United States Patent
Ito et al.

(10) Patent No.: US 10,396,288 B2
(45) Date of Patent: Aug. 27, 2019

(54) ORGANIC ELECTROLUMINESCENT ELEMENT AND ELECTRONIC DEVICE

(71) Applicant: IDEMITSU KOSAN CO., LTD., Chiyoda-ku (JP)

(72) Inventors: Hirokatsu Ito, Ichihara (JP); Masahiro Kawamura, Chiba (JP); Yumiko Mizuki, Basel (CH); Tasuku Haketa, Chiba (JP); Tomoharu Hayama, Utsunomiya (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 86 days.

(21) Appl. No.: 14/909,783

(22) PCT Filed: Sep. 19, 2014

(86) PCT No.: PCT/JP2014/074975
§ 371 (c)(1),
(2) Date: Feb. 3, 2016

(87) PCT Pub. No.: WO2015/041358
PCT Pub. Date: Mar. 26, 2015

(65) Prior Publication Data
US 2016/0181543 A1    Jun. 23, 2016

(30) Foreign Application Priority Data

Sep. 20, 2013 (JP) .................. 2013-196191

(51) Int. Cl.
*H01L 51/50* (2006.01)
*H01L 51/00* (2006.01)
(Continued)

(52) U.S. Cl.
CPC .......... *H01L 51/0056* (2013.01); *C07C 13/62* (2013.01); *C07C 211/61* (2013.01);
(Continued)

(58) Field of Classification Search
None
See application file for complete search history.

(56) References Cited

U.S. PATENT DOCUMENTS

2003/0225234 A1    12/2003    Jaycox et al.
2004/0076853 A1*    4/2004    Jarikov .................. C09K 11/06
                                                            428/690
(Continued)

FOREIGN PATENT DOCUMENTS

CN        1646660 A        7/2005
CN        101550085 A      10/2009
(Continued)

OTHER PUBLICATIONS

Combined Chinese Office Action and Search Report dated Dec. 2, 2016 in Patent Application No. 20148004452.0 (with English Translation of Category of Cited Documents).
(Continued)

*Primary Examiner* — Gregory D Clark
(74) *Attorney, Agent, or Firm* — Oblon, McClelland, Maier & Neustadt, L.L.P.

(57) ABSTRACT

An organic EL device with high emission efficiency, an electronic equipment including the organic EL device, and a compound providing the organic EL device are provided. The compound is represented by formula (1):
(Continued)

US 10,396,288 B2
Page 2

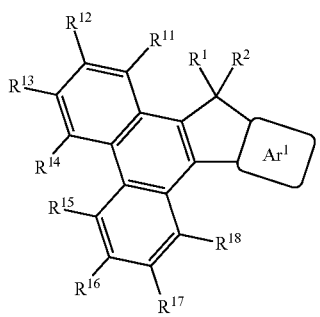

(1)

wherein $Ar^1$ represents a substituted or unsubstituted naphthalene ring; the substituent on the naphthalene ring is at least one selected from a fluorine atom, a cyano group, an alkyl group, a cycloalkyl group, an alkoxy group, an aryloxy group, an alkylthio group, an arylthio group, a group represented by $—Si(R_{101})(R_{102})(R_{103})$, and a group represented by $—Z—R^a$; $R^1$ and $R^2$ each independently represent a hydrogen atom, an alkyl group, a cycloalkyl group, a group represented by $—Si(R_{101})(R_{102})(R_{103})$, an aryl group, or a heteroaryl group; $R^{11}$ to $R^{18}$ each independently represent a hydrogen atom, a fluorine atom, a cyano group, an alkyl group, a cycloalkyl group, an alkoxy group, an aryloxy group, an alkylthio group, an arylthio group, a group represented by $—Si(R_{101})(R_{102})(R_{103})$, or a group represented by $—Z—R^a$; each Z represents a single bond, an arylene group, a heteroarylene group, or a divalent linking group in which 2 to 4 groups selected from the above groups are linked together; $R^a$ represents a group represented by $—N(R_{104})(R_{105})$, an aryl group, or a heteroaryl group; and $R_{101}$ to $R_{105}$ each represent a hydrogen atom, an alkyl group, a cycloalkyl group, aryl group, or a heteroaryl group; provided that at least one selected from the substituent on the naphthalene ring and $R^{11}$ to $R^{18}$ represents a group represented by $—Z—R^a$.

57 Claims, 1 Drawing Sheet

(51) Int. Cl.
| | | |
|---|---|---|
| C07C 211/61 | (2006.01) | |
| C07C 13/62 | (2006.01) | |
| C07C 255/58 | (2006.01) | |
| C07D 333/76 | (2006.01) | |
| C07D 235/08 | (2006.01) | |
| C07D 235/18 | (2006.01) | |
| C07D 237/08 | (2006.01) | |
| C07D 239/26 | (2006.01) | |
| C07D 239/74 | (2006.01) | |
| C07D 251/24 | (2006.01) | |
| C07D 471/04 | (2006.01) | |
| C07D 487/04 | (2006.01) | |
| C07D 209/86 | (2006.01) | |
| C07D 213/16 | (2006.01) | |
| C07D 213/22 | (2006.01) | |
| C07D 307/77 | (2006.01) | |
| C07D 307/91 | (2006.01) | |
| H05B 33/20 | (2006.01) | |
| C09B 57/00 | (2006.01) | |
| C09B 69/00 | (2006.01) | |
| C09B 1/00 | (2006.01) | |
| C09K 11/02 | (2006.01) | |
| C09K 11/06 | (2006.01) | |
| C07F 7/08 | (2006.01) | |

(52) U.S. Cl.
CPC .......... *C07C 255/58* (2013.01); *C07D 209/86* (2013.01); *C07D 213/16* (2013.01); *C07D 213/22* (2013.01); *C07D 235/08* (2013.01); *C07D 235/18* (2013.01); *C07D 237/08* (2013.01); *C07D 239/26* (2013.01); *C07D 239/74* (2013.01); *C07D 251/24* (2013.01); *C07D 307/77* (2013.01); *C07D 307/91* (2013.01); *C07D 333/76* (2013.01); *C07D 471/04* (2013.01); *C07D 487/04* (2013.01); *C07F 7/081* (2013.01); *C09B 1/00* (2013.01); *C09B 57/00* (2013.01); *C09B 57/001* (2013.01); *C09B 57/008* (2013.01); *C09B 69/008* (2013.01); *C09K 11/025* (2013.01); *C09K 11/06* (2013.01); *H05B 33/20* (2013.01); *C07C 2601/14* (2017.05); *C07C 2603/18* (2017.05); *C07C 2603/24* (2017.05); *C07C 2603/26* (2017.05); *C07C 2603/40* (2017.05); *C07C 2603/42* (2017.05); *C07C 2603/50* (2017.05); *C07C 2603/52* (2017.05); *C07C 2603/54* (2017.05); *C09K 2211/1007* (2013.01); *C09K 2211/1011* (2013.01); *C09K 2211/1014* (2013.01); *C09K 2211/1059* (2013.01); *H01L 51/006* (2013.01); *H01L 51/0054* (2013.01); *H01L 51/0058* (2013.01); *H01L 51/0061* (2013.01); *H01L 51/0073* (2013.01); *H01L 51/5012* (2013.01); *H01L 51/5016* (2013.01); *H01L 51/5056* (2013.01); *H01L 51/5072* (2013.01); *H01L 51/5096* (2013.01); *H01L 2251/308* (2013.01)

(56) References Cited

U.S. PATENT DOCUMENTS

| | | |
|---|---|---|
| 2005/0124732 A1 | 6/2005 | Jaycox et al. |
| 2005/0131185 A1 | 6/2005 | Jaycox et al. |
| 2007/0018571 A1 | 1/2007 | Hwang et al. |
| 2009/0273277 A1 | 11/2009 | Lee et al. |
| 2009/0278451 A1 | 11/2009 | Hwang et al. |
| 2012/0181520 A1* | 7/2012 | Kim ............ C07B 59/001 257/40 |
| 2014/0131681 A1 | 5/2014 | Ito et al. |
| 2016/0020407 A1* | 1/2016 | Jung ............ H01L 51/0067 257/40 |

FOREIGN PATENT DOCUMENTS

| | | |
|---|---|---|
| CN | 102617626 A | 8/2012 |
| JP | 2003-229273 A | 8/2003 |
| KR | 10-2007-0012110 A | 1/2007 |
| KR | 10-2012-0083203 A | 7/2012 |
| KR | 10-2012-0116884 A | 10/2012 |
| KR | 10-2012-0135501 A | 12/2012 |
| WO | 2004/061047 A2 | 7/2004 |
| WO | 2004/061048 A1 | 7/2004 |
| WO | 2011/081403 A2 | 7/2011 |
| WO | 2014/069602 A1 | 5/2014 |

OTHER PUBLICATIONS

R. G. Harvey, et al., "A New General Synthesis of Polycyclic Aromatic Compounds Based on Enamine Chemistry," Journal of Organic Chemistry, 1991, vol. 56, No. 3, pp. 1210-1217.
R. N. Jones, "Some Factors Influencing the Ultraviolet Absorption Spectra of Polynuclear Aromatic Compounds. II. The Spectra of

(56) References Cited

OTHER PUBLICATIONS

Aryl Carbinols and Polybenzfluorenes," Journal of the American Chemical Society, 1945, vol. 67, pp. 2021-2027.
International Search Report dated Dec. 16, 2014 in PCT/JP14/74975 Filed Sep. 19, 2014.
Chinese Office Action dated Nov. 15, 2018 in Chinese Patent Application No. 201480044520.0, 5 pages.

* cited by examiner

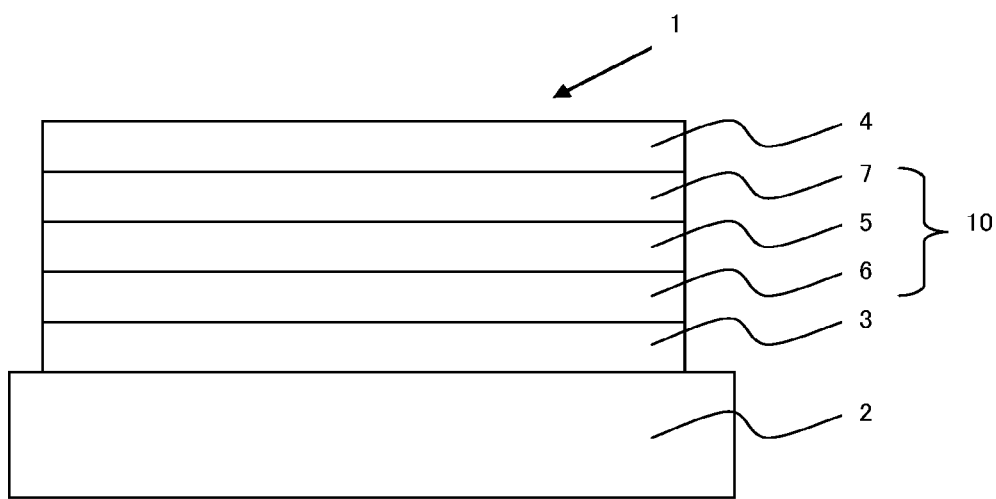

ORGANIC ELECTROLUMINESCENT ELEMENT AND ELECTRONIC DEVICE

CROSS-REFERENCE TO RELATED APPLICATIONS

This application is a National Stage of PCT/JP2014/074975, which was filed on Sep. 19, 2014. This application is based upon and claims the benefit of priority to Japanese Application No. 2013-196191, which was filed on Sep. 20, 2013.

TECHNICAL FIELD

The present invention relates to organic electroluminescence devices and electronic equipment comprising the organic electroluminescence devices and further relates to compounds usable as materials for the organic electroluminescence devices.

BACKGROUND ART

An organic electroluminescence (EL) device is generally composed of an anode, a cathode, and one or more organic thin film layers sandwiched between the anode and the cathode. When a voltage is applied between the electrodes, electrons are injected from the cathode and holes are injected from the anode into a light emitting region. The injected electrons recombine with the injected holes in the light emitting region to form excited states. When the excited states return to the ground state, the energy is released as light.

Many researches have been made on the applications of organic EL device to display, etc. because of its possibility of a wide selection of emission colors by using various emitting materials in a light emitting layer. Particularly, the research on the materials which emit three primary red, green, and blue colors has been made most actively, and the intensive research has been made to improve their properties.

One of the most important problems involved in an organic EL device is how to achieve high emission efficiency. To obtain an organic EL device with high emission efficiency, it has been known to form a light emitting layer by doping a several percent of dopant material into a host material.

As a material for such an organic EL device, Patent Literatures 1 and 2 disclose a compound having a five-membered ring wherein one side is shared with a bicyclic fused ring and another side is shared with a benzene ring, Patent Literature 3 discloses a compound having a five-membered ring wherein one side is shared with a tricyclic fused ring and another side is shared with a benzene ring, and Patent Literature 4 discloses a compound having a five-membered ring wherein one side is shared with a fused ring and another side is shared with a different fused ring.

CITATION LIST

Patent Literature

Patent Literature 1: WO 2004/061047
Patent Literature 2: WO 2004/061048
Patent Literature 3: KR 10-2012-0083203A
Patent Literature 4: KR 10-2012-0116884A

SUMMARY OF INVENTION

Technical Problem

The inventors have examined the compounds disclosed in Patent Literatures 1 to 4 and have found that the improvement in the emission efficiency is still required.

Thus, the technical problem to be solved in the present invention is to provide an organic EL device with high emission efficiency, an electronic equipment comprising the organic EL device, and a compound achieving such an organic EL device.

Solution to Problem

As a result of extensive research to solve the above problem, the inventors have found that the problem can be solved by using a specific compound as the material for an organic EL device. The compound includes a five-membered ring in which one side is shared with a bond between 9-position and 10-position of a phenanthrene ring and another side is shared with a naphthalene ring. The present invention is based on this finding.

In an aspect of the present invention, the following (1) to (4) are provided: (1) a compound represented by formula (1):

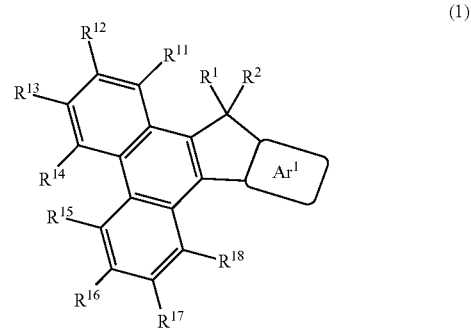

(1)

wherein $Ar^1$ represents a substituted or unsubstituted naphthalene ring, and a substituent on the naphthalene ring is at least one selected from the group consisting of a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a group represented by $-Si(R_{101})(R_{102})(R_{103})$, and a group represented by $-Z-R^a$;

$R^1$ and $R^2$ each independently represent a hydrogen atom, a substituted or unsubstituted alkyl group having 1 to 20 carbon atoms, a substituted or unsubstituted cycloalkyl group having 3 to 20 ring carbon atoms, a group represented by $-Si(R_{101})(R_{102})(R_{103})$, a substituted or unsubstituted aryl group having 6 to 30 ring carbon atoms, or a substituted or unsubstituted heteroaryl group having 5 to 30 ring atoms;

$R^{11}$ to $R^{18}$ each independently represent a hydrogen atom, a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a group represented by —Si($R_{101}$)($R_{102}$)($R_{103}$), or a group represented by —Z—$R^a$;

each Z represents a single bond, a substituted or unsubstituted arylene group having 6 to 30 ring carbon atoms, a substituted or unsubstituted heteroarylene group having 5 to 30 ring atoms, or a divalent linking group in which 2 to 4 groups selected from the above groups are linked together;

when more than one Z occurs, groups Z may be the same or different;

$R^a$ represents a group represented by —N($R_{104}$)($R_{105}$), a substituted or unsubstituted aryl group having 6 to 30 ring carbon atoms, or a substituted or unsubstituted heteroaryl group having 5 to 30 ring atoms;

when more than one $R^a$ occurs, groups $R^a$ may be the same or different;

$R_{101}$ to $R_{105}$ each independently represent a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms;

provided that at least one selected from the substituent on the naphthalene ring and $R^{11}$ to $R^{18}$ represents a group represented by —Z—$R^a$; and more than one —Z—$R^a$ occurs, groups —Z—$R^a$ may be the same or different;

(2) a material for organic electroluminescence devices comprising the compound described in (1);

(3) an organic electroluminescence device comprising an organic thin film layer between a cathode and an anode, wherein the organic thin film layer comprises one or more layers which comprise a light emitting layer and at least one layer of the organic thin film layer comprises the compound described in (1); and (4) an electronic equipment comprising the organic electroluminescence device described in (3).

Advantageous Effects of Invention

The organic EL device of the invention has high emission efficiency. The compound of the invention for use as a material for the organic EL device of the invention has a high carrier mobility, and therefore, is useful not only as a host material of a light emitting layer but also as an electron transporting material or a hole transporting material. In particular, when the compound of the invention is used in a light emitting layer as a dopant material, a high emission efficiency is obtained and an emission of deep blue light is also realized.

Although not particularly limited, among the compounds of the invention, a compound having an amino group is useful particularly as a dopant material, etc.; a compound having a heteroaryl group, particularly a compound having a nitrogen-containing heteroaryl group is useful particularly as an electron transporting material and a material for a blocking layer interposed between a light emitting layer and an electron transporting layer, etc.; and a compound having an anthracene skeleton is useful particularly as a fluorescent host material, etc.

BRIEF DESCRIPTION OF DRAWINGS

FIG. 1 is a schematic view showing an example of the structure of the organic electroluminescence device according to an embodiment of the present invention.

DESCRIPTION OF EMBODIMENTS

The term "a to b carbon atoms" referred to by "a substituted or unsubstituted group X having a to b carbon atoms" used herein is the number of carbon atoms of the unsubstituted group X and does not include any carbon atom in the substituent of the substituted group X.

The number of "ring carbon atoms" referred to herein is the number of the carbon atoms which form a saturated ring, an unsaturated ring, or an aromatic ring, and the carbon atom in a substituent on the ring is not included in the ring carbon atom.

The number of "ring atom" referred to herein is the number of the atoms which form a saturated ring, an unsaturated ring, or an aromatic ring, and a hydrogen atom and the atom in a substituent on the ring are not included in the ring atom.

The definition of "hydrogen atom" used herein includes isotopes different in the neutron numbers, i.e., light hydrogen (protium), heavy hydrogen (deuterium), and tritium.

The optional substituent referred to by "substituted or unsubstituted" used herein is, unless otherwise defined, preferably selected from the group consisting of an alkyl group having 1 to 20, preferably 1 to 10, more preferably 1 to 6 carbon atoms; a cycloalkyl group having 3 to 20, preferably 3 to 6, more preferably 5 or 6 ring carbon atoms; an aryl group having 6 to 30, preferably 6 to 24, more preferably 6 to 12 ring carbon atoms; an aralkyl group having 7 to 30, preferably 7 to 10, more preferably 7 to 12 carbon atoms having an aryl group having 6 to 30, preferably 6 to 24, more preferably 6 to 12 ring carbon atoms; an amino group; a mono- or dialkylamino group having an alkyl group having 1 to 20, preferably 1 to 10, more preferably 1 to 6 carbon atoms; a mono- or diarylamino group having an aryl group having 6 to 30, preferably 6 to 24, more preferably 6 to 12 ring carbon atoms; an alkoxy group having 1 to 30, preferably 1 to 10, more preferably 1 to 6 carbon atoms; an aryloxy group having 6 to 30, preferably 6 to 24, more preferably 6 to 12 ring carbon atoms; an alkylthio group having 1 to 20, preferably 1 to 10, more preferably 1 to 6 carbon atoms; an arylthio group having 6 to 30, preferably 6 to 24, more preferably 6 to 12 ring carbon atoms; a mono-, di- or tri-substituted silyl group, wherein the substituent is selected from an alkyl group having 1 to 20, preferably 1 to 10, more preferably 1 to 6 and an aryl group having 6 to 30, preferably 6 to 24, more preferably 6 to 12 ring carbon atoms; a heteroaryl group having 5 to 30, preferably 5 to 24, more preferably 5 to 12 ring atoms, which comprise 1 to 5, preferably 1 to 3, more preferably 1 to 2 heteroatoms, such as a nitrogen atom, an oxygen atom, and a sulfur atom; a haloalkyl group having 1 to 20, preferably 1 to 10, more preferably 1 to 6 carbon atoms; a halogen atom, such as a fluorine atom, a chlorine, a bromine atom, and a iodine atom; a cyano group; and a nitro group.

Of the above, a substituent selected from the group consisting of an alkyl group having 1 to 6 carbon atoms, a cycloalkyl group having 5 or 6 carbon atom, and an aryl group having 6 to 12 ring carbon atoms is more preferred.

These optional substituents may further include a substituent mentioned above.

The number of the substituent referred to by "substituted or unsubstituted" may be one or more. When two substituents occur, these substituents may be the same or different.

In the present invention, the features which are defined as being preferred can be selected arbitrarily and a combination thereof is a more preferred embodiment.

The compound of the invention is represented by formula (1);

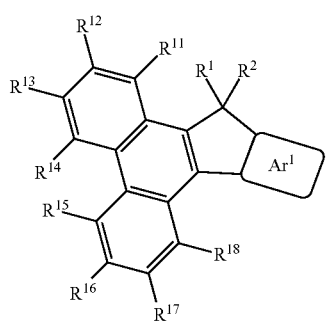

(1)

wherein $Ar^1$ represents a substituted or unsubstituted naphthalene ring, and a substituent on the naphthalene ring is at least one selected from the group consisting of a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a group represented by $—Si(R_{101})(R_{102})(R_{103})$, and a group represented by $—Z—R^a$;

$R^1$ and $R^2$ each independently represent a hydrogen atom, a substituted or unsubstituted alkyl group having 1 to 20 carbon atoms, a substituted or unsubstituted cycloalkyl group having 3 to 20 ring carbon atoms, a group represented by $—Si(R_{101})(R_{102})(R_{103})$, a substituted or unsubstituted aryl group having 6 to 30 ring carbon atoms, or a substituted or unsubstituted heteroaryl group having 5 to 30 ring atoms;

$R^{11}$ to $R^{18}$ each independently represent a hydrogen atom, a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a group represented by $—Si(R_{101})(R_{102})(R_{103})$, or a group represented by $—Z—R^a$;

each Z represents a single bond, a substituted or unsubstituted arylene group having 6 to 30 ring carbon atoms, a substituted or unsubstituted heteroarylene group having 5 to 30 ring atoms, or a divalent linking group in which 2 to 4 groups selected from the above groups are linked together;

when more than one Z occurs, groups Z may be the same or different;

$R^a$ represents a group represented by $—N(R_{104})(R_{105})$, a substituted or unsubstituted aryl group having 6 to 30 ring carbon atoms, or a substituted or unsubstituted heteroaryl group having 5 to 30 ring atoms;

when more than one $R^a$ occurs, groups $R^a$ may be the same or different;

$R_{101}$ to $R_{105}$ each independently represent a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms;

provided that at least one selected from the substituent on the naphthalene ring and $R^{11}$ to $R^{18}$ represents a group represented by $—Z—R^a$; and more than one $—Z—R^a$ occurs, groups $—Z—R^a$ may be the same or different.

$R^1$ and $R^2$ together with the carbon atoms to which $R^1$ and $R^2$ are bonded may form a ring having preferably 3 to 20, more preferably 3 to 6, and still more preferably 5 or 6 ring carbon atoms. On the other hand, none of $R^{11}$ to $R^{18}$ forms a ring.

Examples of the compound in which $R^1$ and $R^2$ together with the carbon atoms to which $R^1$ and $R^2$ are bonded form a ring are shown below.

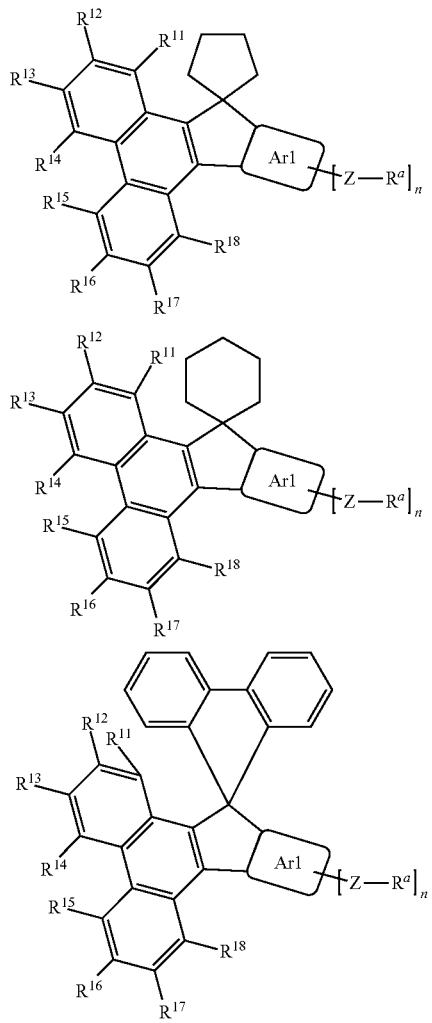

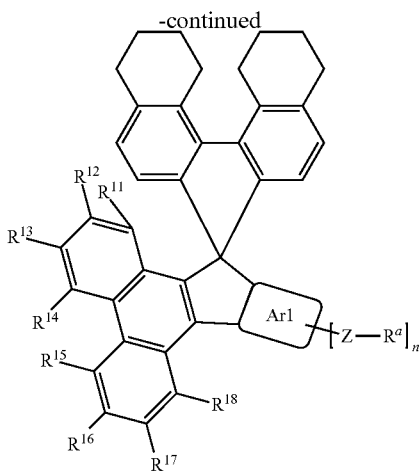

Examples of the alkyl group having 1 to 20, preferably 1 to 10, more preferably 1 to 6 carbon atoms for $R^1$ and $R^2$, $R^{11}$ to $R^{18}$, and $R_{101}$ to $R_{105}$ include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), and a dodecyl group (inclusive of isomeric groups). Preferred are a methyl group, an ethyl group, a n-propyl group, an isopropyl group, a n-butyl group, an isobutyl group, a s-butyl group, a t-butyl group, and a pentyl group (inclusive of isomeric groups). More preferred are a methyl group, an ethyl group, a n-propyl group, an isopropyl group, a n-butyl group, an isobutyl group, a s-butyl group, and a t-butyl group. Particularly preferred are a methyl group, an ethyl group, an isopropyl group, and a t-butyl group.

Examples of the cycloalkyl group having 3 to 20, preferably 3 to 6, more preferably 5 or 6 ring carbon atoms for $R^1$, $R^2$, $R^{11}$ to $R^{18}$, and $R_{101}$ to $R_{105}$ include a cyclopropyl group, a cyclobutyl group, a cyclopentyl group, a cyclohexyl group, a cycloheptyl group, a cyclooctyl group, and an adamantyl group, with a cyclopentyl group and a cyclohexyl group being preferred.

Examples of the alkoxy group having 1 to 20, preferably 1 to 10, and more preferably 1 to 6 carbon atoms for $R^{11}$ to $R^{18}$ include those having an alkyl moiety selected from the alkyl group having 1 to 20 carbon atoms mentioned above. Preferred examples thereof include those having an alkyl moiety selected from the preferred alkyl group mentioned above.

Examples of the aryloxy group having 6 to 30, preferably 6 to 24, more preferably 6 to 18, and still more preferably 6 to 10 ring carbon atoms for $R^{11}$ to $R^{18}$ include those having an aryl moiety selected from the aryl group having 6 to 30 ring carbon atoms to be described below. Preferred examples thereof include those having an aryl moiety selected from the preferred aryl group to be described below.

Examples of the alkylthio group having 1 to 20, preferably 1 to 10, and more preferably 1 to 6 carbon atoms for $R^{11}$ to $R^{18}$ include those having an alkyl moiety selected from the alkyl group having 1 to 20 carbon atoms mentioned above. Preferred examples thereof include those having an alkyl moiety selected from the preferred alkyl group mentioned above.

Examples of the arylthio group having 6 to 30, preferably 6 to 24, more preferably 6 to 18, and still more preferably 6 to 10 ring carbon atoms for $R^{11}$ to $R^{18}$ include those having an aryl moiety selected from the aryl group having 6 to 30 ring carbon atoms to be described below. Preferred examples thereof include those having an aryl moiety selected from the preferred aryl group to be described below.

The group represented by $-Si(R_{101})(R_{102})(R_{103})$ for $R^1$, $R^2$, and $R^{11}$ to $R^{18}$ of formula (1) may include a monoalkylsilyl group, a dialkylsilyl group, a trialkylsilyl group, a monoarylsilyl group, a diarylsilyl group, a triarylsilyl group, a monoalkyldiarylsilyl group, and a dialkylmonoarylsilyl group.

In these substituted silyl groups, the alkyl moiety has preferably 1 to 20, more preferably 1 to 10, and still more preferably 1 to 6, and the aryl moiety has preferably 6 to 30, more preferably 6 to 24, and still more preferably 6 to 18 ring carbon atoms.

Preferred are a trialkylsilyl group and a triarylsilyl group, with a trimethylsilyl group, a triethylsilyl group, a triisopropylsilyl group, a t-butyldimethylsilyl group, a triphenylsilyl group, and a tritolylsilyl group being more preferred.

The group represented by $-N(R_{104})(R_{105})$ for $R^a$ of formula (1) may include a monoalkylamino group, a dialkylamino group, a monoarylamino group, a diarylamino group, a monoheteroarylamino group, a diheteroarylamino group, a monoalkylmonoarylamino group, a monoalkylmonoheteroarylamino group, and a monoarylmonoheteroarylamino group. The aryl moiety of these substituted amino groups may have a substituent, for example, an alkyl group having 1 to 20, preferably 1 to 10, and more preferably 1 to 6 carbon atoms.

In these substituted amino groups, the alkyl moiety has preferably 1 to 20, more preferably 1 to 10, and still more preferably 1 to 6 carbon atoms; the aryl moiety has preferably 6 to 30, more preferably 6 to 24, still more preferably 6 to 18, and particularly preferably 6 to 10 ring carbon atoms; and the heteroaryl moiety has preferably 5 to 30, more preferably 5 to 24, and still more preferably 5 to 12 ring atoms.

Preferred are a dialkylamino group, a diarylamino group, a diheteroarylamino group, and a monoarylmonoheteroarylamino group, with a dimethylamino group, a diethylamino group, a diisopropylamino group, a diphenylamino group, a bis(alkyl-substituted phenyl)amino group, and a bis(aryl-substituted phenyl)amino group being more preferred.

When more than one group which is represented by $-Si(R_{101})(R_{102})(R_{103})$ occurs, these groups may be the same or different. When more than one group which is represented by $-N(R_{104})(R_{105})$ occurs, these groups may be the same or different.

The aryl group having 6 to 30, preferably 6 to 24, more preferably 6 to 18, and still more preferably 6 to 10 ring carbon atoms for $R^1$, $R^2$, $R^{11}$ to $R^{18}$, and $R_{101}$ to $R_{105}$ of formula (1) may be a fused ring or a non-fused ring. Examples thereof include a phenyl group, a biphenylyl group, a terphenylyl group, a naphthyl group, acenaphthylenyl group, an anthryl group, a benzanthryl group, an aceanthryl group, a phenanthryl group, a benzo[c]phenanthryl group, a phenalenyl group, a fluorenyl group, a picenyl group, a pentaphenyl group, a pyrenyl group, a chrysenyl group, a benzo[g]chrysenyl group, a s-indacenyl group, an as-indacenyl group, a fluoranthenyl group, a benzo[k]fluoranthenyl group, a triphenylenyl group, a benzo[b]triphenylenyl group, and a perylenyl group. Preferred are a phenyl group, a biphenylyl group, a terphenylyl group, a naphthyl group, an anthryl group, a pyrenyl group, and a fluoranthenyl group, with a phenyl group, a biphenylyl group, and a terphenylyl group being more preferred and a phenyl group being sill more preferred.

The heteroaryl group having 5 to 30, preferably 5 to 24, and more preferably 5 to 12 ring atoms for $R^1$, $R^2$, $R^{11}$ to $R^{18}$, and $R_{101}$ to $R_{105}$ of formula (1) includes at least one, preferably 1 to 5, more preferably 1 to 4, and still more preferably 1 to 3 heteroatoms, for example, a nitrogen atom, a sulfur atom and an oxygen atom, with a nitrogen atom and an oxygen atom being preferred.

Examples thereof include a pyrrolyl group, a furyl group, a thienyl group, a pyridyl group, an imidazopyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a carbazolyl group, a 9-phenylcarbazolyl group, a phenanthridinyl group, an acridinyl group, a phenanthrolinyl group, a phenazinyl group, a phenothiazinyl group, a phenoxazinyl group, and a xanthenyl group. Preferred are a pyridyl group, an imidazopyridyl group, a pyridazinyl group, a pyrimidinyl group, a pyrazinyl group, a triazinyl group, a benzimidazolyl group, a dibenzofuranyl group, a dibenzothiophenyl group, a carbazolyl group, a 9-phenylcarbazolyl group, a phenanthrolinyl group, and a quinazolinyl group.

Examples of the arylene group having 6 to 30, preferably 6 to 24, more preferably 6 to 18, and still more preferably 6 to 10 ring carbon atoms for Z of formula (1), include divalent groups derived from the aryl group mentioned above by removing one hydrogen atom. Preferred are a phenylene group, a naphthylene group, an anthrylene group, a phenanthrylene group, a pyrenylene group, and a fluorenylene group having two substituents at 9-position, with a 1,4-phenylene group, a 1,3-phenylene group, a 1,2-phenylene group, a 1,4-naphthylene group, a 2,6-naphthylene group, a 9,9-dimethyl-2,7-fluorenylene group, and a 9,9-diphenyl-2,7-fluorenylene group being more preferred.

Examples of the heteroaryl group having 5 to 30, preferably 5 to 24, and more preferably 5 to 12 ring atoms for Z include divalent groups derived from the heteroaryl group mentioned above by removing one hydrogen atom. Preferred are a pyridinylene group, a pyrimidinylene group, a pyrazinylene group, a pyridazinylene group, a triazinylene group, a phenanthrolinylene group, a dibenzofuranylene group, and a dibenzothiophenylene group, with a pyridinylene group, a pyrimidinylene group, a triazinylene group, a dibenzofuranylene group, and a dibenzothiophenylene group being more preferred. Of the substituents mentioned above, the substituent of the heteroarylene group is preferably an aryl group having 6 to 30 ring carbon atoms, more preferably an aryl group having 6 to 24 ring carbon atoms, still more preferably an aryl group having 6 to 12 ring carbon atoms, and particularly preferably a phenyl group.

Z may be a divalent group in which 2 to 4 groups selected from the arylene group and the heteroarylene group are linked together. Examples of such a divalent group include -arylene group-heteroarylene group-, -heteroarylene group-arylene group-, -arylene group-heteroarylene group-arylene group-, -heteroarylene group-arylene group-heteroarylene group-, -arylene group-heteroarylene group-arylene group-heteroarylene group-, and -heteroarylene group-arylene group-heteroarylene group-arylene group-.

Examples and preferred examples of the aryl group and the heteroaryl group for $R^a$ of formula (1) include those mentioned above with respect to $R^{11}$ to $R^{18}$, respectively.

The compound represented by formula (1) is preferably represented by any of formulae (2) to (4):

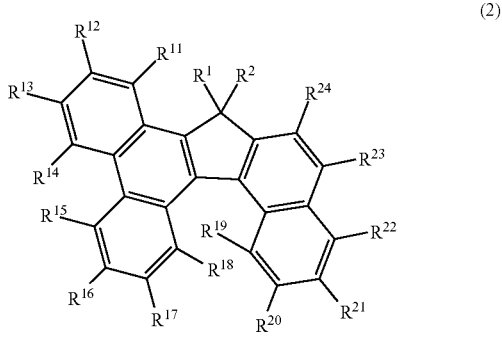

(2)

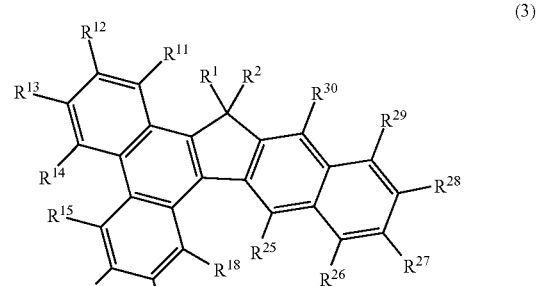

(3)

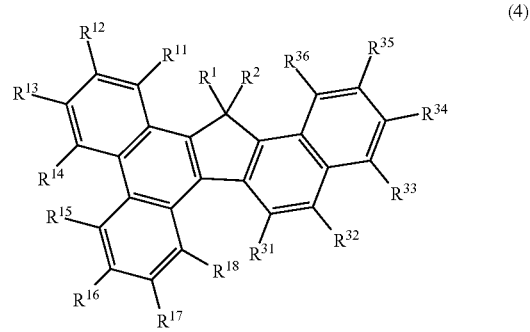

(4)

wherein, $R^1$ and $R^2$ each independently represent a hydrogen atom, a substituted or unsubstituted alkyl group having 1 to 20 carbon atoms, a substituted or unsubstituted cycloalkyl group having 3 to 20 ring carbon atoms, a group represented by —Si($R_{101}$)($R_{102}$)($R_{103}$), a substituted or unsubstituted aryl group having 6 to 30 ring carbon atoms, or a substituted or unsubstituted heteroaryl group having 5 to 30 ring atoms; and $R^{11}$ to $R^{36}$ each independently represent a hydrogen atom, a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a group represented by —Si($R_{101}$)($R_{102}$)($R_{103}$), a group represented by —N($R_{104}$)($R_{105}$), a substituted or unsubstituted aryl group having 6 to 30 ring carbon atoms, a substituted or unsubstituted heteroaryl group having 5 to 30 ring atoms, or a group represented by —Z—$R^a$;

provided that one to four selected from $R^{11}$ to $R^{24}$ of formula (2), one to four selected from $R^{11}$ to $R^{18}$ and $R^{25}$ to $R^{30}$ of formula (3), and one to four selected from $R^{11}$ to $R^{18}$ and $R^{31}$ to $R^{36}$ of formula (4) each represent a group represented by —Z—$R^a$.

$R^1$ and $R^2$ together with the carbon atoms to which $R^1$ and $R^2$ are bonded may form a ring having preferably 3 to 20, more preferably 3 to 6, and still more preferably 5 or 6 ring carbon atoms. Examples of such a ring are those as described above with respect to formula (1). On the other hand, none of $R^{11}$ to $R^{36}$ forms a ring.

Examples and preferred examples of $R^1$, $R^2$, and $R^{11}$ to $R^{18}$ of formulae (2) to (4) are the same as those described above with respect to formula (1), respectively.

Examples and preferred examples of $R^{19}$ to $R^{36}$ are those as described above with respect to $R^{11}$ to $R^{18}$ of formula (1).

As described above, one to four, preferably one or two selected from $R^{11}$ to $R^{24}$ of formula (2), one to four, preferably one or two selected from $R^{11}$ to $R^{18}$ and $R^{25}$ to $R^{30}$ of formula (3), and one to four, preferably one or two selected from $R^{11}$ to $R^{18}$ and $R^{31}$ to $R^{36}$ of formula (4) each represent a group represented by —Z—$R^a$.

Although not particularly limited, in formula (2) preferably at least one selected from $R^{13}$ and $R^{23}$, more preferably $R^{23}$ is the group represented by —Z—$R^a$; in formula (3) preferably at least one selected from $R^{13}$ and $R^{28}$, more preferably $R^{28}$ is the group represented by —Z—$R^a$; and in formula (4) preferably at least one selected from $R^{13}$, $R^{32}$ and $R^{34}$, more preferably $R^{34}$ is the group represented by —Z—$R^a$.

The group represented by —Z—$R^a$ in formulae (2) to (4) is more preferably represented by any of formulae (a) to (c):

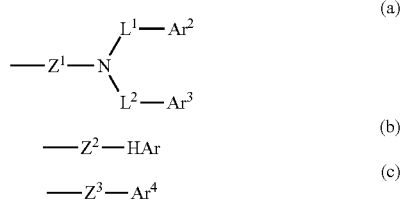

wherein, $Z^1$ to $Z^3$ each independently represent a single bond, a substituted or unsubstituted arylene group having 6 to 30 ring carbon atoms, or a substituted or unsubstituted heteroarylene group having 5 to 30 ring atoms;

$L^1$ and $L^2$ each independently represent a single bond, a substituted or unsubstituted arylene group having 6 to 30 ring carbon atoms, a substituted or unsubstituted heteroarylene group having 5 to 30 ring atoms, or a divalent linking group in which 2 to 4 groups selected from the arylene group and the heteroarylene group are linked together;

$Ar^2$ and $Ar^3$ each independently represent a substituted or unsubstituted aryl group having 6 to 30 ring carbon atoms, or a substituted or unsubstituted heteroaryl group having 5 to 30 ring atoms;

HAr represents a substituted or unsubstituted heteroaryl group having 5 to 30 ring atoms; and $Ar^4$ represents a substituted or unsubstituted aryl group having 14 to 30 ring carbon atoms.

Although not particularly limited, in formula (2) preferably at least one selected from $R^{13}$ and $R^{23}$ is the group represented by any of —Z—$R^a$ and formulae (a) to (c), more preferably $R^{23}$ is the group represented by any of —Z—$R^a$ and formulae (a) to (c), and still more preferably $R^{23}$ is the group represented by formula (b) or (c); in formula (3) preferably at least one selected from $R^{13}$ and $R^{28}$ is the group represented by any of —Z—$R^a$ and formulae (a) to (c), more preferably $R^{28}$ is the group represented by any of —Z—$R^a$ and formulae (a) to (c), and still more preferably $R^{28}$ is the group represented by formula (b) or (c); and in formula (4) preferably at least one selected from $R^{13}$, $R^{32}$, and $R^{34}$ is the group represented by any of —Z—$R^a$ and formulae (a) to (c), more preferably $R^{34}$ is the group represented by any of —Z—$R^a$ and formulae (a) to (c), and still more preferably $R^{34}$ is the group represented by formula (b) or (c).

Examples and preferred examples of $Z^1$ to $Z^3$ in formulae (a) to (c) are the same as those described above with respect to Z in formula (1), respectively. Particularly, in formula (a) $Z^1$ is preferably a single bond or an arylene group having 6 to 30 ring carbon atoms and more preferably a single bond; in formula (2) $Z^2$ is preferably a single bond or an arylene group having 6 to 30 ring carbon atoms; and in formula (c) $Z^3$ is preferably a single bond or an arylene group having 6 to 30 ring carbon atoms and more preferably an arylene group having 6 to 30 ring carbon atoms.

Examples and preferred examples of the arylene group having 6 to 30, preferably 6 to 24, more preferably 6 to 18, and still more preferably 6 to 10 ring carbon atoms and the heteroarylene group having 5 to 30, preferably 5 to 24, and more preferably 5 to 12 ring atoms each for $L^1$ and $L^2$ in formula (a) are the same as those described above with respect to the arylene group and the heteroarylene group for Z in formula (1), respectively. Examples of the divalent group in which 2 to 4 groups selected from the arylene group and the heteroarylene group are linked together for $L^1$ and $L^2$ include -arylene group-heteroarylene group-, -heteroarylene group-arylene group-, -arylene group-heteroarylene group-arylene group-, -heteroarylene group-arylene group-heteroarylene group-, -arylene group-heteroarylene group-arylene group-heteroarylene group-, and -heteroarylene group-arylene group-heteroarylene group-arylene group-.

Examples of the aryl group having 6 to 30, preferably 6 to 20, and more preferably 6 to 14 ring carbon atoms for $Ar^2$ and $Ar^3$ in formula (a) include a phenyl group, a biphenylyl group (2-biphenylyl group, 4-biphenylyl group), a terphenylyl group, a naphthyl group, acenaphthylenyl group, an anthryl group, a benzanthryl group, an aceanthryl group, a phenanthryl group, a benzo[c]phenanthryl group, a phenalenyl group, a fluorenyl group, a picenyl group, a pentaphenyl group, a pyrenyl group, a chrysenyl group, a benzo[g]chrysenyl group, a s-indacenyl group, an as-indacenyl group, a fluoranthenyl group, a benzo[k]fluoranthenyl group, a triphenylenyl group, a benzo[b]triphenylenyl group, and a perylenyl group. In view of the emission efficiency, the device lifetime, and the driving voltage, a phenyl group, a biphenylyl group (2-biphenylyl group, 4-biphenylyl group), a terphenylyl group, a naphthyl group, and an anthryl group are preferred, a phenyl group and a biphenylyl group (2-biphenylyl group, 4-biphenylyl group) are more preferred, a biphenylyl group (2-biphenylyl group, 4-biphenylyl group) is still more preferred, and a 4-biphenylyl group is particularly preferred.

Particularly in view of the device lifetime, the aryl group preferably has a substituent. When the aryl group, particularly a phenyl group, has a substituent, for example, an alkyl group having 1 to 20 carbon atoms, a cycloalkyl group having 3 to 20 ring carbon atoms and an alkoxy group having 1 to 30 carbon atoms, the device lifetime tends to be largely improved.

Examples and preferred examples of the heteroaryl group having 5 to 30, preferably 5 to 20, and more preferably 5 to 14 ring atoms for $Ar^2$ and $Ar^3$ are the same as those described above with respect to the heteroaryl group for $R^1$ in formula (1).

$L^1$ and $L^2$ are both preferably single bonds, namely, formula (a) is preferably represented by formula (a'):

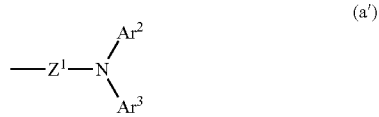

wherein $Z^1$, $Ar^2$ and $Ar^3$ are the same as $Z^1$, $Ar^2$ and $Ar^3$ of formula (a).

Examples and preferred examples of the heteroaryl group having 5 to 30 ring atoms for HAr in formula (b) are the same as those described above with respect to the heteroaryl group for $R^{11}$ to $R^{36}$ in formulae (2) to (4). HAr is more preferably a pyridinyl group, a pyrimidinyl group, or a triazinyl group.

Examples of the aryl group having 14 to 30 ring carbon atoms for $Ar^4$ in formula (c) are those having 14 to 30 ring carbon atoms selected from the aryl group described above with respect to $R^{11}$ to $R^{36}$ in formulae (2) to (4). Preferred is an aryl group having 14 to 25 ring carbon atoms and more preferred is an aryl group having 14 to 20 ring carbon atoms. Specific examples thereof include an anthryl group, a phenanthryl group, a fluoranthenyl group, and a benzo[k]fluoranthenyl group, with an anthryl group being more preferred. Although not particularly limited, $Ar^4$ preferably has a substituent and more preferably has a substituent particularly when $Z^3$ is a single bond. The substituent is preferably an aryl group having 6 to 25 ring carbon atoms and more preferably an aryl group having 6 to 12 ring carbon atoms, such as a phenyl group, a naphthyl group, and a biphenylyl group.

—HAr in formula (b) is preferably a group selected from the following groups:

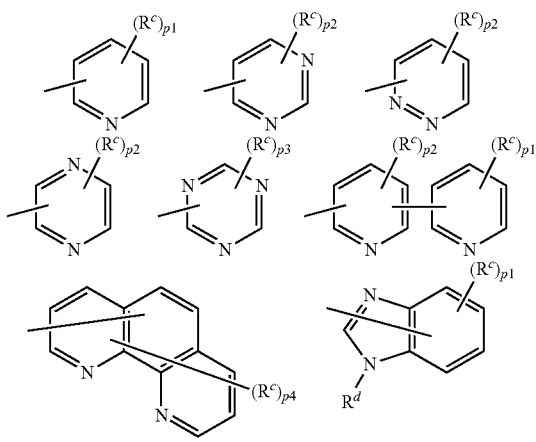

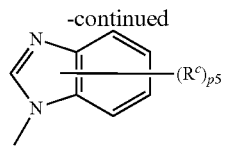

wherein each $R^c$ independently represents a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 ring carbon atoms, a substituted or unsubstituted aralkyl group having 7 to 30 carbon atoms which has an aryl group having 6 to 30 ring carbon atoms, an amino group, a mono- or dialkylamino group having an alkyl group having 1 to 20 carbon atoms, a mono- or diarylamino group having an aryl group having 6 to 30 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a mono-, or tri-substituted silyl group having a substituent selected from an alkyl group having 1 to 20 carbon atoms and an aryl group having 6 to 30 ring carbon atoms, a substituted or unsubstituted heteroaryl group having 5 to 30 ring atoms, a halogen atom, a cyano group, or a nitro group;

When more than one $R^c$ occurs in each group, groups $R^c$ may be the same or different;

$R^d$ represents a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 ring carbon atoms, or a substituted or unsubstituted heteroaryl group having 5 to 30 ring atoms; and each p1 independently represents an integer of 0 to 4, each p2 independently represents an integer of 0 to 3, p3 represents an integer of 0 to 2, p4 represents an integer of 0 to 7, and p5 represents an integer of 0 to 5.

$R^c$ in each group may be bonded to any of the ring carbon atoms.

Examples and preferred examples of the group for $R^c$ and $R^d$ are the same as those described above with respect to $R^{11}$ to $R^{24}$ in formulae (2) to (4), respectively.

Preferably, p1 to p5 are each an integer of 0 to 2.

Of the above, —HAR in formula (b) is preferably the following group:

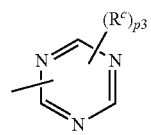

wherein $R^c$ and p3 are as defined above.

In formula (2),
(A) a compound wherein only one or two selected from $R^{11}$ to $R^{24}$ are independently represented by any of formulae (a) to (c) is preferred;
(B) a compound wherein only one or two selected from $R^{11}$ to $R^{24}$ are independently represented by formula (a) is more preferred;
(C) a compound wherein only one or two selected from $R^{11}$ to $R^{24}$ are independently represented by formula (b) is also more preferred; and (D) a compound wherein only one or two selected from $R^{11}$ to $R^{24}$ are independently represented by formula (c) is also more preferred.

In formula (3),
(E) a compound wherein only one or two selected from $R^{11}$ to $R^{18}$ and $R^{25}$ to $R^{30}$ are independently represented by any of formulae (a) to (c) is preferred;
(F) a compound wherein only one or two selected from $R^{11}$ to $R^{18}$ and $R^{25}$ to $R^{30}$ are independently represented by formula (a) is more preferred;
(G) a compound wherein only one or two selected from $R^{11}$ to $R^{18}$ and $R^{25}$ to $R^{30}$ are independently represented by formula (b) is also more preferred; and
(H) a compound wherein only one or two selected from $R^{11}$ to $R^{18}$ and $R^{25}$ to $R^{30}$ are independently represented by formula (c) is also more preferred.

In formula (4),
(I) a compound wherein only one or two selected from $R^{11}$ to $R^{18}$ and $R^{31}$ to $R^{36}$ are independently represented by any of formulae (a) to (c) is preferred;
(J) a compound wherein only one or two selected from $R^{11}$ to $R^{18}$ and $R^{31}$ to $R^{36}$ are independently represented by formula (a) is more preferred;
(K) a compound wherein only one or two selected from $R^{11}$ to $R^{18}$ and $R^{31}$ to $R^{36}$ are independently represented by formula (b) is also more preferred; and
(L) a compound wherein only one or two selected from $R^{11}$ to $R^{18}$ and $R^{31}$ to $R^{36}$ are independently represented by formula (c) is also more preferred.

A compound wherein only one or two selected from $R^{11}$ to $R^{24}$ in formula (2), only one or two selected from $R^{11}$ to $R^{18}$ and $R^{25}$ to $R^{30}$ in formula (3), and only one or two selected from $R^{11}$ to $R^{18}$ and $R^{31}$ to $R^{36}$ in formula (4) are represented by formula (a) is also one of preferred embodiments of the invention.

A compound wherein only one or two selected from $R^{11}$ to $R^{24}$ in formula (2), only one or two selected from $R^{11}$ to $R^{18}$ and $R^{25}$ to $R^{30}$ in formula (3), and only one or two selected from $R^{11}$ to $R^{18}$ and $R^{31}$ to $R^{36}$ in formula (4) are represented by formula (b) is also one of preferred embodiments of the invention.

A compound wherein only one or two selected from $R^{11}$ to $R^{24}$ in formula (2), only one or two selected from $R^{11}$ to $R^{18}$ and $R^{25}$ to $R^{30}$ in formula (3), and only one or two selected from $R^{11}$ to $R^{18}$ and $R^{31}$ to $R^{36}$ in formula (4) are represented by formula (c) is also one of preferred embodiments of the invention.

Of the compound of the invention, also preferred is a compound represented by any of formulae (2-1) to (4-1) and (2-2) to (4-2);

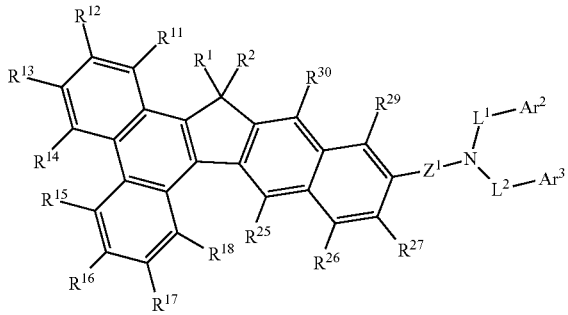
(3-1)

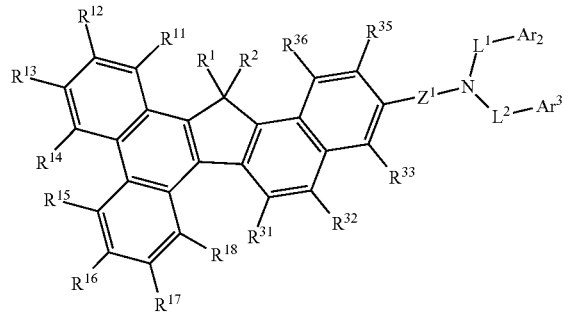
(4-1)

wherein $R^1$, $R^2$, $R^{11}$ to $R^{22}$, $R^{24}$ to $R^{27}$, $R^{29}$ to $R^{33}$, $R^{35}$, $R^{36}$, $Z^1$, $L^1$, $L^2$, $Ar^2$, and $Ar^3$ are as defined above, and examples and preferred examples thereof are the same as those described above; and

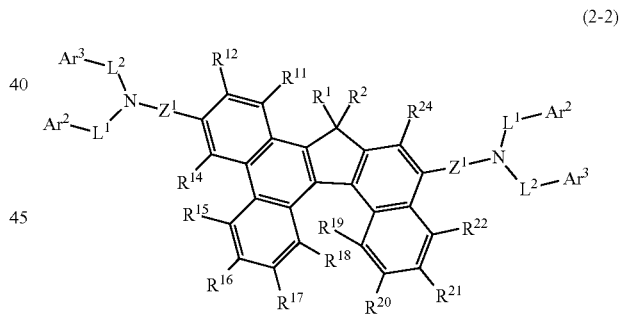
(2-2)

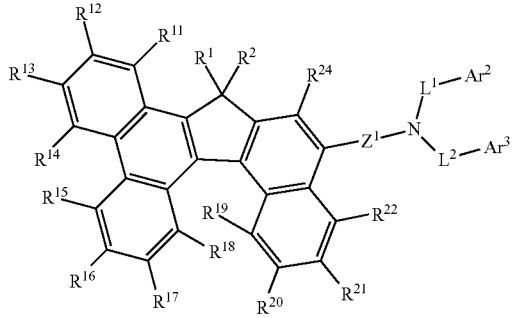
(2-1)

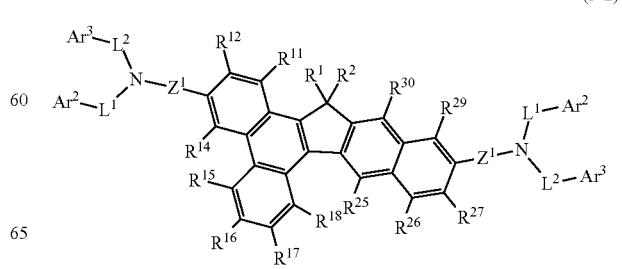
(3-2)

-continued

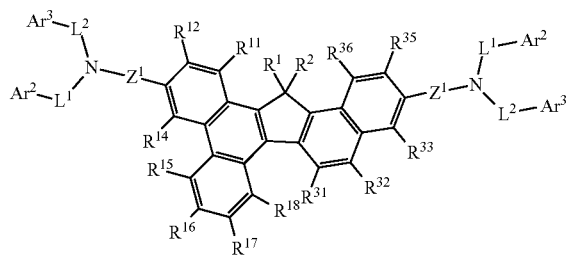

(4-2)

wherein $R^1$, $R^2$, $R^{11}$, $R^{12}$, $R^{14}$ to $R^{22}$, $R^{24}$ to $R^{27}$, $R^{29}$ to $R^{33}$, $R^{35}$, $R^{36}$, $Z^1$, $L^1$, $L^2$, $Ar^2$, and $Ar^3$ are as defined above, and examples and preferred examples thereof are the same as those described above; and more than one $Z^1$, $L^1$, $L^2$, $Ar^2$, and $Ar^3$ may be the same or different, respectively.

Examples of the compound of the invention are shown below, although not limited thereto.

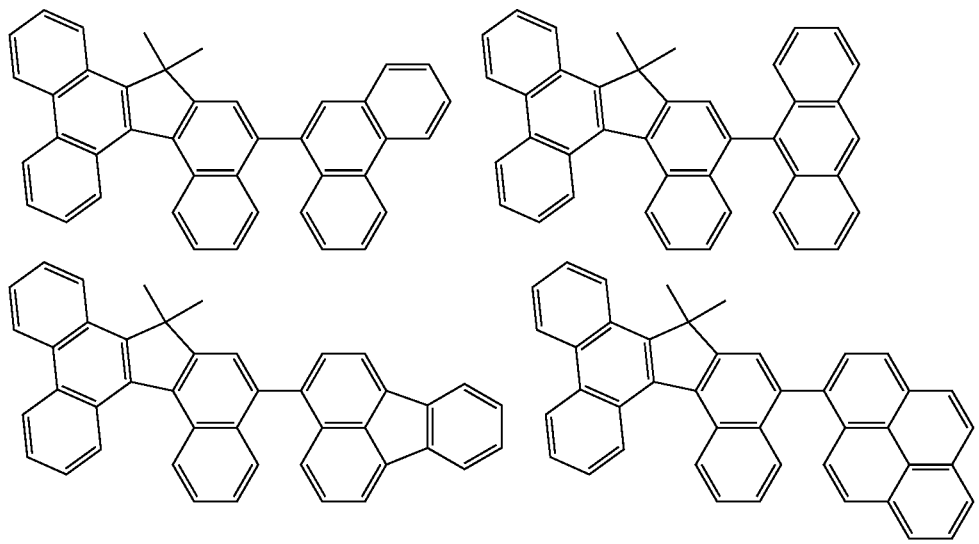

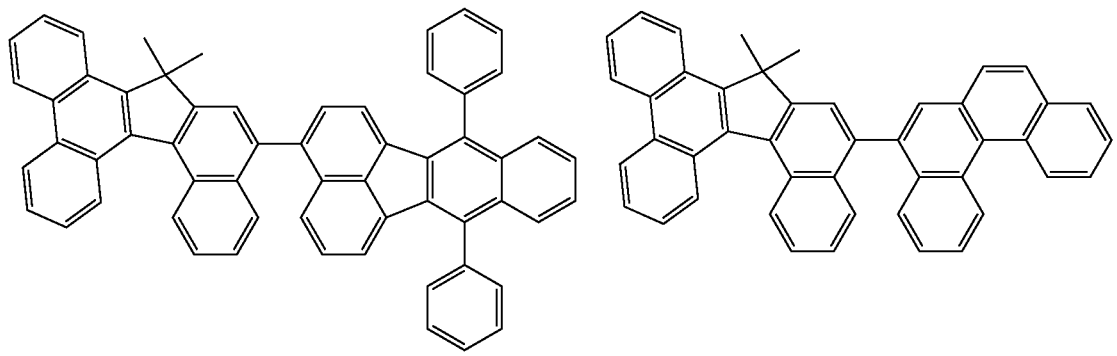

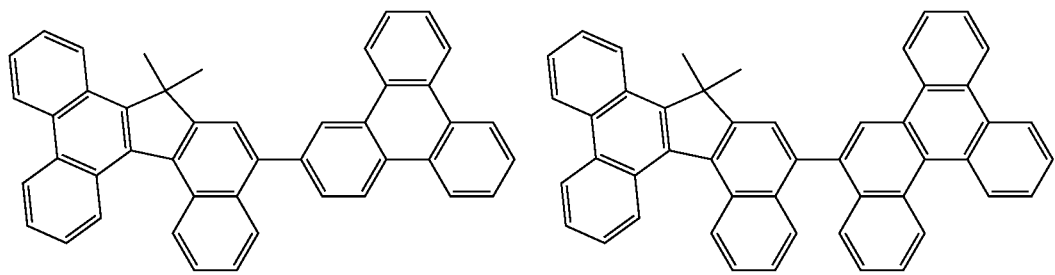

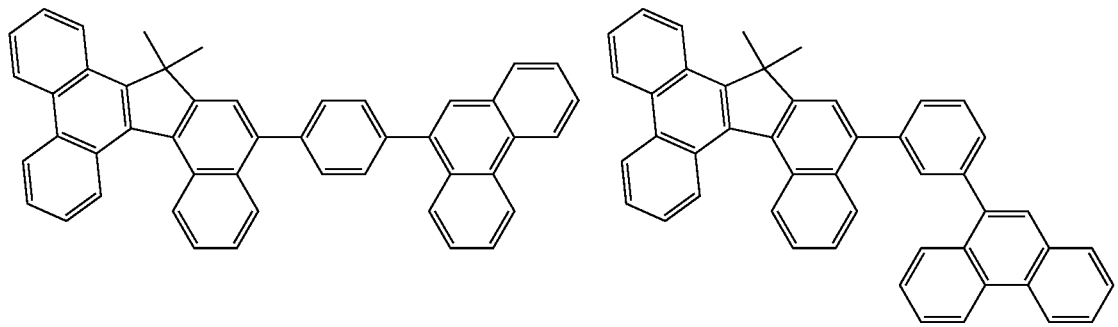
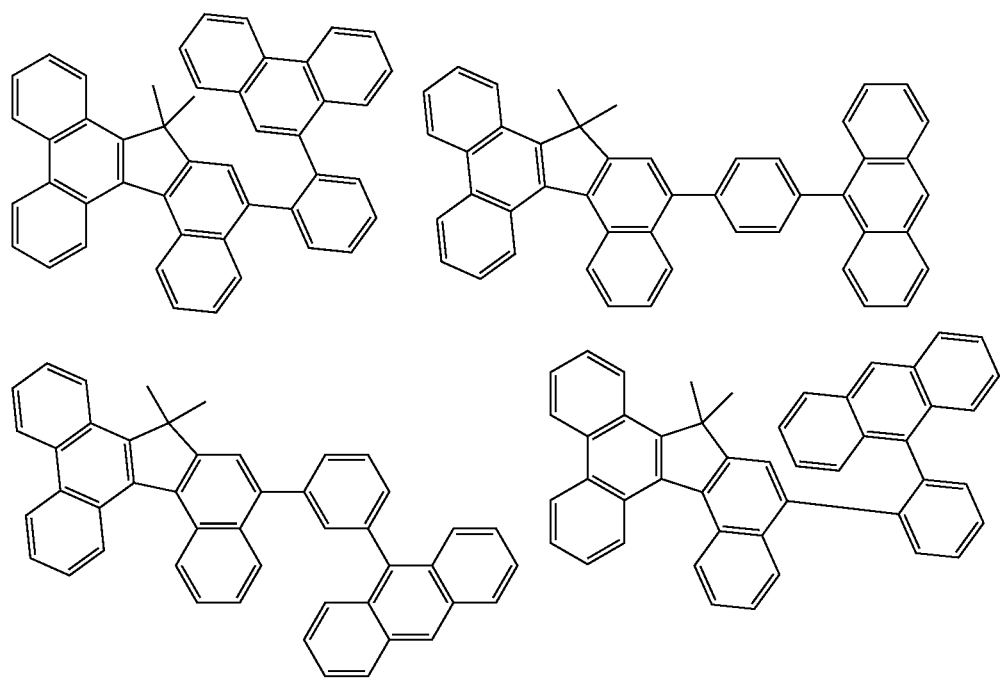
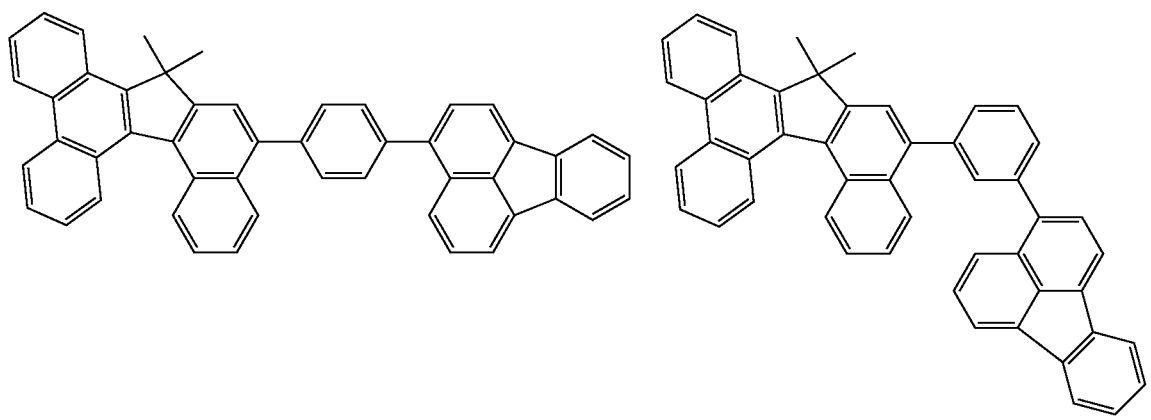

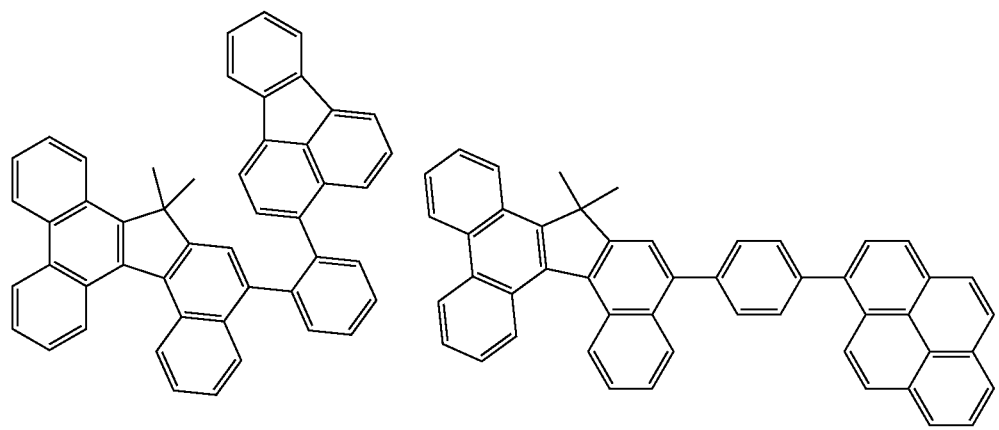
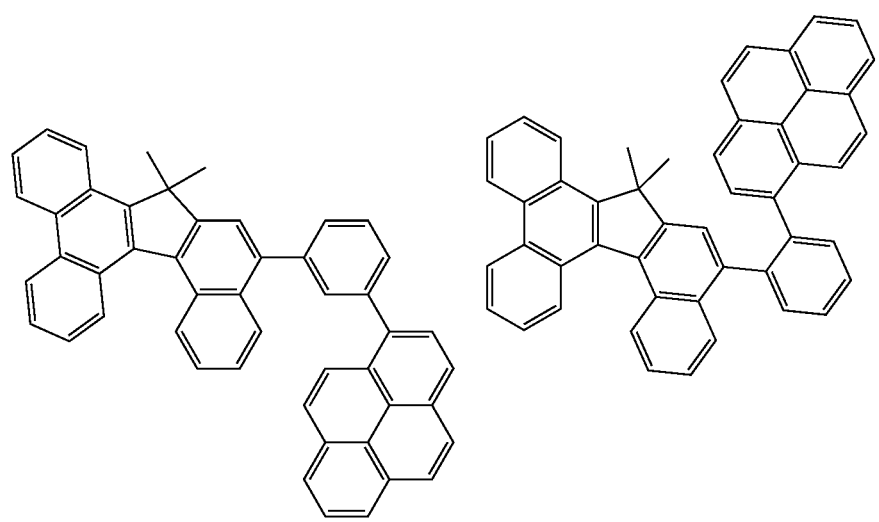
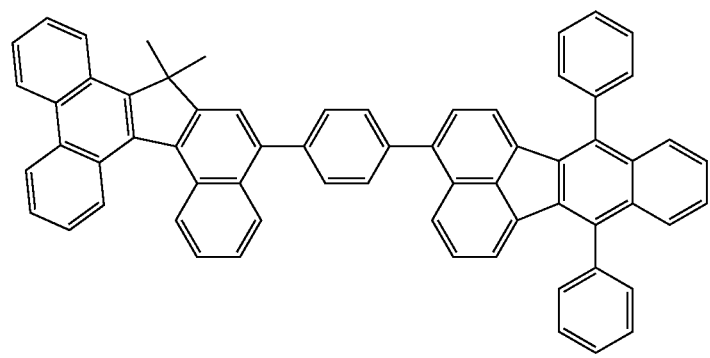

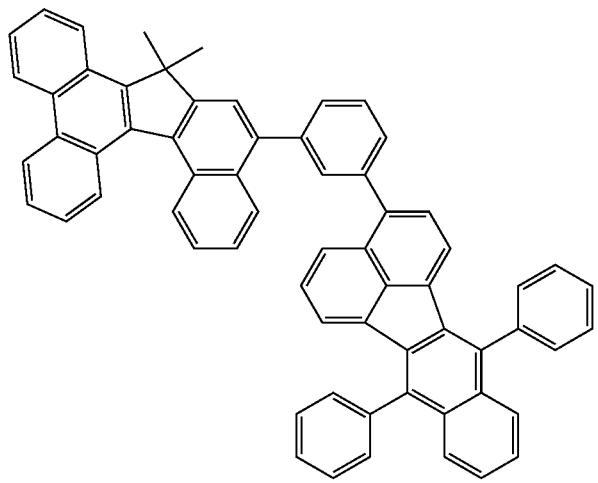
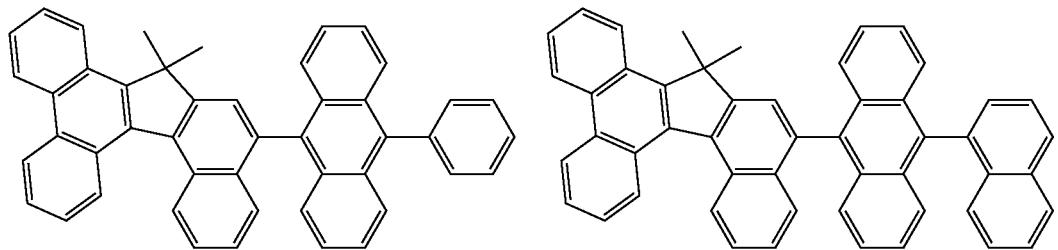
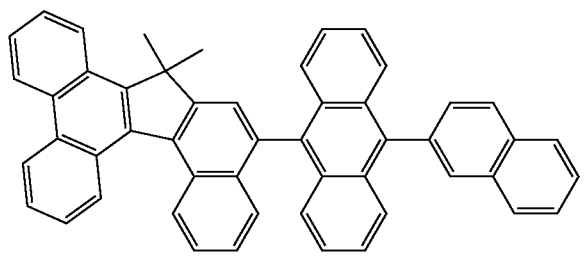
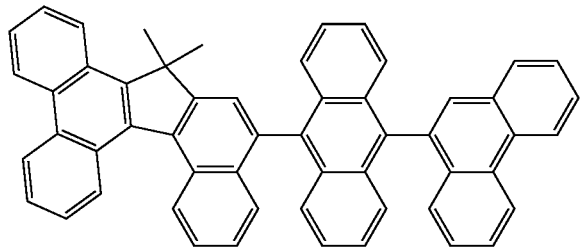
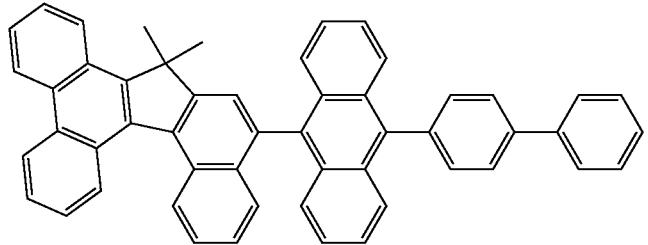

-continued
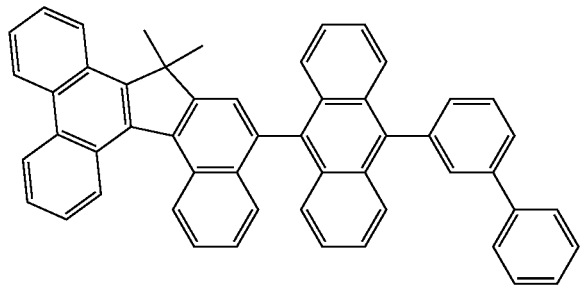
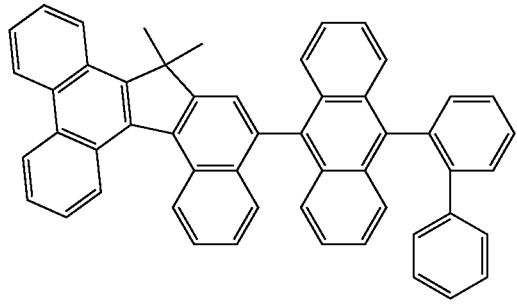
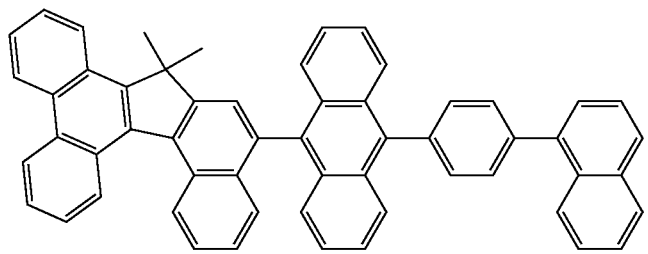
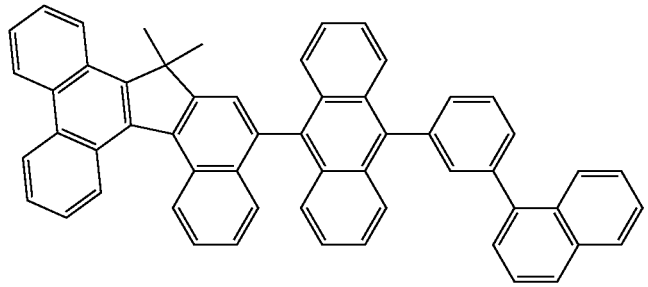
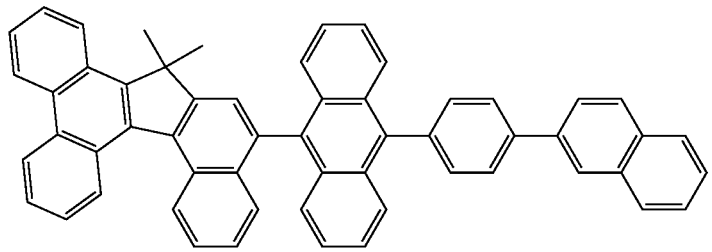
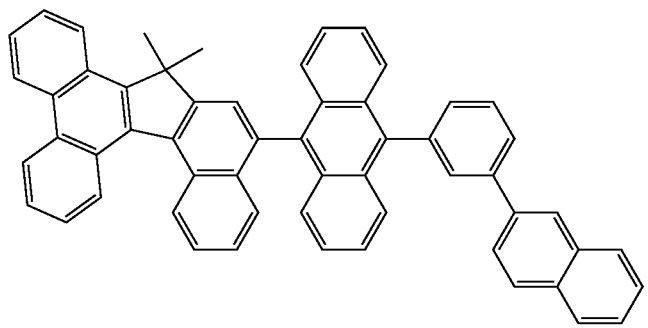

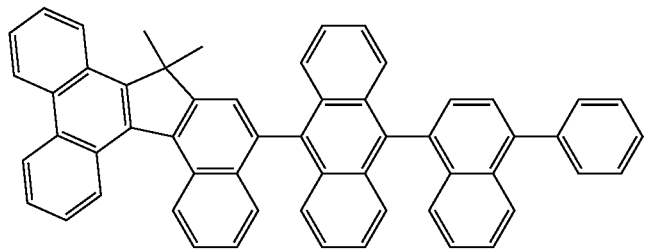
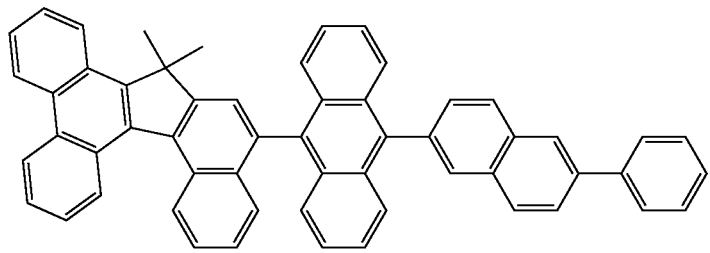
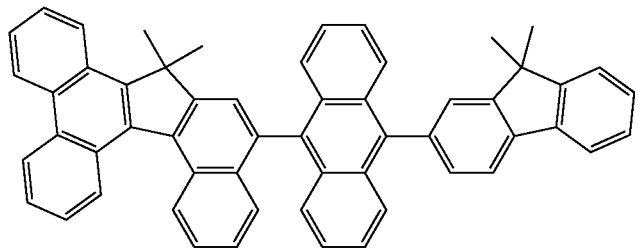
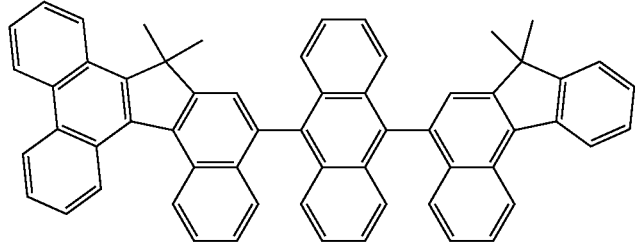
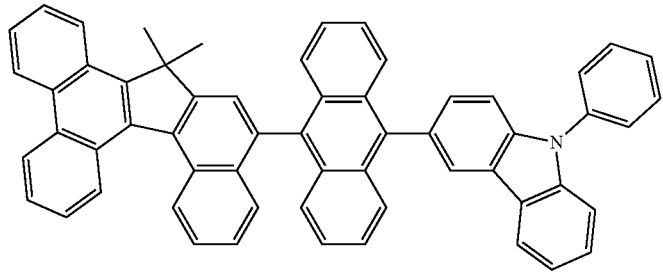
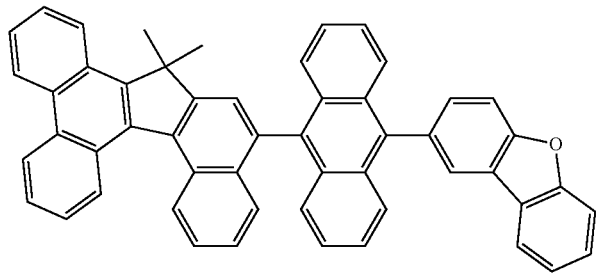

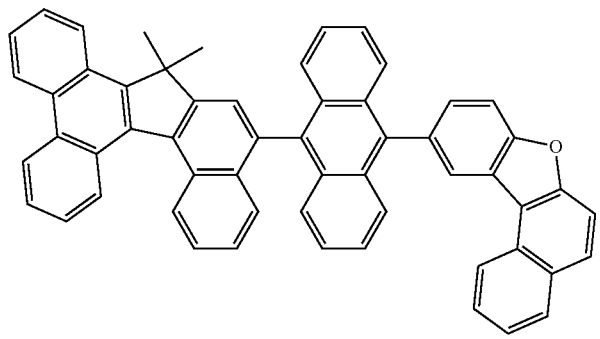
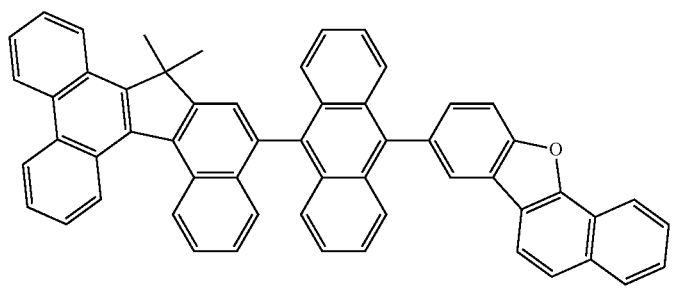
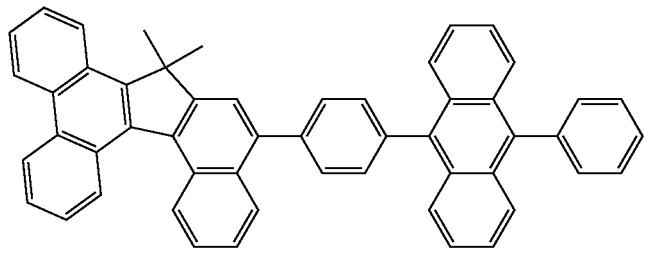
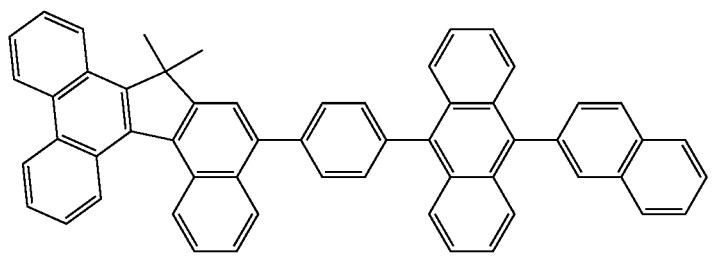
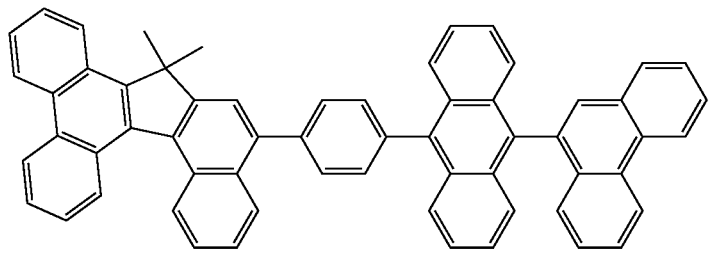

-continued
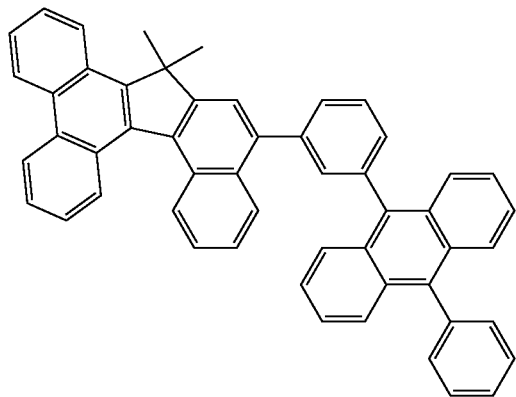
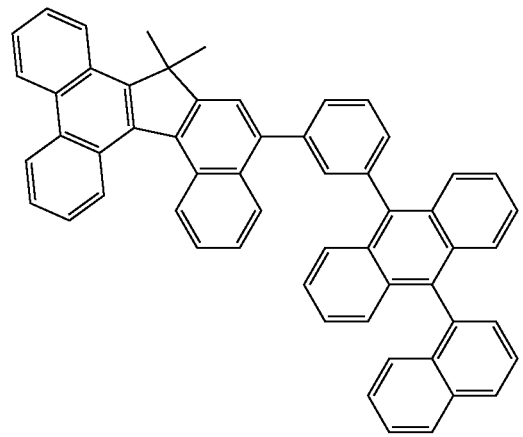
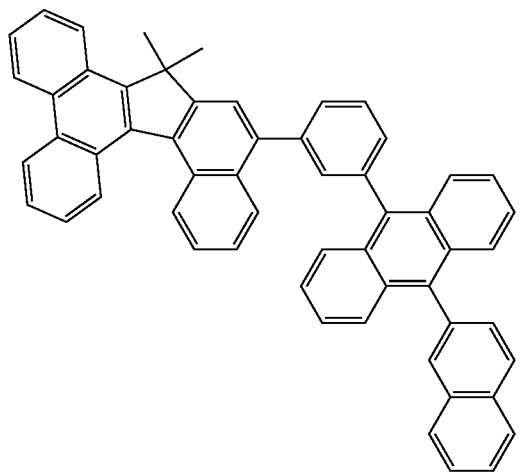
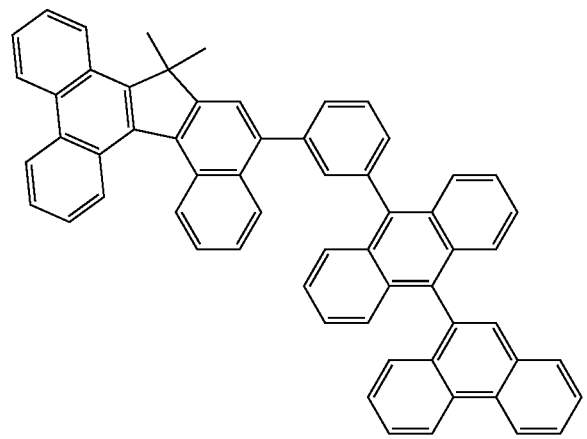
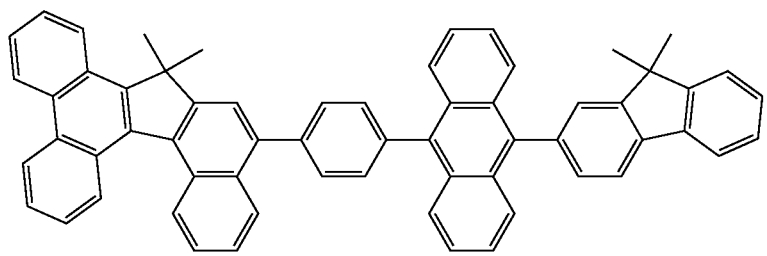
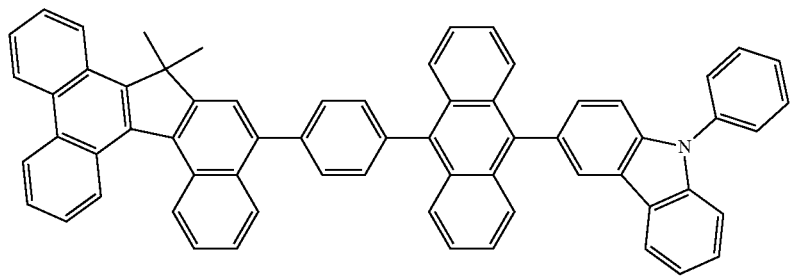
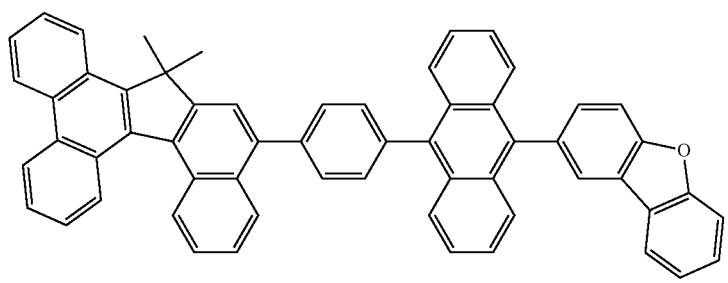

-continued
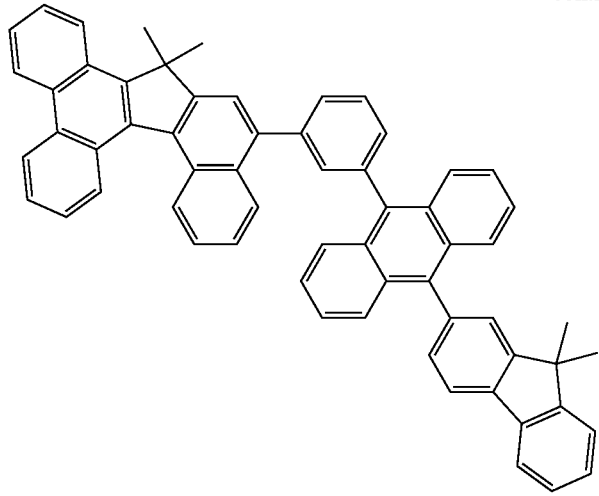
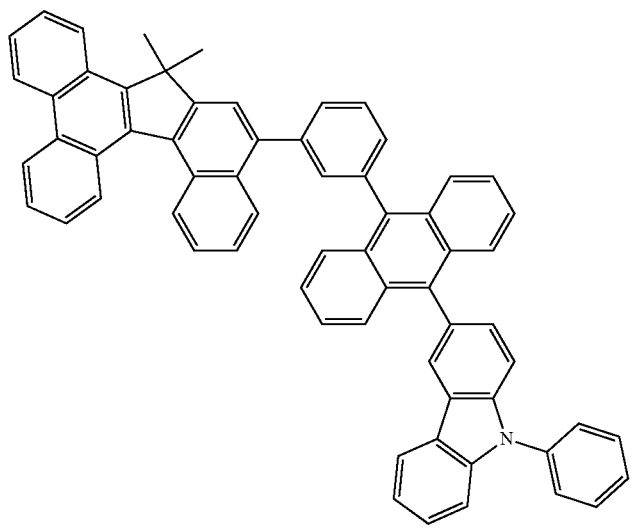
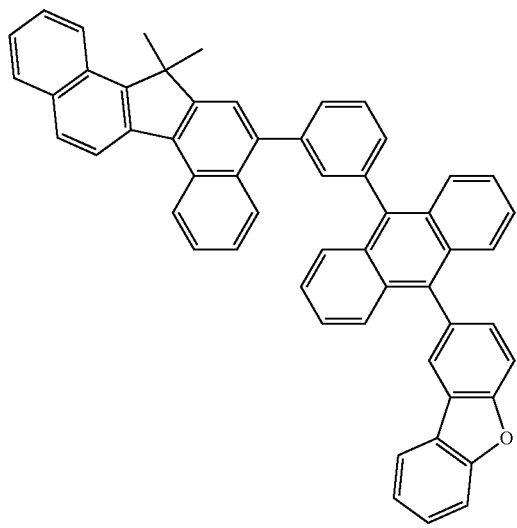

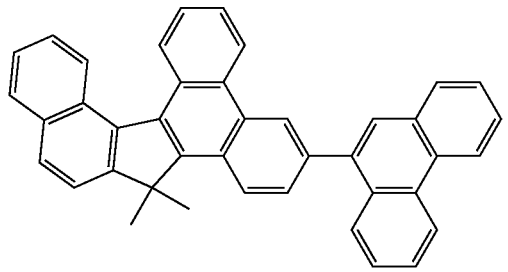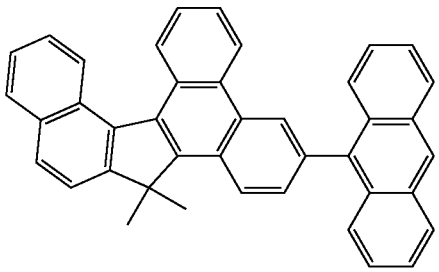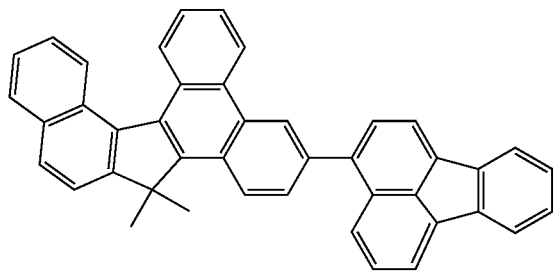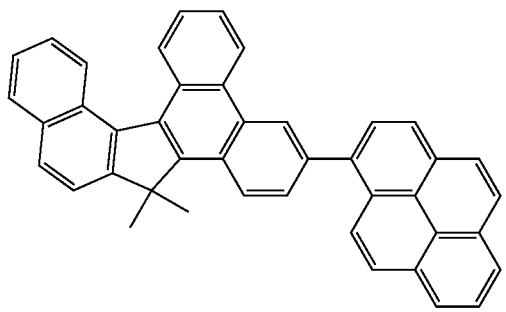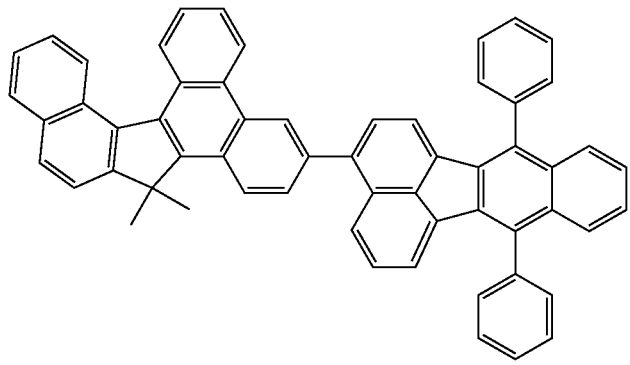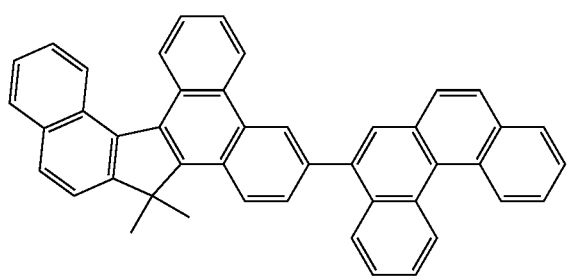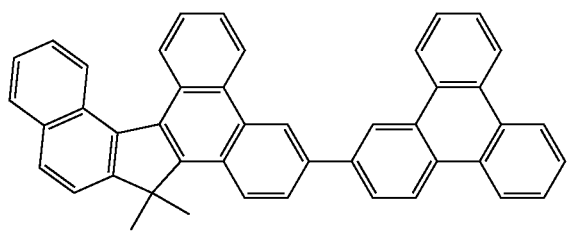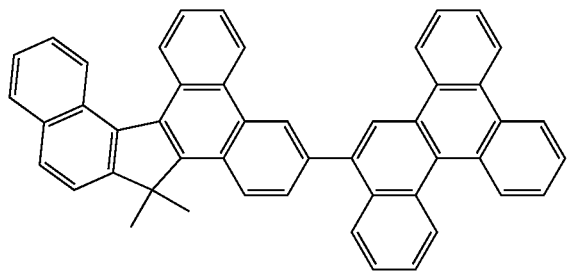

-continued
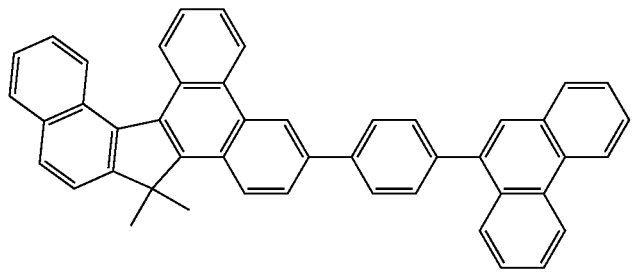
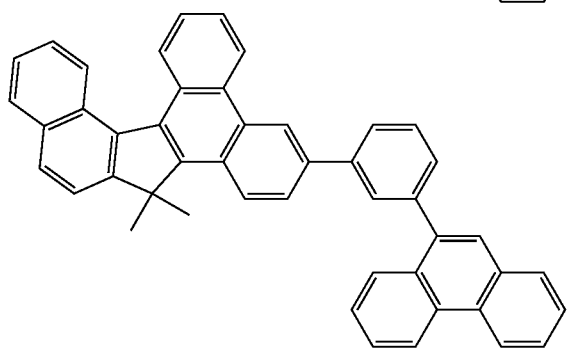
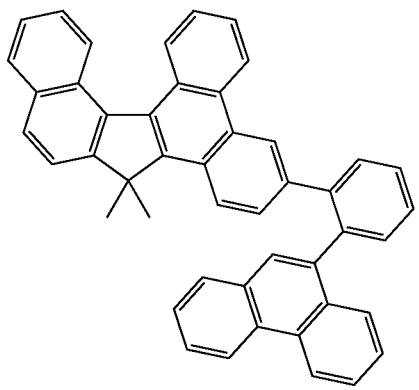
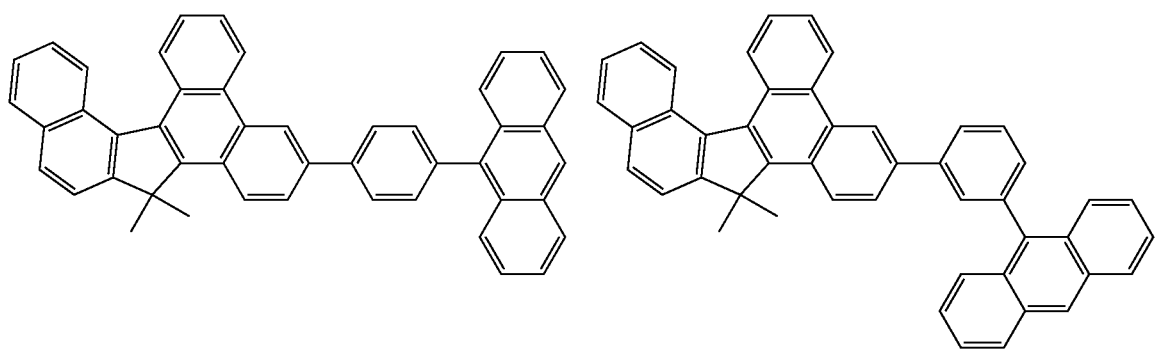
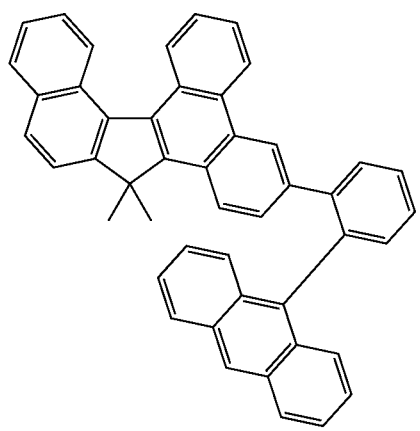
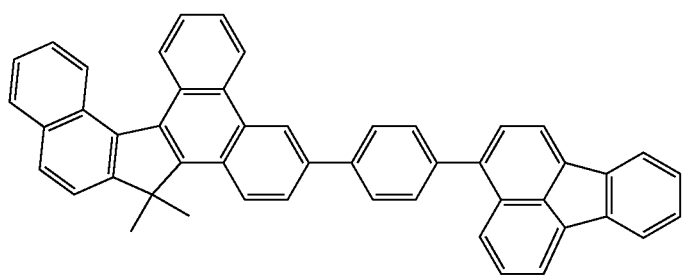

-continued
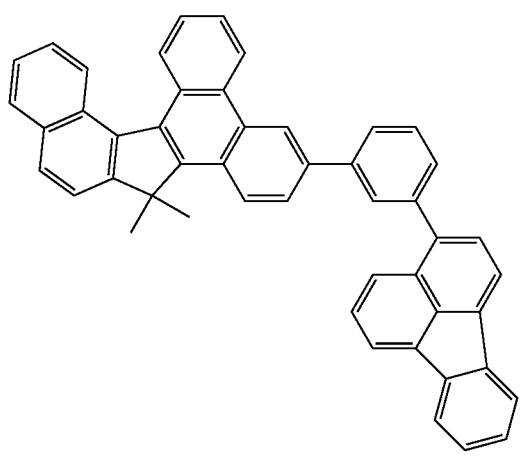
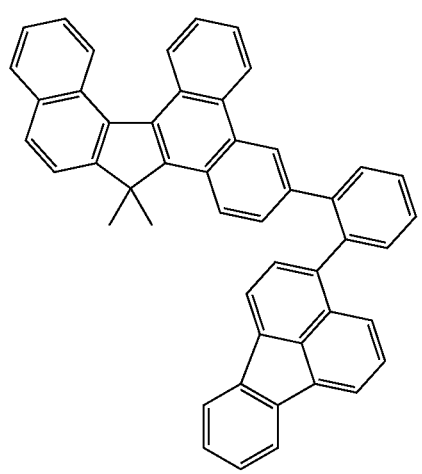
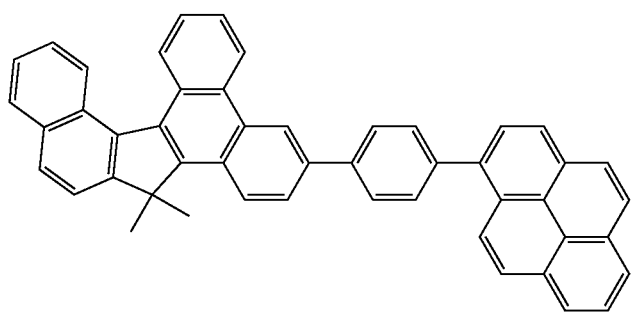
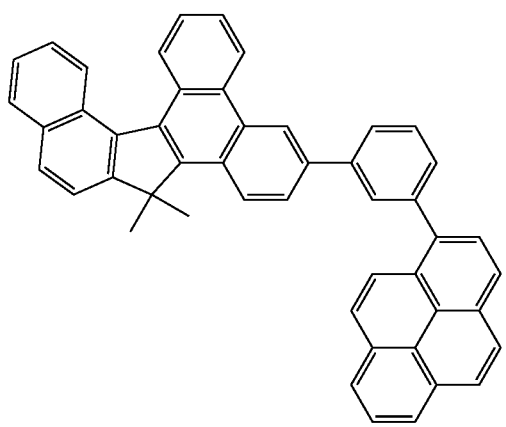
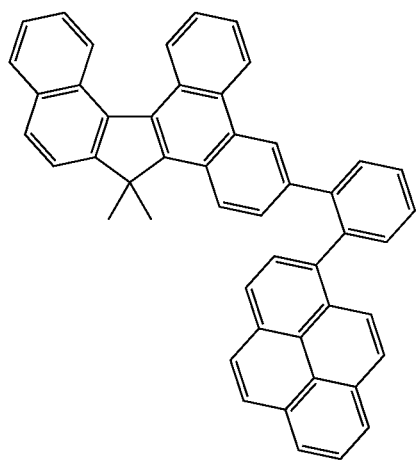

-continued
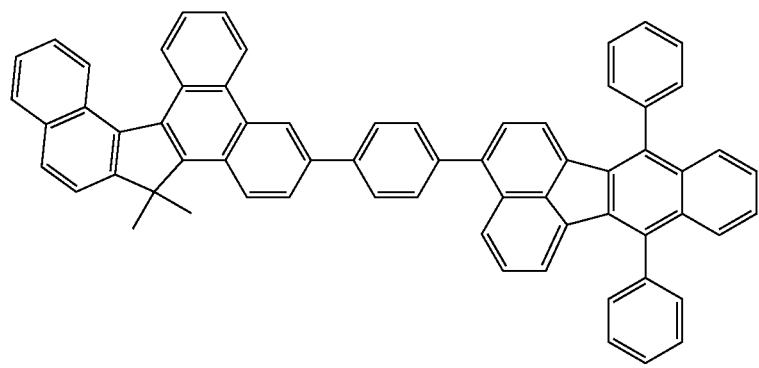
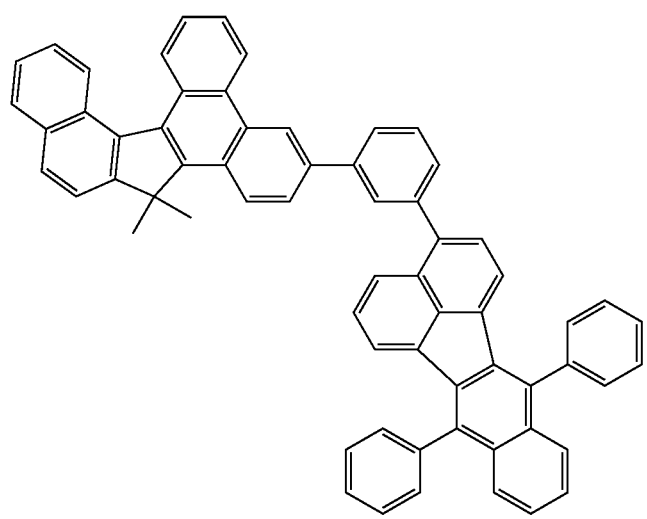
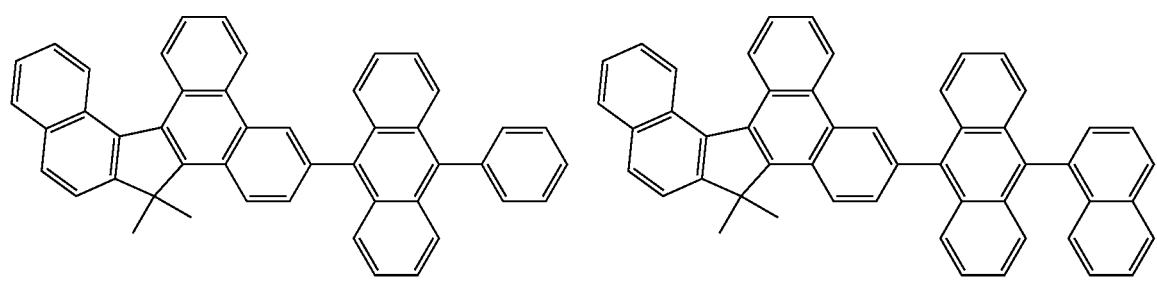
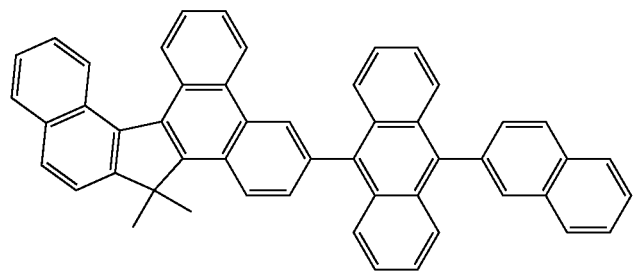
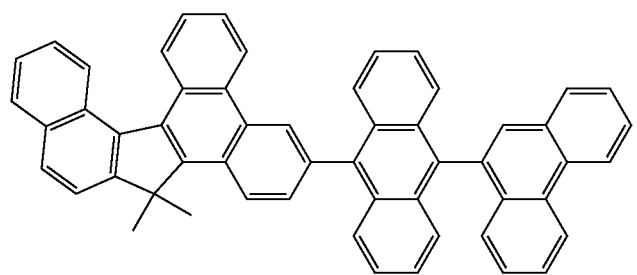

-continued
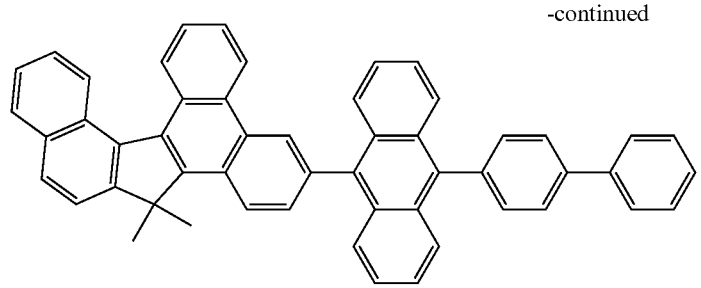
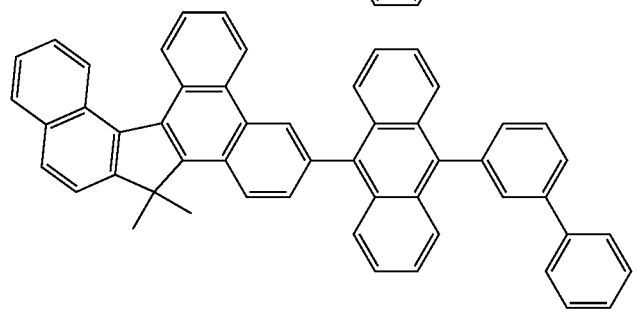
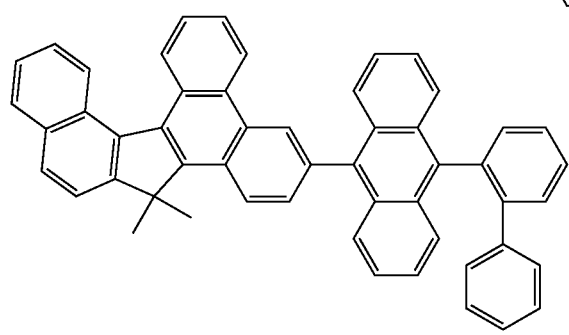
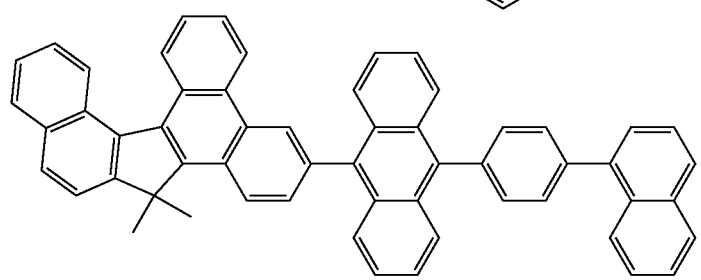
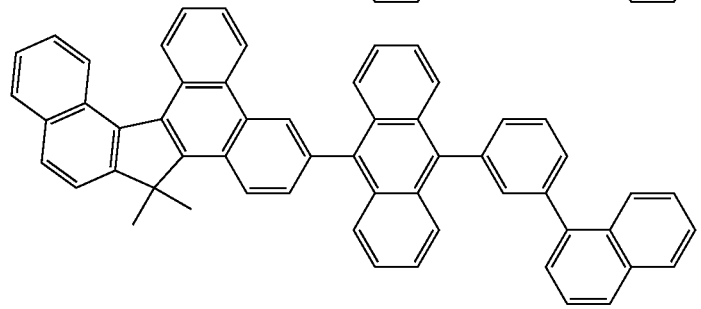
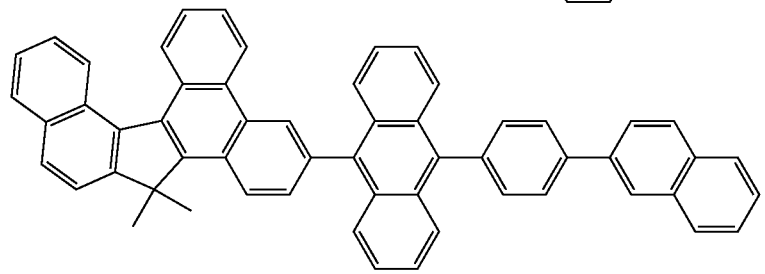

-continued
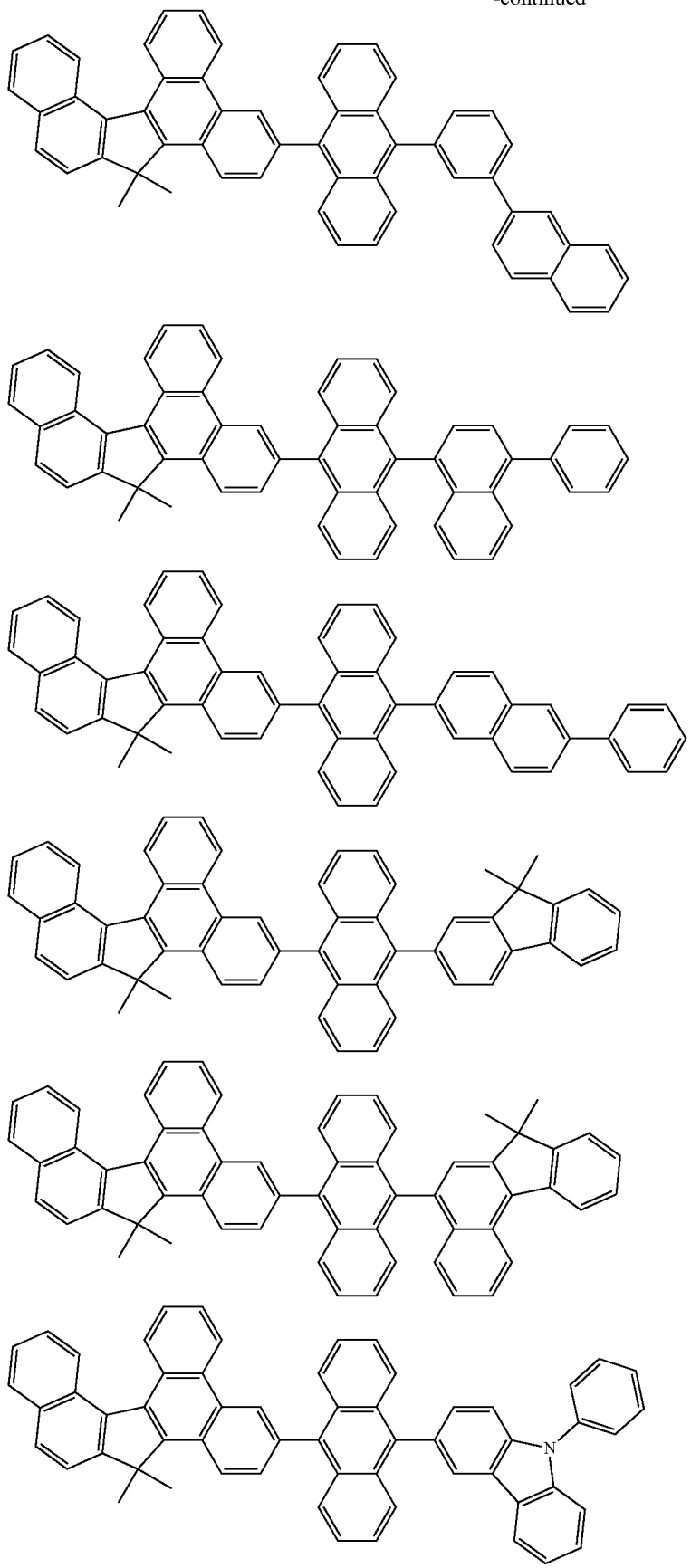

-continued
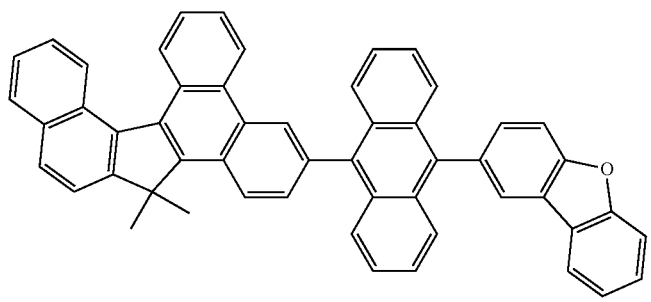
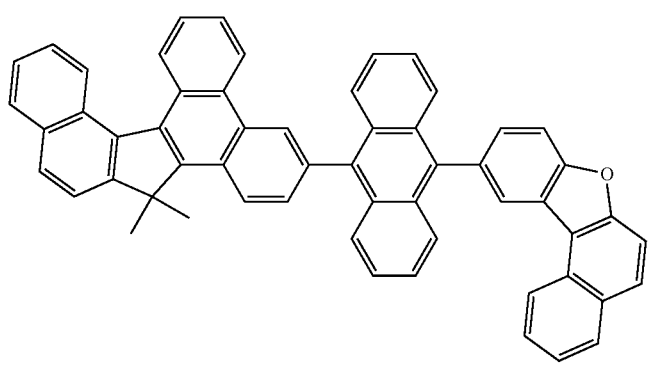
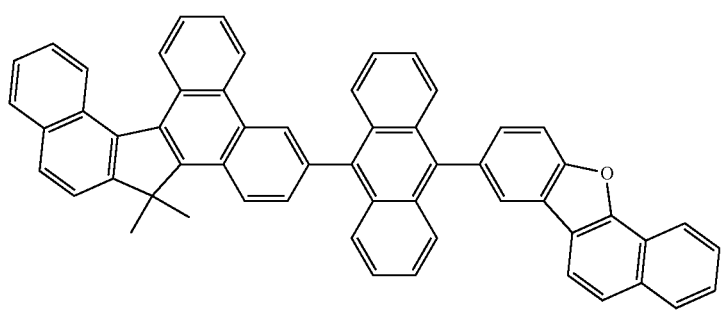
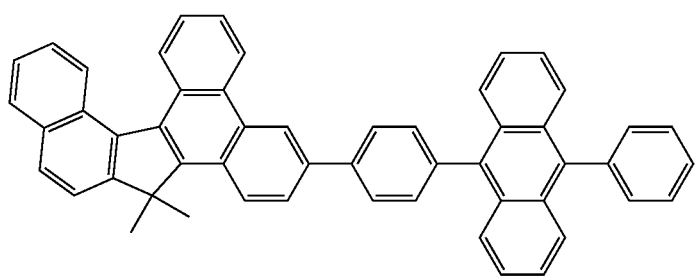
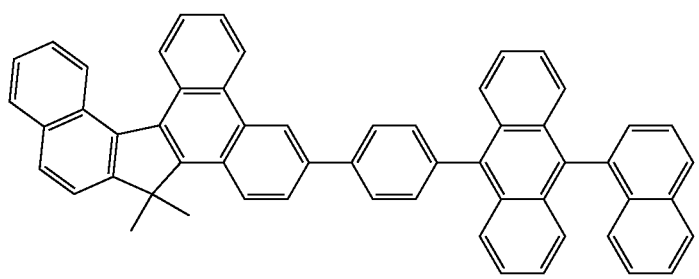

-continued
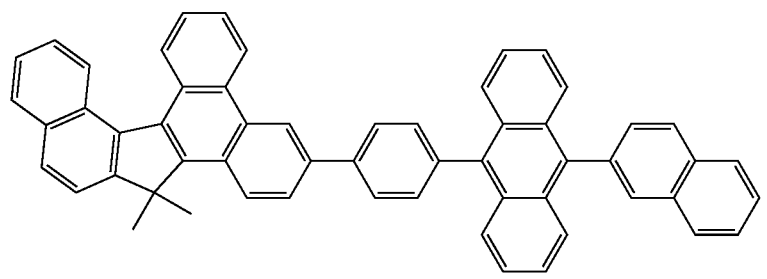
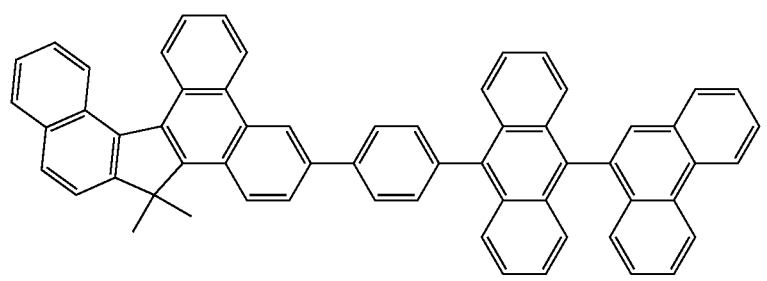
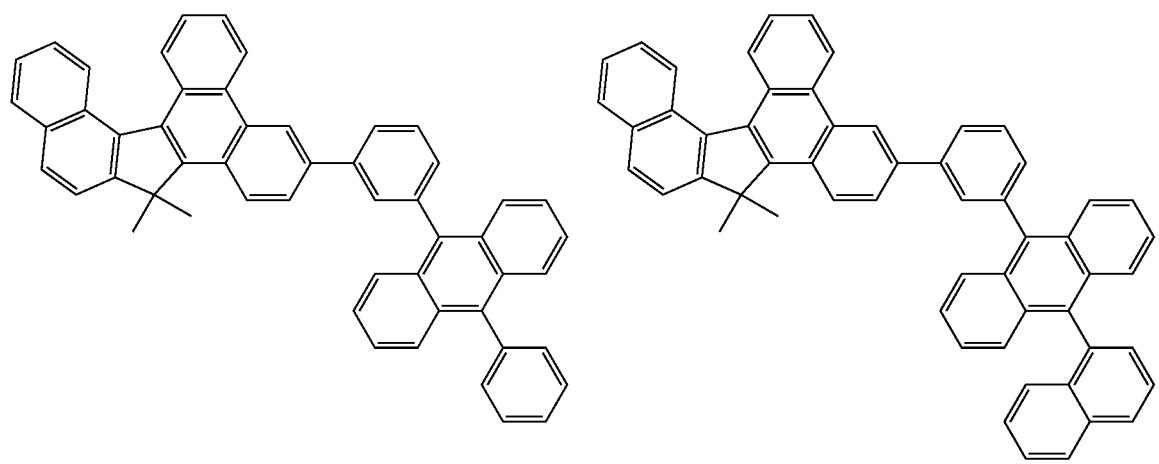
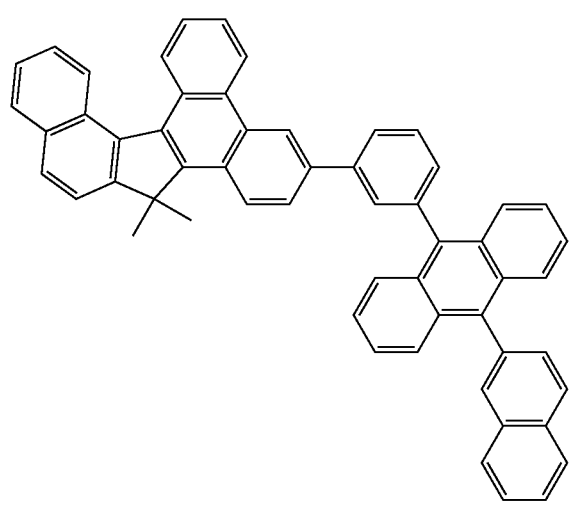

-continued
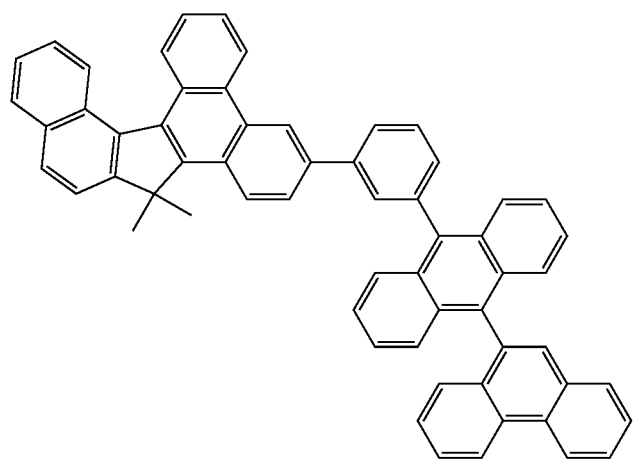
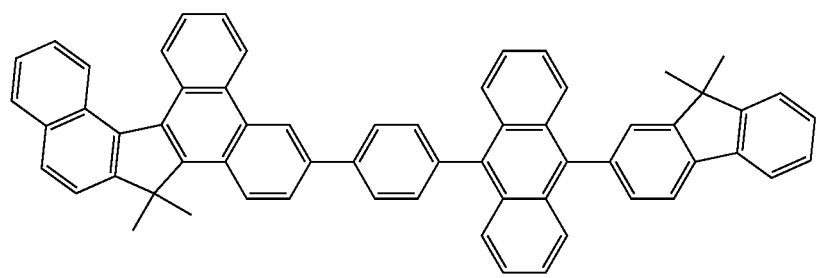
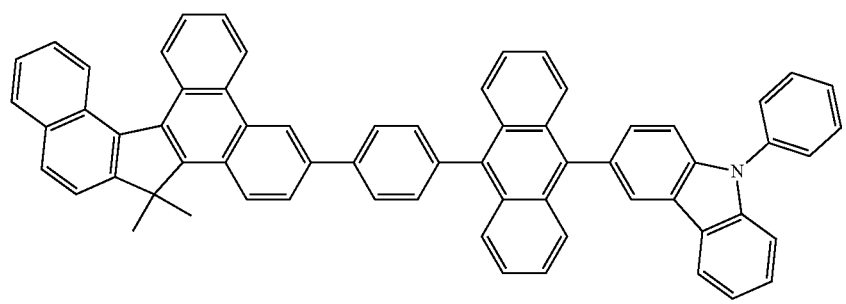
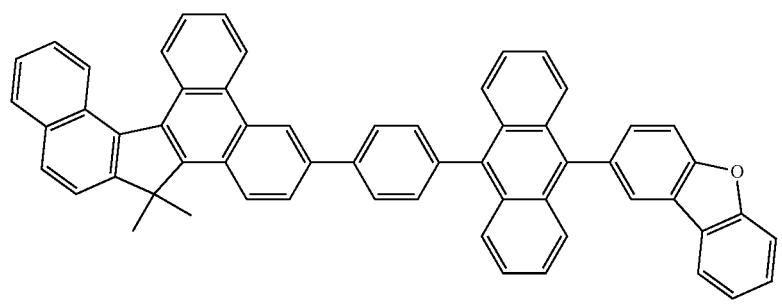

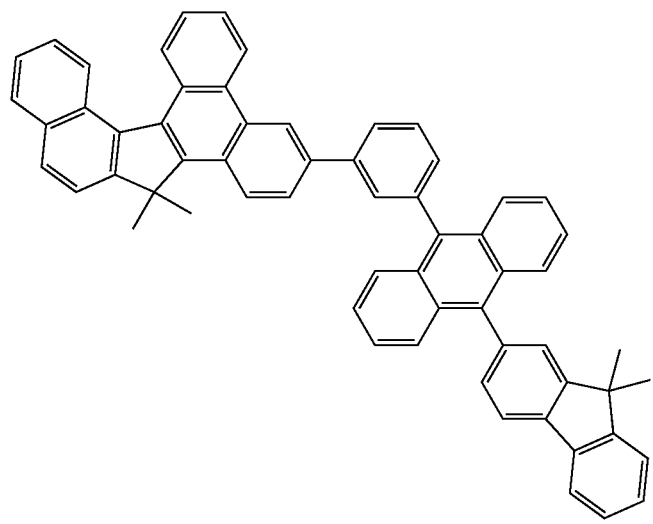
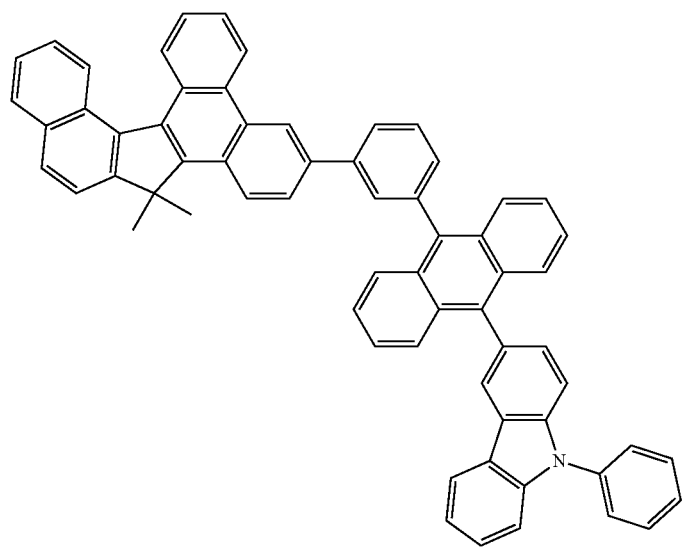
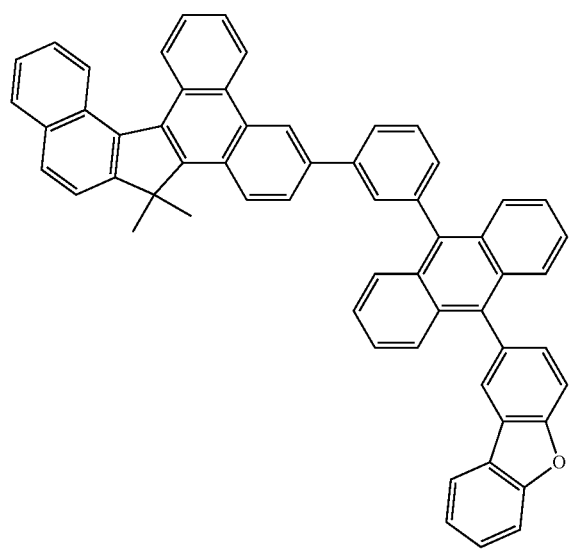

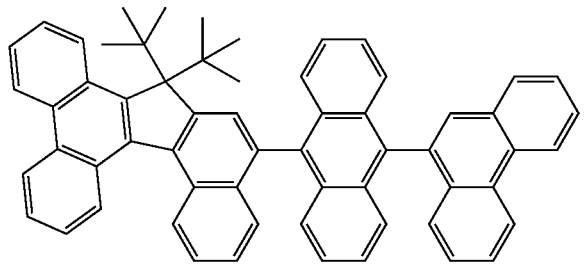
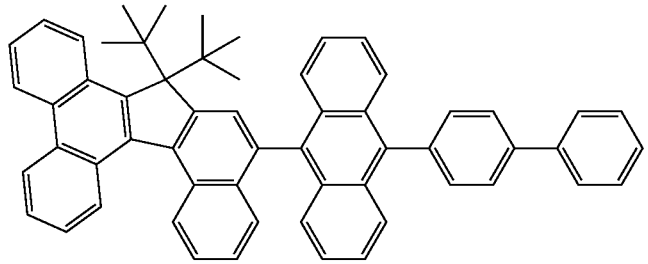
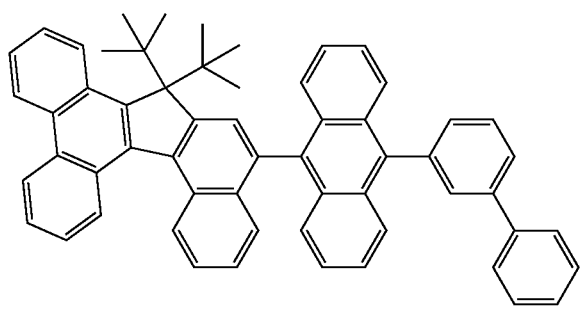

-continued
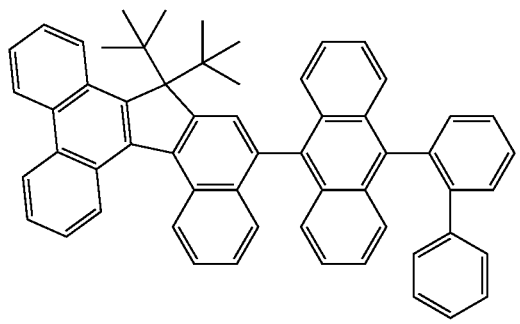
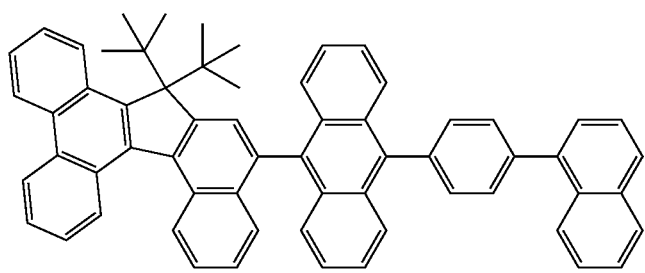
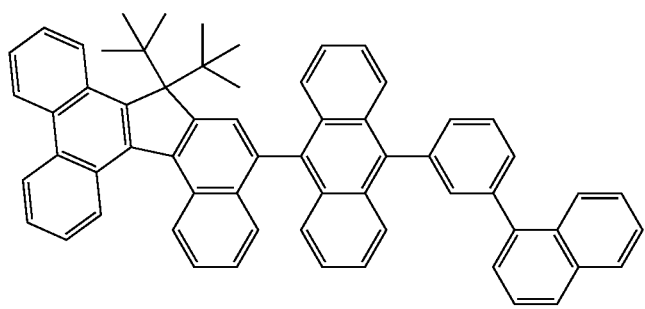
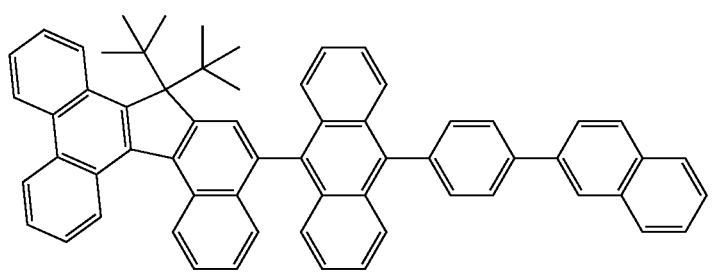
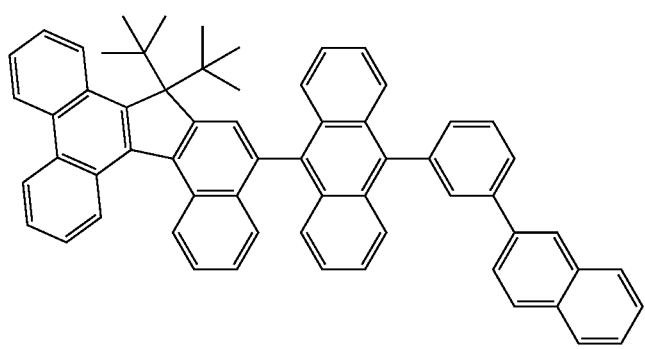

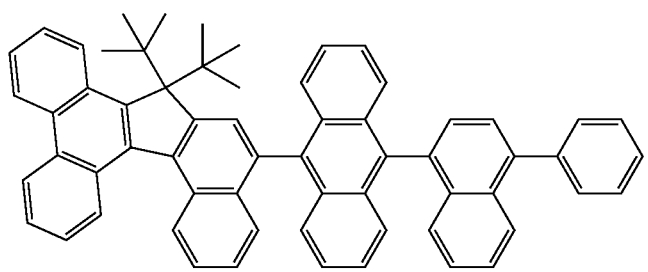
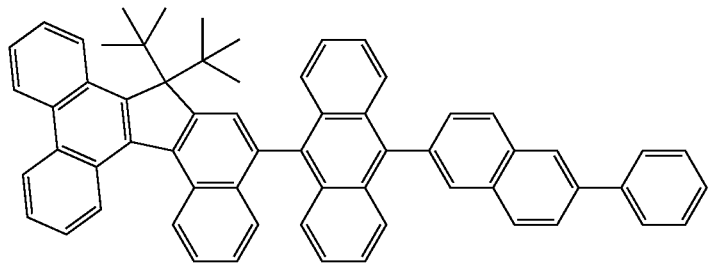
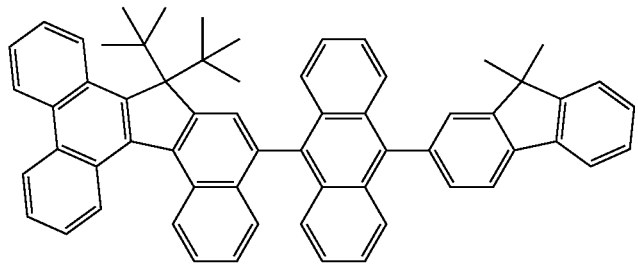
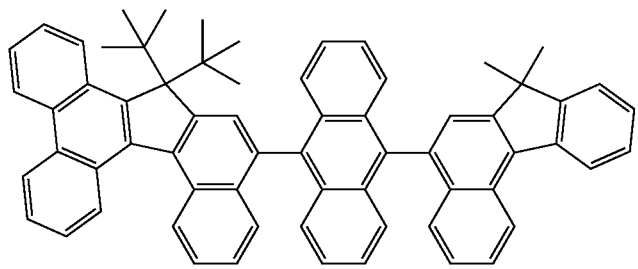
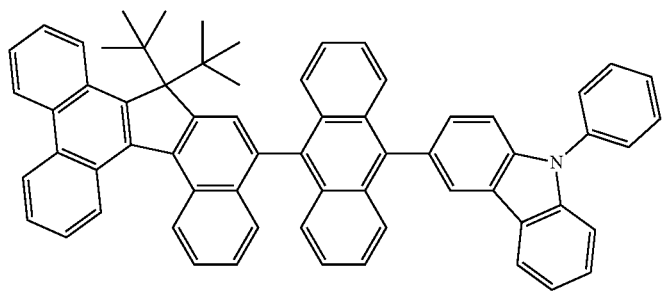
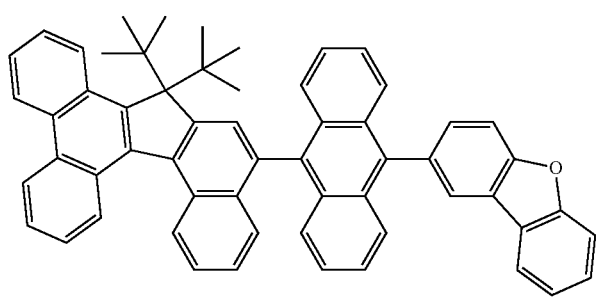

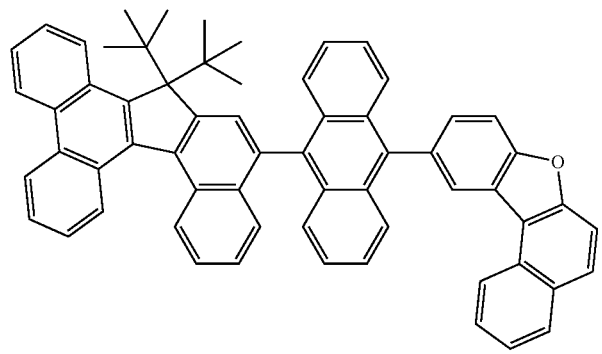
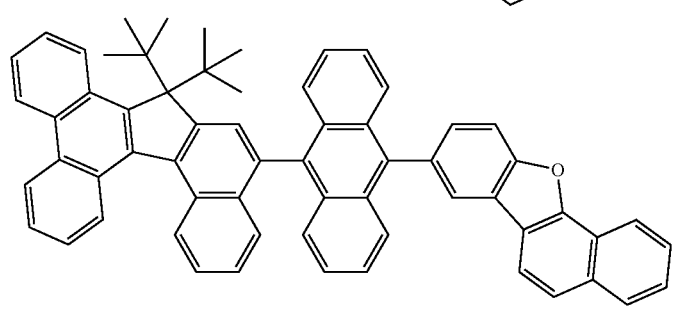
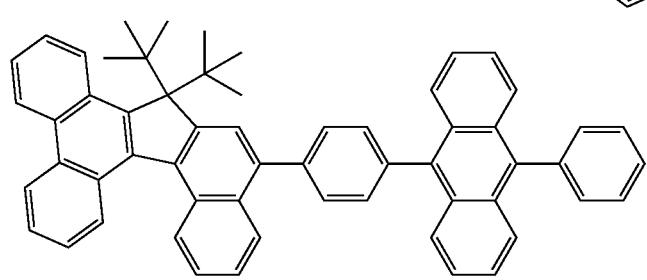
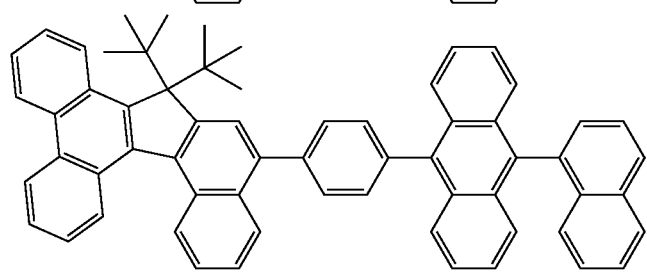
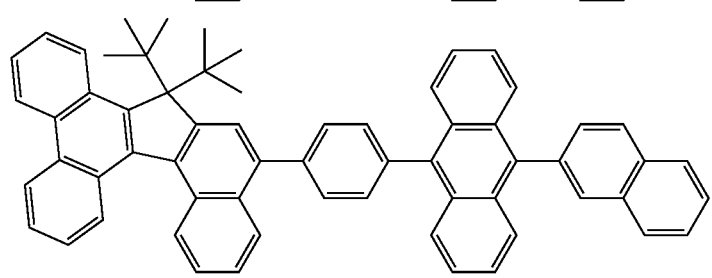
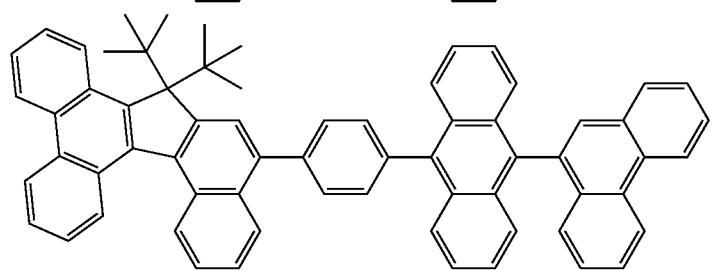

-continued
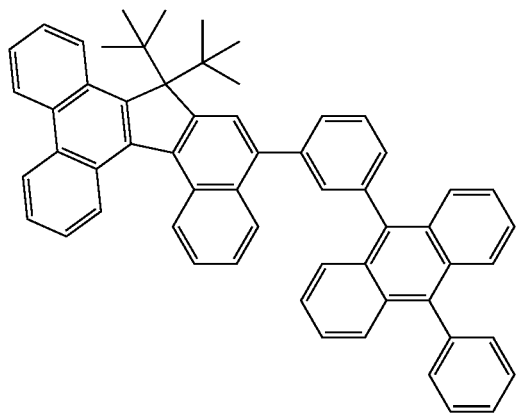
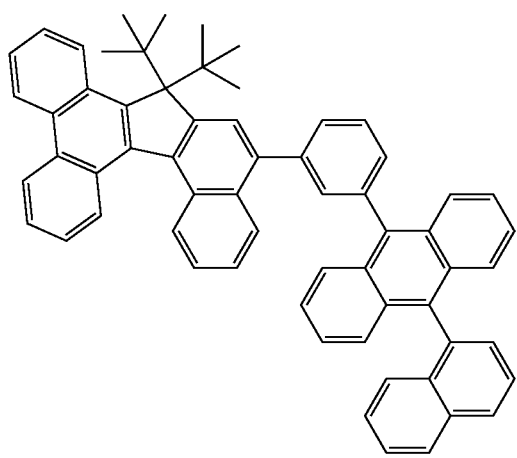
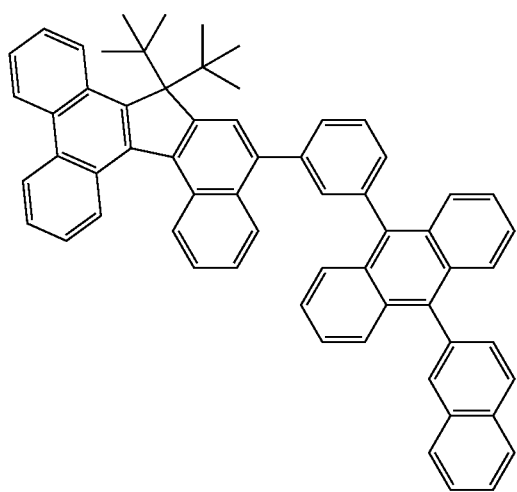

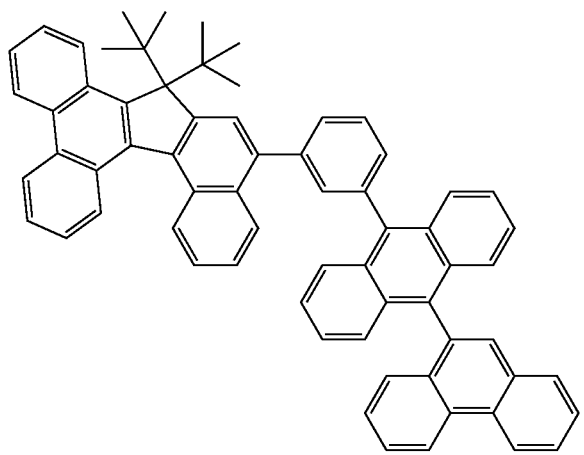
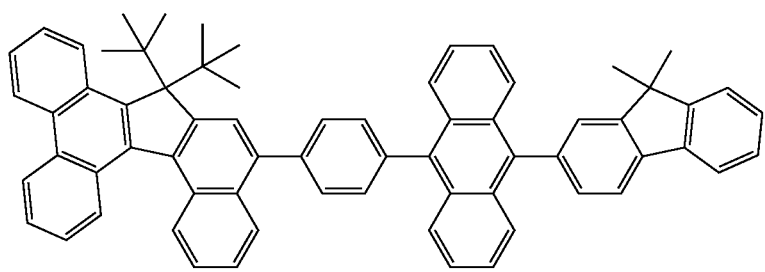
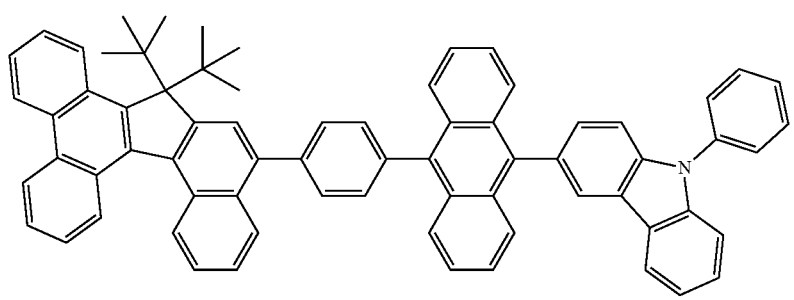
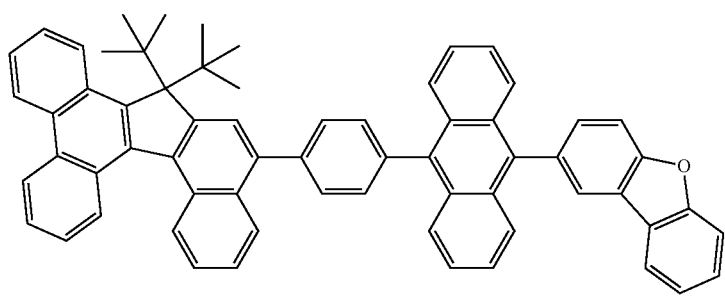

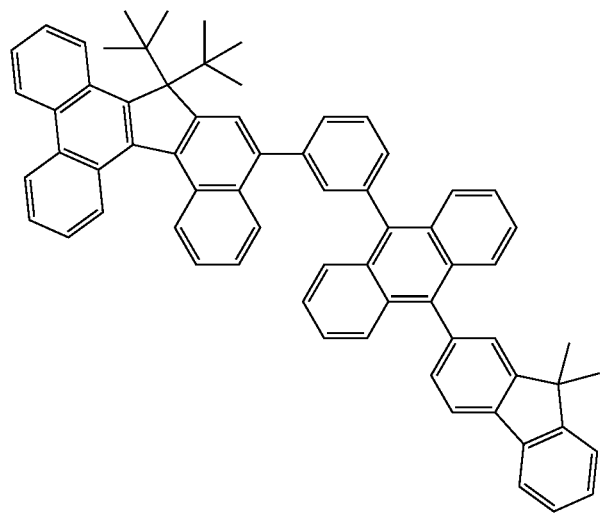
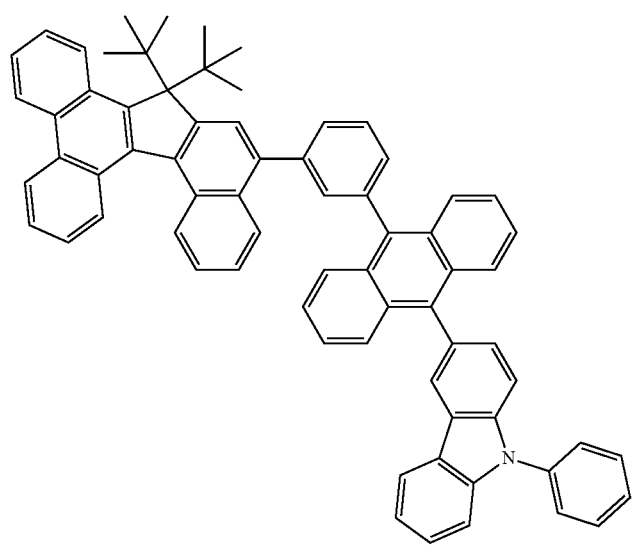
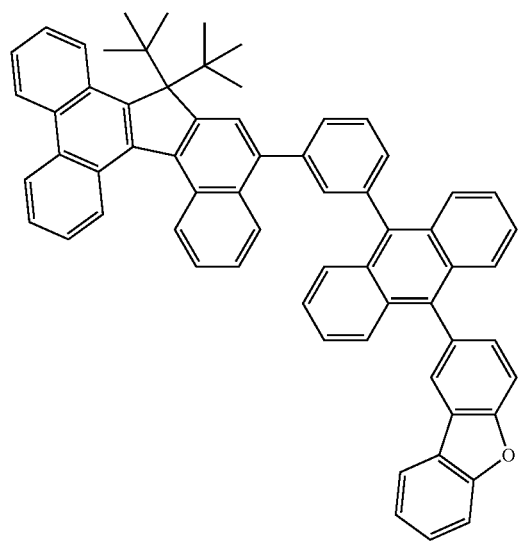

-continued
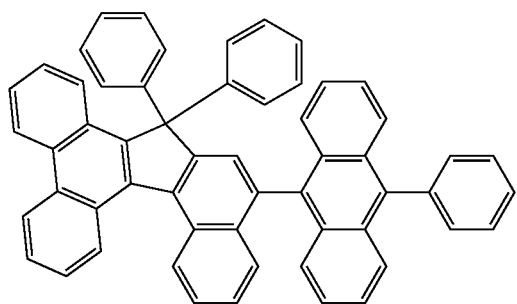
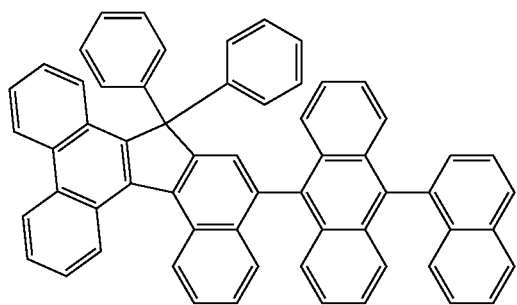
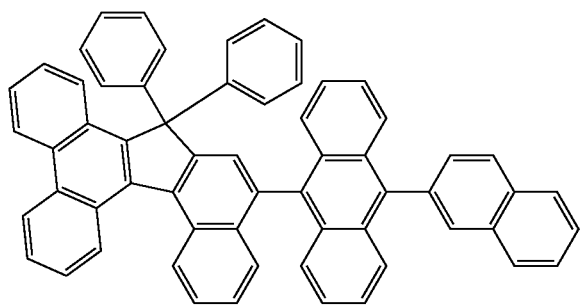
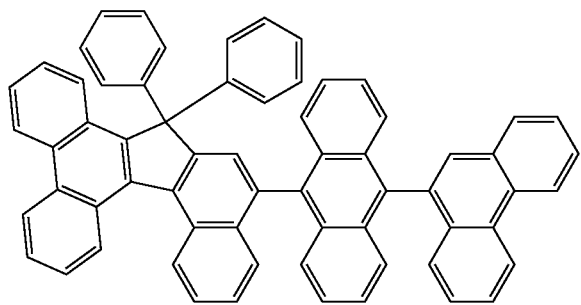
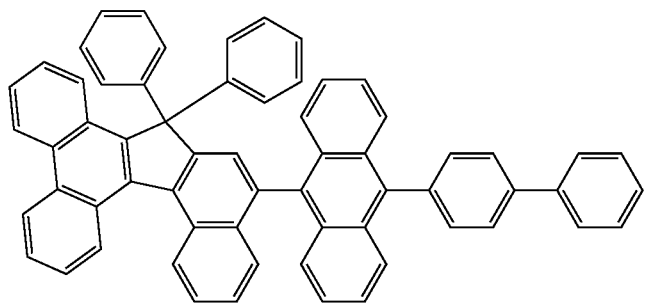

-continued
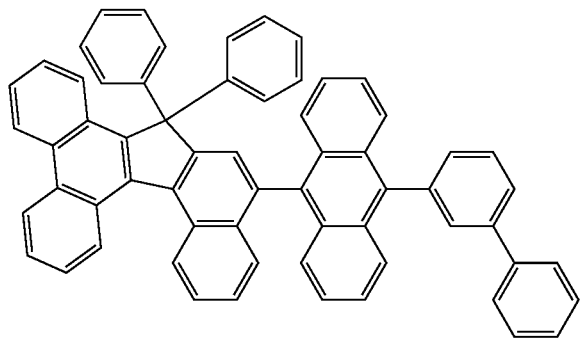

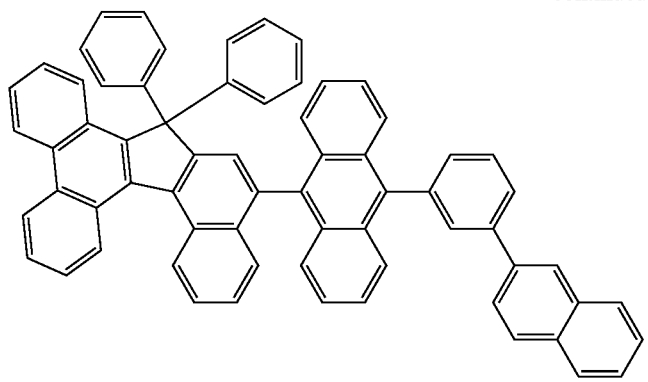
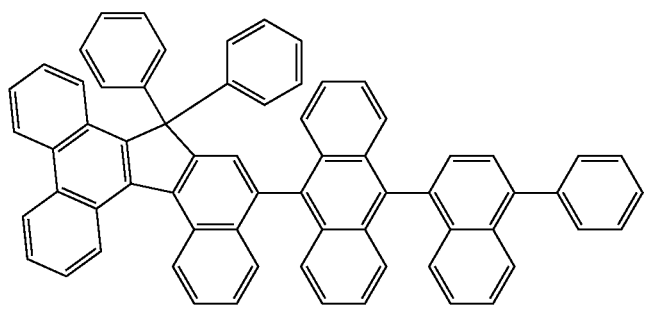
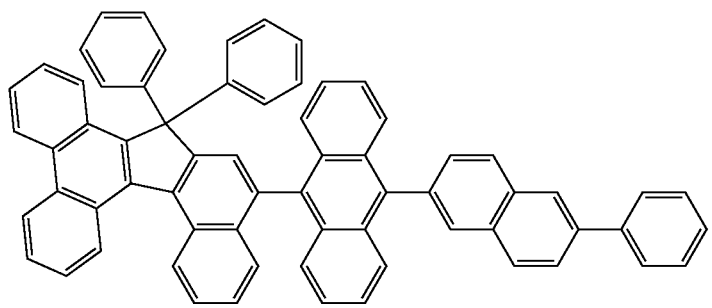
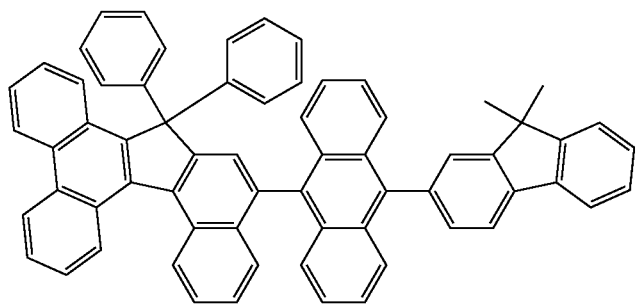
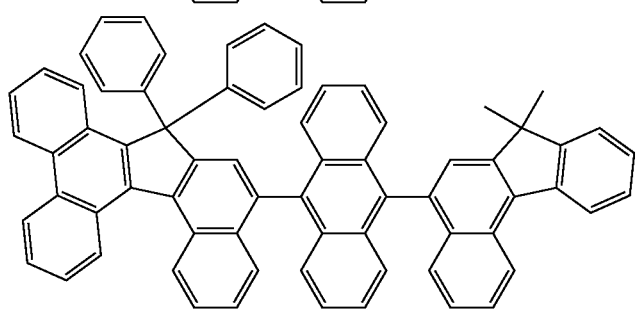

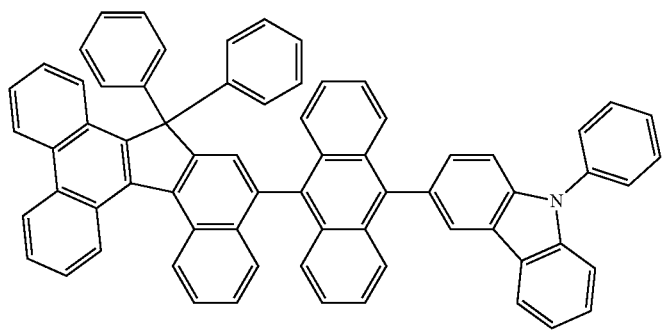
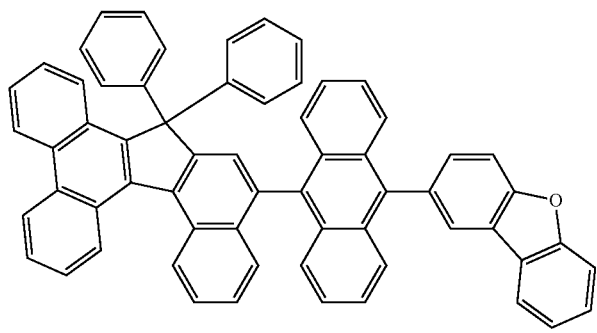
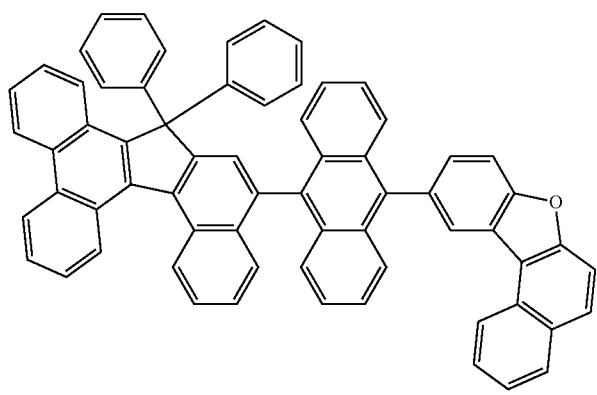
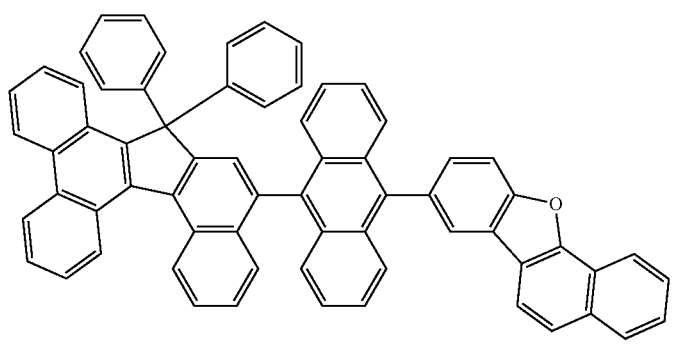
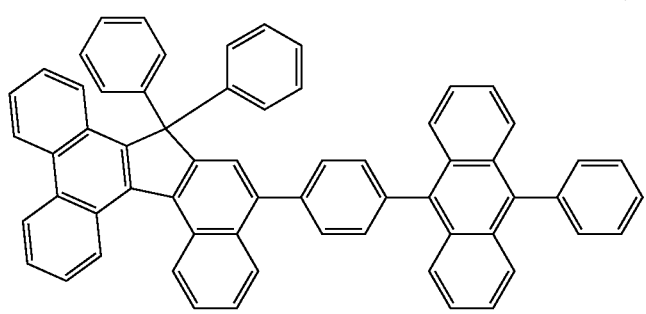

-continued
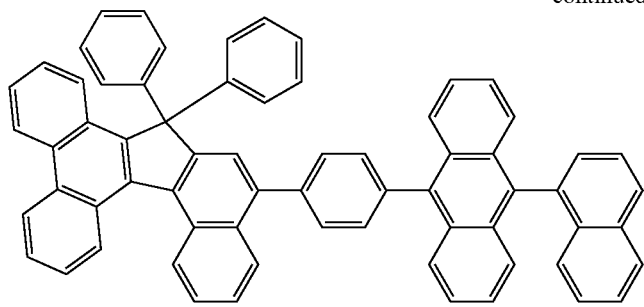

-continued
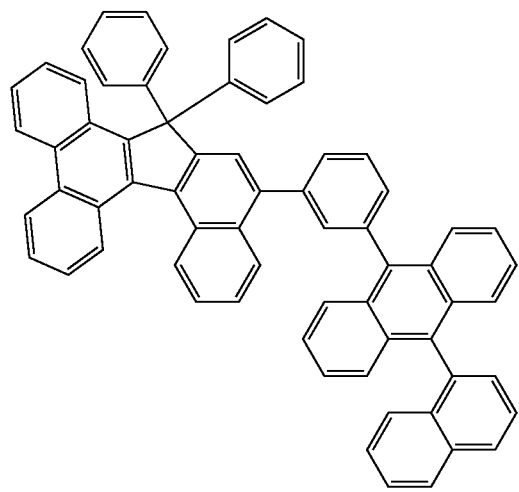
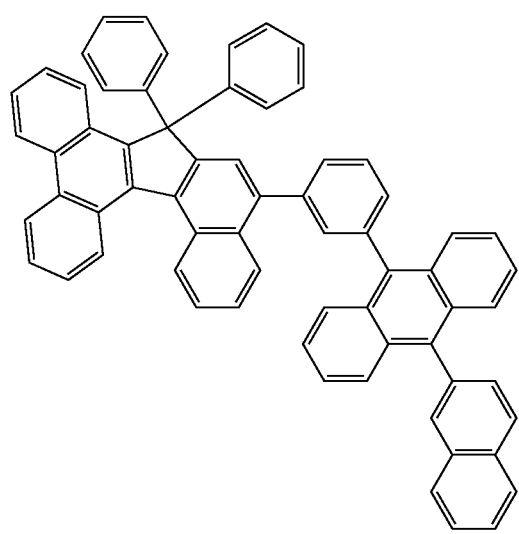
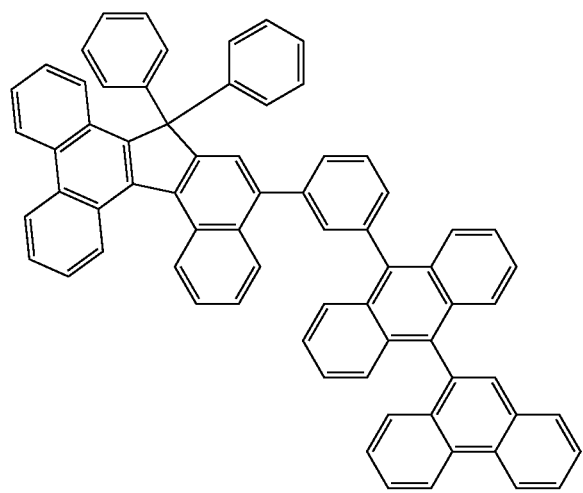

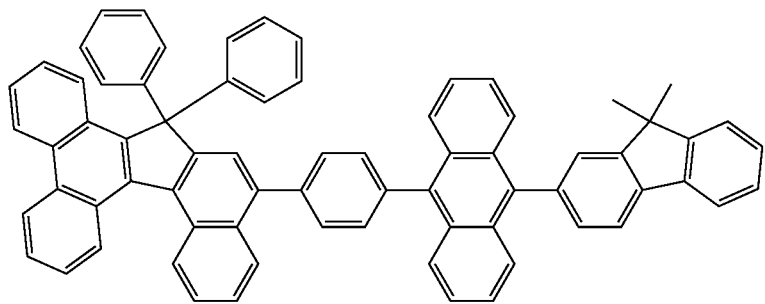
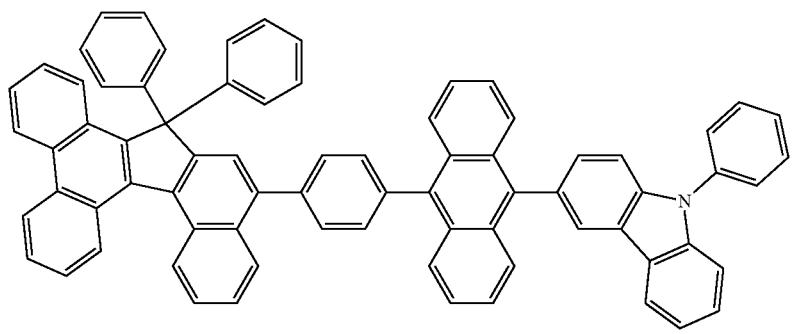
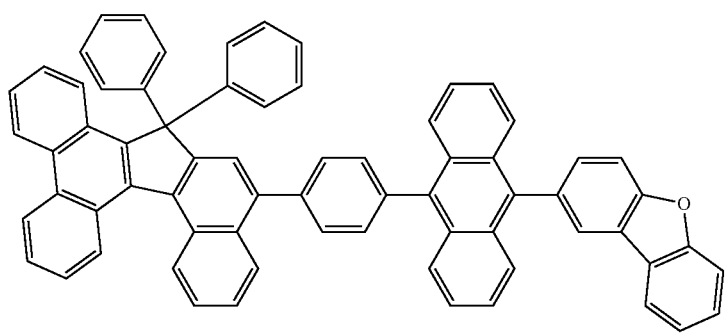
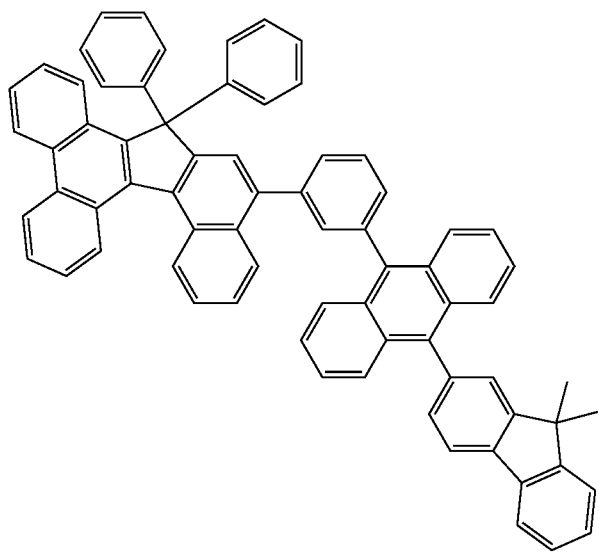

-continued
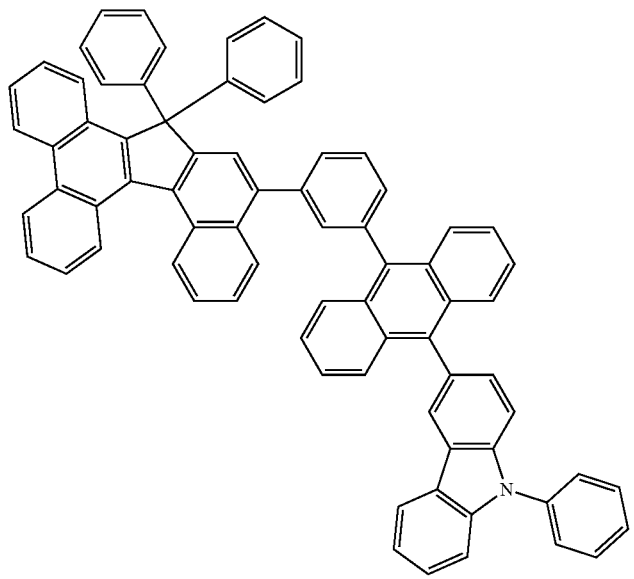
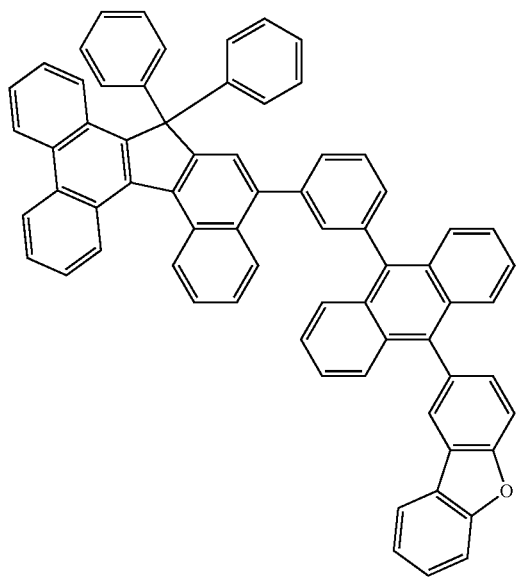
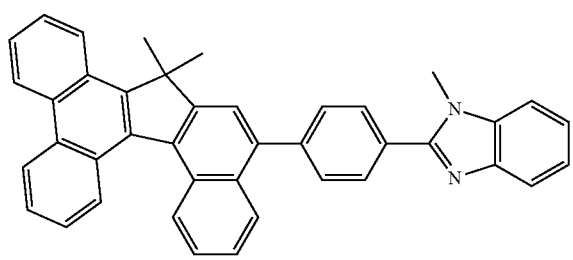
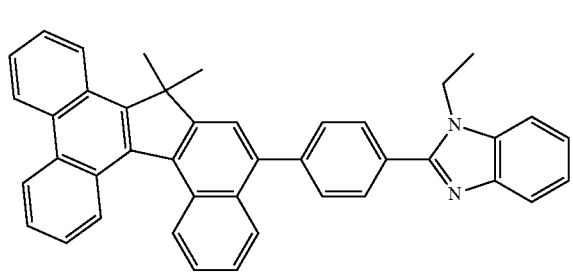
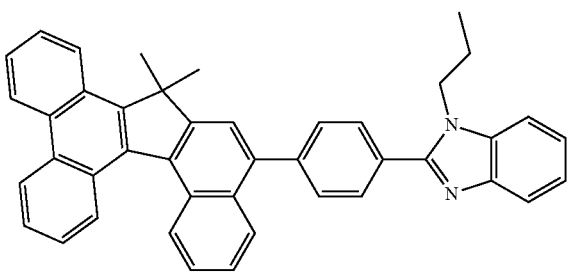

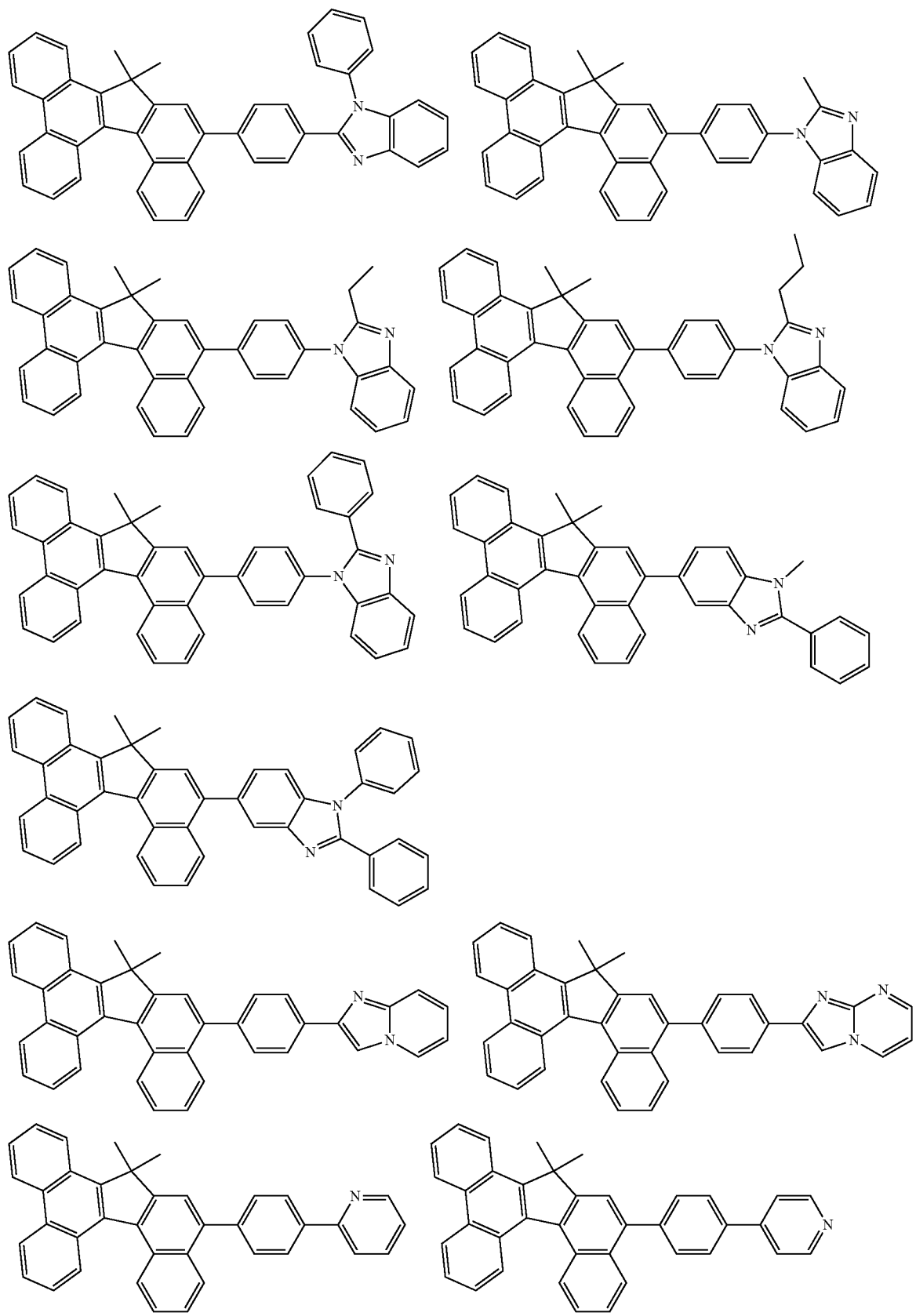

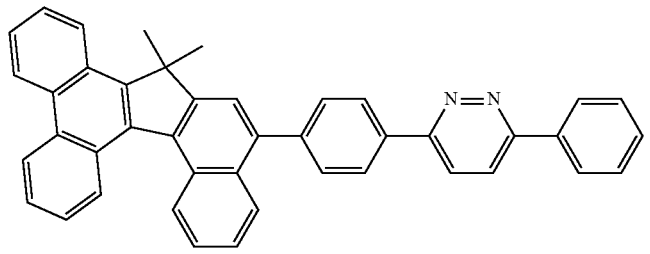
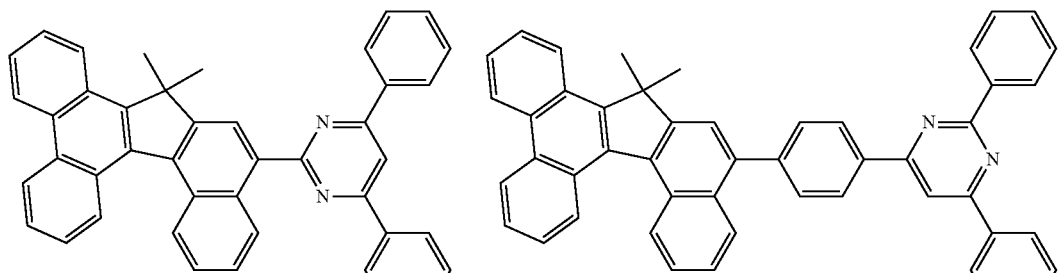
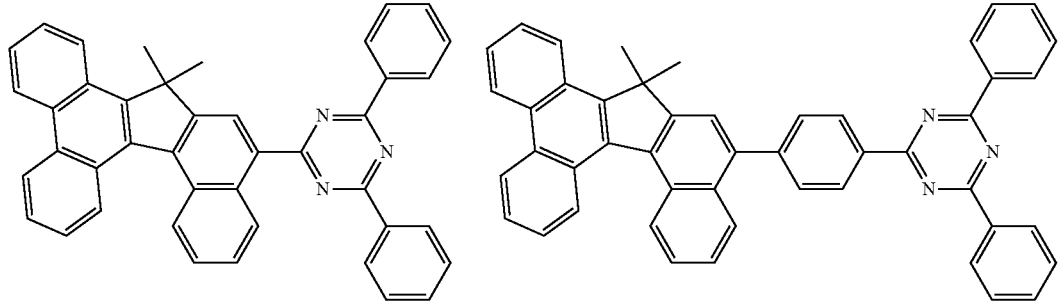
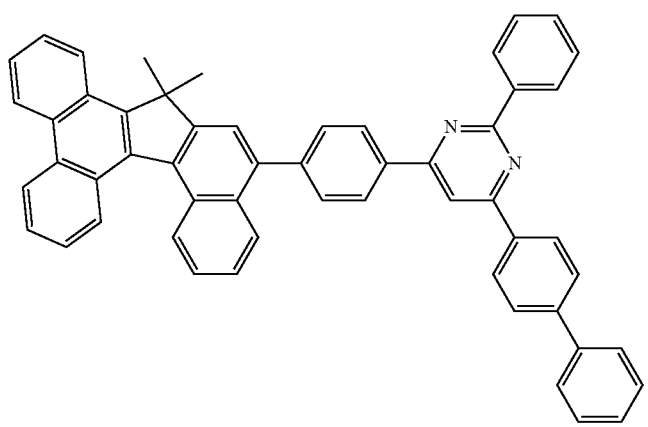

-continued
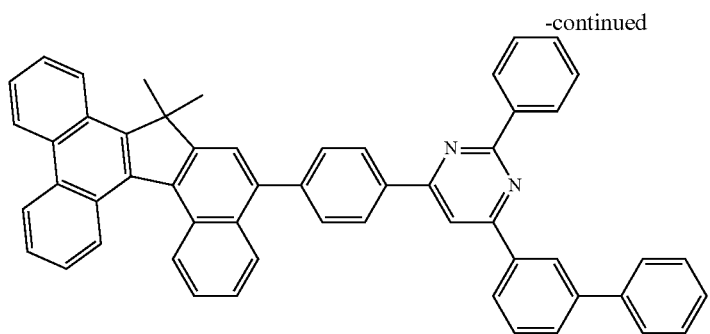
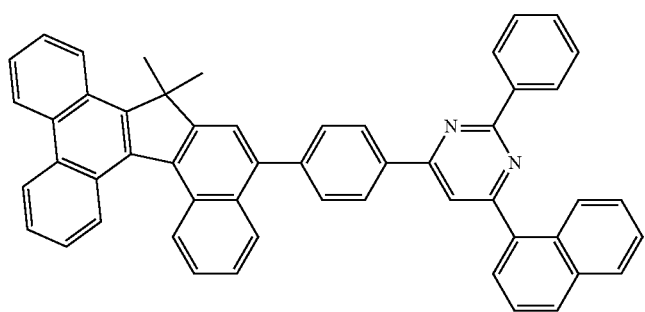
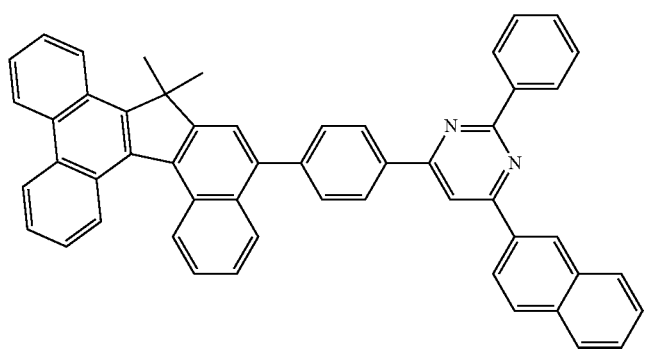
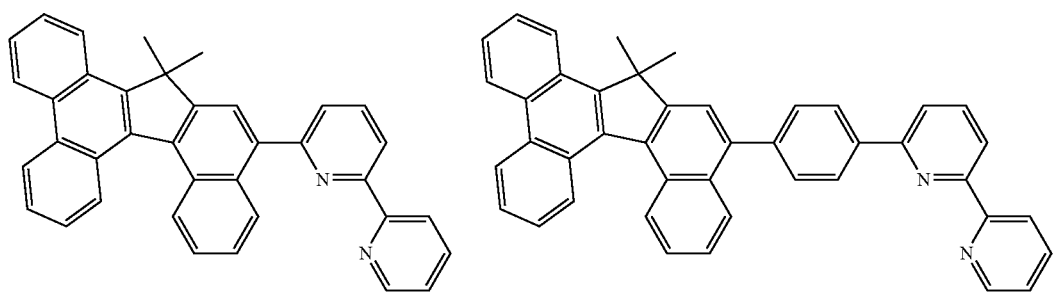
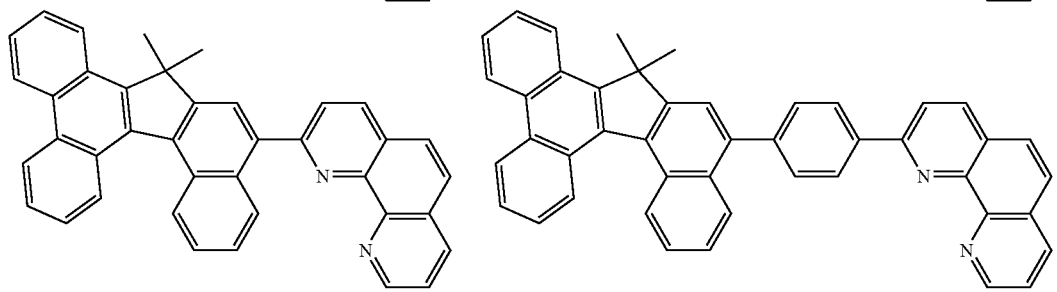

-continued
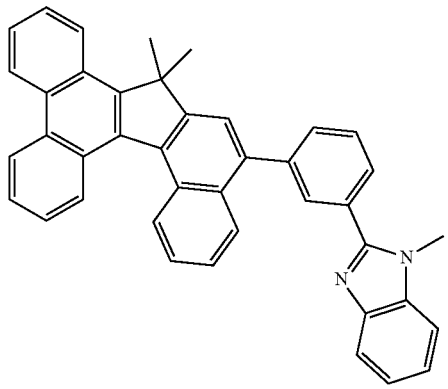
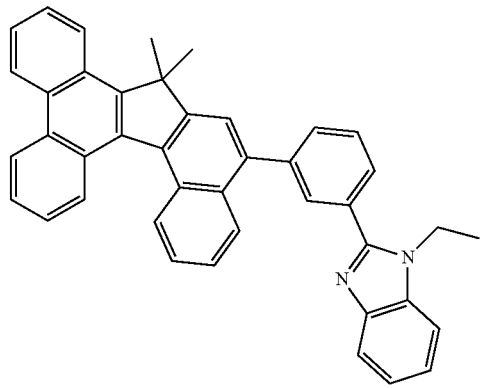
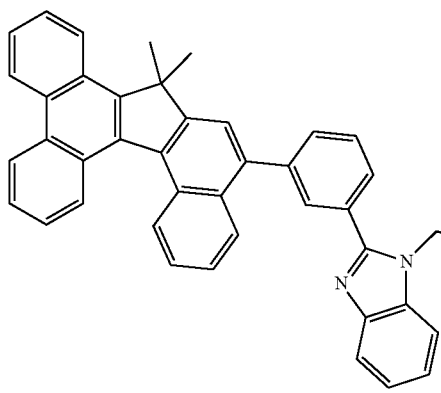
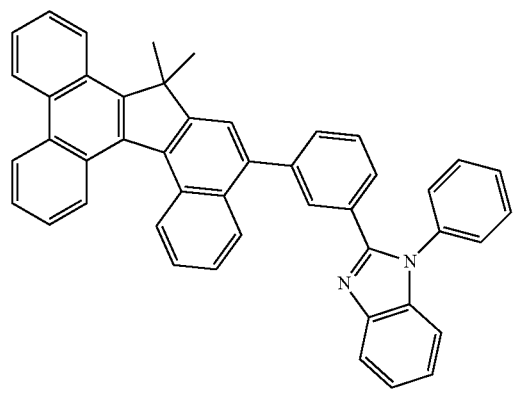
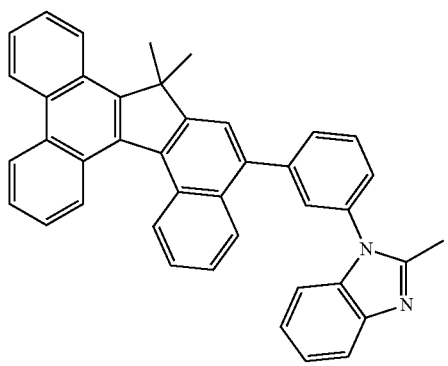
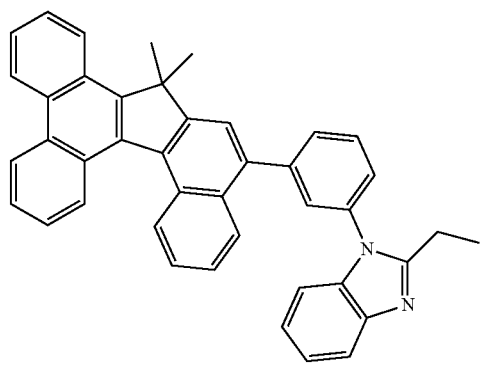
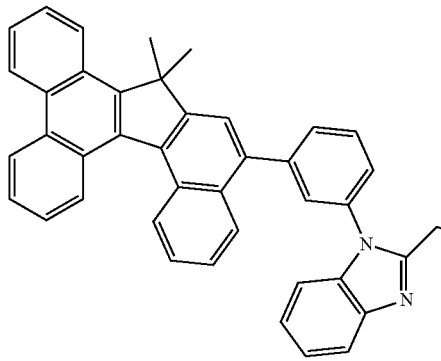
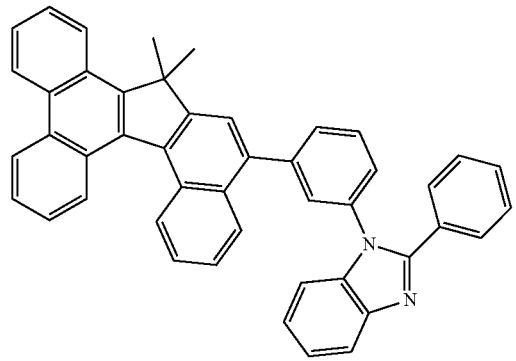

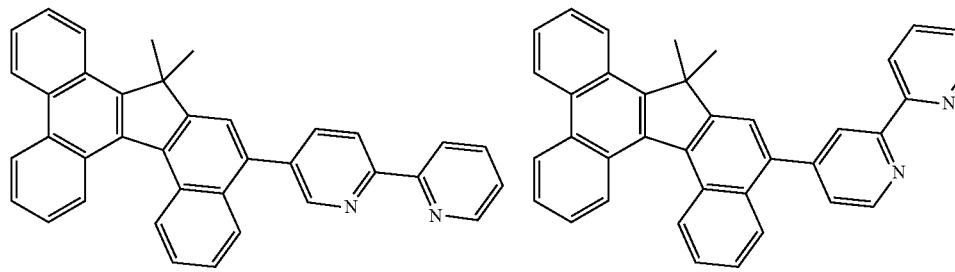

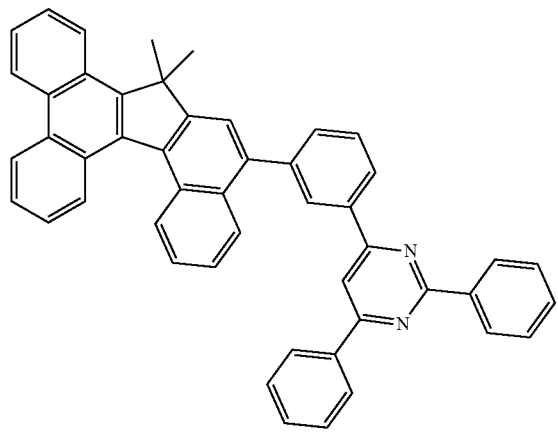
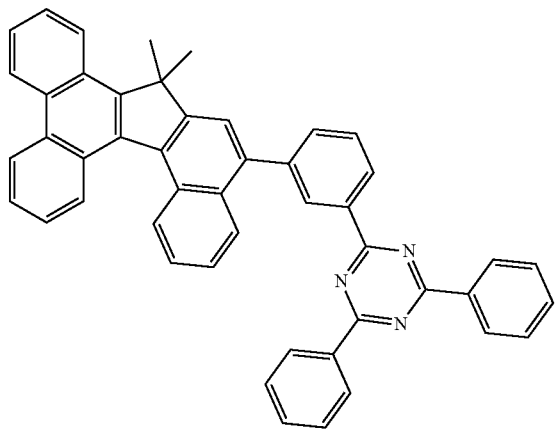
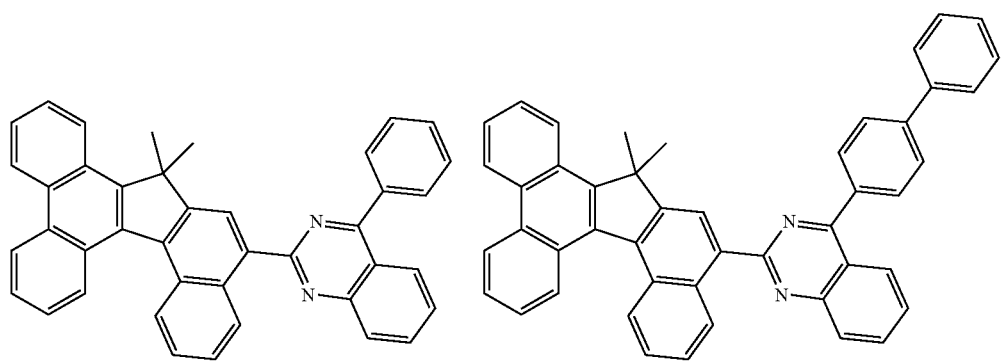
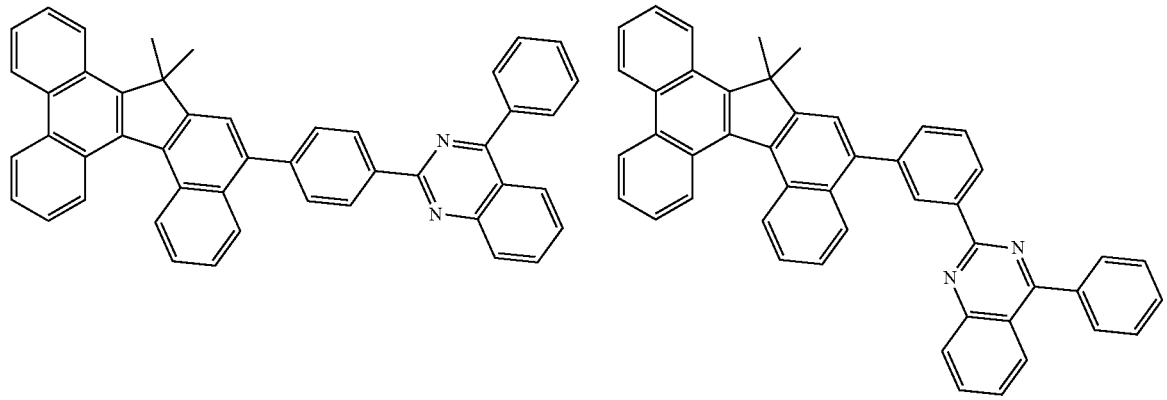
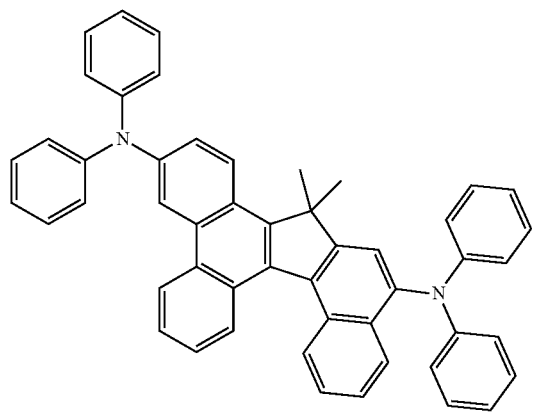
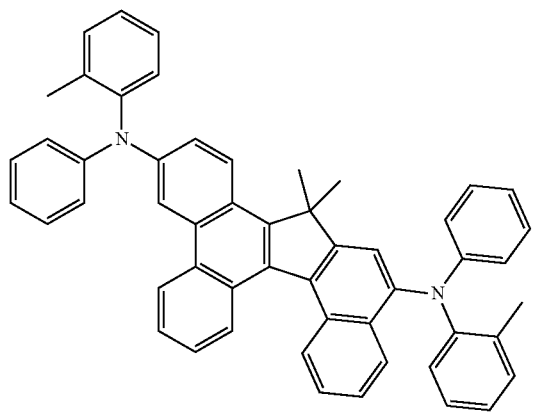

-continued
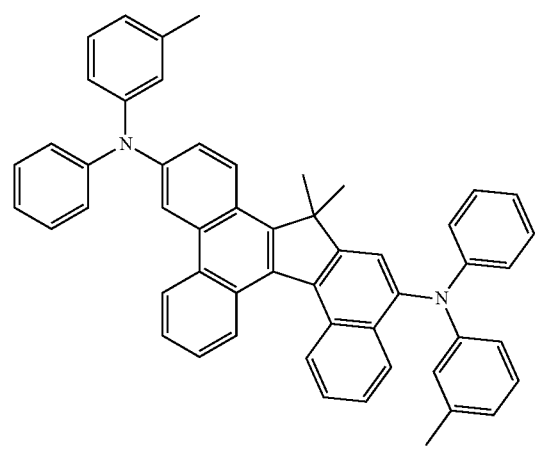
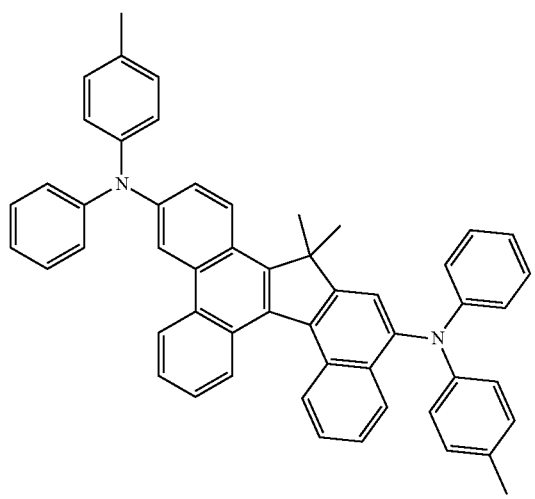
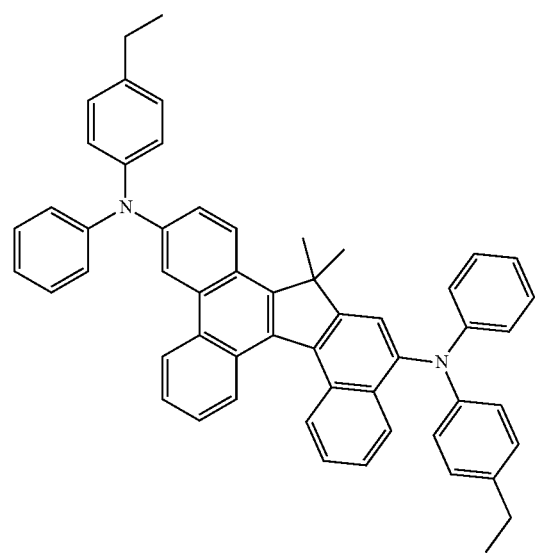
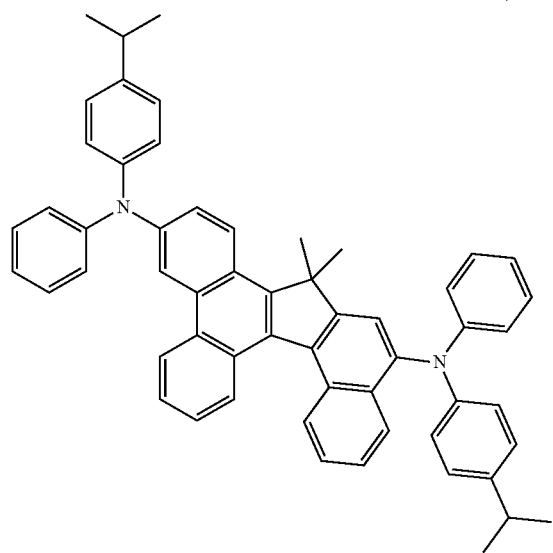
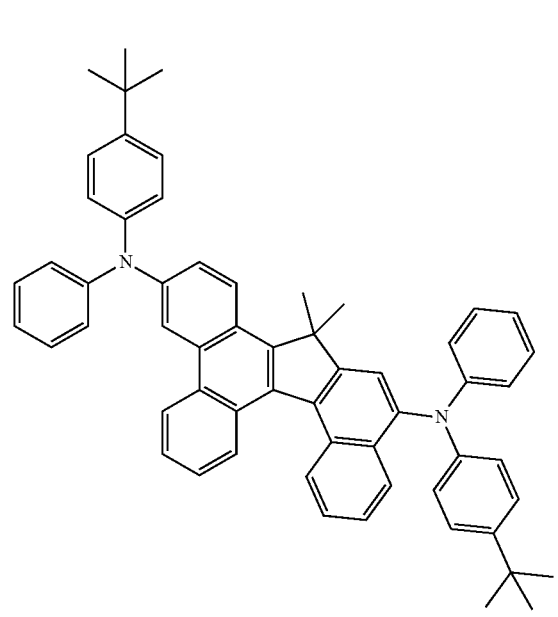
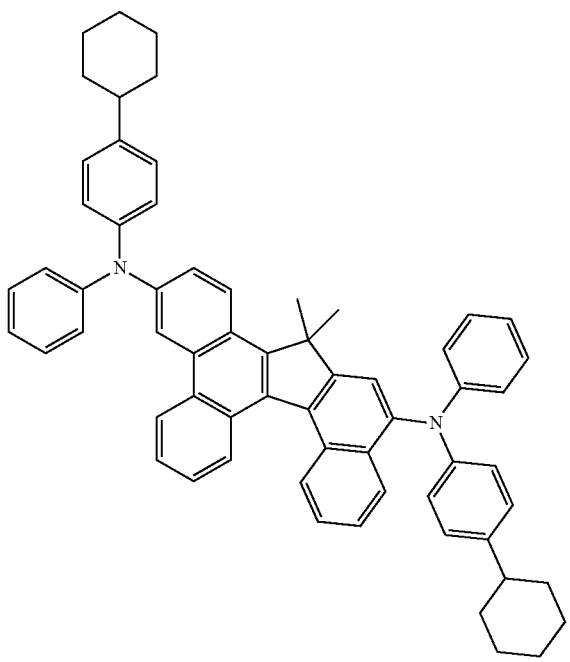

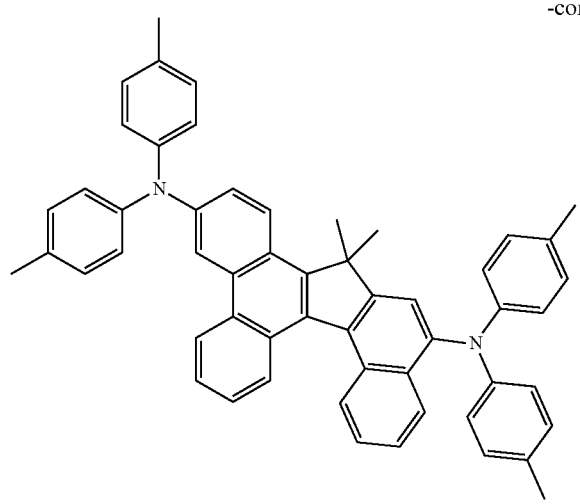
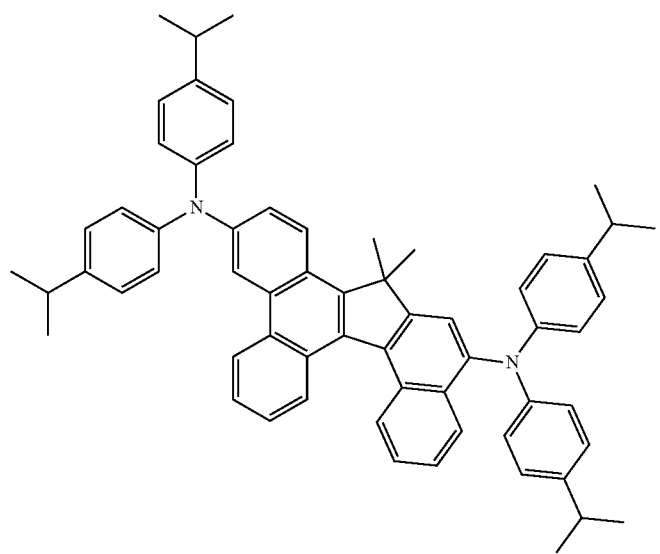
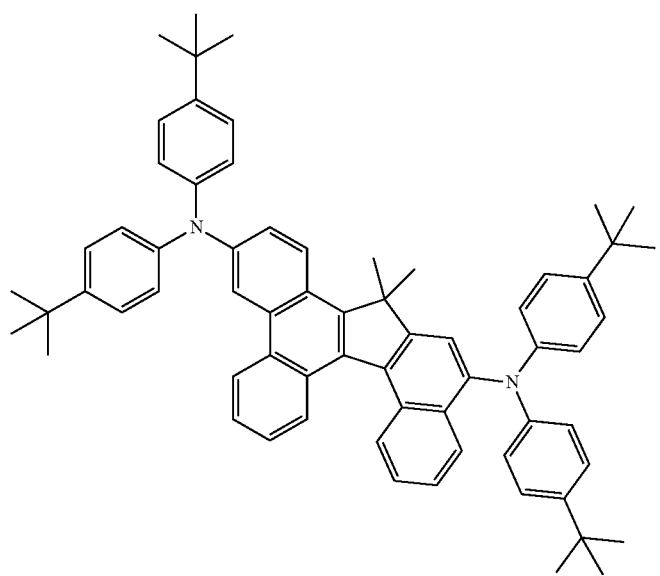

101 102
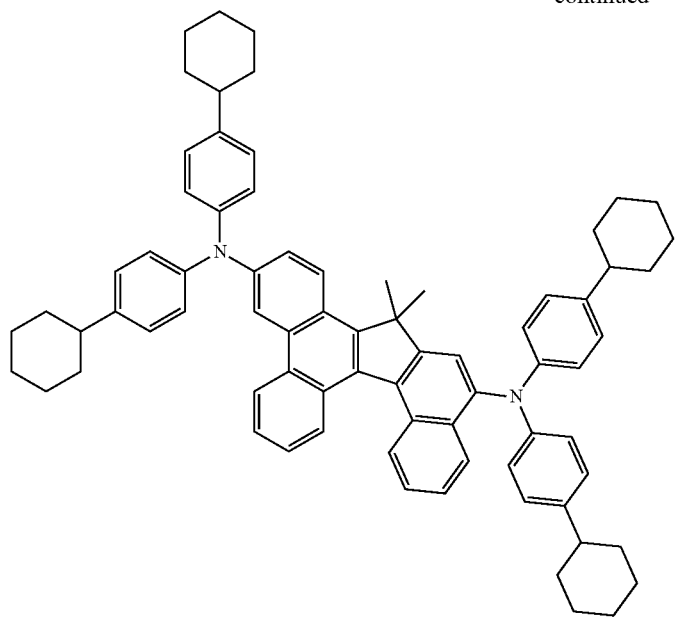
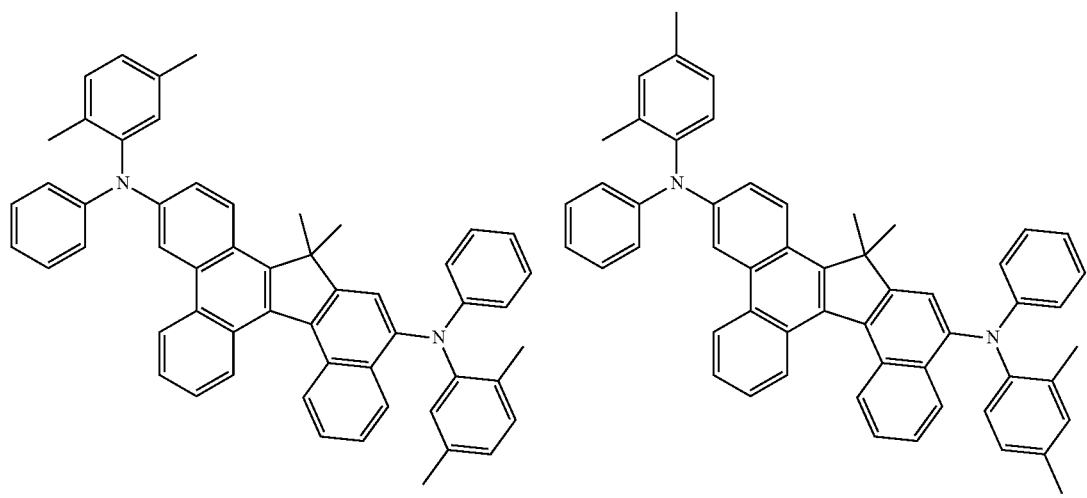
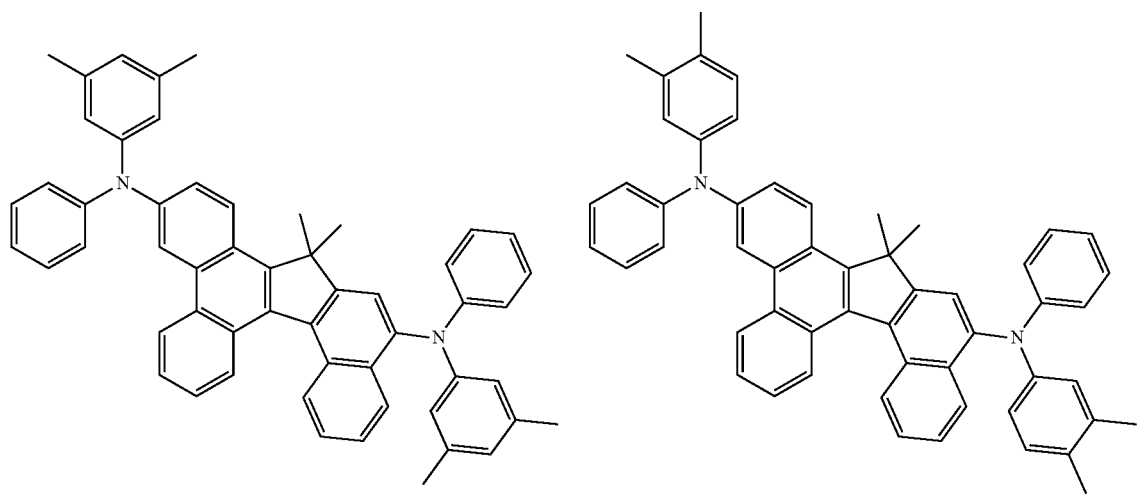

103
104
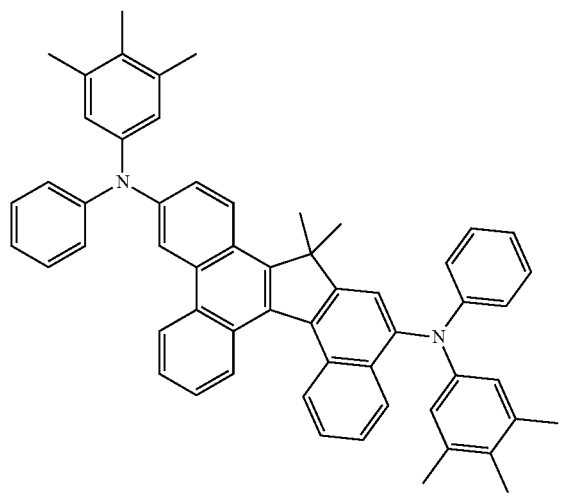
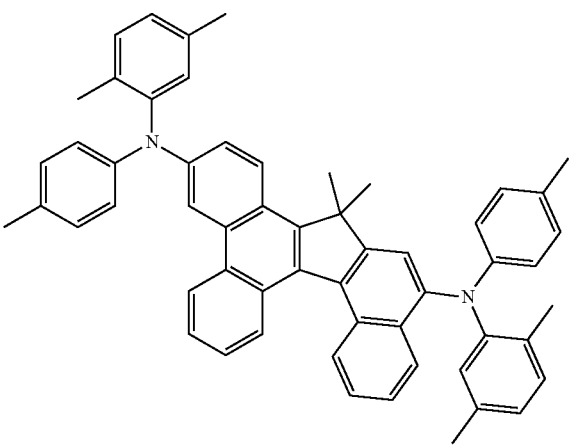
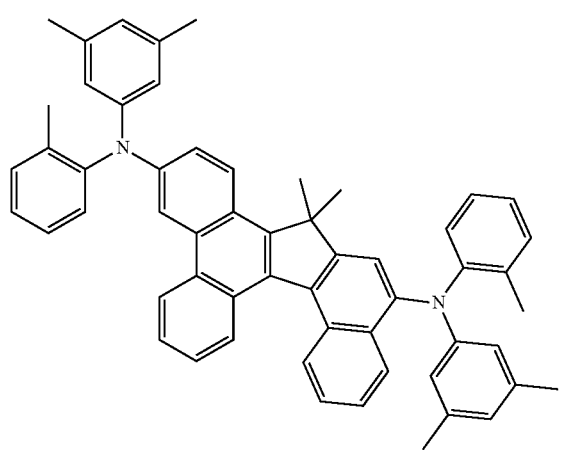
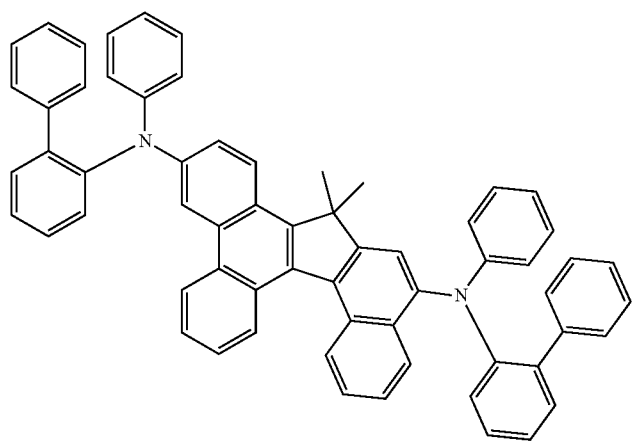

105
106
-continued
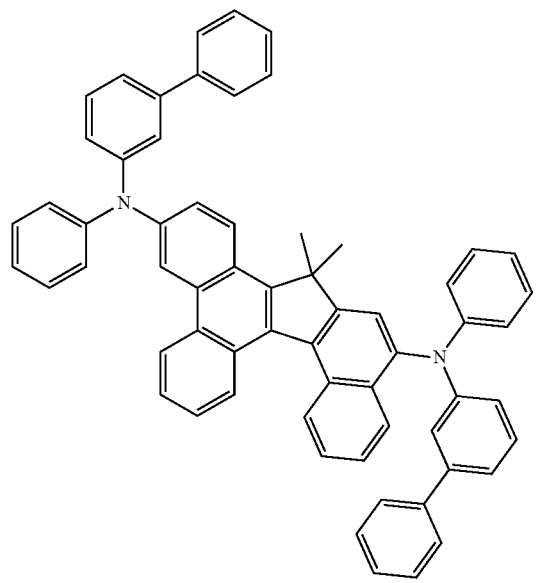
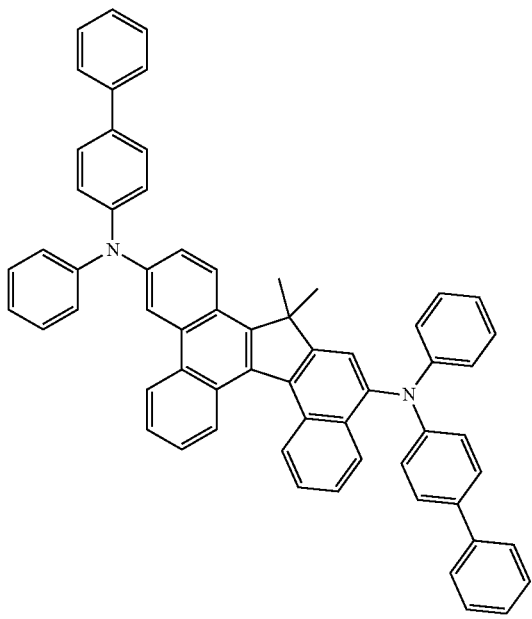
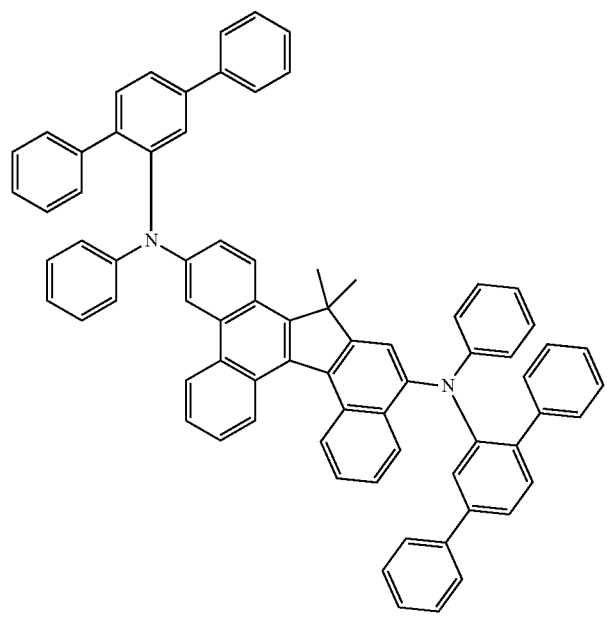

-continued
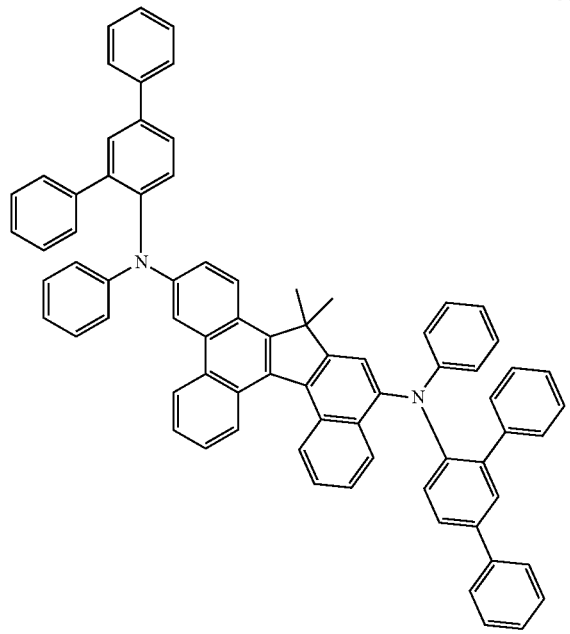
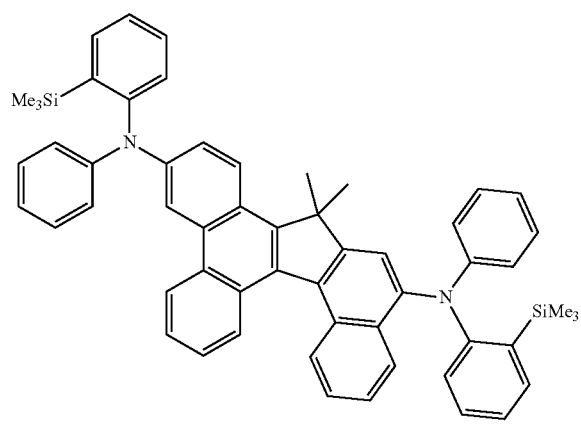
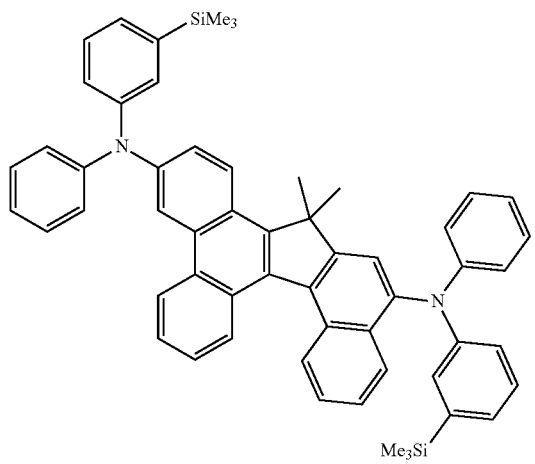
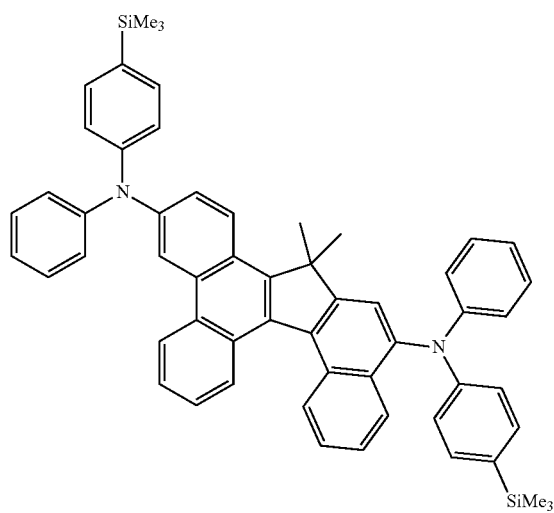

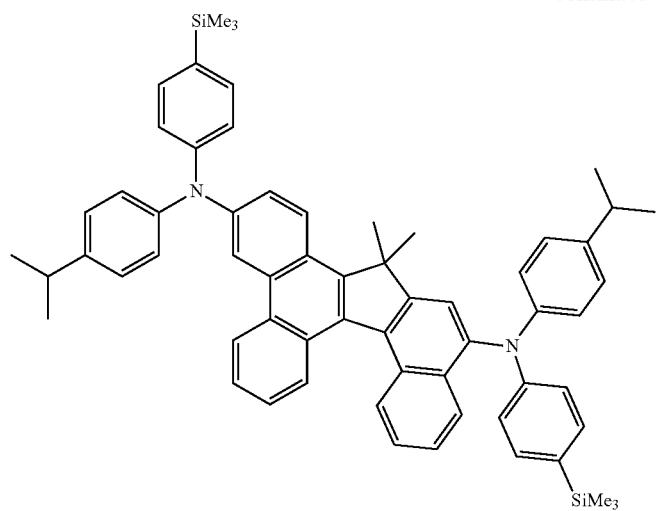
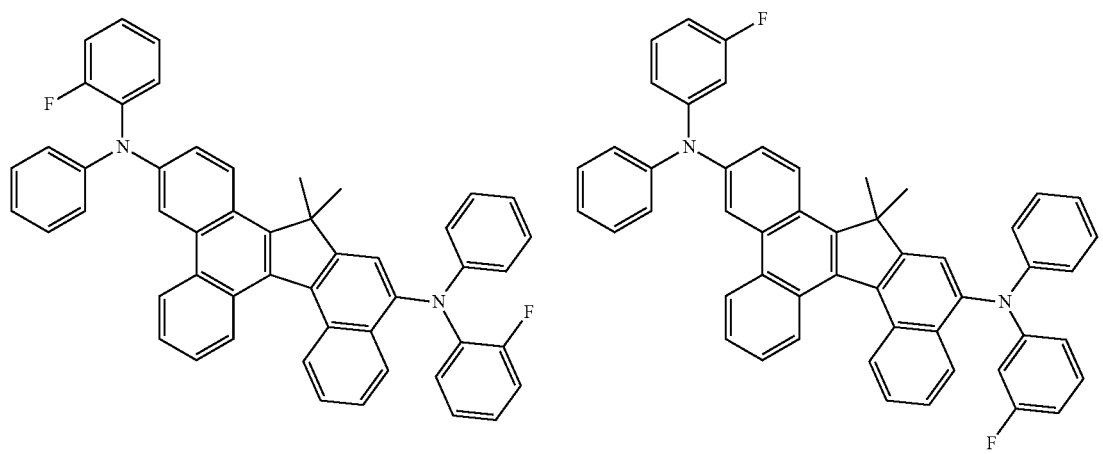
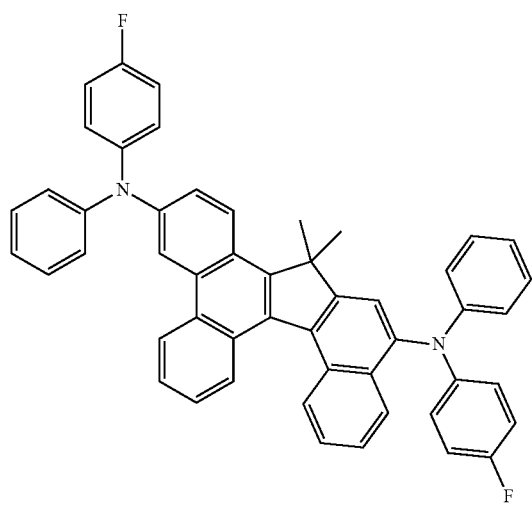

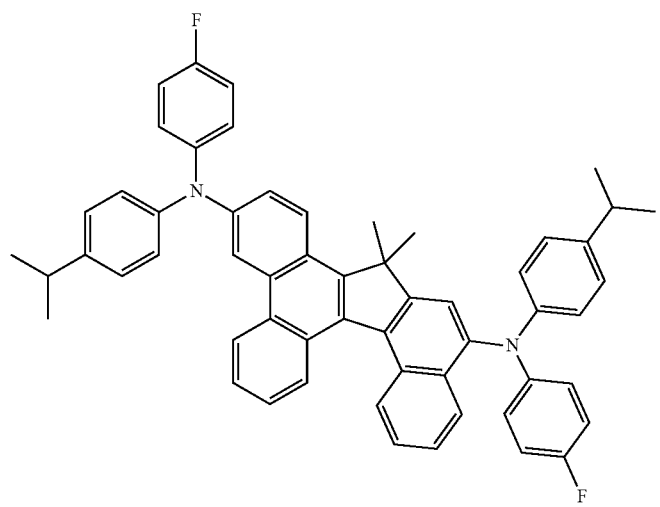
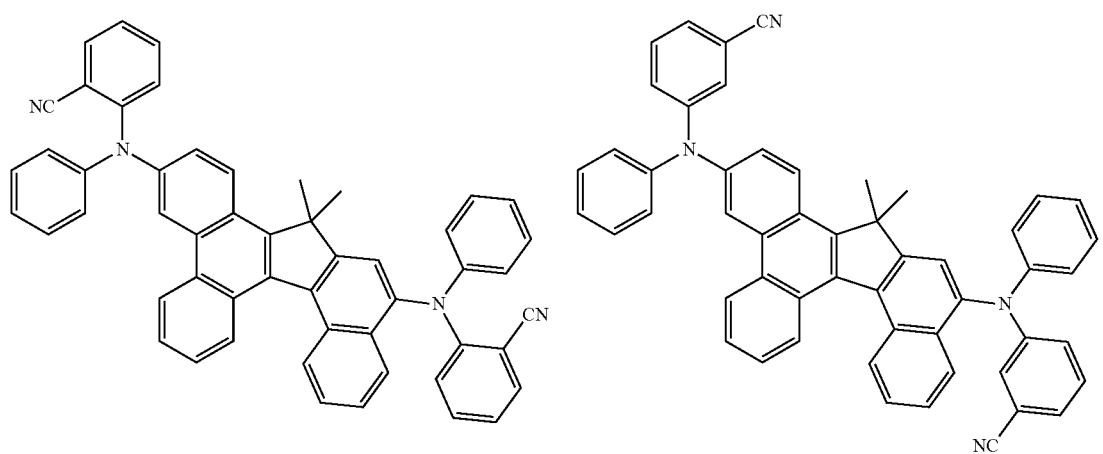
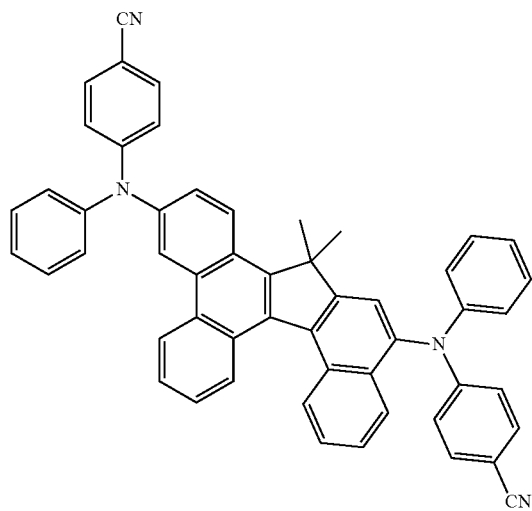

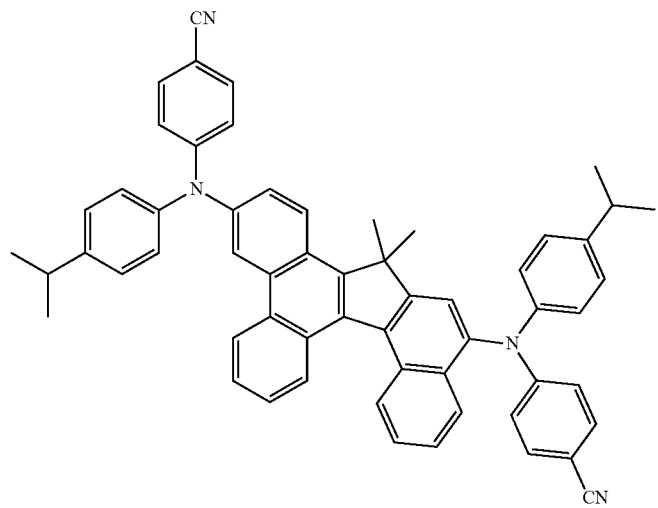
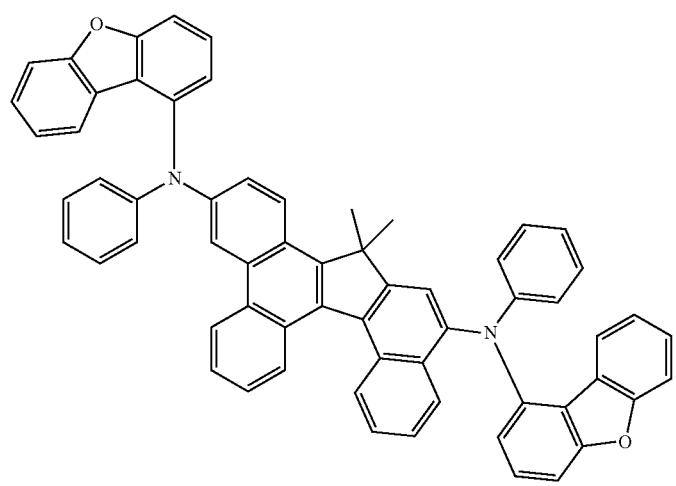
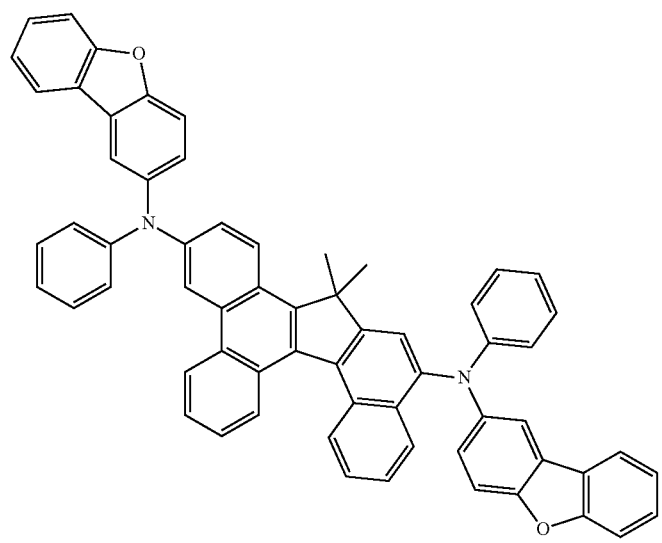

-continued
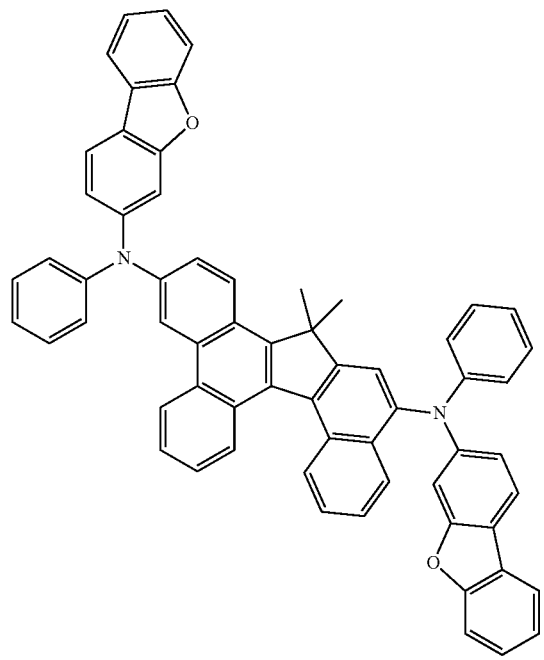
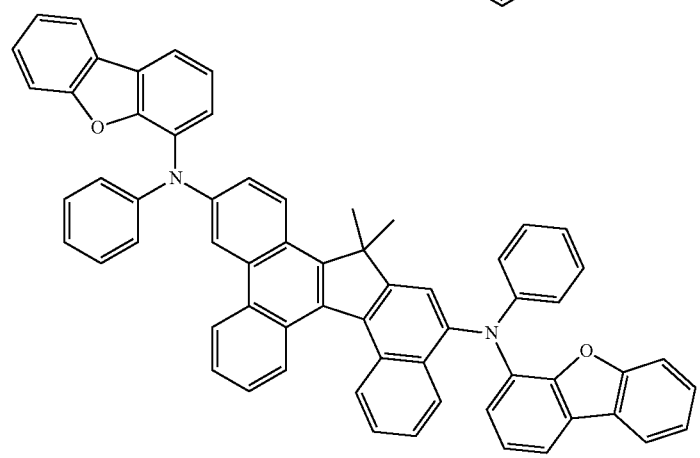
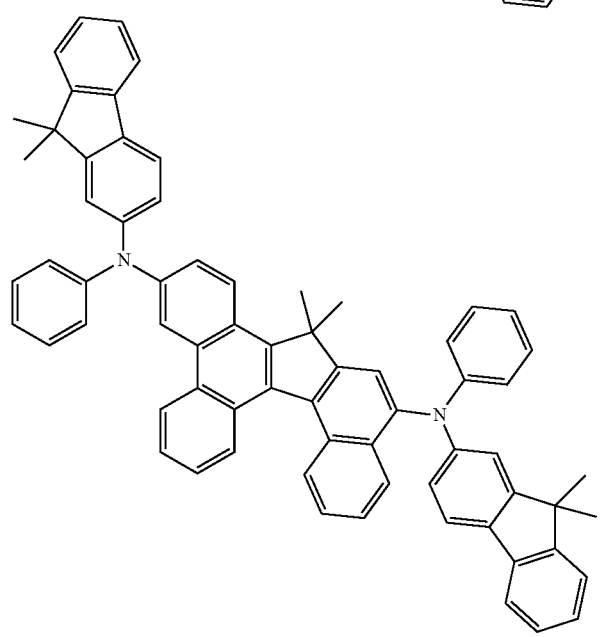

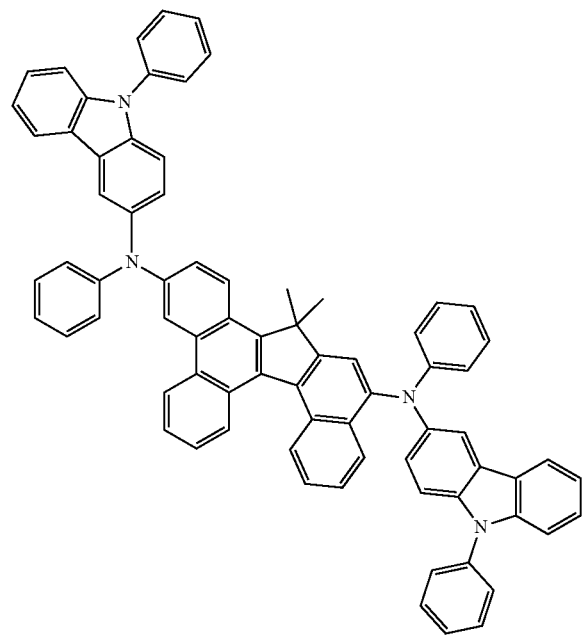
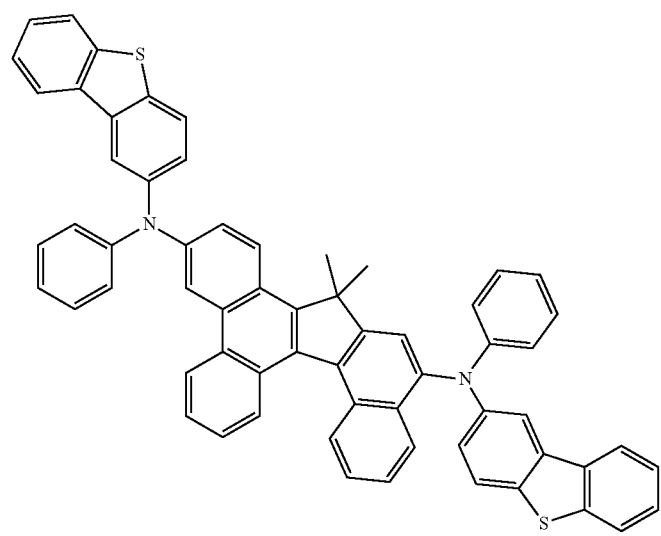

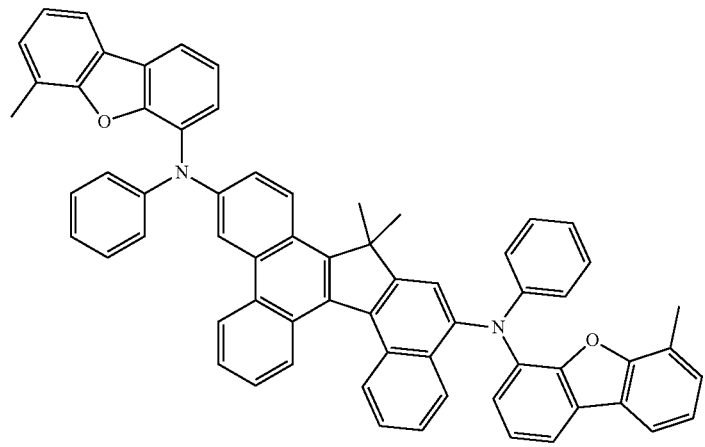
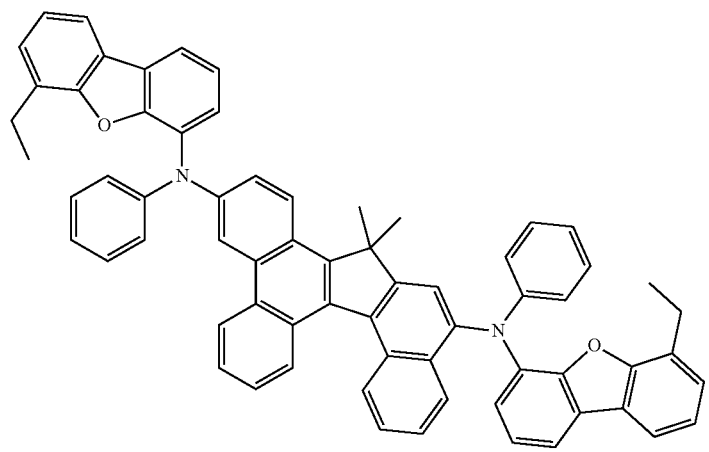
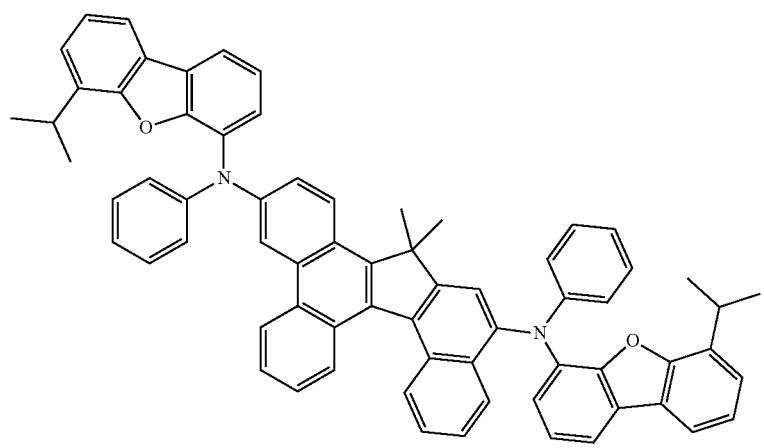

-continued
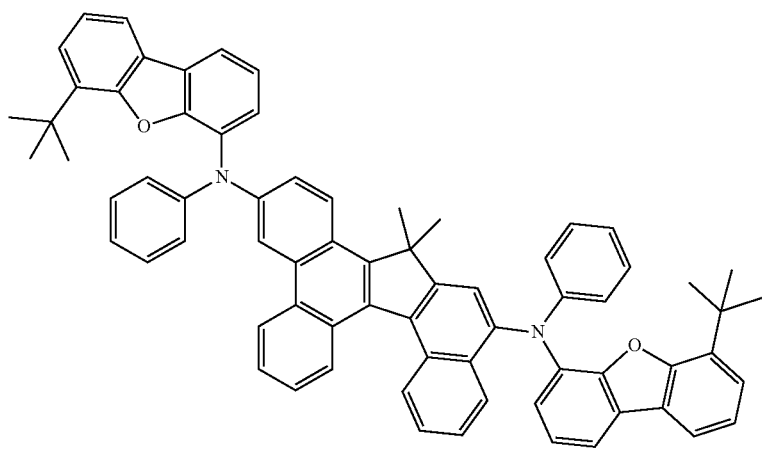
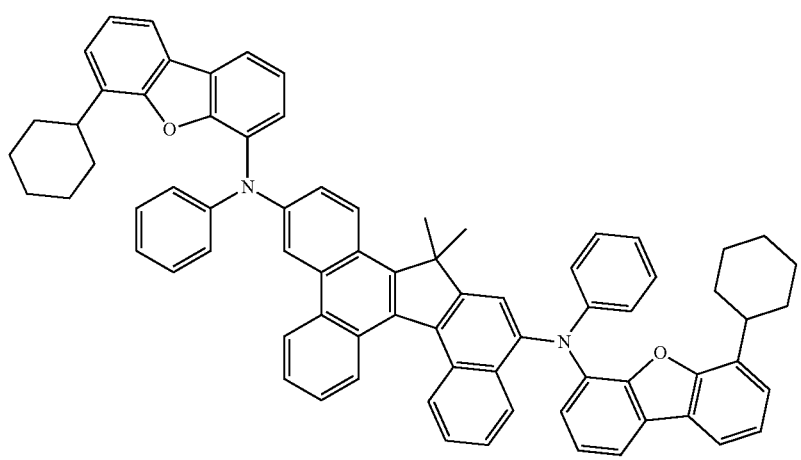
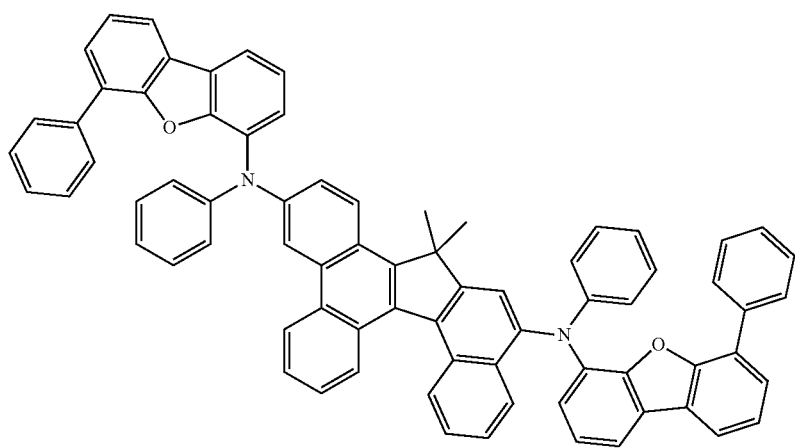

-continued
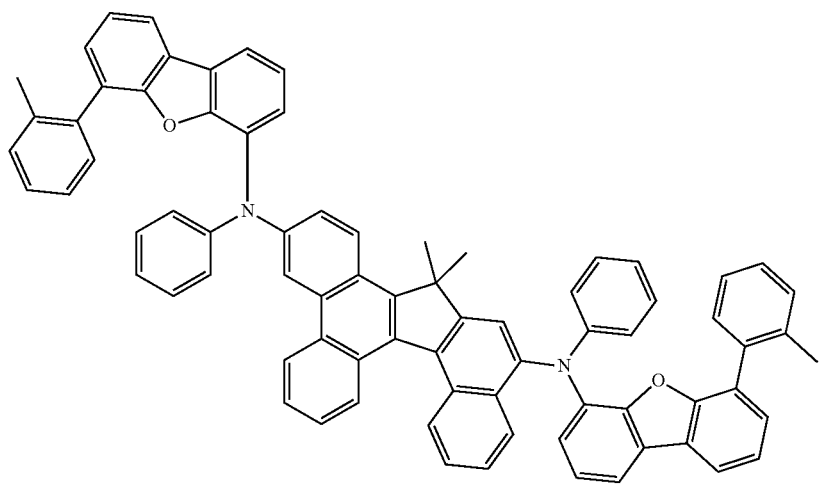
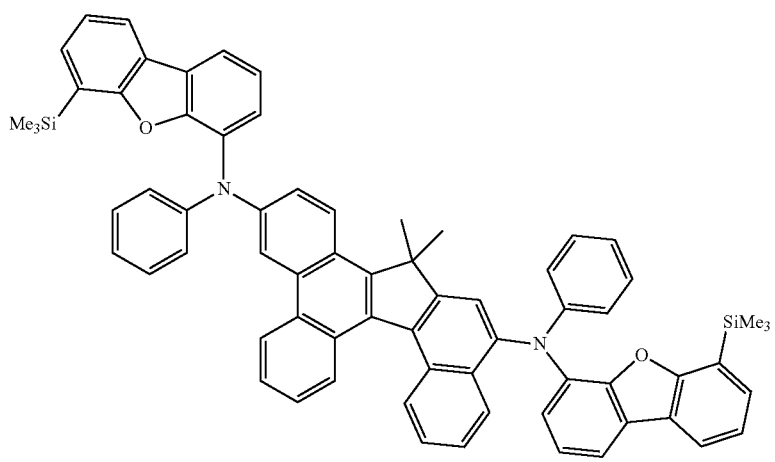
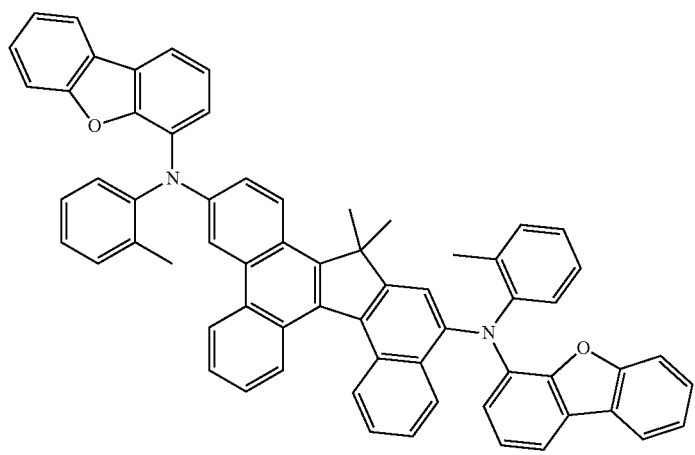

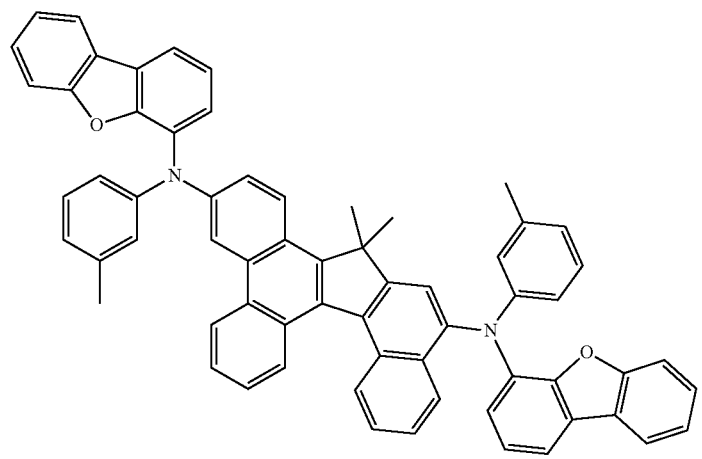
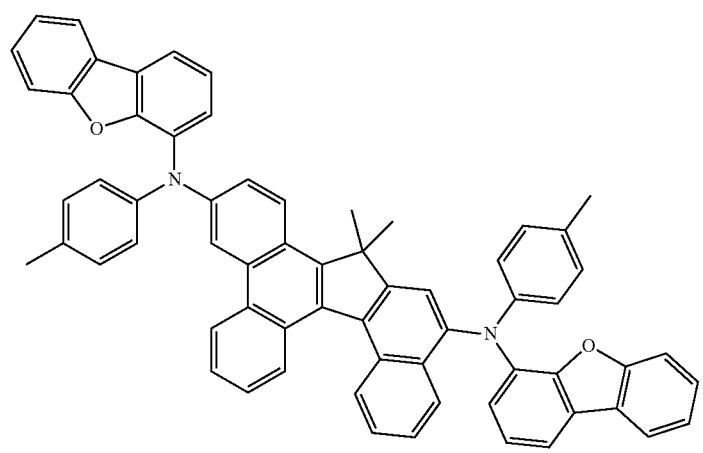
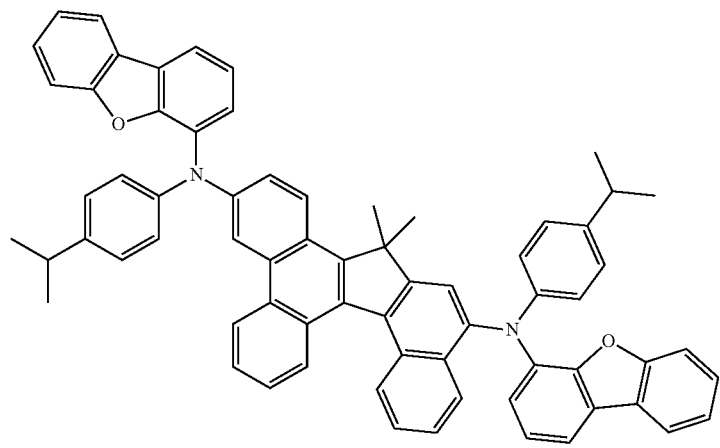

-continued
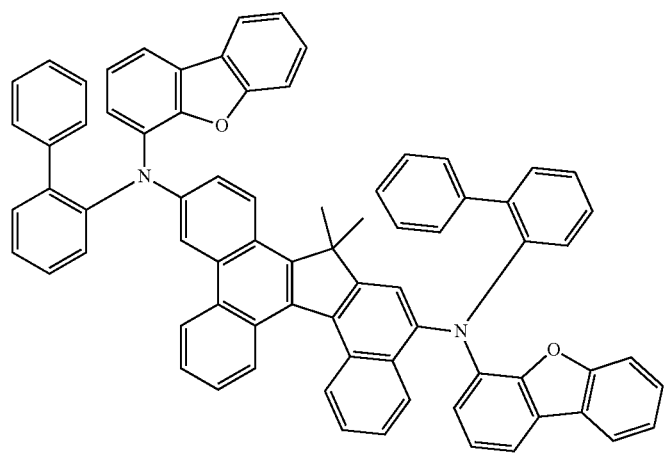
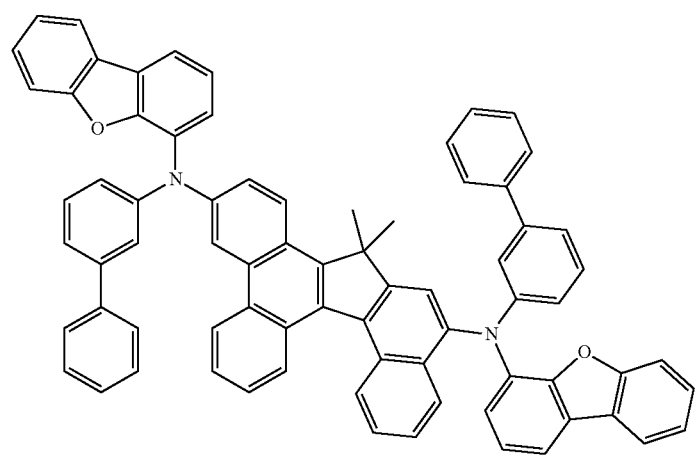
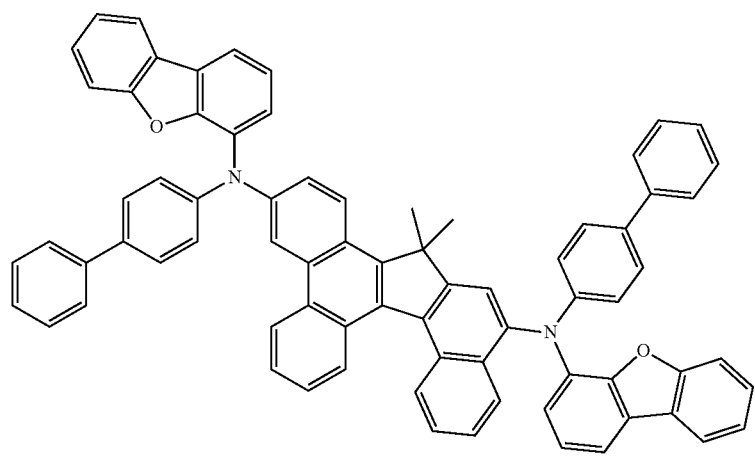

-continued
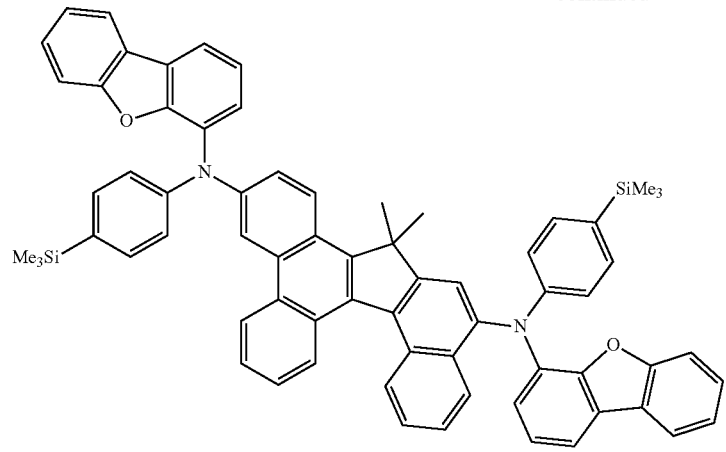
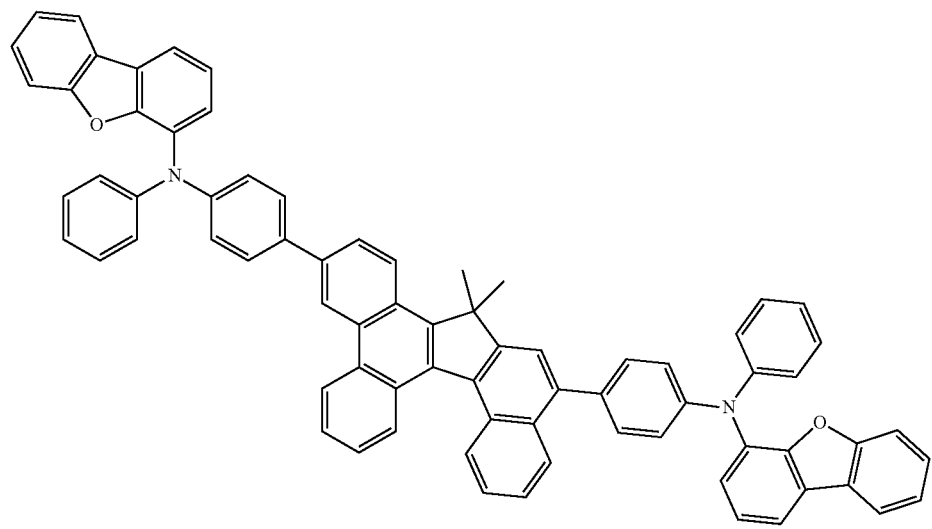
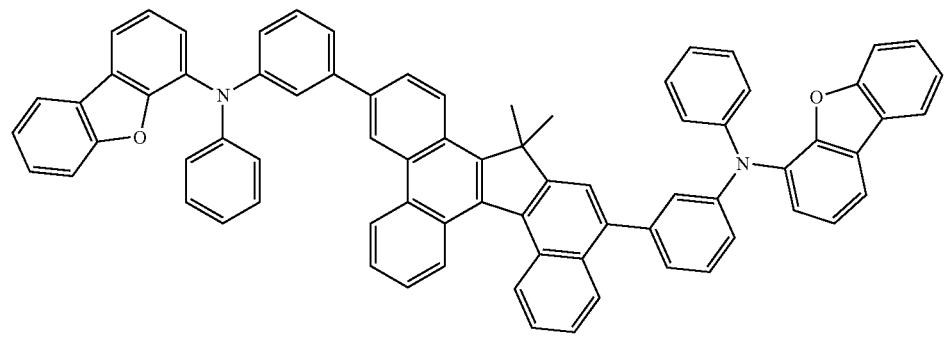

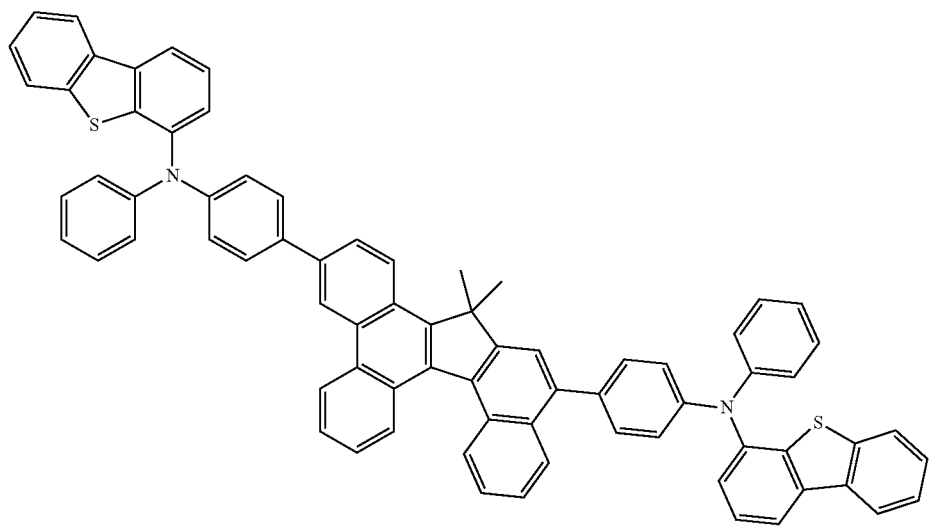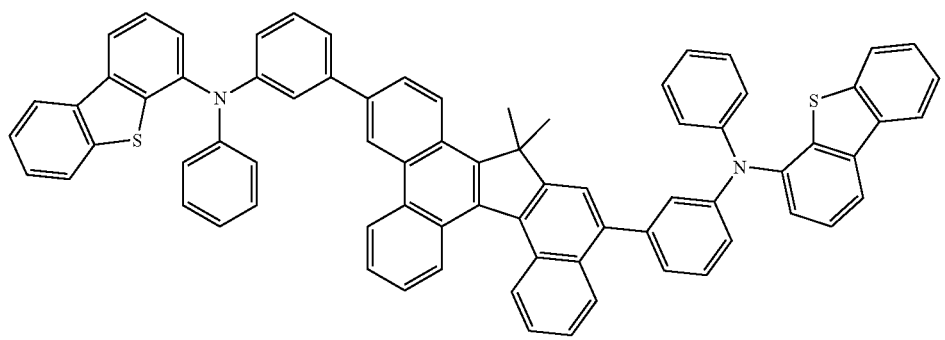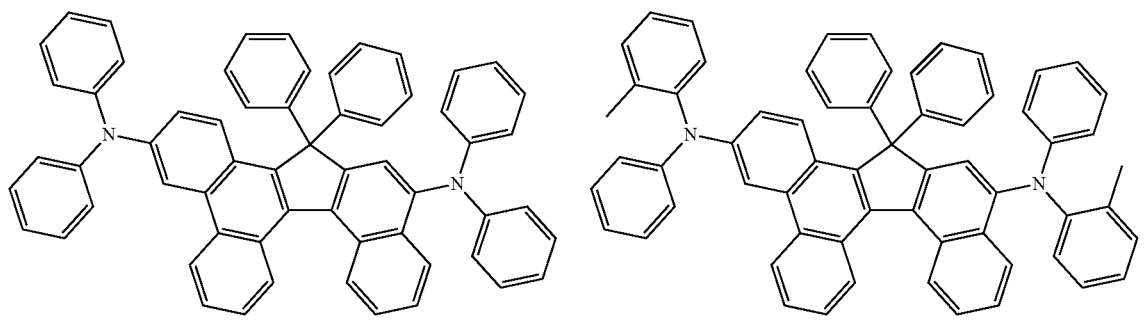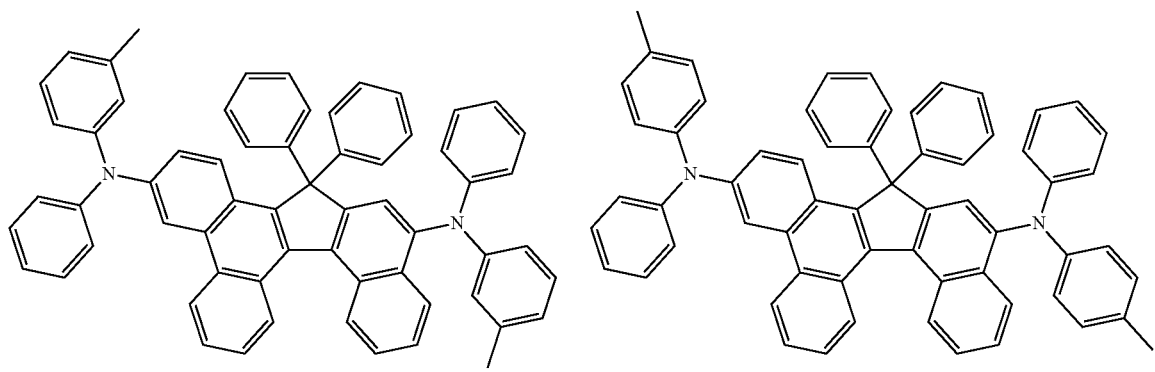

-continued
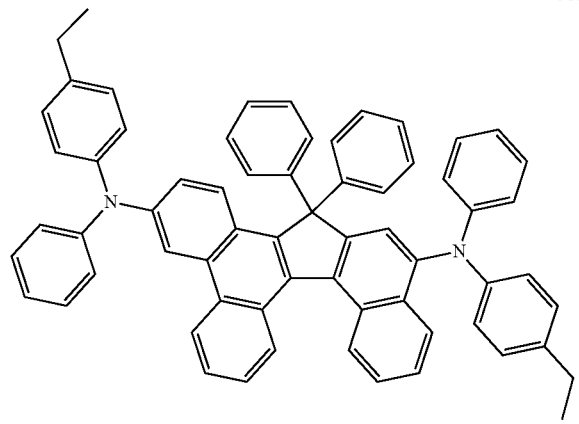
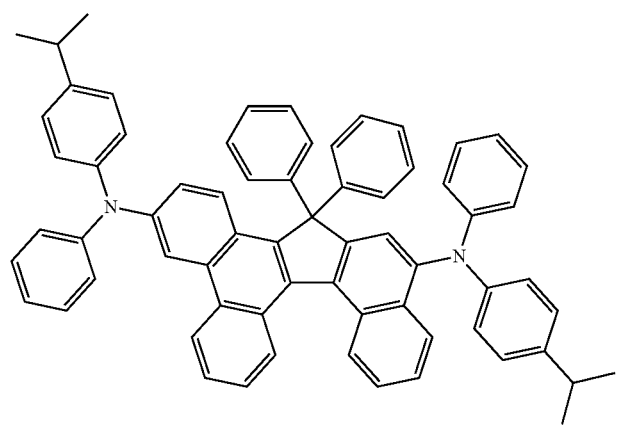
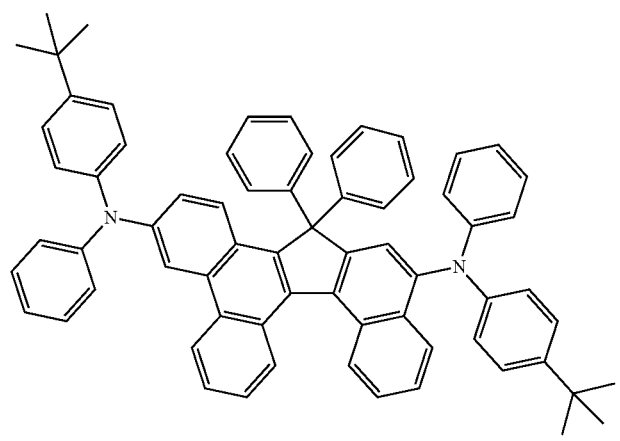

-continued
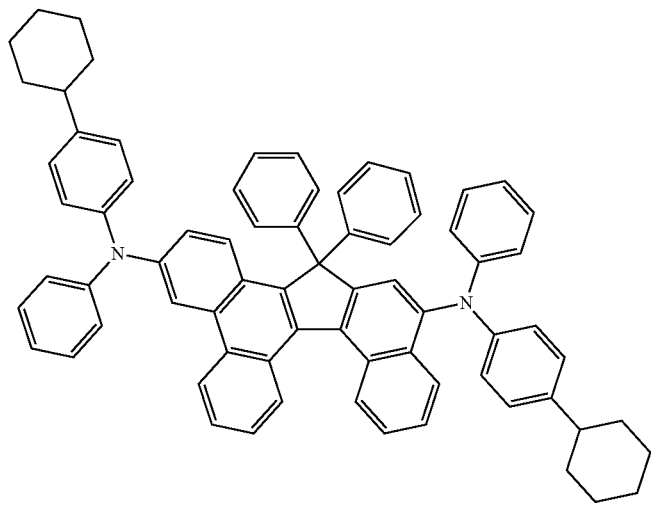
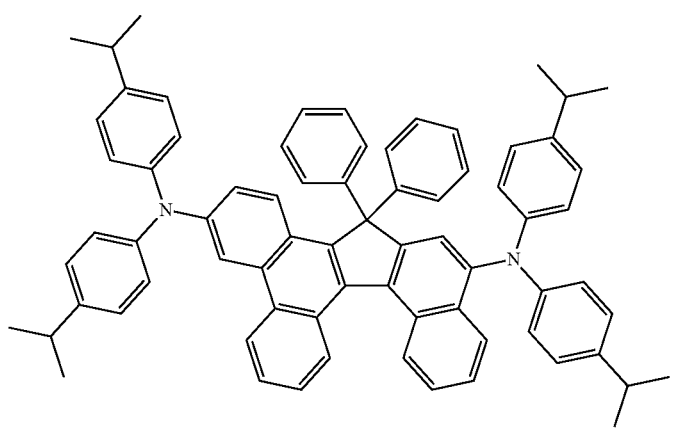
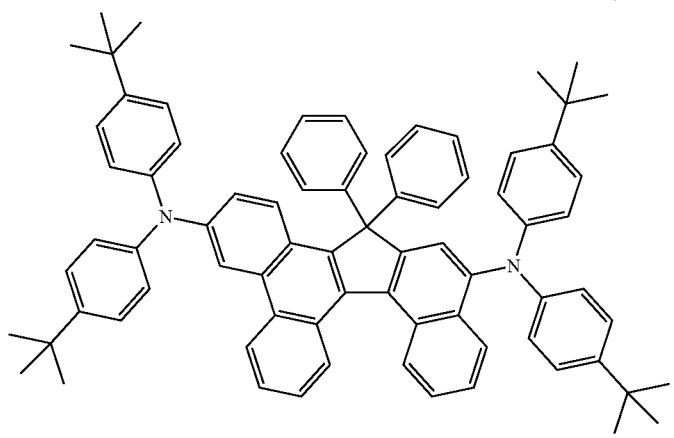

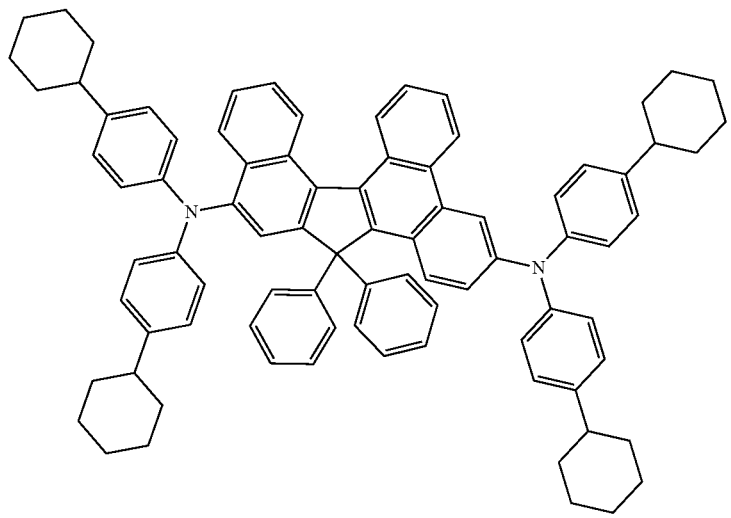
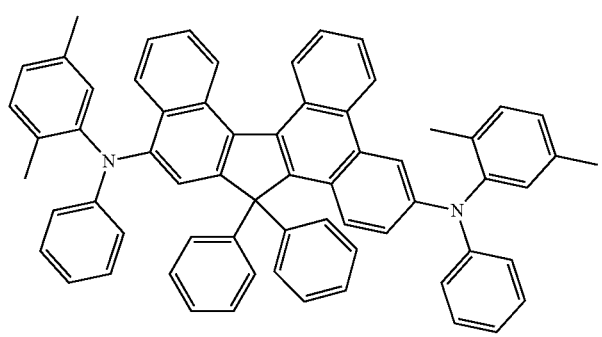
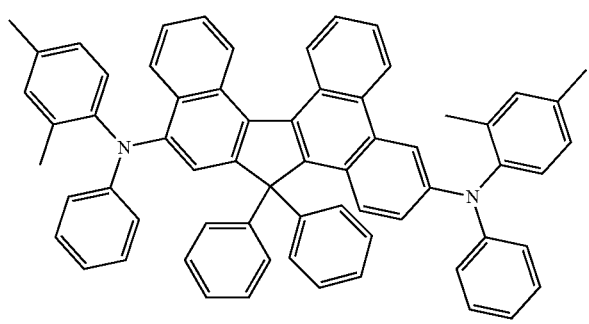
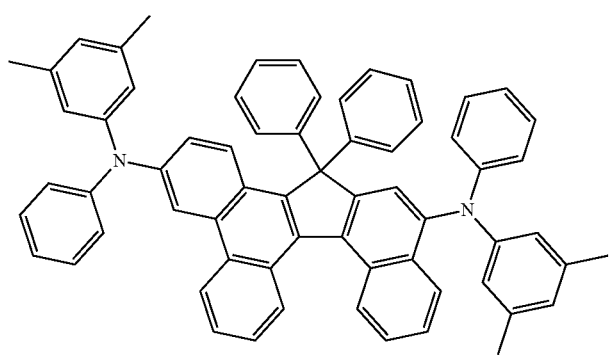

-continued
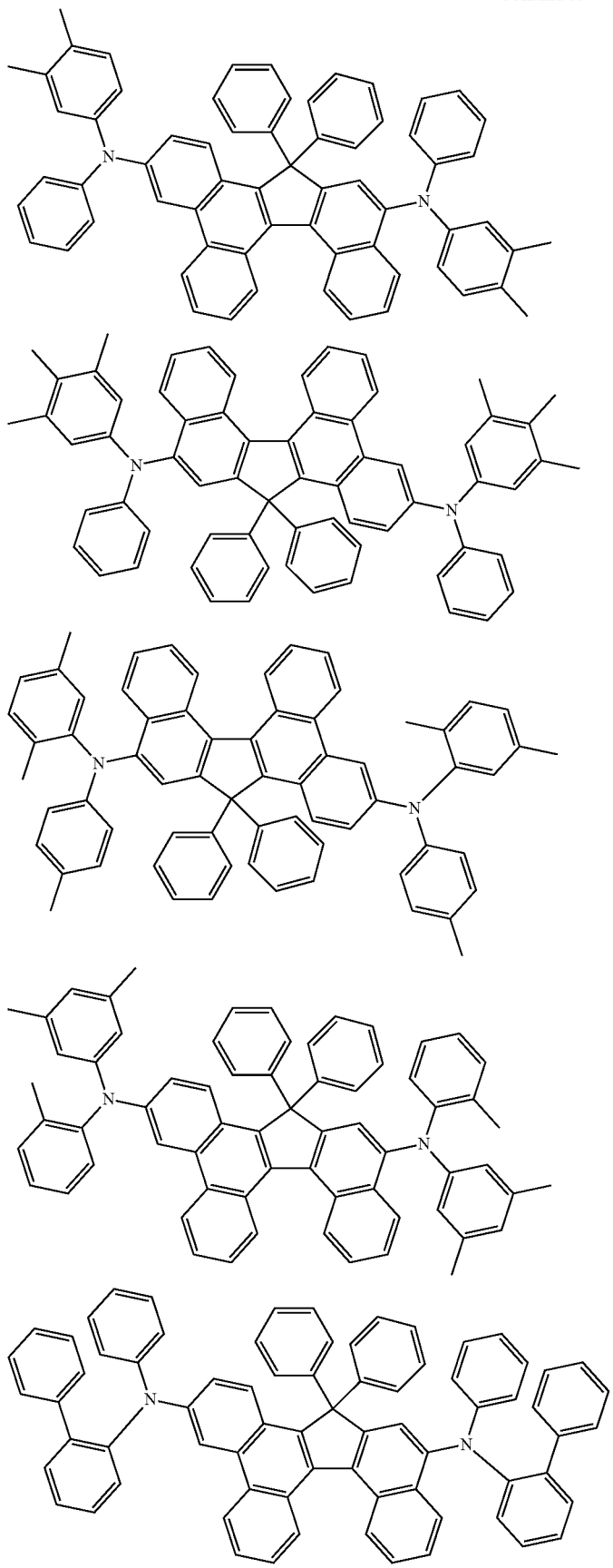

-continued
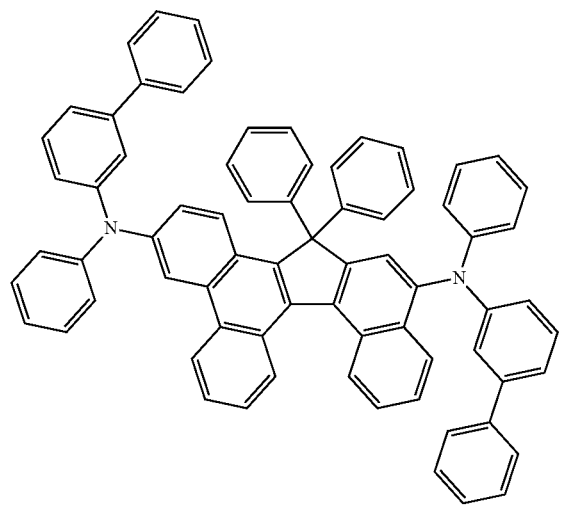
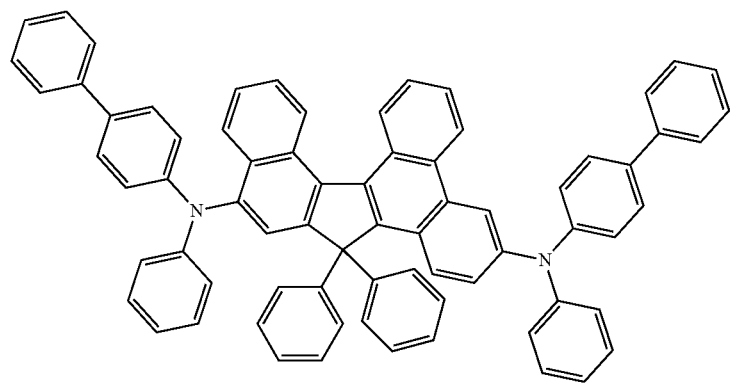
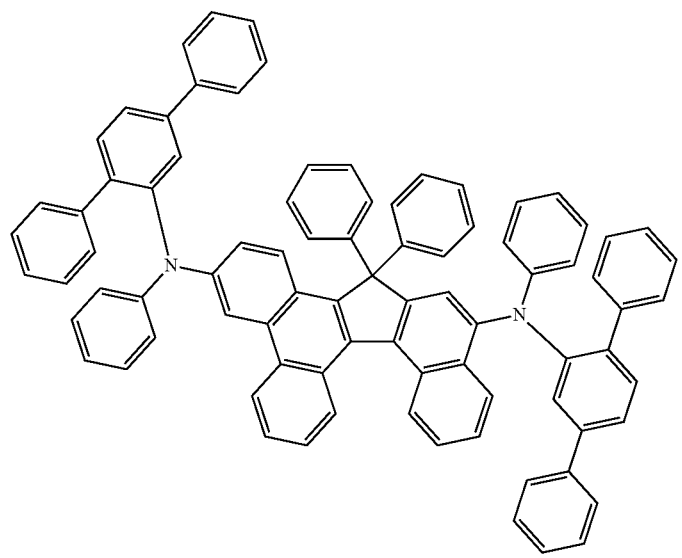

-continued
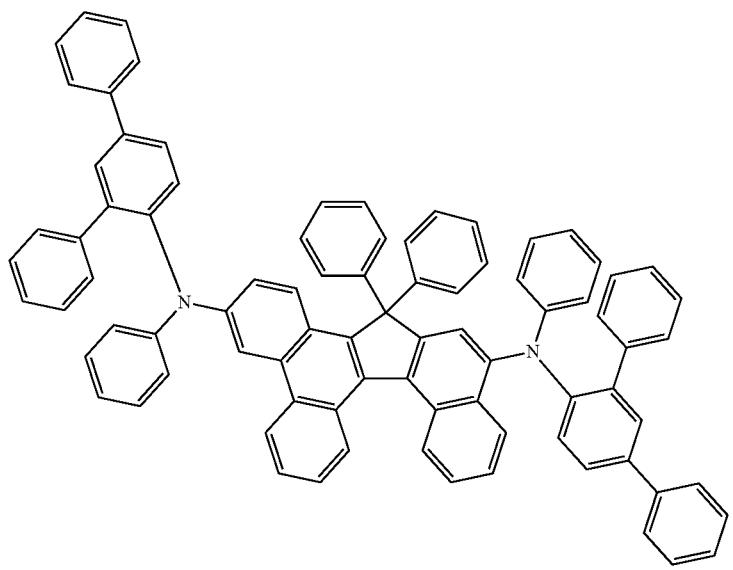
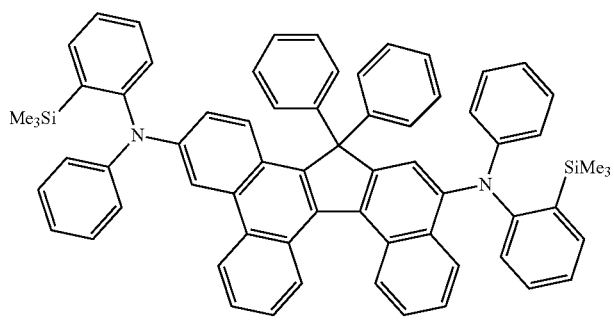
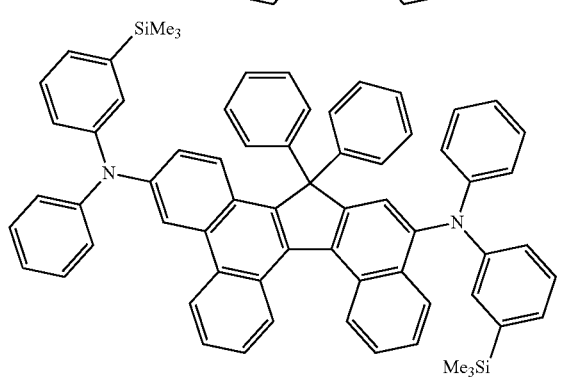
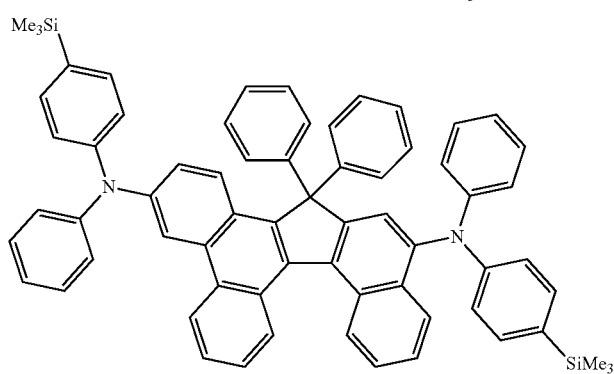

-continued
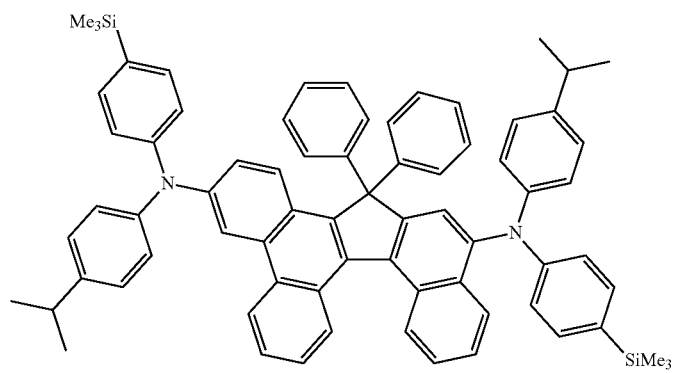
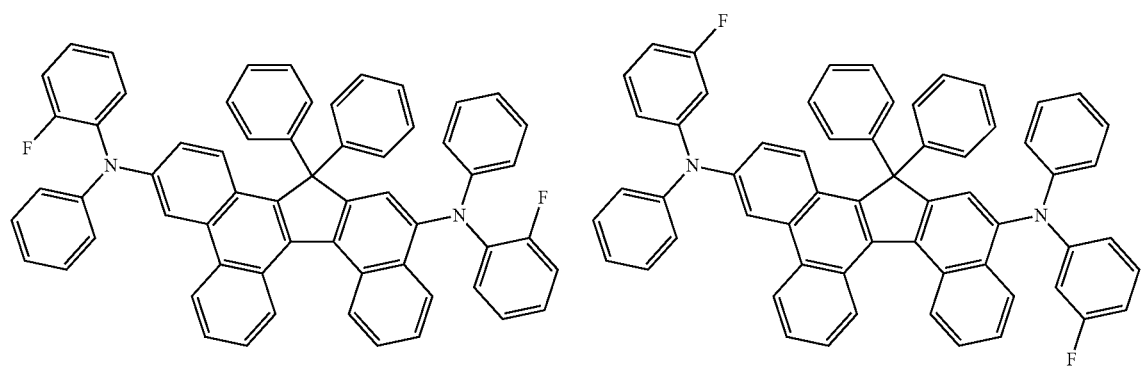
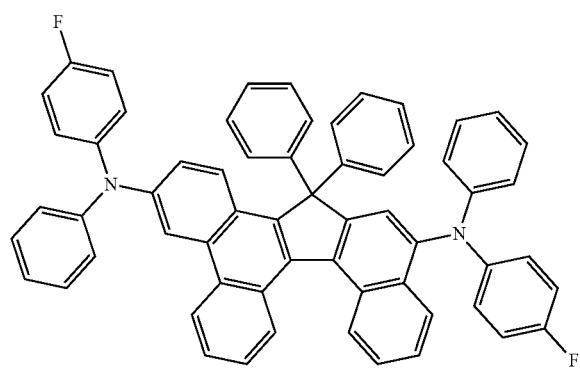
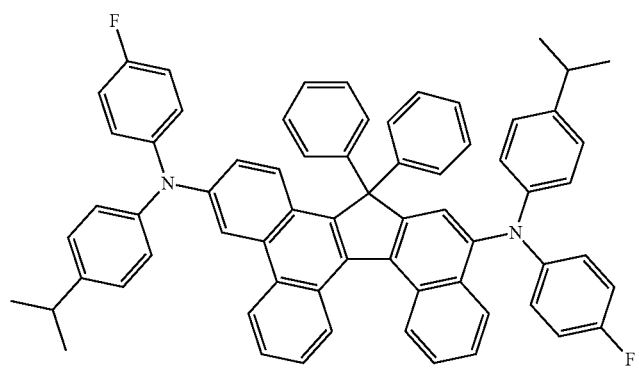

-continued
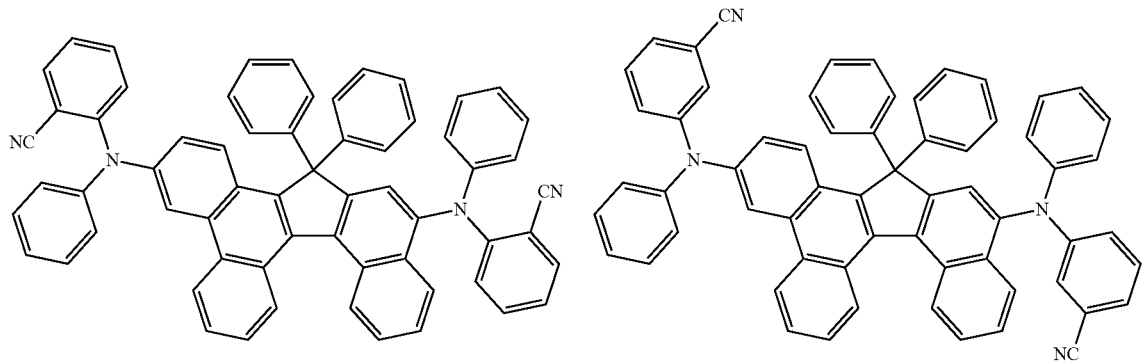
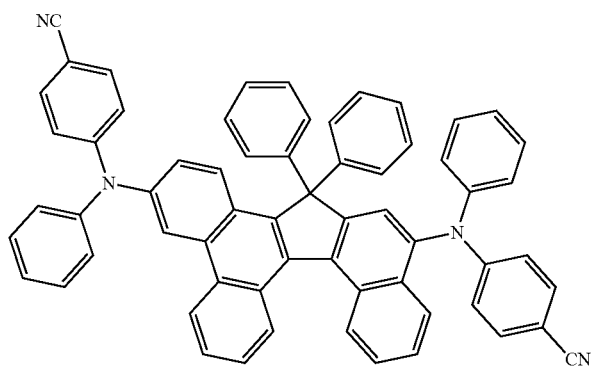
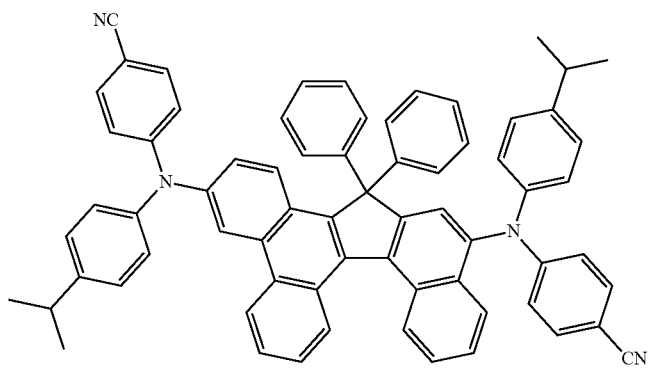
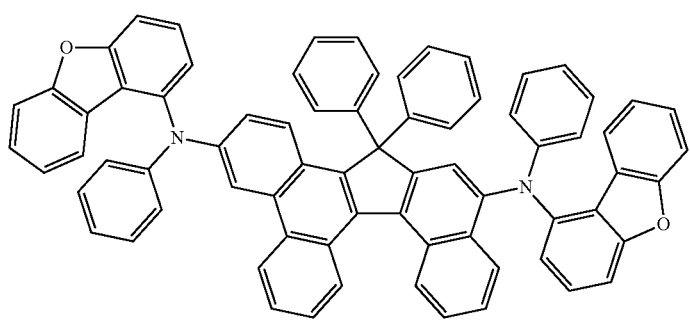

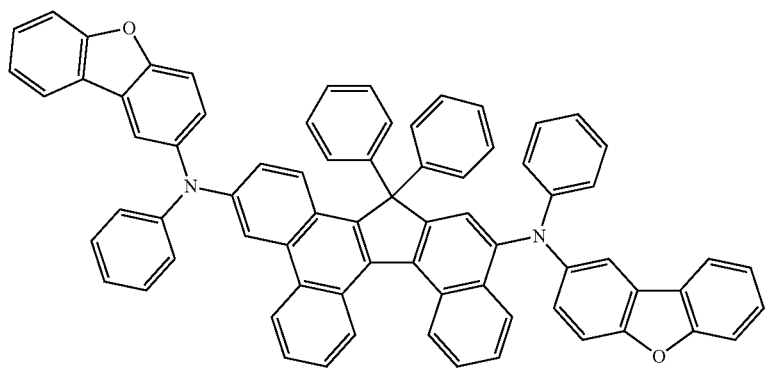
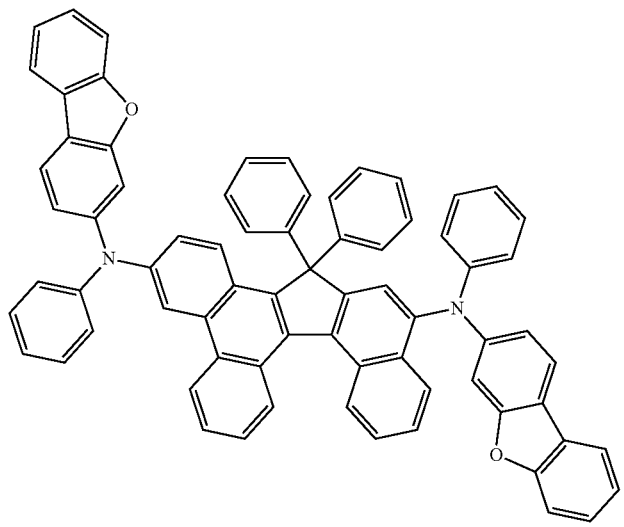
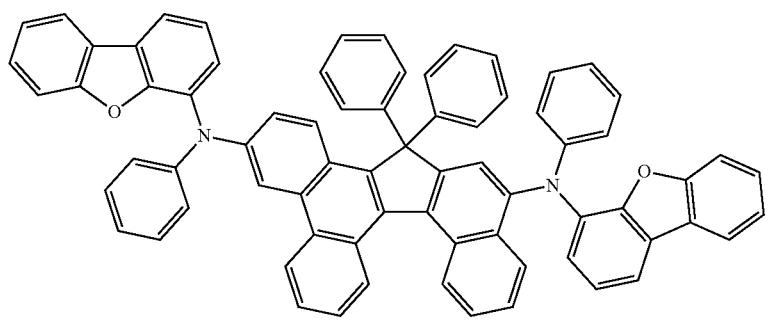
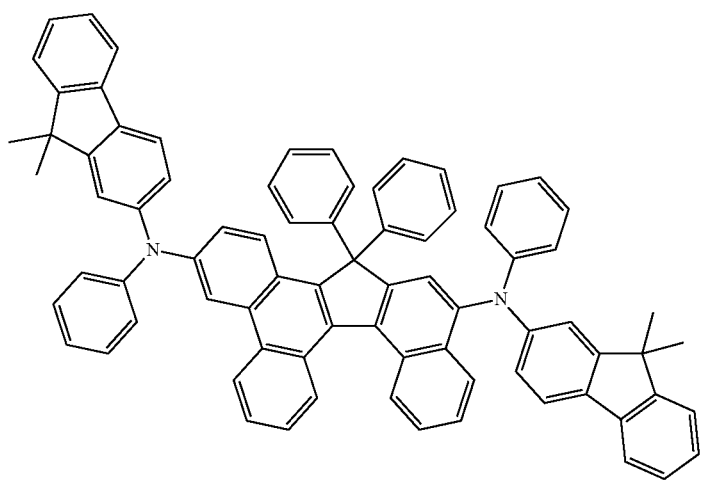

-continued
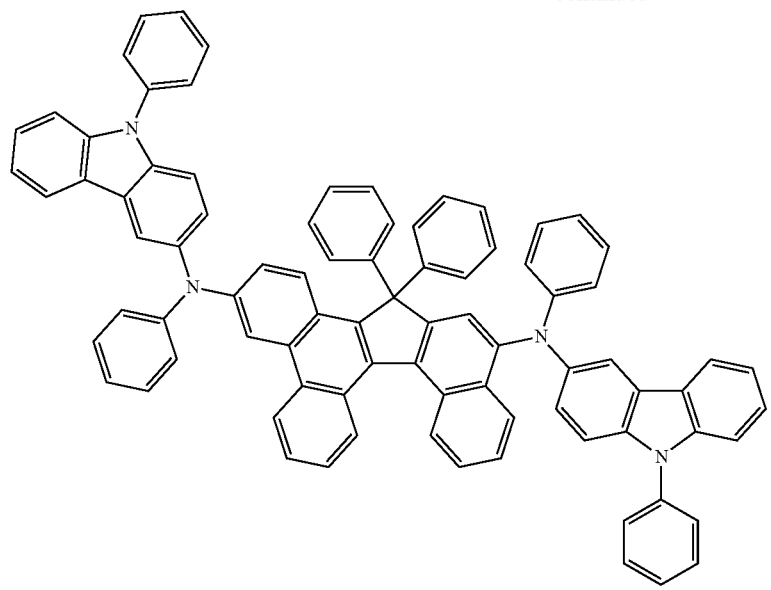
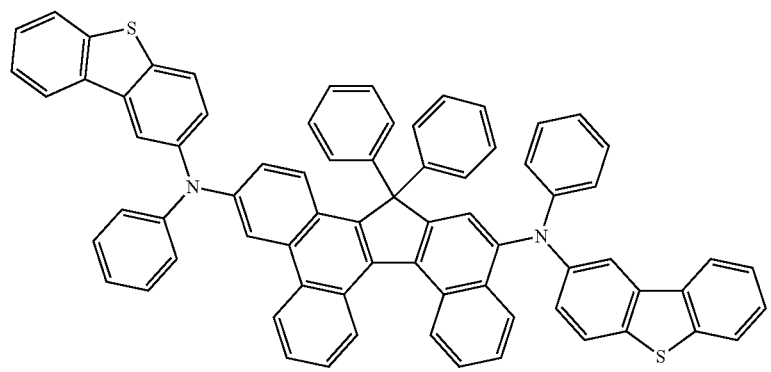
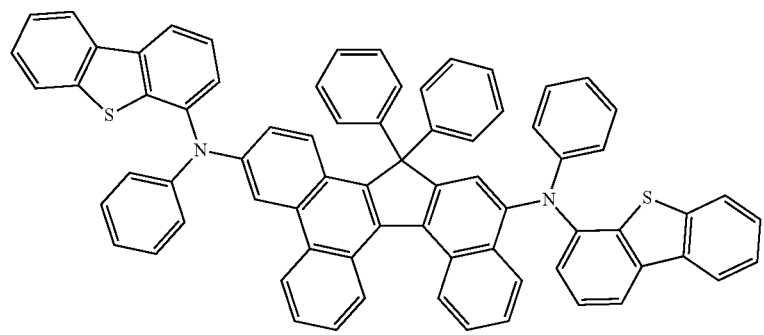
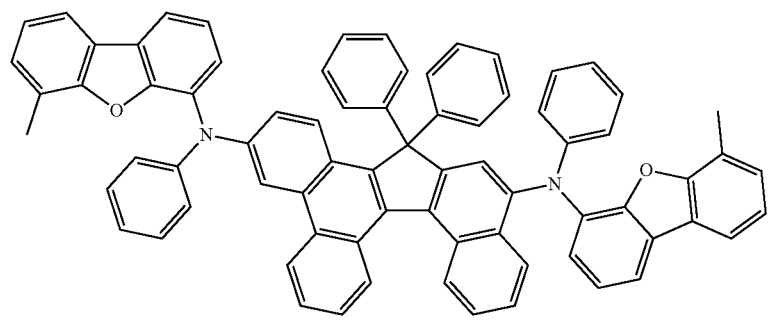

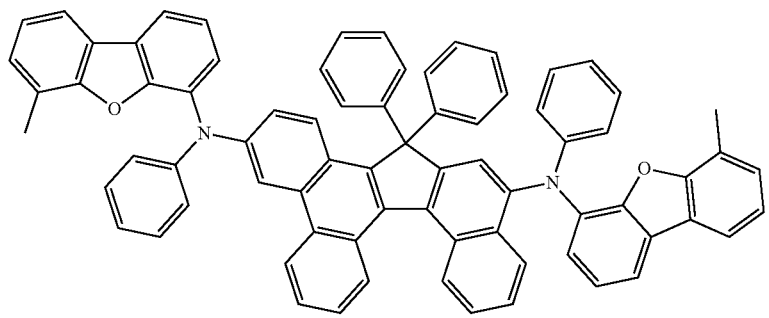
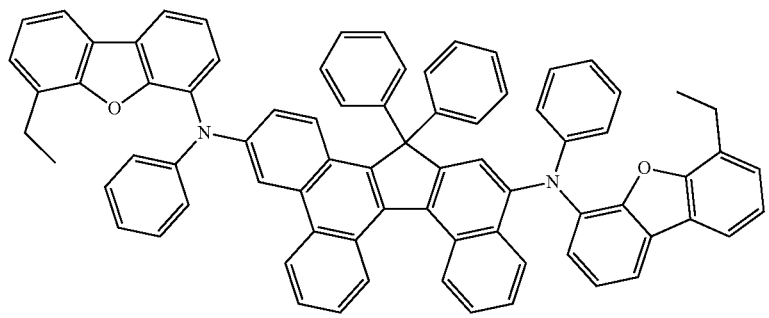
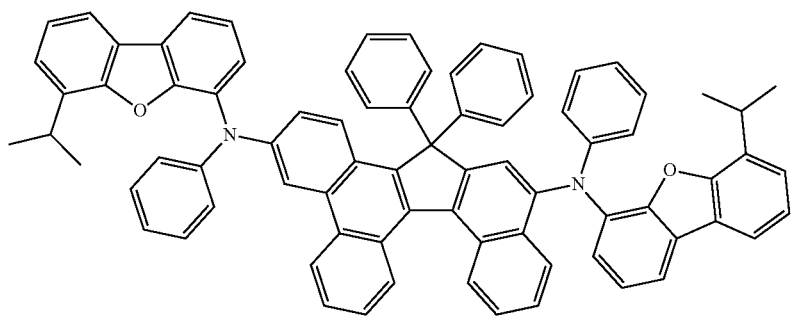
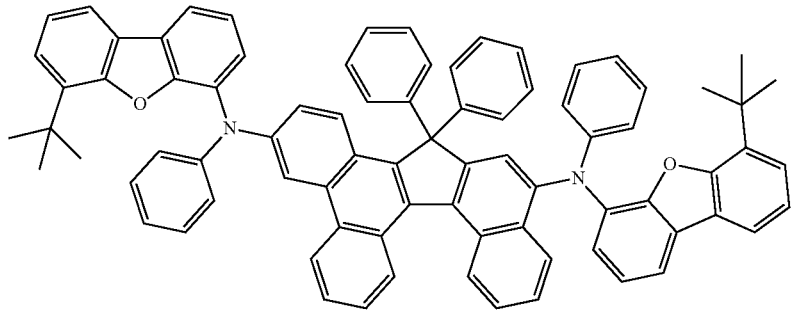
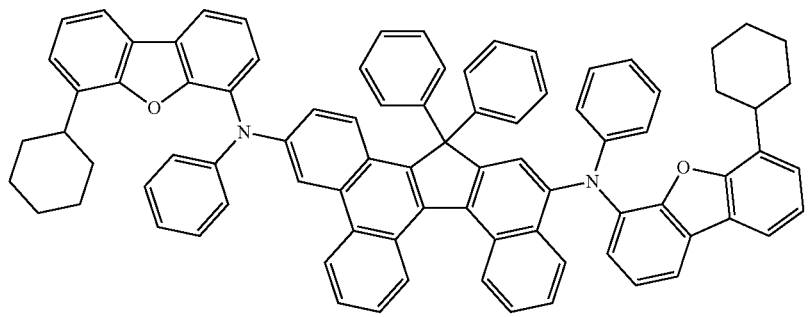

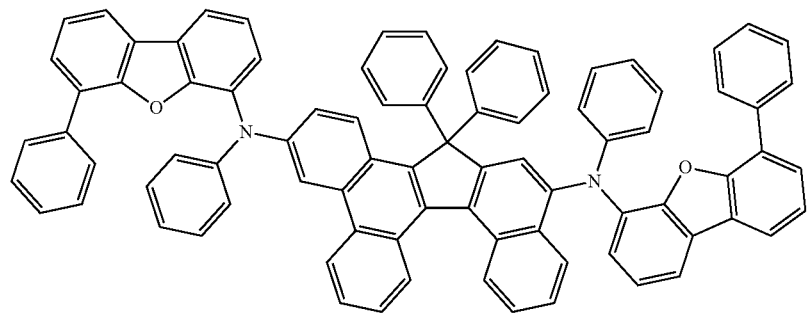
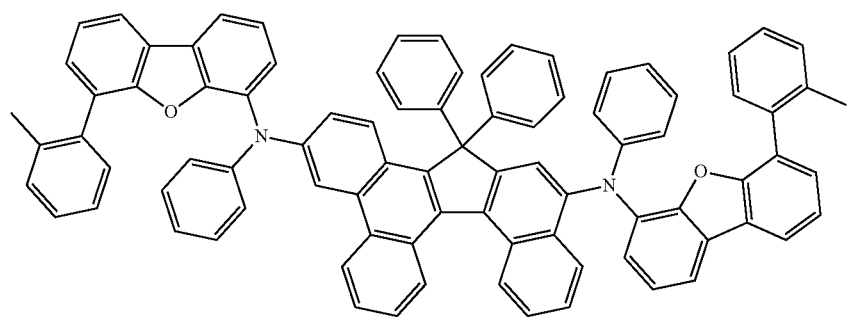
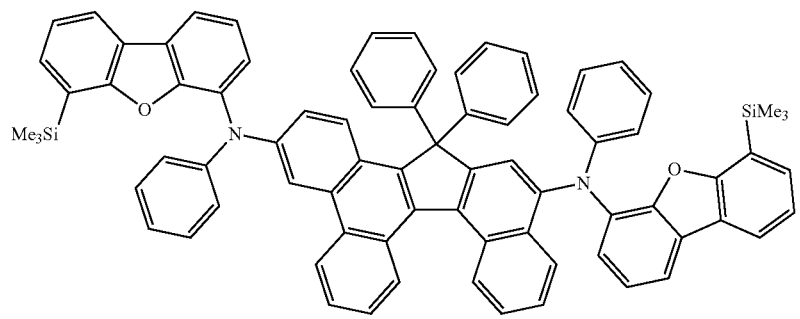
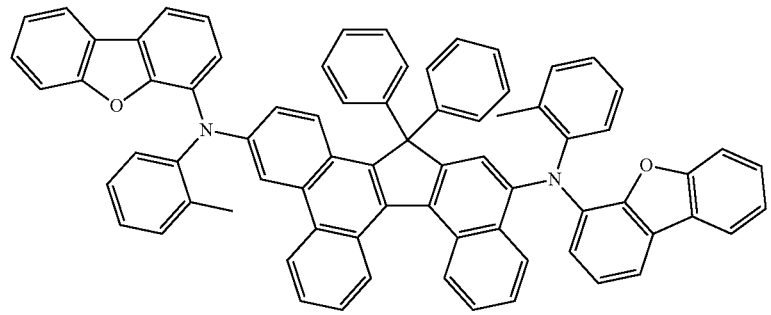
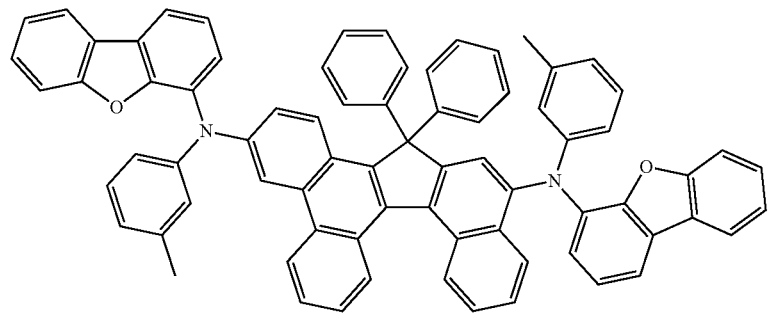

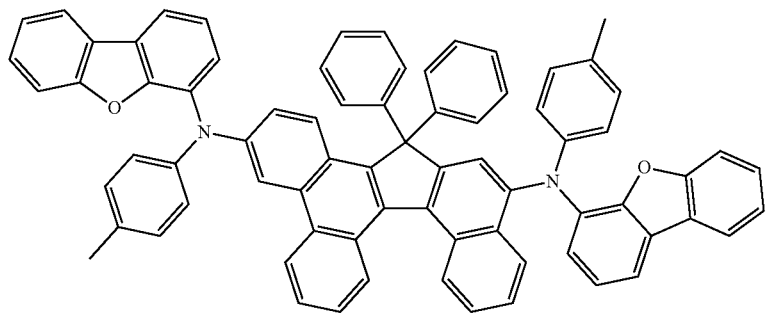
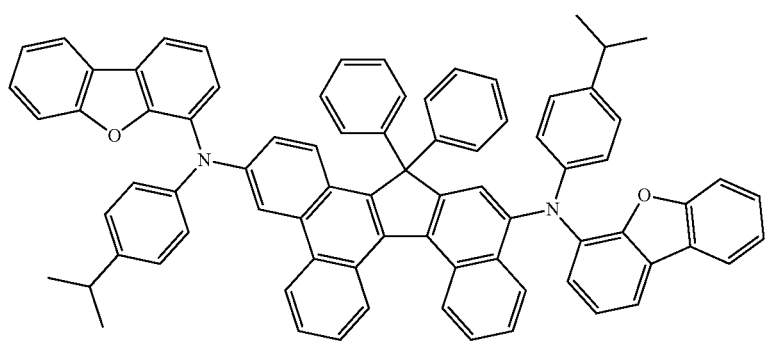
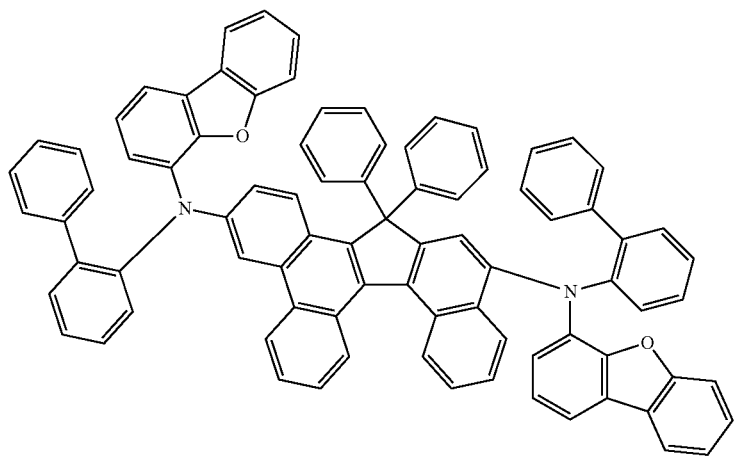
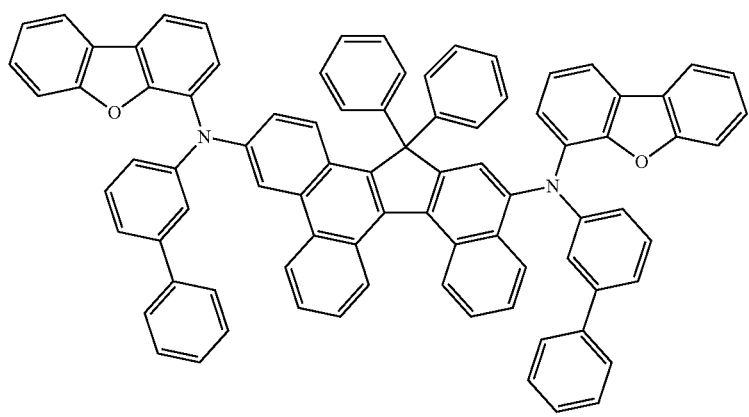

-continued
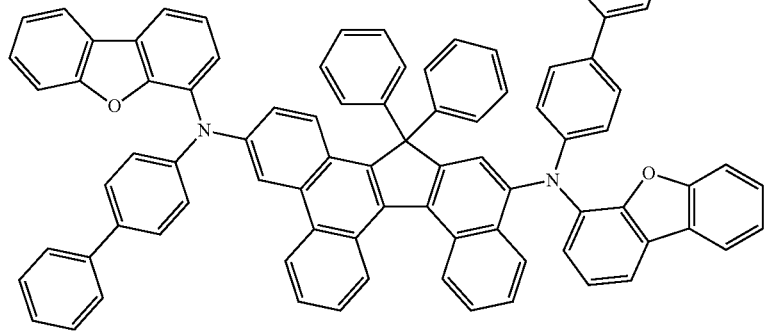
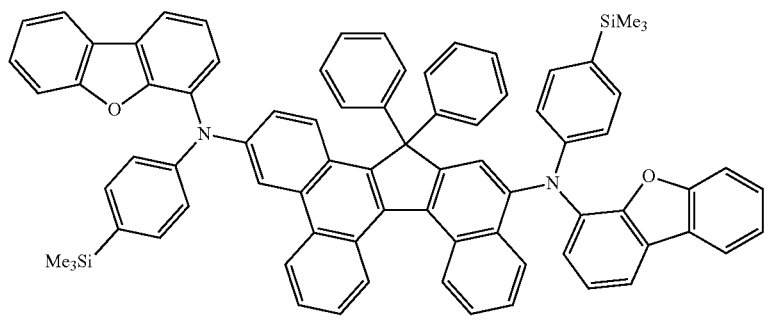
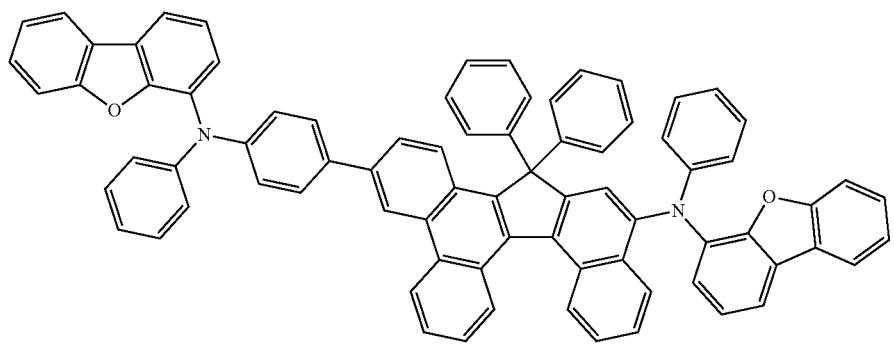
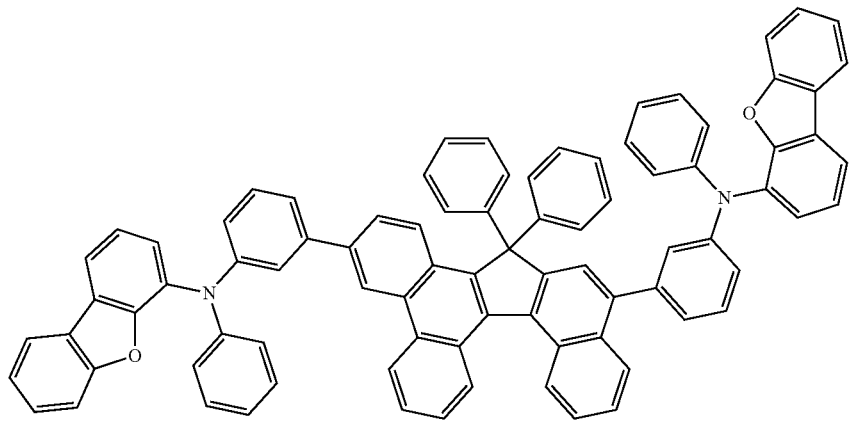

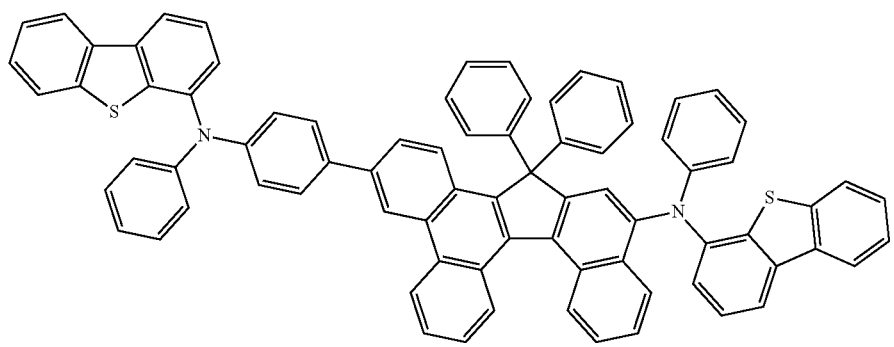
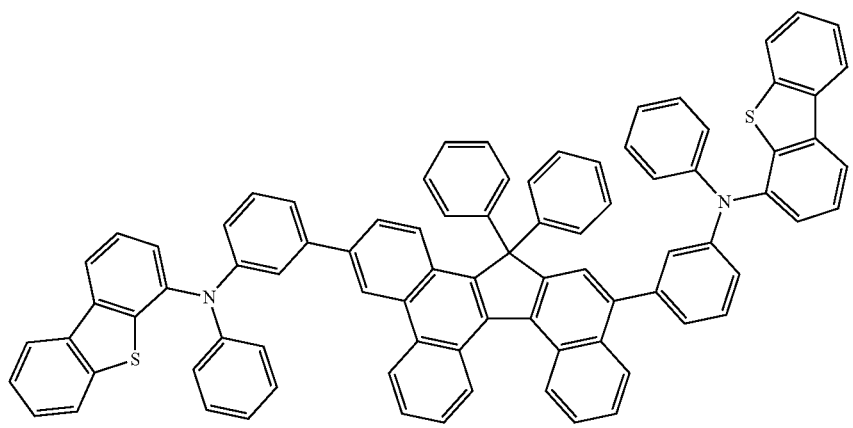
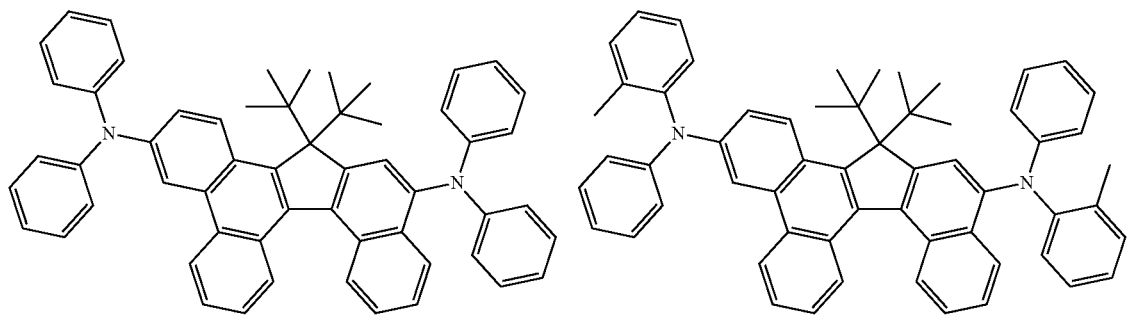
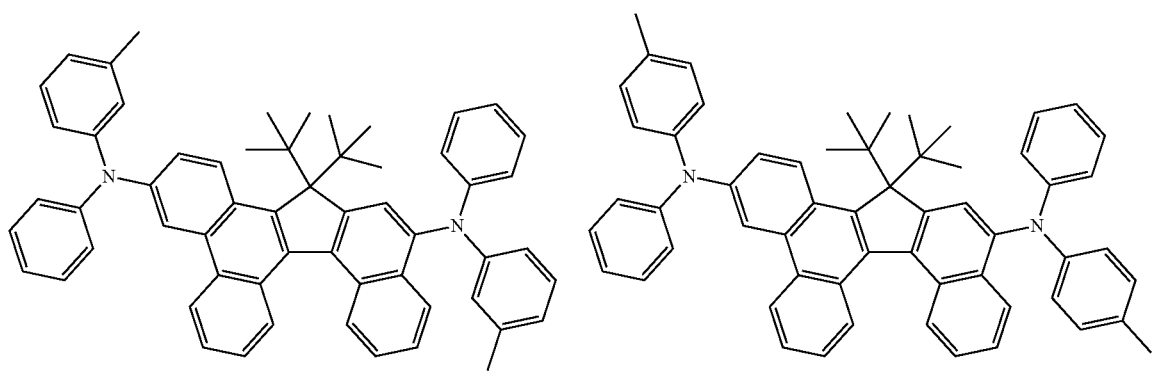

-continued
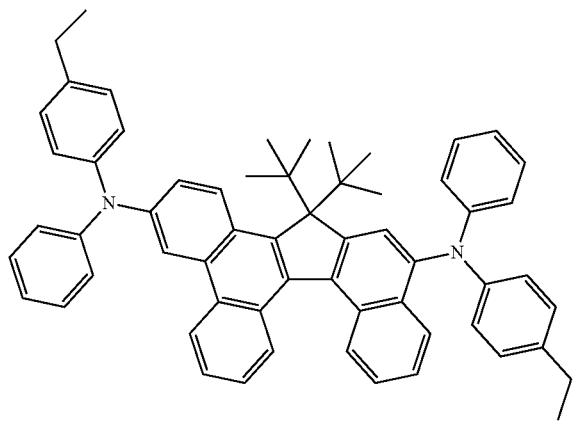
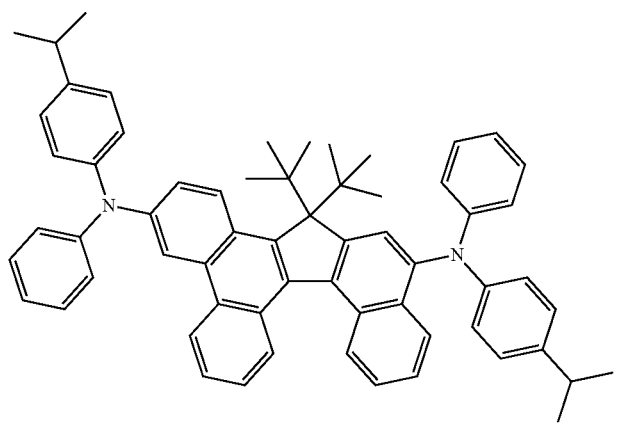
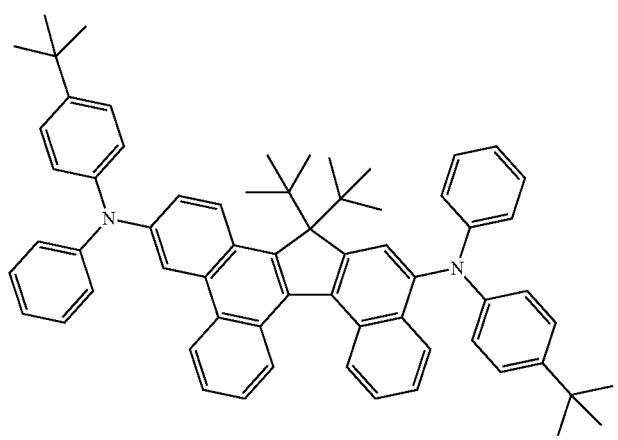

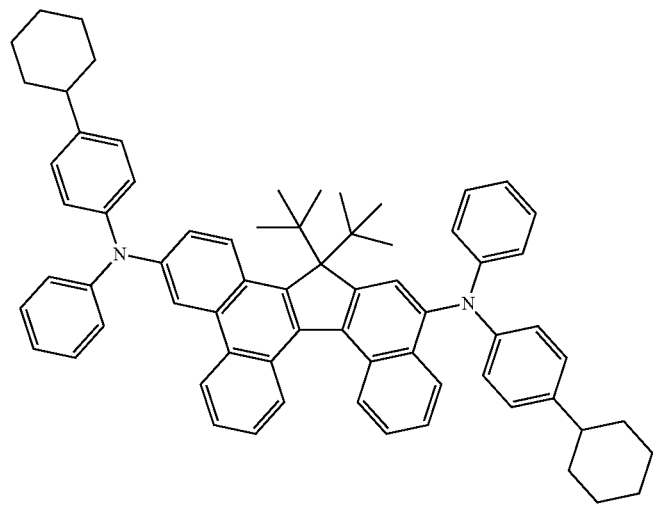
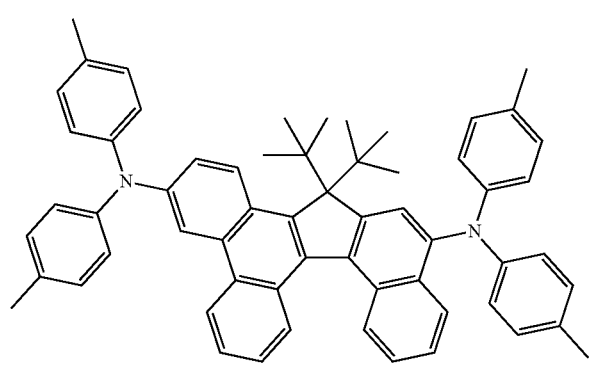
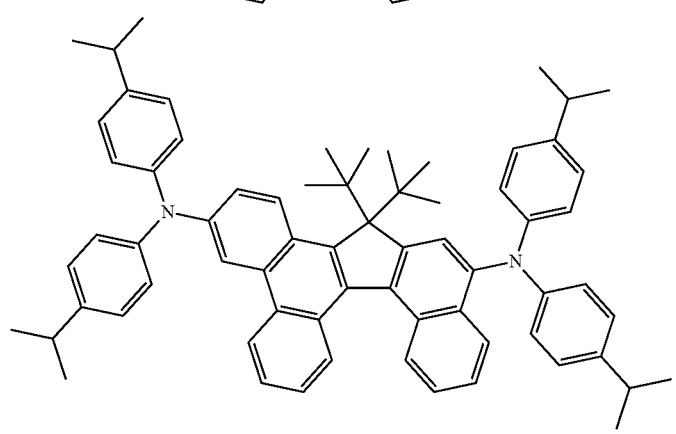
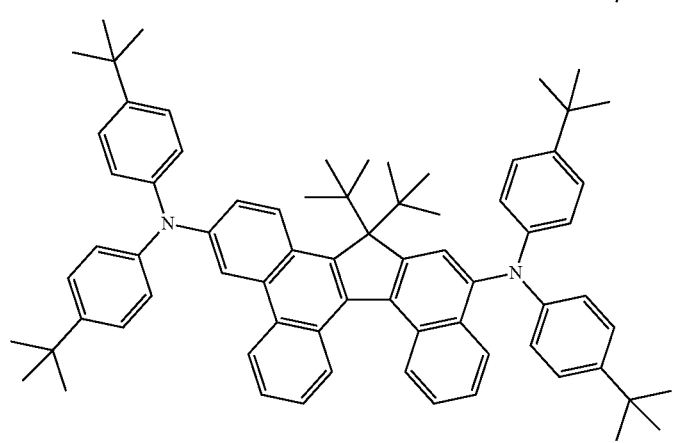

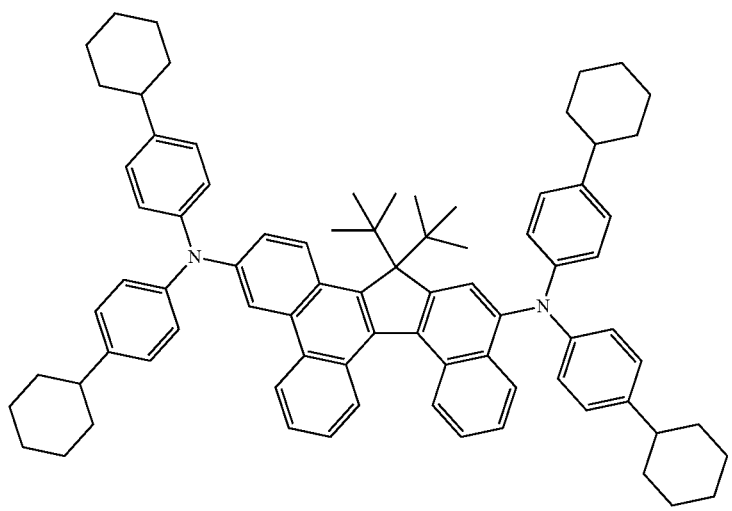
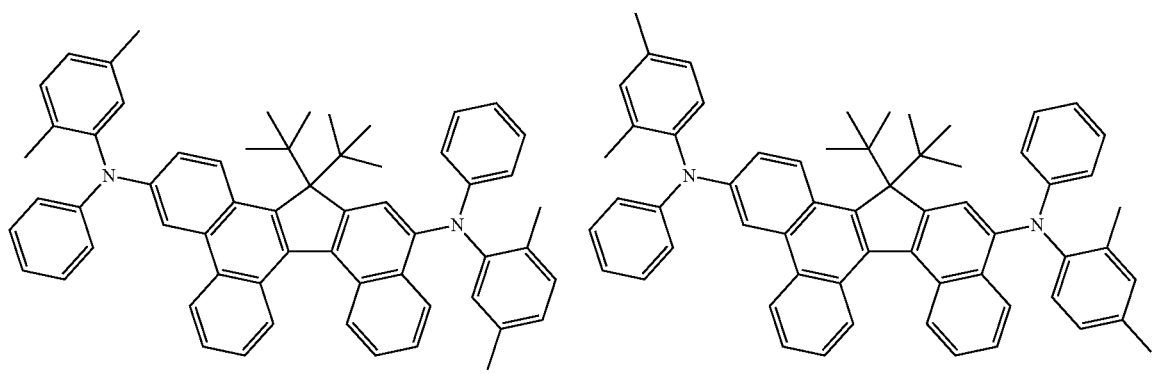

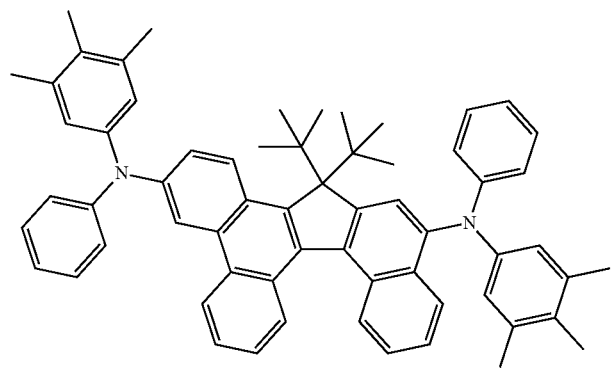
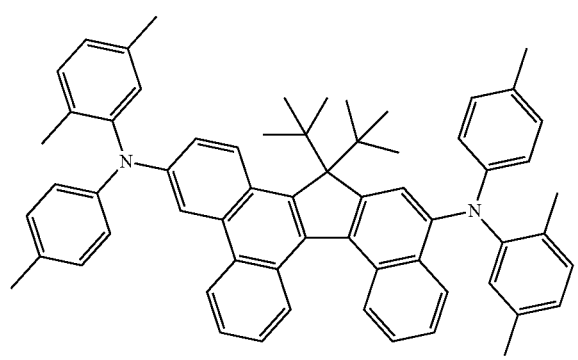
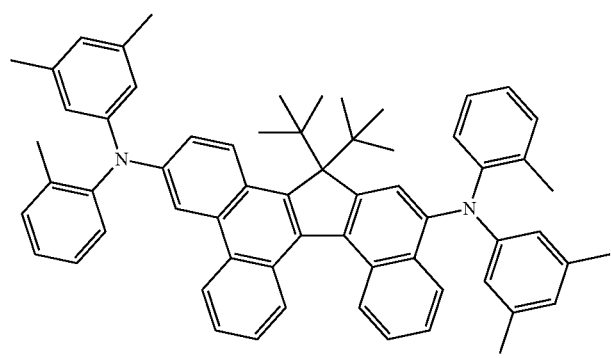
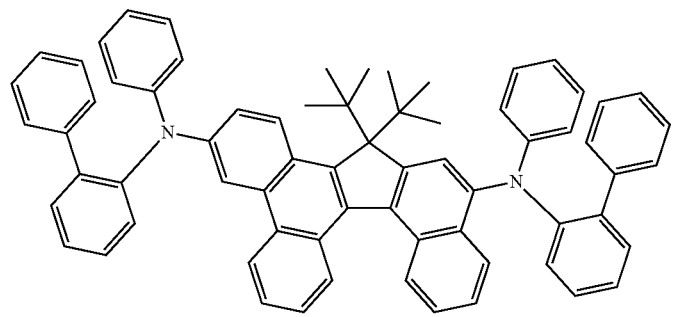

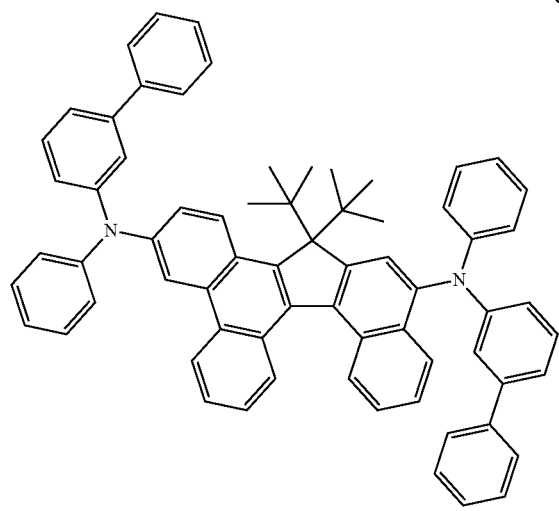
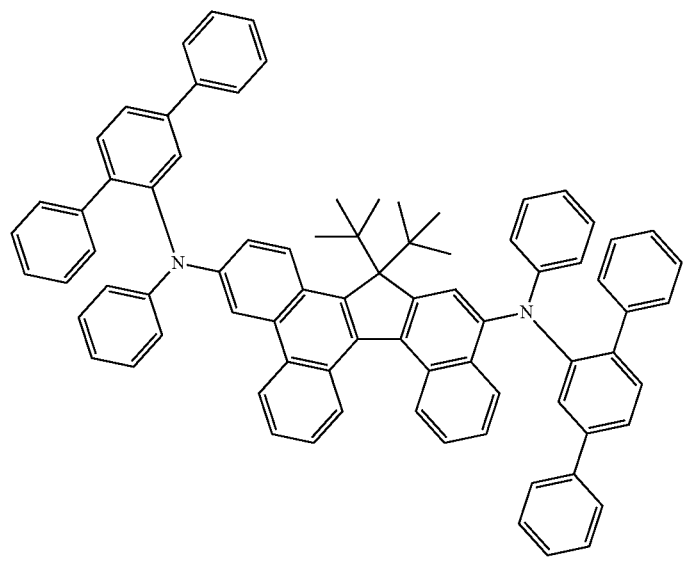
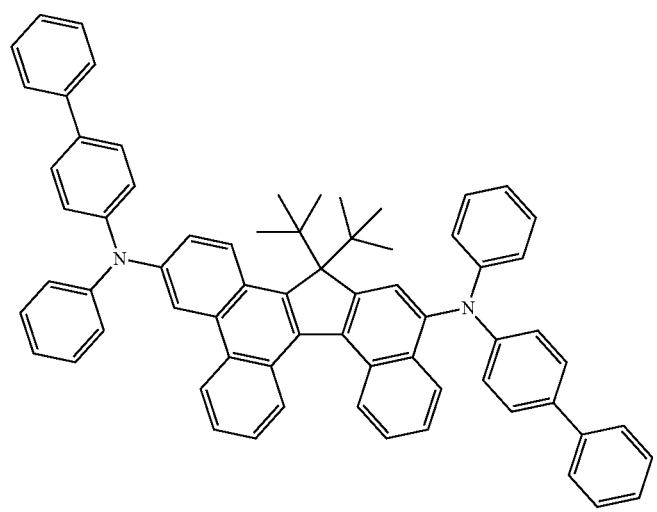

-continued
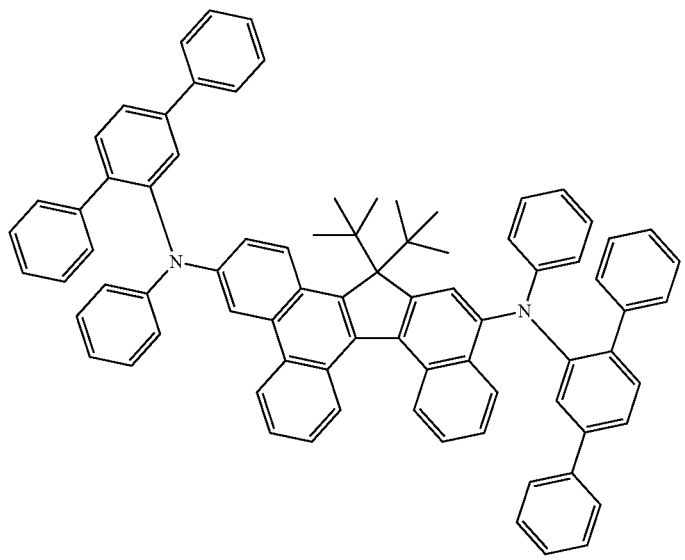
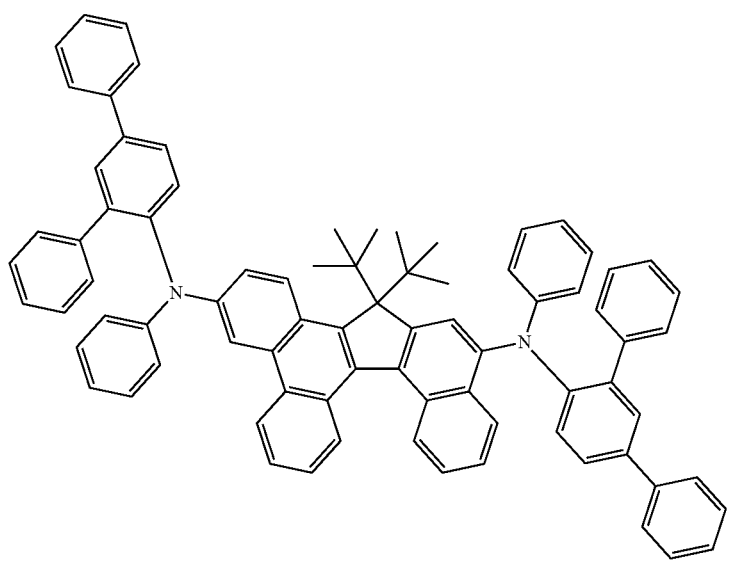
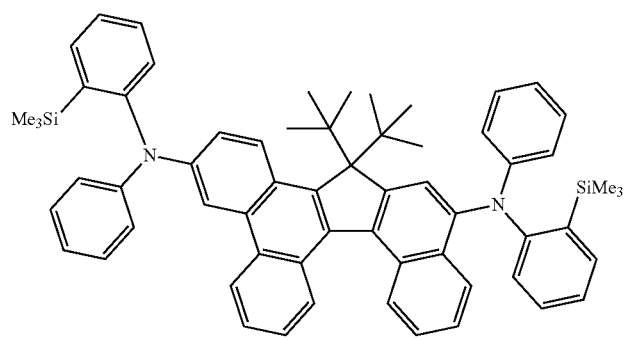

-continued
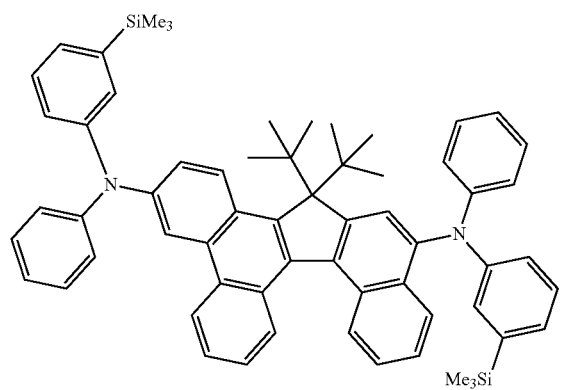
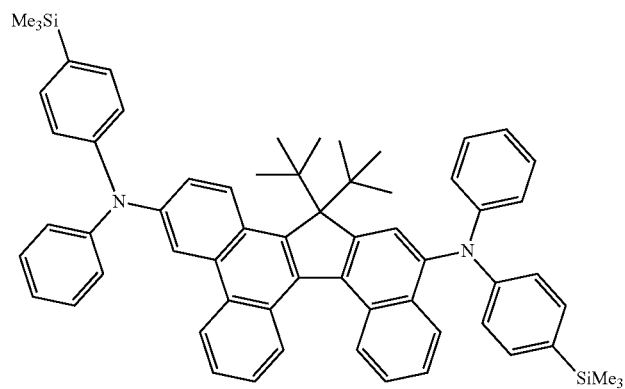
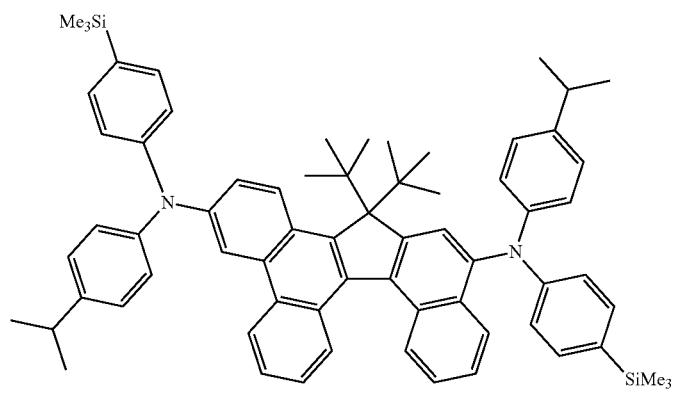
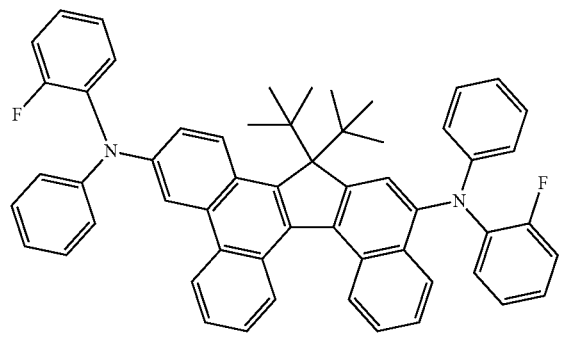

-continued
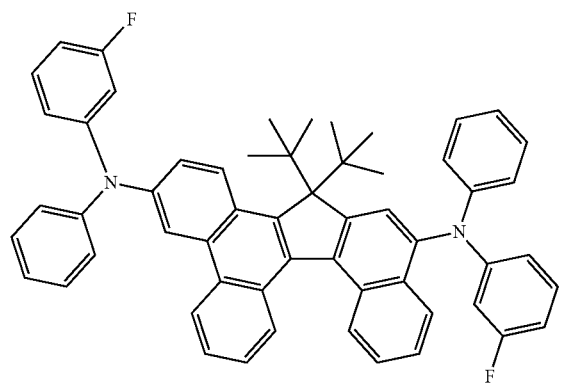
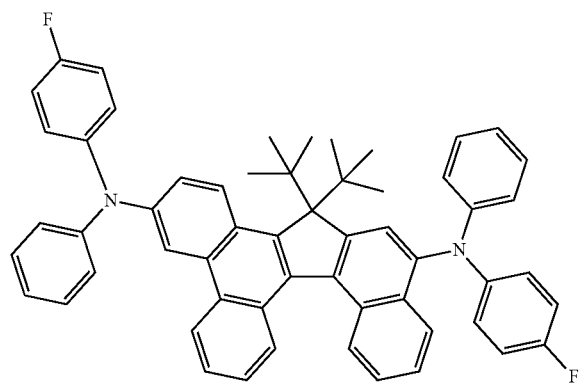
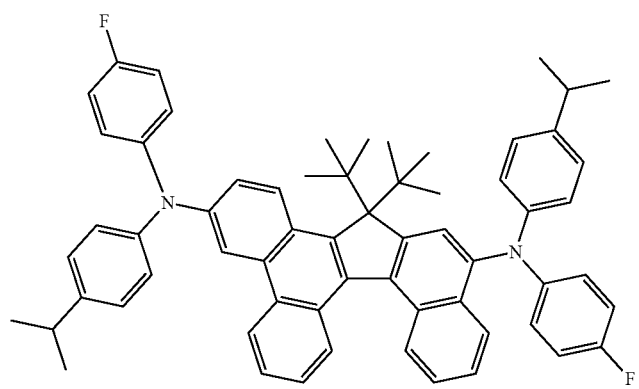
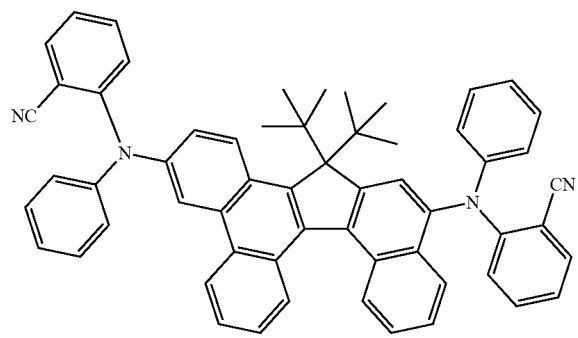

-continued
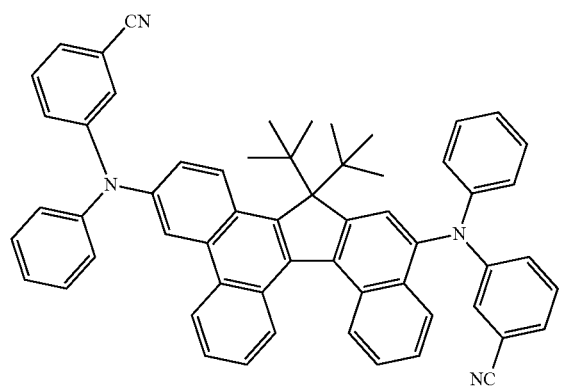
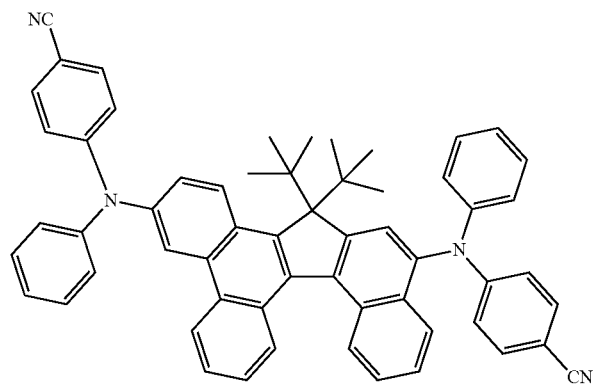
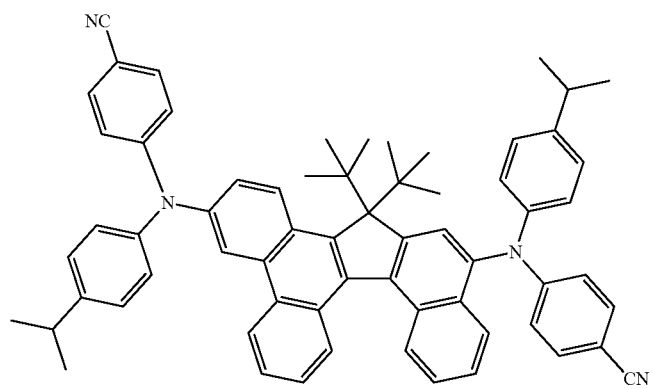
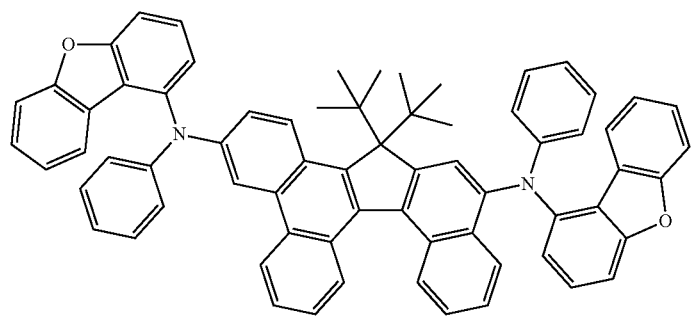

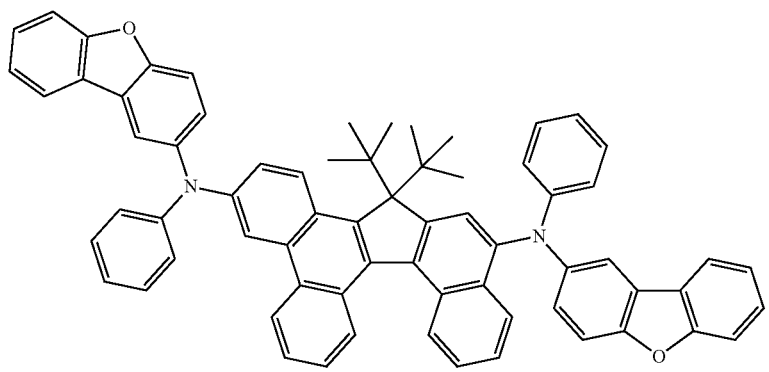
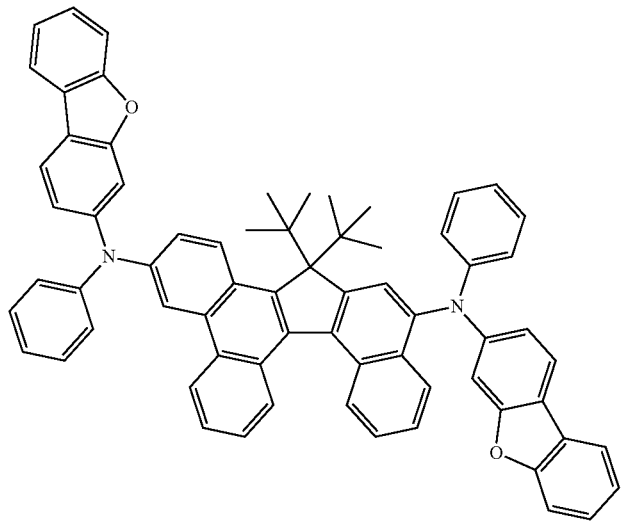
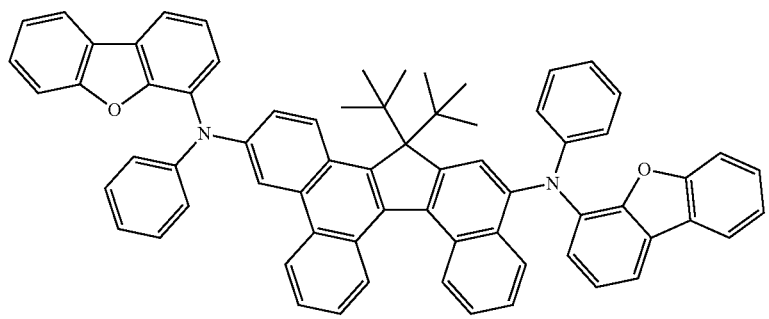 [SMILES: CC(C)(C)C1(C(C)(C)C)c2cc(N(c3ccccc3)c3cccc4c3sc3ccccc34)c3ccccc3c2-c2c1c1ccc(N(c3ccccc3)c3cccc4c3sc3ccccc34)cc1c1ccccc21]
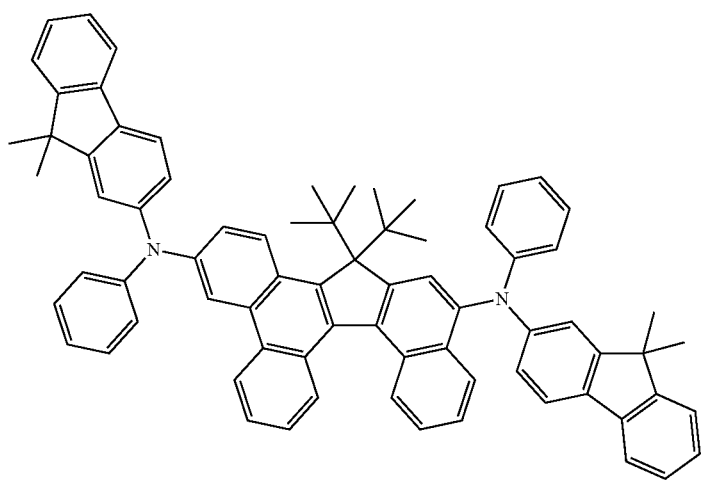

-continued
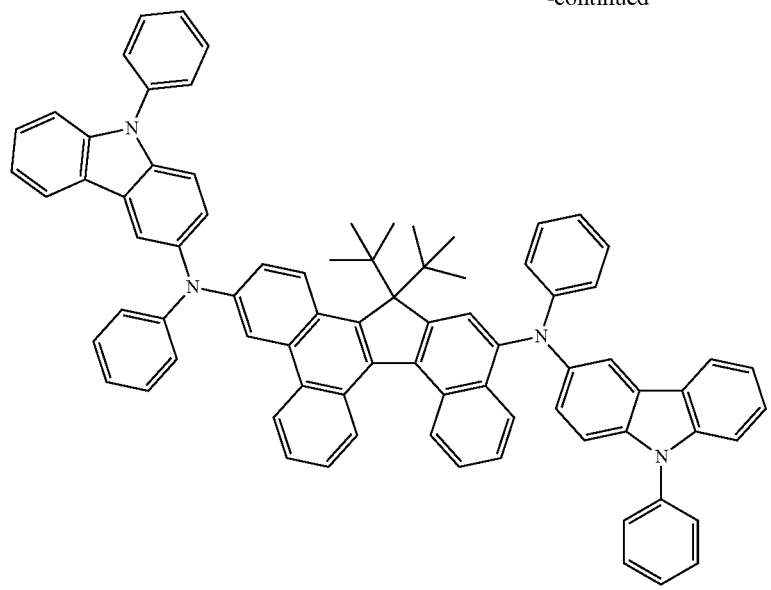
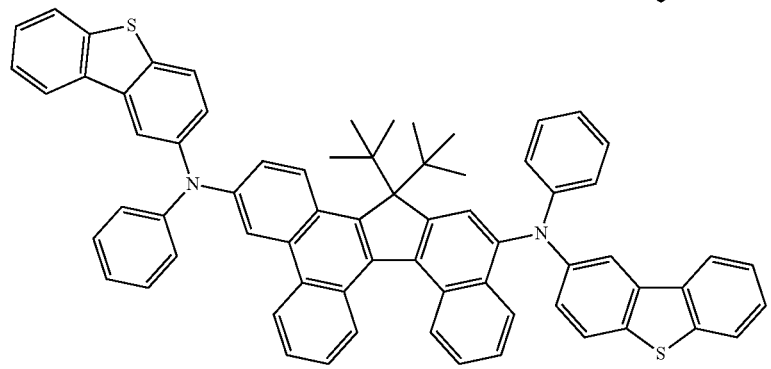
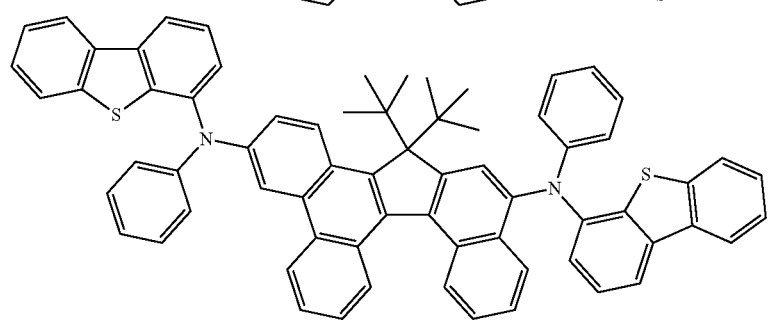
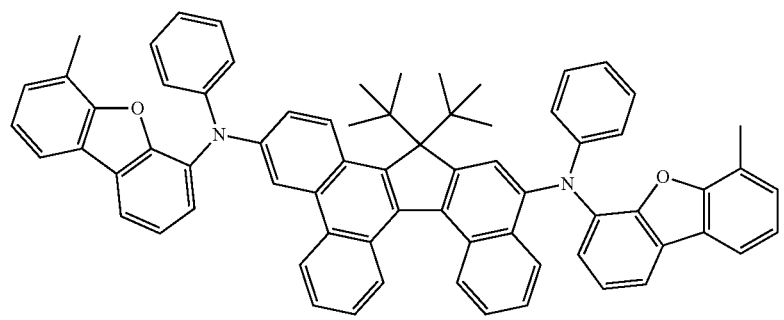

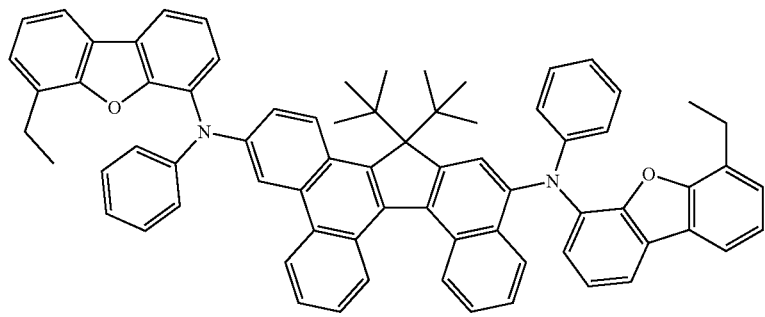
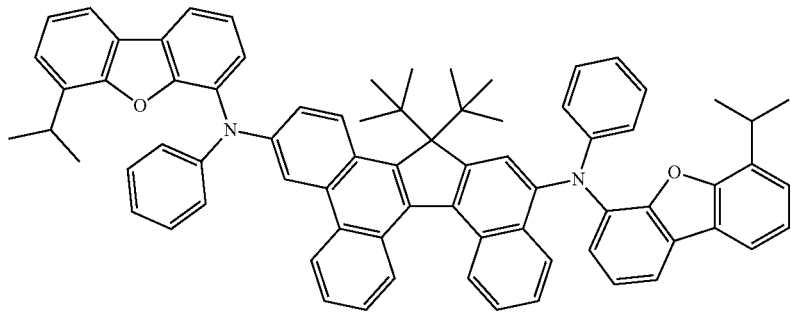
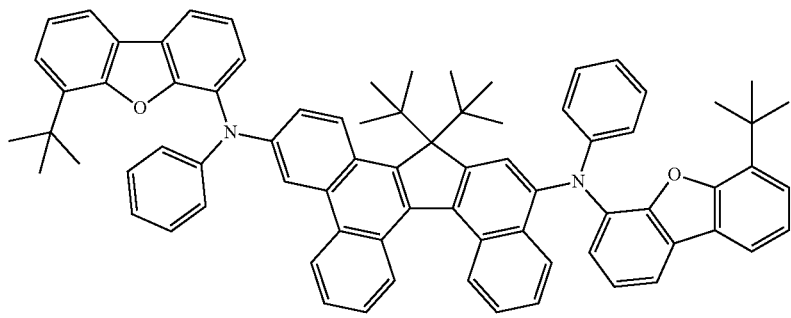
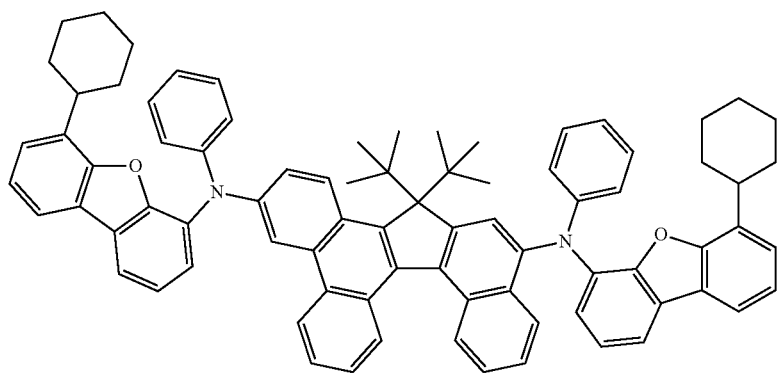
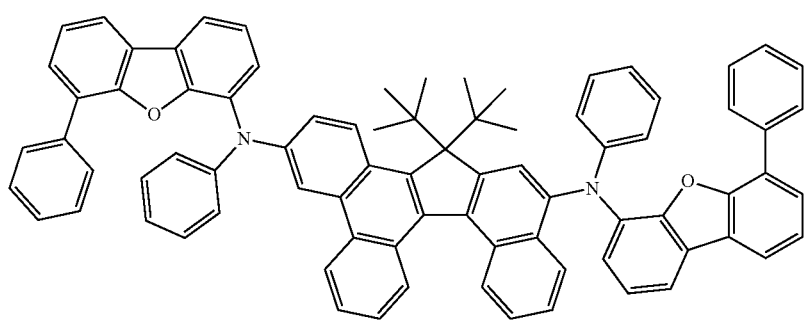

-continued
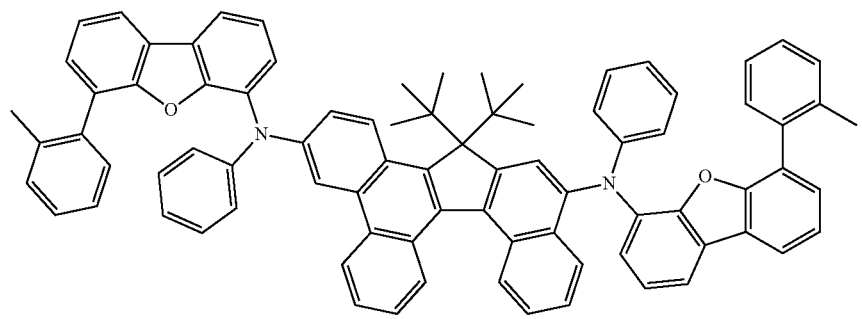
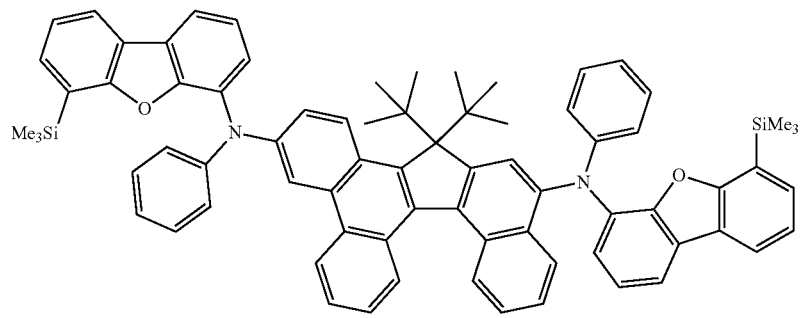
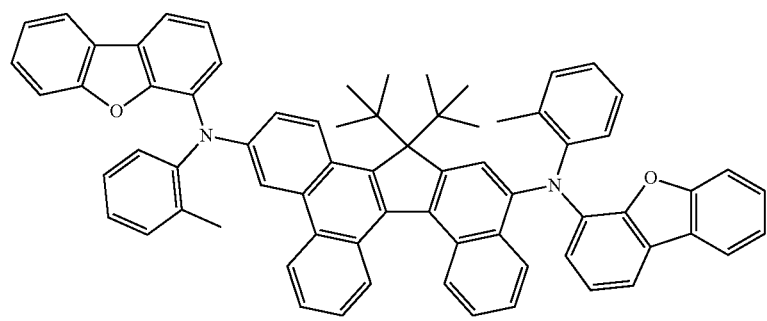
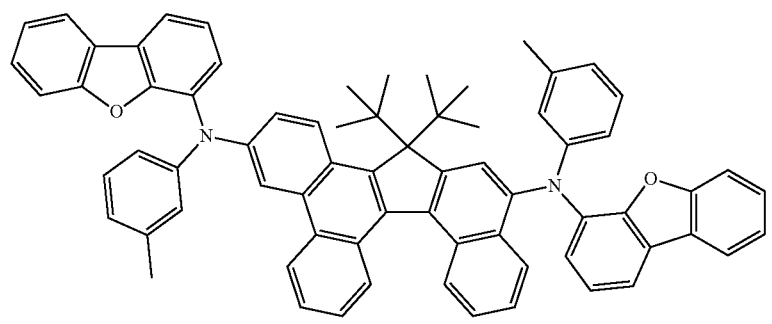
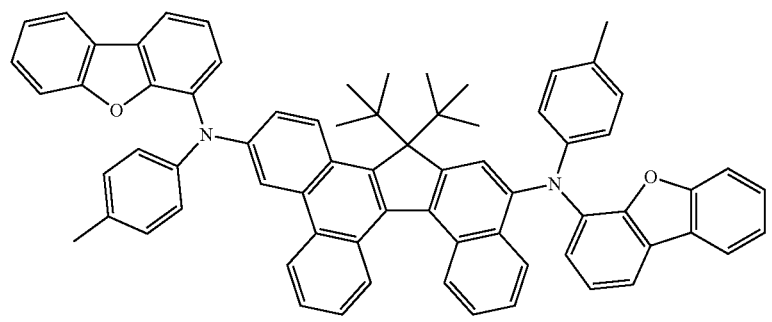

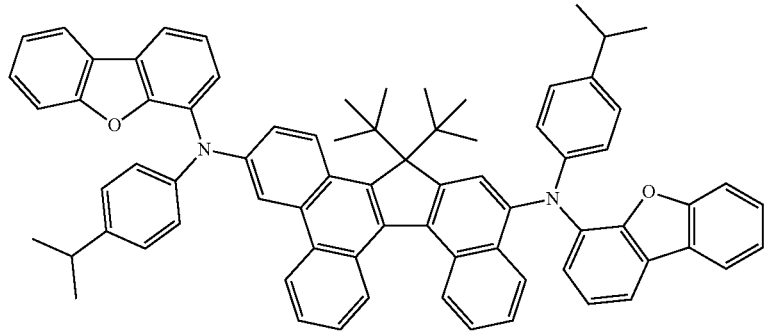
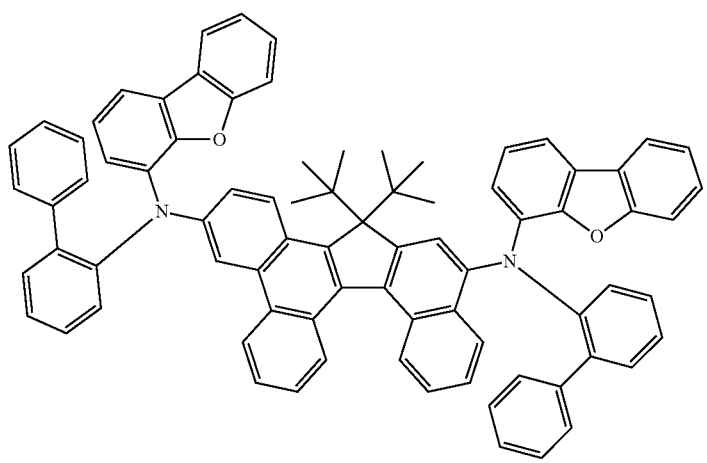
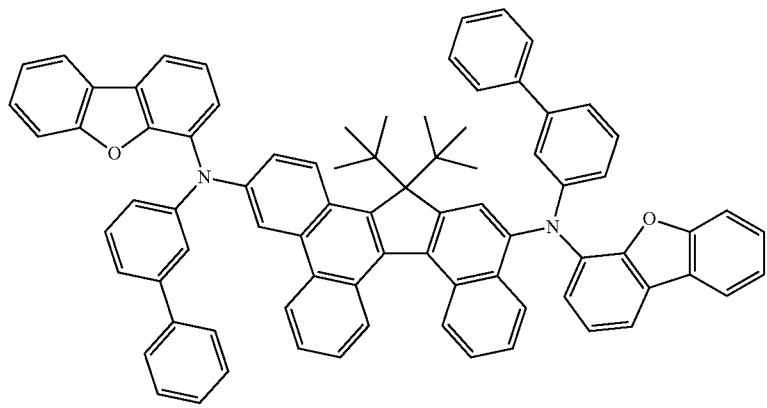
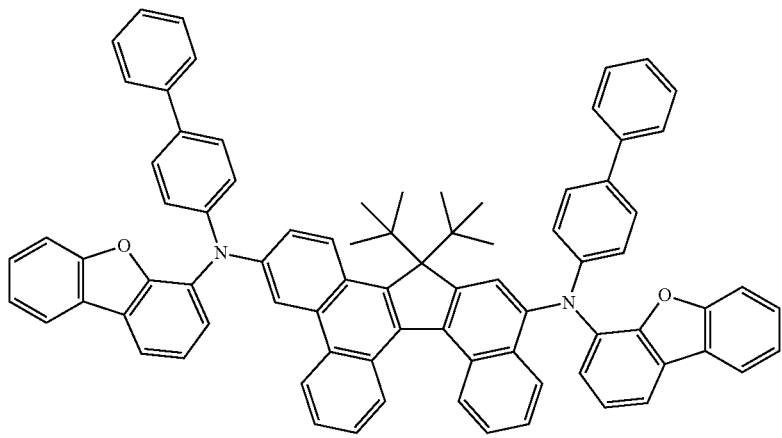

-continued
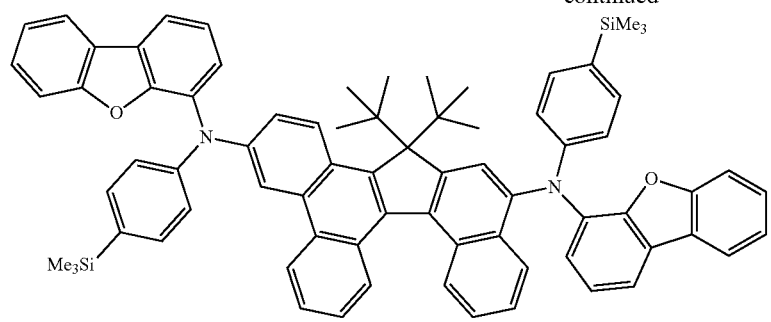
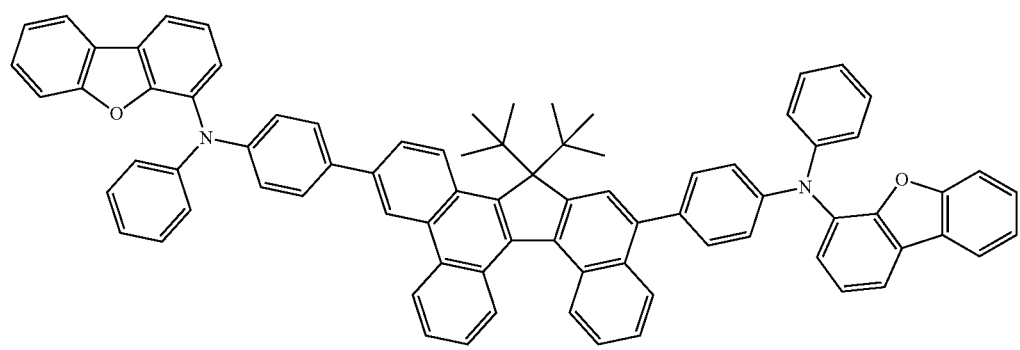
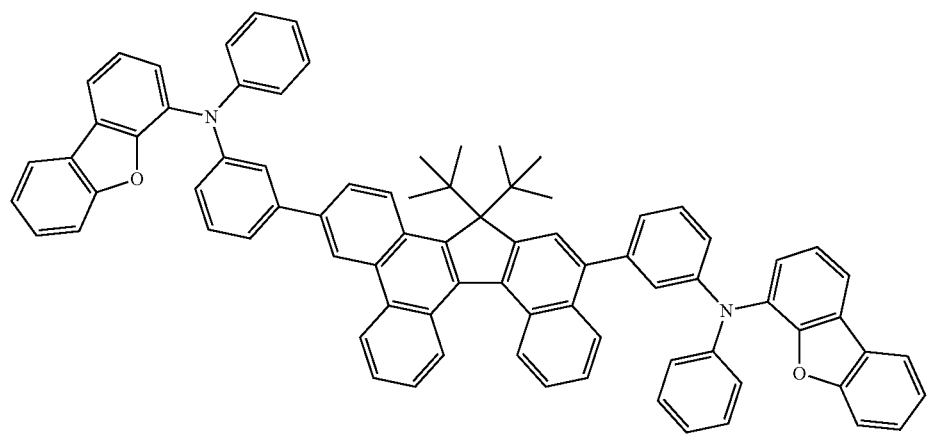
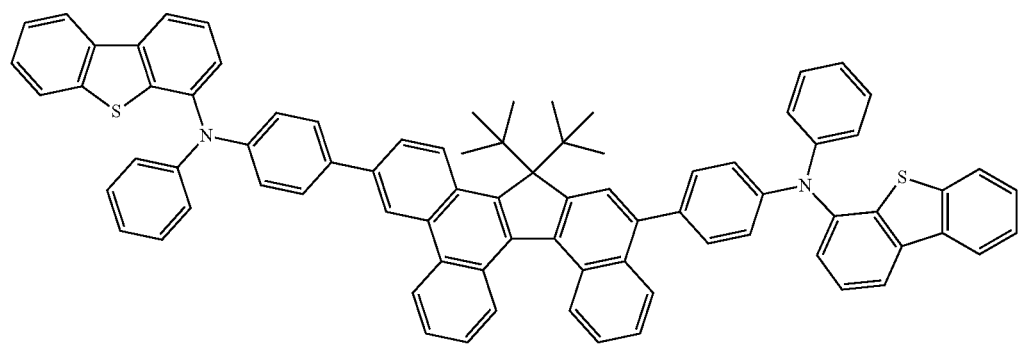

-continued
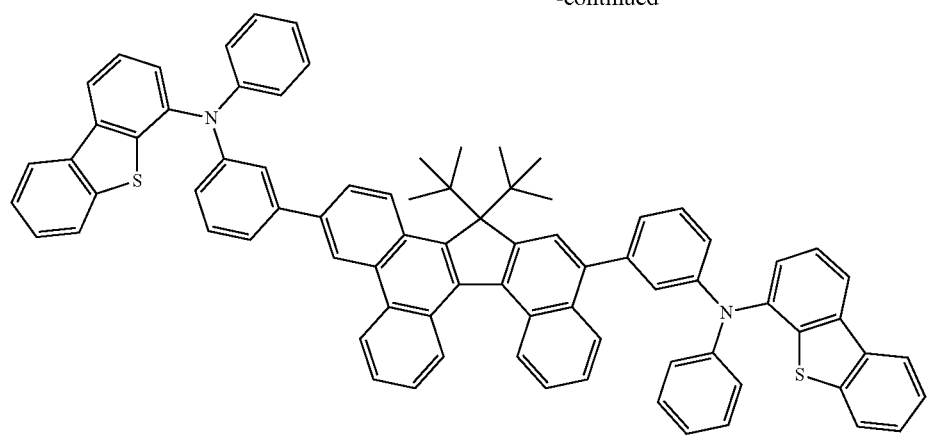
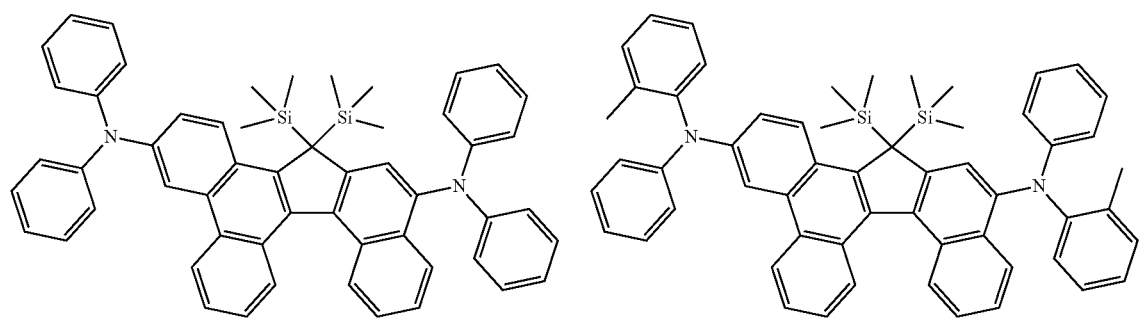
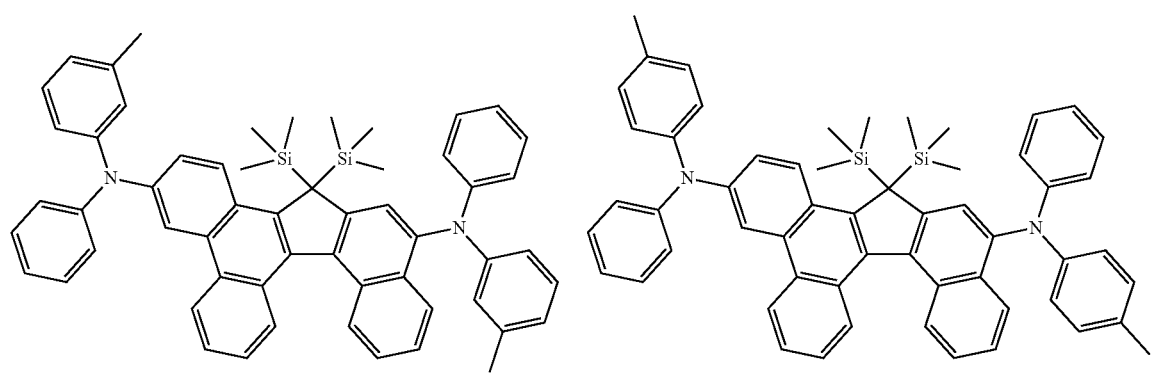
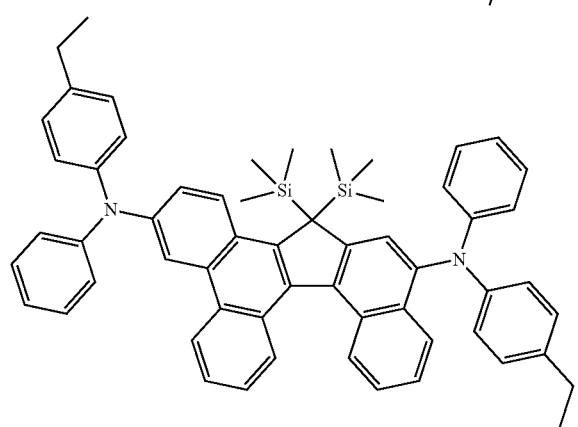

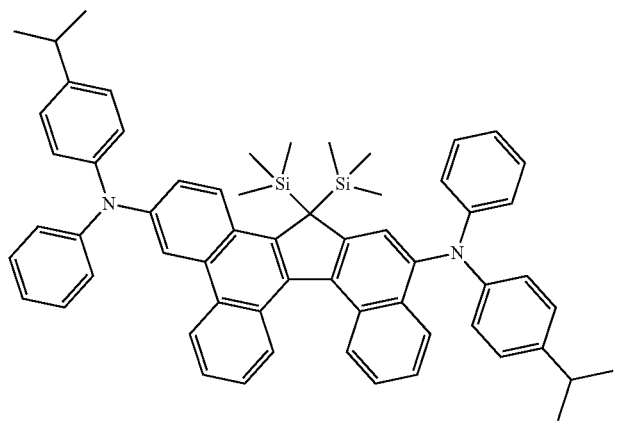
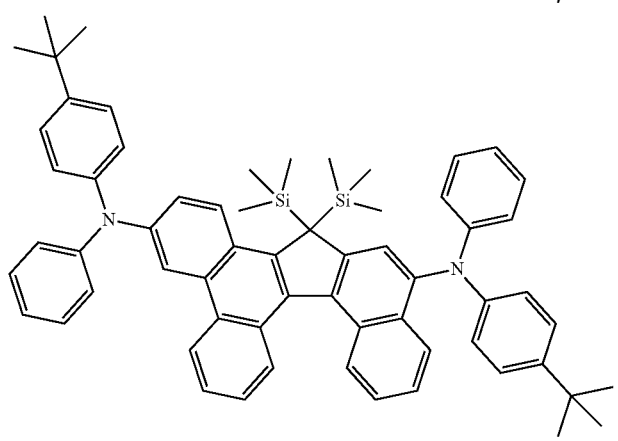
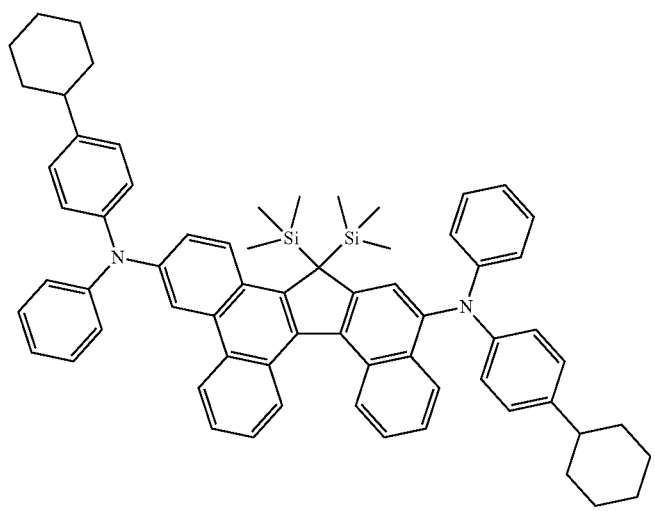
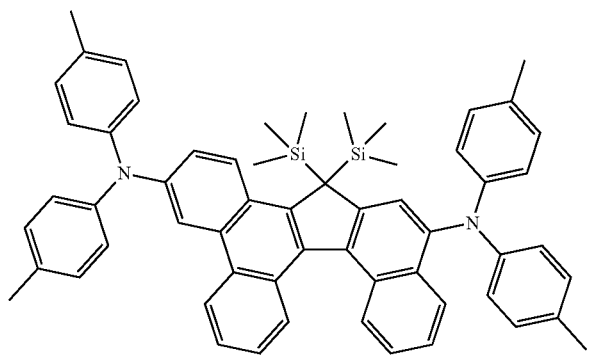

-continued
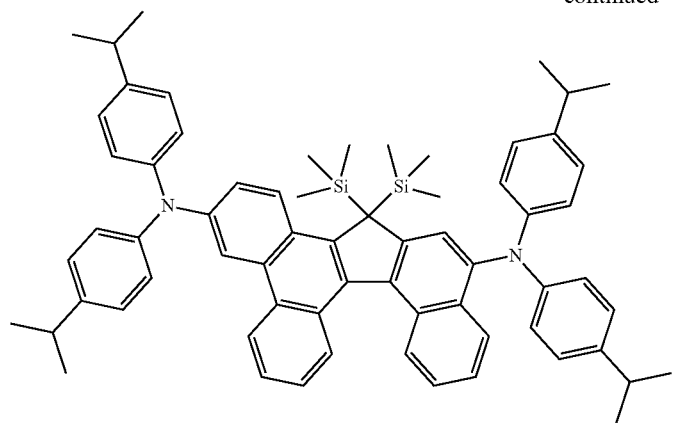
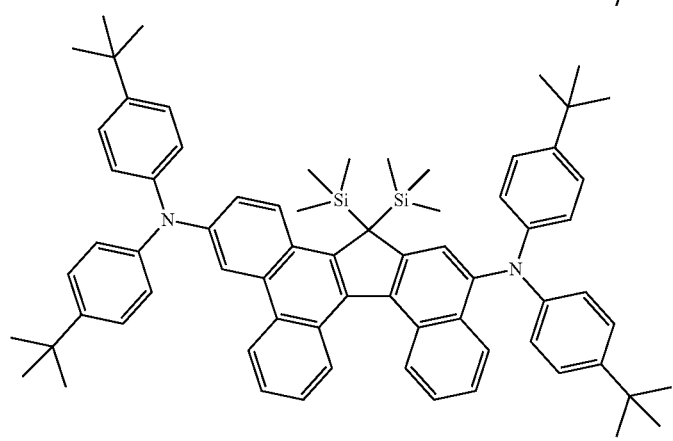
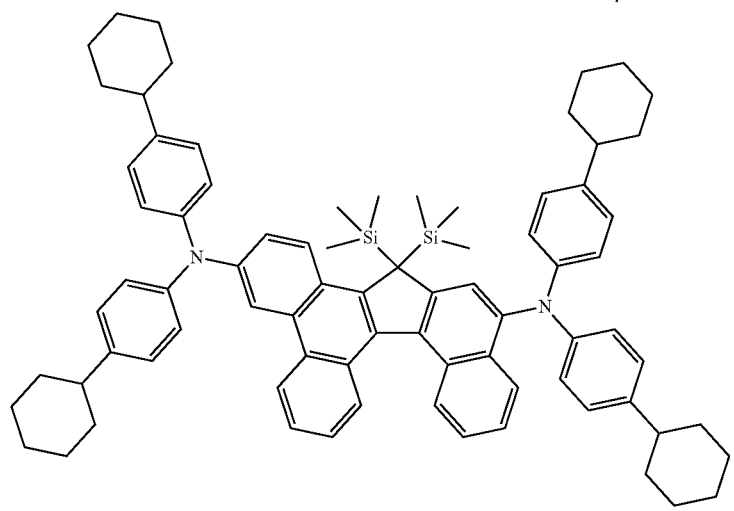
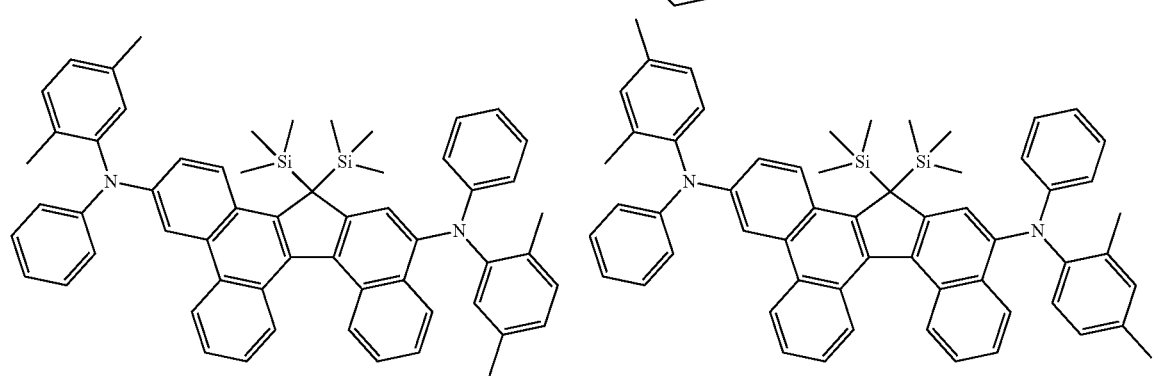

-continued
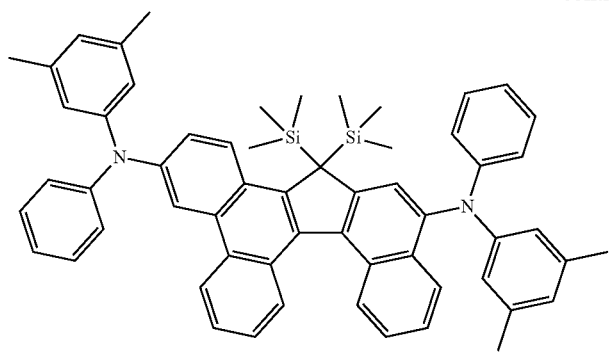
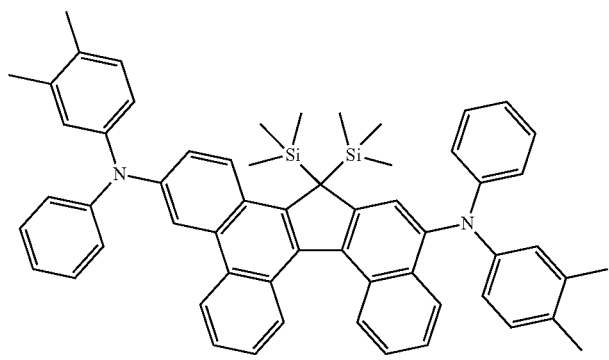
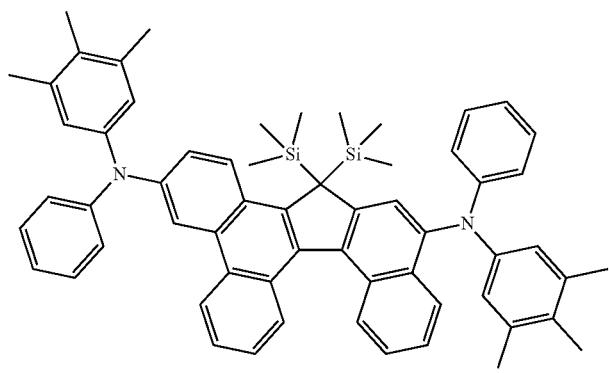
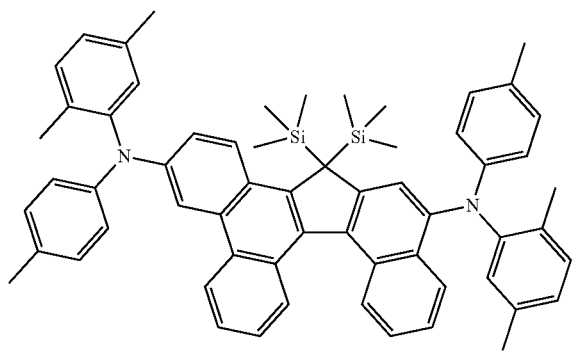

-continued
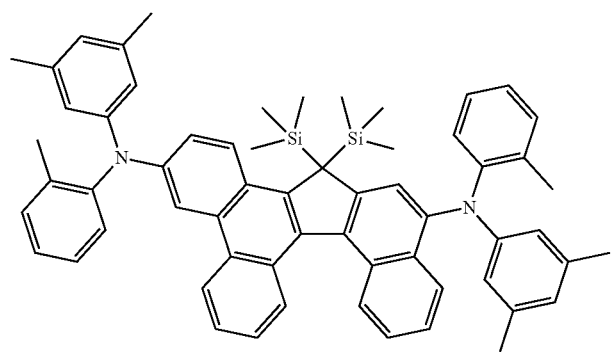
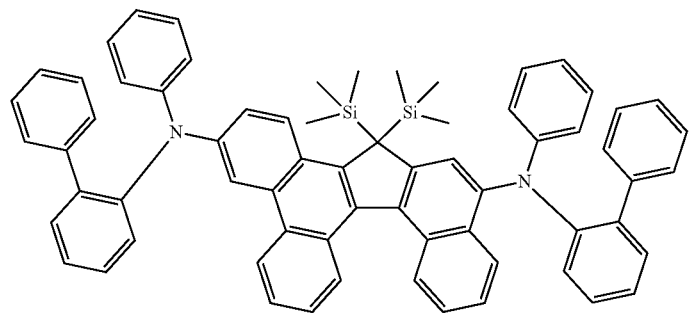
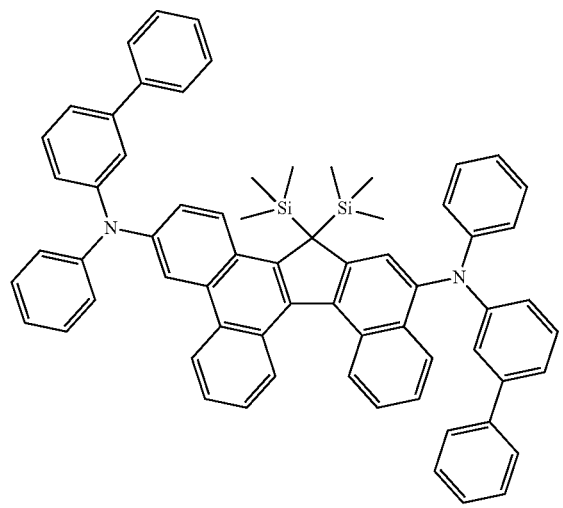
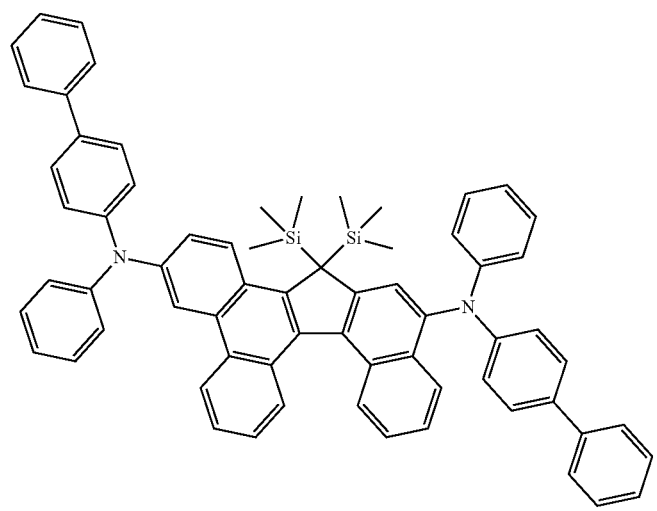

-continued
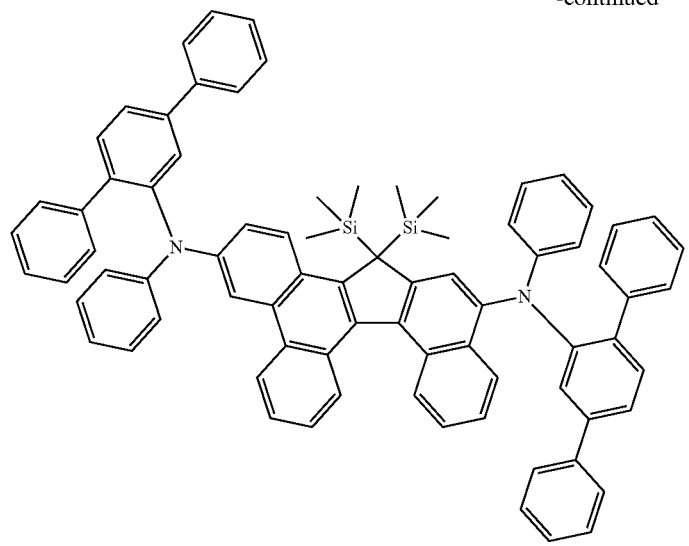
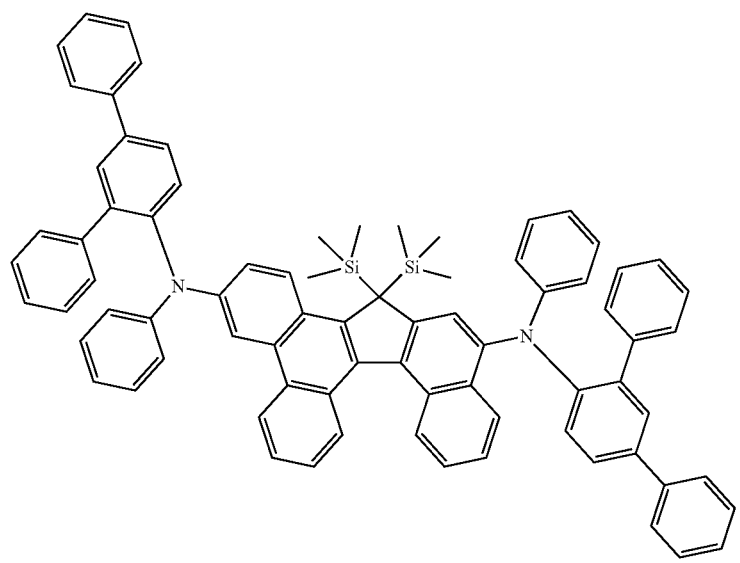
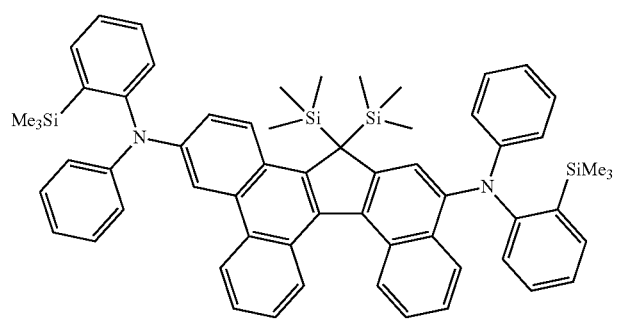

-continued
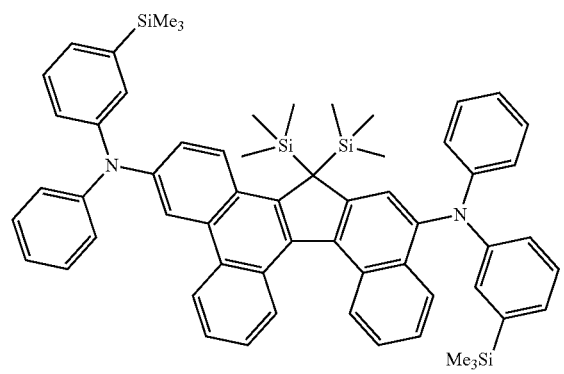
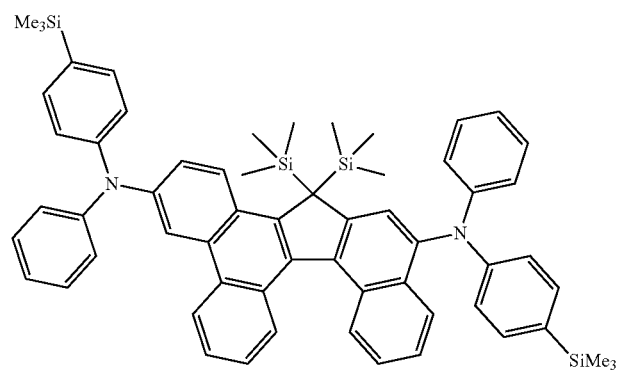
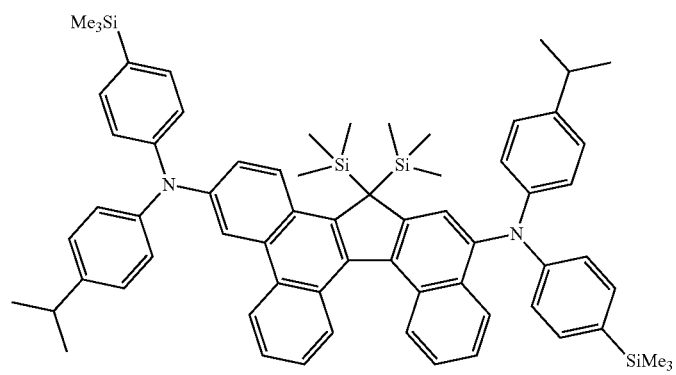
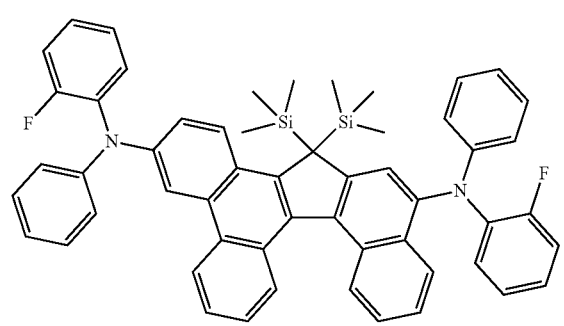

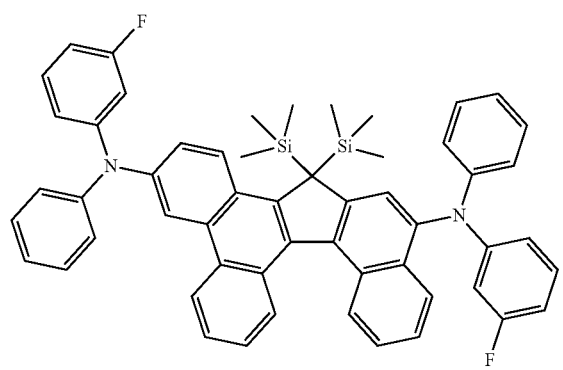
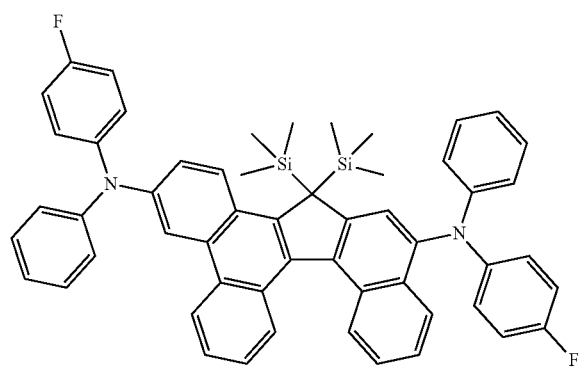
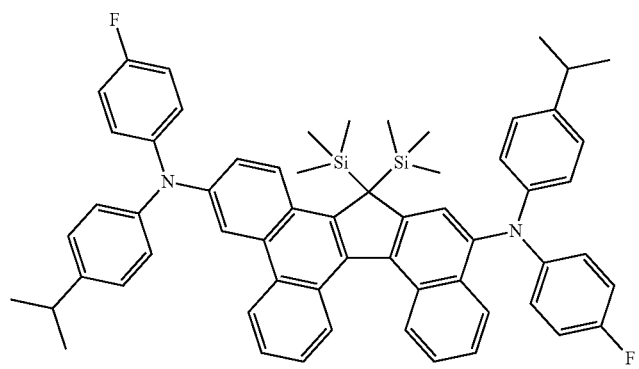
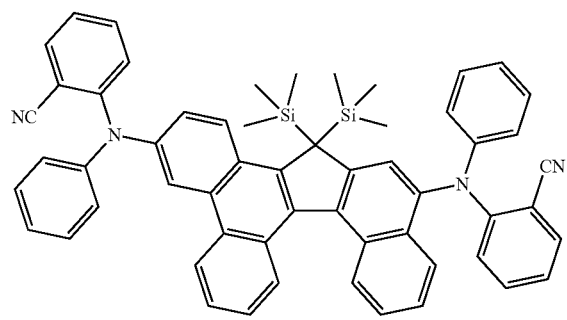

-continued
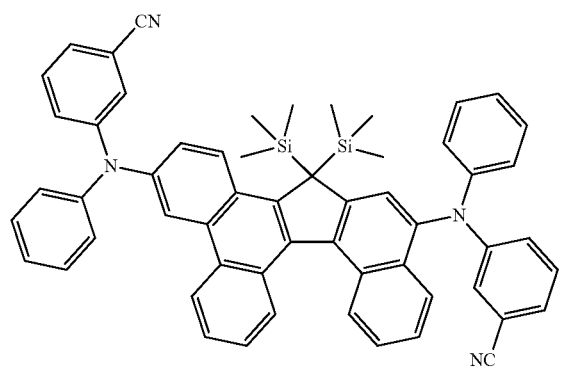
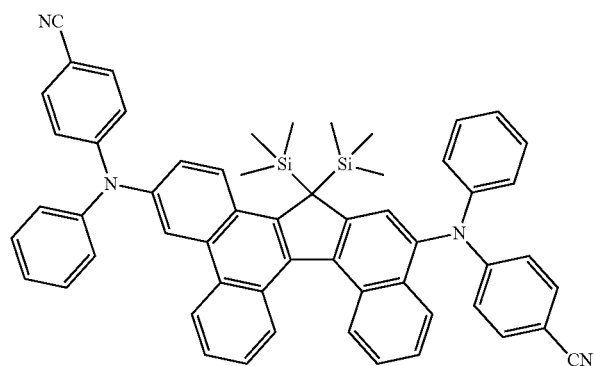
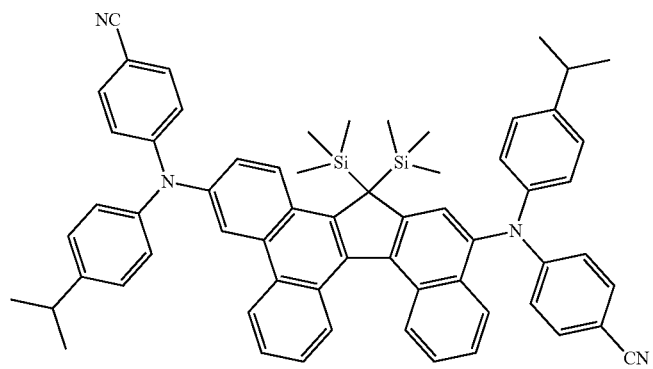
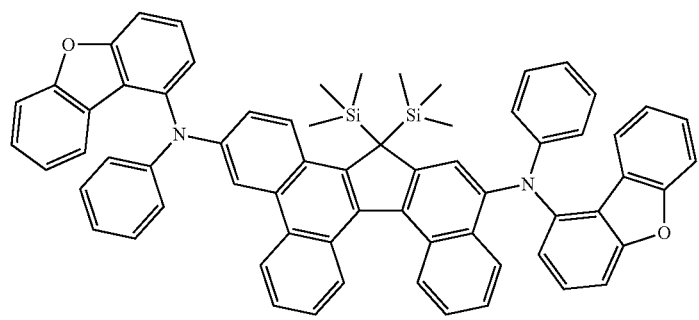

-continued
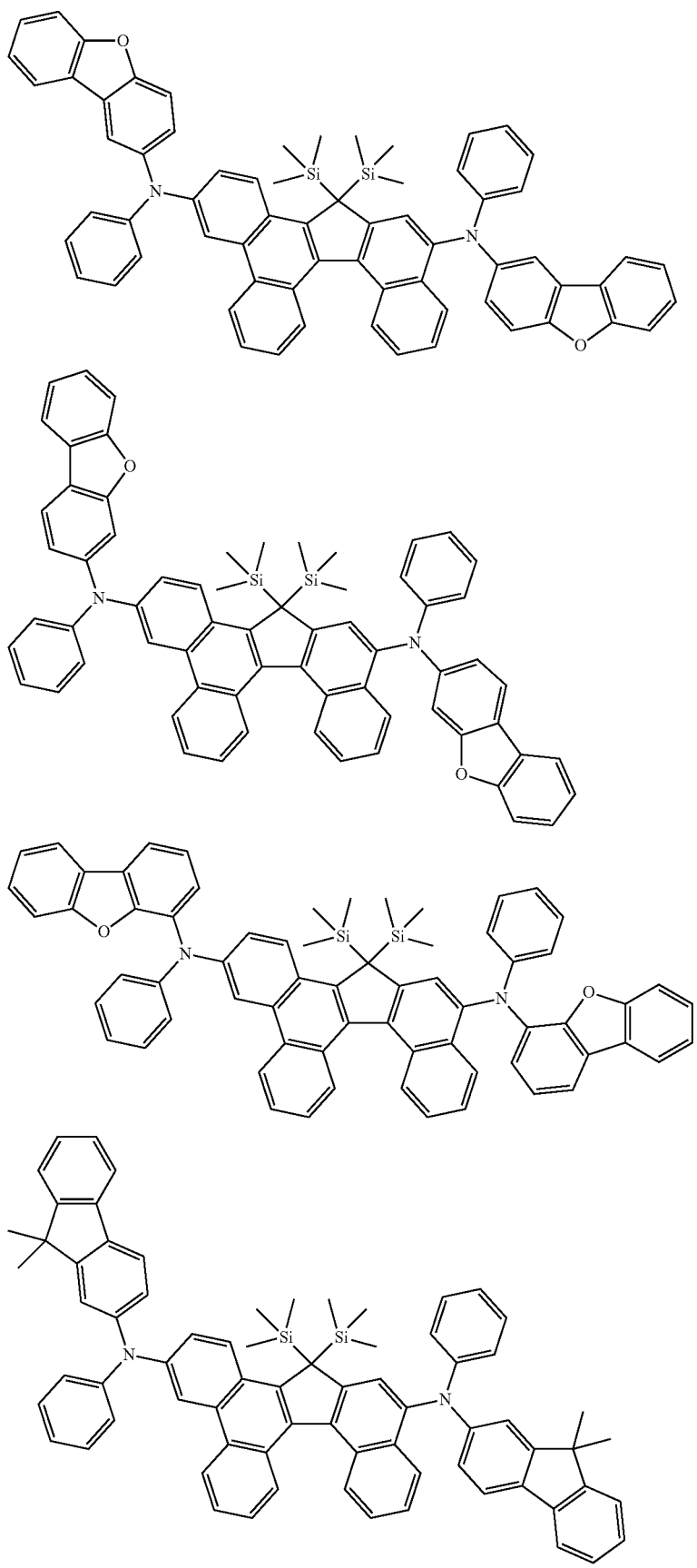

-continued
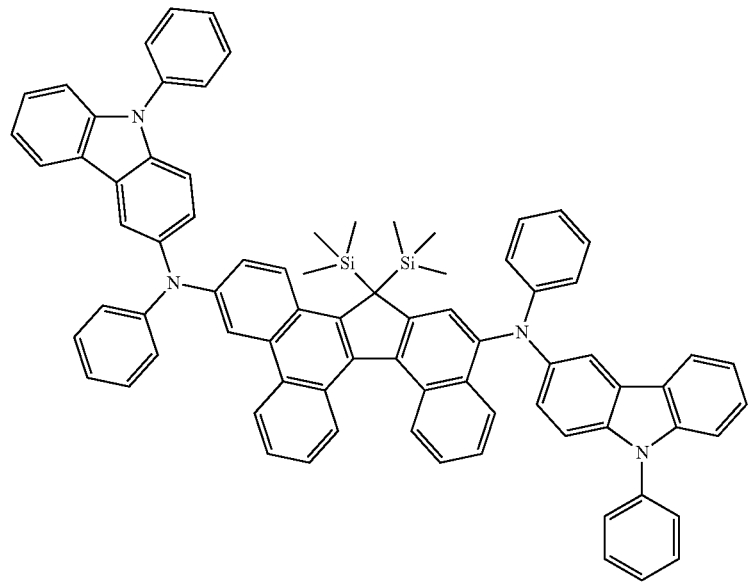
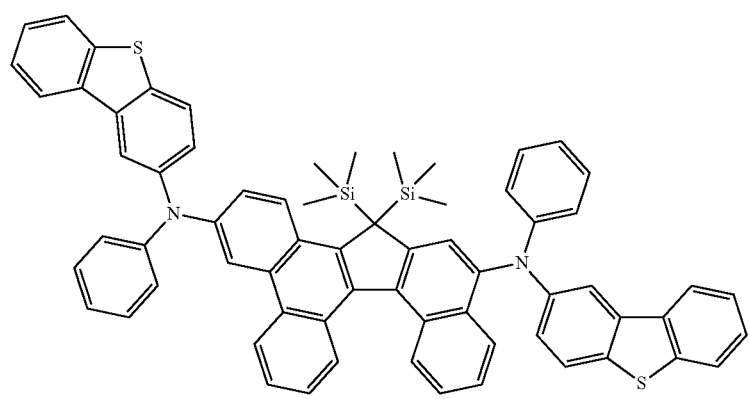
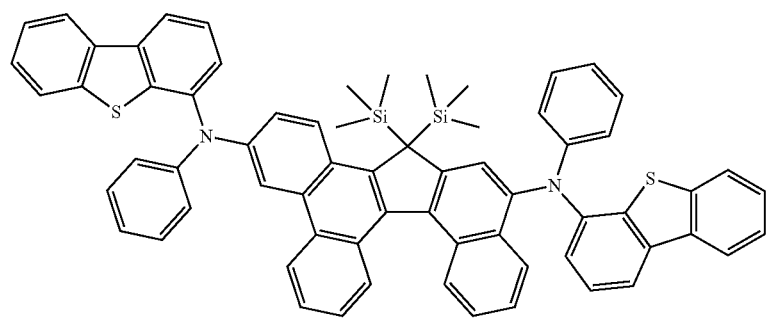
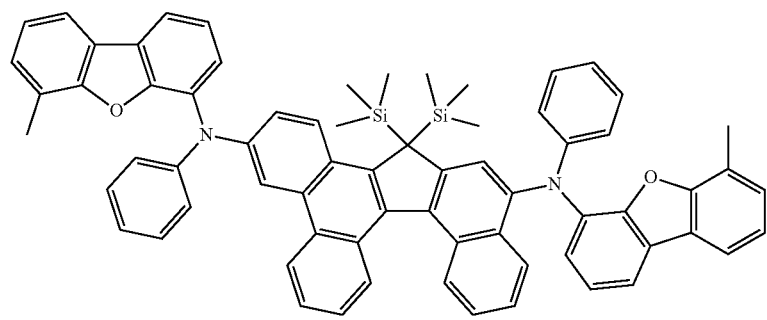

-continued
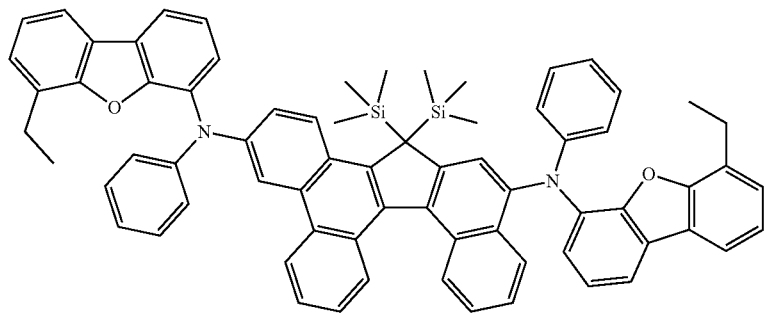
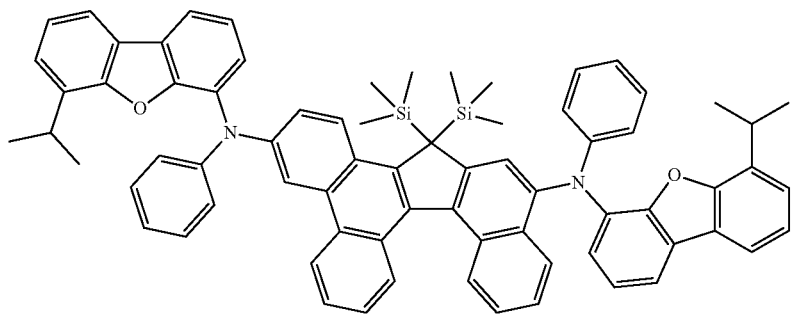
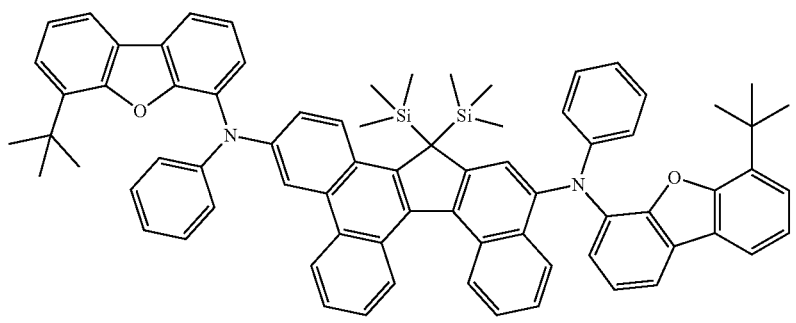
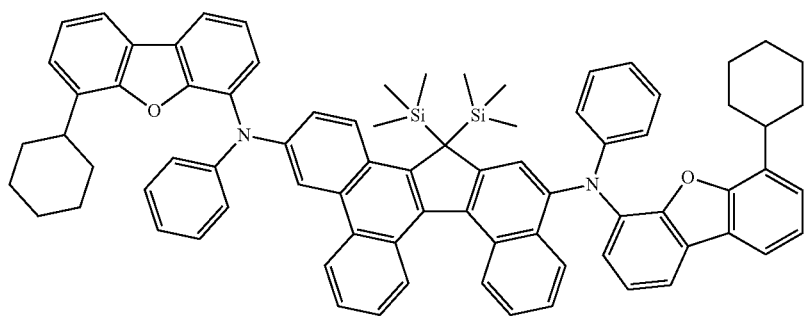
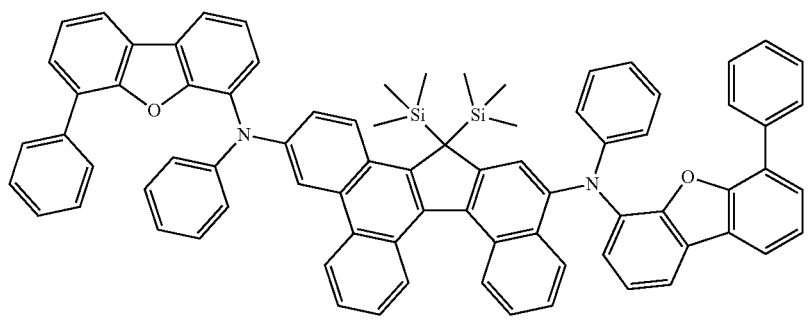

-continued
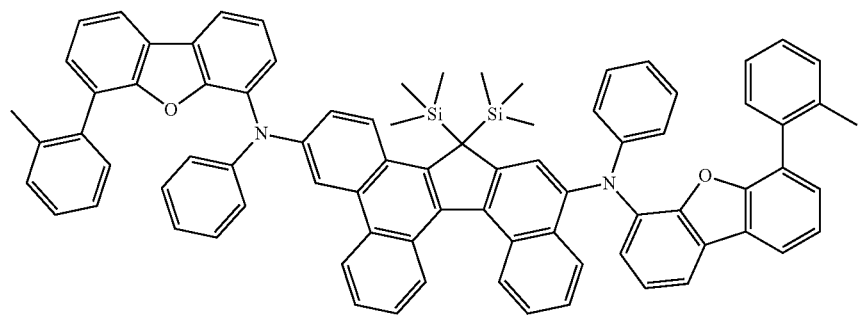
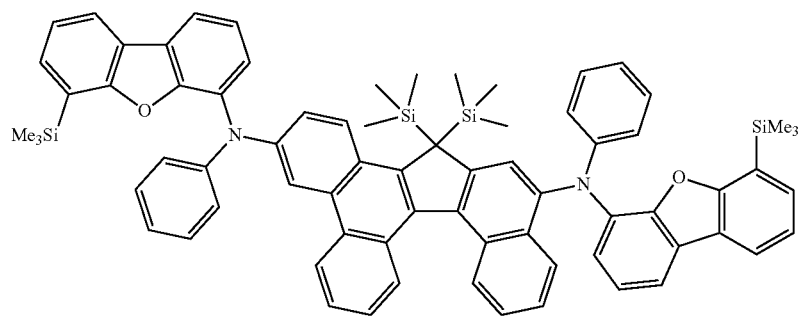
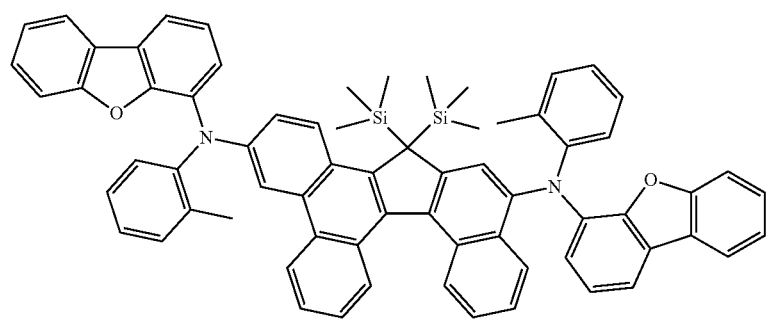

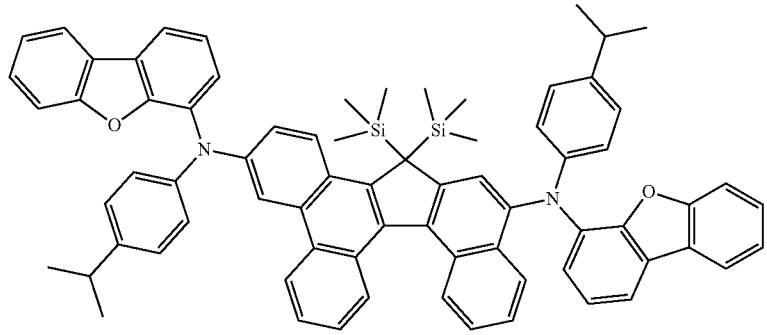
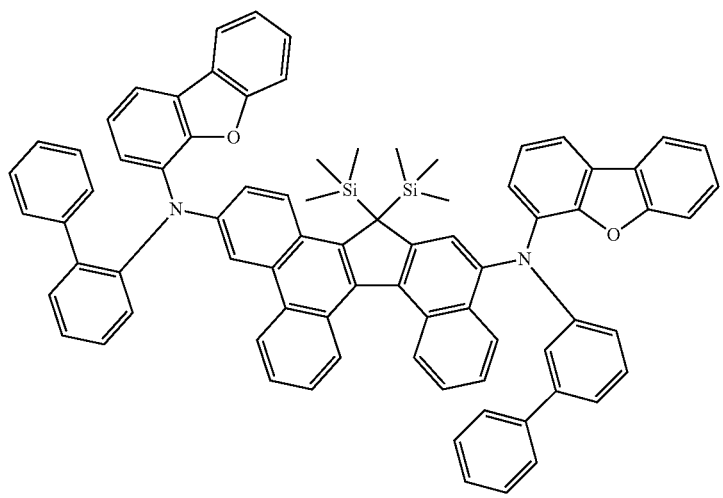
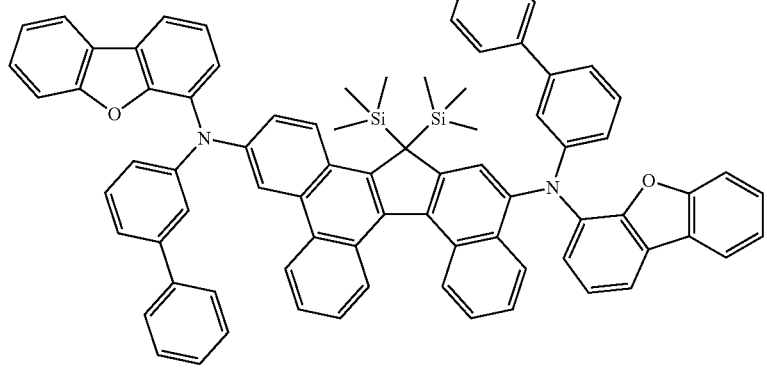
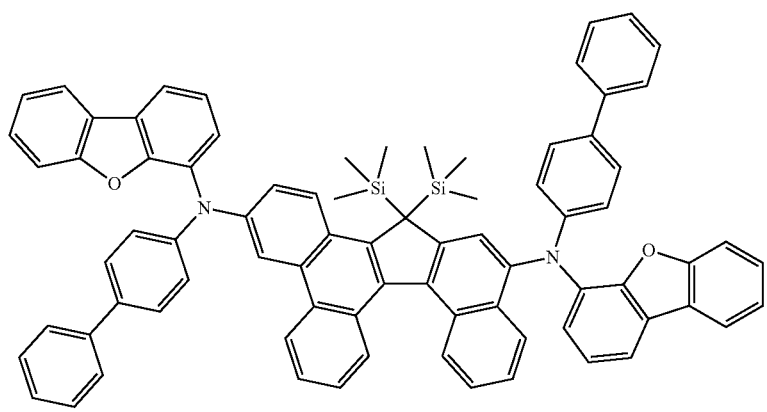

-continued
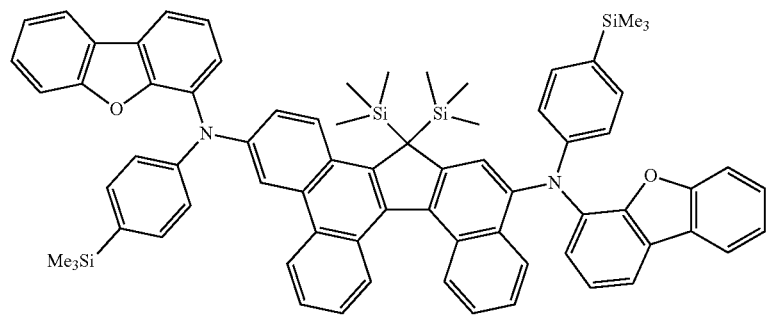
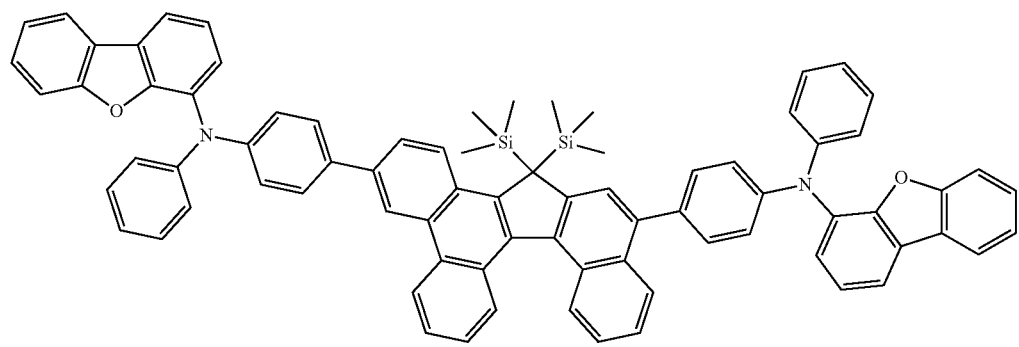
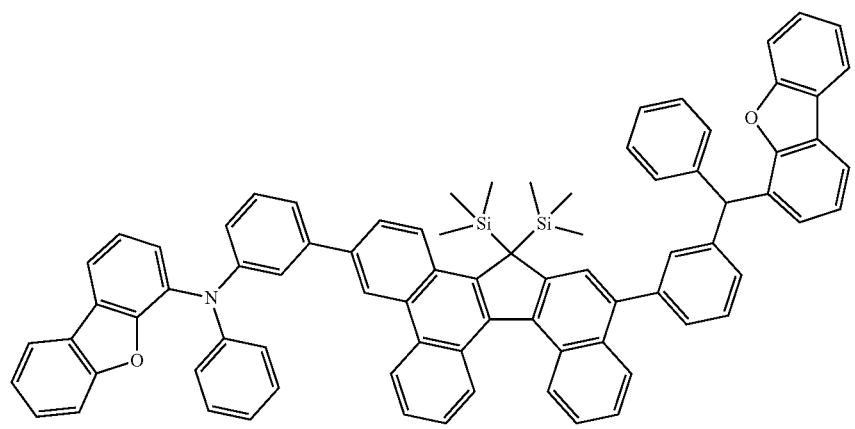
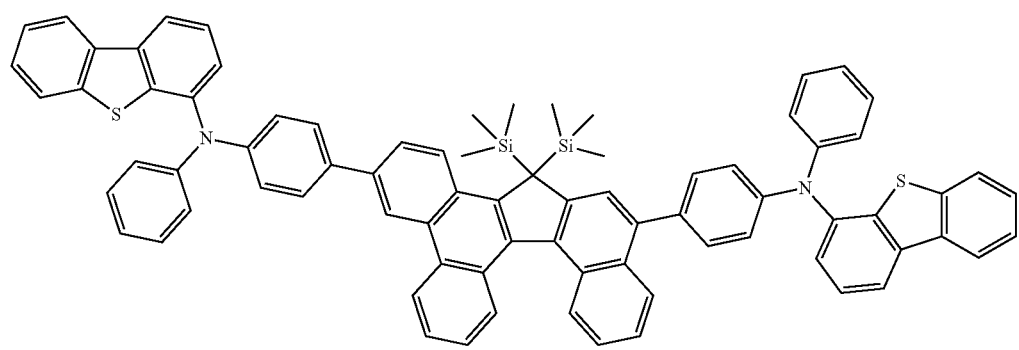

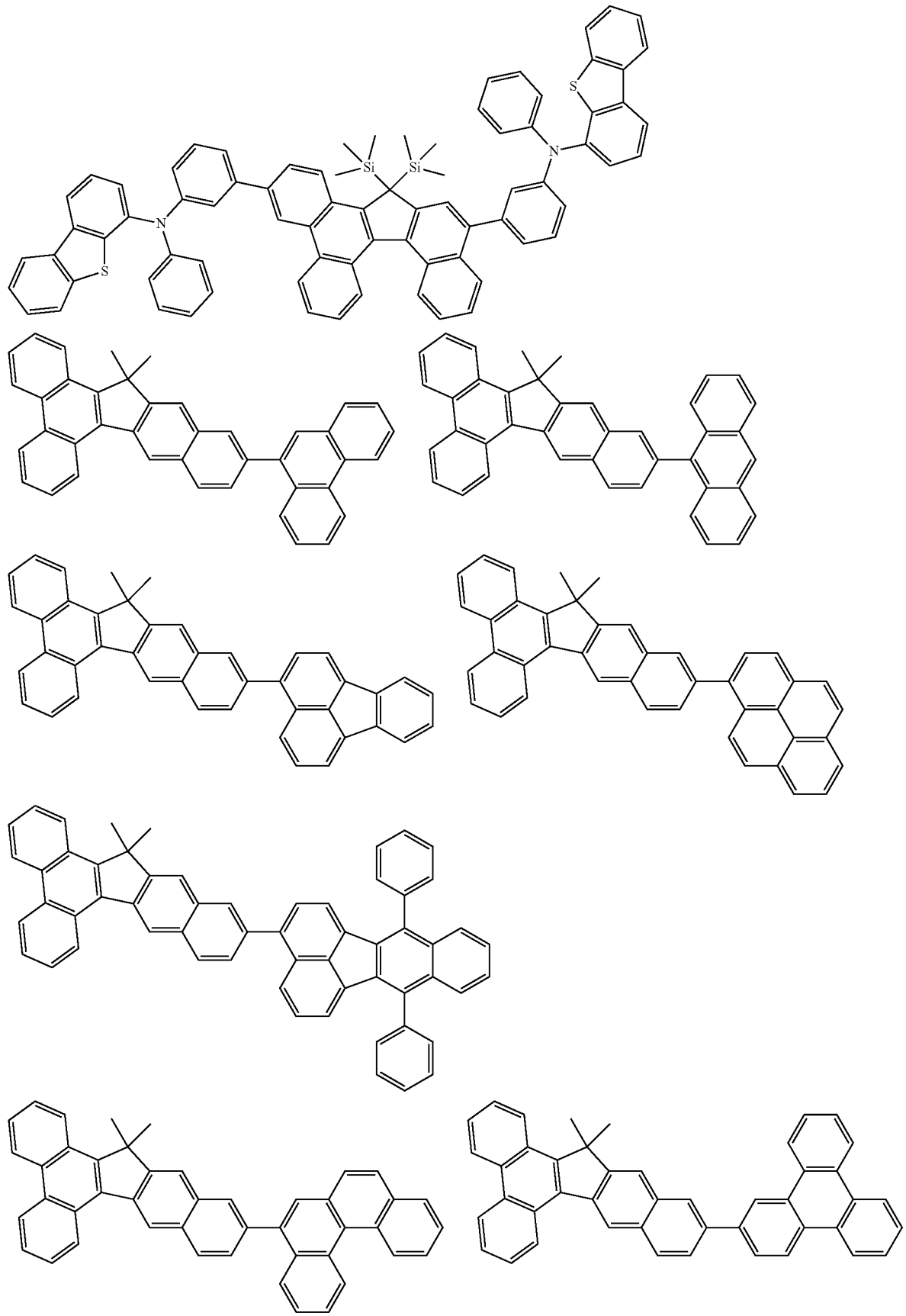

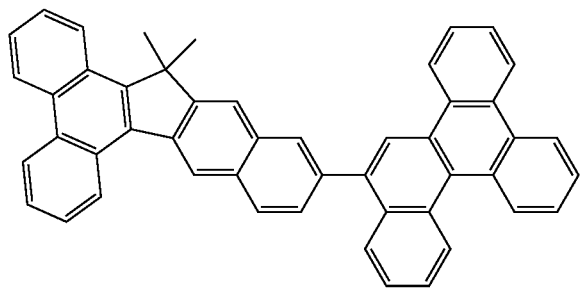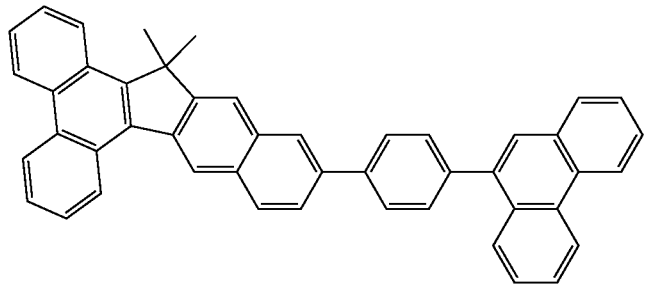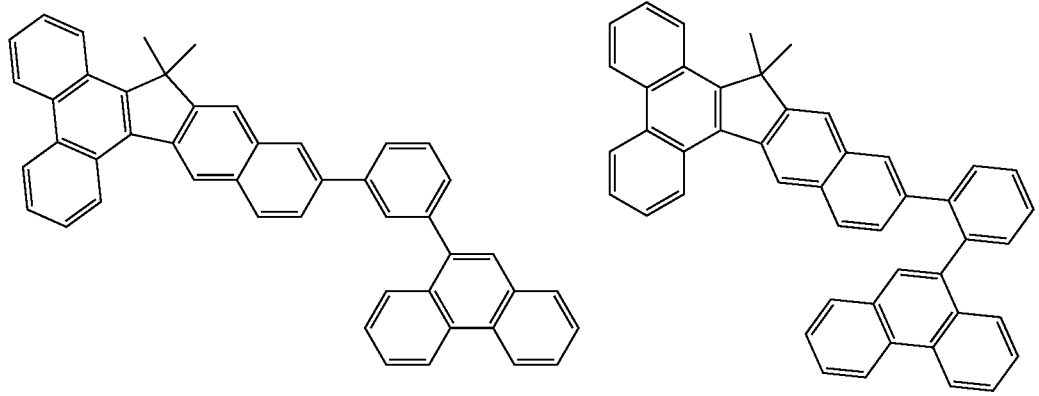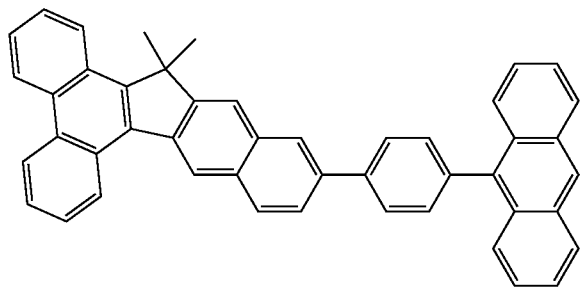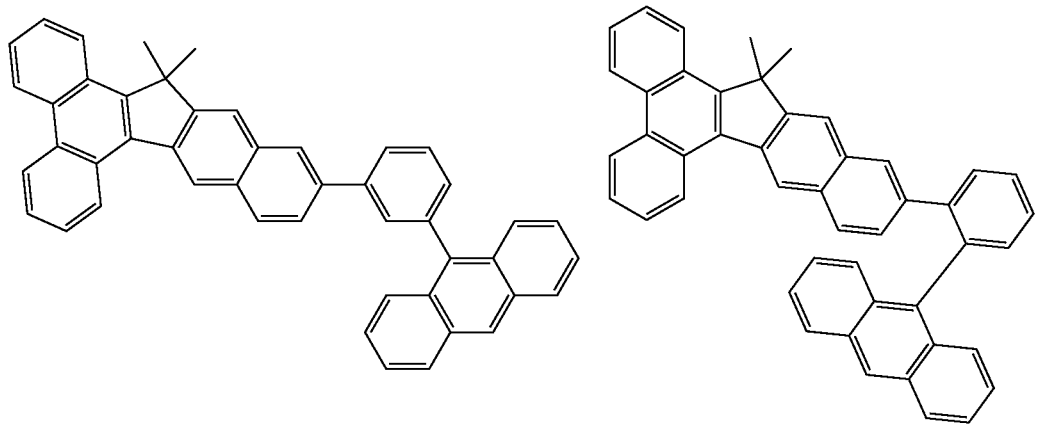

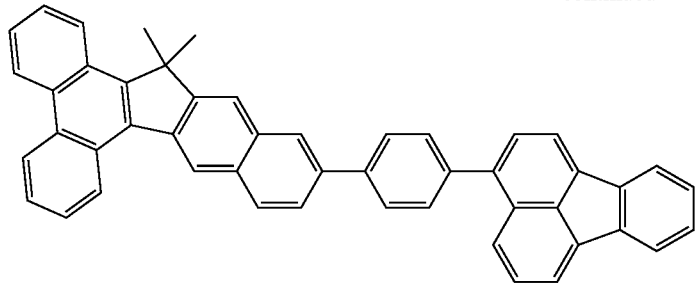
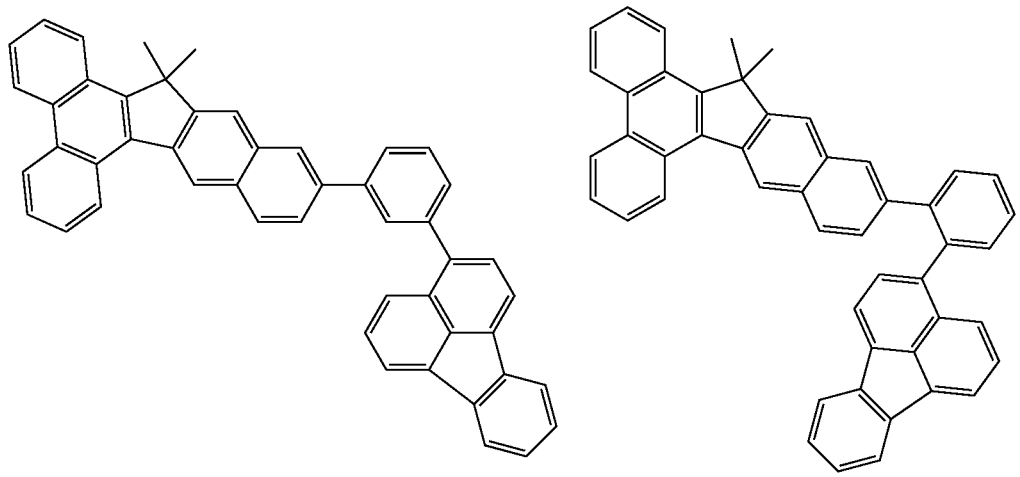
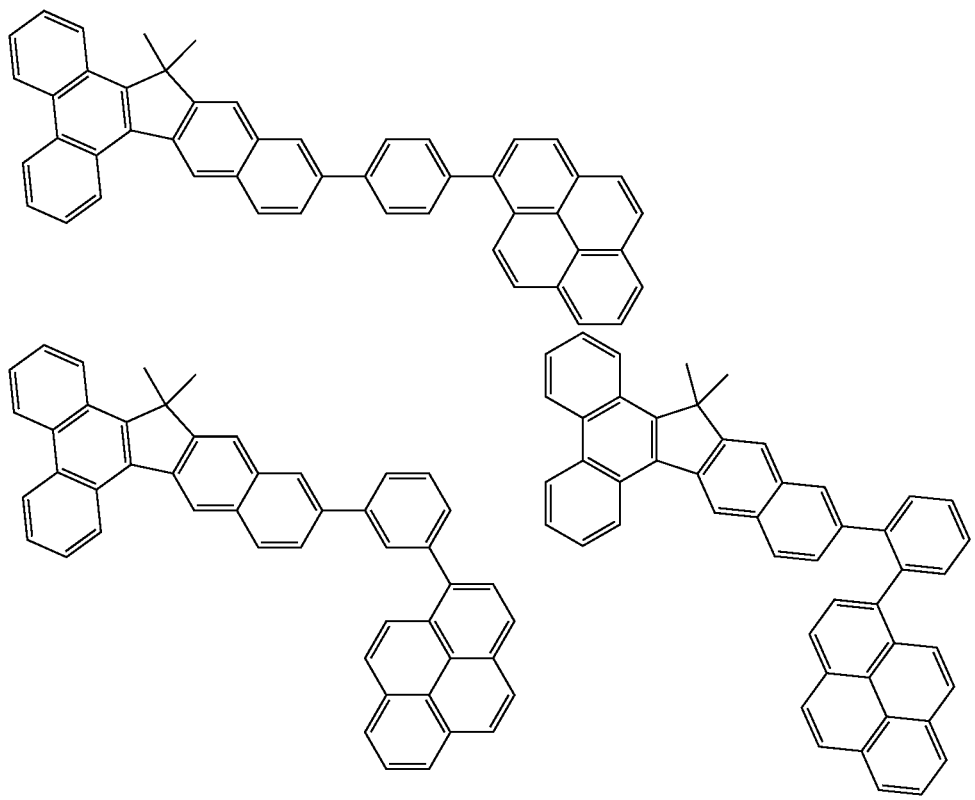

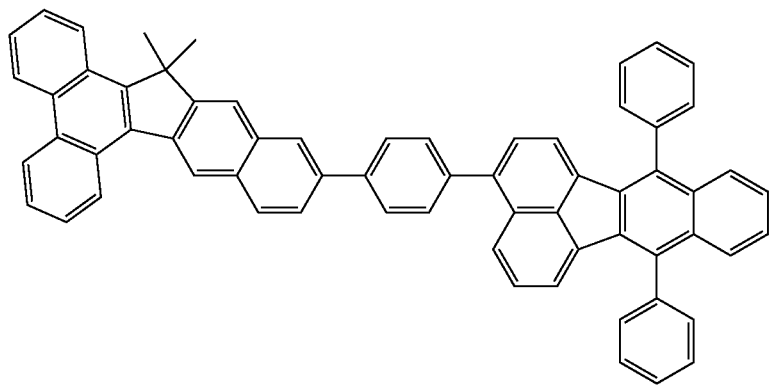
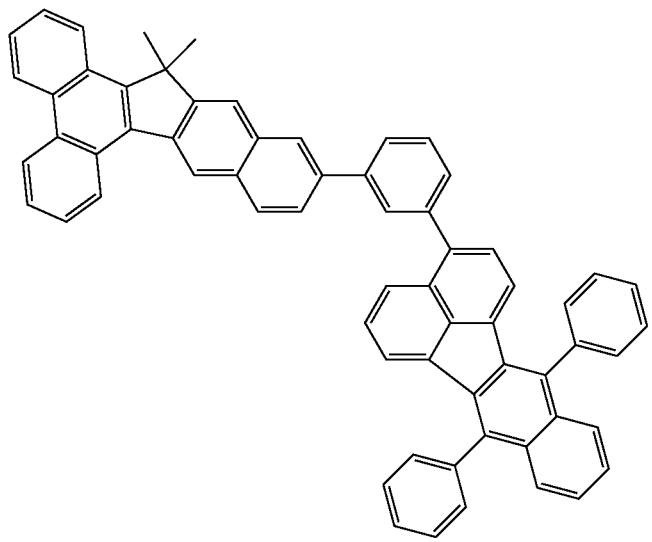
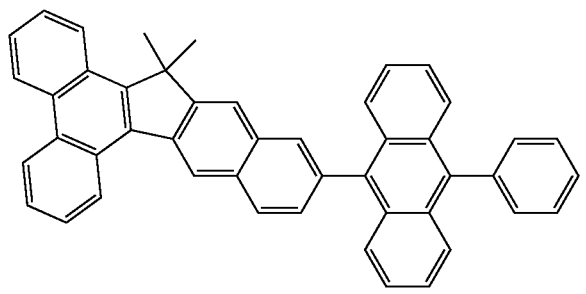
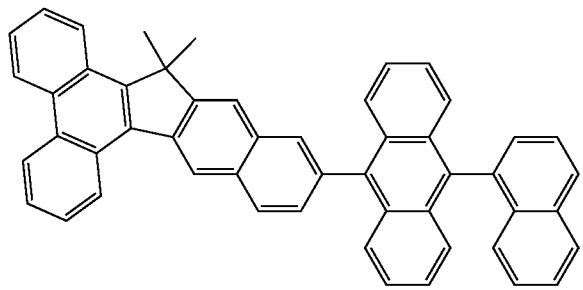

-continued
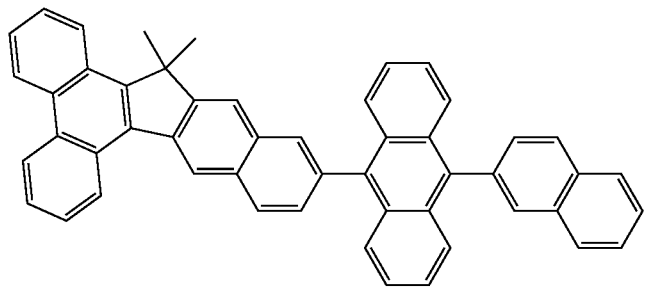
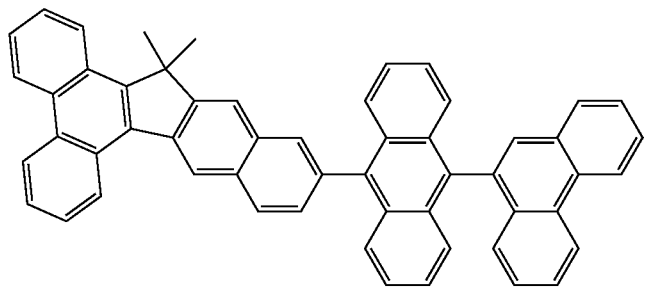
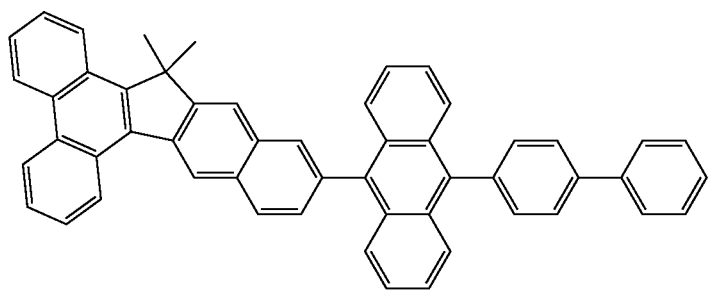
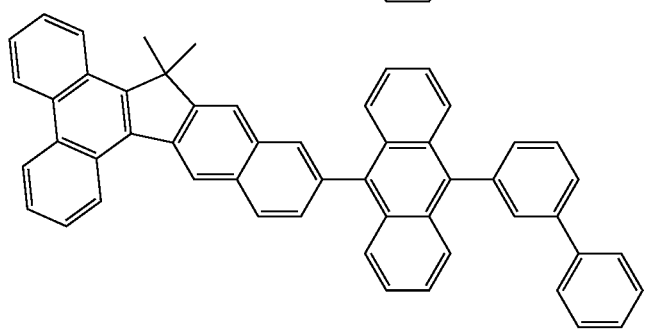
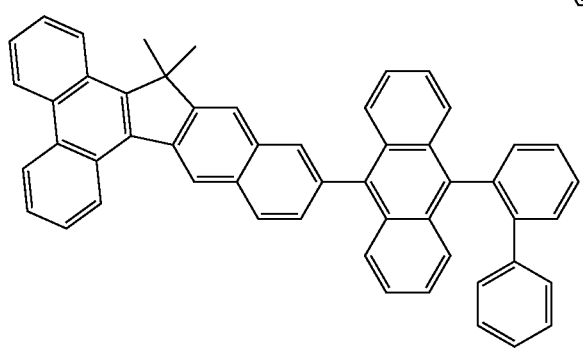

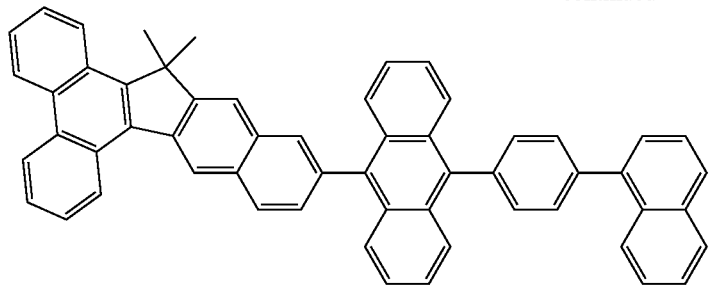
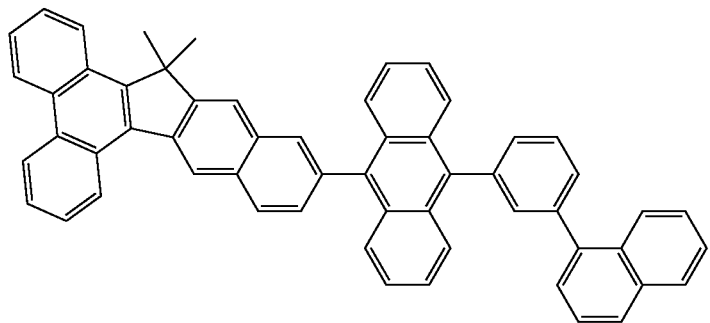
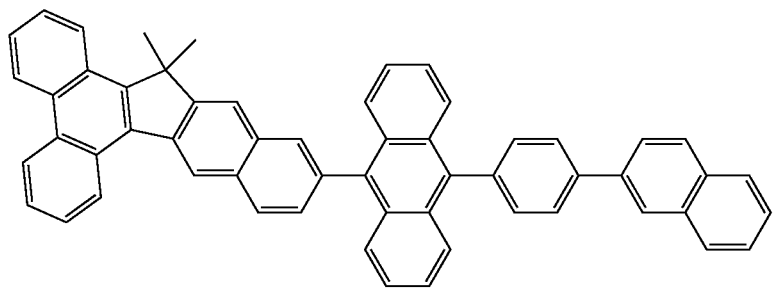
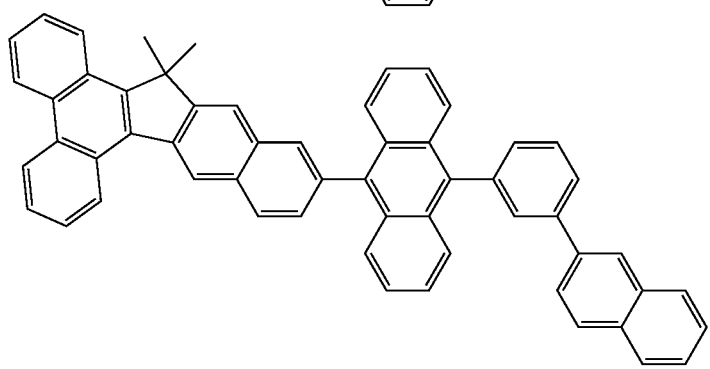
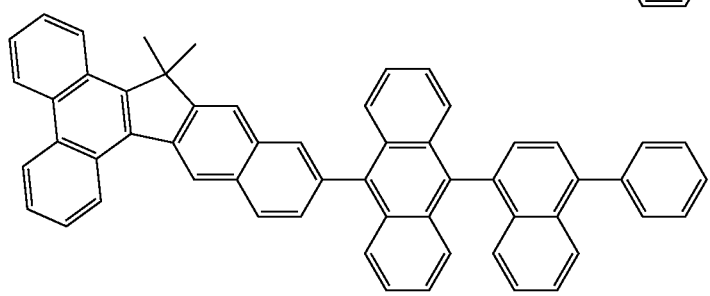

-continued
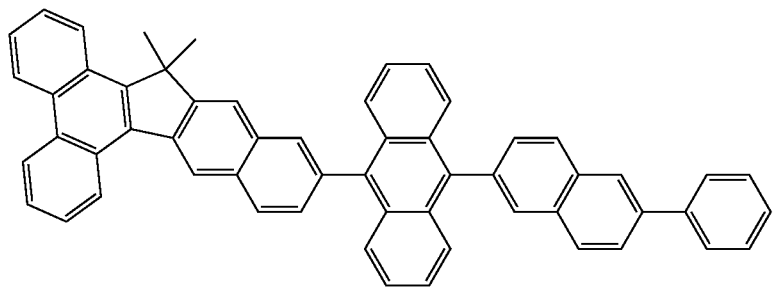
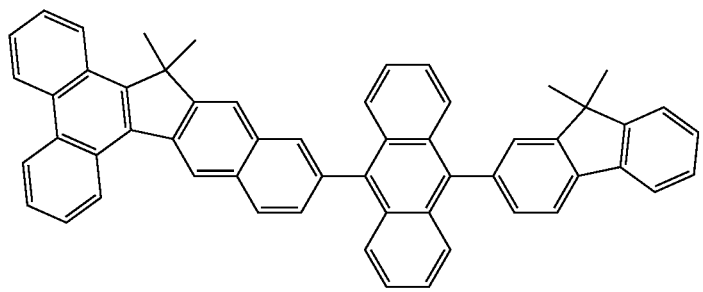
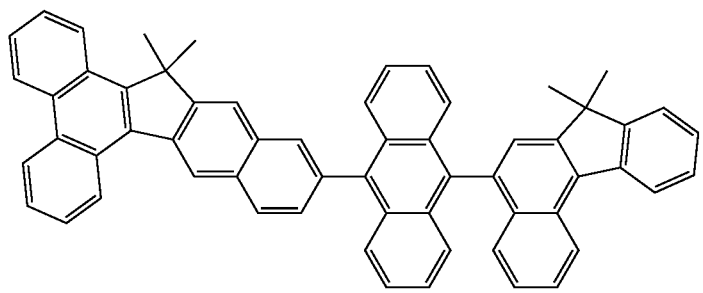
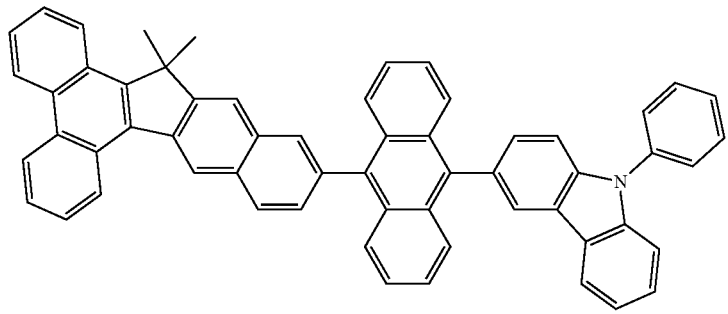
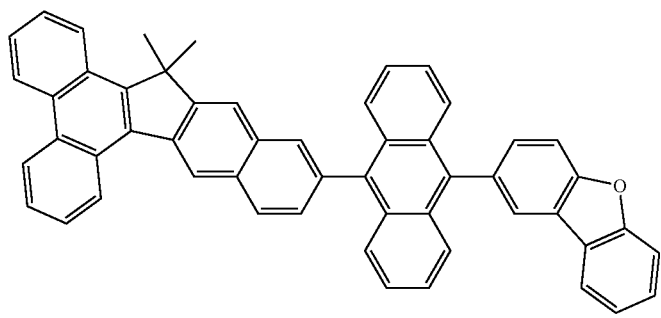

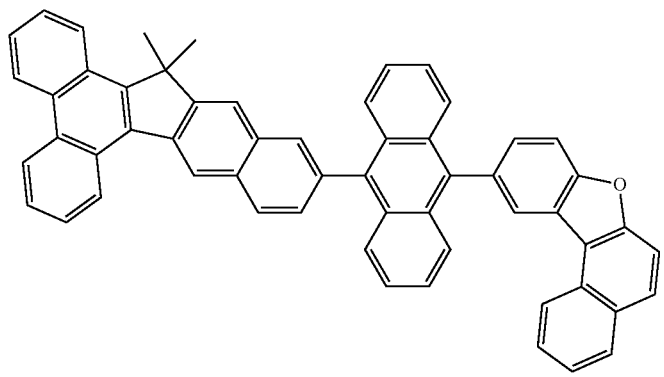
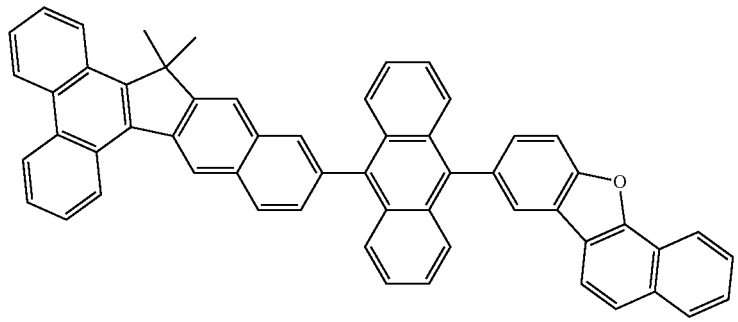
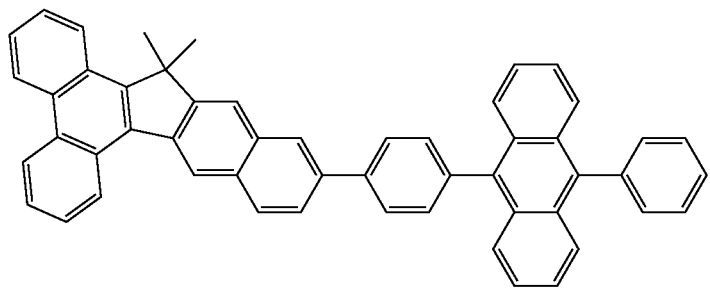
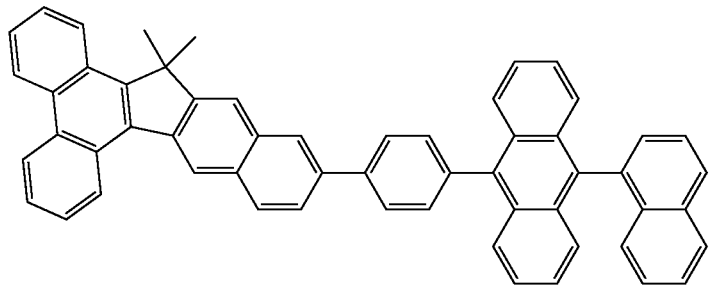
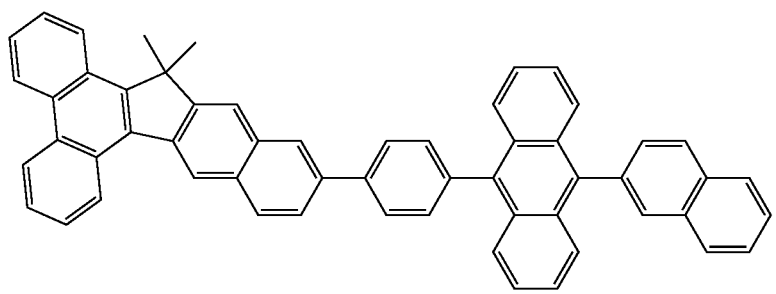

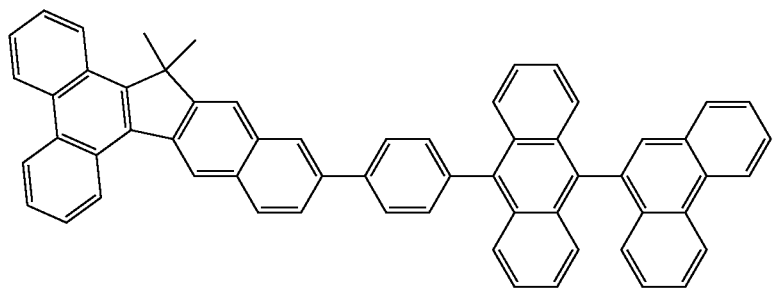
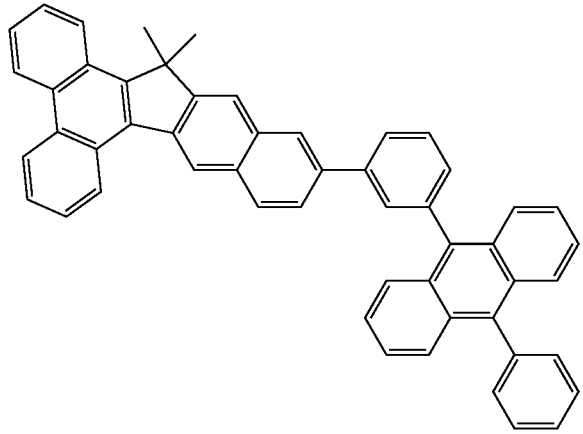
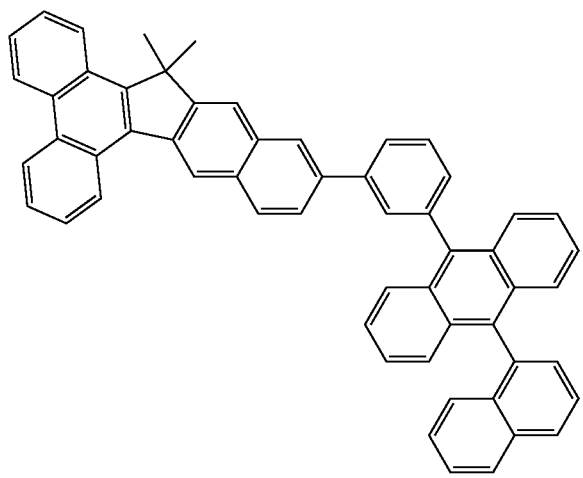
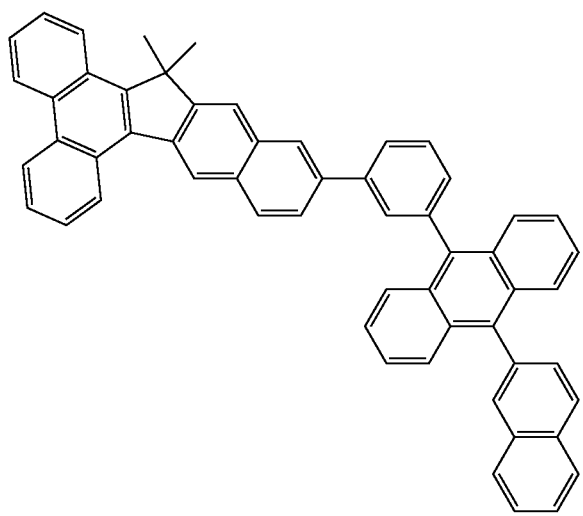

-continued
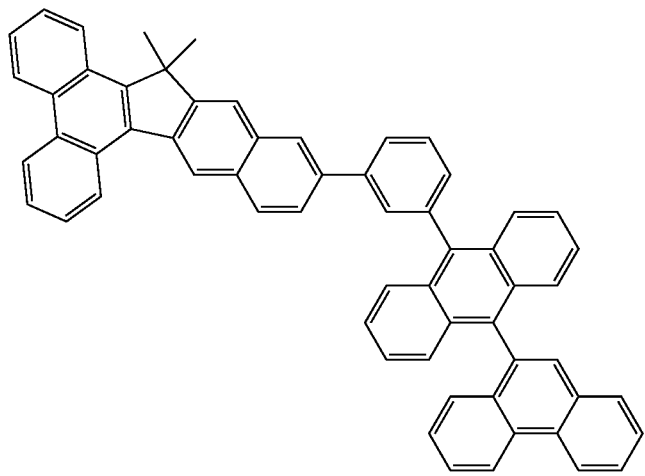
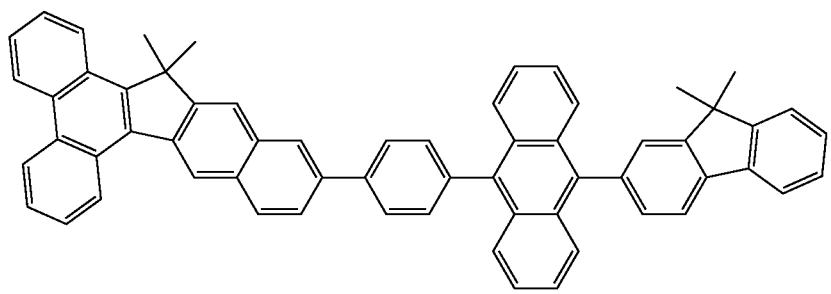
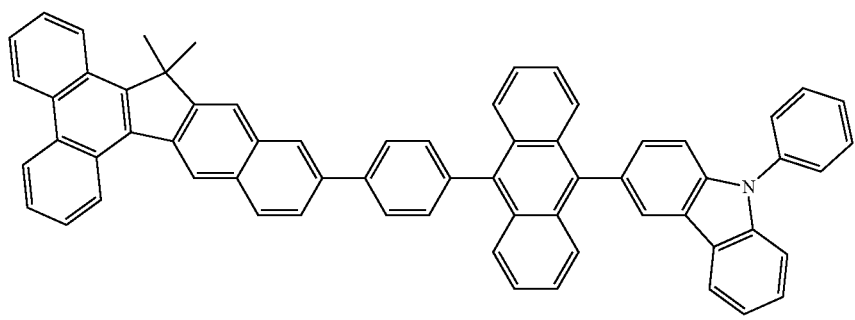
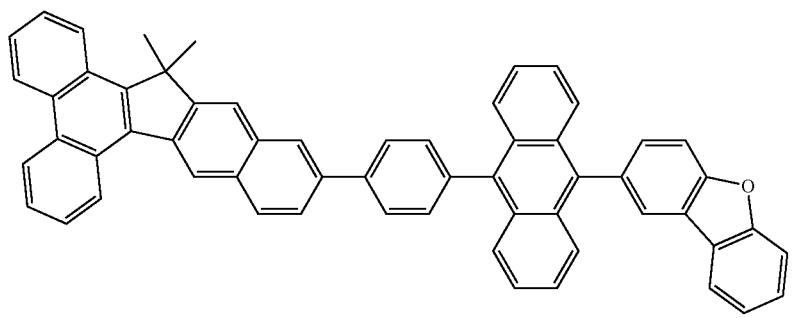

-continued
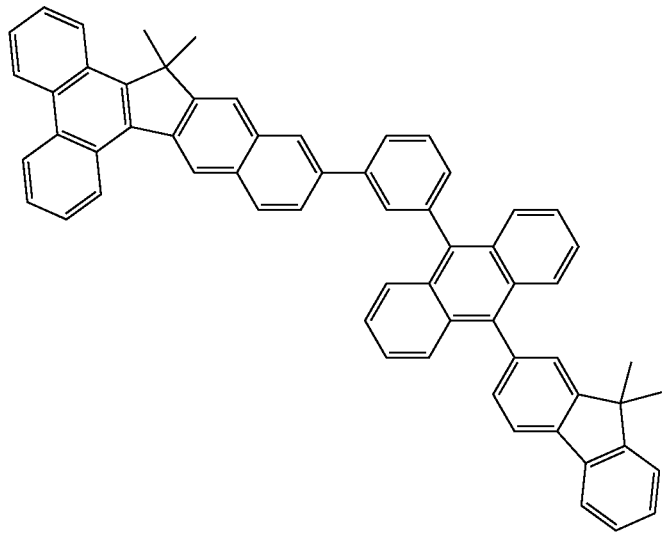
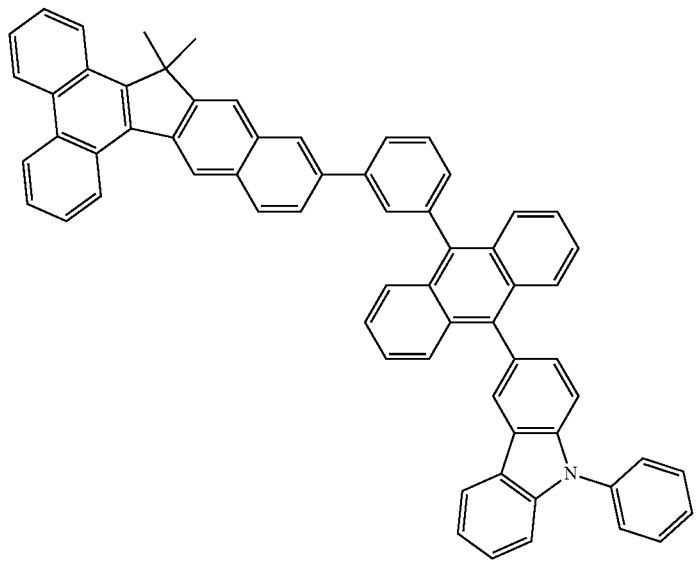
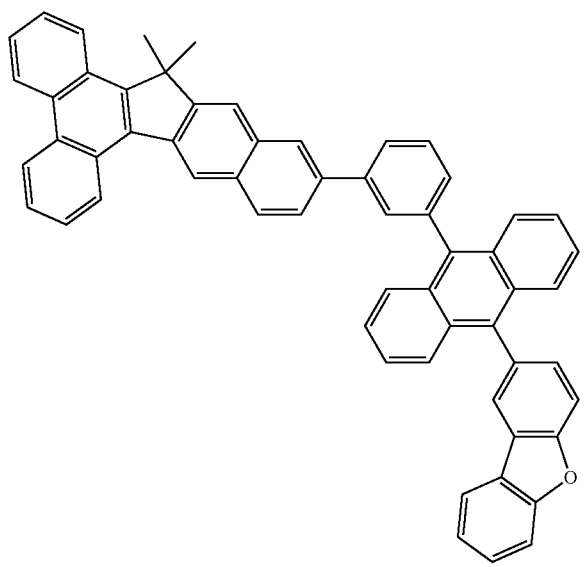

245
246
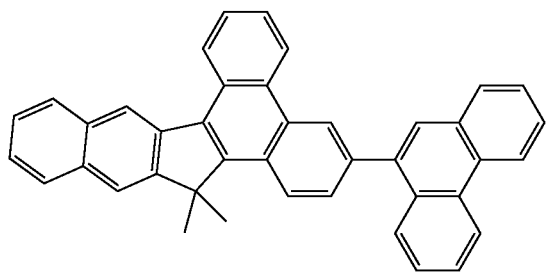
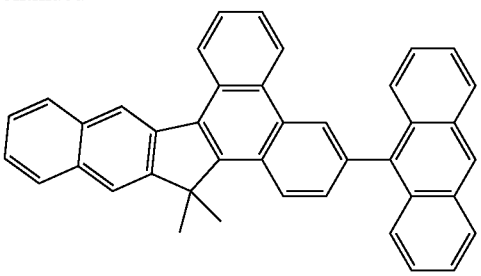
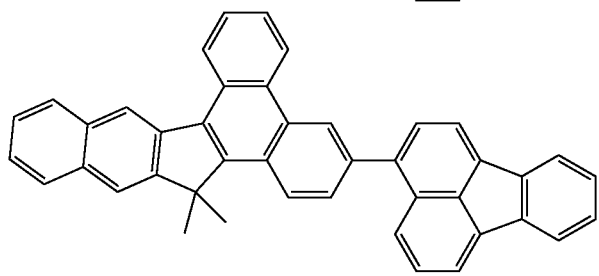
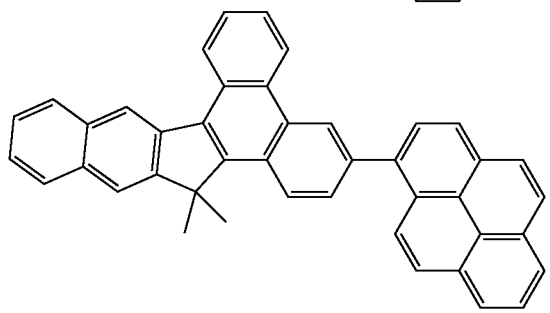
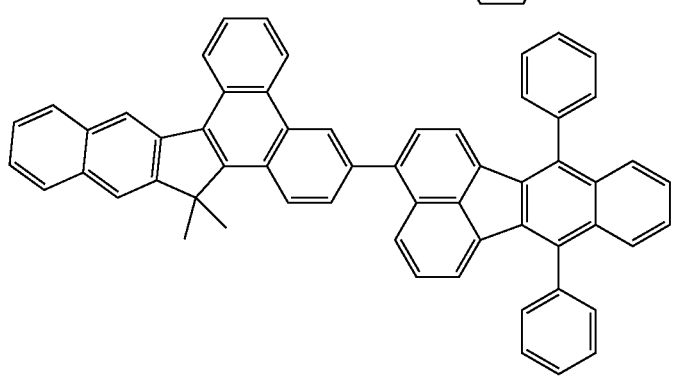
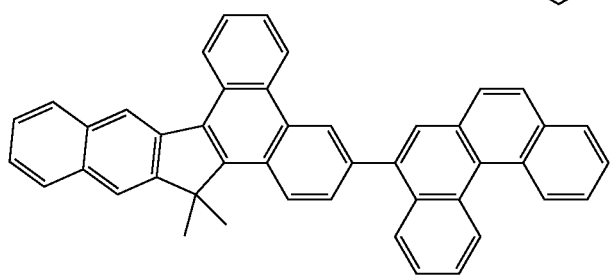
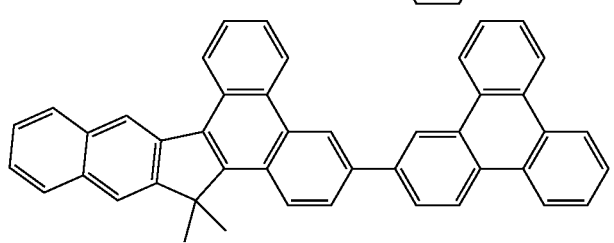

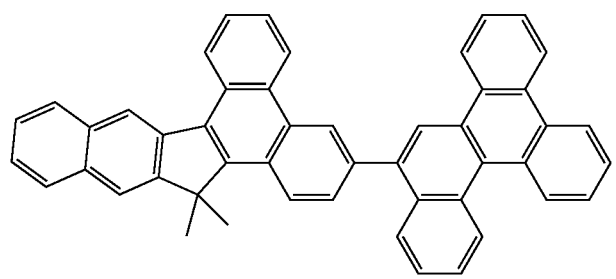
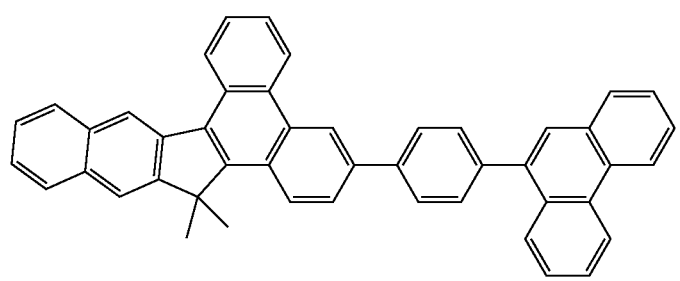
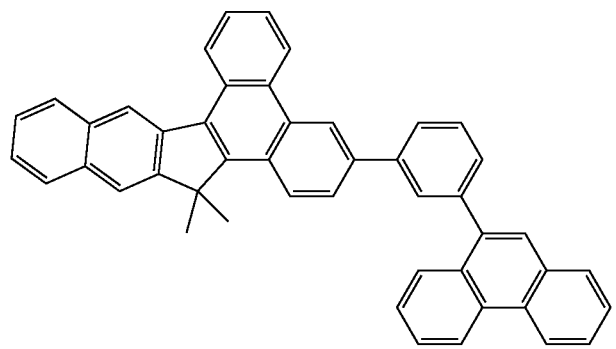
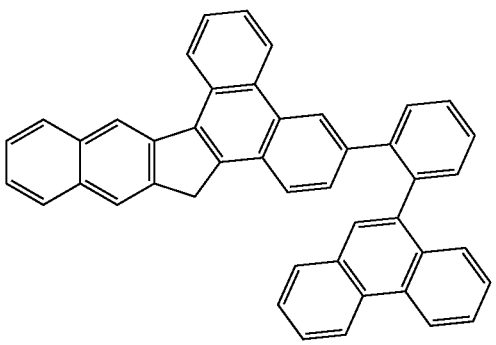
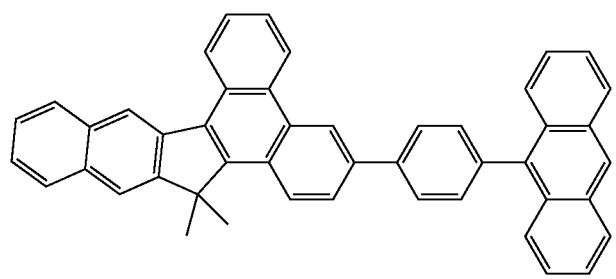
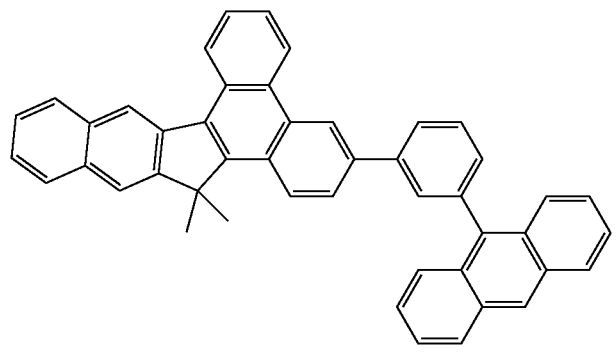
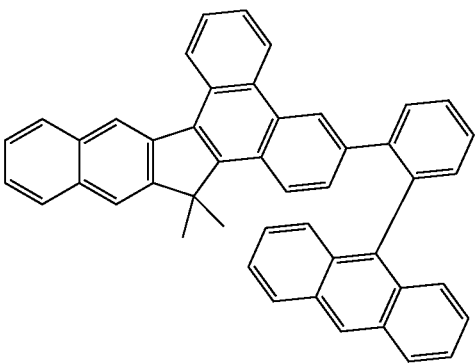

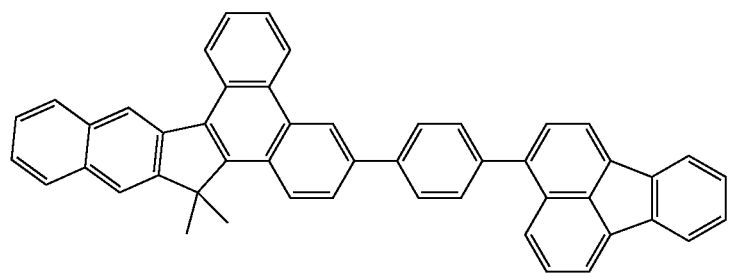
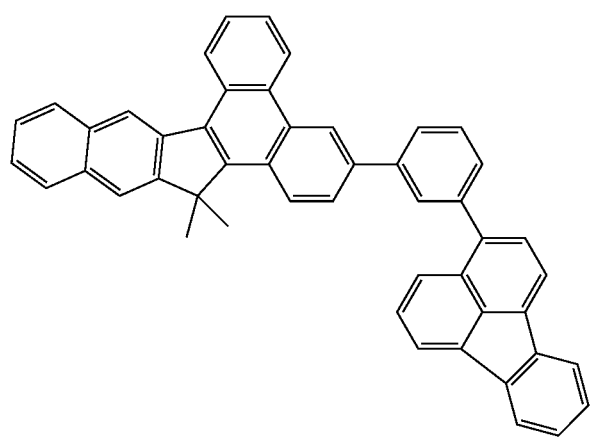
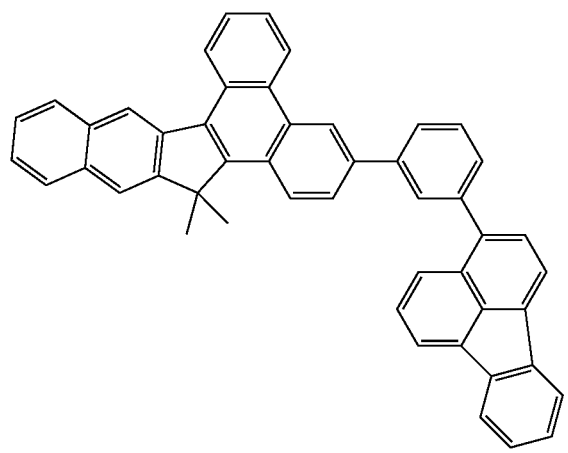
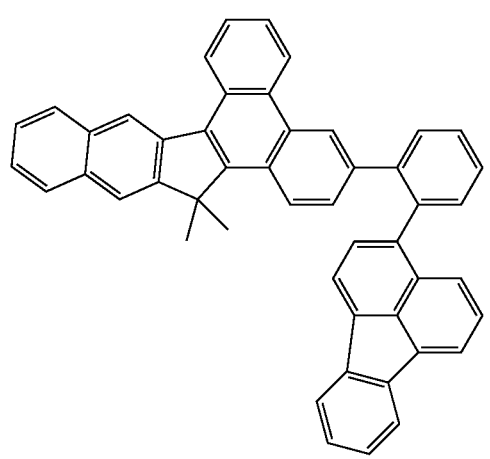

-continued
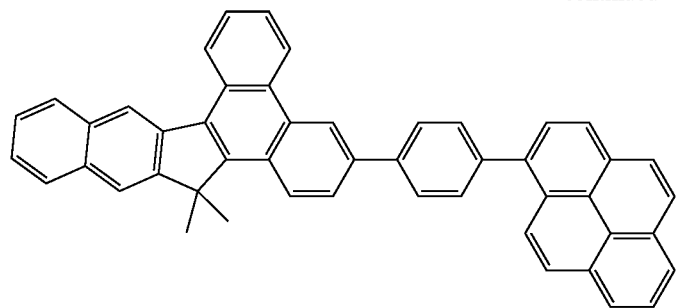
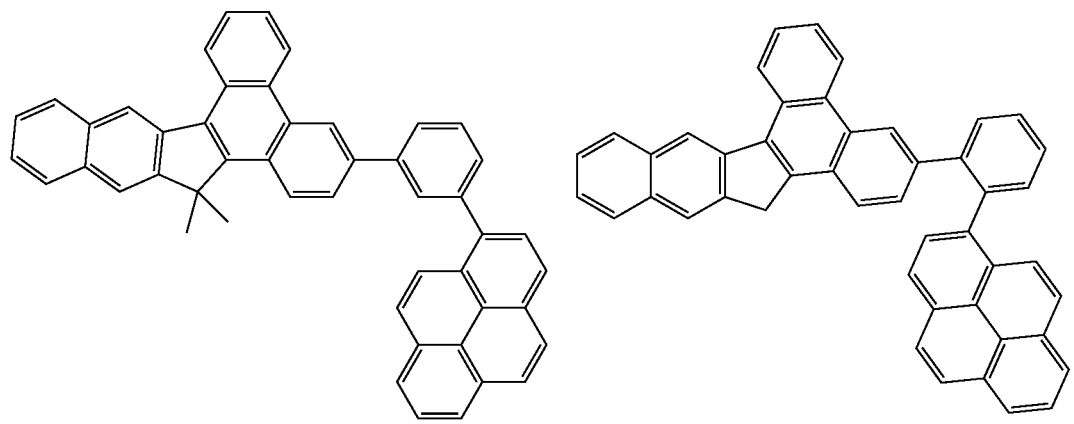
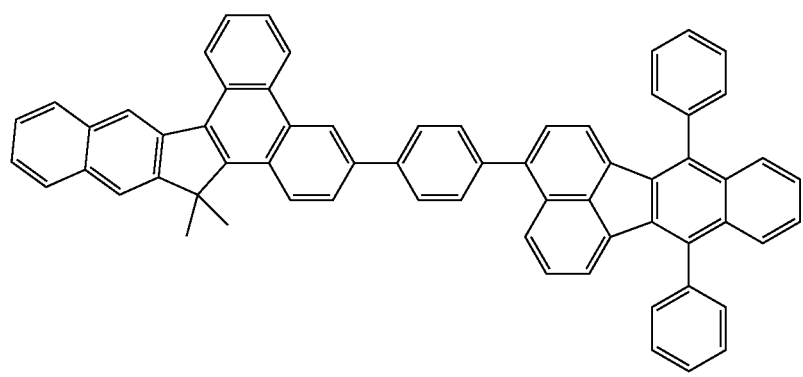
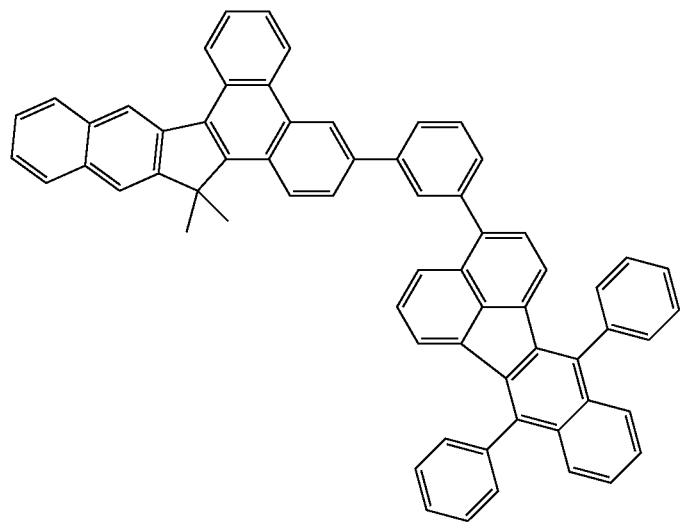

-continued
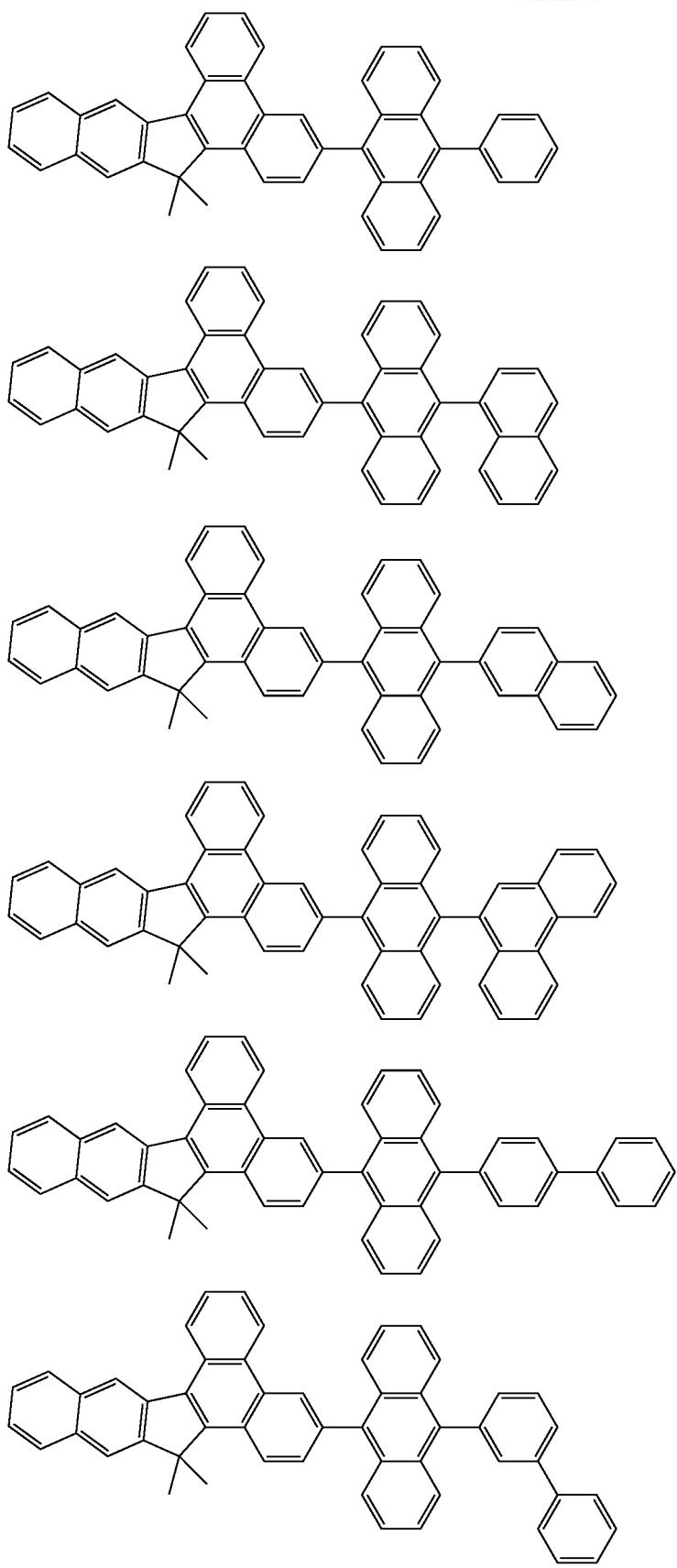

-continued
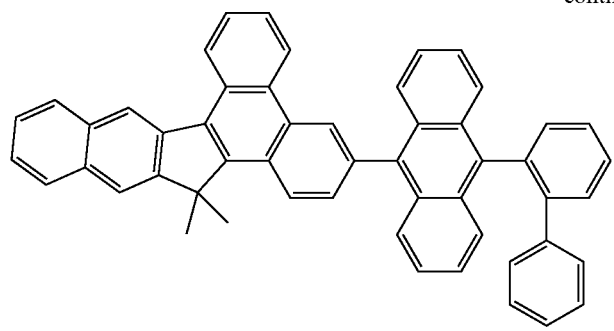
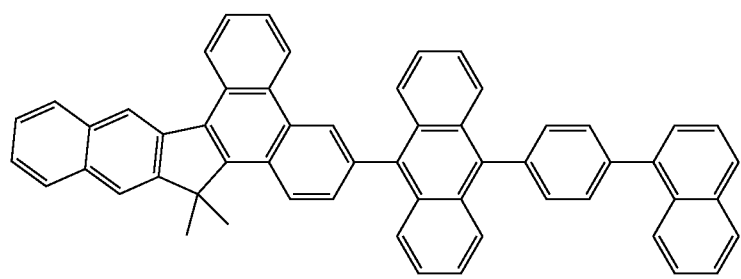
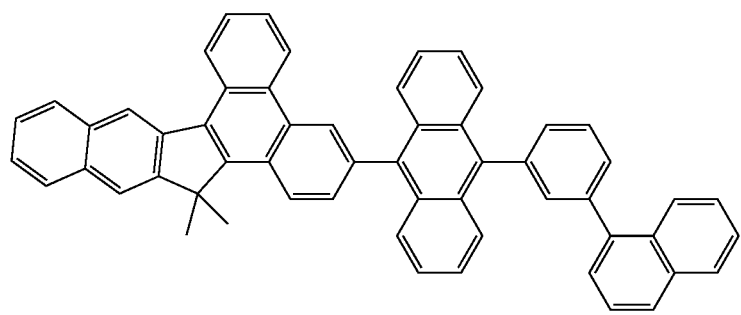
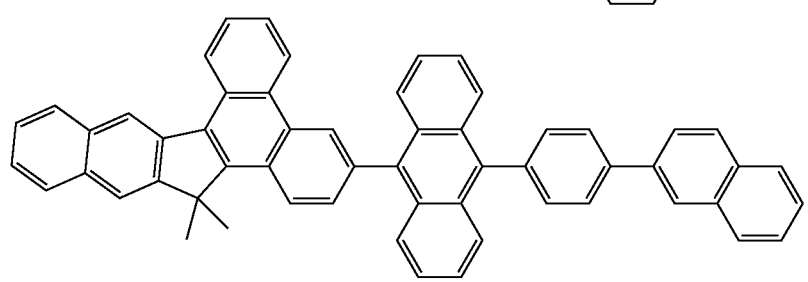
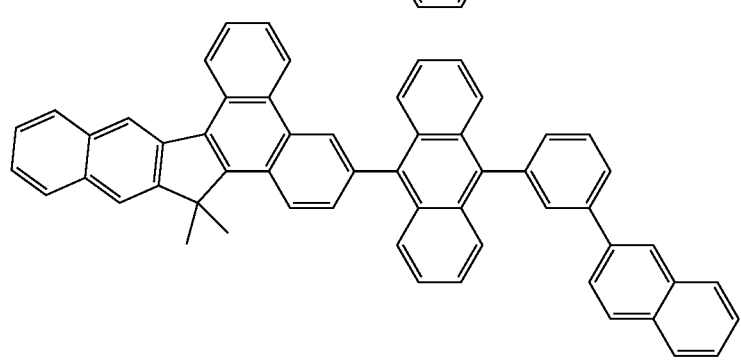

-continued
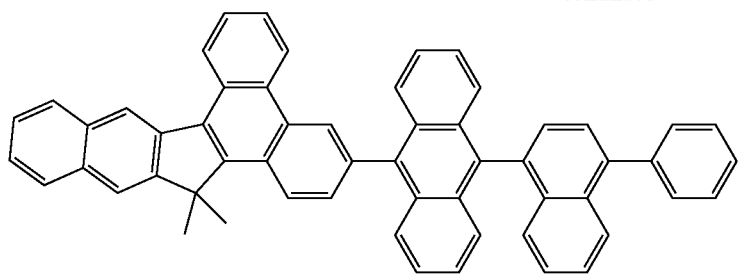
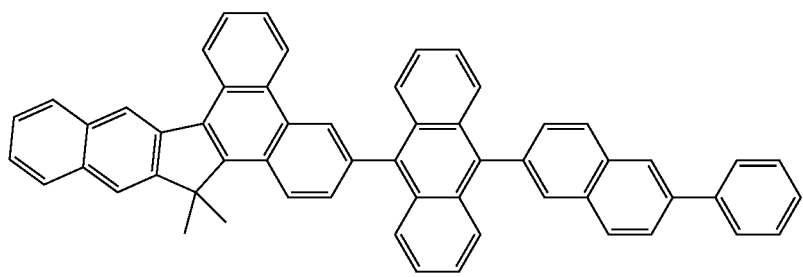
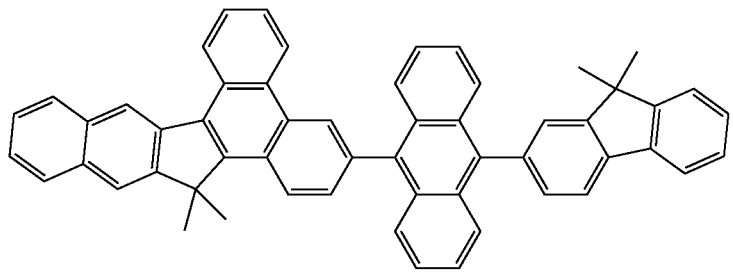
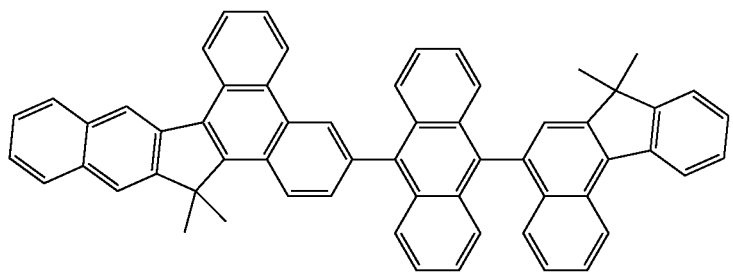
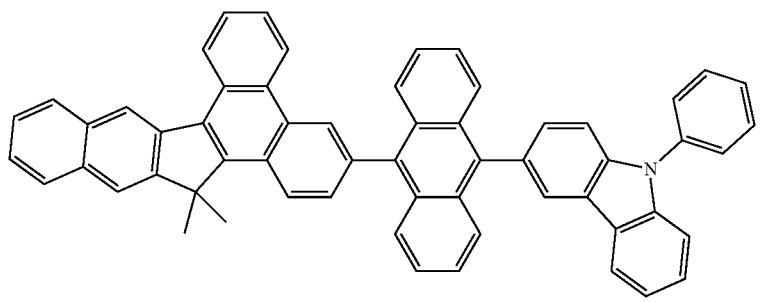
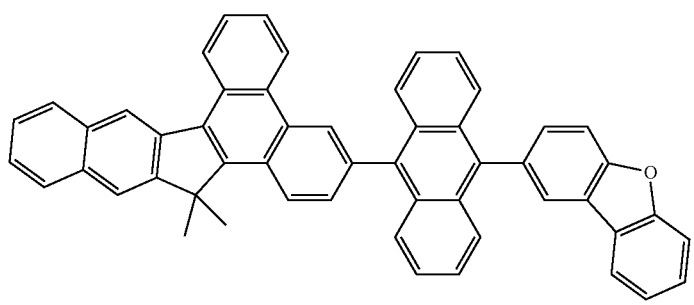

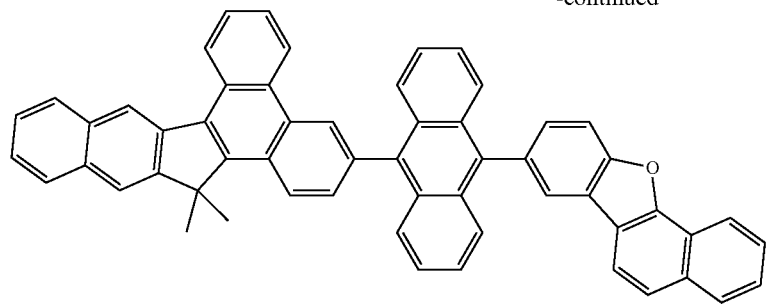
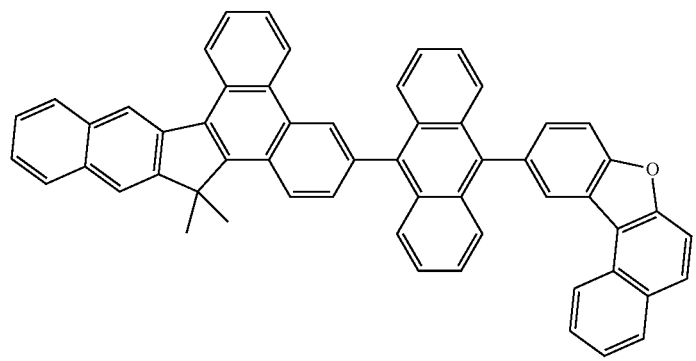
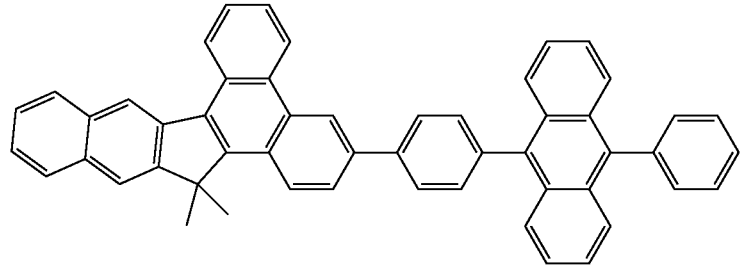
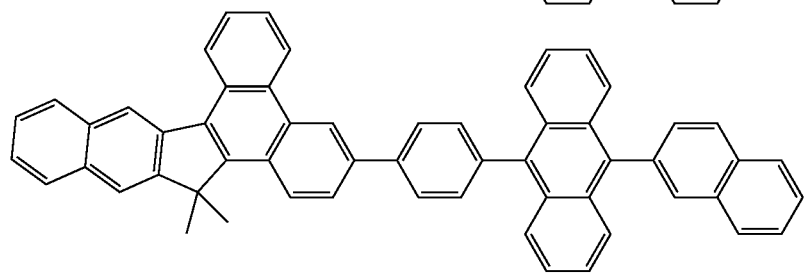
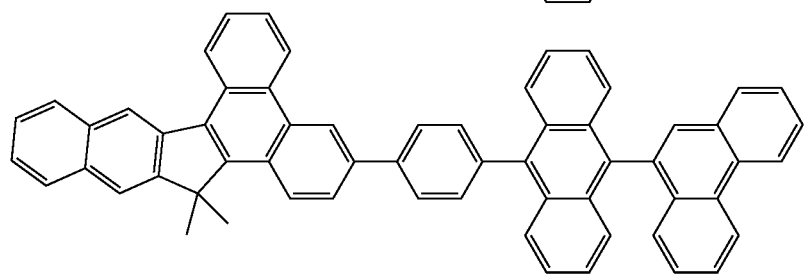

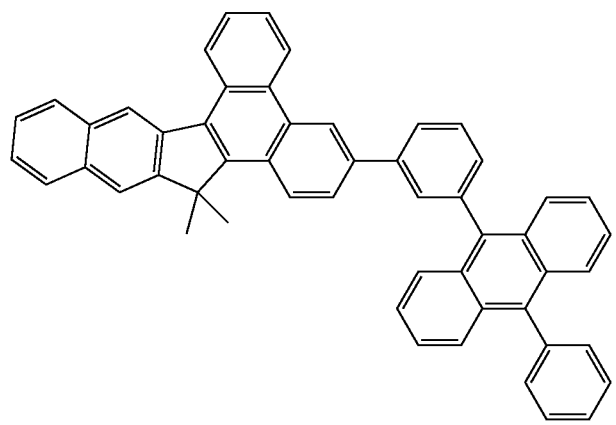
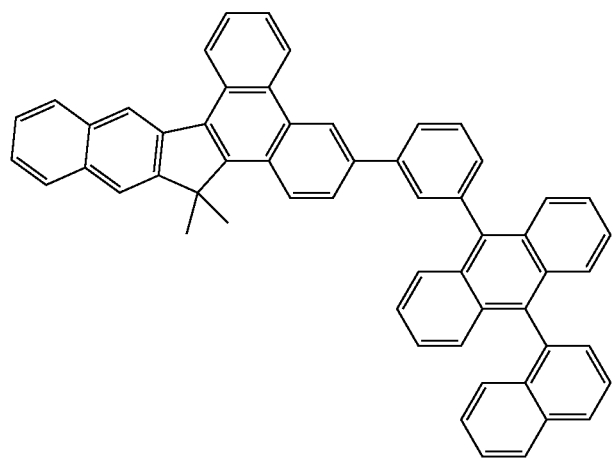
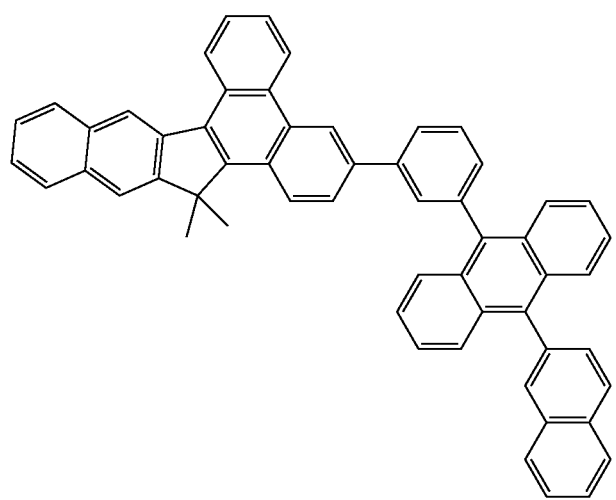

-continued
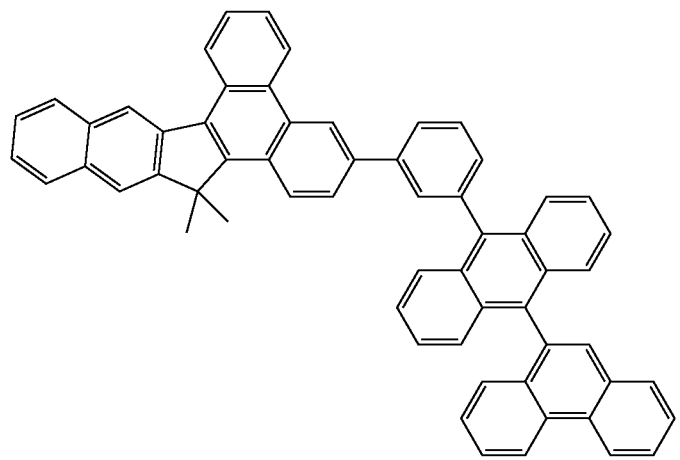
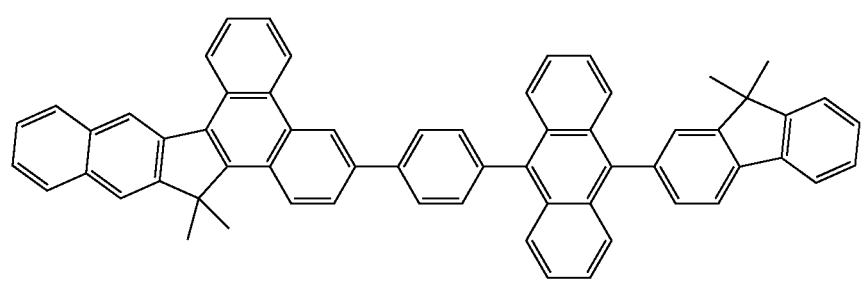
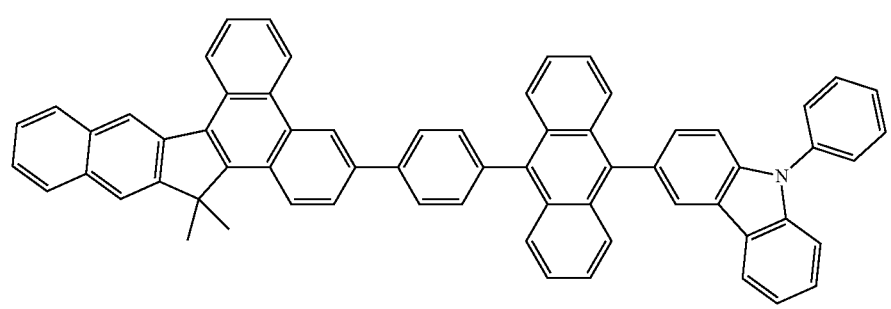
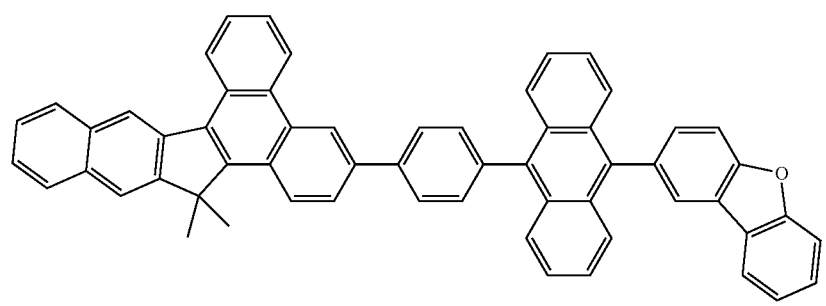

-continued
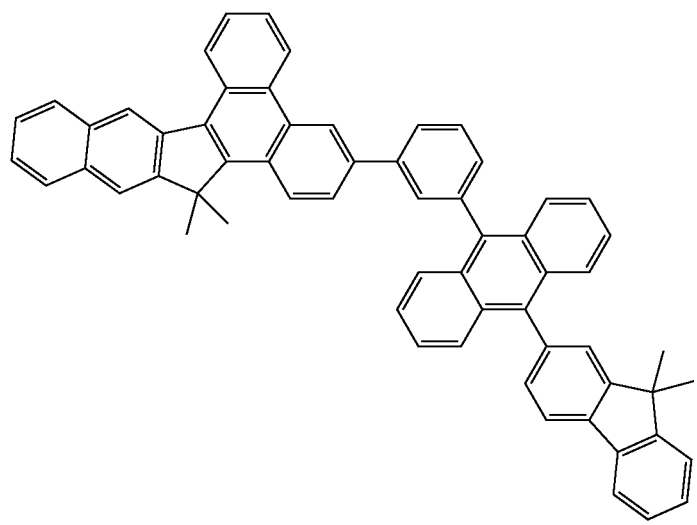
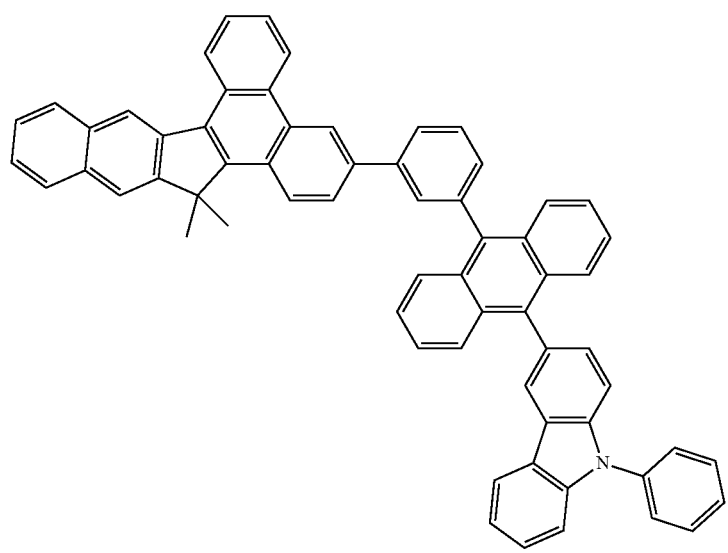
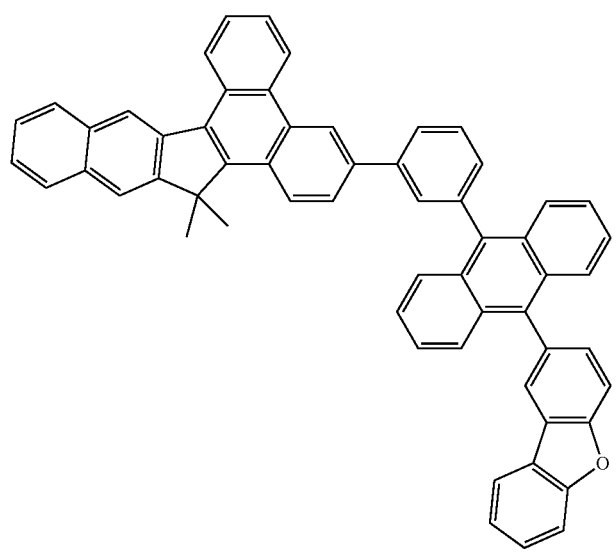

-continued
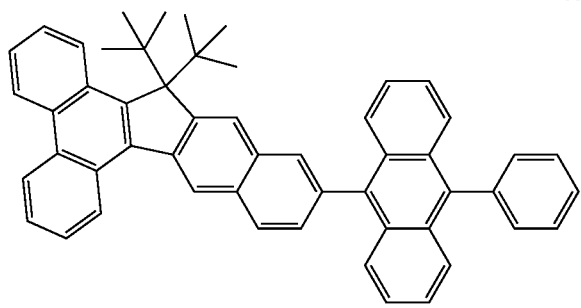
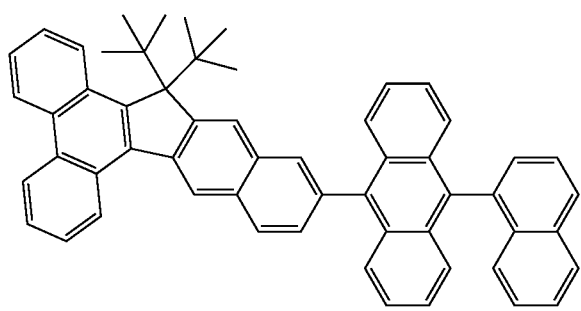
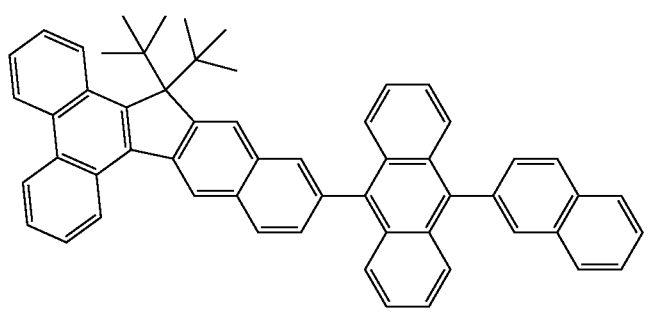
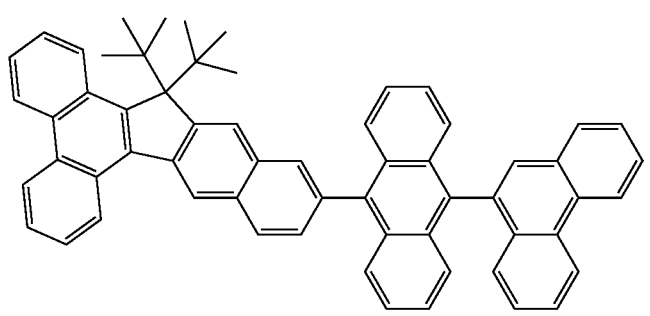
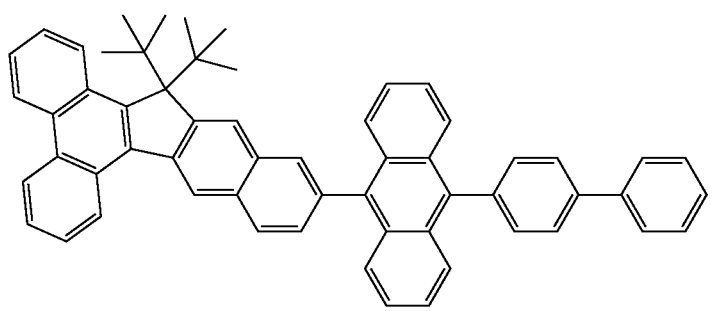

-continued
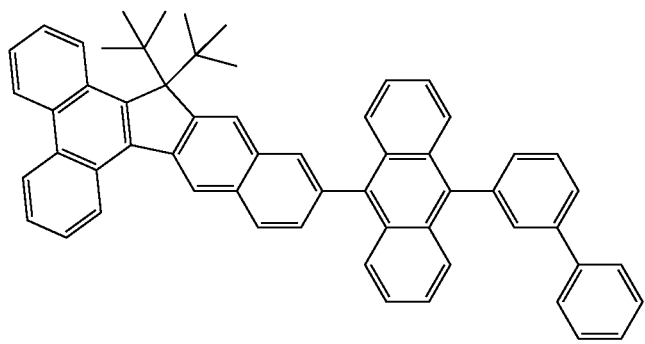
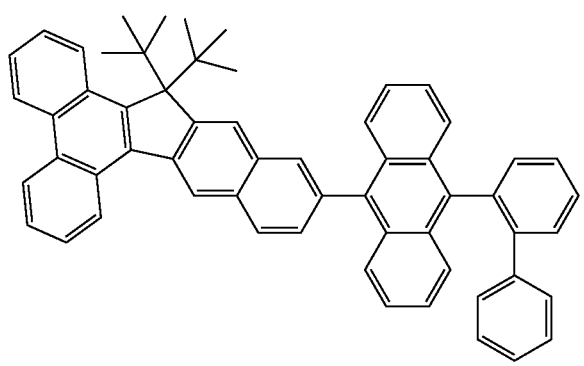
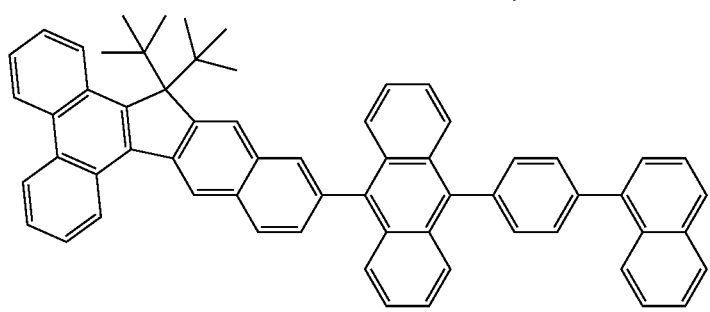
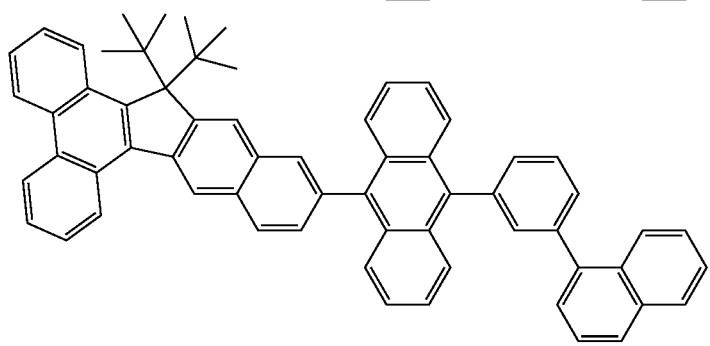
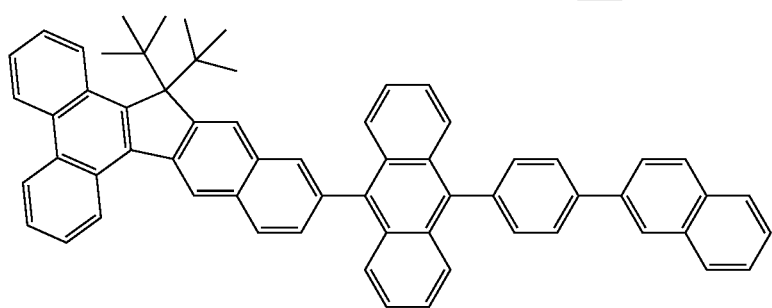

-continued
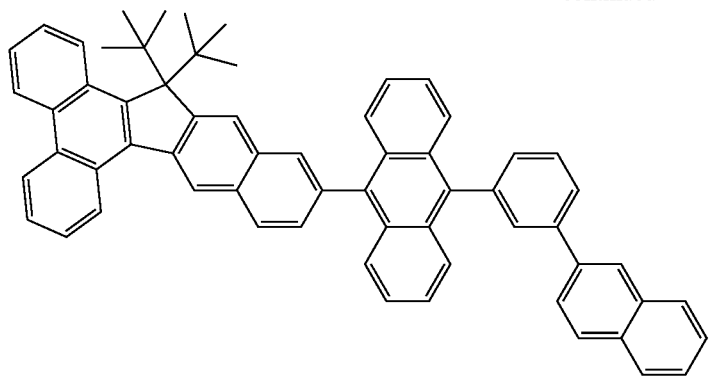
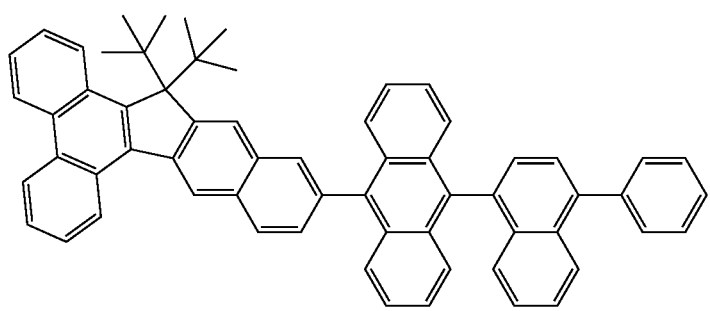
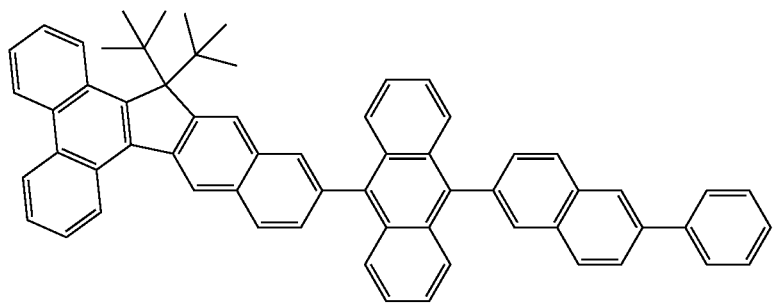
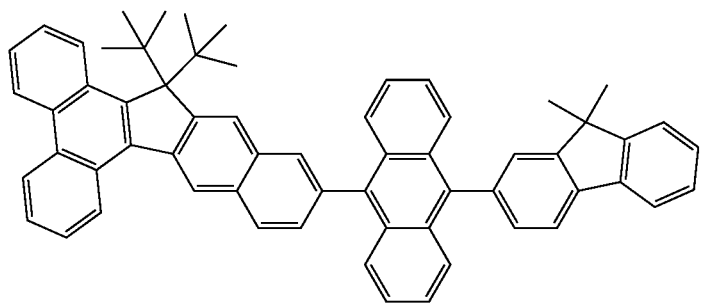
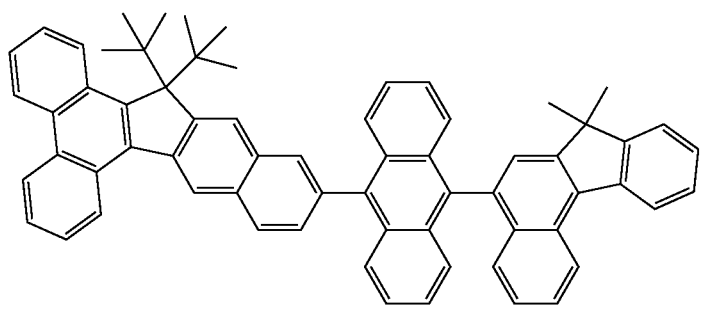

-continued
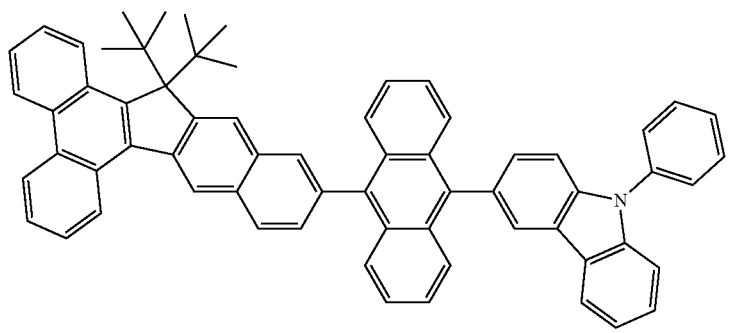
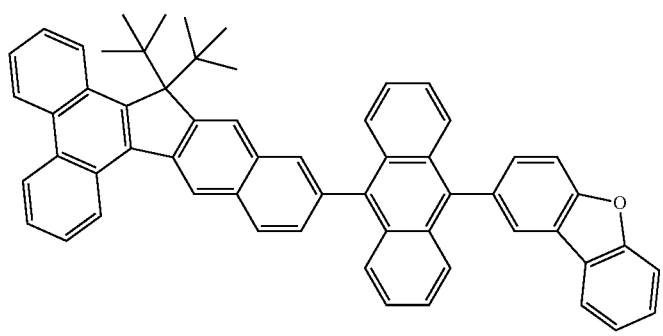
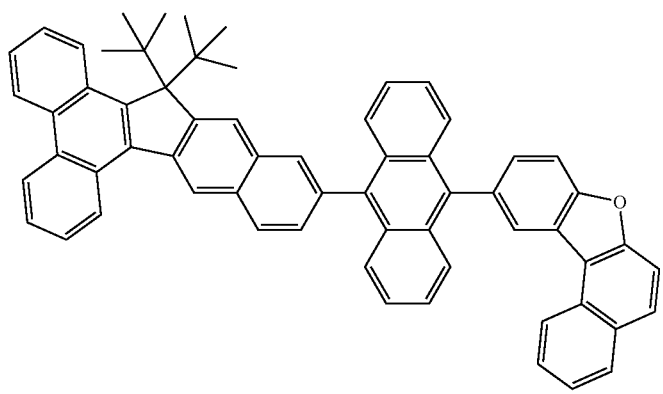
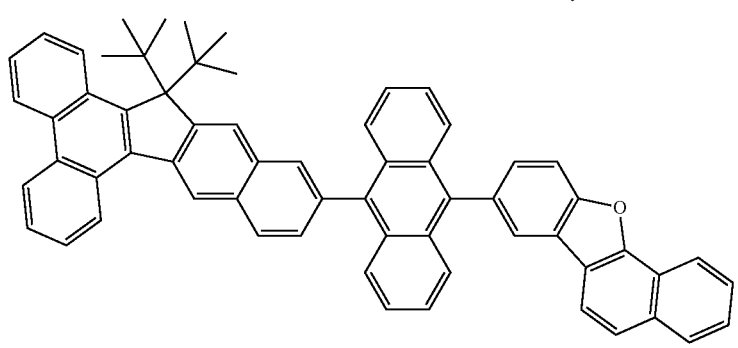
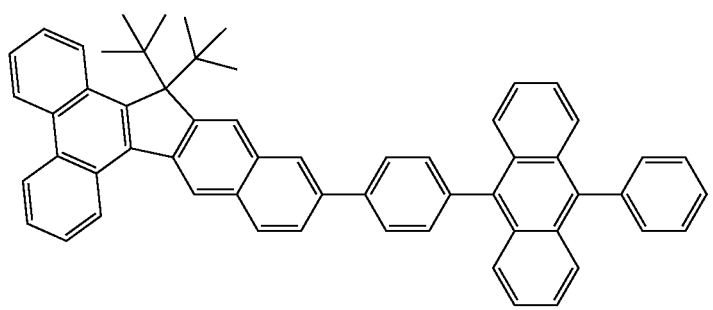

-continued
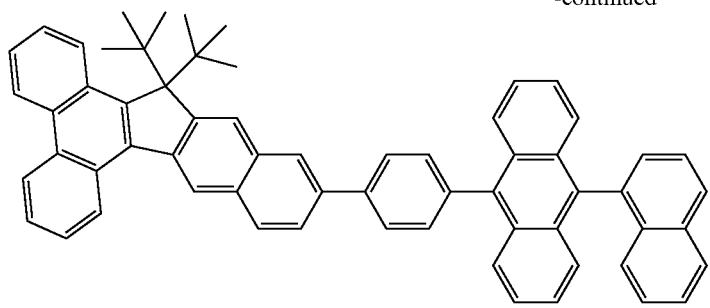
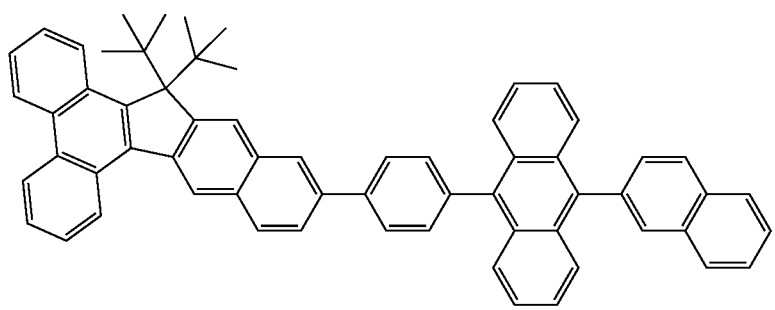
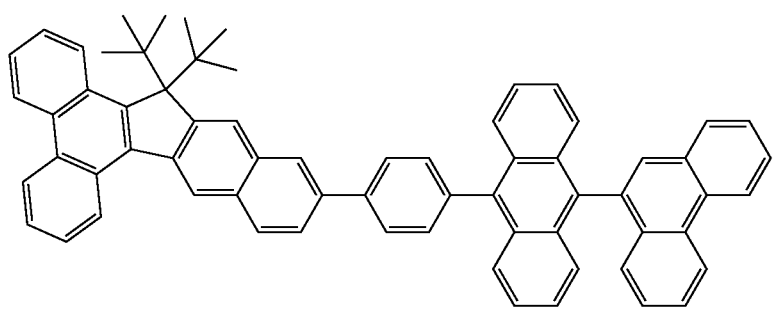
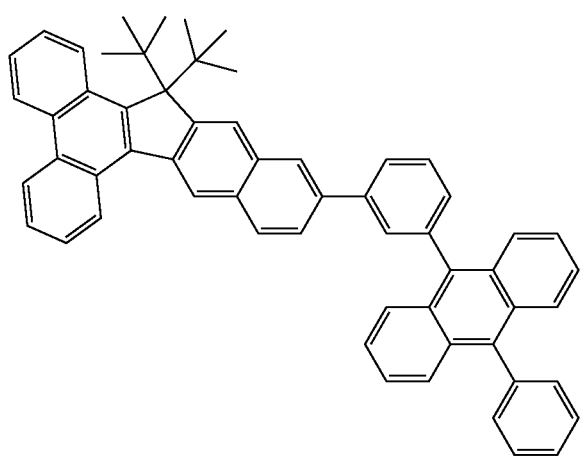

-continued
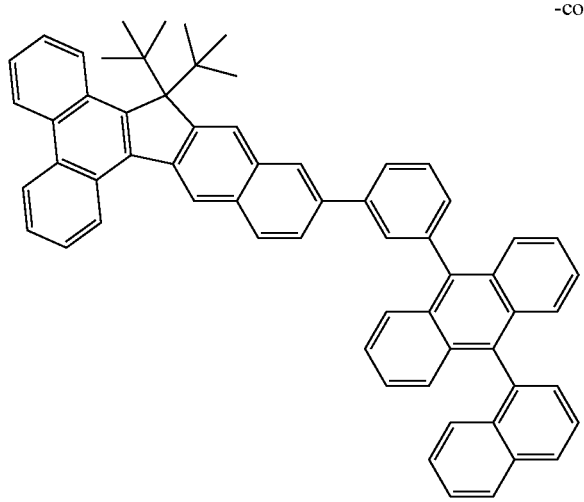
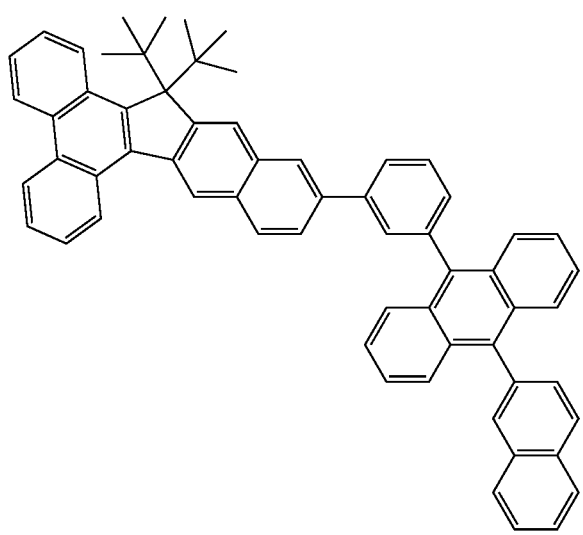
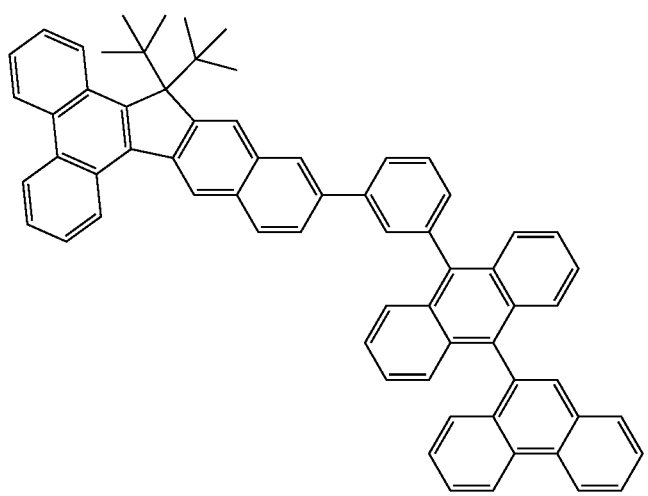

-continued
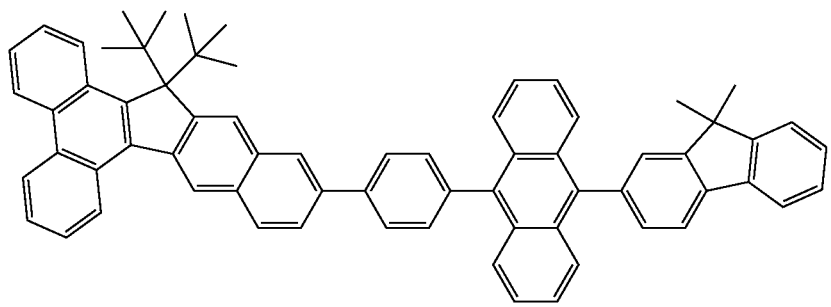
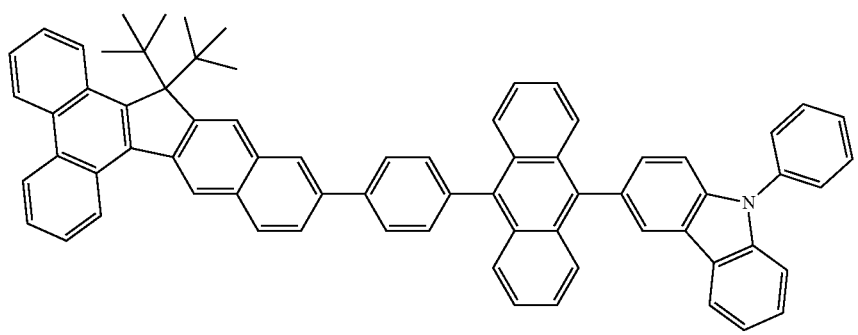
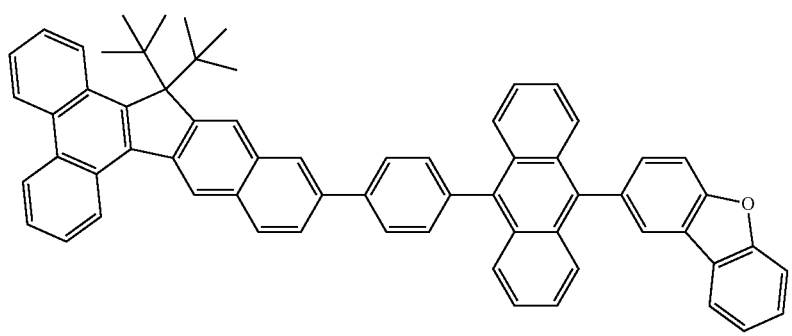
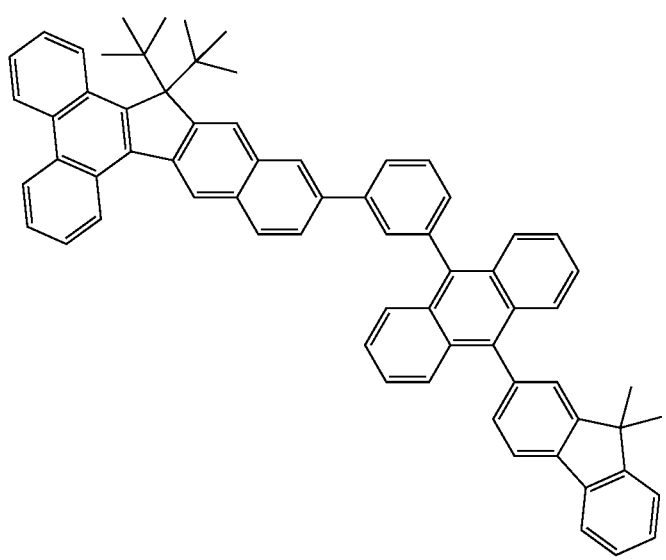

-continued
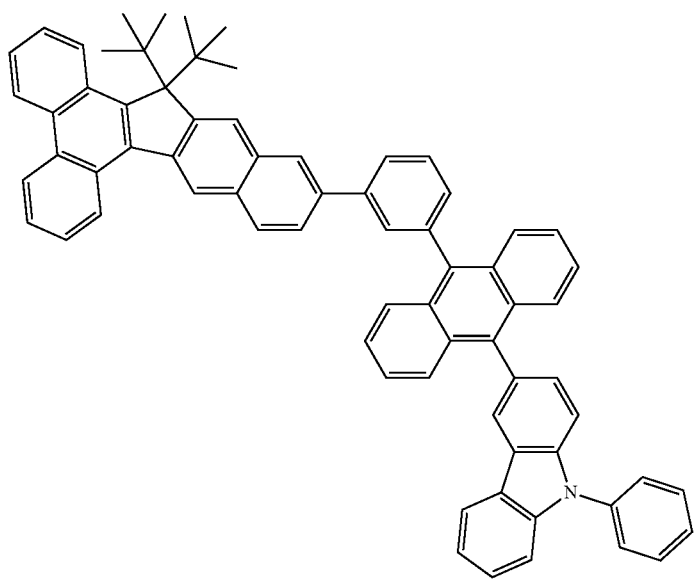
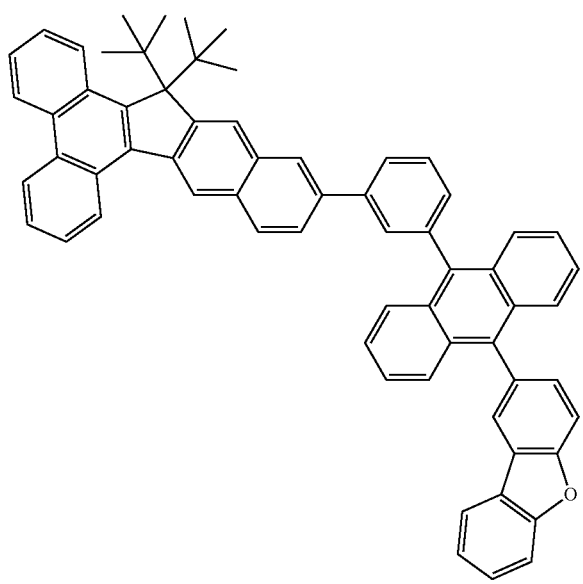
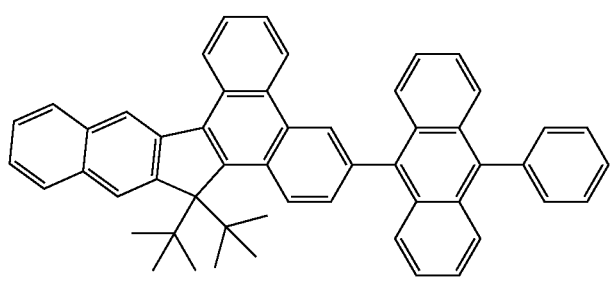
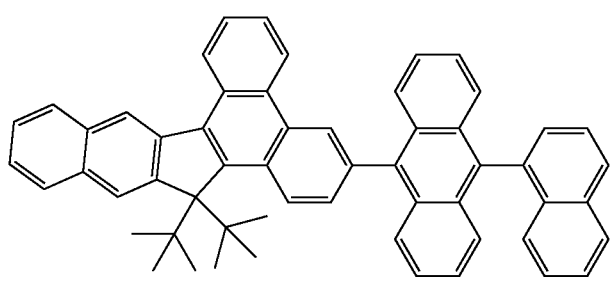

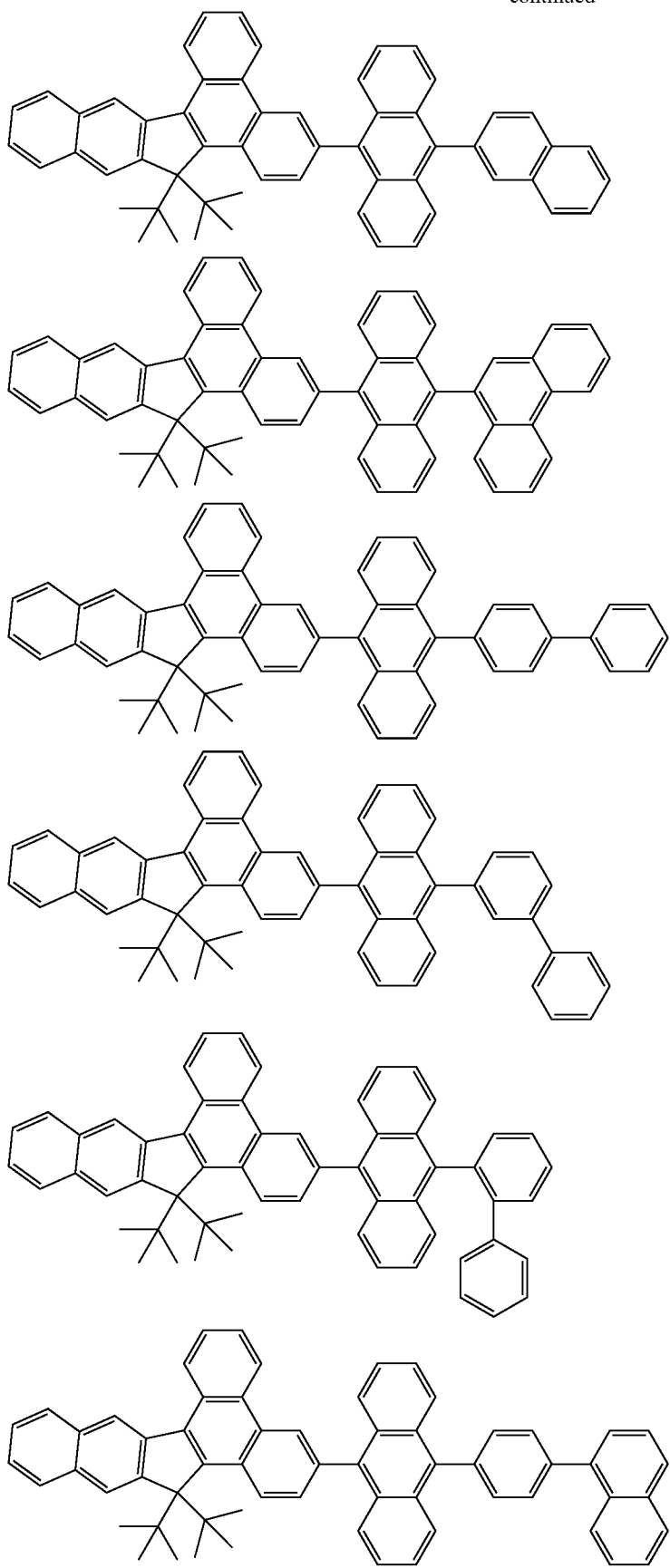

-continued
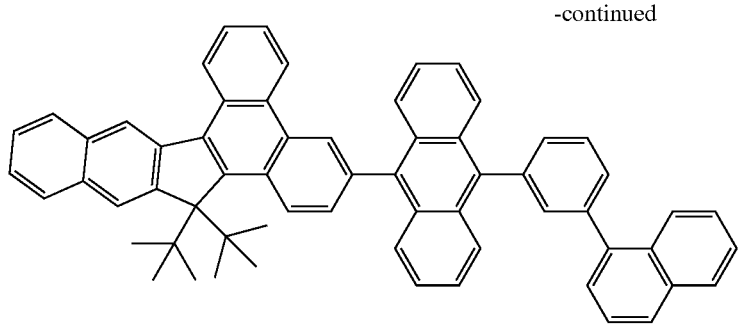
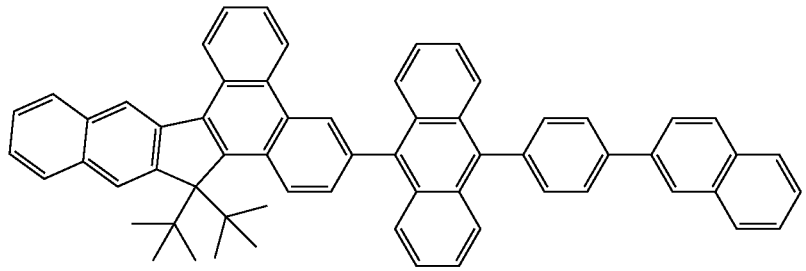
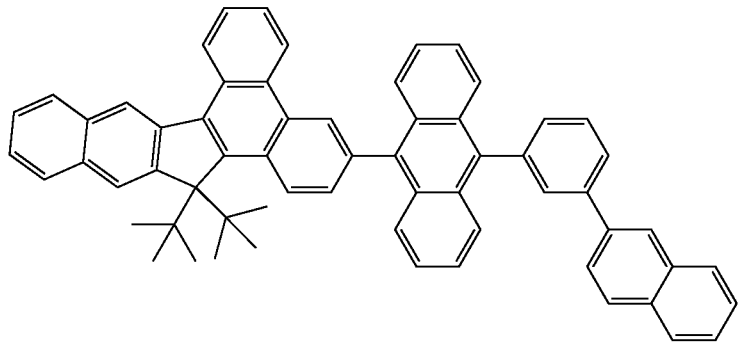
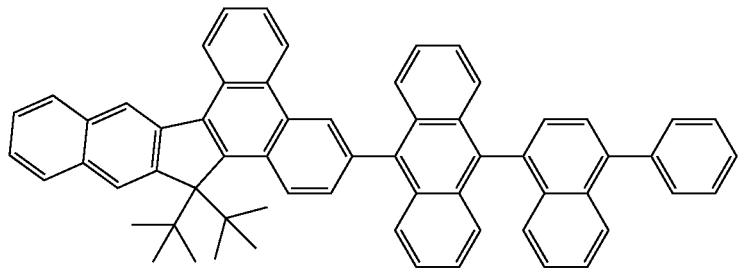
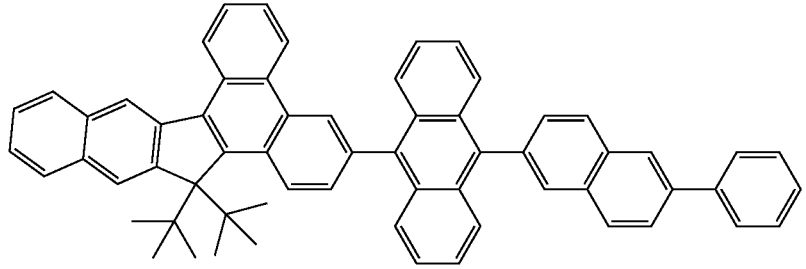
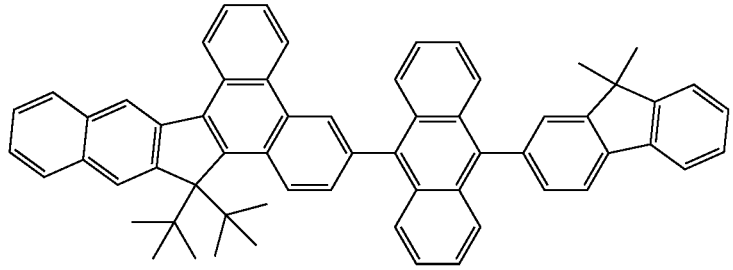

-continued
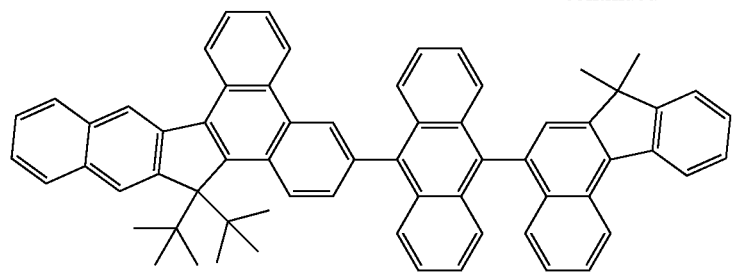
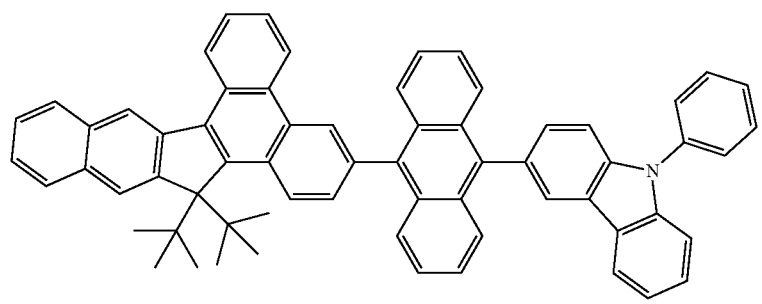
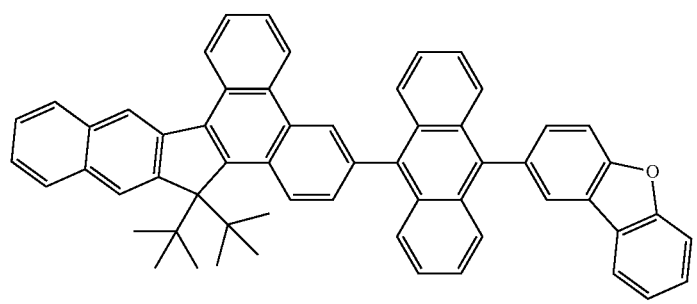
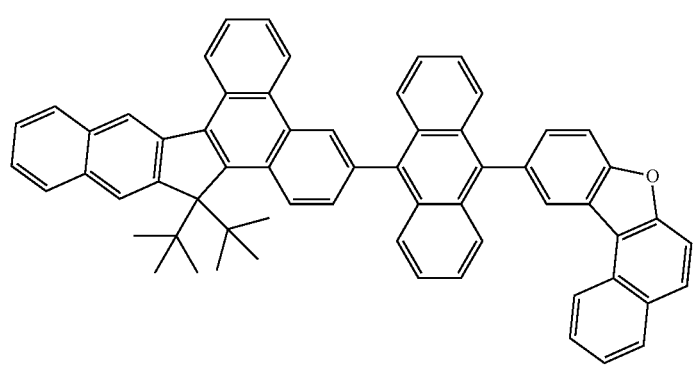
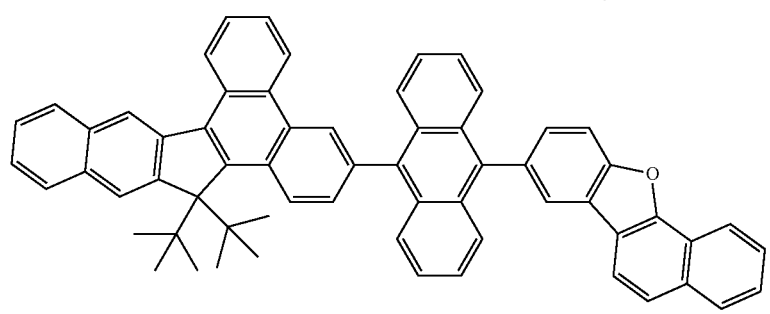

-continued
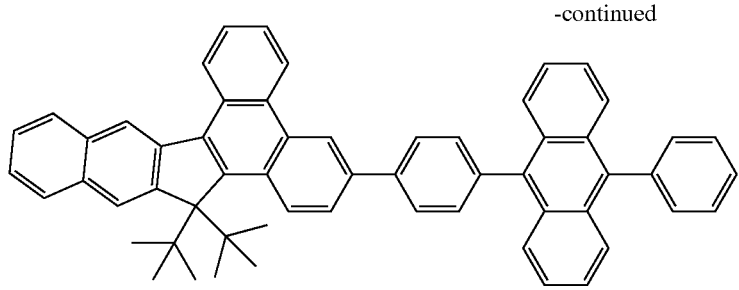
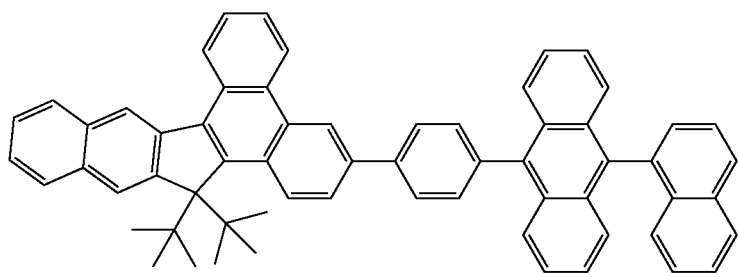
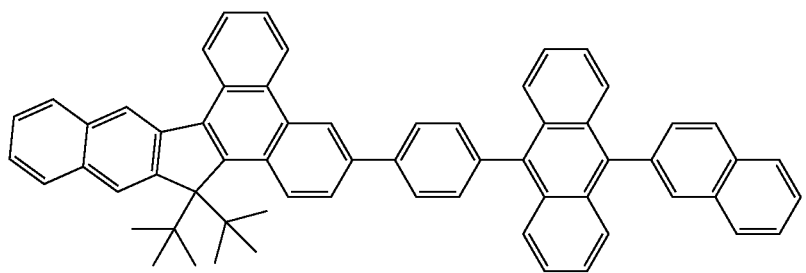
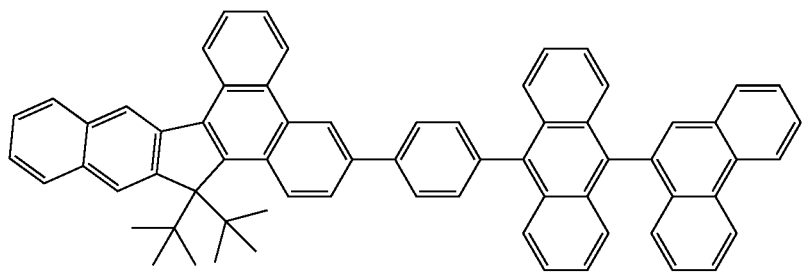
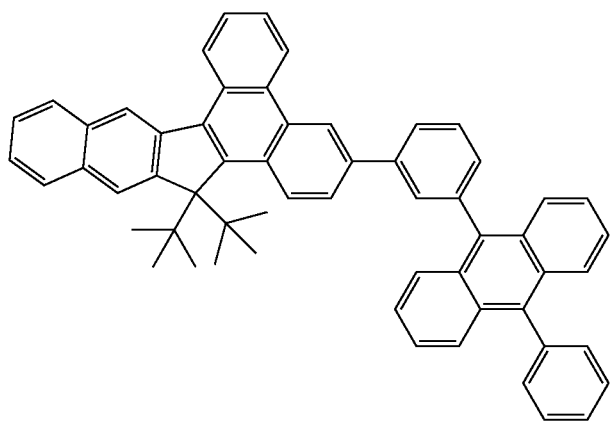

-continued
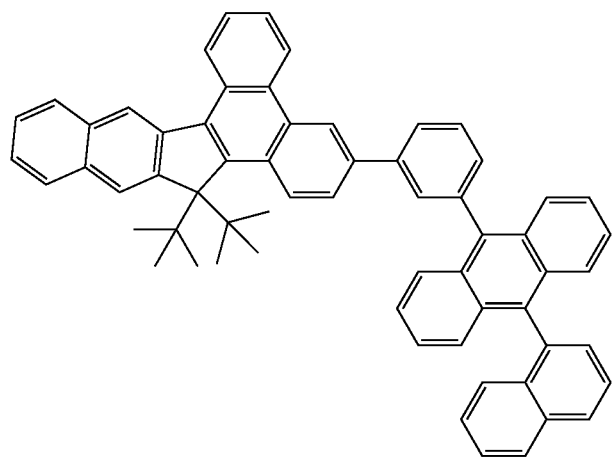
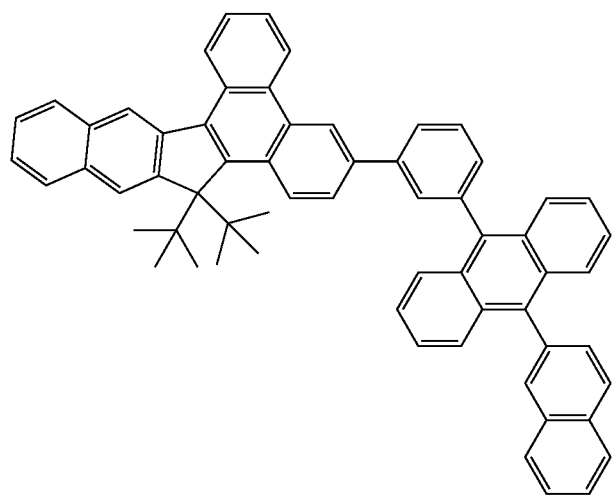
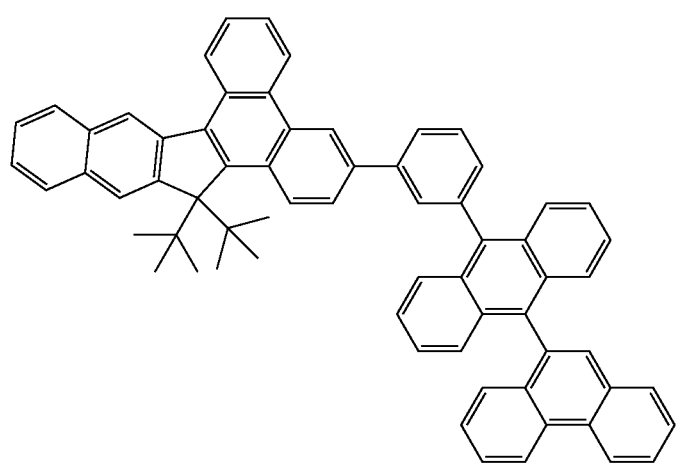
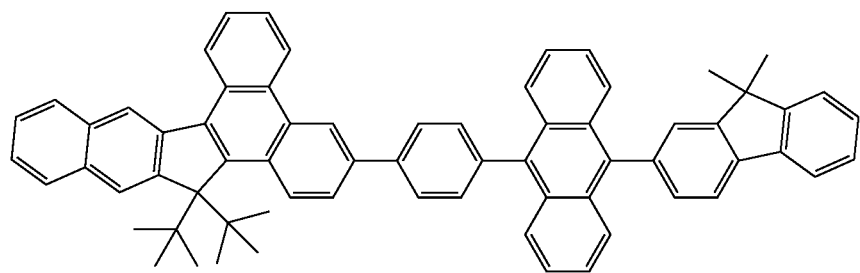

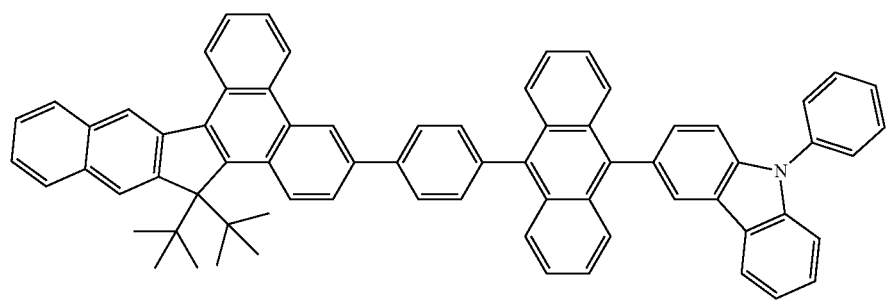
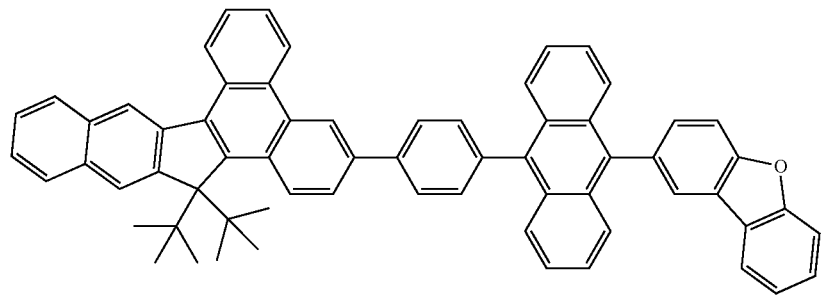
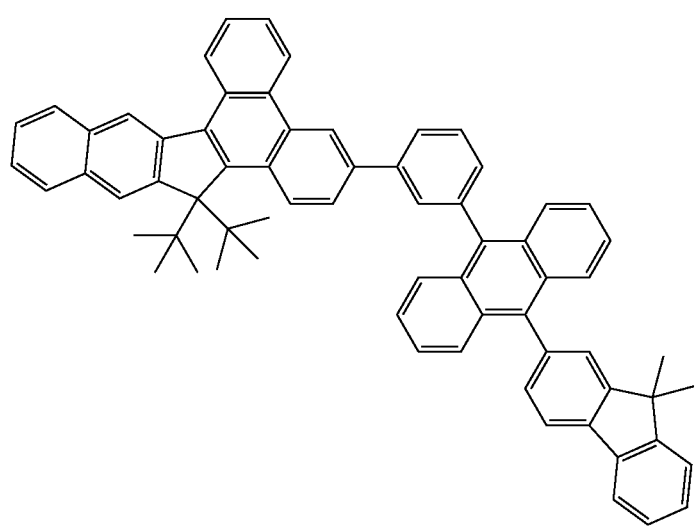
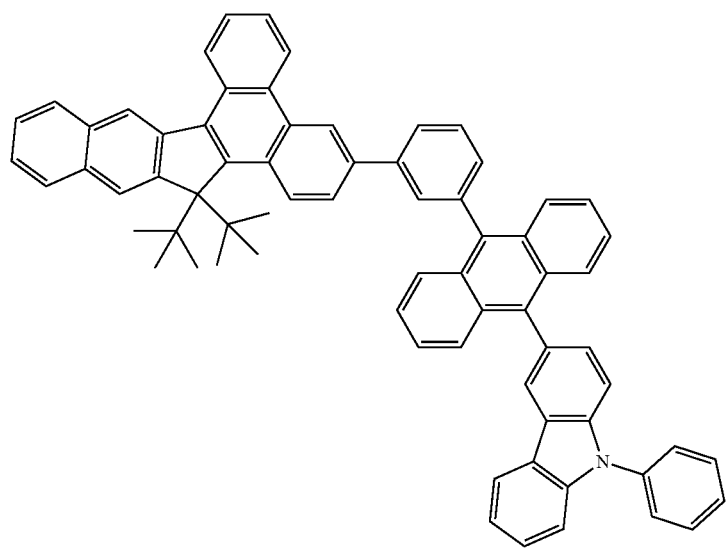

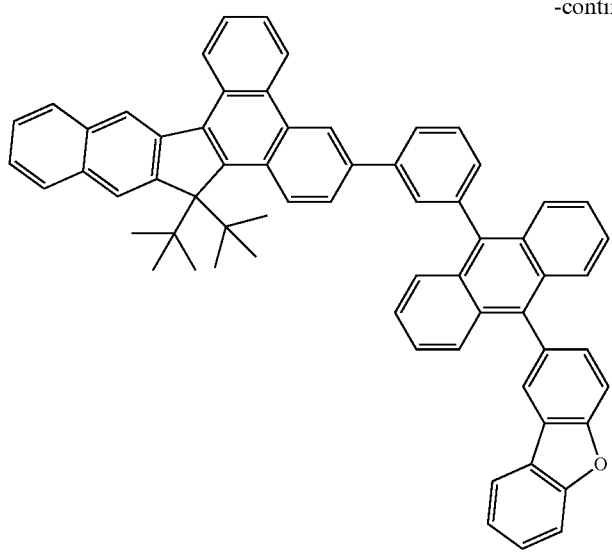
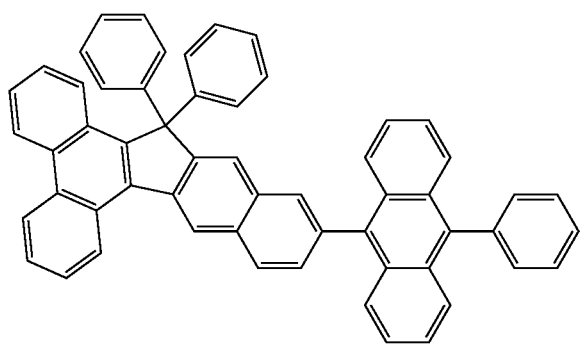
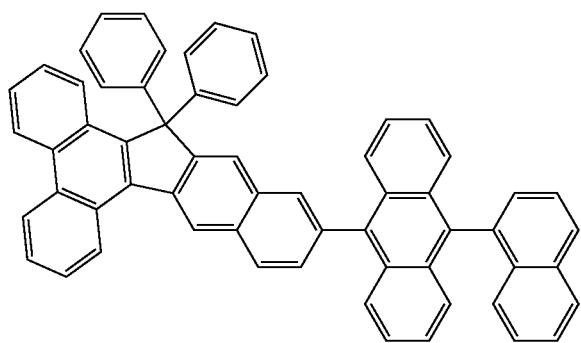
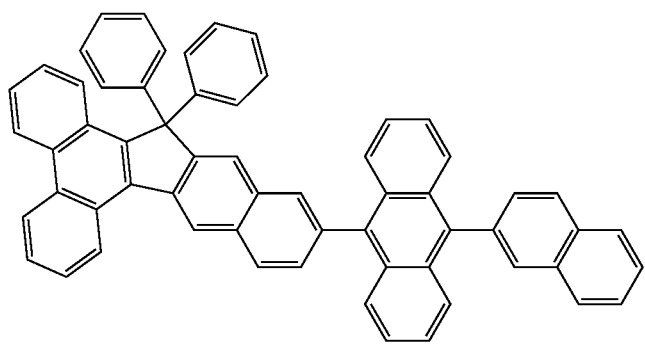

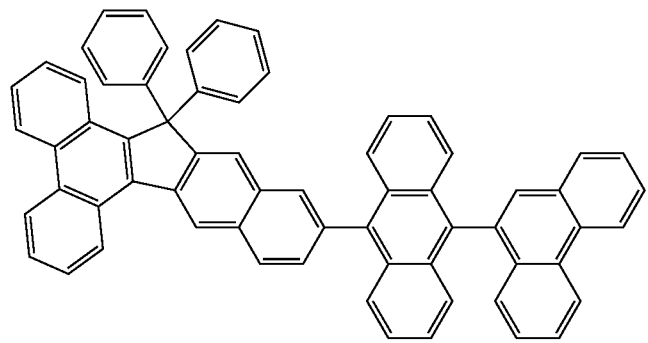
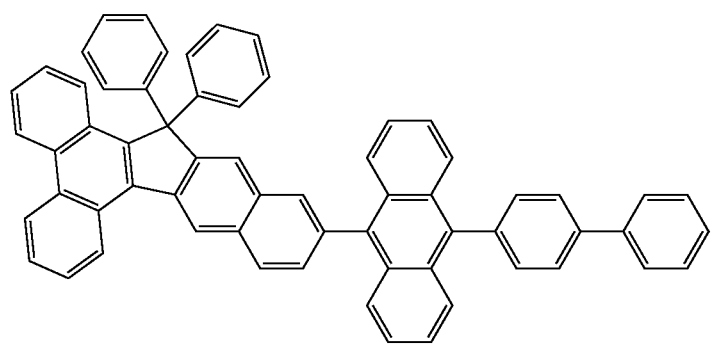
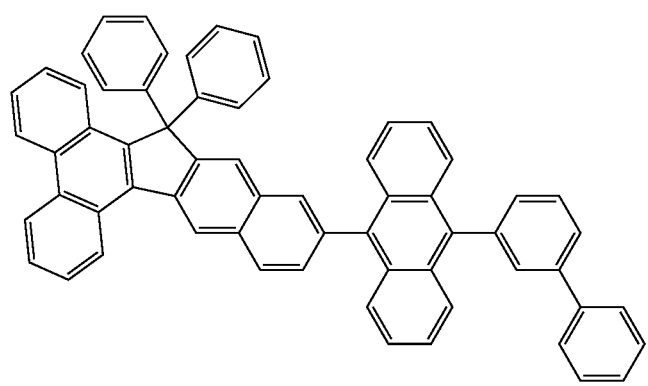
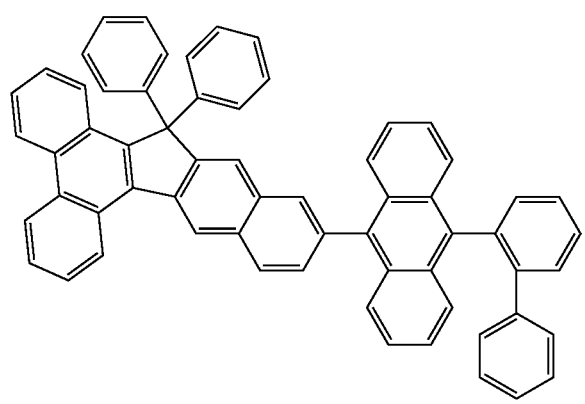

-continued
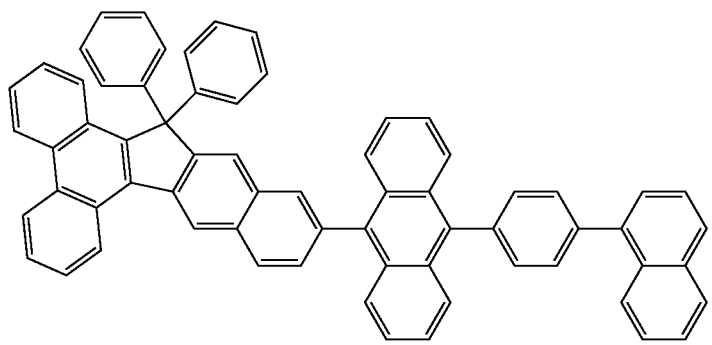
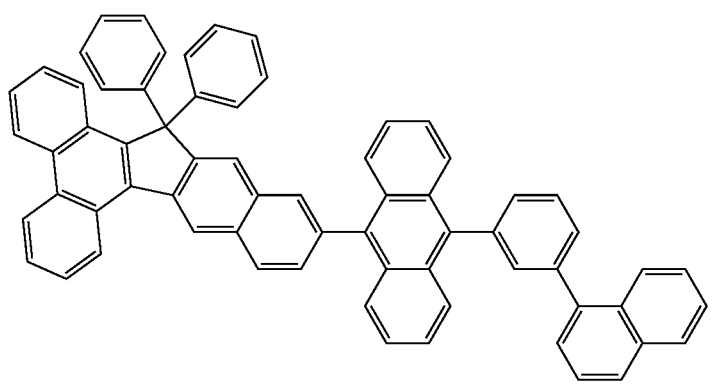
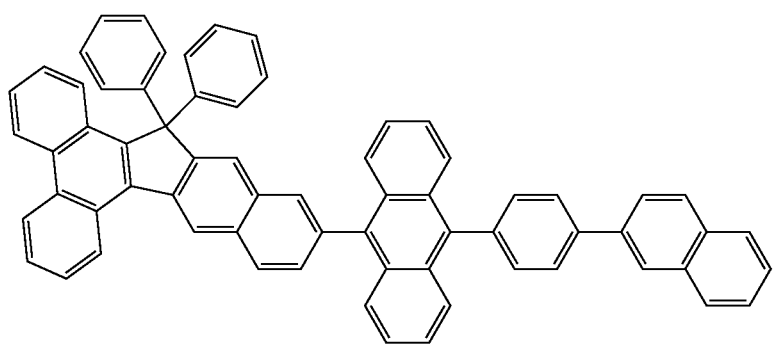
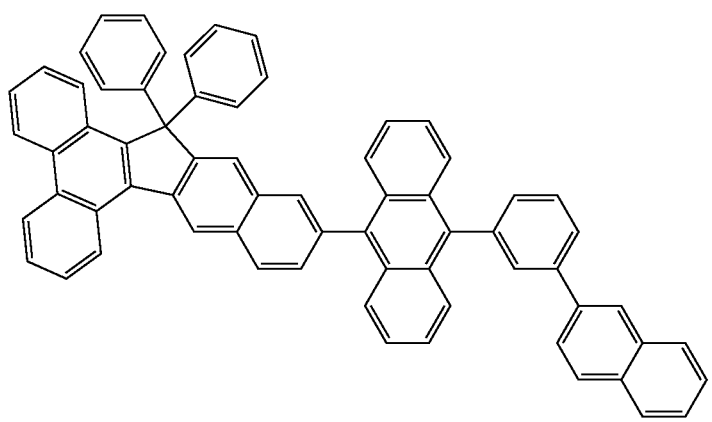

-continued
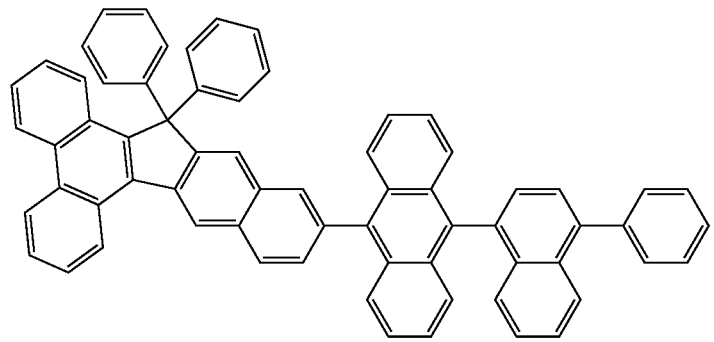
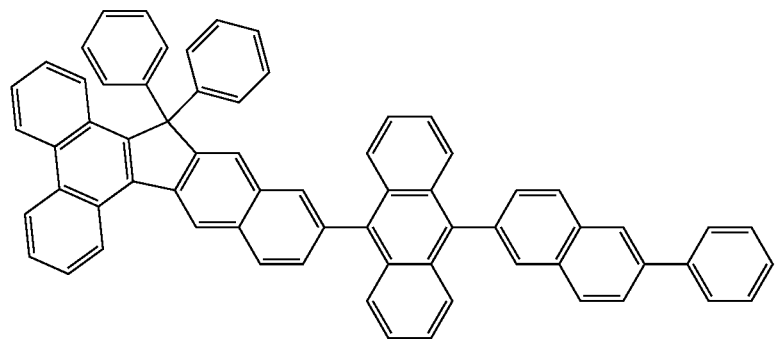
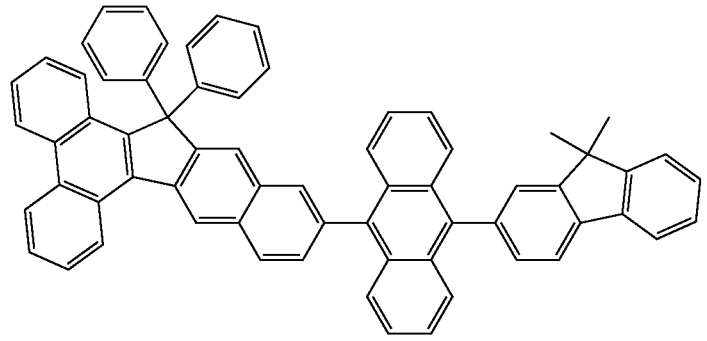
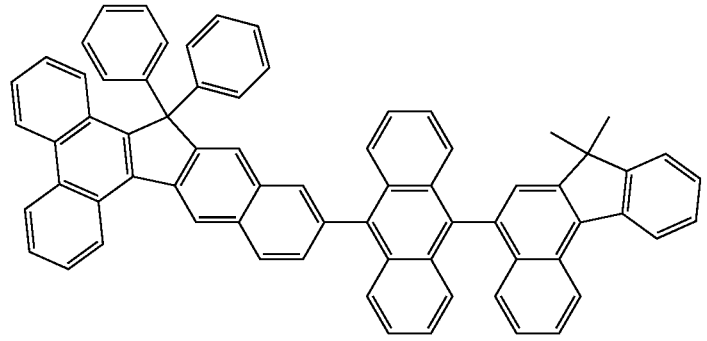
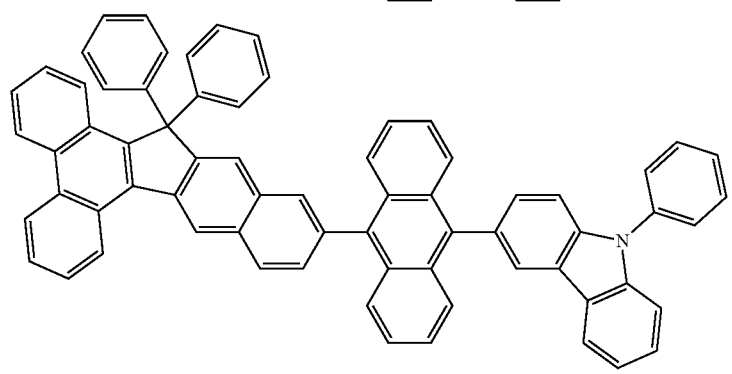

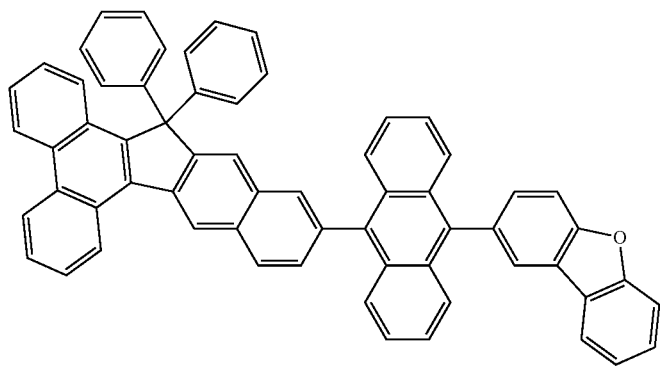
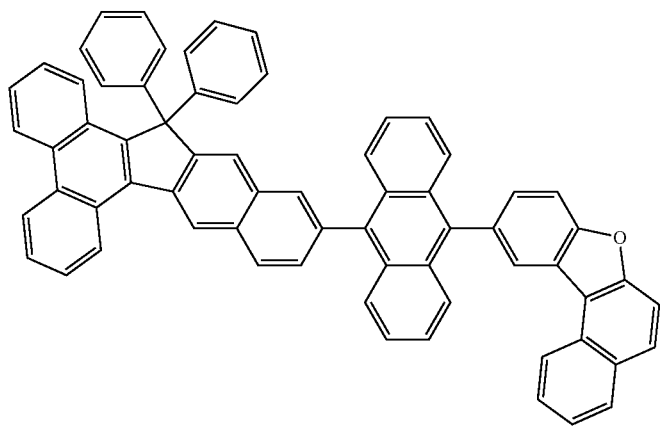
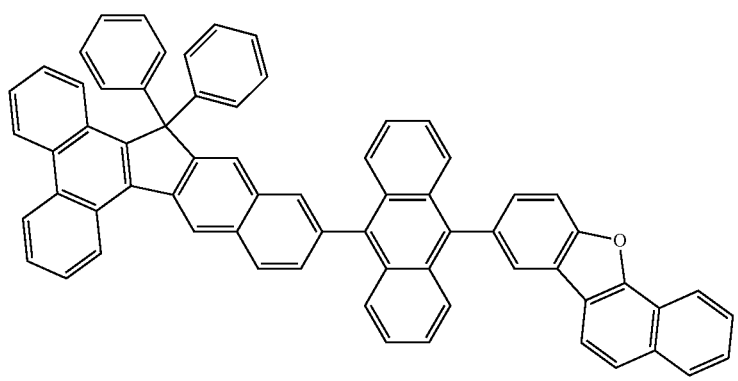
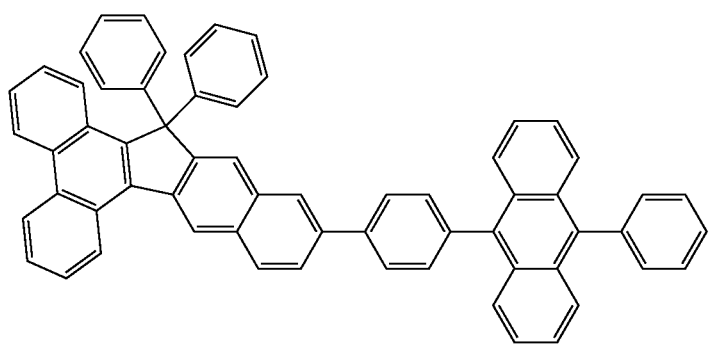

-continued

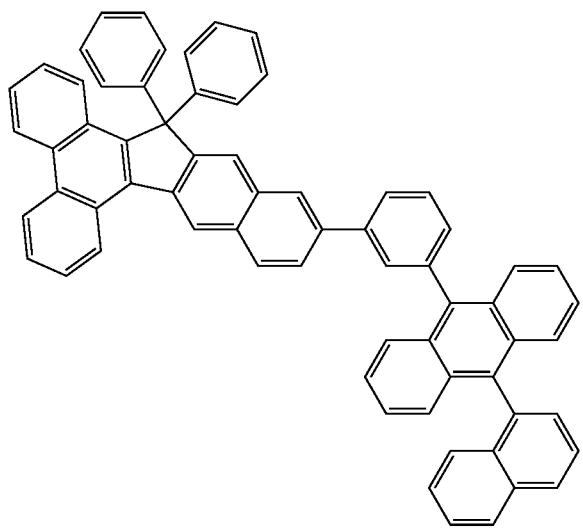
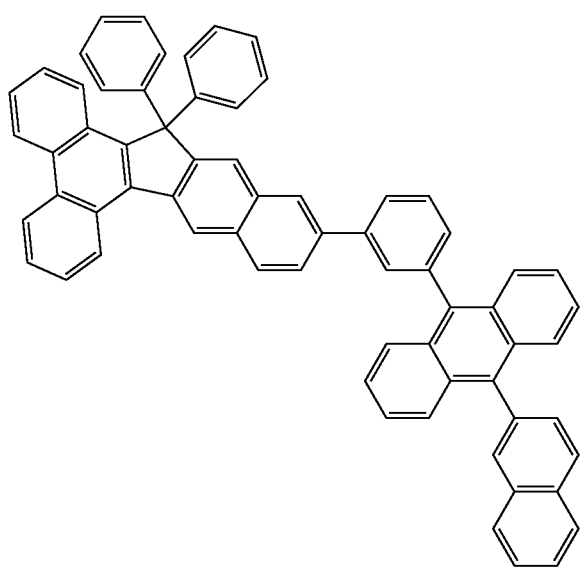
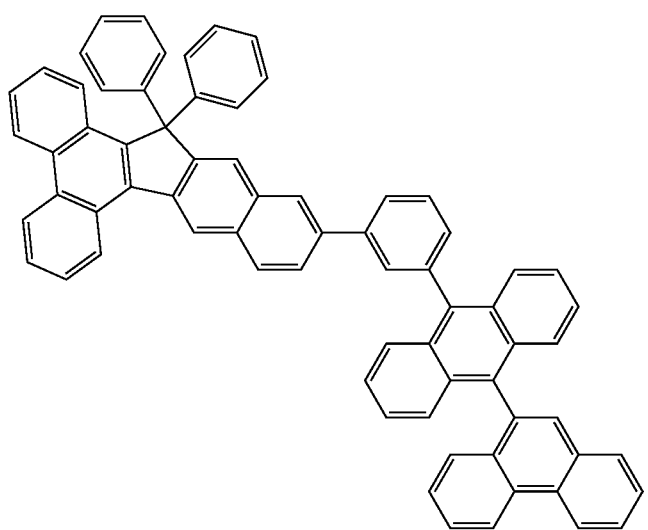

-continued
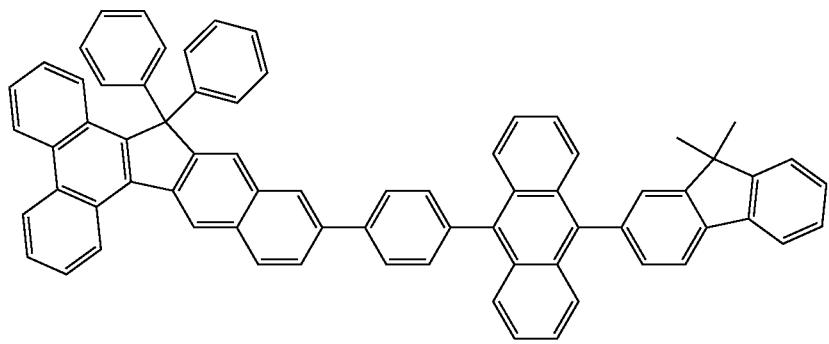
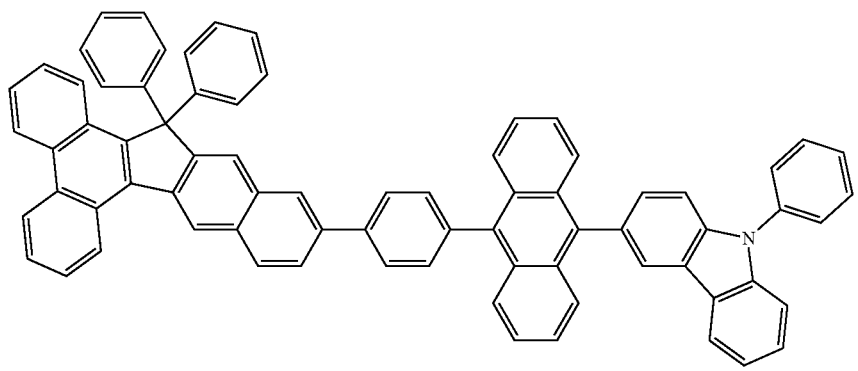
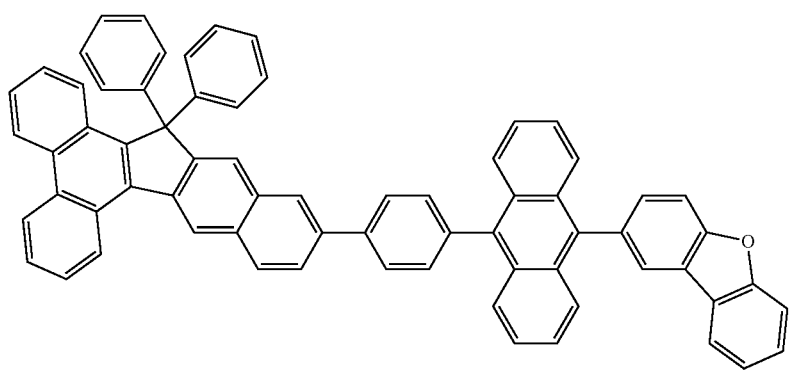
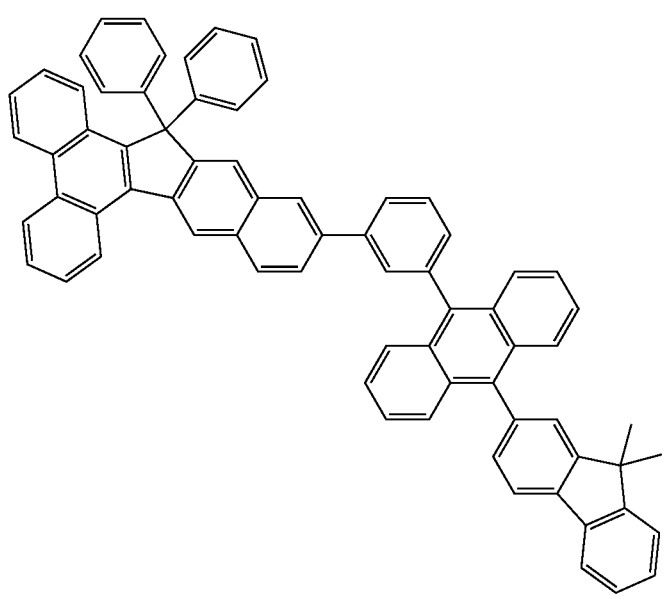

-continued
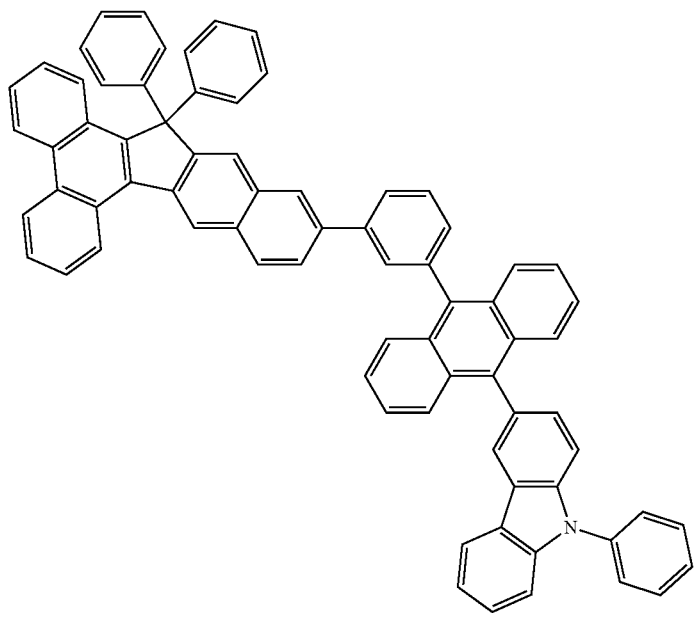
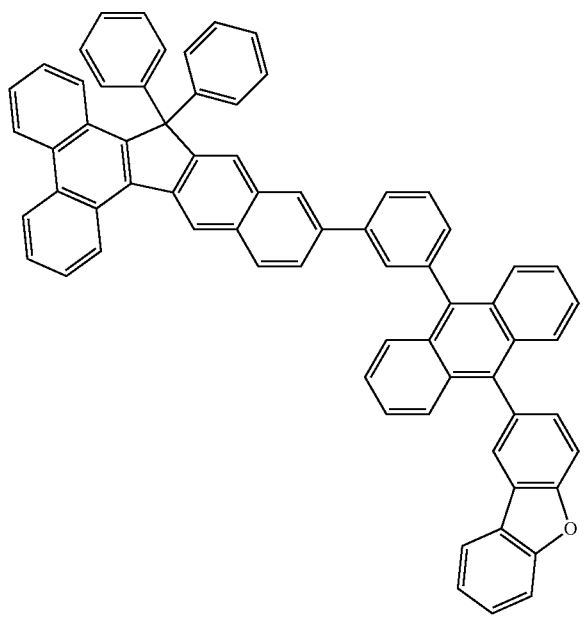
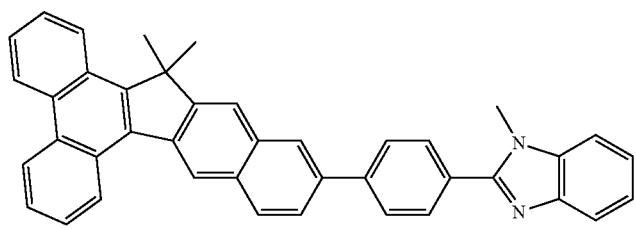
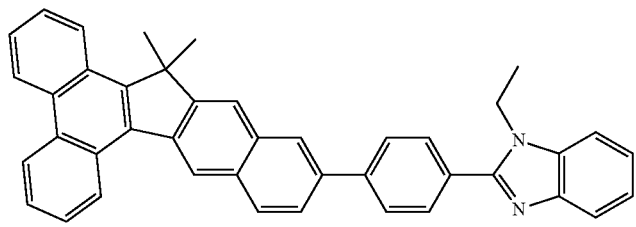

-continued
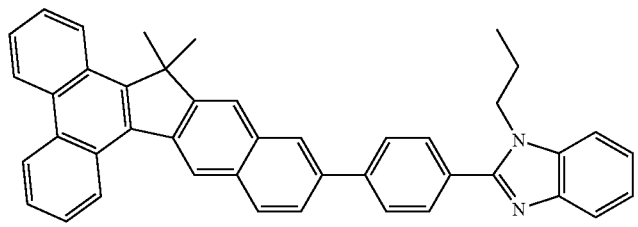
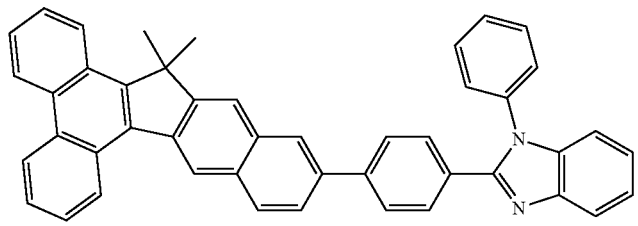
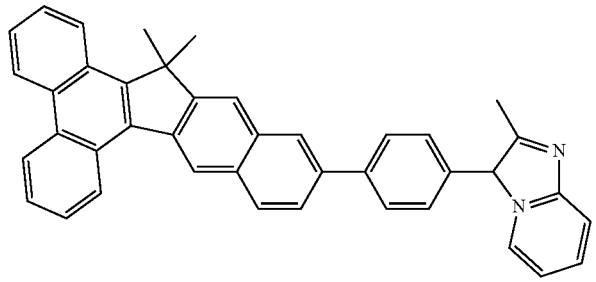
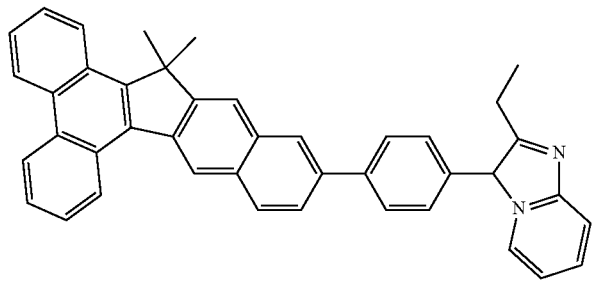
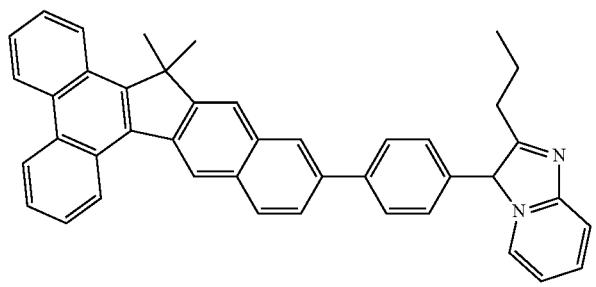
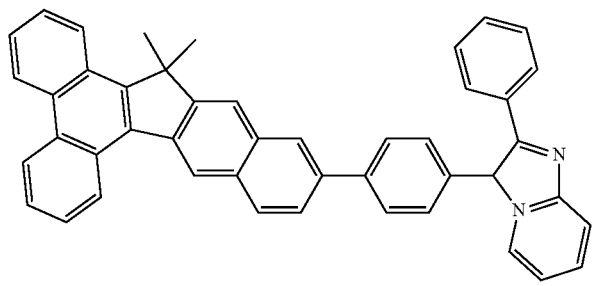

-continued
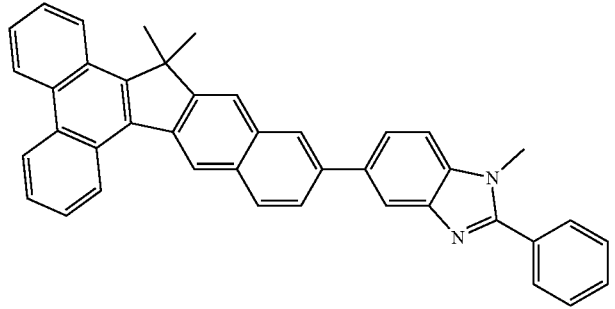
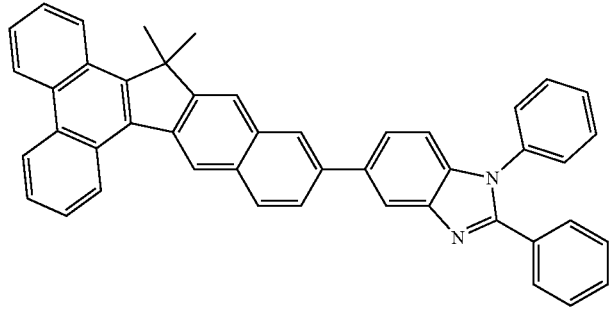
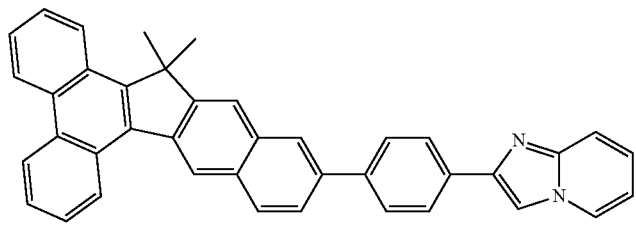
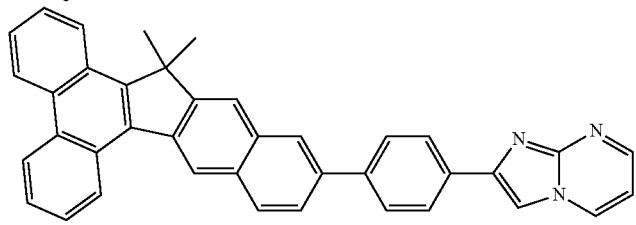
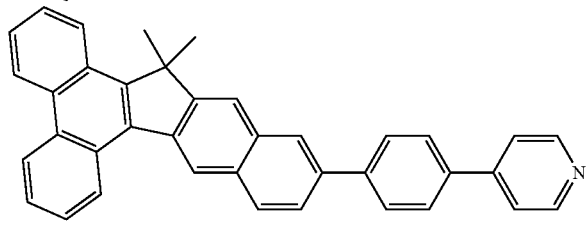
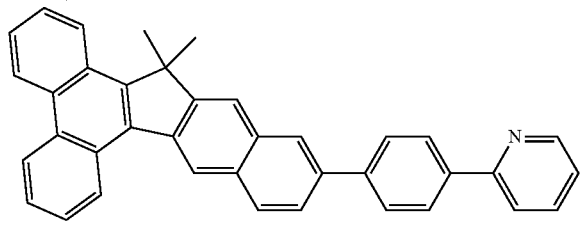
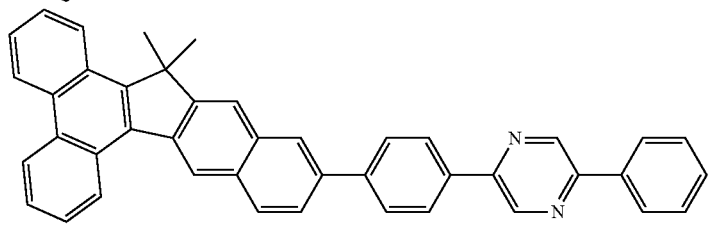

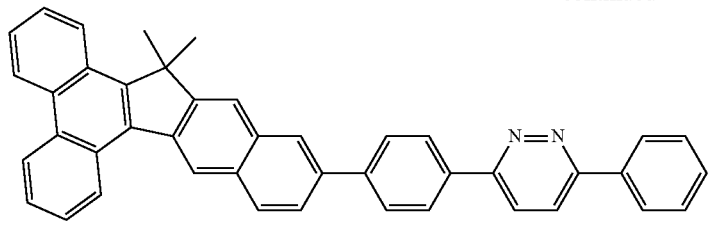
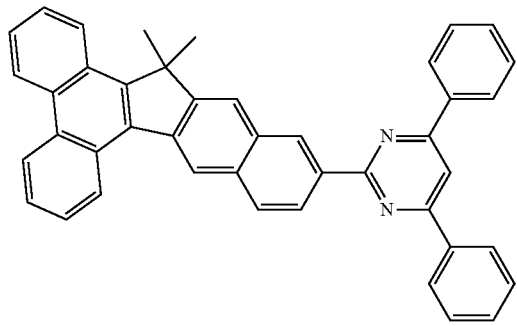
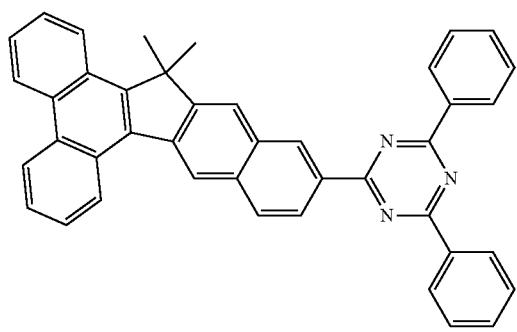
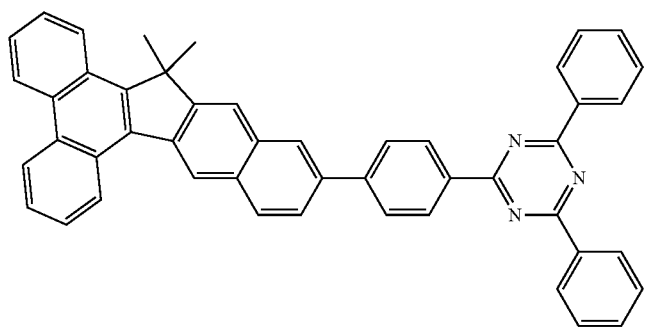

-continued
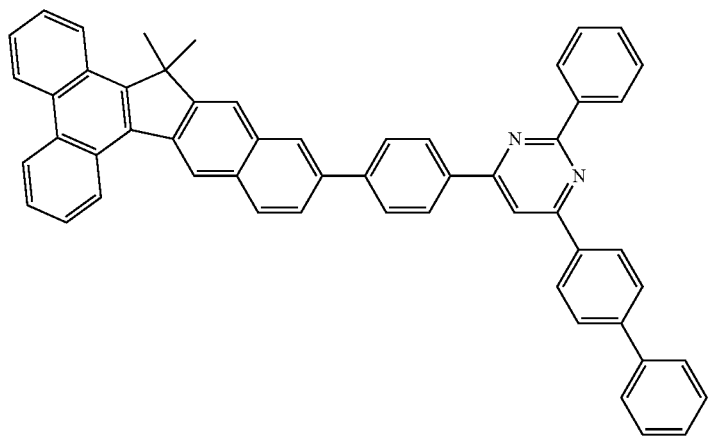
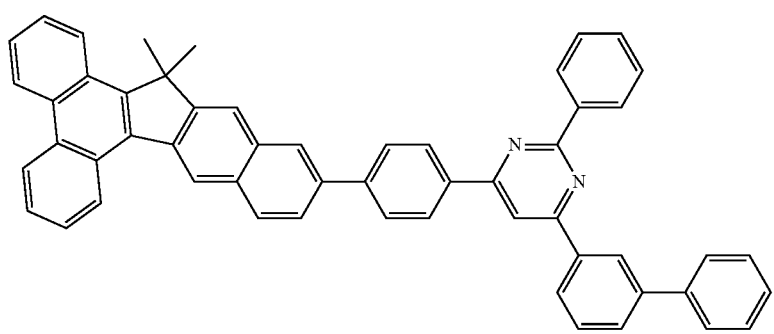
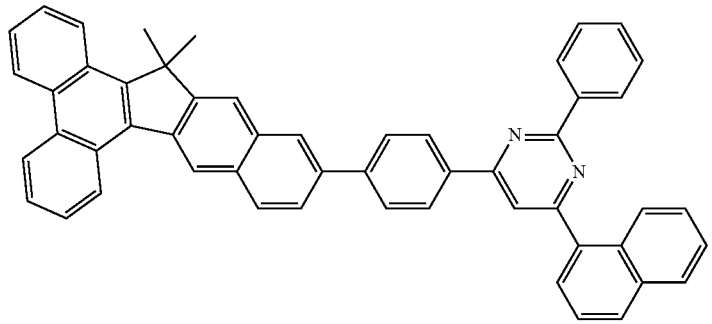
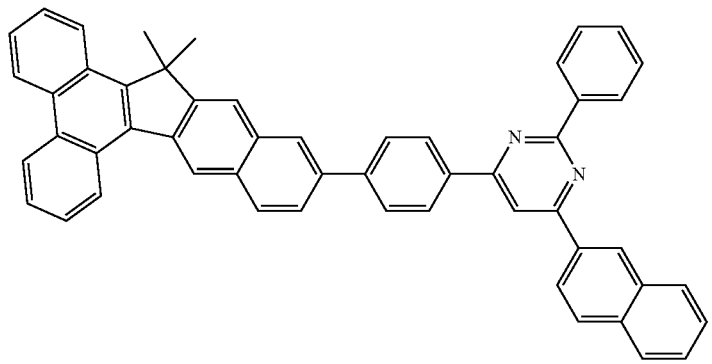

-continued
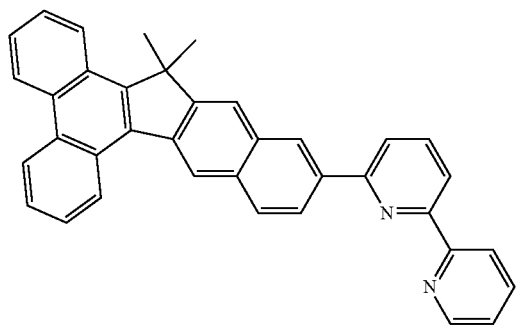
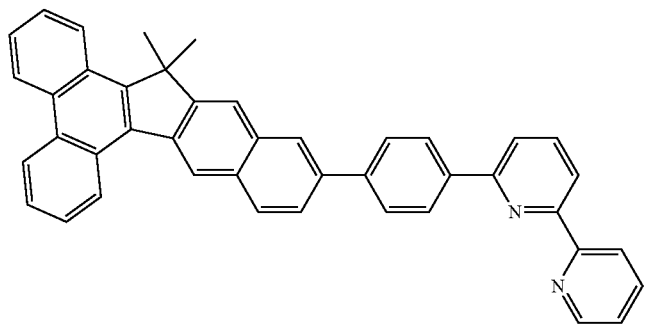
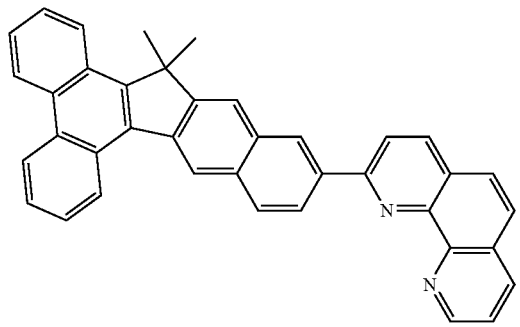
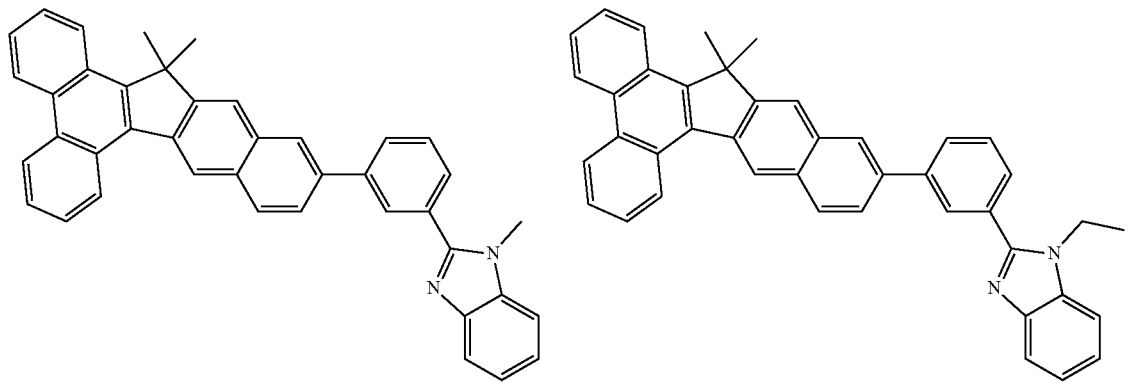

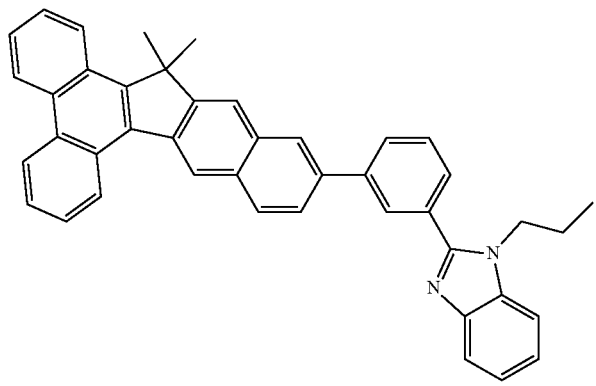
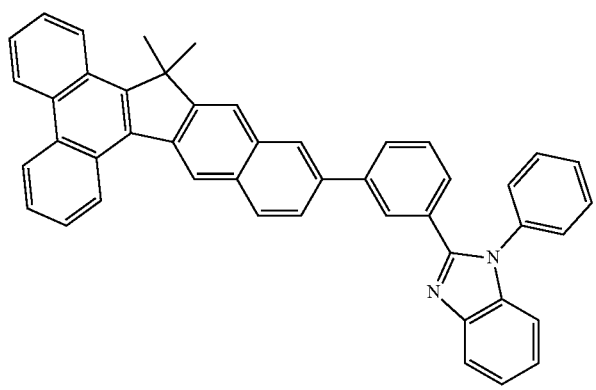
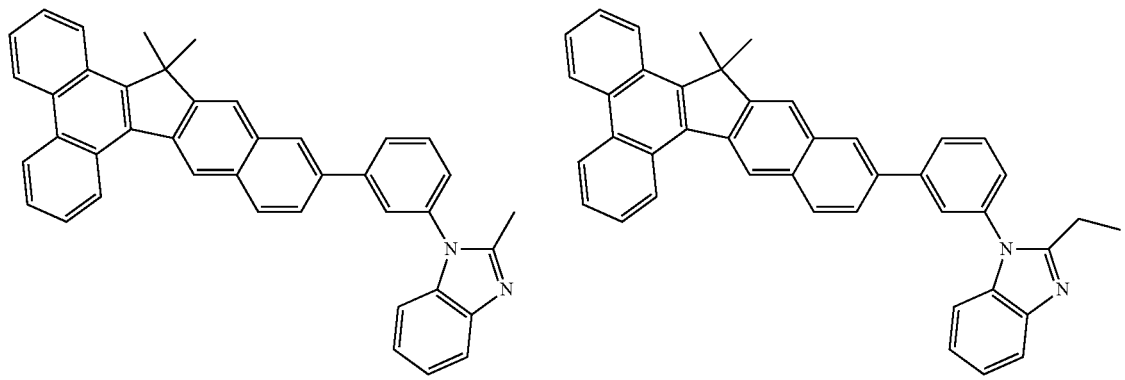
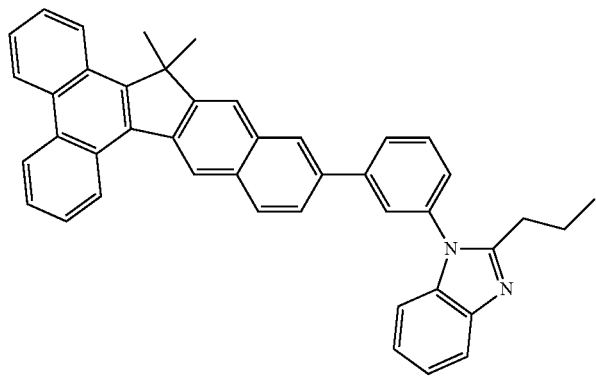

-continued
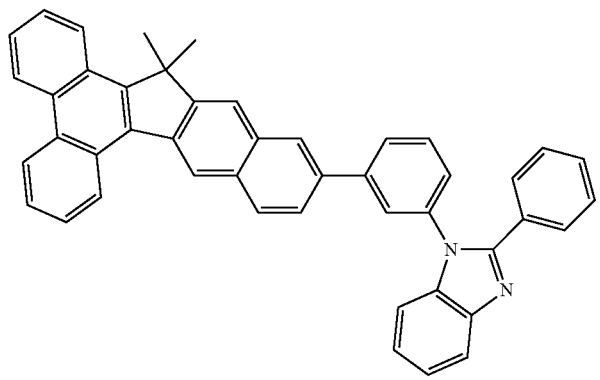
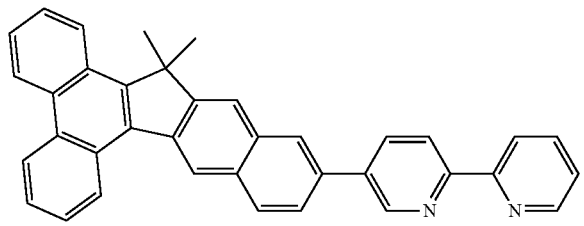
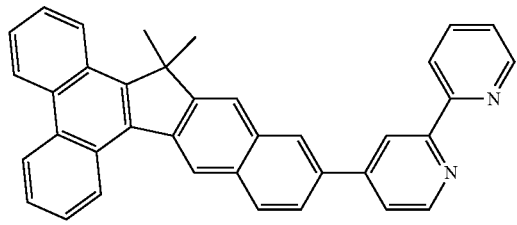
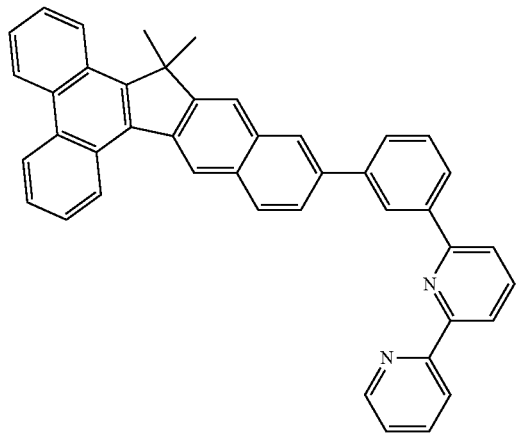
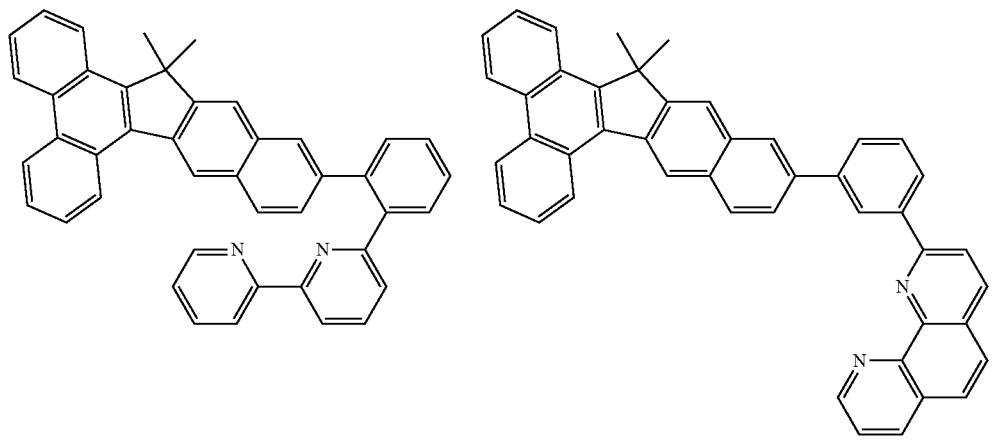

327
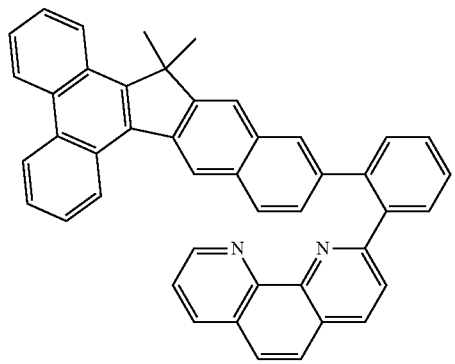
328
-continued
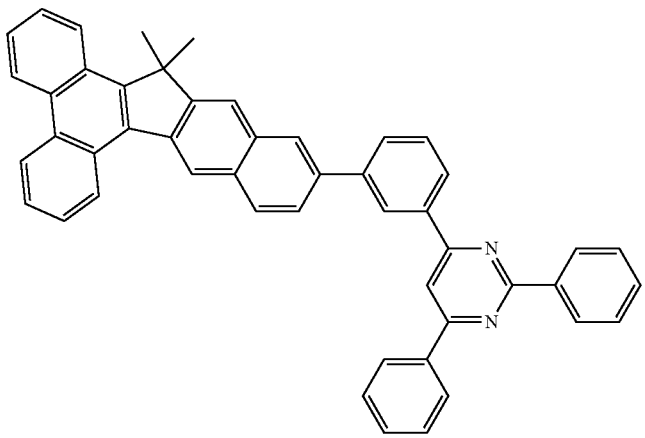
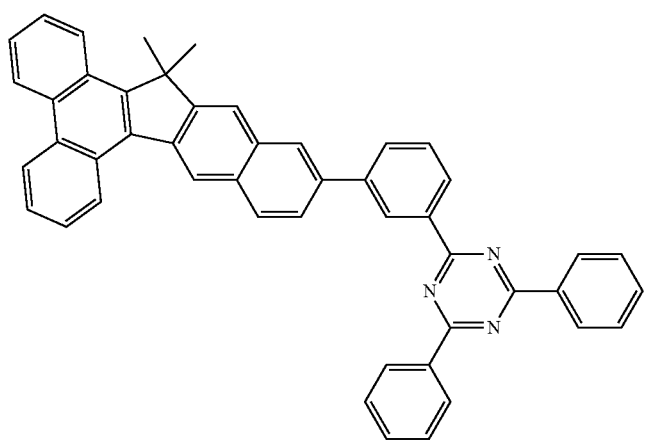
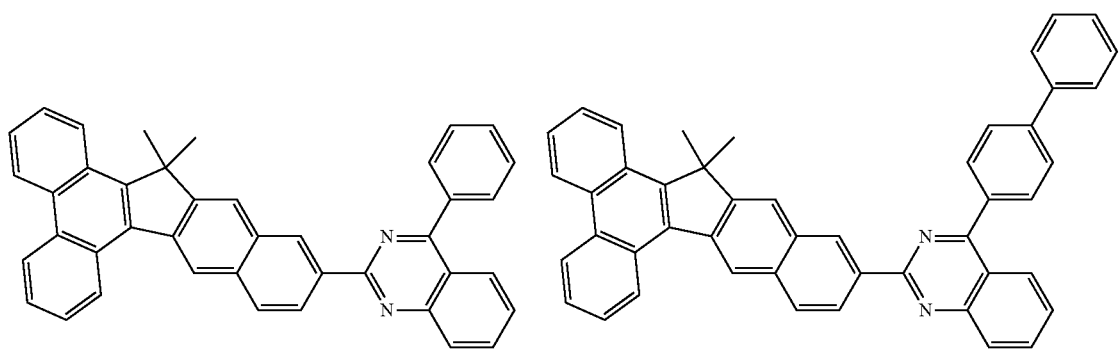
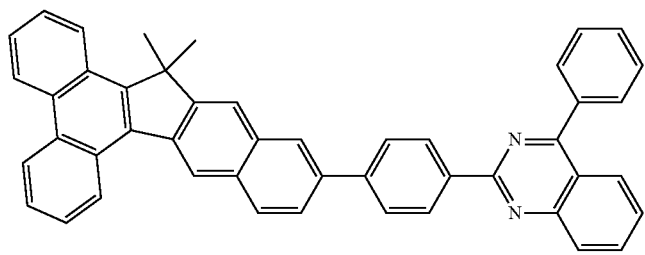

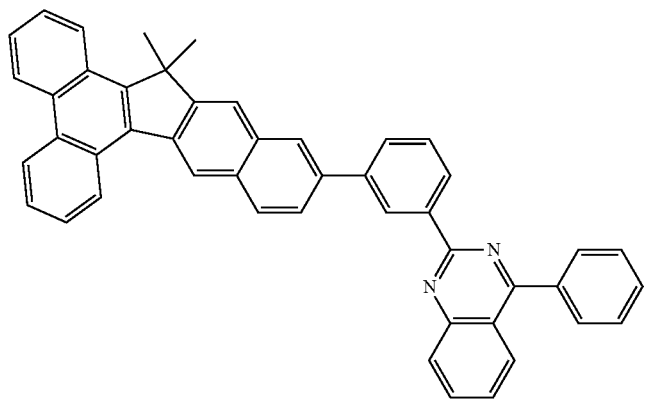
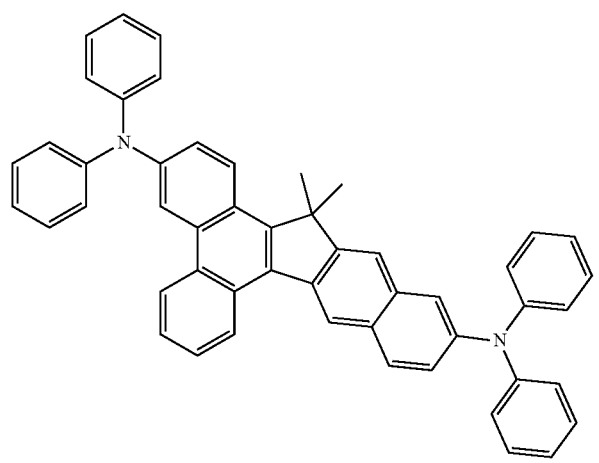
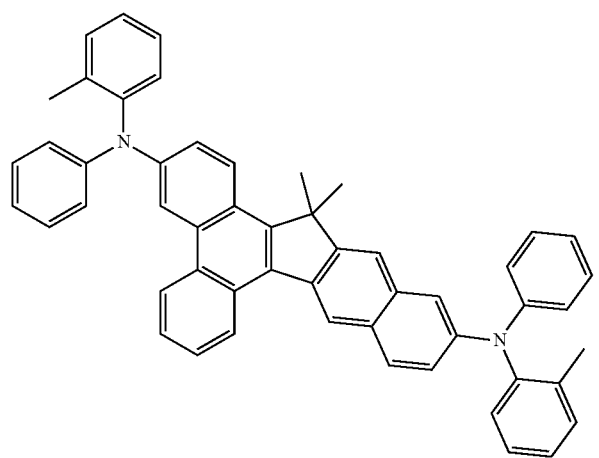

-continued
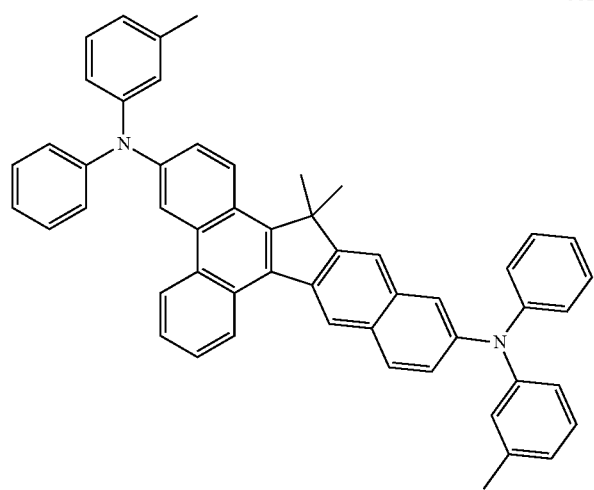
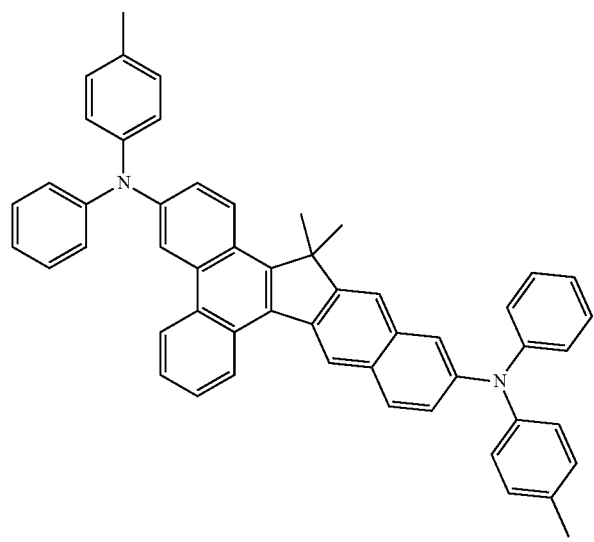
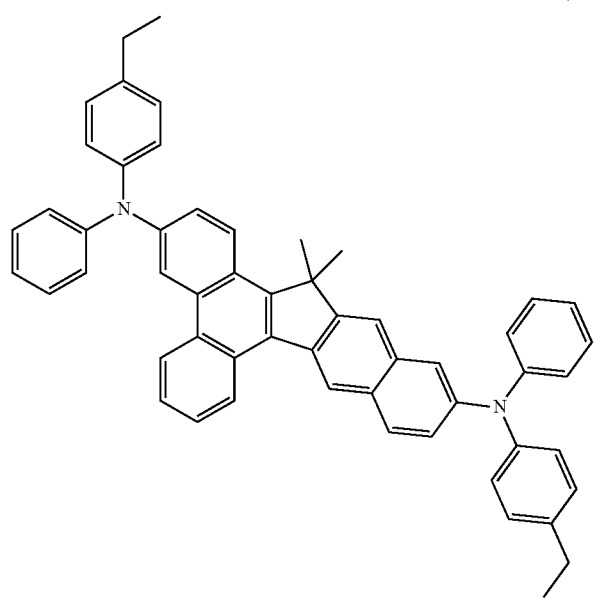

-continued
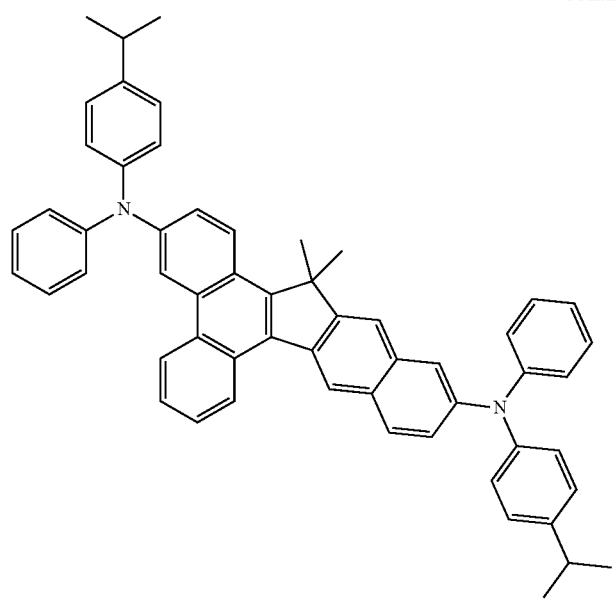
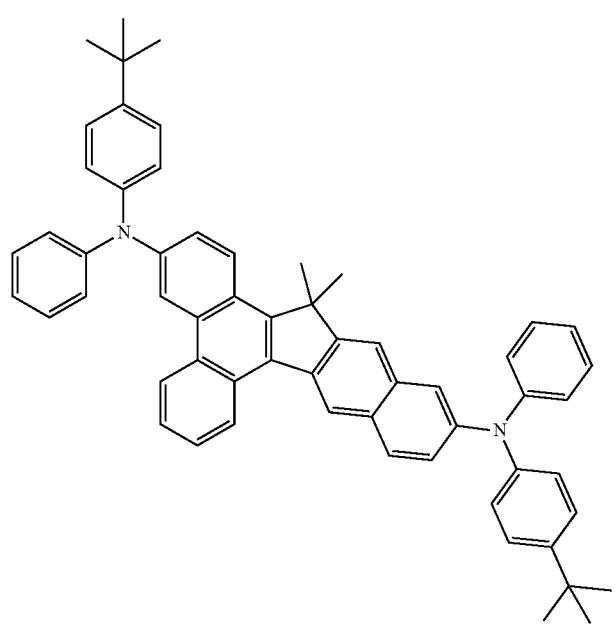

-continued
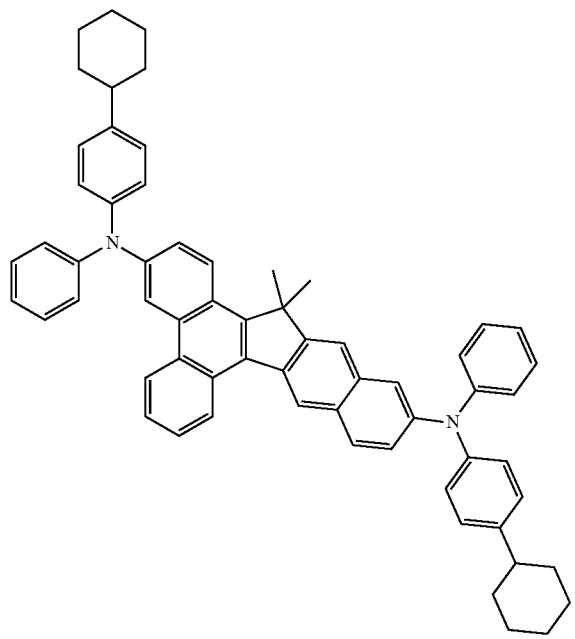

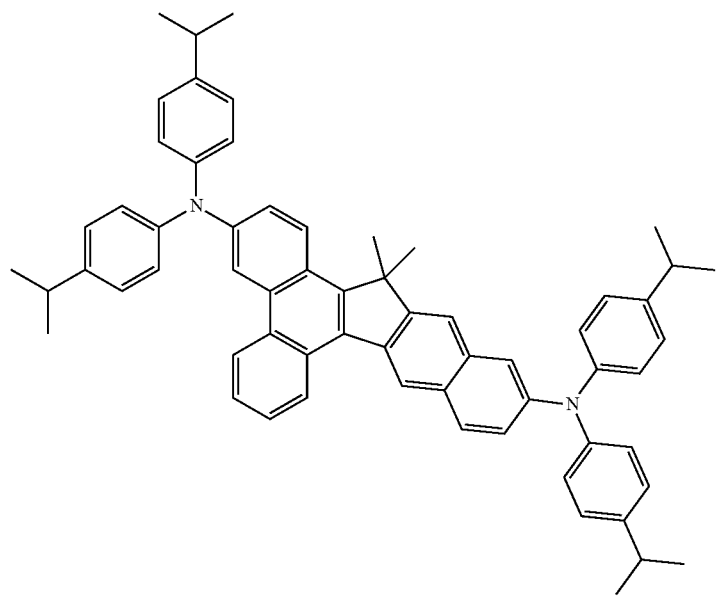
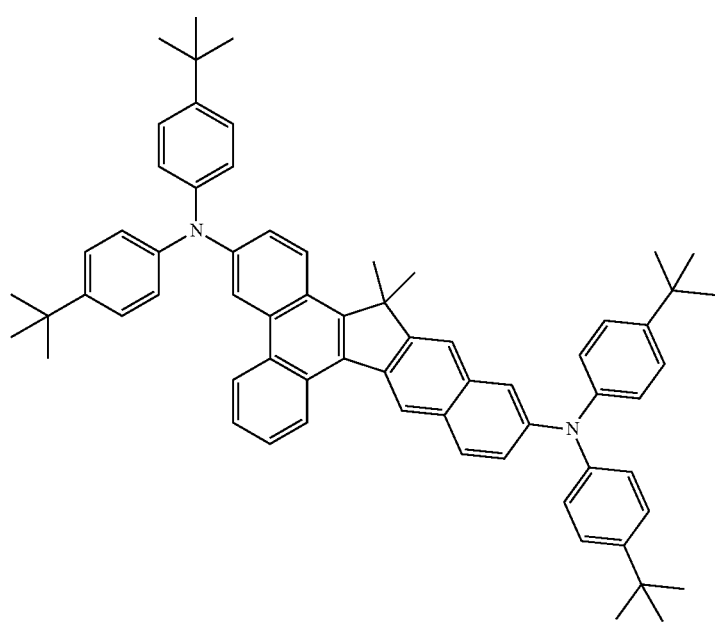

-continued
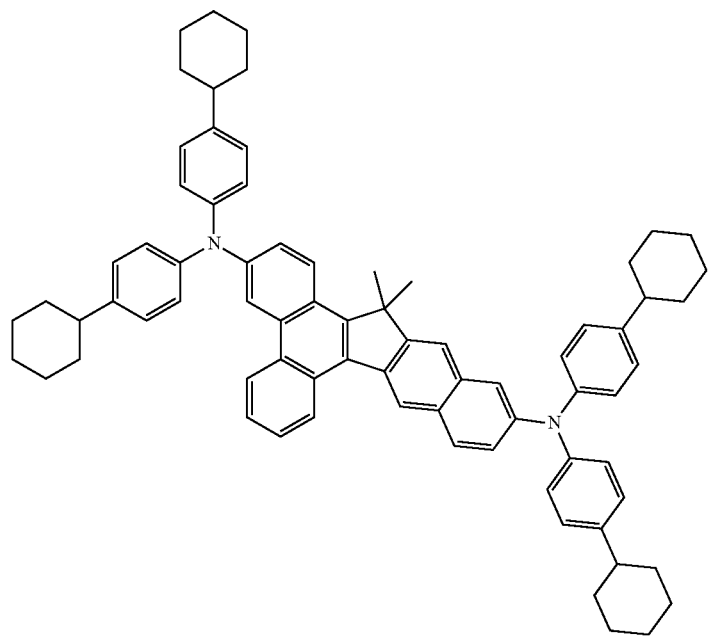
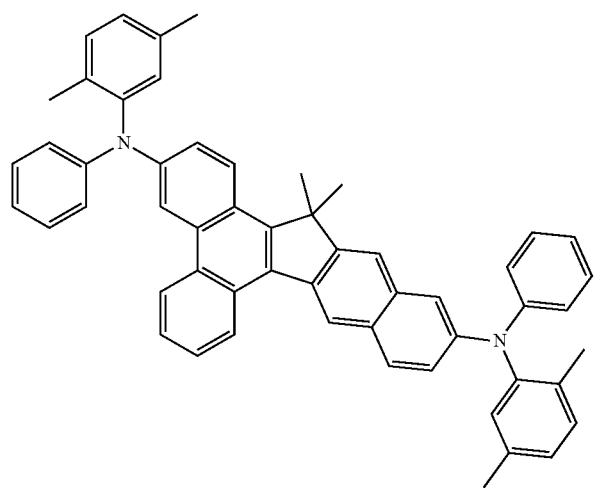
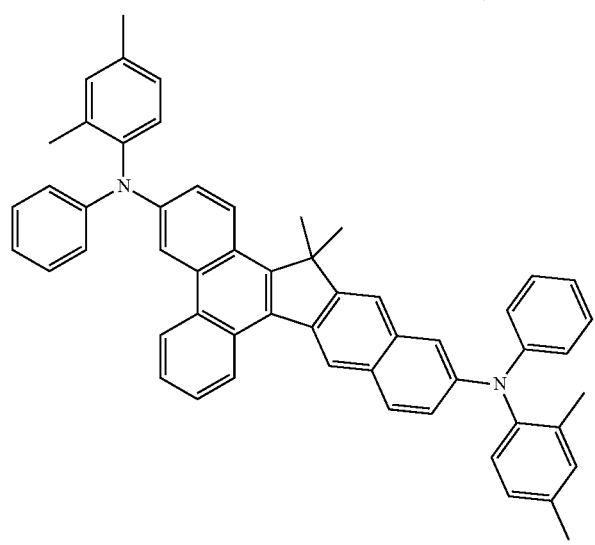

-continued
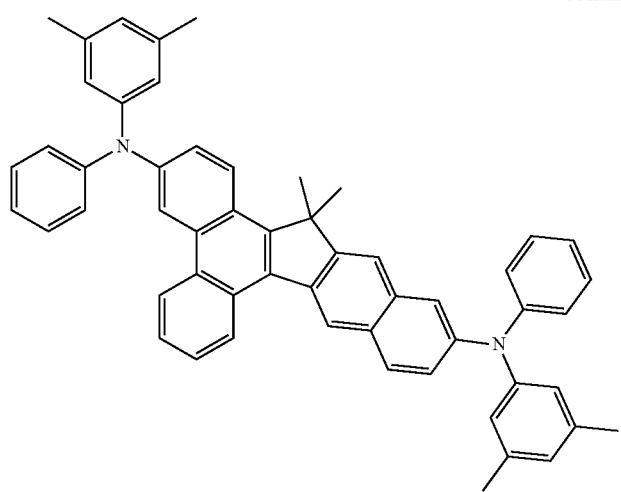
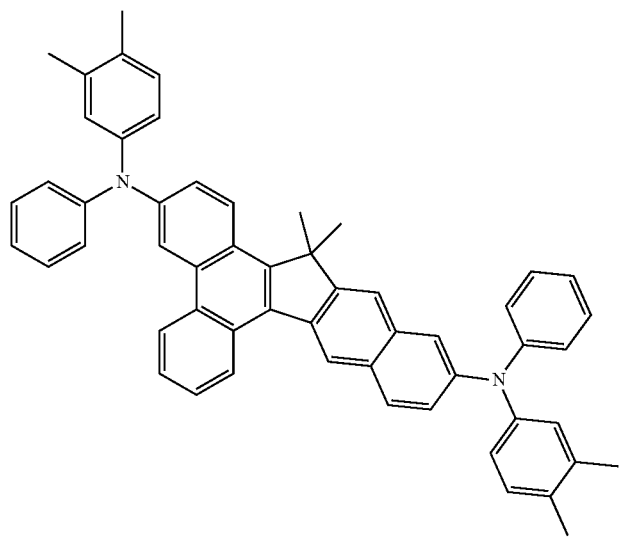
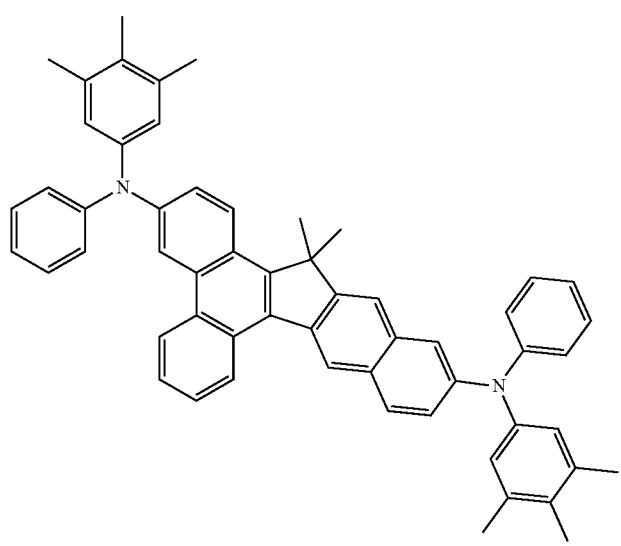

-continued
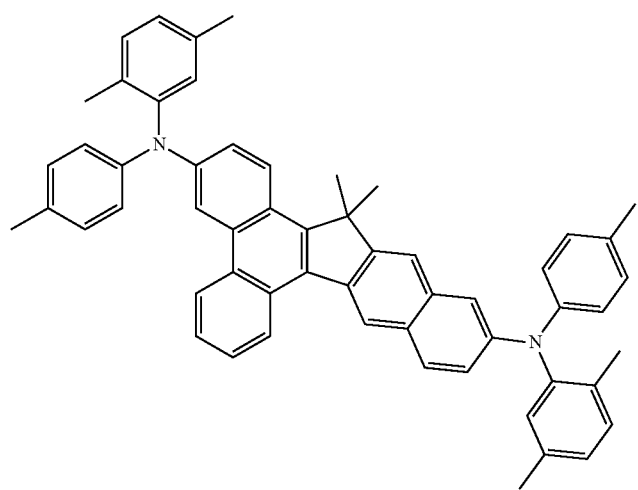
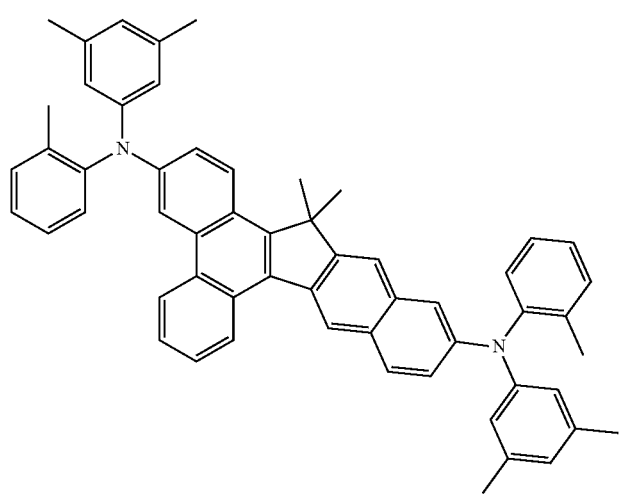
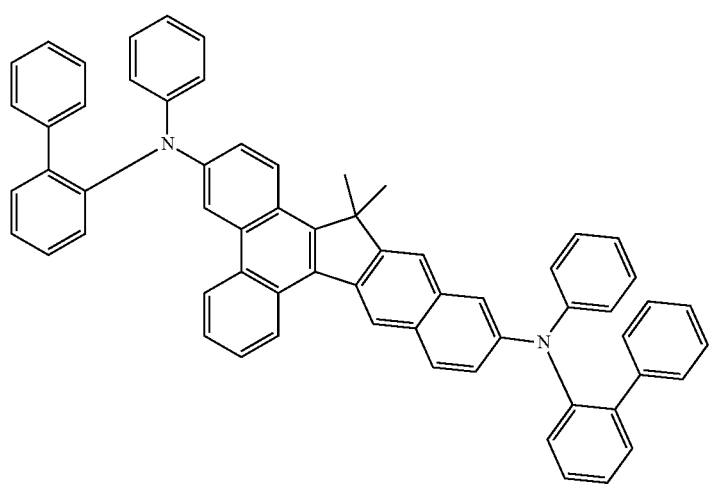

-continued
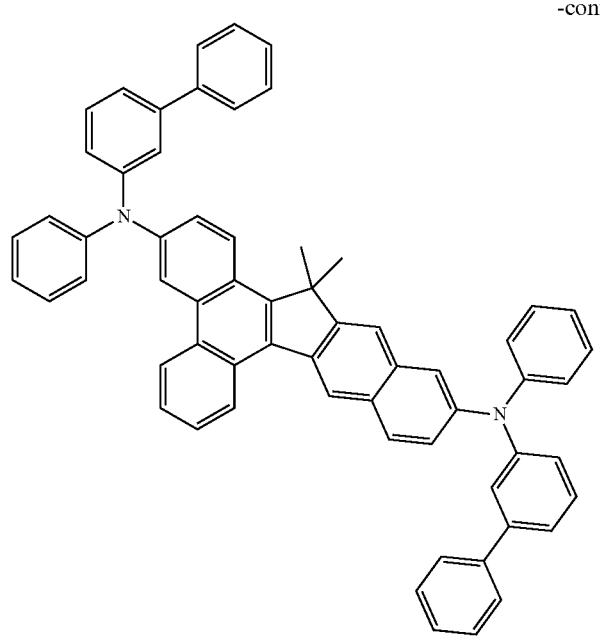
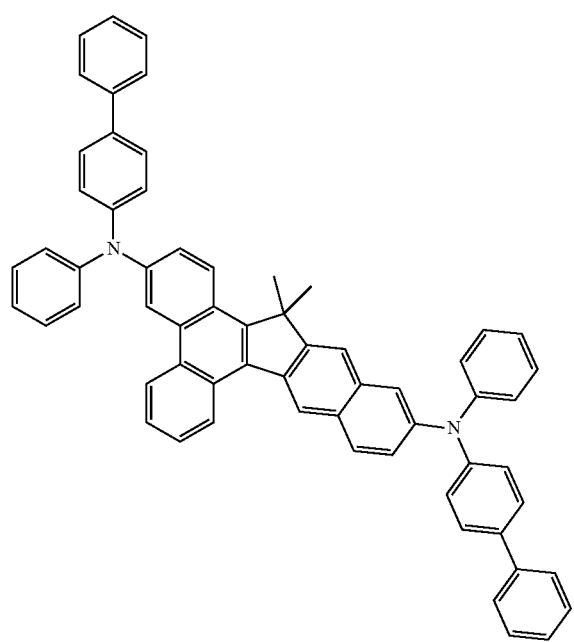

-continued
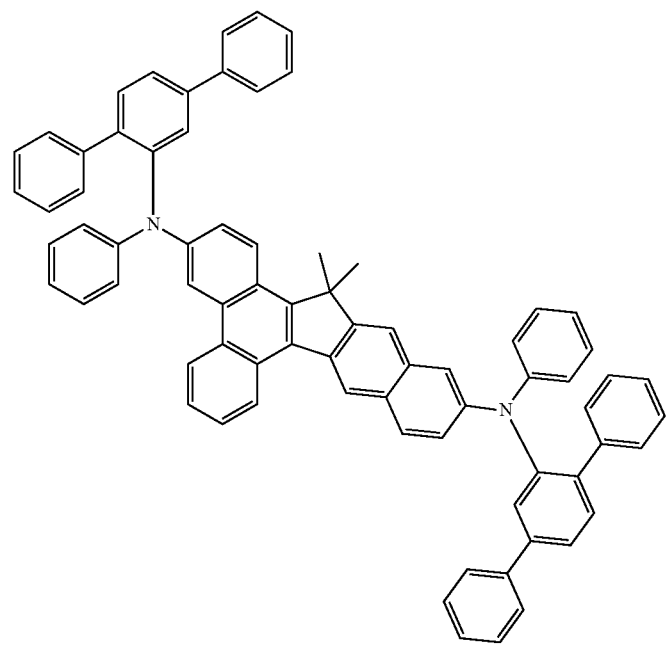
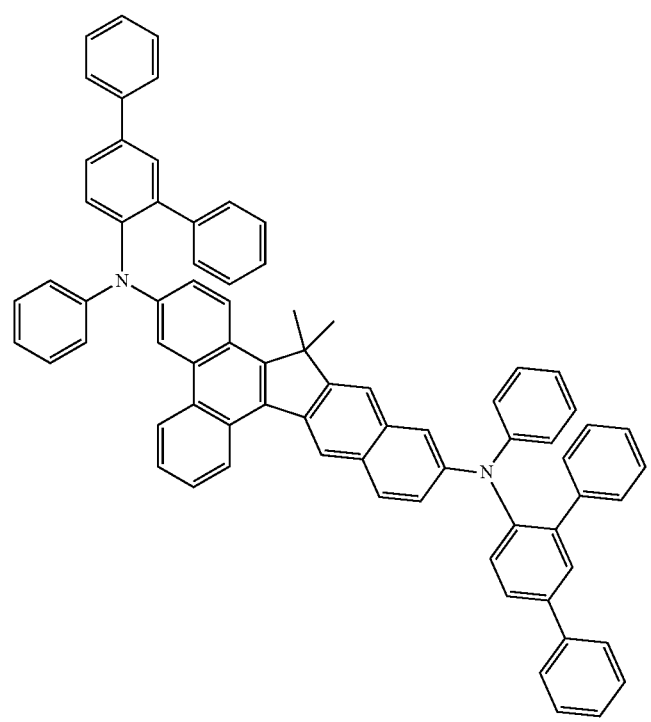

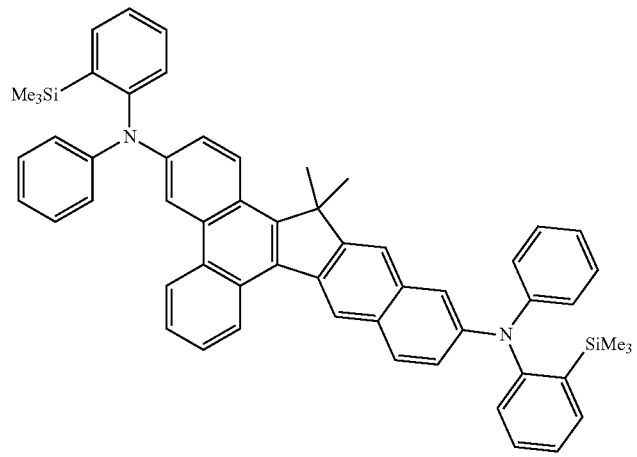
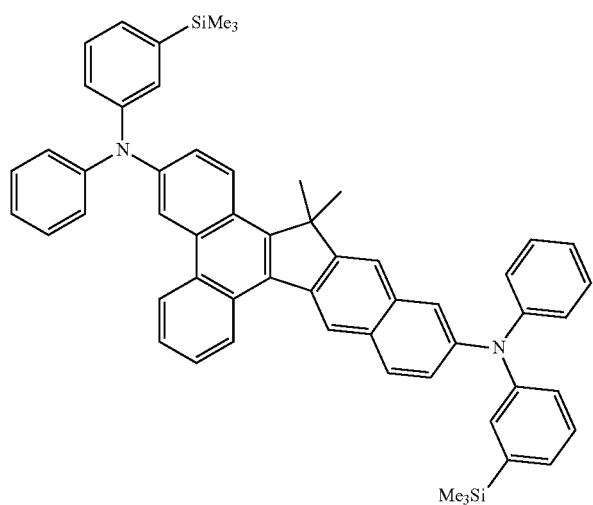
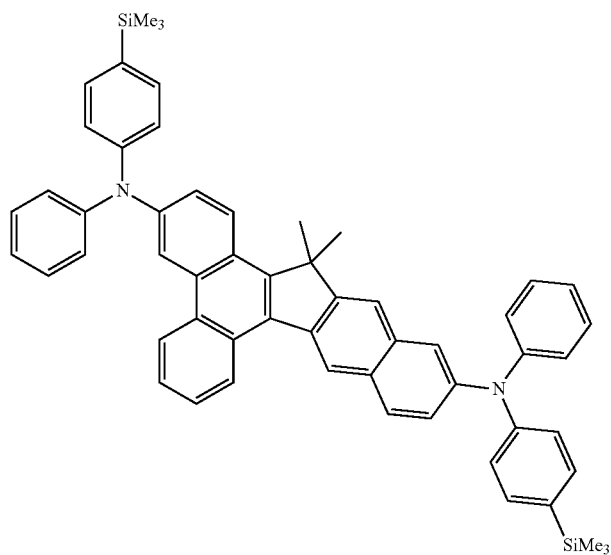

-continued
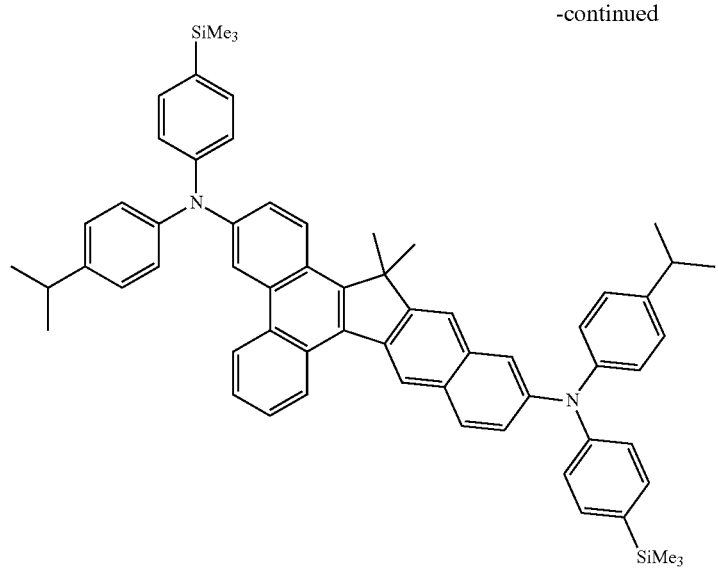
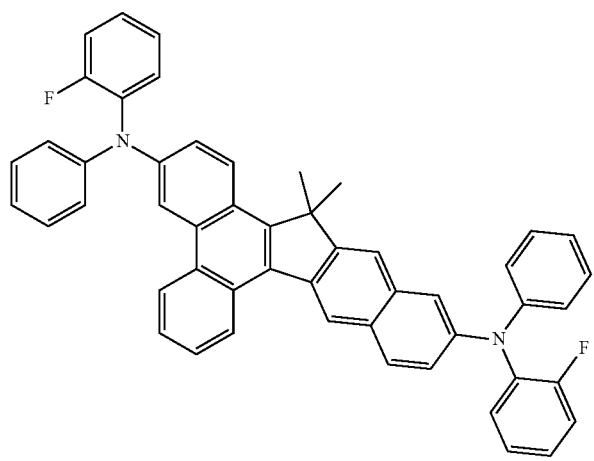
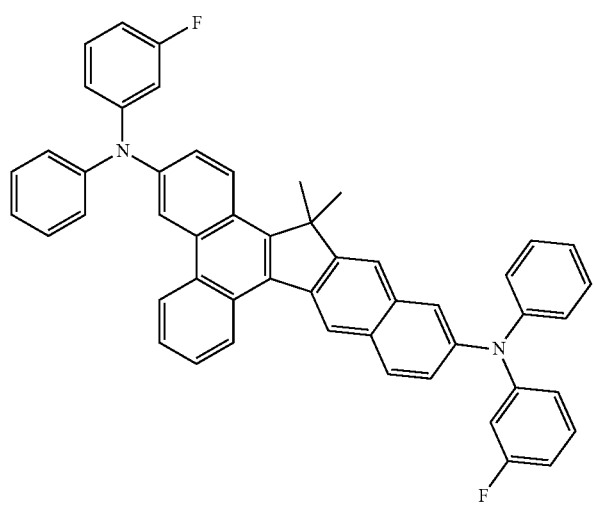

-continued
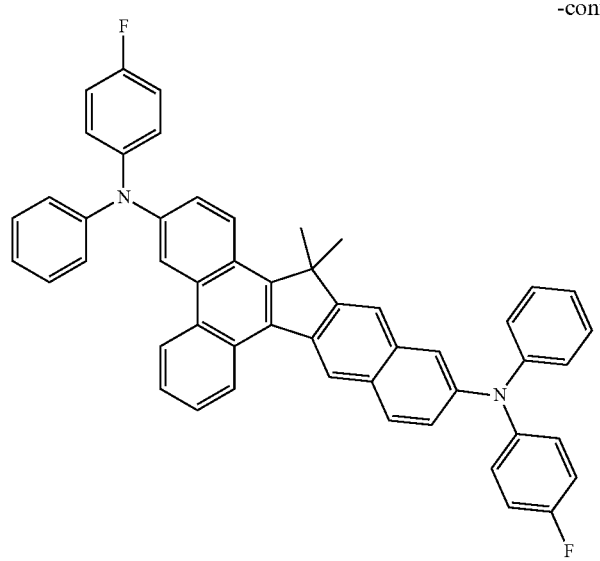
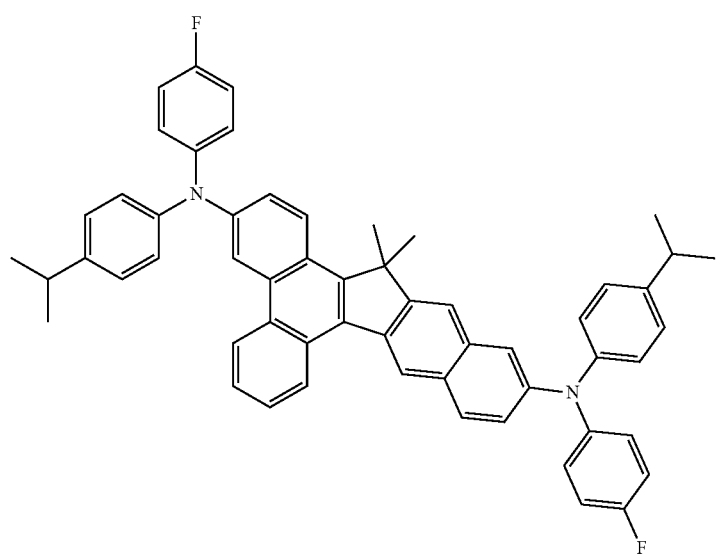
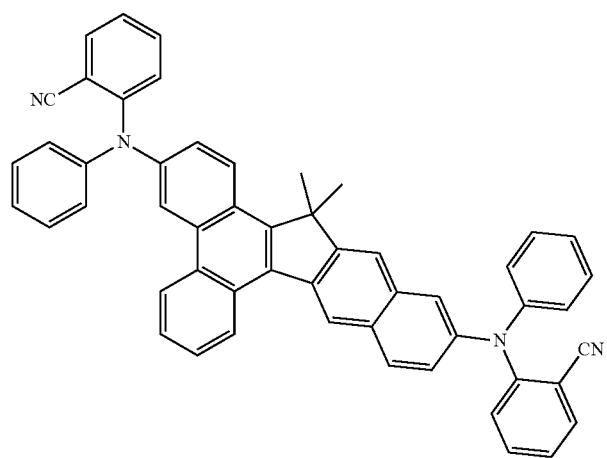

-continued
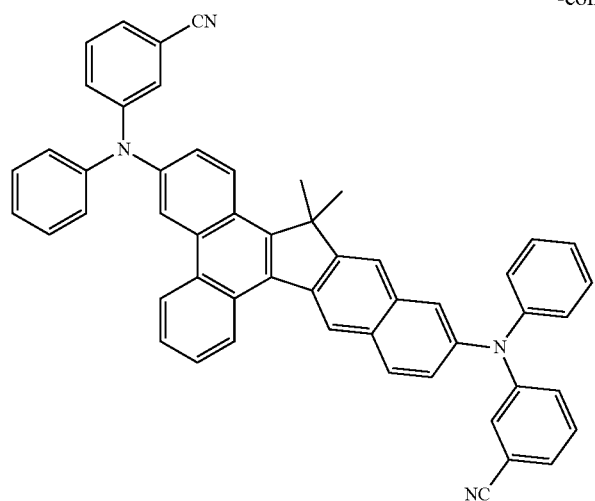
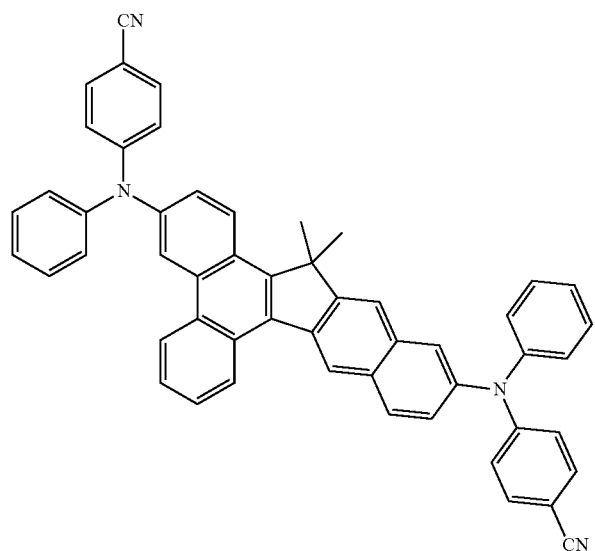
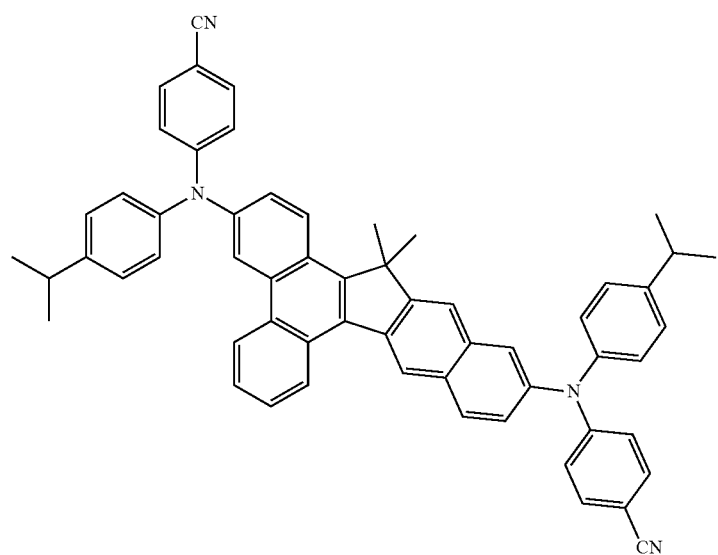

-continued
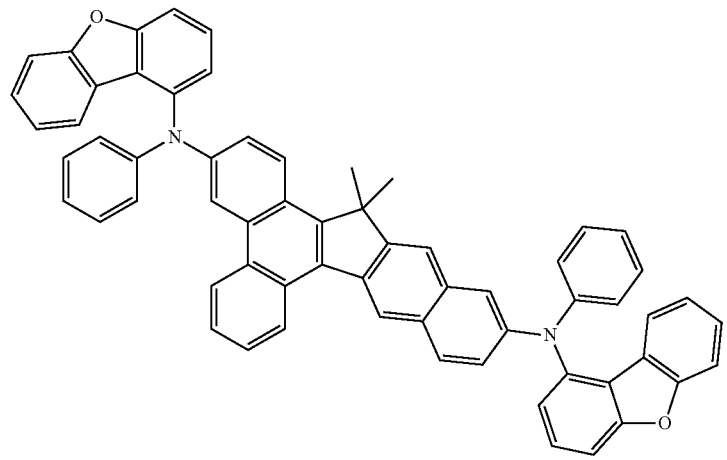
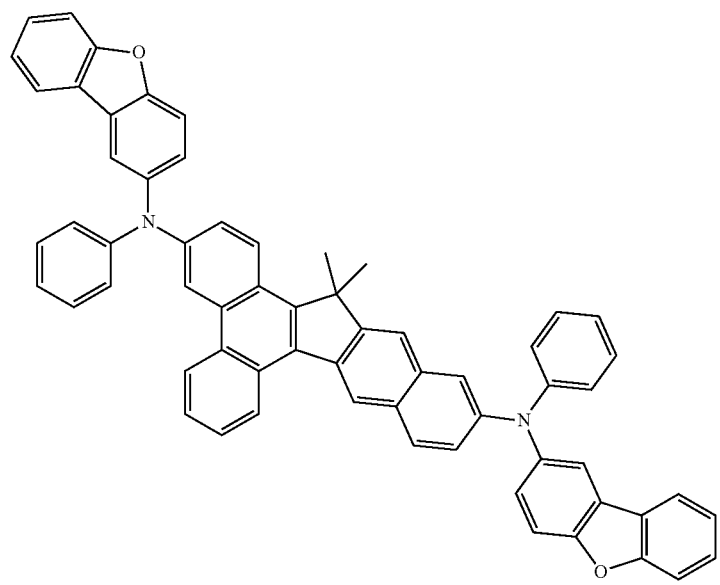
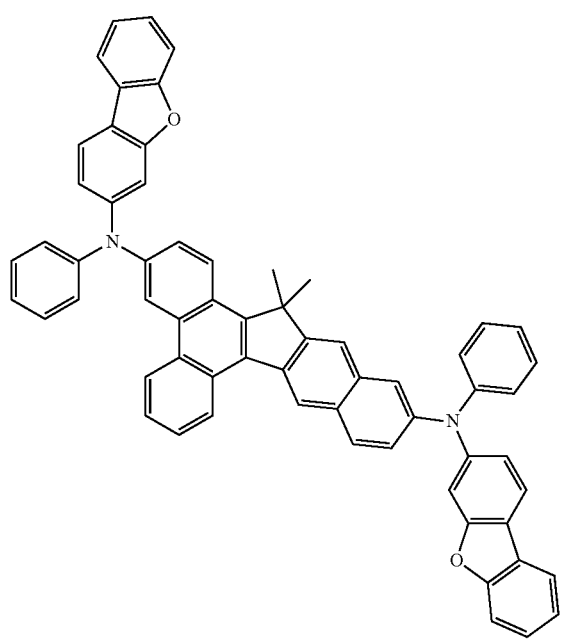

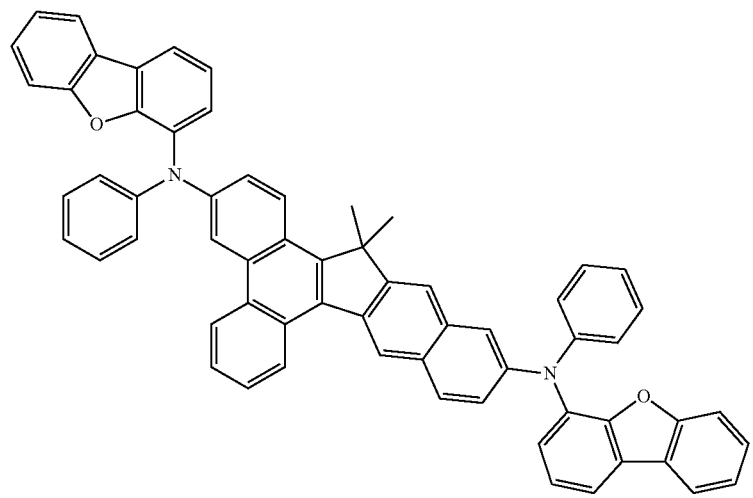
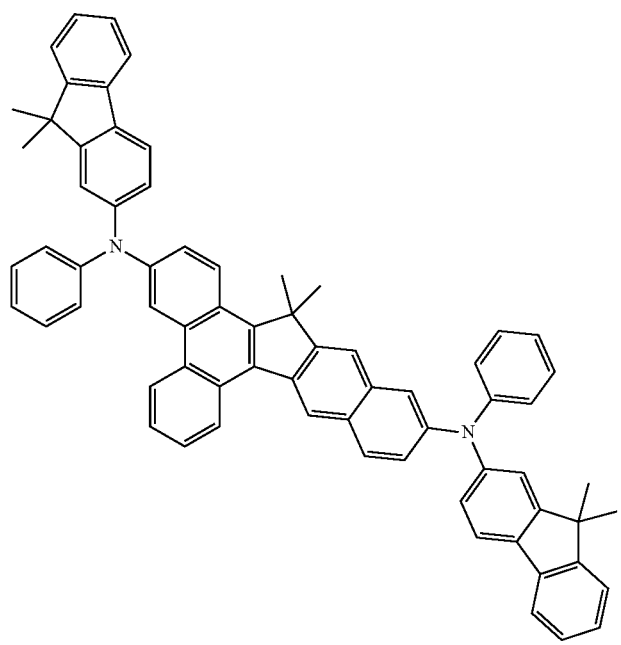

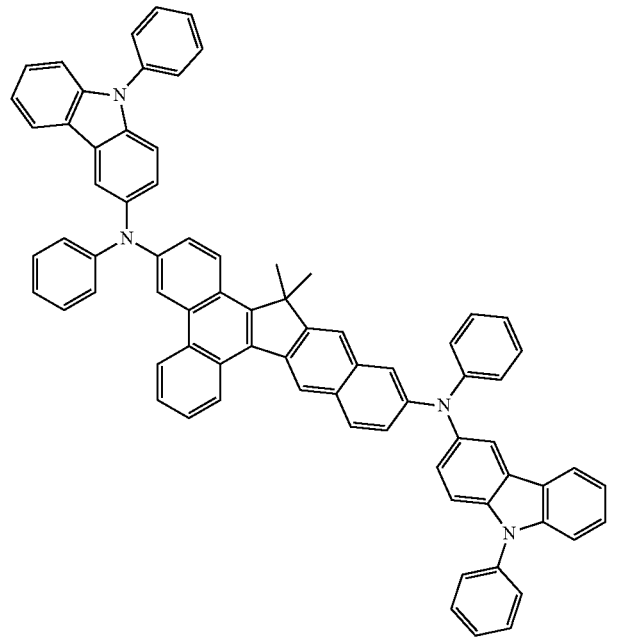
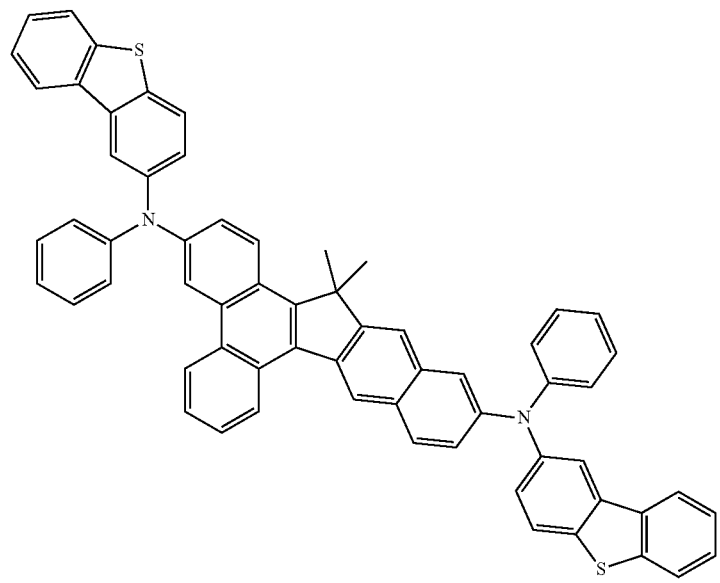
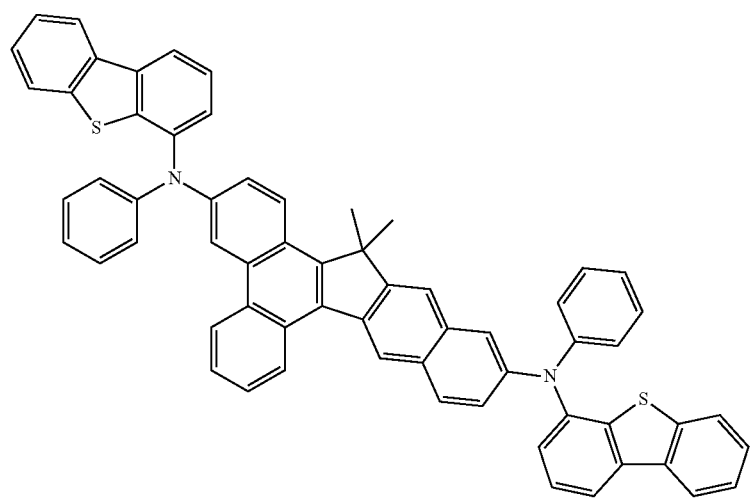

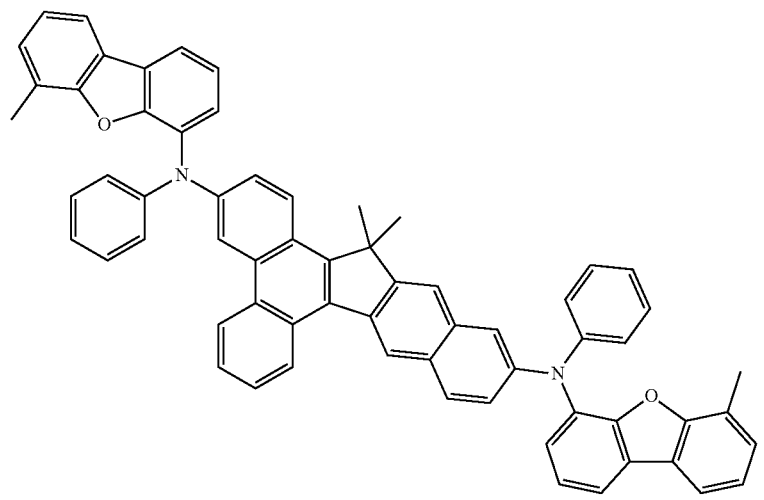
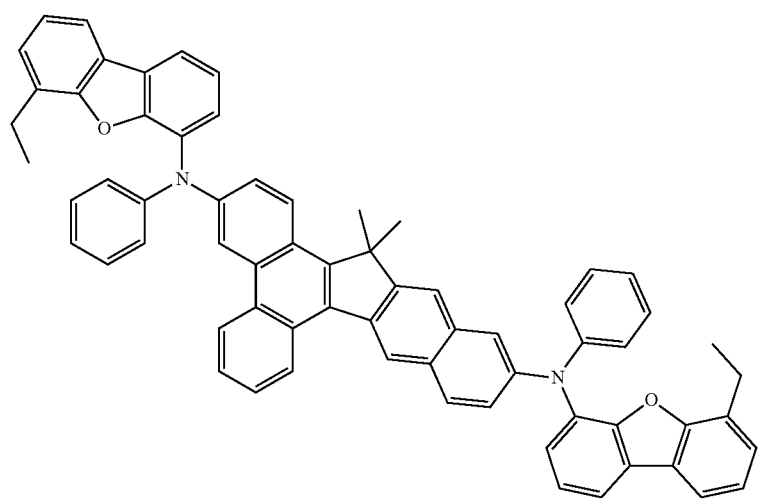
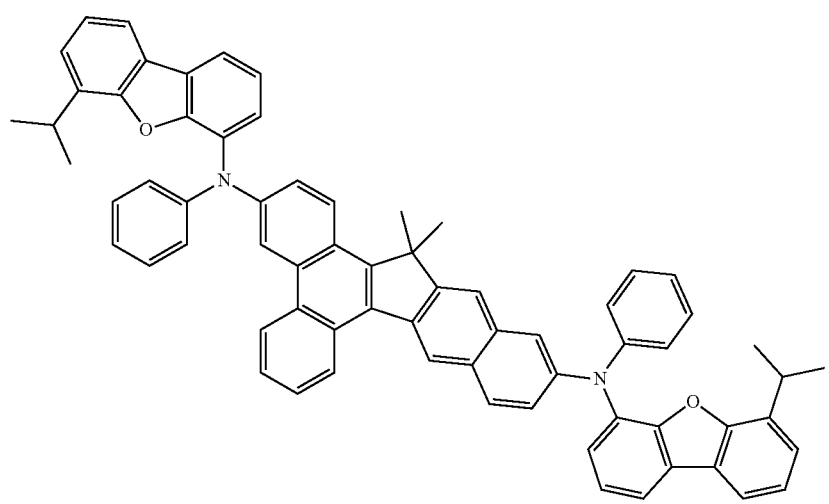

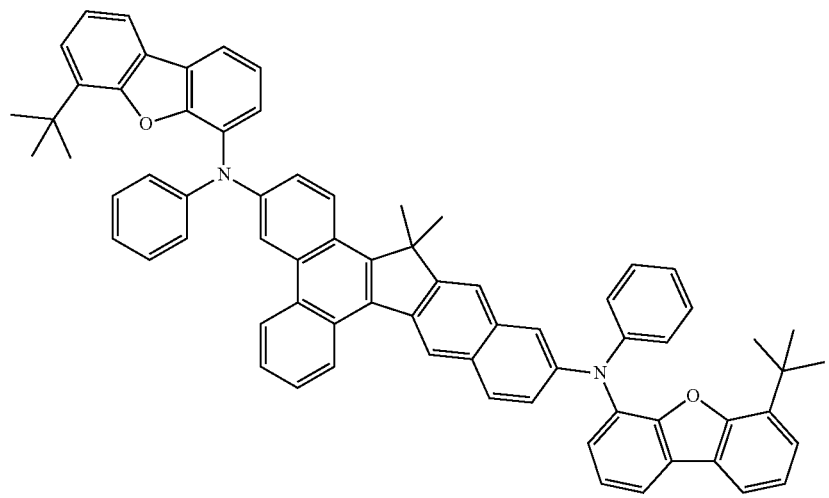
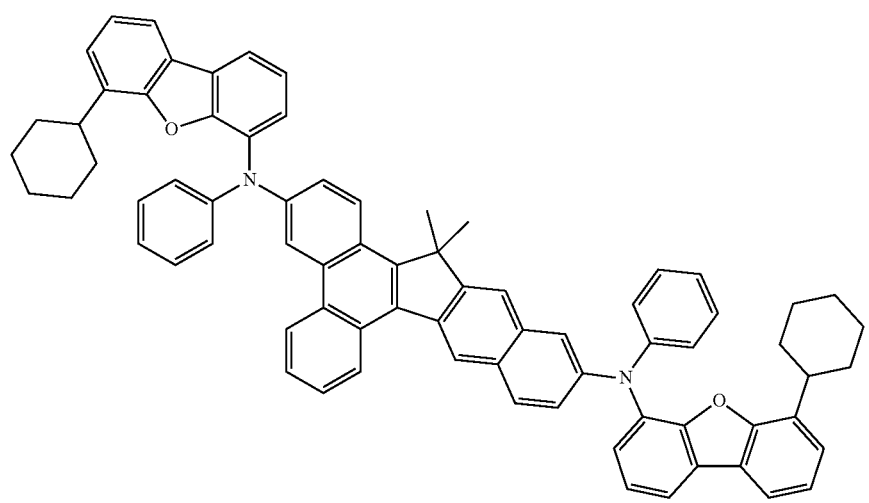
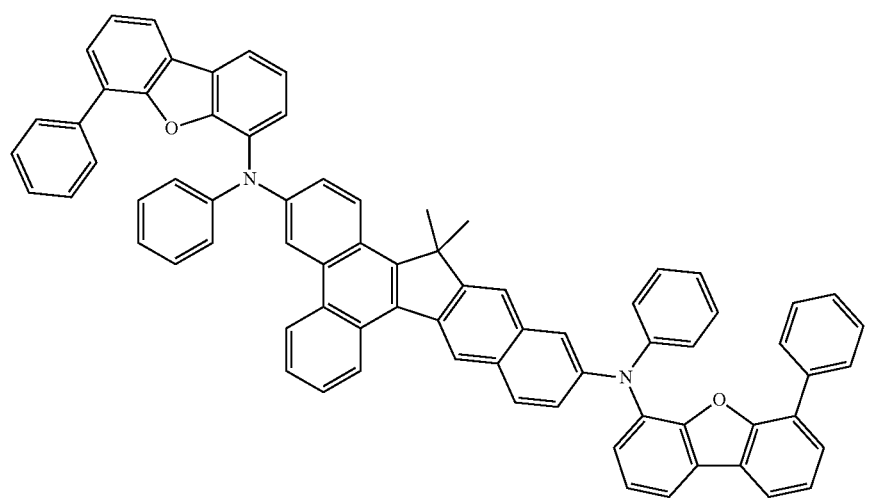

-continued
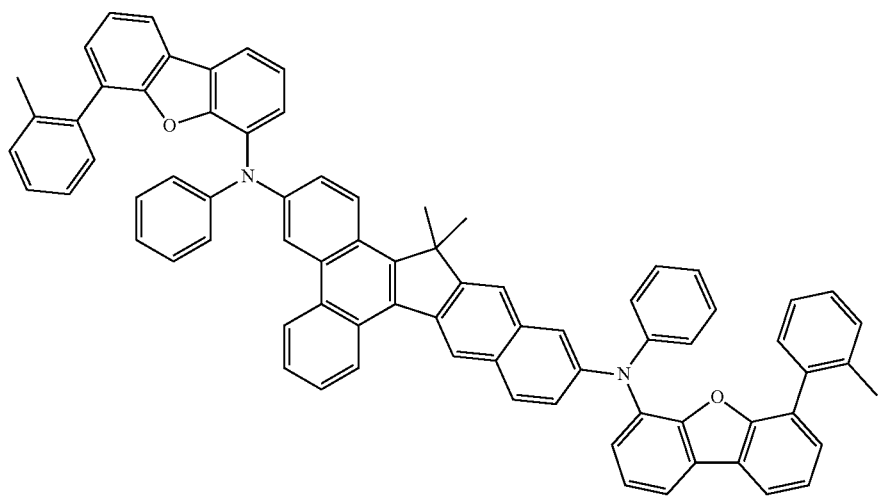
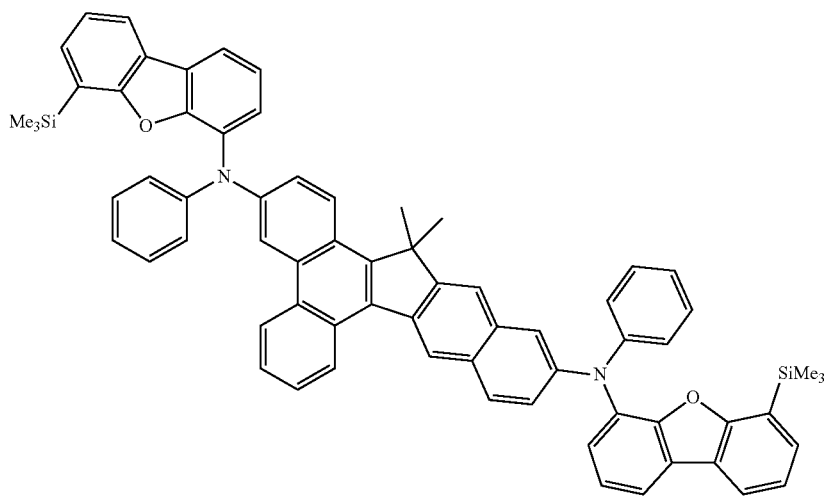
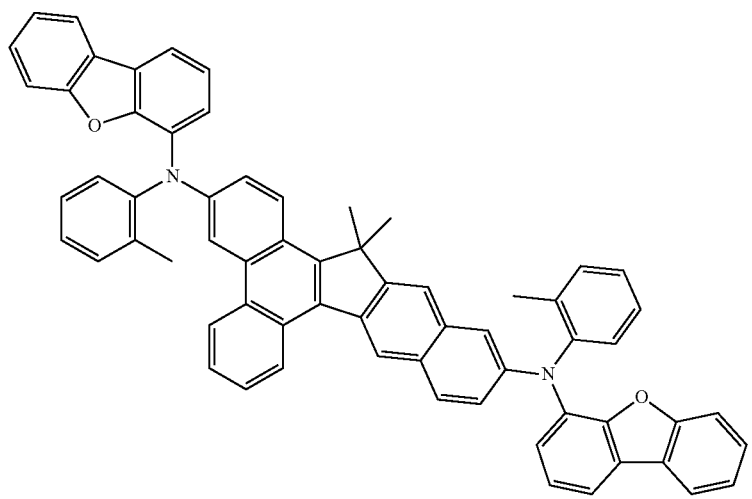

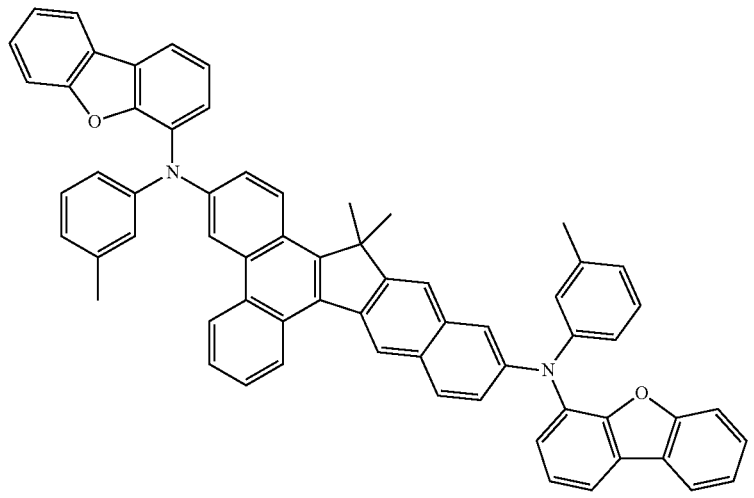
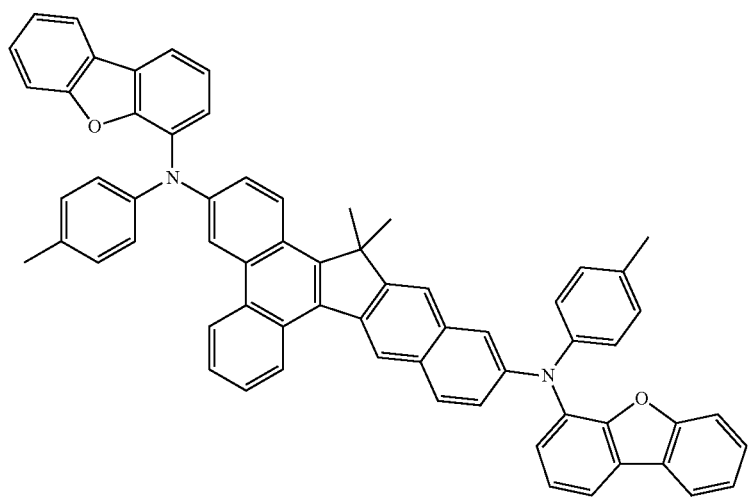
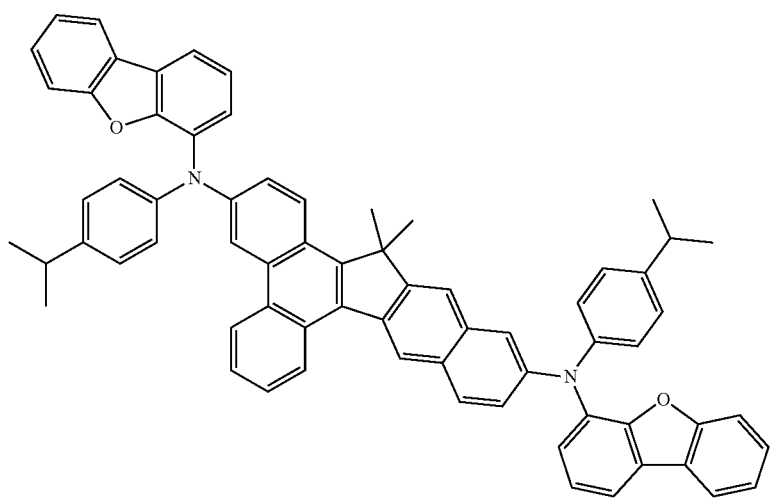

-continued
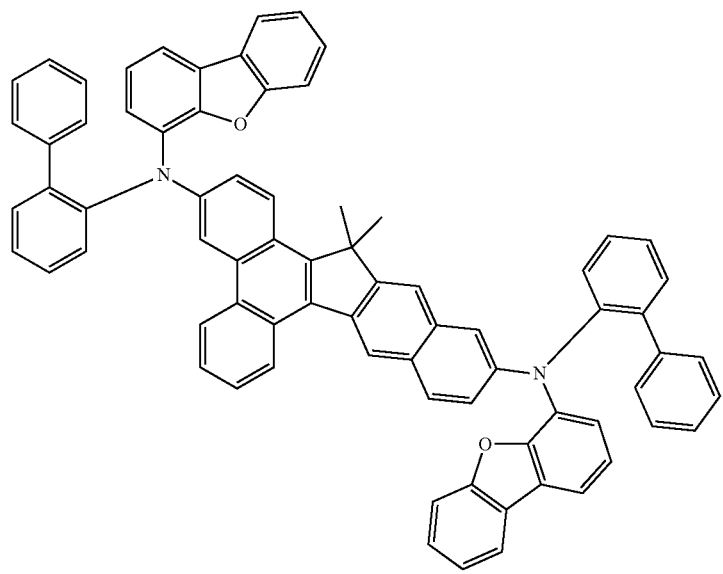
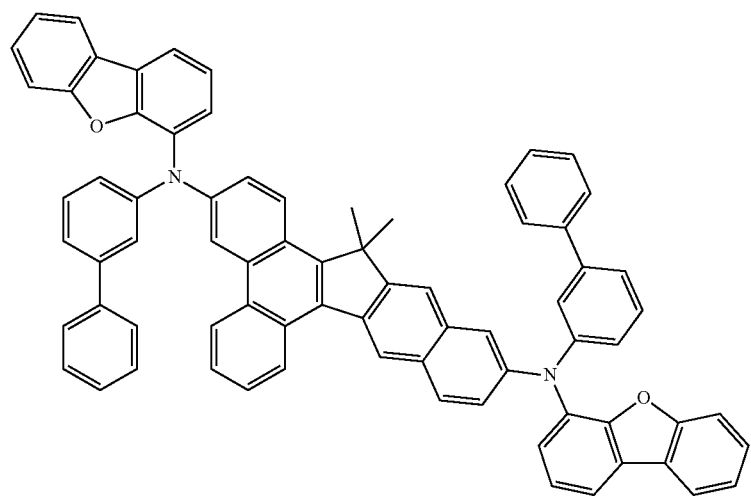
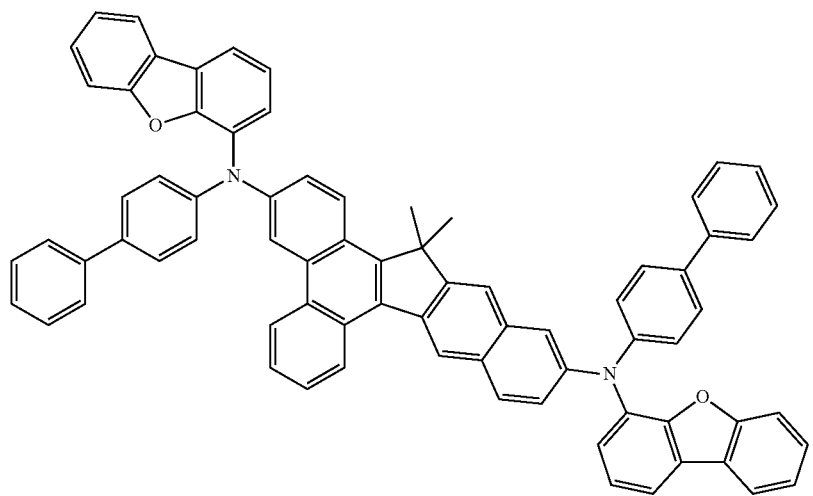

-continued
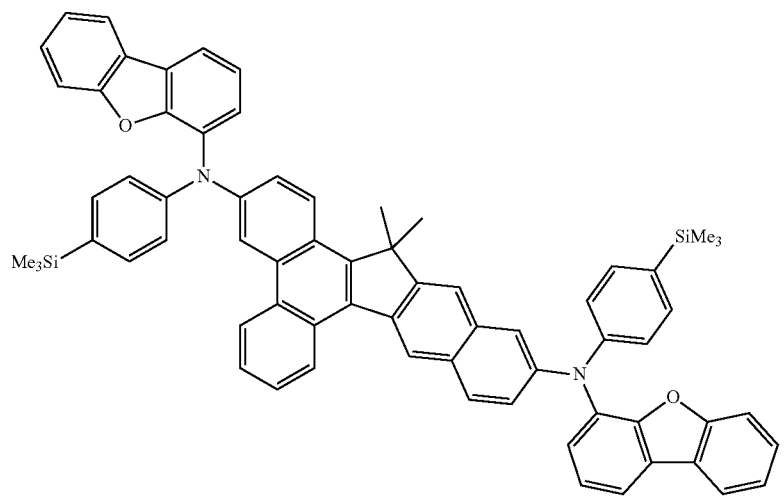
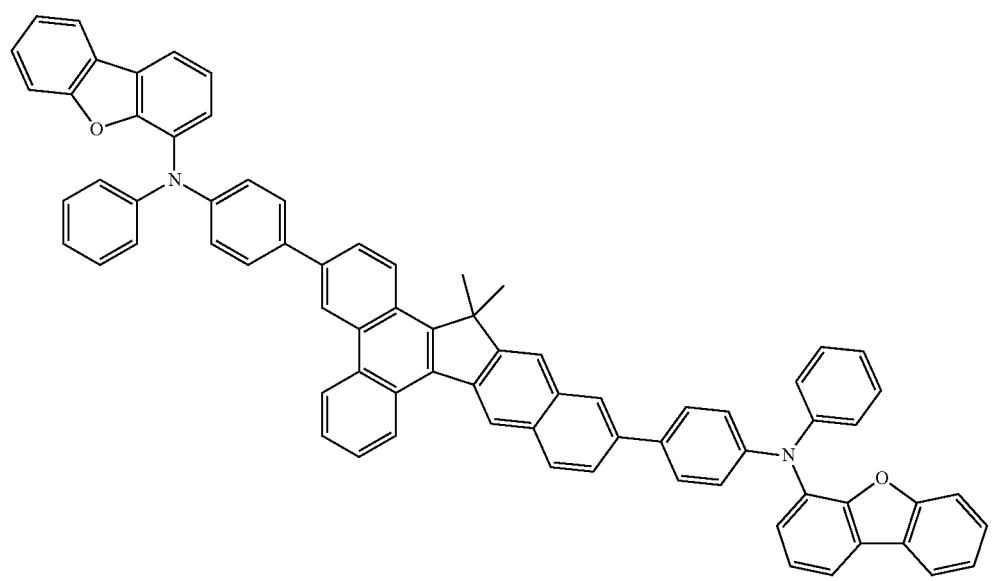
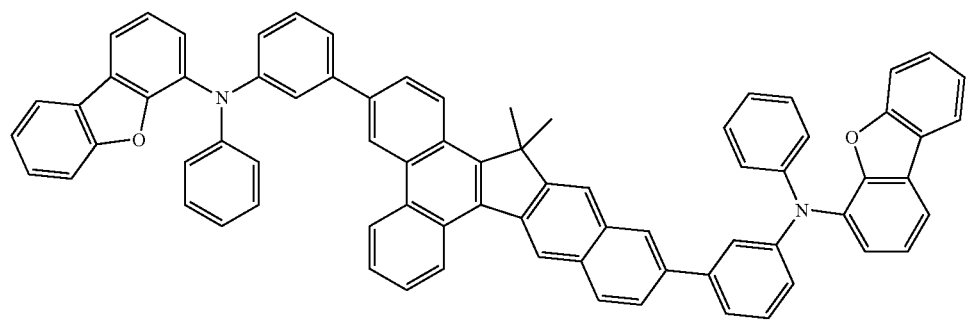

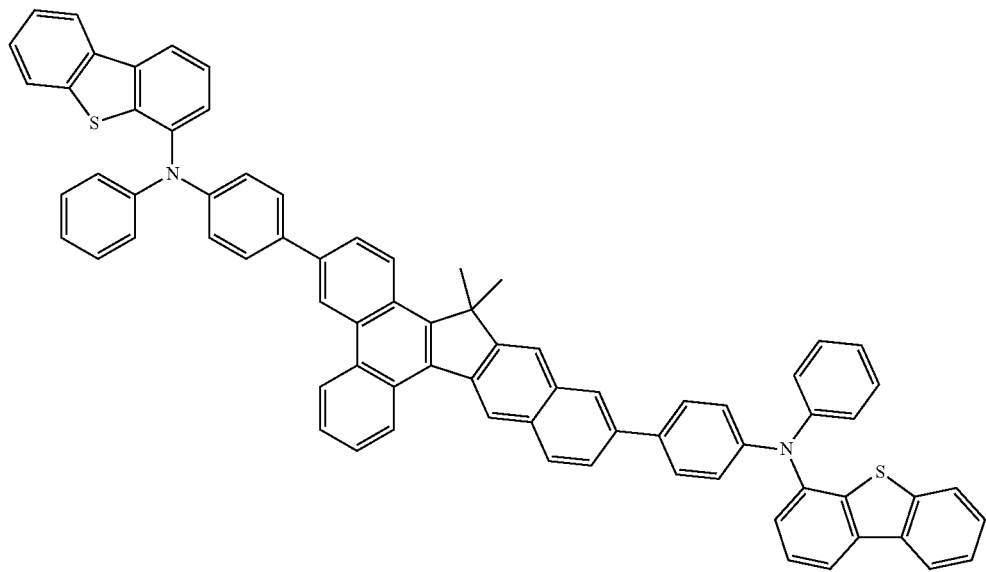
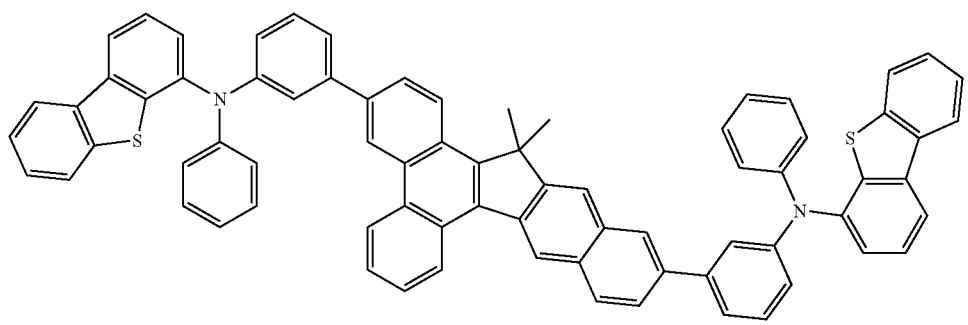
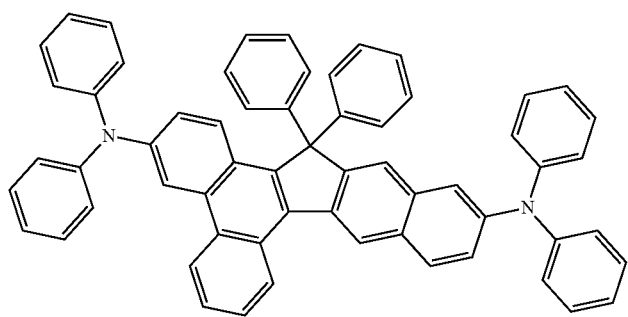
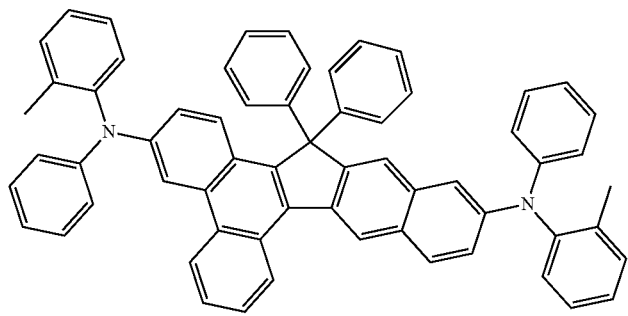

-continued
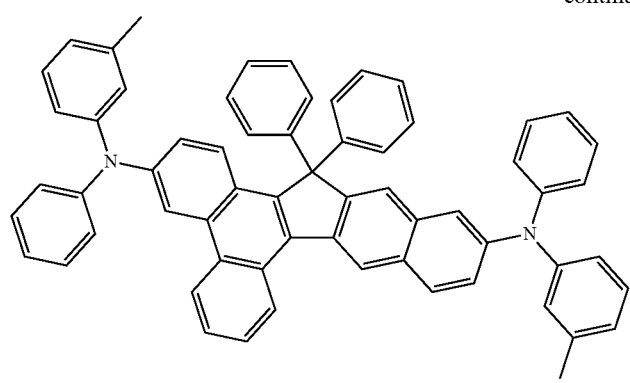
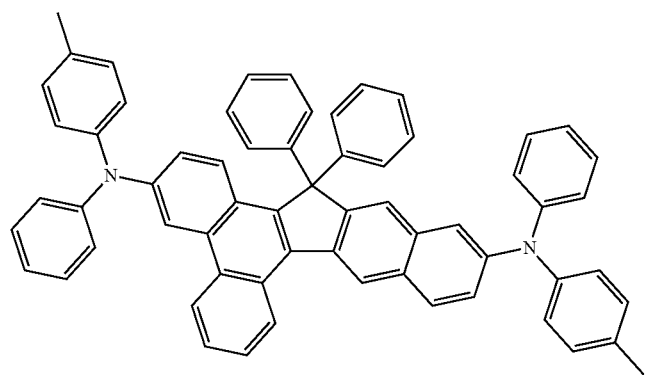
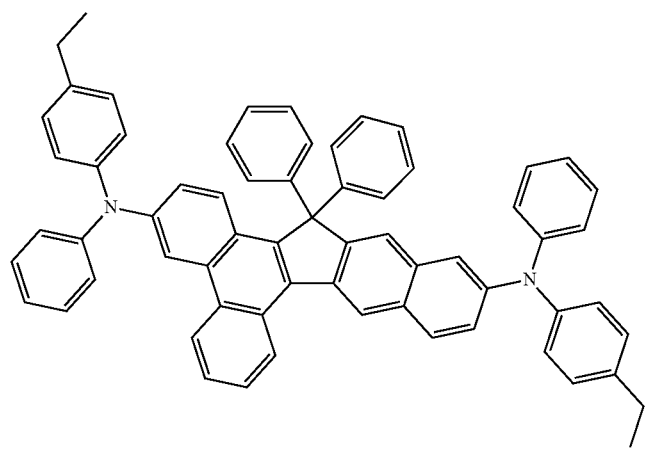
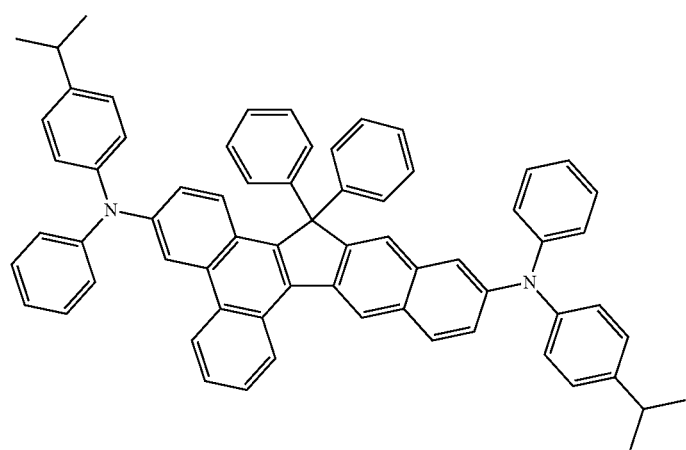

-continued
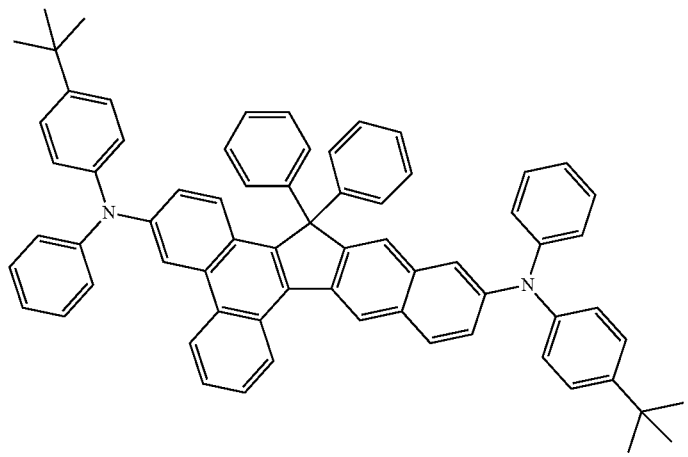
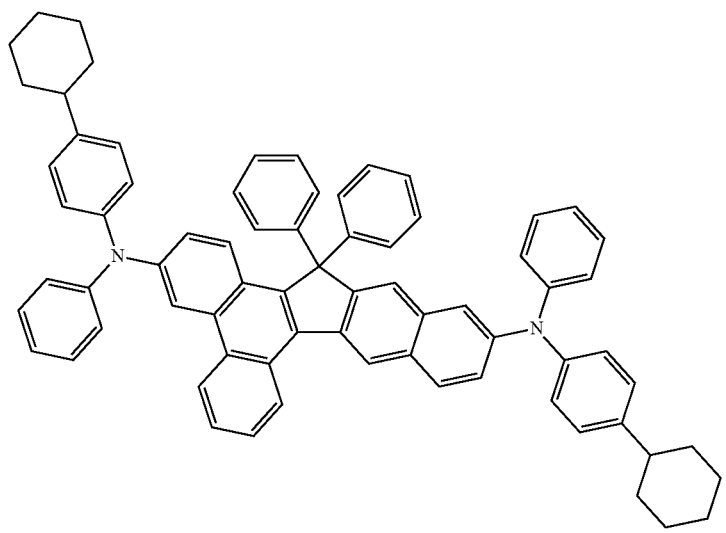
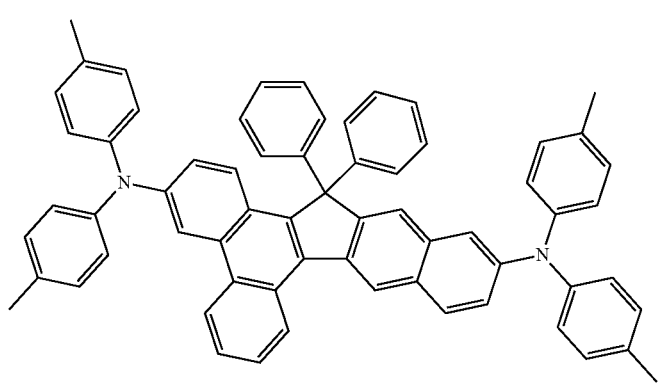

-continued
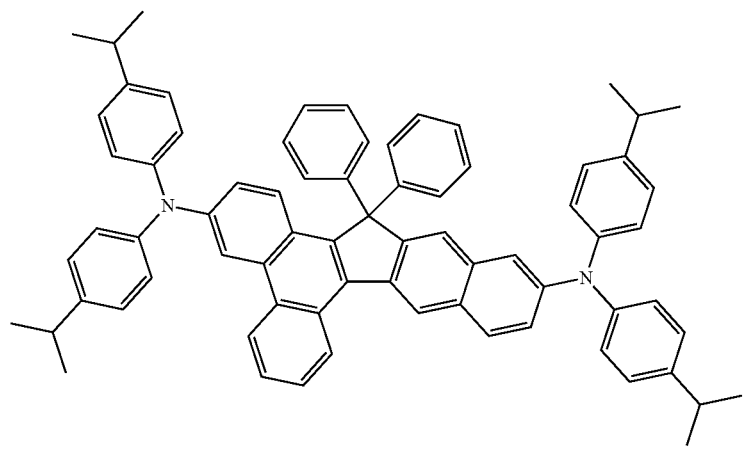
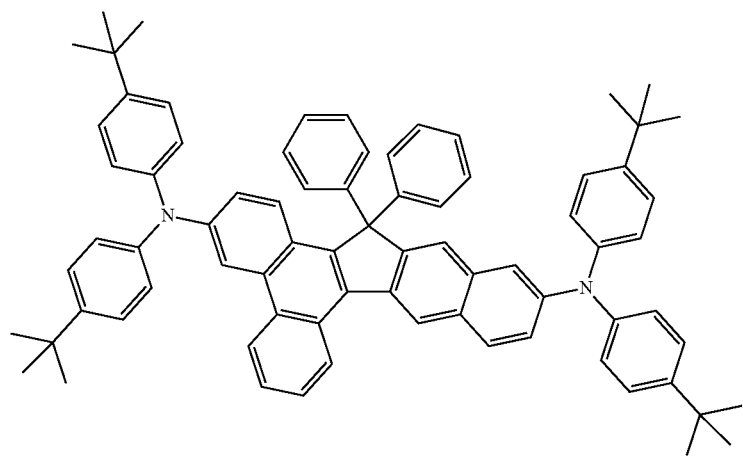
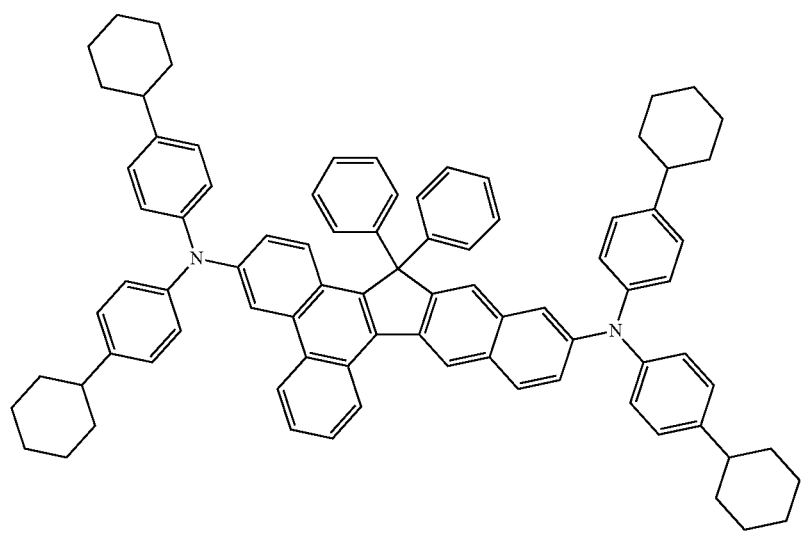

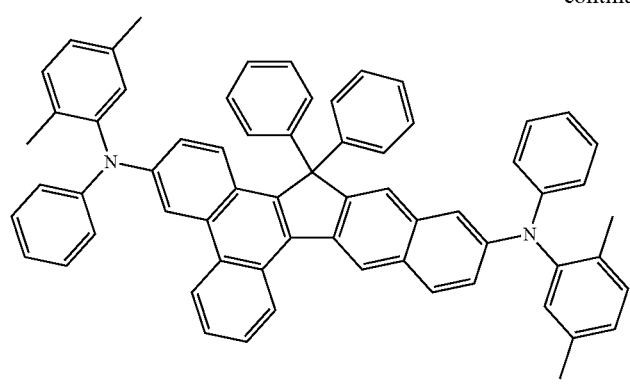
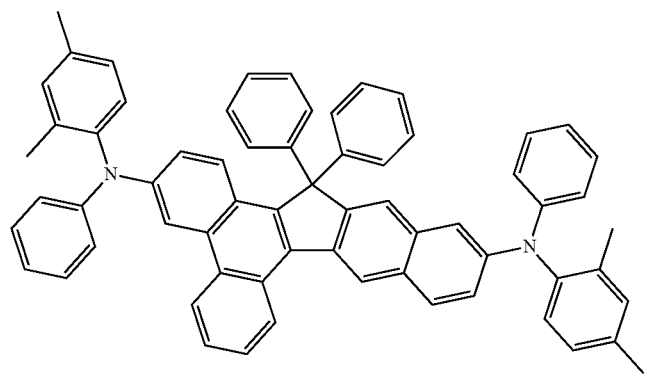
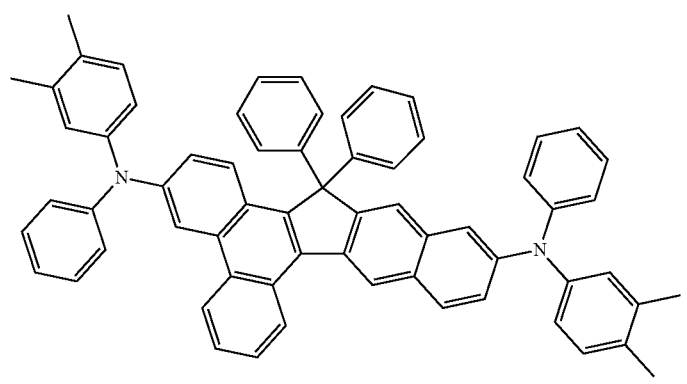

-continued
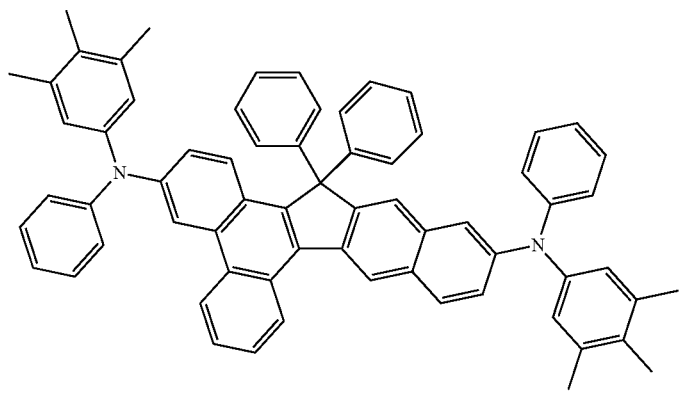
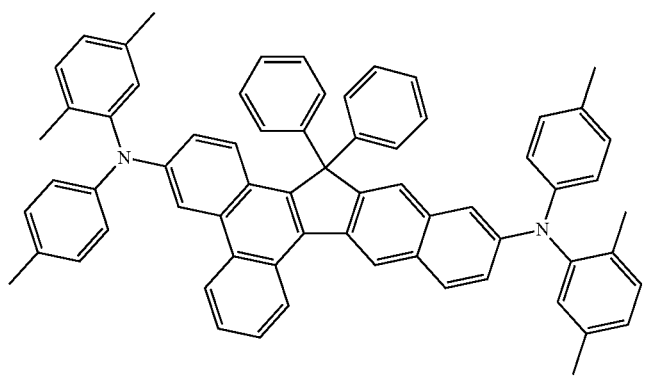
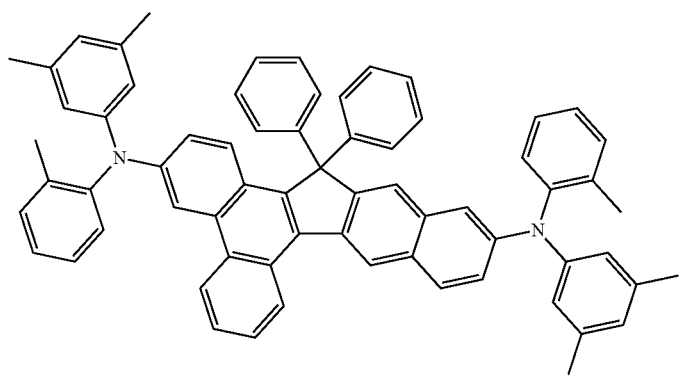
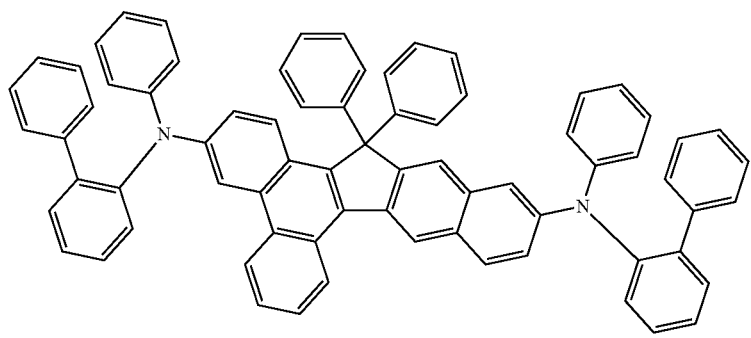

-continued
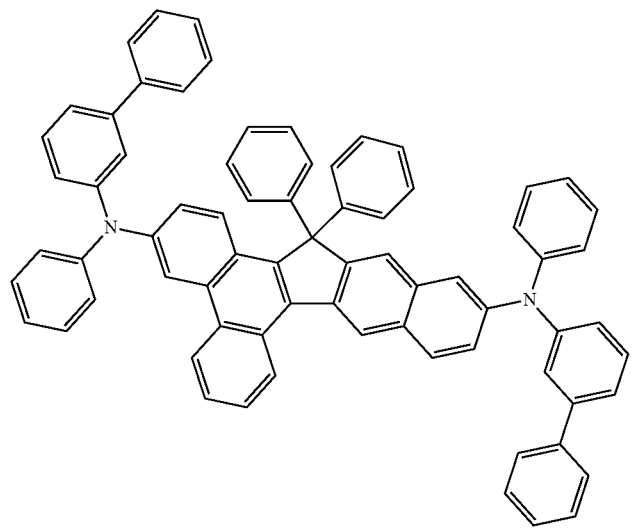
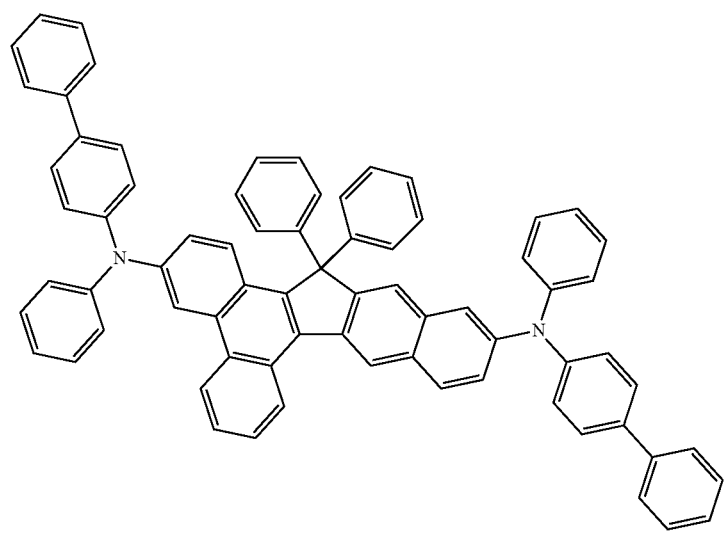
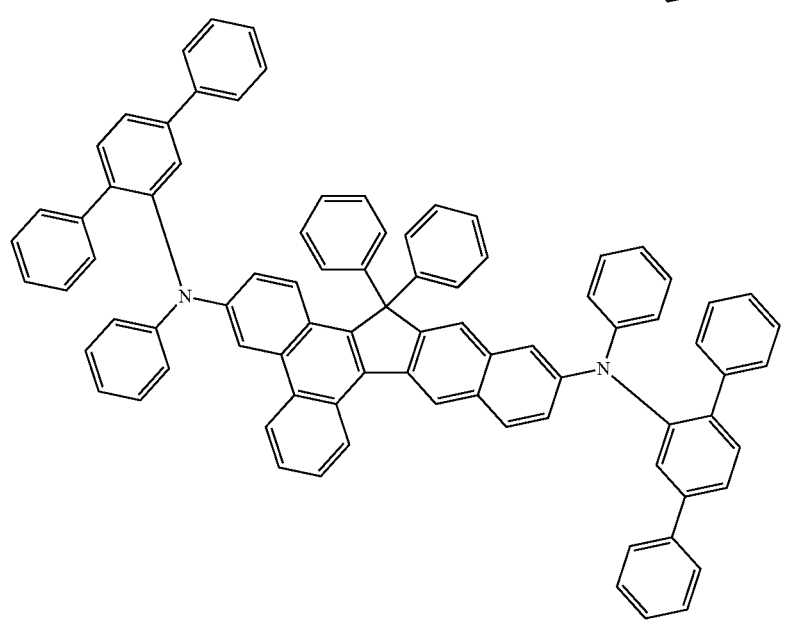

-continued
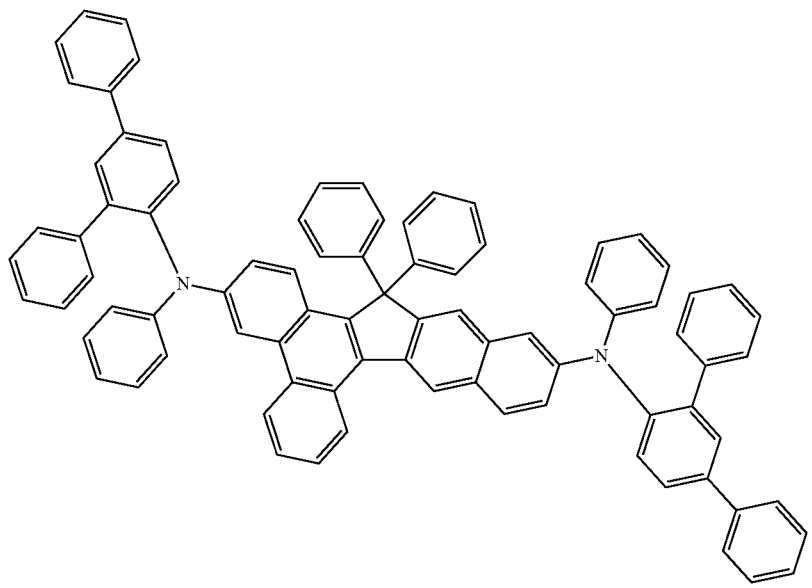
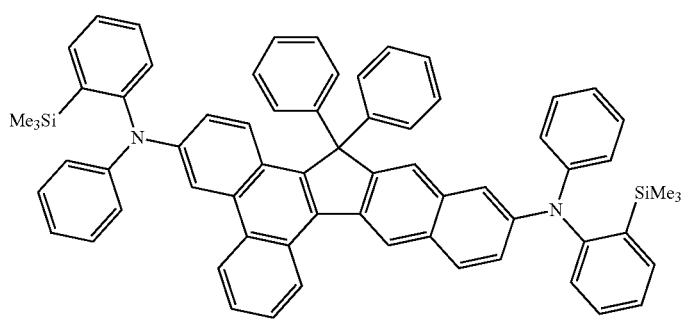
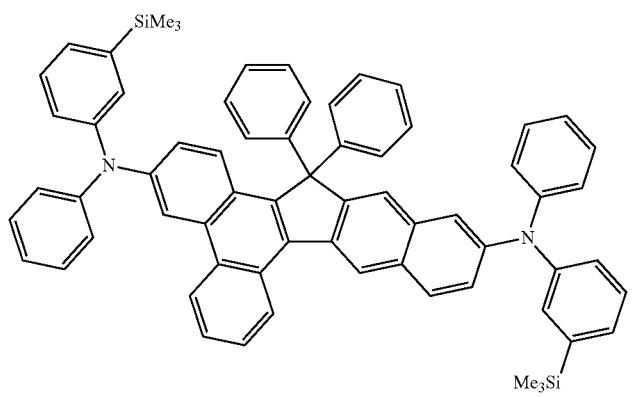
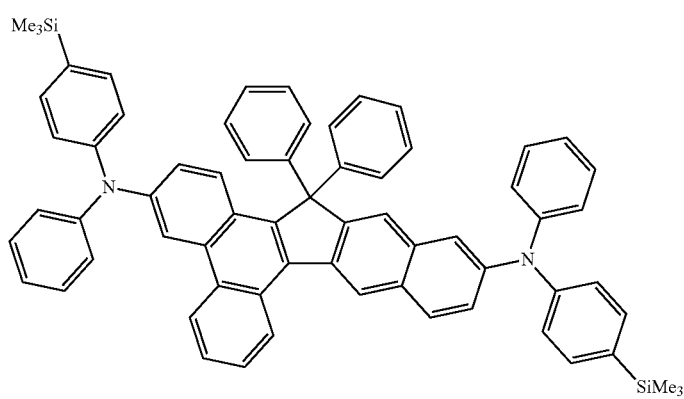

-continued
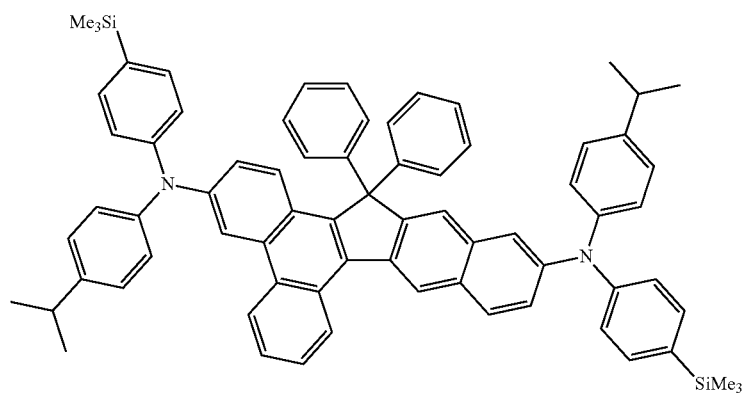
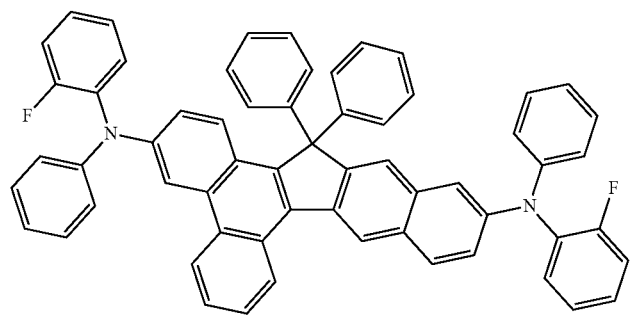
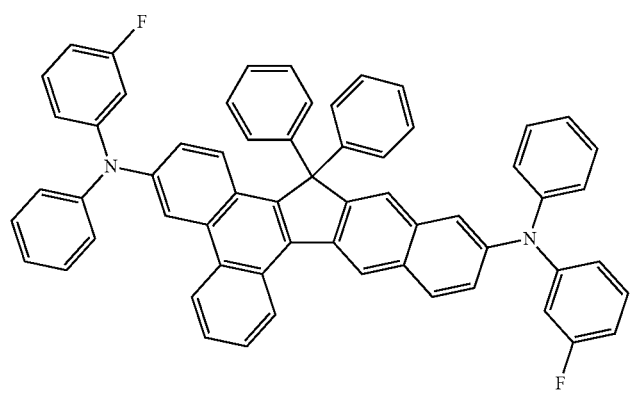
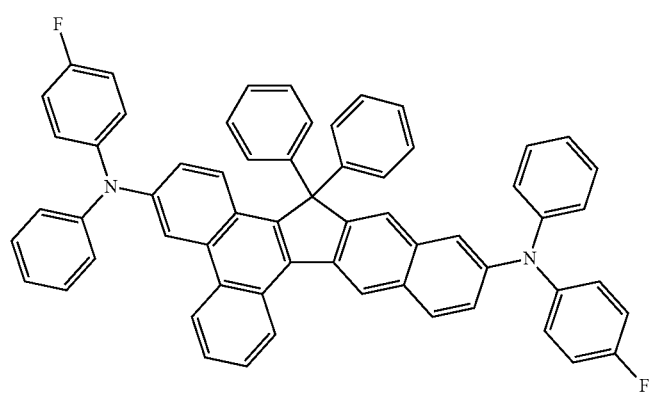

-continued
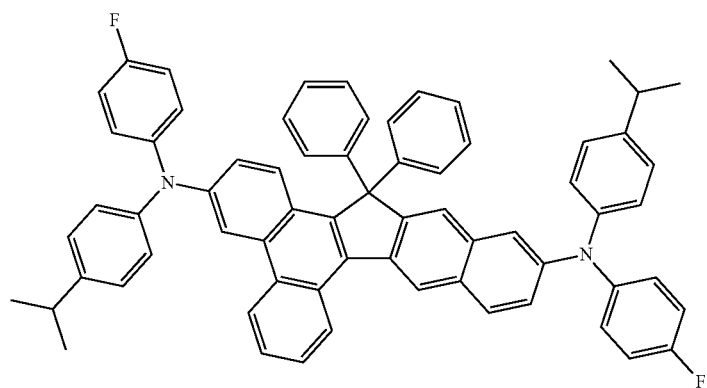
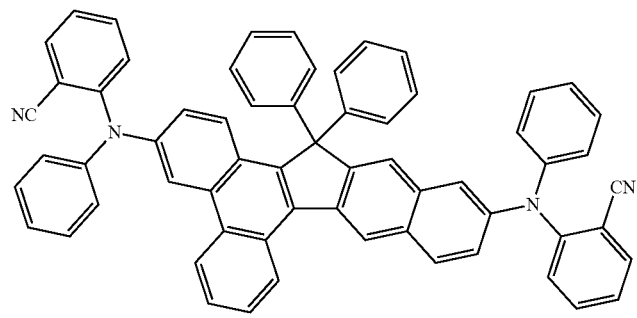
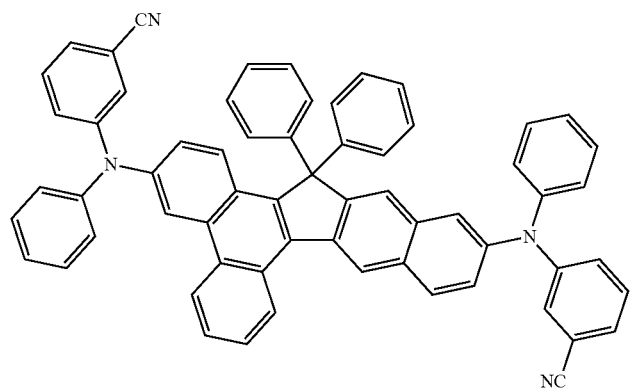
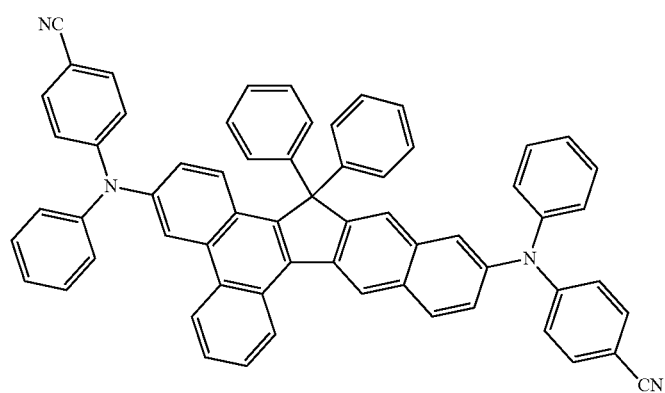

-continued
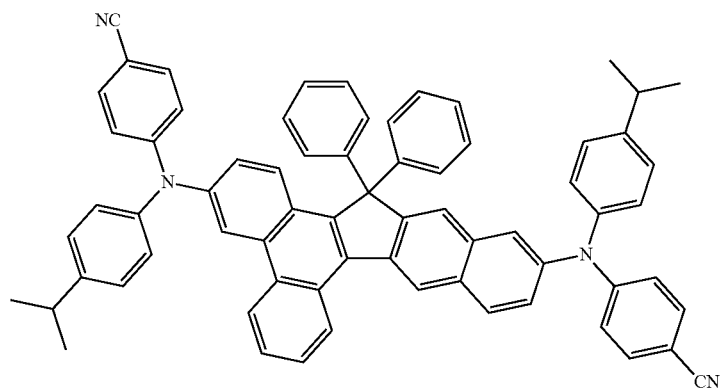
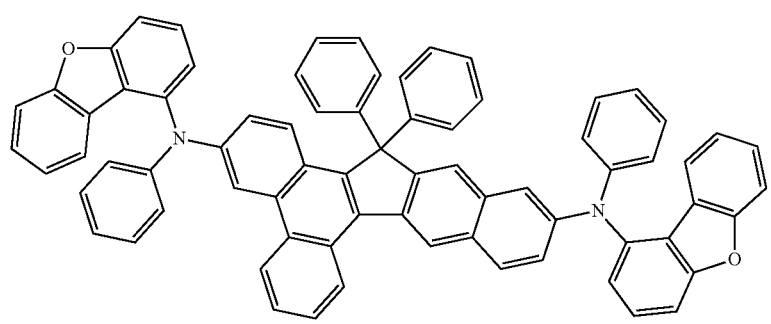
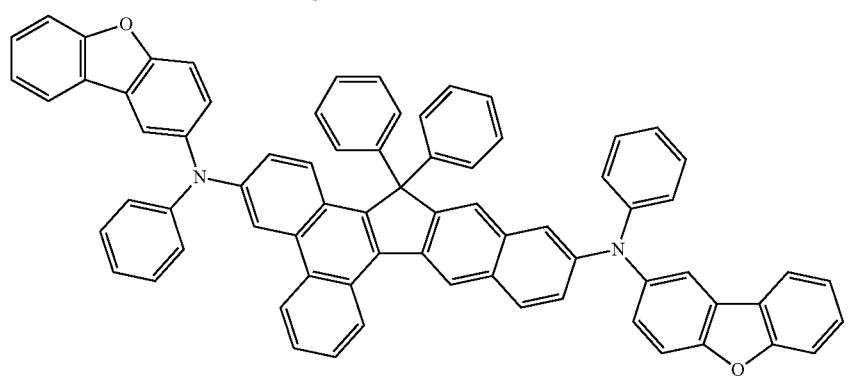
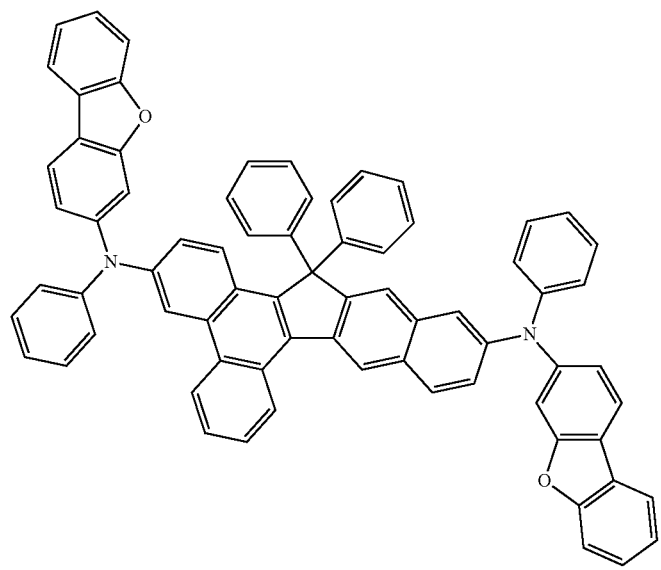

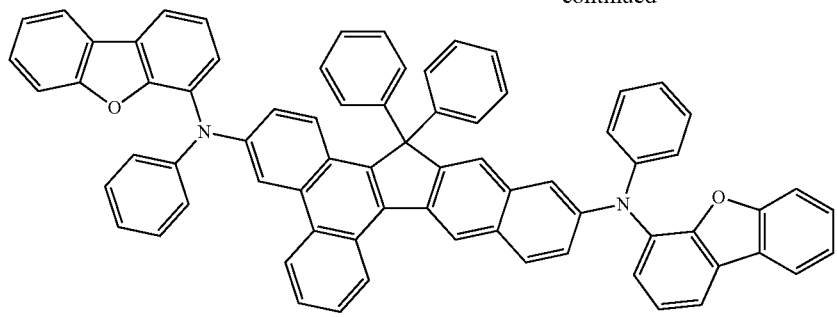
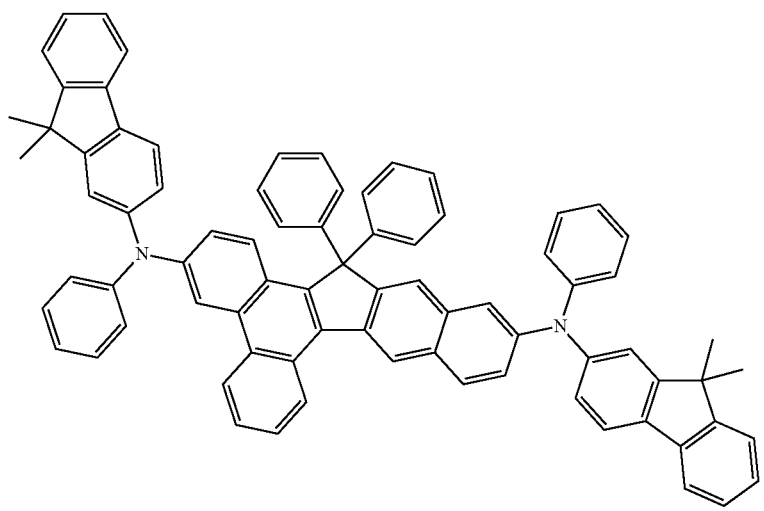
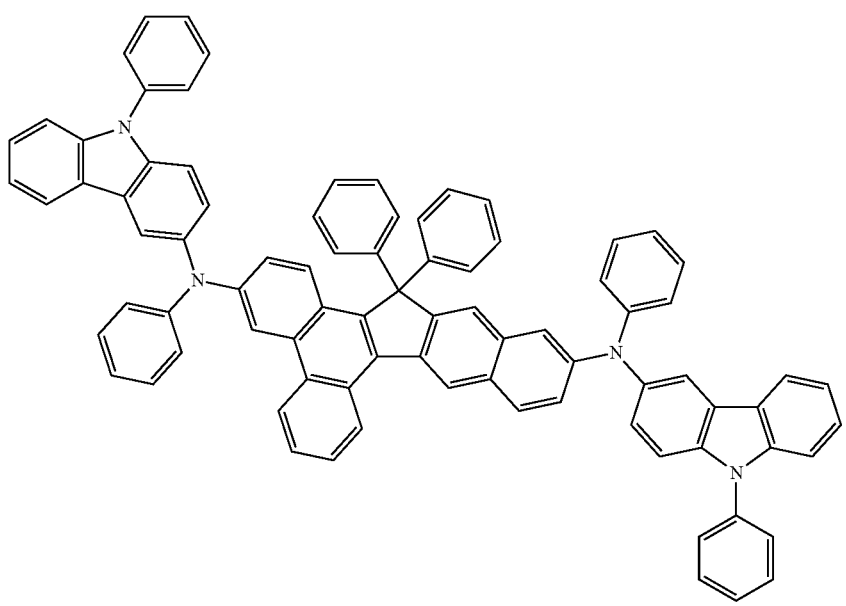

-continued
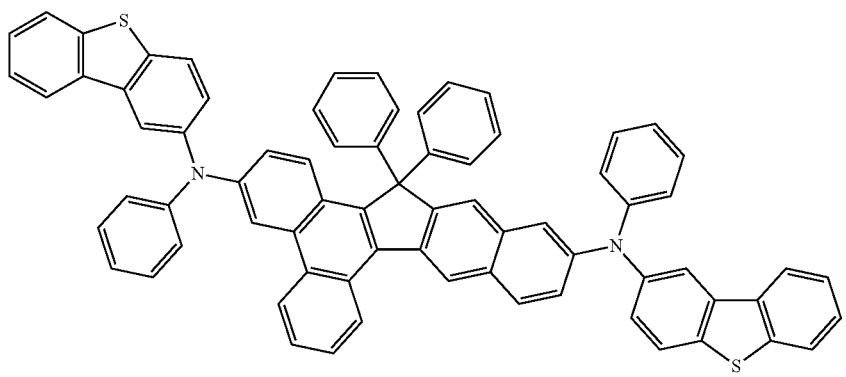
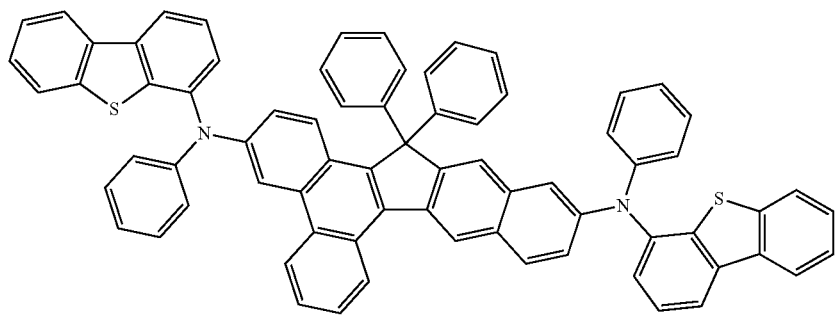
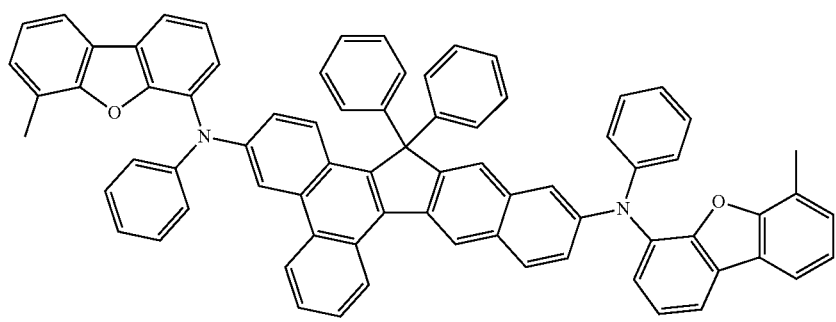
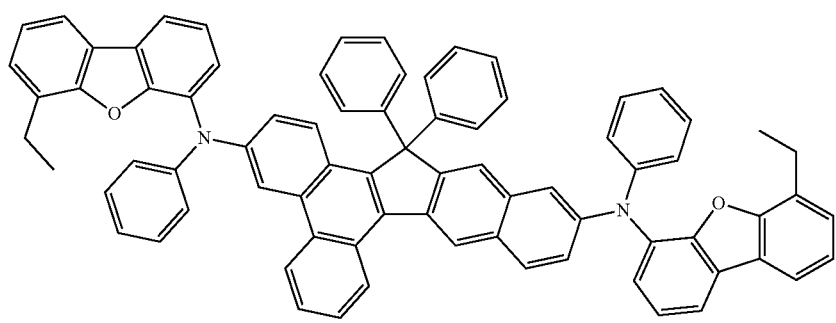
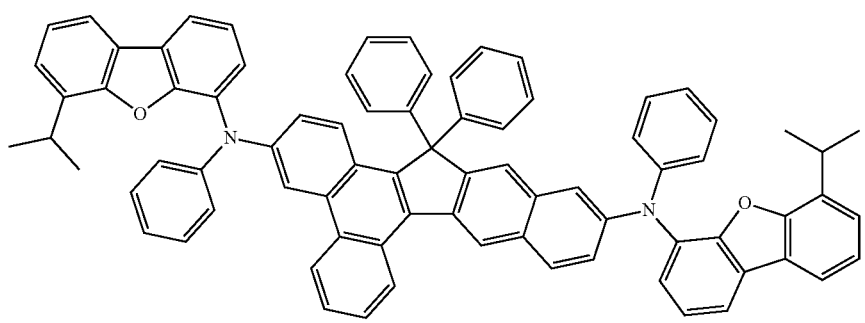

-continued
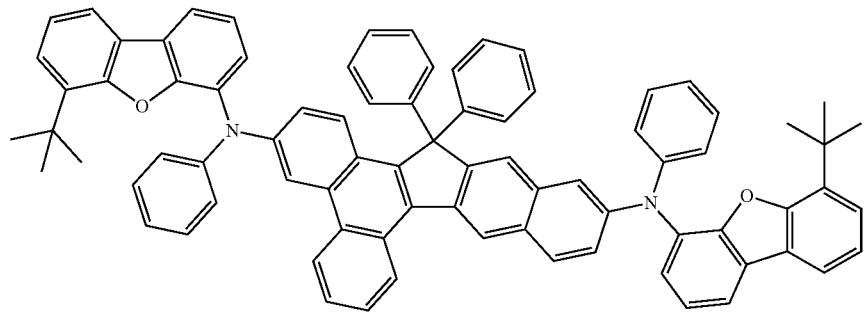
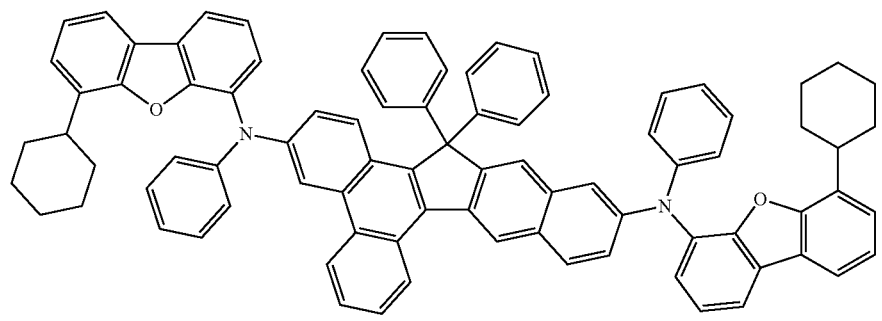
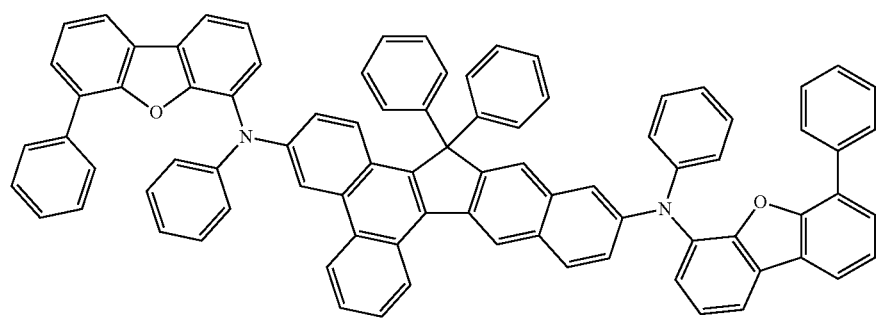
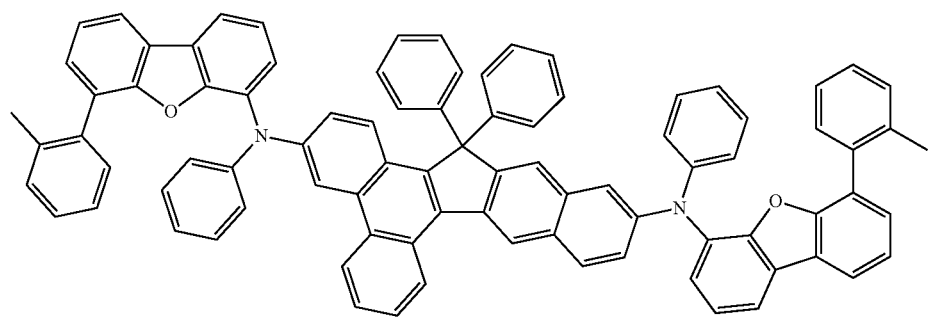
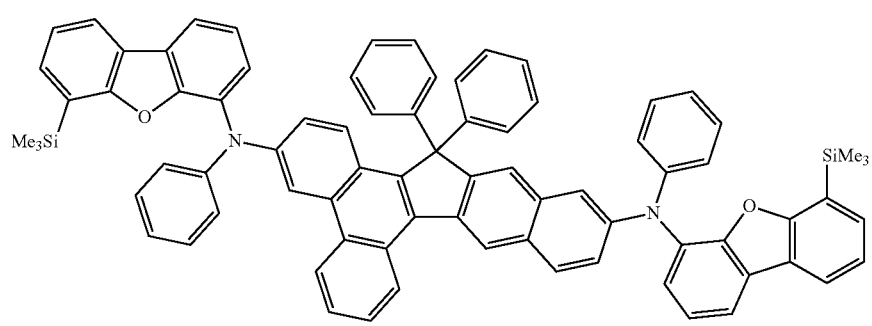

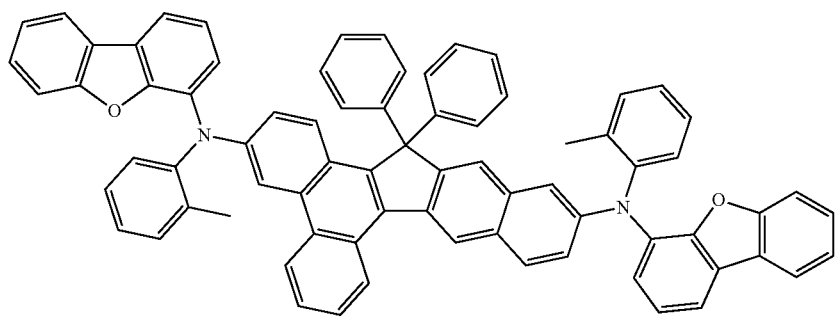
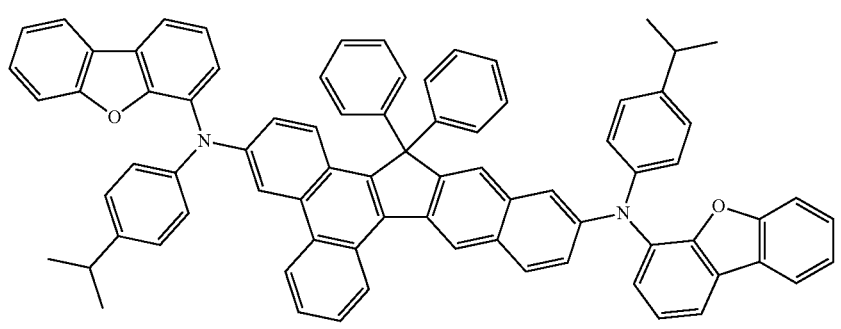

-continued
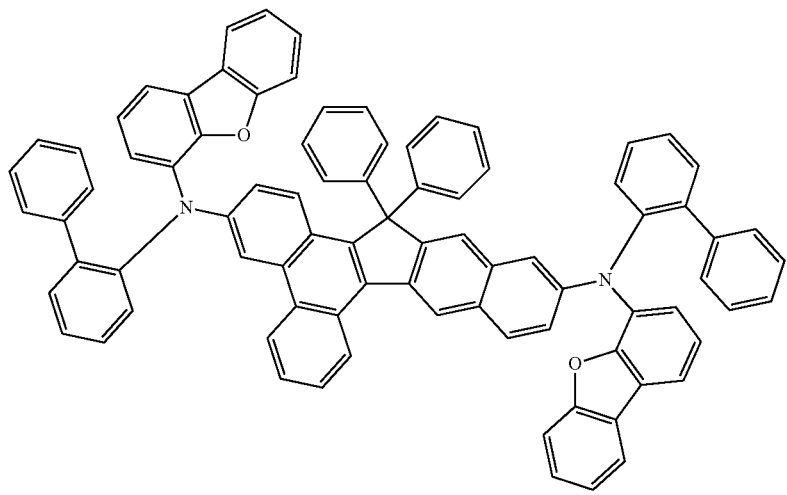
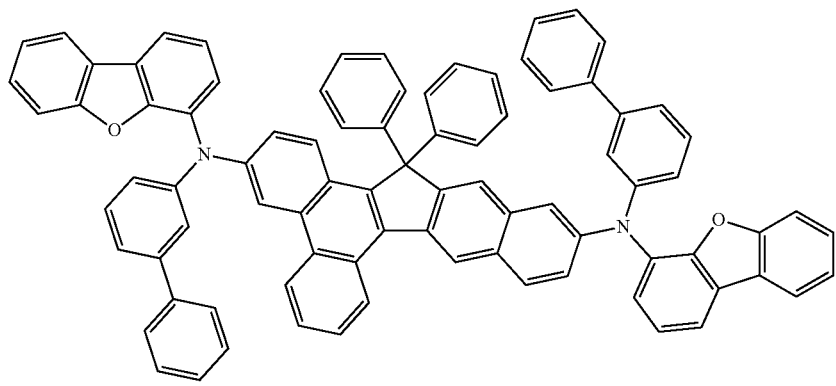
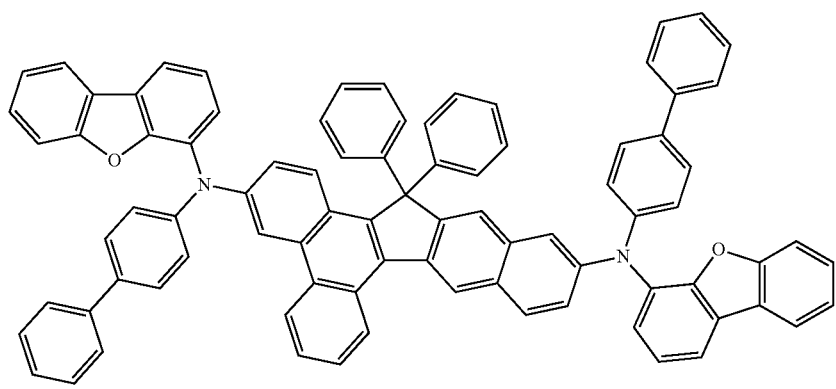
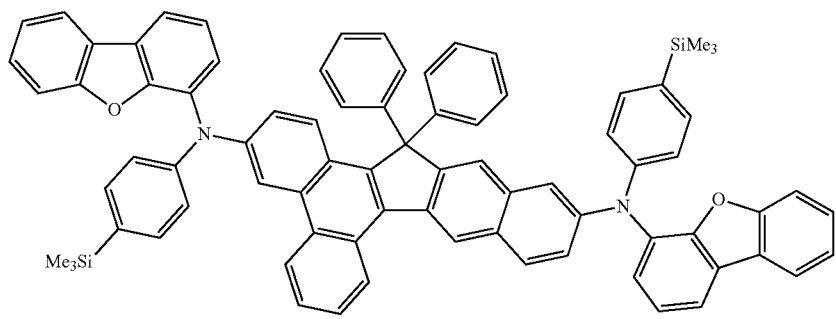

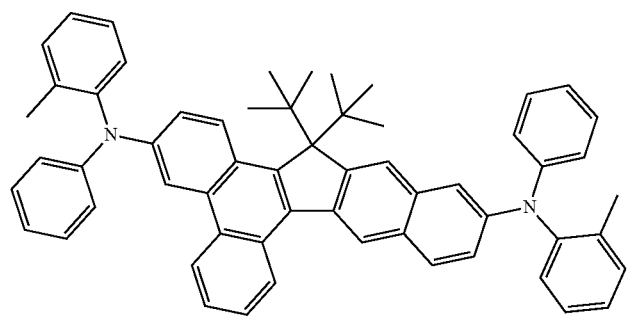
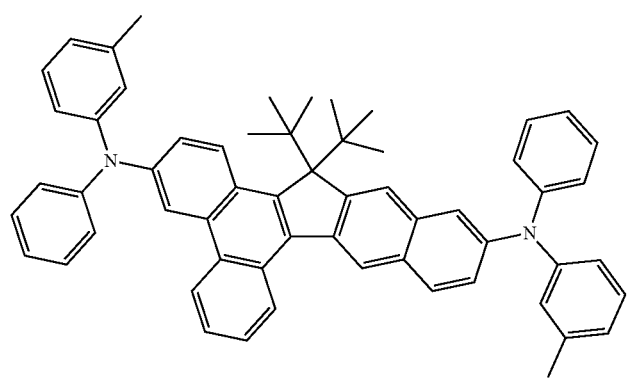
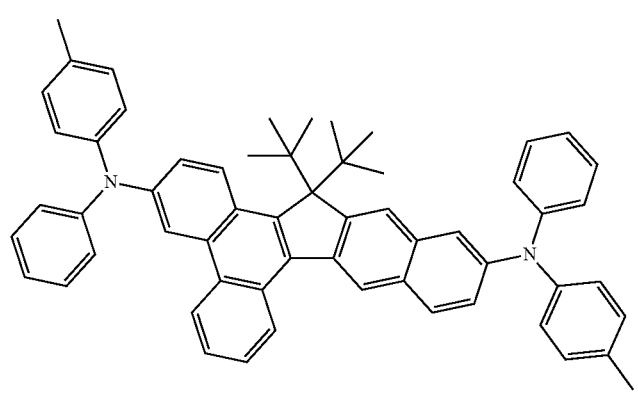

-continued
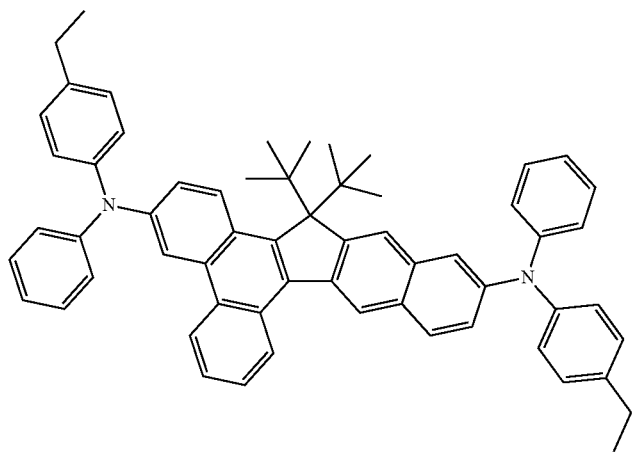
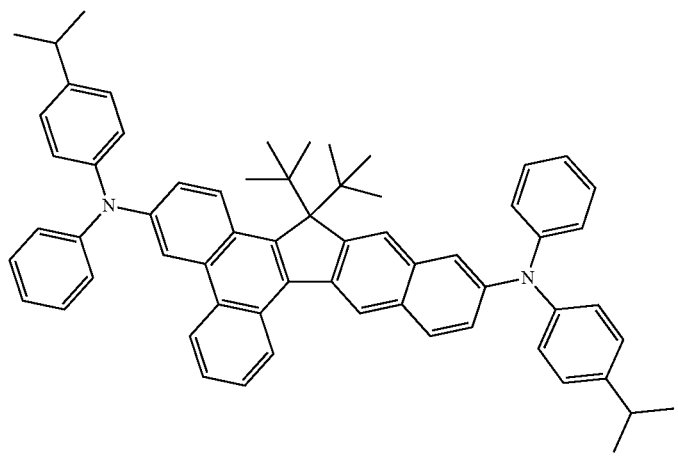
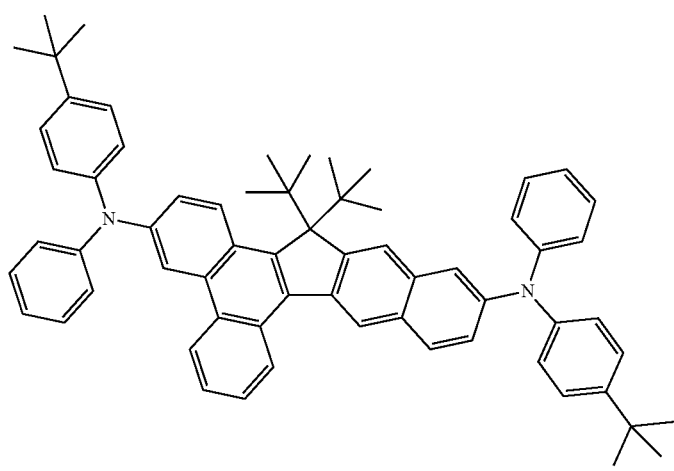

-continued
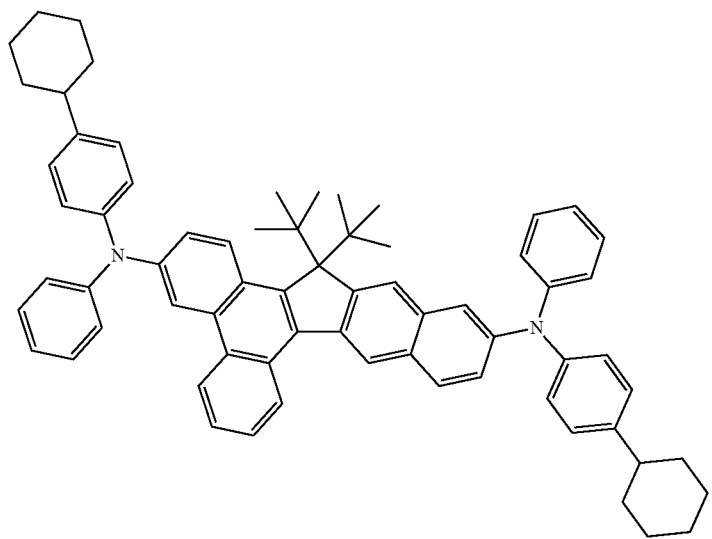
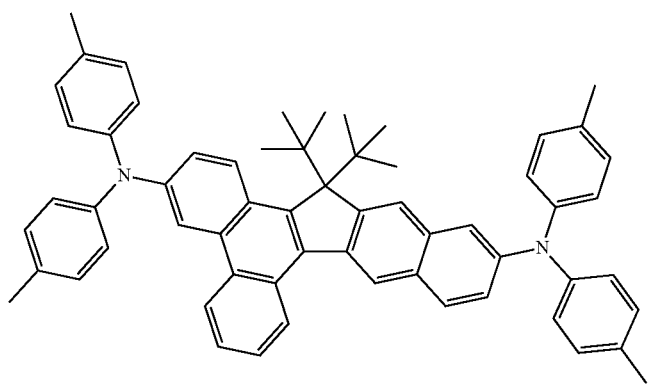
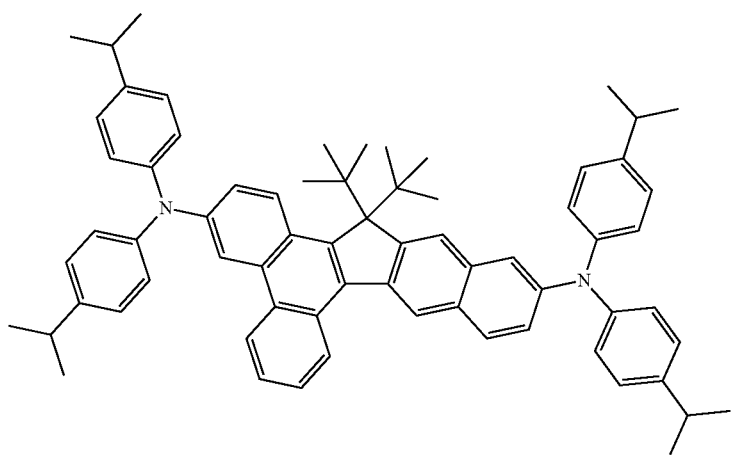

-continued
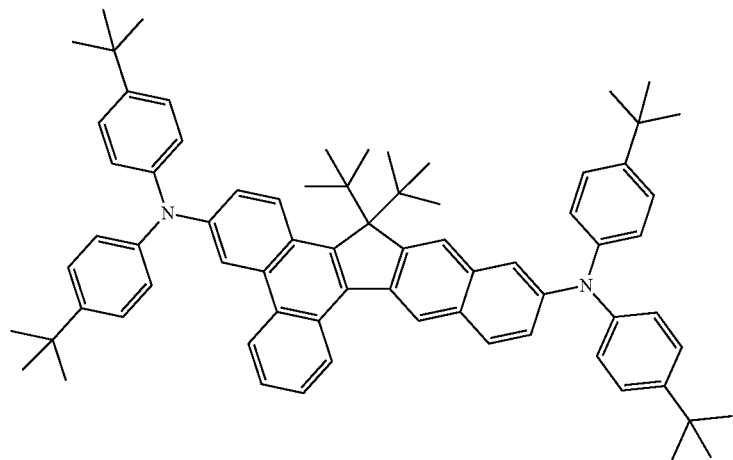
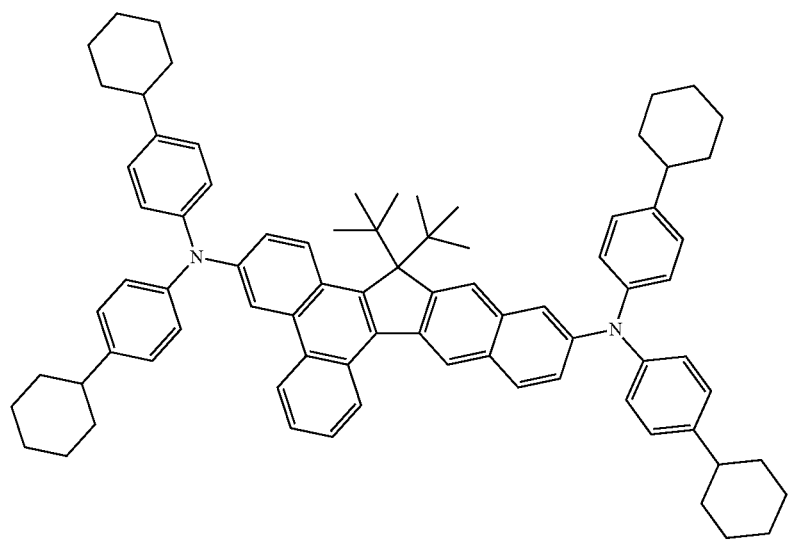
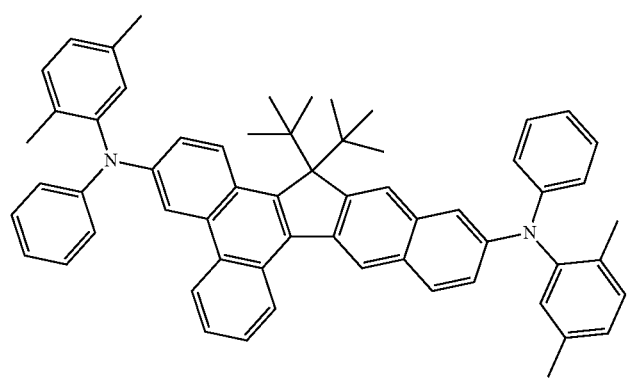

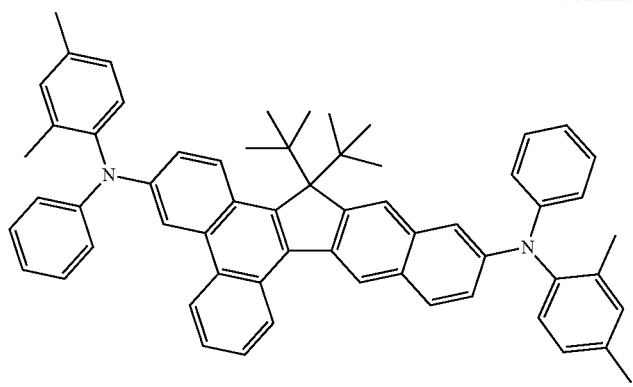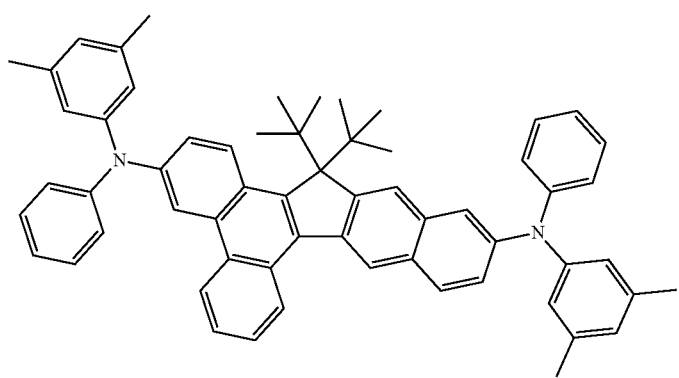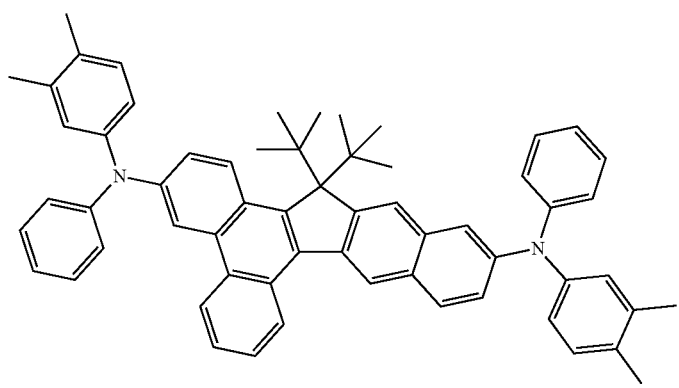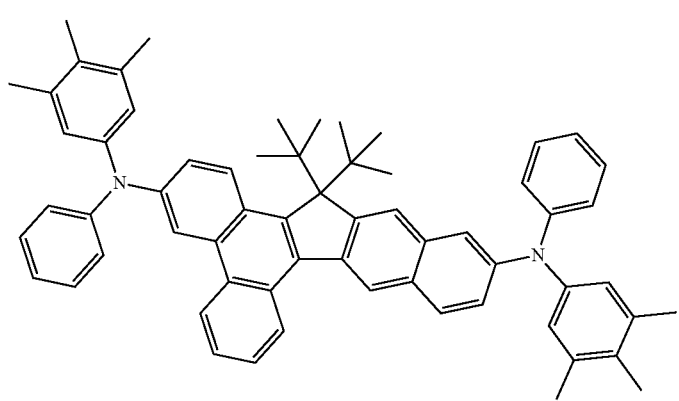

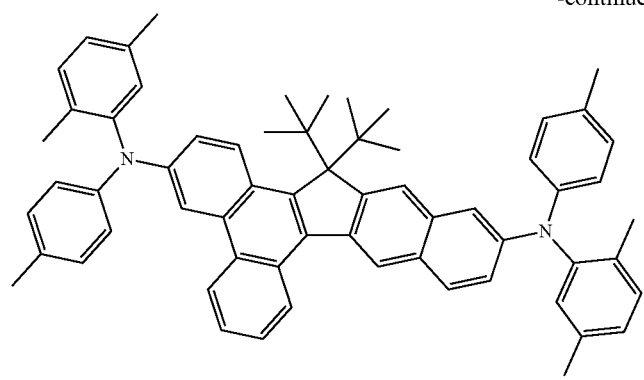
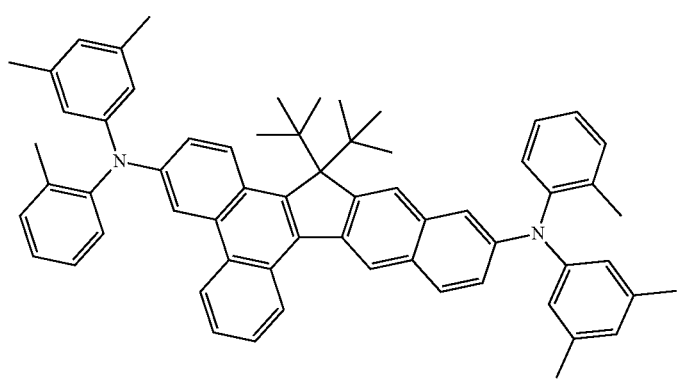
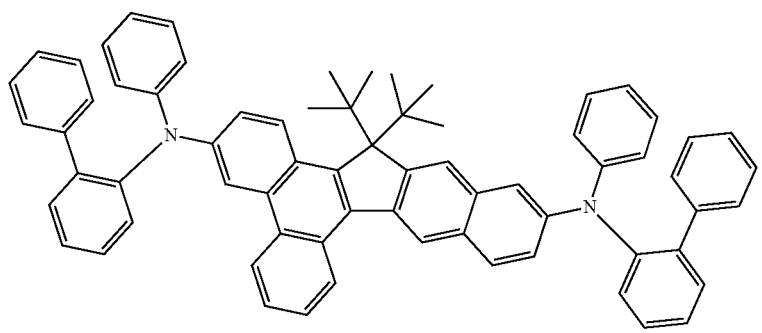
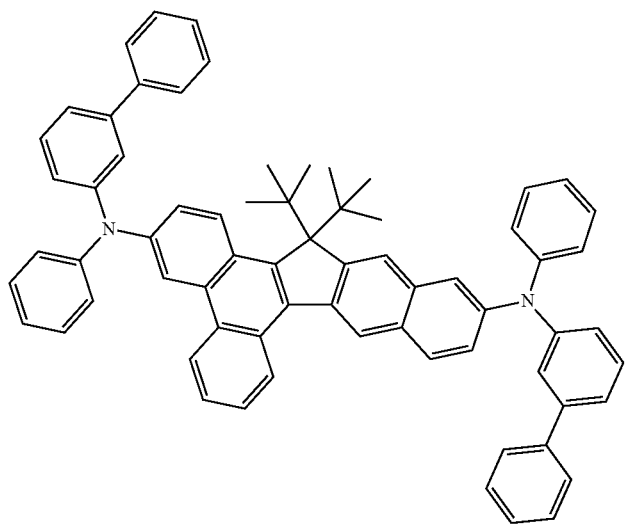

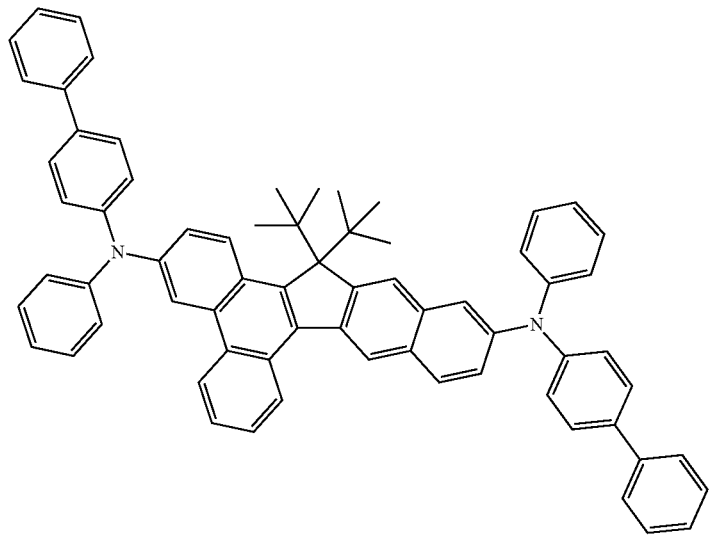
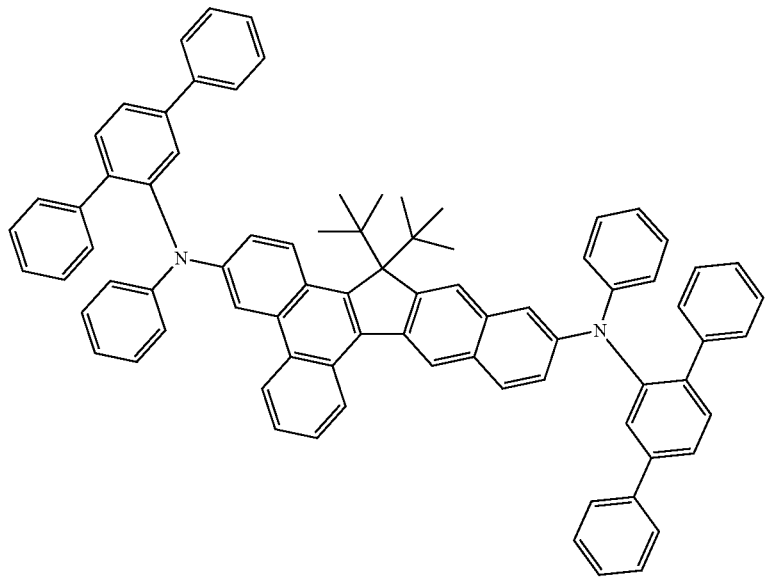
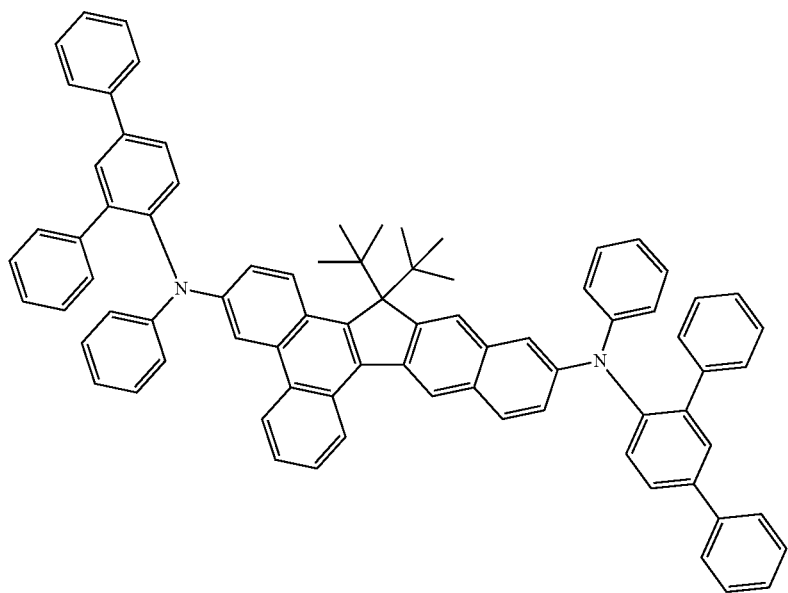

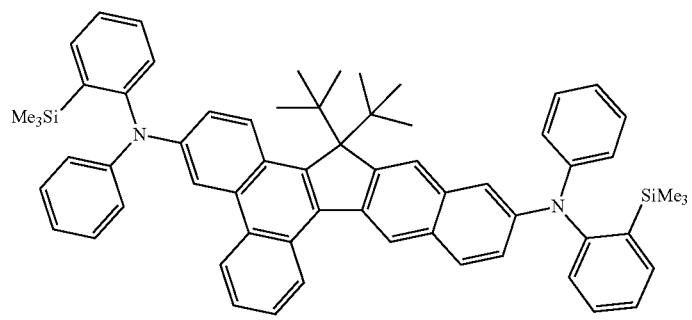
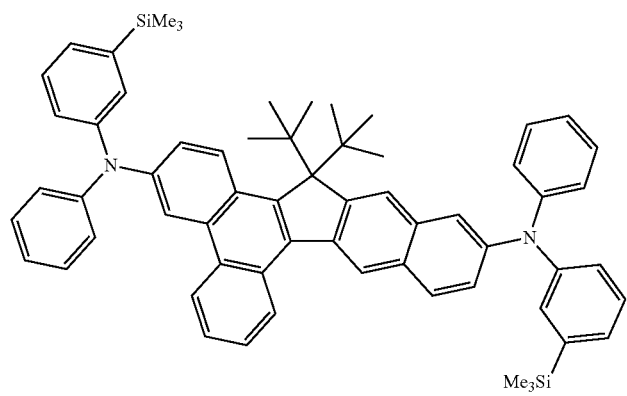
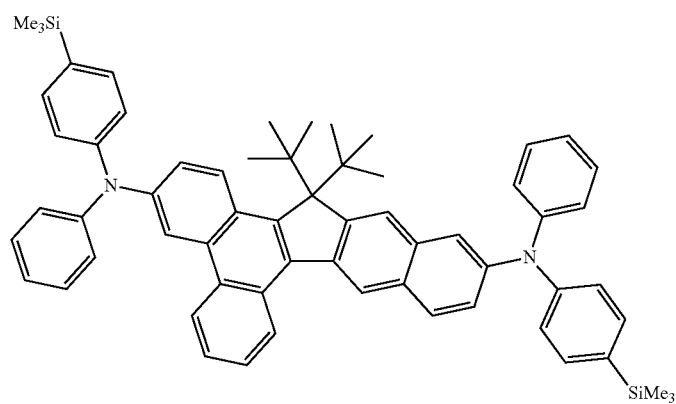
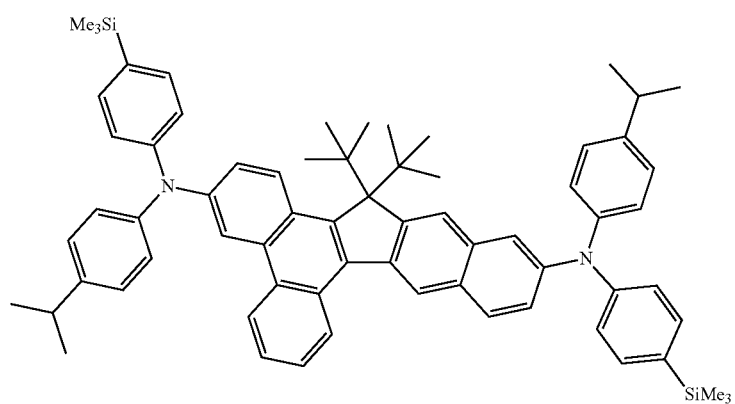

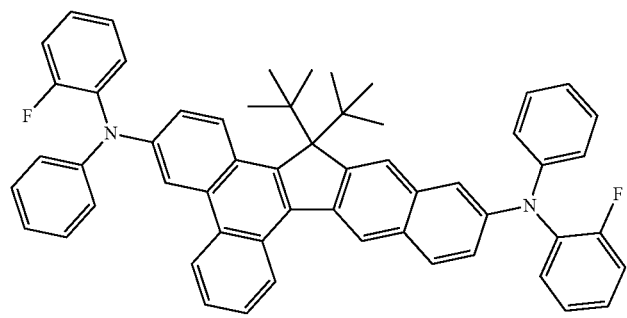
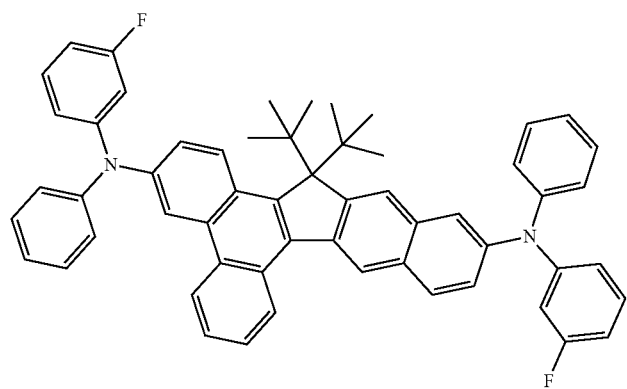
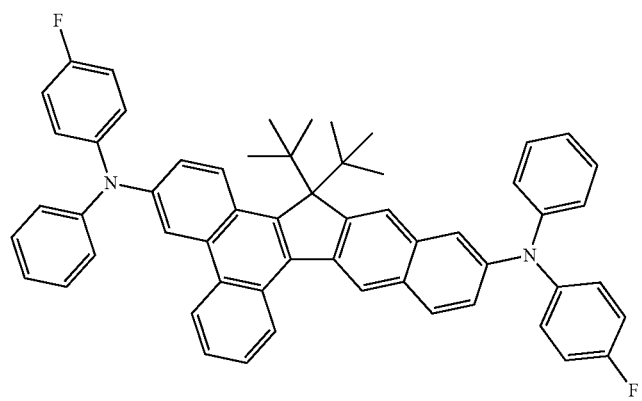
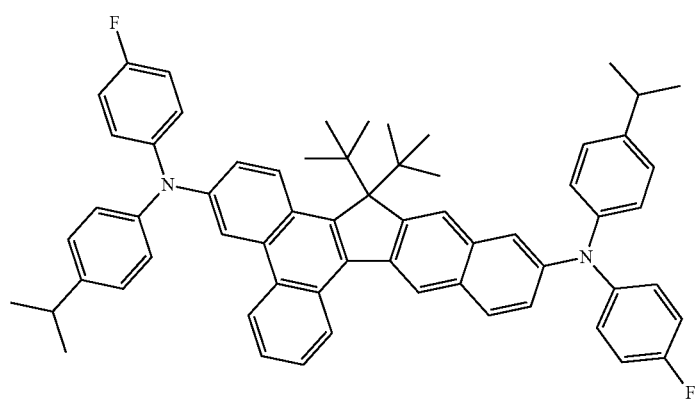

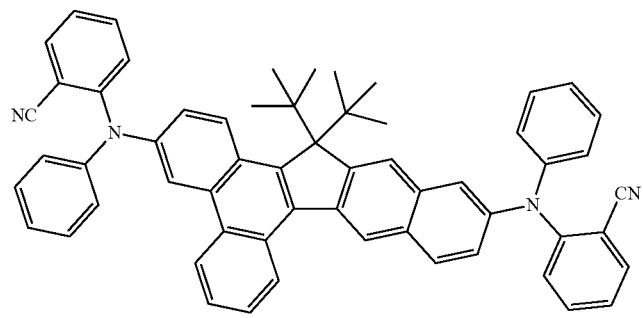
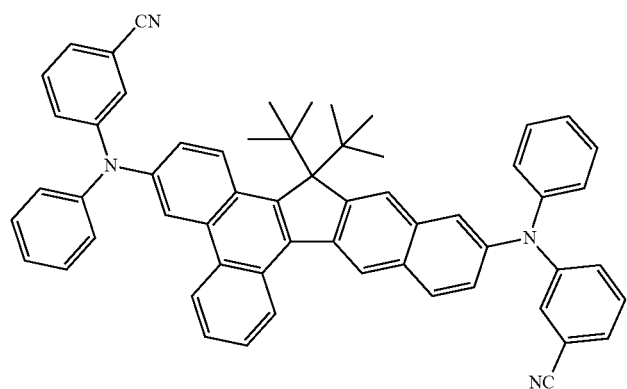
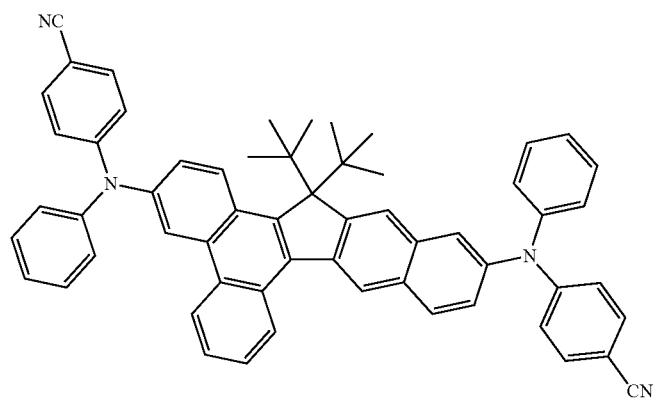
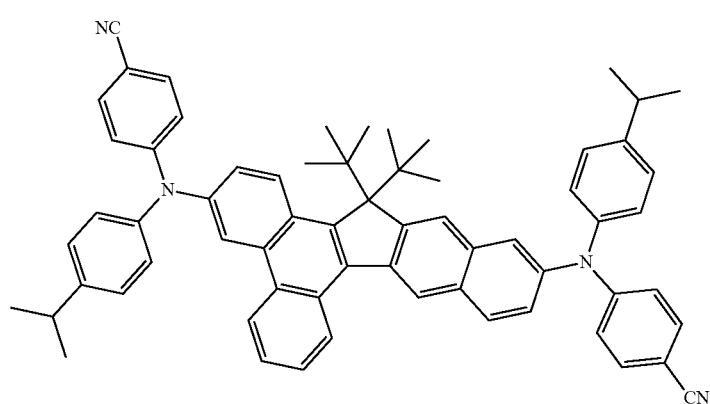

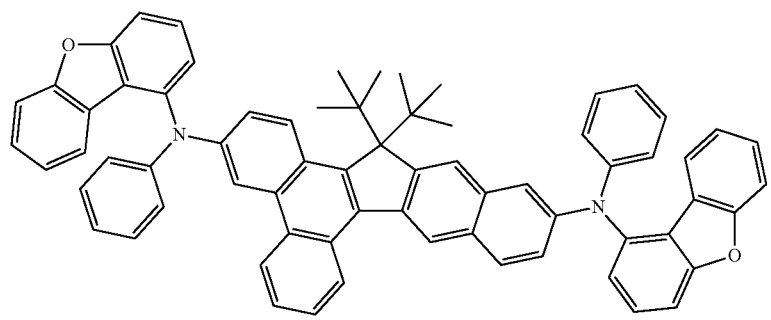
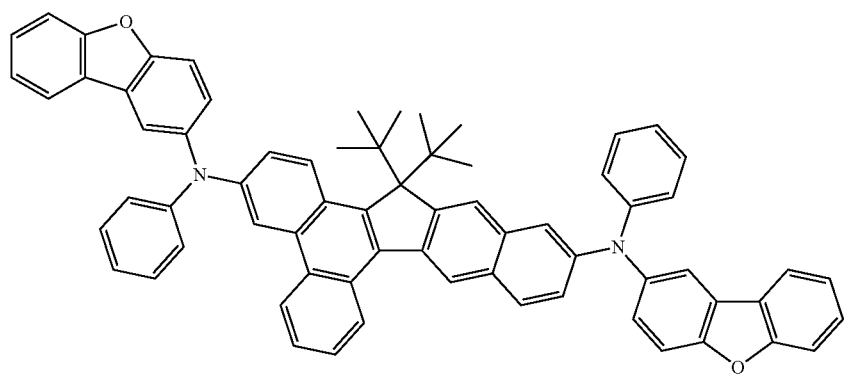
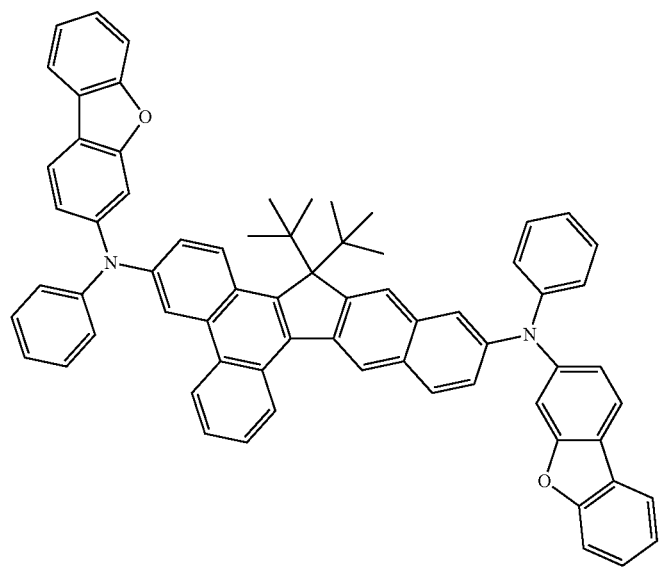
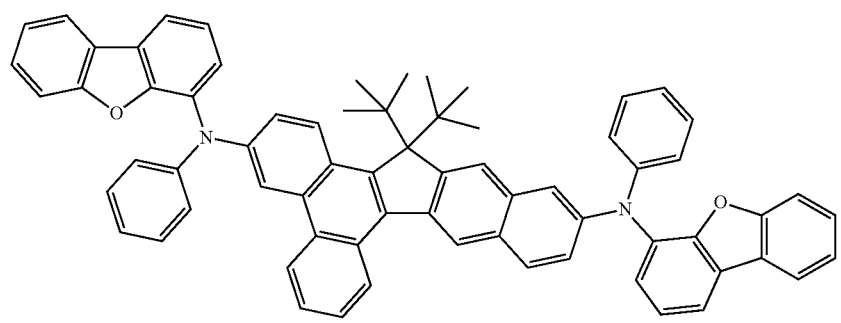

-continued
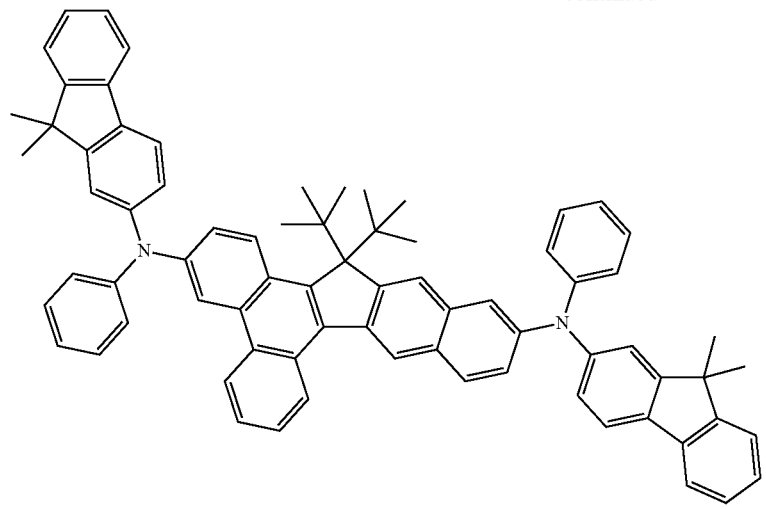
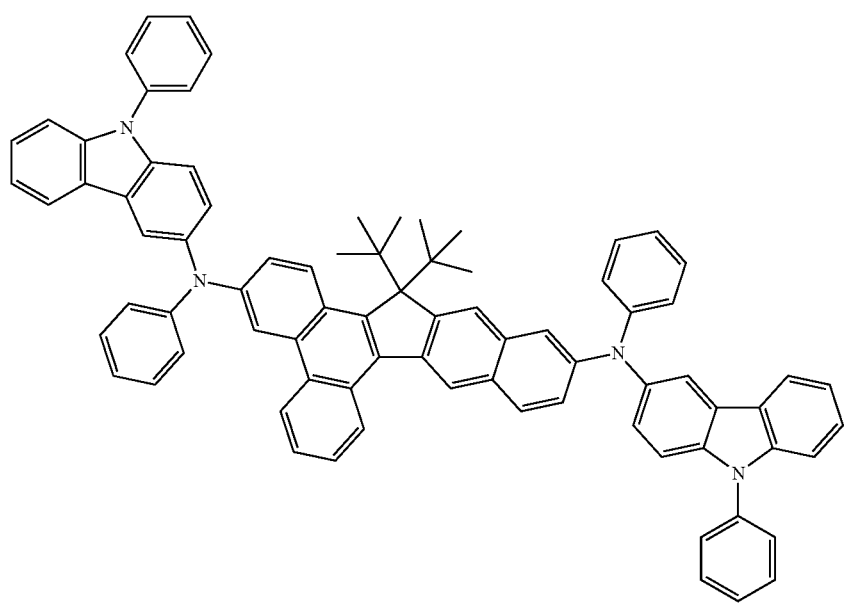
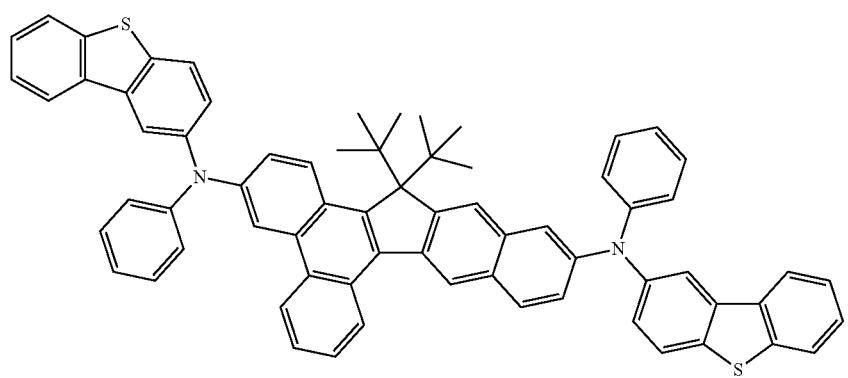

-continued
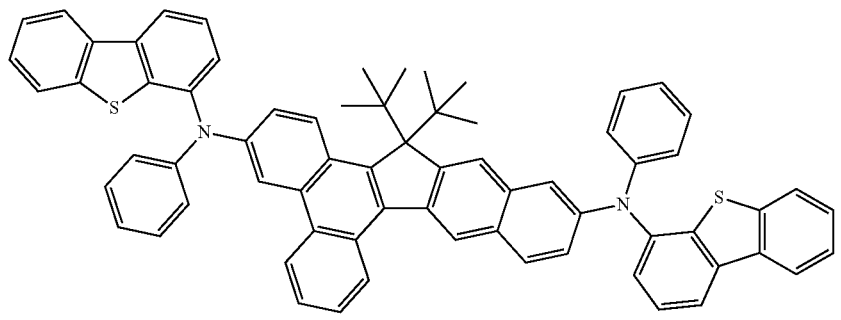
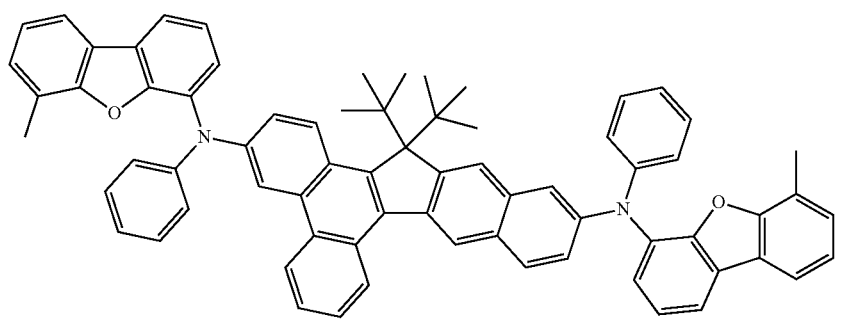
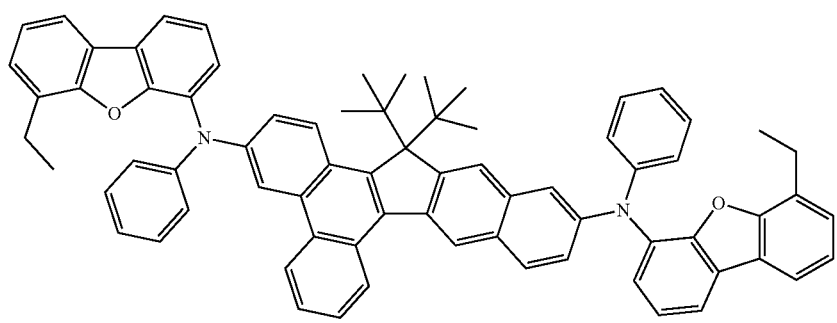
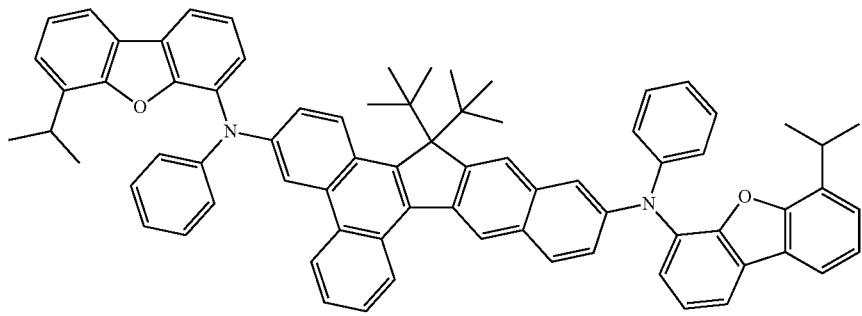
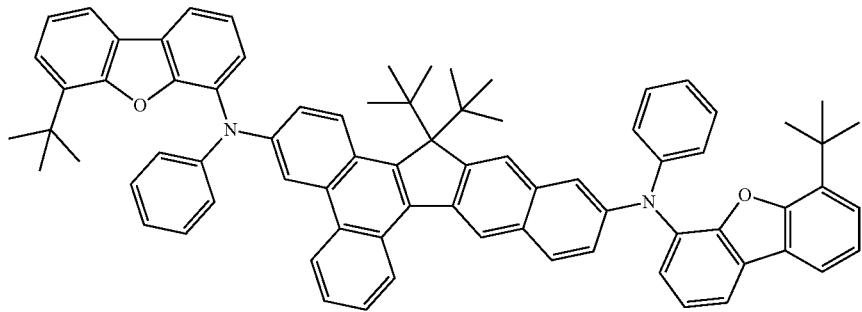

-continued
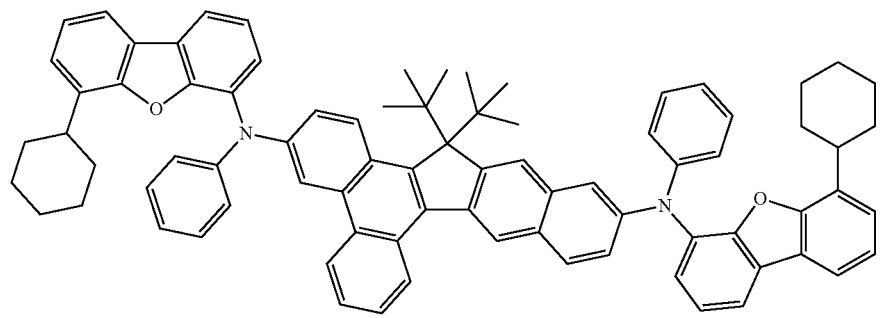
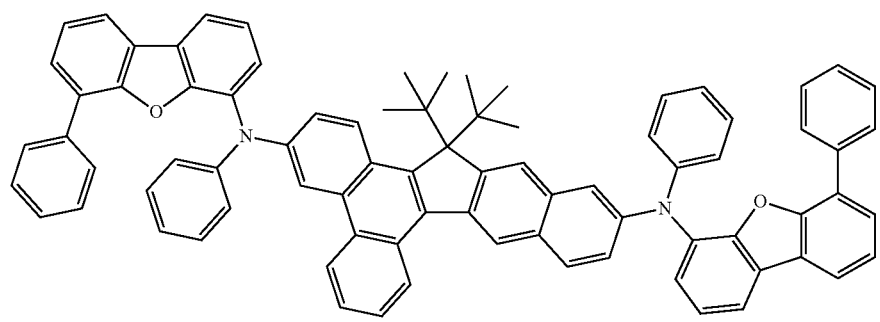
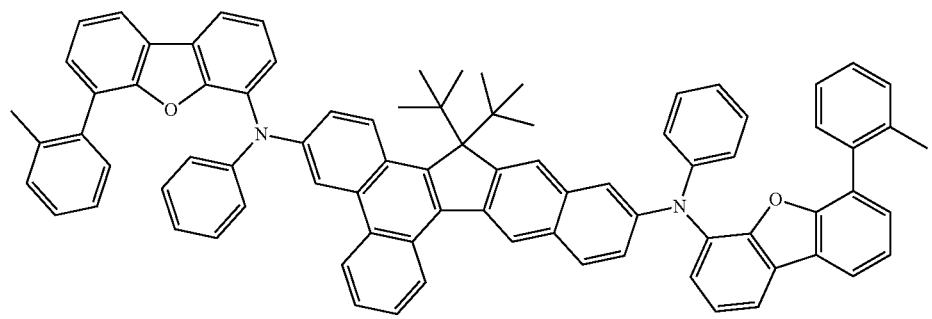
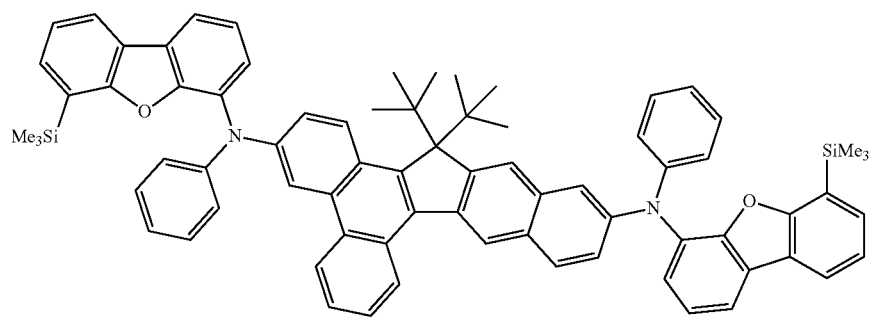
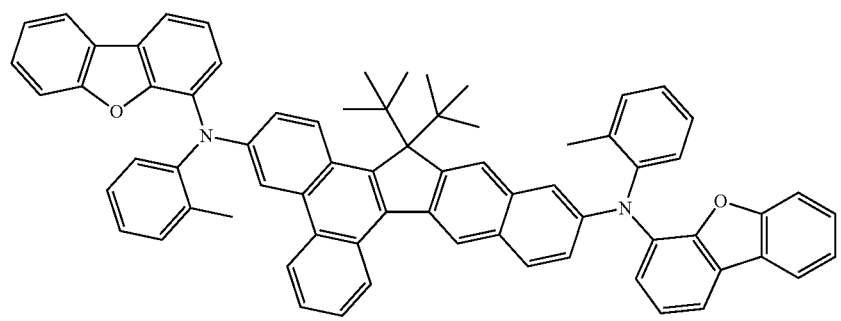

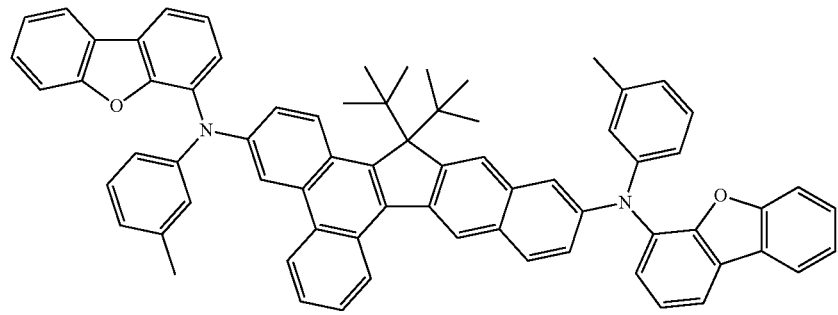
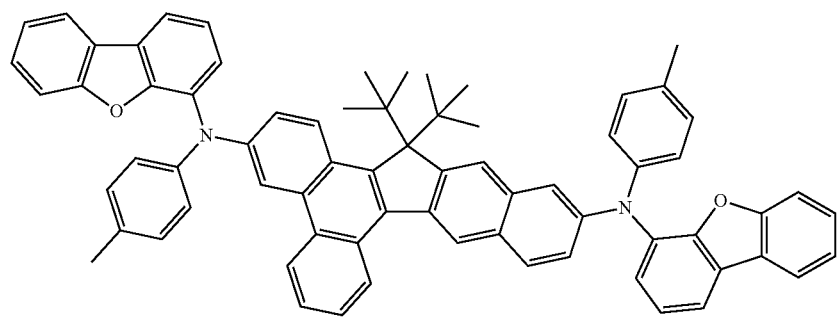
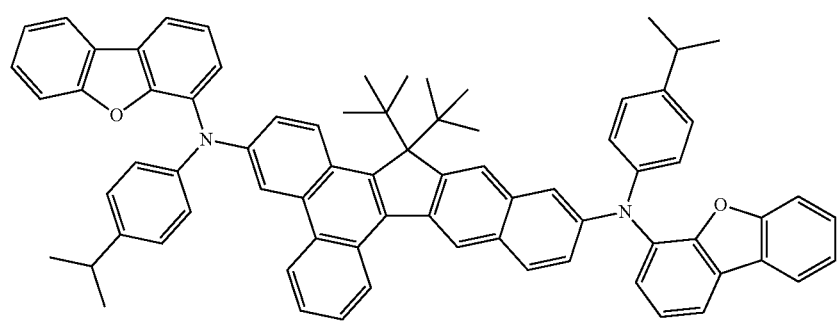
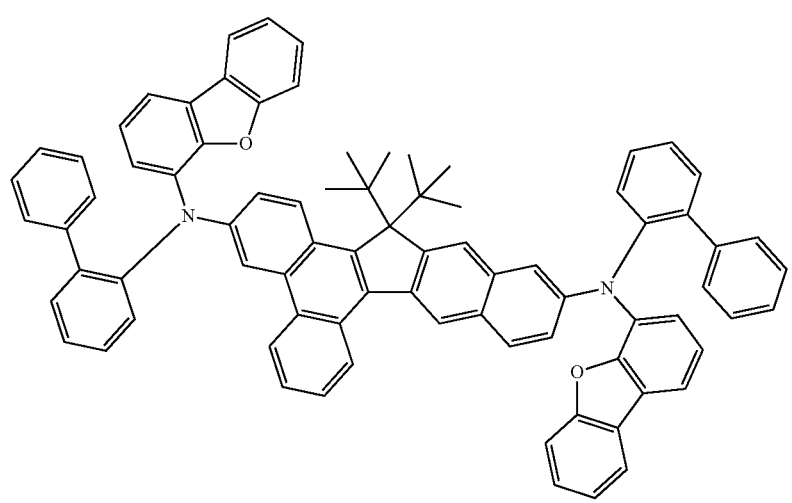

-continued
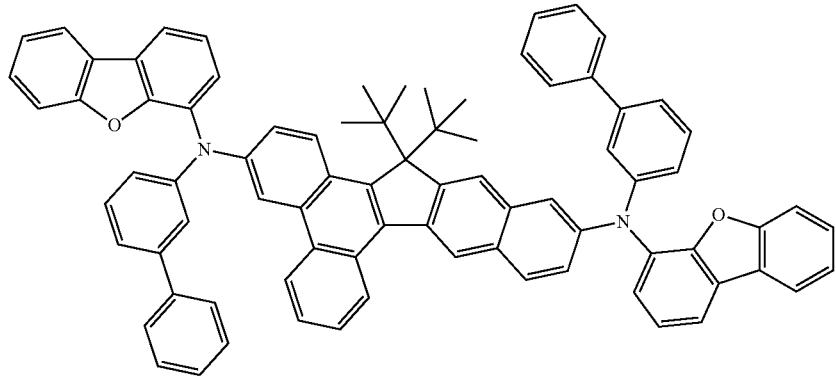
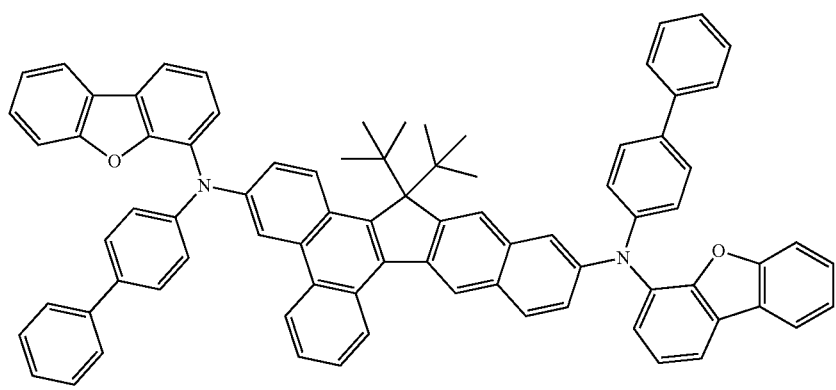
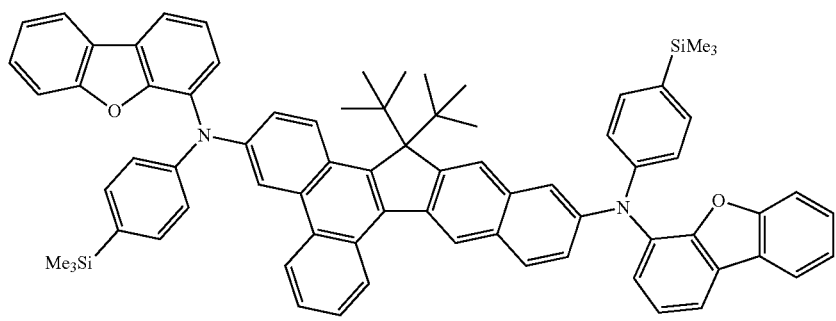
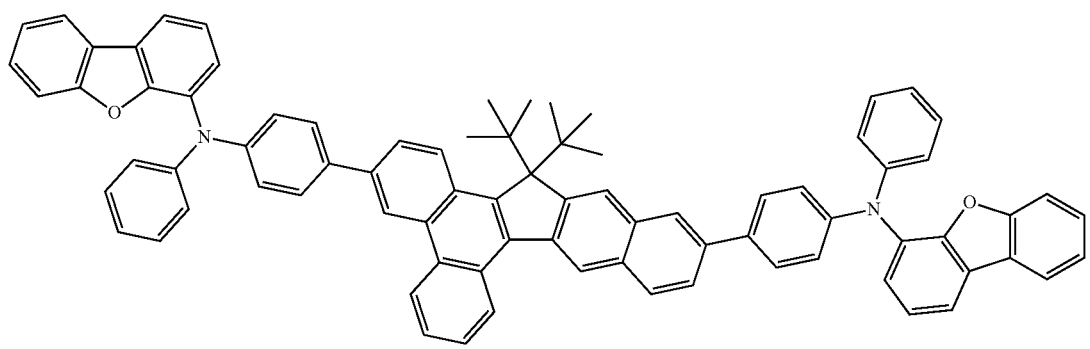

-continued
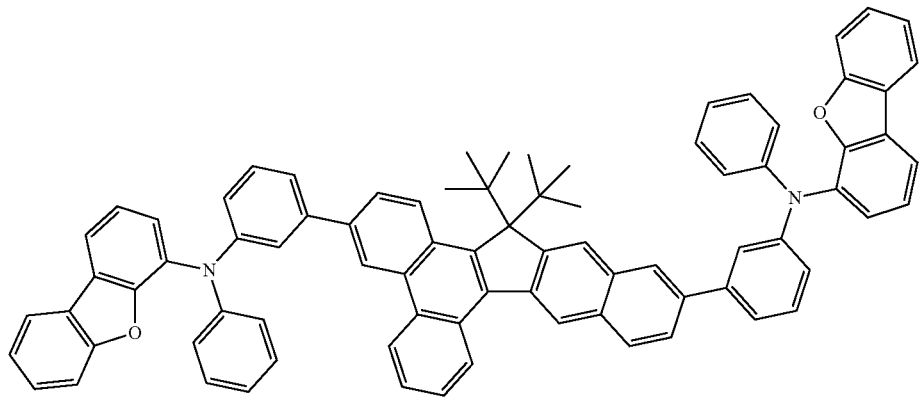
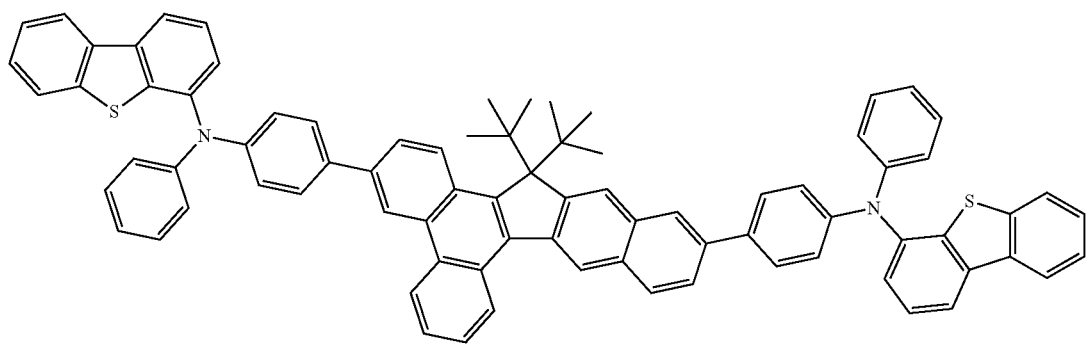
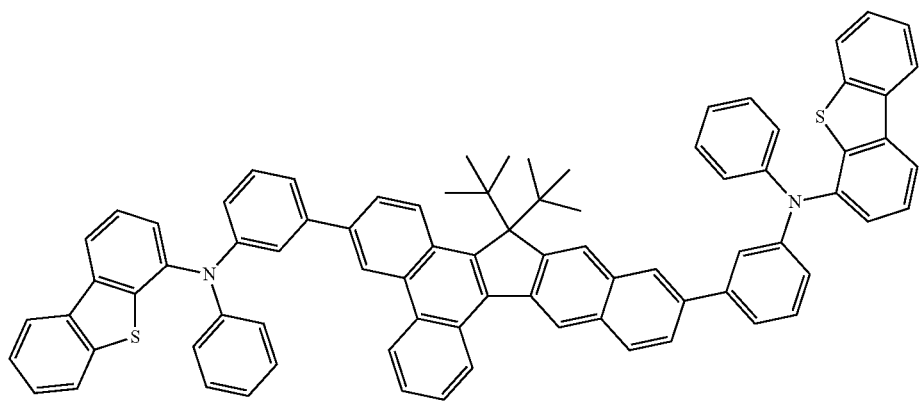
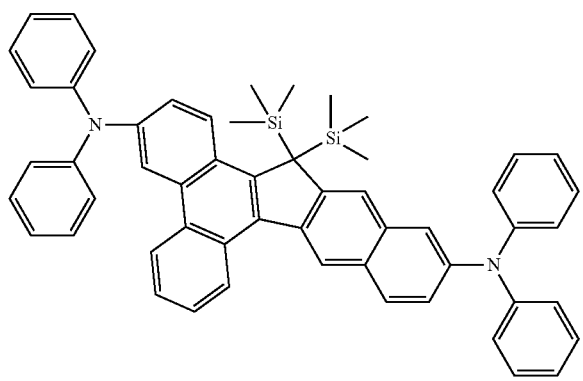

-continued
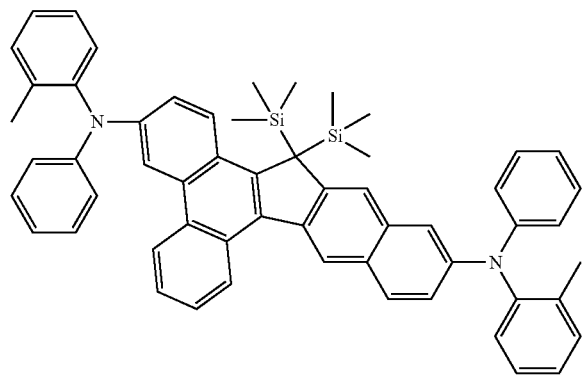
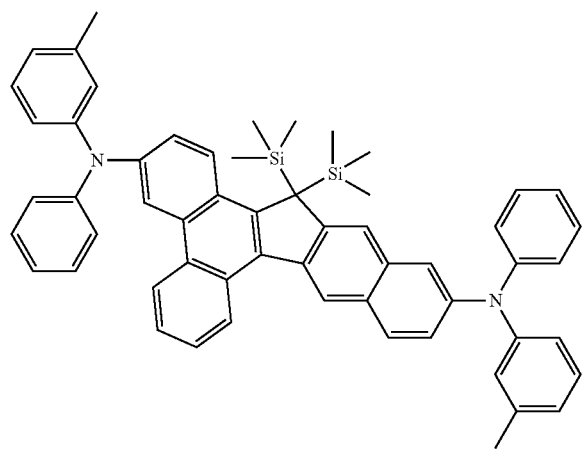
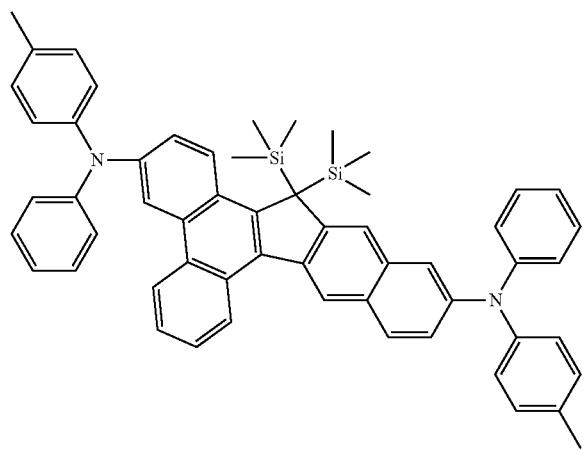

-continued
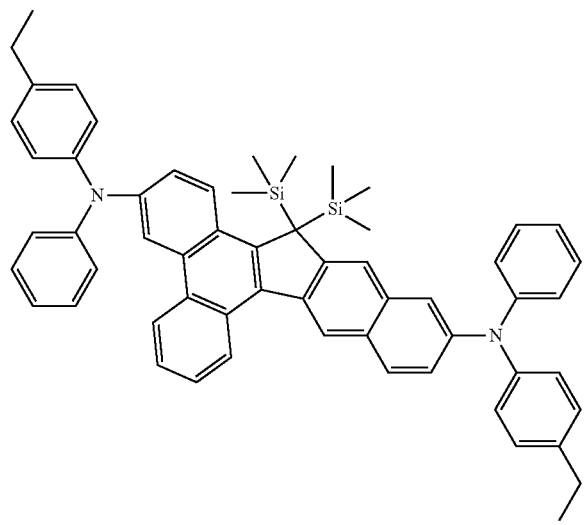
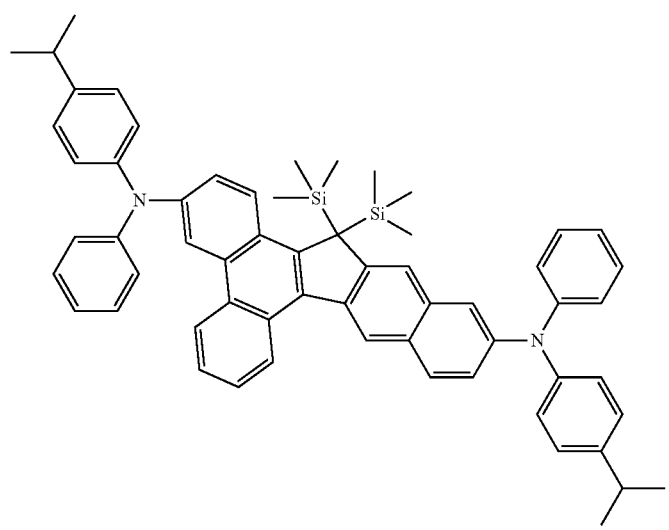
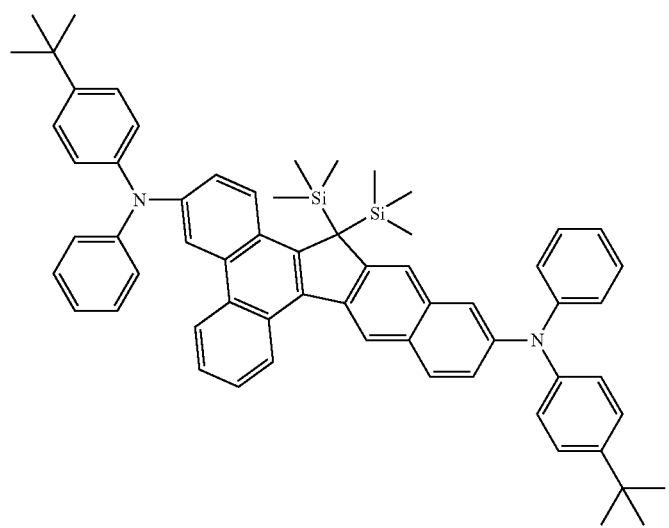

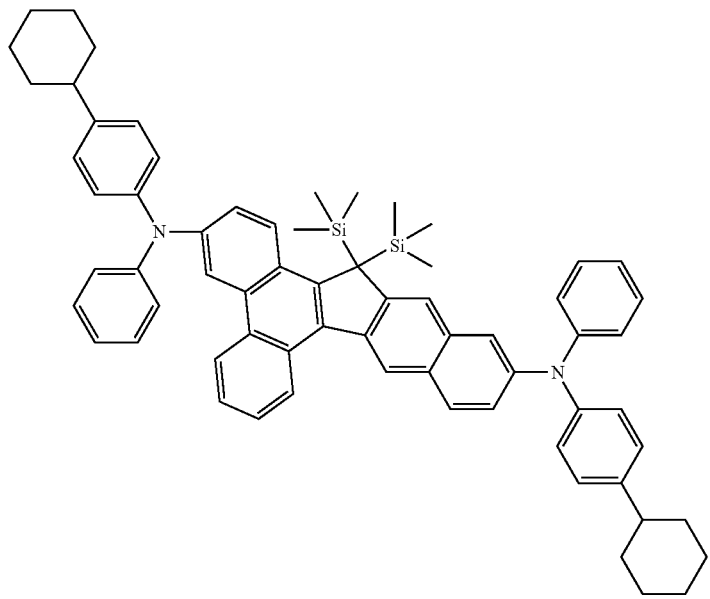
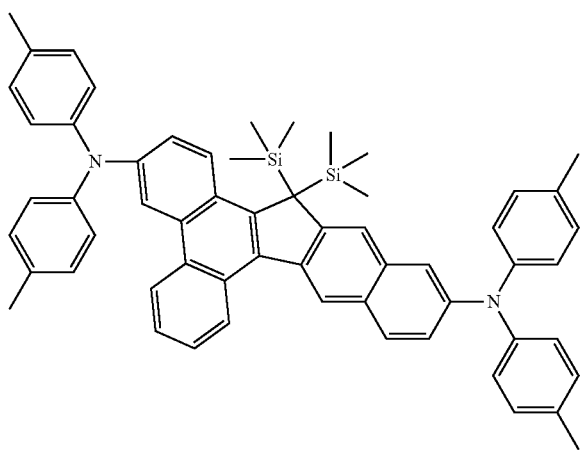
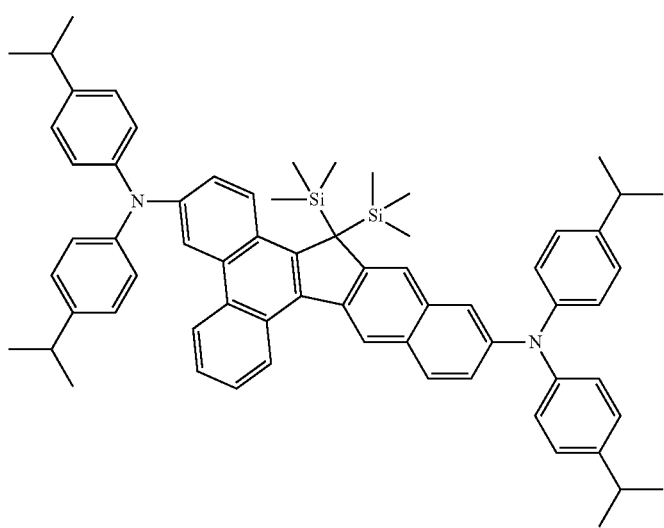

-continued
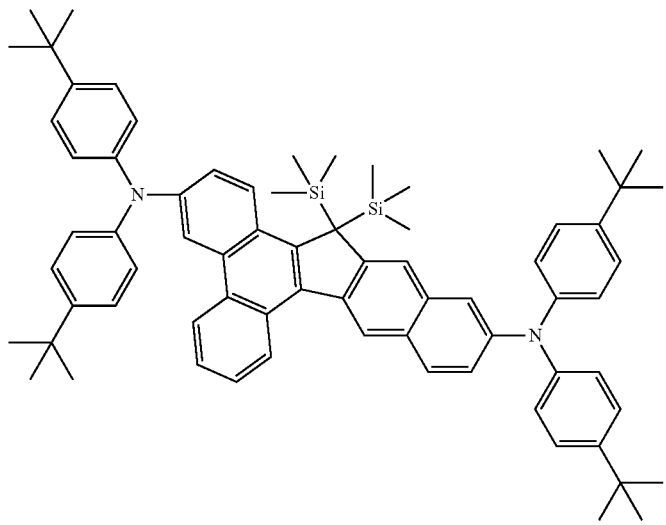
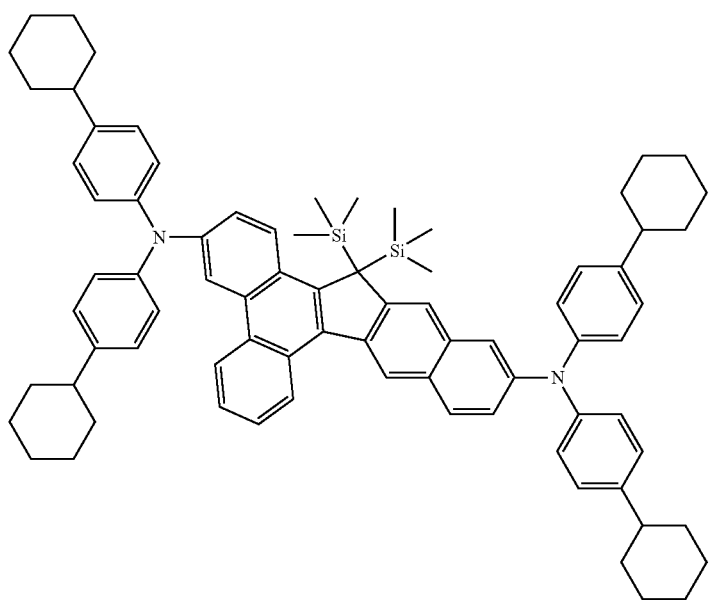
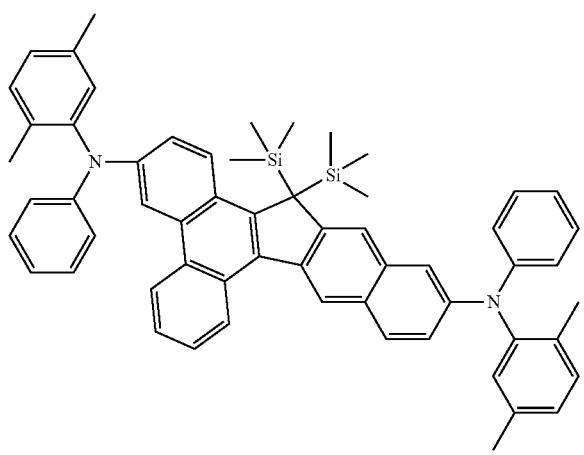

-continued
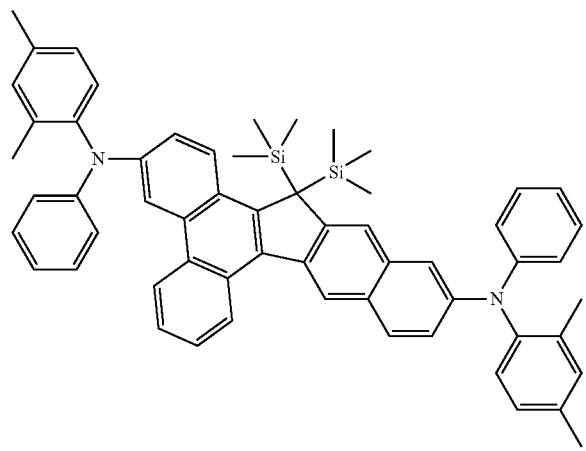
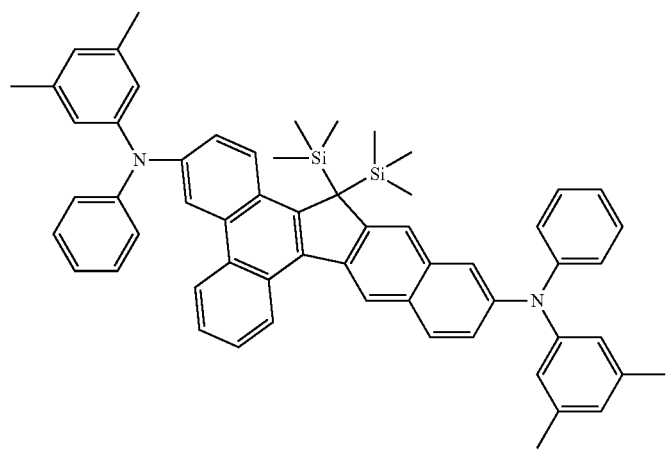
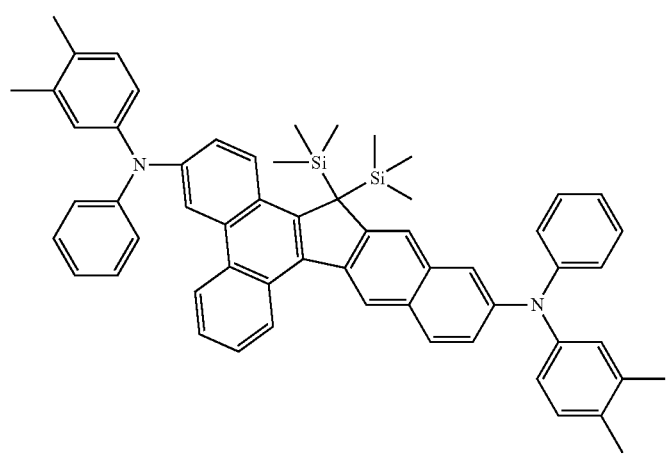

-continued
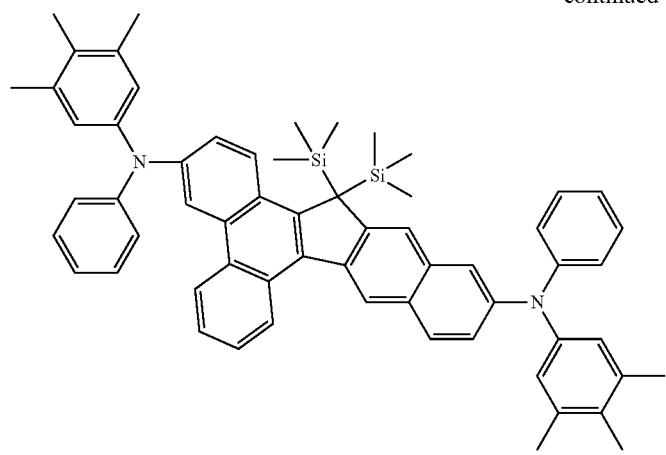
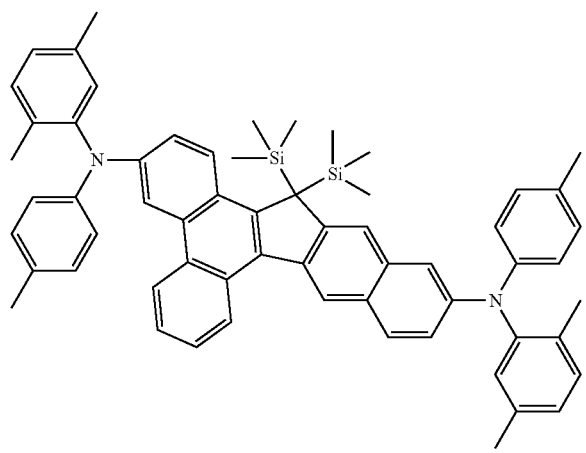
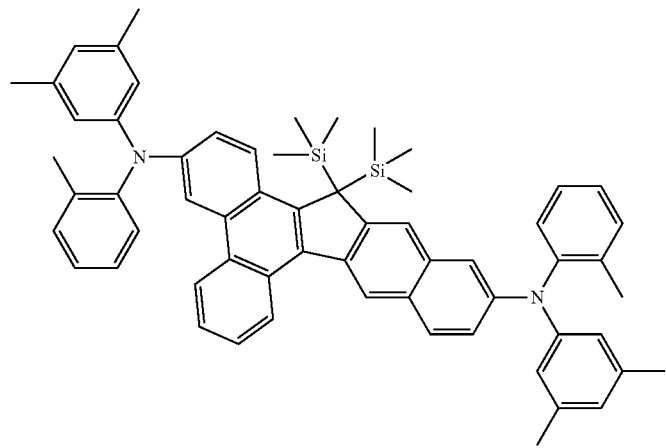
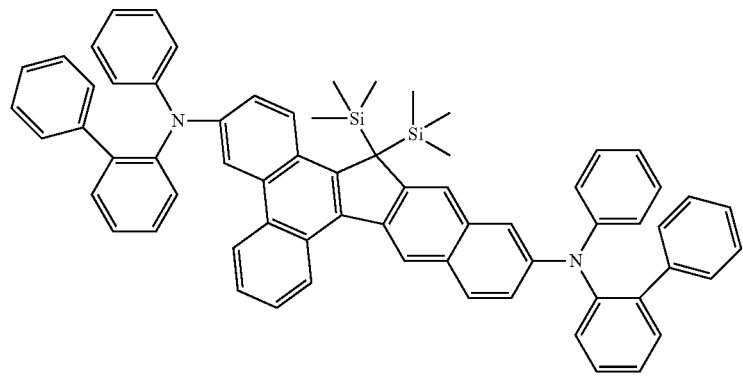

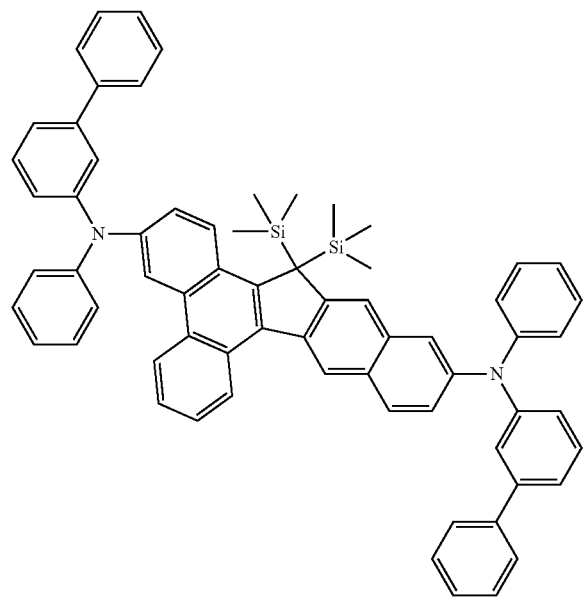
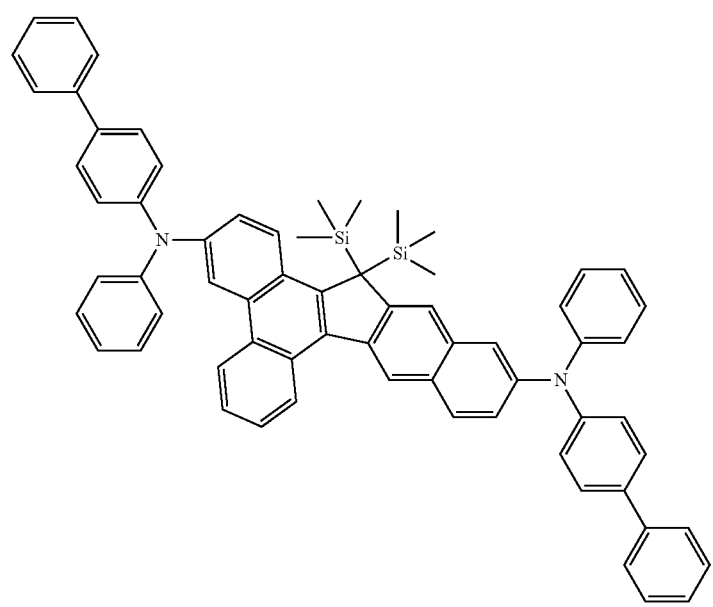

-continued
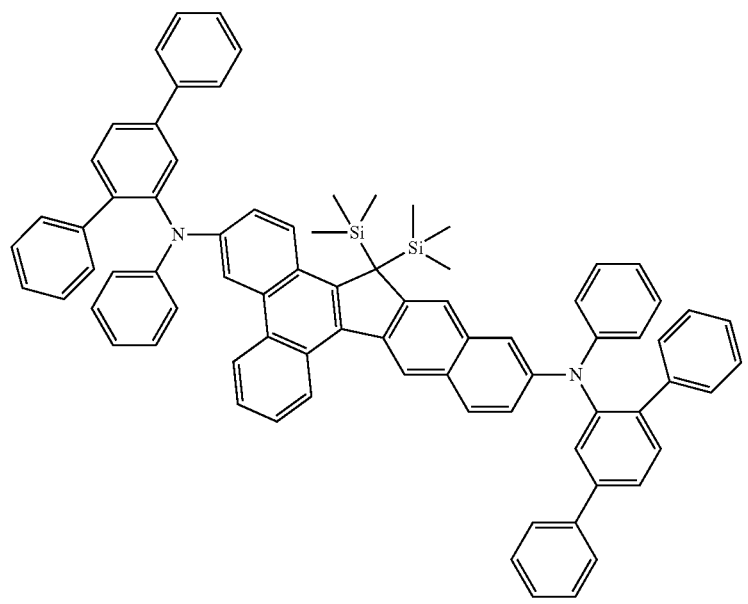
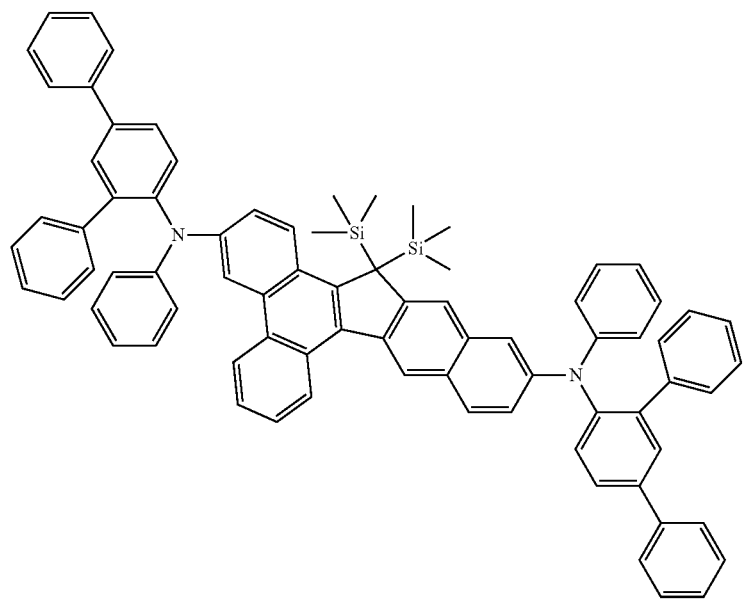
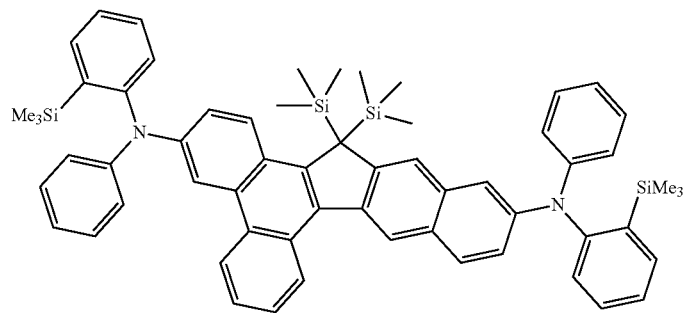

-continued
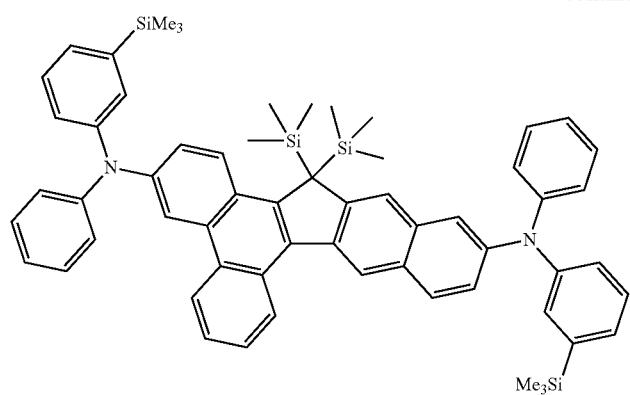
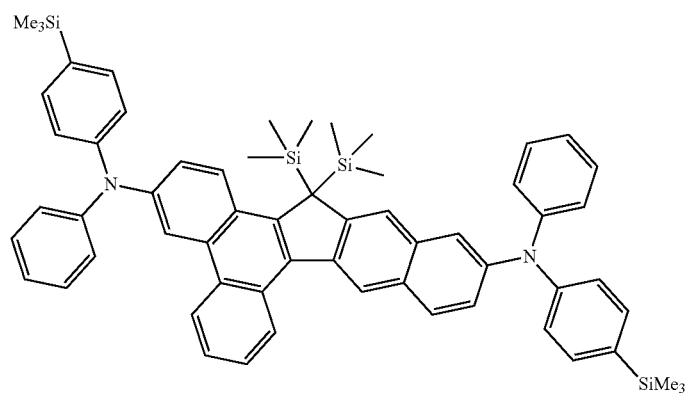
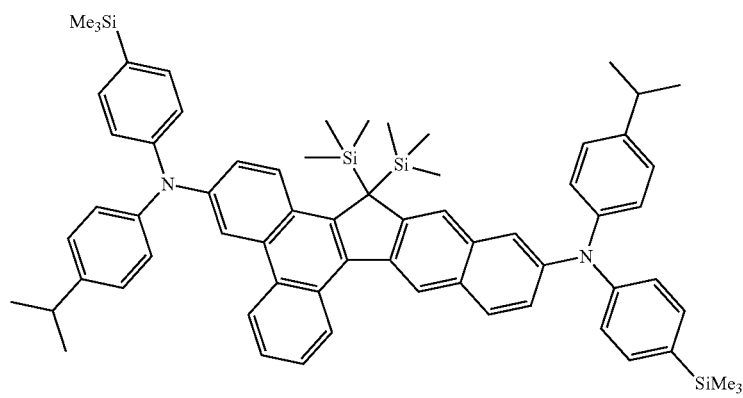
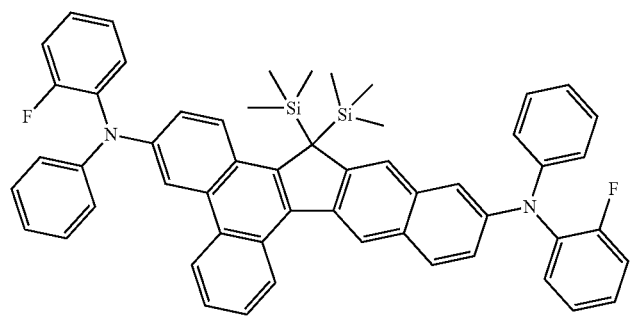

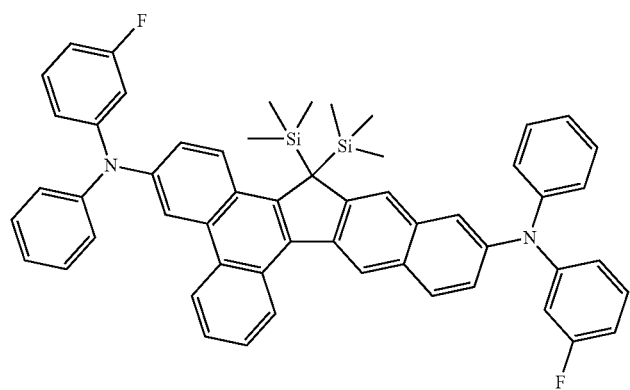
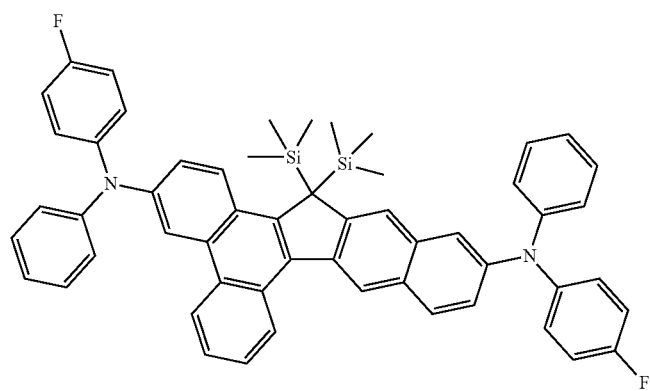
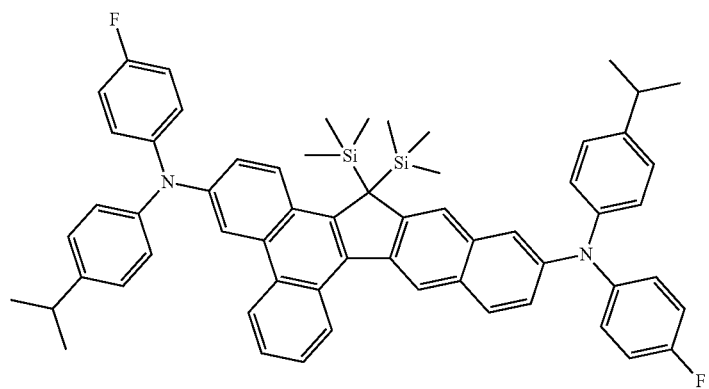
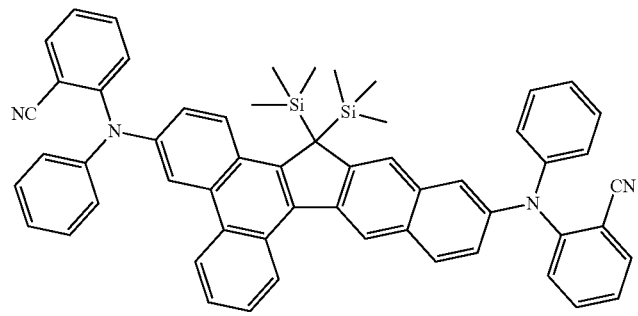

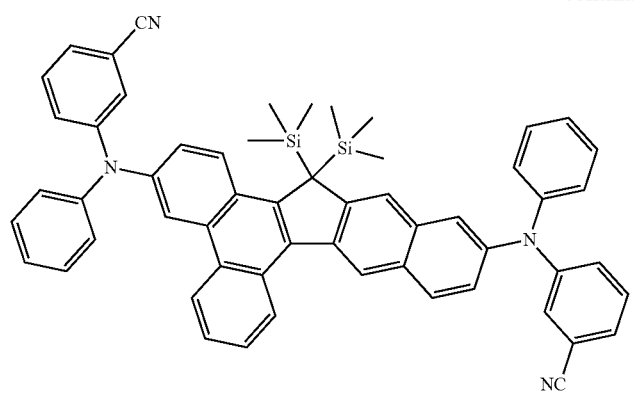
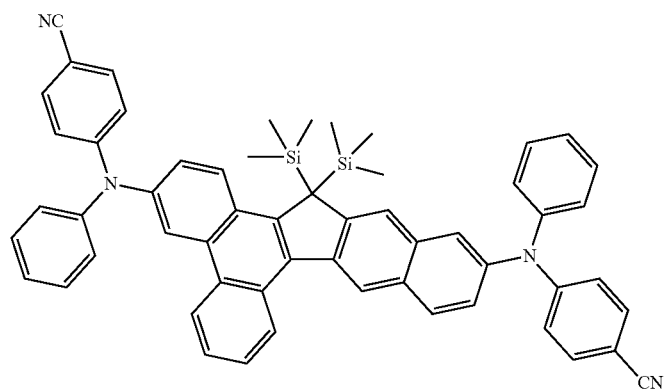
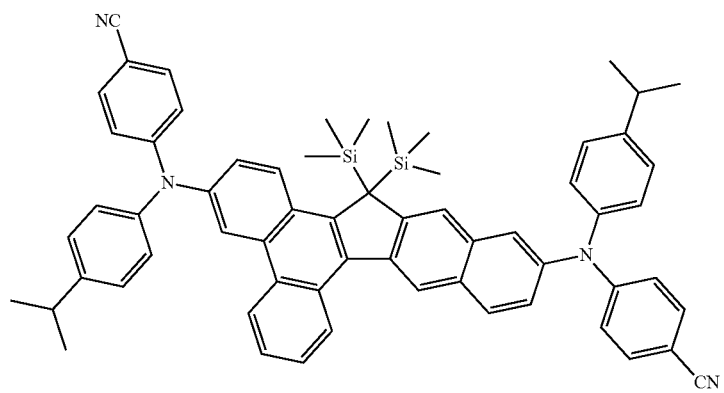
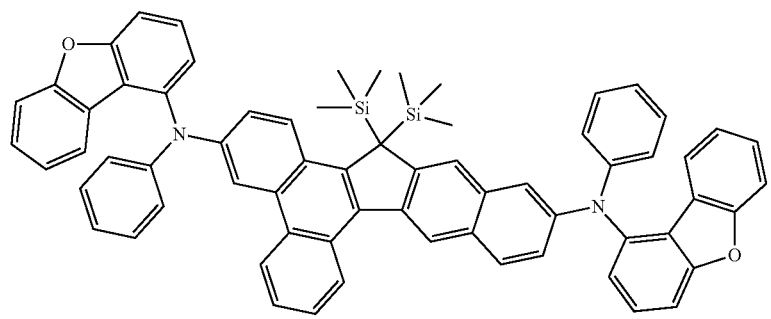

-continued
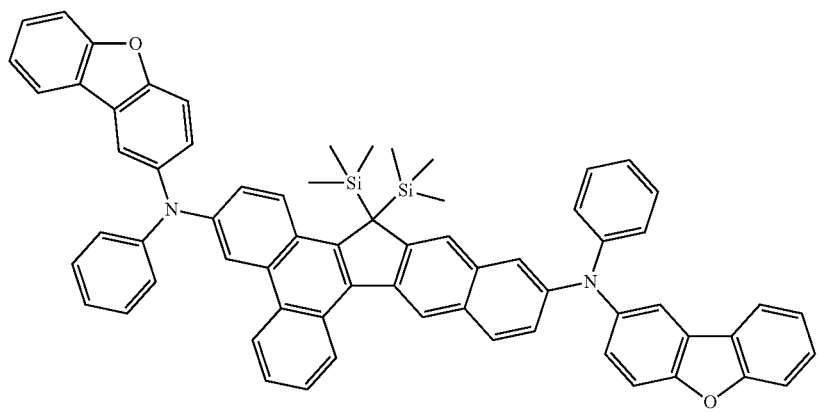
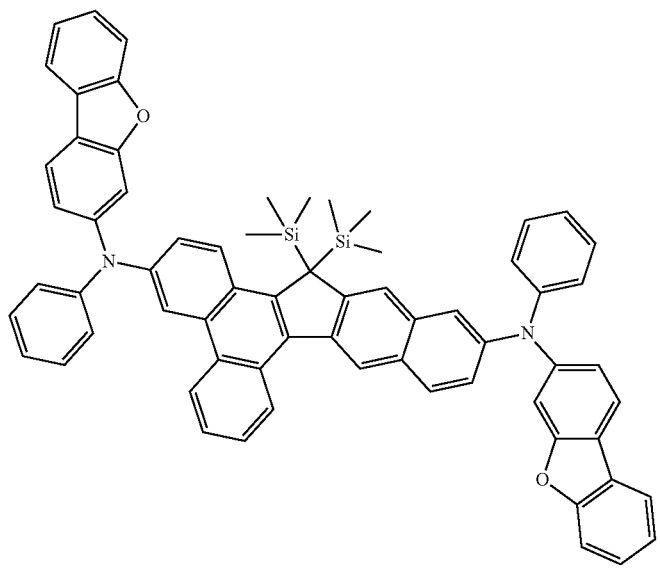
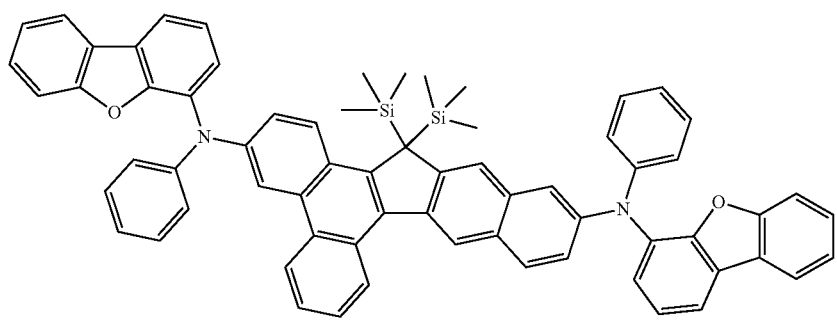

-continued
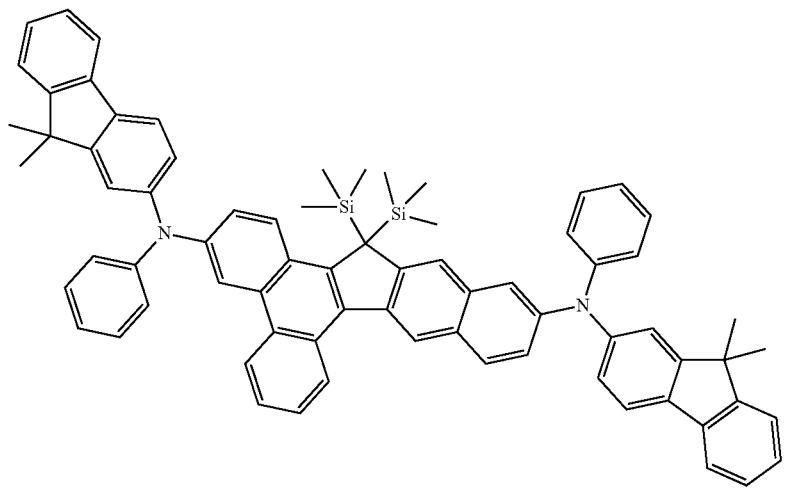
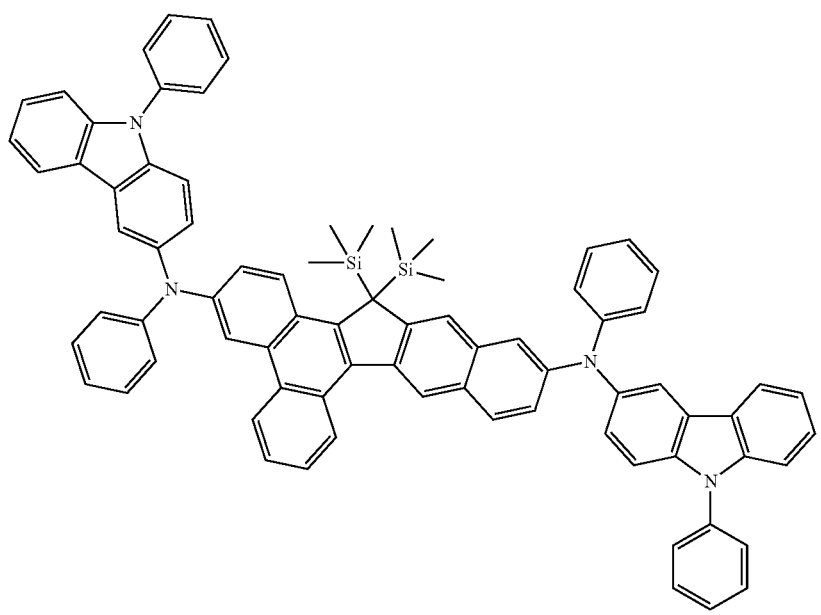
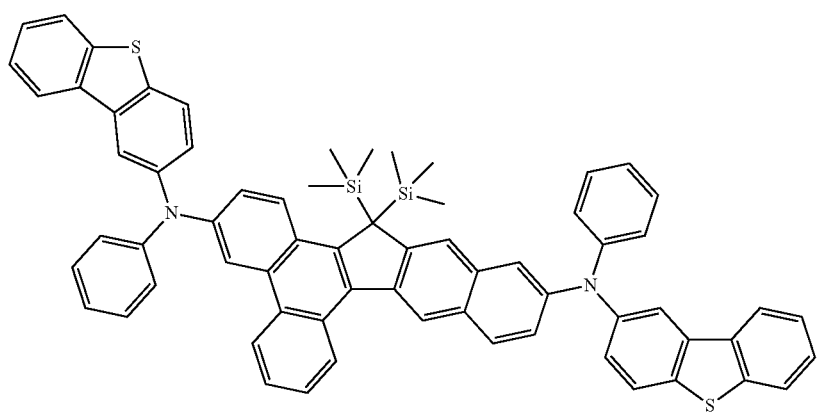

-continued
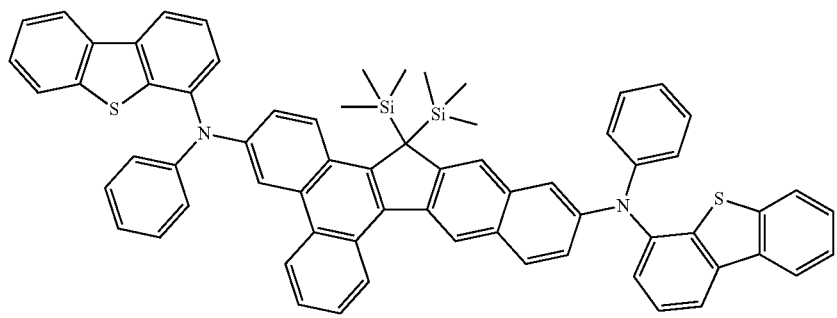
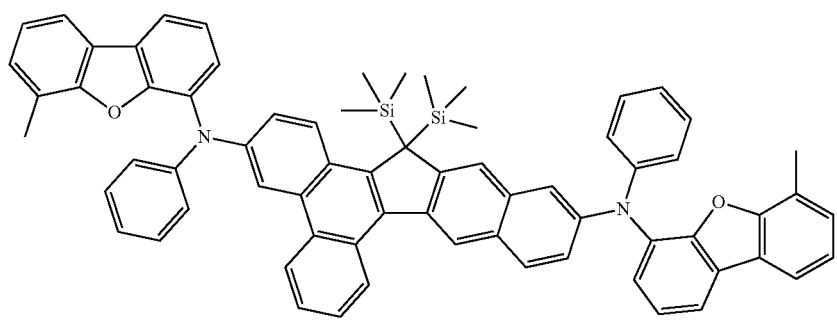
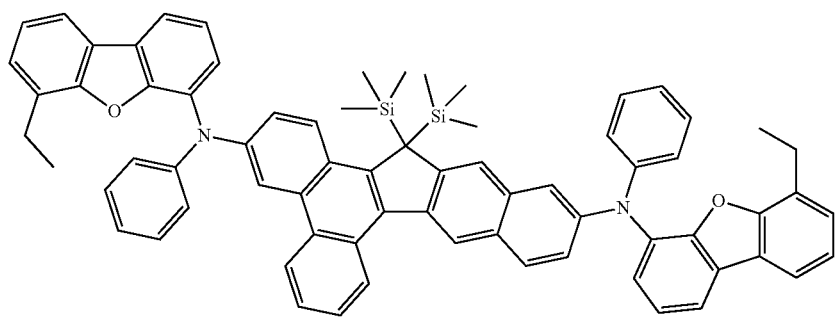
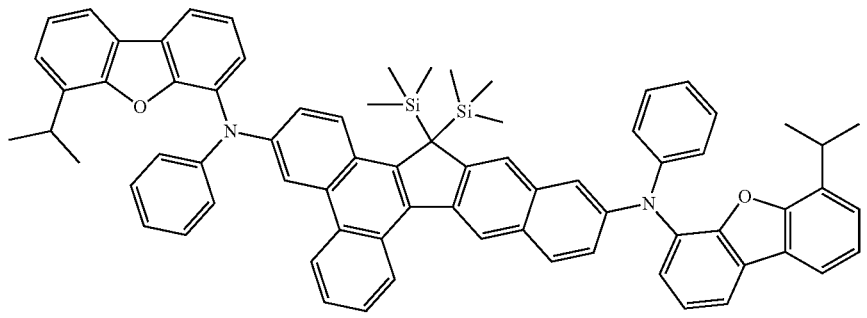
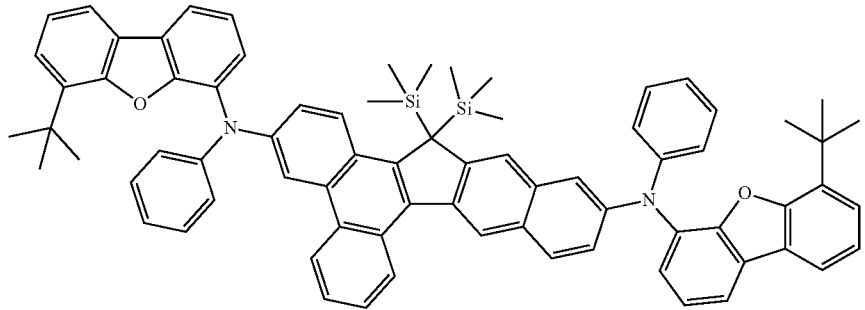

-continued
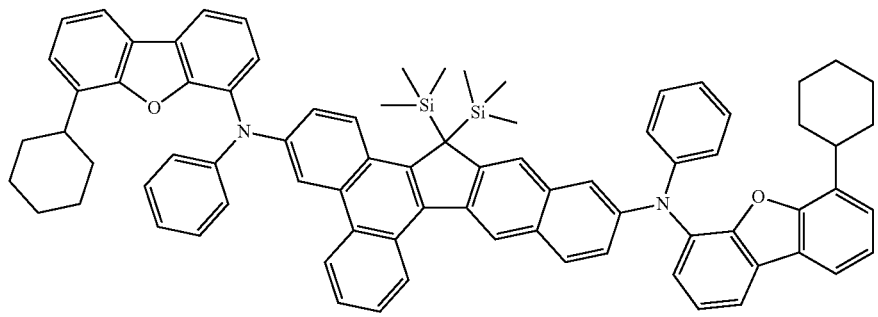
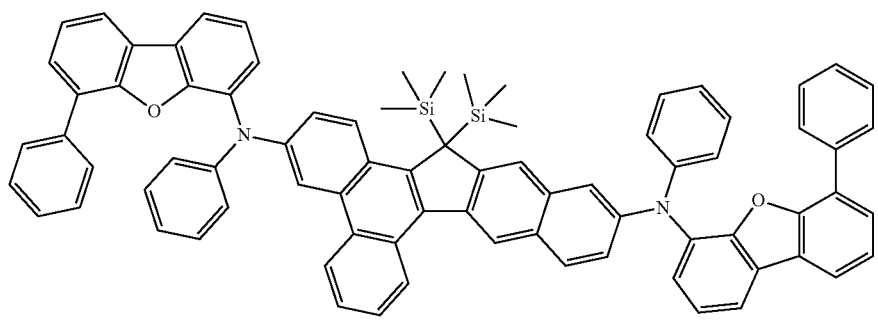
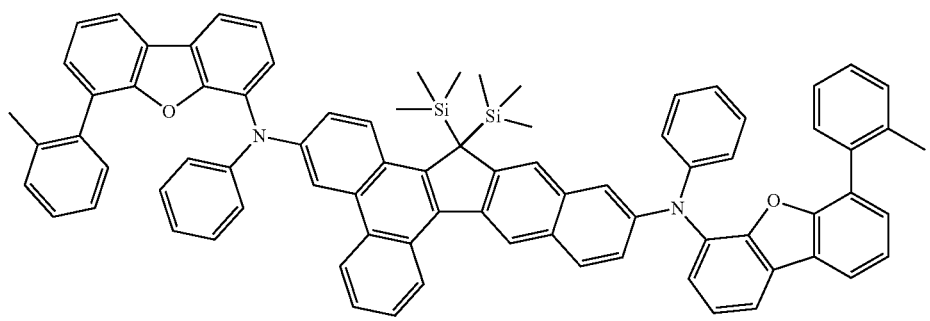
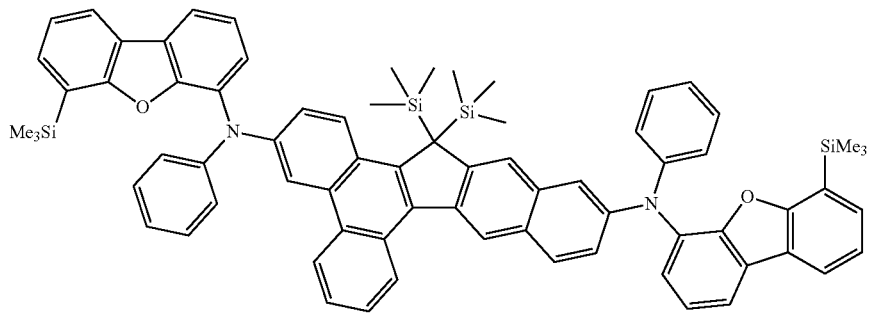
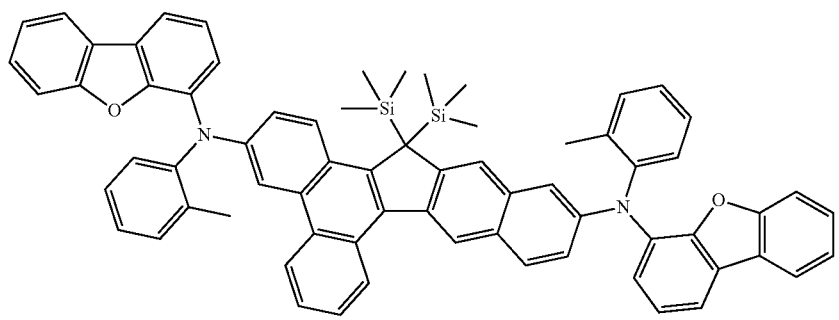

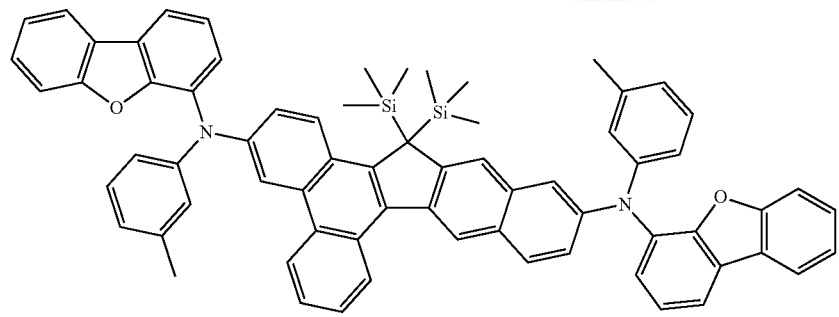
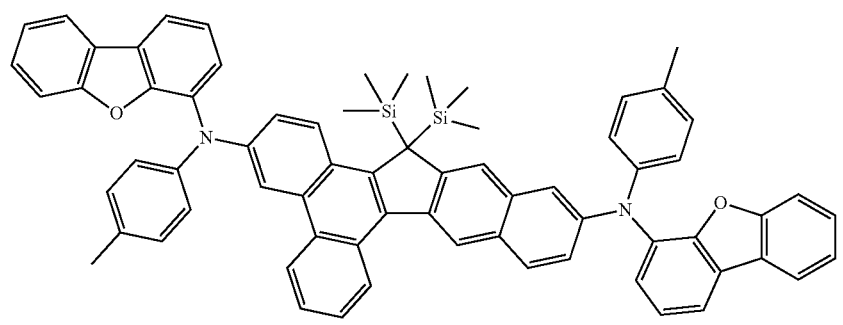
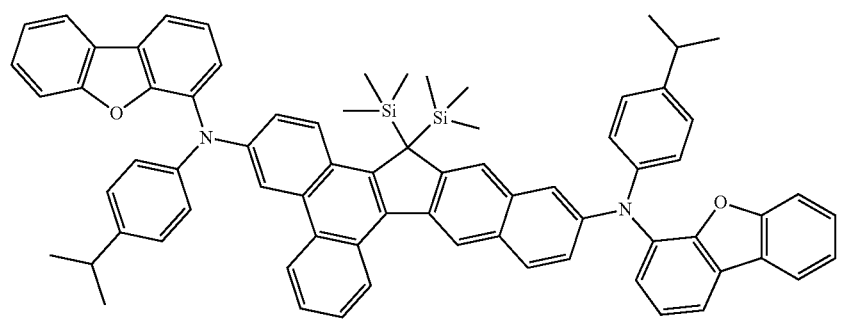
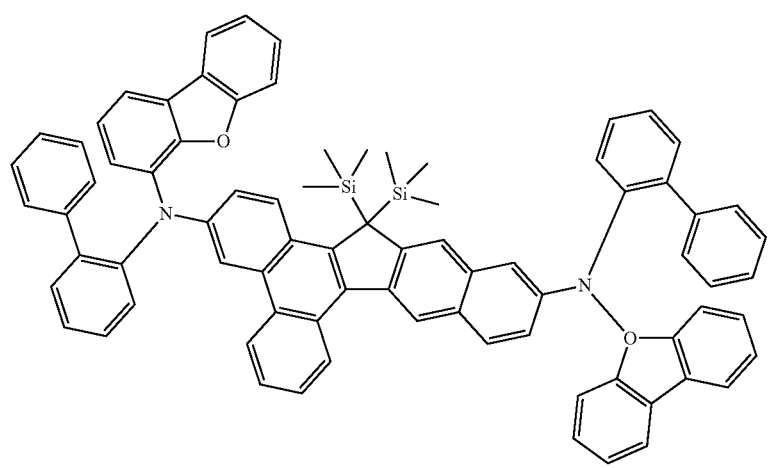

-continued
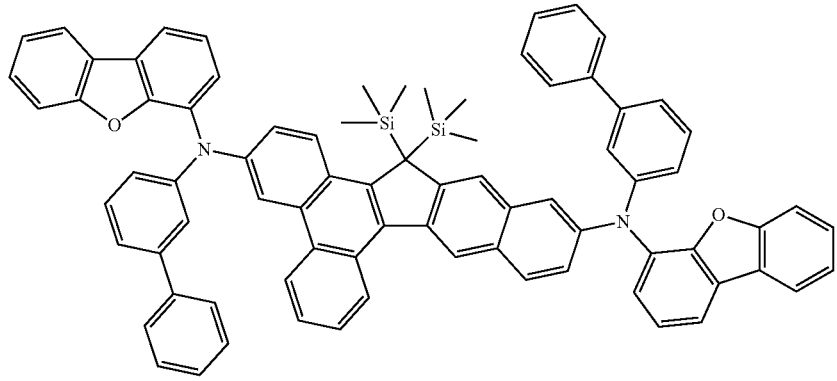
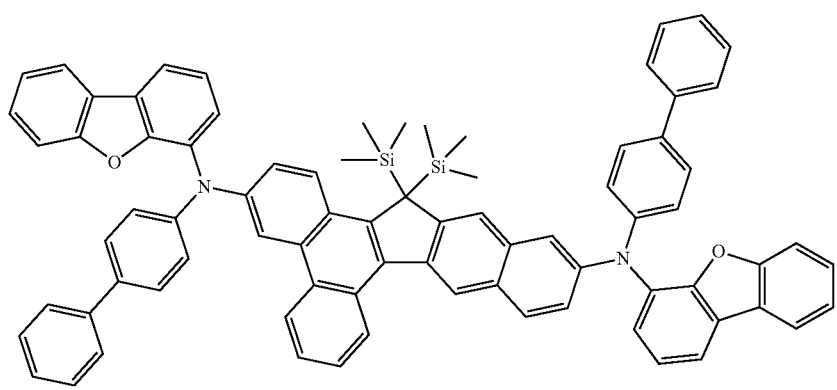
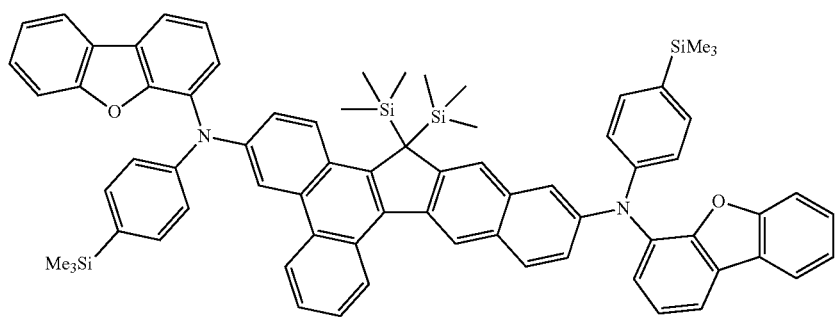
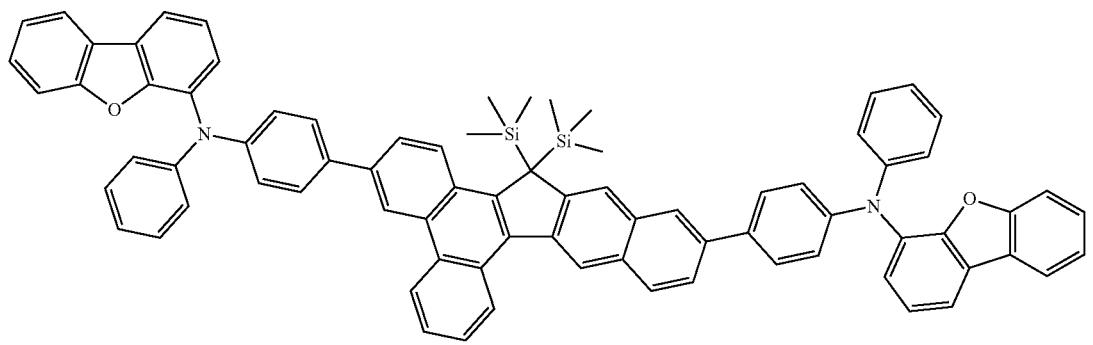

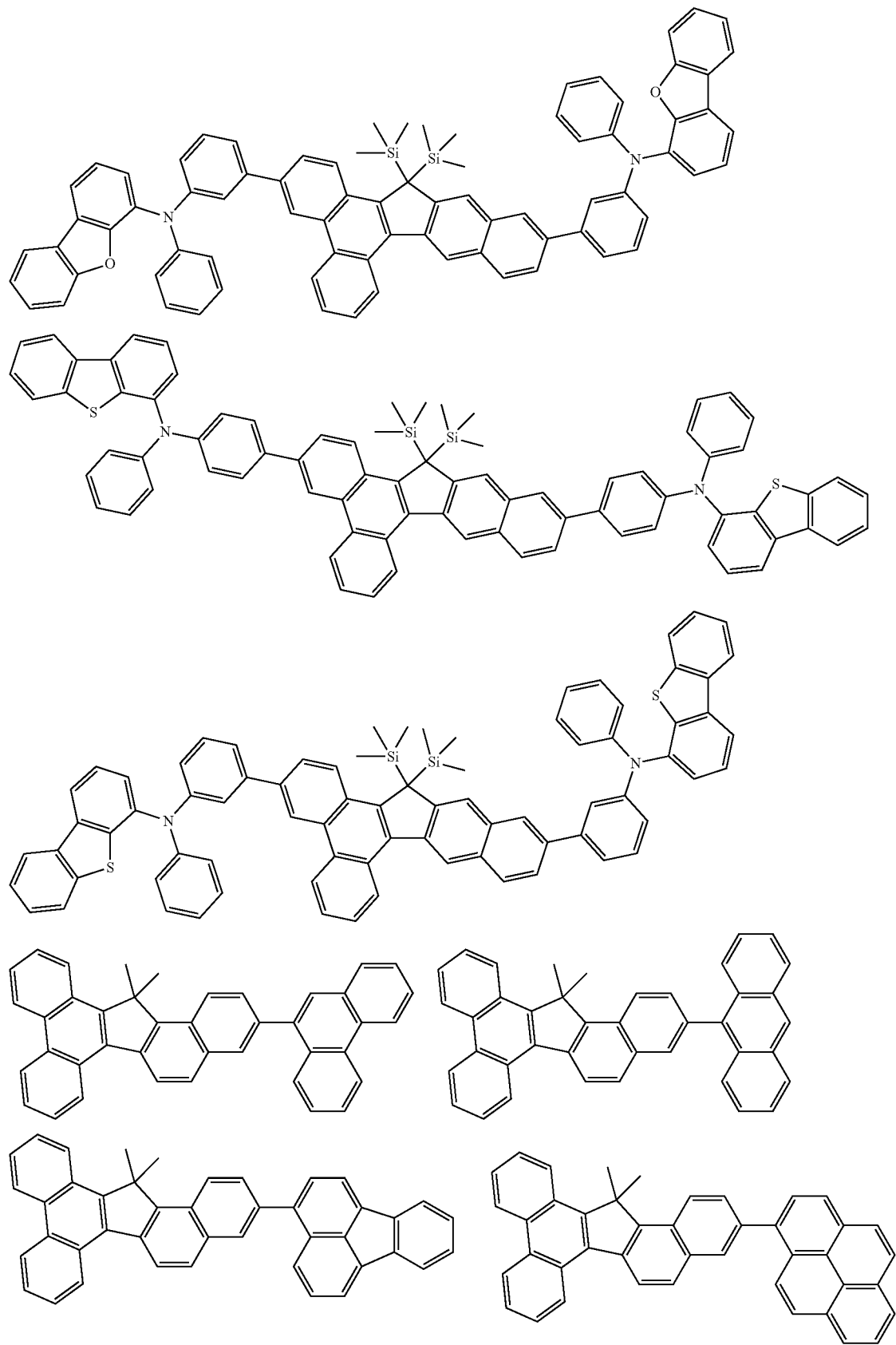

-continued
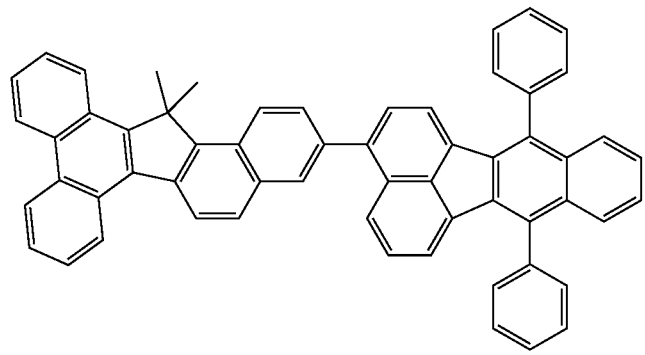
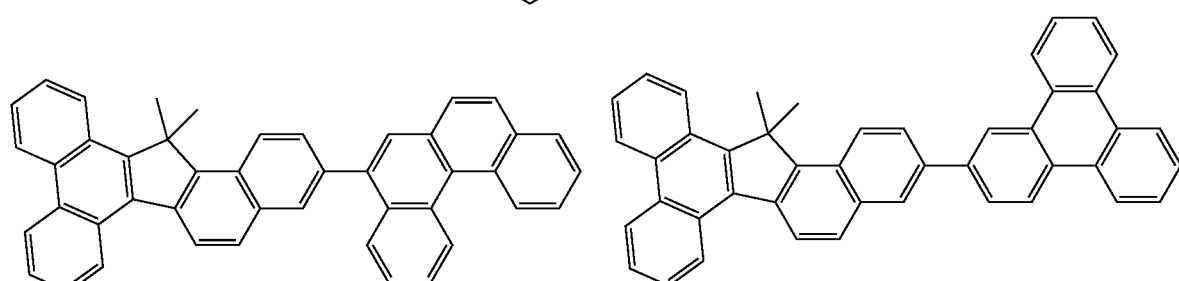
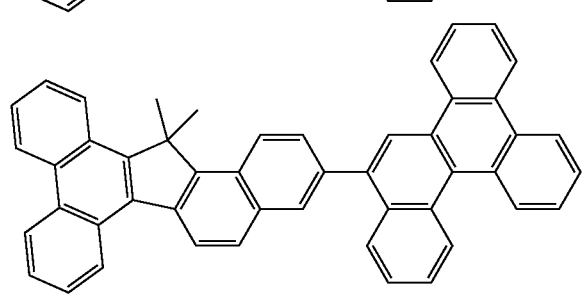
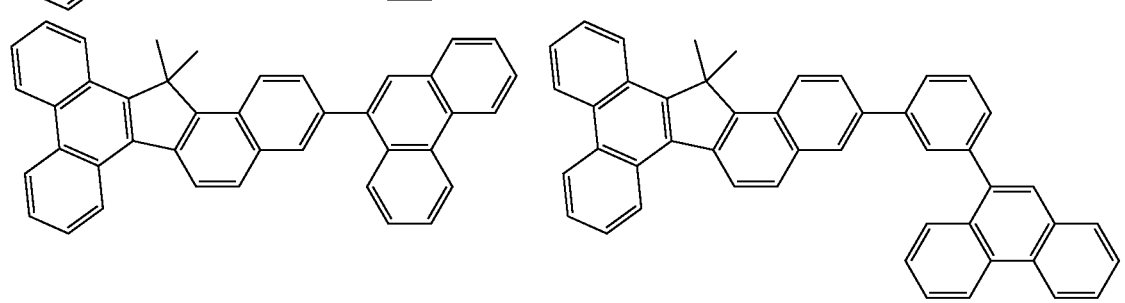
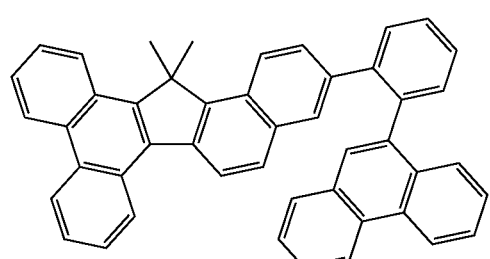
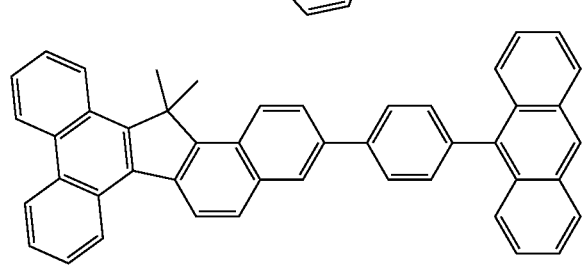

479 480
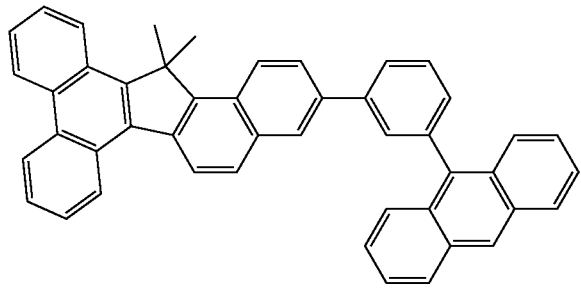
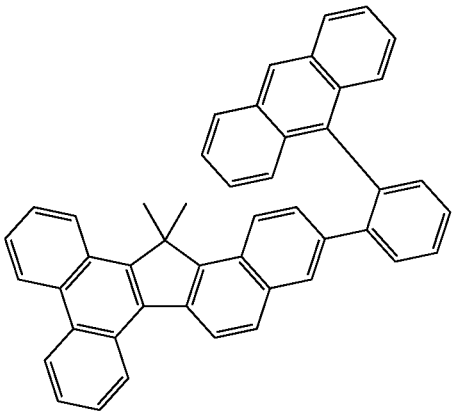
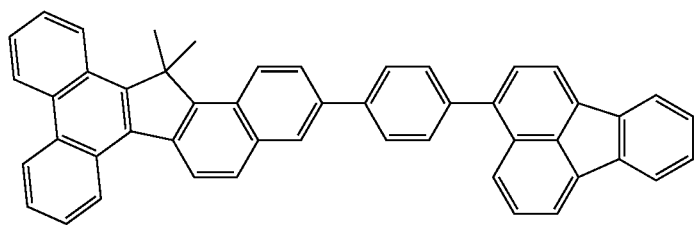
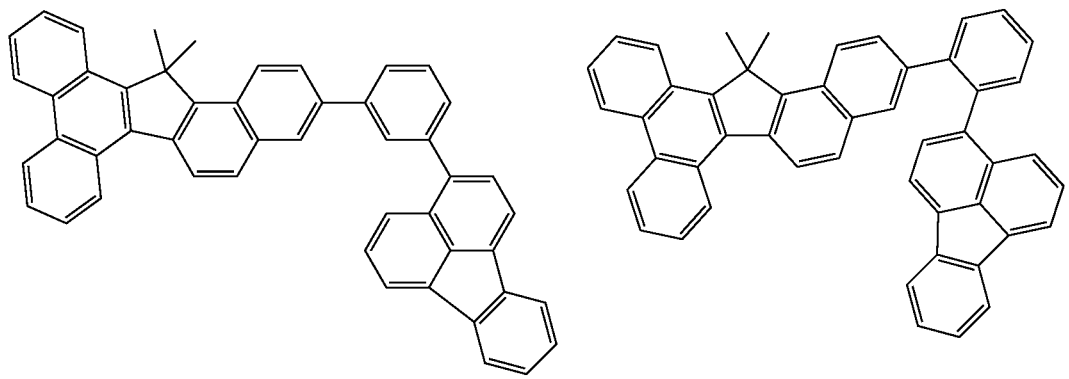
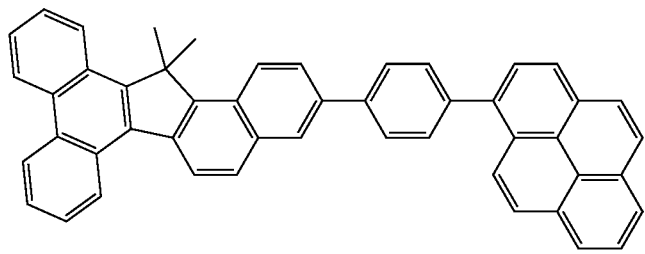

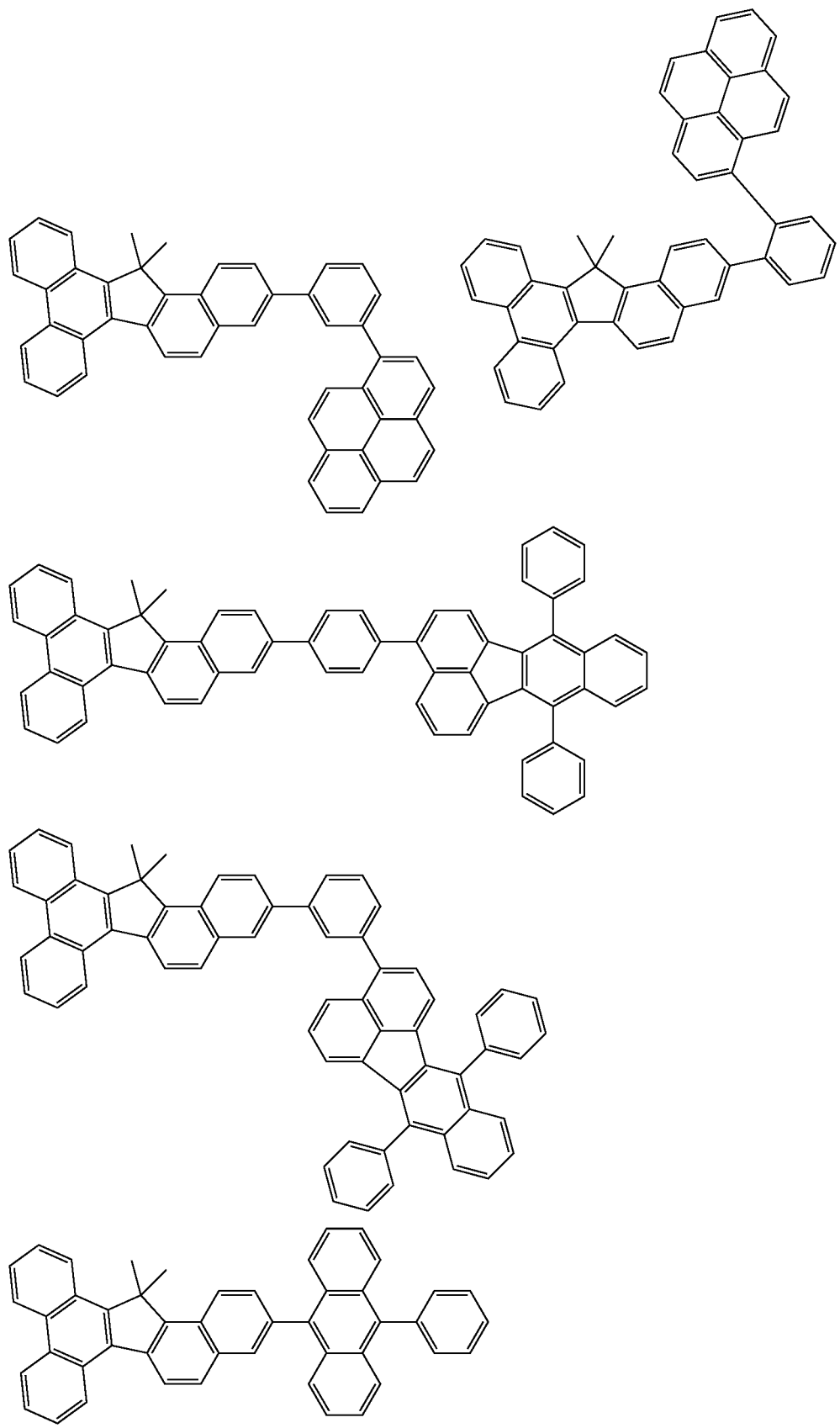

-continued
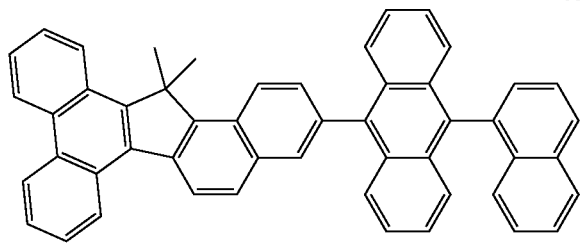
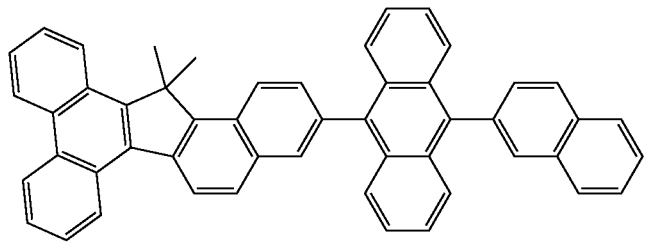
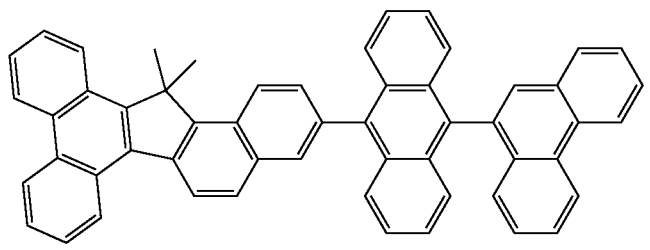
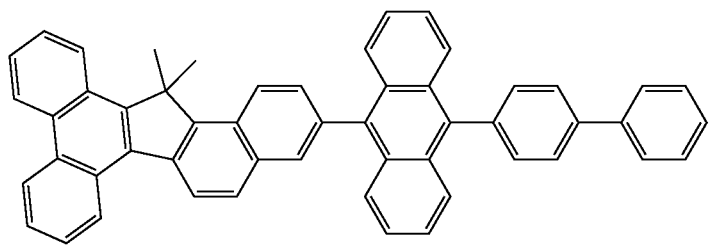
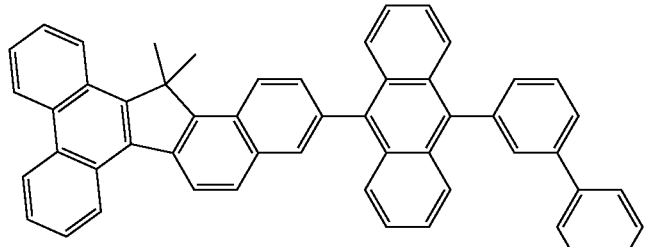
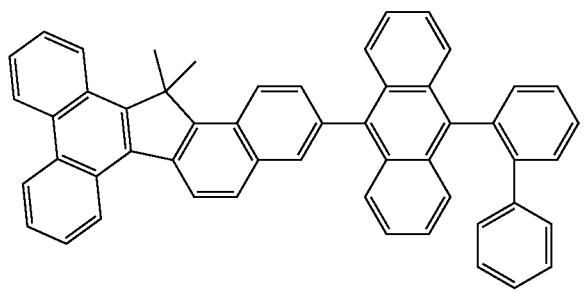

-continued
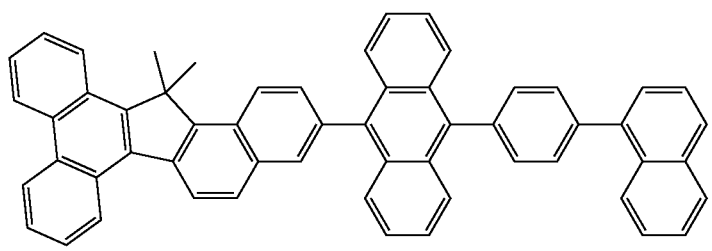
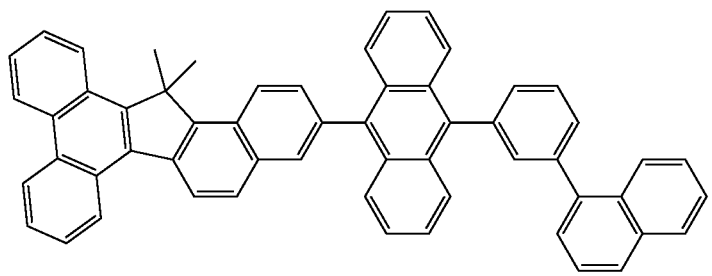
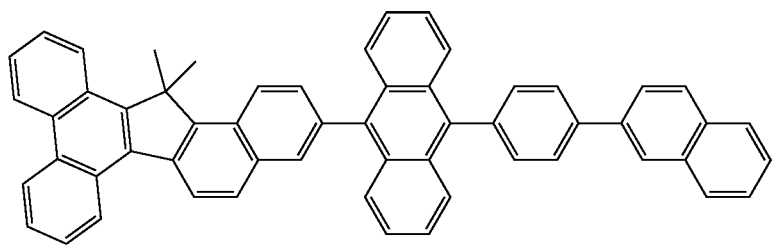
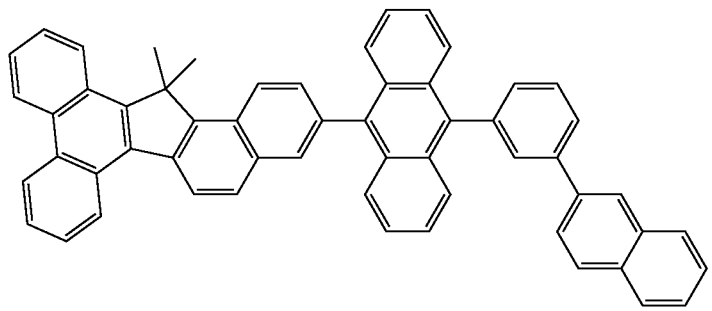
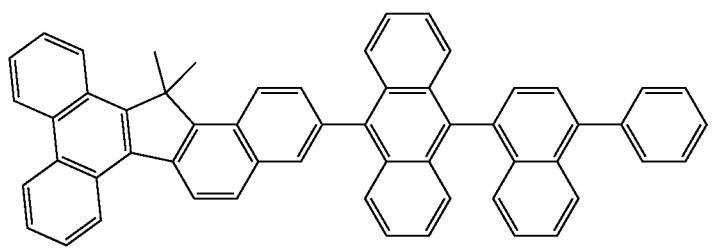
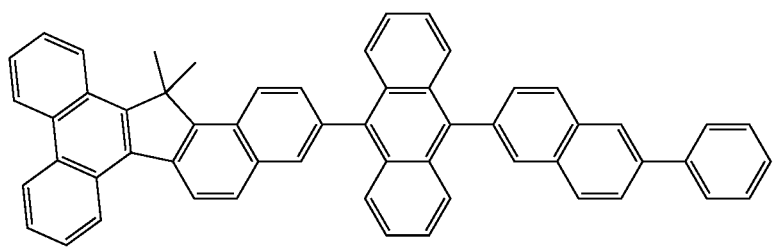

487
-continued
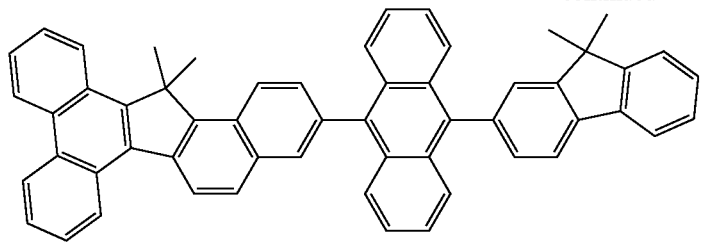
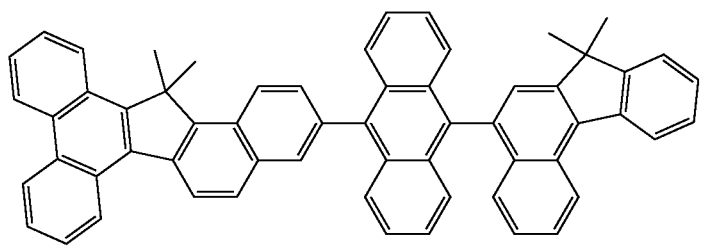
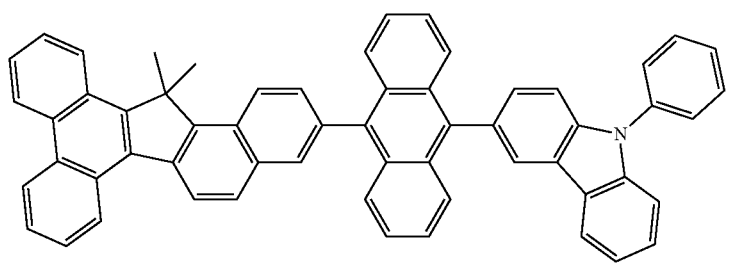
488
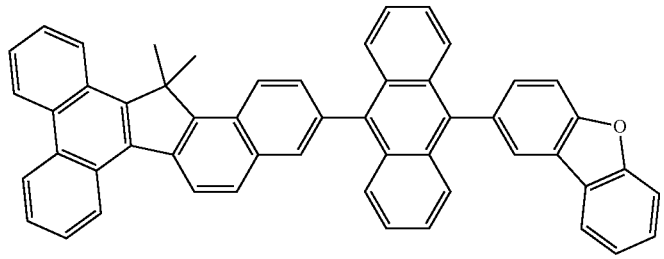
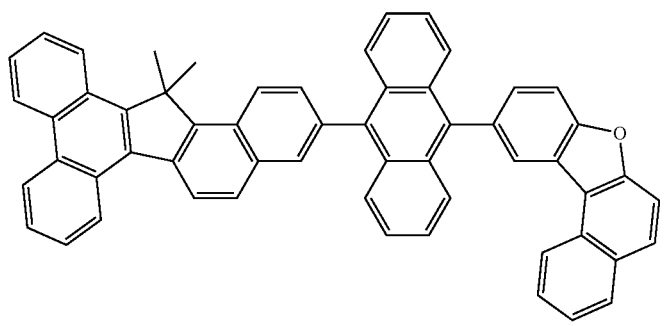
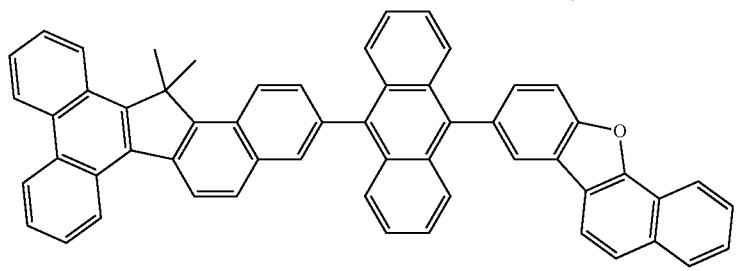

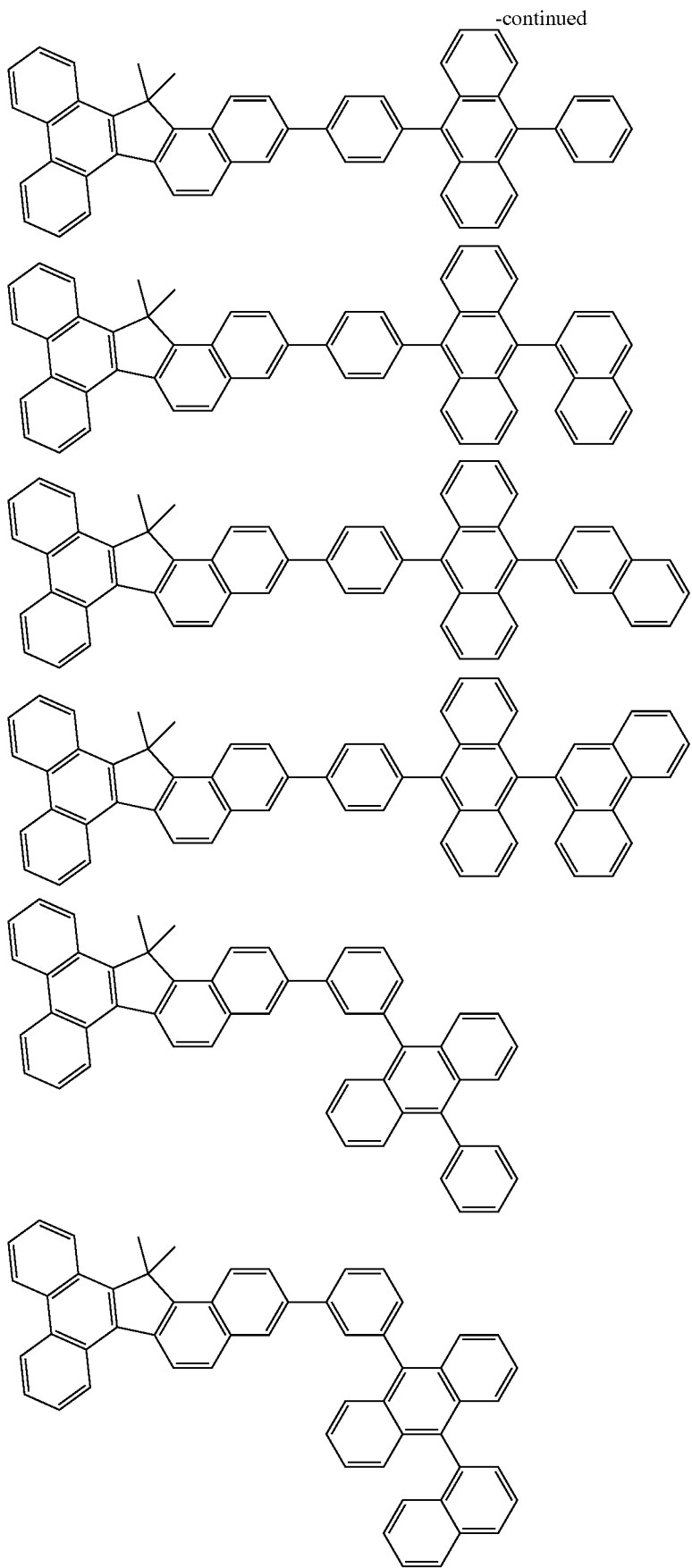

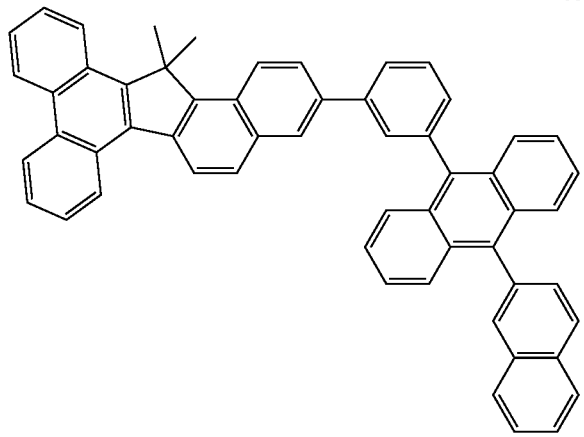
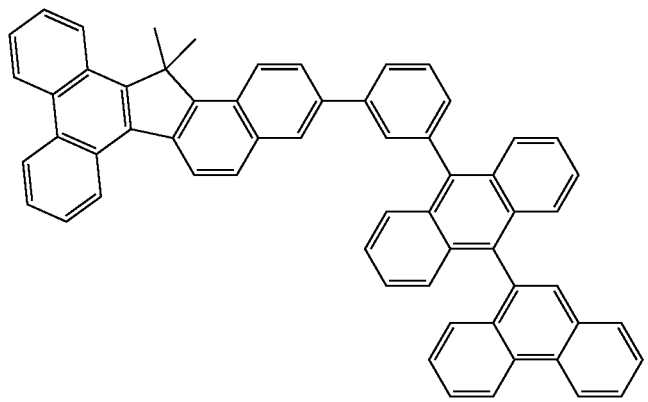
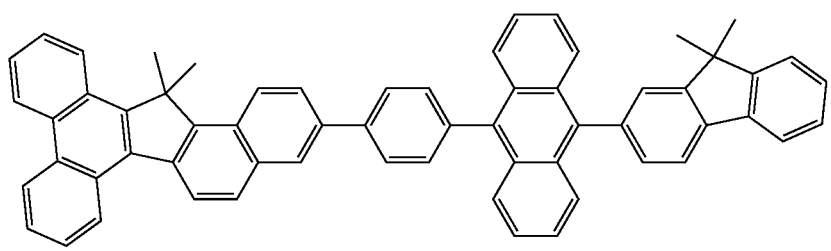
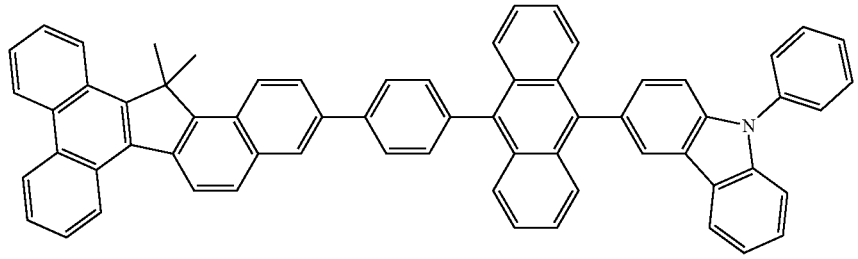
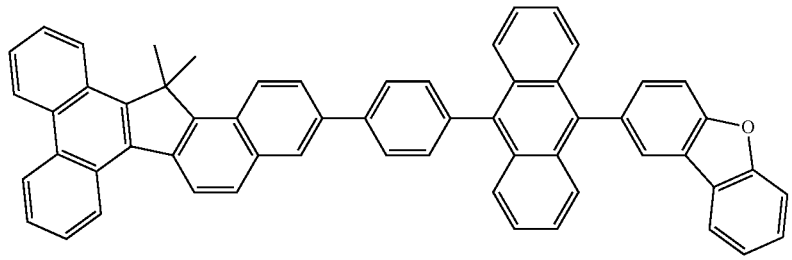

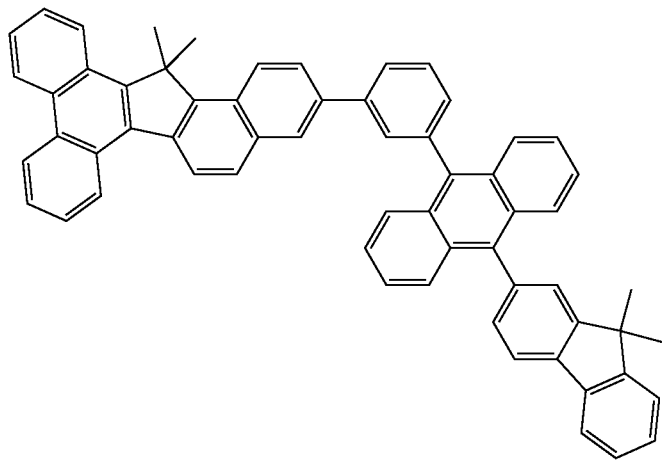
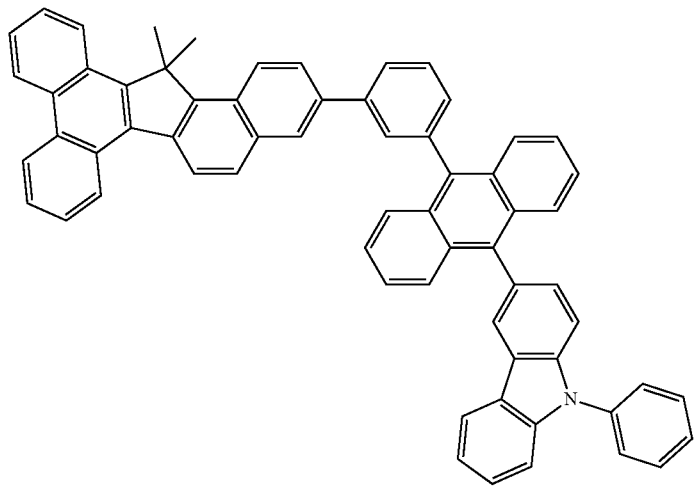
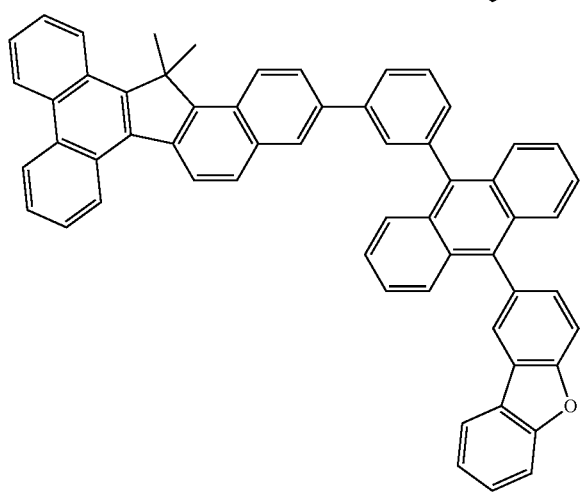
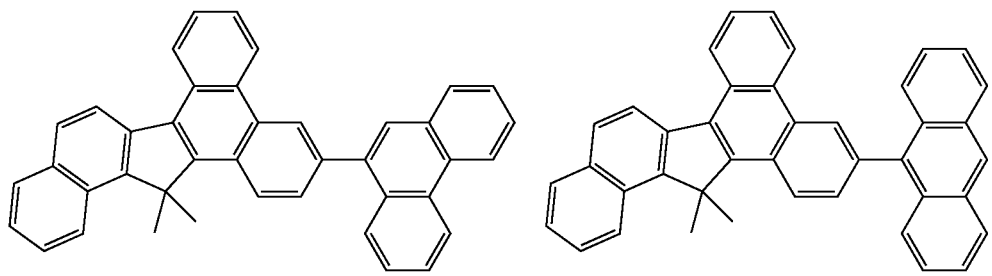

495 496
-continued
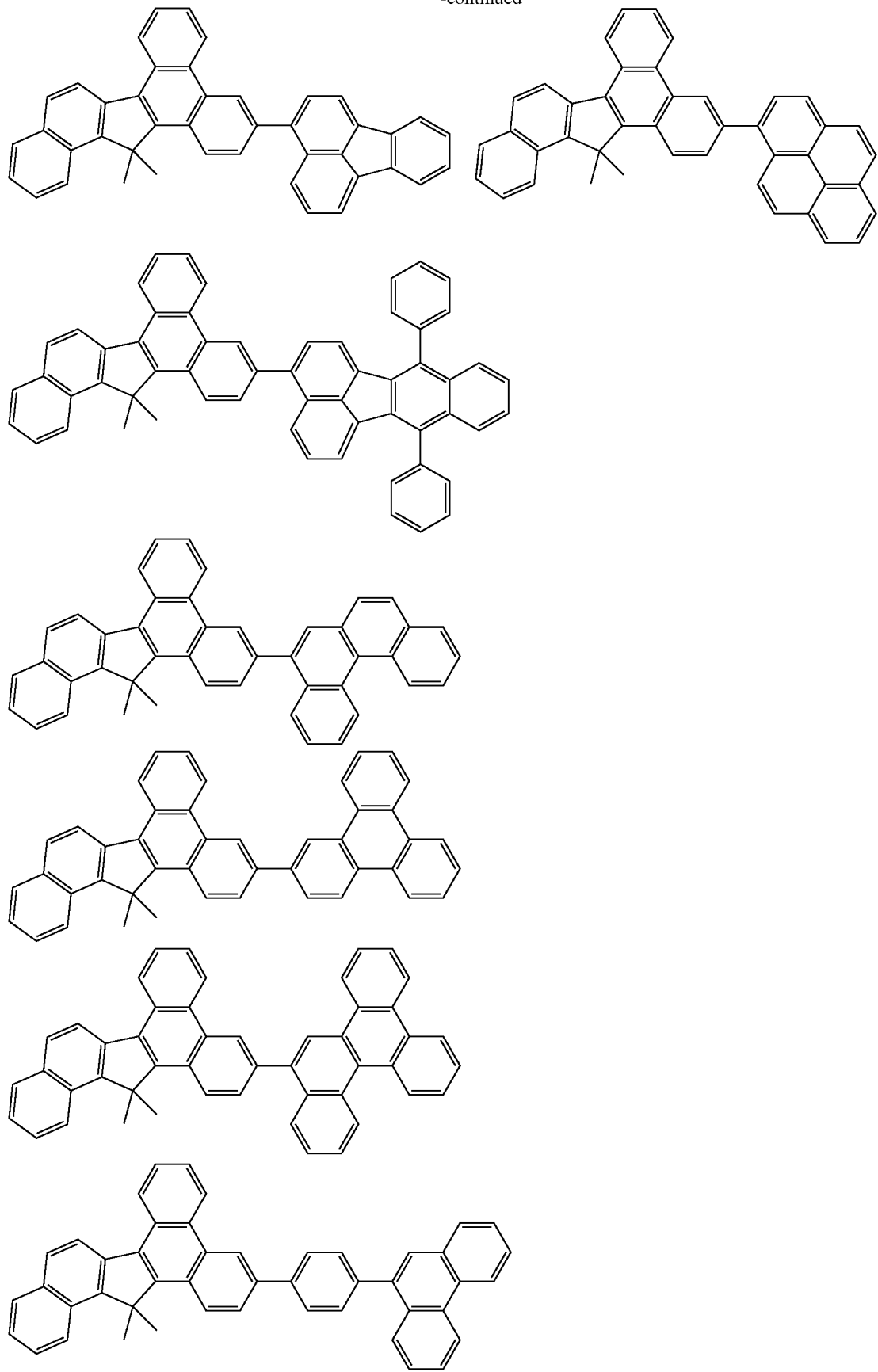

497  498
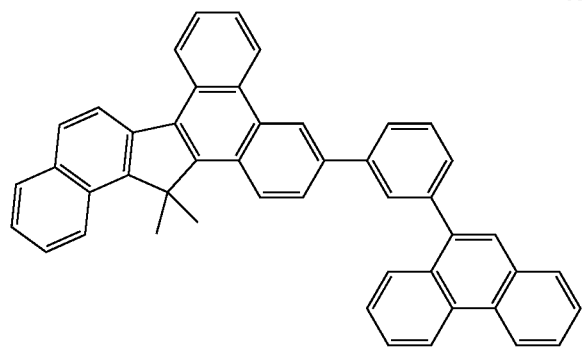 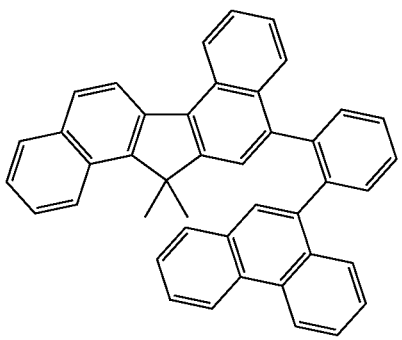
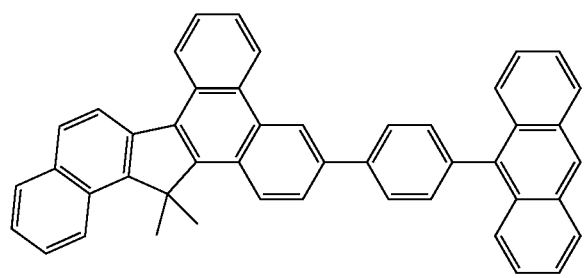
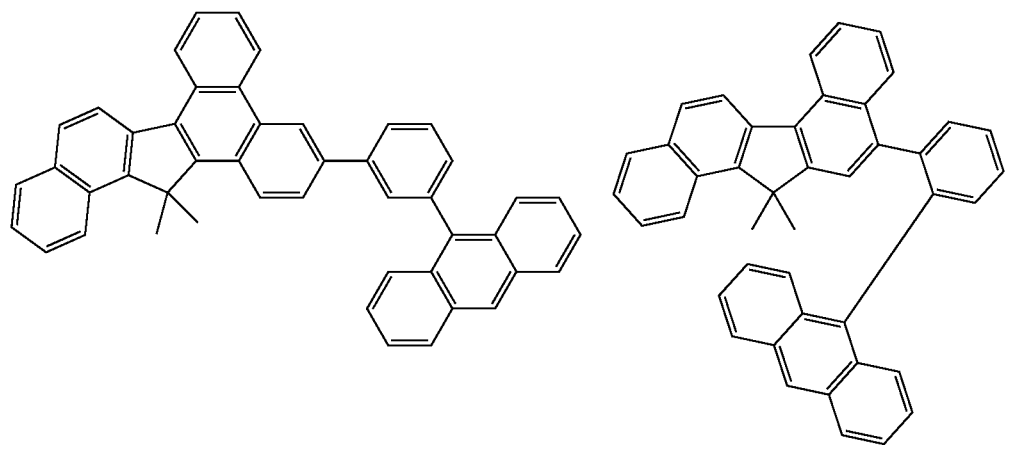
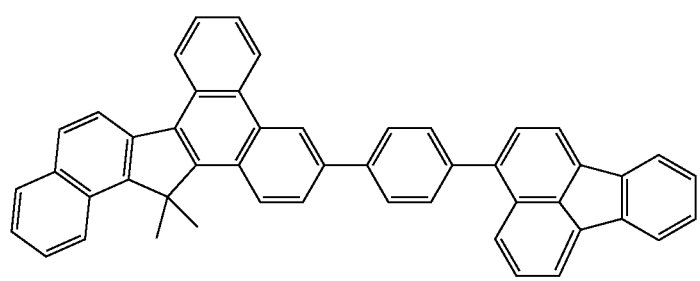

499
500
-continued
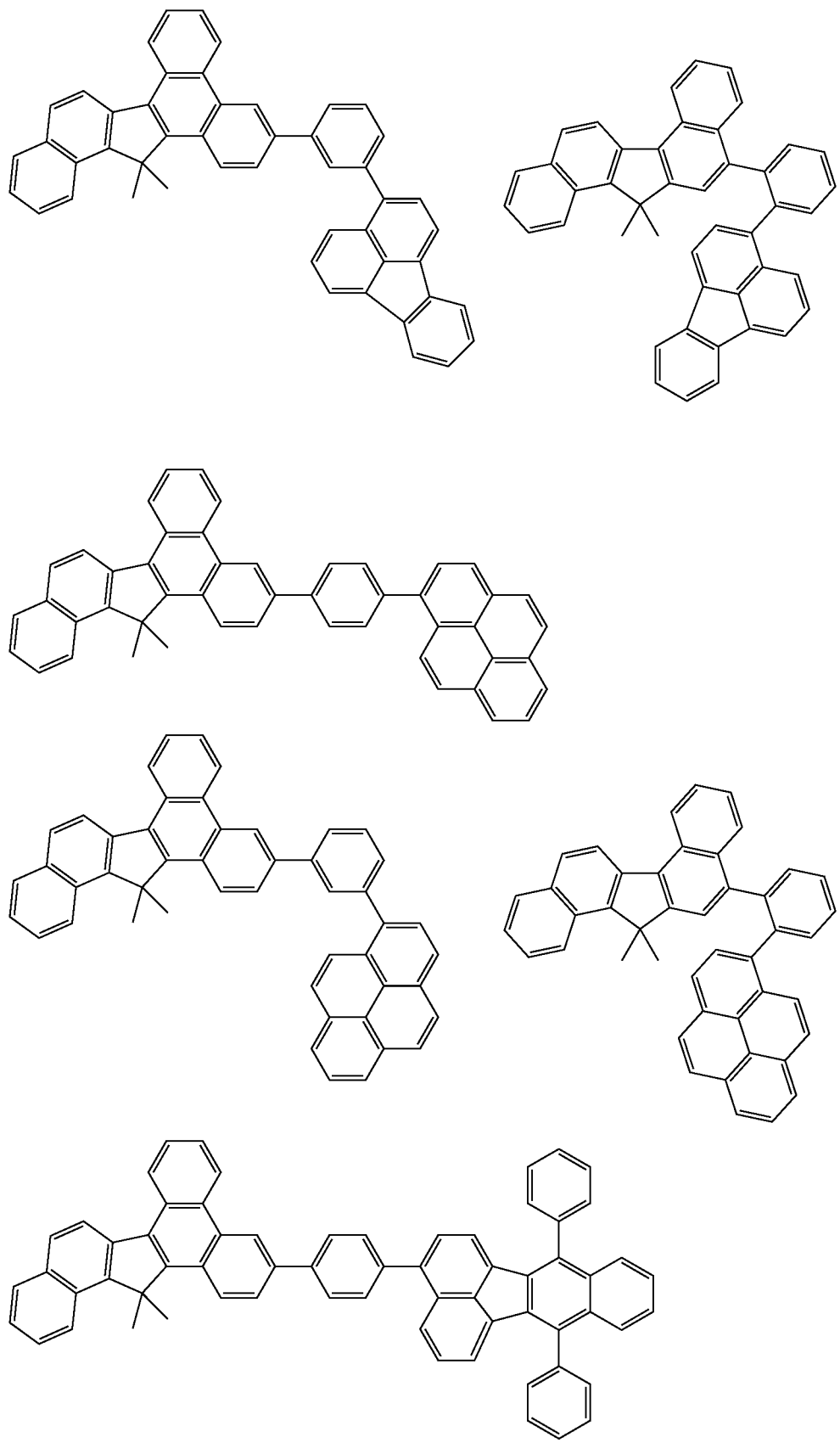

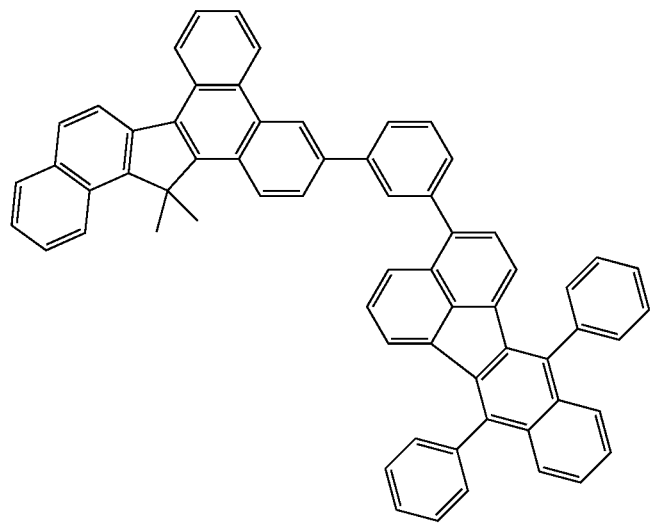
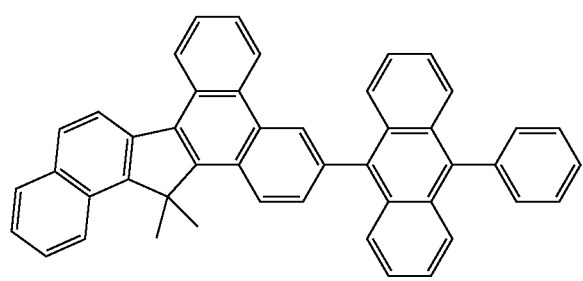
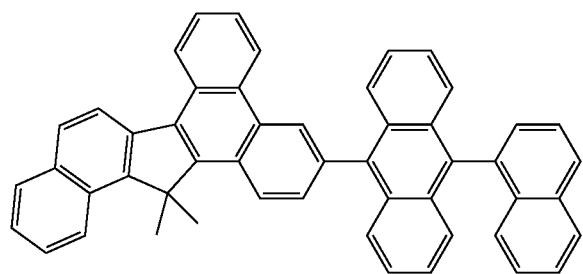
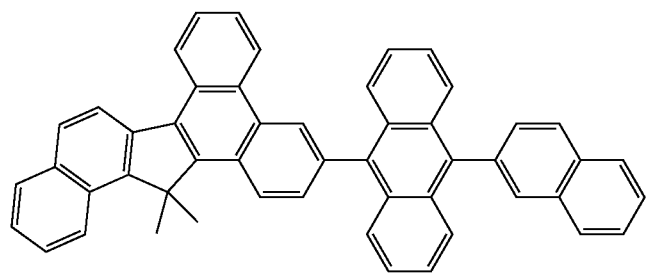
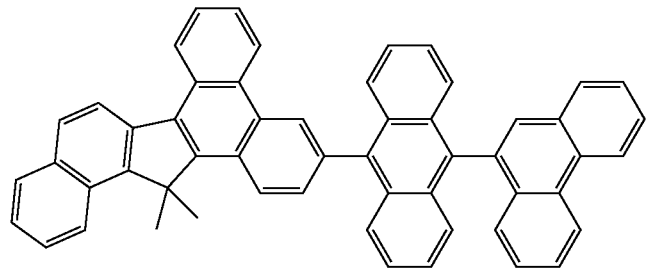

-continued
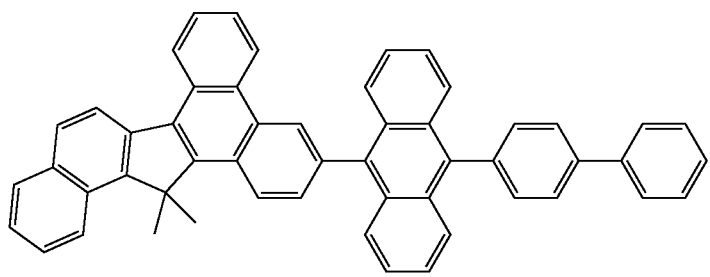
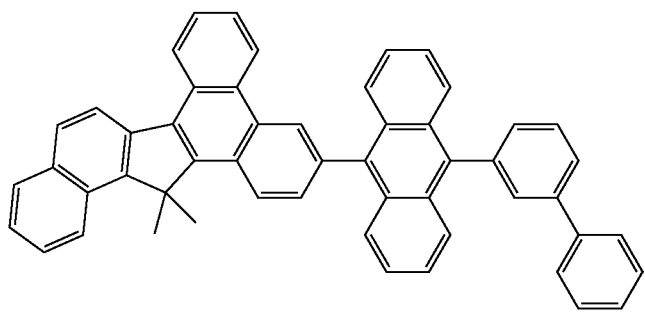
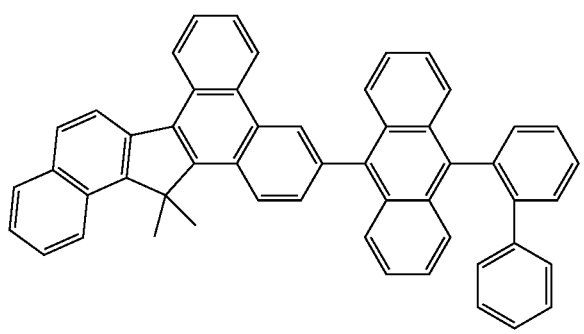
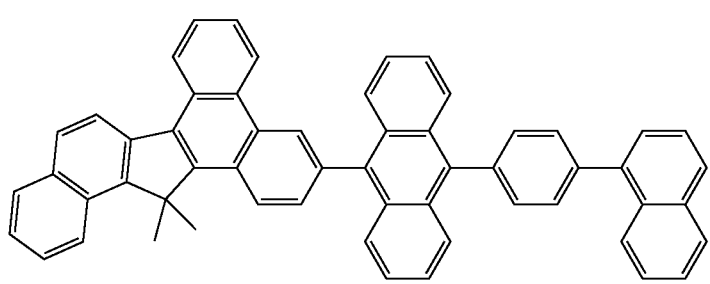
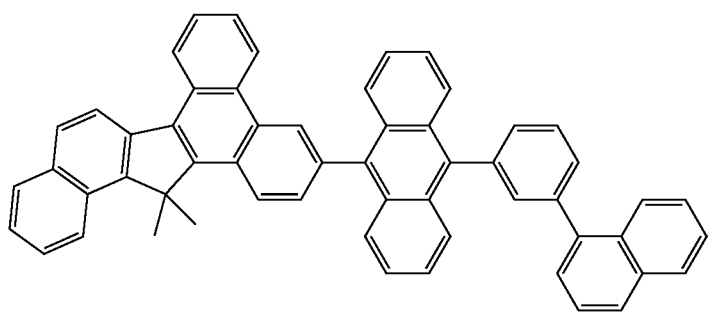

-continued
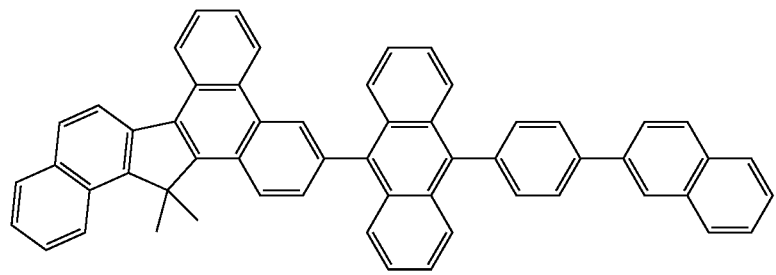
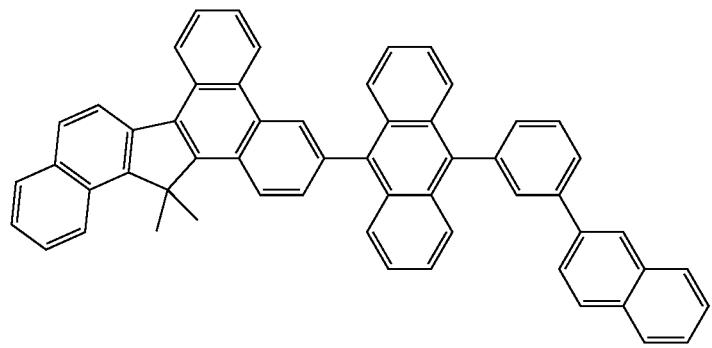
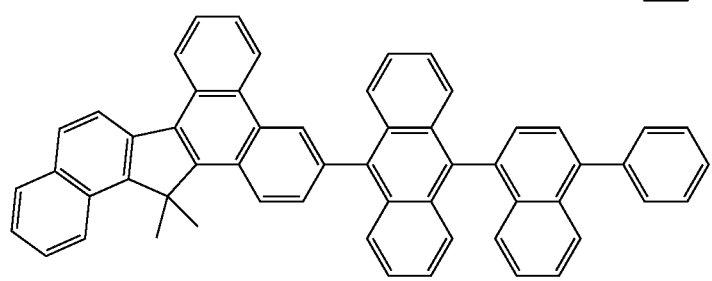
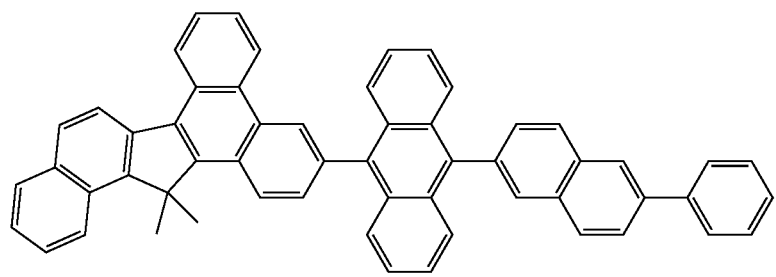
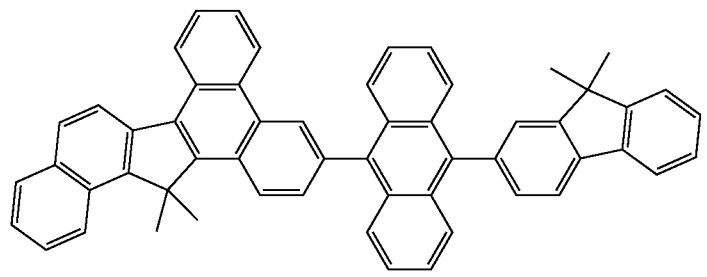
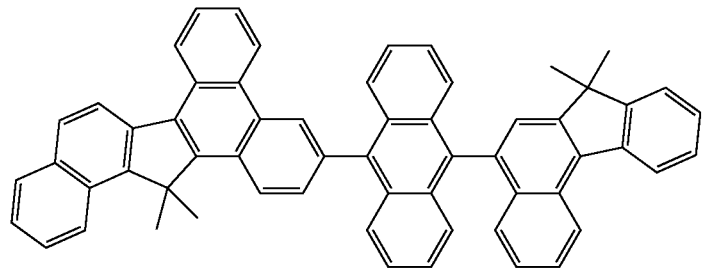

-continued
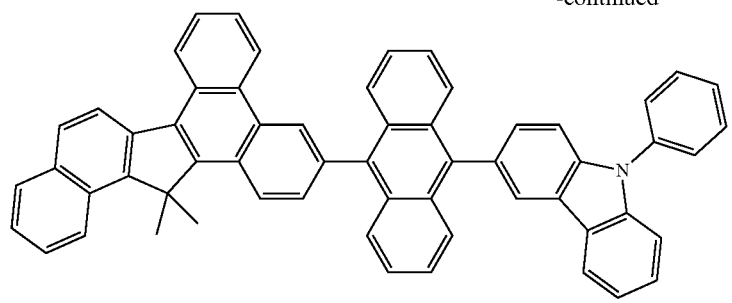
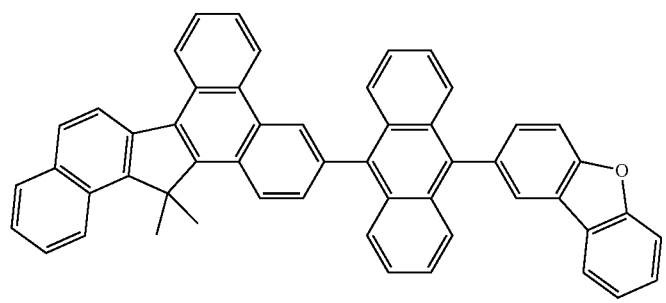
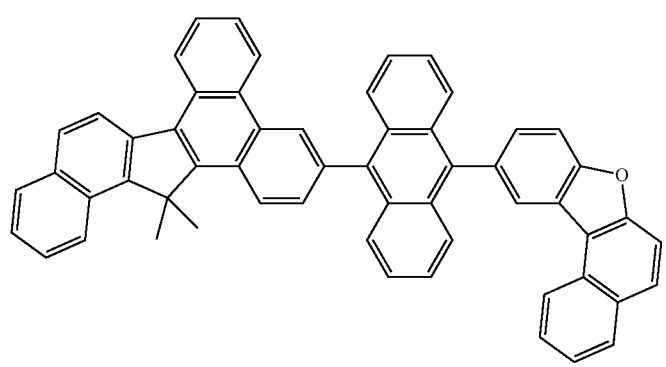
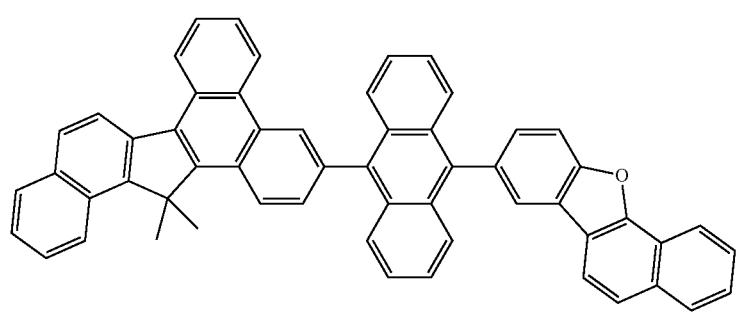
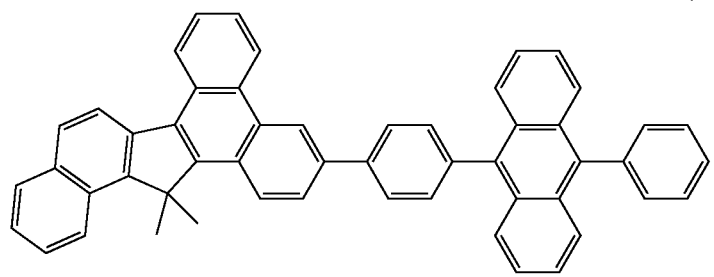

-continued
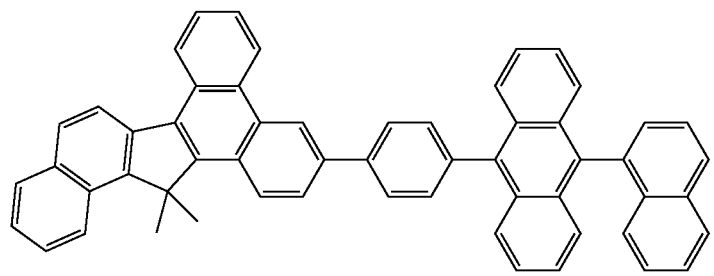
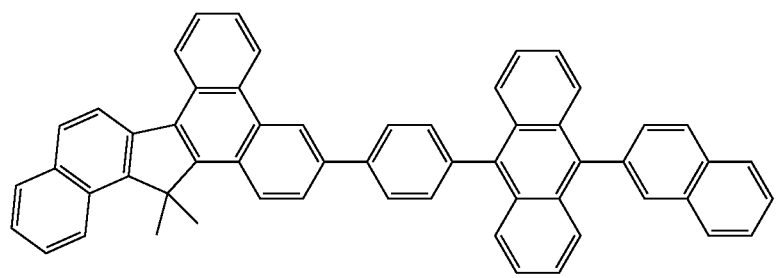
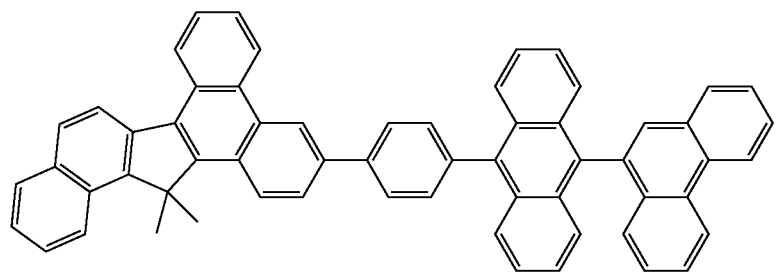
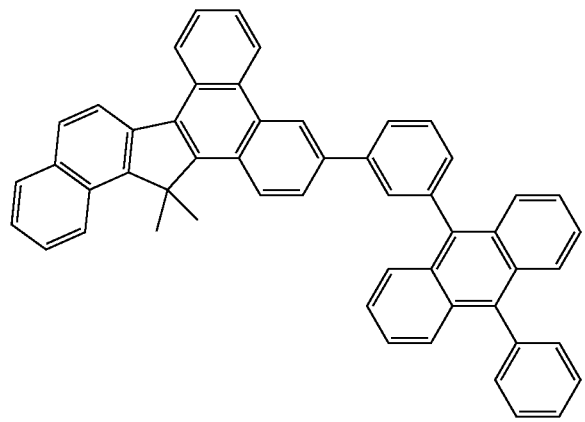
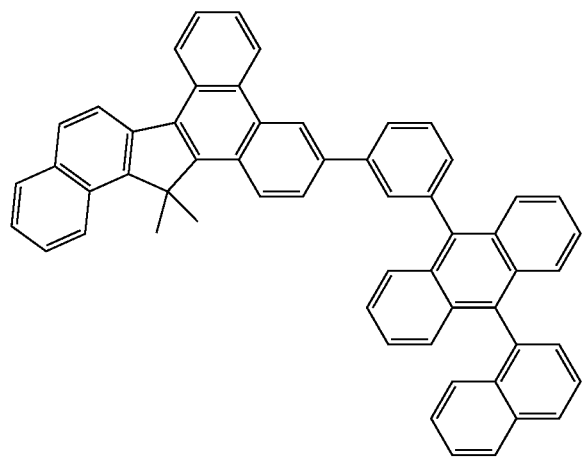

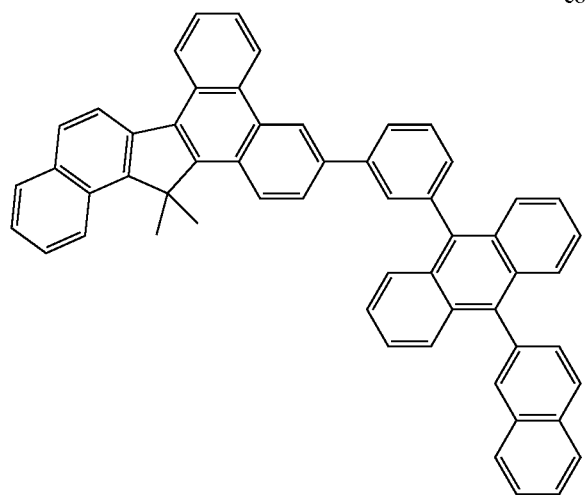
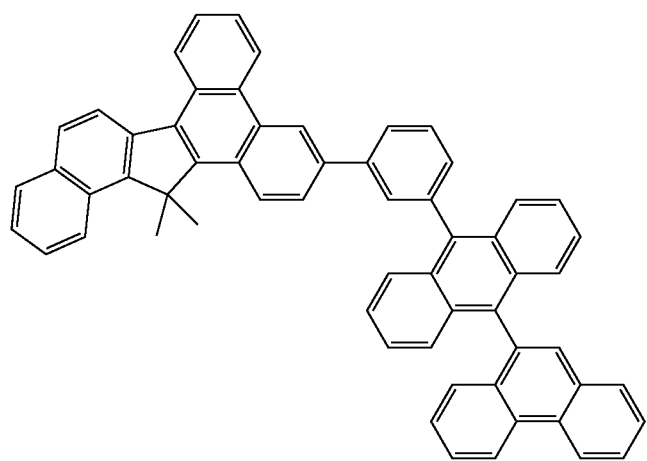
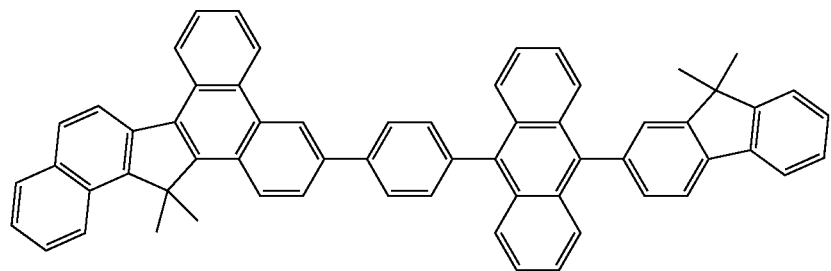
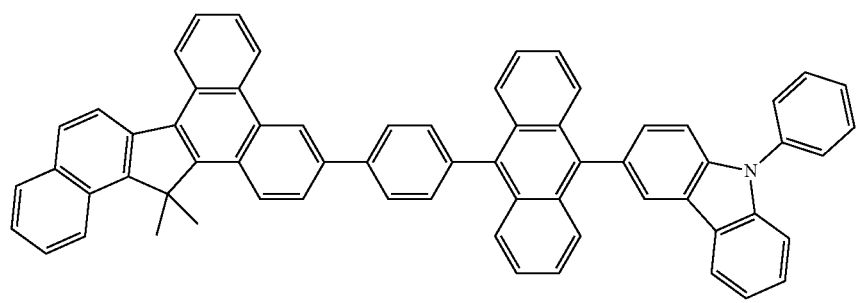

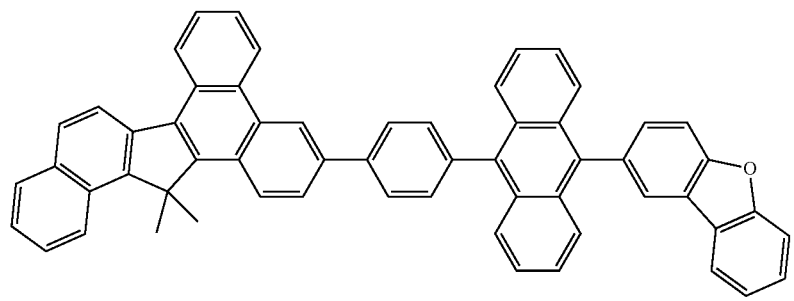
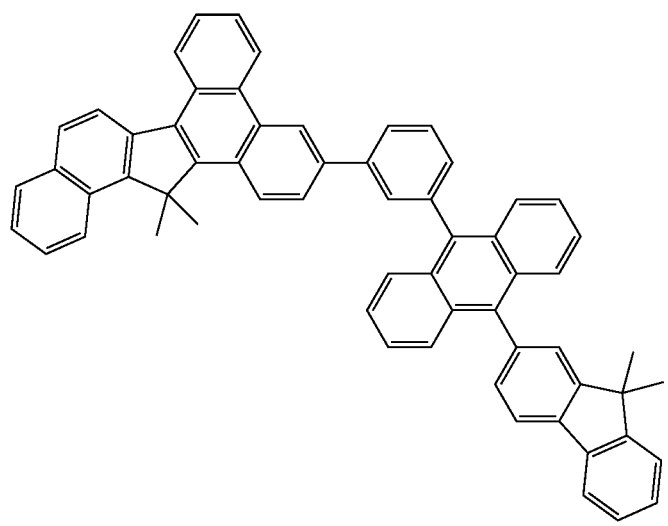
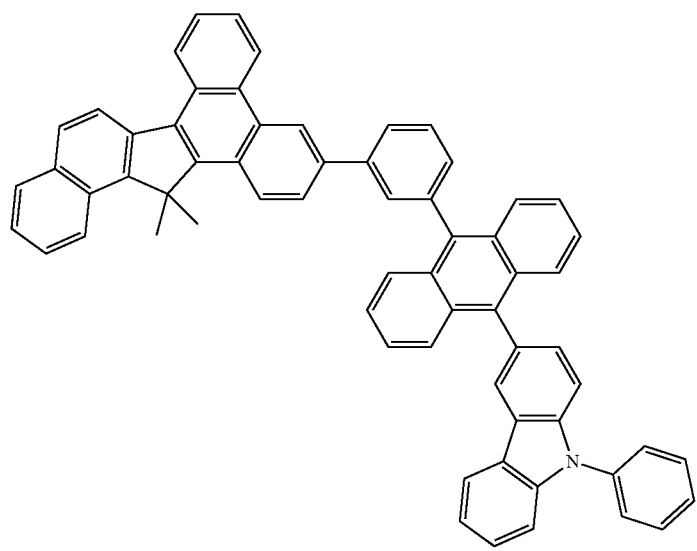

-continued
515
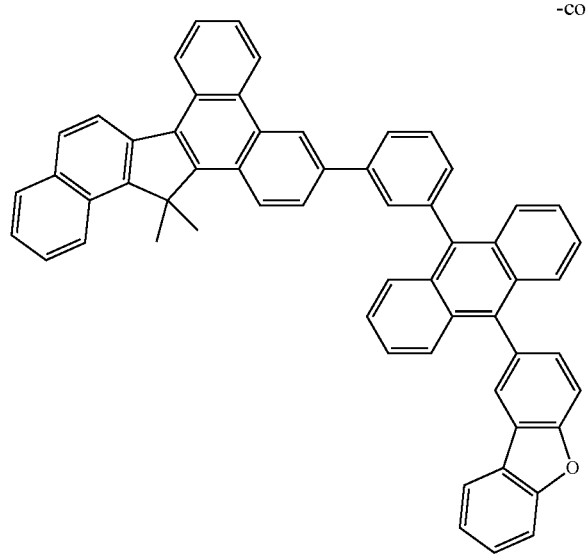
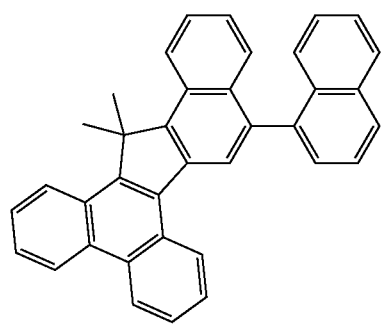
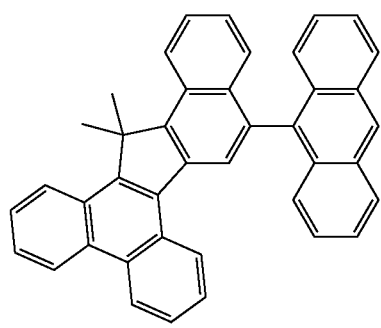
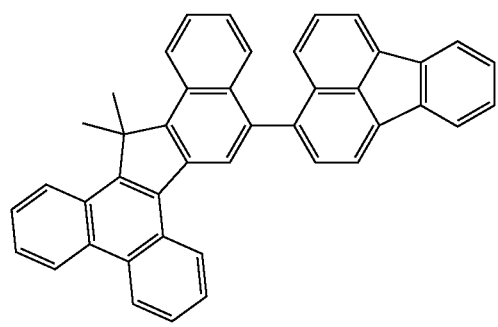
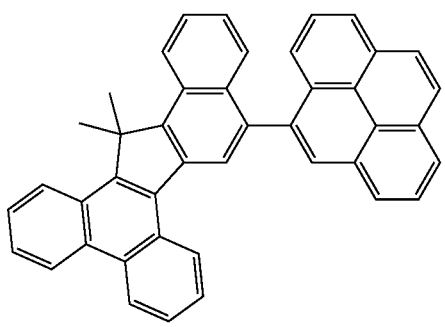
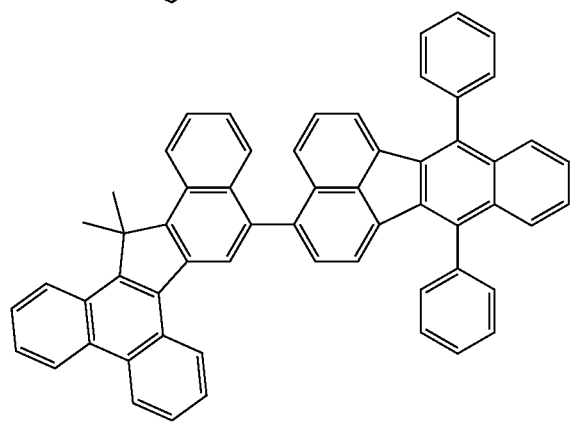
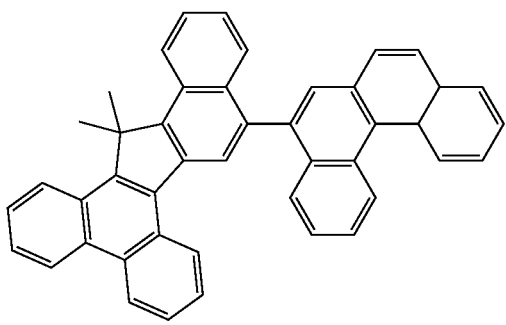
516

-continued
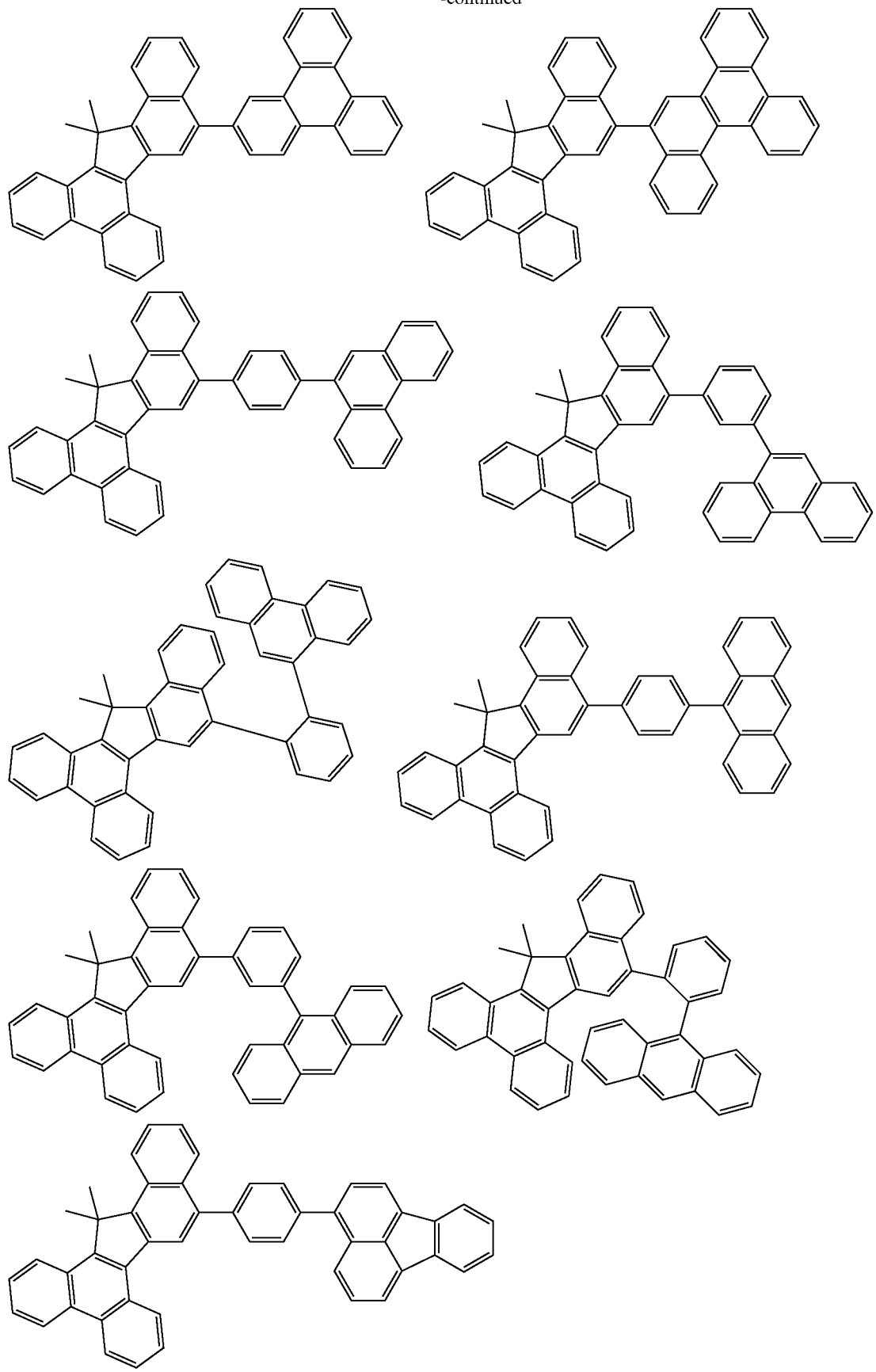

519
520
-continued
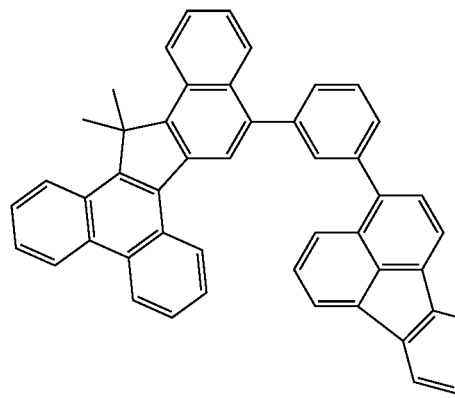
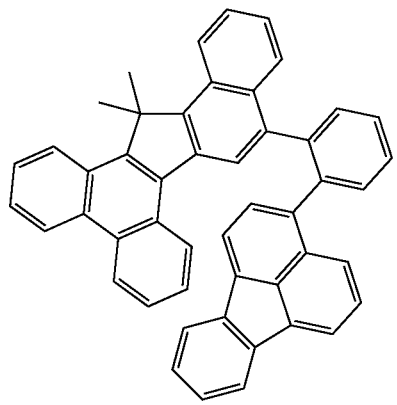
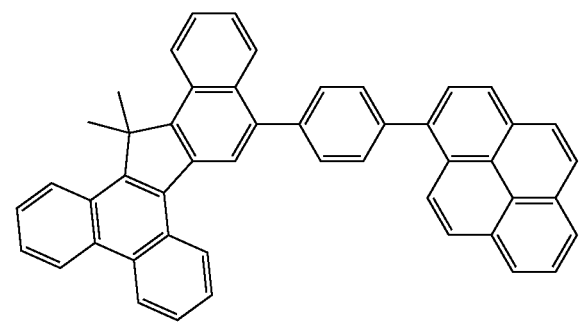
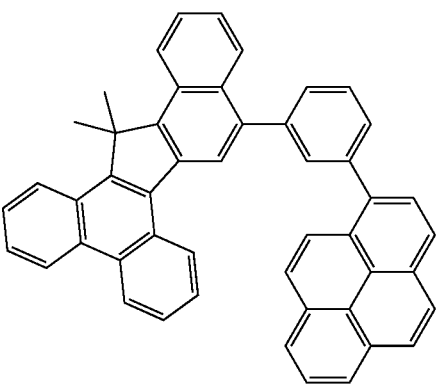
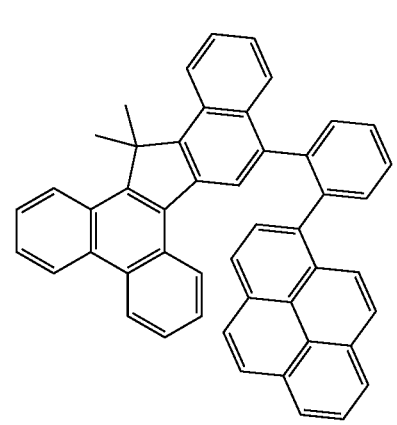
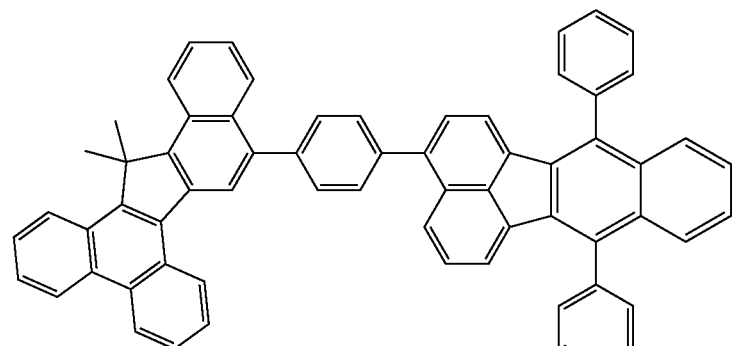

-continued
521
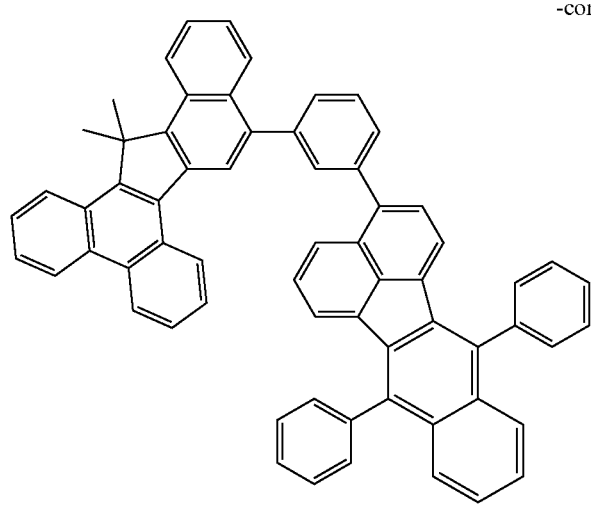
522
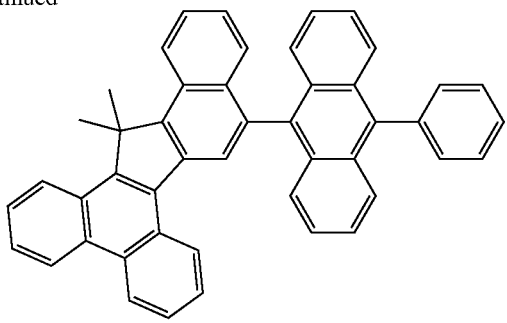
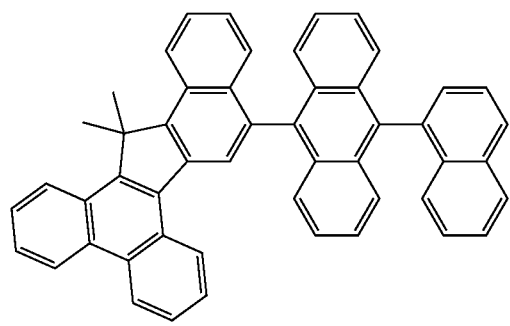
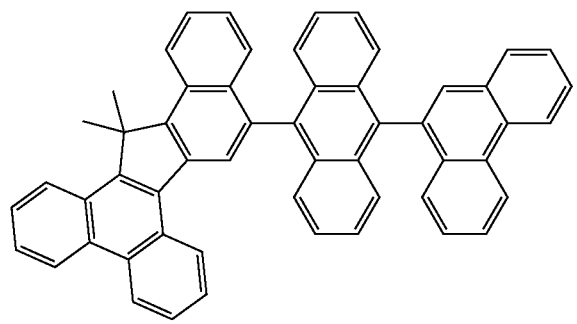
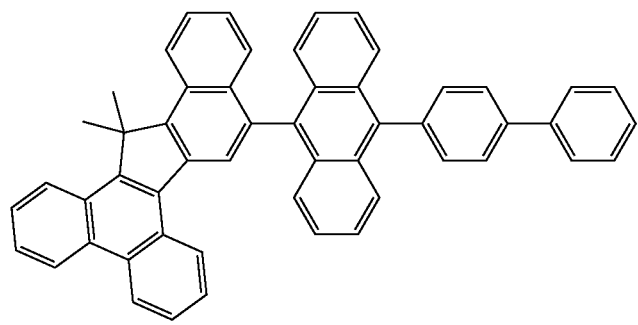

-continued
523 524
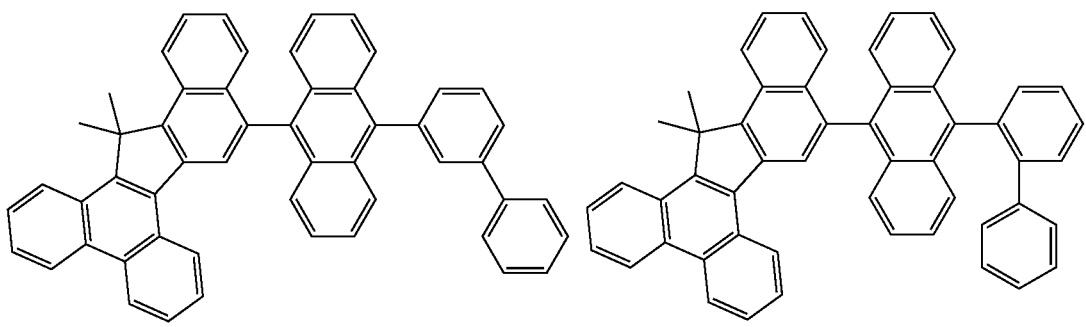
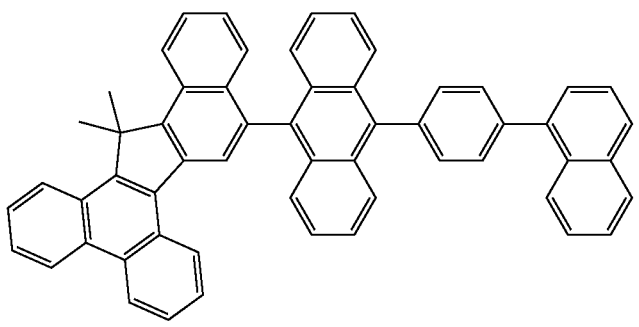
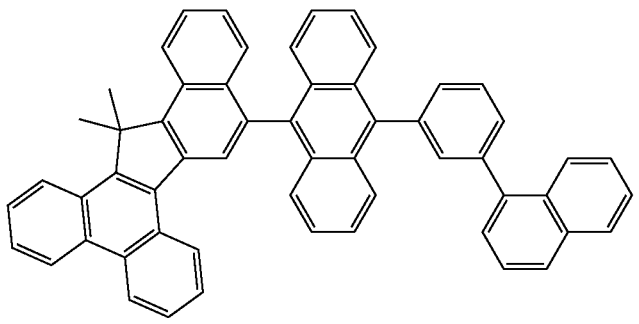
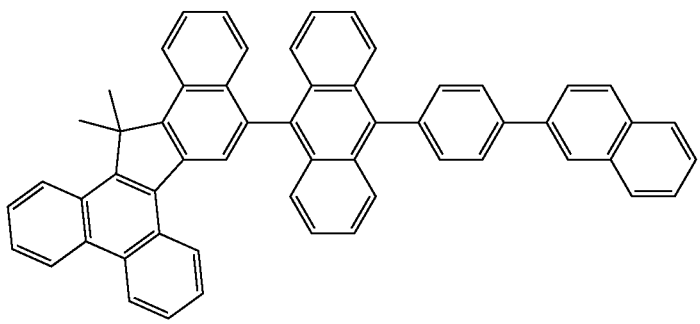
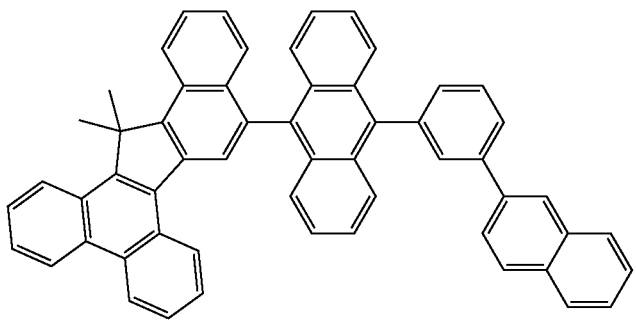

525
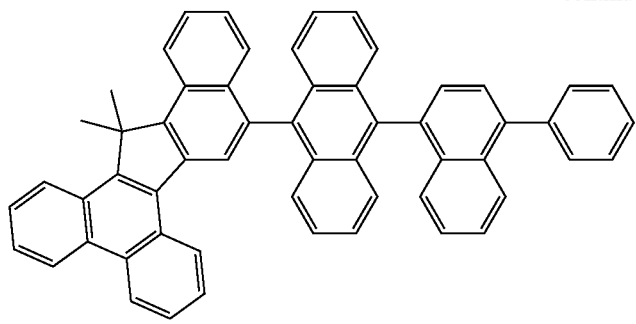
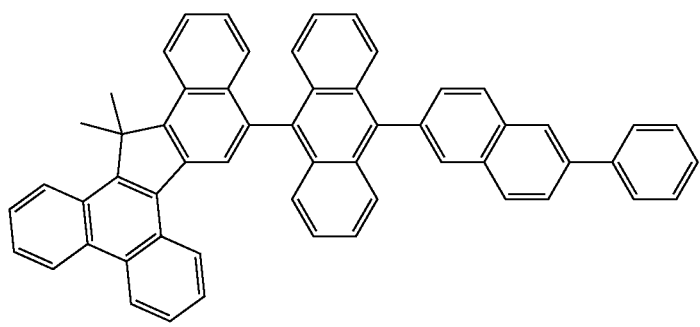

526
-continued
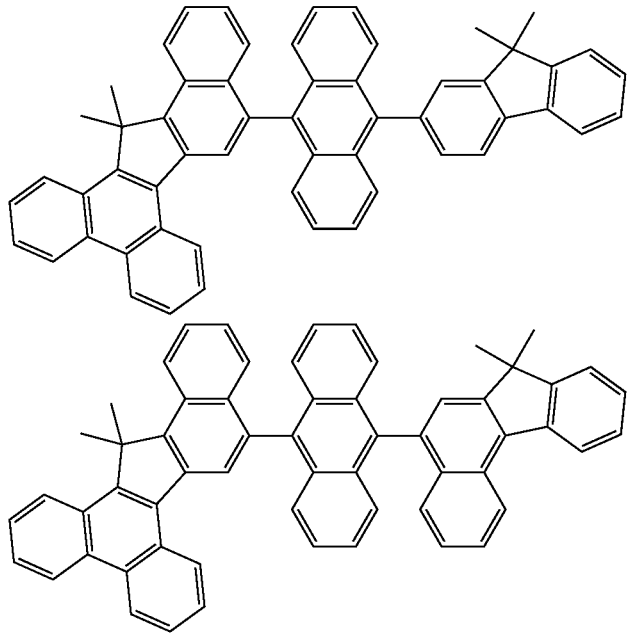
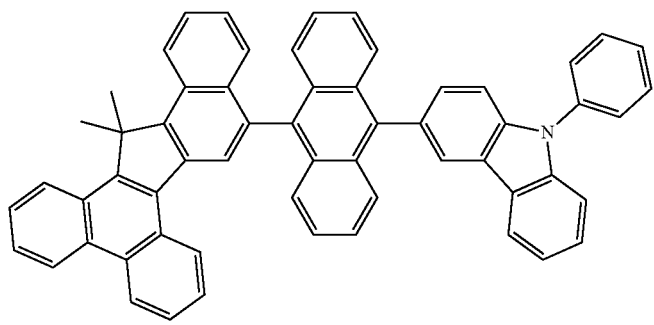

-continued
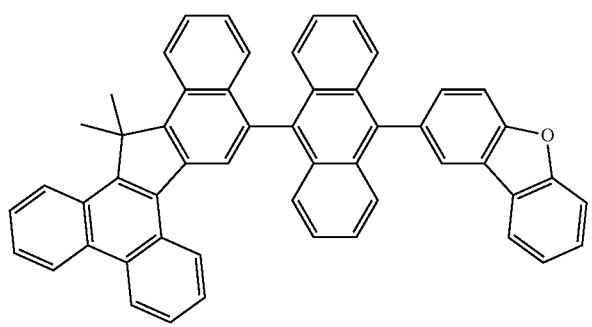
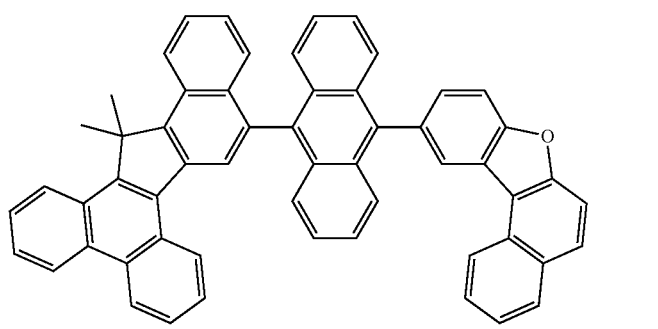
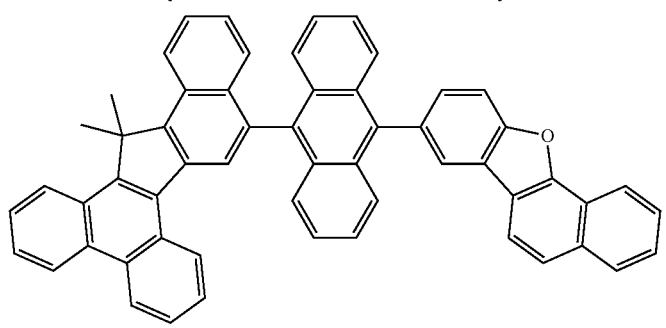
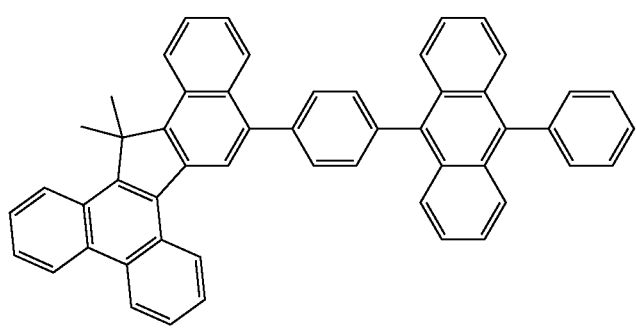
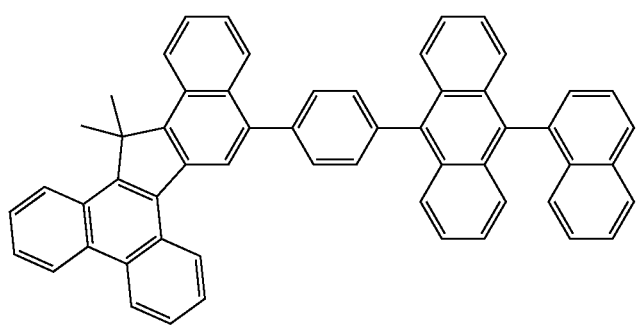

-continued
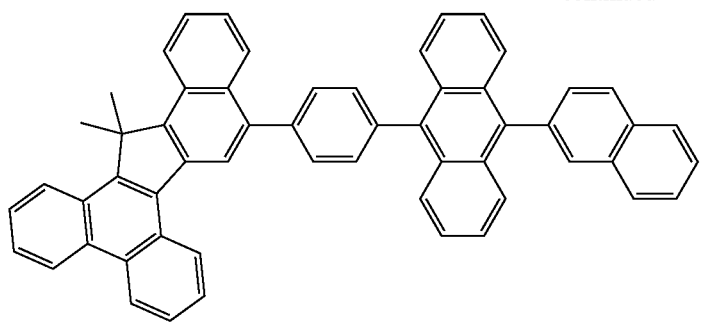
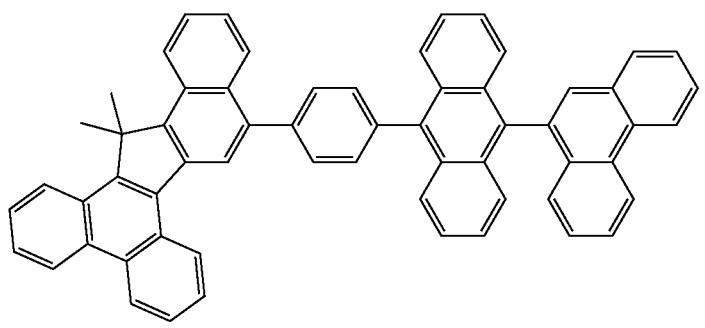
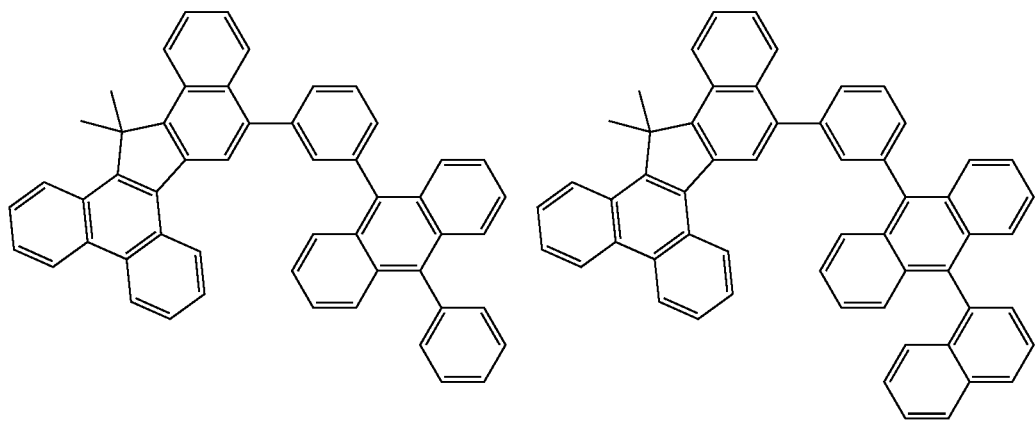
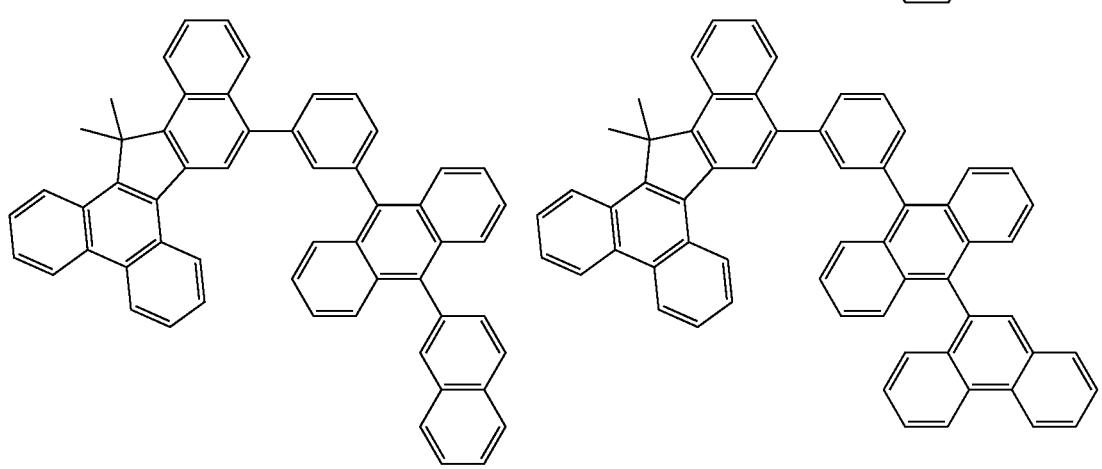

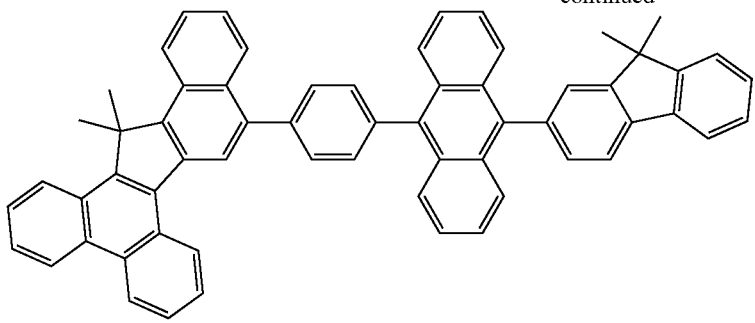

533 534
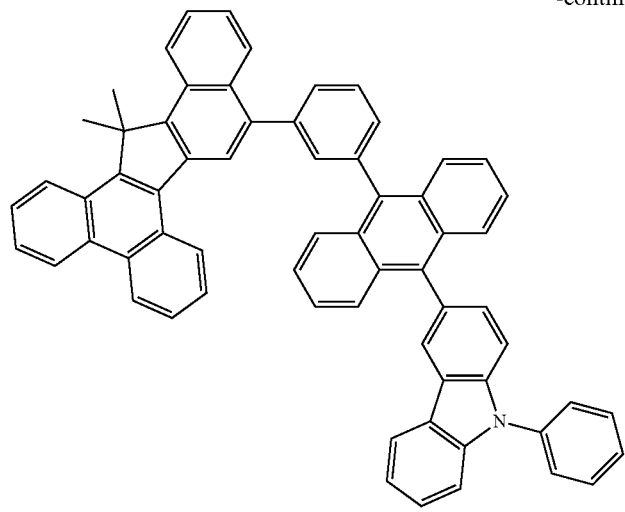
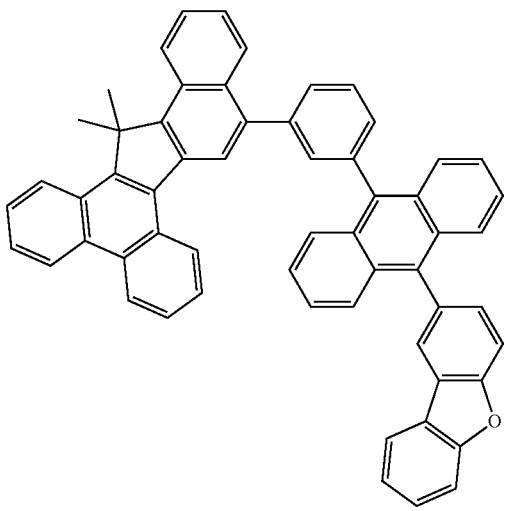
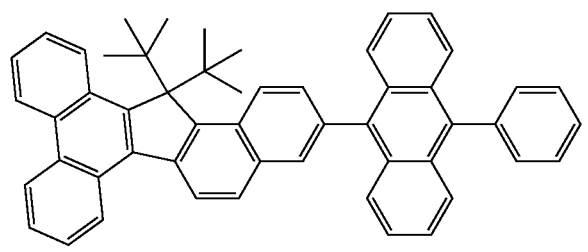
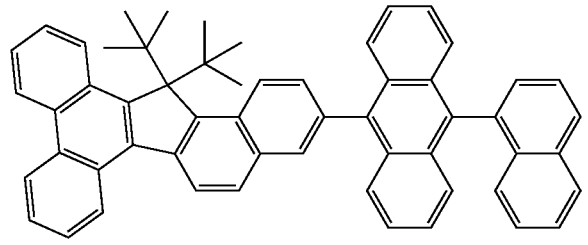
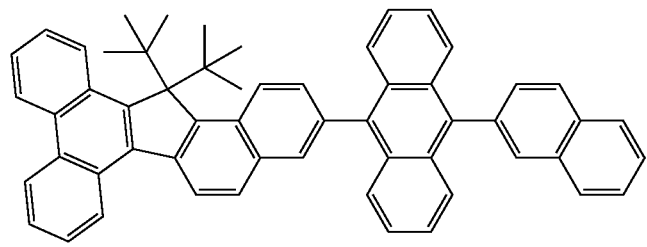
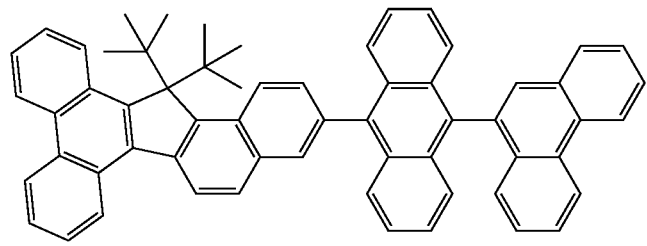
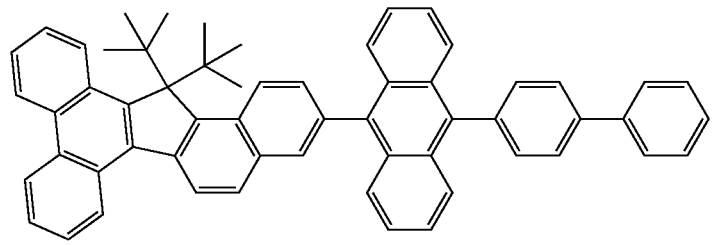

-continued
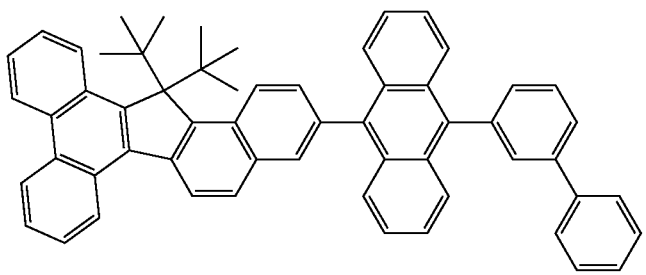
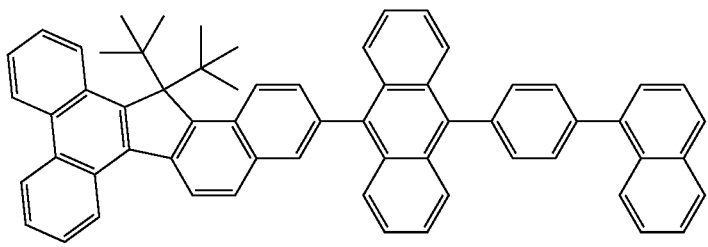
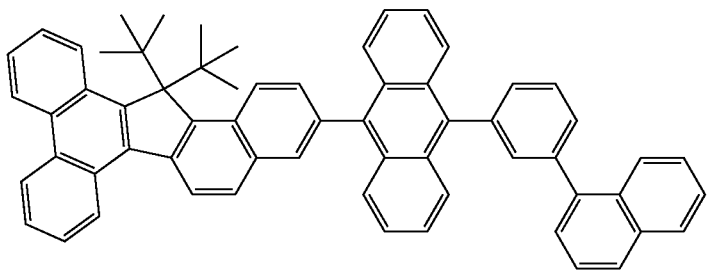
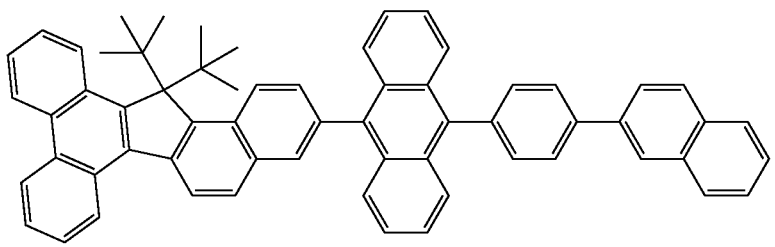
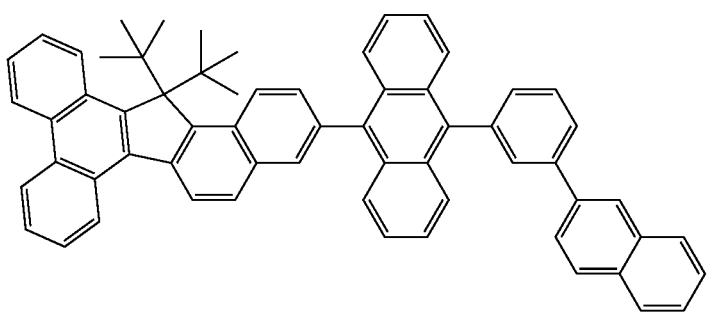

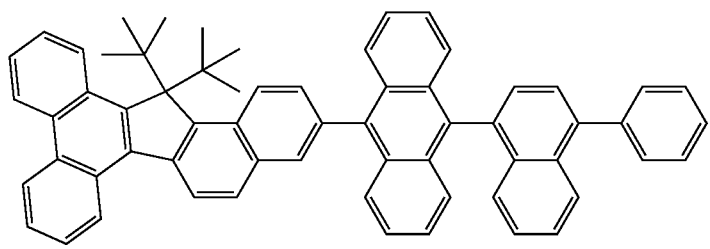
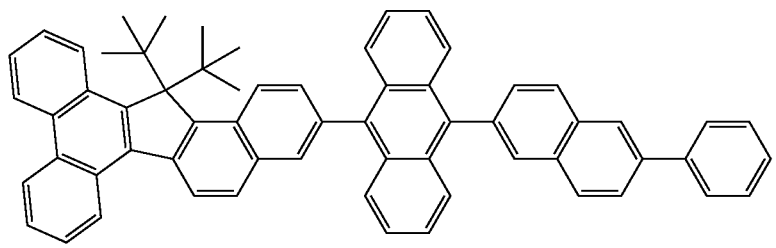
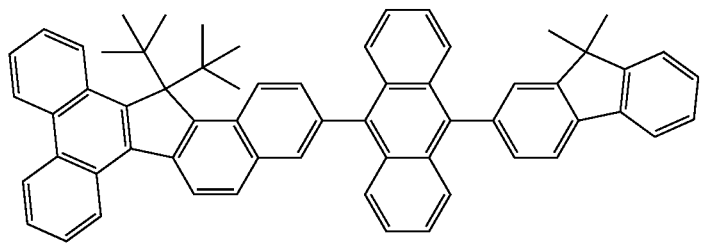
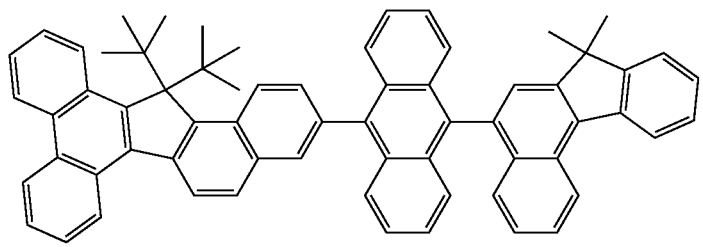
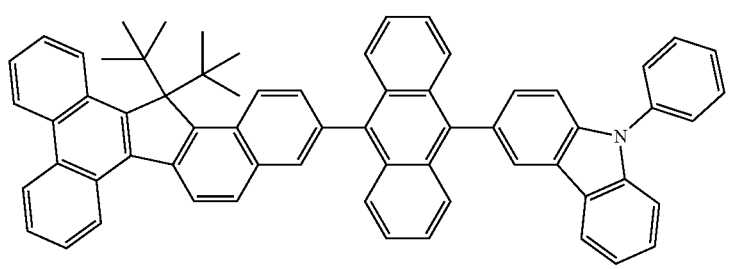
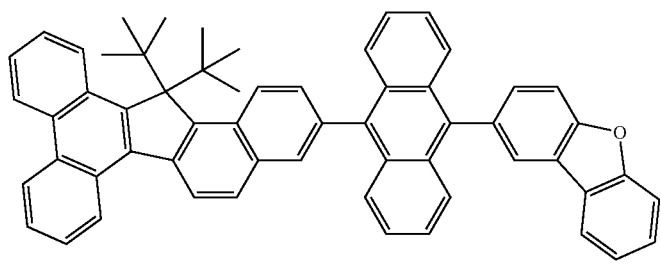

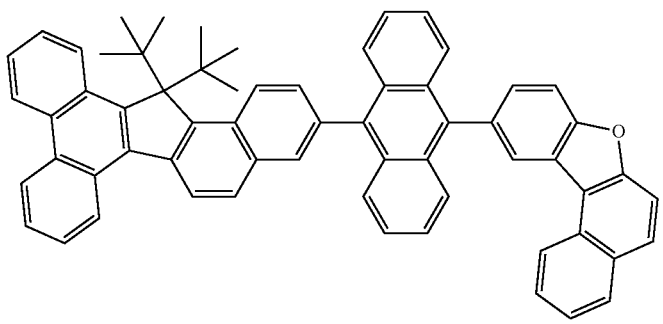
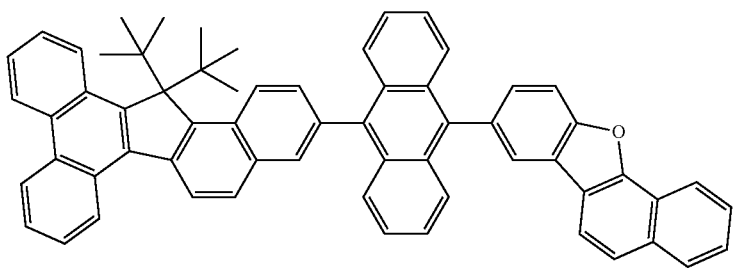
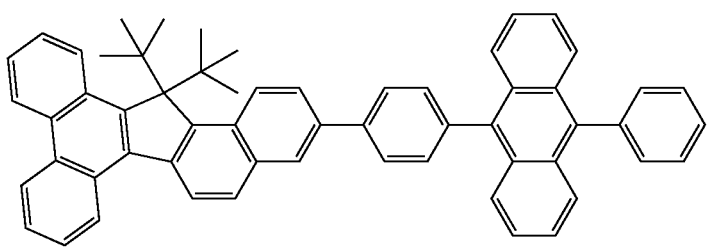
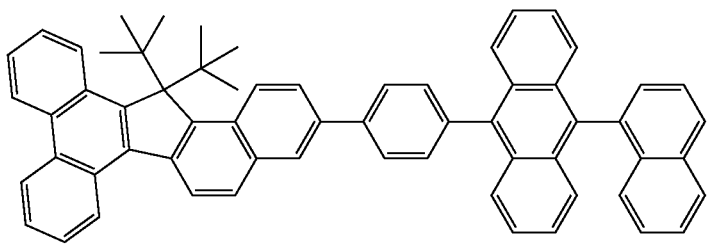
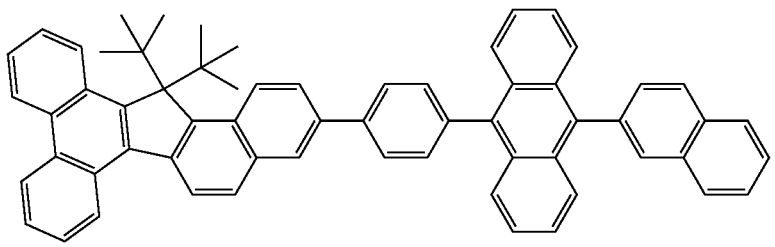
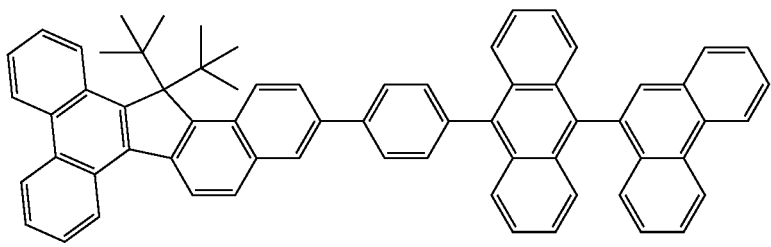

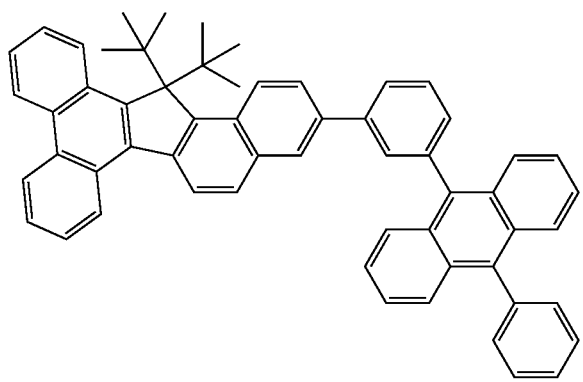
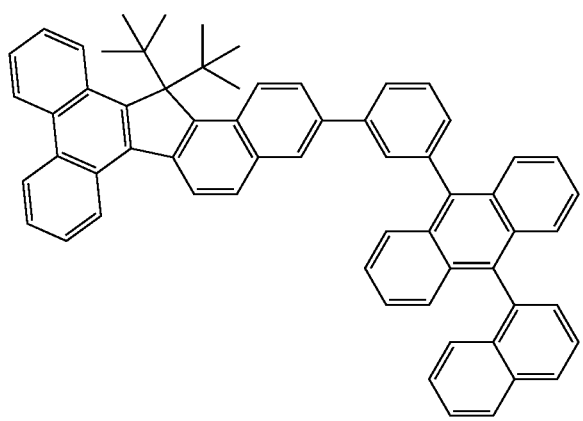
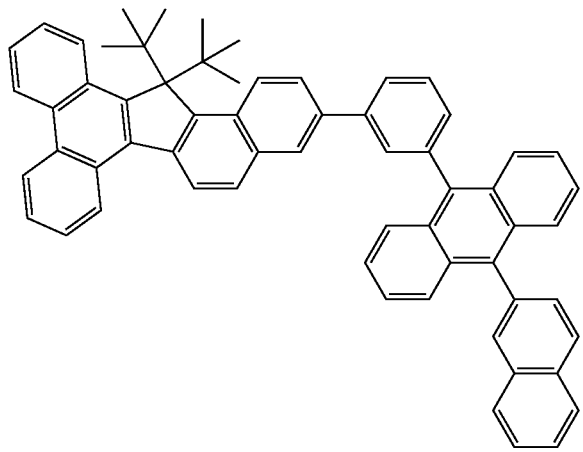
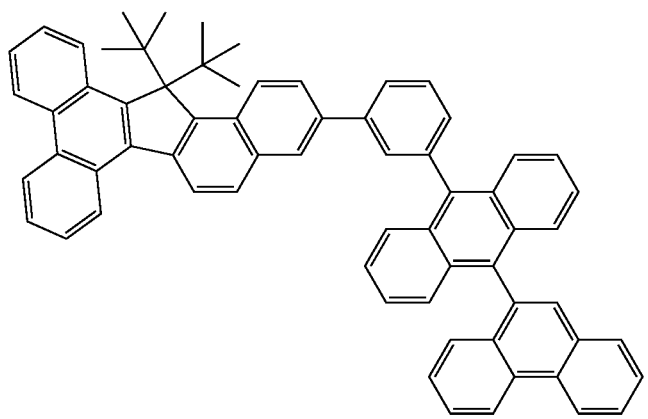

-continued
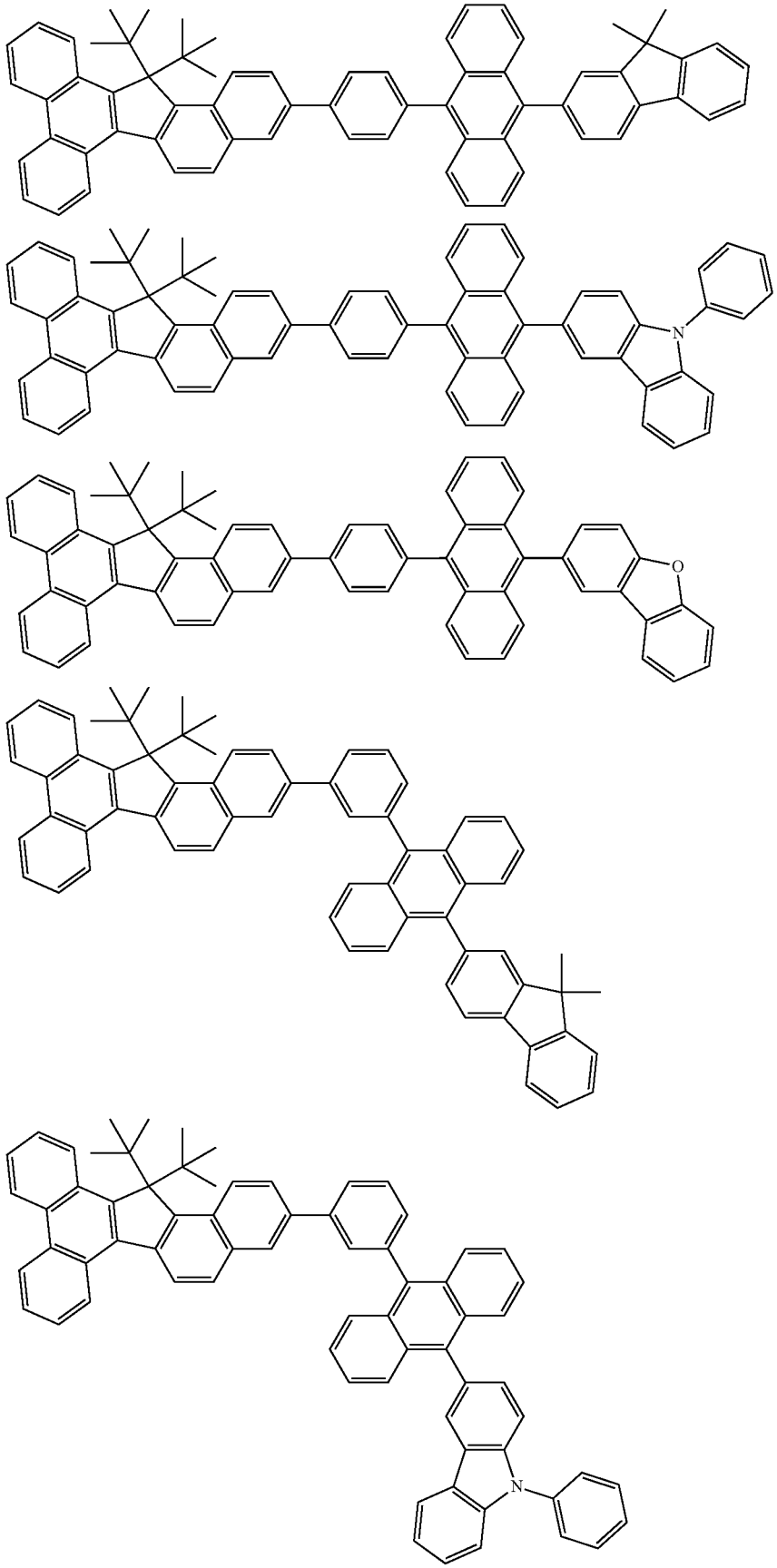

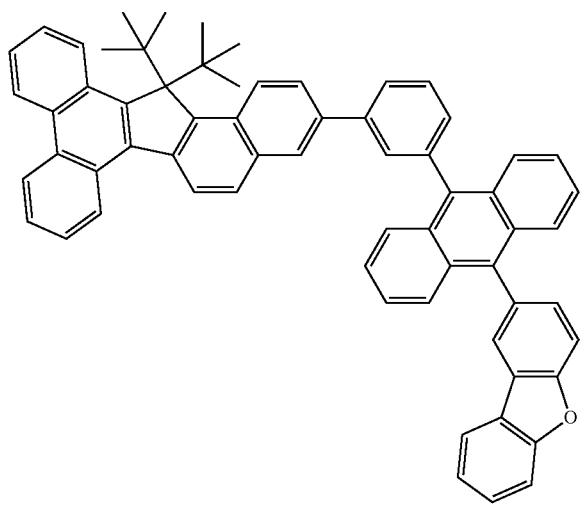
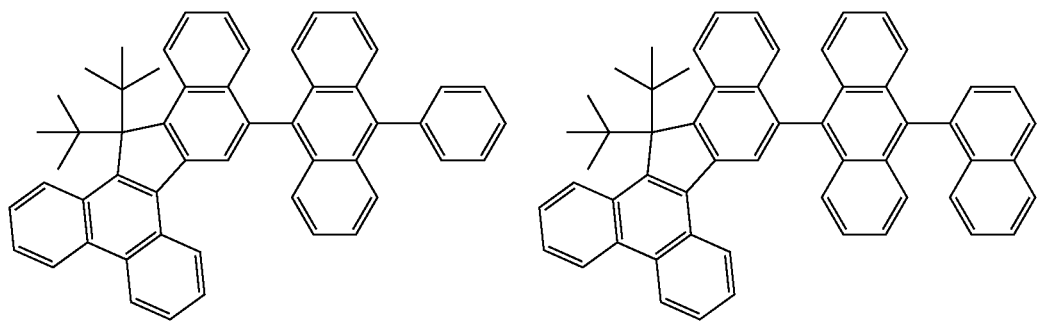
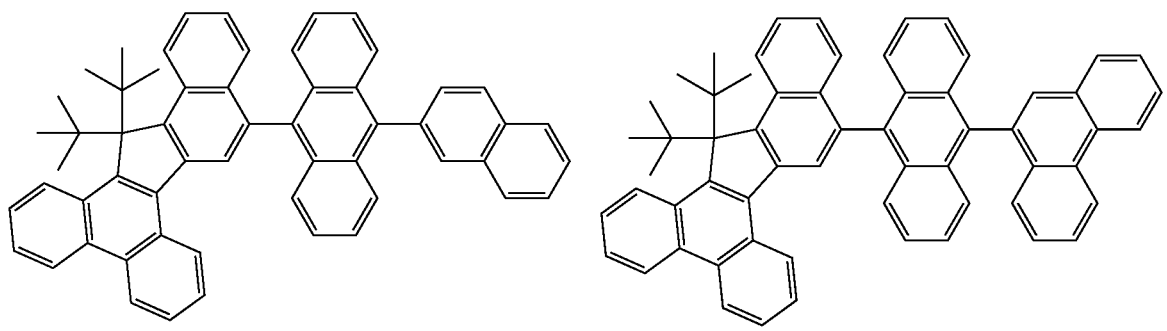
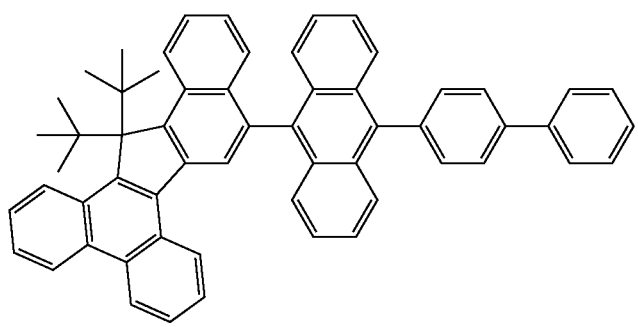

547 548
-continued
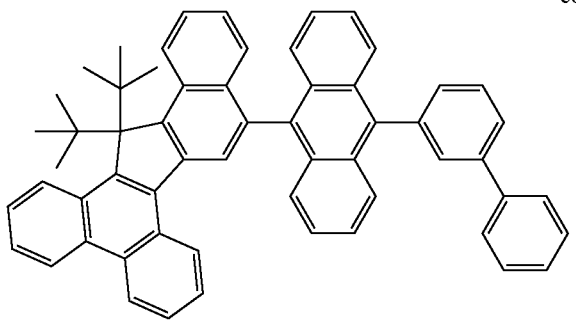 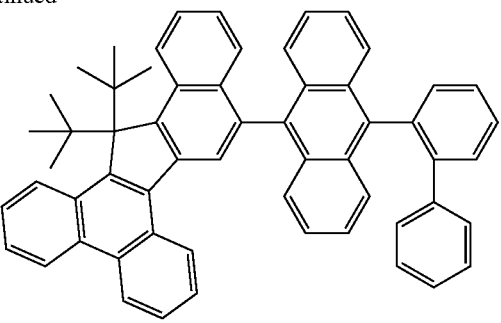
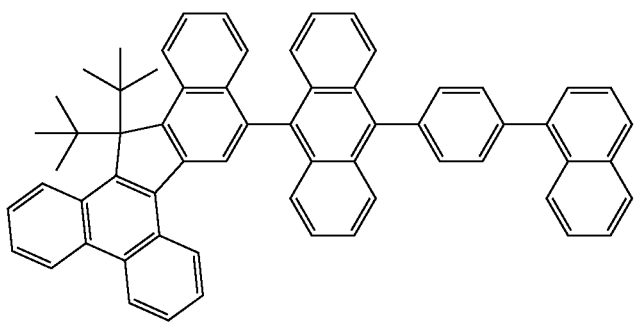
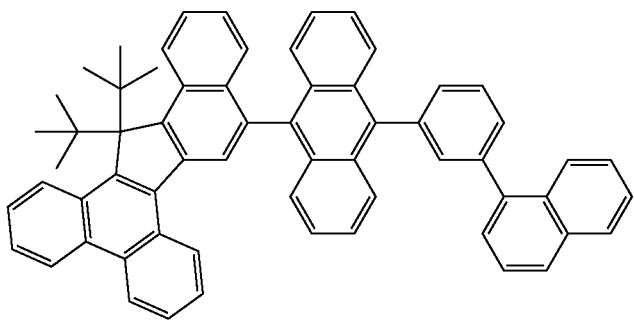
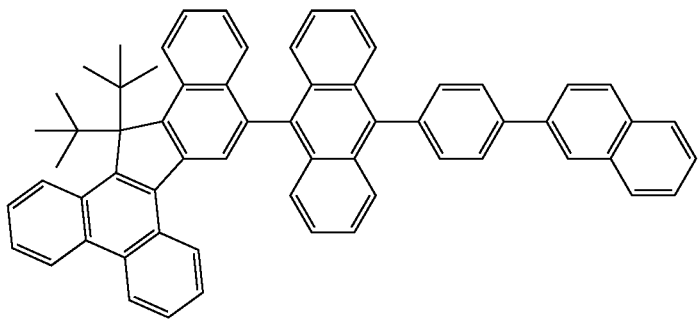
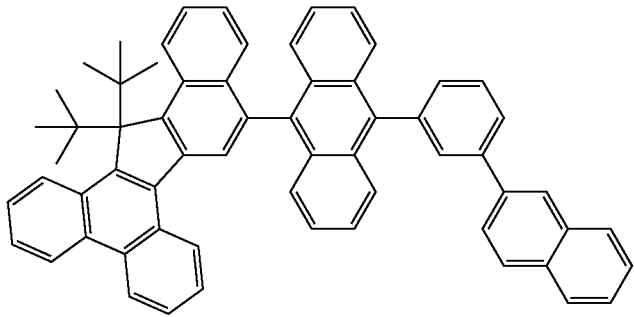

-continued
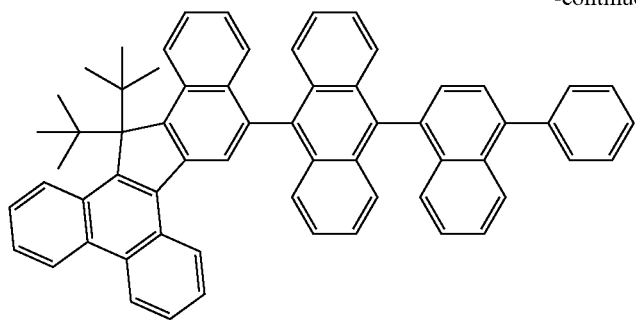
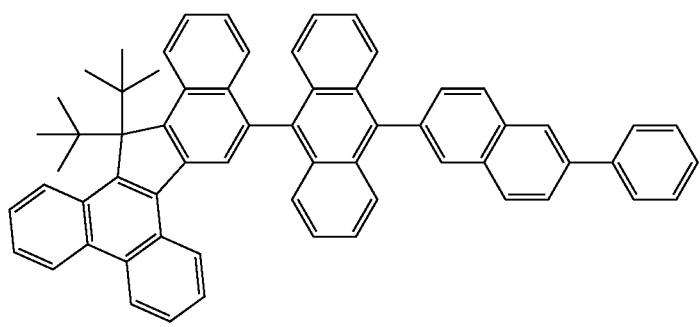
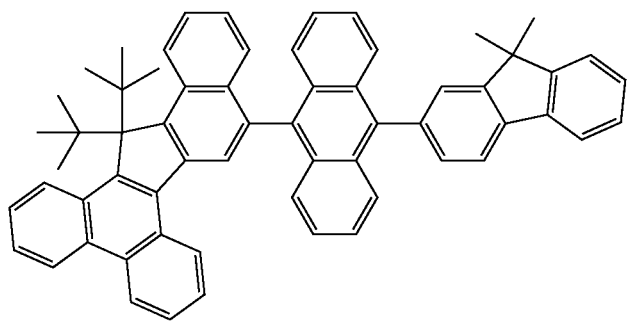
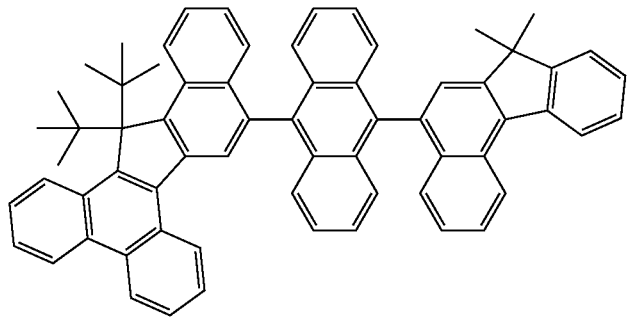
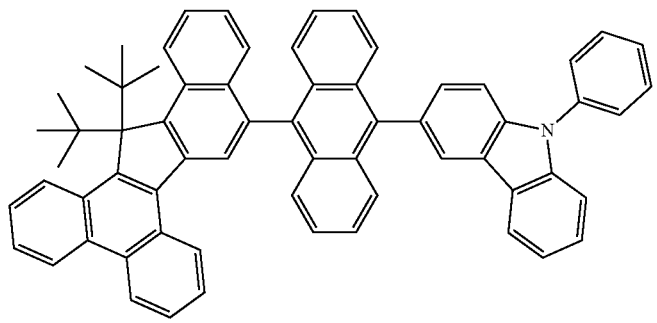

551
552
-continued
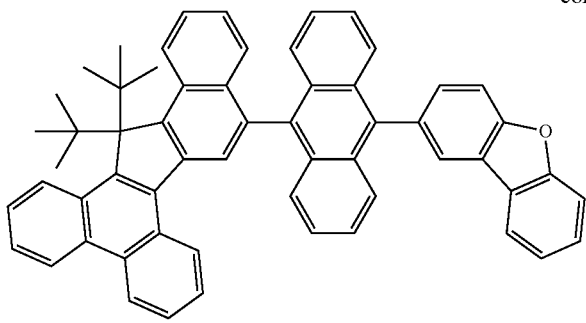
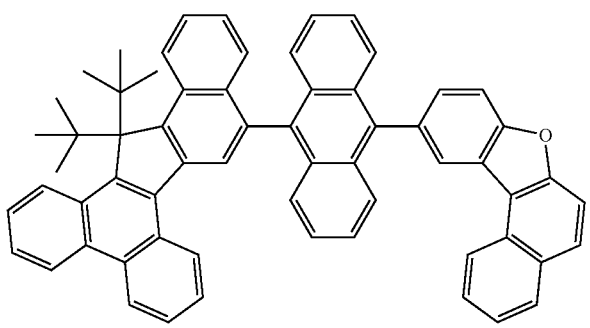
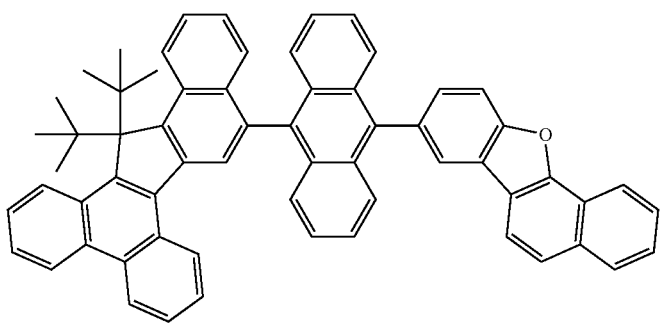
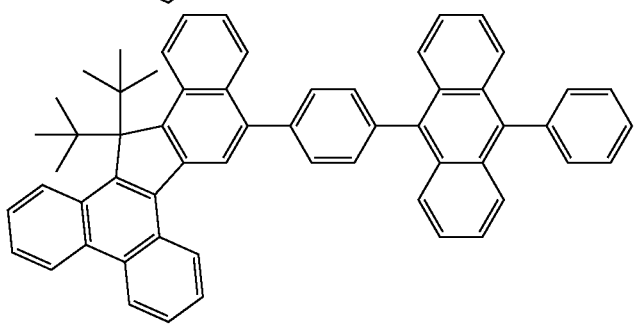
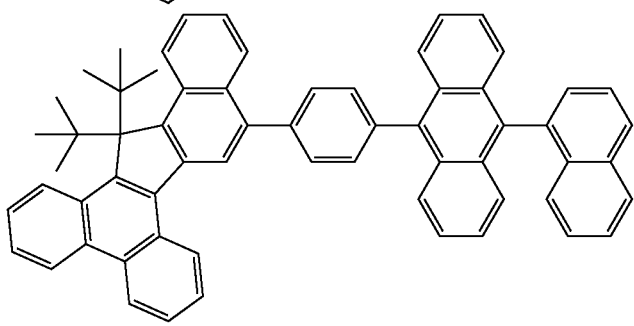

553
554
-continued
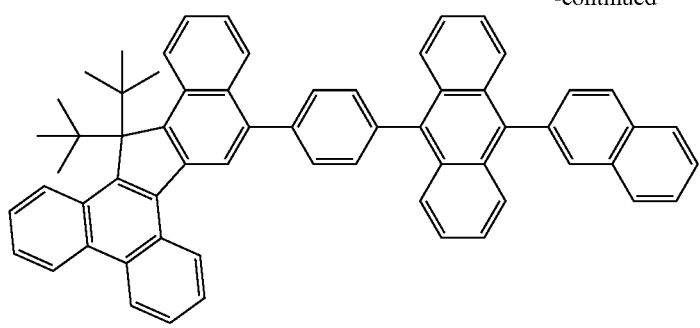
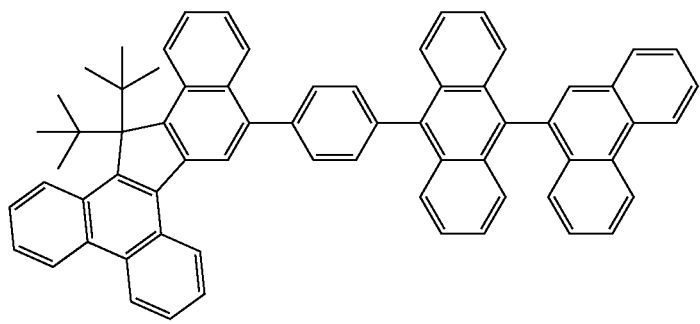
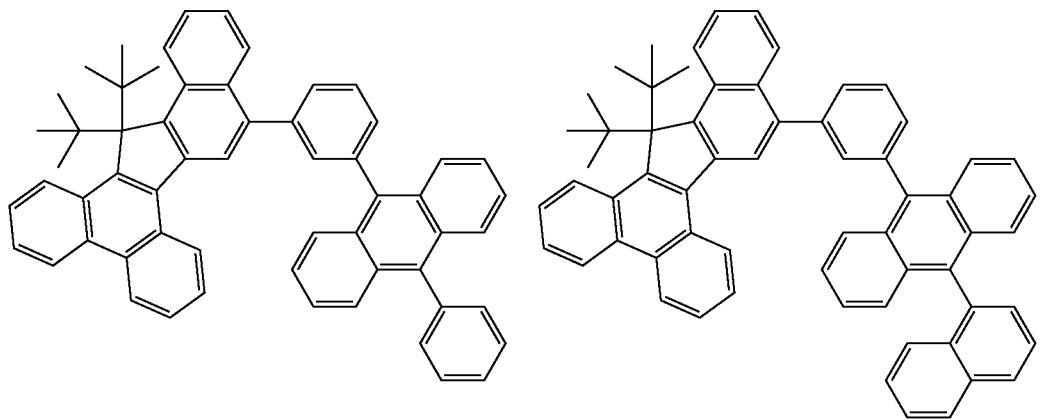
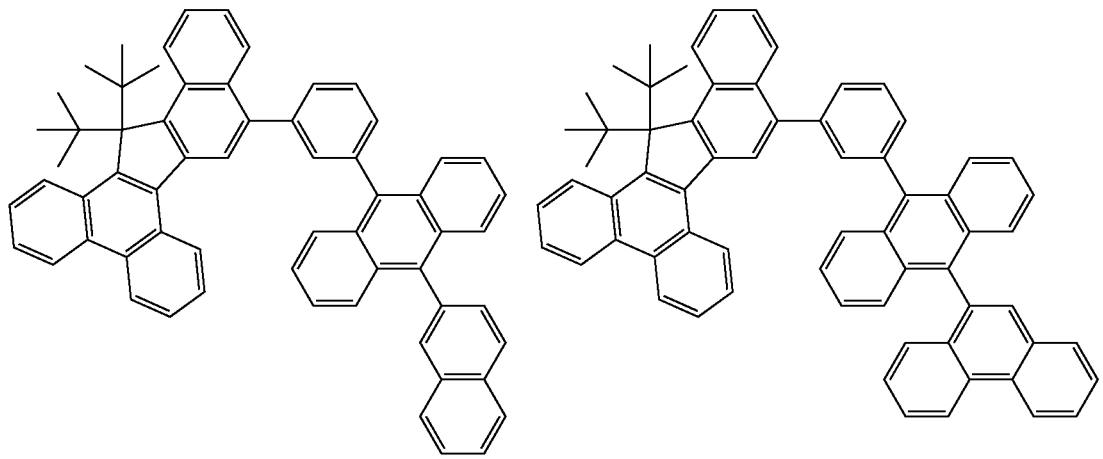

555
-continued
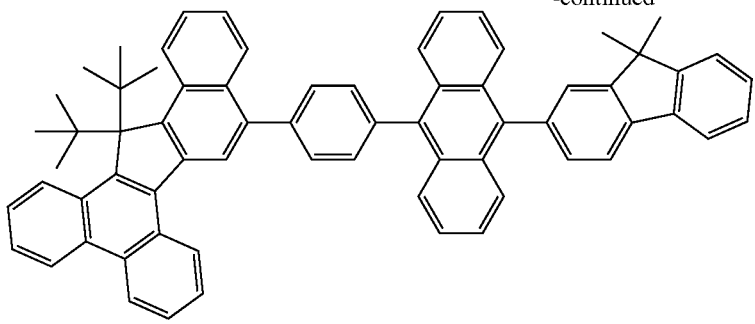
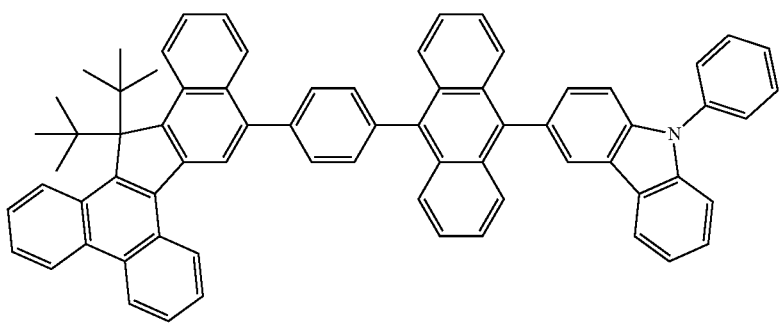
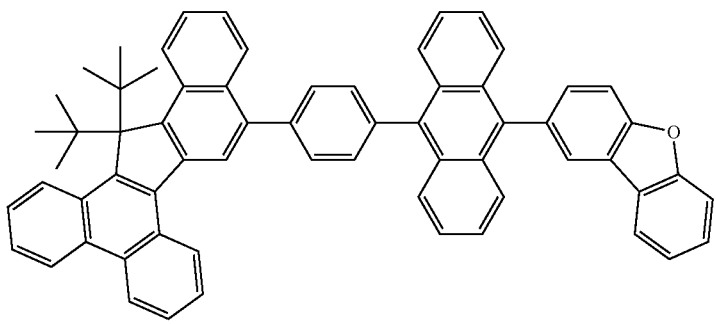
556
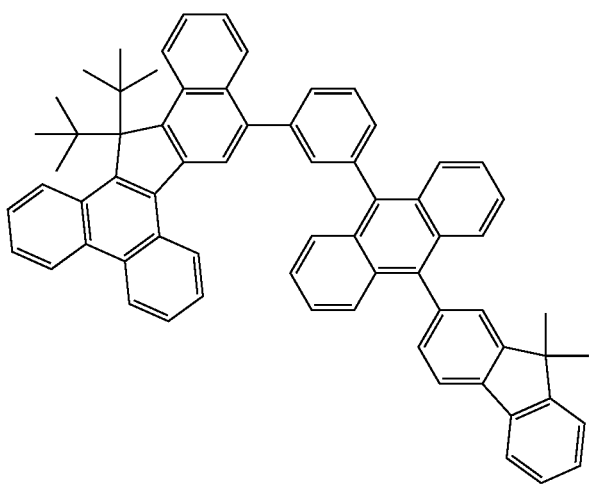

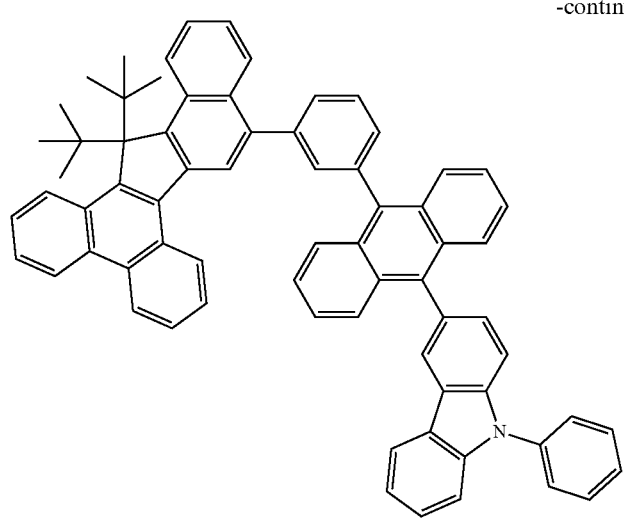
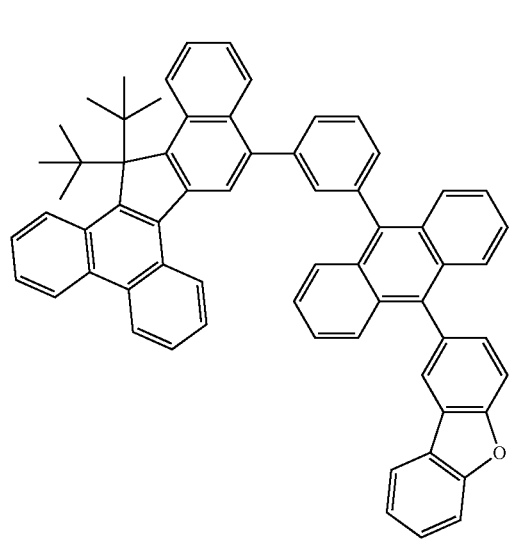
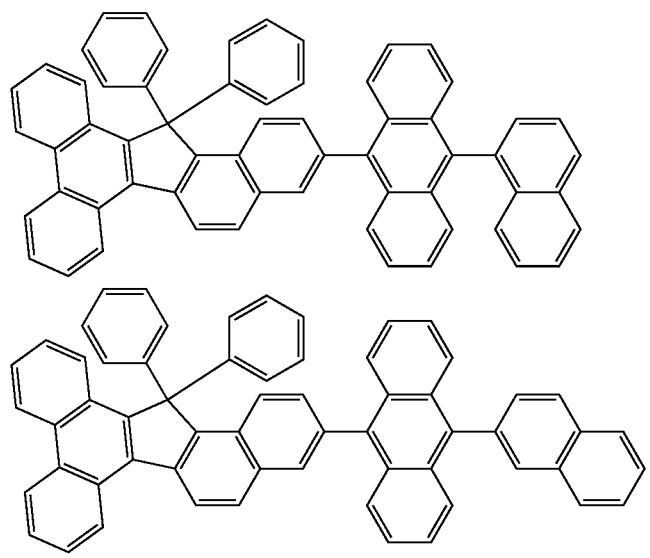

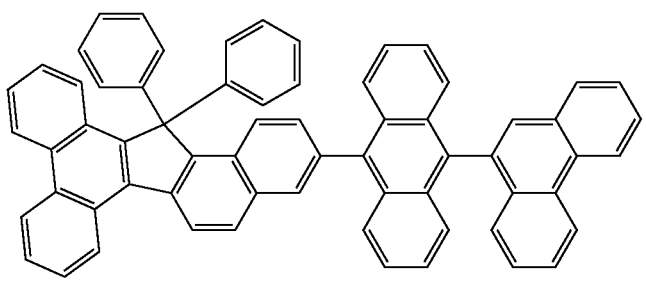
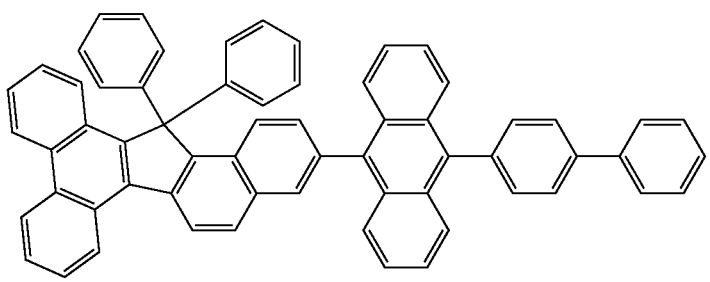
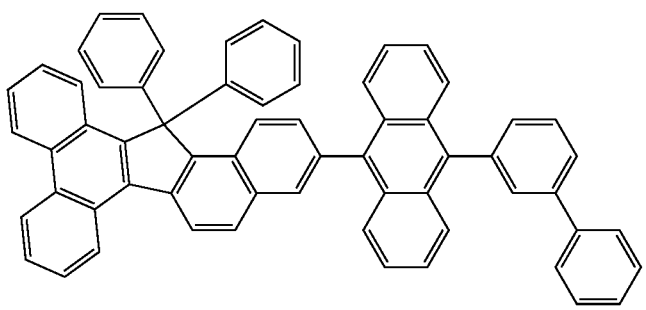
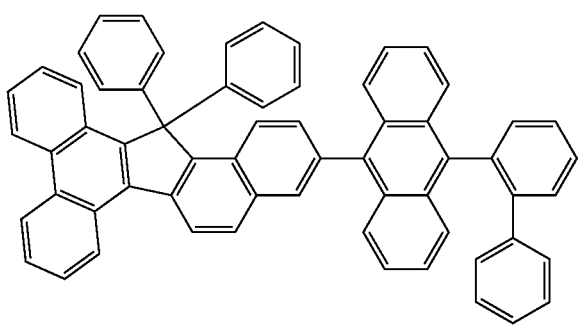
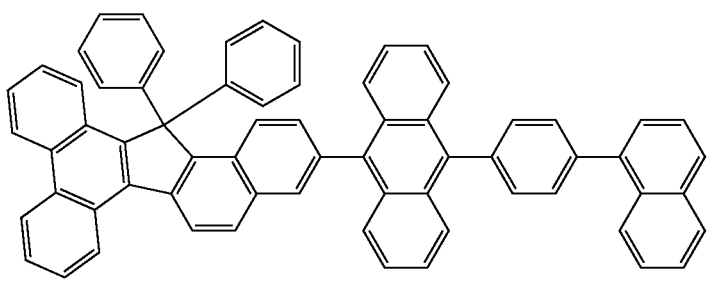

-continued
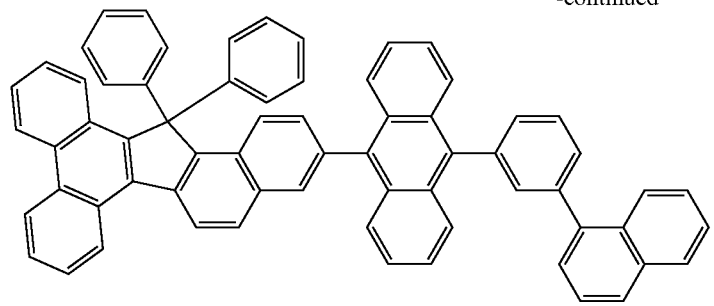
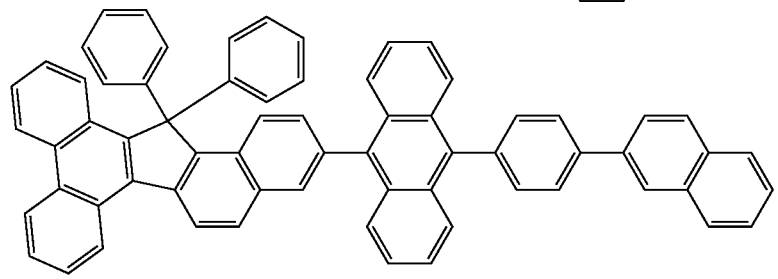
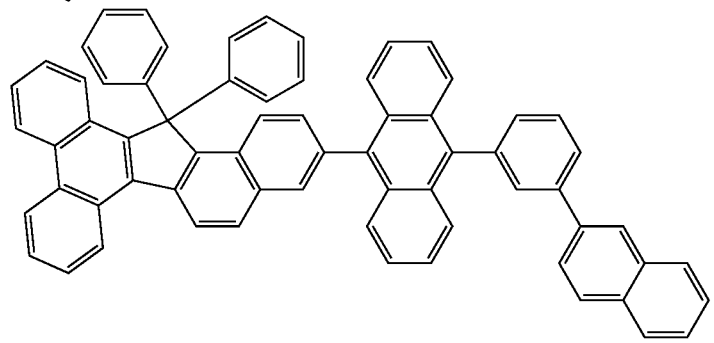
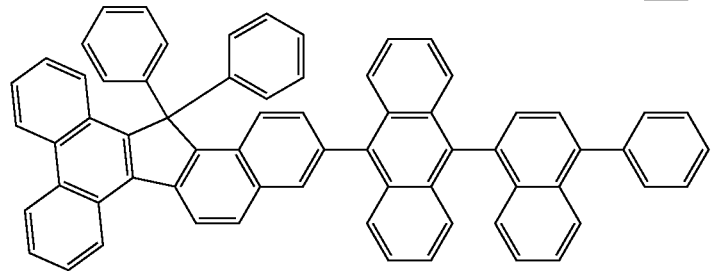
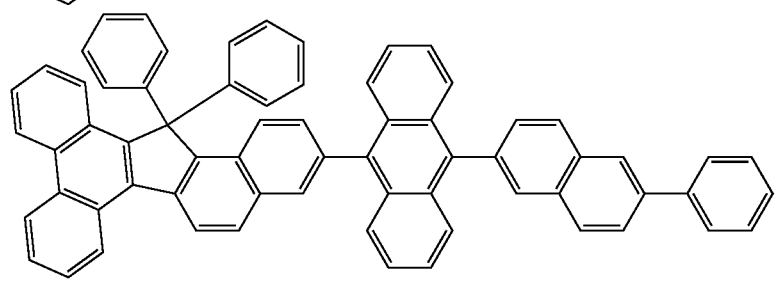
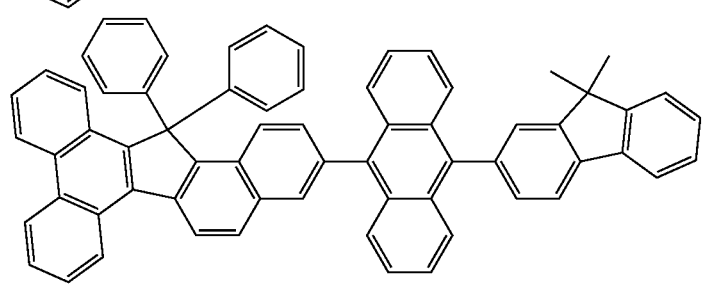

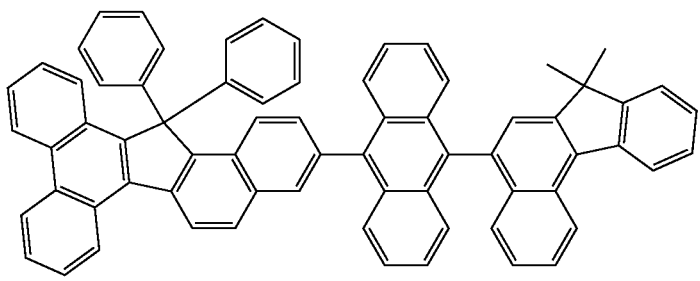
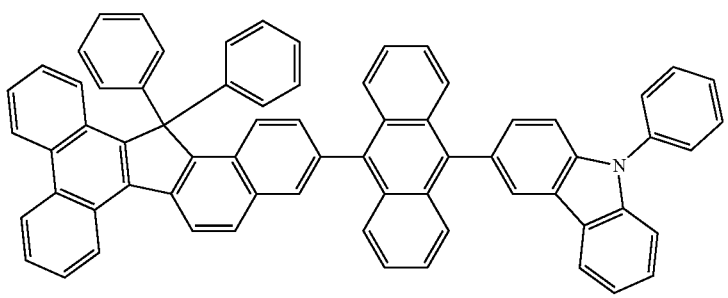
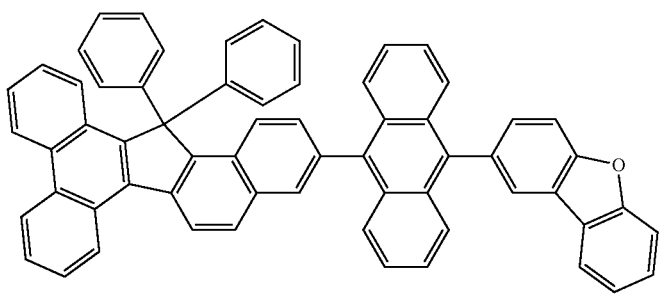
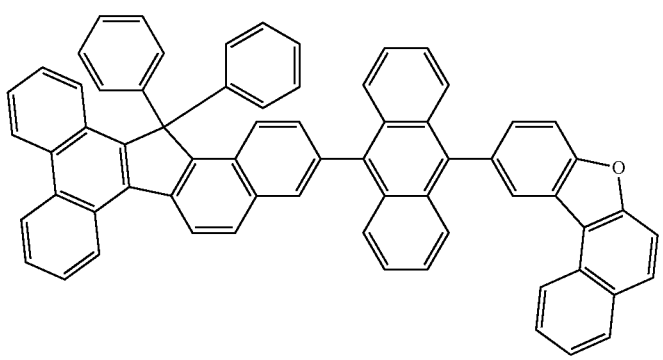
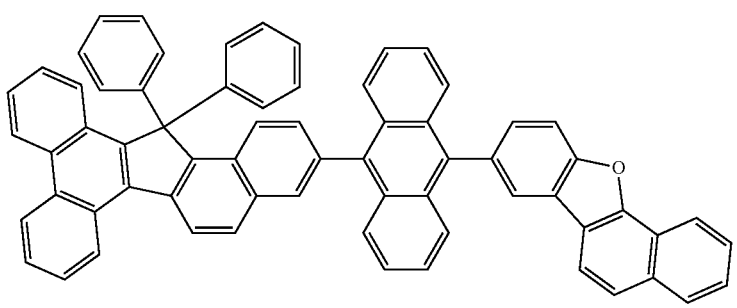

-continued
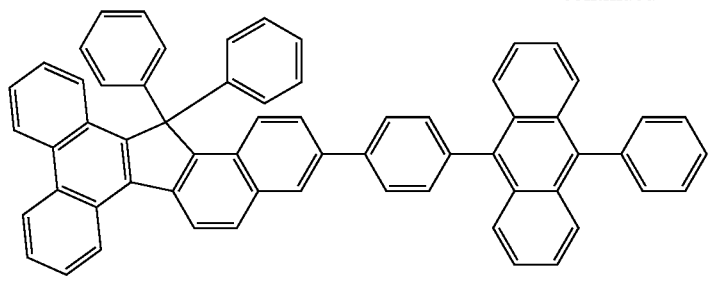
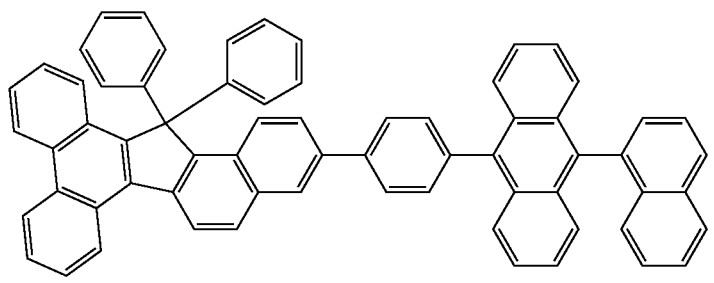
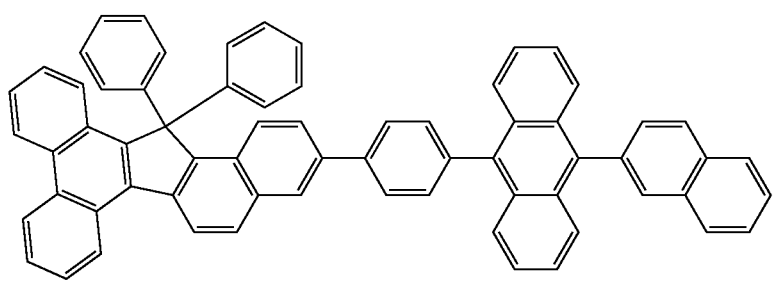
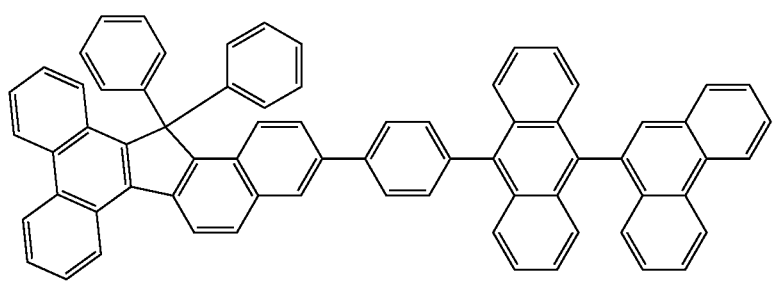
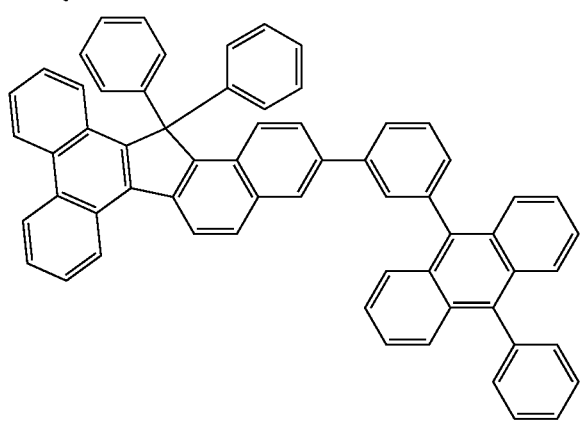

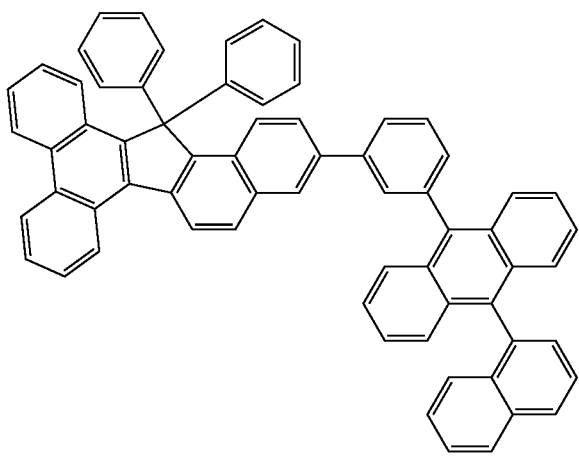
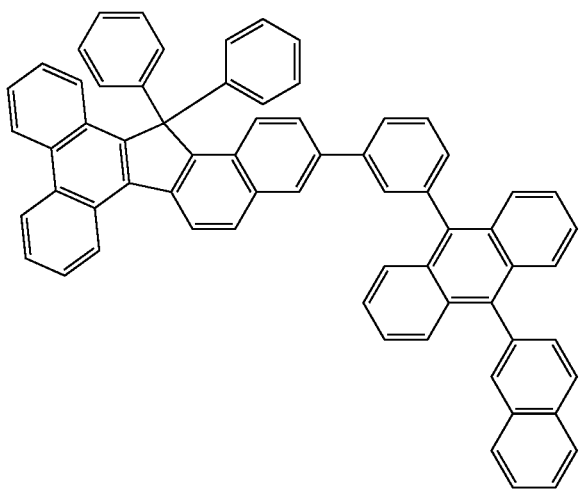
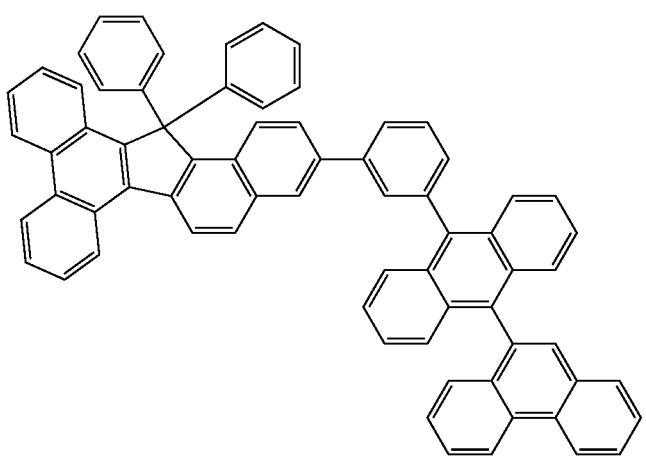
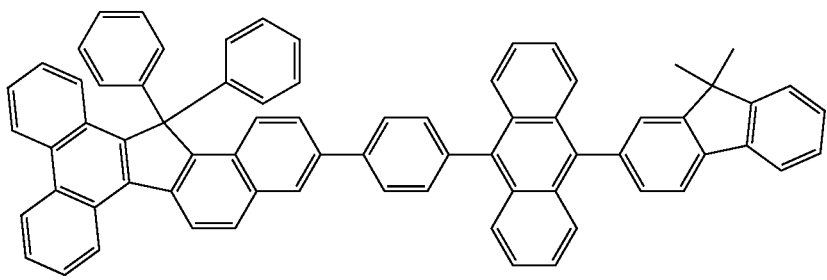

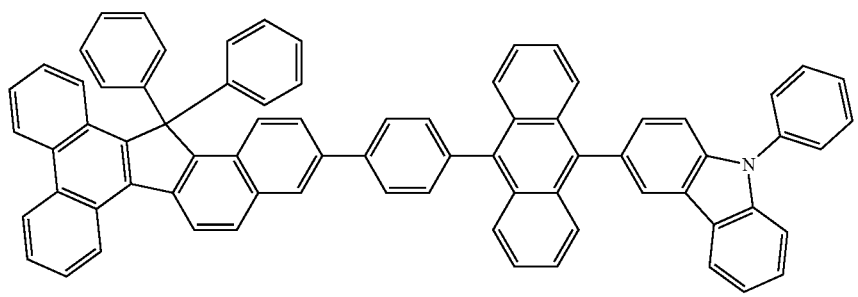
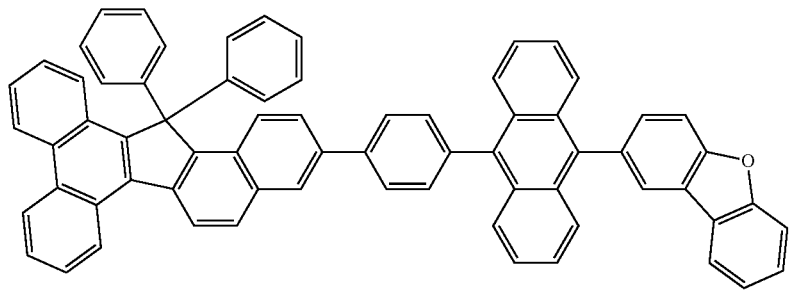
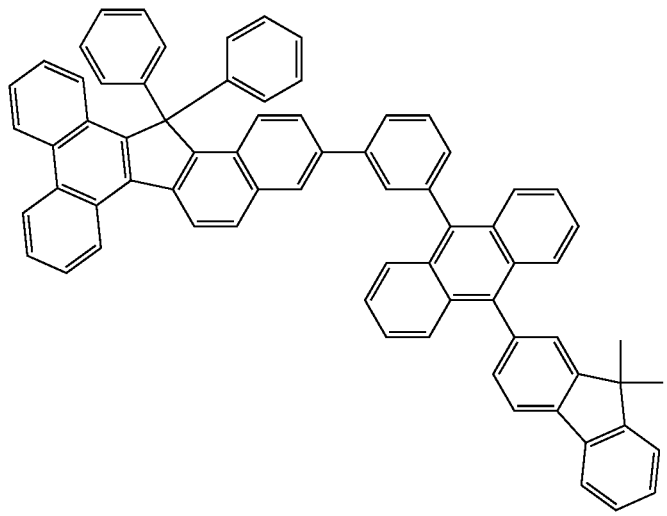
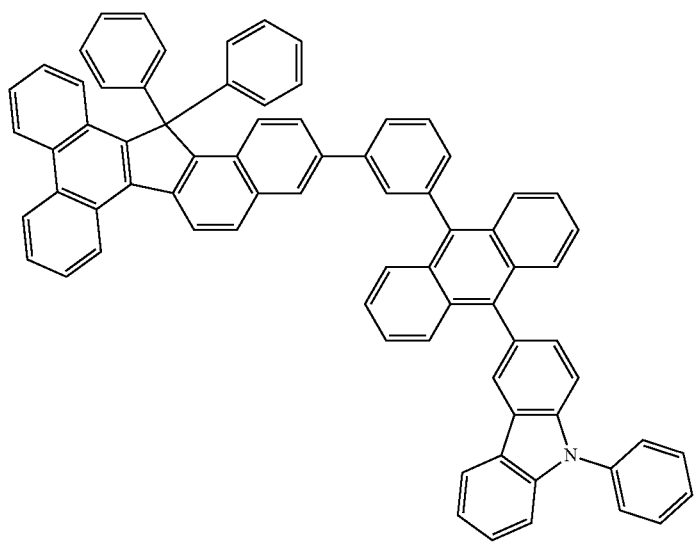

-continued
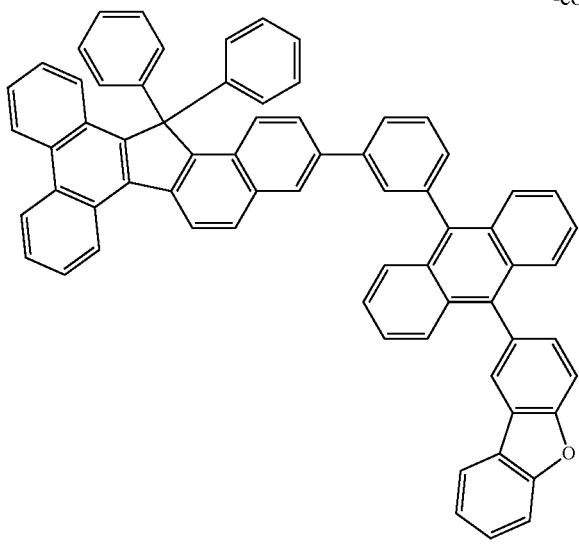

-continued
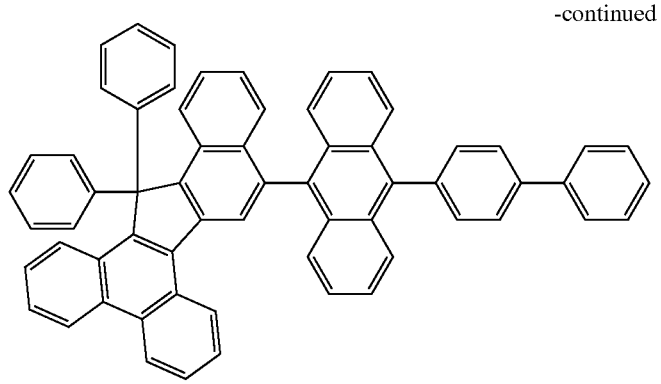
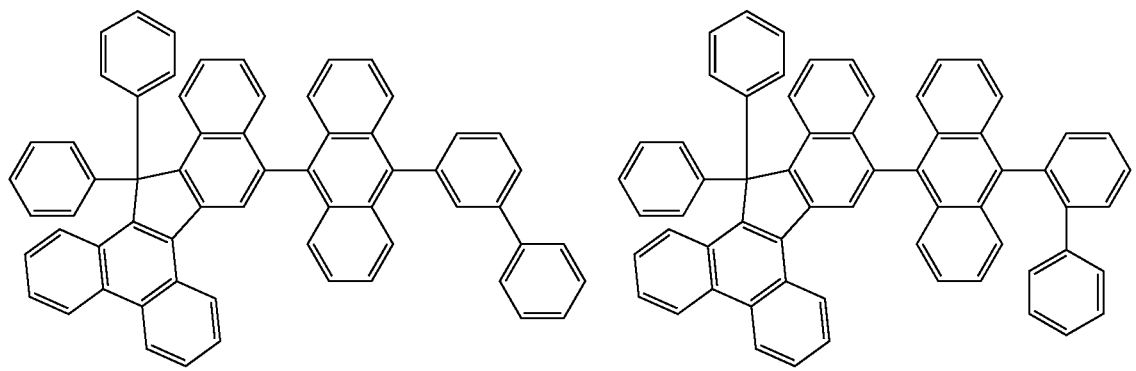
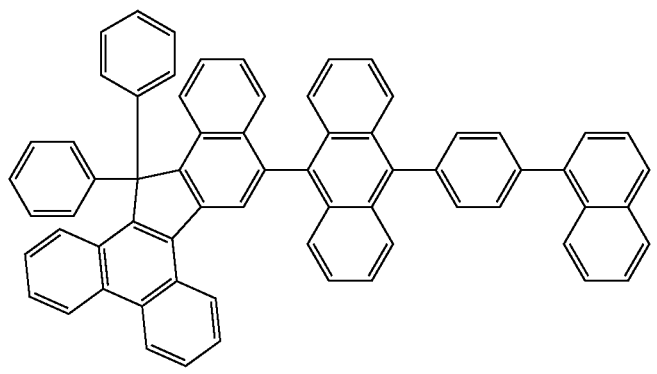
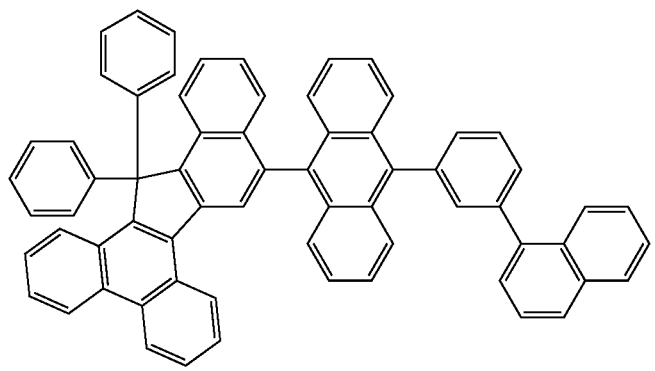

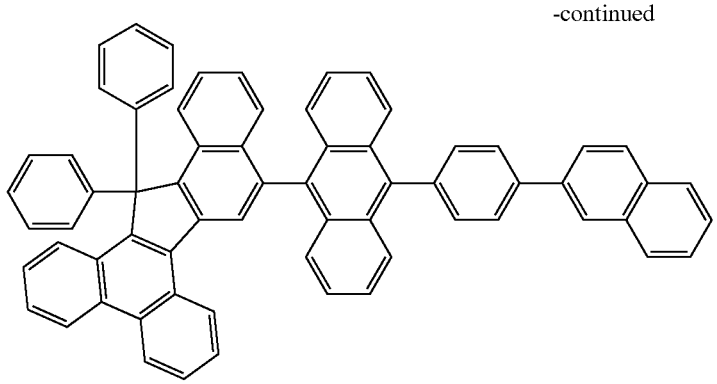
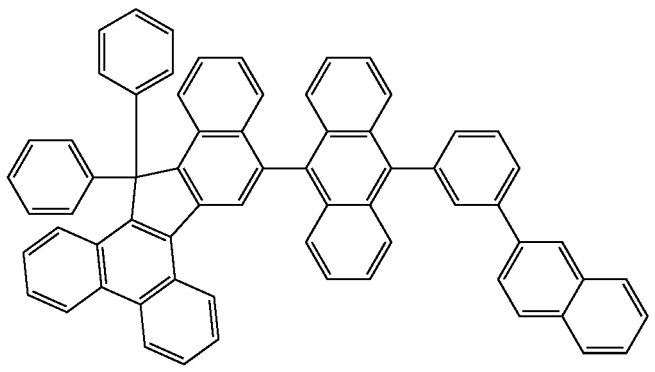
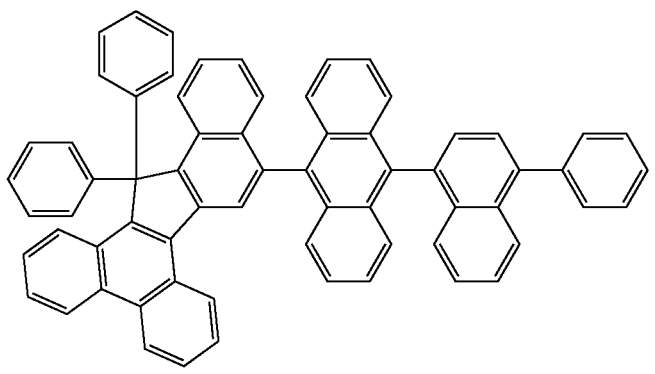
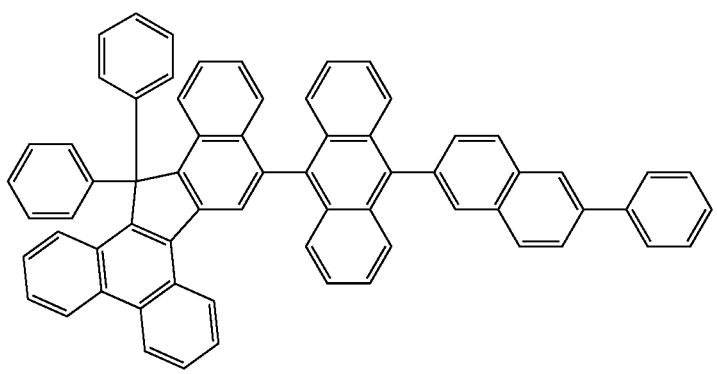

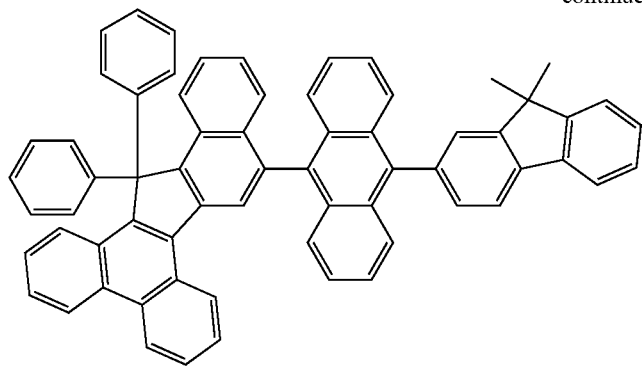
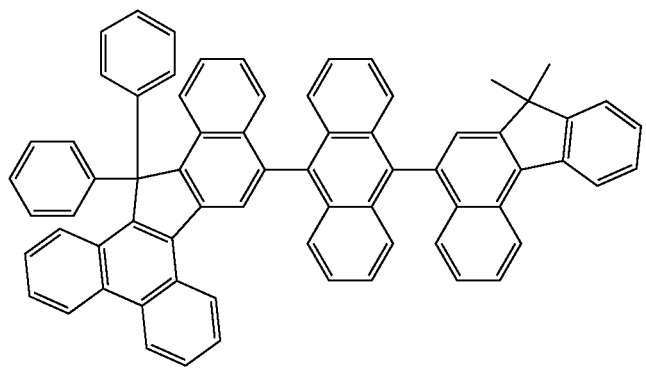
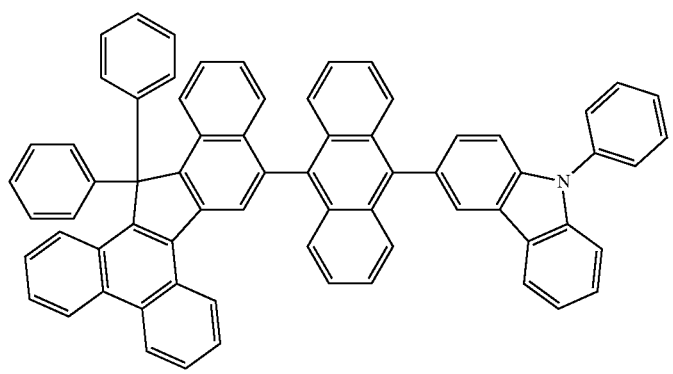
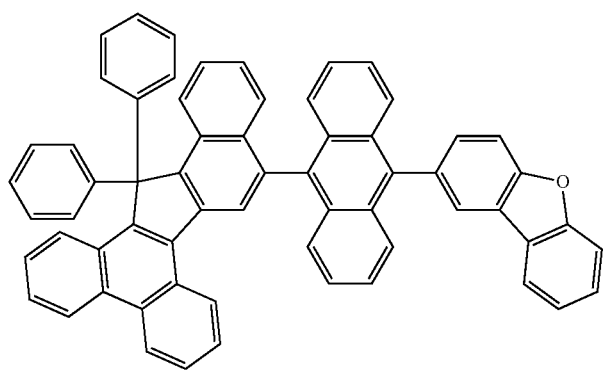

-continued
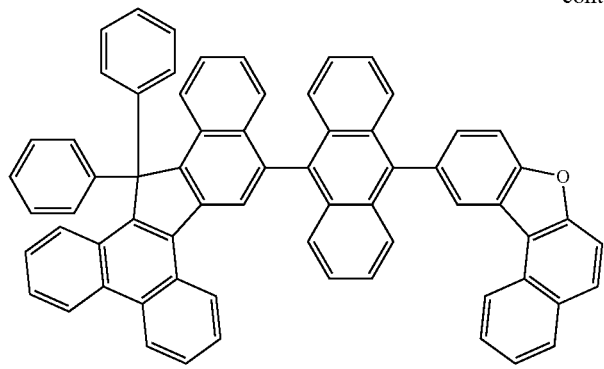
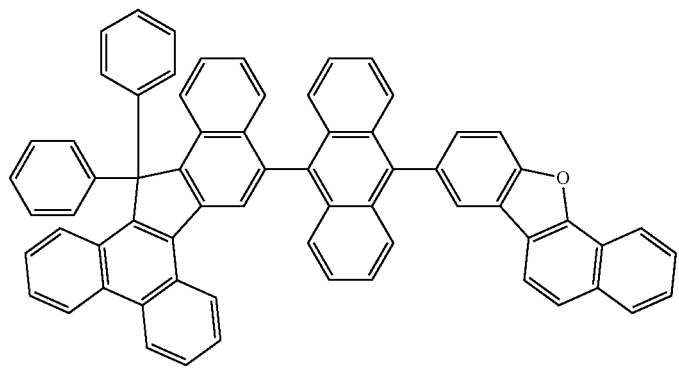
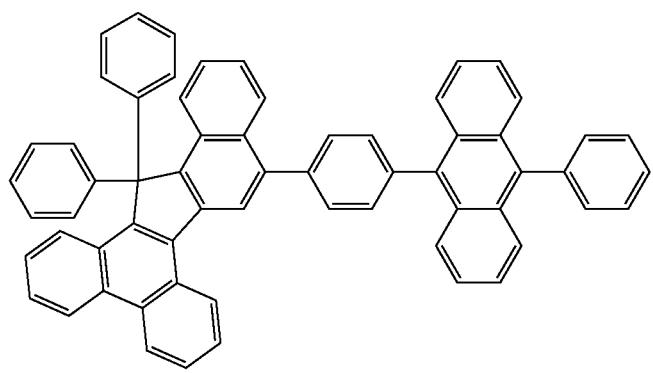
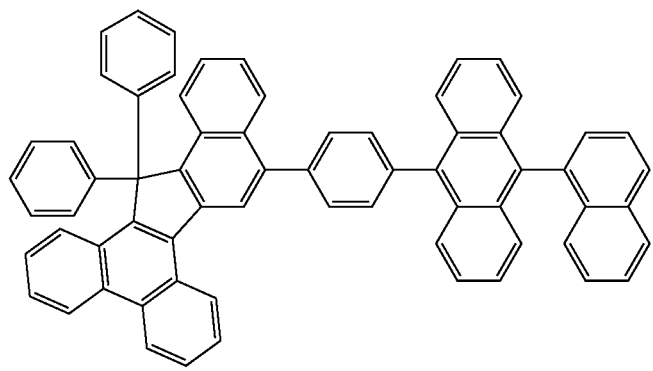

-continued
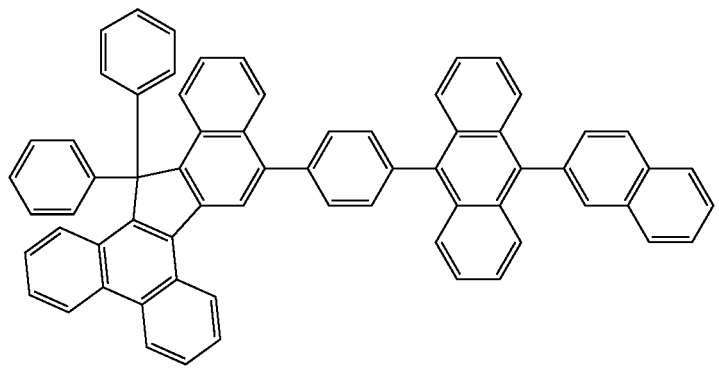
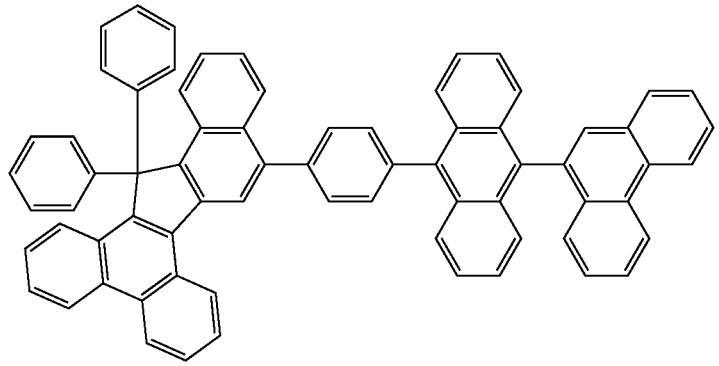
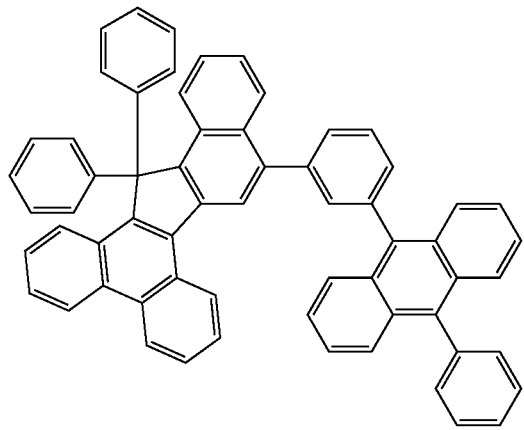
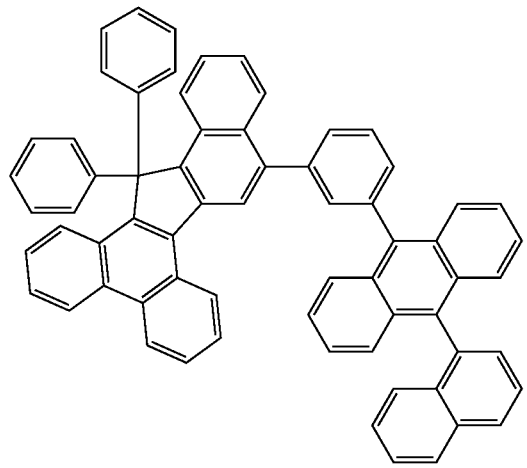
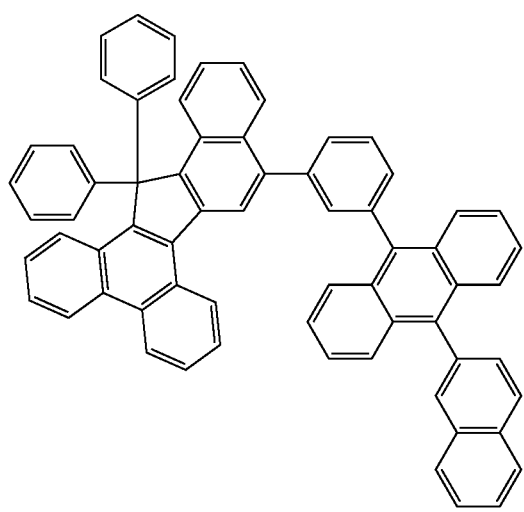
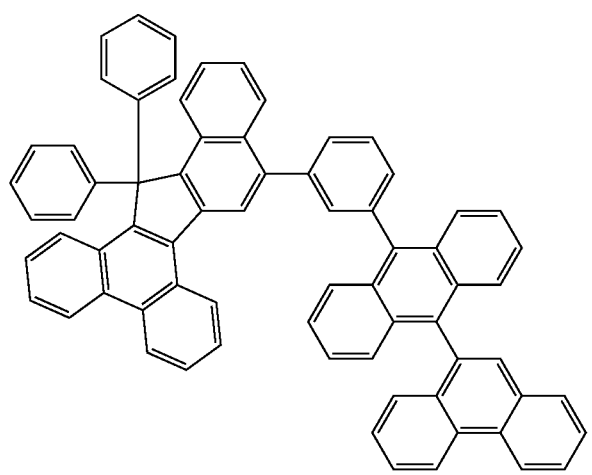

-continued
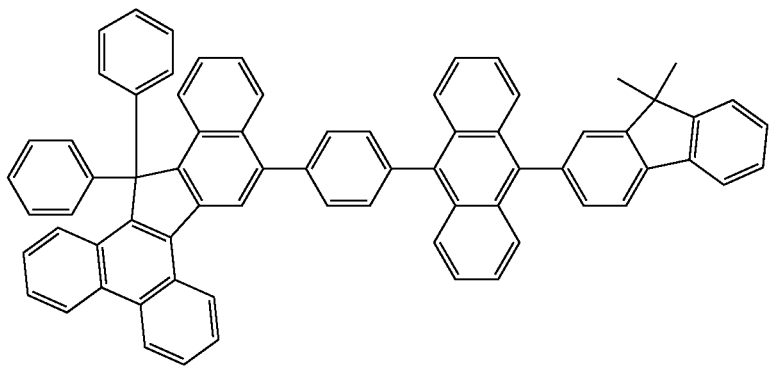
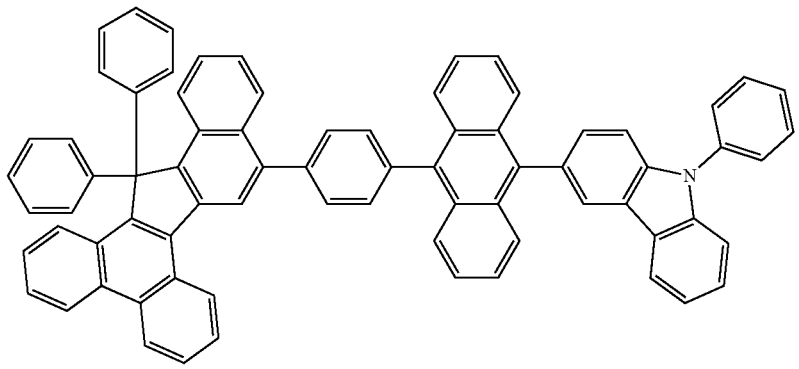
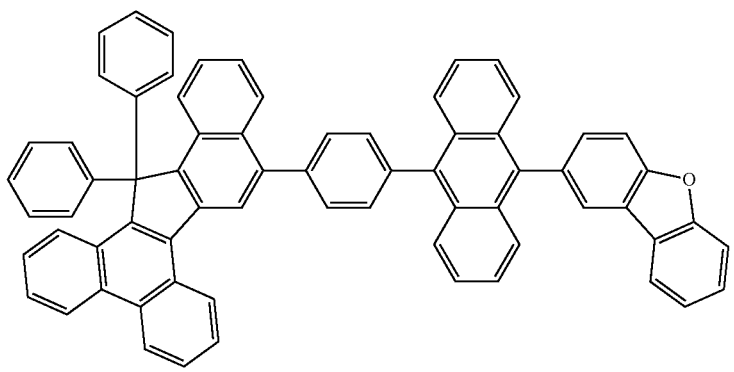
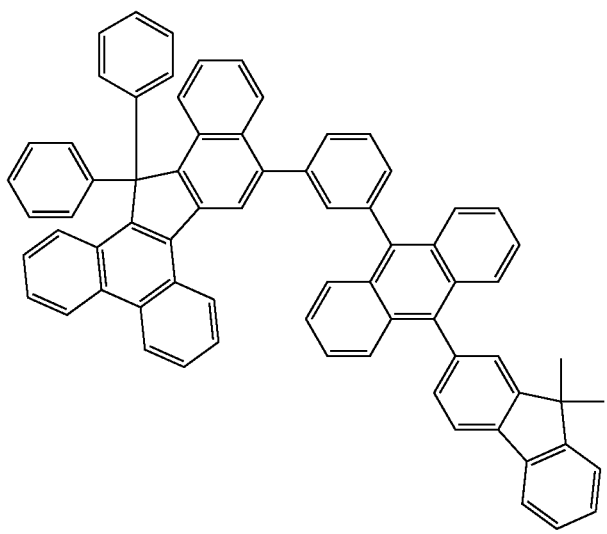

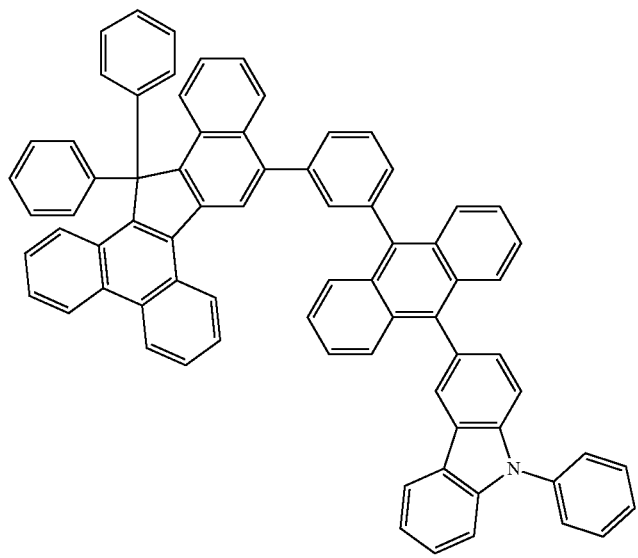
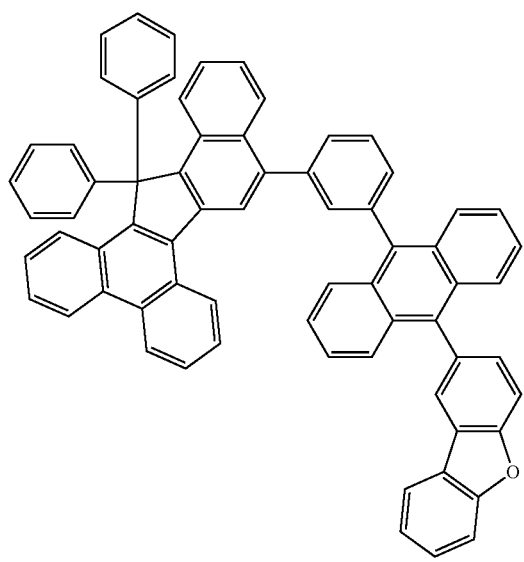
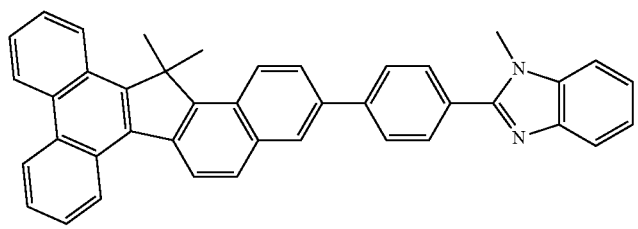
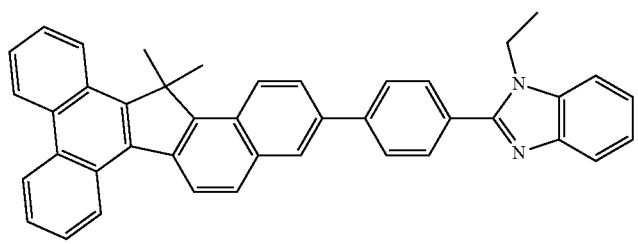

-continued
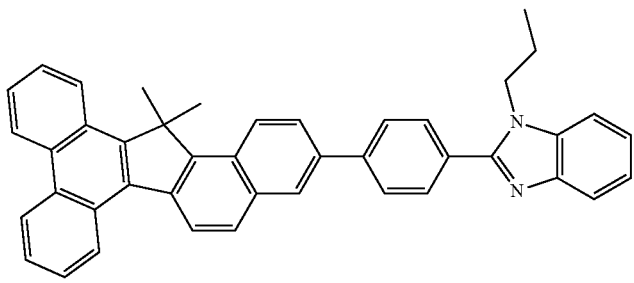
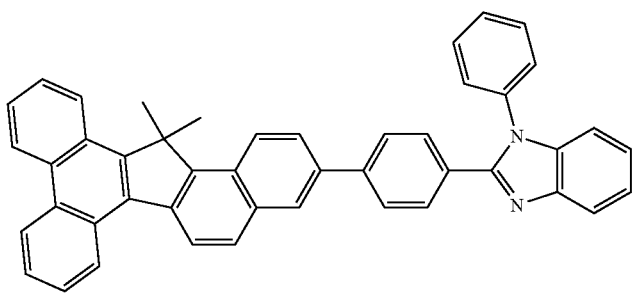
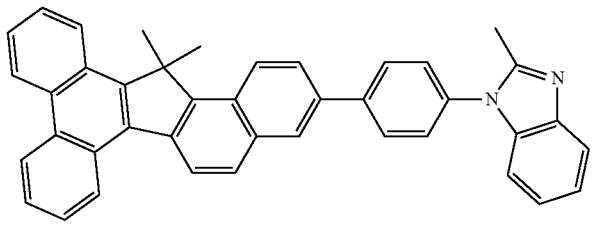
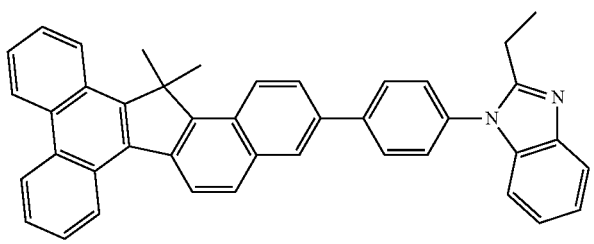
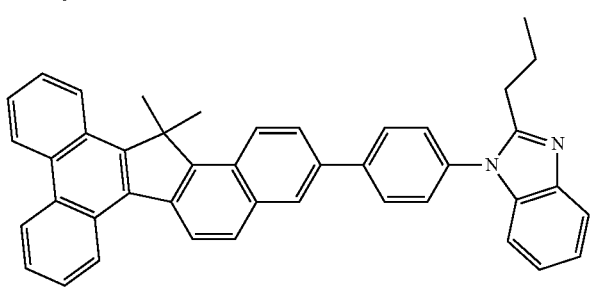
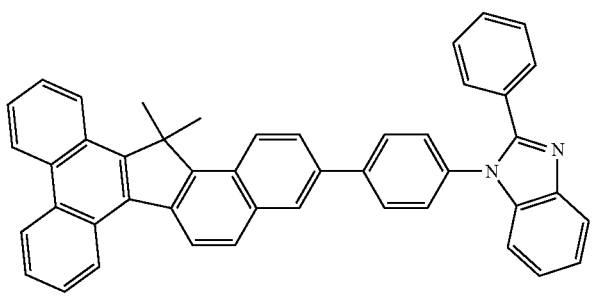

-continued
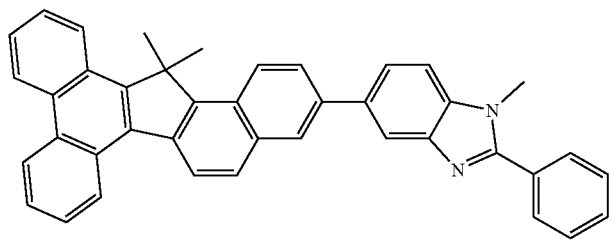
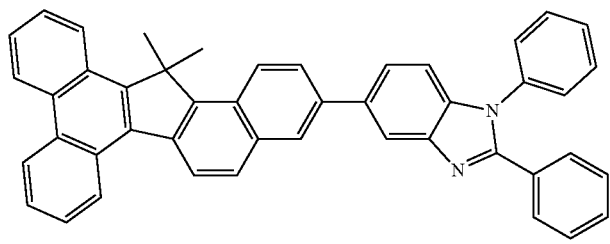
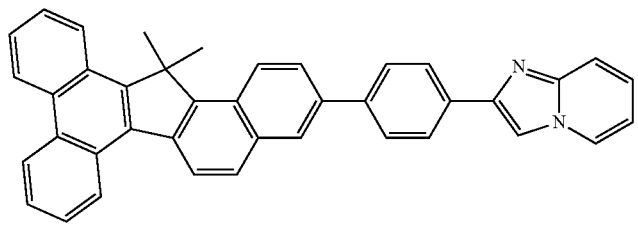
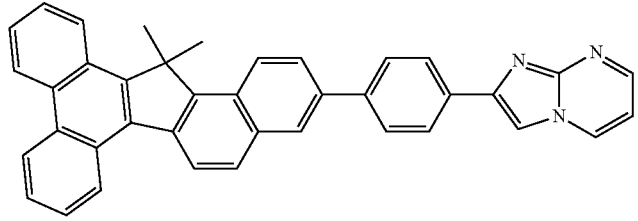
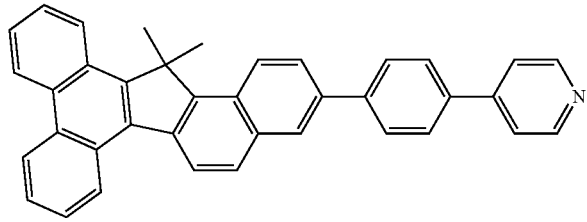
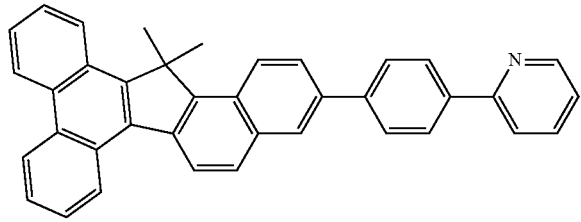
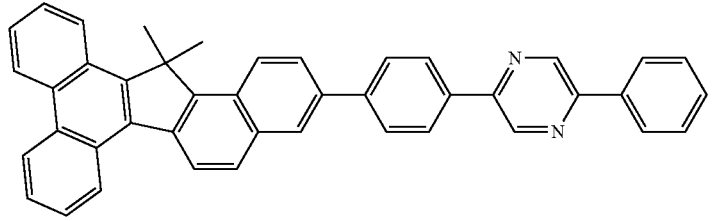

-continued
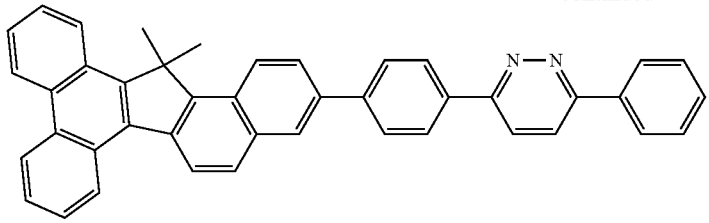
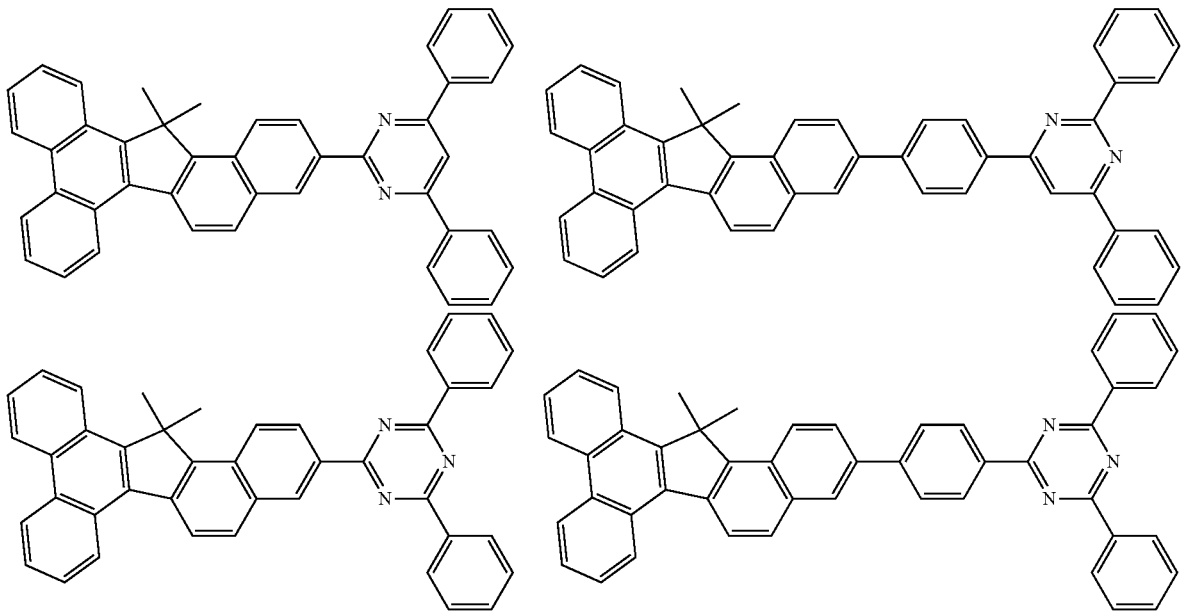
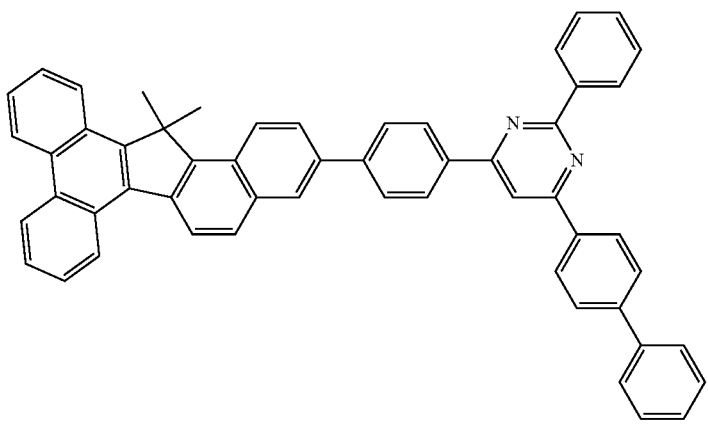
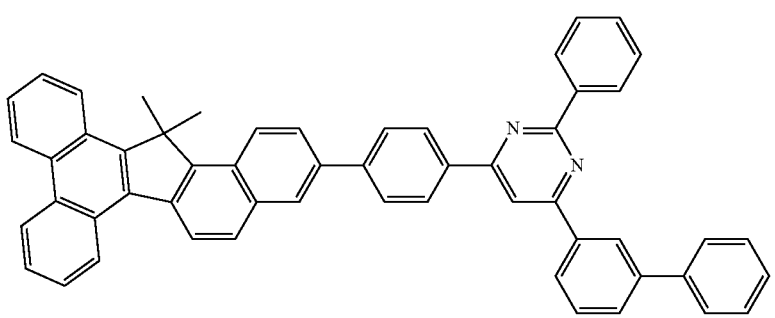

-continued
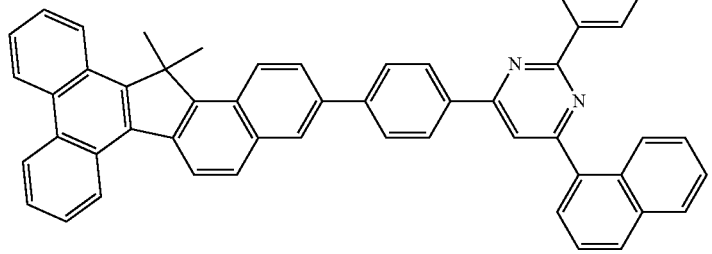
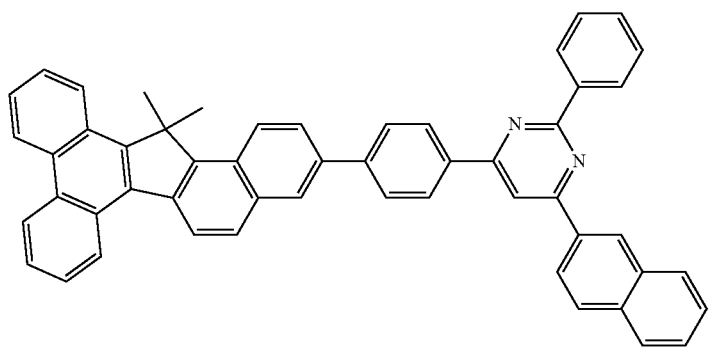
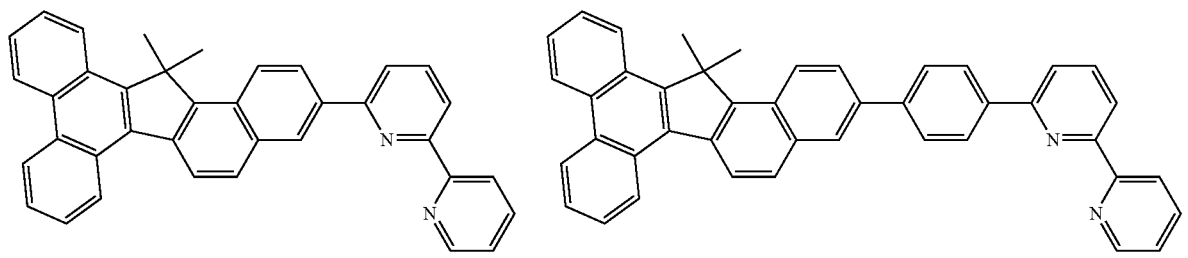
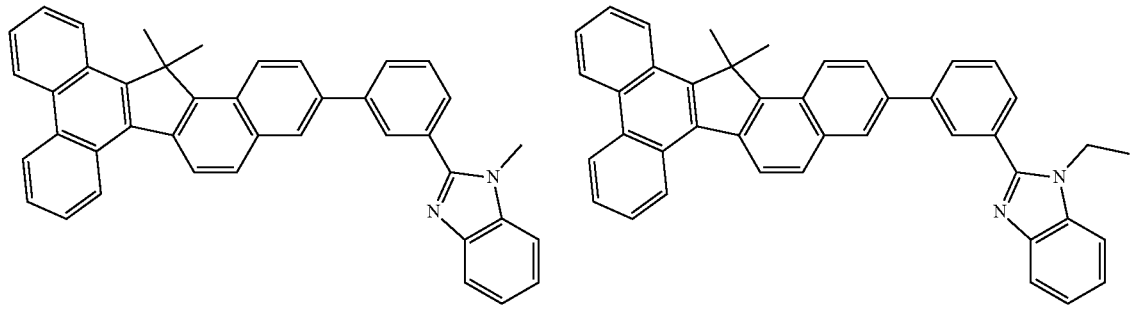

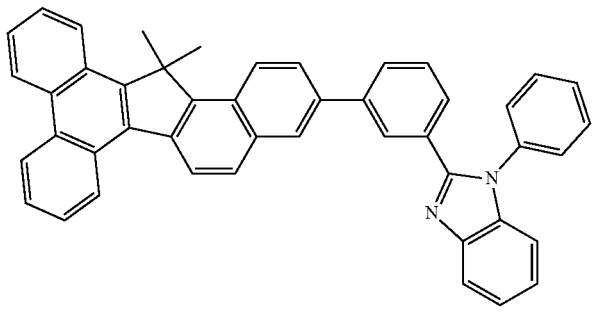
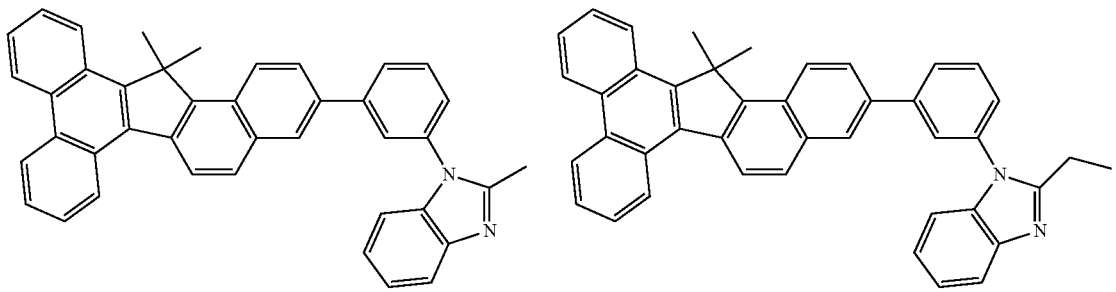
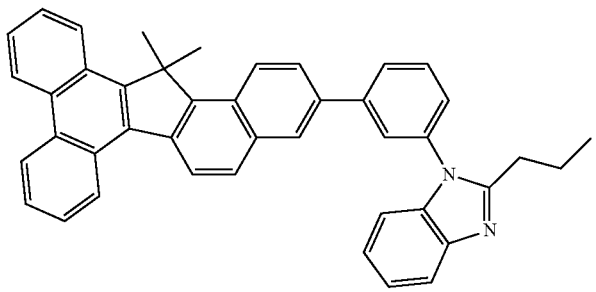
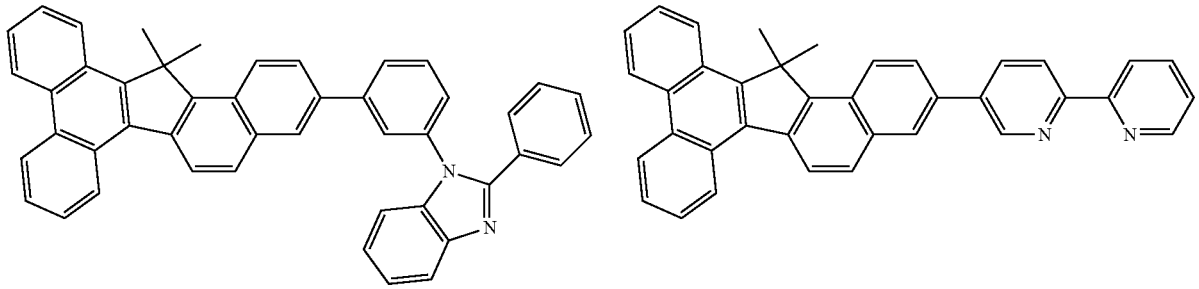

-continued

599
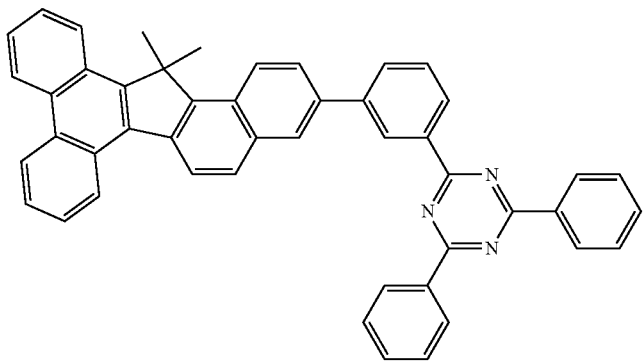
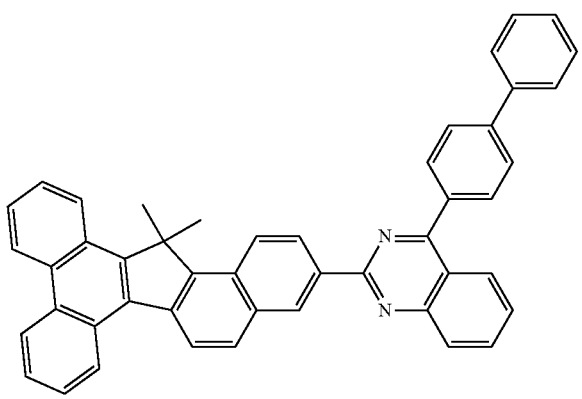
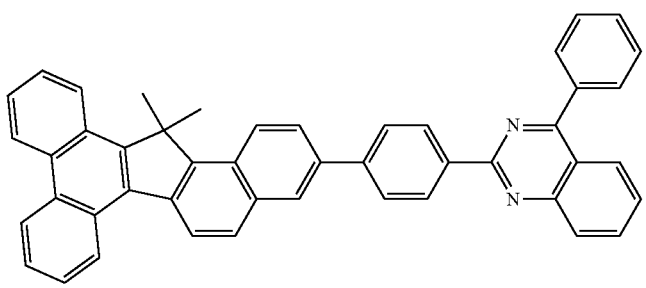
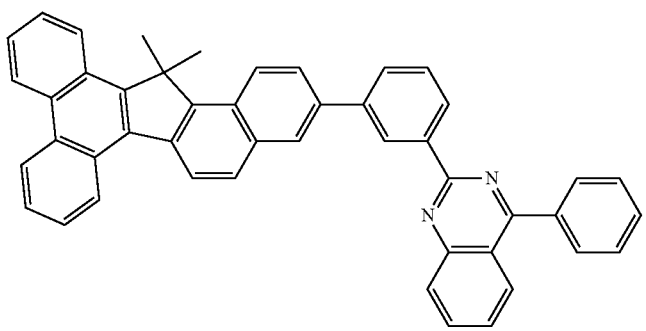
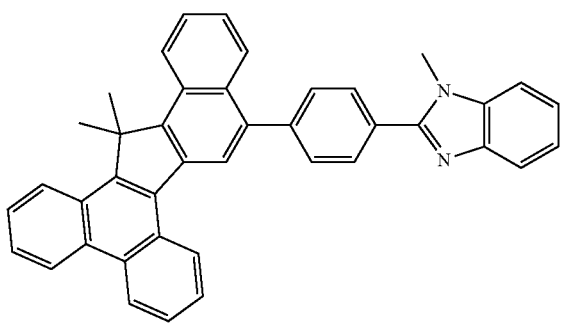
600
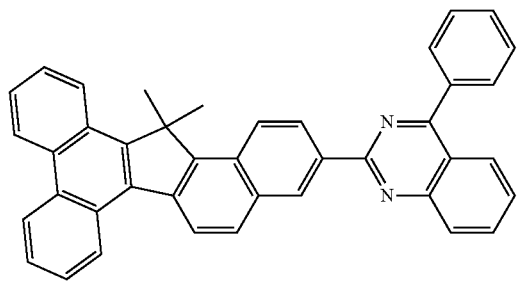
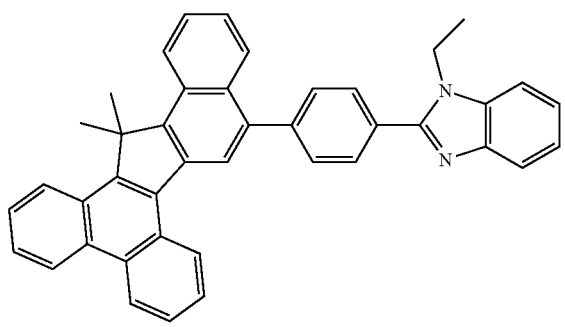

-continued
| 601 | 602 |
|---|---|
| 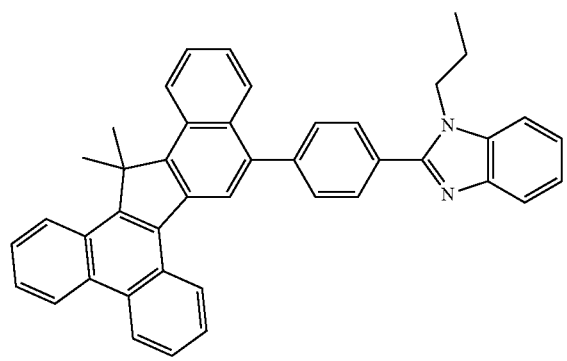 | 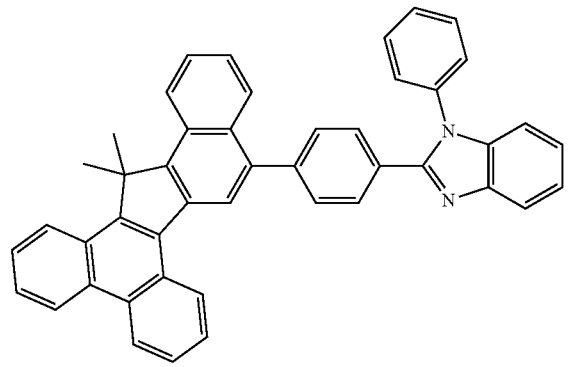 |
| 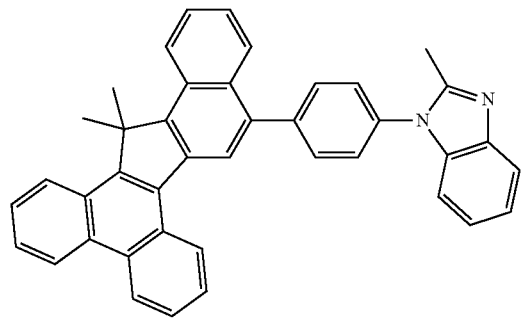 | 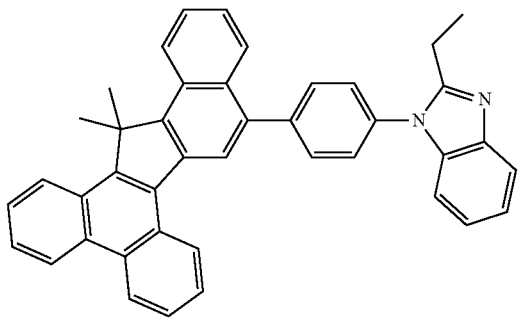 |
| 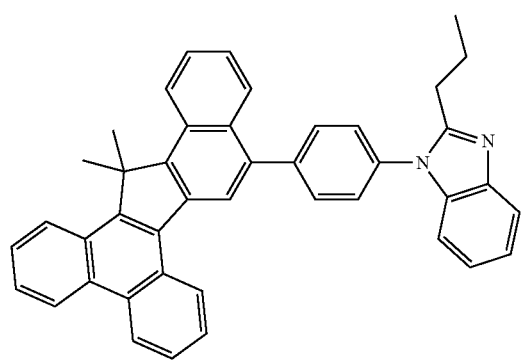 | 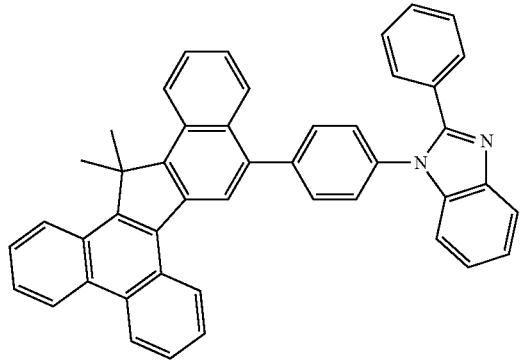 |
| 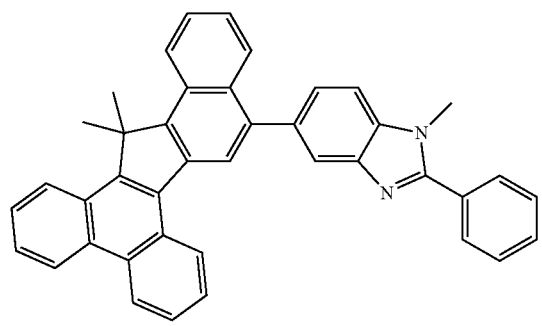 | 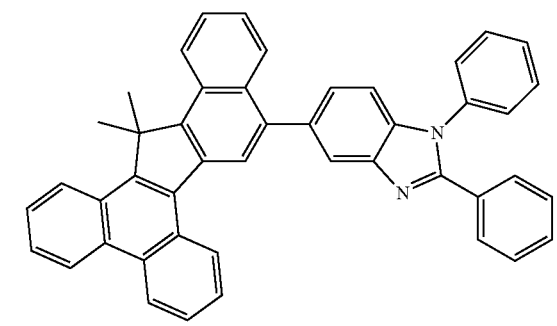 |
| 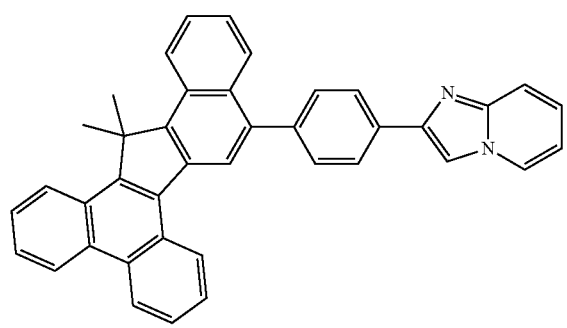 | 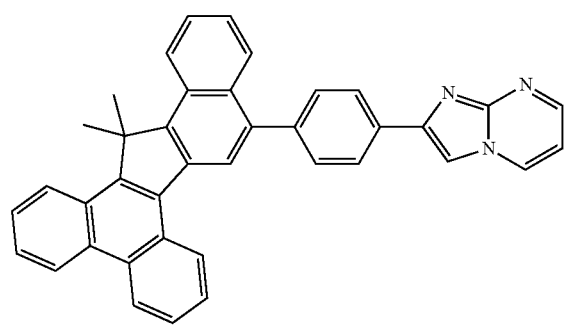 |

-continued
| 603 | 604 |
|---|---|
| 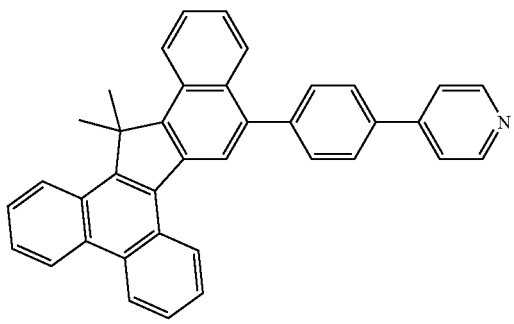 | 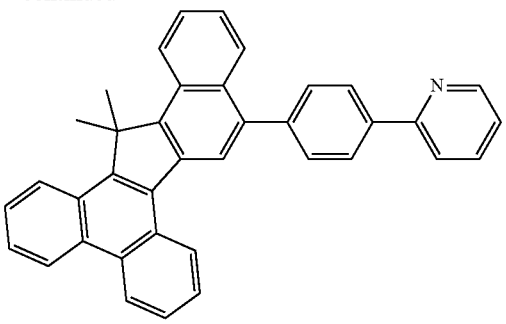 |
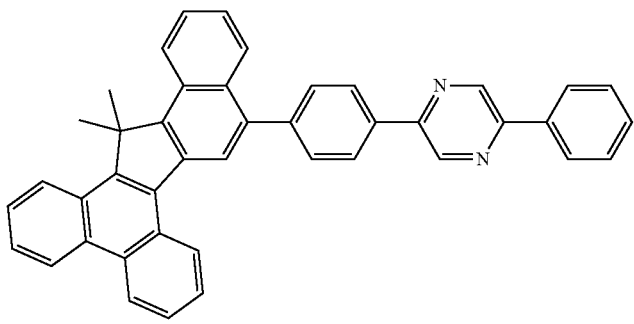
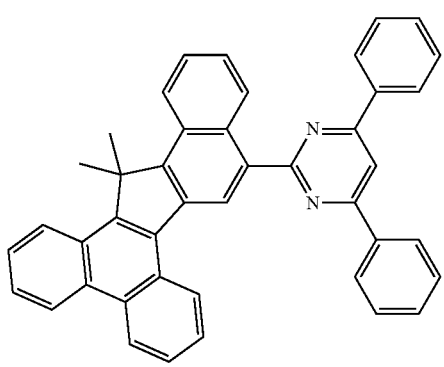
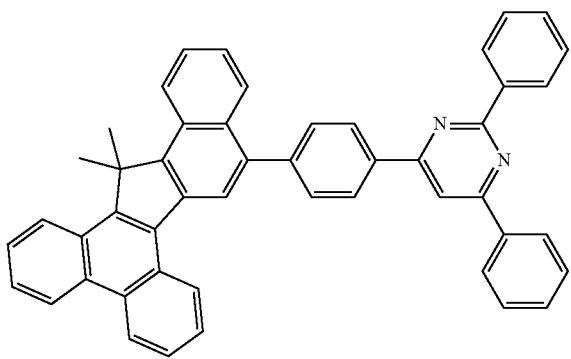
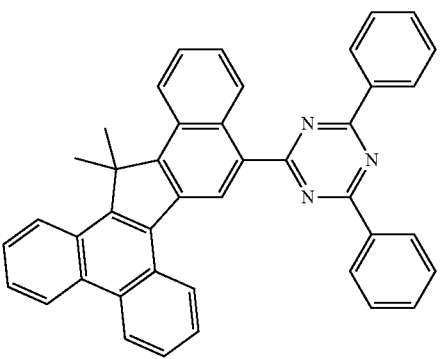
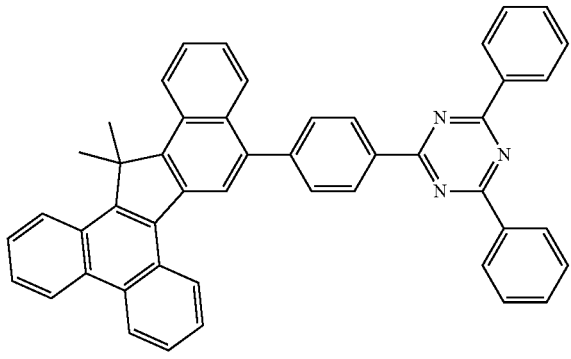

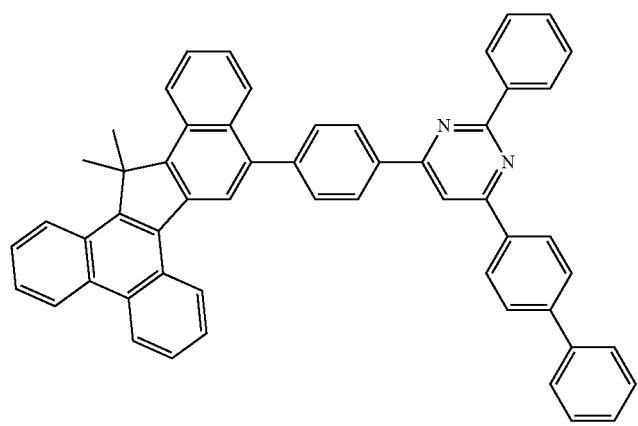
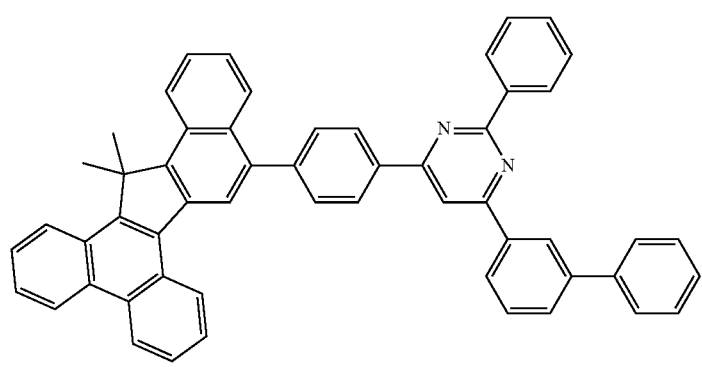
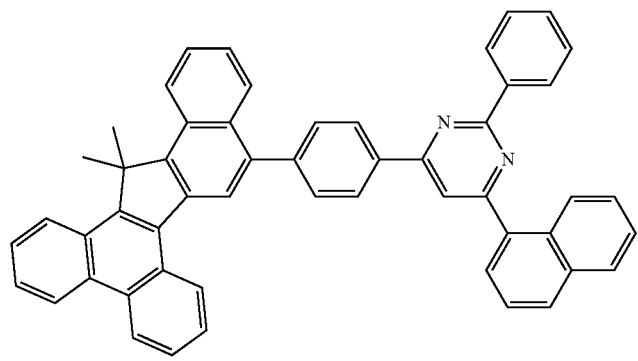
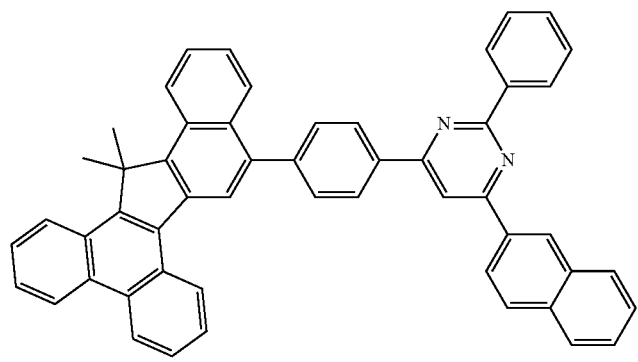

607
608
-continued
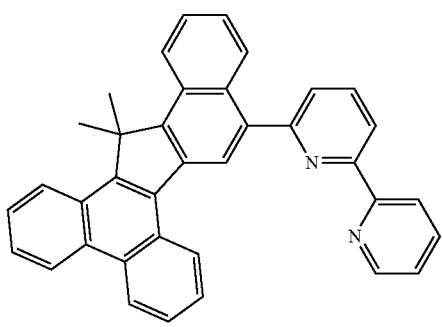
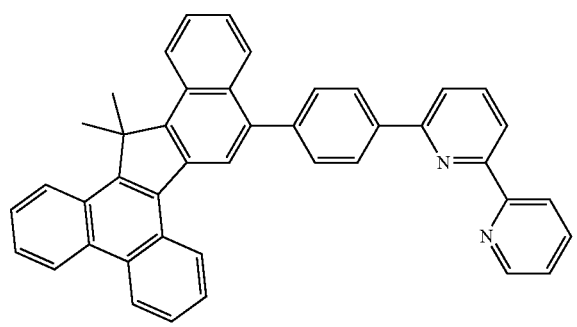
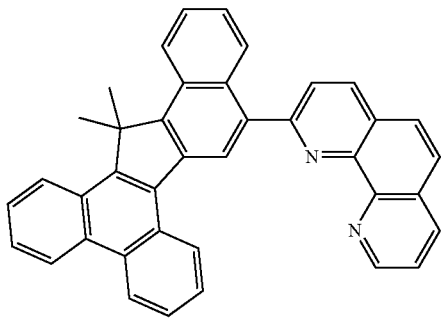
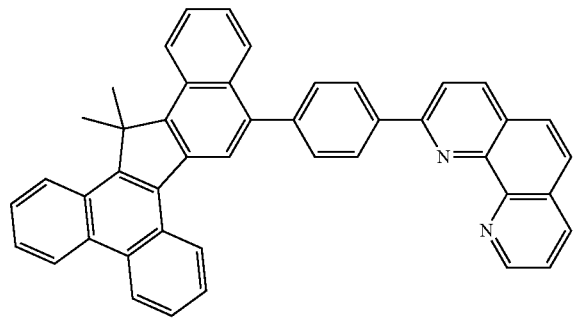
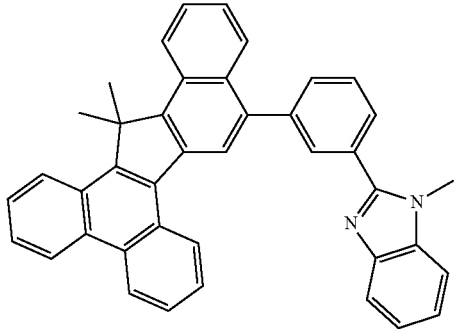
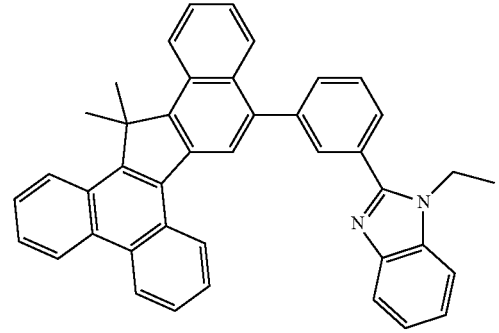
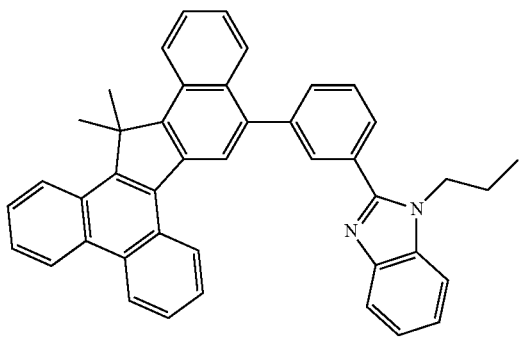
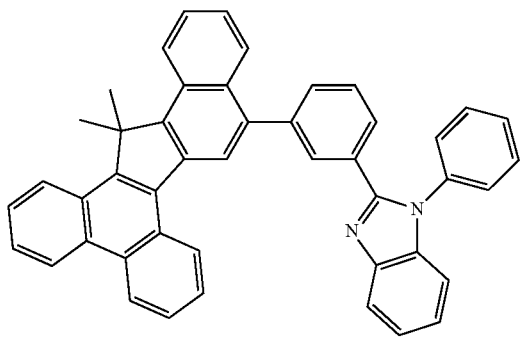
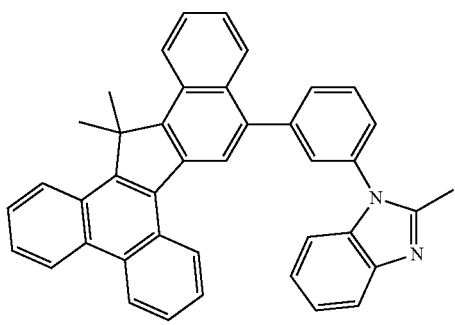
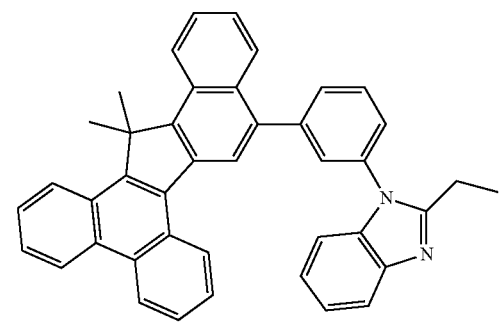

-continued
609  610
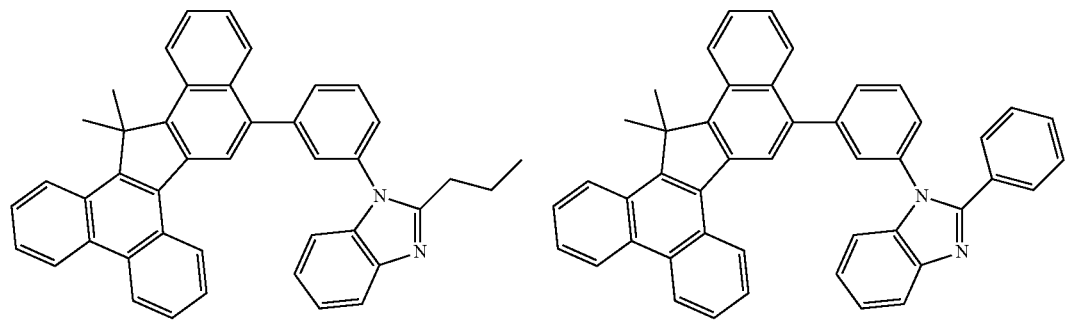
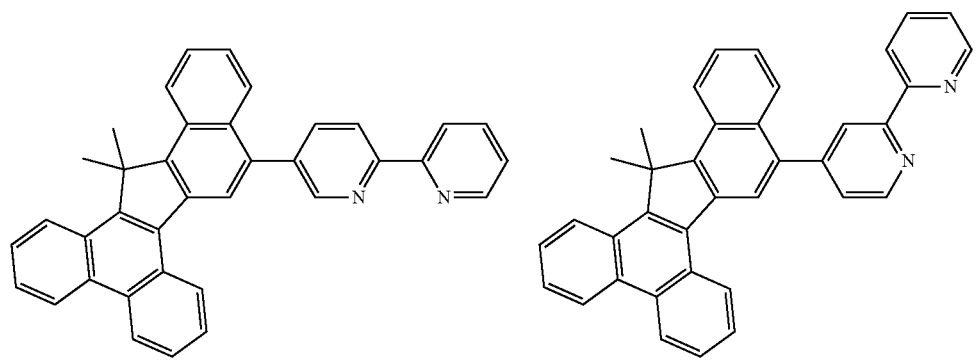
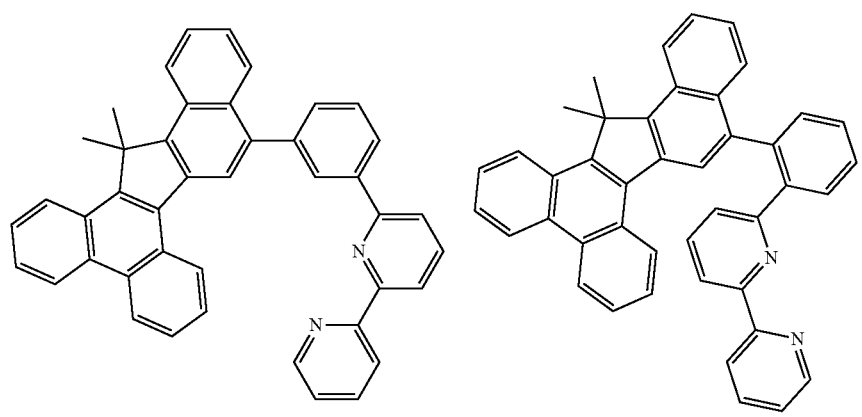
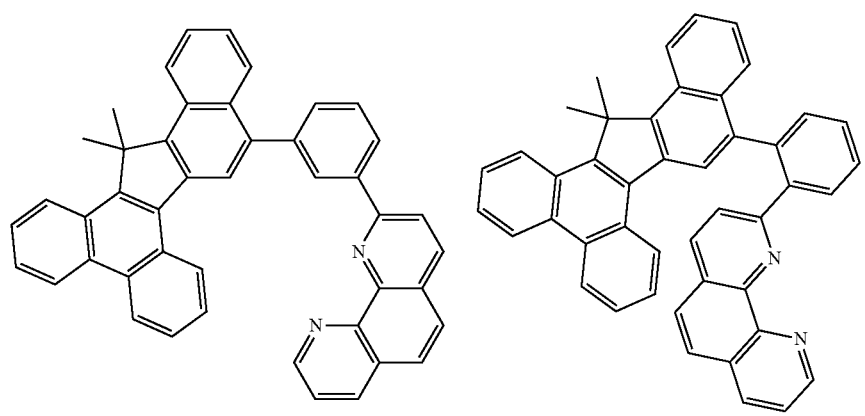

-continued
611
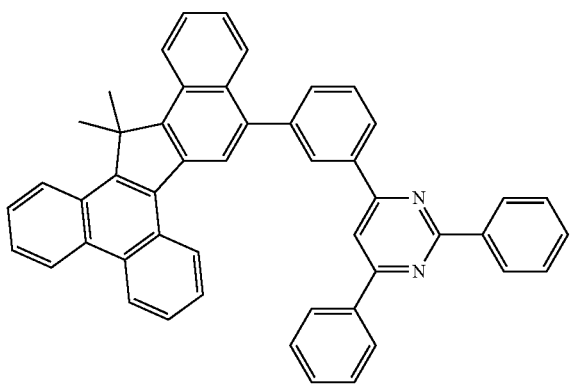
612
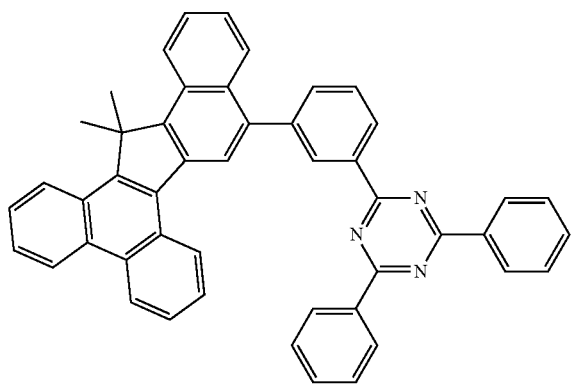
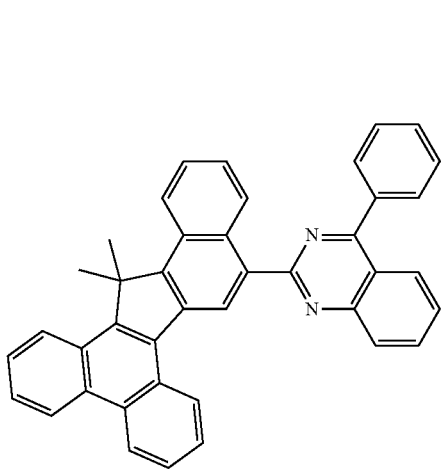
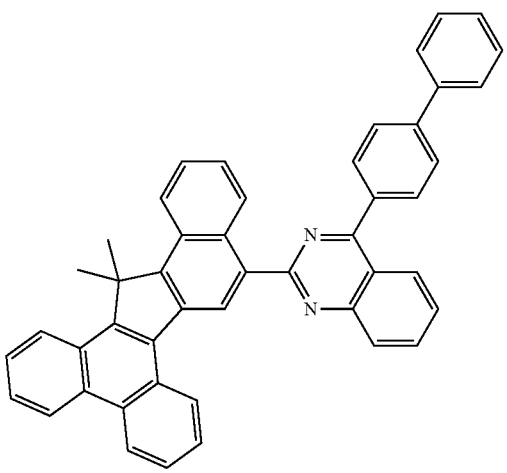
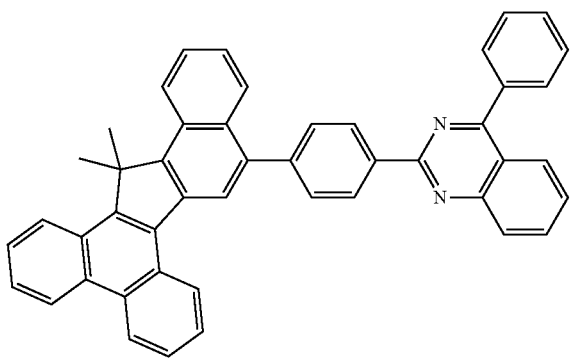
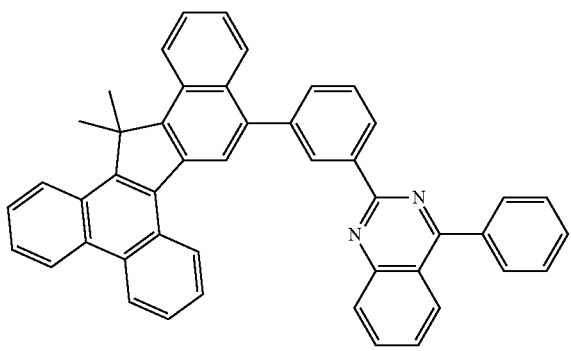

-continued
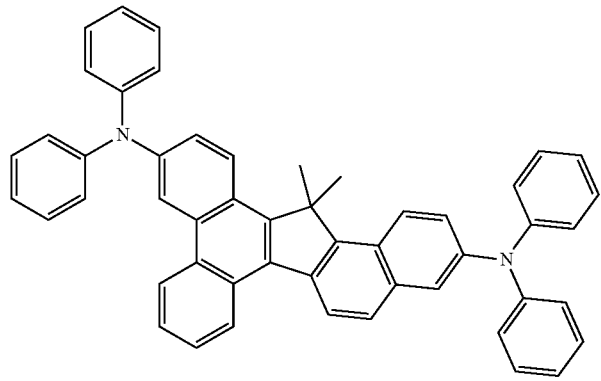
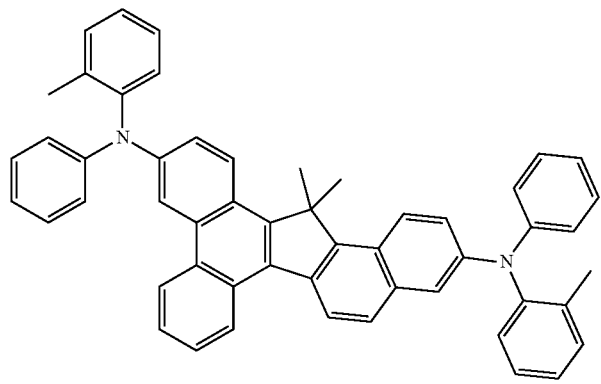
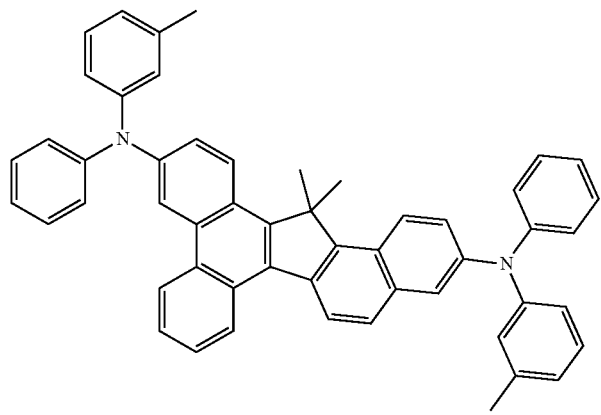
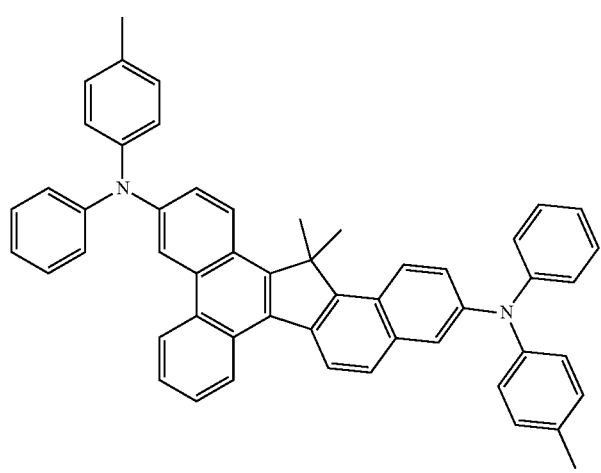

-continued
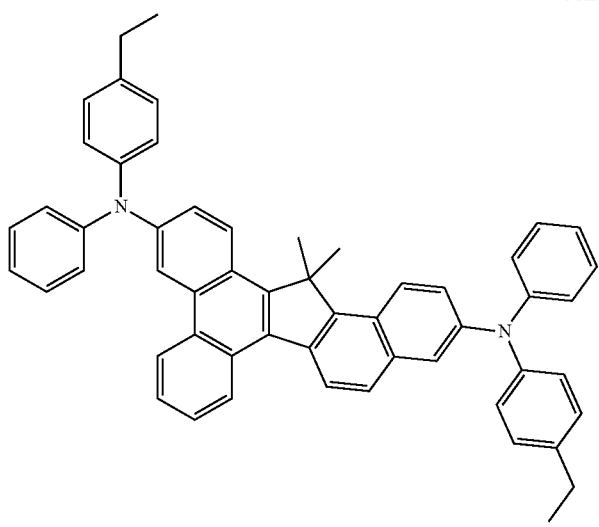
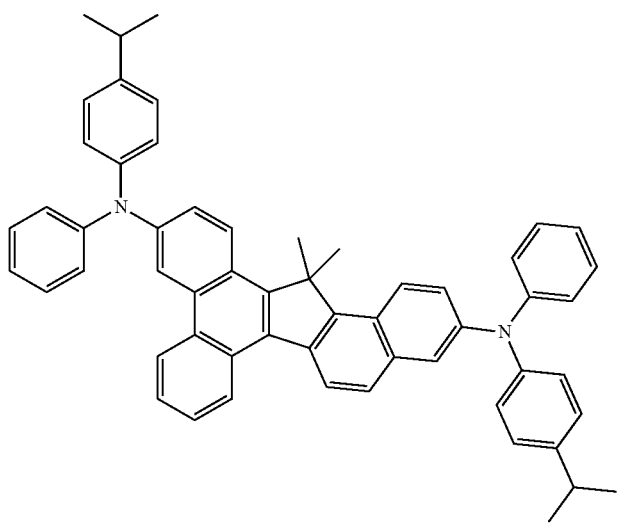
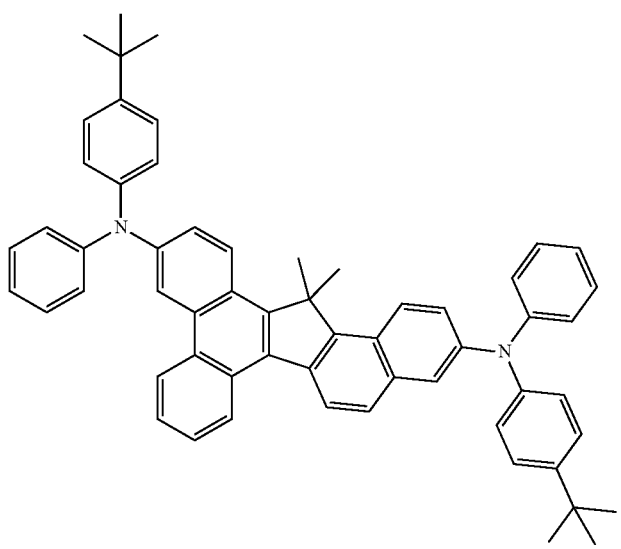

-continued
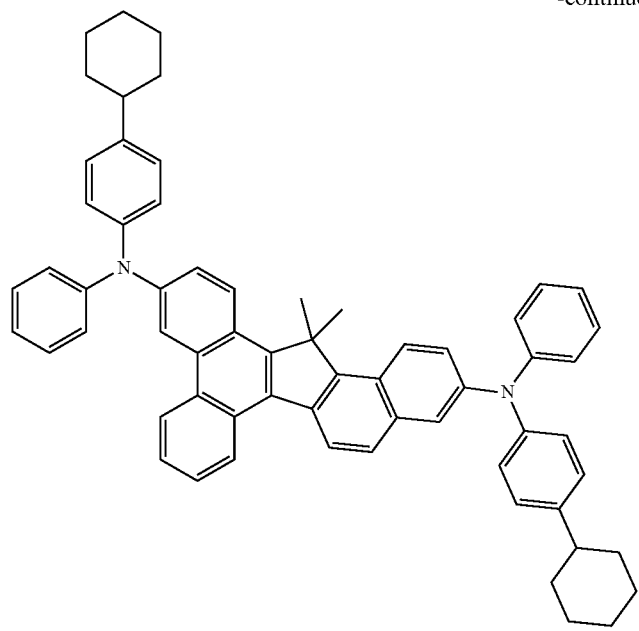
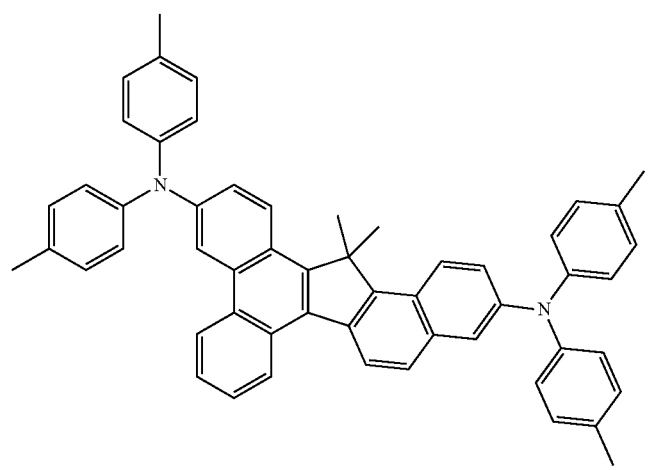
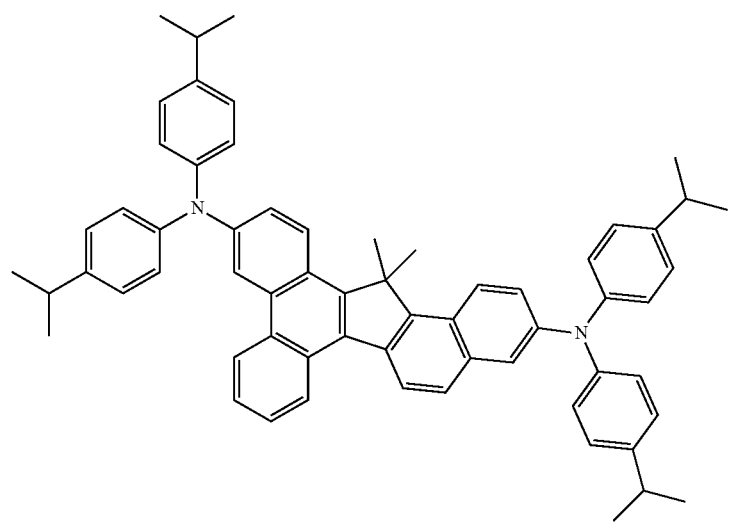

-continued
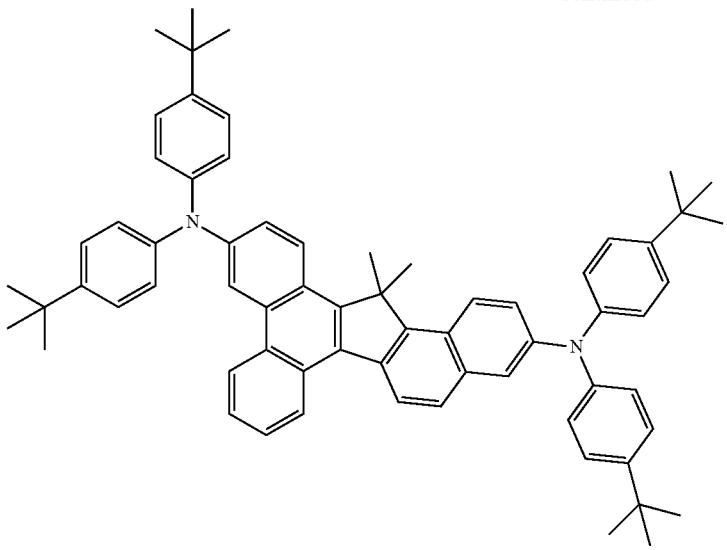
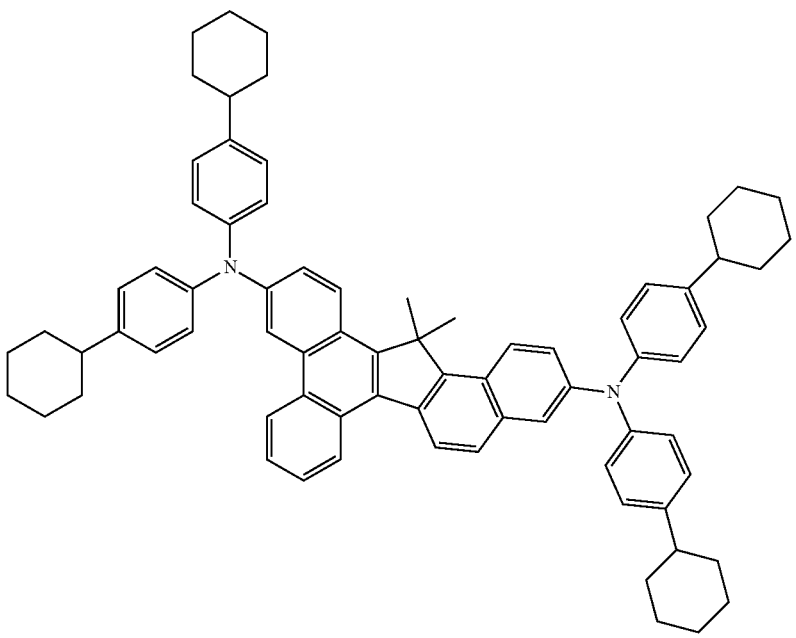
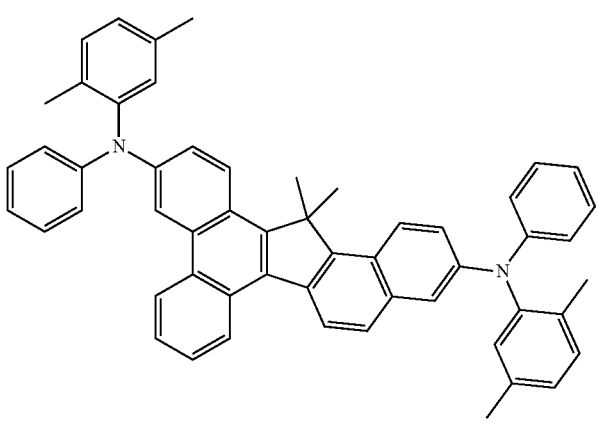

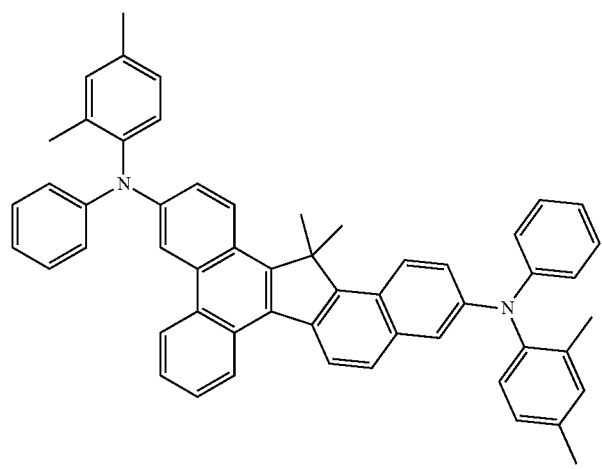
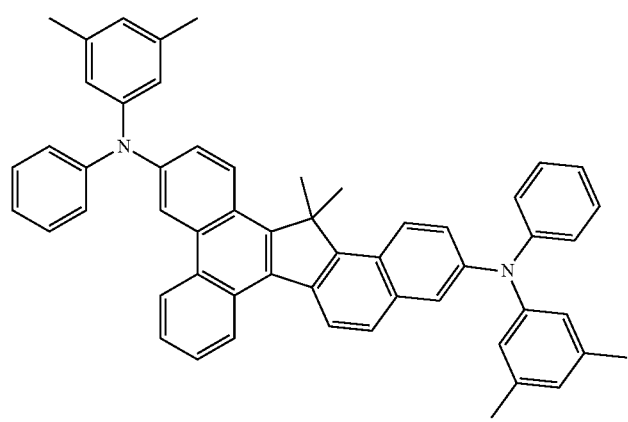
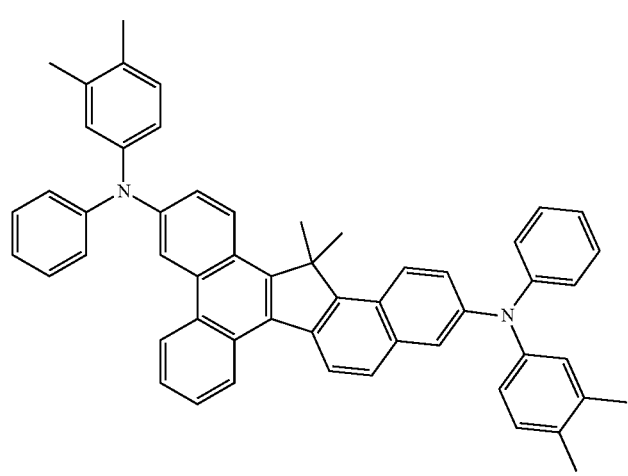

-continued
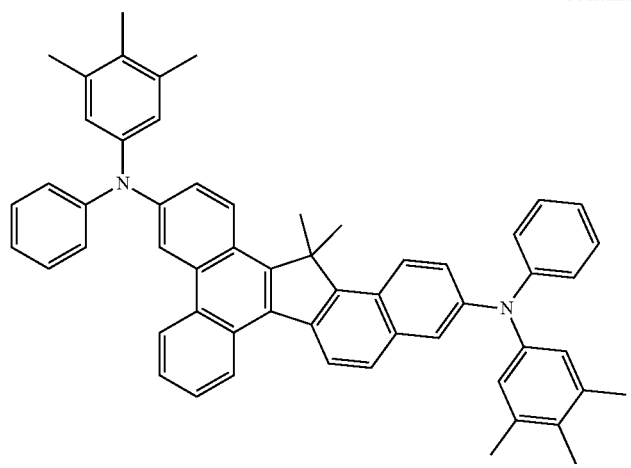
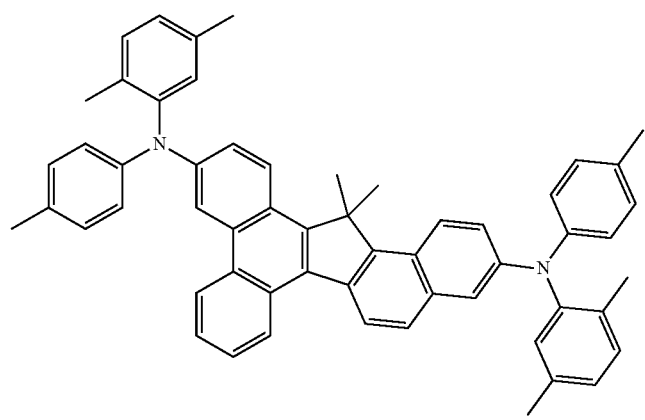
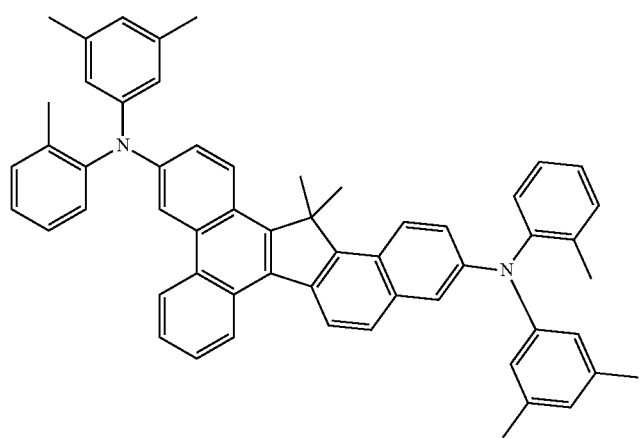

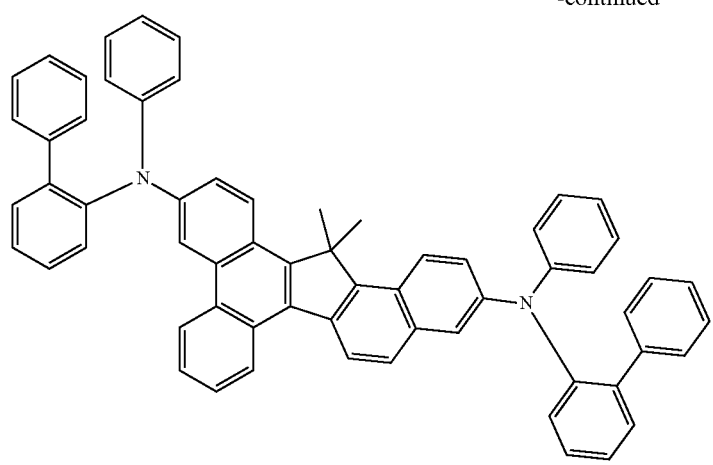
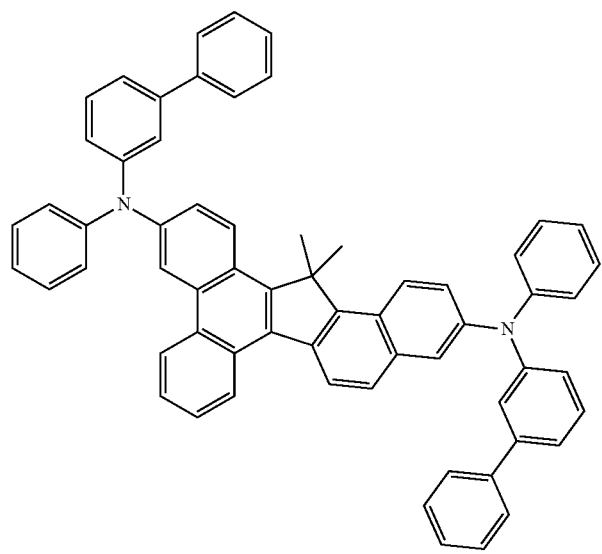
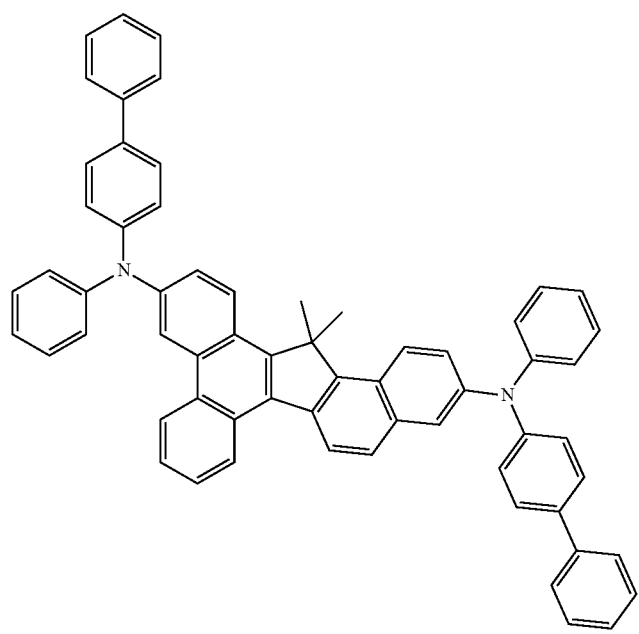

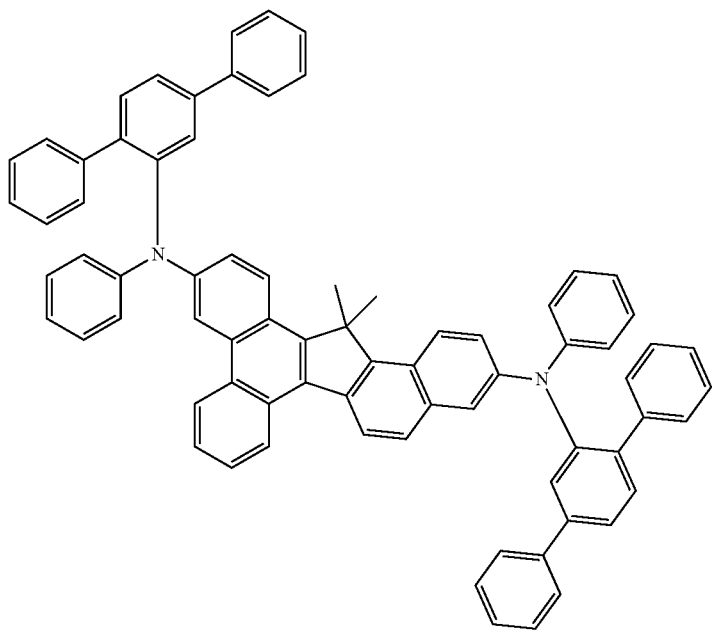
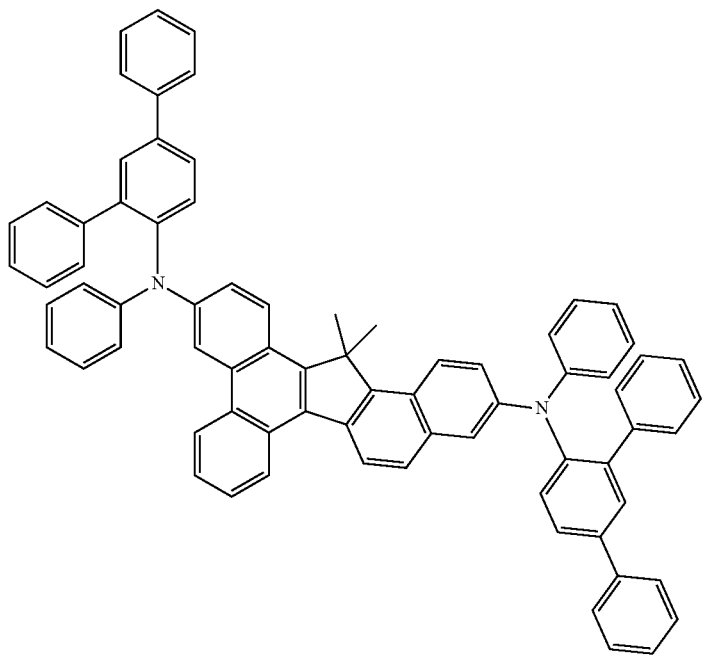
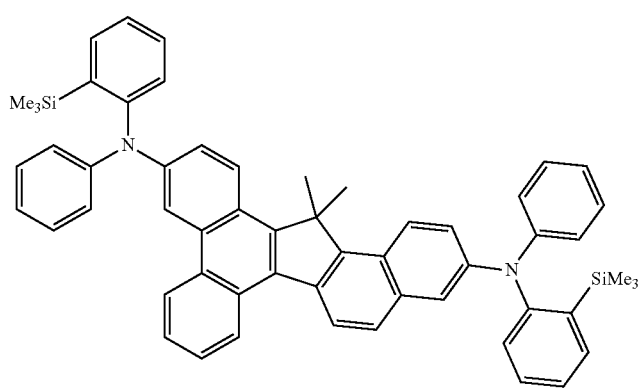

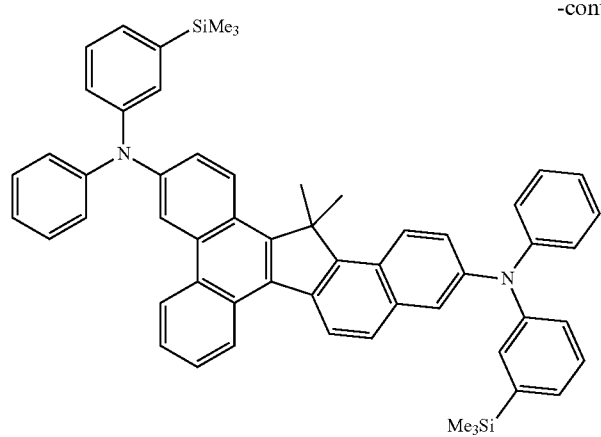
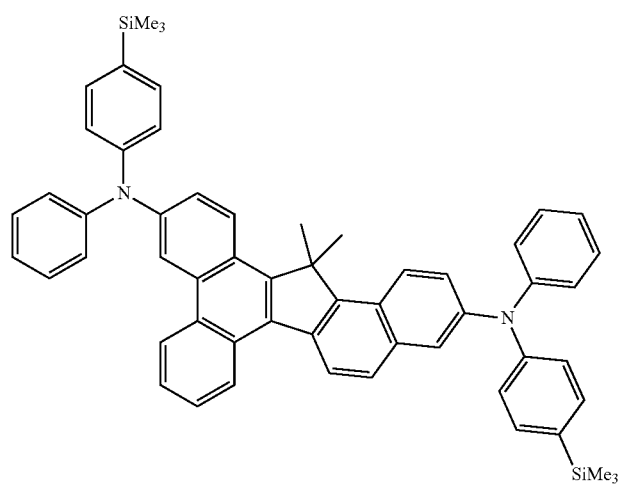
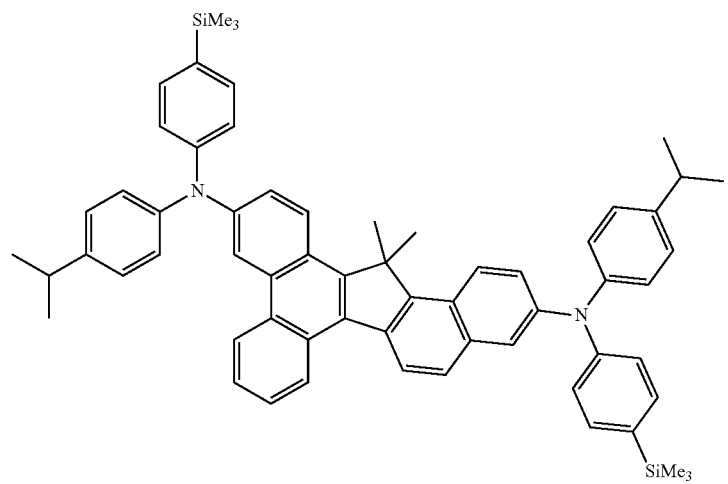

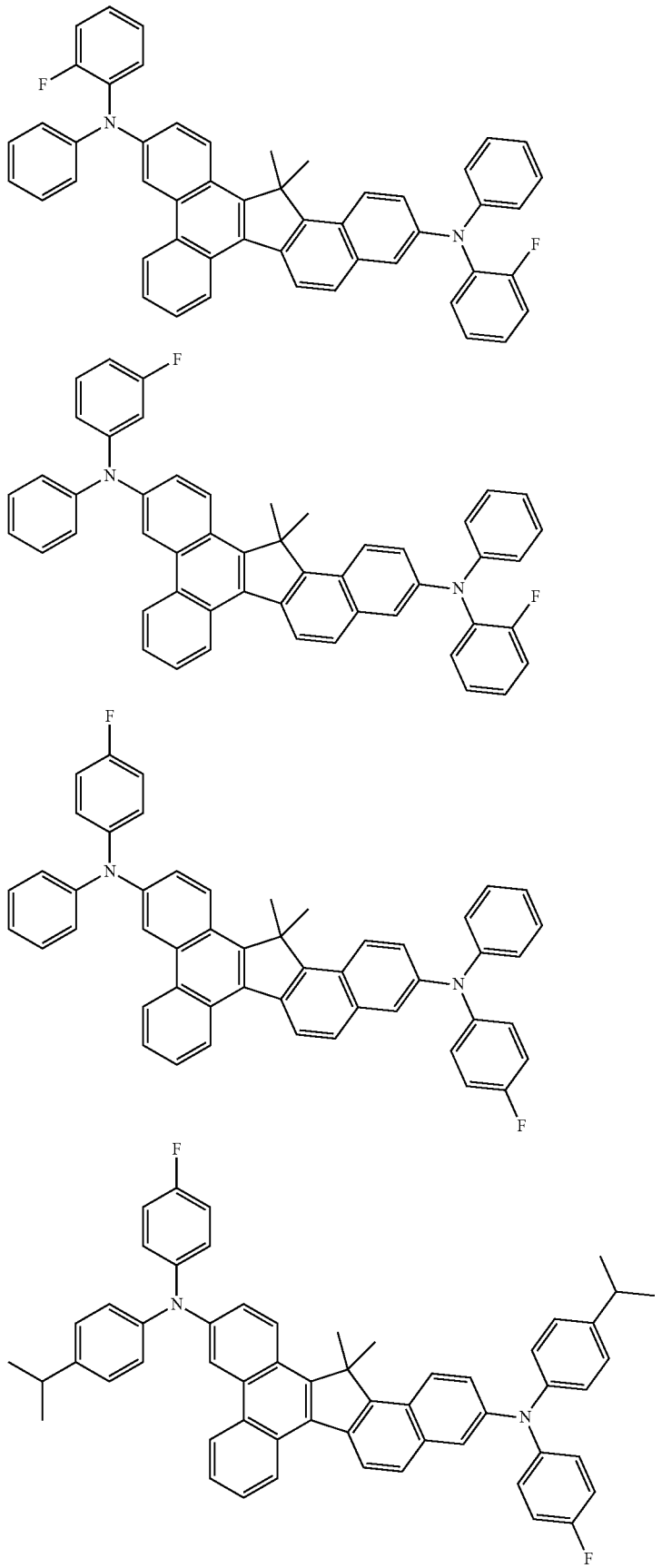

-continued
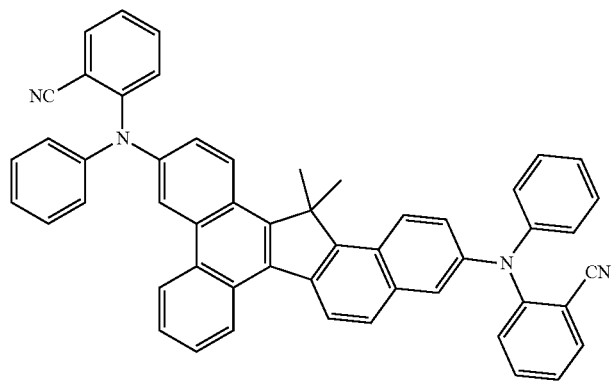
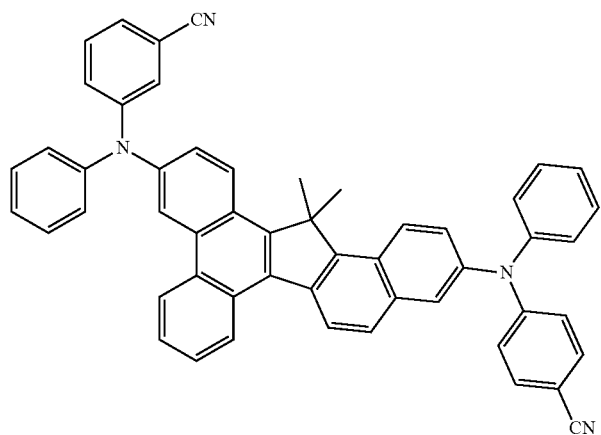
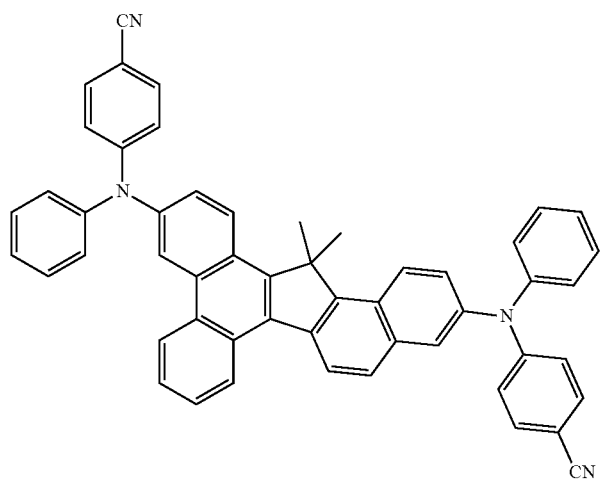

-continued
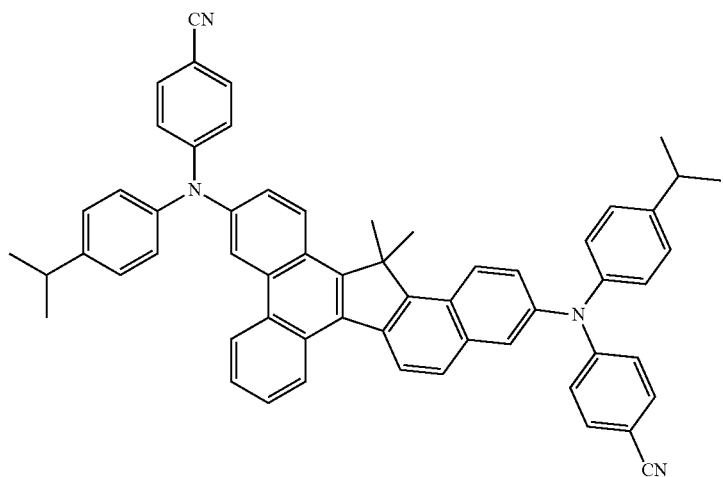
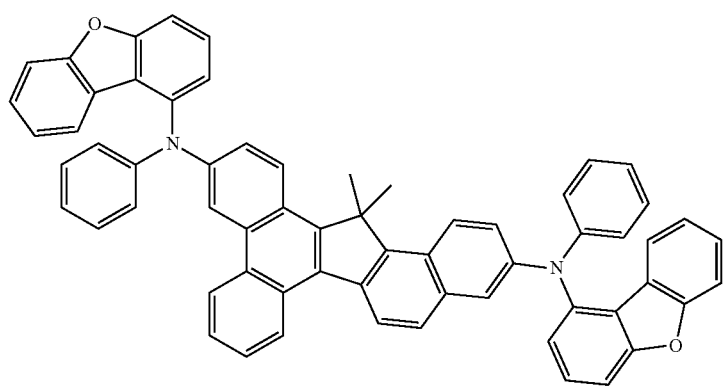
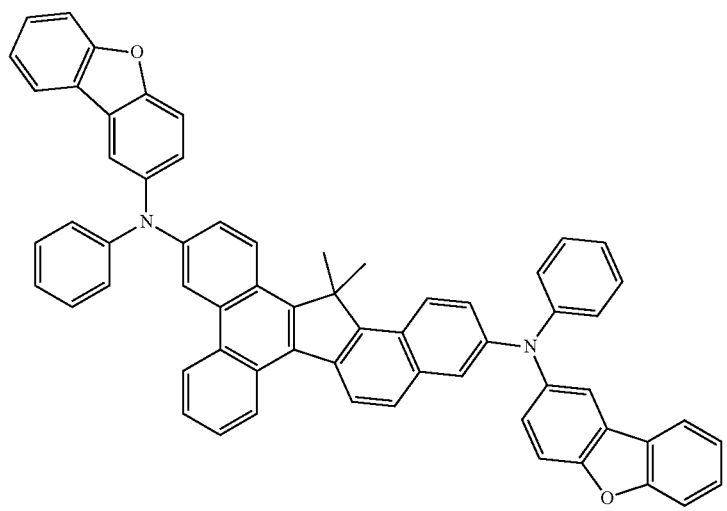

-continued
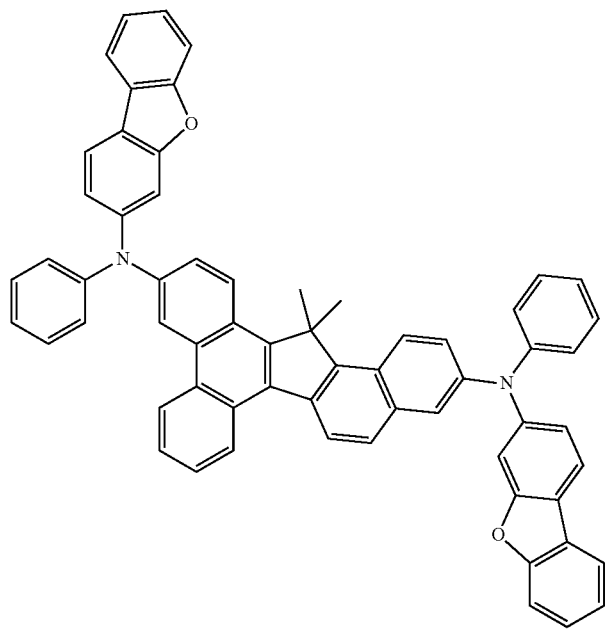
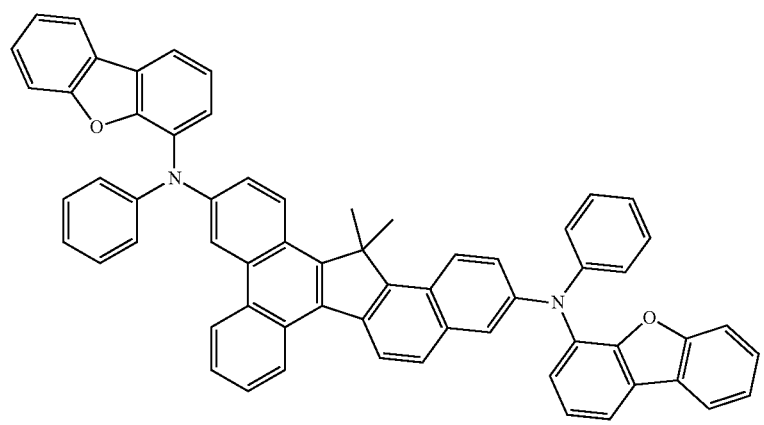
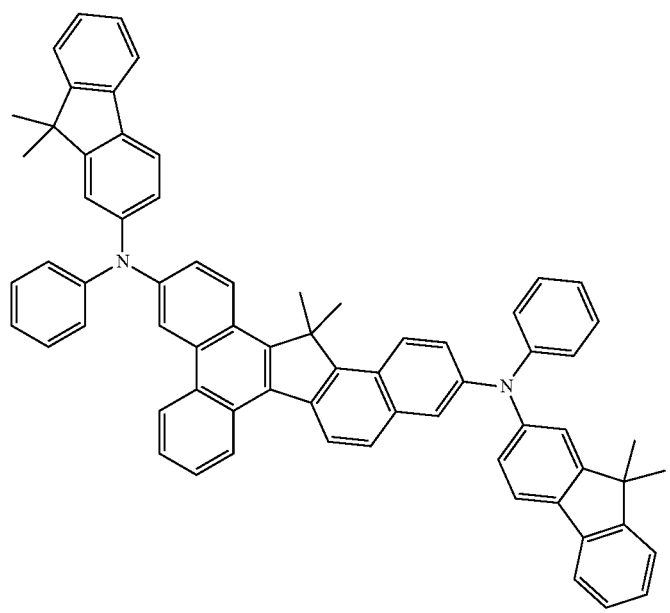

-continued
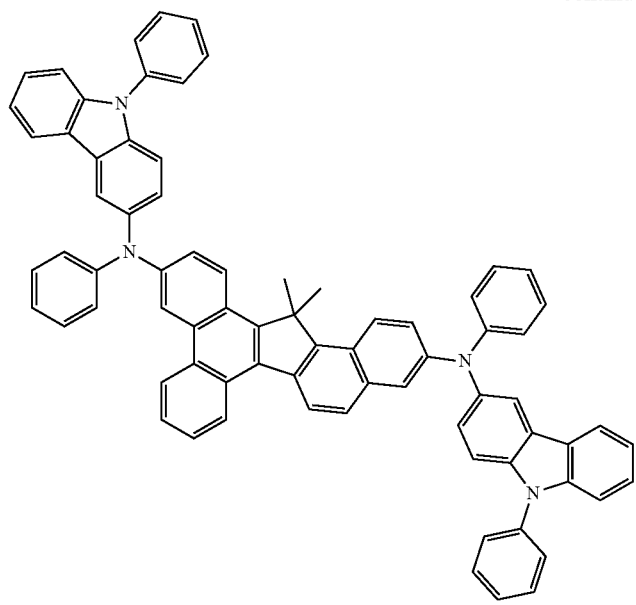
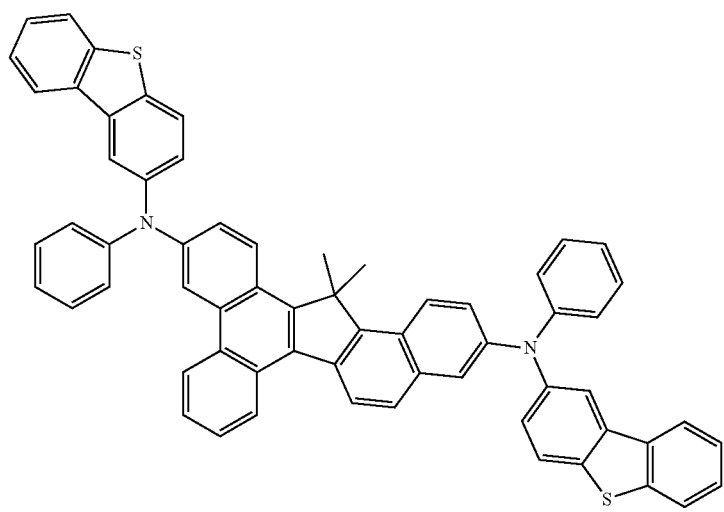
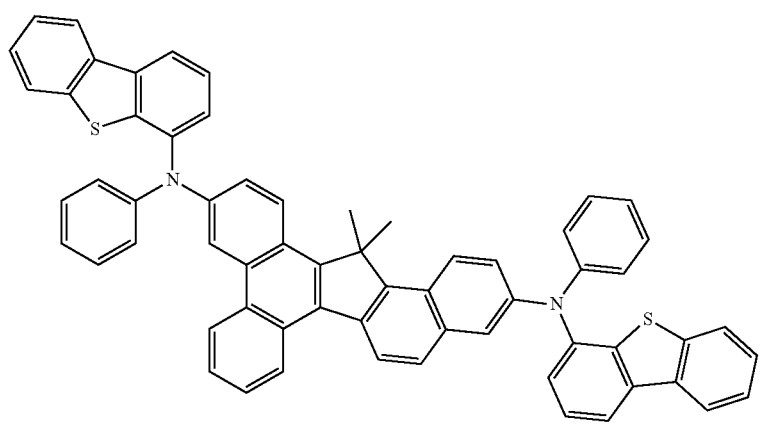

-continued
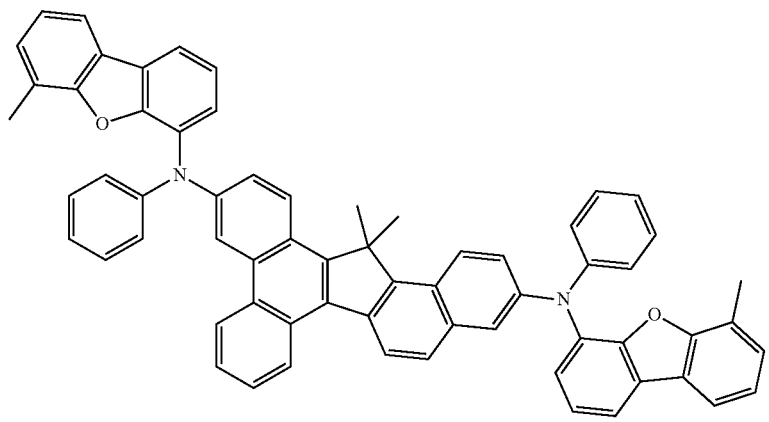
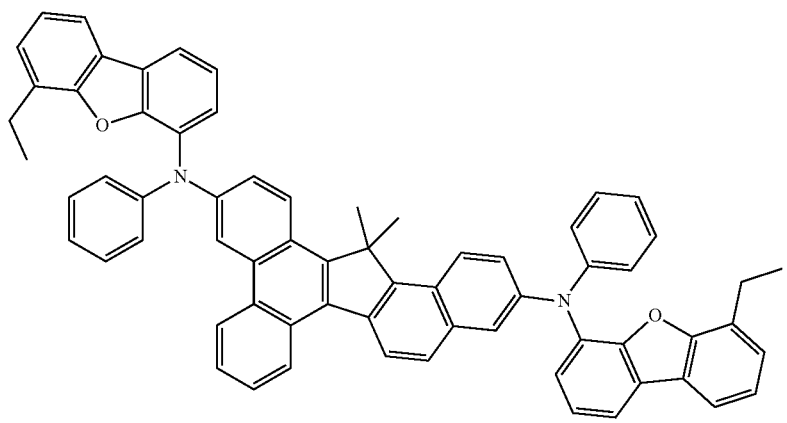
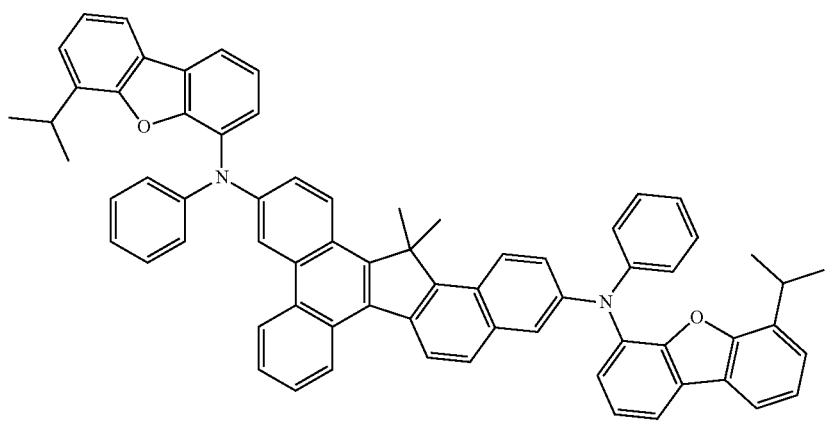
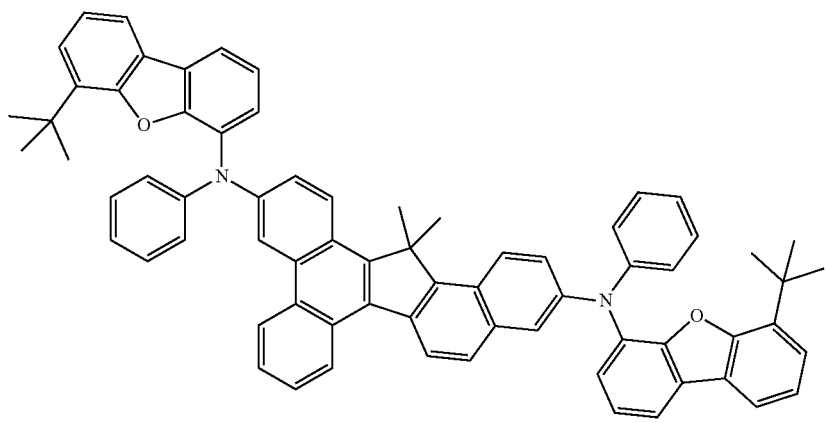

-continued
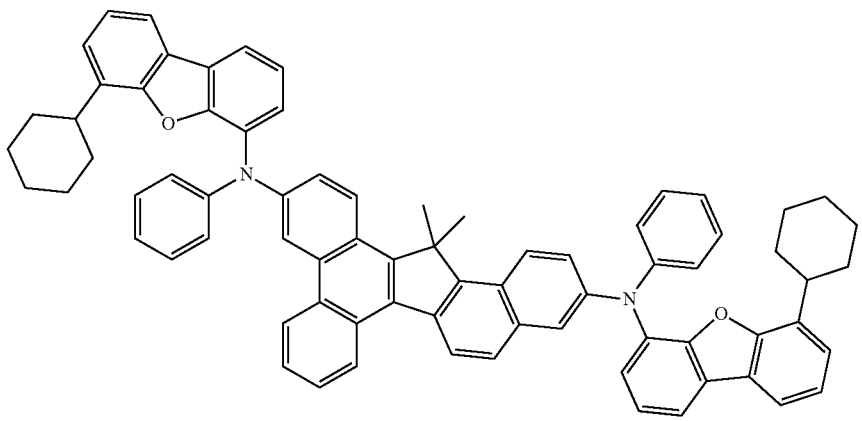
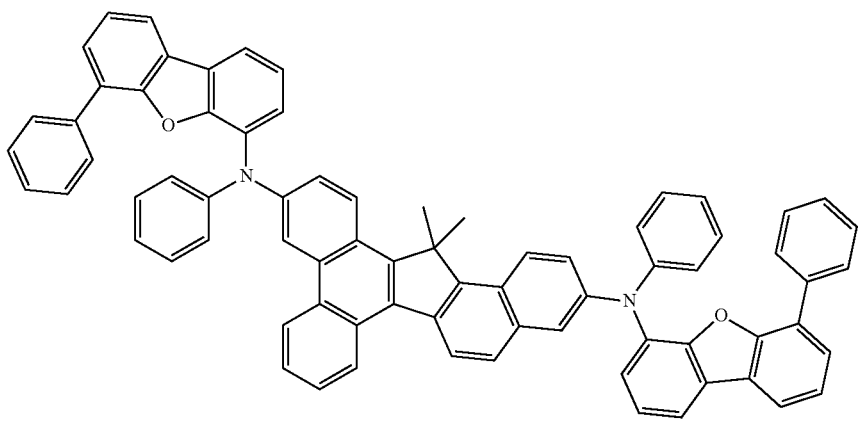
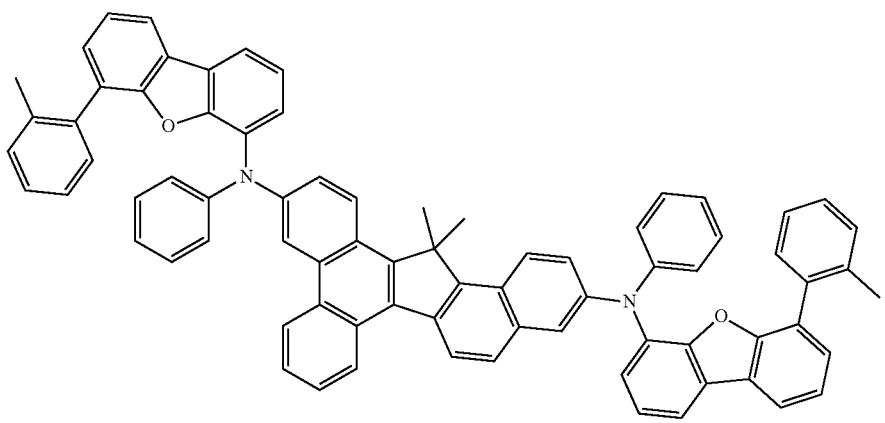
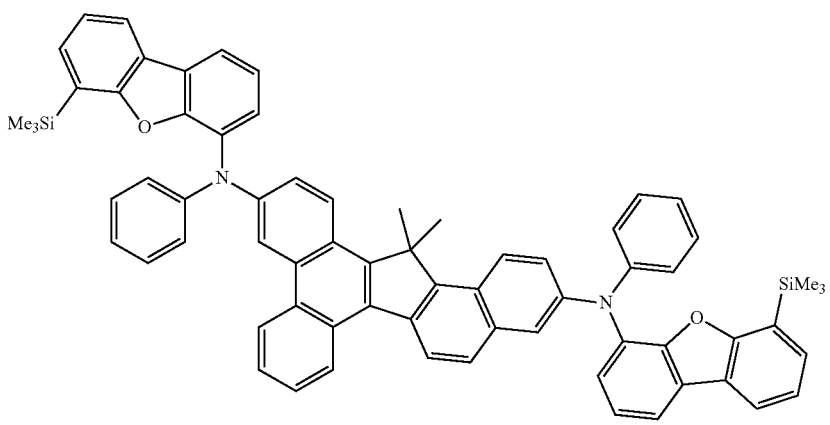

-continued
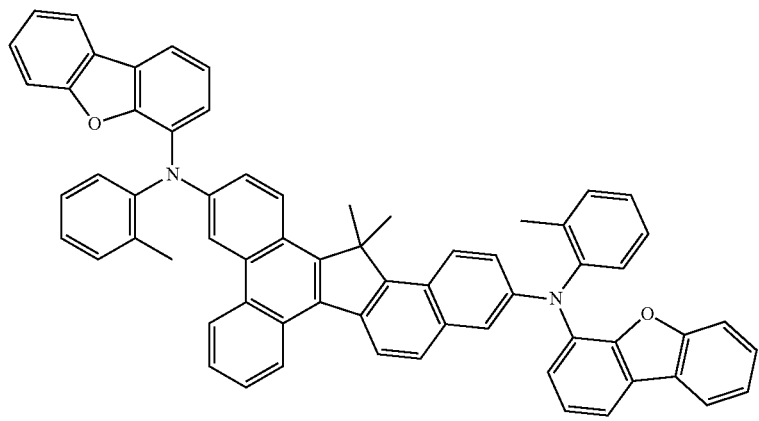
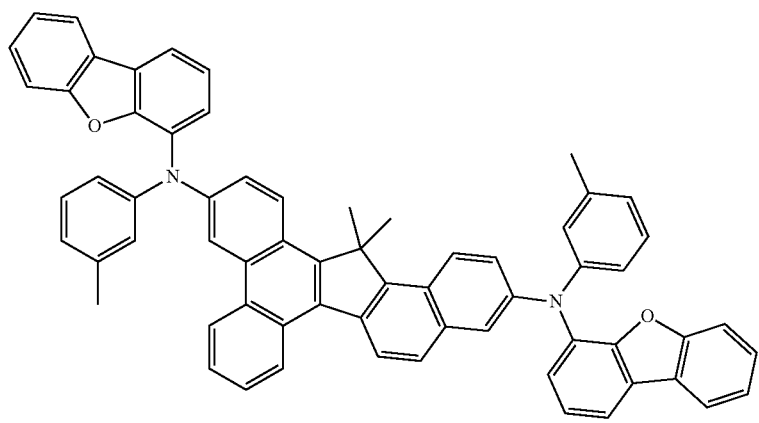
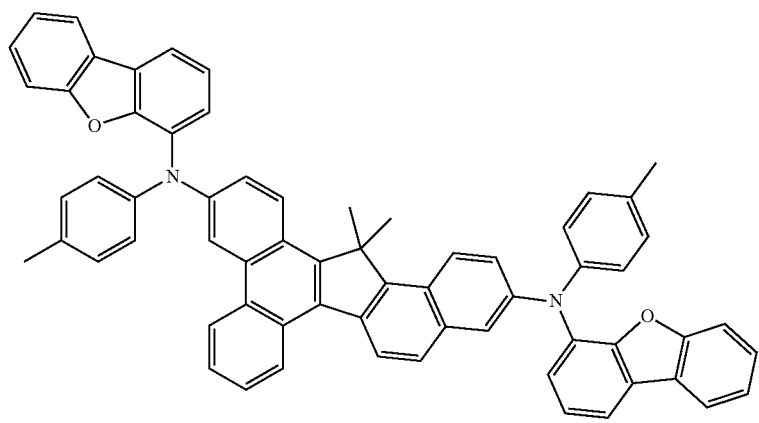
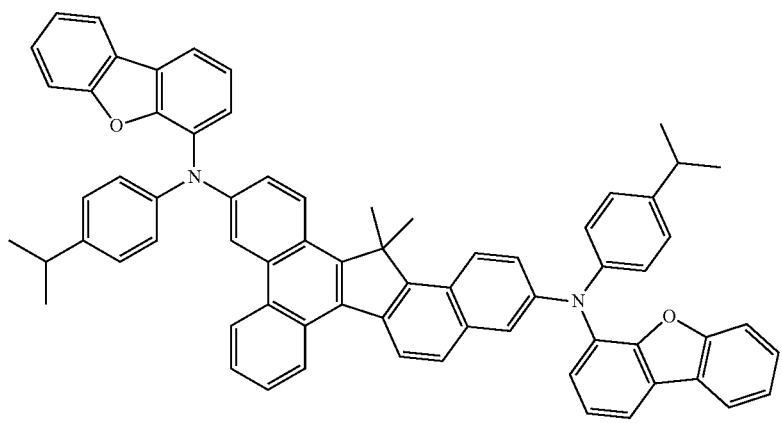

-continued
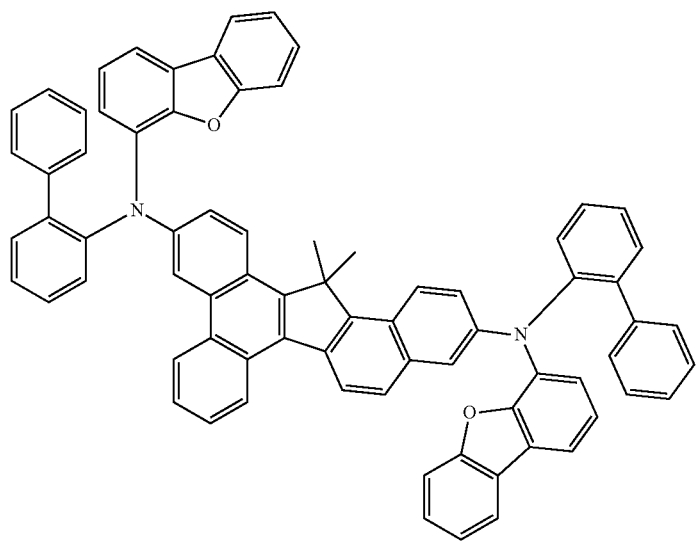
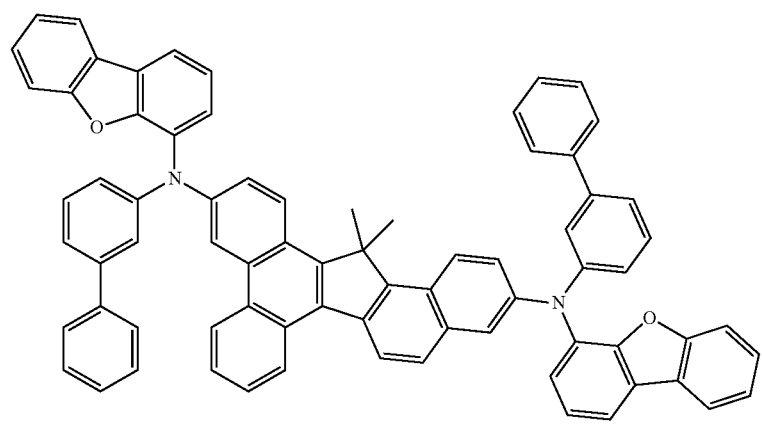
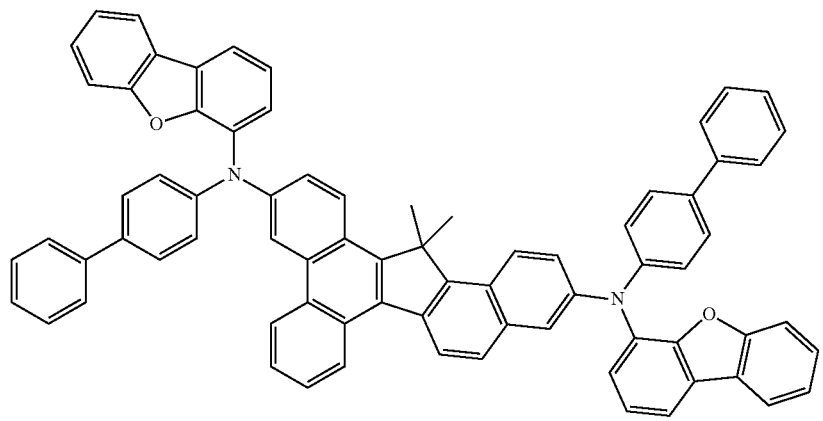

-continued
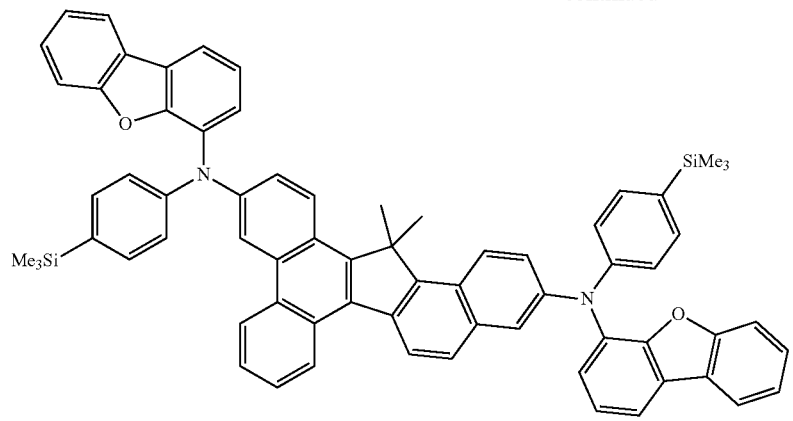
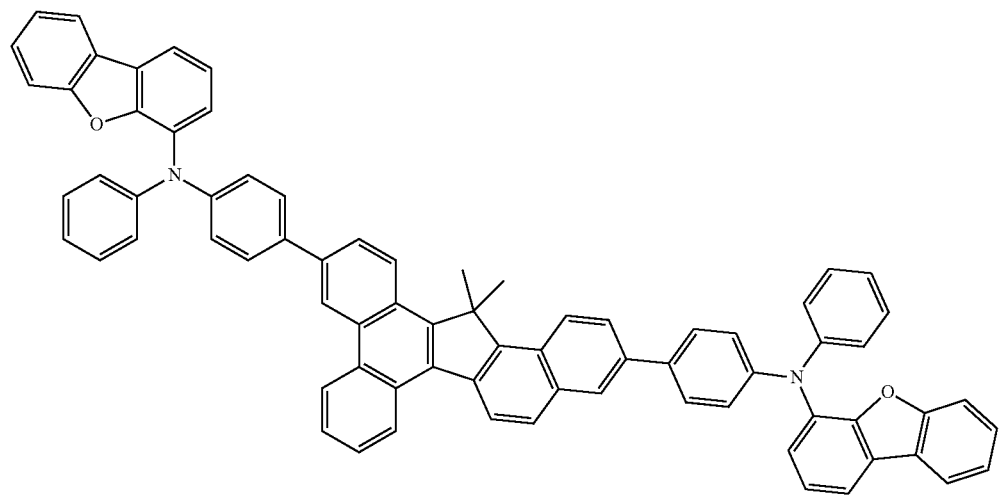
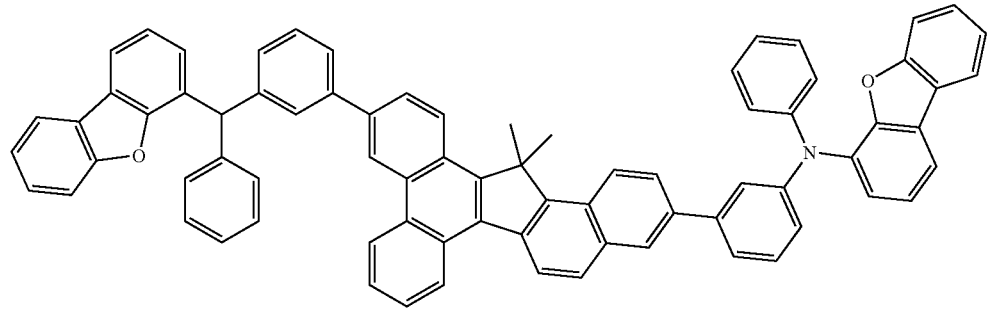
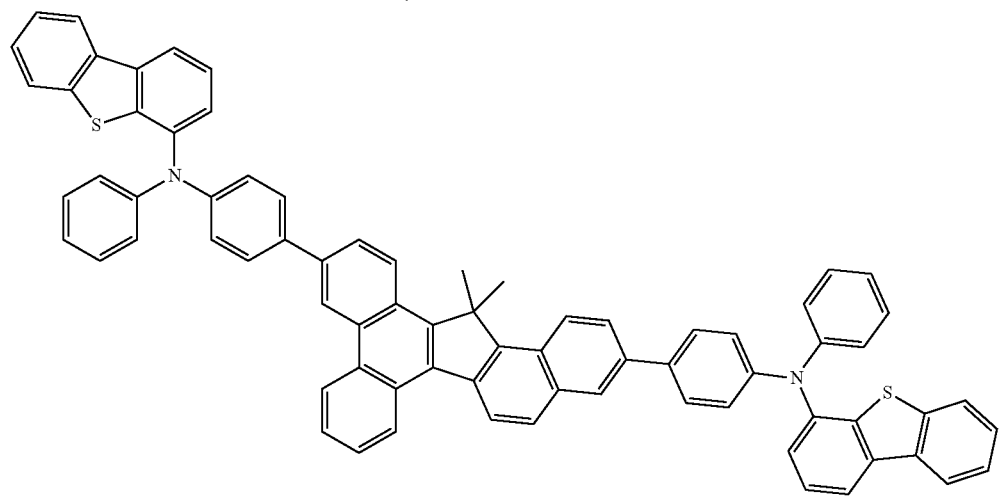

651
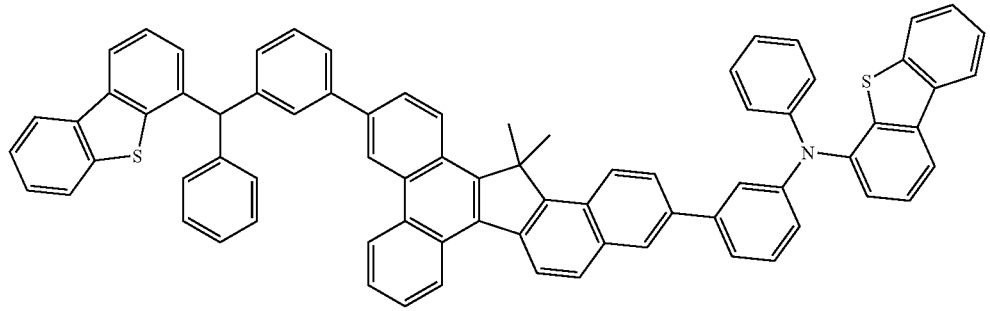
652
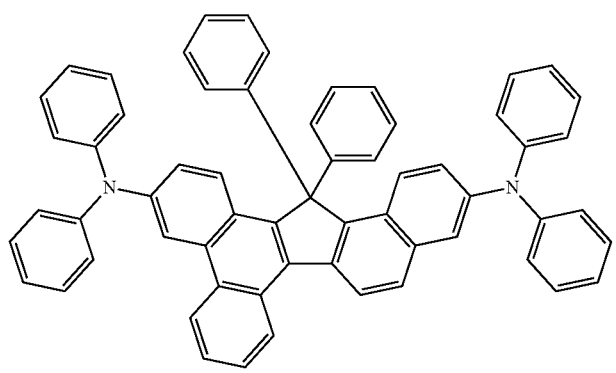
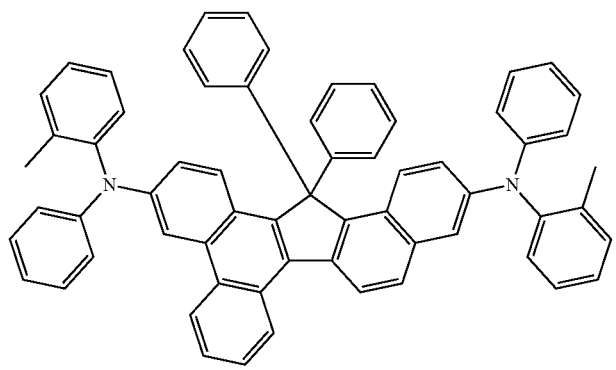
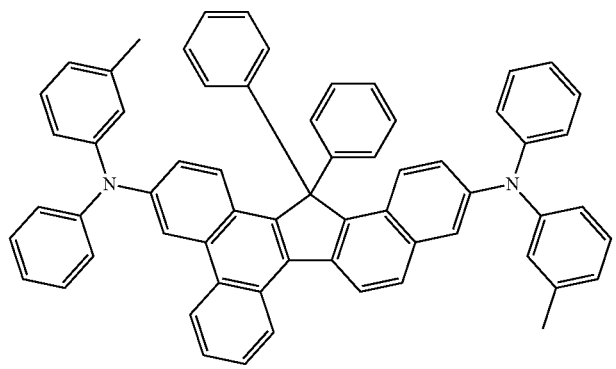

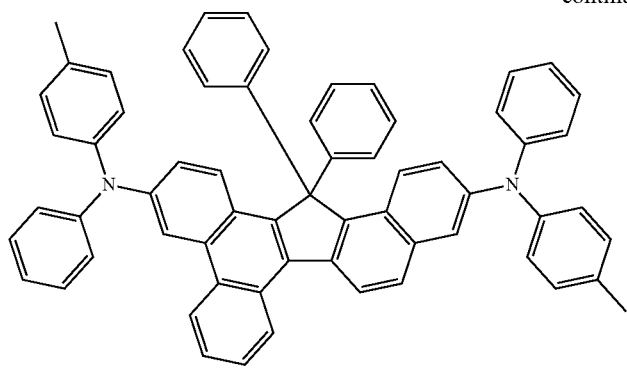
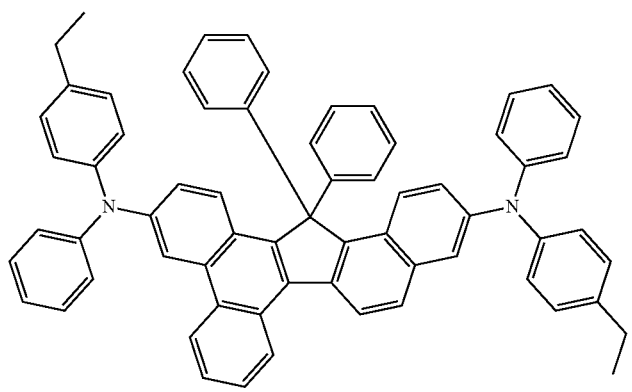
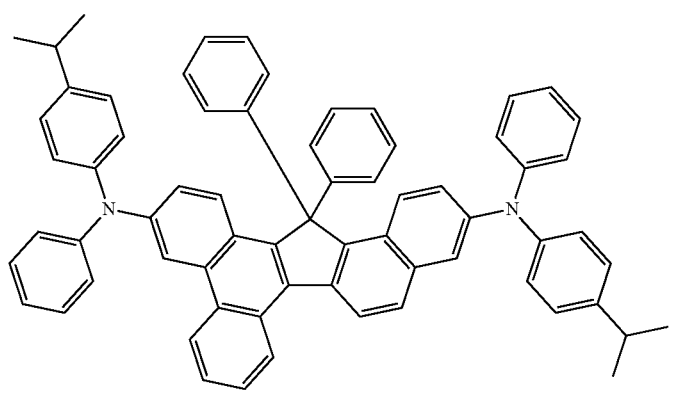
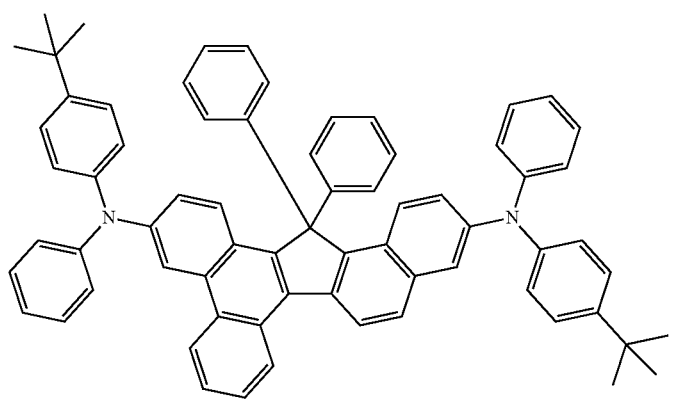

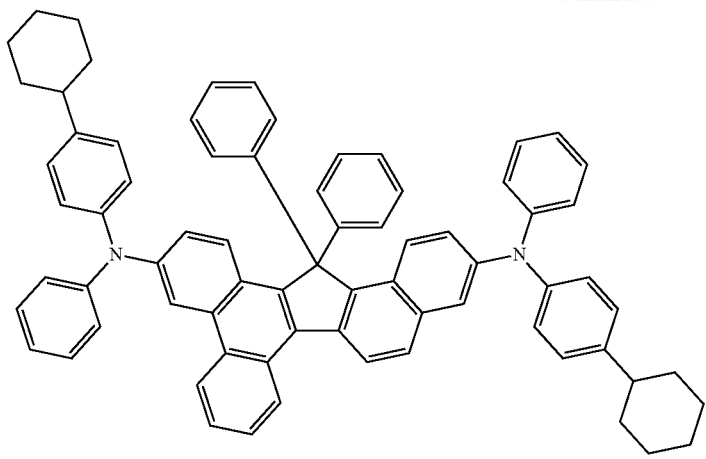
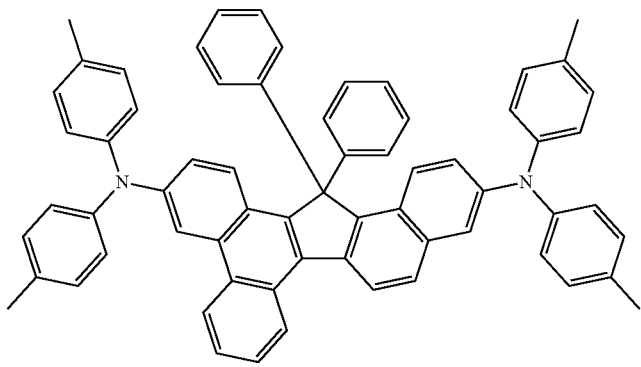
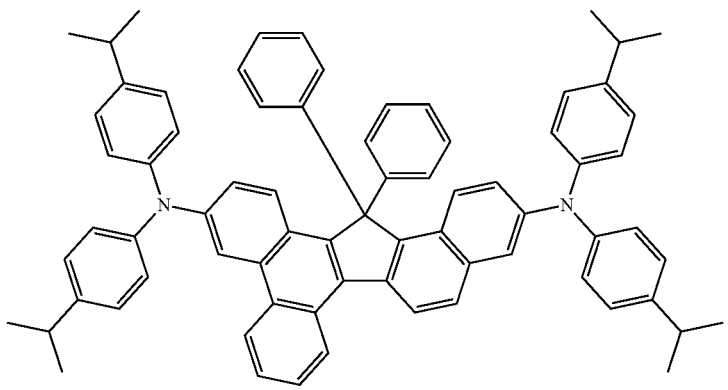
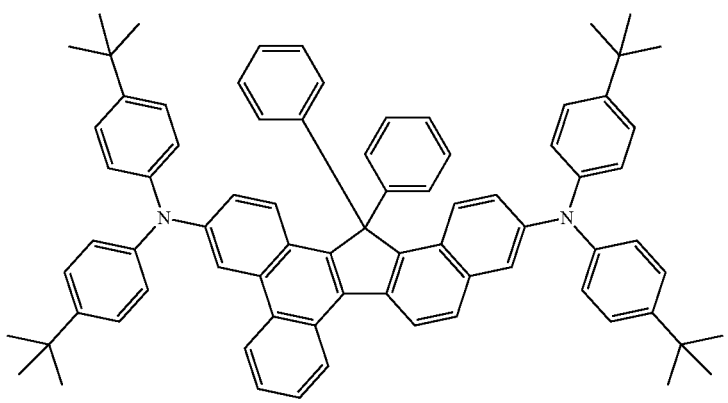

-continued
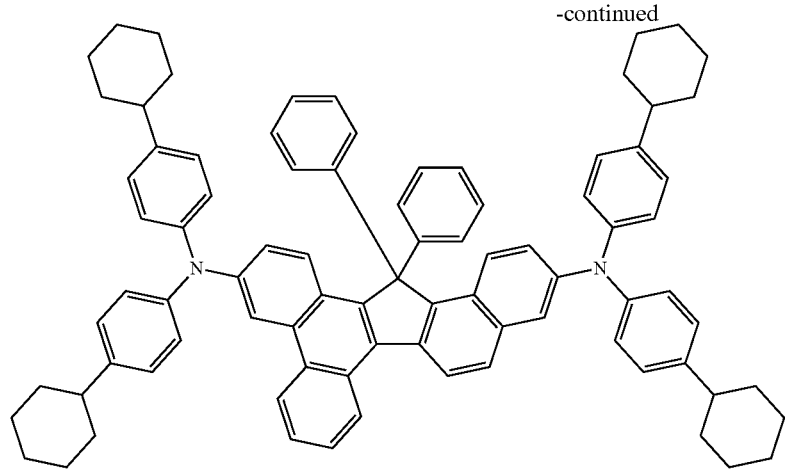
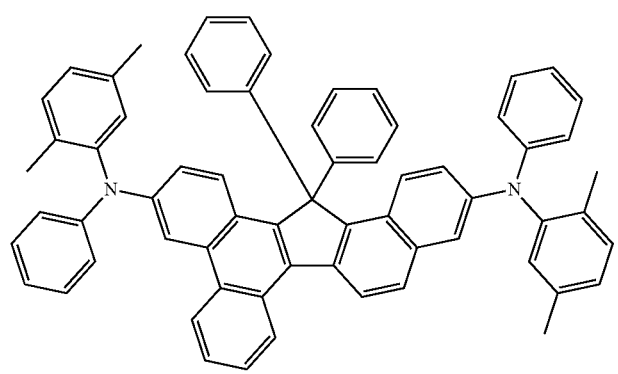
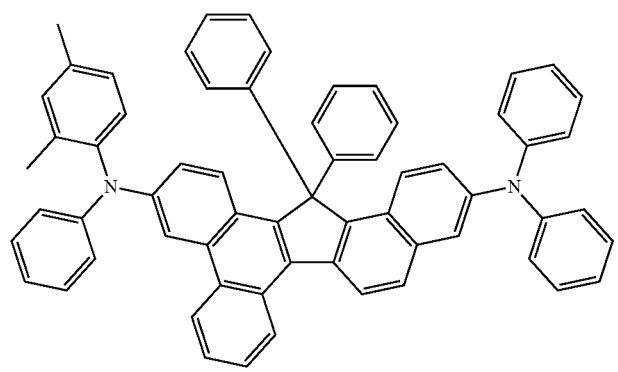
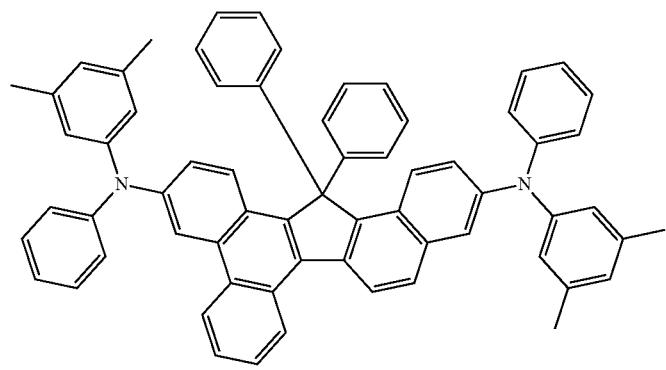

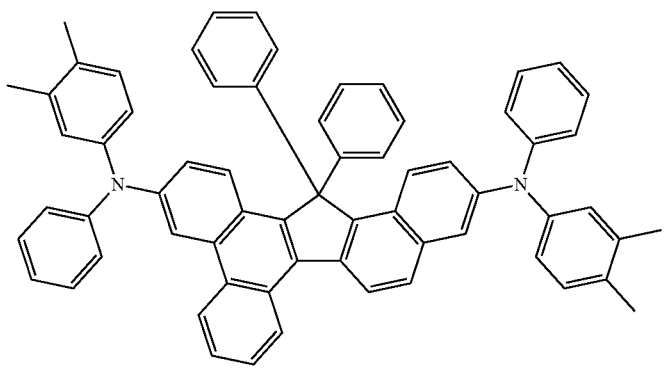
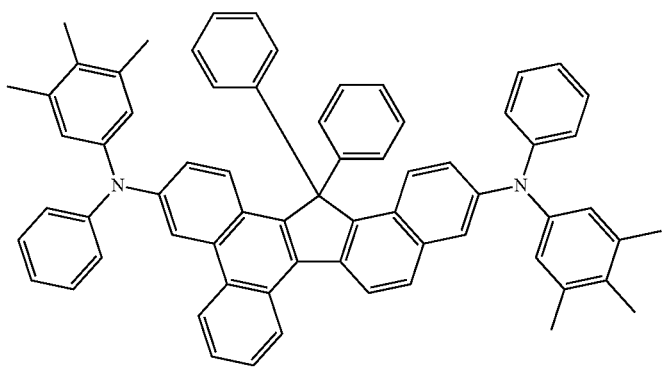
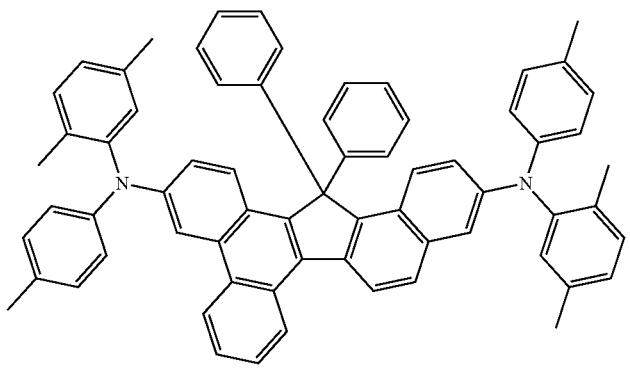
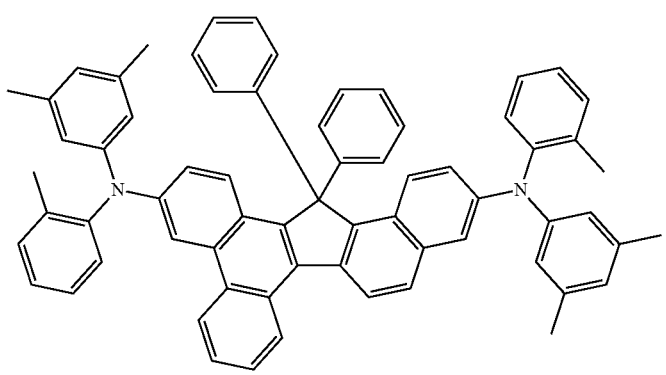

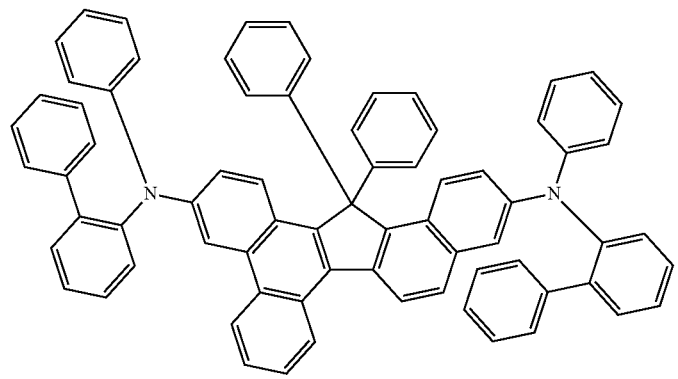
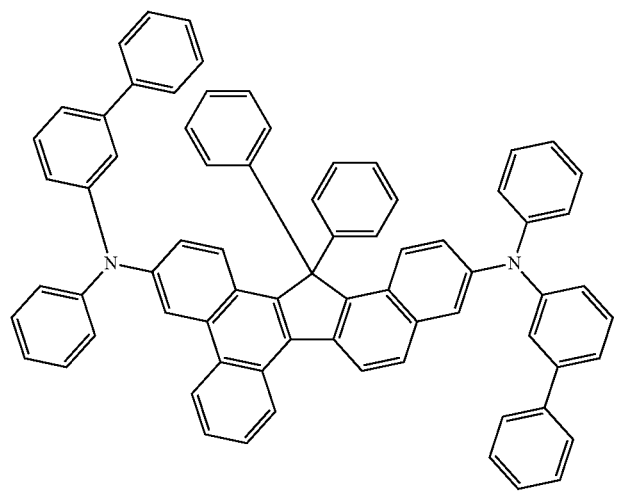
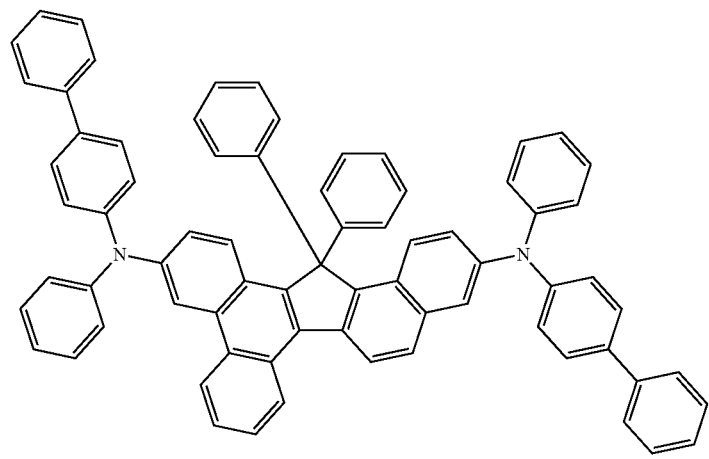

-continued
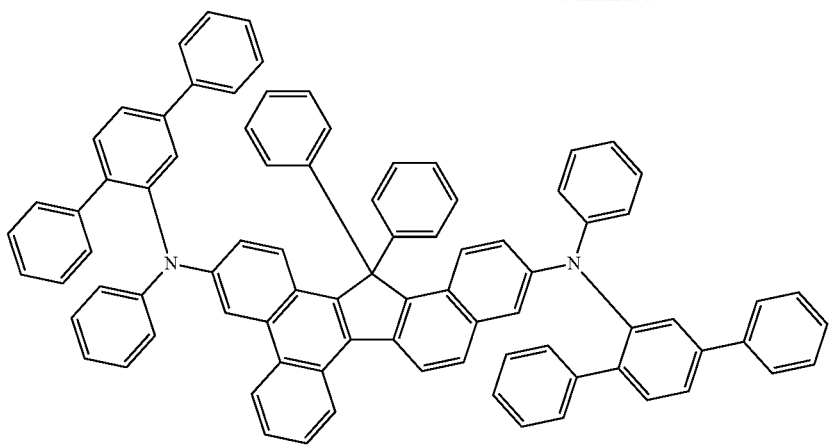
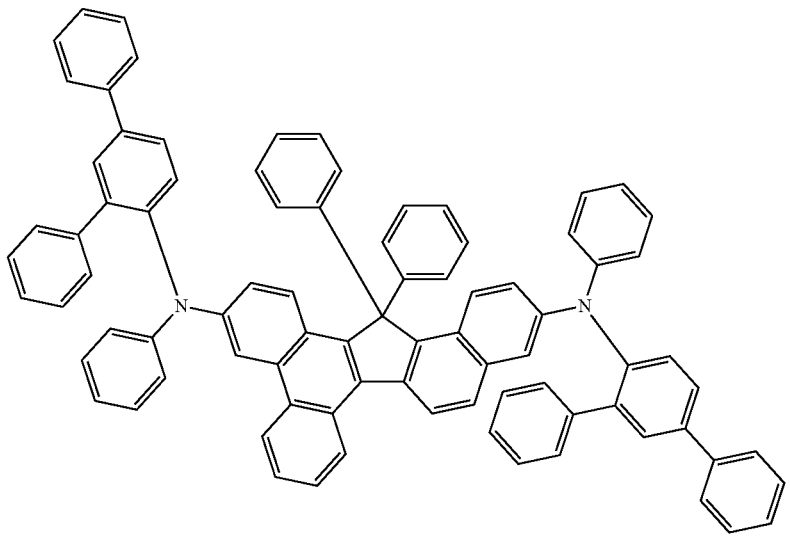
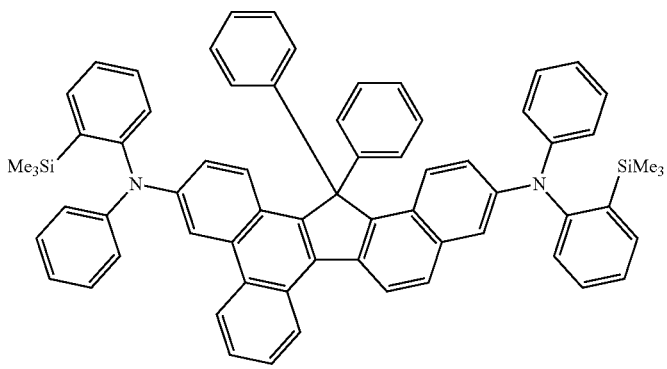
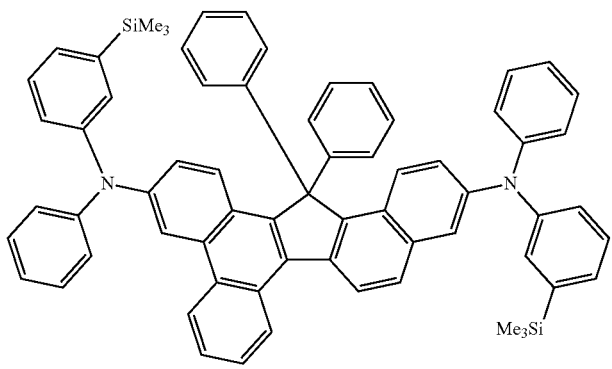

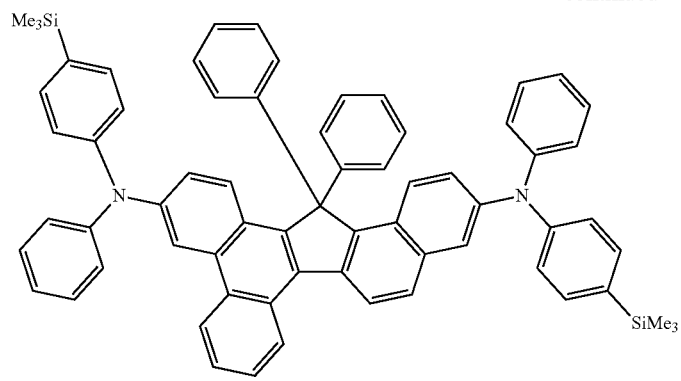
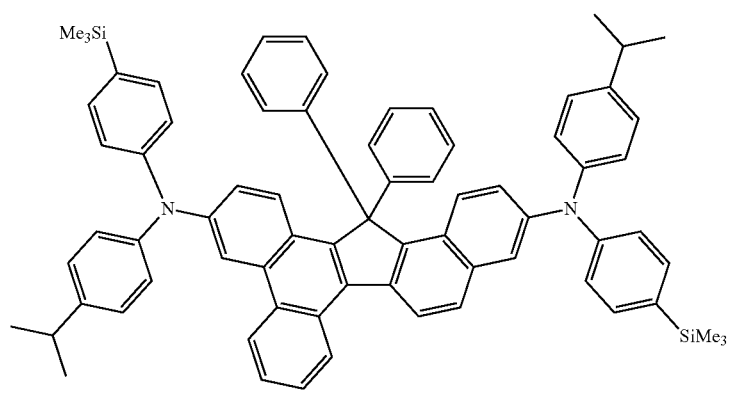
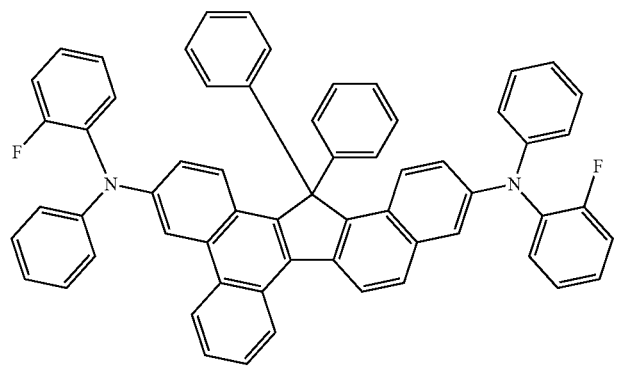
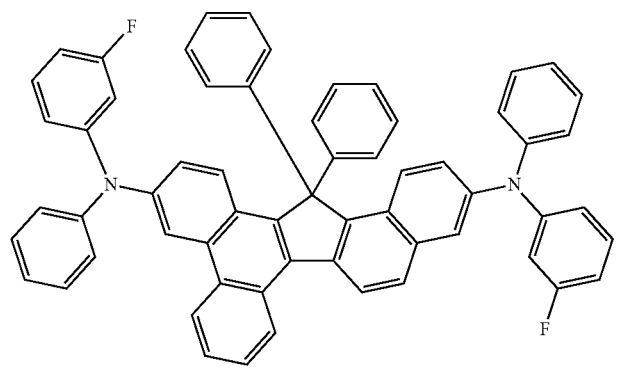

-continued
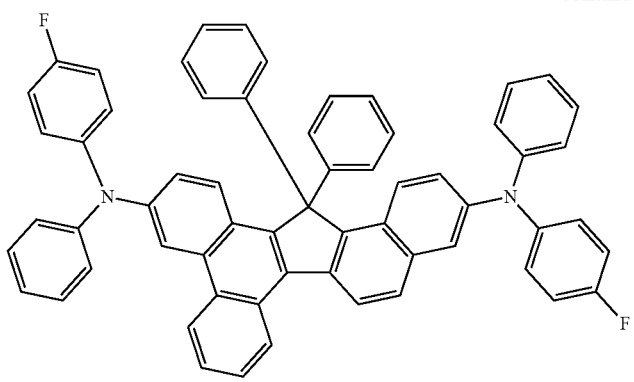
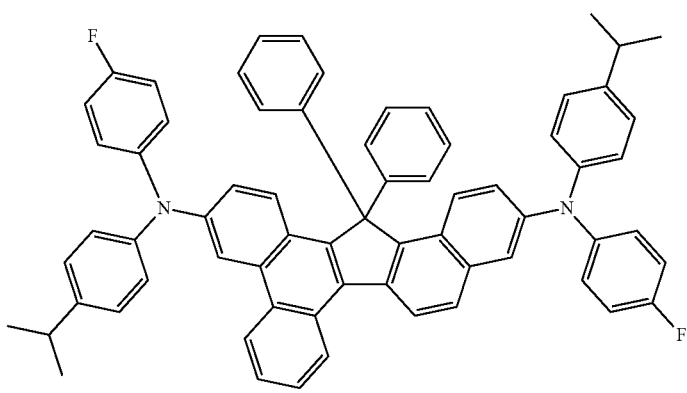
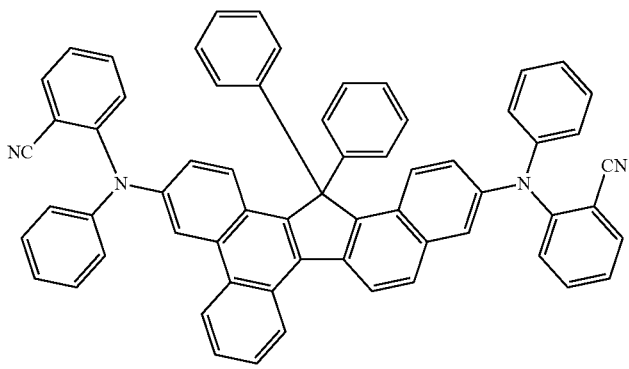
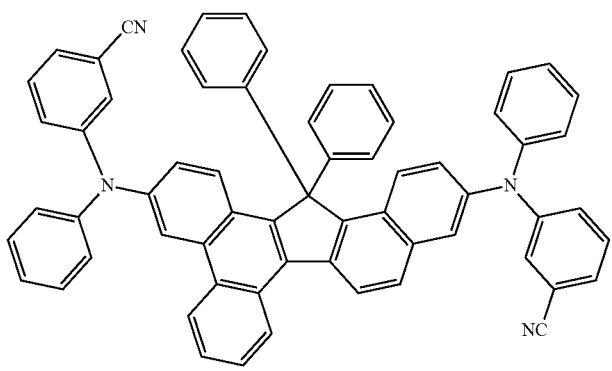

-continued
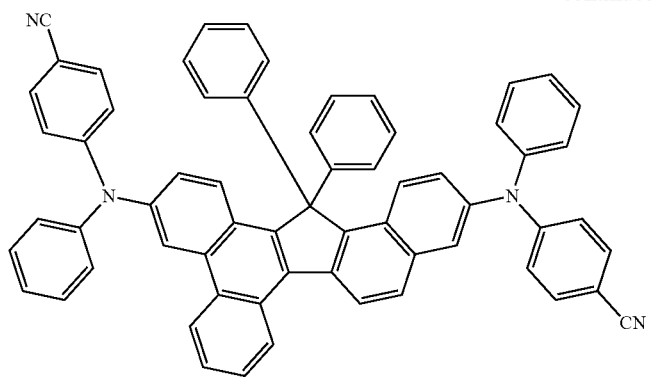
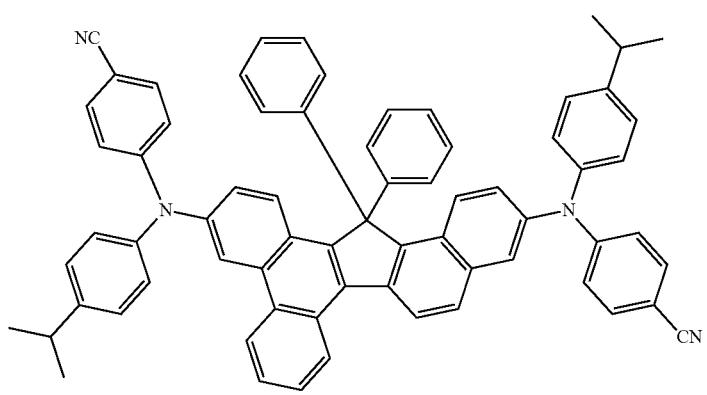
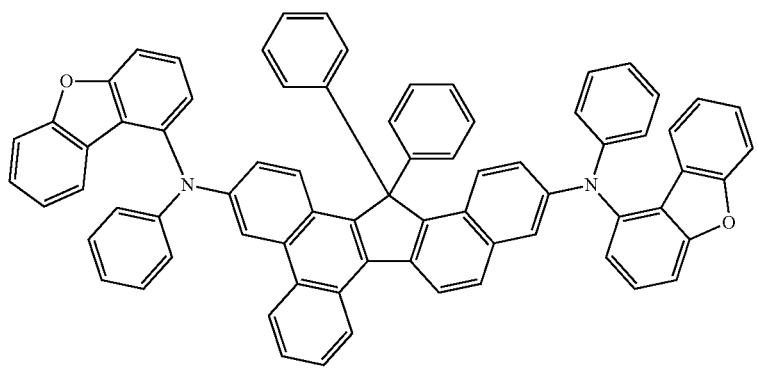
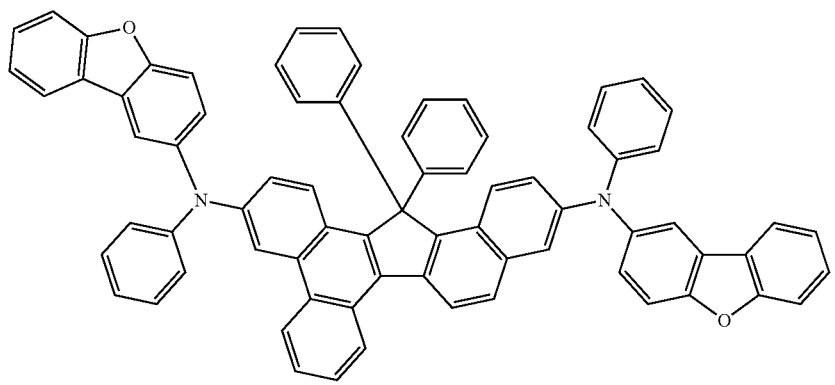

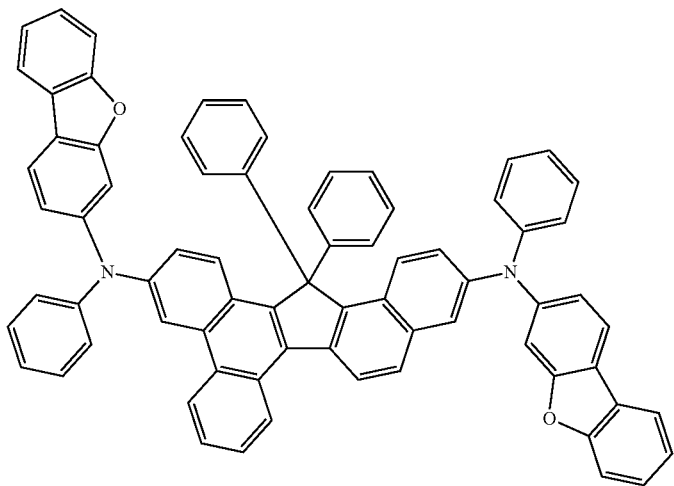
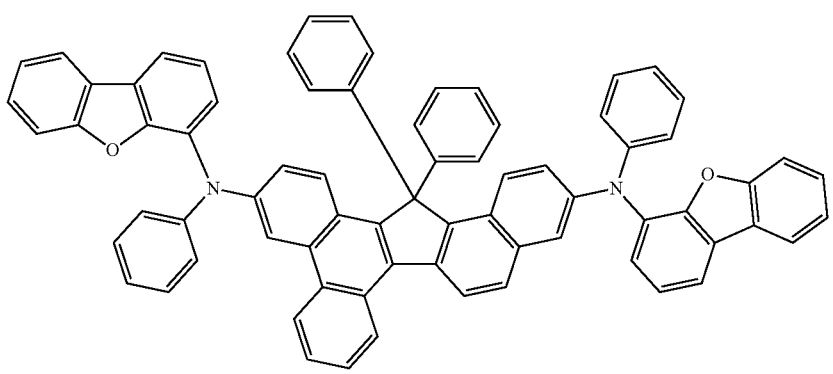
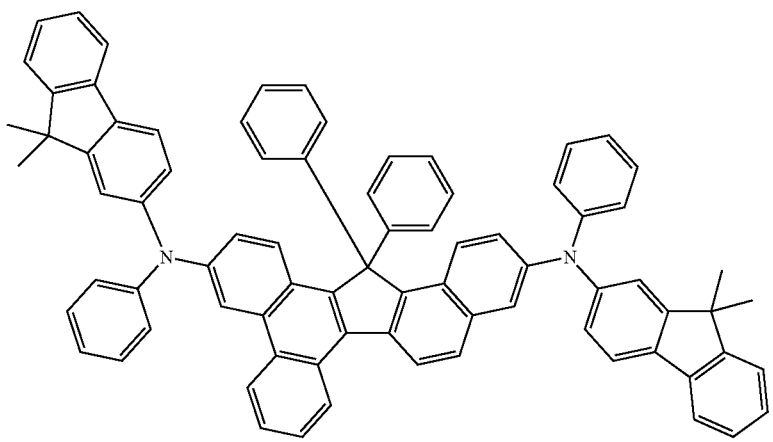

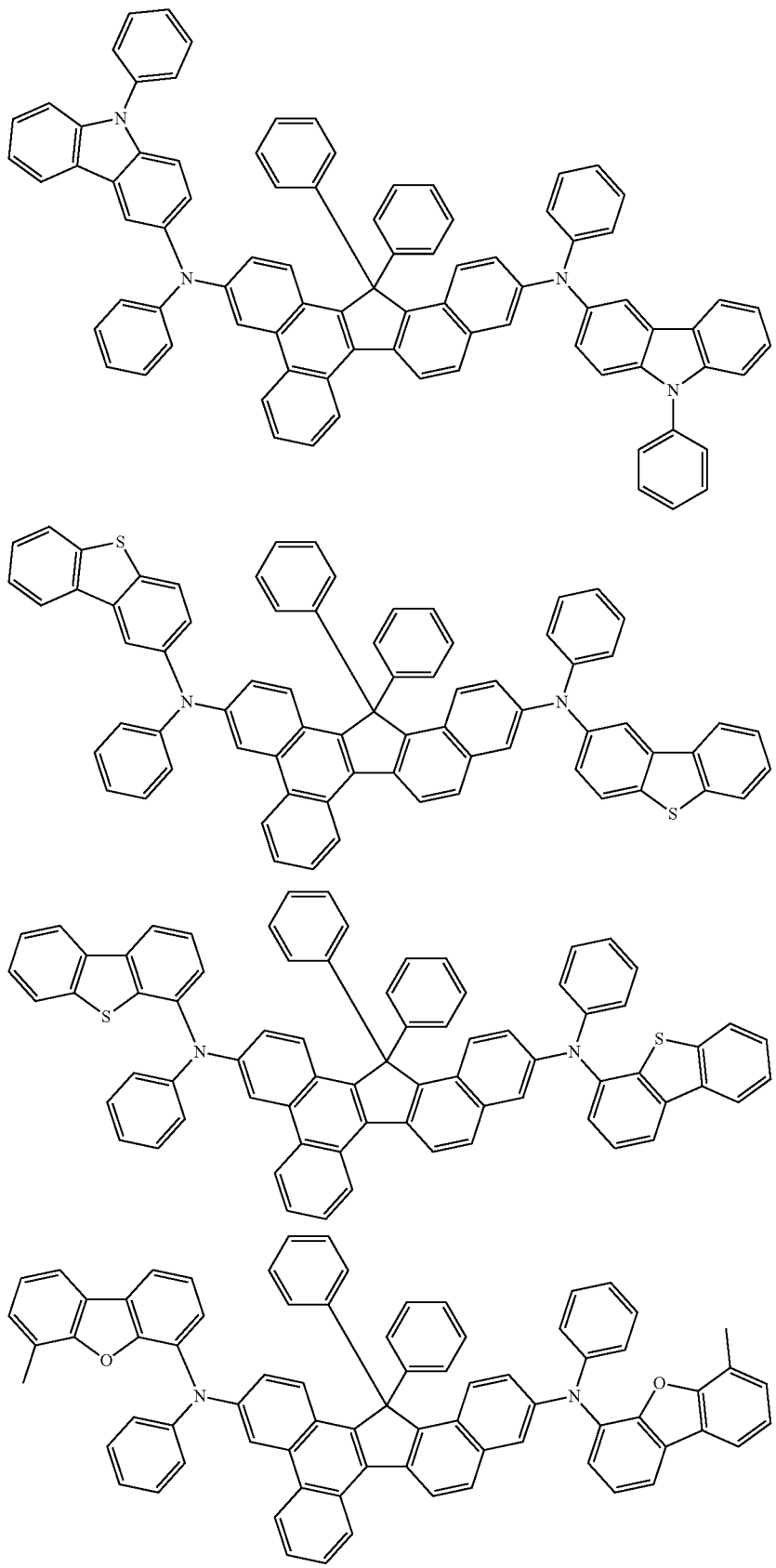

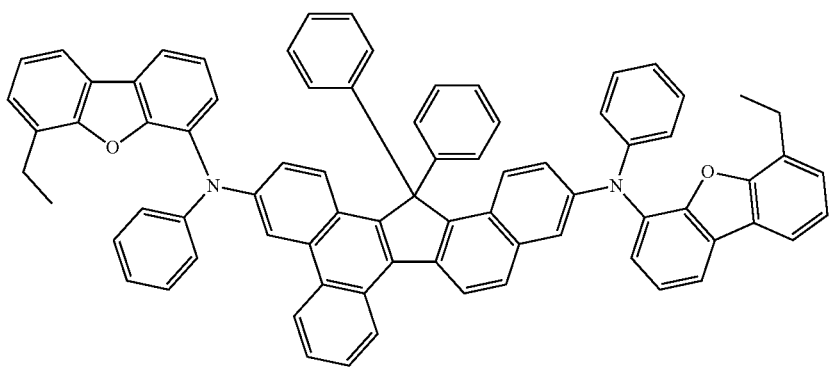
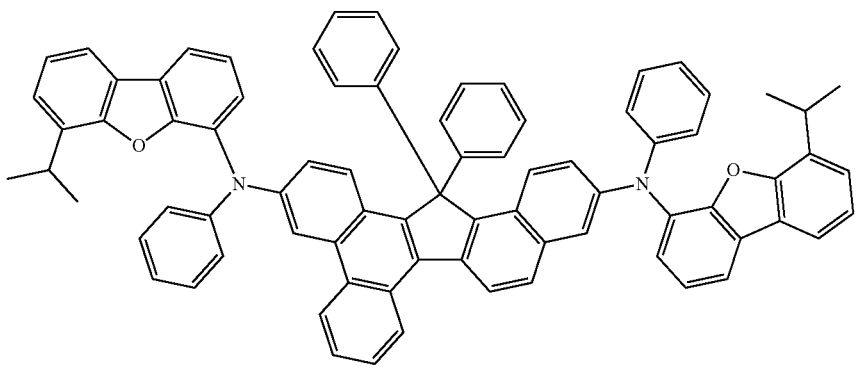
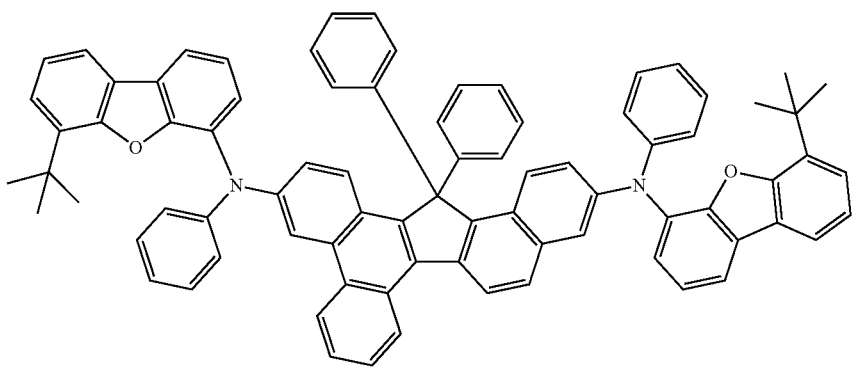
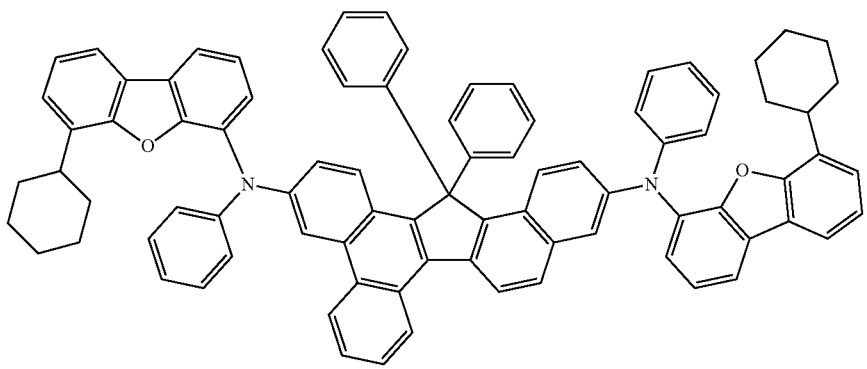

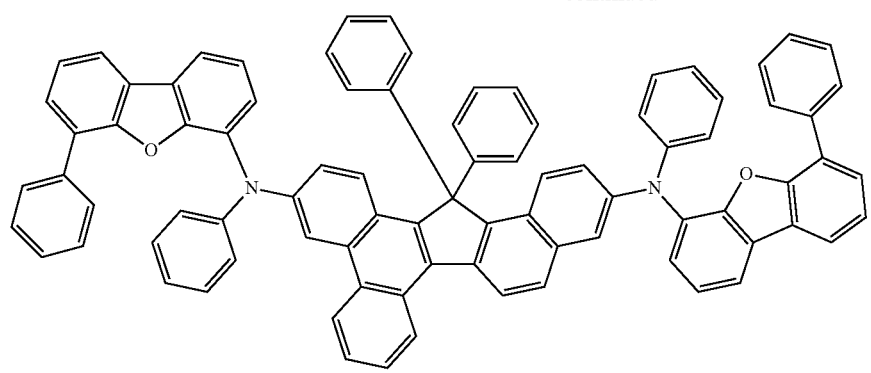
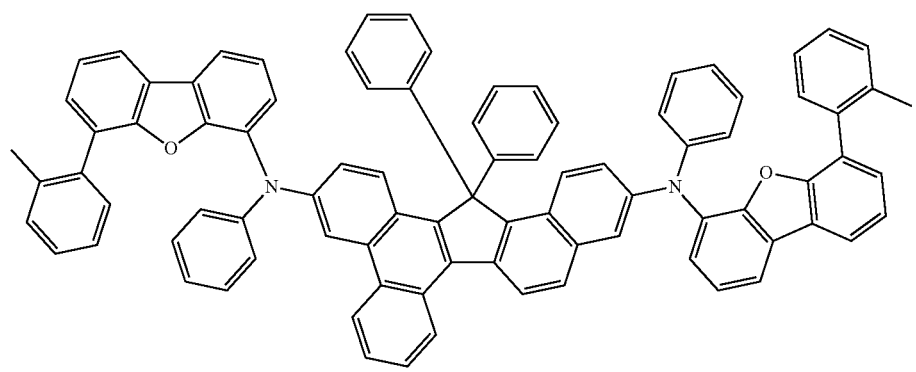
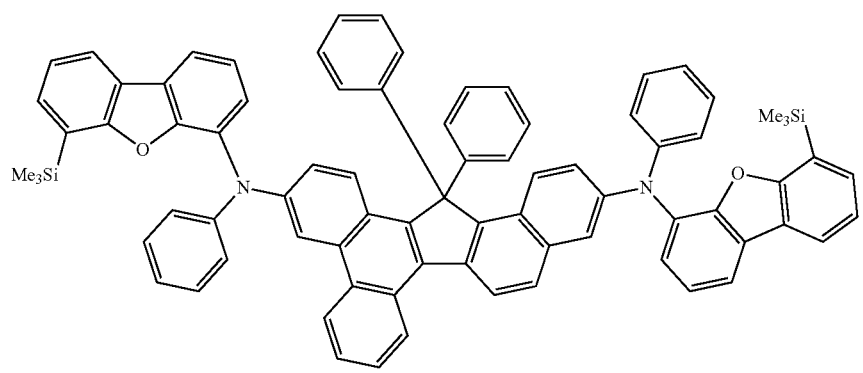
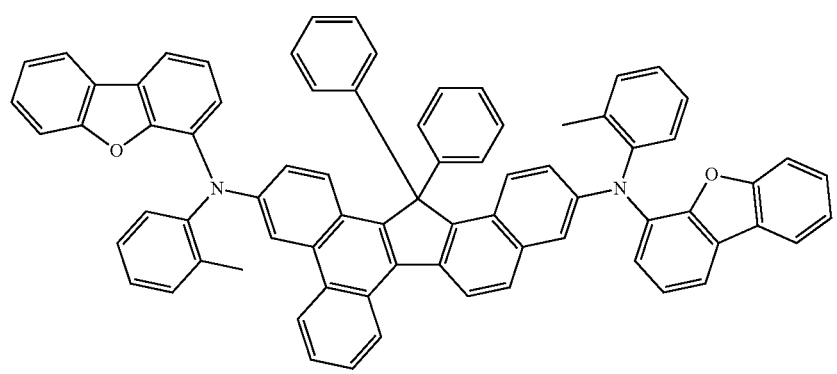

-continued
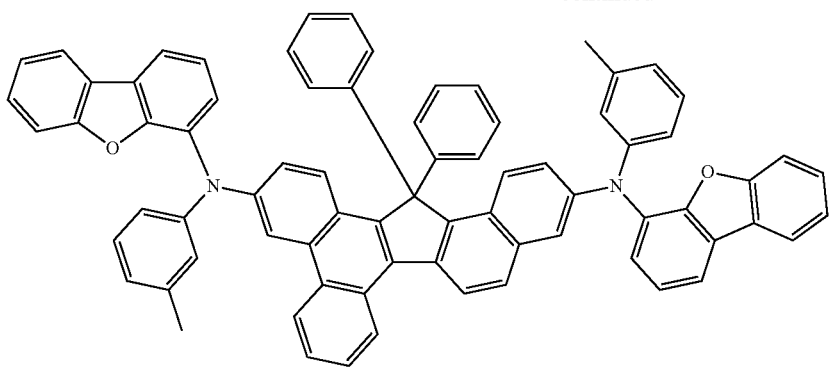
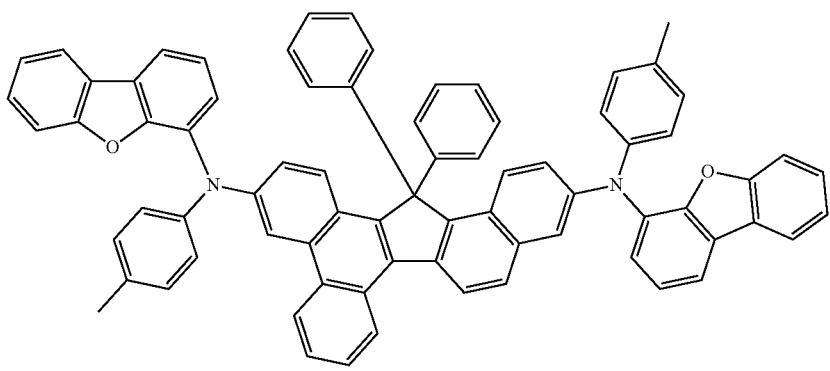
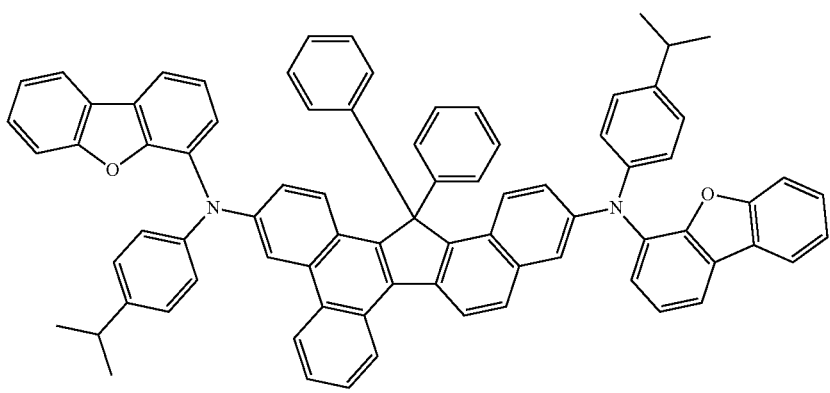
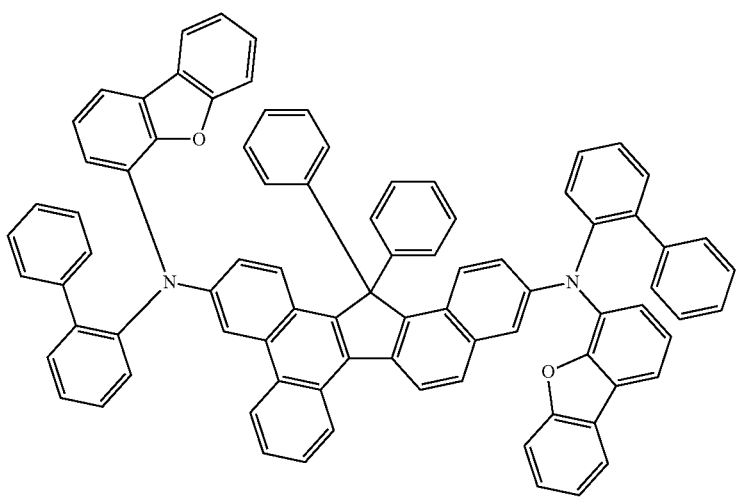

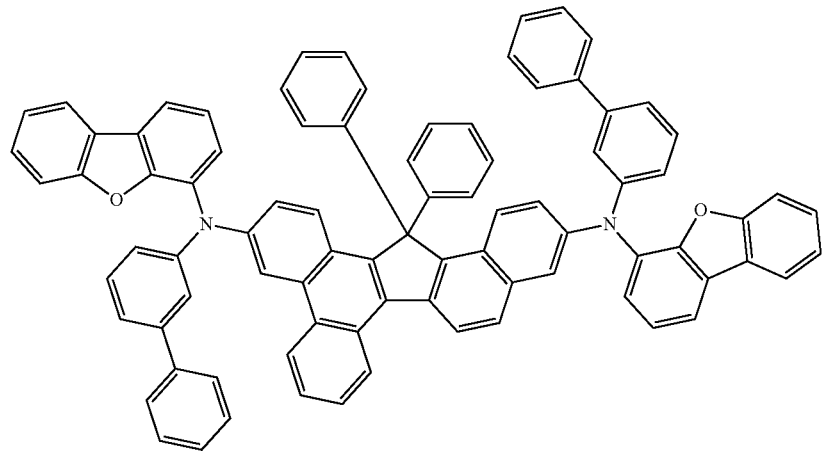
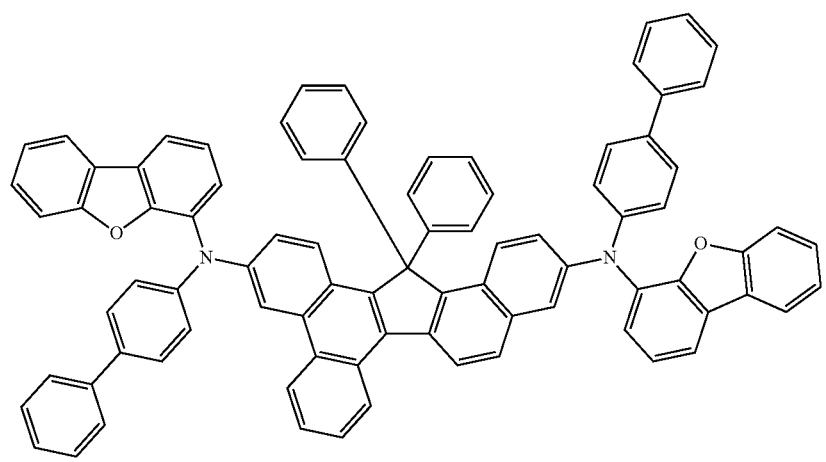
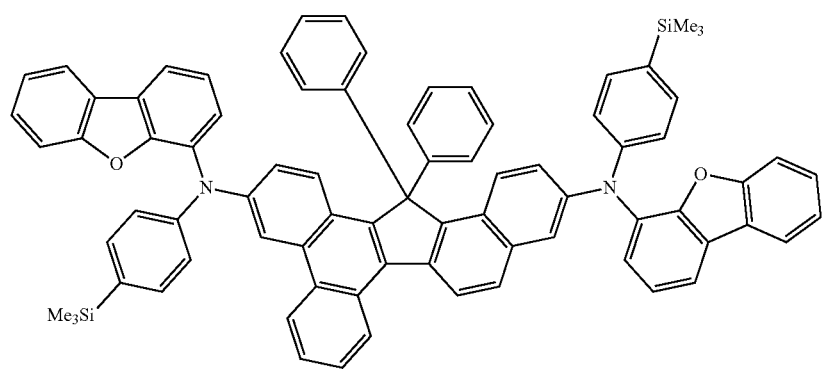
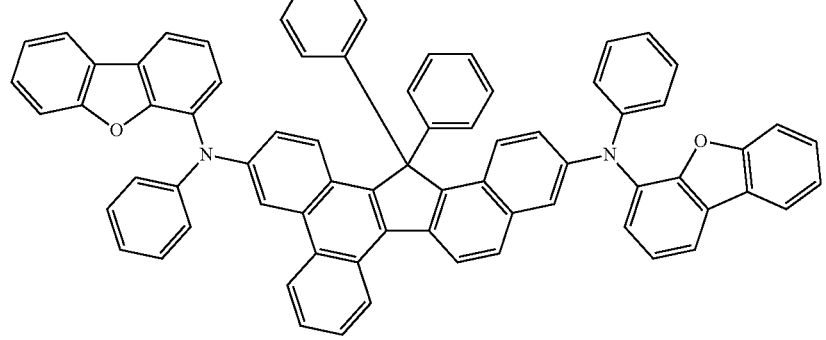

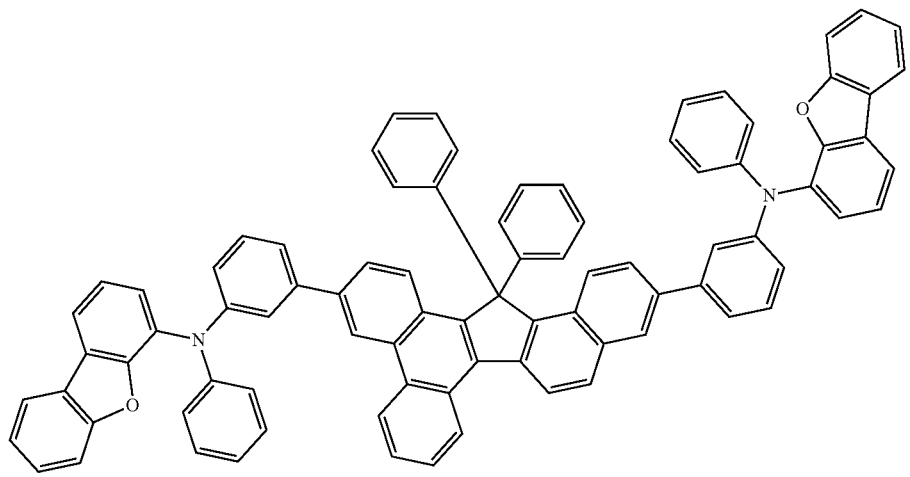
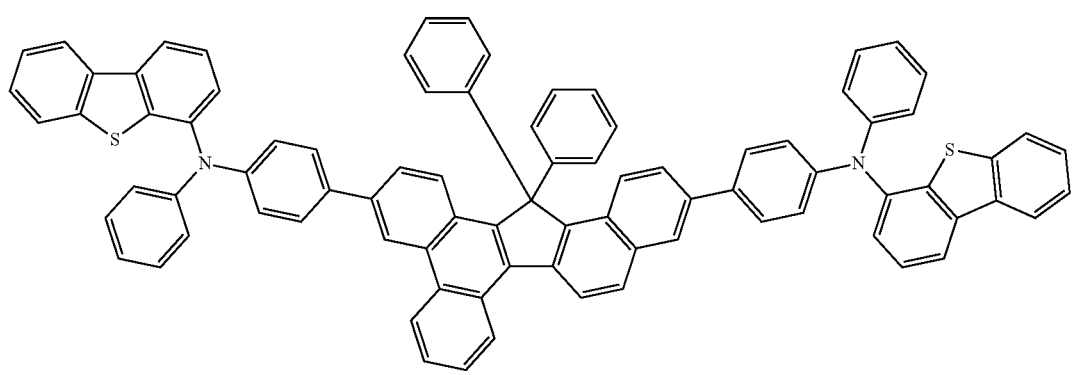
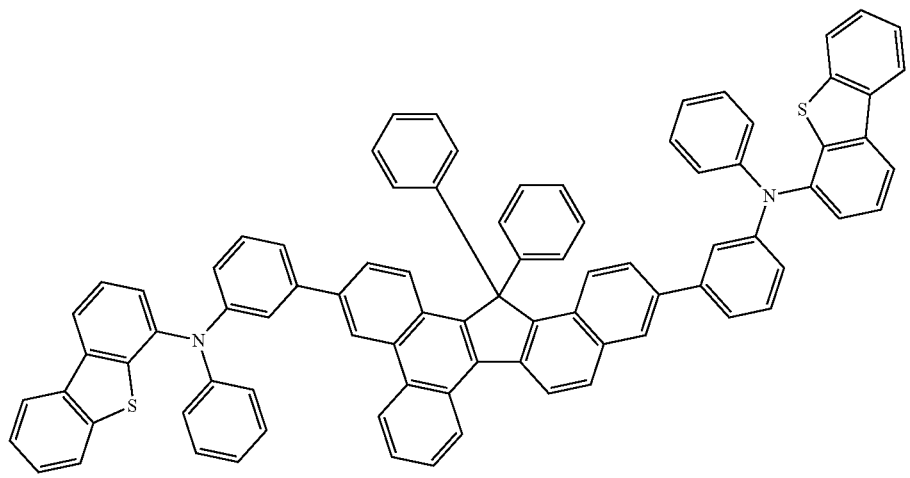
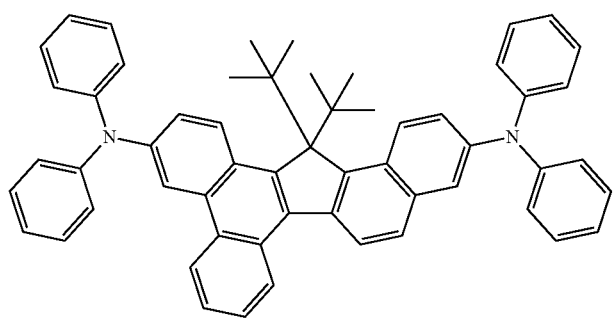

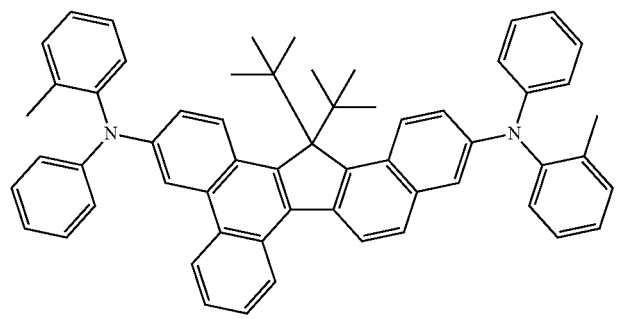
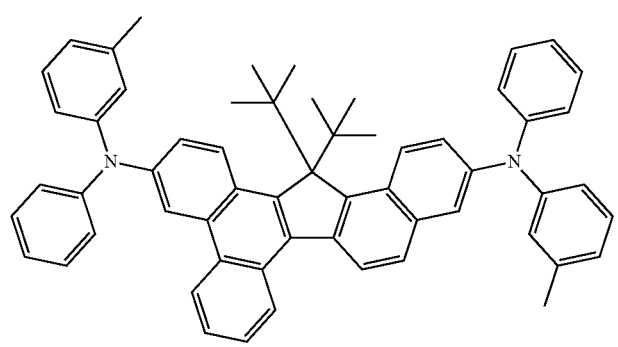
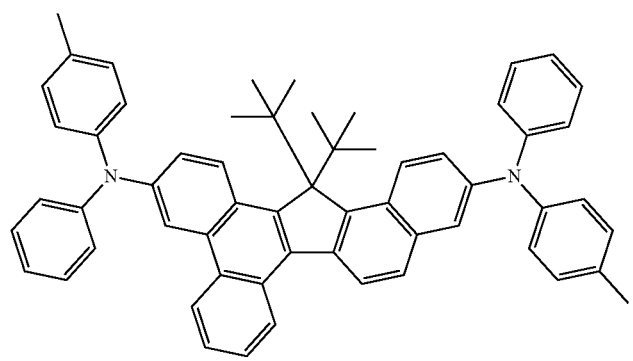
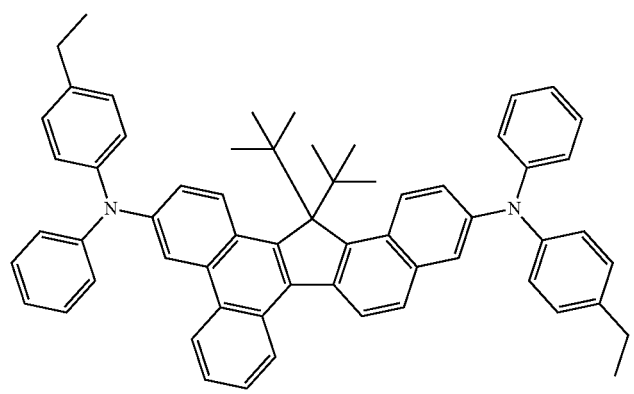

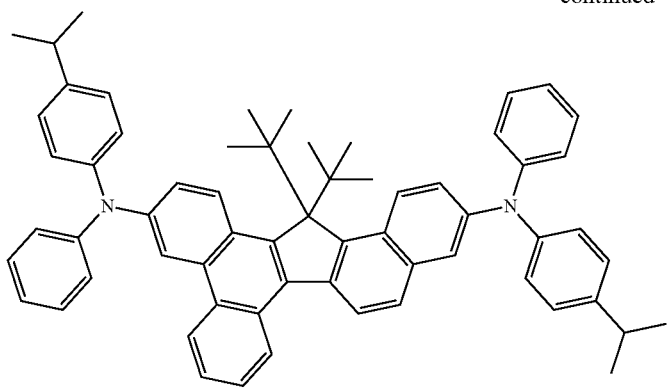
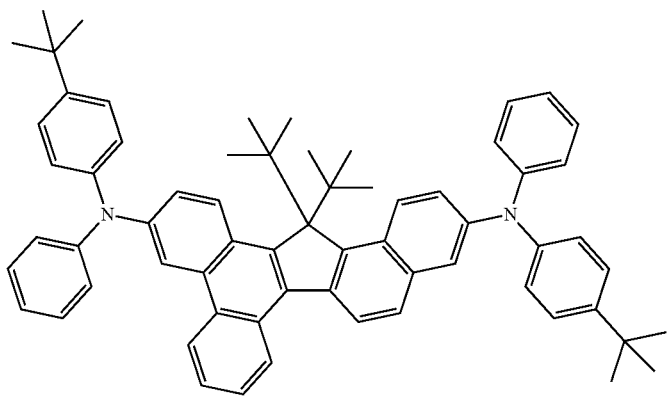
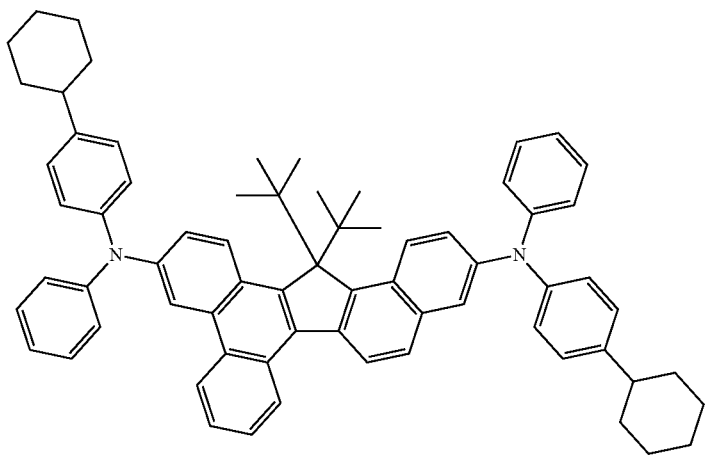
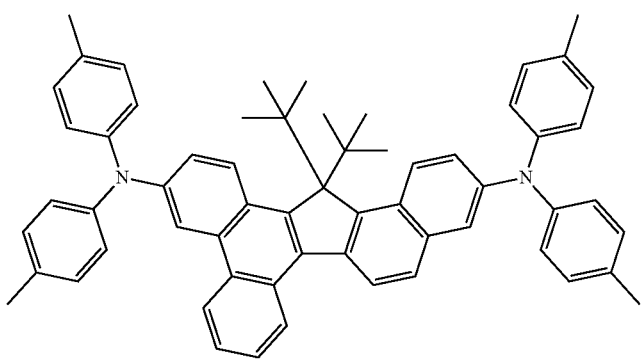

-continued
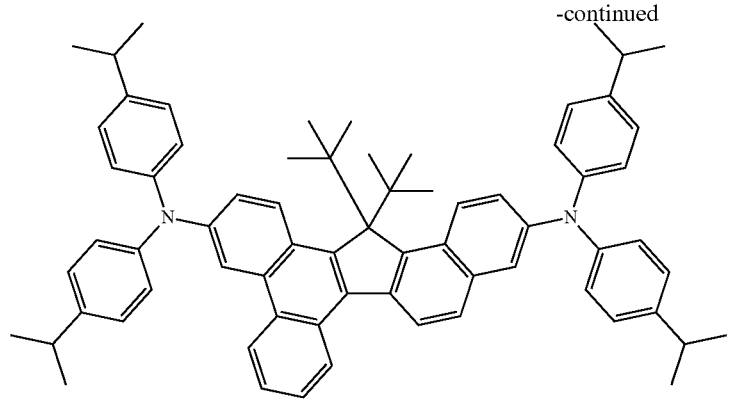
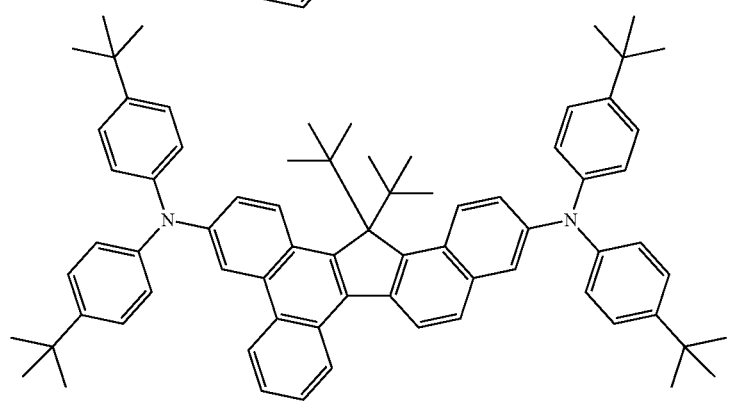
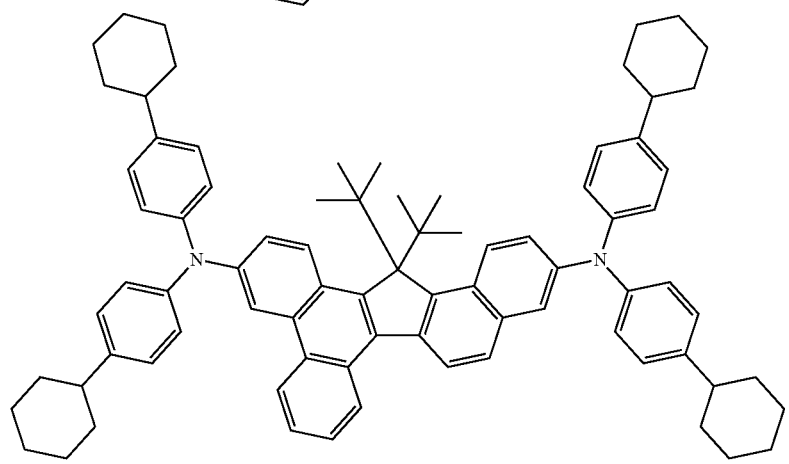
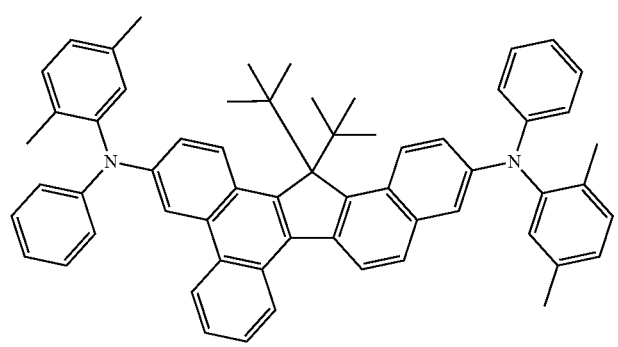

-continued
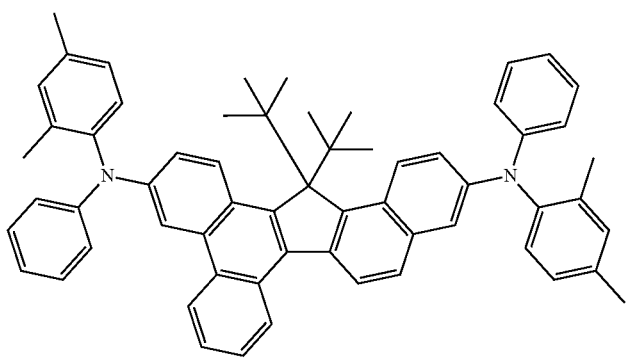
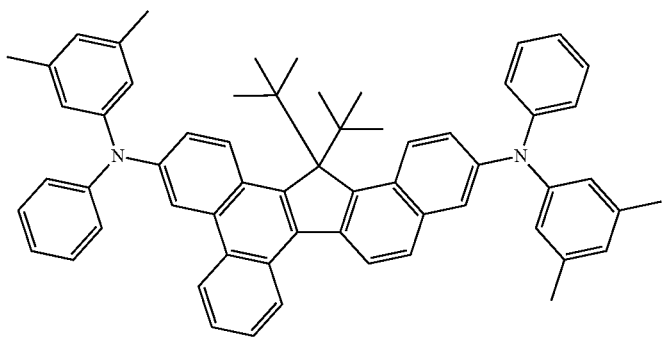
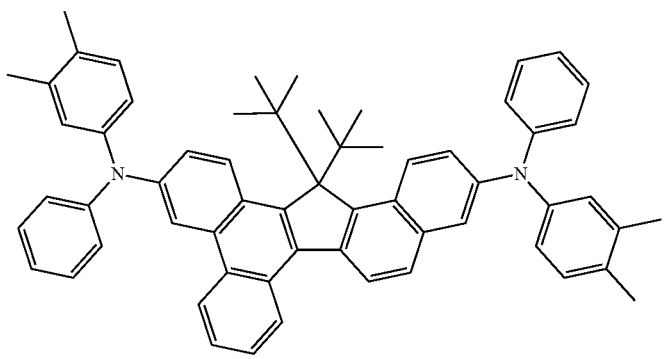
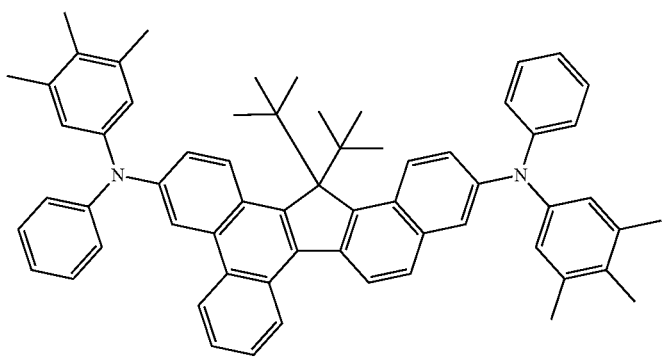

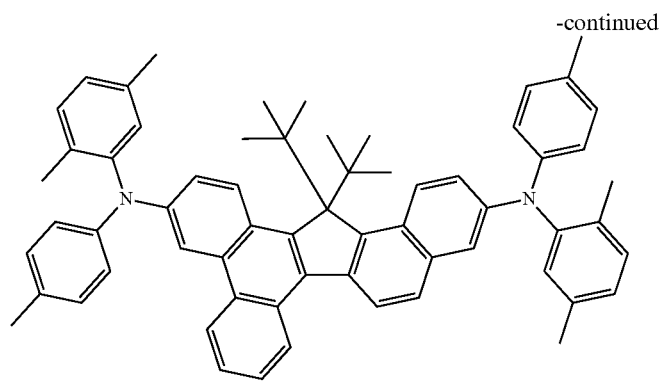
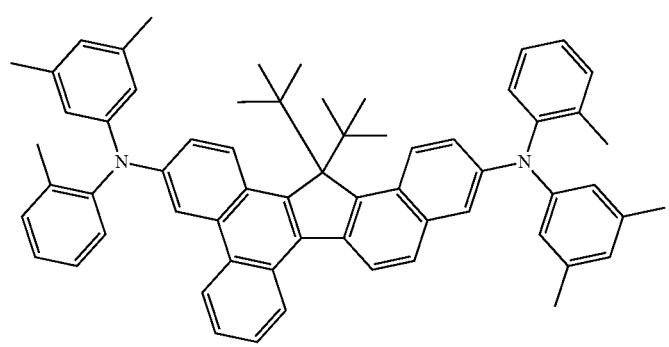
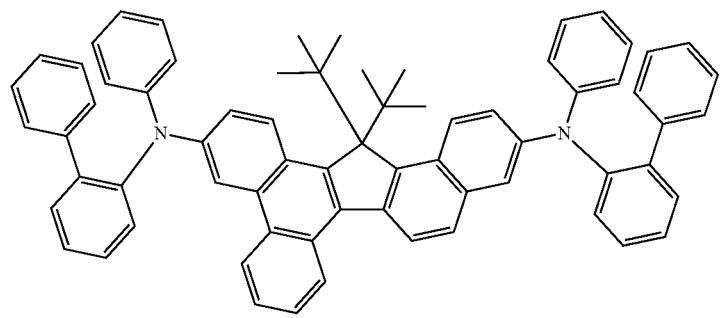
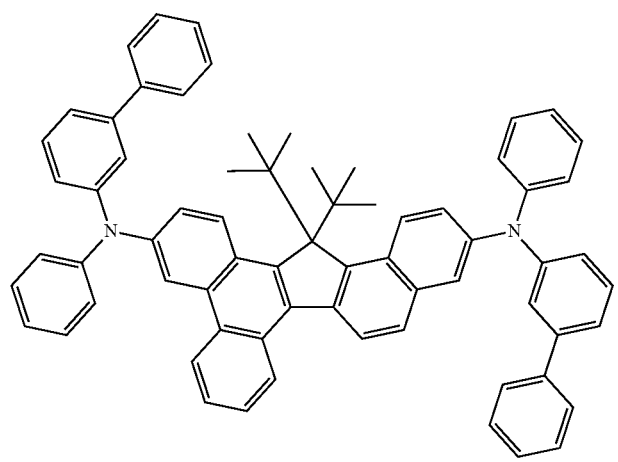

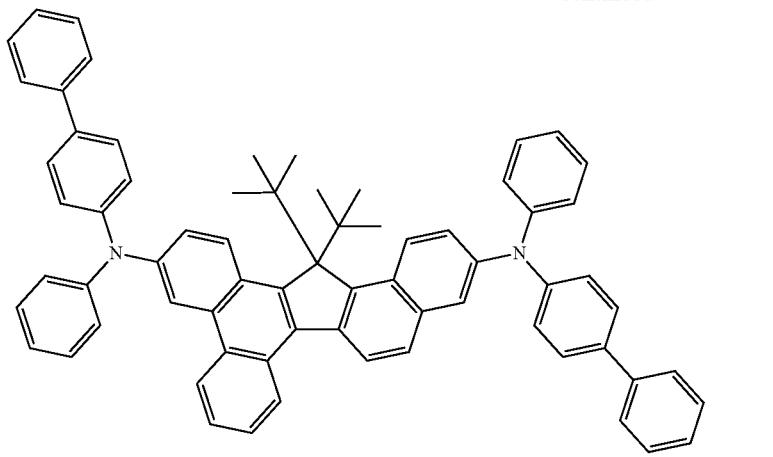
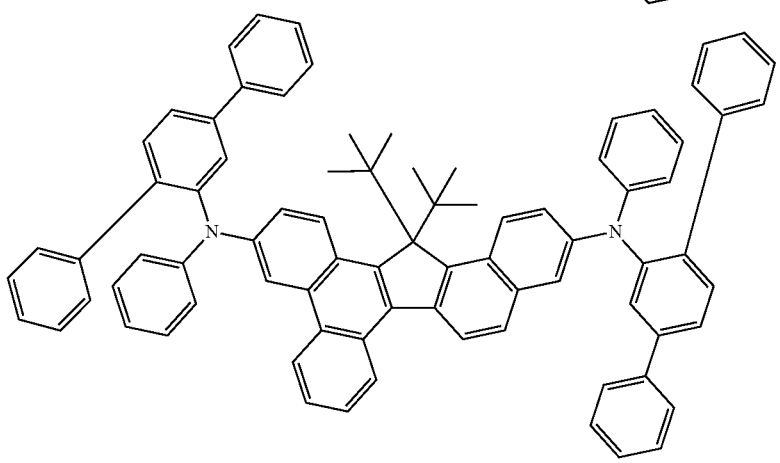
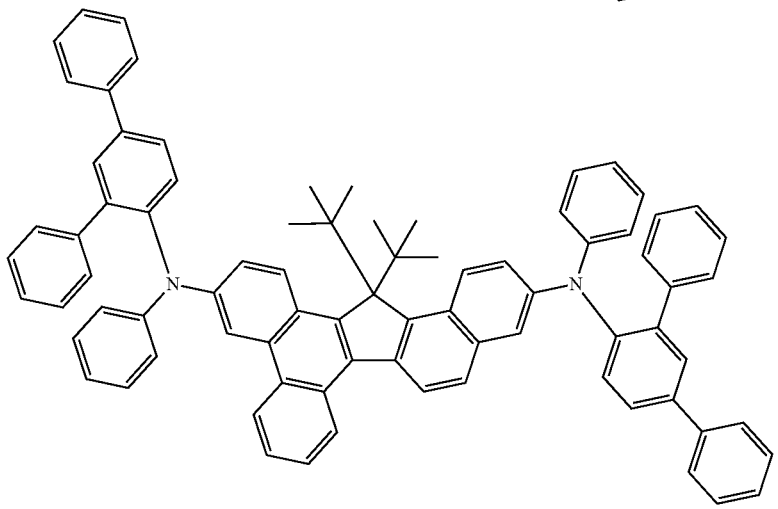
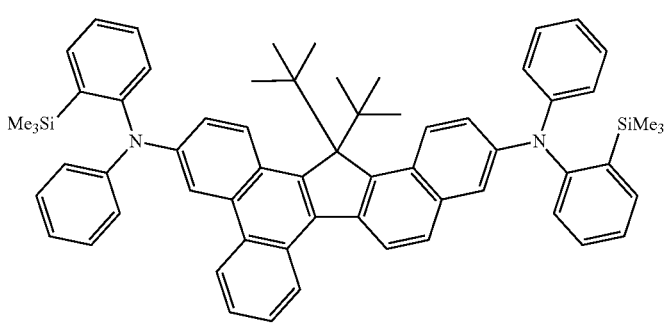

-continued
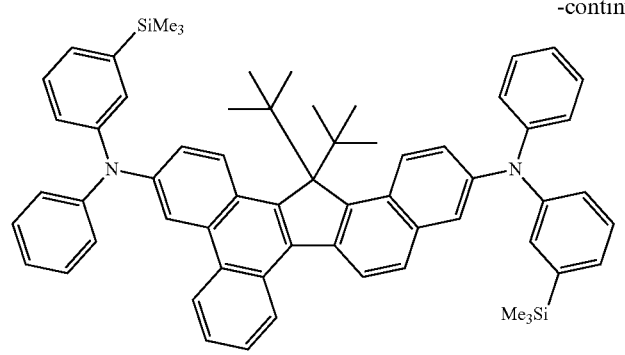
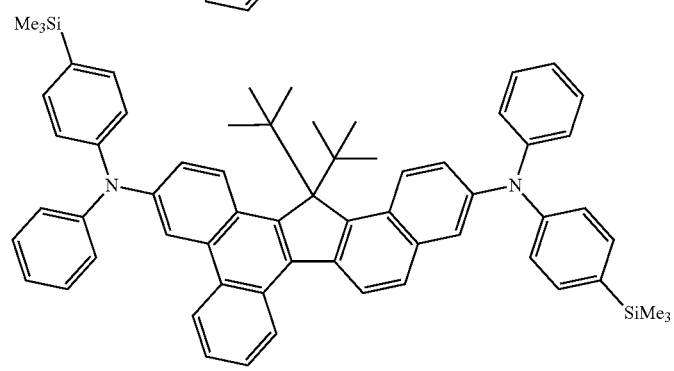
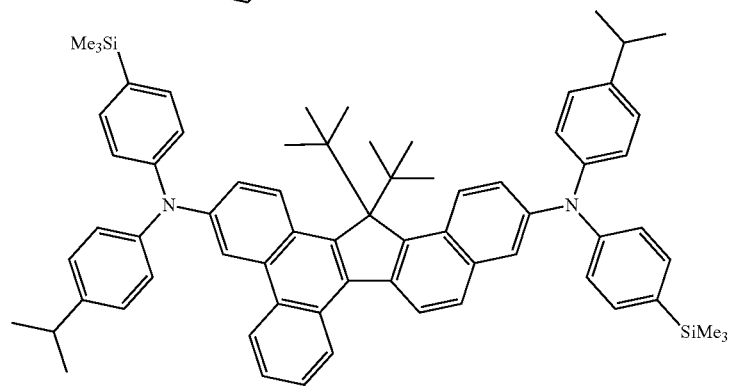
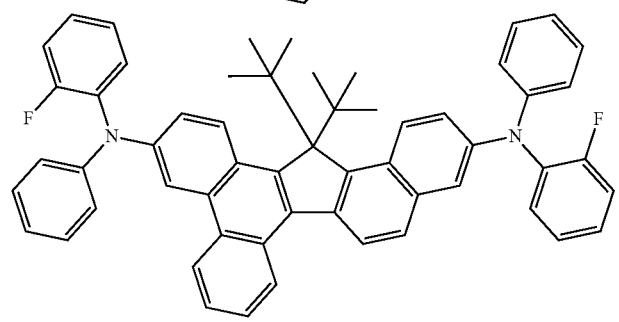
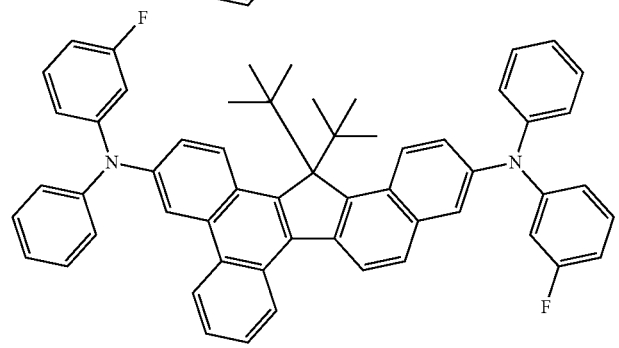

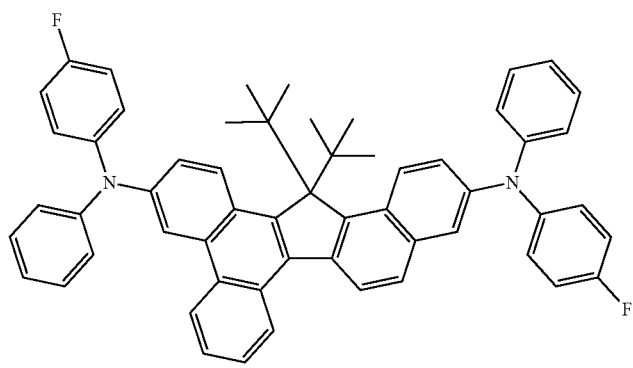
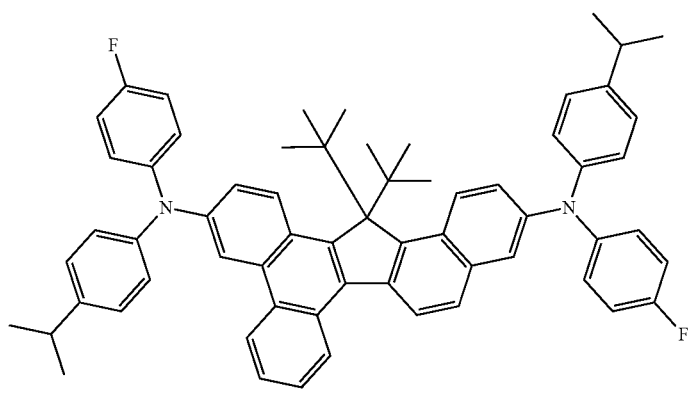
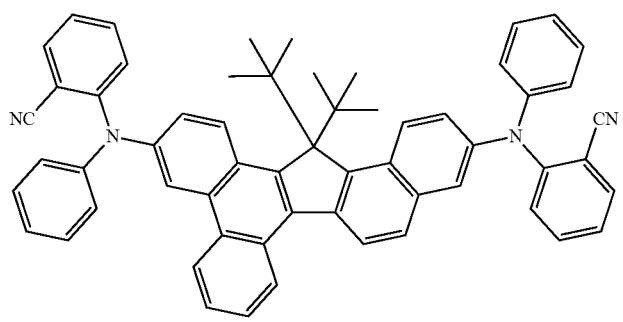
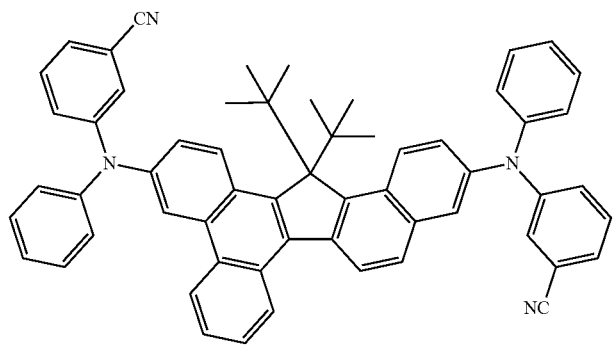

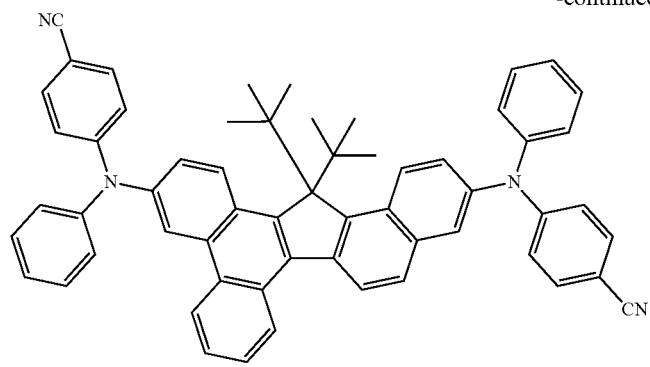
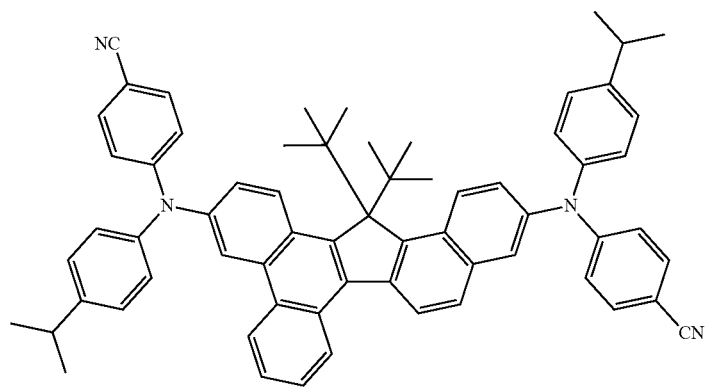
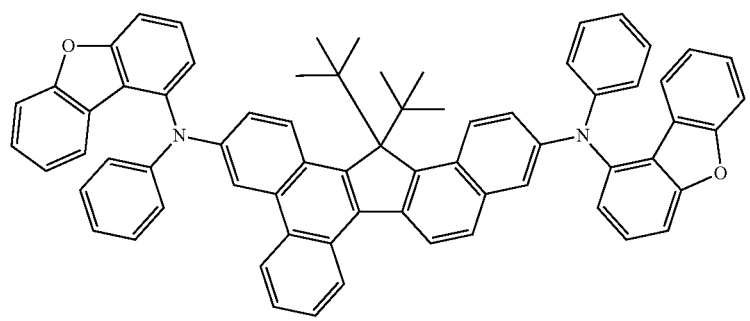
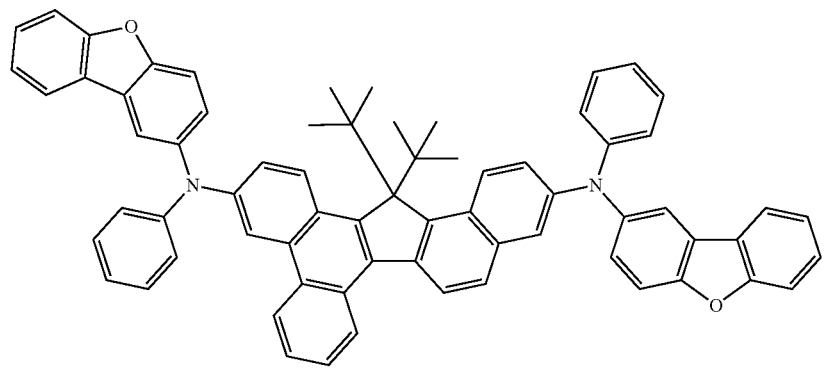

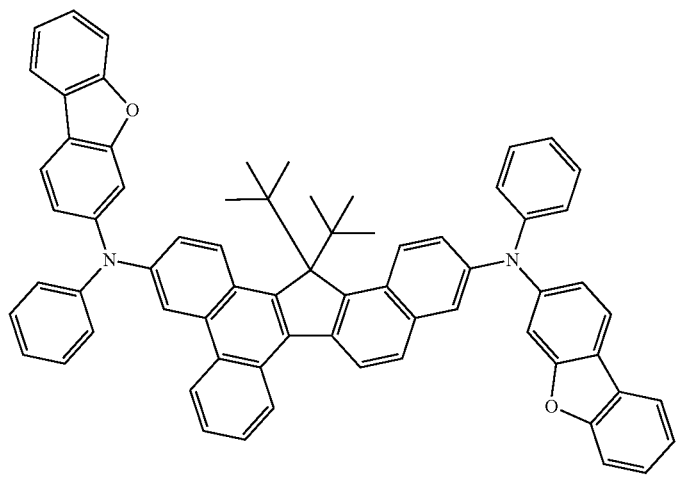
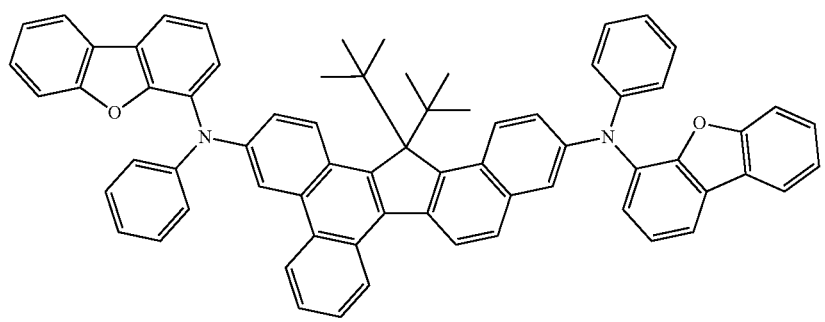
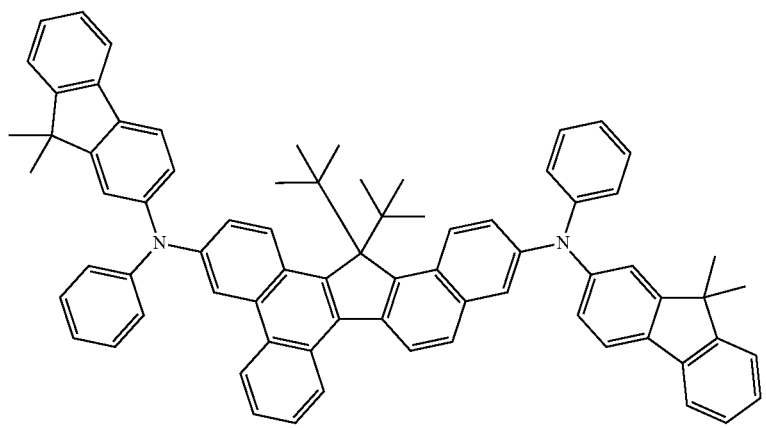

-continued
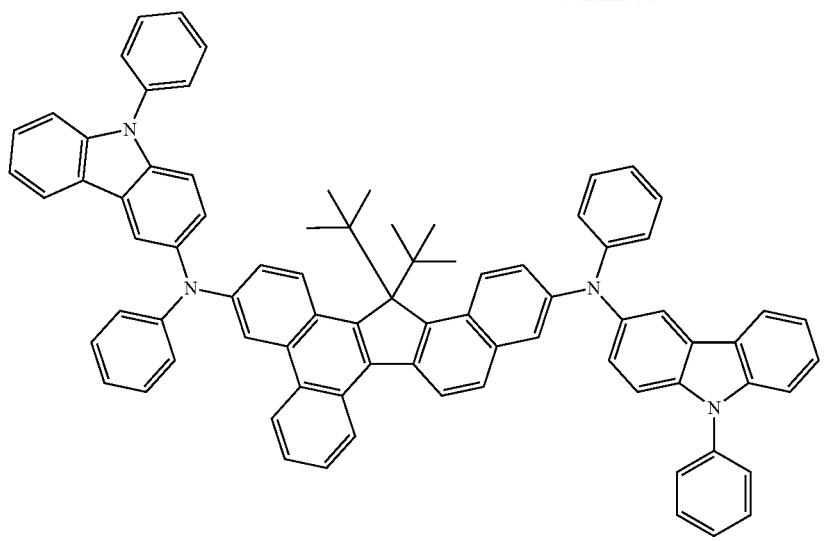
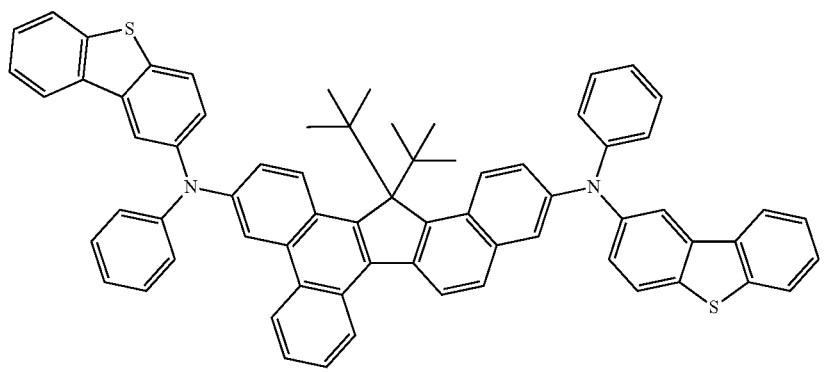
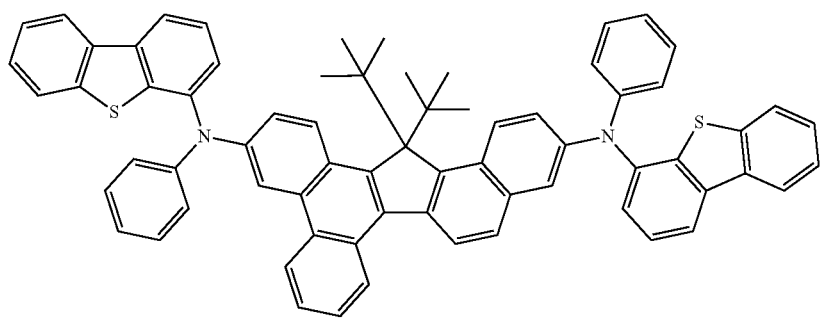
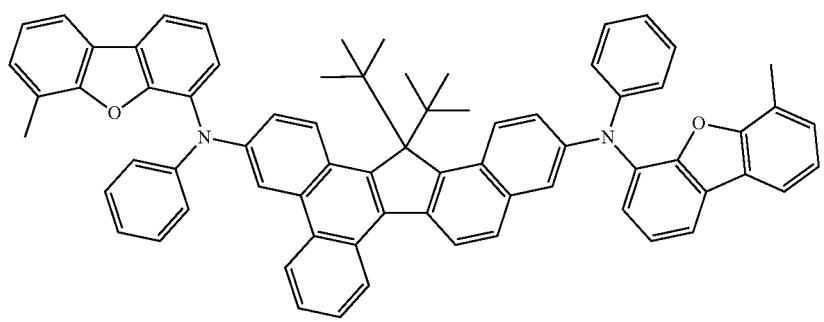

-continued
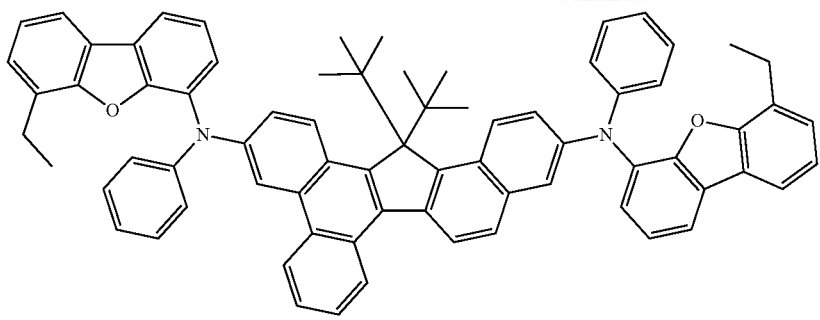
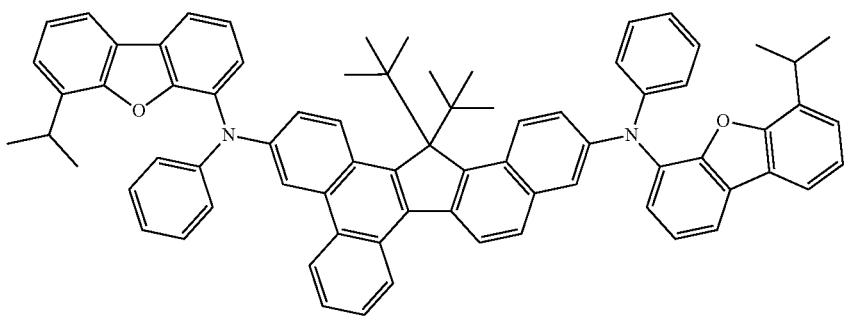
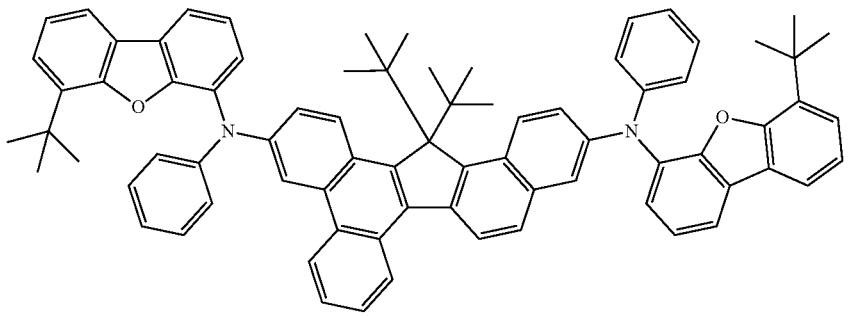
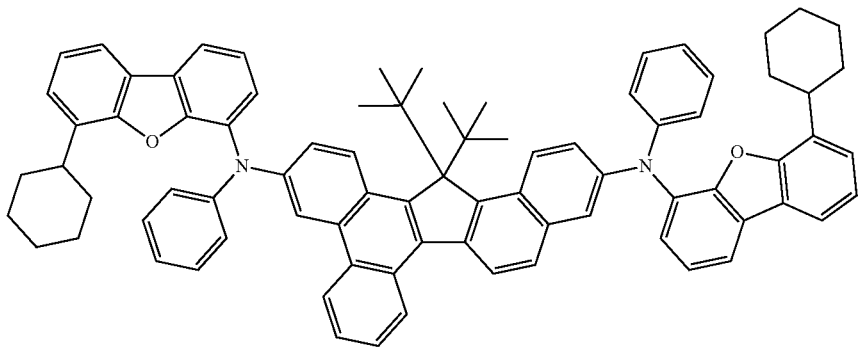
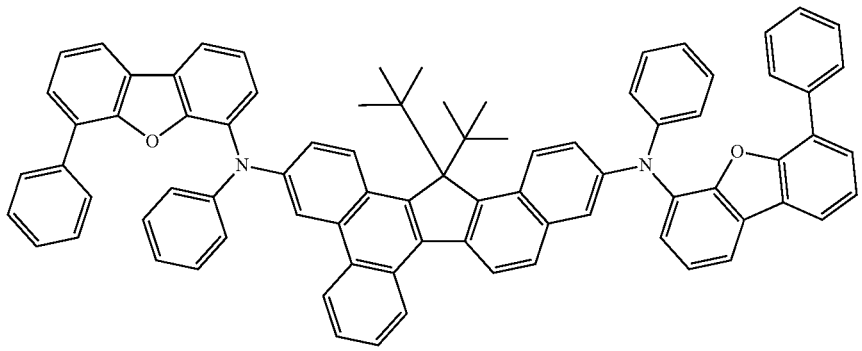

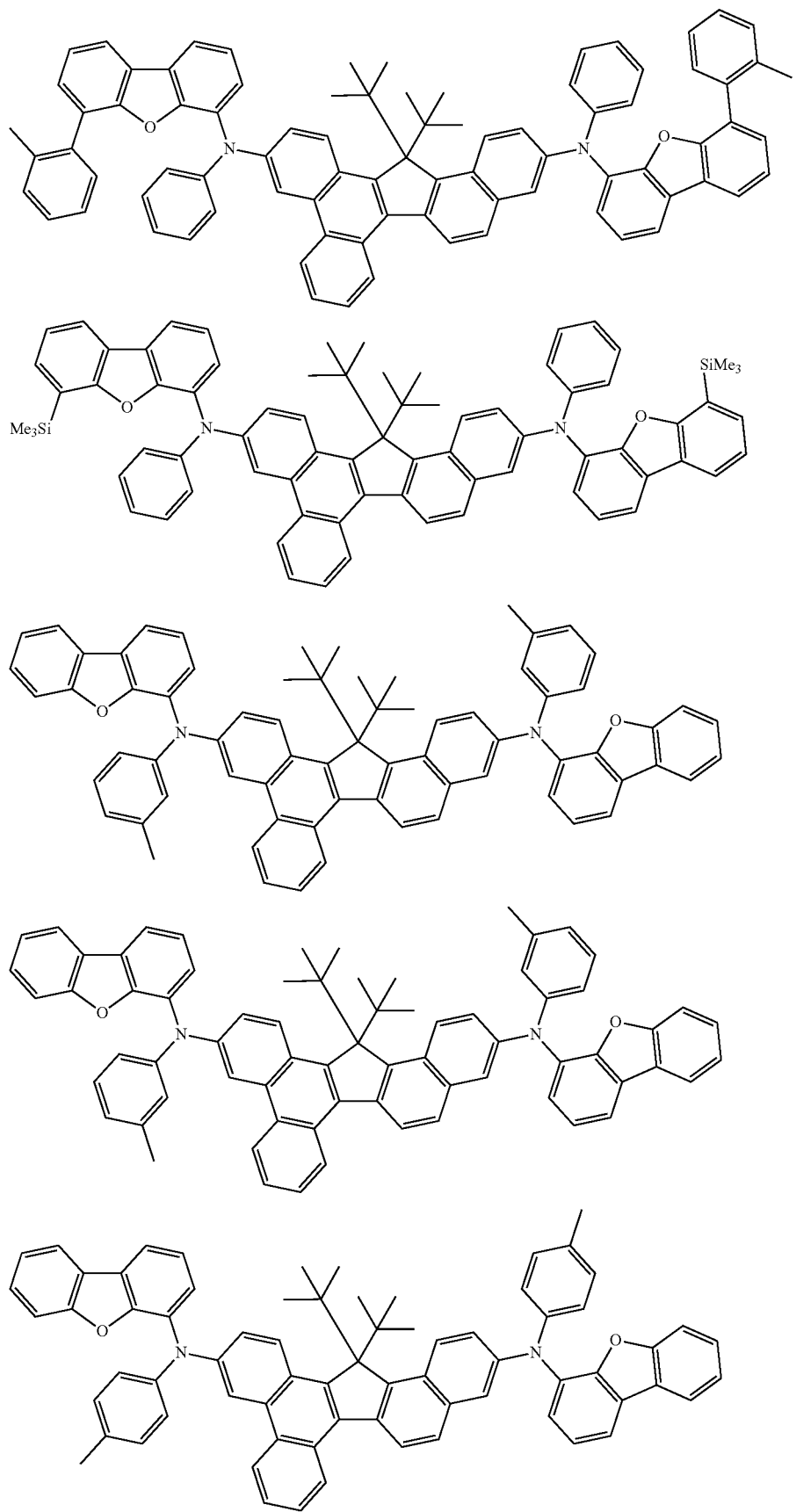

-continued
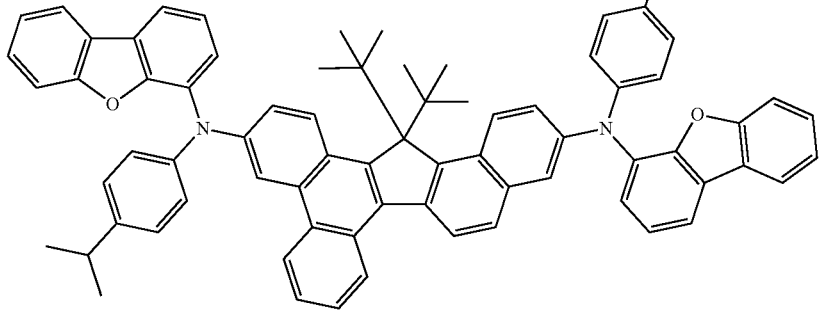
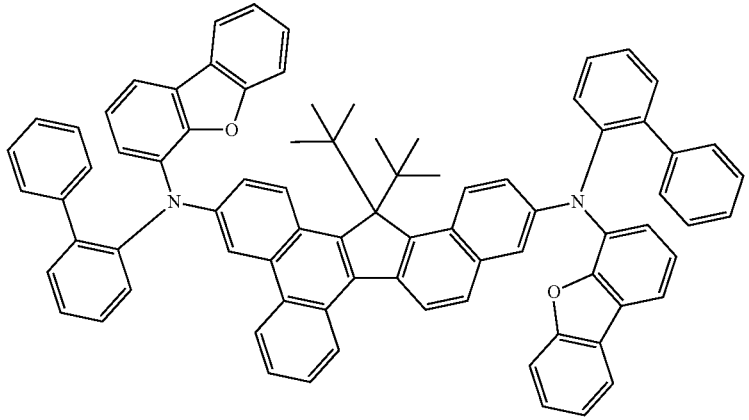
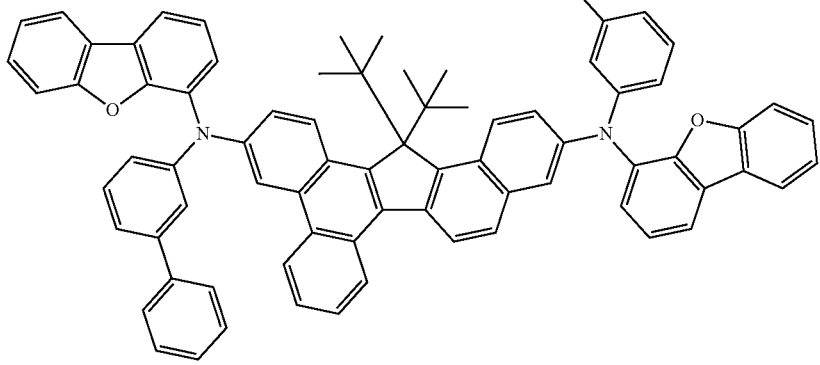
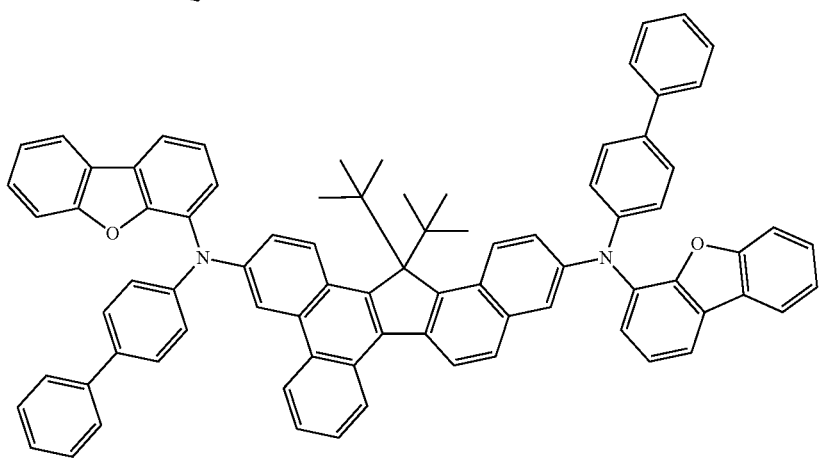

-continued
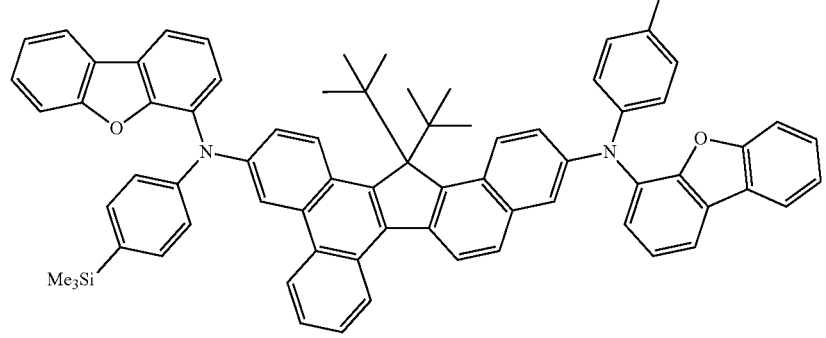
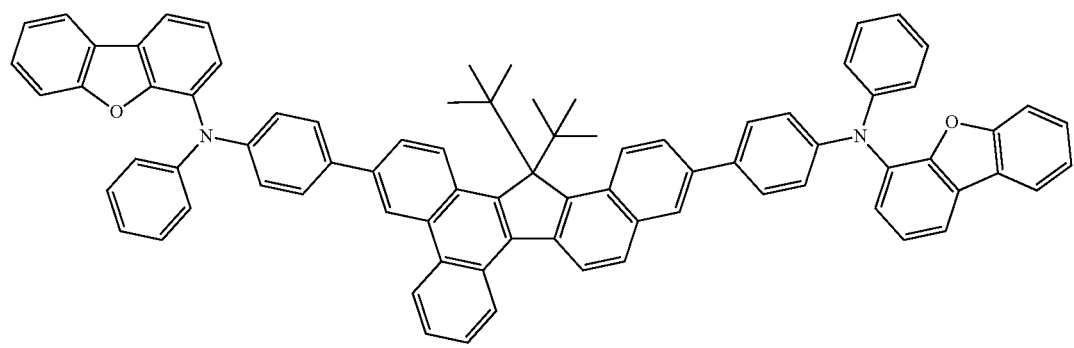
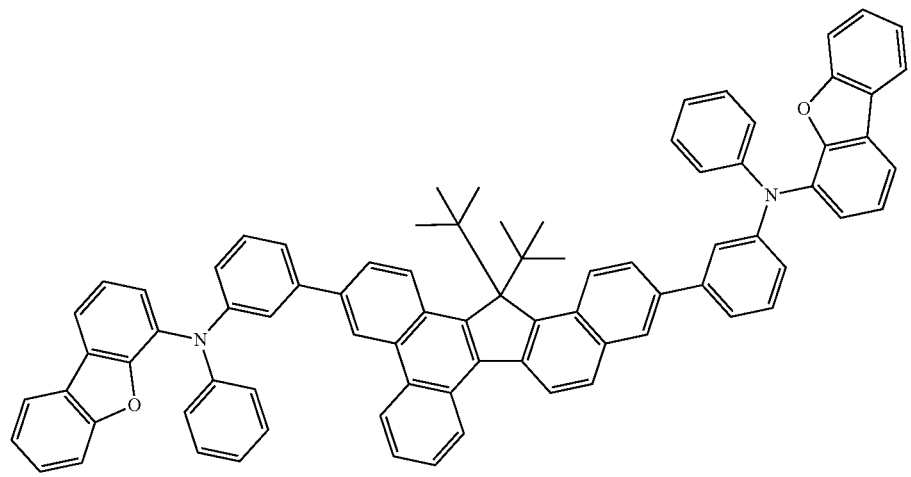
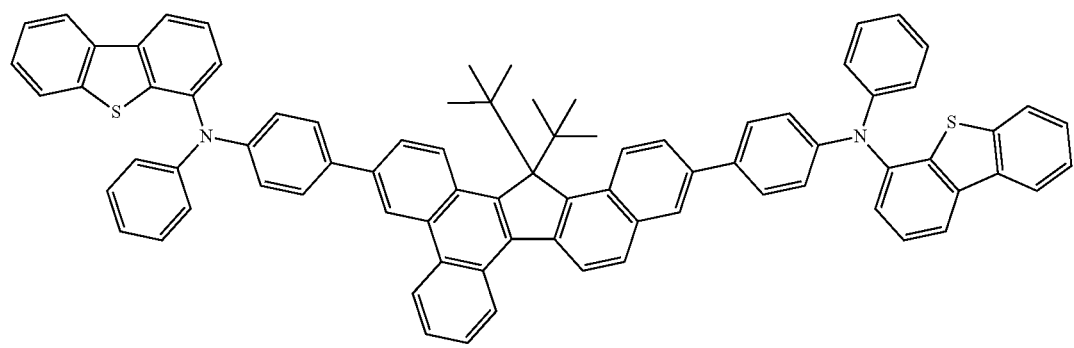

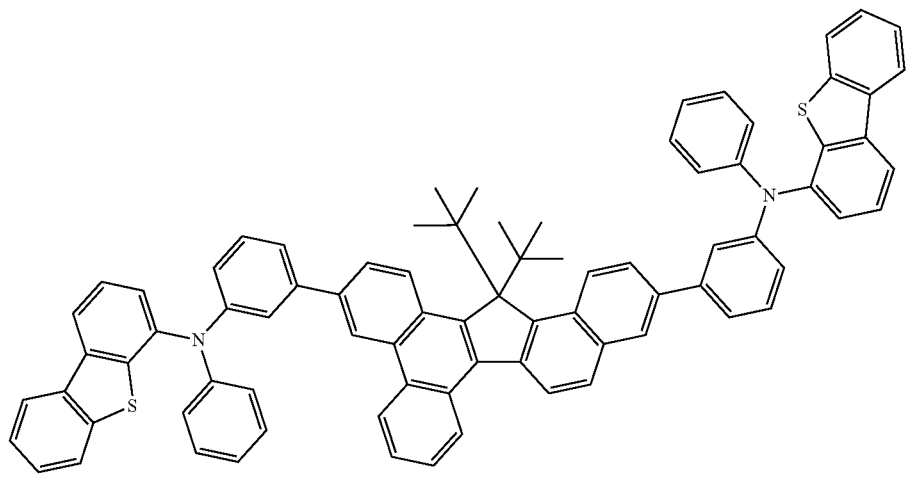
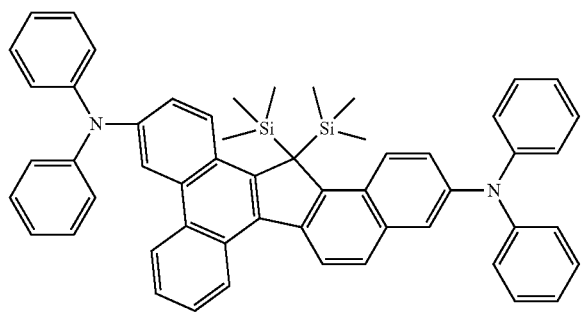
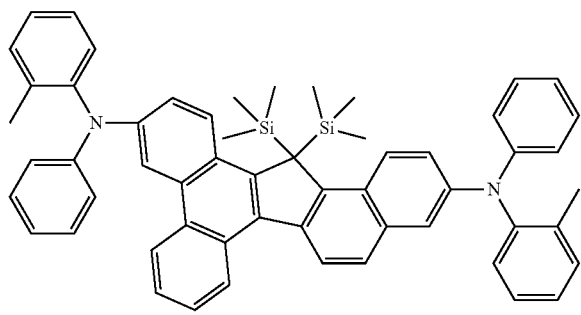
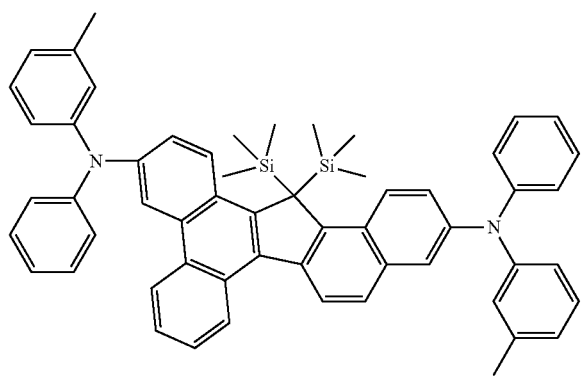

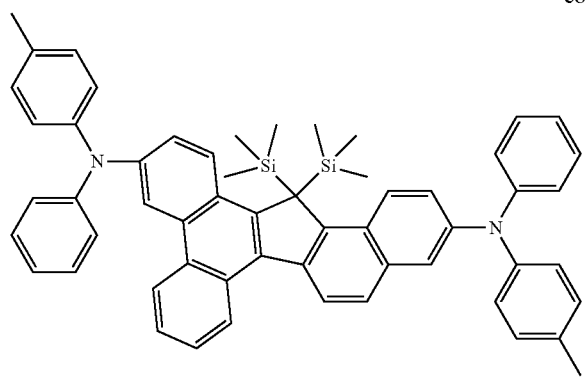
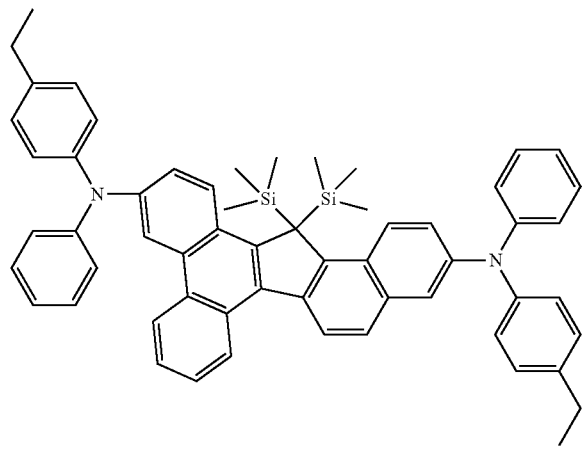
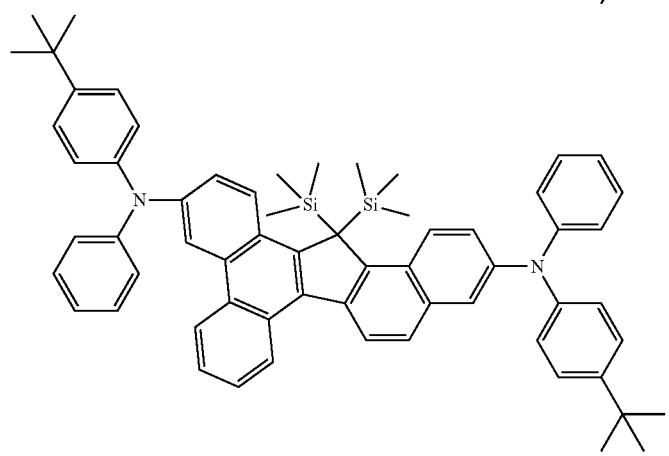

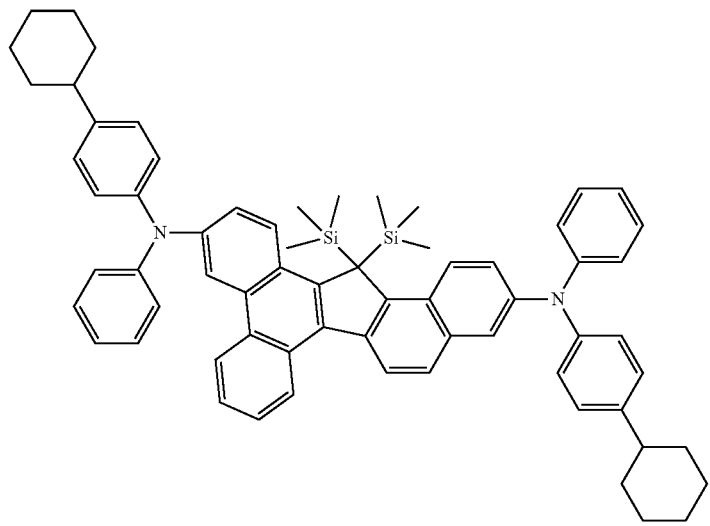
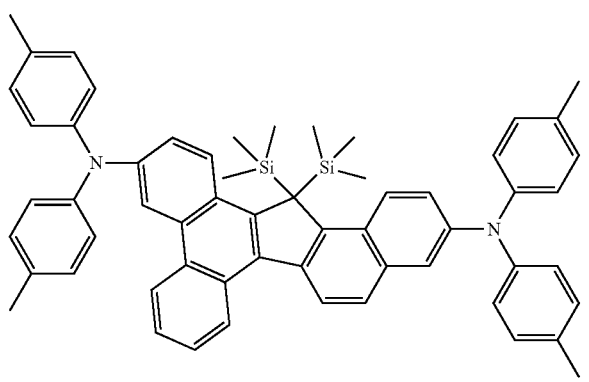
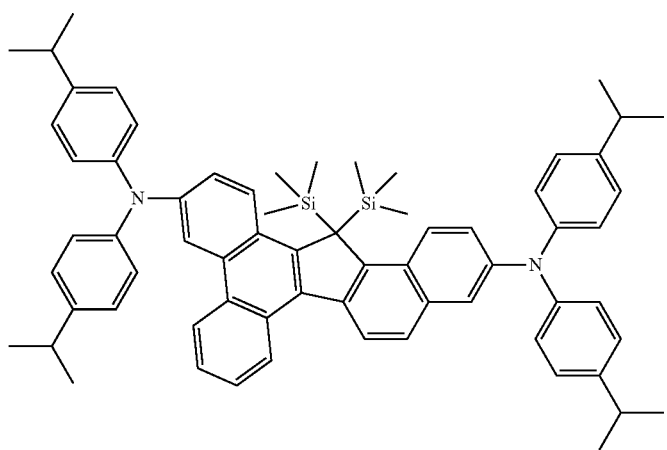

-continued
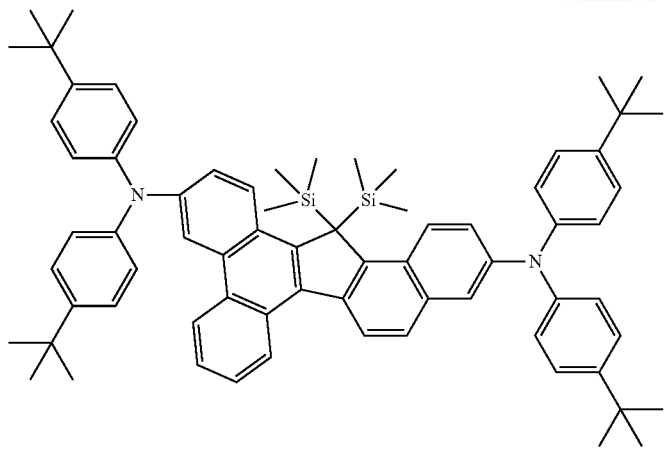
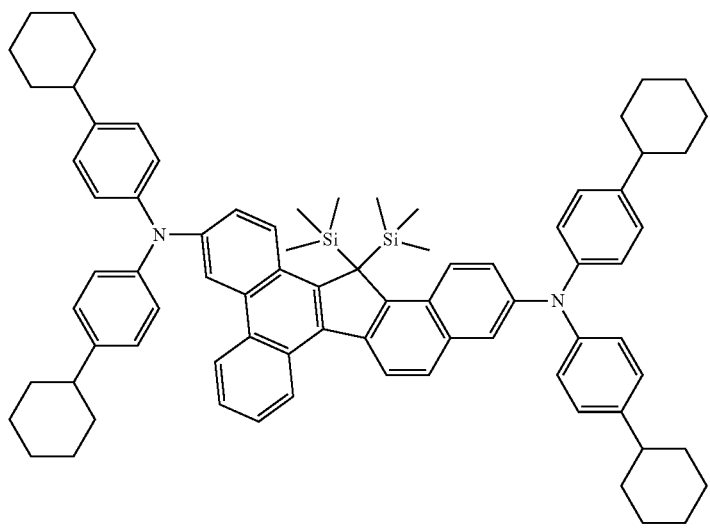
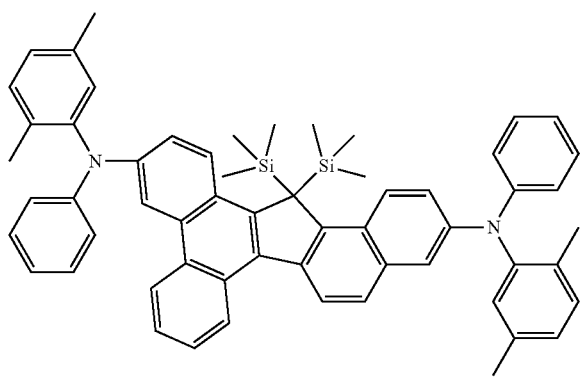

-continued
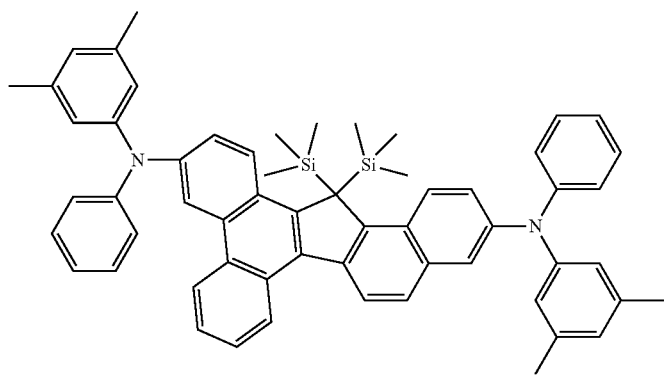
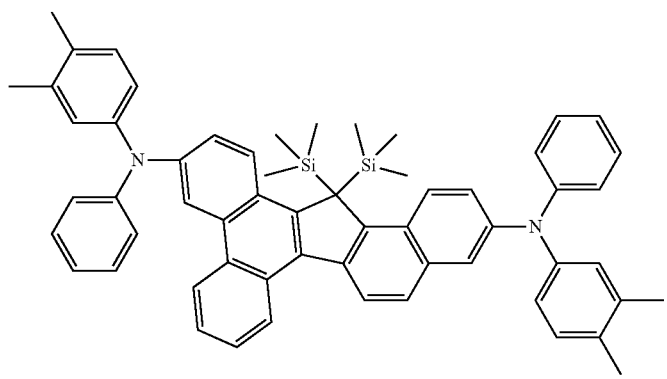
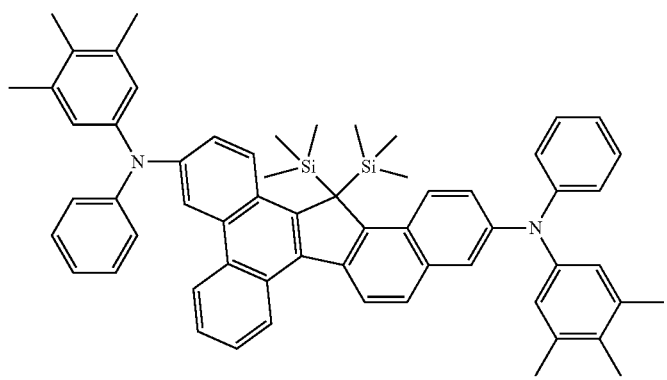
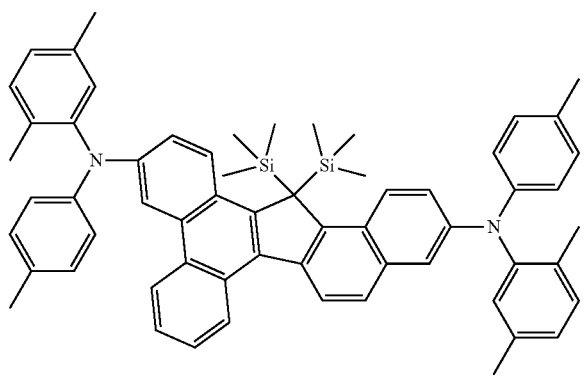

-continued
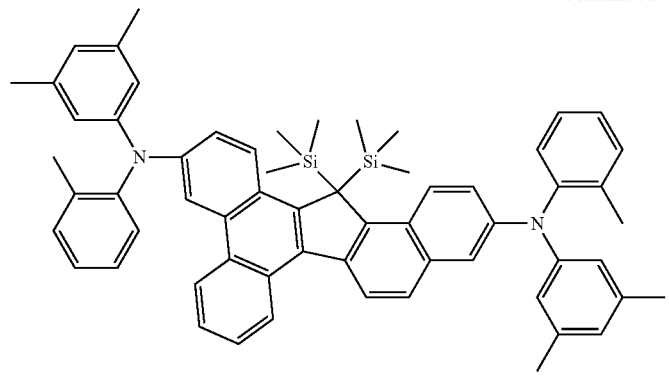
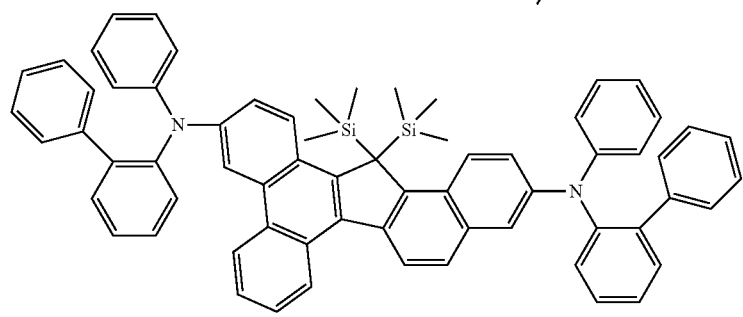
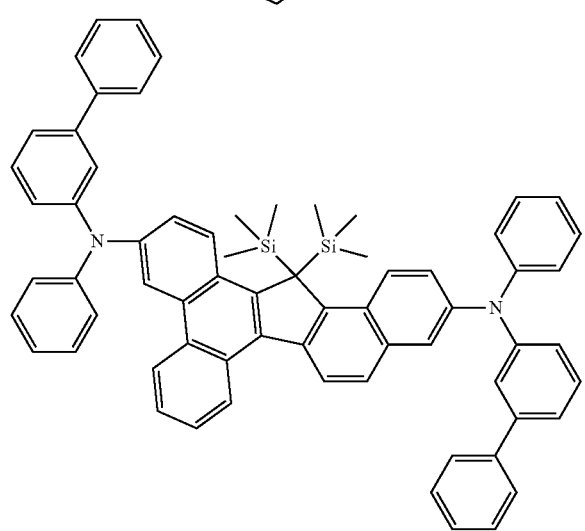
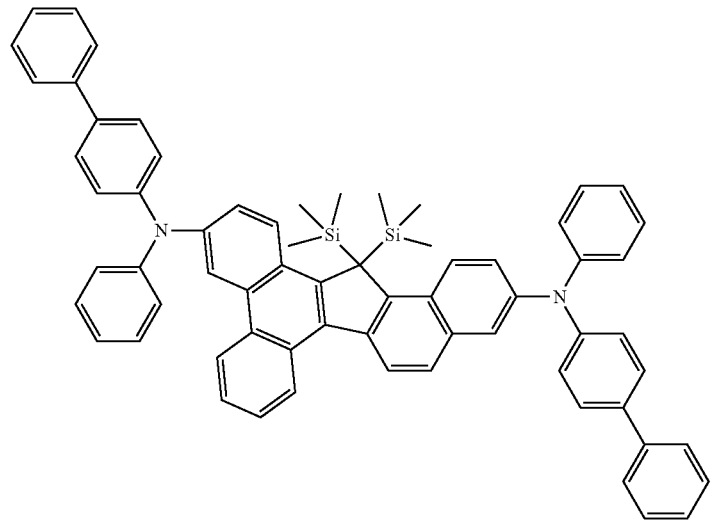

-continued
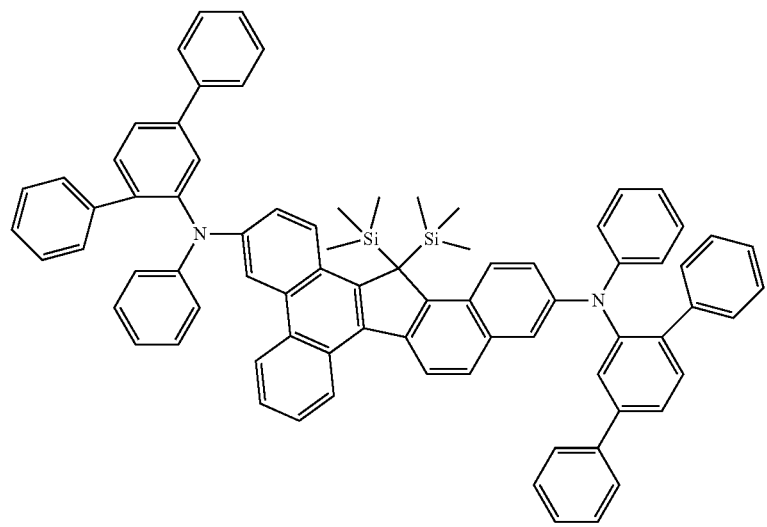
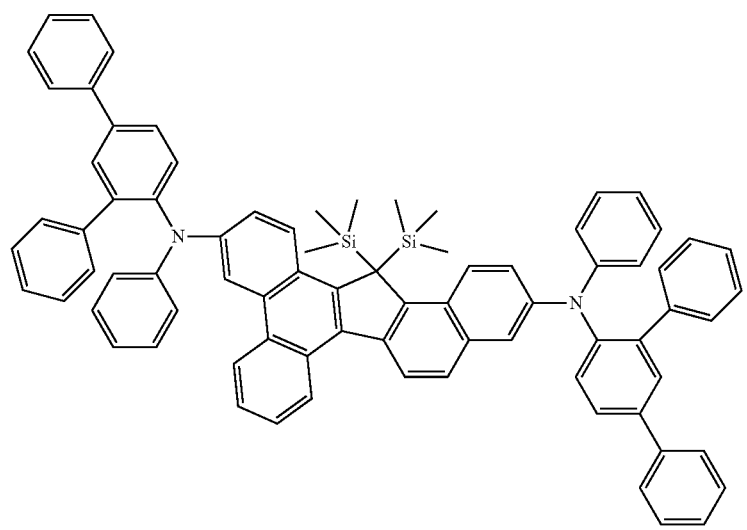
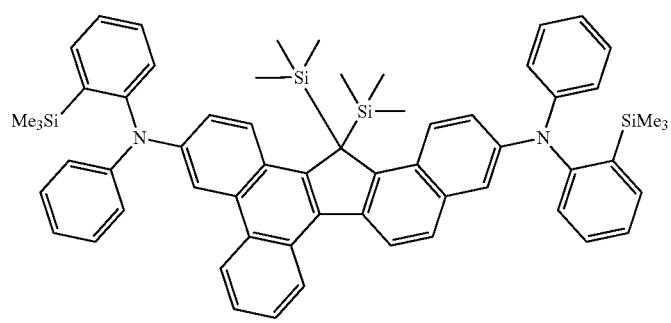
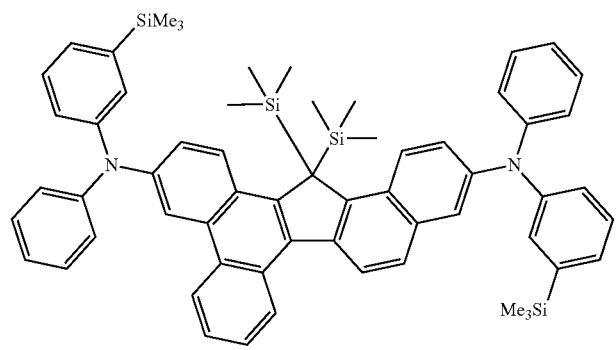

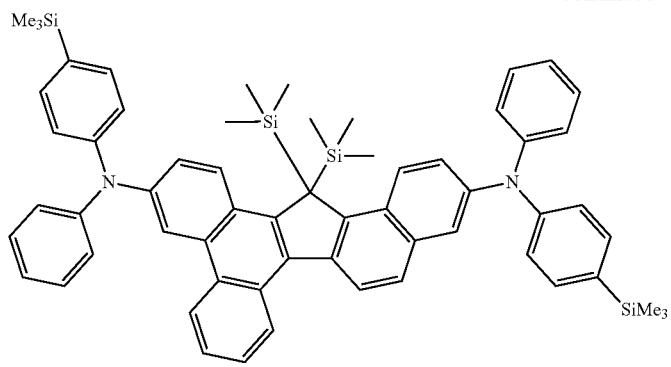
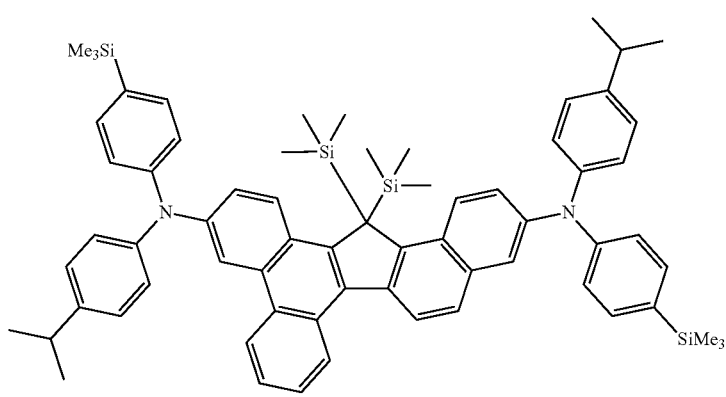
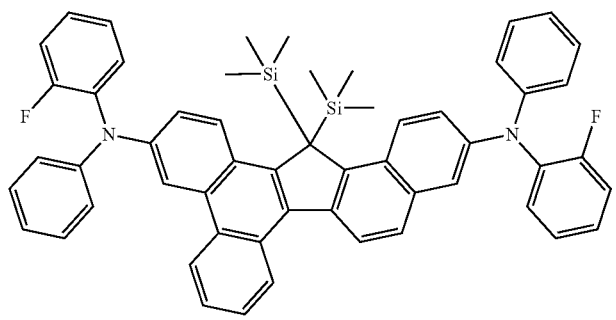
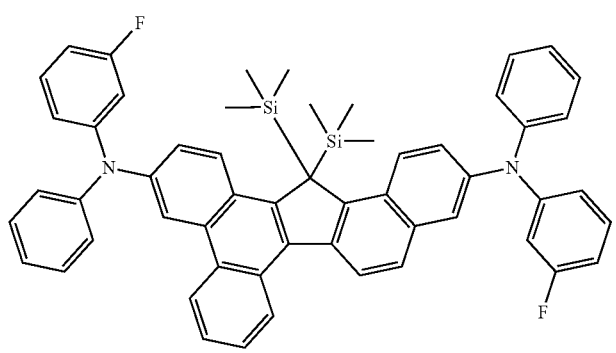

-continued
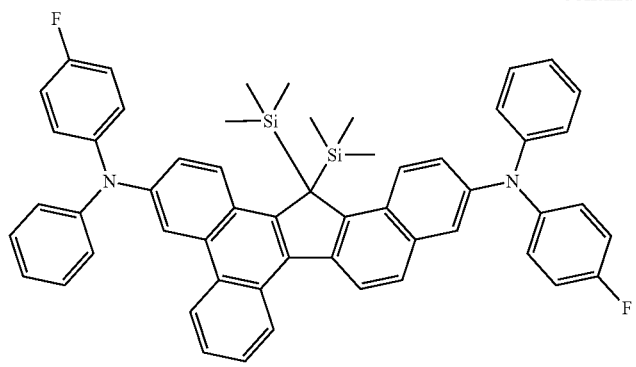
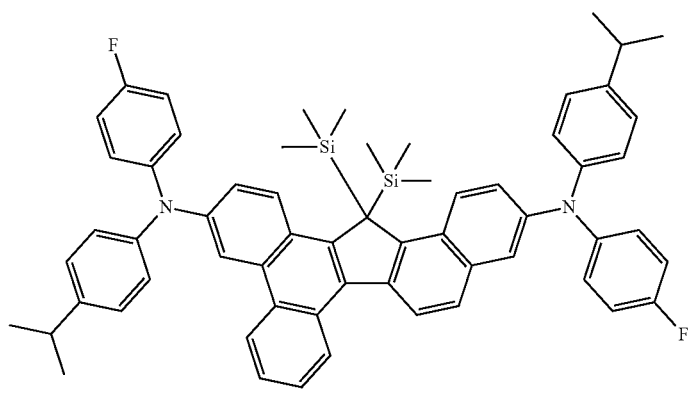
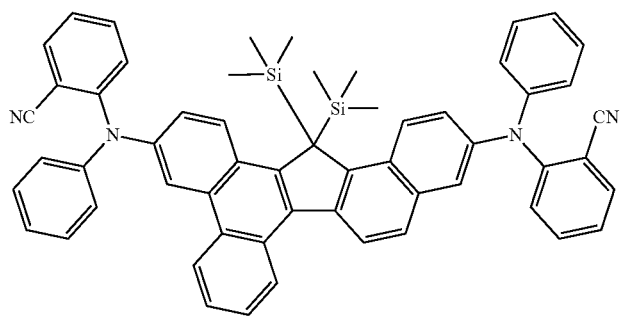
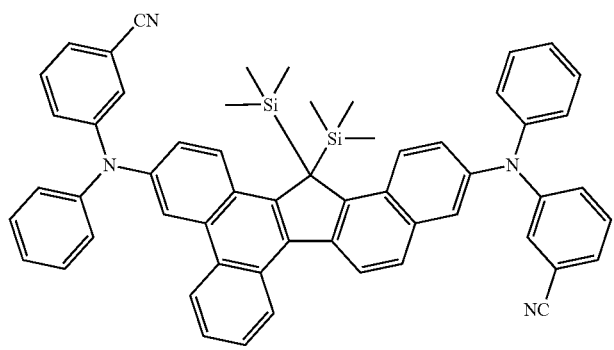

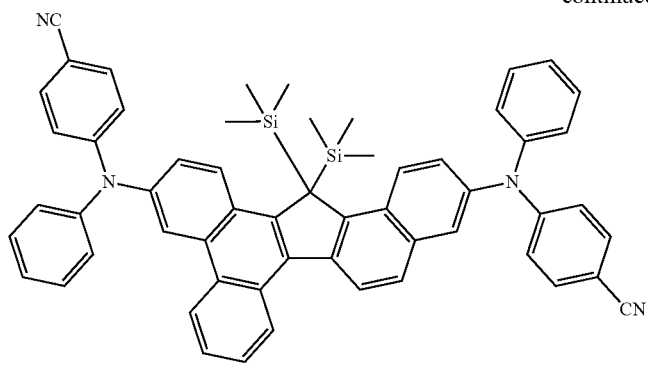
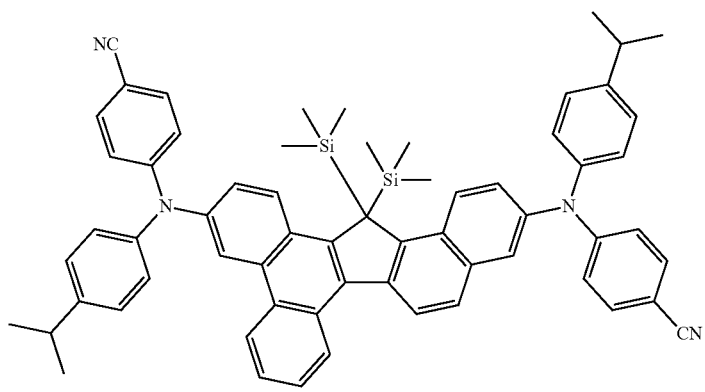
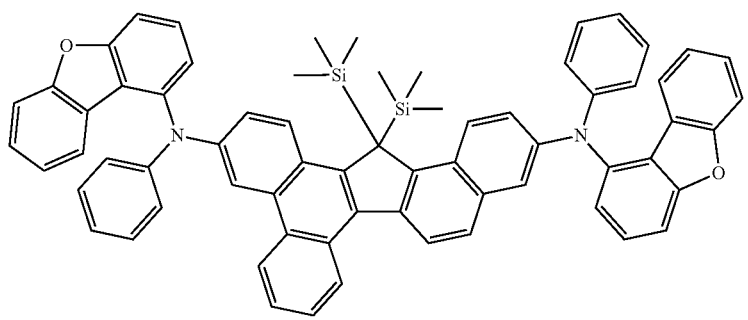
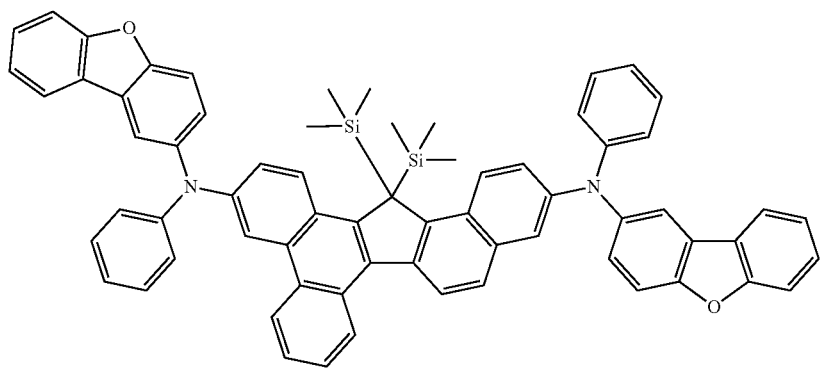

-continued
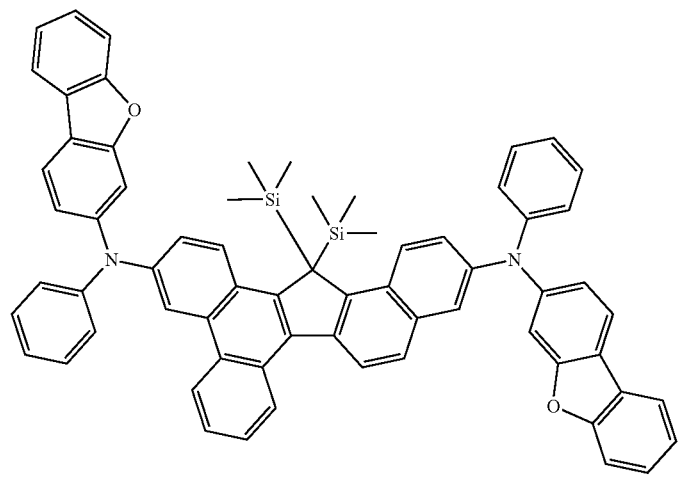
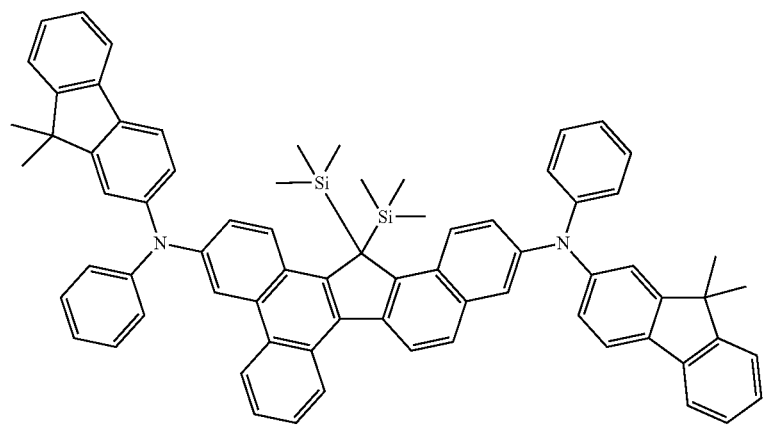

-continued
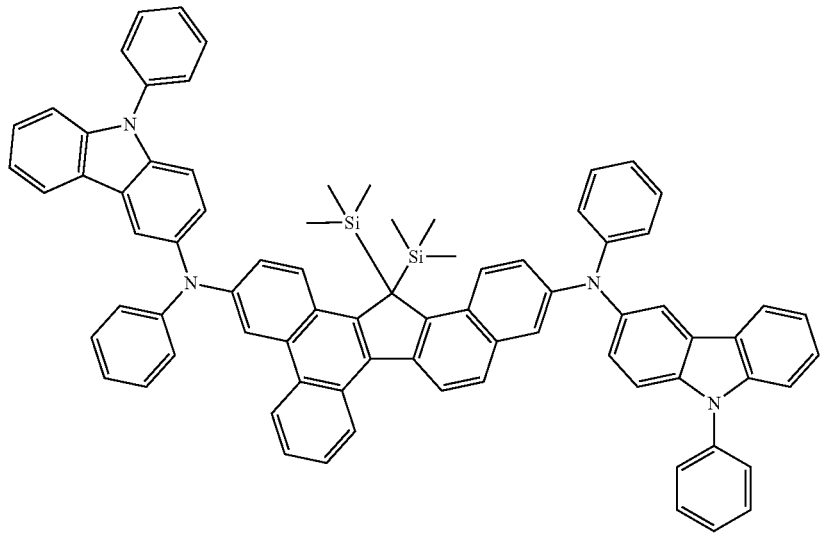
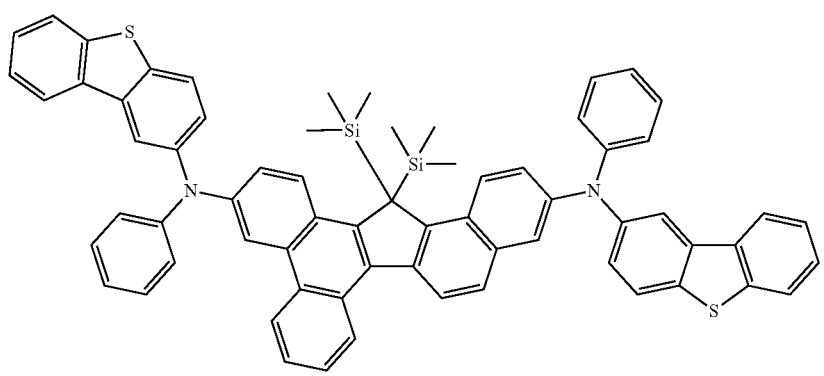
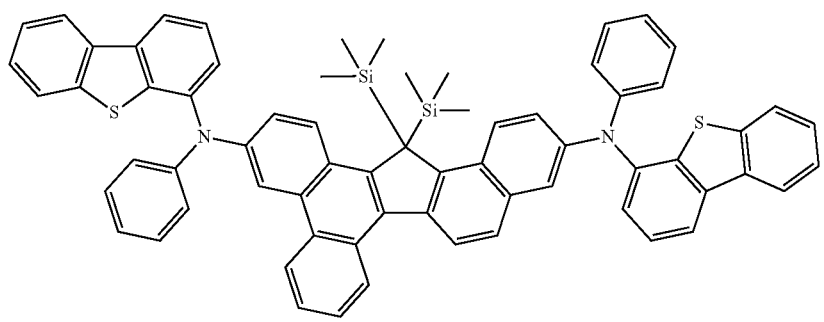
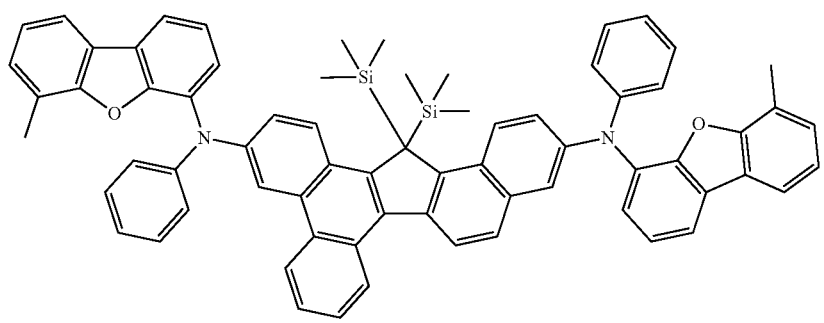

-continued
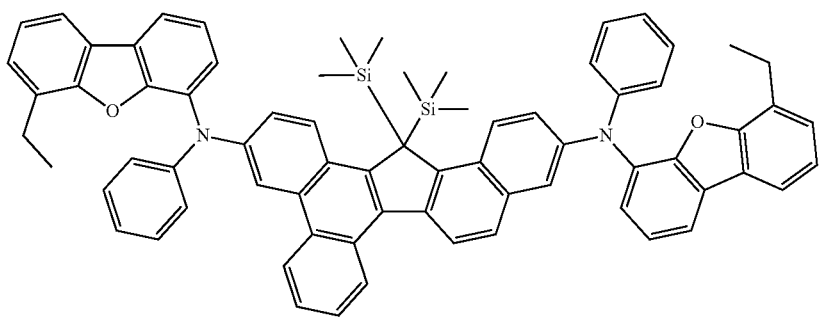
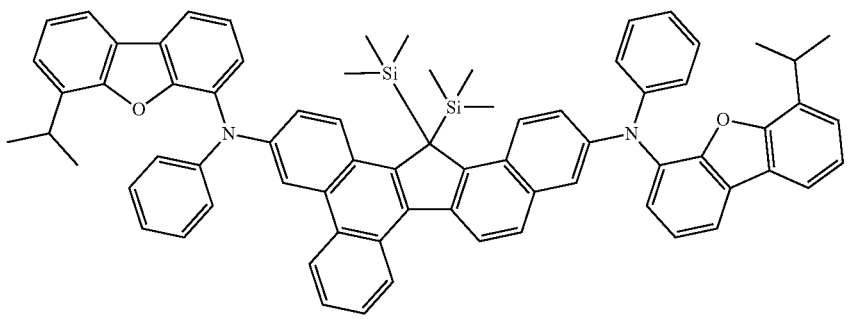
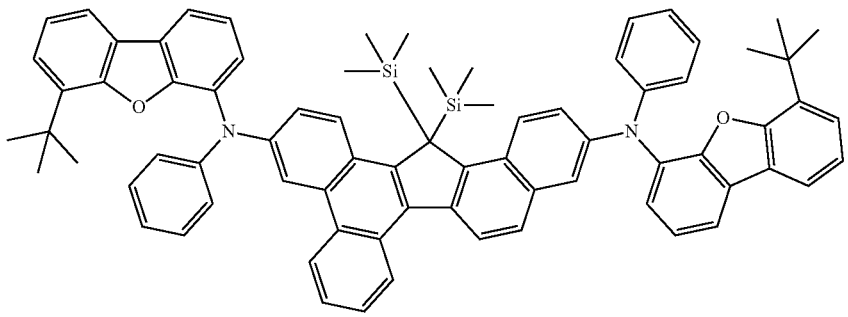
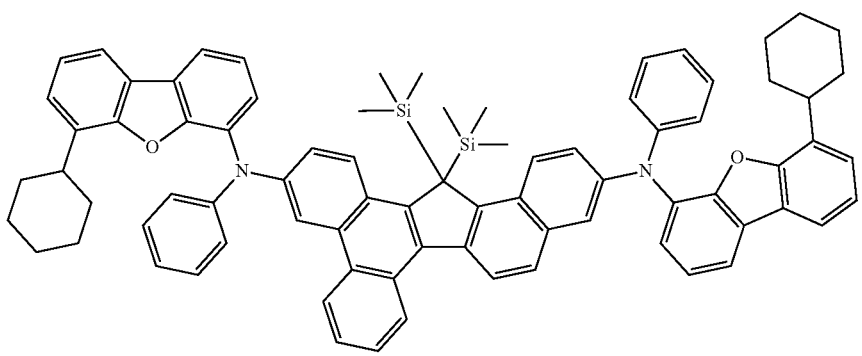
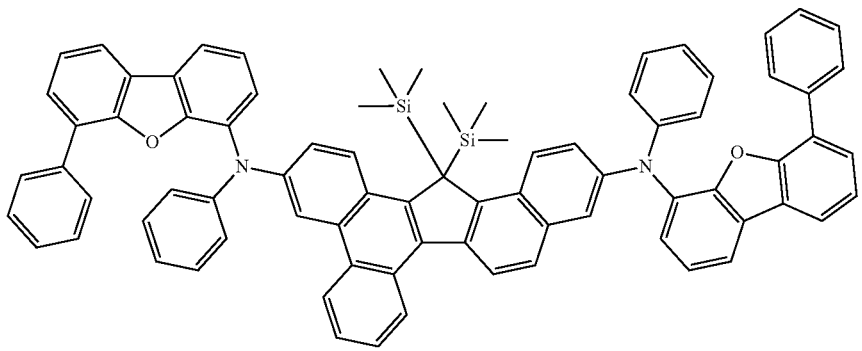

-continued
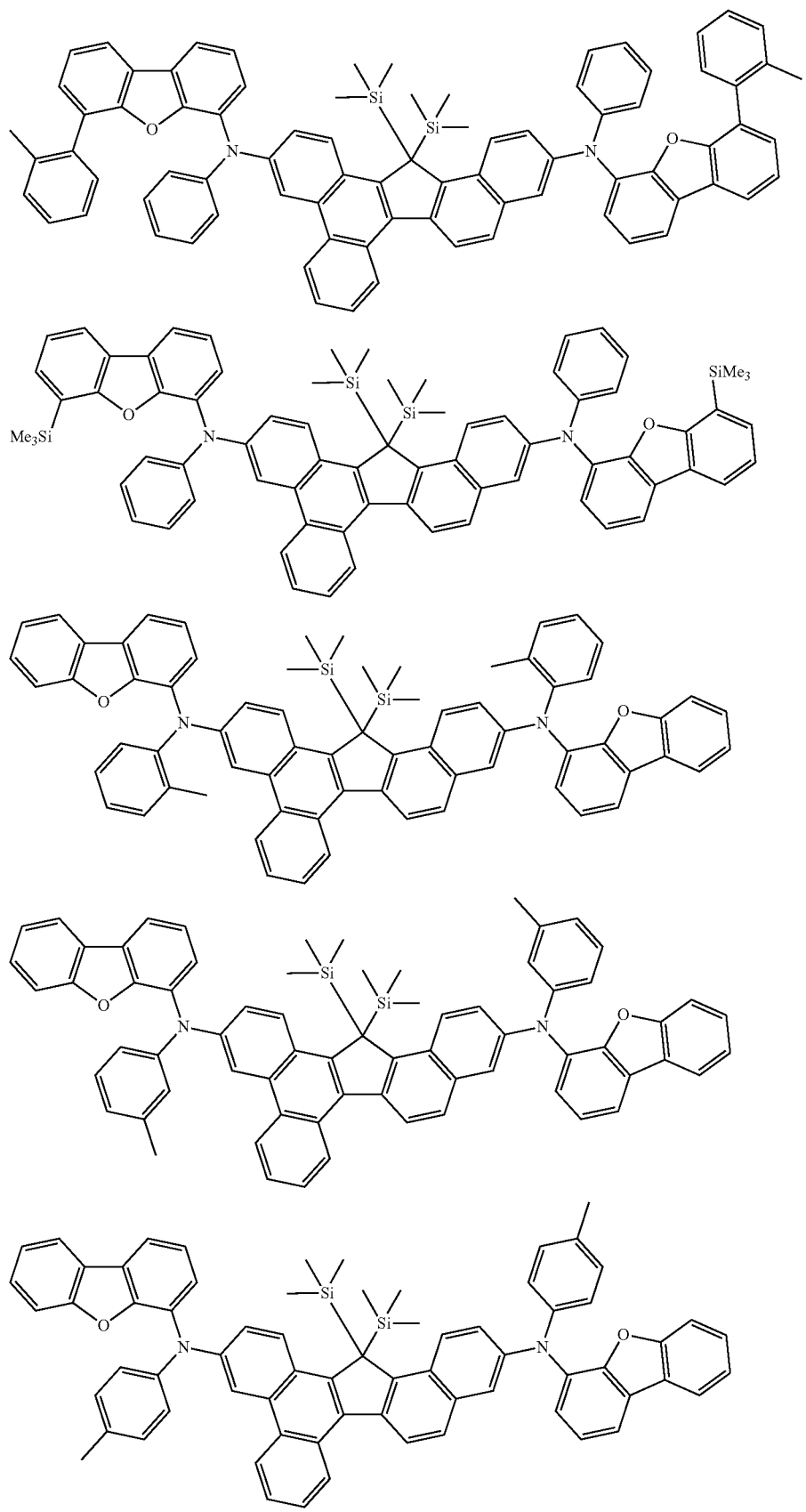

-continued
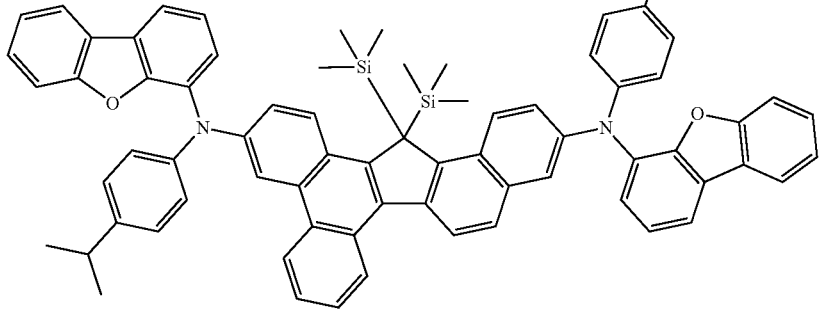
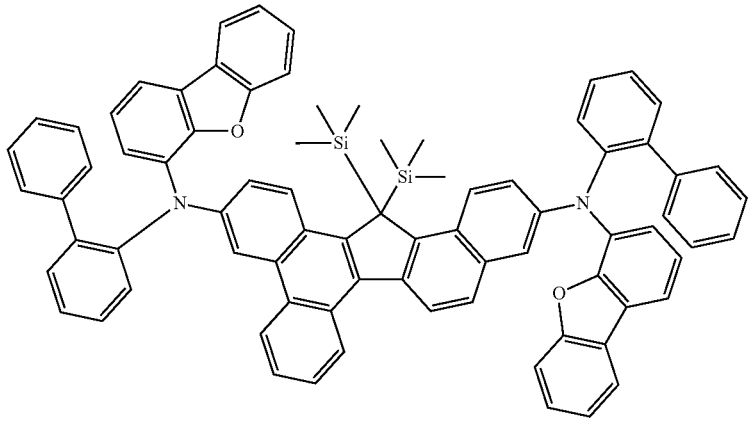
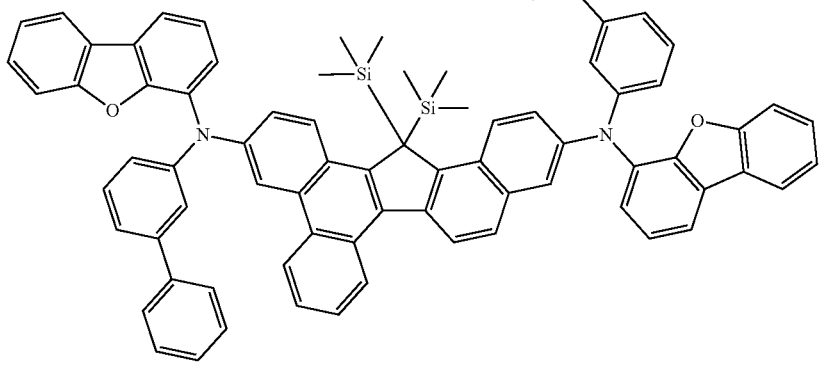
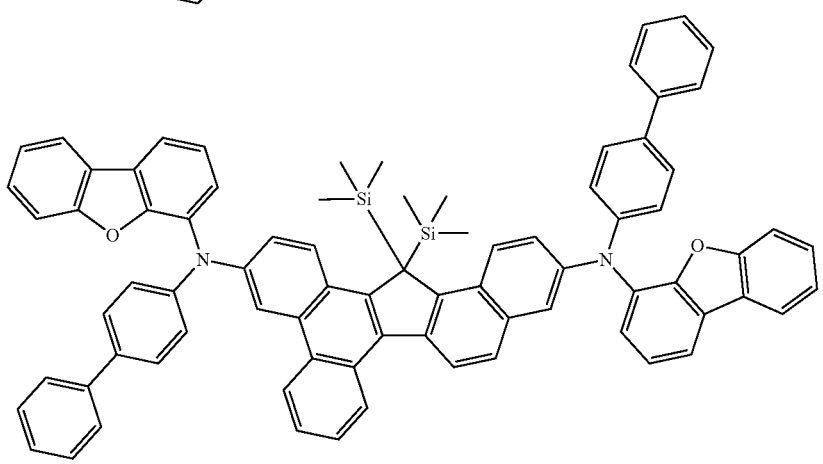

-continued
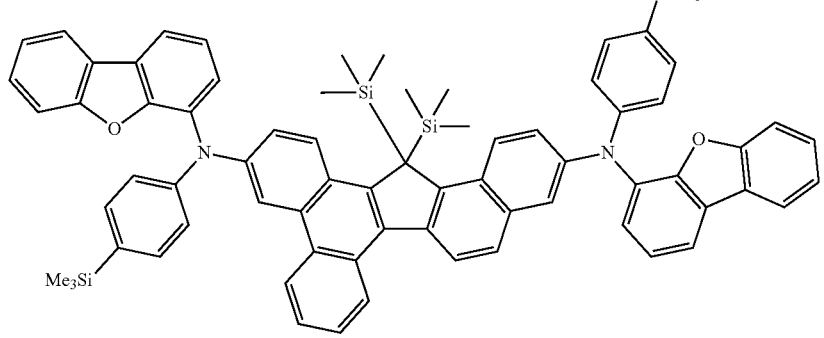
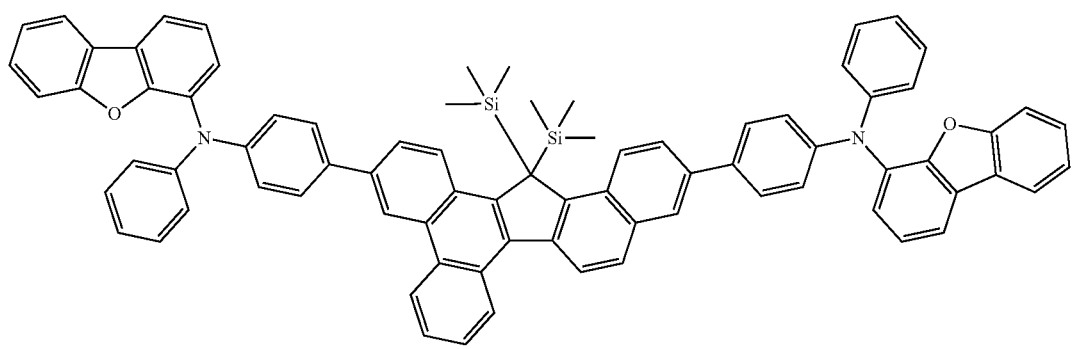
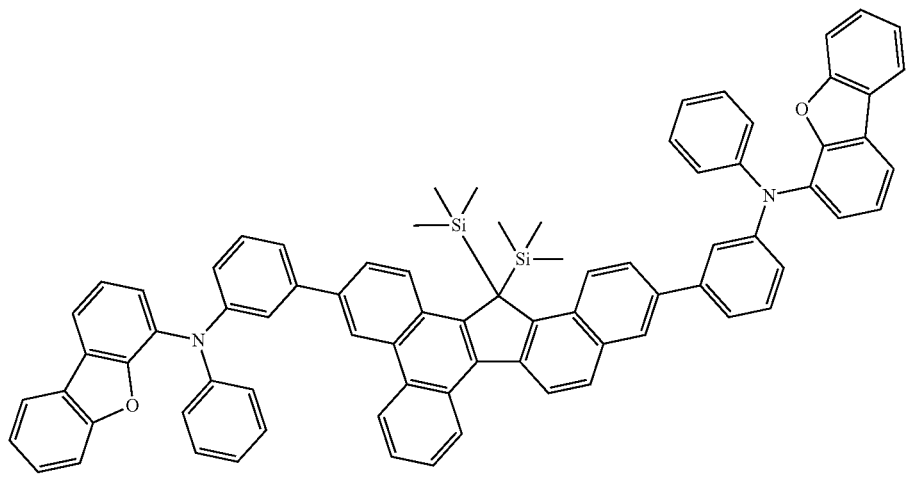
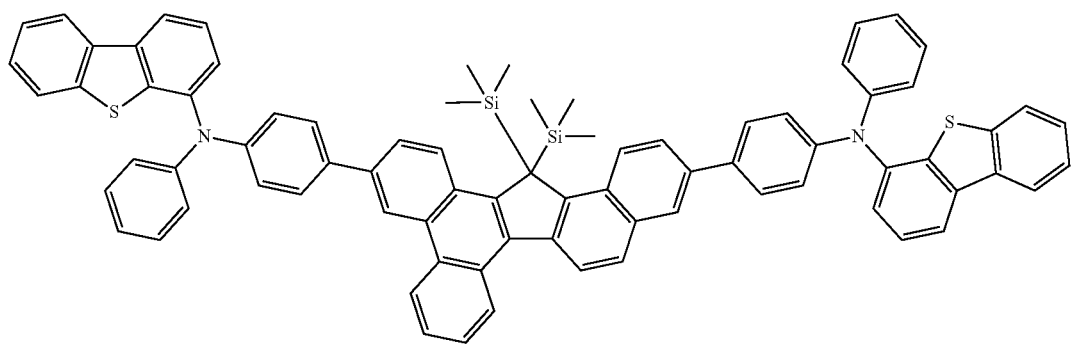

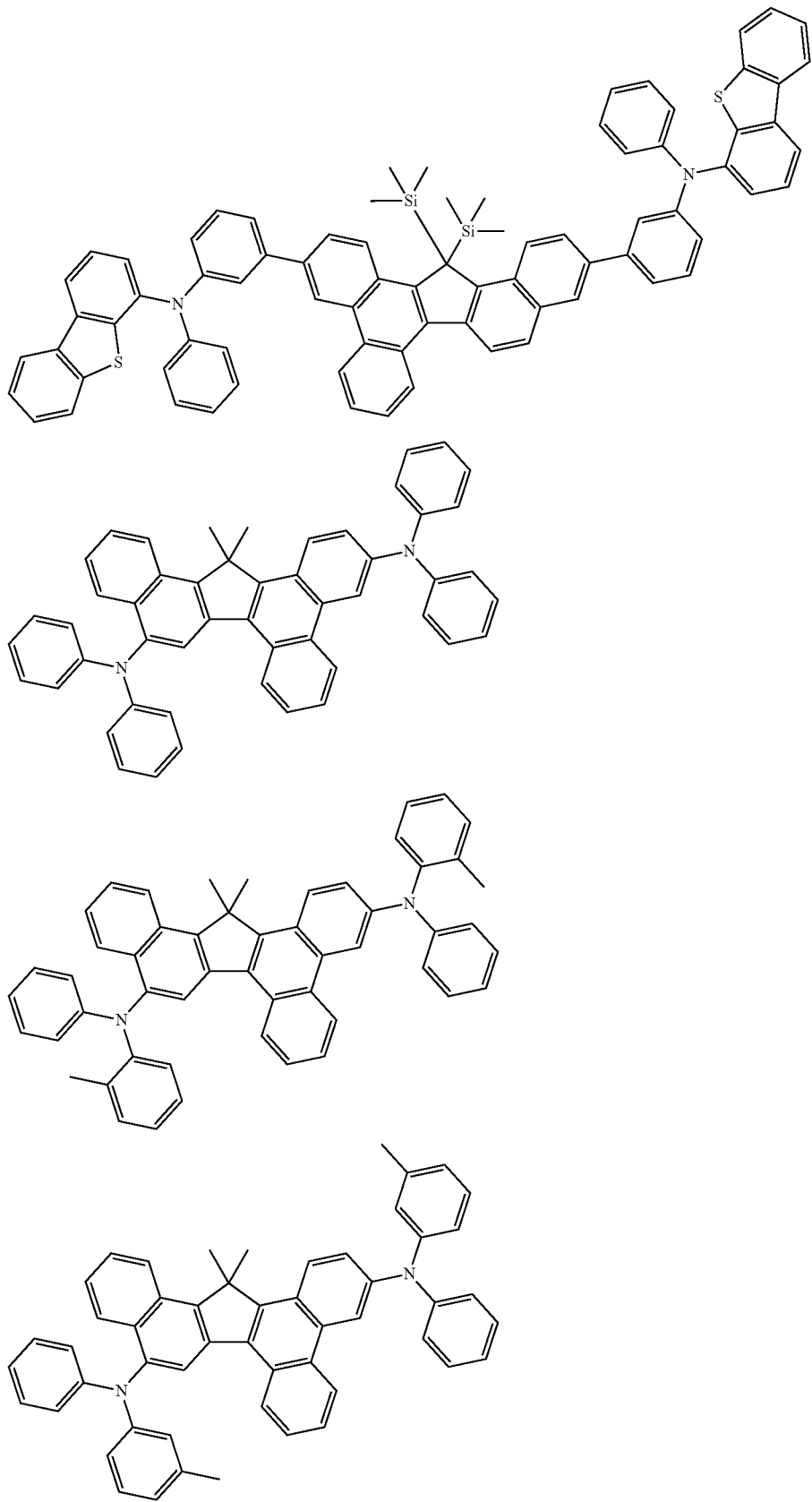

-continued
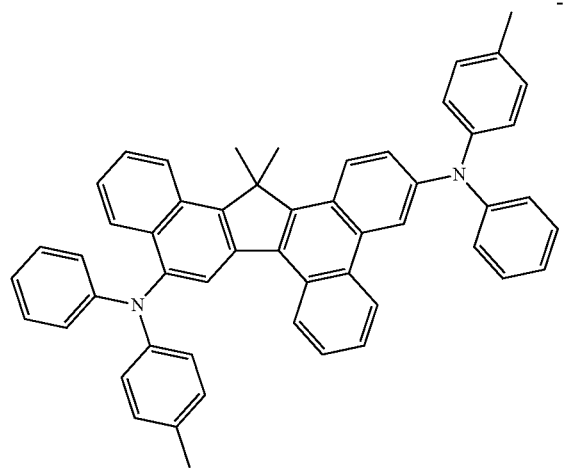
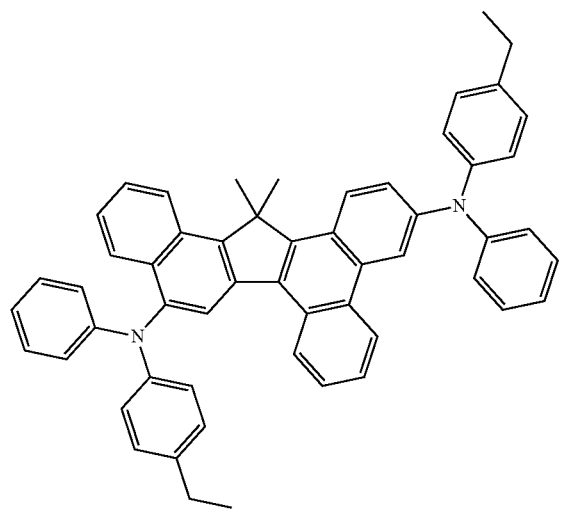
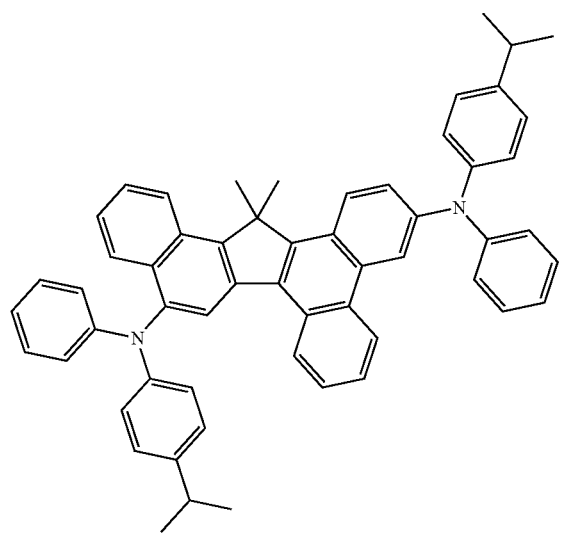

-continued
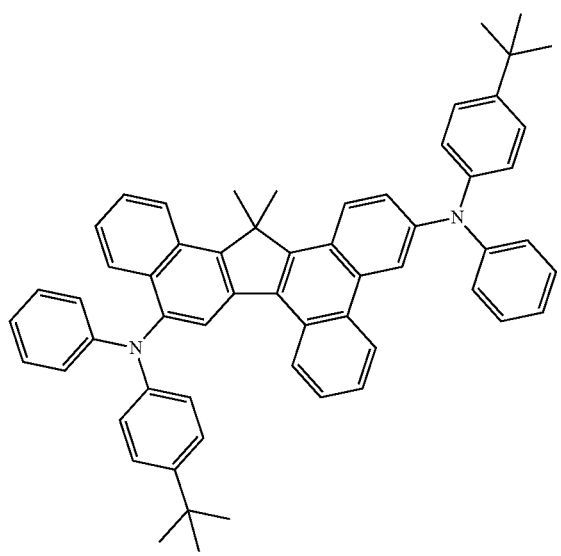
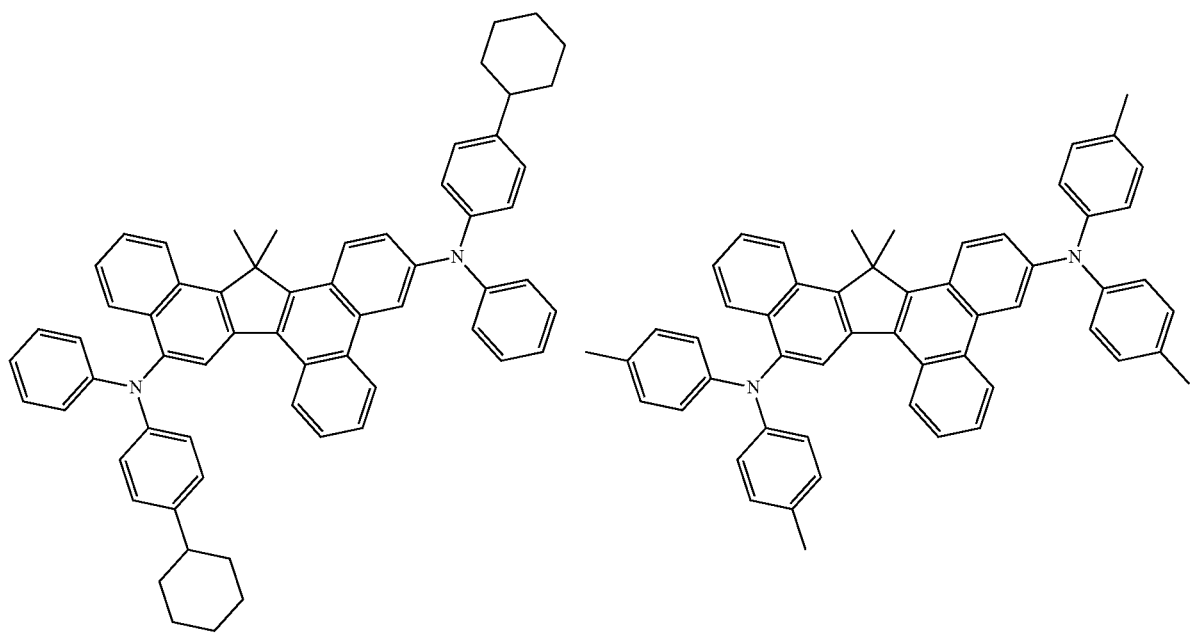
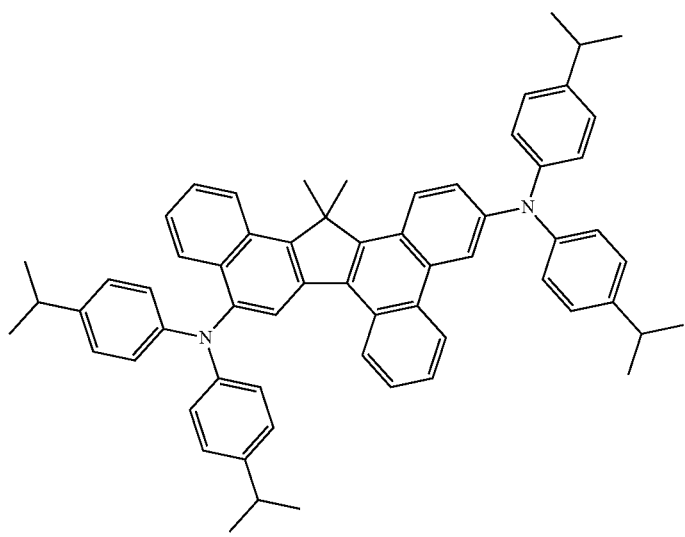

753
-continued
754
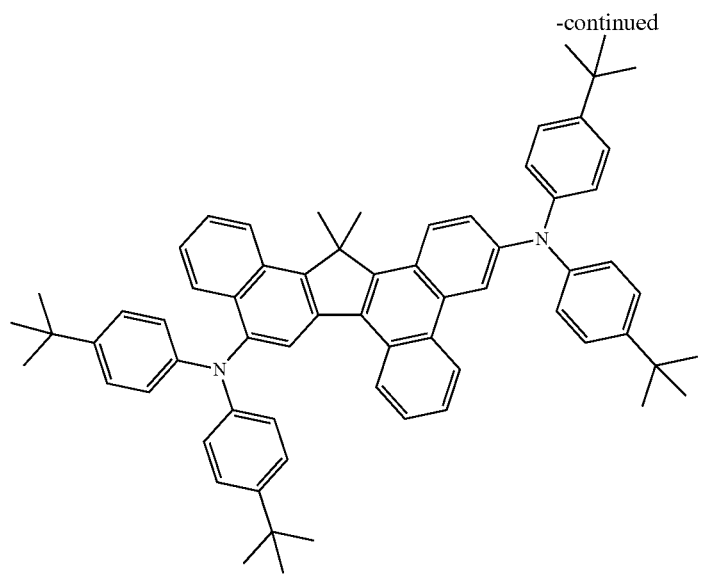
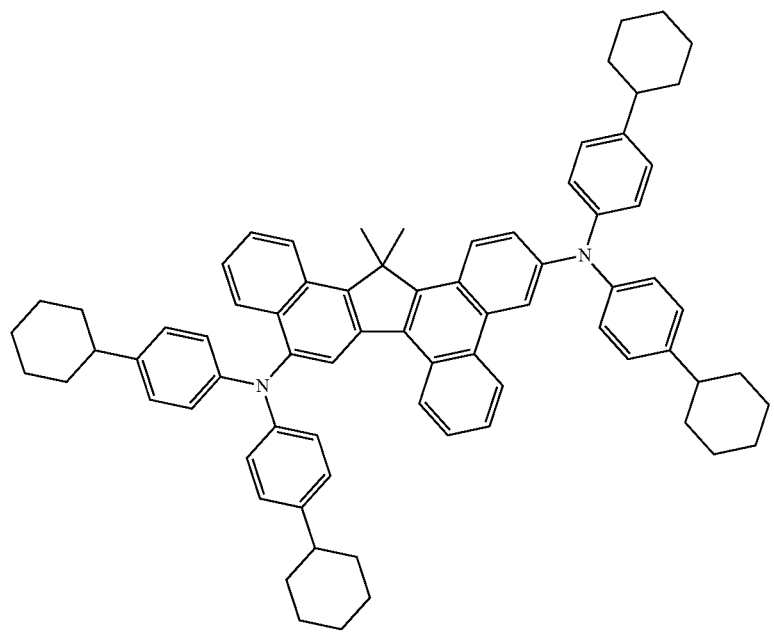
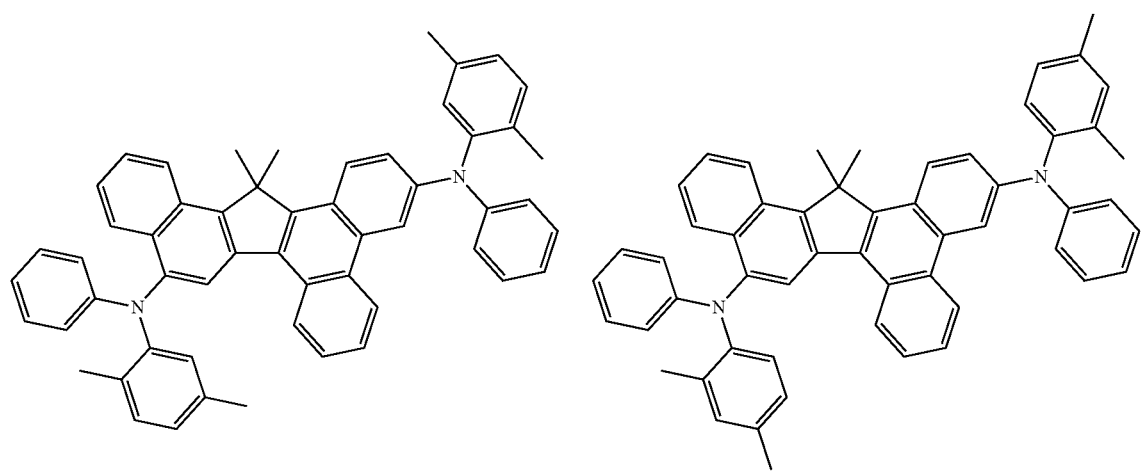

-continued
755
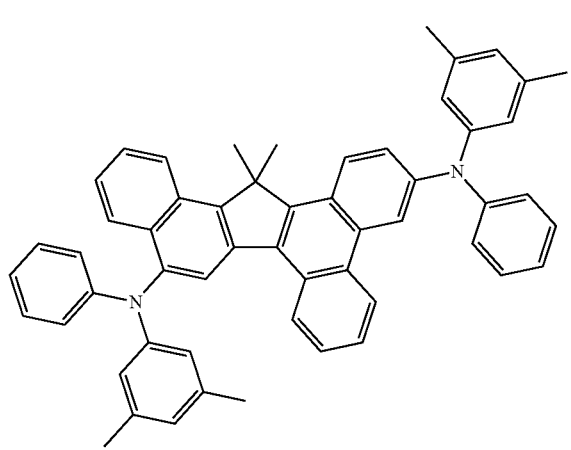
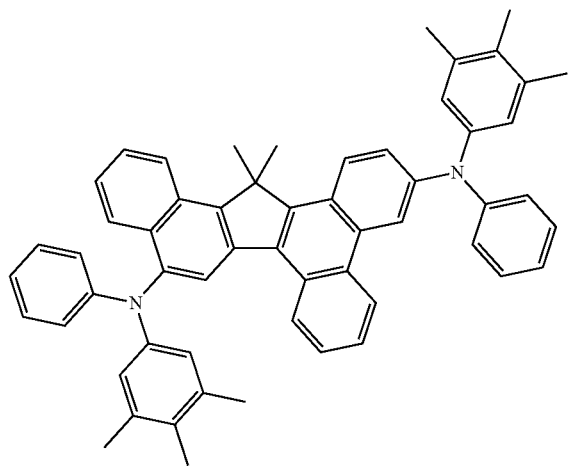
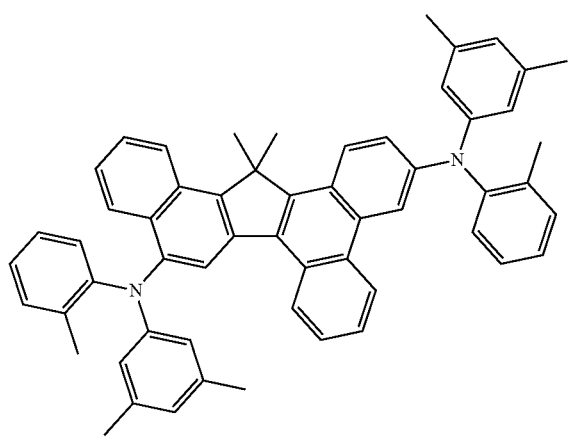
756
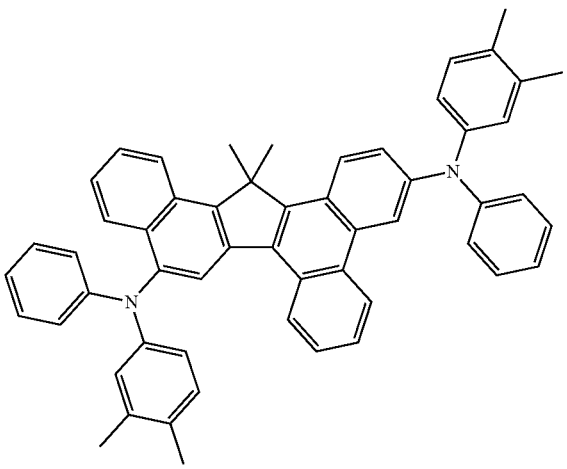
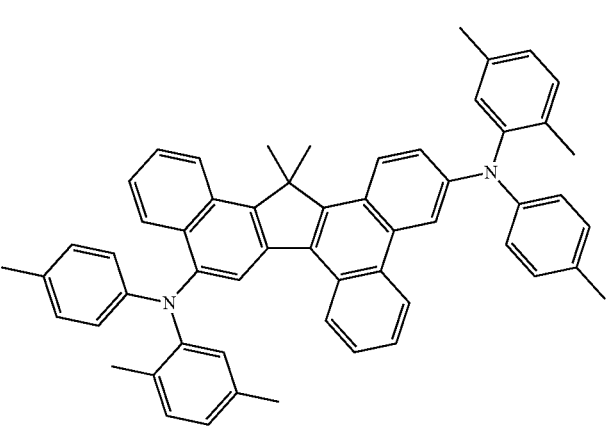
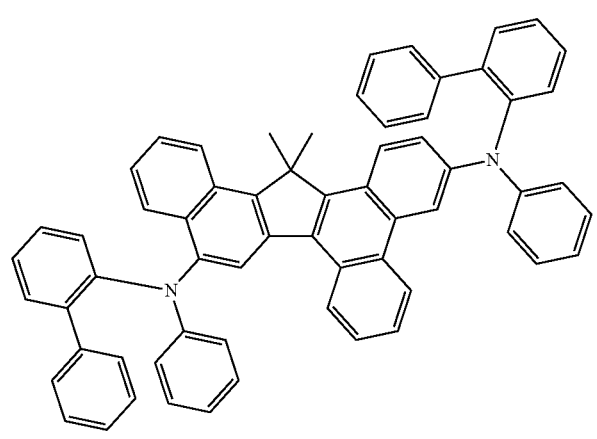

757
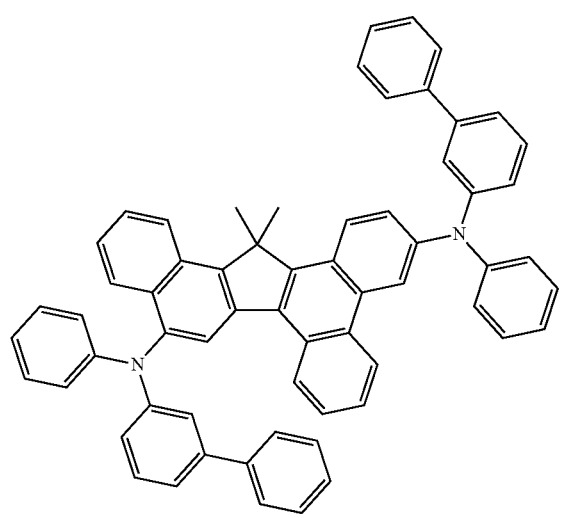
758
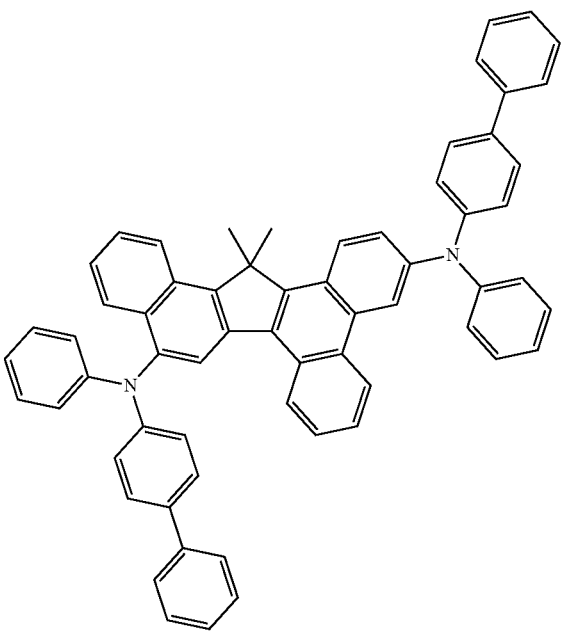
-continued
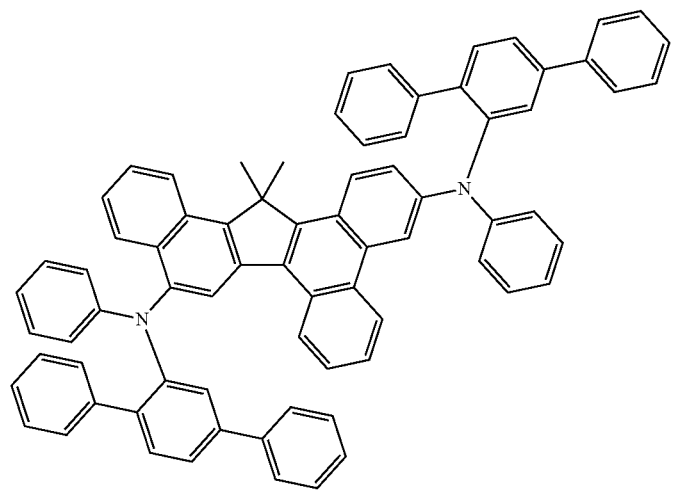

-continued
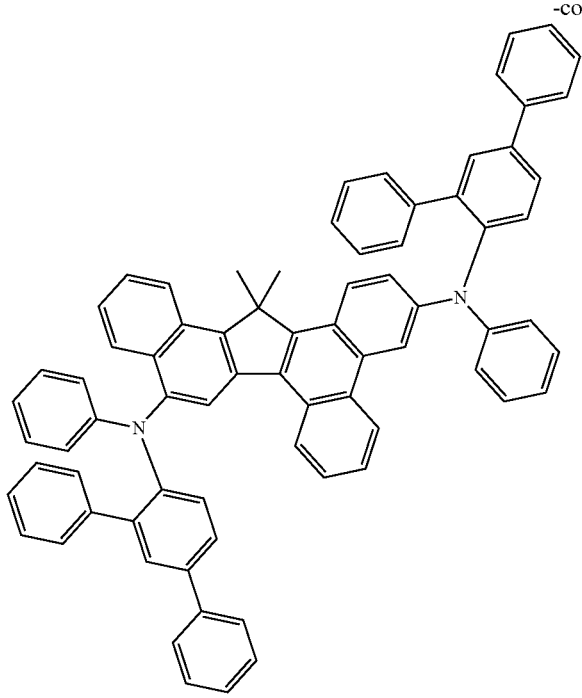
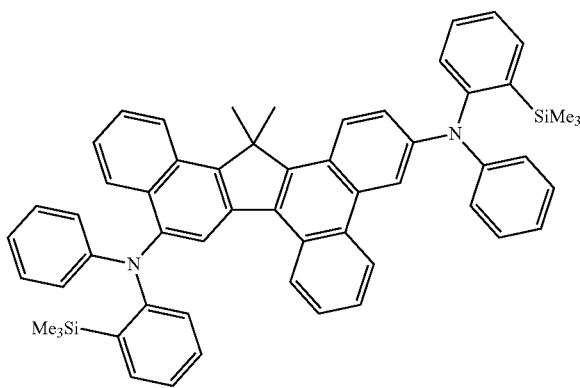
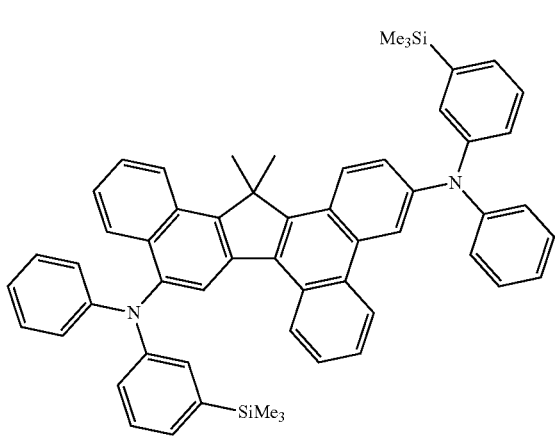 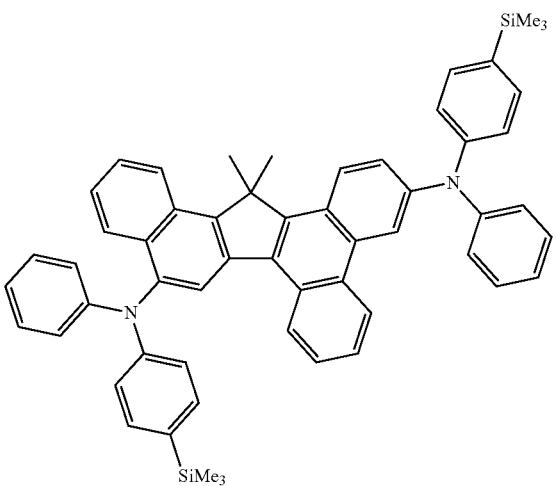

761
-continued
762
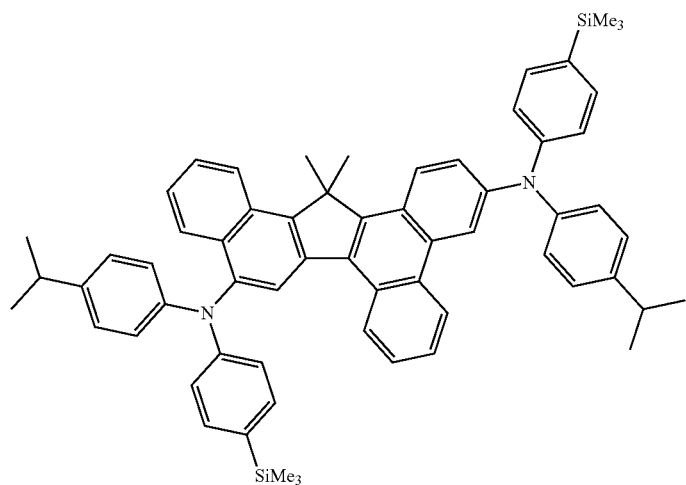
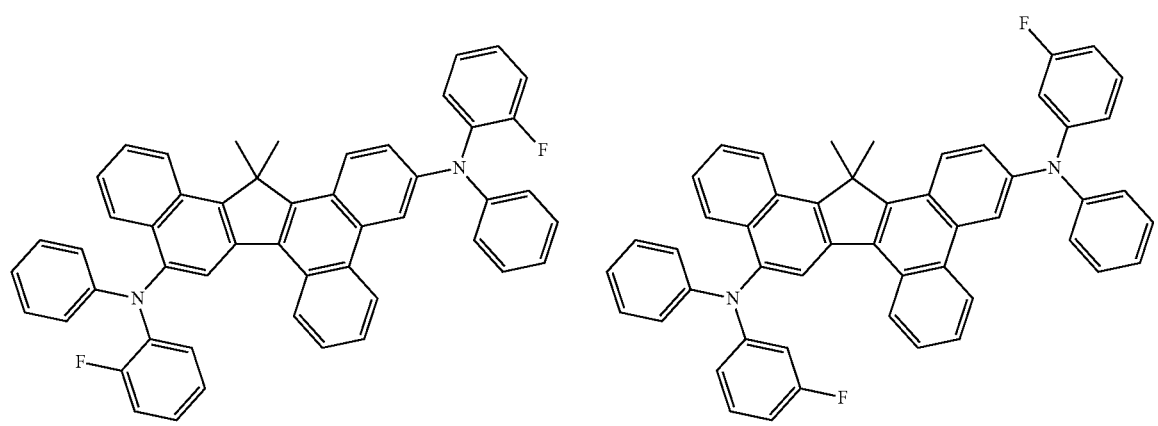
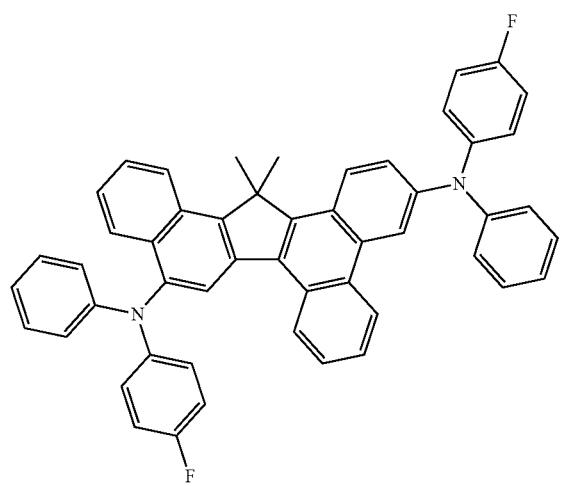

763
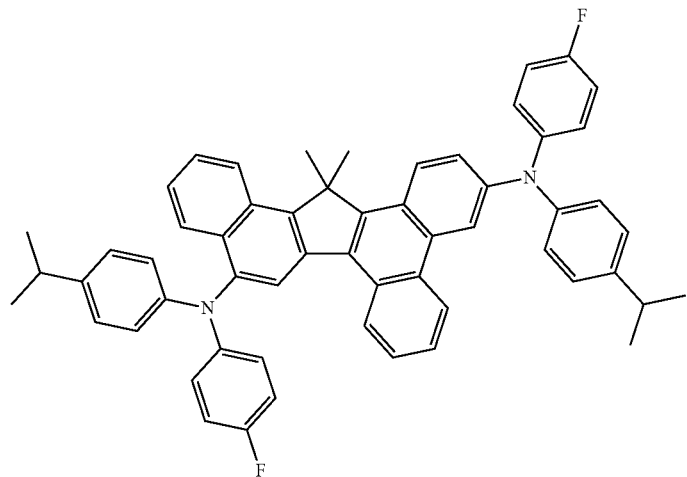
764
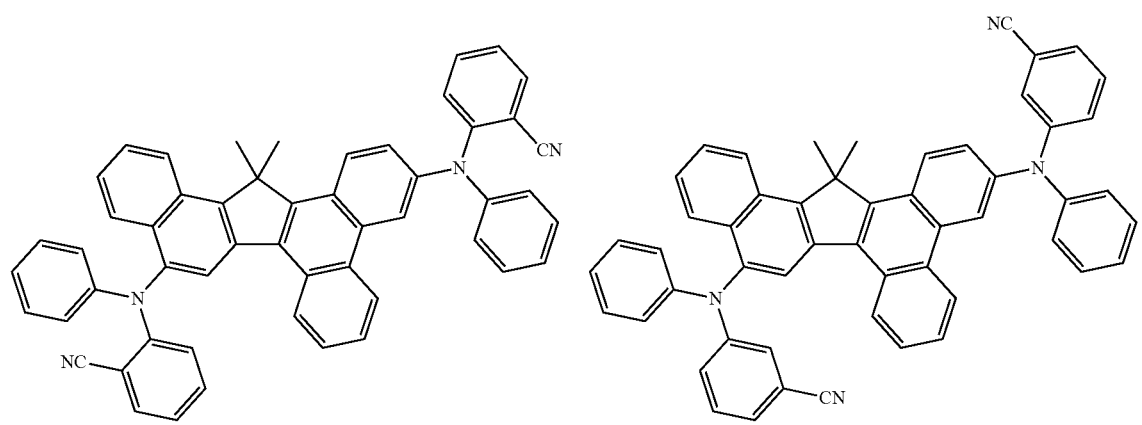
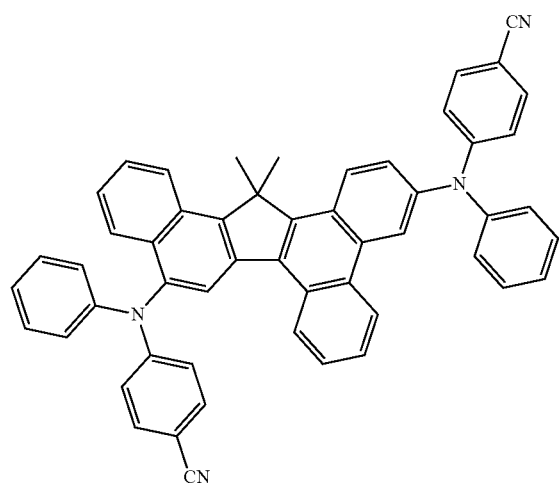

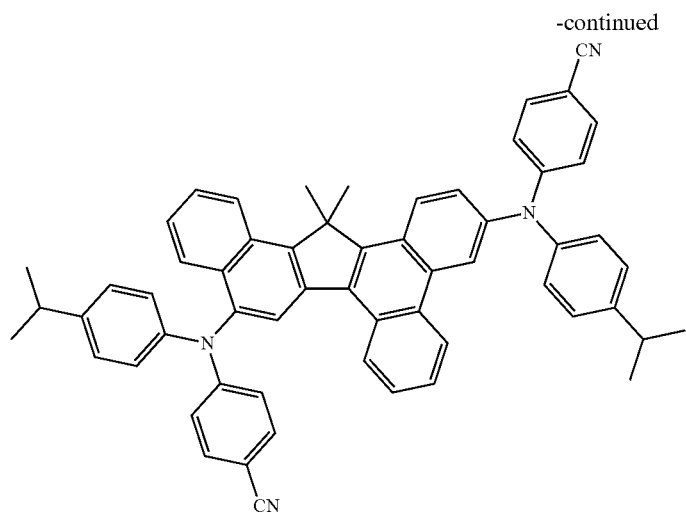
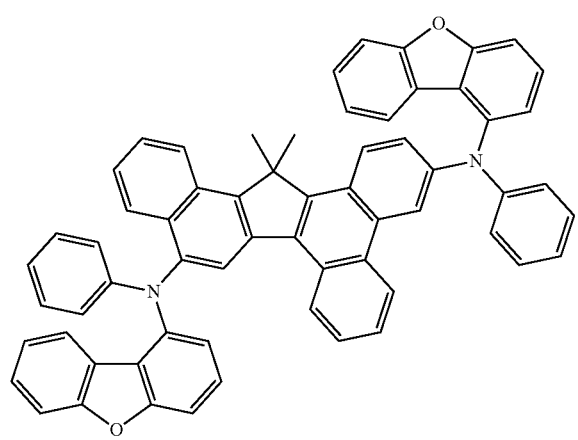
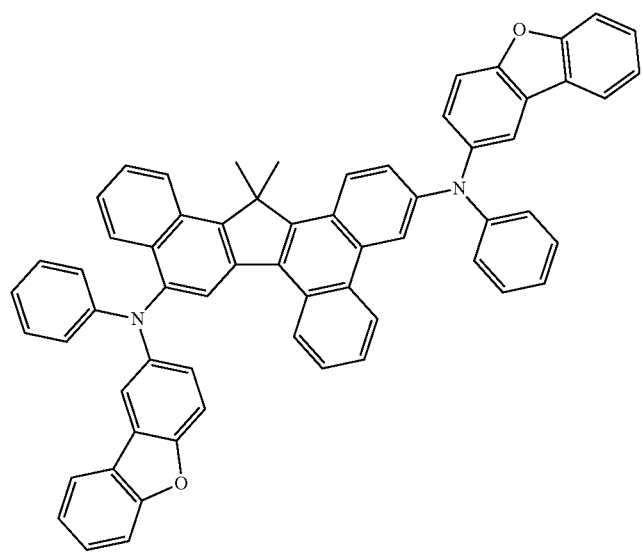

-continued
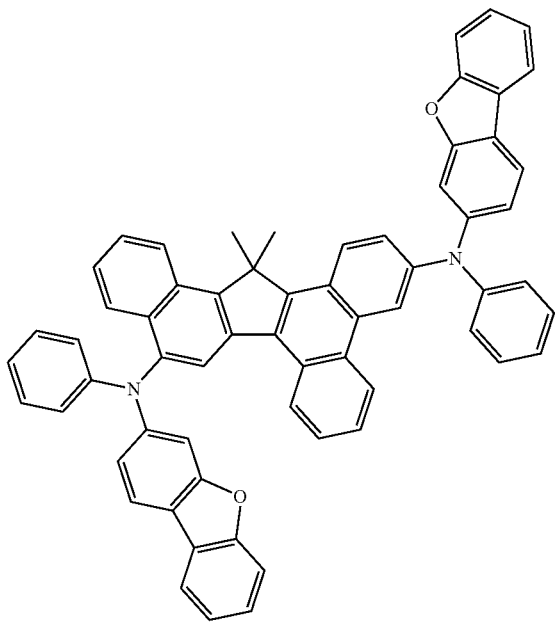
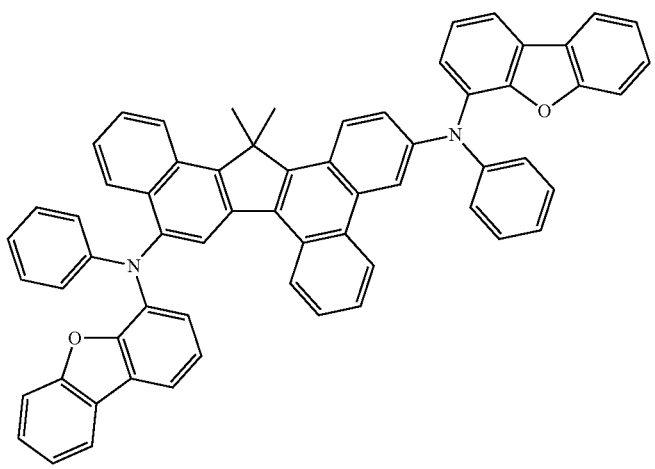
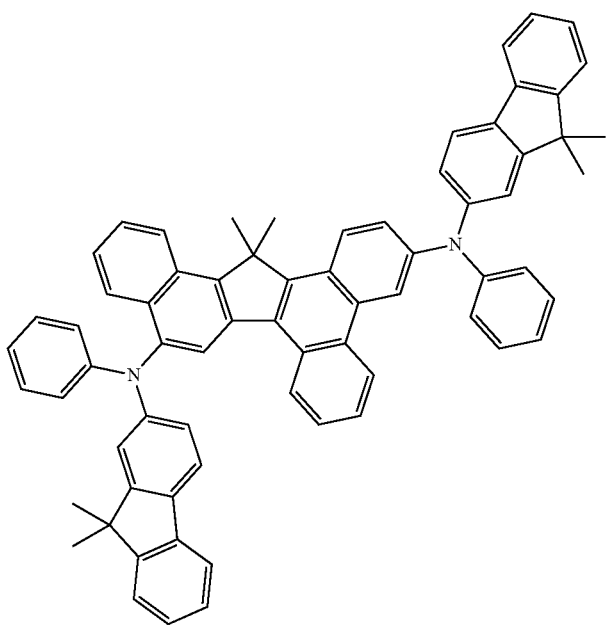

-continued
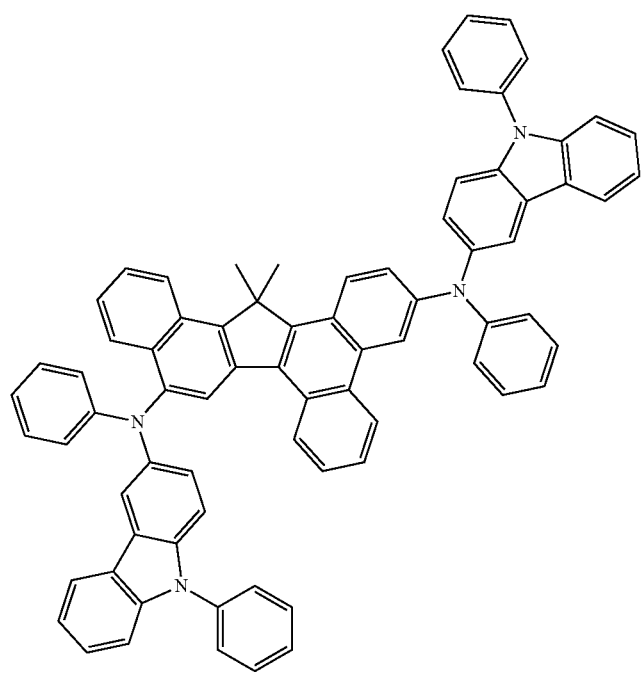
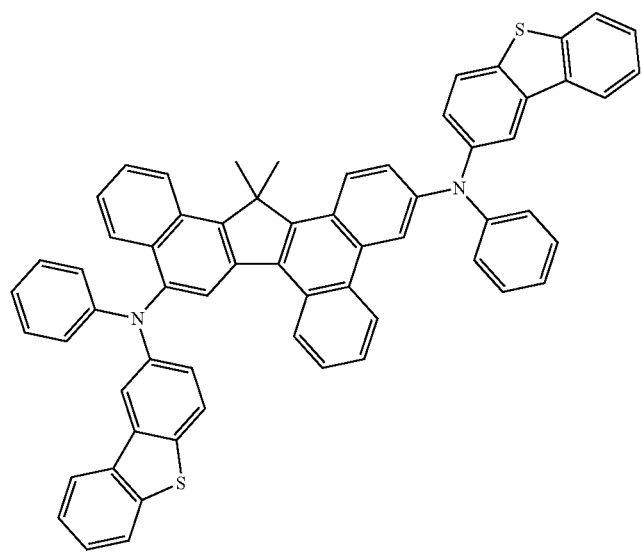
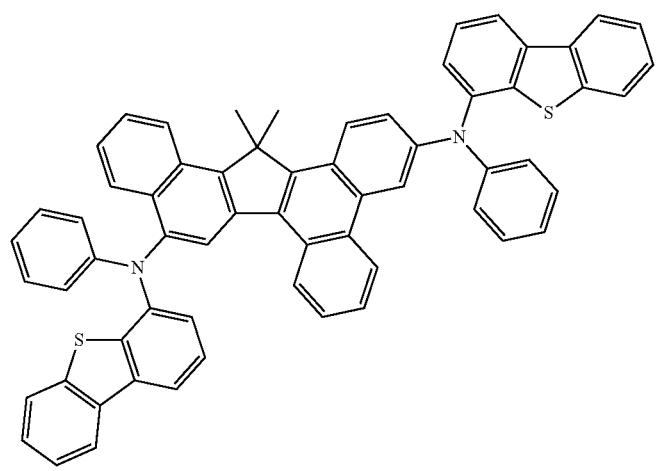

-continued
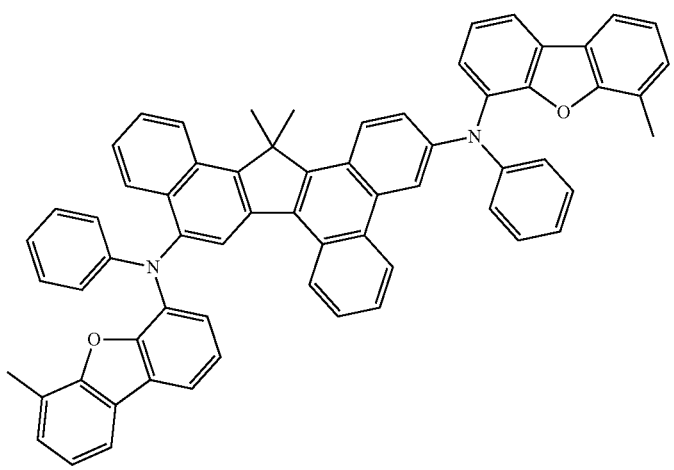
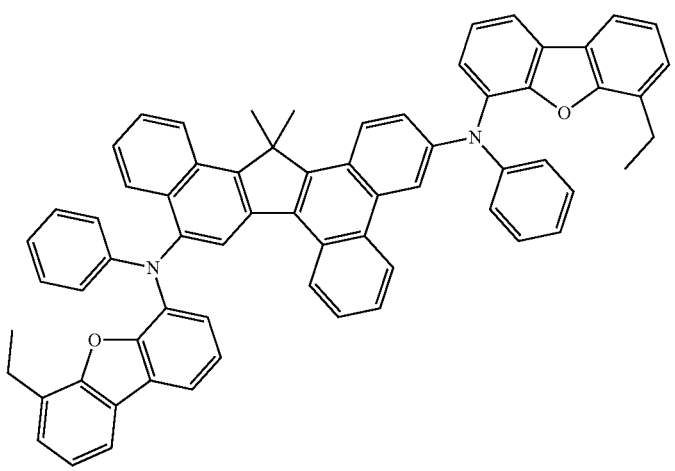
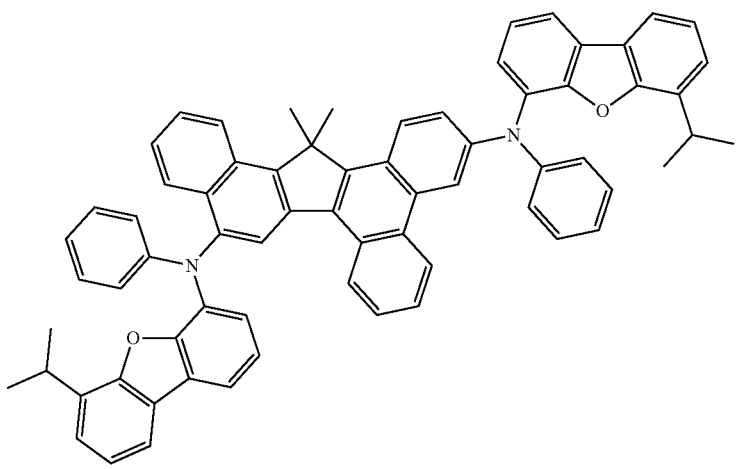

-continued
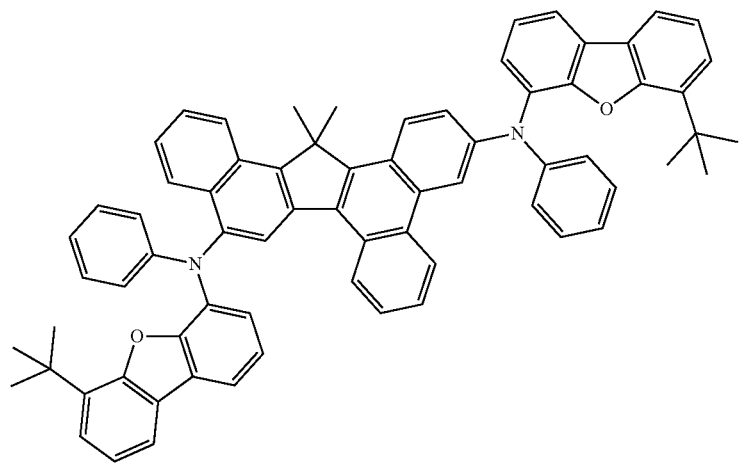
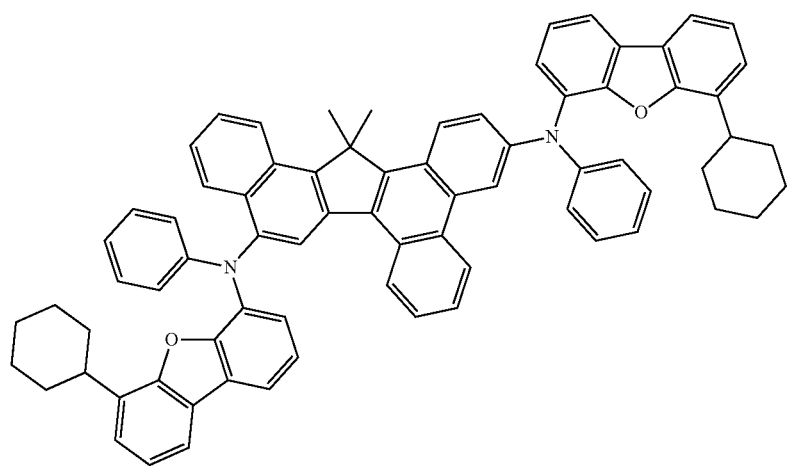
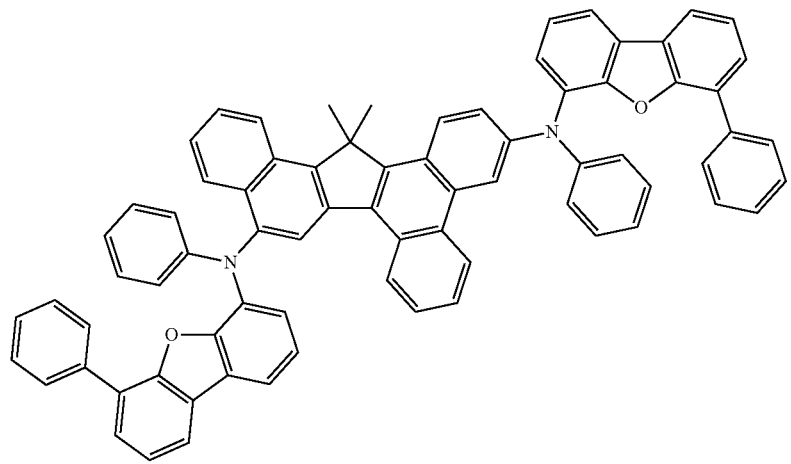

-continued
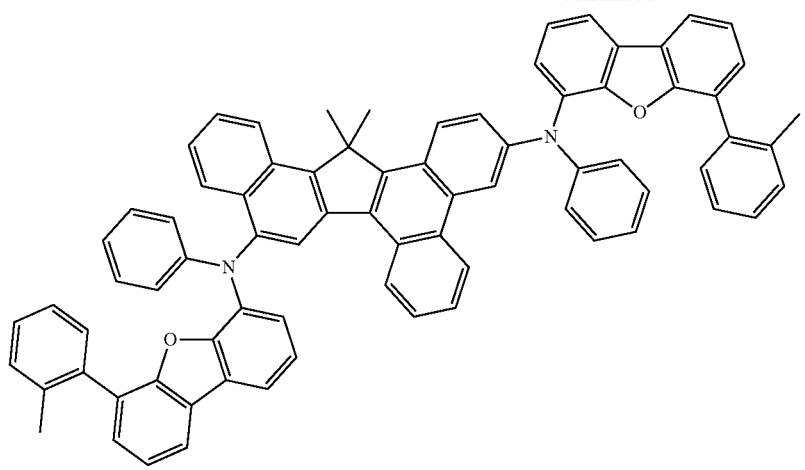
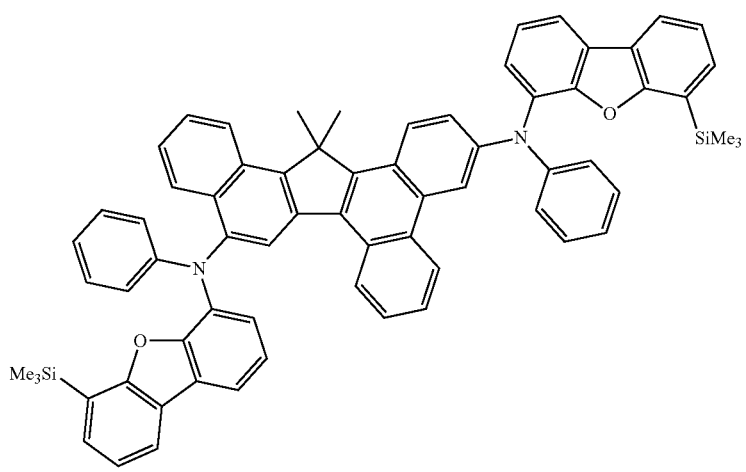
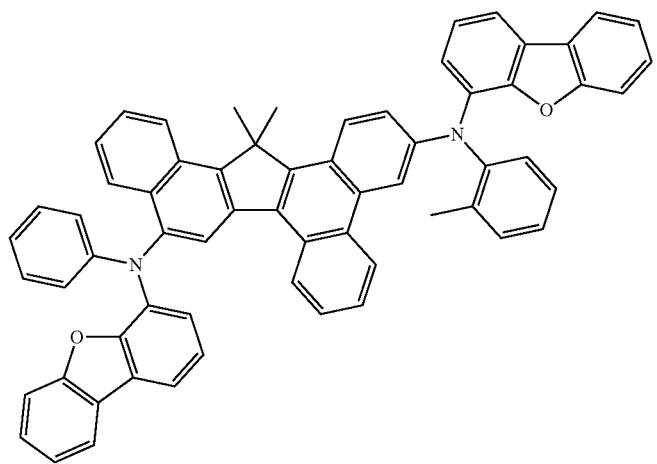

-continued
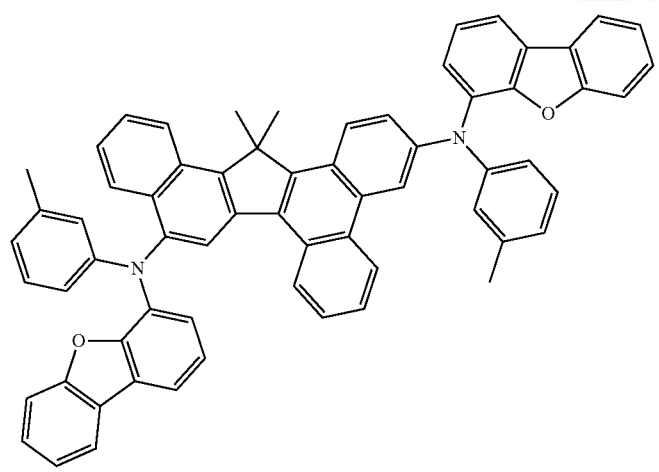
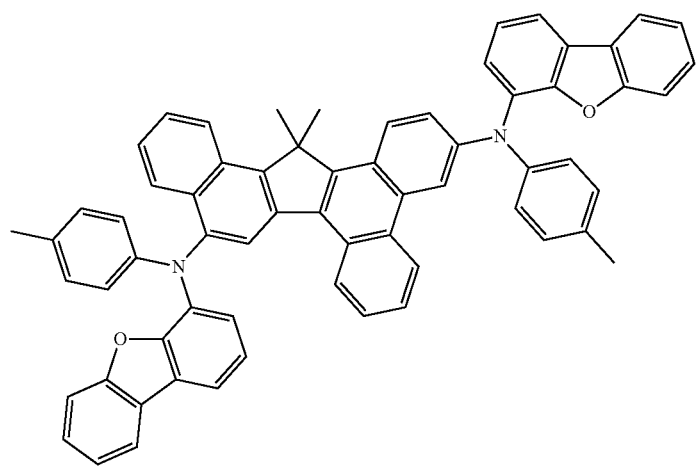
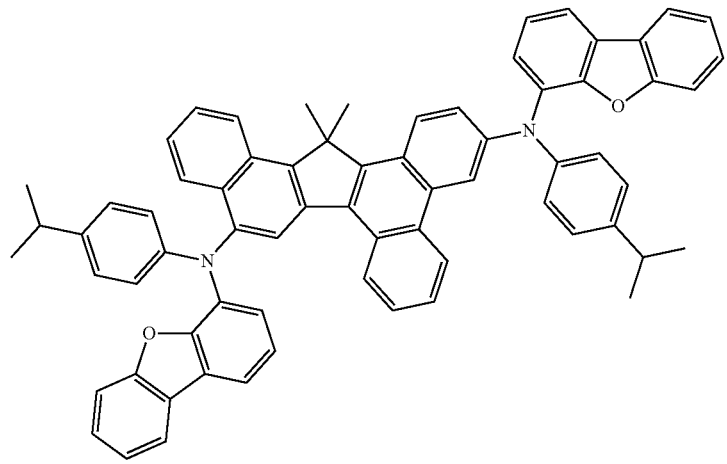

-continued
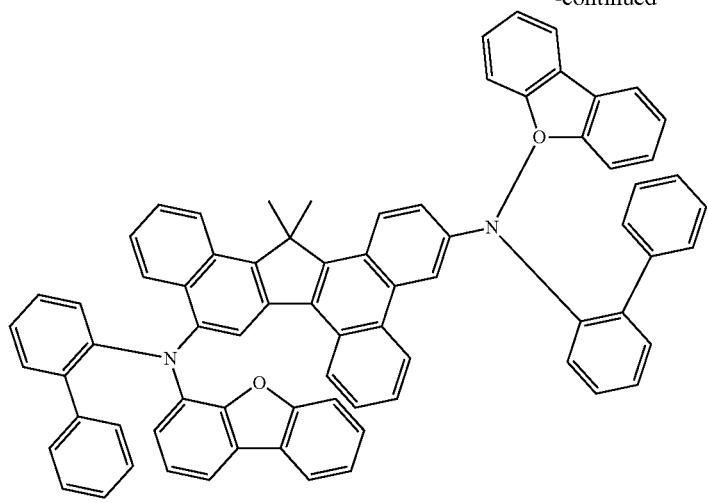
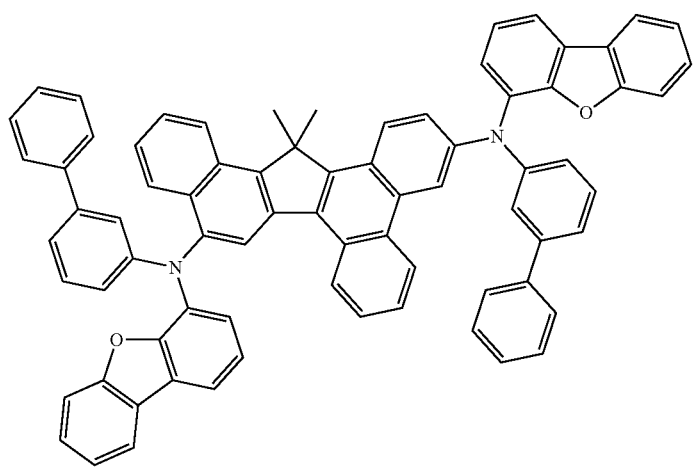
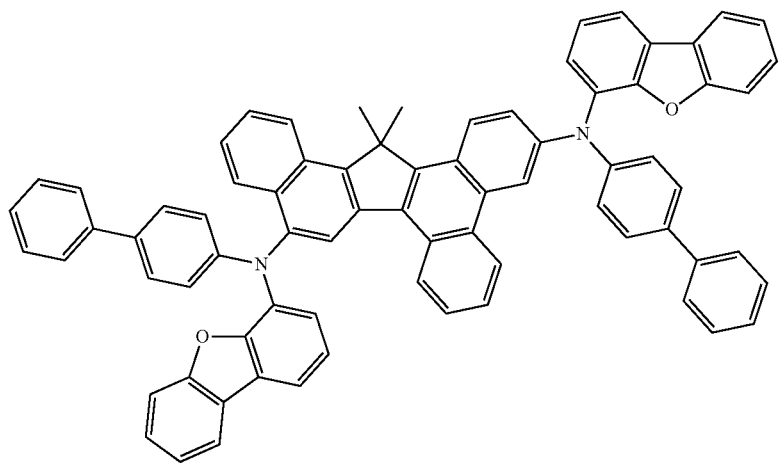 [SMILES: CC1(C)c2c(cc(N(c3ccc(-c4ccccc4)cc3)c3cccc4c3oc3ccccc34)c3ccccc23)-c2c1c1ccc(N(c3ccc(-c4ccccc4)cc3)c3cccc4c3oc3ccccc34)cc1c1ccccc21]

-continued
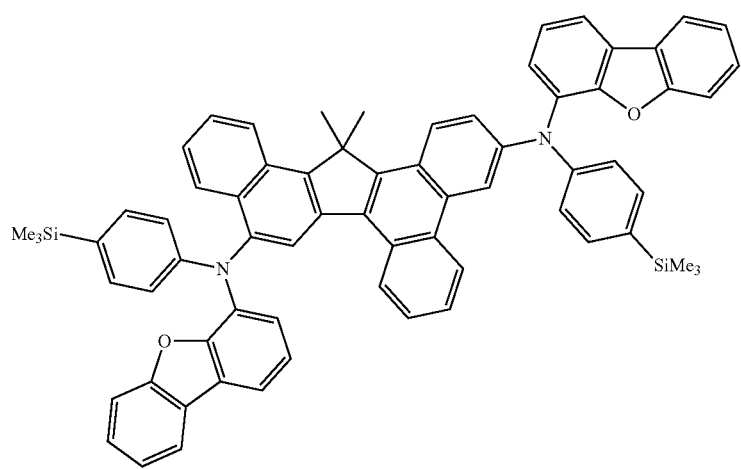
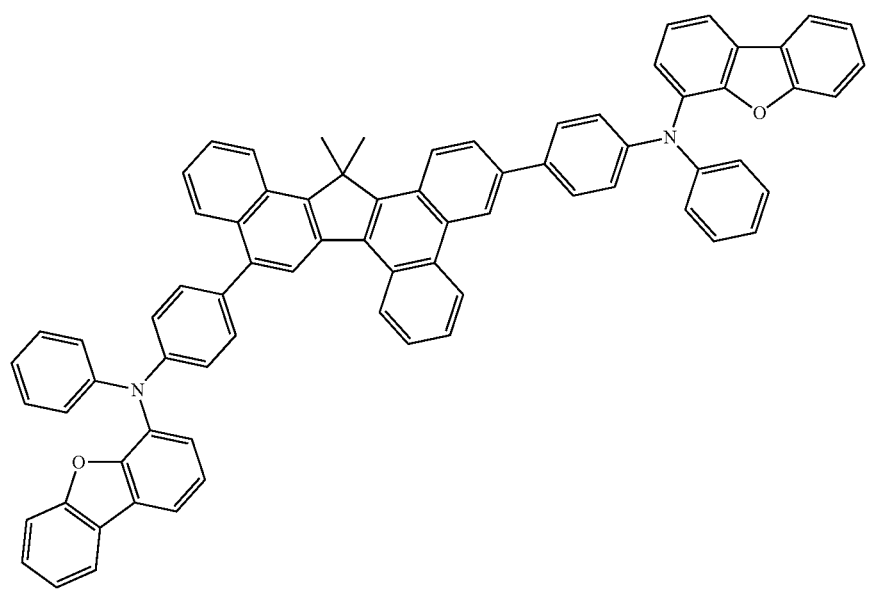
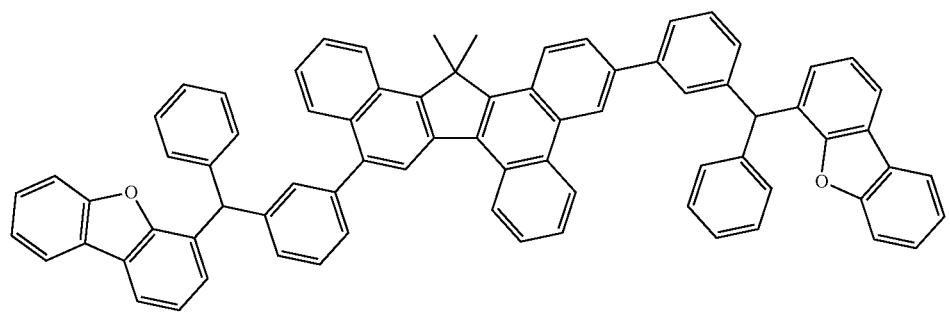

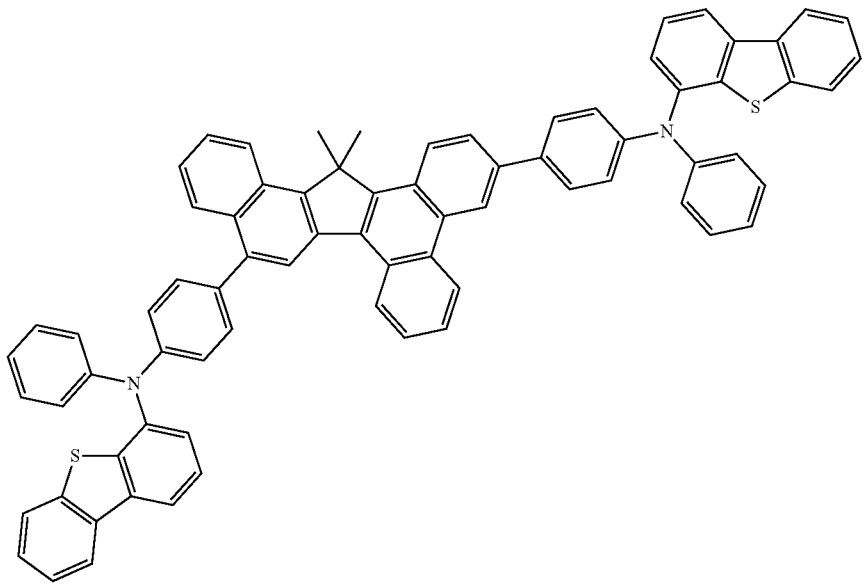
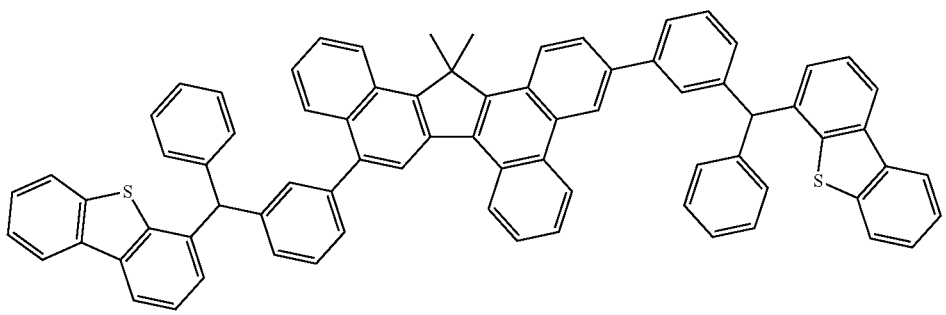
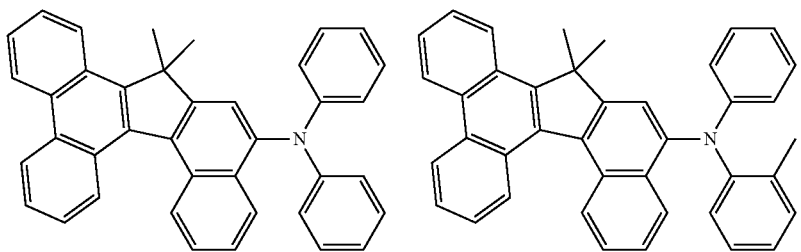
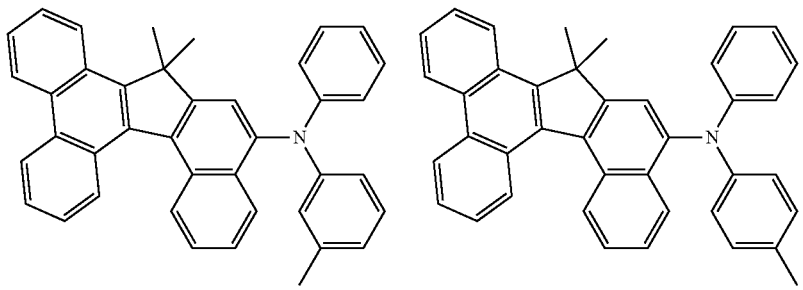

-continued
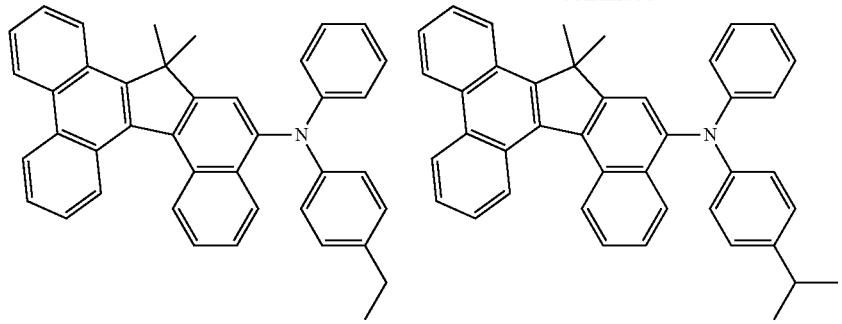
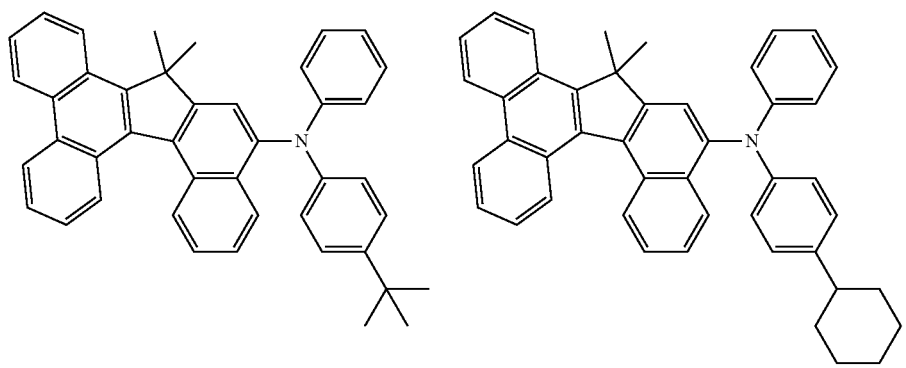
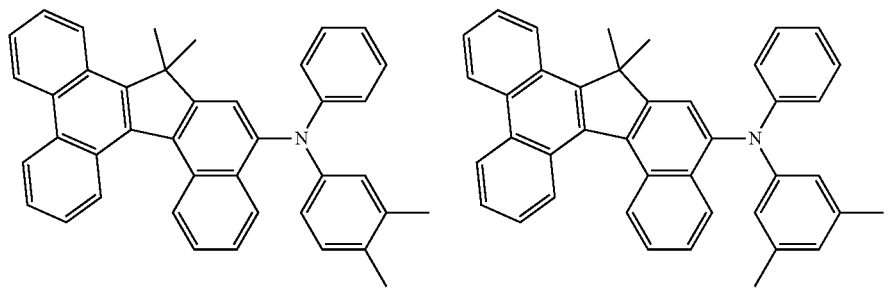
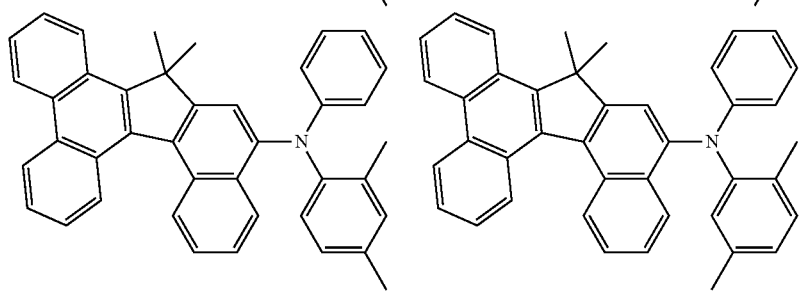
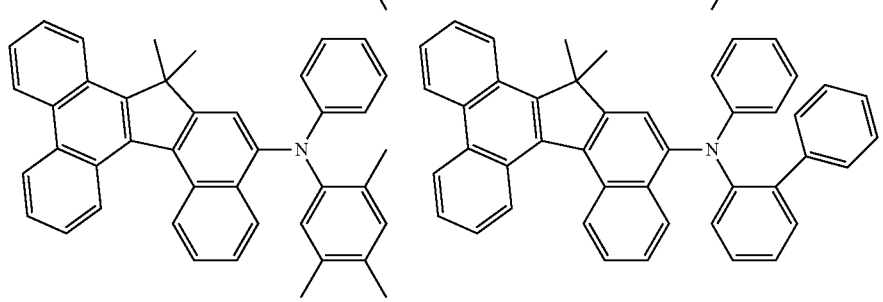

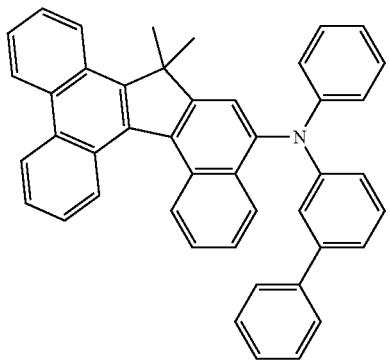
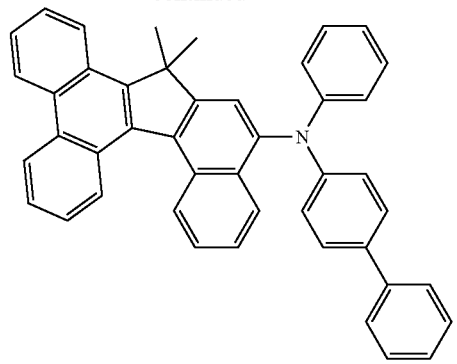
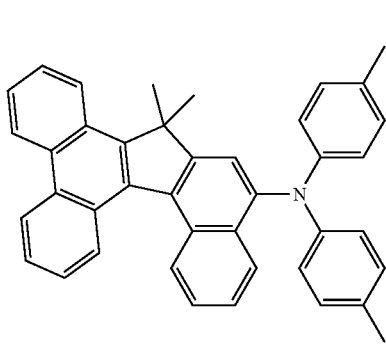
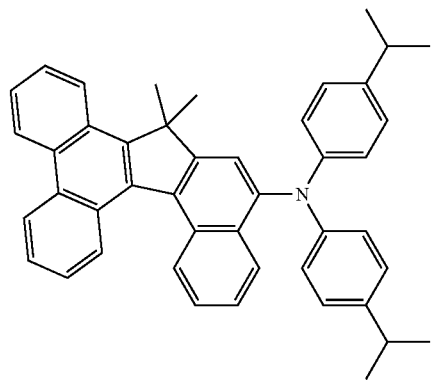
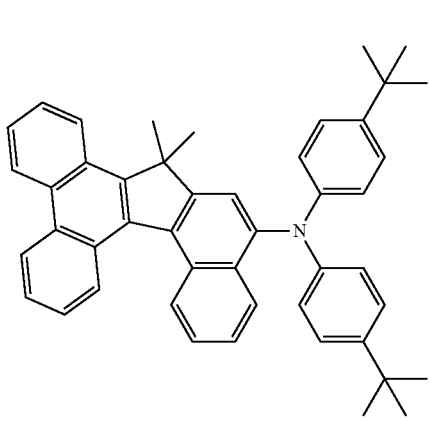
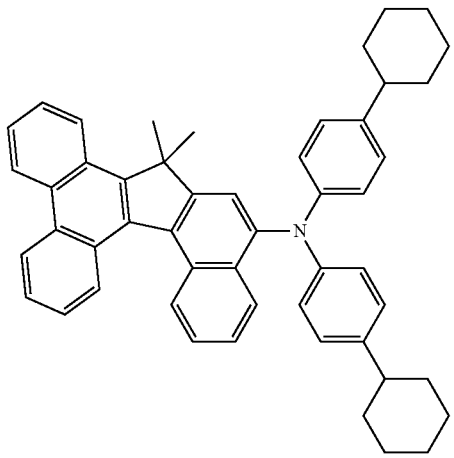
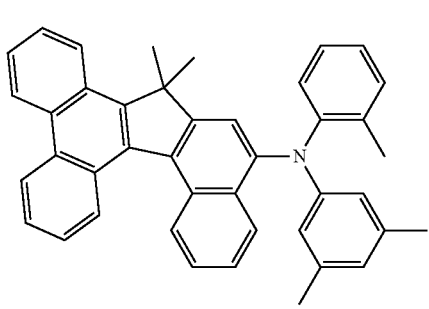
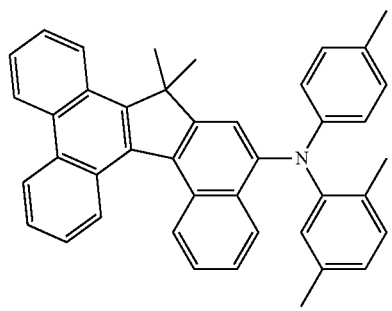

-continued
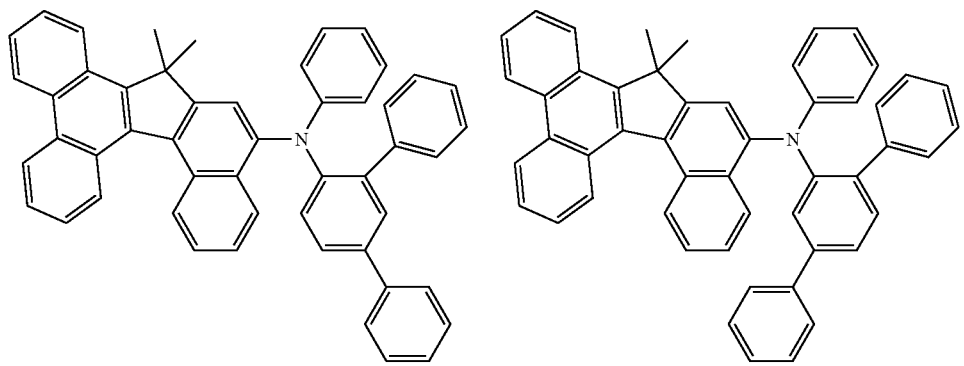
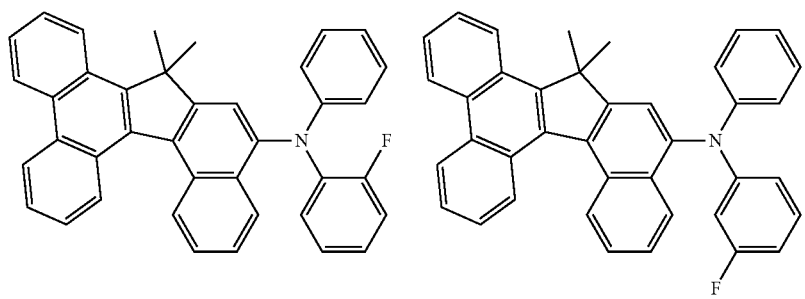
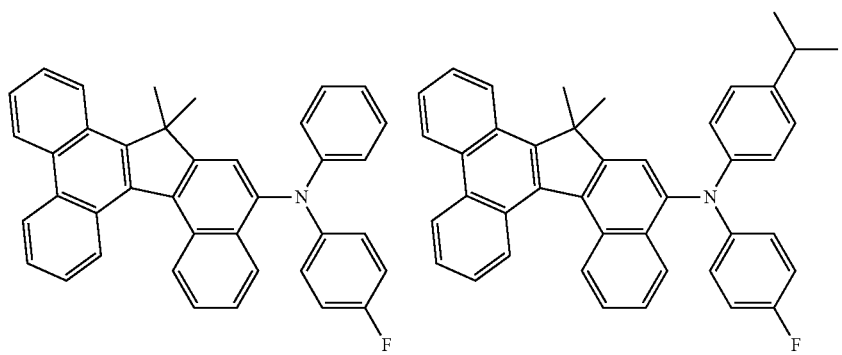
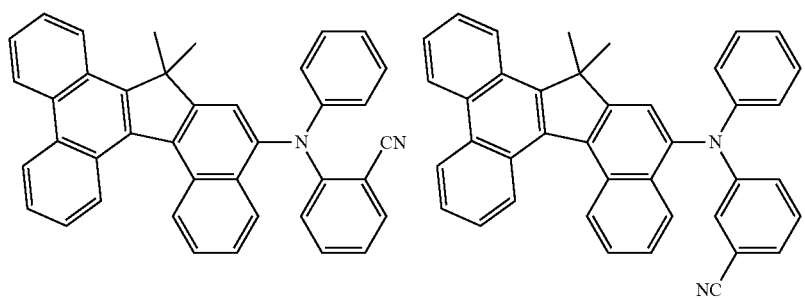
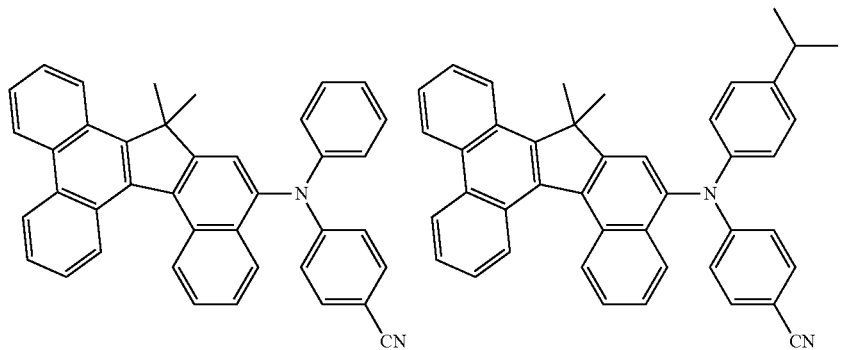

-continued
791
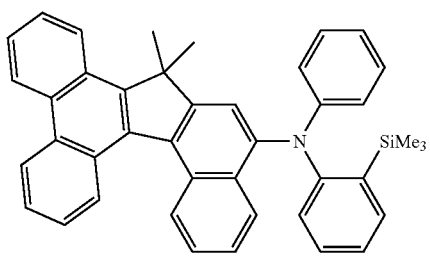
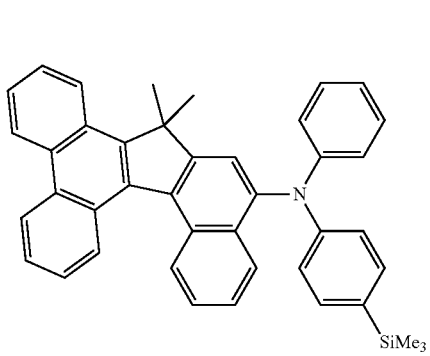
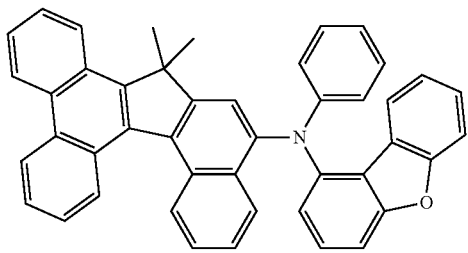
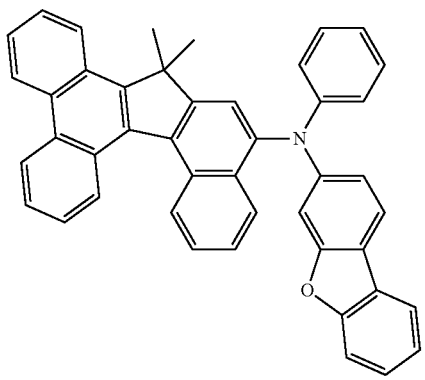
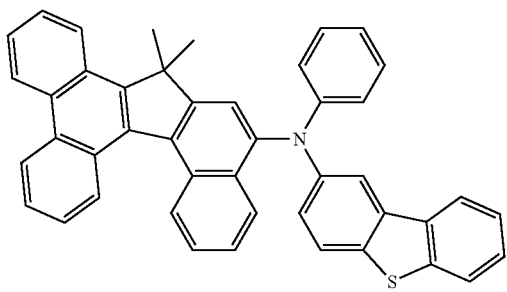
792
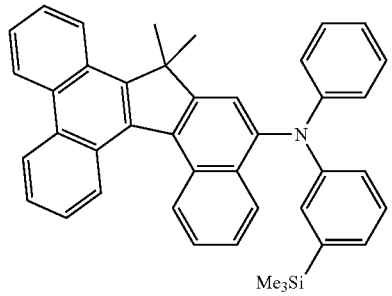
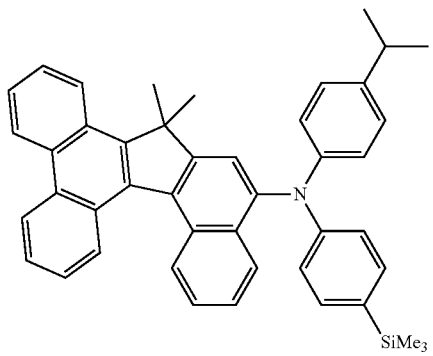
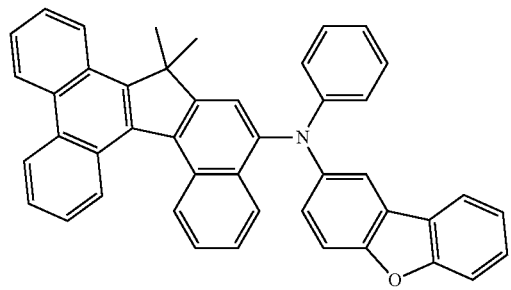
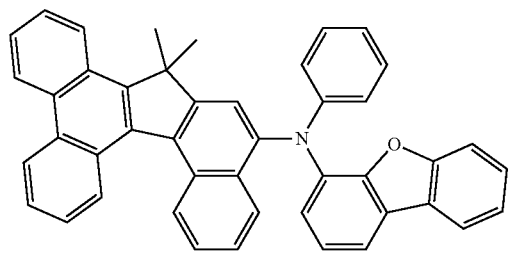
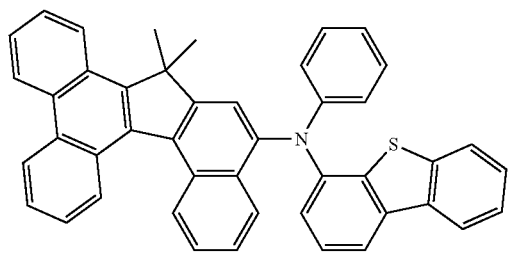

-continued
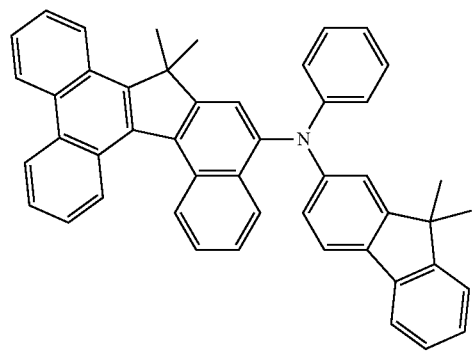
793
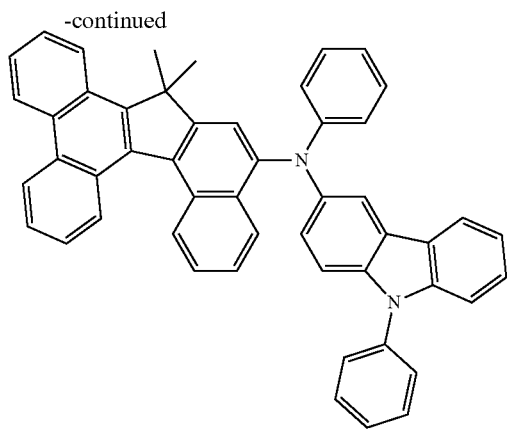
794
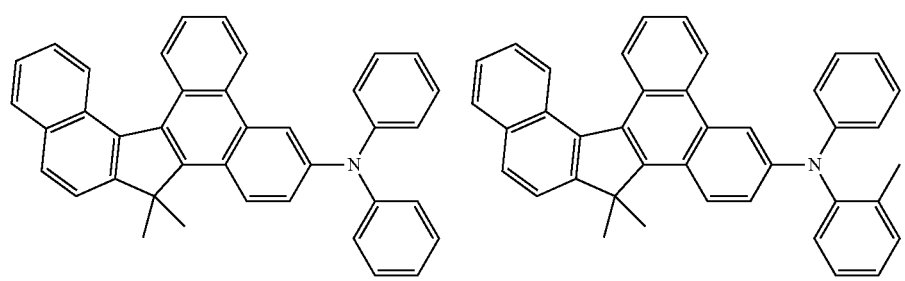
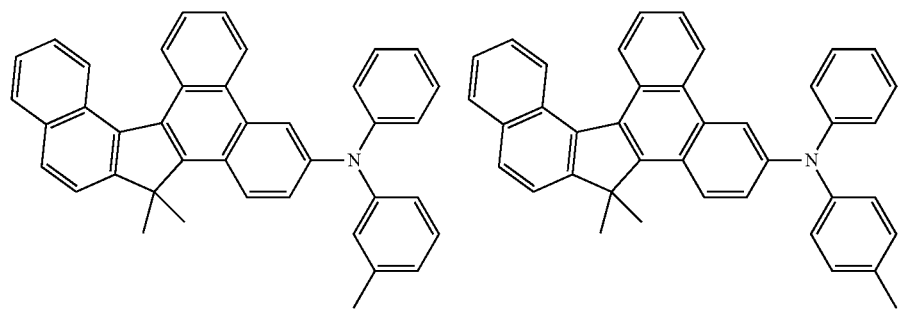
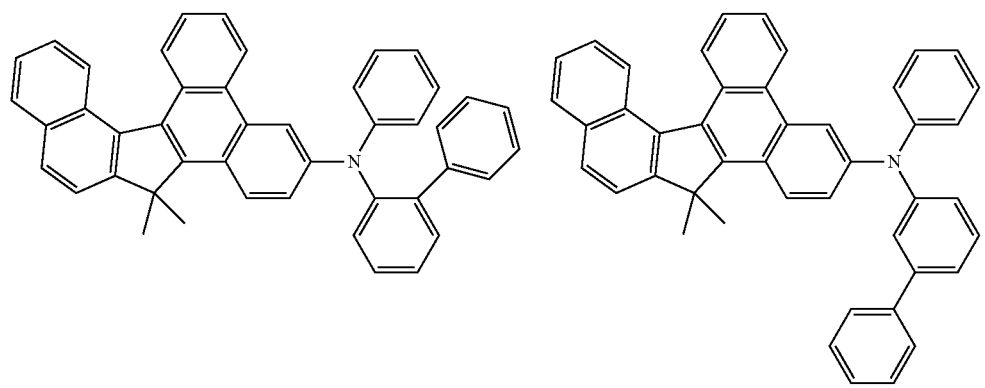

| 795 | 796 |
|---|---|
| 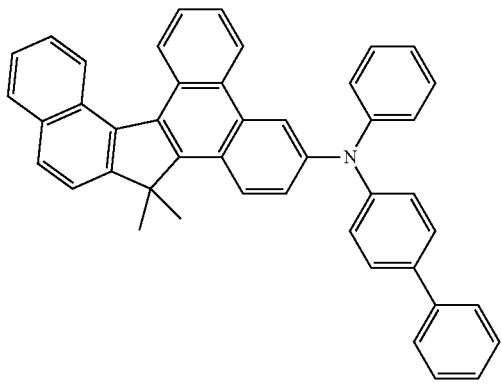 | 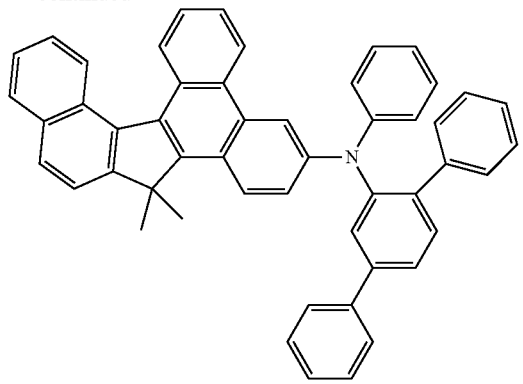 |
| 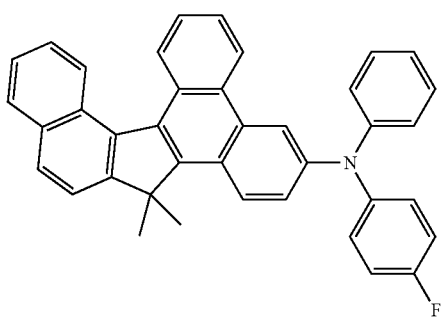 | 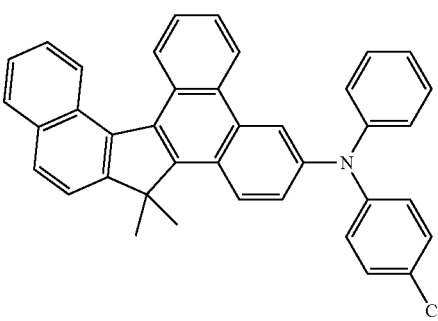 |
| 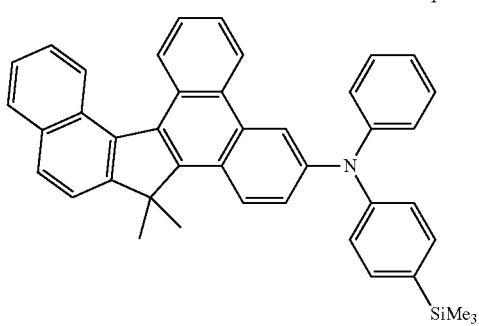 | 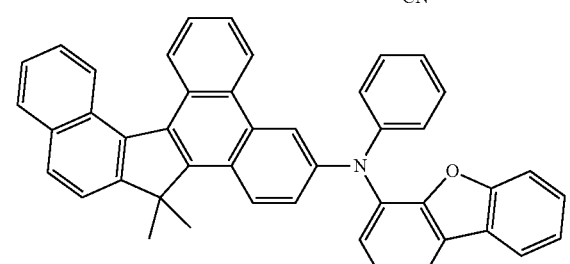 |
| 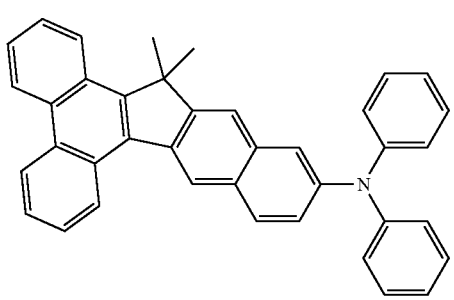 | 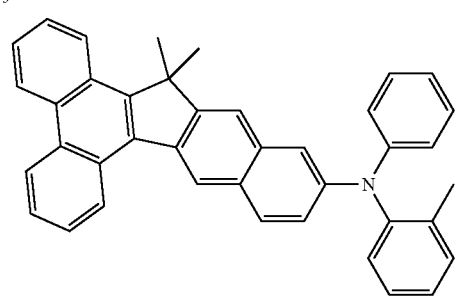 |
| 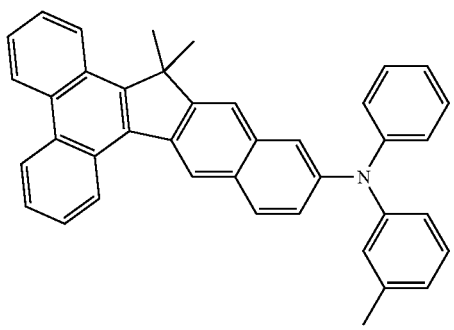 | 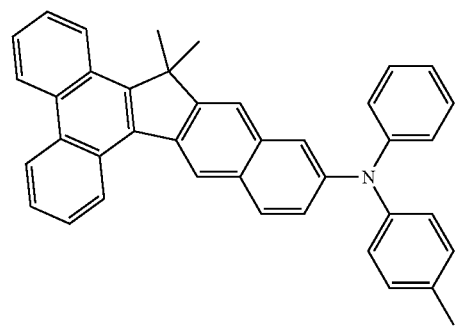 |

-continued
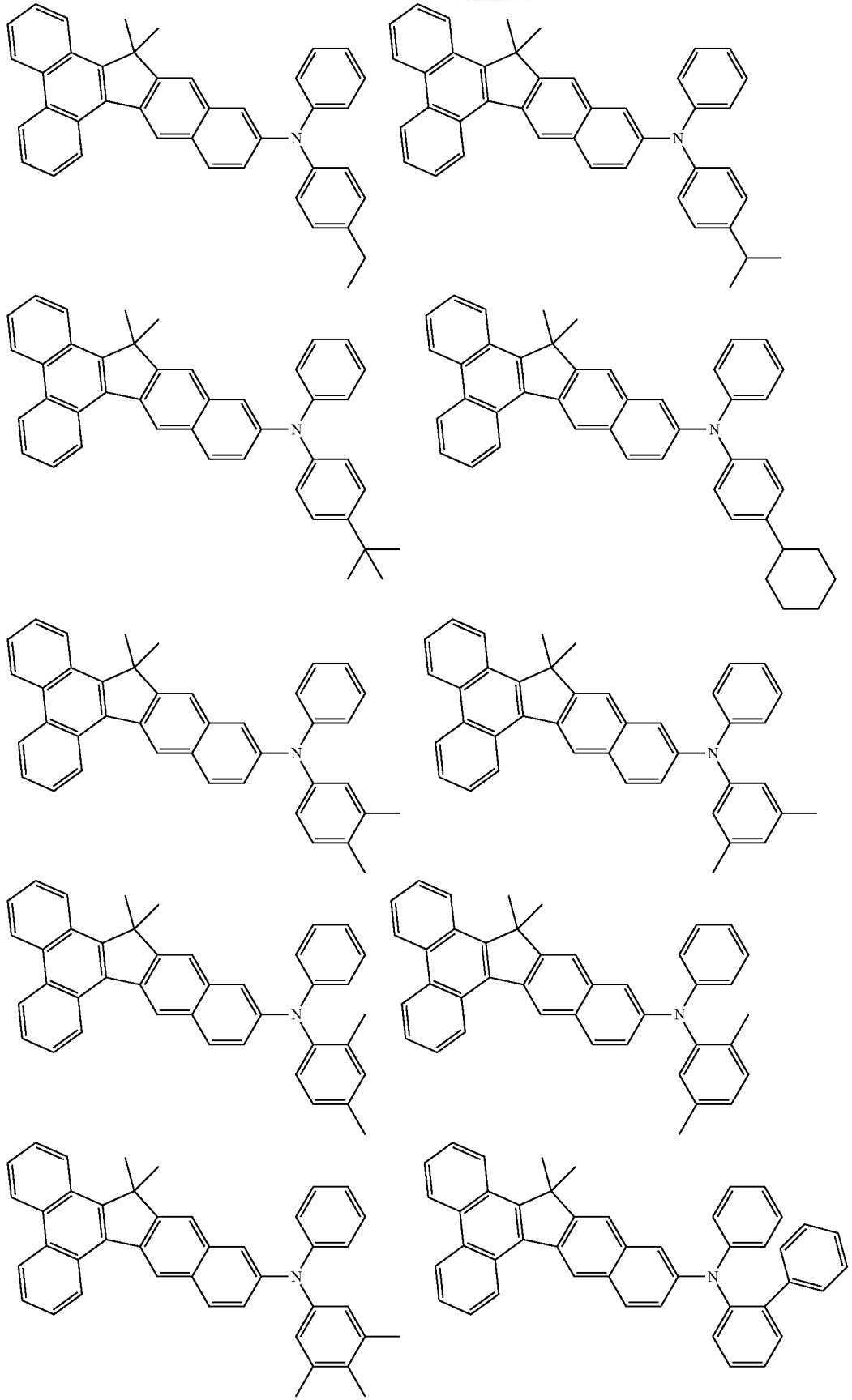

799   800
-continued
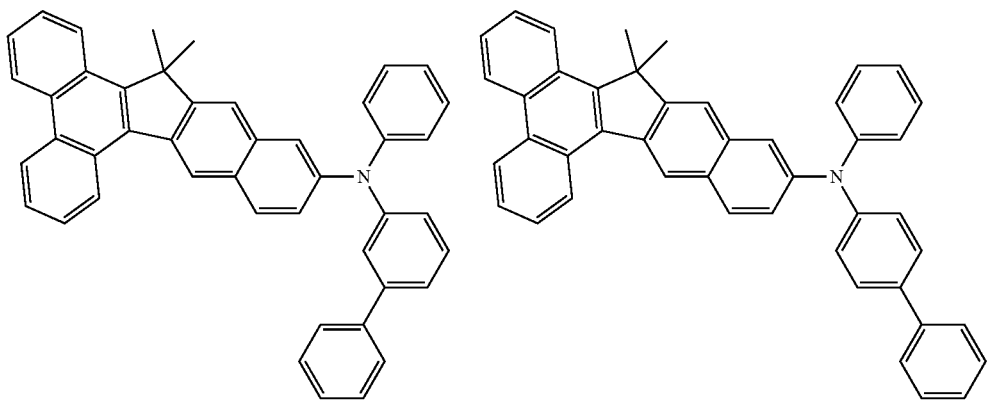
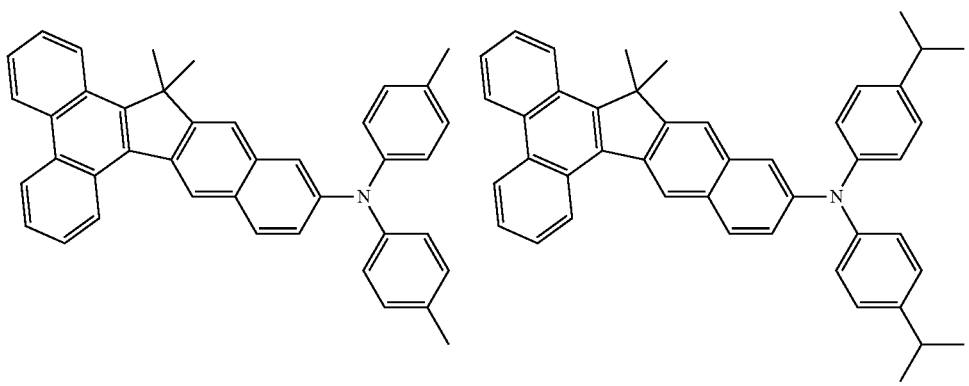
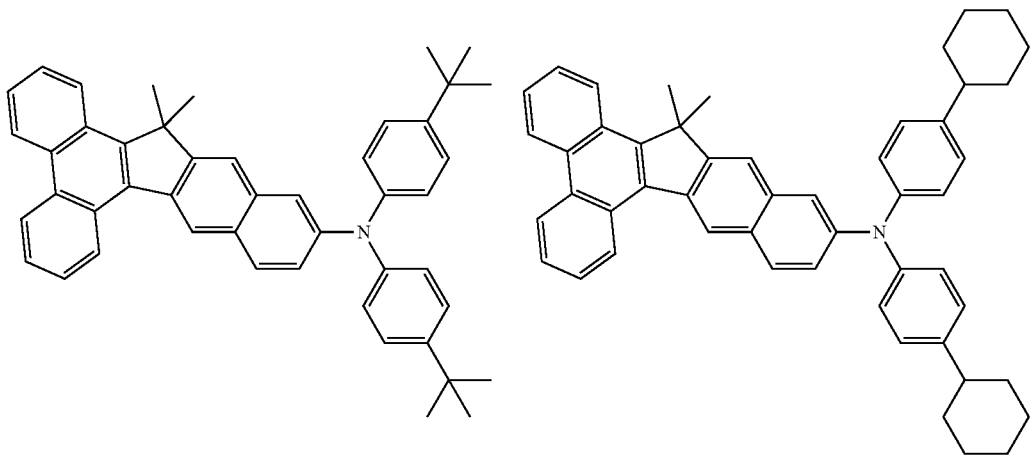
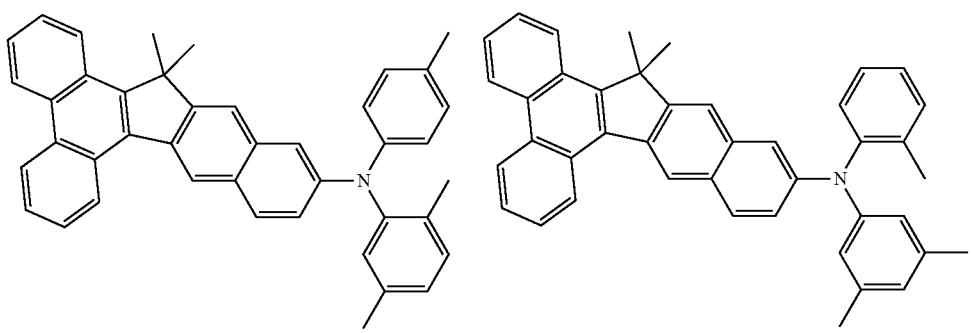

-continued
| 801 | 802 |
|---|---|
| 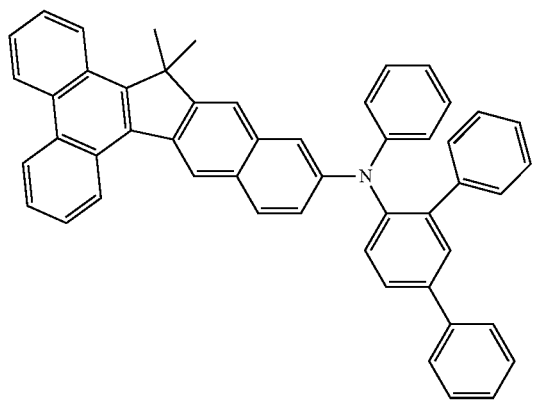 | 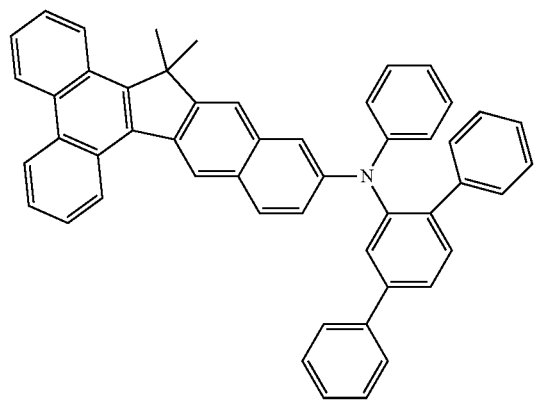 |
| 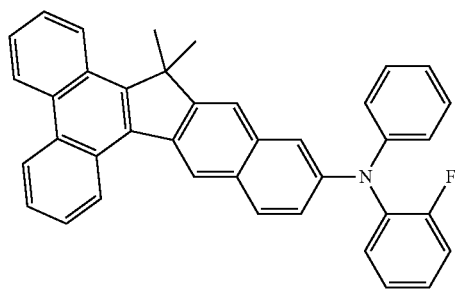 | 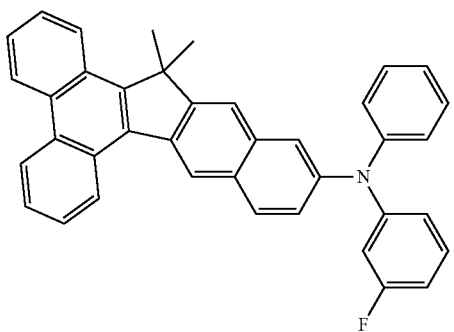 |
| 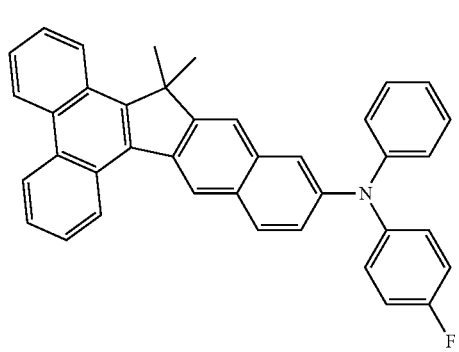 | 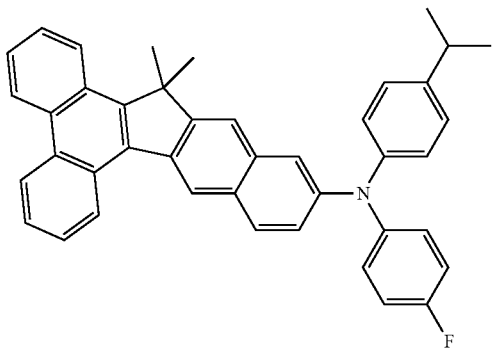 |
| 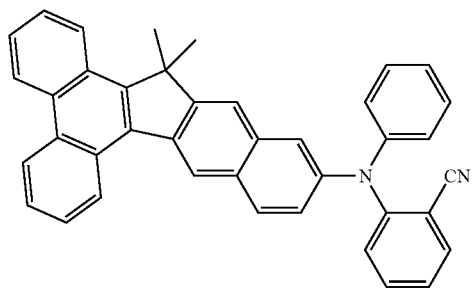 | 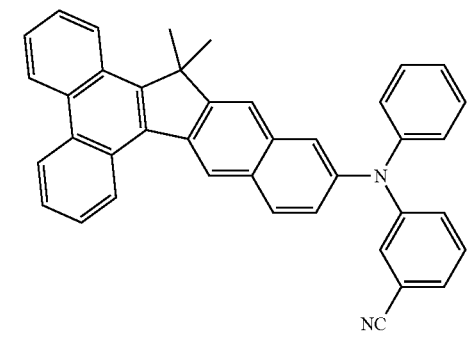 |

-continued
| 803 | 804 |
|---|---|
| 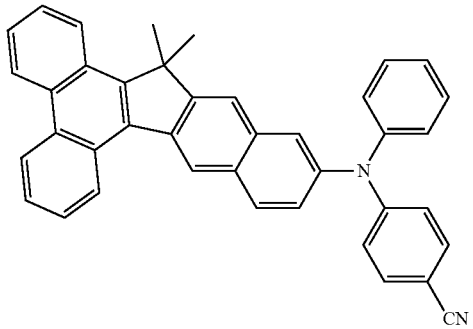 | 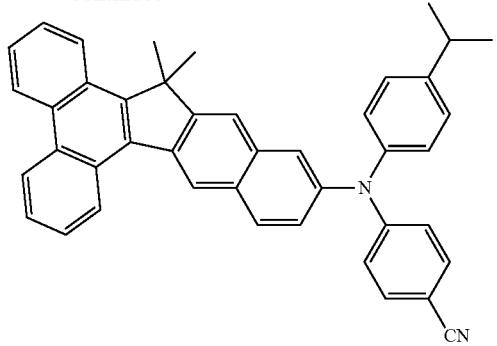 |
| 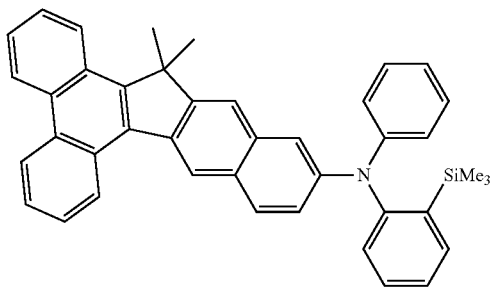 | 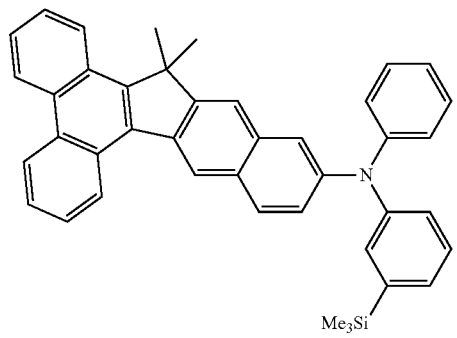 |
| 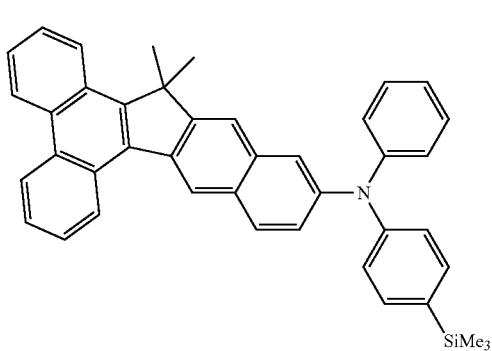 | 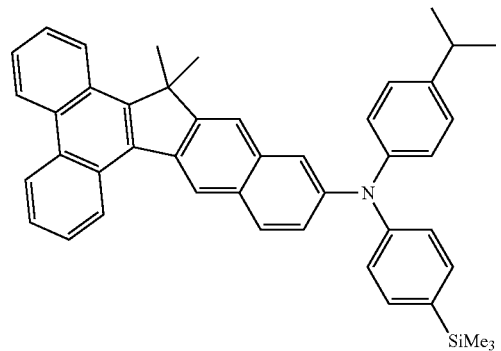 |
| 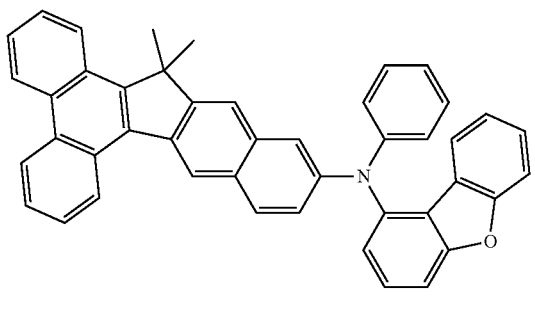 | 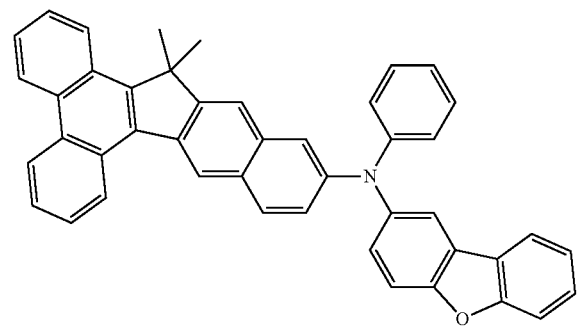 |

-continued
805
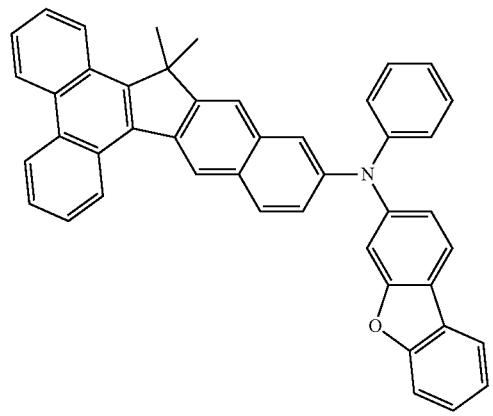
806
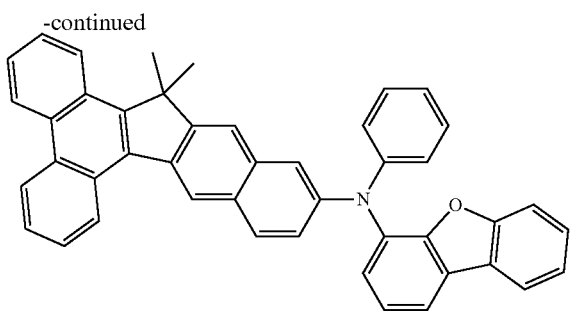
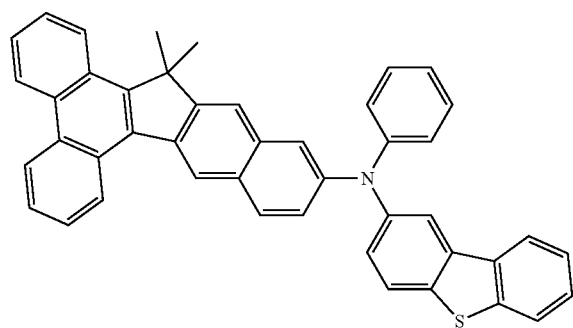
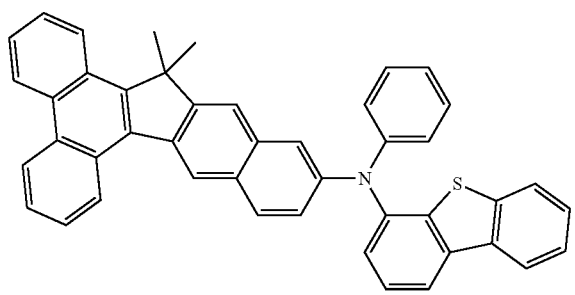
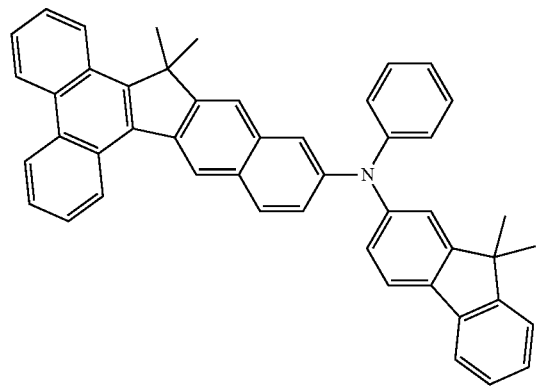
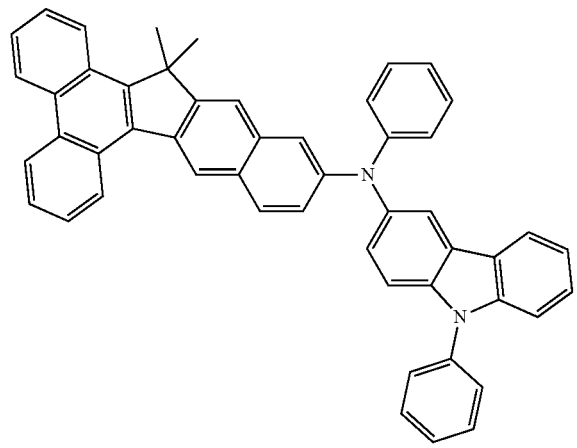
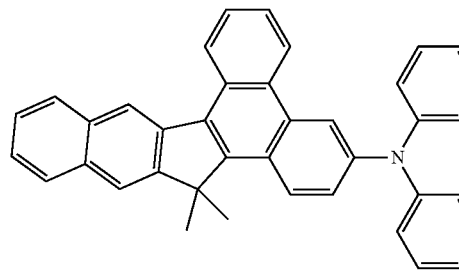
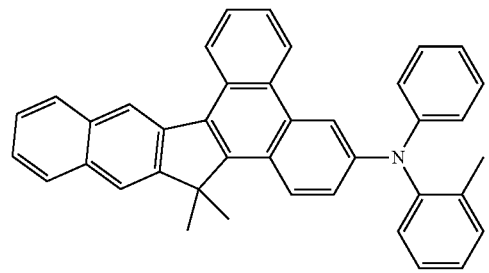

-continued
807
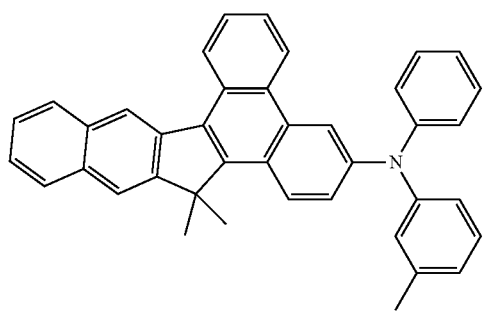
808
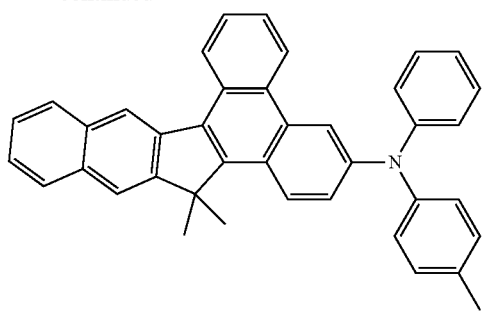
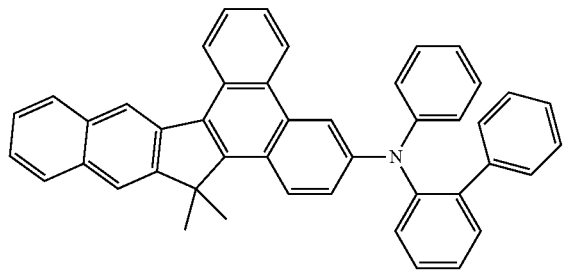
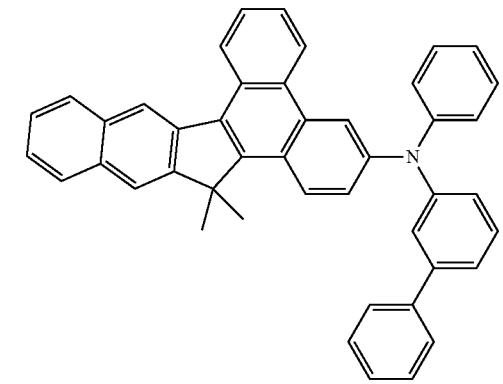
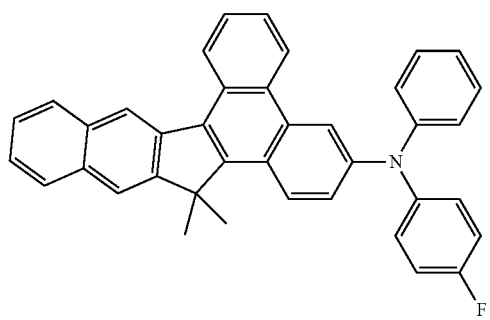
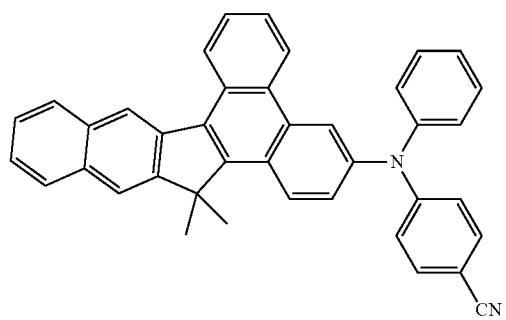
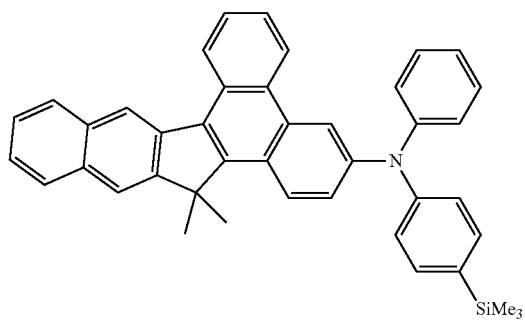
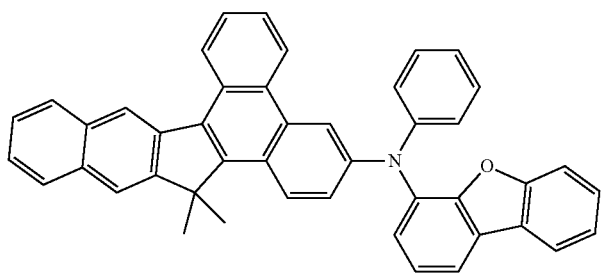
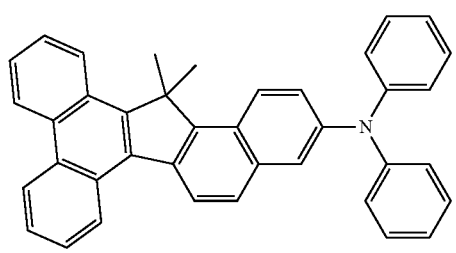
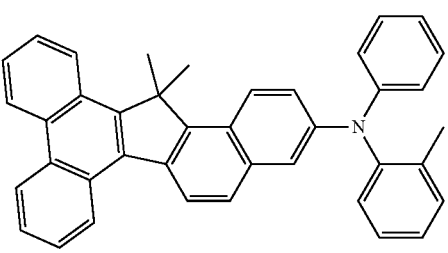

809 810
-continued
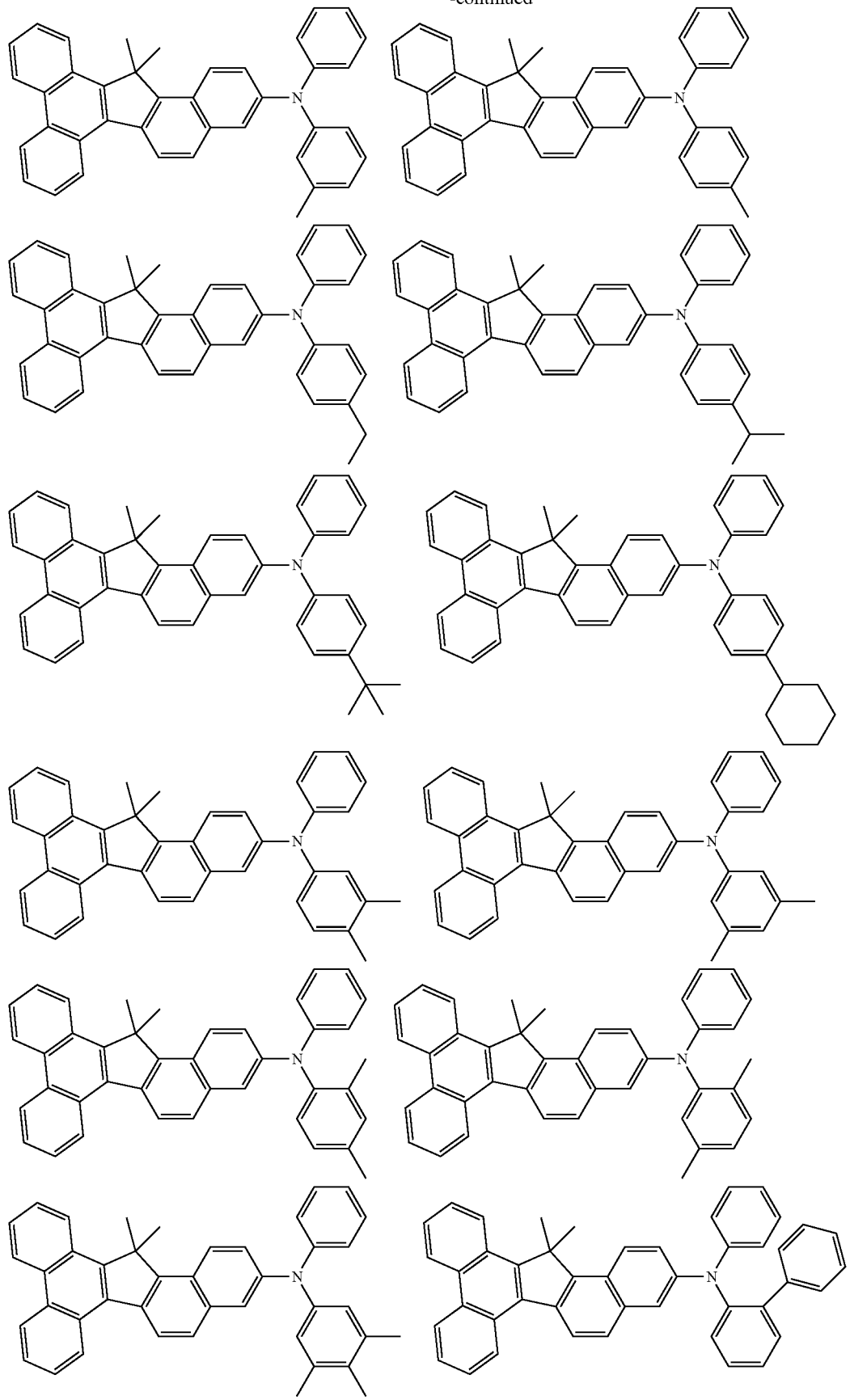

-continued
| 811 | 812 |
|---|---|
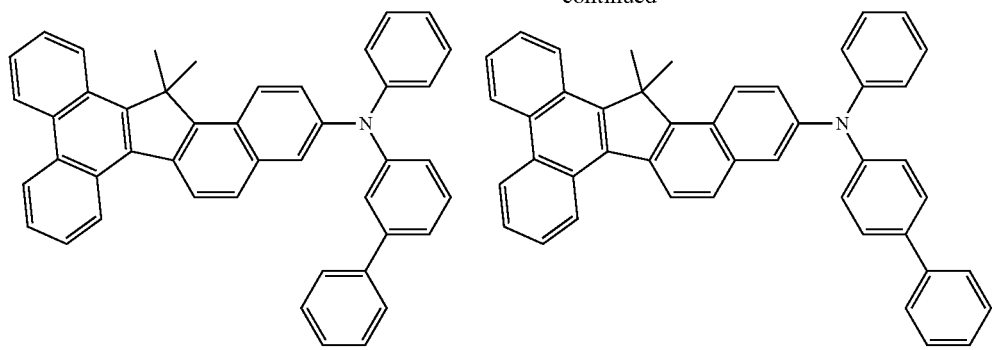
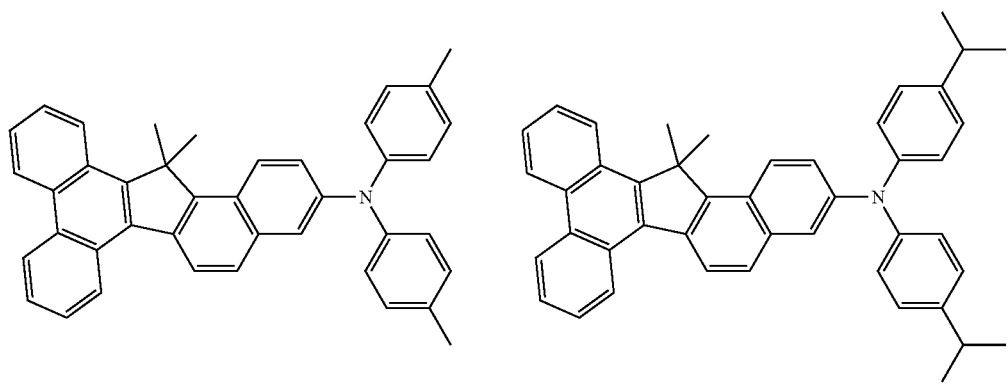
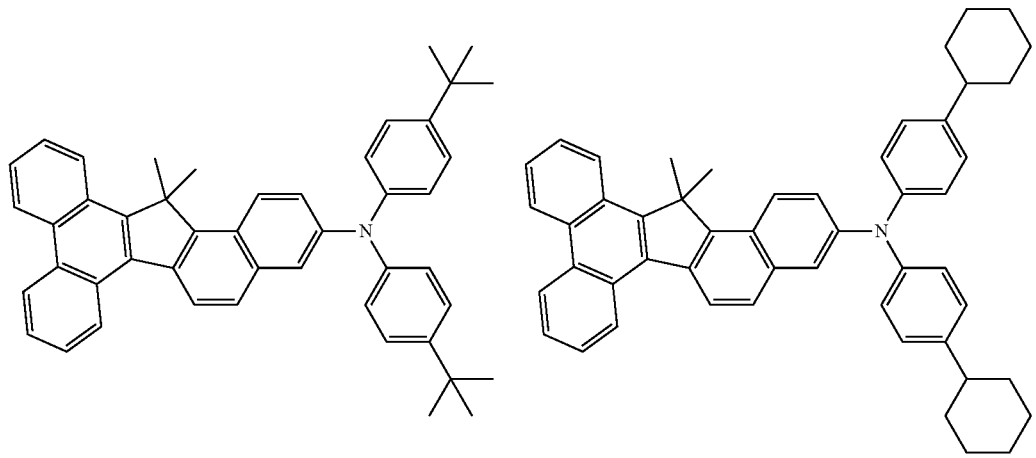
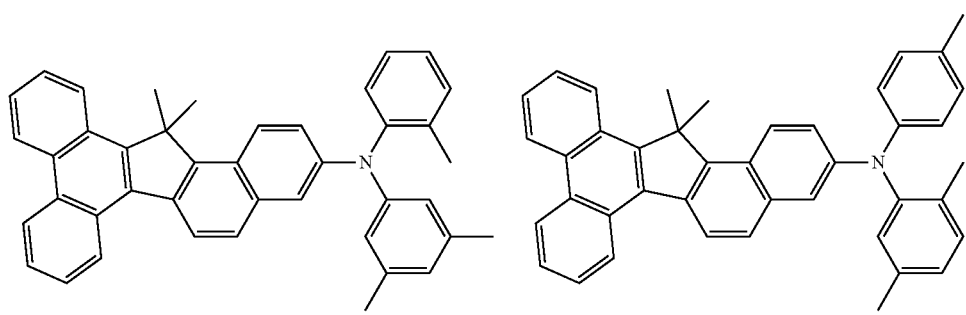

-continued
| 813 | 814 |
|---|---|
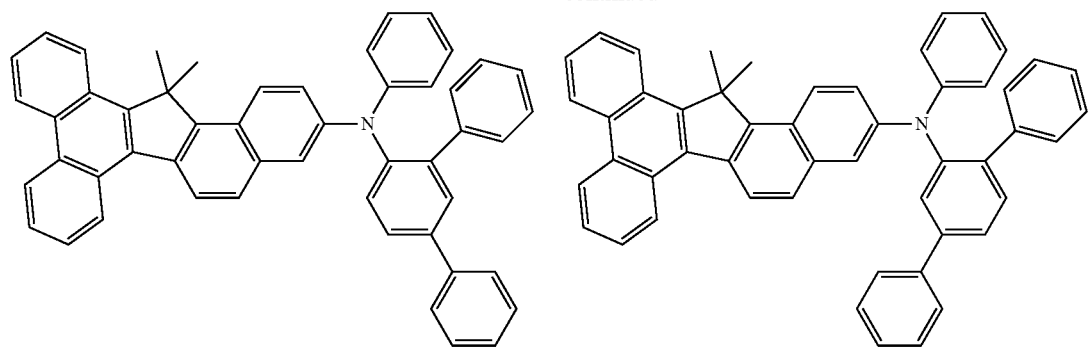
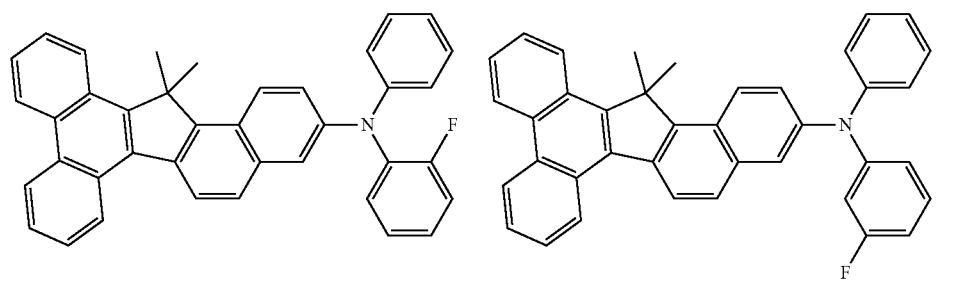
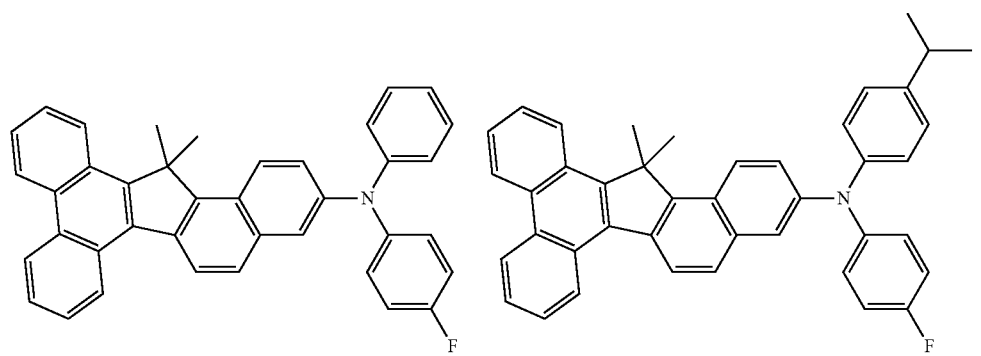
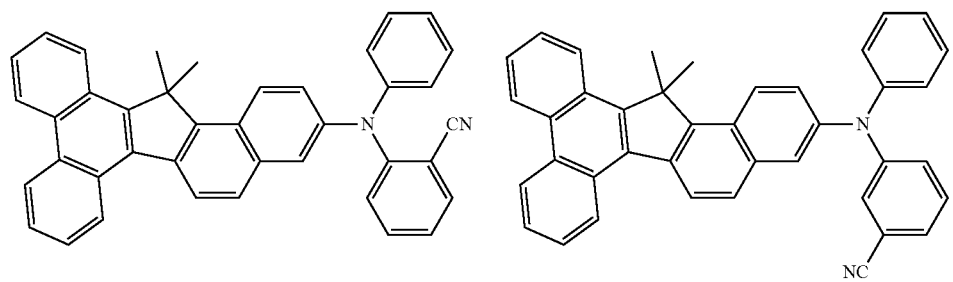
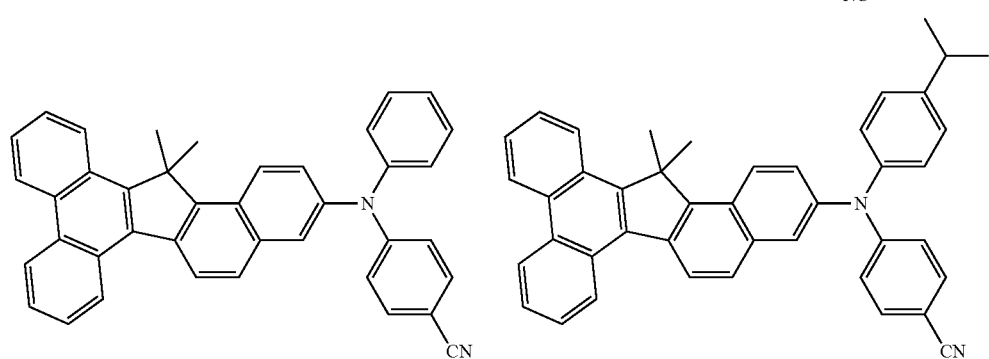

815 816
-continued
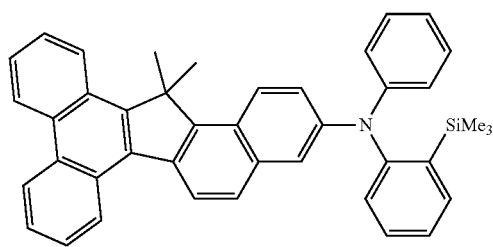 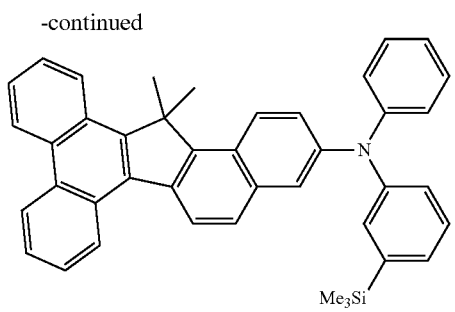
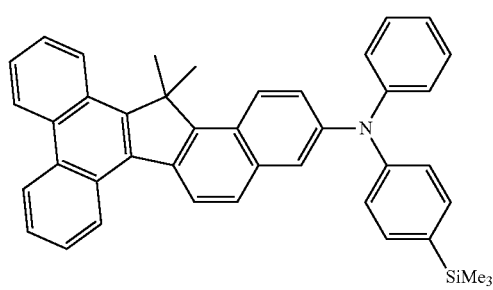 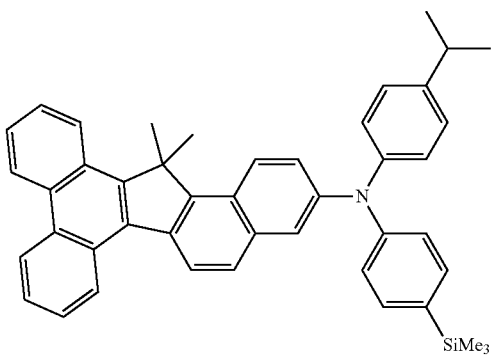
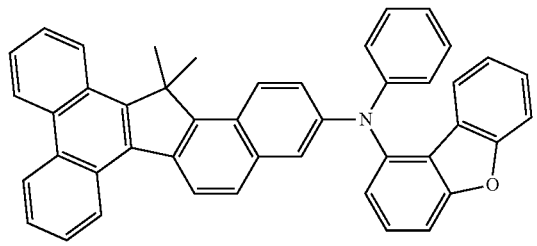 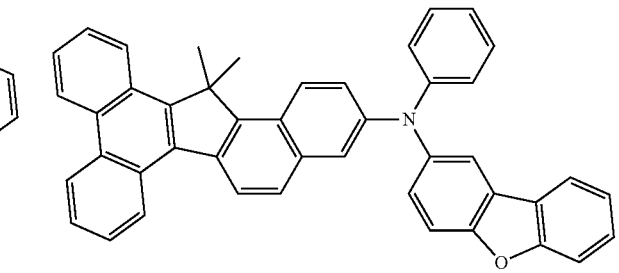
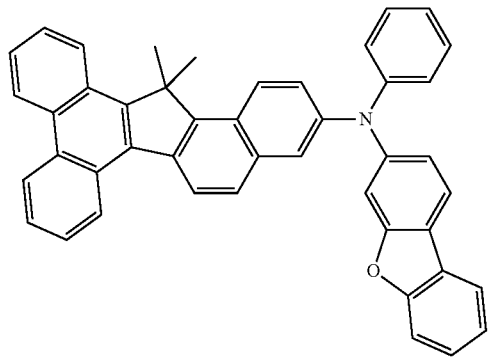 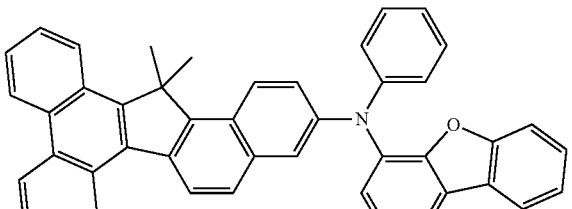
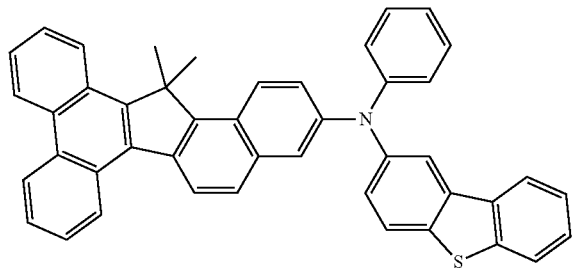 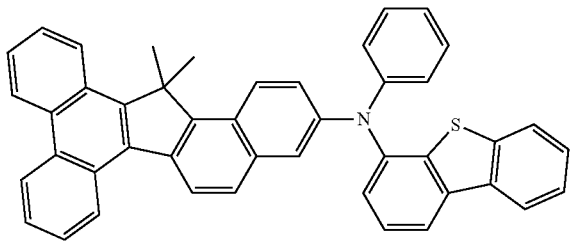

-continued
| 817 | 818 |
|---|---|
| 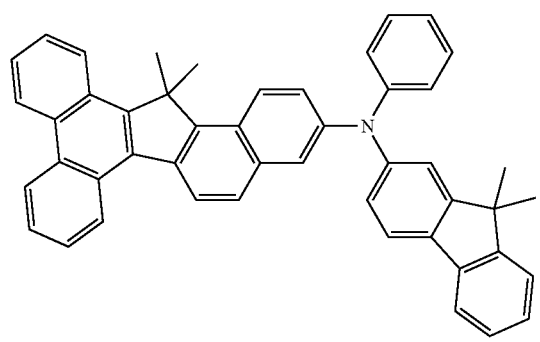 | 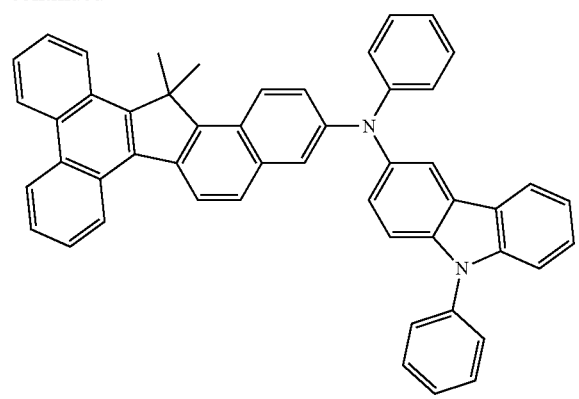 |
| 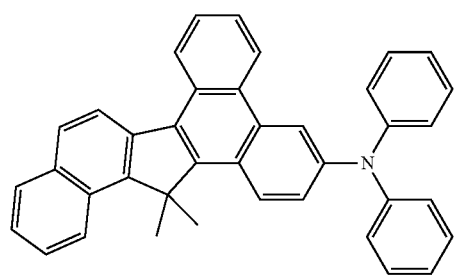 | 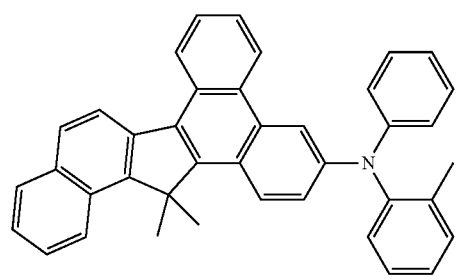 |
| 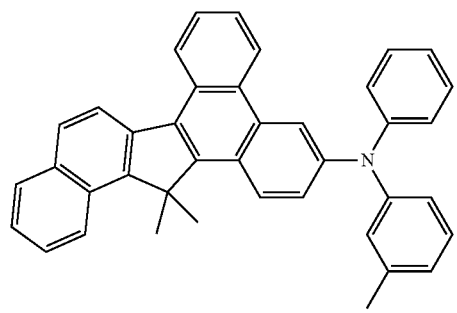 | 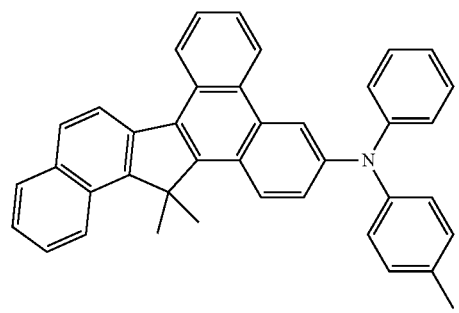 |
| 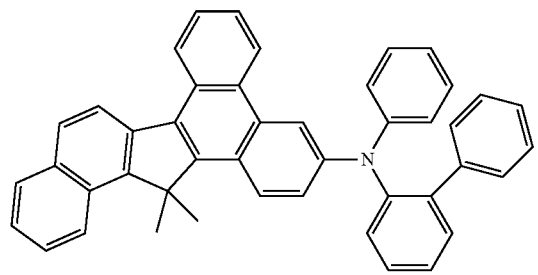 | 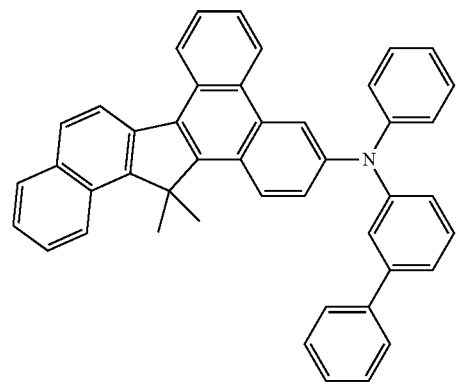 |

-continued
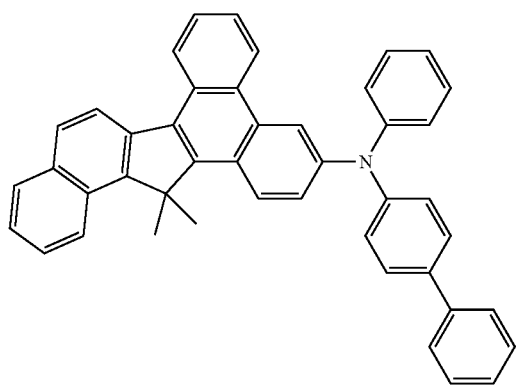
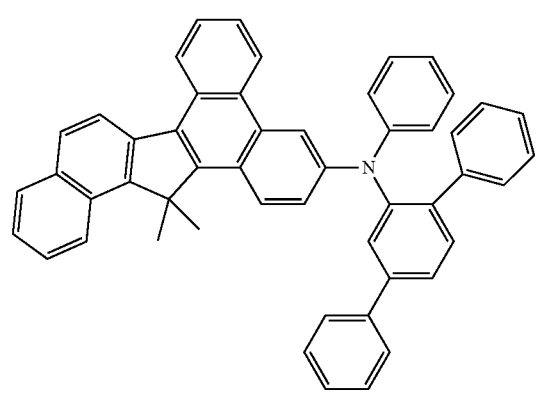
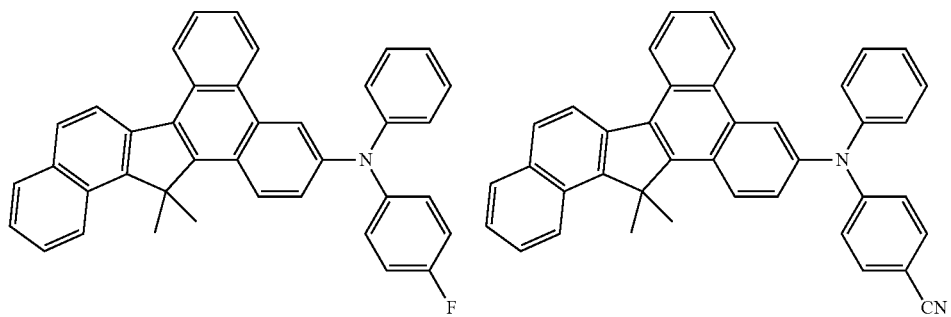
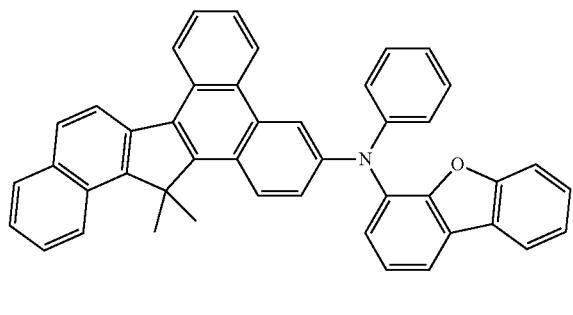
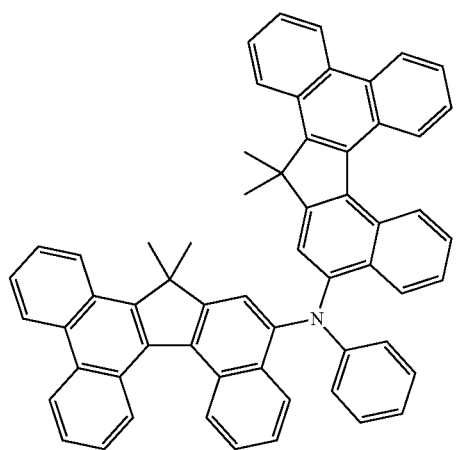

-continued
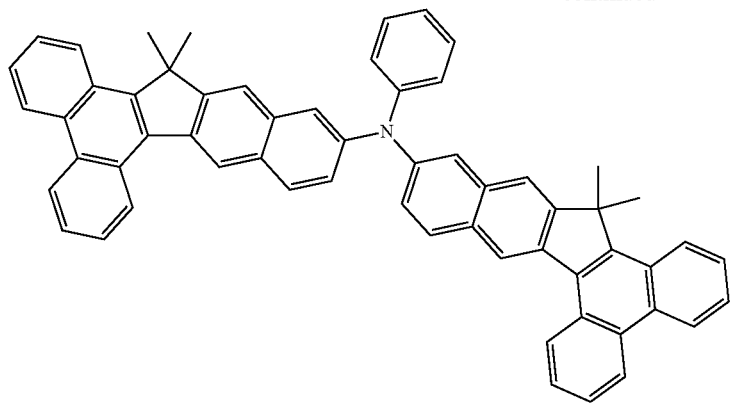
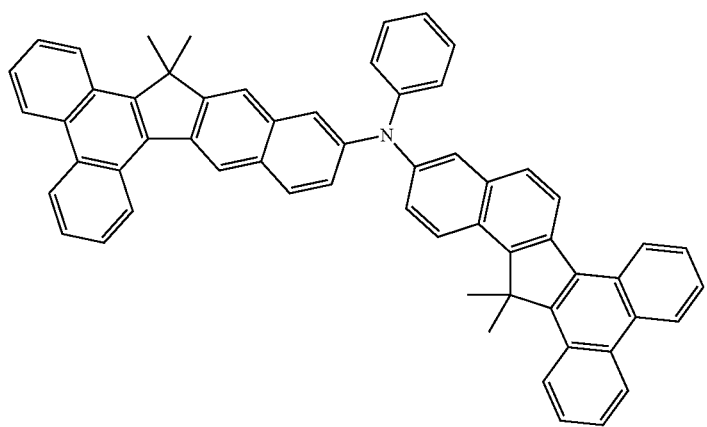
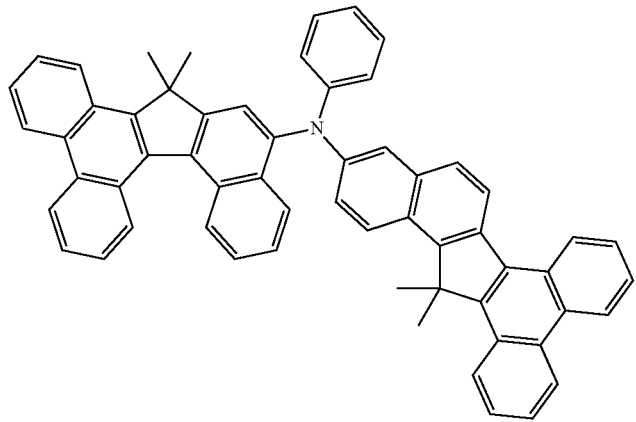
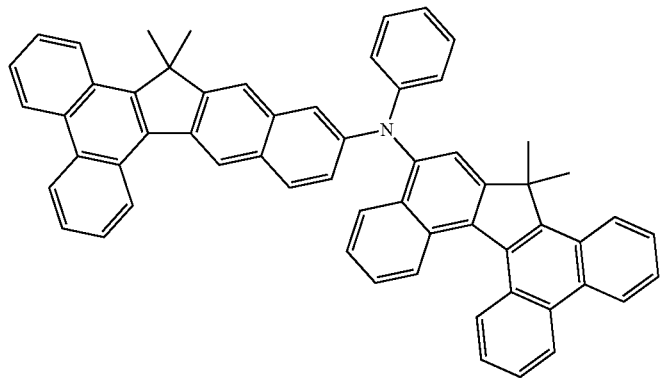

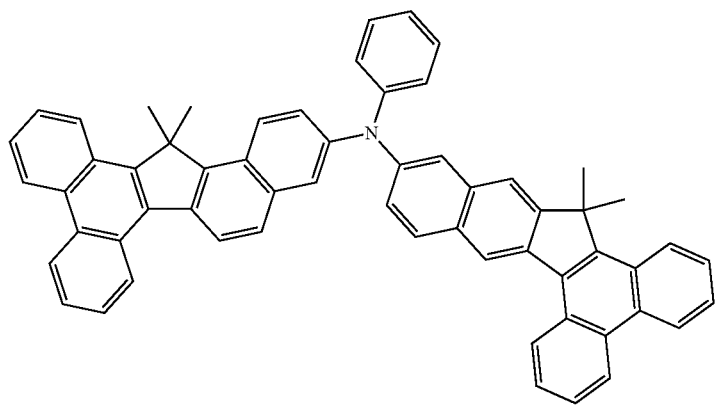
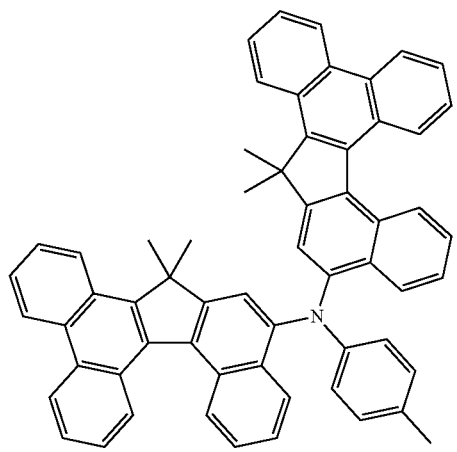
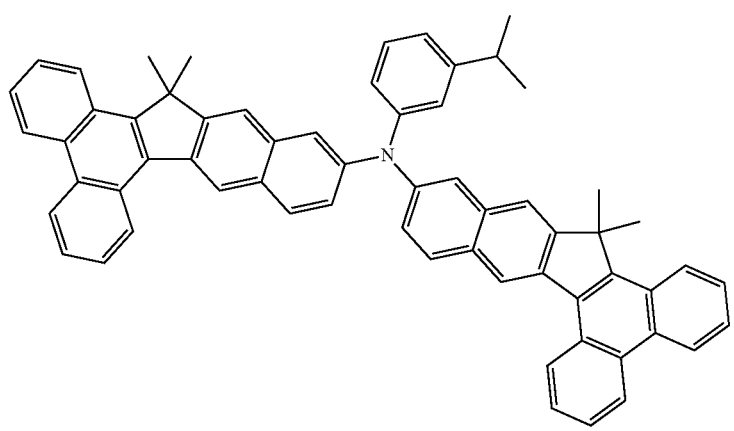
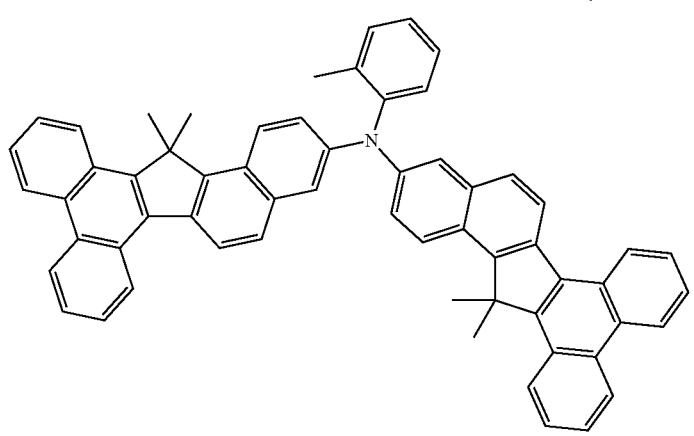

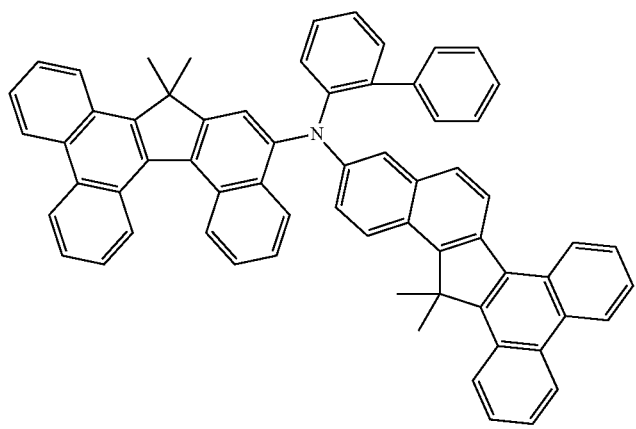
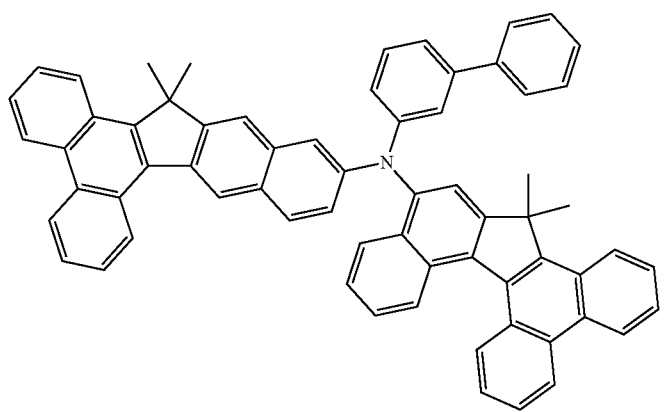
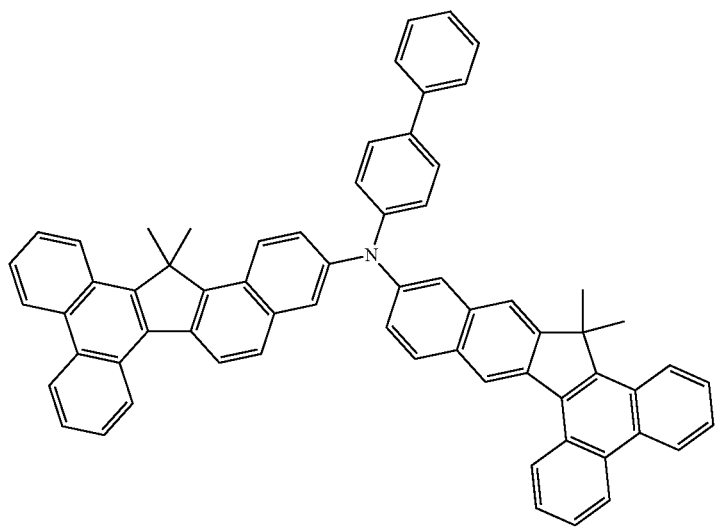

-continued
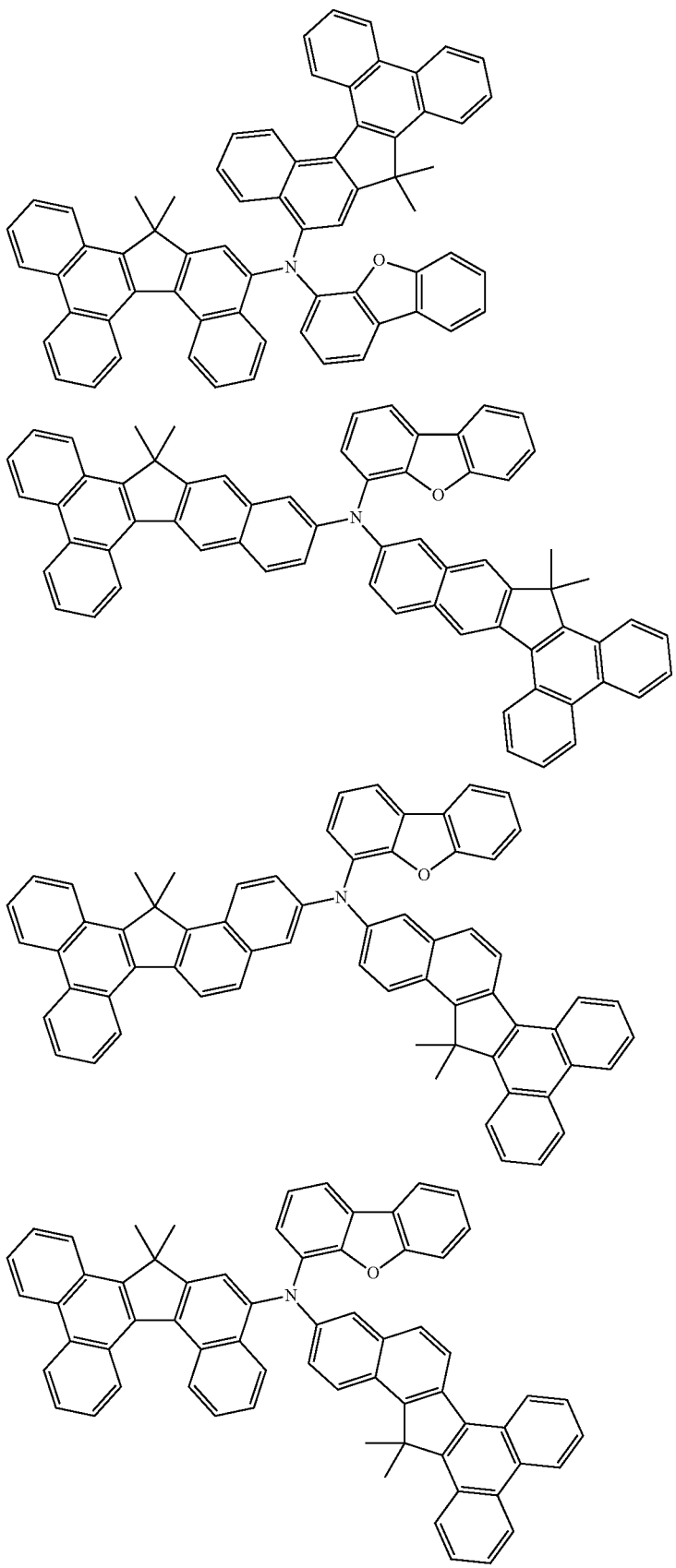

-continued
| 829 | 830 |
|---|---|
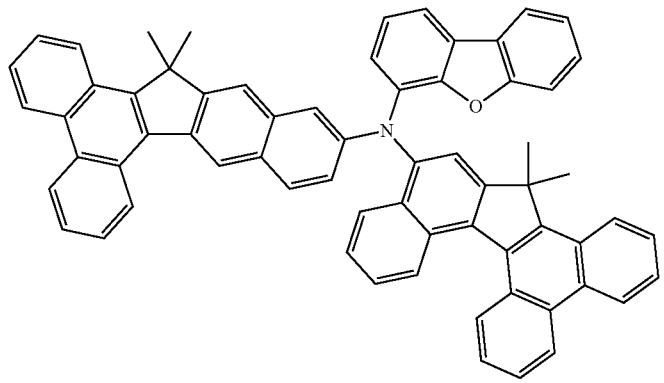
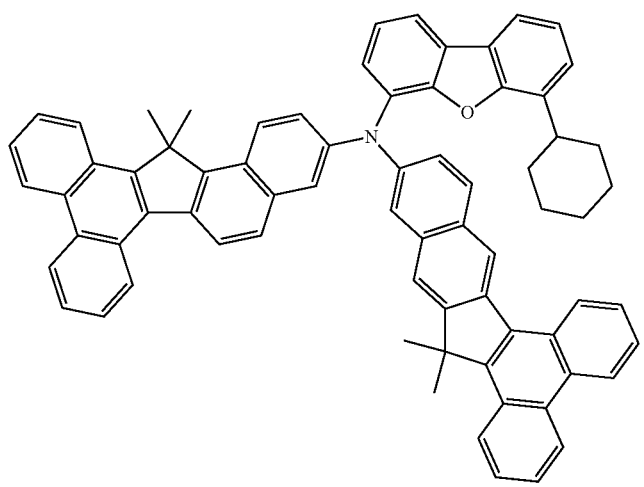
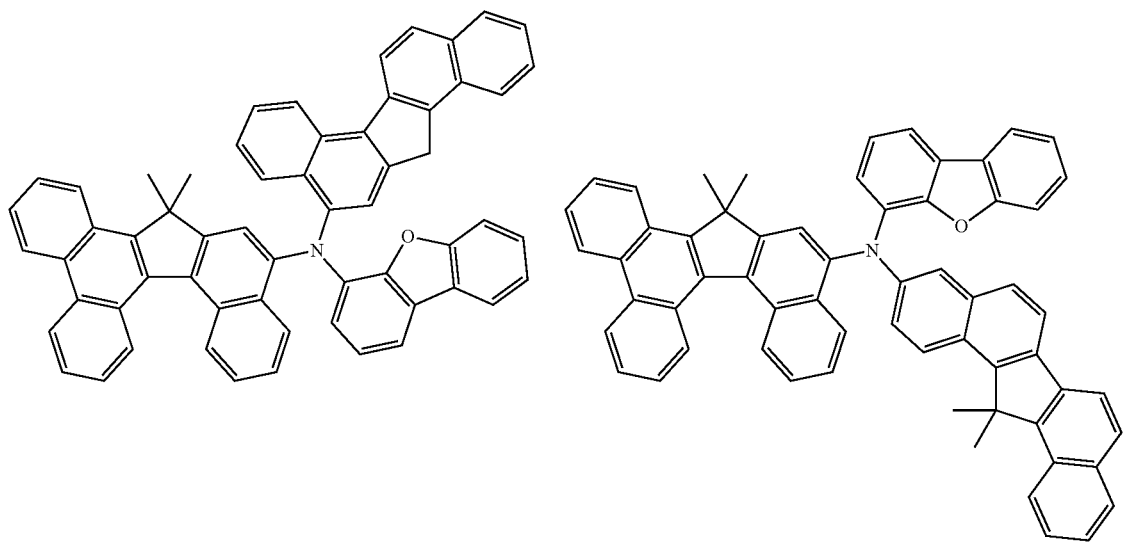

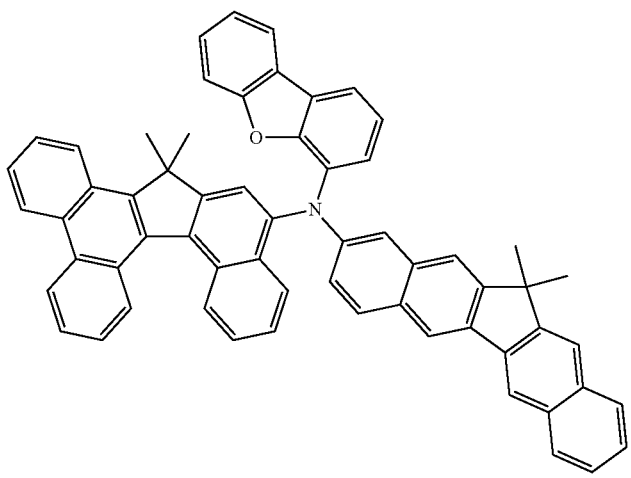
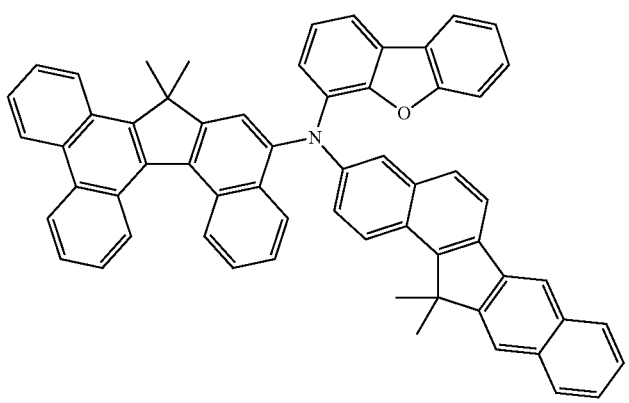
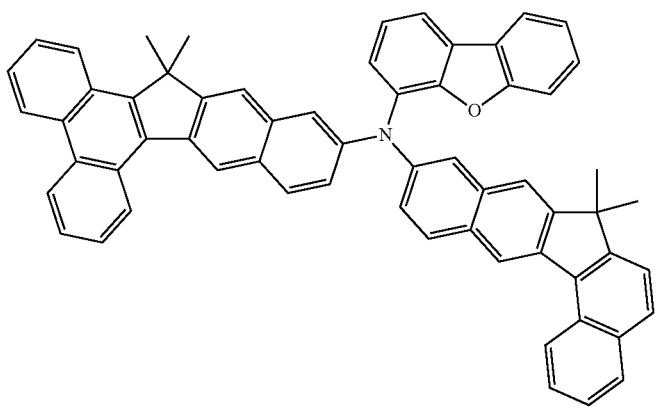
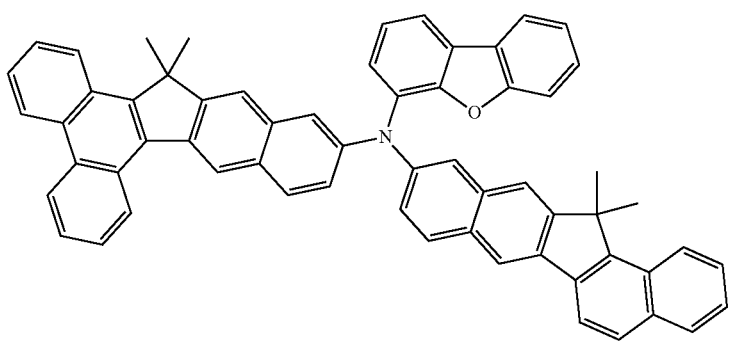

-continued
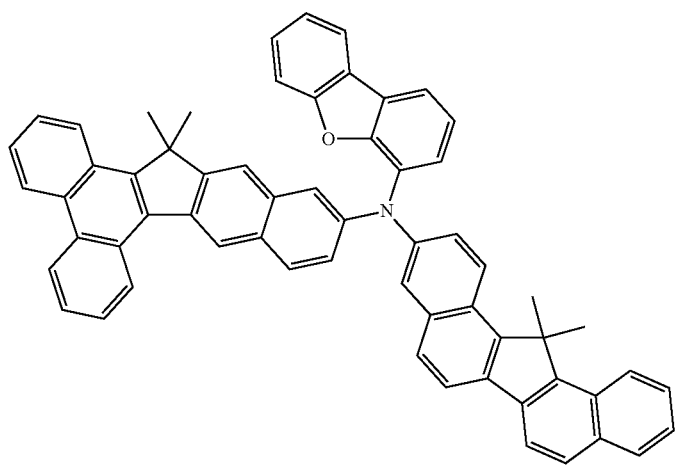

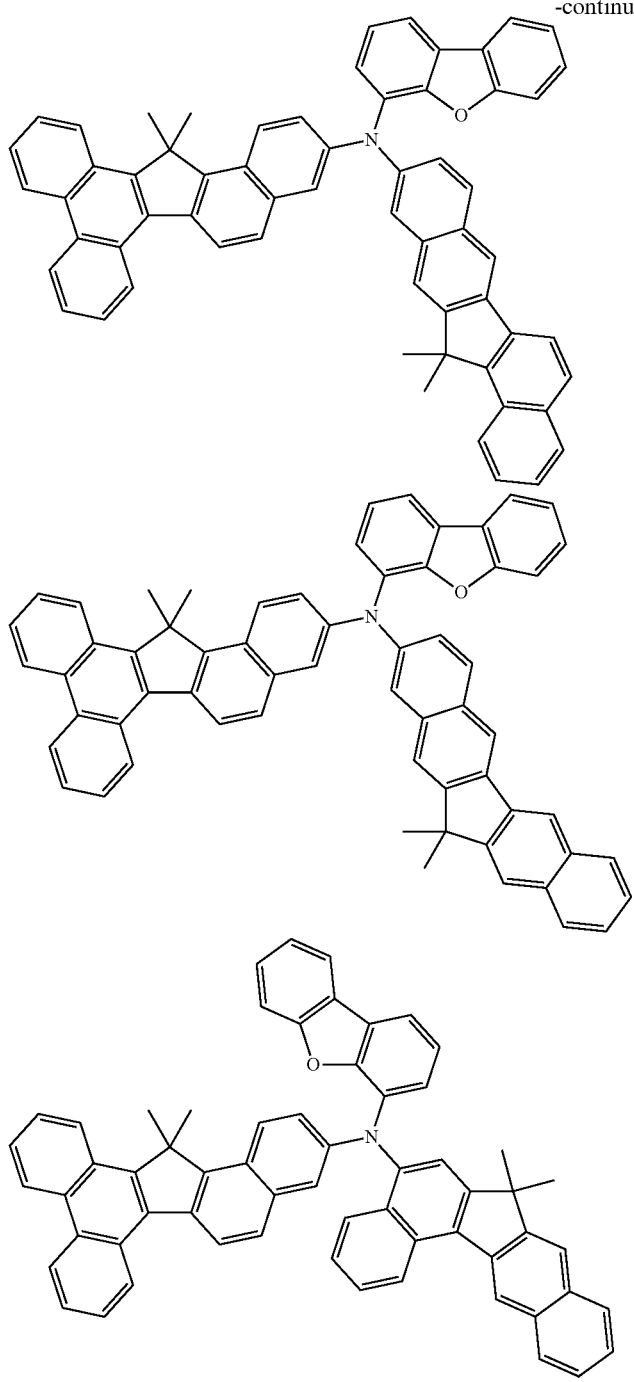

The compound of the invention mentioned above is useful as a material for organic EL devices.

The production method thereof is not particularly limited and can be easily produced by utilizing or modifying known synthetic reactions while taking the examples, etc. in the present specification into consideration.

Organic EL Device

The organic EL device of the invention will be described below.

The organic EL device of the invention comprises an organic thin film layer between a cathode and an anode. The organic thin film layer comprises a light emitting layer and at least one layer of the organic thin film layer comprises the compound of the invention mentioned above. Some of the organic EL devices of the invention can be operated at a lower driving voltage and have a long lifetime. Some of the organic EL devices emit blue light with high color purity.

Examples of the organic thin film layer which comprises the material for organic EL device include a hole transporting layer, a light emitting layer, an electron transporting, a space layer, and a blocking layer, although not limited thereto.

Particularly in view of the emission efficiency and the device lifetime, a compound of the invention having an amino group is preferably used in a light emitting layer and more preferably used in a light emitting layer as a dopant material. A compound of the invention having a heteroaryl group, particularly having a nitrogen-containing heteroaryl group is preferably used in an electron transporting layer or a blocking layer interposed between a light emitting layer and an electron transporting layer. In addition, particularly in view of the driving voltage and the emission efficiency, a compound of the invention having an anthracene skeleton is preferably used in a light emitting layer and more preferably in a light emitting layer as a host material, particularly as a fluorescent host material.

The organic EL device of the invention may be any of a single color emitting device of fluorescent or phosphorescent type, a white-emitting device of fluorescent/phosphorescent hybrid type, an emitting device of a simple type having a single emission unit, and an emitting device of a tandem type having two or more emission units. The "emission unit" referred to herein is the smallest unit for emitting light by the recombination of injected holes and injected electrons, which comprises one or more organic layers wherein at least one layer is a light emitting layer.

A representative device structures of the simple-type organic EL device is:
(1) anode/emission unit/cathode.

The emission unit may be a laminate comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the emission unit are shown below:

(a) hole transporting layer/light emitting layer (/electron transporting layer);
(b) hole transporting layer/first fluorescent emitting layer/second fluorescent emitting layer (/electron transporting layer);
(c) hole transporting layer/phosphorescent emitting layer/space layer/fluorescent emitting layer (/electron transporting layer);
(d) hole transporting layer/first phosphorescent emitting layer/second phosphorescent emitting layer/space layer/fluorescent emitting layer (/electron transporting layer);
(e) hole transporting layer/first phosphorescent emitting layer/space layer/second phosphorescent emitting layer/space layer/fluorescent emitting layer (/electron transporting layer); and
(f) hole transporting layer/phosphorescent emitting layer/space layer/first fluorescent emitting layer/second fluorescent emitting layer (/electron transporting layer).

The emission color of the phosphorescent light emitting layer and that of the fluorescent light emitting layer may be different. For example, the layered structure of the laminated light emitting layer (d) mentioned above may be hole transporting layer/first phosphorescent emitting layer (red emission)/second phosphorescent emitting layer (green emission)/space layer/fluorescent emitting layer (blue emission)/electron transporting layer.

An electron blocking layer may be disposed between the light emitting layer and the hole transporting layer or between the light emitting layer and the space layer, if necessary. Also, a hole blocking layer may be disposed between the light emitting layer and the electron transporting layer, if necessary. With such an electron blocking layer or a hole blocking layer, electrons and holes are confined in the light emitting layer to facilitate the charge recombination in the light emitting layer, thereby improving the lifetime.

A representative device structure of the tandem-type organic EL device is:
(2) anode/first emission unit/intermediate layer/second emission unit/cathode.

The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer may be formed by known materials so as to supply electrons to the first emission unit and holes to the second emission unit.

A schematic structure of an example of the organic EL device of the invention is shown in FIG. 1, wherein the organic EL device 1 comprises a substrate 2, an anode 3, a cathode 4, and an emission unit 10 (organic thin film layer) disposed between the anode 3 and the cathode 4. The emission unit 10 comprises a light emitting layer 5 which comprises at least one fluorescent emitting layer containing a fluorescent host material and a fluorescent dopant material. A hole injecting layer/transporting layer 6 may be disposed between the light emitting layer 5 and the anode 3, and an electron injecting layer/transporting layer 7 may be disposed between the light emitting layer 5 and the cathode 4. An electron blocking layer may be disposed on the anode 3 side of the light emitting layer 5, and a hole blocking layer may be disposed on the cathode 4 side of the light emitting layer 5. With these blocking layers, electrons and holes are confined in the light emitting layer 5 to facilitate the exciton generation in the light emitting layer 5.

In the present invention, a host material is referred to as a fluorescent host material when combinedly used with a fluorescent dopant material and referred to as a phosphorescent host material when combinedly used with a phosphorescent dopant material. Therefore, the fluorescent host material and the phosphorescent host material are not distinguished from each other merely by the difference in their molecular structures. Namely, in the present invention, the term "fluorescent host material" means a material for constituting a fluorescent emitting layer containing a fluorescent dopant material and does not mean a material that cannot be used as a material for a phosphorescent emitting layer. The same applies to the phosphorescent host material.

Substrate

The organic EL device of the invention is formed on a light-transmissive substrate. The light-transmissive substrate serves as a support for the organic EL device and preferably a flat substrate having a transmittance of 50% or more to 400 to 700 nm visible light. Examples of the substrate include a glass plate and a polymer plate. The glass plate may include a plate made of soda-lime glass, barium-strontium-containing glass, lead glass, aluminosilicate glass, borosilicate glass, barium borosilicate glass, or quartz. The polymer plate may include a plate made of polycarbonate, acryl, polyethylene terephthalate, polyether sulfide, or polysulfone.

Anode

The anode of the organic EL device injects holes to the hole transporting layer or the light emitting layer, and an anode having a work function of 4.5 eV or more is effective. Examples of the material for anode include indium tin oxide alloy (ITO), tin oxide (NESA), indium zinc oxide alloy, gold, silver, platinum, and copper. The anode is formed by making the electrode material into a thin film by a method, such as a vapor deposition method and a sputtering method. When getting the light emitted from the light emitting layer through the anode, the transmittance of anode to visible light is preferably 10% or more. The sheet resistance of anode is preferably several hundreds Ω/or less. The film thickness of anode depends upon the kind of material and generally 10 nm to 1 μm, preferably 10 to 200 nm.

Cathode

The cathode injects electrons to the electron injecting layer, the electron transporting layer or the light emitting layer, and formed preferably by a material having a small work function. Examples of the material for cathode include, but not limited to, indium, aluminum, magnesium, magnesium-indium alloy, magnesium-aluminum alloy, aluminum-lithium alloy, aluminum-scandium-lithium alloy, and magnesium-silver alloy. Like the anode, the cathode is formed by making the material into a thin film by a method, such as a vapor deposition method and a sputtering method. The emitted light may be taken through the cathode, if necessary.

The material other than the compound of the invention usable in each layer will be described below.

Light Emitting Layer

The light emitting layer is an organic layer having a light emitting function and comprises a host material and a dopant material when a doping system is employed. The major function of the host material is to promote the recombination of electrons and holes and confine excitons in the light emitting layer. The dopant material causes the excitons generated by recombination to emit light efficiently.

In case of a phosphorescent device, the major function of the host material is to confine the excitons generated on the dopant material in the light emitting layer.

To control the carrier balance in the light emitting layer, the light emitting layer may be a double host material (host/co-host) layer, for example, a layer in which an electron transporting host material and a hole transporting host material are combinedly used.

The light emitting layer may be a double dopant layer in which two or more kinds of dopant materials having high quantum yield are combinedly used and each dopant material emits light with its own color. For example, to obtain a yellow emission, a light emitting layer formed by co-depositing a host material, a red-emitting dopant material and a green-emitting dopant material is used.

In a laminate of two or more light emitting layers, electrons and holes are accumulated in the interface between the light emitting layers, and therefore, the recombination region is localized in the interface between the light emitting layers, to improve the quantum efficiency.

The easiness of hole injection to the light emitting layer and the easiness of electron injection to the light emitting layer may be different from each other. Also, the hole transporting ability and the electron transporting ability each being expressed by mobility of holes and electrons in the light emitting layer may be different from each other.

The light emitting layer is formed, for example, by a known method, such as a vapor deposition method, a spin coating method, and LB method. The light emitting layer can be formed also by making a solution of a binder, such as resin, and the material for the light emitting layer in a solvent into a thin film by a method, such as spin coating.

The light emitting layer is preferably a molecular deposit film. The molecular deposit film is a thin film formed by depositing a vaporized material or a film formed by solidifying a material in the state of solution or liquid. The molecular deposit film can be distinguished from a thin film formed by LB method (molecular build-up film) by the differences in the assembly structures and higher order structures and the functional difference due to the structural differences.

The thickness of the light emitting layer is preferably 5 to 50 nm, more preferably 7 to 50 nm, and still more preferably 10 to 50 nm. If 5 nm or more, the light emitting layer can be formed easily. If 50 nm or less, the increase in the driving voltage can be prevented.

Dopant Material

The fluorescent dopant material (phosphorescent emitting material) used in the light emitting layer is a compound which emits light by releasing the energy of excited singlet state and is not particularly limited as long as emitting light by releasing the energy of excited singlet state. Examples there of include a fluoranthene derivative, a styrylarylene derivative, a pyrene derivative, an arylacetylene derivative, a fluorene derivative, a boron complex, a perylene derivative, an oxadiazole derivative, an anthracene derivative, a styrylamine derivative, and an arylamine derivative, with an anthracene derivative, a fluoranthene derivative, a styrylamine derivative, an arylamine derivative, a styrylarylene derivative, a pyrene derivative, and a boron complex being preferred, and an anthracene derivative, a fluoranthene derivative, a styrylamine derivative, an arylamine derivative, and a boron complex being more preferred.

The content of the fluorescent dopant material in the light emitting layer is not particularly limited and selected according to the use of the device, and preferably 0.1 to 70% by mass, more preferably 1 to 30% by mass, and still more preferably 1 to 20% by mass, and still further preferably 1 to 10% by mass. If being 0.1% by mass or more, the amount of light emission is sufficient. If being 70% by mass or less, the concentration quenching can be avoided.

Host Material

An anthracene derivative or a compound having a polycyclic aromatic skeleton, preferably an anthracene derivative is preferably used as the host material for the light emitting layer.

For example, the following anthracene derivative represented by formula (5) is used as the host material for a blue emitting layer:

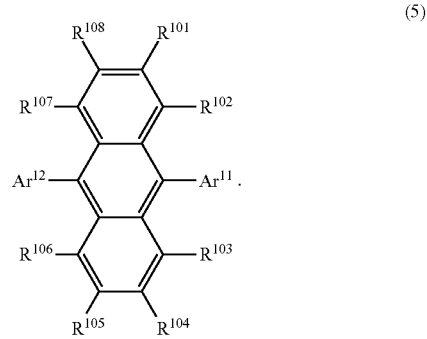

(5)

In formula (5), $Ar^{11}$ and $Ar^{12}$ each independently represent a substituted or unsubstituted monocyclic group having 5 to 50 ring atoms or a substituted or unsubstituted fused ring group having 8 to 50 ring atoms.

$R^{101}$ to $R^{108}$ each independently selected from a hydrogen atom; a substituted or unsubstituted monocyclic group having 5 to 50, preferably 5 to 30, more preferably 5 to 20, and still more preferably 5 to 12 ring atoms; a substituted or unsubstituted fused ring group having 8 to 50, preferably 8 to 30, more preferably 8 to 20, and still more preferably 8 to 14 ring atoms; a group comprising a combination of the monocyclic group and the fused ring group; a substituted or unsubstituted alkyl group having 1 to 50, preferably 1 to 20, more preferably 1 to 10, and still more preferably 1 to 6 carbon atoms; a substituted or unsubstituted cycloalkyl group having 3 to 50, preferably 3 to 20, more preferably 3 to 10, and still more preferably 5 to 8 ring carbon atoms; a substituted or unsubstituted alkoxy group having 1 to 50, preferably 1 to 20, more preferably 1 to 10, and still more preferably 1 to 6 carbon atoms; a substituted or unsubstituted aralkyl group having 7 to 50, preferably 7 to 20, more preferably 7 to 14 carbon atoms; a substituted or unsubstituted aryloxy group having 6 to 50, preferably 6 to 20, more preferably 6 to 12 ring carbon atoms; a substituted or unsubstituted silyl group; a halogen atom; and a cyano group.

Preferred is the anthracene derivative wherein $R^{101}$ to $R^{108}$ are all hydrogen atoms, or one of $R^{101}$ and $R^{108}$, one of $R^{104}$ and $R^{105}$, both of $R^{101}$ and $R^{105}$, or both of $R^{108}$ and $R^{104}$ are selected from a monocyclic group having 5 to 50 ring atoms, preferably a phenyl group, a biphenylyl group, and a terphenylyl group; a substituted or unsubstituted alkyl group having 1 to 50 carbon atoms, preferably a methyl group, an ethyl group, a n-propyl group, an isopropyl group, a n-butyl group, an isobutyl group, a s-butyl group, and a t-butyl group; or a substituted silyl group, preferably a trimethylsilyl group. More preferred is the anthracene derivative wherein $R^{101}$ to $R^{108}$ are all hydrogen atoms.

The monocyclic group of formula (5) is a group composed of only a ring structure having no fused ring structure.

Examples of the monocyclic group having 5 to 50 ring atoms include an aromatic group, such as a phenyl group, a biphenylyl group, a terphenylyl group, and a quaterphenylyl group; and a heterocyclic group, such as a pyridyl group, a pyrazyl group, a pyrimidyl group, a triazinyl group, a furyl group, and a thienyl group, with a phenyl group, a biphenylyl group, and a terphenylyl group being preferred.

The fused ring group of formula (5) is a group wherein two or more ring structures are fused to each other.

Examples of the fused ring group having 8 to 50 ring atoms include a fused aromatic ring group, such as a naphthyl group, a phenanthryl group, an anthryl group, a chrysenyl group, a benzanthryl group, a bonzophenanthryl group, a triphenylenyl group, a benzochrysenyl group, an indenyl group, a fluorenyl group, a 9,9-dimethylfluorenyl group, a benzofluorenyl group, a dibenzofluorenyl group, a fluoranthenyl group, and a benzofluoranthenyl group; and a fused heterocyclic group, such as a benzofuranyl group, a benzothiophenyl group, an indolyl group, a dibenzofuranyl group, a dibenzothiophenyl group, a carbazolyl group, a quinolyl group, and a phenanthrolinyl group; with a naphthyl group, a phenanthryl group, an anthryl group, a 9,9-dimethylfluorenyl group, a fluoranthenyl group, a benzanthryl group, a dibenzothiophenyl group, a dibenzofuranyl group, and a carbazolyl group being preferred.

The substituent of $Ar^{11}$ and $Ar^{12}$ is preferably selected from the monocyclic groups and the fused ring groups mentioned above.

In formula (5), examples of the alkyl group, the cycloalkyl group, the alkoxy group, the alkyl portion and the aryl portion of the aralkyl group, the aryloxy group, the substituted silyl group (alkylsilyl group and arylsilyl group), and the halogen atom are as defined above with respect to $R^1$ to $R^8$ and $R^a$ to $R^d$ of formula (2).

In formula (5a), $R^{101}$ to $R^{108}$ are preferably all hydrogen atoms, or one of $R^{101}$ and $R^{108}$, one of $R^{104}$ and $R^{105}$, both of $R^{101}$ and $R^{105}$, or both of $R^{108}$ and $R^{104}$ are preferably selected from a monocyclic group having 5 to 50 ring atoms, for example, a phenyl group, a biphenylyl group, or a terphenylyl group; a substituted or unsubstituted alkyl group having 1 to 50 carbon atoms, for example, a methyl group, an ethyl group, a n-propyl group, an isopropyl group, a n-butyl group, an isobutyl group, a s-butyl group, and a t-butyl group; and a substituted silyl group, for example, a trimethylsilyl group, with $R^{101}$ to $R^{108}$ wherein all are hydrogen atoms being more preferred.

The anthracene derivative represented by formula (5) is preferably any of the following anthracene derivatives (A), (B) and (C), and it is selected depending upon the constitution of the organic EL device to be applied or the required properties.

Anthracene Derivative (A)

The anthracene derivative (A) is represented by formula (5) wherein $Ar^{11}$ and $Ar^{12}$ each independently represent a substituted or unsubstituted fused ring group having 8 to 50 ring atoms. $Ar^{11}$ and $Ar^{12}$ may be the same or different.

The anthracene derivative represented by formula (5) wherein $Ar^{11}$ and $Ar^{12}$ are different substituted or unsubstituted fused ring groups (inclusive of the difference in the positions connecting to the anthracene ring) is particularly preferable. Examples of the fused ring are as described above, with a naphthyl group, a phenanthryl group, a benzanthryl group, a 9,9-dimethylfluorenyl group, and a dibenzofuranyl group being preferred.

Anthracene Derivative (B)

The anthracene derivative (B) is represented by formula (5) wherein one of $Ar^{11}$ and $Ar^{12}$ is a substituted or unsubstituted monocyclic group having 5 to 50 ring atoms and the other is a substituted or unsubstituted fused ring group having 8 to 50 ring atoms.

In a preferred anthracene derivative (B), $Ar^{12}$ is a naphthyl group, a phenanthryl group, a benzanthryl group, a 9,9-dimethylfluorenyl group, or a dibenzofuranyl group; and $Ar^{11}$ is an unsubstituted phenyl group or a substituted phenyl group having a substituent selected from a monocyclic group and a fused ring group, for example, a phenyl group, a biphenyl group, a naphthyl group, a phenanthryl group, a 9,9-dimethylfluorenyl group, and a dibenzofuranyl group.

Preferred examples of the monocyclic group and the fused ring group are as described above.

In another preferred anthracene derivative (B), $Ar^{12}$ is a substituted or unsubstituted fused ring group having 8 to 50 ring atoms and $Ar^{11}$ is an unsubstituted phenyl group. The fused ring group is particularly preferably a phenanthryl group, a 9,9-dimethylfluorenyl group, a dibenzofuranyl group, or a benzanthryl group.

Anthracene Derivative (C)

The anthracene derivative (C) is represented by formula (5) wherein $Ar^{11}$ and $Ar^{12}$ each independently represent a substituted or unsubstituted monocyclic group having 5 to 50 ring atoms.

In a preferred anthracene derivative (C), both of $Ar^{11}$ and $Ar^{12}$ are substituted or unsubstituted phenyl groups.

In a more preferred anthracene derivative (C), $Ar^{11}$ is an unsubstituted phenyl group and $Ar^{12}$ is a phenyl group having a substituent selected from a monocyclic group and a condensed ring group; or $Ar^{11}$ and $Ar^{12}$ each independently represent a phenyl group having a substituent selected from a monocyclic group and a condensed ring group.

Examples of the monocyclic group and the fused ring group which are preferable as the substituent are as described above. The monocyclic ring as the substituent is more preferably a phenyl group and a biphenyl group, and the fused ring group as the substituent is more preferably a naphthyl group, a phenanthryl group, a 9,9-dimethylfluorenyl group, a dibenzofuranyl group, and a benzanthryl group.

Examples of the anthracene derivative represented by formula (5) are described below.

843 844
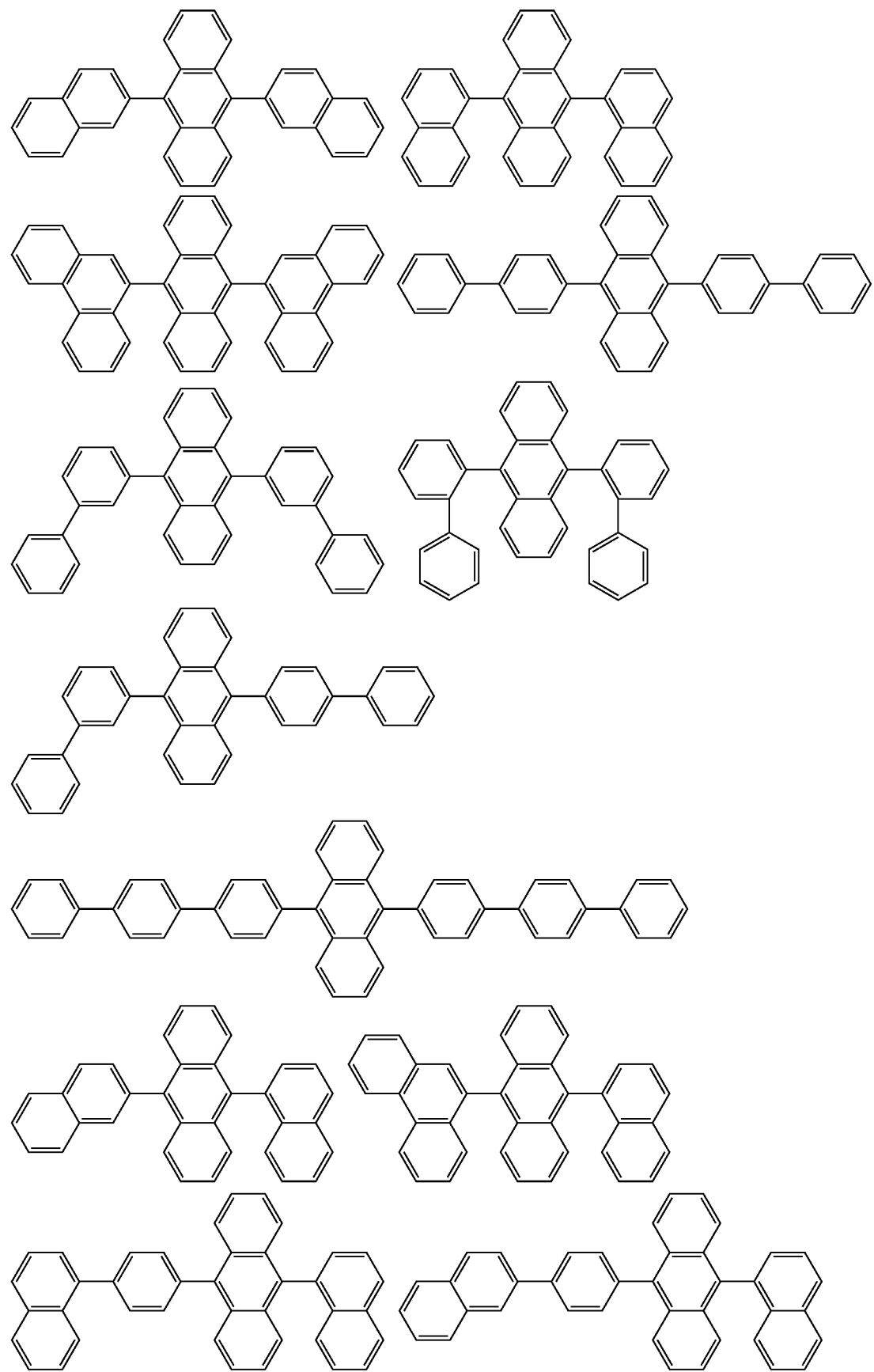

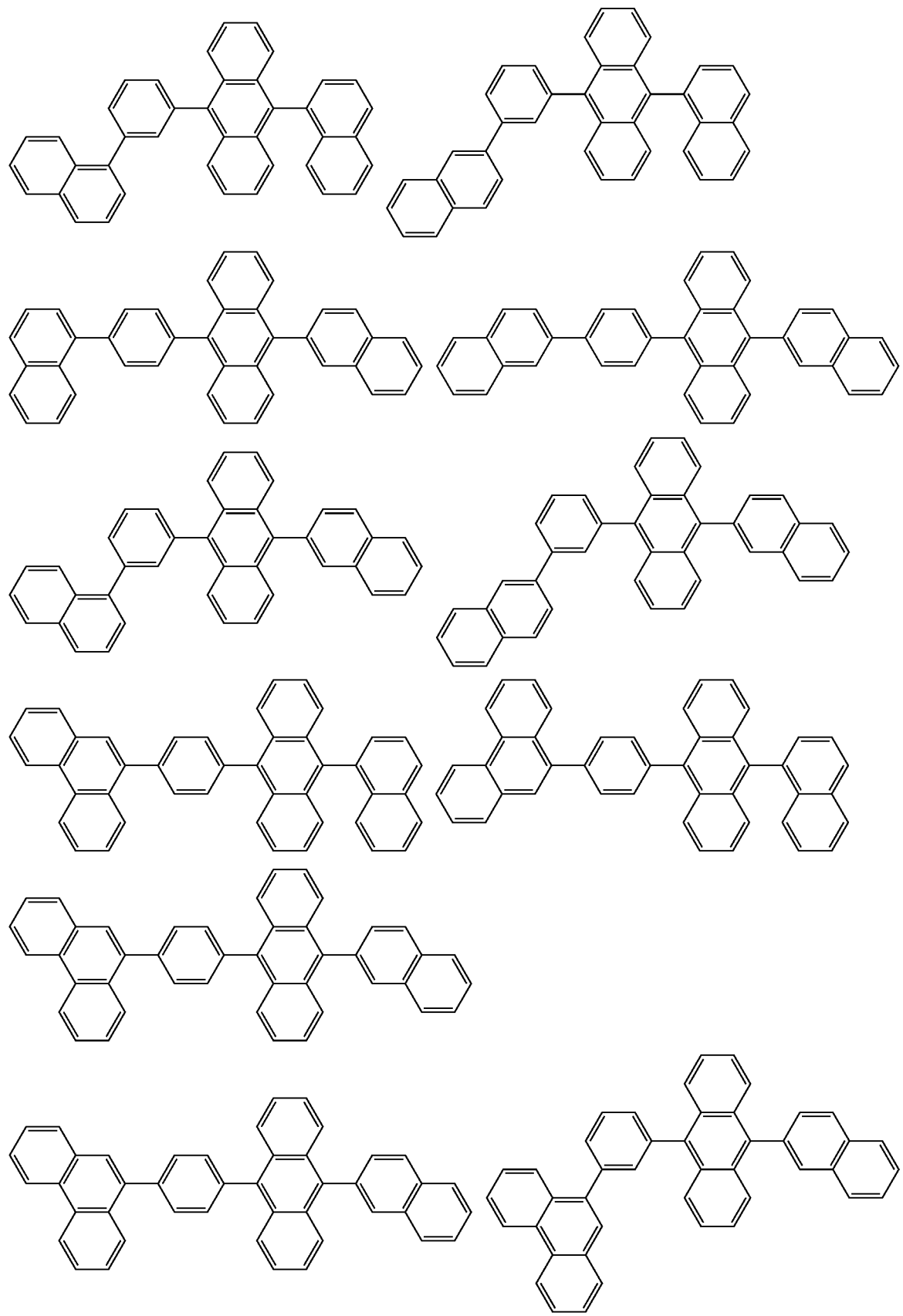

-continued
847    848
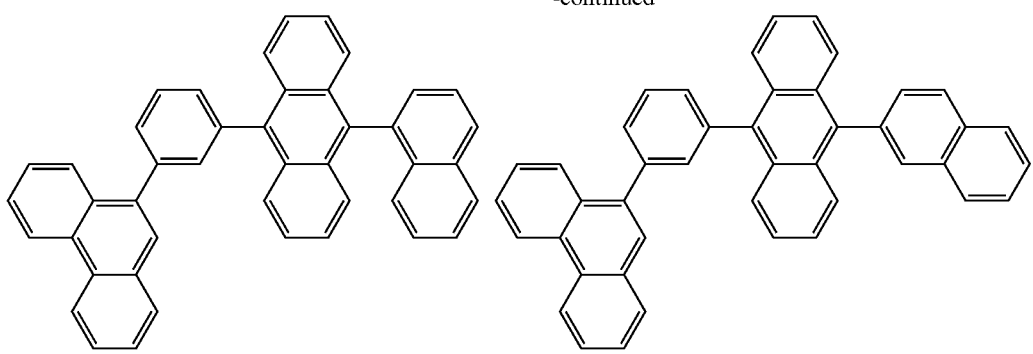
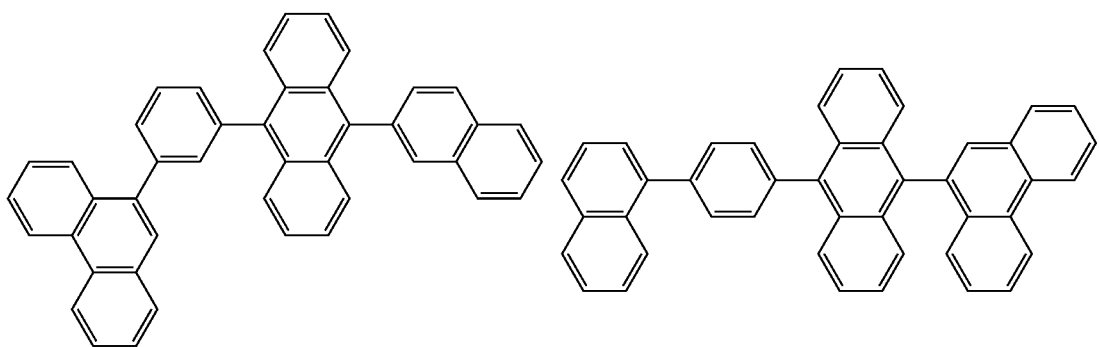
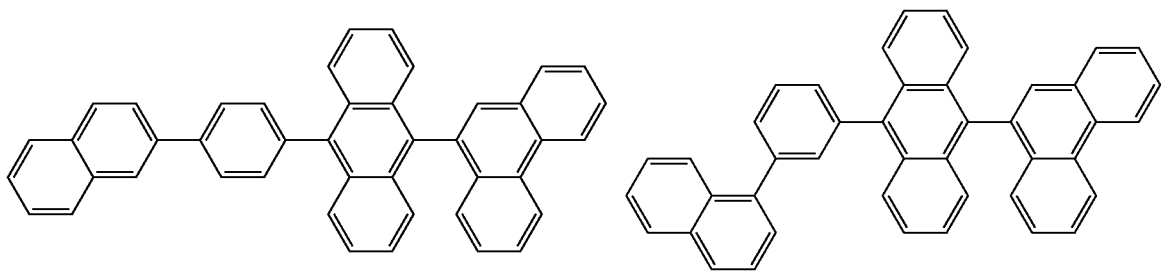
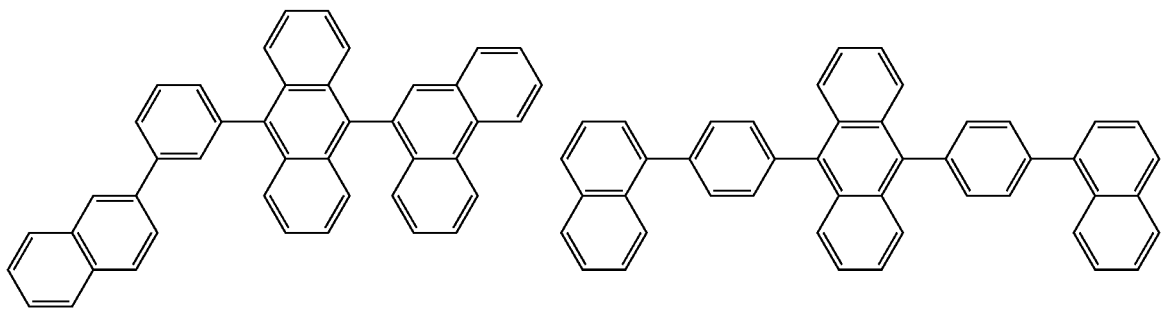
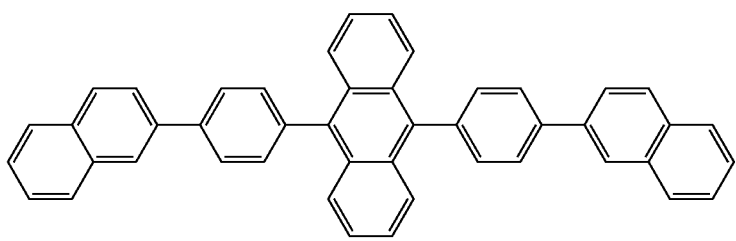

849 850
-continued
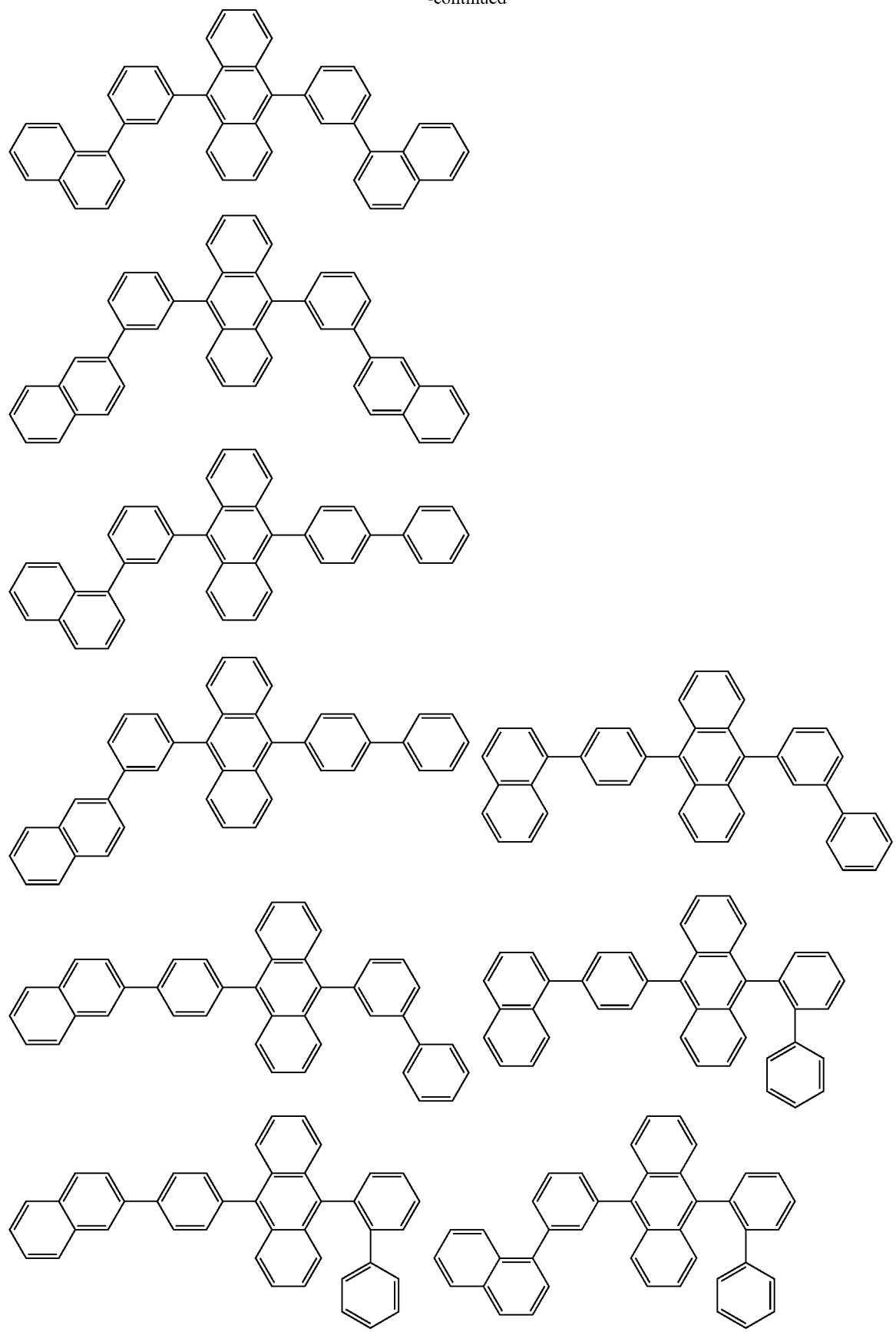

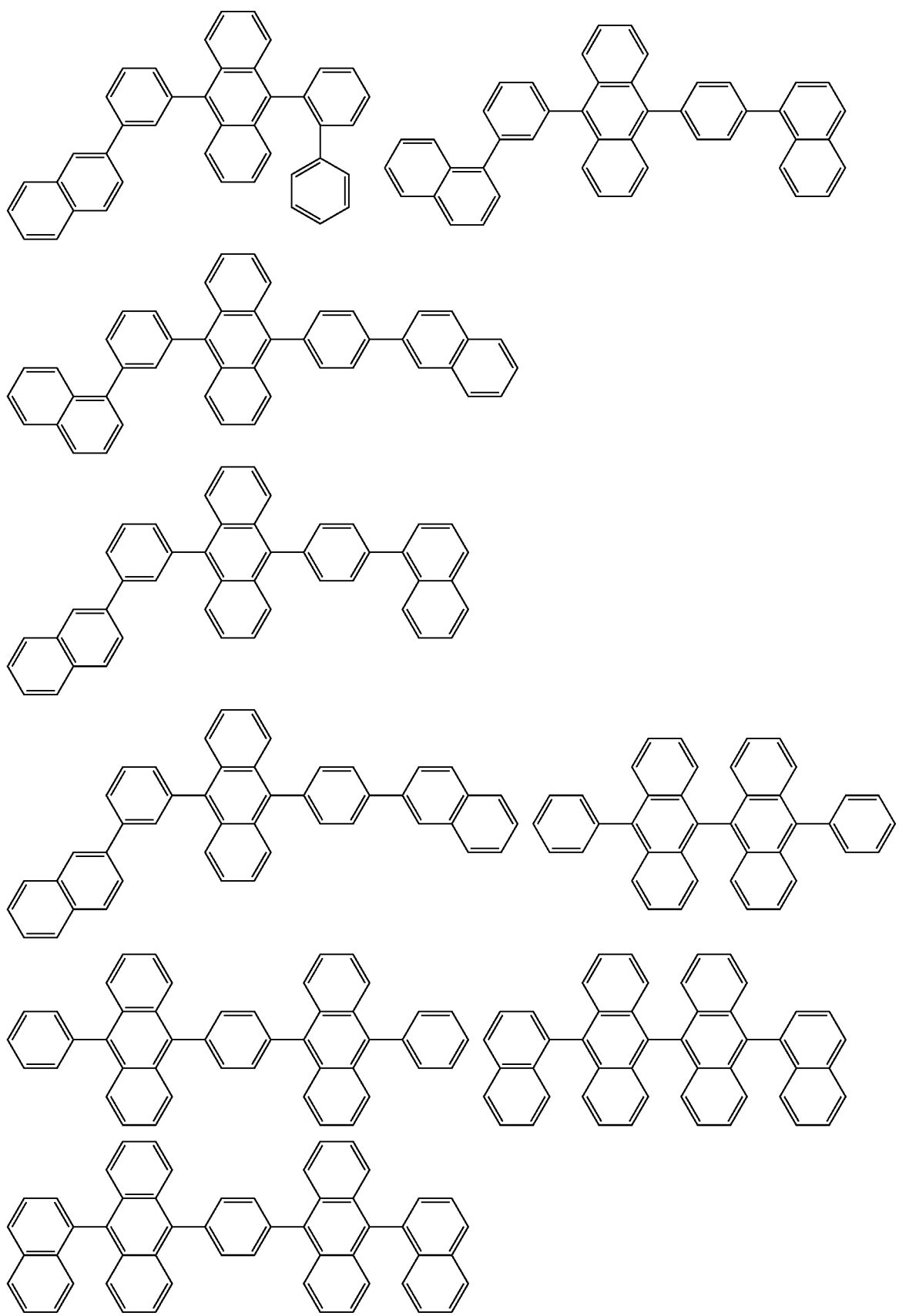

-continued
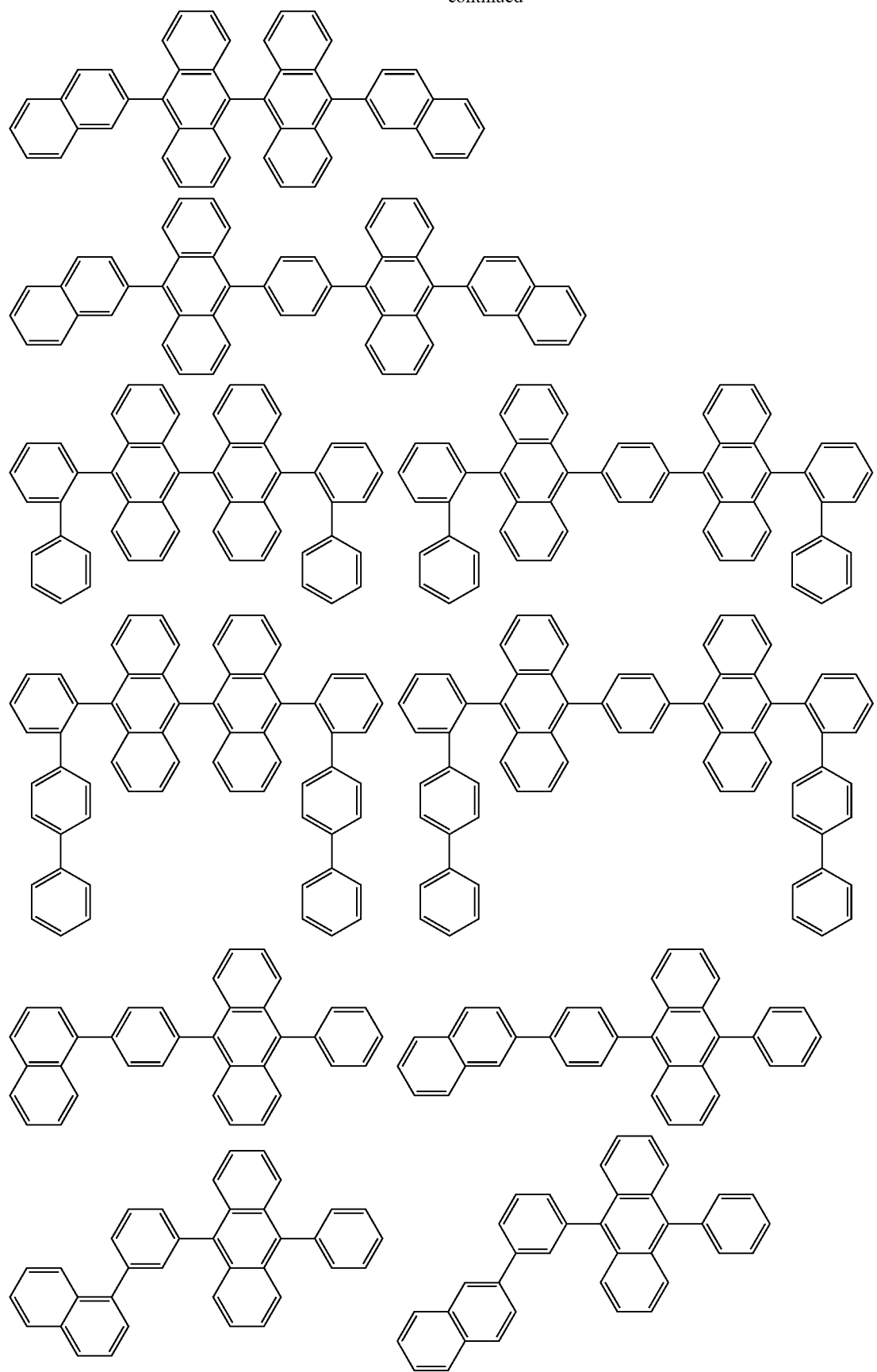

-continued
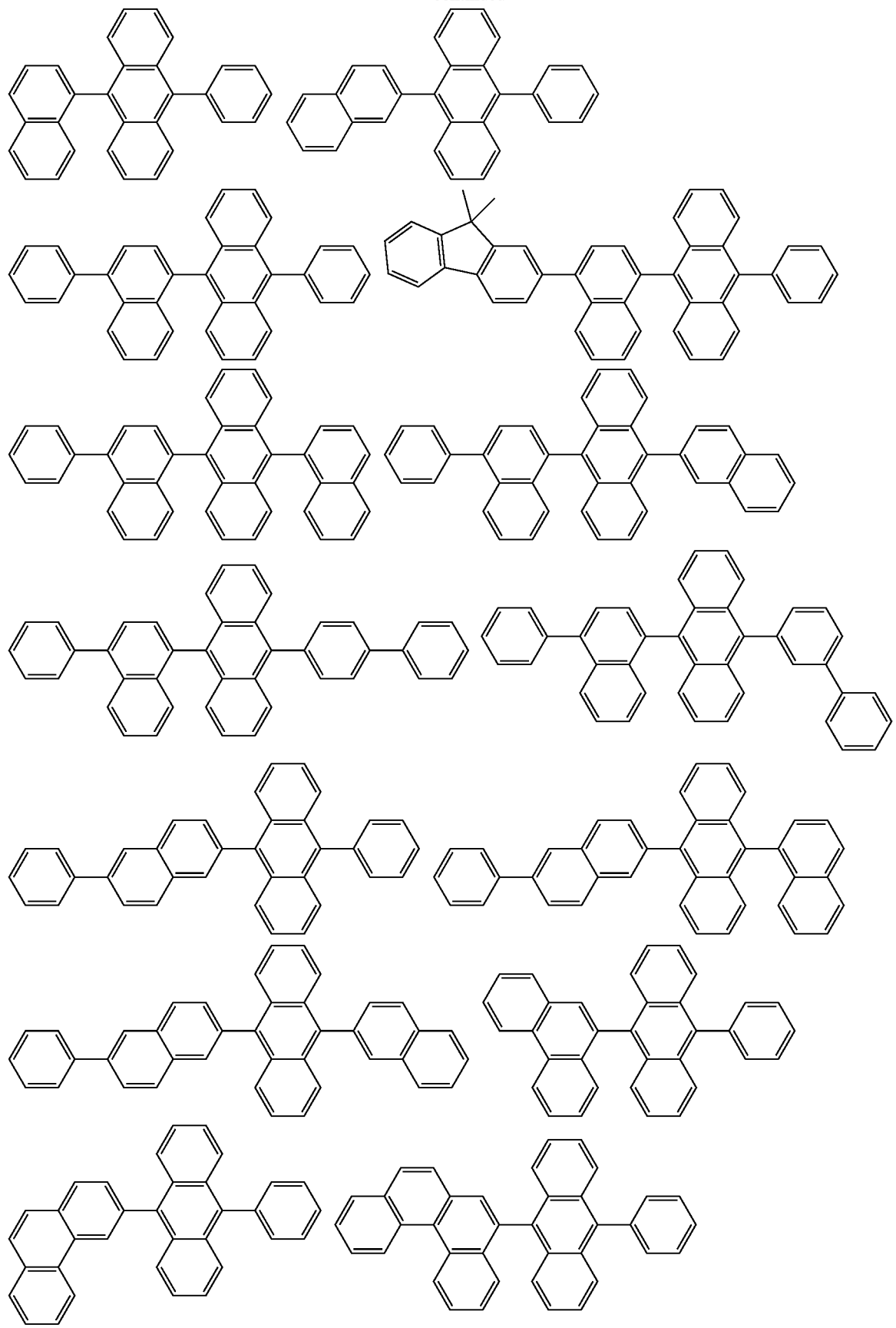

-continued
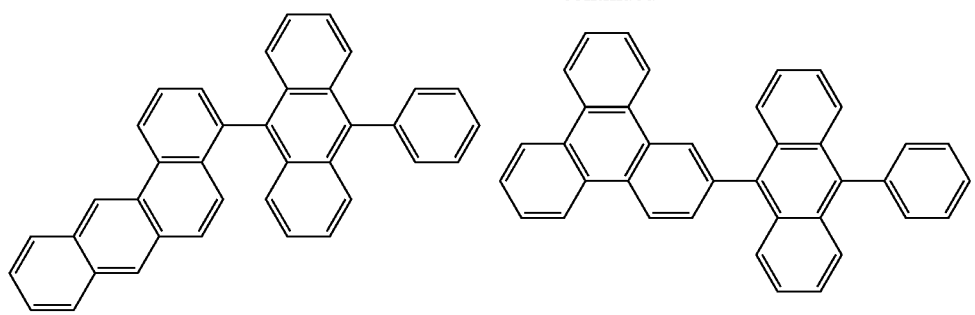
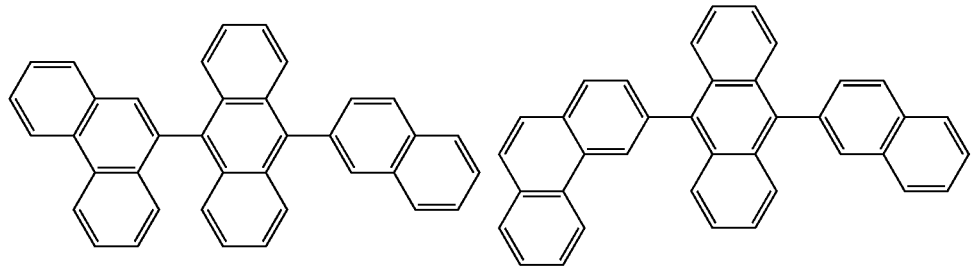
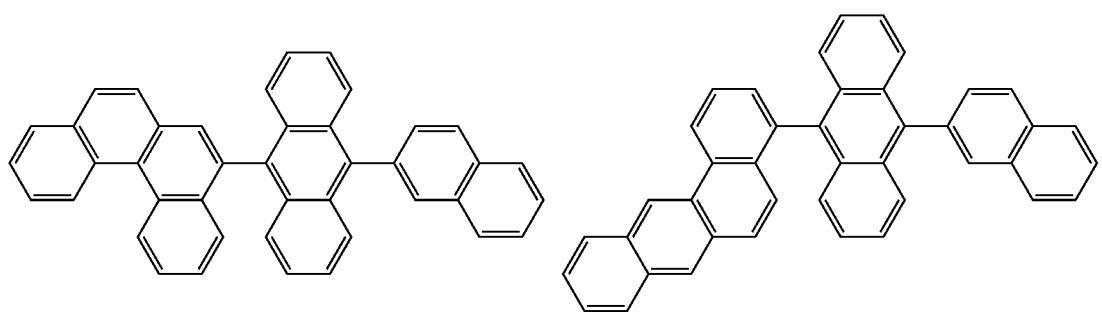
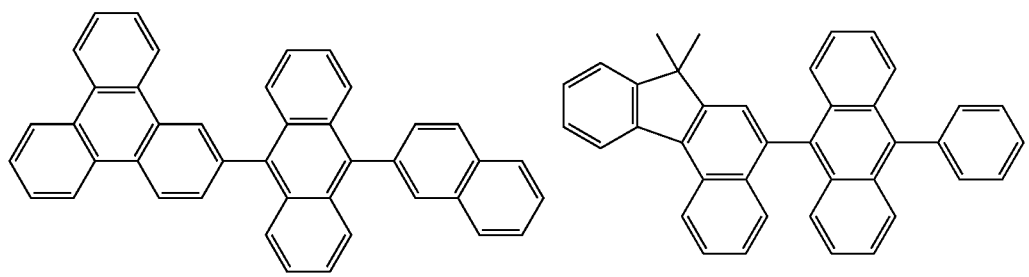
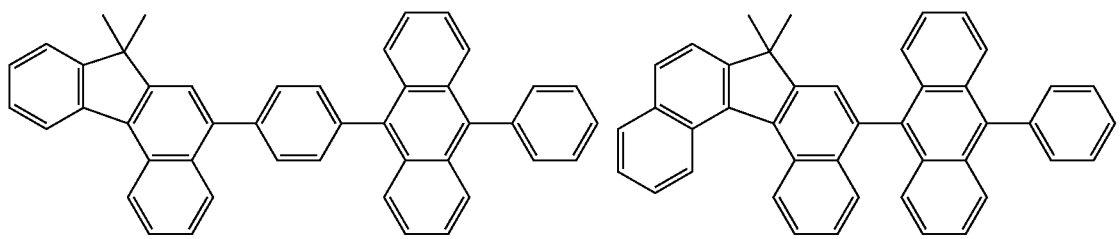
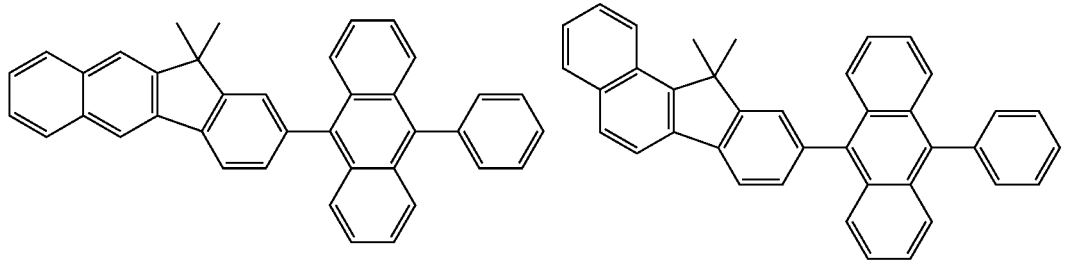

-continued
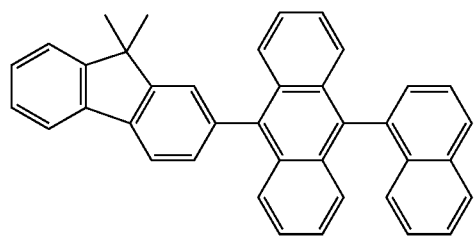
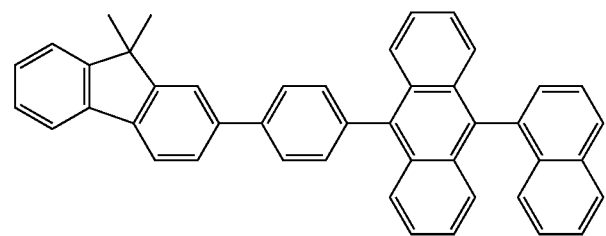
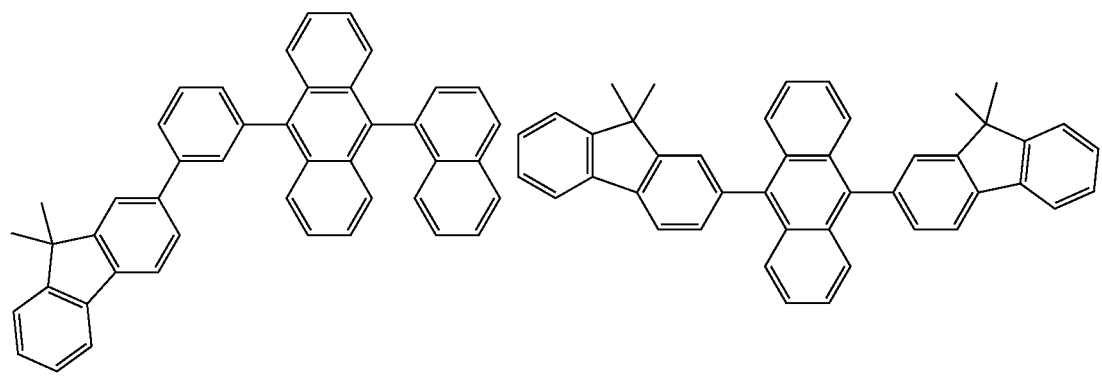
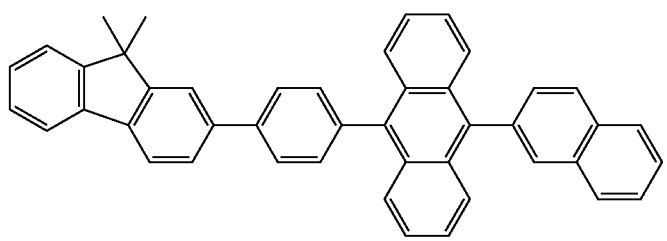
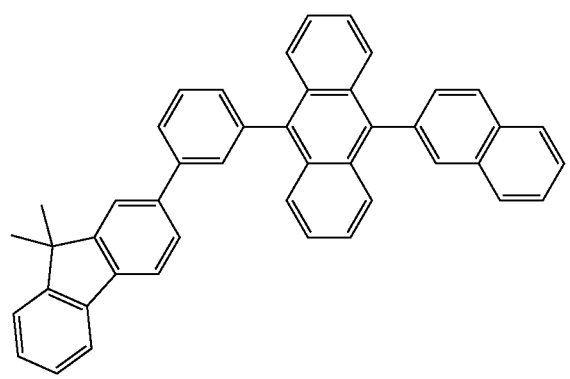
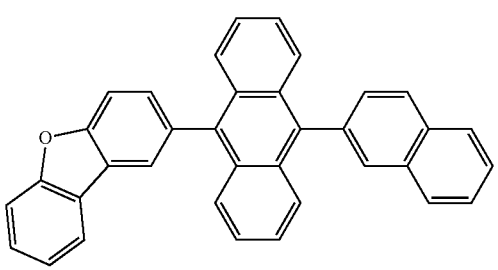
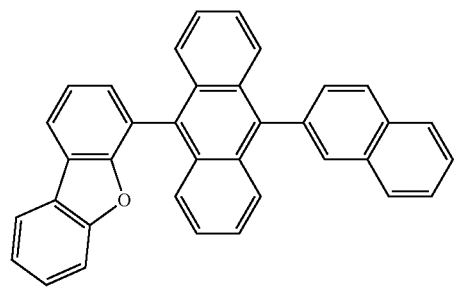
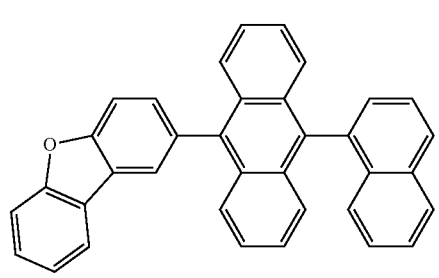

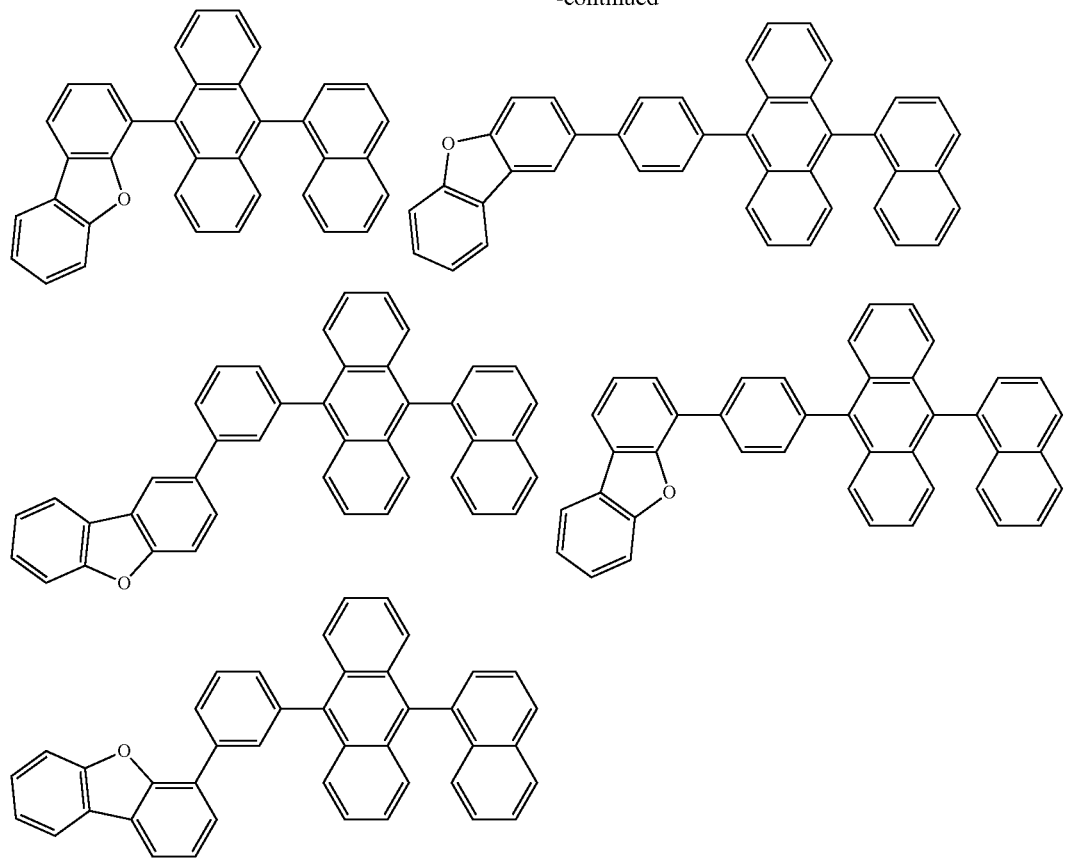

Electron-Donating Dopant Material

The organic EL device of the invention preferably comprises an electron-donating dopant material in the interfacial region between the cathode and the light emitting unit. With such a construction, the organic EL device has an improved luminance and an elongated lifetime. The electron-donating dopant material is a metal having a work function of 3.8 eV or less or a compound containing such a metal. Examples thereof include at least one compound selected from alkali metal, alkali metal complex, alkali metal compound, alkaline earth metal, alkaline earth metal complex, alkaline earth metal compound, rare earth metal, rare earth metal complex, and rare earth metal compound.

Examples of the alkali metal include Na (work function: 2.36 eV), K (work function: 2.28 eV), Rb (work function: 2.16 eV), and Cs (work function: 1.95 eV), with those having a work function of 2.9 eV or less being particularly preferred. Examples of the alkaline earth metal include Ca (work function: 2.9 eV), Sr (work function: 2.0 to 2.5 eV), and Ba (work function: 2.52 eV), with those having a work function of 2.9 eV or less being particularly preferred. Examples of the rare earth metal include Sc, Y, Ce, Tb, and Yb, with those having a work function of 2.9 eV or less being particularly preferred.

Examples of the alkali metal compound include alkali oxide, such as $Li_2O$, $Cs_2O$, $K_2O$, and alkali halide, such as LiF, NaF, CsF, and KF, with LiF, $Li_2O$, and NaF being preferred. Examples of the alkaline earth metal compound include BaO, SrO, CaO, and a mixture thereof, such as $Ba_xSr_{1-x}O$ (0<x<1) and $Ba_xCA^1_{-x}O$ (0<x<1), with BaO, SrO, and CaO being preferred. Examples of the rare earth metal compound include $YbF_3$, $ScF_3$, $ScO_3$, $Y_2O_3$, $Ce_2O_3$, $GdF_3$, and $TbF_3$, with $YbF_3$, $ScF_3$, and $TbF_3$ being preferred.

Examples of the alkali metal complex, alkaline earth metal complex, and rare earth metal are not particularly limited as long as containing at least one metal ion selected from alkali metal ions, alkaline earth metal ions, and rare earth metal ions, respectively. Examples of the ligand include quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bipyridyl, phenanthroline, phthalocyanine, porphyrin, cyclopentadiene, β-diketones, azomethines, and a derivative thereof.

The electron-donating dopant material is added to the interfacial region preferably into a form of layer or island. The electron-donating dopant material is added preferably by co-depositing the electron-donating dopant material with the organic compound (light emitting material, electron injecting material, etc.) for forming the interfacial region by a resistance heating deposition method, thereby dispersing the electron-donating dopant material into the organic material. The disperse concentration expressed by the molar ratio of the organic material and the electron-donating dopant material is 100:1 to 1:100.

When the electron-donating dopant material is formed into a form of layer, a light emitting material or an electron injecting material is made into a layer to form an interfacial organic layer, and then, the electron-donating dopant material alone is deposited by a resistance heating deposition method into a layer having a thickness preferably 0.1 to 15 nm. When the electron-donating dopant material is formed into a form of island, a light emitting material or an electron injecting material is made into a form of island to form an interfacial organic layer, and then, the electron-donating dopant material alone is deposited by a resistance heating deposition method into a form of island having a thickness preferably 0.05 to 1 nm.

The molar ratio of the main component and the electron-donating dopant material in the organic EL device is preferably 5:1 to 1:5.

Electron Transporting Layer

The electron transporting layer is an organic layer disposed between the light emitting layer and the cathode and transports electrons from the cathode to the light emitting layer. If two or more electron transporting layers are provided, the organic layer closer to the cathode may be called an electron injecting layer in some cases. The electron injecting layer injects electrons from the cathode to the organic layer unit efficiently.

An aromatic heterocyclic compound having one or more heteroatoms in its molecule is preferably used as the electron transporting material for the electron transporting layer, with a nitrogen-containing ring derivative being particularly preferred. The nitrogen-containing ring derivative is preferably an aromatic ring compound having a nitrogen-containing 6- or 5-membered ring or a fused aromatic ring compound having a nitrogen-containing 6- or 5-membered ring.

The nitrogen-containing ring derivative is preferably, for example, a chelate metal complex having a nitrogen-containing ring represented by formula (A):

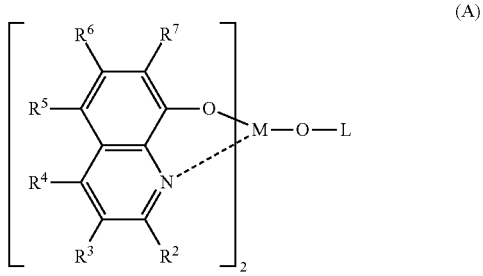

wherein $R^2$ to $R^7$ each independently represent a hydrogen atom, a halogen atom, a hydroxyl group, an amino group, a hydrocarbon group having 1 to 40, preferably 1 to 20, more preferably 1 to 10, and still more preferably 1 to 6 carbon atoms, an alkoxy group having 1 to 40, preferably 1 to 20, more preferably 1 to 10, and still more preferably 1 to 6 carbon atoms, an aryloxy group having 6 to 40, preferably 6 to 20, more preferably 6 to 12 ring carbon atoms, an alkoxycarbonyl group having 2 to 40, preferably 2 to 20, more preferably 2 to 10, and still more preferably 2 to 5 carbon atoms, or an aromatic heterocyclic group having 9 to 40, preferably 9 to 30, more preferably 9 to 20 ring atoms, each optionally having a substituent.

M is aluminum (Al), gallium (Ga), or indium (In), with In being preferred.

L is a group represented by formula (A') or (A"):

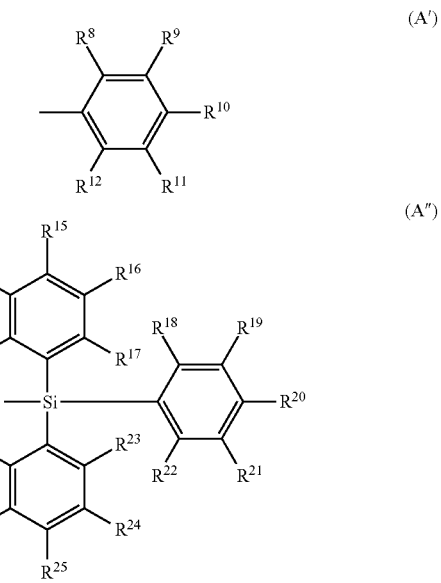

wherein $R^8$ to $R^{12}$ in formula (A') each independently represent a hydrogen atom or a substituted or unsubstituted hydrocarbon group having 1 to 40, preferably 1 to 20, more preferably 1 to 10, and still more preferably 1 to 6 carbon atoms, and adjacent groups may form a ring structure; and $R^{13}$ to $R^{27}$ in formula (A") each independently represent a hydrogen atom or a substituted or unsubstituted hydrocarbon group having 1 to 40, preferably 1 to 20, more preferably 1 to 10, and still more preferably 1 to 6 carbon atoms, and adjacent two groups may form a ring structure.

Examples of the hydrocarbon group having 1 to 40 carbon atoms represented by $R^8$ to $R^{12}$ of formula (A') and $R^{13}$ to $R^{27}$ of formula (A") are as defined above with respect to $R^2$ to $R^7$ of formula (A).

Examples of the divalent group to be formed when adjacent groups selected from $R^8$ to $R^{12}$ and $R^{13}$ to $R^{27}$ form a ring structure include a tetramethylene group, a pentamethylene group, a hexamethylene group, a diphenylmethane-2,2'-diyl group, a diphenylethane-3,3'-diyl group, and a diphenylpropane-4,4'diyl group.

The electron transporting compound for the electron transporting layer is preferably a metal complex including 8-hydroxyquinoline or its derivative, an oxadiazole derivative, and a nitrogen-containing heterocyclic derivative.

Electron transporting compounds which have a good thin film-forming property are preferably used. Examples of the electron transporting compound are shown below.

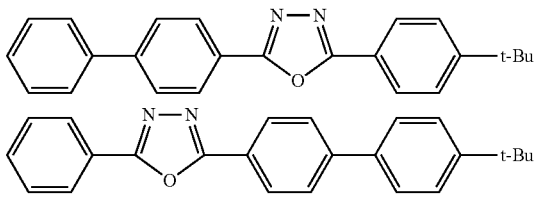

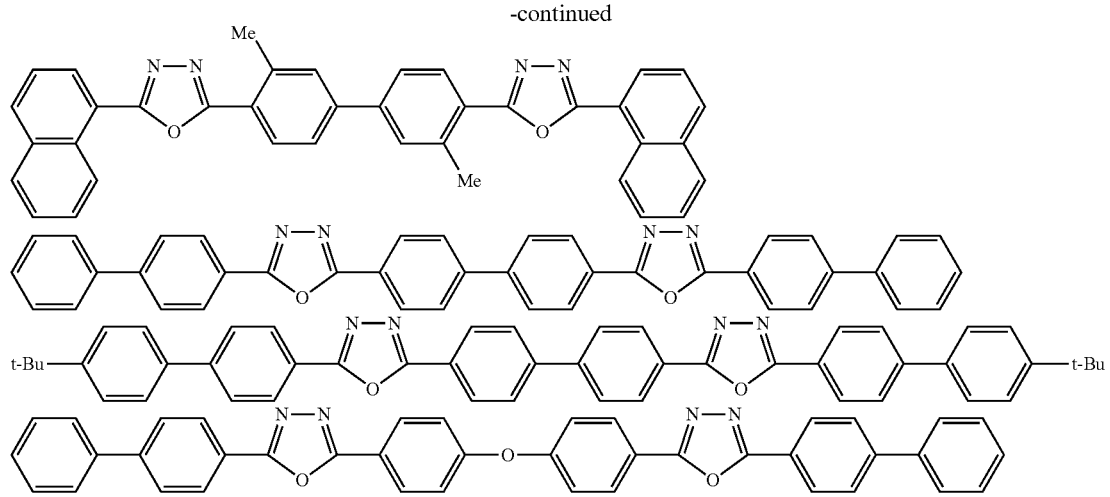

Examples of the nitrogen-containing heterocyclic derivative for use as the electron transporting compound include a nitrogen-containing compound other than a metal complex. For example, a compound having the following nitrogen-containing heterocyclic group is preferred:

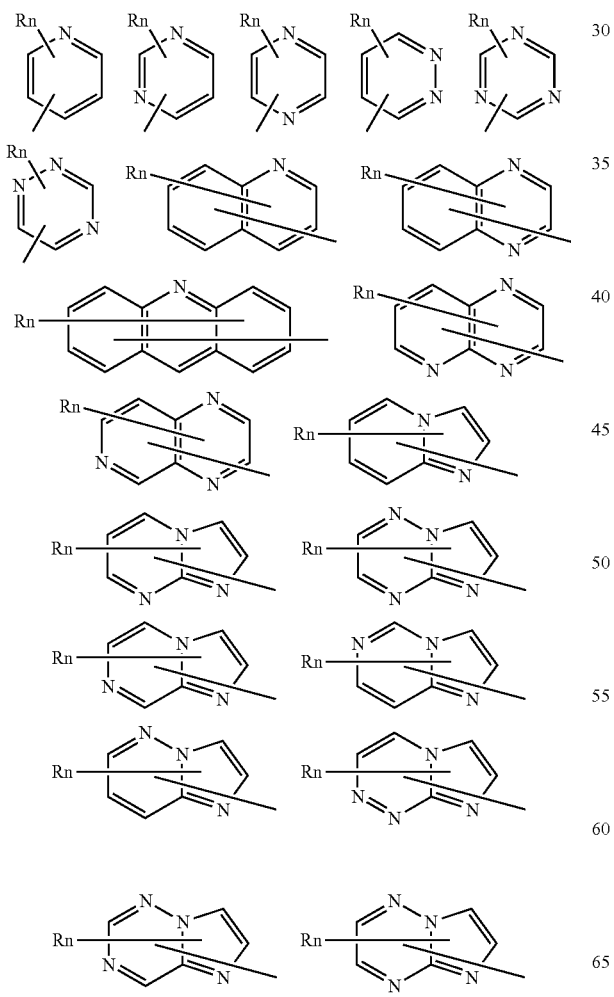

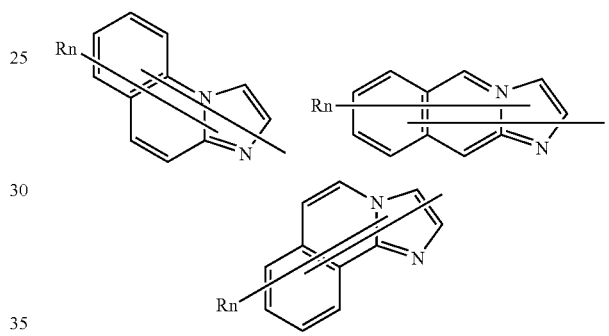

wherein R is an aromatic hydrocarbon group or a fused aromatic hydrocarbon group each having 6 to 40 carbon atoms, an aromatic heterocyclic group or a fused aromatic heterocyclic group each having 3 to 40 carbon atoms, an alkyl group having 1 to 20 carbon atoms, or an alkoxy group having 1 to 20 carbon atoms; and n is an integer of 0 to 5, and when n is an integer of 2 or more, groups R may be the same or different.

The electron transporting layer of the organic EL of the invention particularly preferably comprises at least one of the nitrogen-containing heterocyclic derivatives represented by formulae (60) to (62);

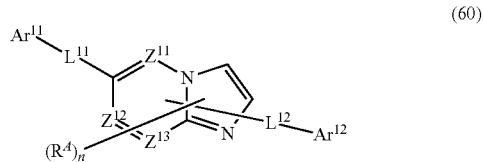

(60)

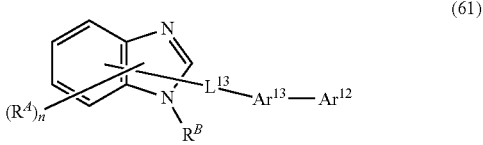

(61)

-continued (62)

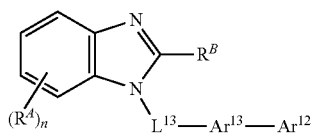

wherein $Z^{11}$, $Z^{12}$, and $Z^{13}$ each independently represent a nitrogen atom or a carbon atom;

$R^A$ and $R^B$ each independently represent a substituted or unsubstituted aryl group having 6 to 50, preferably 6 to 30, more preferably 6 to 20, and still more preferably 6 to 12 ring carbon atoms, a substituted or unsubstituted heterocyclic group having 5 to 50, preferably 5 to 30, more preferably 5 to 20, and still more preferably 5 to 12 ring atoms, a substituted or unsubstituted alkyl group having 1 to 20, preferably 1 to 10, and more preferably 1 to 6 carbon atoms, a substituted or unsubstituted haloalkyl group having 1 to 20, preferably 1 to 10, and more preferably 1 to 6 carbon atoms, or a substituted or unsubstituted alkoxyl group having 1 to 20, preferably 1 to 10, and more preferably 1 to 6 carbon atoms;

n is an integer of 0 to 5, when n is an integer of 2 or more, groups $R^A$ may be the same or different from each other, and adjacent two groups $R^A$ may bond to each other to form a substituted or unsubstituted hydrocarbon ring;

$Ar^{11}$ represents a substituted or unsubstituted aryl group having 6 to 50, preferably 6 to 30, more preferably 6 to 20, and still more preferably 6 to 12 ring carbon atoms or a substituted or unsubstituted heterocyclic group having 5 to 50, preferably 5 to 30, more preferably 5 to 20, and still more preferably 5 to 12 ring atoms;

$Ar^2$ represents a hydrogen atom, a substituted or unsubstituted alkyl group having 1 to 20, preferably 1 to 10, and more preferably 1 to 6 carbon atoms, a substituted or unsubstituted haloalkyl group having 1 to 20, preferably 1 to 10, and more preferably 1 to 6 carbon atoms, a substituted or unsubstituted alkoxyl group having 1 to 20, preferably 1 to 10, and more preferably 1 to 6 carbon atoms, a substituted or unsubstituted aryl group having 6 to 50, preferably 6 to 30, more preferably 6 to 20, and still more preferably 6 to 12 ring carbon atoms, or a substituted or unsubstituted heterocyclic group having 5 to 50, preferably 5 to 30, more preferably 5 to 20, and still more preferably 5 to 12 ring atoms;

provided that one of $Ar^{11}$ and $Ar^{12}$ is a substituted or unsubstituted fused aromatic hydrocarbon group having 10 to 50, preferably 10 to 30, more preferably 10 to 20, and still more preferably 10 to 14 ring carbon atoms or a substituted or unsubstituted fused aromatic heterocyclic group having 9 to 50, preferably 9 to 30, more preferably 9 to 20, and still more preferably 9 to 14 ring atoms;

$Ar^{13}$ represents a substituted or unsubstituted arylene group having 6 to 50, preferably 6 to 30, more preferably 6 to 20, and still more preferably 6 to 12 ring carbon atoms or a substituted or unsubstituted heteroarylene group having 5 to 50, preferably 5 to 30, more preferably 5 to 20, and still more preferably 5 to 12 ring atoms; and $L^{11}$, $L^{12}$, and $L^{13}$ each independently represent a single bond, a substituted or unsubstituted arylene group having 6 to 50, preferably 6 to 30, more preferably 6 to 20, and still more preferably 6 to 12 ring carbon atoms or a substituted or unsubstituted divalent fused aromatic heterocyclic group having 9 to 50, preferably 9 to 30, more preferably 9 to 20, and still more preferably 9 to 14 ring atoms.

Examples of the nitrogen-containing heterocyclic derivatives represented by formulae (60) to (62) are shown below.

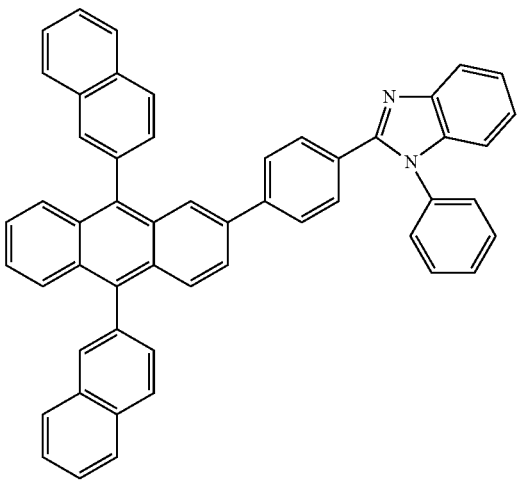

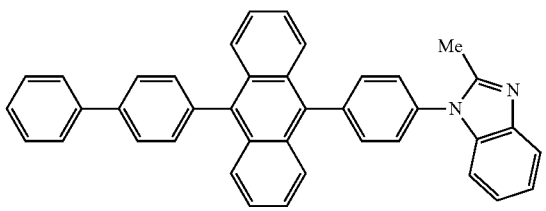

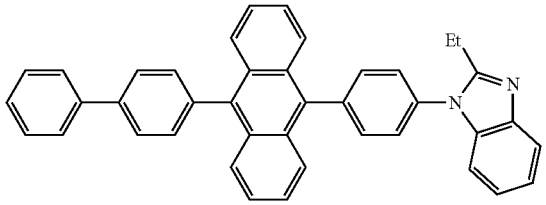

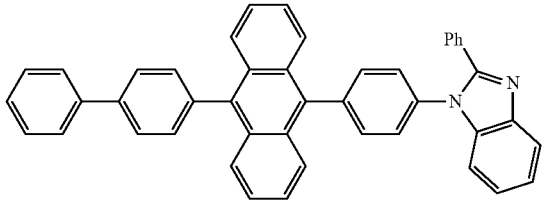

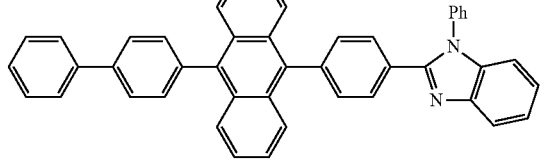

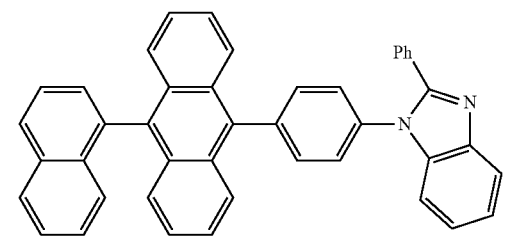

-continued

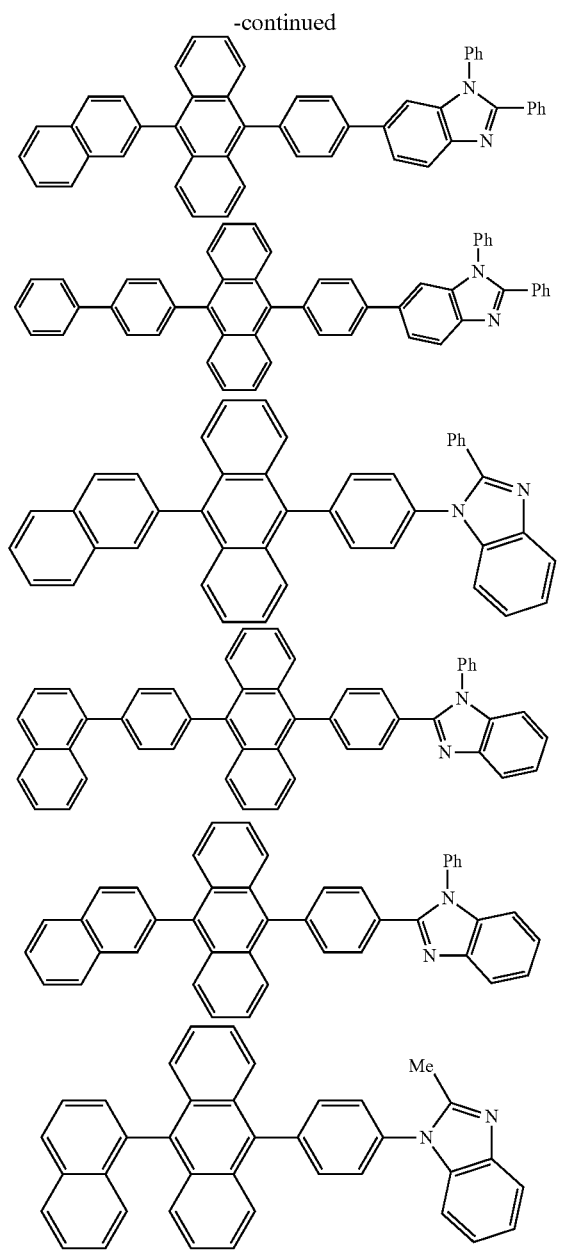

The electron transporting layer of the organic EL device of the invention may be made into a two-layered structure of a first electron transporting layer (anode side) and a second electron transporting layer (cathode side).

The thickness of the electron transporting layer is preferably 1 to 100 nm, although not particularly limited thereto. In a two-layered structure of a first electron transporting layer (anode side) and a second electron transporting layer (cathode side), the thickness of the first electron transporting is preferably 5 to 60 nm and more preferably 10 to 40 nm, and the thickness of the second electron transporting layer is preferably 1 to 20 nm and more preferably 1 to 10 nm.

The electron injecting layer which may be formed adjacent to the electron transporting layer preferably includes an inorganic compound, such as an insulating material and a semiconductor in addition to the nitrogen-containing ring derivative. The insulating material or semiconductor incorporated into the electron injecting layer effectively prevents the leak of electric current to enhance the electron injecting properties.

The insulating material is preferably at least one metal compound selected from the group consisting of an alkali metal chalcogenide, an alkaline earth metal chalcogenide, an alkali metal halide, and an alkaline earth metal halide. The alkali metal chalcogenide, etc. incorporated into the electron injecting layer further enhances the electron injecting properties. Preferred examples of the alkali metal chalcogenides include $Li_2O$, $K_2O$, $Na_2S$, $Na_2Se$, and $Na_2O$, and preferred examples of the alkaline earth metal chalcogenides include CaO, BaO, SrO, BeO, BaS, and CaSe. Preferred examples of the alkali metal halides include LiF, NaF, KF, LiCl, KCl, and NaCl. Examples of the alkaline earth metal halides include fluorides such as $CaF_2$, $BaF_2$, $SrF_2$, $MgF_2$, and $BeF_2$ and halides other than fluorides.

Examples of the semiconductor may include an oxide, a nitride or an oxynitride each containing at least one element selected from the group consisting of Ba, Ca, Sr, Yb, Al, Ga, In, Li, Na, Cd, Mg, Si, Ta, Sb and Zn. The semiconductor may be used singly or in combination of two or more. The inorganic compound forming the electron injecting layer preferably forms a microcrystalline or amorphous insulating thin film. When the electron injecting layer is formed from such an insulating thin film, the thin film is made more uniform to decrease the pixel defects such as dark spots. Examples of such an inorganic compound include an alkali metal chalcogenide, an alkaline earth metal chalcogenide, an alkali metal halide, and an alkaline earth metal halide, each being described above.

The thickness of the layer including the insulating material or the semiconductor is preferably about 0.1 to 15 nm. The electron injecting layer may include the electron-donating dopant material described above.

Hole Transporting Layer

The hole transporting layer is an organic layer formed between the light emitting layer and the anode and has a function of transporting holes from the anode to the light emitting layer. When the hole transporting layer is formed by two or more layers, the layer closer to the anode may be defined as the hole injecting layer in some cases. The hole injecting layer has a function of efficiently injecting holes from the anode to the organic layer unit.

An aromatic amine compound, for example, an aromatic amine derivative represented by formula (I), is preferably used as the material for forming the hole transporting layer:

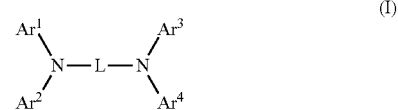

(I)

wherein $Ar^1$ to $Ar^4$ each represent a substituted or unsubstituted aromatic hydrocarbon group having 6 to 50, preferably 6 to 30, more preferably 6 to 20, and still more preferably 6 to 12 ring carbon atoms; a substituted or unsubstituted fused aromatic hydrocarbon group having 6 to 50, preferably 6 to 30, more preferably 6 to 20, and still more preferably 6 to 12 ring carbon atoms; a substituted or unsubstituted aromatic heterocyclic group having 5 to 50, preferably 5 to 30, more preferably 5 to 20, and still more preferably 5 to 12 ring atoms; a fused aromatic heterocyclic group having 5 to 50, preferably 5 to 30, more preferably 5 to 20, and still more preferably 5 to 12 ring atoms; or a group wherein the aromatic hydrocarbon group or fused aromatic hydrocarbon group is bonded to the aromatic heterocyclic group or fused aromatic heterocyclic group;

Ar$^1$ and Ar$_2$, or Ar$_3$ and Ar$^4$ may form a ring; and

L represents a substituted or unsubstituted aromatic hydrocarbon group having 6 to 50, preferably 6 to 30, more preferably 6 to 20, and still more preferably 6 to 12 ring carbon atoms; a substituted or unsubstituted fused aromatic hydrocarbon group having 6 to 50, preferably 6 to 30, more preferably 6 to 20, and still more preferably 6 to 12 ring carbon atoms; a substituted or unsubstituted aromatic heterocyclic group having 5 to 50, preferably 5 to 30, more preferably 5 to 20, and still more preferably 5 to 12 ring atoms; or a fused aromatic heterocyclic group having 5 to 50, preferably 5 to 30, more preferably 5 to 20, and still more preferably 5 to 12 ring atoms.

Examples of the compound represented by formula (I) are shown below.

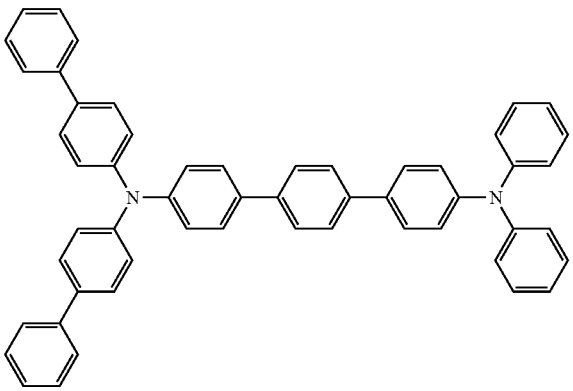

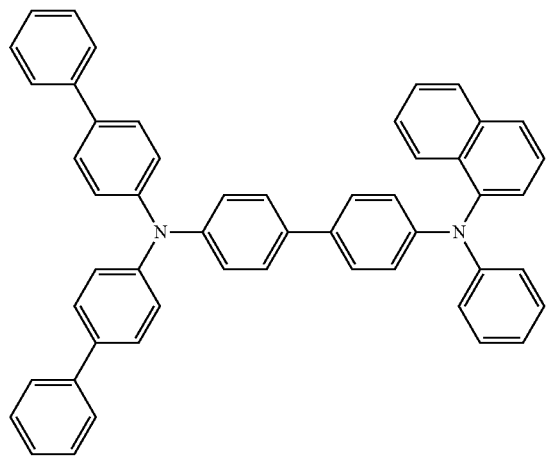

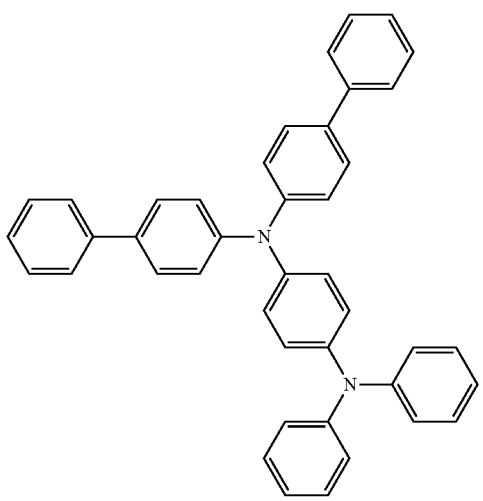

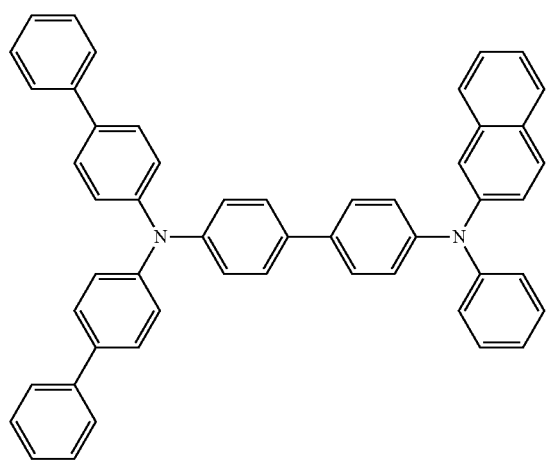

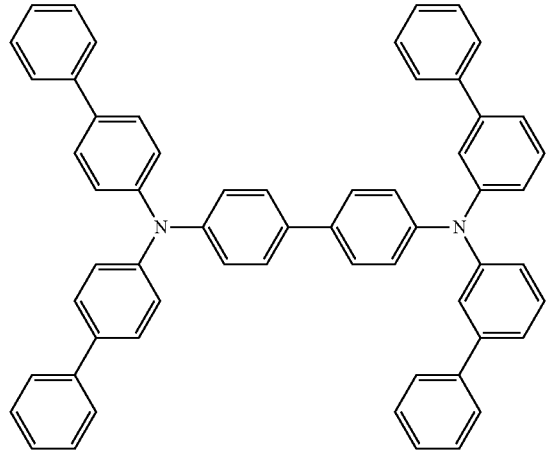

873
-continued
874
-continued
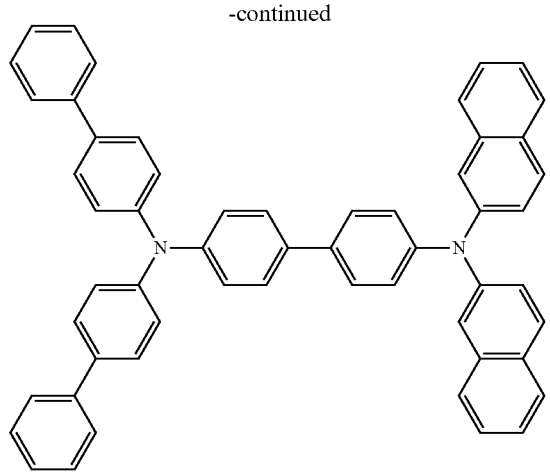
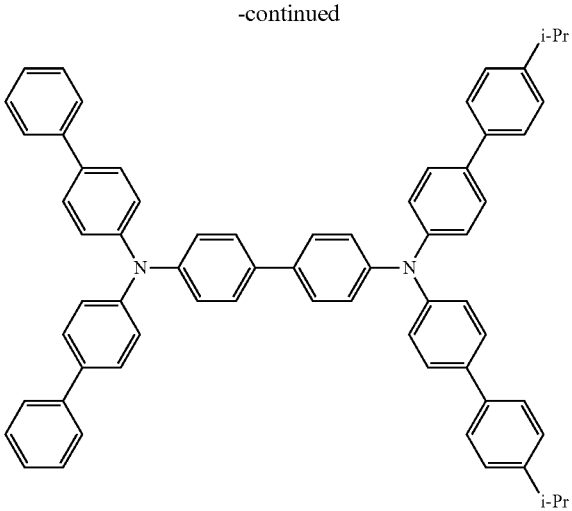
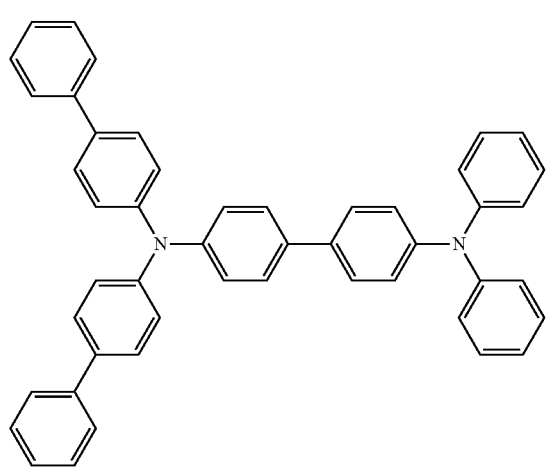
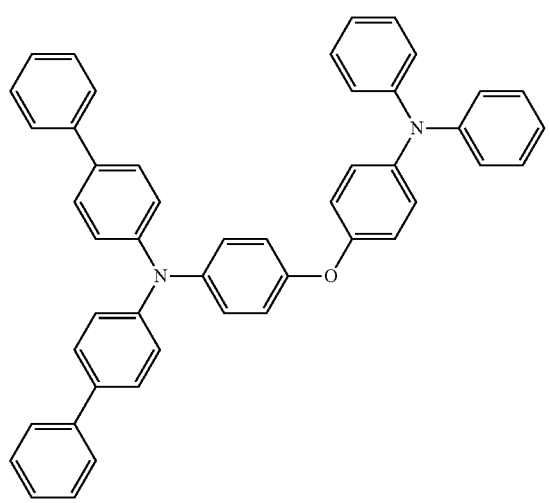
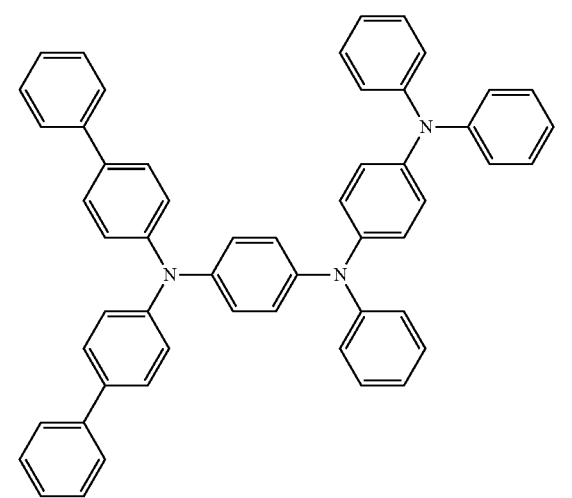

875
-continued
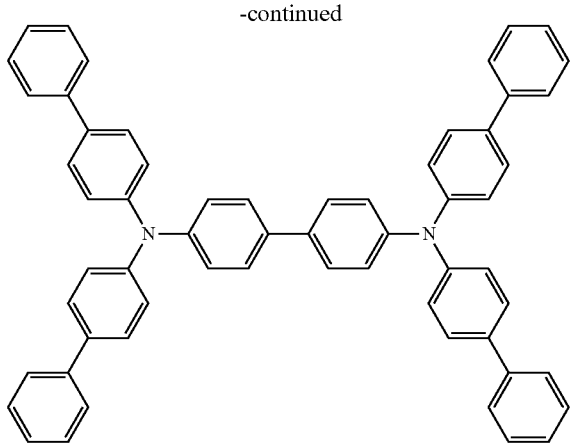
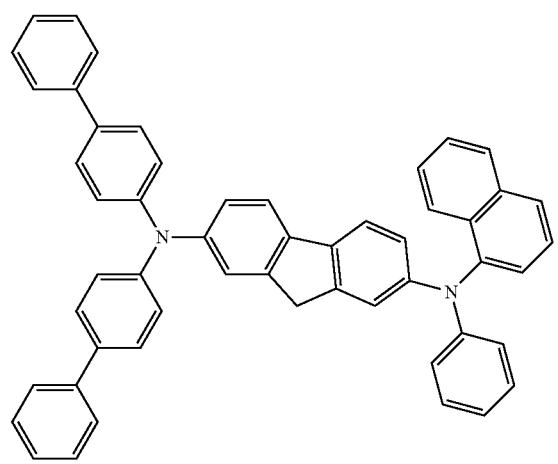
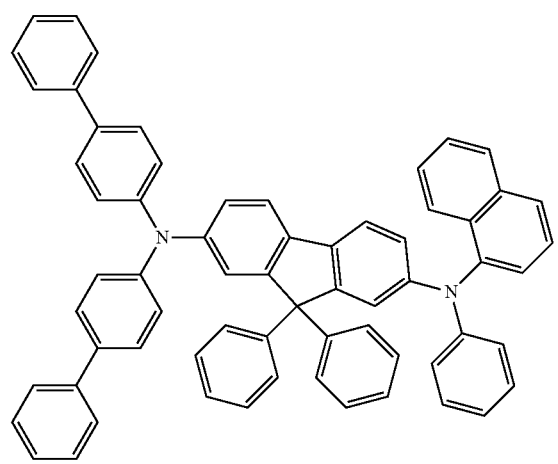
876
-continued
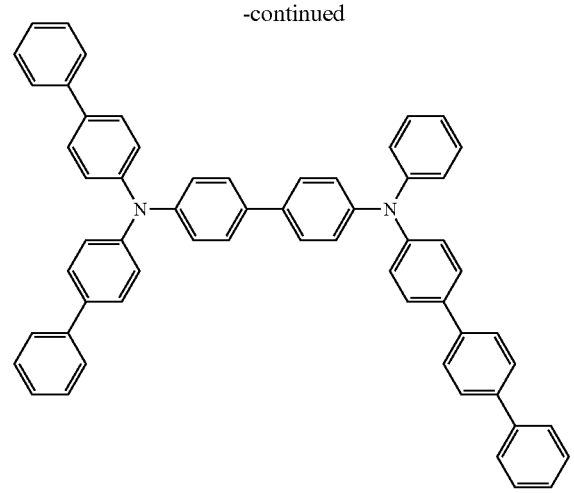
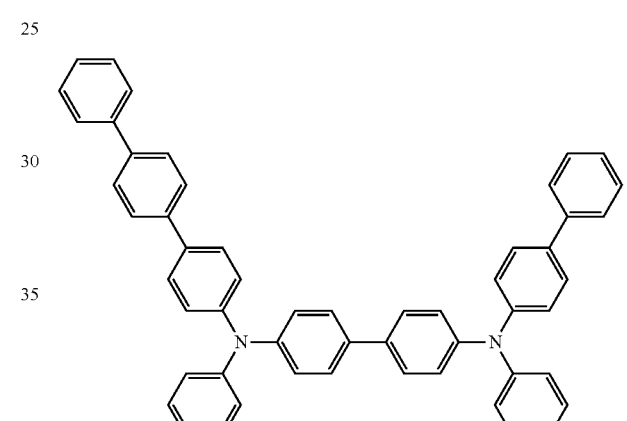
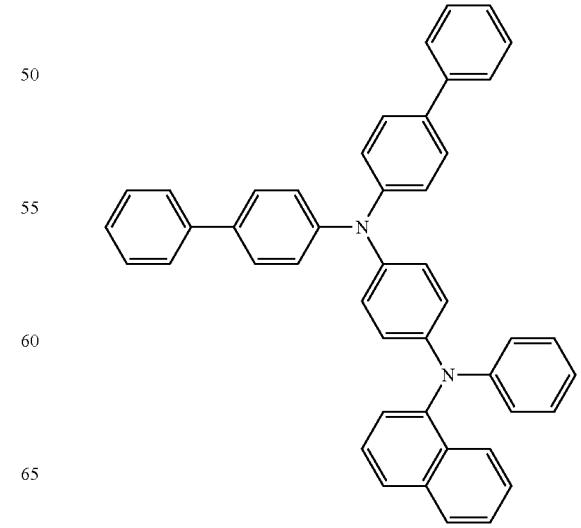

877
-continued
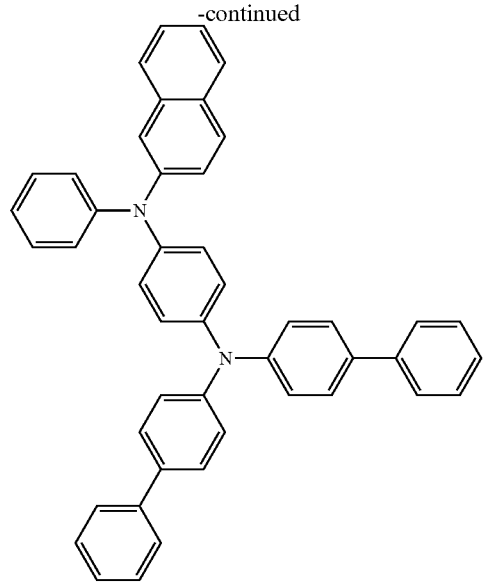
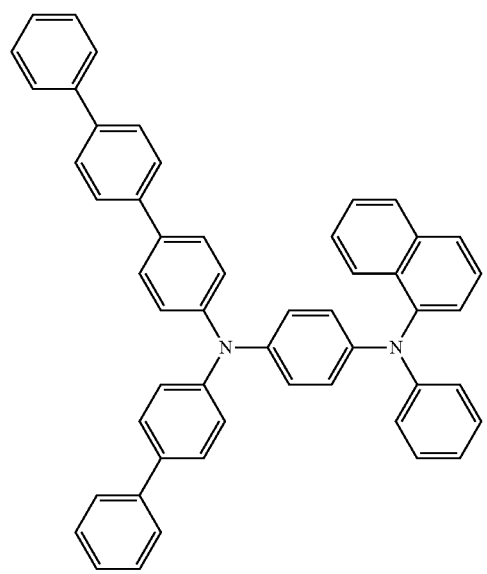
878
-continued
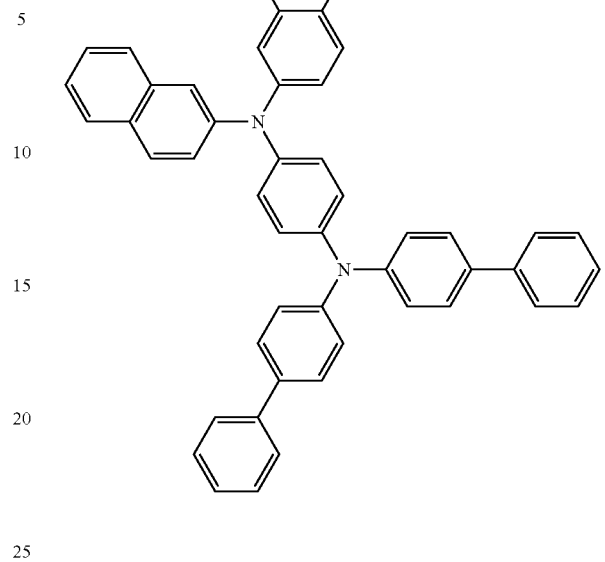
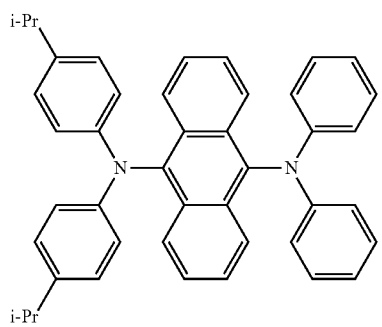
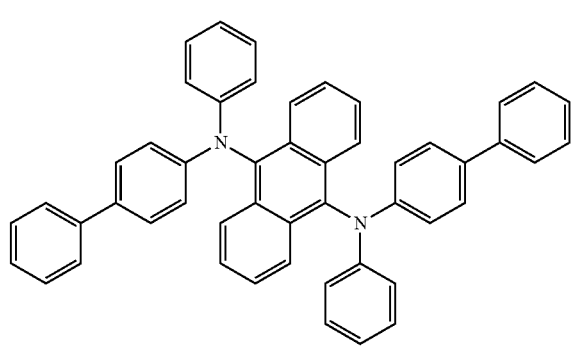
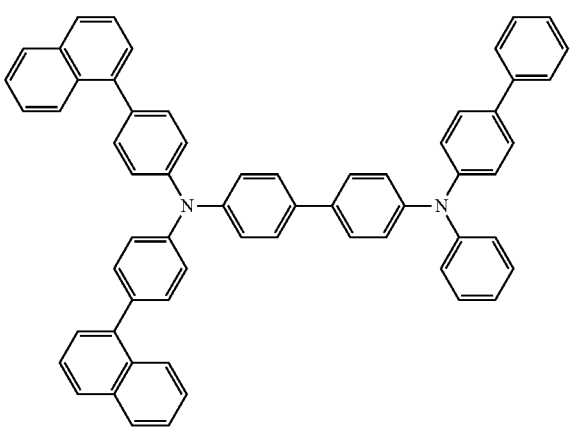

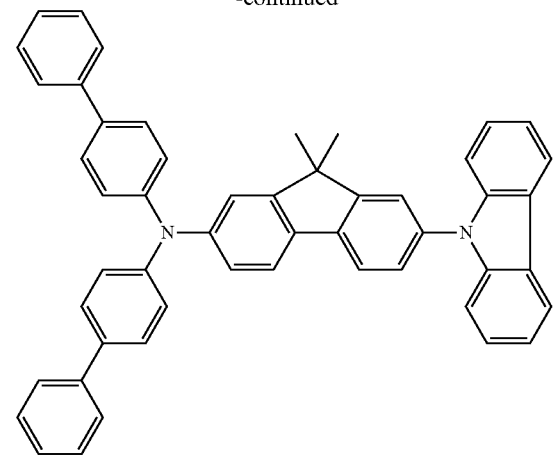
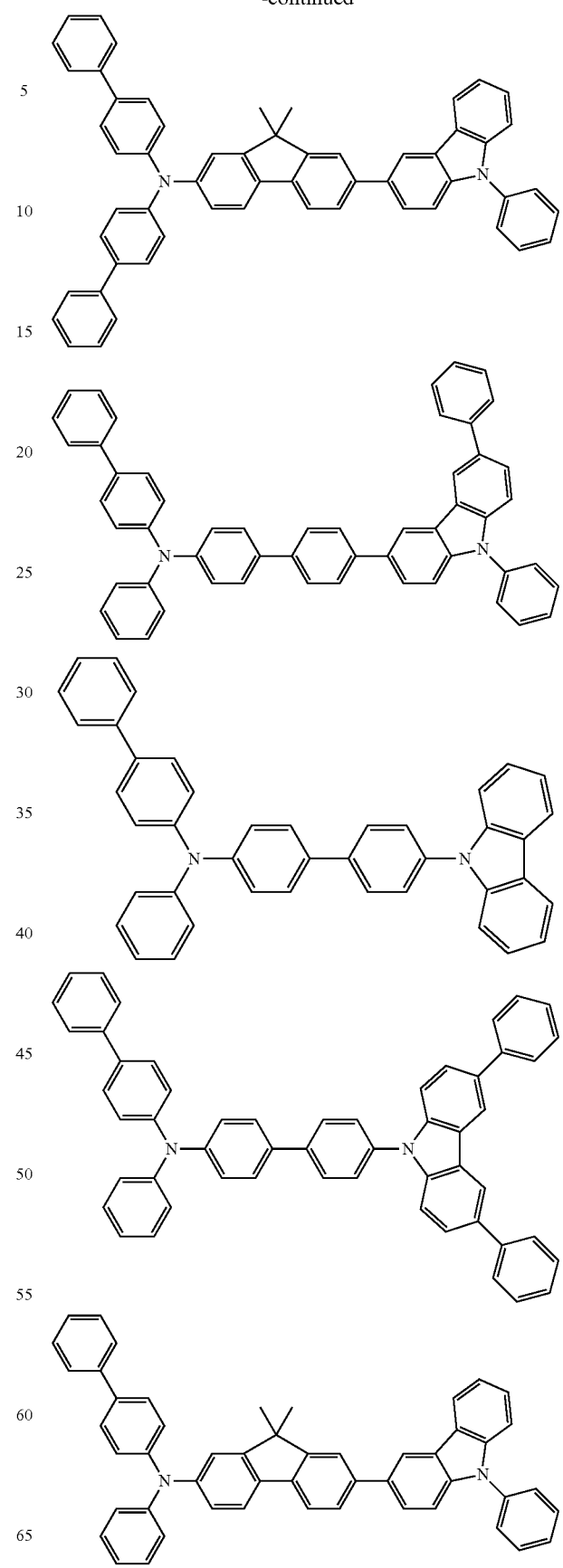

881
-continued
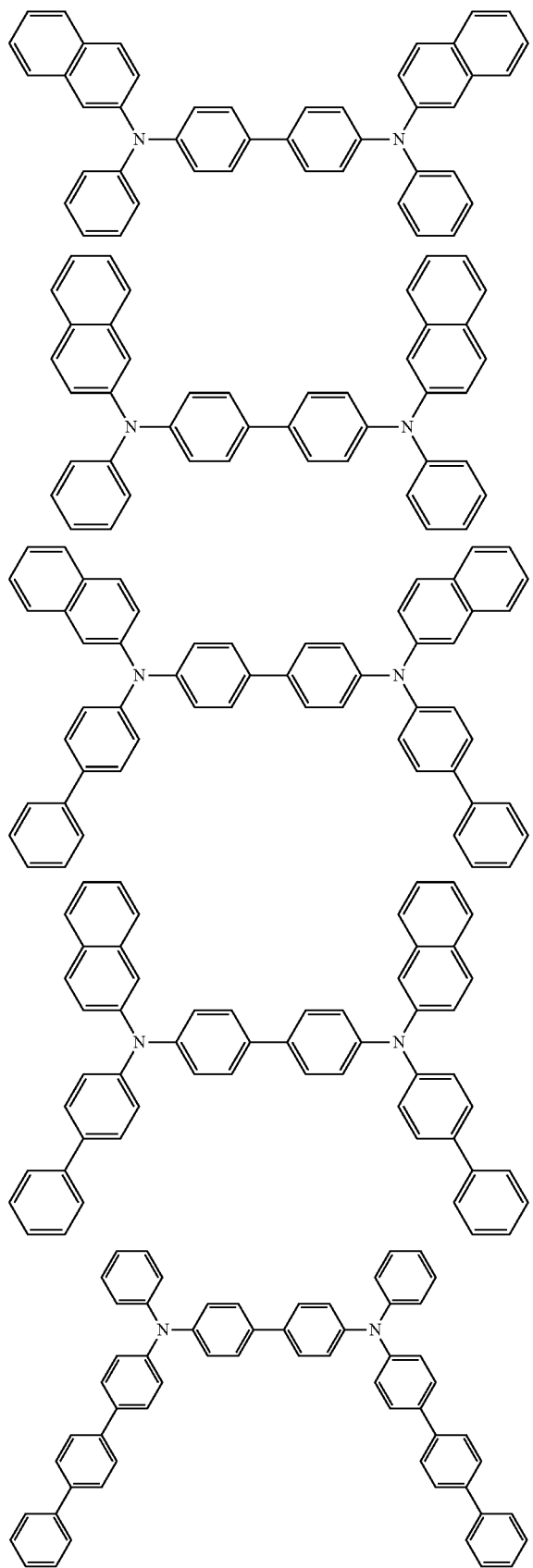
882
-continued
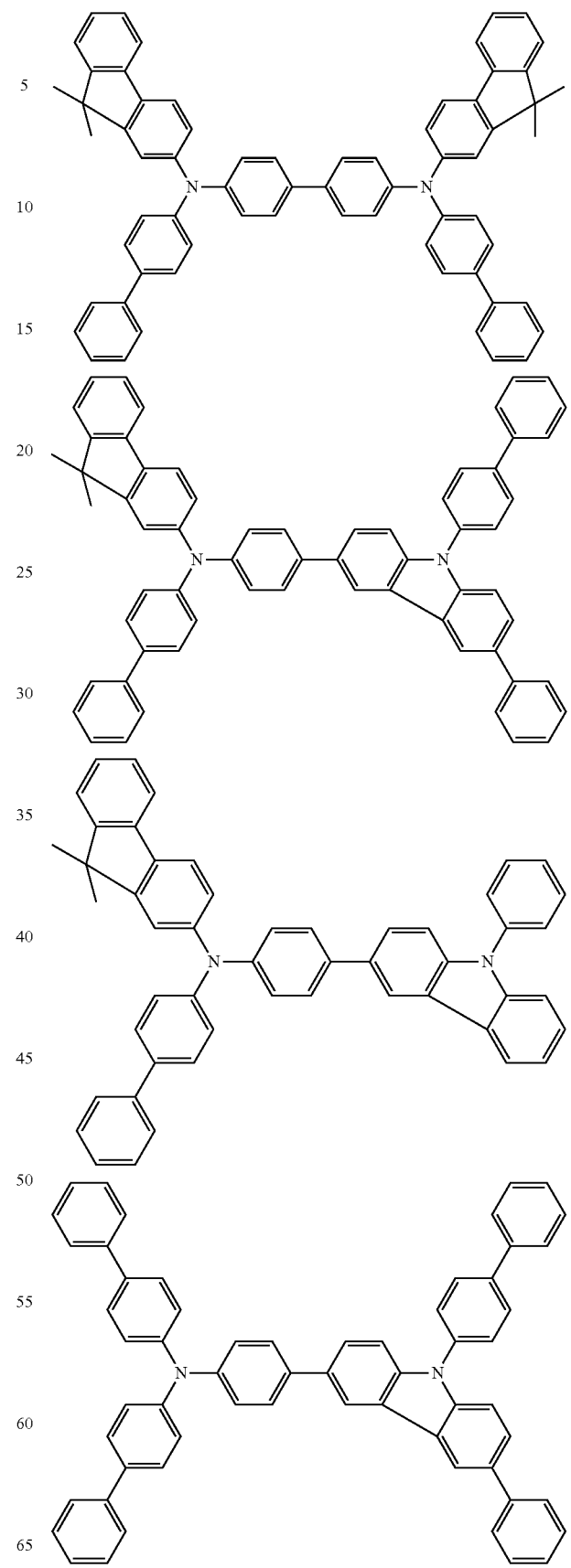

883
-continued
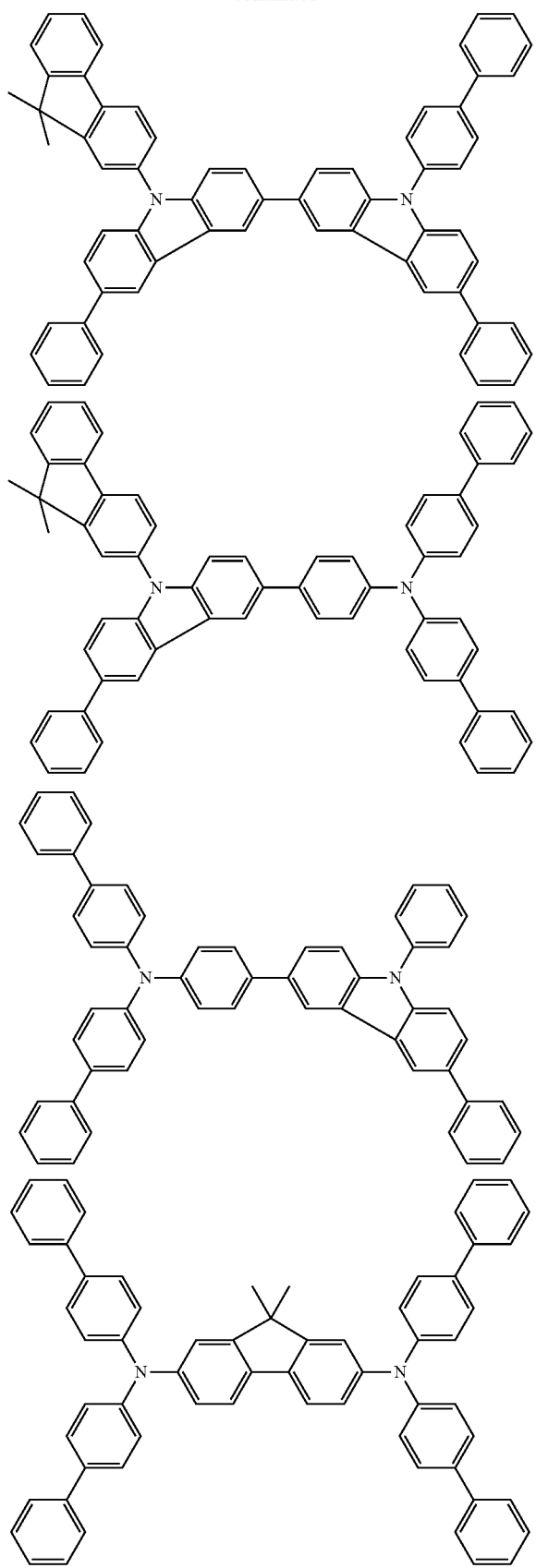
884
-continued
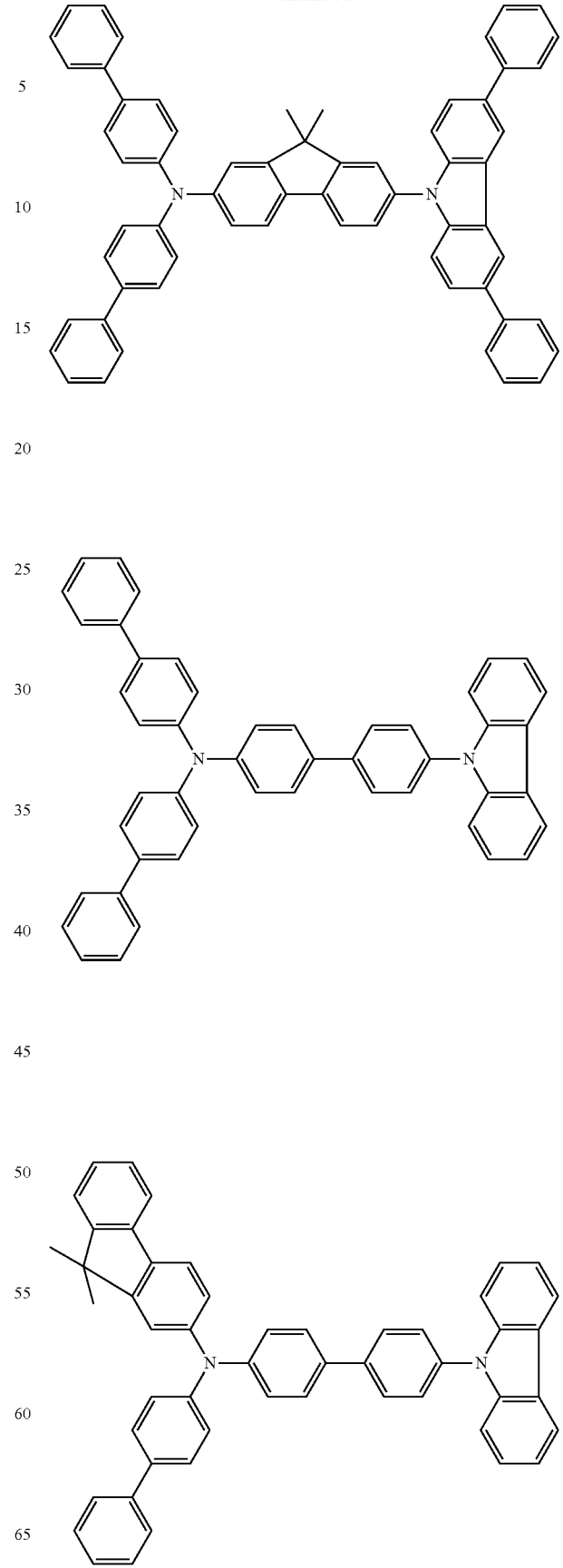

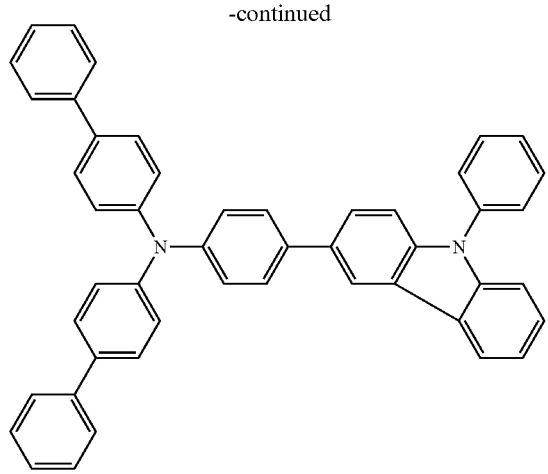
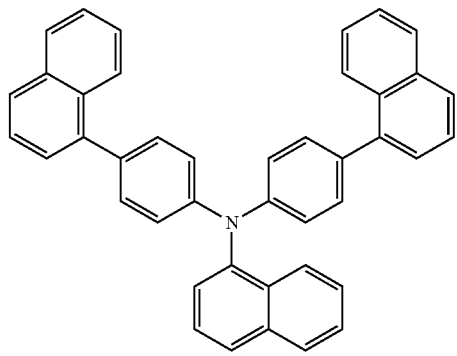
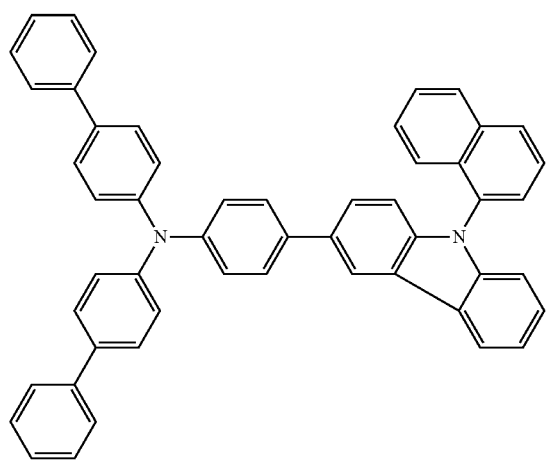 [SMILES: c1ccc(-c2ccc(N(c3ccc(-c4ccccc4)cc3)c3ccc(-c4ccc5c(c4)c4ccccc4n5-c4cccc5ccccc45)cc3)cc2)cc1]
The aromatic amine represented by formula (II) is also preferably used as the material for forming the hole transporting layer.
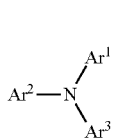
(II)
In formula (II), Ar$^1$ to Ar$^3$ are as defined above with respect to Ar$^1$ to Ar$^4$ of formula (I). Examples of the compounds represented by formula (II) are shown below, although not limited thereto.

887
-continued
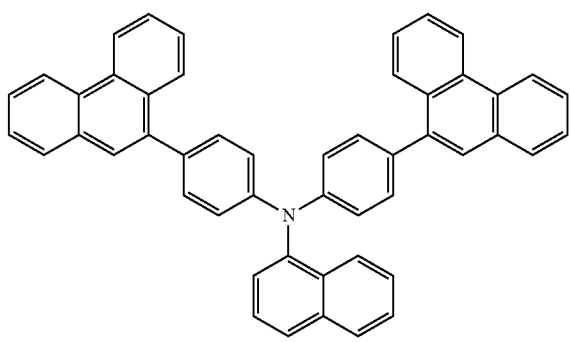
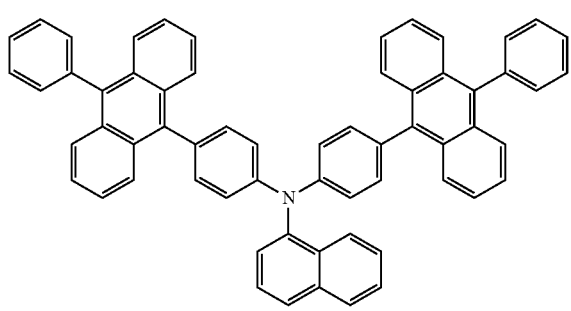
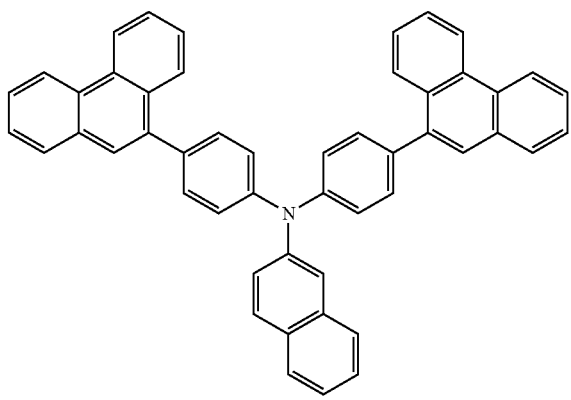
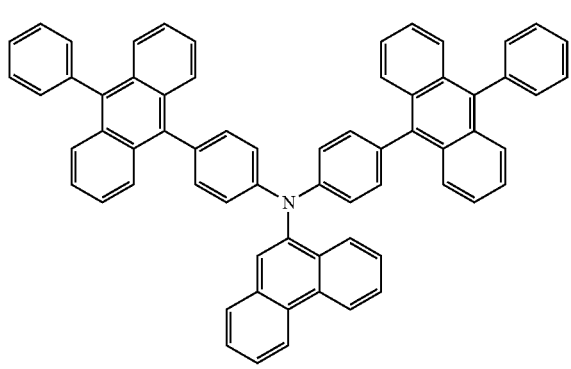
888
-continued
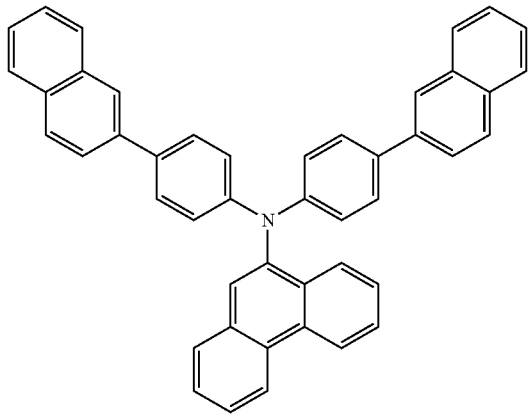
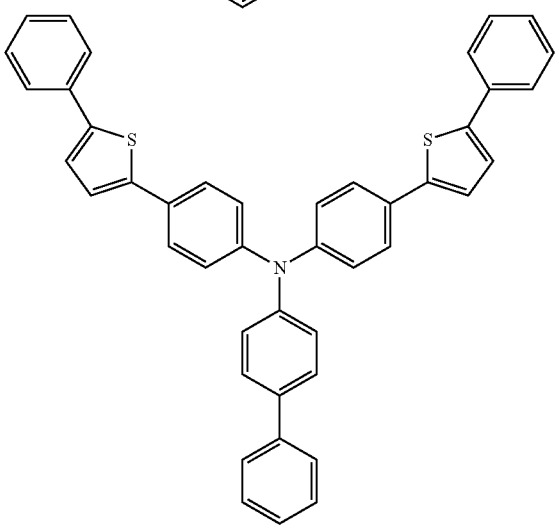
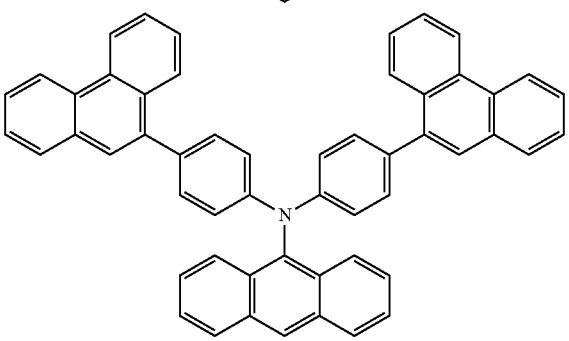
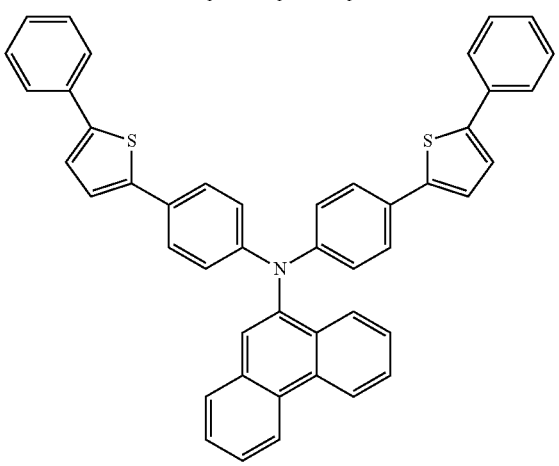

889
-continued
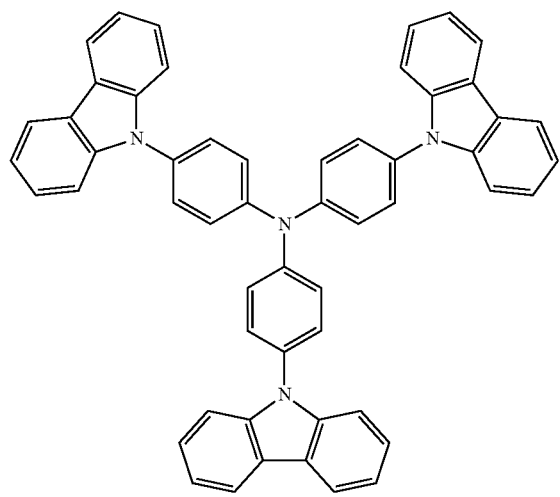
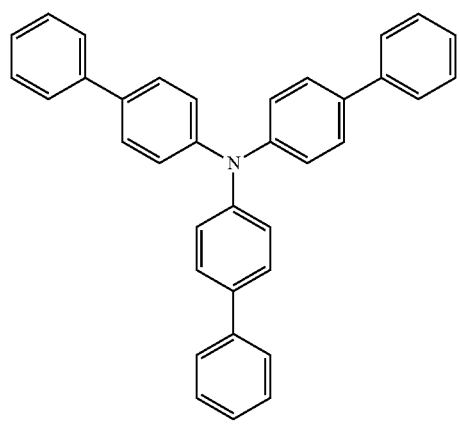
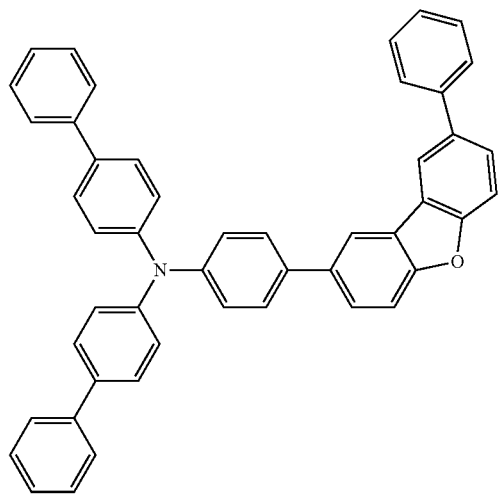
890
-continued
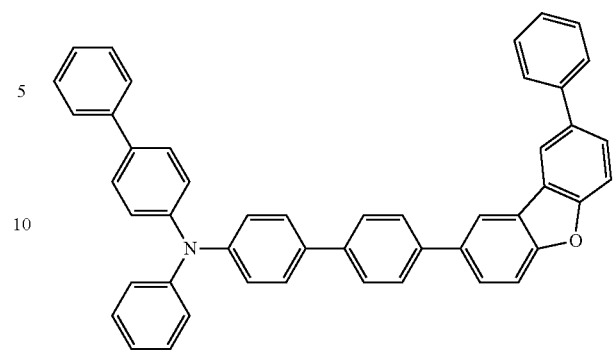
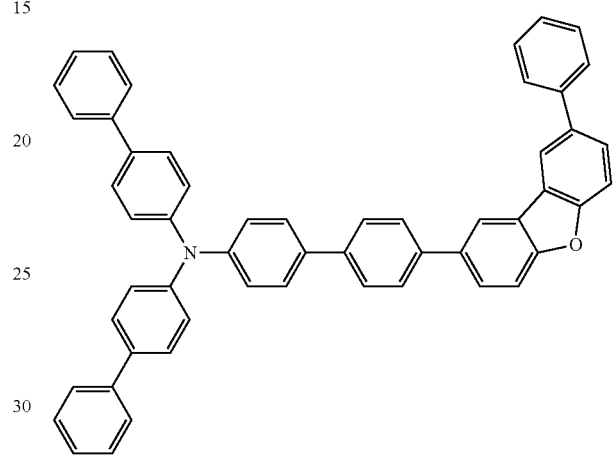
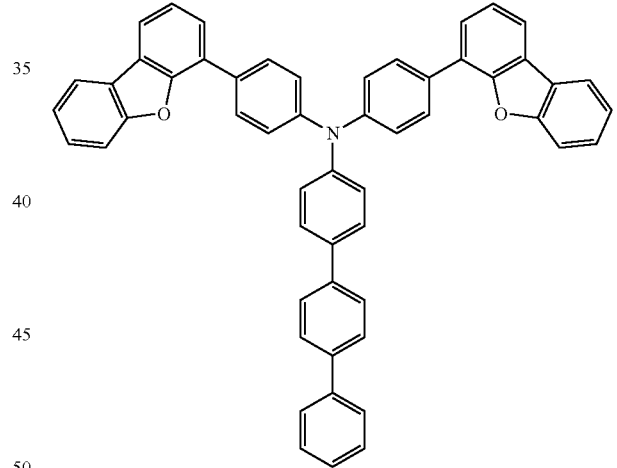
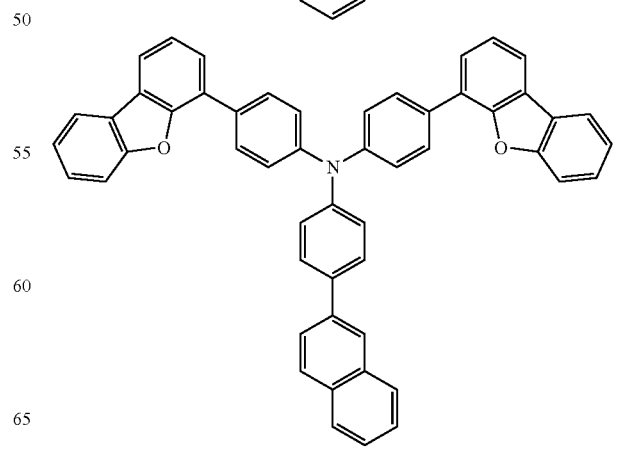

891
-continued

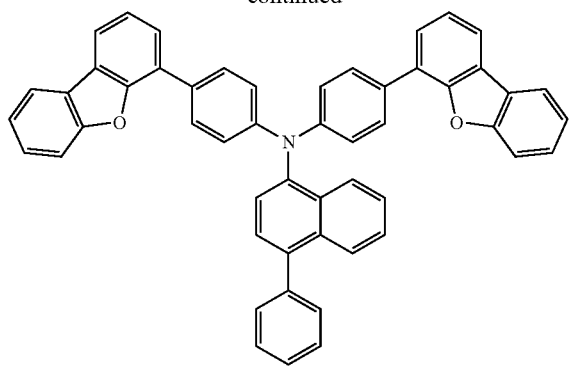
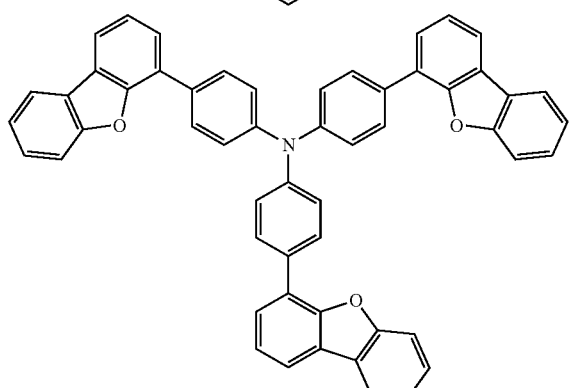
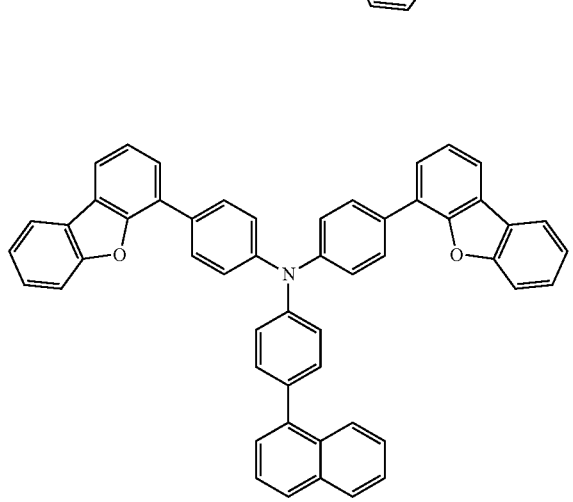
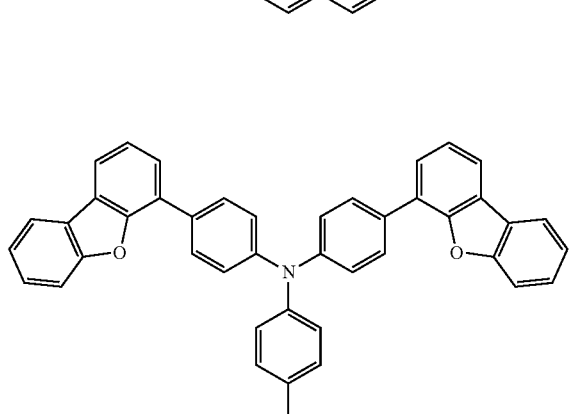

892
-continued

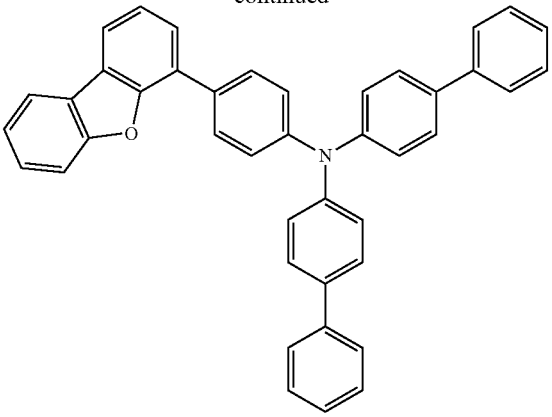
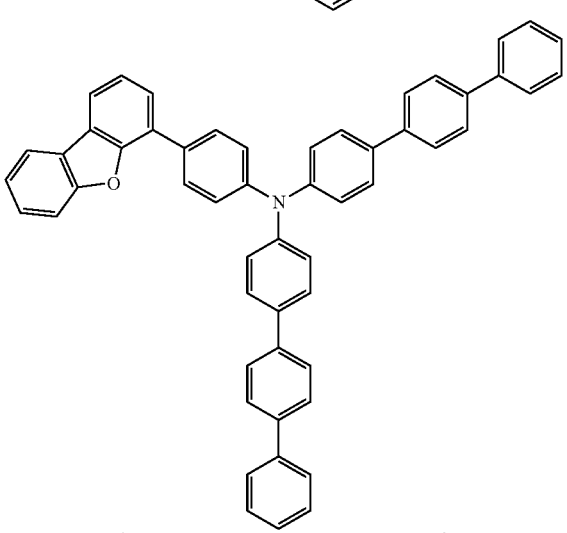
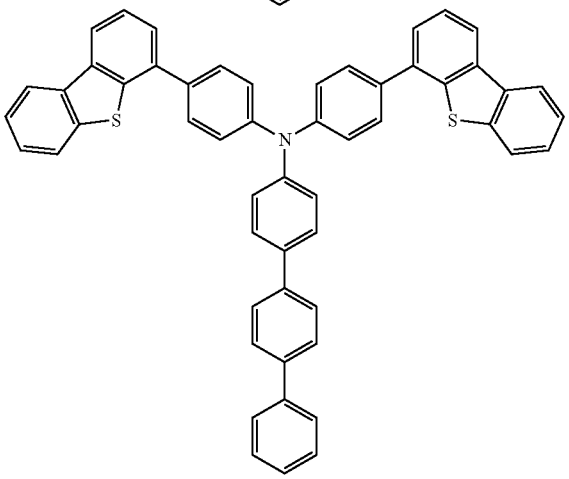

The hole transporting layer of the organic EL device of the invention may be made into a two-layered structure of a first hole transporting layer (anode side) and a second hole transporting layer (cathode side).

The thickness of the hole transporting layer is preferably 10 to 200 nm, although not particularly limited thereto. In a two-layered structure of a first hole transporting layer (anode side) and a second hole transporting layer (cathode side), the thickness of the first hole transporting is preferably 50 to 150 nm and more preferably 50 to 110 nm, and the thickness of the second hole transporting layer is preferably 5 to 50 nm and more preferably 5 to 30 nm.

The organic EL device of the invention may have a layer comprising an acceptor material which is attached to the anode side of the hole transporting layer or the first hole transporting layer. With such a layer, it is expected that the driving voltage is lowered and the production cost is reduced.

The acceptor material is preferably a compound represented by the following formula:

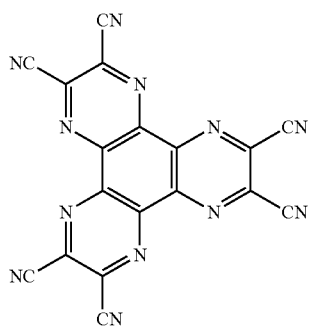 [SMILES: N#Cc1nc2c3nc(C#N)c(C#N)nc3c3nc(C#N)c(C#N)nc3c2nc1C#N]

The thickness of the layer comprising the acceptor material is preferably 5 to 20 nm, although not particularly limited thereto.

N/P Doping

The carrier injecting properties of the hole transporting layer and the electron transporting layer can be controlled by, as described in JP 3695714B, the doping (n) with a donor material or the doping (p) with an acceptor material.

A typical example of the n-doping is an electron transporting material doped with a metal, such as Li and Cs, and a typical example of the p-doping is a hole transporting material doped with an acceptor material such as, $F_4TCNQ$.

Space Layer

For example, in an organic EL device wherein a fluorescent emitting layer and a phosphorescent emitting layer are laminated, a space layer is disposed between the fluorescent emitting layer and the phosphorescent emitting layer to prevent the diffusion of excitons generated in the phosphorescent emitting layer to the fluorescent emitting layer or to control the carrier balance. The space layer may be disposed between two or more phosphorescent emitting layers.

Since the space layer is disposed between the light emitting layers, a material combining the electron transporting ability and the hole transporting ability is preferably used for forming the space layer. To prevent the diffusion of triplet energy in the adjacent phosphorescent emitting layer, the triplet energy of the material for the space layer is preferably 2.6 eV or more. The materials described with respect to the hole transporting layer are usable as the material for the space layer.

Blocking Layer

The organic EL device of the invention preferably comprises a blocking layer, such as an electron blocking layer, a hole blocking layer, and a triplet blocking layer, which is disposed adjacent to the light emitting layer. The electron blocking layer is a layer which prevents the diffusion of electrons from the light emitting layer to the hole transporting layer and is formed between the light emitting layer and the hole transporting layer. The hole blocking layer is a layer which prevents the diffusion of holes from the light emitting layer to the electron transporting layer and is formed between the light emitting layer and the electron transporting layer.

The triplet blocking layer prevents the diffusion of triplet excitons generated in the light emitting layer to adjacent layers and has a function of confining the triplet excitons in the light emitting layer, thereby preventing the deactivation of energy on molecules other than the emitting dopant material of triplet excitons, for example, on molecules in the electron transporting layer.

The electron mobility of the electron injecting layer is preferably $10^{-6}$ cm$^2$/Vs or more at an electric field strength in a range of 0.04 to 0.5 MV/cm. Within the above range, the injection of electrons from the cathode to the electron transporting layer is promoted and the injection of electrons to the adjacent blocking layer and light emitting layer is also promoted, thereby enabling to drive a device at lower voltage.

Electronic Equipment

Since the organic EL device employing the compound of the invention has a further improve emission efficiency, it is usable in electronic equipment, for example, as display parts, such as organic EL panel module, display devices of television sets, mobile phones, personal computer, etc., and light emitting sources of lighting equipment and vehicle lighting equipment.

EXAMPLES

The present invention will be described in more detail with reference to the examples. However, it should be noted that the scope of the invention is not limited thereto.

Synthesis Example 1: Synthesis of Intermediate A

The intermediate A was synthesized according to the following methods (1-1) to (1-6).

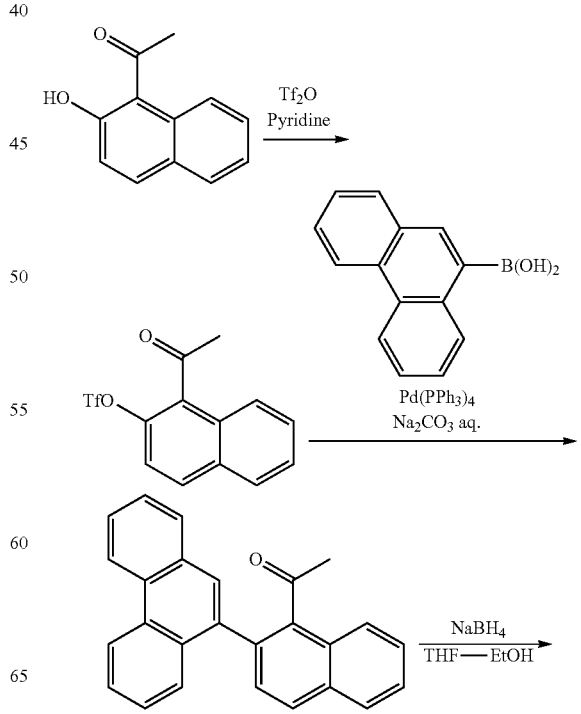

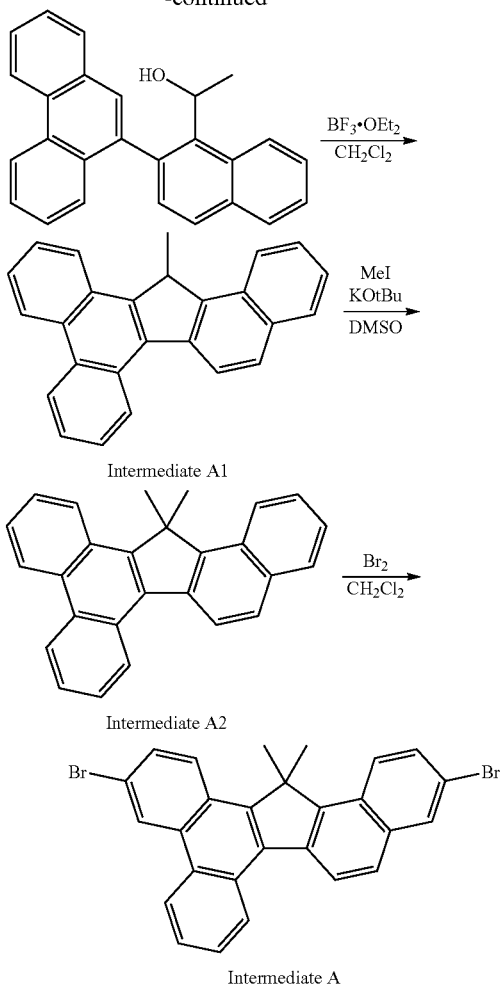

Intermediate A1

Intermediate A2

Intermediate A (1-1): Synthesis of
1-acetyl-2-trifluoromethylsulfoxynaphthalene

Under an argon atmosphere, trifluoromethanesulfonic anhydride (34.3 mL) was added dropwise into a solution of 1-acetyl-2-naphthol (25.3 g) and pyridine (33 mL) in dichloromethane (250 mL) under ice cooling. The resultant solution was stirred at room temperature for 2 h. After adding water, the reaction solution was stirred under ice cooling. The obtained mixed solution was successively washed with water, a 1 M hydrochloric acid, and then water. The dichloromethane layer was dried over anhydrous magnesium sulfate, and then the solvent was evaporated off under reduced pressure. The obtained residue was dissolved in ethyl acetate. The resultant solution was washed with a 1 M hydrochloric acid and water and then dried over anhydrous magnesium sulfate. Thereafter, the solvent was evaporated off under reduced pressure to obtain 1-acetyl-2-trifluoromethylsulfoxynaphthalene (42.0 g) in a yield of 97%.

(1-2): Synthesis of
1-acetyl-2-(9-phenanthryl)naphthalene

Under an argon atmosphere, a mixture of 1-acetyl-2-trifluoromethylsulfoxynaphthalene (42.0 g), 9-phenanthrene boronic acid (29.3 g), tetrakis(triphenylphosphine) palladium(0) (3.1 g), a 2 M aqueous solution of sodium carbonate (200 mL), and 1,2-dimethoxyethane (400 mL) was refluxed under heating for 7 h. The reaction mixture was cooled to room temperature and the solvent was evaporated off under reduced pressure. The obtained residue was washed with methanol and then purified by recrystallization to obtain 1-acetyl-2-(9-phenanthryl)naphthalene (31.2 g) in a yield of 68%.

(1-3): Synthesis of 1-[2-(9-phenanthryl)-1-naphthyl]ethanol

Into a solution of 1-acetyl-2-(9-phenanthryl)naphthalene (10.5 g) in a mixed solvent of THF (200 mL) and ethanol (50 mL), sodium borohydride (5.73 g) was added. The obtained solution was allowed to react at room temperature for 48 h. The obtained reaction mixture was poured into crushed ice and extracted with acetic acid. The obtained ethyl acetate layer was washed water and dried over anhydrous magnesium sulfate. Then, the solvent was evaporated off under reduced pressure to obtain a crude product (11.4 g) of 1-[2-(9-phenanthryl)-1-naphthyl]ethanol, which was used in the next process without purification.

(1-4): Synthesis of Intermediate A1

Under an argon atmosphere, boron trifluoride diethyl ether complex (5.4 mL) was added dropwise into a solution of the crude product (11.4 g) of 1-[2-(9-phenanthryl)-1-naphthyl]ethanol in dichloromethane (100 mL) under ice cooling. The resultant solution was stirred at room temperature for 6 h. Water was added to the obtained reaction mixture under ice cooling and then the dichloromethane layer was separated. After adding a saturated aqueous solution of sodium hydrogen carbonate, the dichloromethane layer was stirred and allowed to phase separation. The obtained dichloromethane layer was washed with water and dried over anhydrous magnesium sulfate. Thereafter, the solvent was evaporated off under reduced pressure and the obtained residue was purified by crystallization to obtain the intermediate A1 (10.1 g) in a yield of 93%.

(1-5): Synthesis of Intermediate A2

Under an argon atmosphere, potassium t-butoxide (4.5 g) was added to a solution of the intermediate A1 (10.1 g) in 200 mL of DMSO, and then methyl iodide (2.48 mL) was further added under water cooling. The resultant mixture was allowed to react overnight at room temperature. Toluene was added to the reaction mixture, and the toluene layer was washed with water and dried over anhydrous magnesium sulfate. Thereafter, the solvent was evaporated off under reduced pressure. The obtained residue was washed by dispersing in methanol to obtain the intermediate A2 (9.39 g) in a yield of 89%.

(1-6): Synthesis of Intermediate A

Under an argon atmosphere, a solution of bromine (0.4 g) in dichloromethane (8 mL) was added to a solution of the intermediate A2 (1.22 g) in dichloromethane (12 mL) under ice cooling. The resultant solution was allowed to react overnight. After adding an aqueous solution of sodium hydrogen carbonate, the obtained reaction mixture was extracted with dichloromethane. After evaporating off the solvent under reduced pressure, the obtained residue was purified by recrystallization to obtain the intermediate A (1.13 g) in a yield of 64%.

Synthesis Example 2: Synthesis of Intermediate B

The intermediate B was synthesized according to the following methods (2-1) to (2-5).

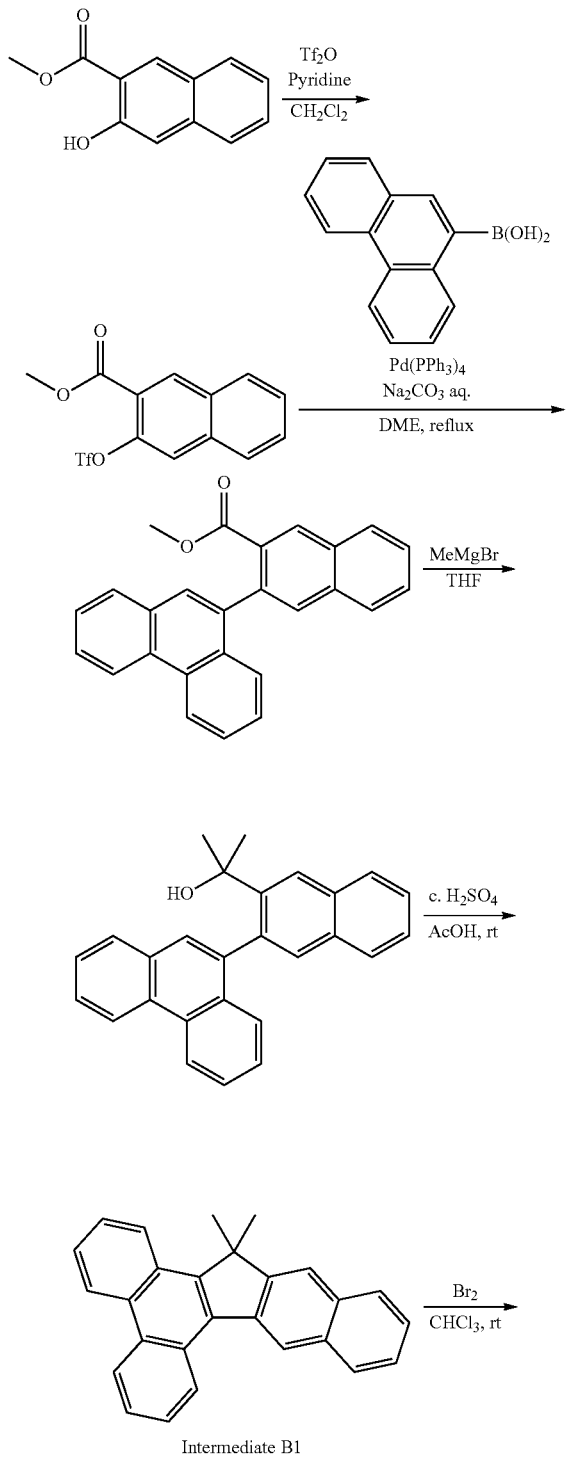

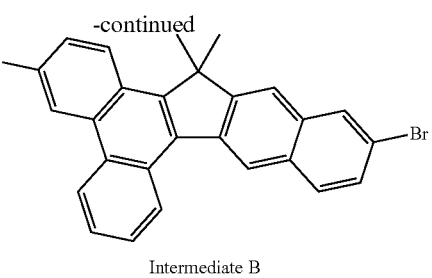

Intermediate B (2-1): Synthesis of methyl 3-trifluoromethylsulfonyloxy-2-naphthoate Under an argon atmosphere, trifluoromethanesulfonic anhydride (10.6 mL) was added dropwise into a solution of methyl 3-hydroxy-2-naphthoate (8.5 g) and triethylamine (8.8 mL) in dichloromethane (210 mL) under ice cooling. The resultant solution was stirred at room temperature for 6 h. The obtained reaction mixture was cooled on ice, stirred after adding water, and then extracted with dichloromethane. The dichloromethane layer was washed with a saturated saline and dried over anhydrous sodium sulfate. Then, the solvent was evaporated off under reduced pressure. The obtained residue was purified by a silica gel chromatography to obtain methyl 3-trifluoromethylsulfonyloxy-2-naphthoate (13.3 g) in a yield of 95%.

(2-2): Synthesis of methyl 3-(9-phenanthryl)-2-naphthoate

Under an argon atmosphere, a mixture of methyl 3-(9-phenanthryl)-2-naphthoate (13.0 g), 9-phenanthrene boronic acid (10.4 g), tetrakis(triphenylphosphine) palladium(0) (2.2 g), a 2 M aqueous solution of sodium carbonate (78 mL), and 1,2-dimethoxyethane (194 mL) was refluxed under heating for 7.5 h. The obtained reaction mixture was cooled to room temperature, filtered through celite, and then extracted with toluene. The toluene layer was washed with a saturated saline and dried over anhydrous sodium sulfate. Then, the solvent was evaporated off under reduced pressure. The obtained residue was purified by a silica gel chromatography to obtain methyl 3-(9-phenanthryl)-2-naphthoate (12.9 g) in a yield of 91%.

(2-3): Synthesis of 2-[3-(9-phenanthryl)-2-naphthyl]propane-2-ol

Under an argon atmosphere, a 0.97 M of solution of methylmagnesium bromide in tetrahydrofuran (43 mL) was added dropwise at 50° C. to a solution of methyl 3-(9-phenanthryl)-2-naphthoate (5.0 g) in tetrahydrofuran (38 mL). The resultant solution was stirred at 50° C. for 7 h. The obtained reaction mixture was cooled on ice, stirred after adding water, and then extracted with toluene. The toluene layer was washed with a saturated saline and dried over anhydrous sodium sulfate. Then, the solvent was evaporated off under reduced pressure. The obtained residue was purified by silica gel chromatography and recrystallization to obtain 2-[3-(9-phenanthryl)-2-naphthyl]propane-2-ol (3.36 g) in a yield of 67%.

(2-4): Synthesis of Intermediate B1

Into a solution of 2-[3-(9-phenanthryl)-2-naphthyl]propane-2-ol (3.36 g) in acetic acid (62 mL), concentrated sulfuric acid (0.5 mL) was added dropwise. The resultant solution was stirred at room temperature for 8 h. After adding water (100 mL) and toluene (100 mL), the obtained reaction mixture was stirred. The separated toluene layer was washed with water, a saturated aqueous solution of sodium hydrogen carbonate, and a saturated saline and then dried over anhydrous sodium sulfate. Then, the solvent was evaporated off under reduced pressure. The obtained residue was purified by silica gel chromatography and recrystallization to obtain the intermediate B1 (1.50 g) in a yield of 47%.

(2-5): Synthesis of Intermediate B

Under an argon atmosphere, bromine (0.15 g) was added to a solution of the intermediate B1 (0.5 g) in chloroform (21 mL). The resultant solution was stirred at room temperature for 7.5 h. After adding water, the obtained reaction mixture was extracted with chloroform. The separated chloroform layer was washed with a saturated aqueous solution of sodium hydrogen carbonate, a saturated aqueous solution of sodium thiosulfate, and a saturated saline, and then dried over anhydrous sodium sulfate. Then, the solvent was evaporated off under reduced pressure. The obtained residue was purified by silica gel chromatography and recrystallization to obtain the intermediate B (0.20 g) in a yield of 27%.

Synthesis Example 3: Synthesis of Intermediate C

The intermediate C was synthesized according to the following methods (3-1) to (3-6).

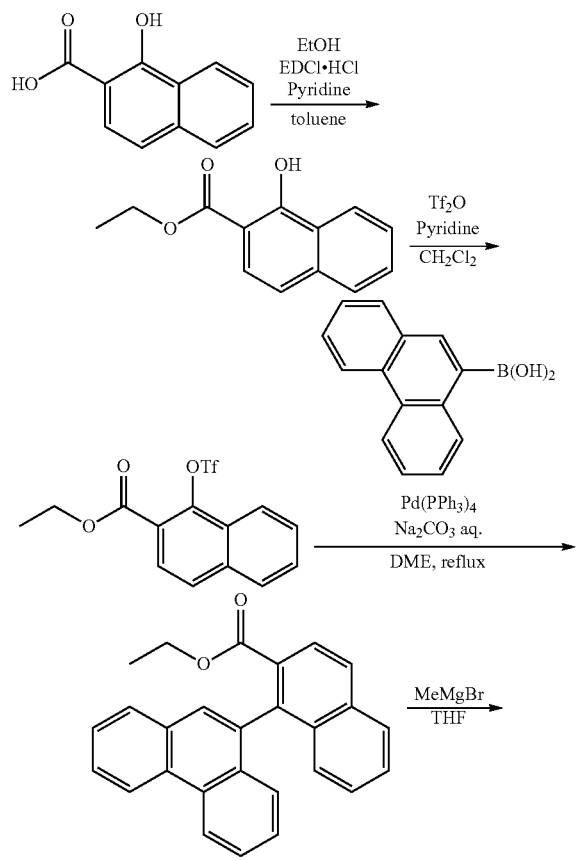

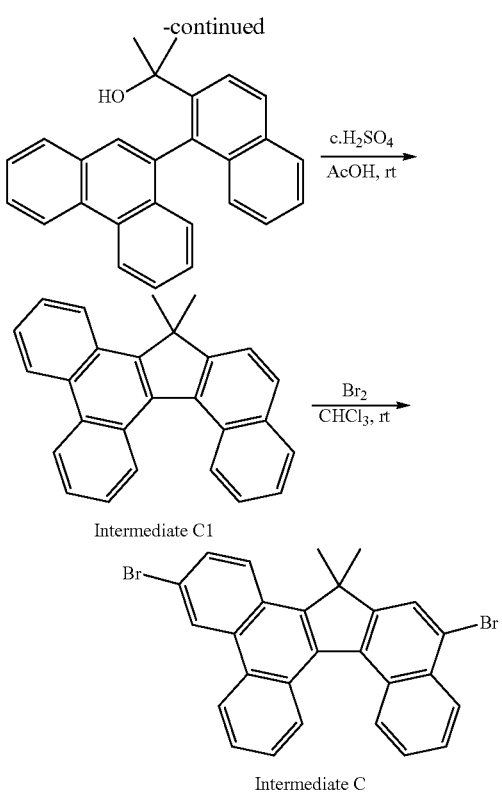

Intermediate C1

Intermediate C (3-1): Synthesis of ethyl 1-hydroxy-2-naphthoate

Under an argon atmosphere, a mixture of 1-hydroxynaphthoic acid (7.5 g) and ethanol (148 mL) was added dropwise to a solution of 1-ethyl-3-(3-dimethylaminopropyl)carbodiimide hydrochloride (9.2 g) and pyridine (9.7 mL) in toluene (199 mL). The resultant solution was stirred at room temperature for 7.5 h. The solvent in the obtained reaction mixture was evaporated off under reduced pressure. The obtained residue was dissolved in dichloromethane, and the dichloromethane layer was successively washed with a 5% hydrochloric acid and a saturated saline and dried over anhydrous sodium sulfate. Then, the solvent was evaporated off under reduced pressure. The obtained residue was purified by silica gel chromatography to obtain ethyl 1-hydroxy-2-naphthoate (7.98 g) in a yield of 93%.

(3-2): Synthesis of ethyl 1-trifluoromethylsulfonyloxy-2-naphthoate

Under an argon atmosphere, trifluoromethanesulfonic anhydride (10.3 mL) was added dropwise to a solution of ethyl 1-hydroxy-2-naphthoate (8.8 g) and triethylamine (8.5 mL) in dichloromethane (203 mL) under ice cooling. The resultant solution was stirred at room temperature for 6.5 h. The obtained reaction mixture was cooled on ice, stirred after adding water, and then extracted with dichloromethane. The separated dichloromethane layer was washed with a saturated saline and dried over anhydrous sodium sulfate. Then, the solvent was evaporated off under reduced pressure. The obtained residue was purified by a silica gel chromatography to obtain ethyl 1-trifluoromethanesulfoxy-2-naphthoate (11.4 g) in a yield of 80%.

(3-3): Synthesis of ethyl 1-(9-phenanthryl)-2-naphthoate

Under an argon atmosphere, a mixture of ethyl 1-trifluoromethylsulfonyloxy-2-naphthoate (11.4 g), 9-phenanthrene boronic acid (8.7 g), tetrakis(triphenylphosphine) palladium (0) (1.9 g), a 2 M aqueous solution of sodium carbonate (65 mL), and 1,2-dimethoxyethane (163 mL) was refluxed under heating for 8 h. After cooling to room temperature, the obtained reaction mixture was filtered through celite and extracted with toluene. The toluene layer was washed with a saturated saline and dried over anhydrous sodium sulfate. Then, the solvent was evaporated off under reduced pressure. The obtained residue was purified by silica gel chromatography to obtain ethyl 1-(9-phenanthryl)-2-naphthoate (12.3 g) in a yield of 99%.

(3-4): Synthesis of 2-[1-(9-phenanthryl)-2-naphthyl]propane-2-ol

Under an argon atmosphere, a 0.97 M solution of methylmagnesium bromide in tetrahydrofuran (41 mL) was added dropwise at 50° C. to a solution of ethyl 1-(9-phenanthryl)-2-naphthoate (5.0 g) in tetrahydrofuran (37 mL). The resultant solution was stirred for 8 h at 50° C. The obtained reaction mixture was cooled to room temperature, stirred after adding water, and then extracted with toluene. The separated toluene layer was washed with a saturated saline and dried over anhydrous sodium sulfate. Then, the solvent was evaporated off under reduced pressure. The obtained residue was purified by silica gel chromatography and recrystallization to obtain 2-[1-(9-phenanthryl)-2-naphthyl]propane-2-ol (4.21 g) in a yield of 87%.

(3-5): Synthesis of Intermediate C1

Concentrated sulfuric acid (0.6 mL) was added dropwise to a solution of 2-[1-(9-phenanthryl)-2-naphthyl]propane-2-ol (4.21 g) in acetic acid (77 mL). The resultant solution was stirred at room temperature for 6 h. After adding water (100 mL) and toluene (100 mL), the obtained reaction mixture was stirred. The separated toluene layer was washed with water, a saturated aqueous solution of sodium hydrogen carbonate, and a saturated saline, and then dried over anhydrous sodium sulfate. The, the solvent was evaporated off under reduced pressure. The obtained residue was purified by a silica gel chromatography to obtain the intermediate C1 (2.11 g) in a yield of 53%.

(3-6): Synthesis of Intermediate C

Under an argon atmosphere, bromine (0.15 g) was added to a solution of the intermediate C1 (0.5 g) in chloroform (21 mL). The resultant solution was stirred at room temperature for 7.5 h. After adding water, the obtained reaction mixture was extracted with chloroform. The separated chloroform layer was washed with a saturated aqueous solution of sodium hydrogen carbonate, a saturated aqueous solution of sodium thiosulfate, and a saturated saline, and then dried over anhydrous sodium sulfate. Then, the solvent was evaporated off under reduced pressure. The obtained residue was purified by silica gel chromatography and recrystallization to obtain the intermediate C (0.58 g) in a yield of 80%.

Synthesis Example 4: Synthesis of Compound 1

The compound 1 was synthesized according to the following method.

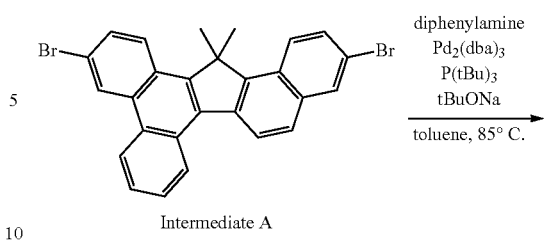

Intermediate A

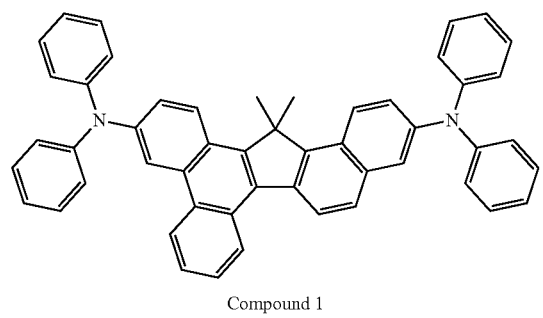

Compound 1

Under an argon atmosphere, a mixture of the intermediate A (1.84 g) obtained in Synthesis Example 1, diphenylamine (1.37 g), tris(dibenzylideneacetone) dipalladium(0) (0.07 g), tri-t-butylphosphine (0.036 g), sodium t-butoxide (0.85 g), and toluene (64 mL) was stirred at 85° C. for 7 h. The obtained reaction mixture was cooled to room temperature and filtered through celite, and then the solvent was evaporated off under reduced pressure. The obtained residue was purified by silica gel column chromatography and recrystallization to obtain the compound 1 (1.34 g) in a yield of 54%. The obtained compound was identified by mass spectrometry: m/e=678 to the molecular weight of 678.30.

Synthesis Example 5: Synthesis of Compound 2

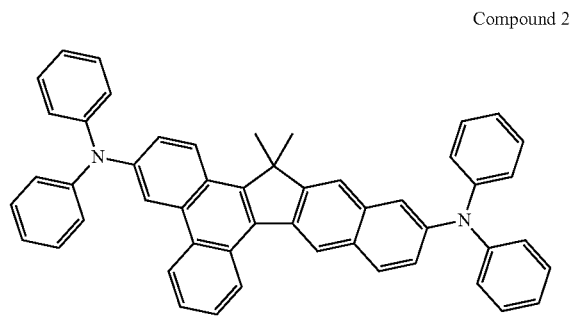 [SMILES: CC1(C)c2cc3cc(N(c4ccccc4)c4ccccc4)ccc3cc2-c2c1c1ccc(N(c3ccccc3)c3ccccc3)cc1c1ccccc21]

Compound 2

The compound 2 was obtained in the same manner as in Synthesis Example 4 except for using the intermediate B obtained in Synthesis Example 2 in place of the intermediate A. The obtained compound was identified by mass spectrometry: m/e=678 to the molecular weight of 678.30.

Synthesis Example 6: Synthesis of Compound 3

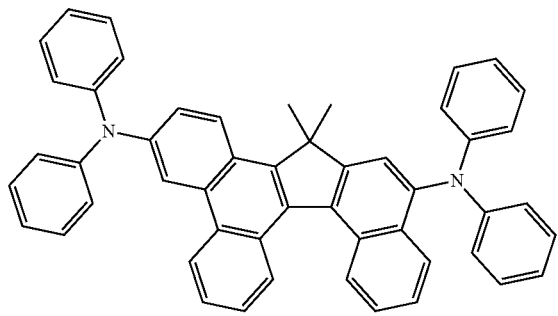

Compound 3

The compound 3 was obtained in the same manner as in Synthesis Example 4 except for using the intermediate C obtained in Synthesis Example 3 in place of the intermediate A. The obtained compound was identified by mass spectrometry: m/e=678 to the molecular weight of 678.30.

Synthesis Example 7: Synthesis of Compound 4

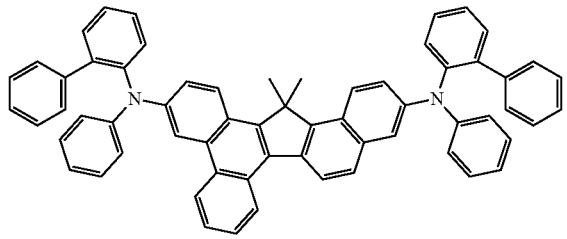

Compound 4

The compound 4 was obtained in the same manner as in Synthesis Example 4 except for using N-phenyl-2-biphenylamine in place of diphenylamine. The obtained compound was identified by mass spectrometry: m/e=830 to the molecular weight of 830.37.

Synthesis Example 8: Synthesis of Compound 5

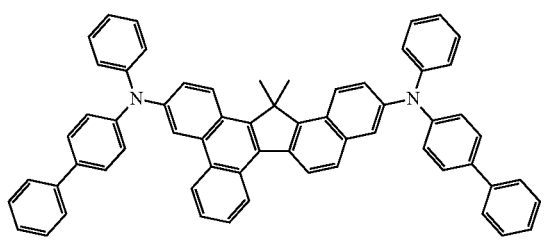

Compound 5

The compound 5 was obtained in the same manner as in Synthesis Example 4 except for using N-phenyl-4-biphenylamine in place of diphenylamine. The obtained compound was identified by mass spectrometry: m/e=830 to the molecular weight of 830.37.

Synthesis Example 9: Synthesis of Compound 6

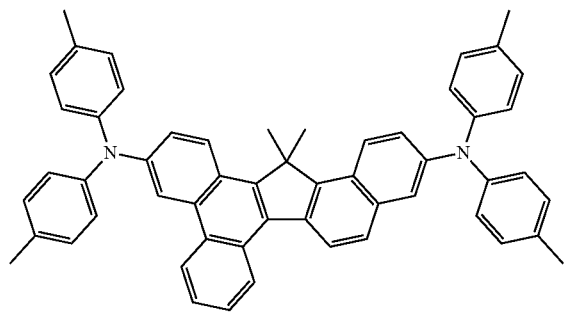

Compound 6

The compound 6 was obtained in the same manner as in Synthesis Example 4 except for using p,p'-ditolylamine in place of diphenylamine. The obtained compound was identified by mass spectrometry: m/e=734 to the molecular weight of 734.37.

Synthesis Example 10: Synthesis of Compound 7

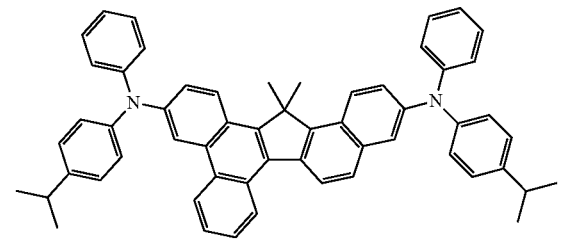

Compound 7

The compound 7 was obtained in the same manner as in Synthesis Example 4 except for using 4-isopropyl-N-phenylaniline in place of diphenylamine. The obtained compound was identified by mass spectrometry: m/e=762 to the molecular weight of 762.40.

Synthesis Example 11: Synthesis of Intermediate D

The intermediate D was synthesized according to the following method.

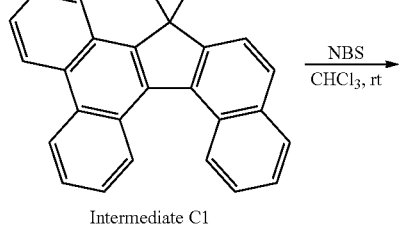

Intermediate C1

$\xrightarrow{\text{NBS}}_{\text{CHCl}_3, \text{rt}}$

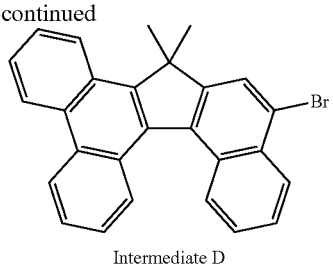

Intermediate D

Under an argon atmosphere, a solution of N-bromosuccinimide (0.71 g) in chloroform (10 mL) was added dropwise under ice cooling to a solution of the intermediate C1 (1.38 g) synthesized according to the method of Synthesis Example 3 in chloroform (50 mL). The resultant solution was stirred at room temperature for 6 h. The obtained reaction mixture was extracted with dichloromethane. The dichloromethane layer was dried over anhydrous sodium sulfate and then the dichloromethane was evaporated off under reduced pressure. The obtained residue was purified by silica gel column chromatography and recrystallization to obtain the intermediate D (1.27 g) in a yield of 75%.

Synthesis Example 12: Synthesis of Intermediate E

The intermediate E was synthesized according to the following method.

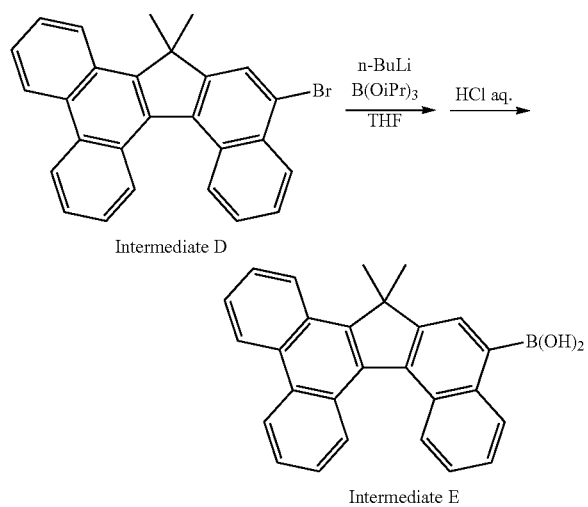

Under an argon atmosphere, a solution of the intermediate D (0.74 g) synthesized according to the method of Synthesis Example 11 in tetrahydrofuran (20 ml) was cooled to −78° C. After adding a hexane solution of n-butyl lithium (1.57 M, 1.4 mL), the solution was stirred for 2 h. After adding triisopropyl borate (1.0 mL), the reaction solution was stirred at room temperature for 3 h and further stirred at room temperature for 3 h after adding 10 mL of a 2 M hydrochloric acid. The obtained reaction mixture was extracted with toluene, and the toluene layer was washed with a saturated saline and dried over anhydrous sodium sulfate. Then, the toluene solvent was evaporated off under reduced pressure. The obtained residue was purified by recrystallization to obtain the intermediate E (0.44 g) in a yield of 66%.

Synthesis Example 13: Synthesis of Compound 8

The compound 8 was synthesized according to the following method.

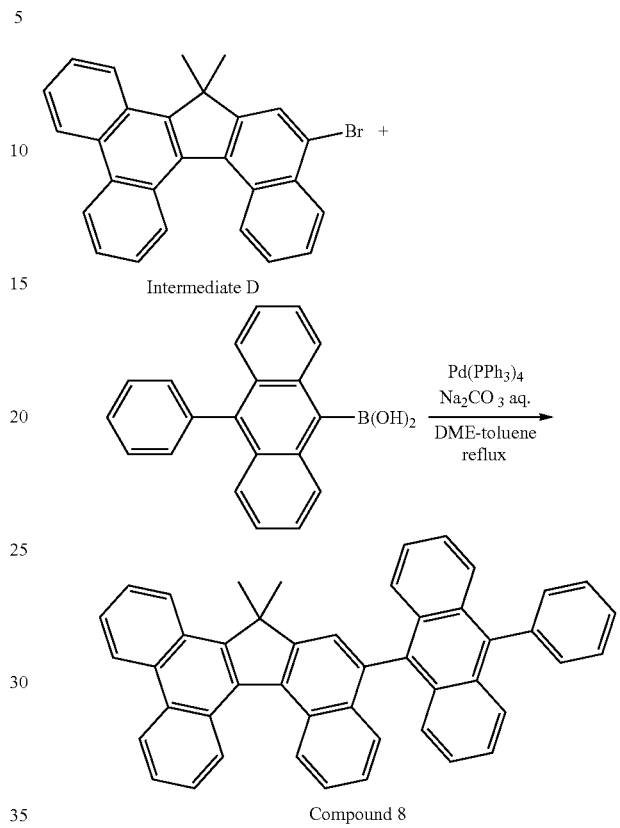

Under an argon atmosphere, a mixture of the intermediate D (0.53 g), 9-phenylanthracene-10-ylboronic acid (0.45 g), tetrakis(triphenylphosphine) palladium(0) (43 mg), a 2 M aqueous solution of sodium carbonate (2 mL), toluene (3 mL), and 1,2-dimethoxyethane (3 mL) was refluxed for 8 h. The obtained reaction mixture was extracted with toluene. The toluene layer was washed with a saturated saline and dried over anhydrous sodium sulfate. Then, the toluene solvent was evaporated off under reduced pressure. The obtained residue was purified by silica gel column chromatography and recrystallization to obtain the compound 8 (0.40 g) in a yield of 53%. The obtained compound was identified by mass spectrometry: m/e=596 to the molecular weight of 596.25.

Synthesis Example 14: Synthesis of Compound 9

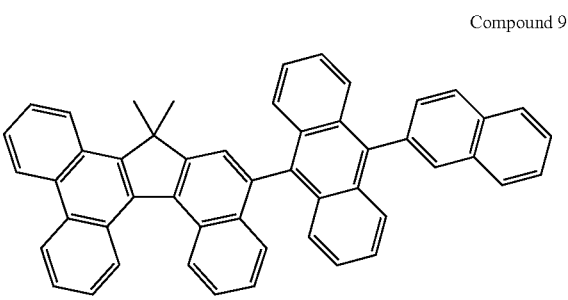 [SMILES: CC1(C)c2cc(-c3c4ccccc4c(-c4ccc5ccccc5c4)c4ccccc34)c3ccccc3c2-c2c1c1ccccc1c1ccccc21]

Compound 9

The compound 9 was obtained in the same manner as in Synthesis Example 13 except for using 9-(2-naphthy)anthracene-10-ylboronic acid in place of 9-phenylanthracene-10-ylboronic acid. The obtained compound was identified by mass spectrometry: m/e=646 to the molecular weight of 646.27.

Synthesis Example 15: Synthesis of Compound 10

Compound 10

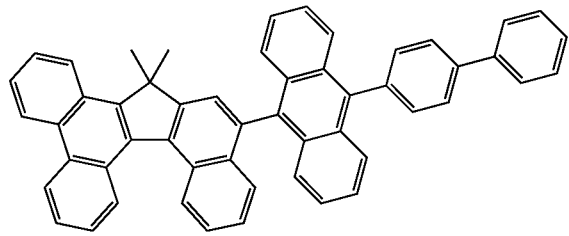

The compound 10 was obtained in the same manner as in Synthesis Example 13 except for using 9-(4-biphenyl)anthracene-10-ylboronic acid in place of 9-phenylanthracene-10-ylboronic acid. The obtained compound was identified by mass spectrometry: m/e=672 to the molecular weight of 672.28.

Synthesis Example 16: Synthesis of Compound 11

The compound 11 was synthesized according to the following method.

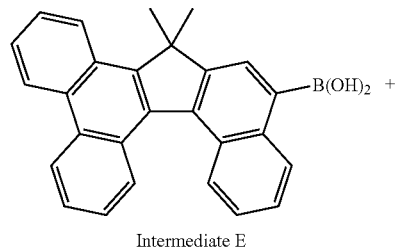

Intermediate E

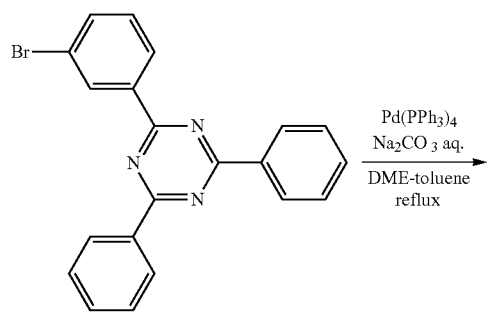

Pd(PPh$_3$)$_4$
Na$_2$CO$_3$ aq.
DME-toluene
reflux

Compound 11

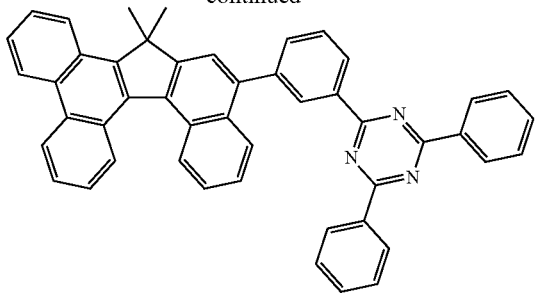

Under an argon atmosphere, a mixture of the intermediate E (0.44 g), 2-(3-bromophenyl)-4,6-phenyl-1,3,5-triazine (0.39 g), tetrakis(triphenylphosphine) palladium(0) (35 mg), a 2 M aqueous solution of sodium carbonate (1.5 mL), toluene (2 mL), and 1,2-dimethoxyethane (2 mL) was refluxed for 8 h. The obtained reaction mixture was extracted with toluene. The toluene layer was washed with a saturated saline and dried over anhydrous sodium sulfate. Then, the toluene solvent was evaporated off under reduced pressure. The obtained residue was purified by silica gel column chromatography and recrystallization to obtain the compound 11 (0.38 g) in a yield of 58%. The obtained compound was identified by mass spectrometry: m/e=651 to the molecular weight of 651.27.

Example 1

Production of Organic EL Device

A glass substrate of 25 mm×75 mm×1.1 mm thickness having an ITO transparent electrode (product of Geomatec Company) was cleaned by ultrasonic cleaning in isopropyl alcohol for 5 min and then UV ozone cleaning for 30 min. The thickness of the ITO transparent electrode was 130 nm.

The cleaned glass substrate having an ITO transparent electrode line was mounted to a substrate holder of a vacuum vapor deposition apparatus. The following compound HI-1 was vapor-deposited so as to cover the transparent electrode to form a film HI-1 with a thickness of 5 nm, thereby forming a hole injecting layer.

On the film HI-1, the following compound HT-1 was vapor-deposited to form a film HT-1 with a thickness of 80 nm, thereby forming a first hole transporting layer. On the film HT-1, the following compound HT-2 was vapor-deposited to form a film HT-2 with a thickness of 15 nm, thereby forming a second hole transporting layer.

On the second hole transporting layer, the compound BH-1 (host material) and the compound 1 (dopant material) were vapor co-deposited to form a co-deposited film with a thickness of 25 nm. The concentration of the compound 1 was 5.0% by mass. The co-deposited film works as a light emitting layer.

On the light emitting layer, the following compound ET-1 was vapor-deposited to form a film ET-1 with a thickness of 20 nm, thereby forming a first electron transporting layer.

On the film ET-1, the following compound ET-2 was vapor-deposited to form a film ET-2 with a thickness of 5 nm, thereby forming a second electron transporting layer.

On the film ET-2, LiF was vapor-deposited to form a film of LiF with a thickness of 1 nm at a film-forming speed of 0.1 Å/min, thereby forming an electron injecting electrode (cathode).

On the film of LiF, metallic Al was vapor-deposited to from a film of metallic Al with a thickness of 80 nm, thereby forming a metallic Al cathode.

Thus, an organic EL device was produced.

Evaluation of Organic EL Device

By applying a voltage to the organic EL device thus produced so as to adjust the current density to 10 mA/cm², the external quantum efficiency (EQE) was evaluated. In addition, the time taken until the luminance was reduced to 80% of the initial luminance (LT80) was measured at a current density of 50 mA/cm². The results are shown in Table 1.

HI-1

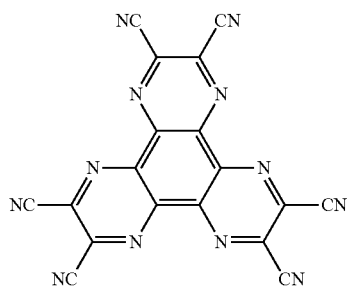

HT-1

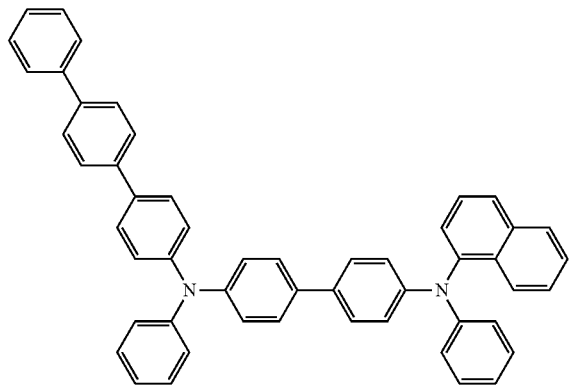

HT-2

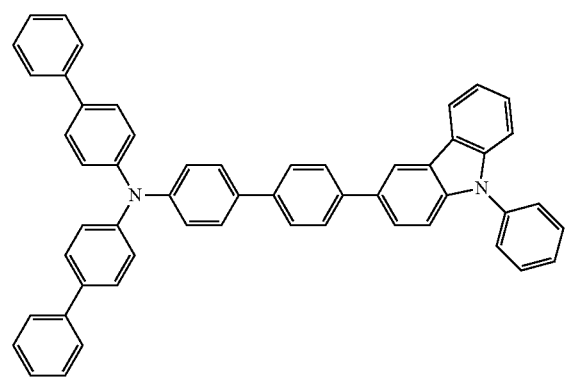

BH-1

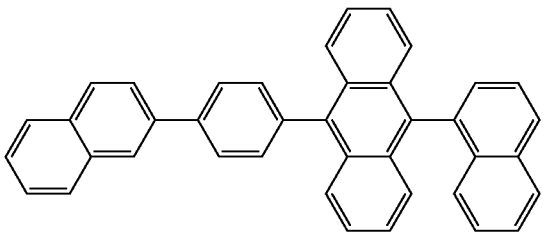

ET-1

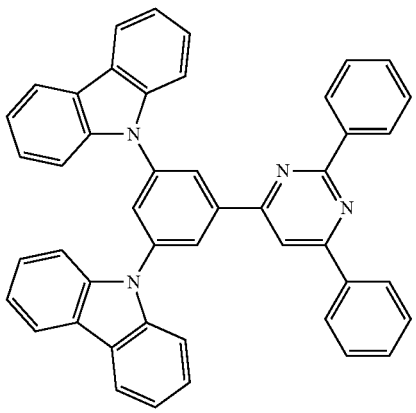

ET-2

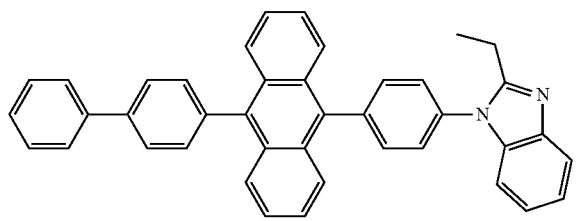

Examples 2 to 3 and Comparative Examples 1 to 2

Each device was produced in the same manner as in Example 1 except for using each compound shown in Table 1 in place of the compound 1. The results of evaluation are shown in Table 1.

TABLE 1

|  | Dopant material | External quantum efficiency (%) | LT80 (h) |
| --- | --- | --- | --- |
| Example 1 | Compound 1 | 9.3 | 140 |
| Example 2 | Compound 2 | 9.5 | 130 |
| Example 3 | Compound 3 | 9.2 | 160 |
| Comparative example 1 | Comparative compound 1 | 7.4 | 95 |
| Comparative example 2 | Comparative compound 2 | 8.5 | 85 |

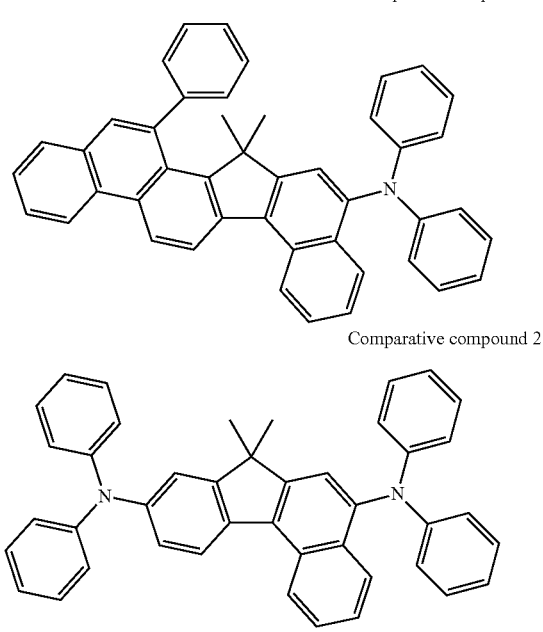

Comparative compound 1

Comparative compound 2

The comparative compound 1 and the compounds 1 to 3 used in Examples 1 to 3 are different in the fuse manner of the three-membered ring in the fluorene ring moiety. The comparative compound 2 and the compounds 1 to 3 used in Examples 1 to 3 are different in the aromatic rings of the fluorene ring moiety. By employing the fused ring system specified in the present invention, the exciton generated on the host material is smoothly transferred into the compounds 1 to 3 used as the dopant material, and the energy of the excited compounds 1 to 3 is efficiently converted into light. These effects are considered to result in the high efficiency.

The compounds 1 to 3 are excellent in the carrier transporting ability. Therefore, the carriers are well balanced in the light emitting layer which is formed by combinedly using the host material, this being considered to contribute to the improved emission efficiency and the elongated lifetime.

Example 4

Production of Organic EL Device

A glass substrate of 25 mm×75 mm×1.1 mm thickness having an ITO transparent electrode (product of Geomatec Company) was cleaned by ultrasonic cleaning in isopropyl alcohol for 5 min and then UV ozone cleaning for 30 min. The thickness of the ITO transparent electrode was 130 nm.

The cleaned glass substrate having an ITO transparent electrode line was mounted to a substrate holder of a vacuum vapor deposition apparatus. The following compound HI-1 was vapor-deposited so as to cover the transparent electrode to form a film HI-1 with a thickness of 5 nm, thereby forming a hole injecting layer.

On the hole injecting layer, the following compound HT-3 was vapor-deposited to form a film HT-3 with a thickness of 80 nm, thereby forming a first hole transporting layer.

On the first hole transporting layer, the following compound HT-4 was vapor-deposited to form a film HT-4 with a thickness of 15 nm, thereby forming a second hole transporting layer. Further, on the second hole transporting layer, the compound BH-1 (host material) and the compound 1 (dopant material) were vapor co-deposited to form a co-deposited film with a thickness of 25 nm. The concentration of the compound 1 was 5.0% by mass. The co-deposited film works as a light emitting layer.

On the light emitting layer, the following compound ET-3 was vapor-deposited to form a film ET-3 with a thickness of 20 nm, thereby forming a first electron transporting layer.

On the first electron transporting layer, the following compound ET-2 was vapor-deposited to form a film ET-2 with a thickness of 5 nm, thereby forming a second electron transporting layer.

On the second electron transporting layer, LiF was vapor-deposited to form a film of LiF with a thickness of 1 nm at a film-forming speed of 0.01 nm/sec, thereby forming an electron injecting electrode (cathode).

On the film of LiF, metallic Al was vapor-deposited to from a film of metallic Al with a thickness of 80 nm, thereby forming a metallic Al cathode.

Evaluation of Organic EL Device

By applying a voltage to the organic EL device thus produced so as to adjust the current density to 10 mA/cm$^2$, an emission spectrum was measured. In addition, the time taken until the luminance was reduced to 80% of the initial luminance (LT80) was measured at a current density of 50 mA/cm$^2$. The results are shown in Table 2.

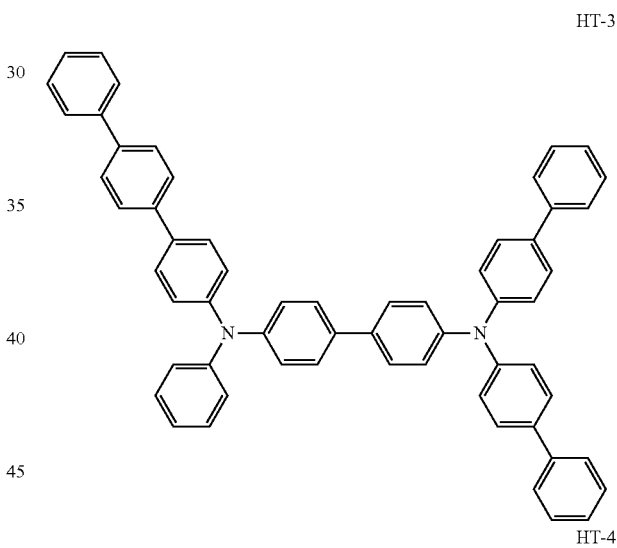

HT-3

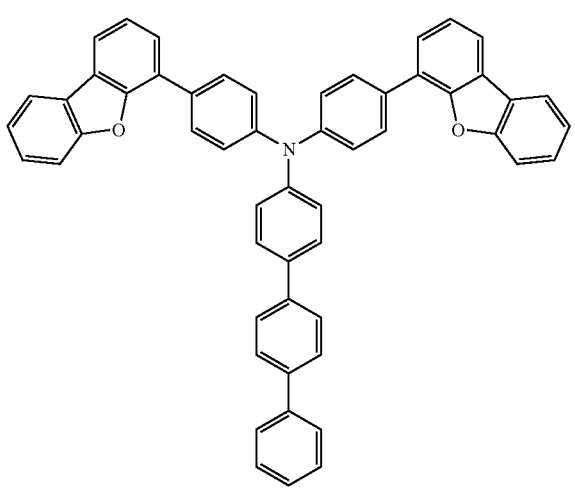

HT-4

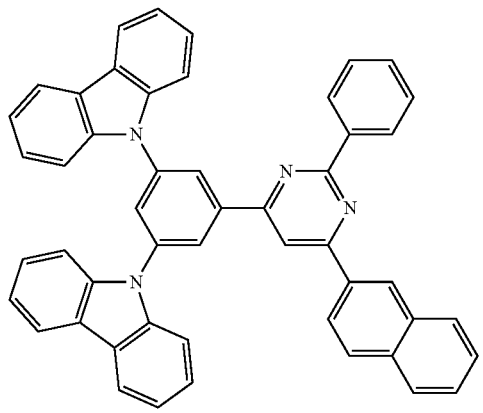

ET-3

Examples 5 to 8 and Comparative Example 3

Each device was produced in the same manner as in Example 4 except for using each compound shown in Table 2 in place of the compound 1. The results of evaluation are shown in Table 2.

TABLE 2

|  | Dopant material | Emission peak wavelength (nm) | LT80 (h) |
| --- | --- | --- | --- |
| Example 4 | Compound 1 | 446 | 350 |
| Example 5 | Compound 4 | 445 | 480 |
| Example 6 | Compound 5 | 450 | 730 |
| Example 7 | Compound 6 | 452 | 500 |
| Example 8 | Compound 7 | 449 | 430 |
| Comparative example 3 | Comparative compound 2 | 457 | 120 |

As seen from Table 2, the compounds 1 and 4 to 7 each used as a dopant material of the light emitting layer largely increase the device lifetime. As descried above, the compounds are excellent in the carrier transporting ability and favorably interact with the host material. These properties probably contribute to the prolonged lifetime of each organic EL device. $Ar^2$ of the compound 1 is a phenyl group. In the compounds 4 and 5, $Ar^2$ is changed to a biphenylyl group and changed to an alkyl-substituted phenyl group in the compounds 6 and 7. These changes would lead to the protection of the amino moiety which is susceptible to chemical reaction because of its molecular structure. This protection probably contributes to the further improvement in the device lifetime.

As compared with the device employing the comparative compound 2, the devices employing the compounds 1 and 4 to 7 emit a light with shorter wavelength, showing that the compounds of the invention are suitable for use in a deep blue-emitting organic EL device.

Example 9

Production of Organic EL Device

A glass substrate of 25 mm×75 mm×1.1 mm thickness having an ITO transparent electrode (product of Geomatec Company) was cleaned by ultrasonic cleaning in isopropyl alcohol for 5 min and then UV ozone cleaning for 30 min. The thickness of the ITO transparent electrode was 130 nm.

The cleaned glass substrate having an ITO transparent electrode line was mounted to a substrate holder of a vacuum vapor deposition apparatus. The following compound HI-1 was vapor-deposited so as to cover the transparent electrode to form a film HI-1 with a thickness of 5 nm, thereby forming a hole injecting layer.

On the hole injecting layer, the following compound HT-5 was vapor-deposited to form a film HT-5 with a thickness of 80 nm, thereby forming a first hole transporting layer. Further, on the first hole transporting layer, the following compound HT-4 was vapor-deposited to form a film HT-4 with a thickness of 15 nm, thereby forming a second hole transporting layer.

Then, on the second hole transporting layer, the compound 8 (host material) and the compound BD-1 (dopant material) were vapor co-deposited to form a co-deposited film with a thickness of 25 nm. The concentration of the compound BD-1 was 5.0% by mass. The co-deposited film works as a light emitting layer.

On the light emitting layer, the following compound ET-1 was vapor-deposited to form a film ET-1 with a thickness of 20 nm, thereby forming a first electron transporting layer.

On the first electron transporting layer, the following compound ET-2 was vapor-deposited to form a film ET-2 with a thickness of 5 nm, thereby forming a second electron transporting layer.

On the second electron transporting layer, LiF was vapor-deposited to form a film of LiF with a thickness of 1 nm at a film-forming speed of 0.01 nm/sec, thereby forming an electron injecting electrode (cathode).

On the film of LiF, metallic Al was vapor-deposited to from a film of metallic Al with a thickness of 80 nm, thereby forming a metallic Al cathode.

Evaluation of Organic EL Device

By applying a voltage to the organic EL device thus produced so as to adjust the current density to 10 mA/cm², the driving voltage and the external quantum efficiency (EQE) were measured. The results are shown in Table 3.

BD-1

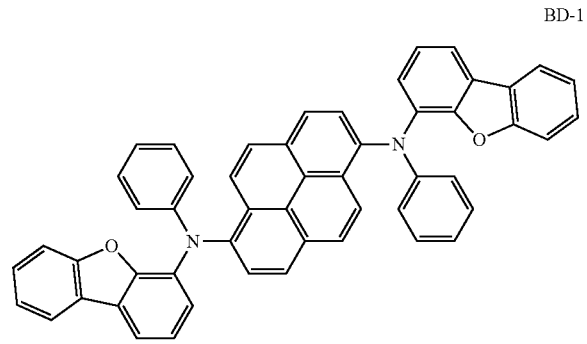

HT-5

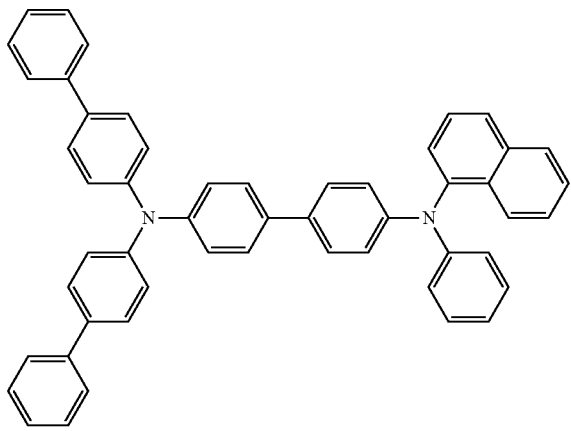

Examples 10 to 11 And Comparative Example 4

Each device was produced in the same manner as in Example 9 except for using each compound shown in Table 3 in place of the compound 8. The results of evaluation are shown in Table 3.

TABLE 3

|  | Host material | Driving voltage (V) | External quantum efficiency (%) |
| --- | --- | --- | --- |
| Example 9 | Compound 8 | 3.3 | 8.5 |
| Example 10 | Compound 9 | 3.2 | 8.4 |
| Example 11 | Compound 10 | 3.2 | 8.5 |
| Comparative example 4 | Comparative compound 3 | 3.4 | 7.5 |

Comparative compound 3

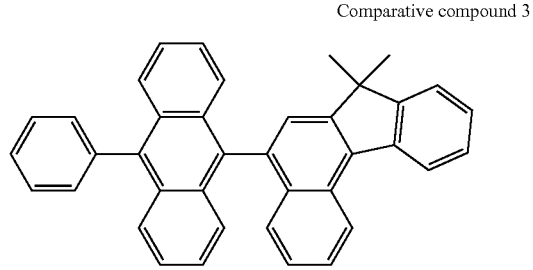 [SMILES: CC1(C)c2ccccc2-c2c1cc(-c1c3ccccc3c(-c3ccccc3)c3ccccc13)c1ccccc21]

As seen from Table 3, the organic EL devices comprising the compounds 8 to 10 in the light emitting layer as the host material are operated at lower driving voltage and emit light with high efficiency. The broad π-plane of the structure in which the anthracene skeleton further includes a substituent is considered to enhance the interaction between the host materials in the light emitting layer to increase the carrier transporting ability. Probably with this effect, the driving voltage is reduced, and simultaneously, a more efficient emission is obtained because the energy is transferred to the dopant material smoothly. Thus, the compounds 8 to 10 of the invention are also useful as a host material of the light emitting layer.

REFERENCE SIGNS LIST

1: Organic EL device
2: Substrate
3: Anode
4: Cathode
5: Light emitting layer
6: Hole injecting layer/hole transporting layer
7: Electron injecting layer/electron transporting layer
10: Emission unit

What is claimed is:
1. A compound is represented by any of formulae (3) and (4-2):

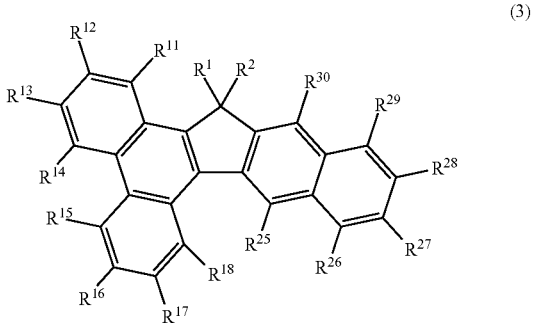

(3)

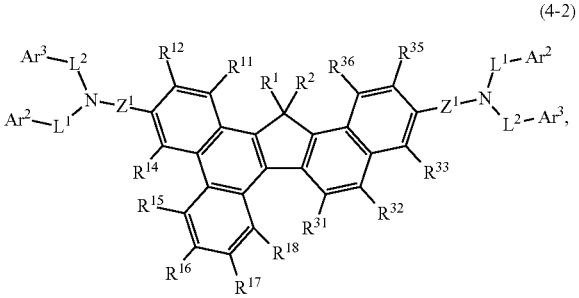

(4-2)

wherein:
$R^1$ and $R^2$ each independently represent a hydrogen atom, a substituted or unsubstituted alkyl group having 1 to 20 carbon atoms, a substituted or unsubstituted cycloalkyl group having 3 to 20 ring carbon atoms, a group represented by —Si($R_{101}$)($R_{102}$)($R_{103}$), a substituted or unsubstituted aryl group having 6 to 30 ring carbon atoms, or a substituted or unsubstituted heteroaryl group having 5 to 30 ring atoms; and
$R^{11}$ to $R^{18}$, and $R^{25}$ to $R^{36}$ each independently represents a hydrogen atom, a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a group represented by —Si($R_{101}$)($R_{102}$)($R_{103}$), a group represented by —N($R_{104}$)($R_{105}$), a substituted or unsubstituted aryl group having 6 to 30 ring carbon atoms, a substituted or unsubstituted heteroaryl group having 5 to 30 ring atoms, or a group represented by —Z—$R^a$;

$R_{101}$ to $R_{105}$ each independently represent a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms;

$L^1$ and $L^2$ each independently represent a single bond, a substituted or unsubstituted arylene group having 6 to 30 ring carbon atoms, a substituted or unsubstituted heteroarylene group having 5 to 30 ring atoms, or a divalent linking group in which 2 to 4 groups selected from the arylene group and the heteroarylene group are linked together;

$Ar^2$ and $Ar^1$ each independently represent a substituted or unsubstituted aryl group having 6 to 30 ring carbon atoms, or a substituted or unsubstituted heteroaryl group having 5 to 30 ring atoms the group represented by —Z—$R^a$ is represented by formula (b):

$$—Z^2—HAr \qquad (b);$$

—HAr in formula (b) is a group selected from the following groups:

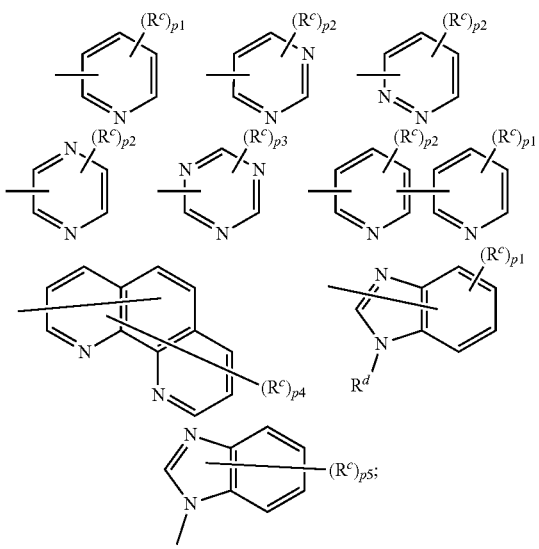

$Z^1$ and $Z^2$ each independently represent a single bond, a substituted or unsubstituted arylene group having 6 to 30 ring carbon atoms, a substituted or unsubstituted heteroarylene group having 5 to 30 ring atoms, or a divalent linking group in which 2 to 4 groups selected from the arylene group and the heteroarylene group are linked together;

each $R^c$ independently represents a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 ring carbon atoms, a substituted or unsubstituted aralkyl group having 7 to 30 carbon atoms which has an aryl group having 6 to 30 ring carbon atoms, an amino group, a mono- or dialkylamino group having an alkyl group having 1 to 20 carbon atoms, a mono- or diarylamino group having an aryl group having 6 to 30 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a mono-, di- or tri-substituted silyl group having a substituent selected from an alkyl group having 1 to 20 carbon atoms and an aryl group having 6 to 30 ring carbon atoms, a substituted or unsubstituted heteroaryl group having 5 to 30 ring atoms, a halogen atom, a cyano group, or a nitro group;

when more than one $R^c$ occurs in each group, groups $R^c$ may be the same or different;

$R^d$ represents a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 ring carbon atoms, or a substituted or unsubstituted heteroaryl group having 5 to 30 ring atoms; and each p1 independently represents an integer of 0 to 4, each p2 independently represents an integer of 0 to 3, p3 represents an integer of 0 to 2, p4 represents an integer of 0 to 7, and p5 represents an integer of 0 to 5, provided that one to four selected from $R^{11}$ to $R^{18}$ and $R^{25}$ to $R^{30}$ of formula (3) each represent a group represented by —Z—$R^a$.

2. The compound according to claim 1, wherein only one or two selected from $R^{11}$ to $R^{18}$ and $R^{25}$ to $R^{30}$ in formula (3), and only one or two selected from $R^{11}$ to $R^{12}$ and $R^{14}$ to $R^{18}$ and $R^{31}$ to $R^{33}$ and $R^{35}$ to $R^{36}$ in formula (4-2) are represented by formula (b).

3. The compound according to claim 1, wherein $R^{28}$ in formula (3) is represented by formula (b).

4. The compound according to claim 1, wherein $Z^1$ is a single bond.

5. The compound according to claim 1, wherein $Ar^2$ and $Ar^3$ each represent a substituted or unsubstituted aryl group having 6 to 30 ring carbon atoms.

6. The compound according to claim 1, wherein $L^1$ and $L^2$ are both single bonds, and $Ar^2$ and $Ar^3$ each independently represent a substituted or unsubstituted phenyl group, a substituted or unsubstituted naphthyl group, a substituted or unsubstituted phenanthrenyl group, a substituted or unsubstituted fluorenyl group, a substituted or unsubstituted dibenzofuranyl group, or a substituted or unsubstituted dibenzothiophenyl group.

7. A material for organic electroluminescence devices, the material comprising the compound according to claim 1.

8. An organic electroluminescence device, comprising:
an organic thin film layer between a cathode and an anode, wherein:
the organic thin film layer comprises one or more layers comprising a light emitting layer; and
at least one layer of the organic thin film layer comprises the compound represented by formula (3) or (4-2) according to claim 1.

9. The organic electroluminescence device according to claim 8, wherein the light emitting layer comprises the compound represented by formula (3) or (4-2).

10. The organic electroluminescence device according to claim 8, wherein the at least one layer of the organic thin film layer comprises the compound represented by formula (3) or (4-2) and an anthracene derivative represented by formula (5):

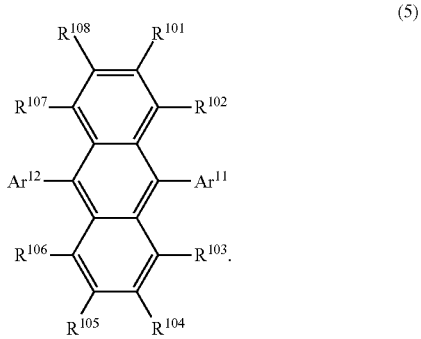

wherein:
$Ar^{11}$ and $Ar^{12}$ each independently represent a substituted or unsubstituted monocyclic group having 5 to 50 ring atoms or a substituted or unsubstituted fused ring group having 8 to 50 ring atoms; and
$R^{101}$ to $R^{108}$ are each independently selected from a hydrogen atom, a substituted or unsubstituted monocyclic group having 5 to 50 ring atoms, a substituted or unsubstituted fused ring group having 8 to 50 ring atoms, a group comprising a combination of the monocyclic group and the fused ring group, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted silyl group, a halogen atom, and a cyano group.

11. The organic electroluminescence device according to claim 8, wherein the organic thin film layer comprises an electron transporting layer, and the electron transporting layer comprises said compound represented by formula (3) or (4-2).

12. The organic electroluminescence device according to claim 8, wherein the organic thin film layer comprises a hole transporting layer comprising the compound represented by formula (3) or (4-2).

13. The organic electroluminescence device according to claim 8, wherein the organic thin film layer comprises an electron transporting layer and a blocking layer between the electron transporting layer and the light emitting layer, and the blocking layer comprises the compound represented by formula (3) or (4-2).

14. An electronic equipment, comprising the organic electroluminescence device according to claim 8.

15. A compound represented by formula (2):

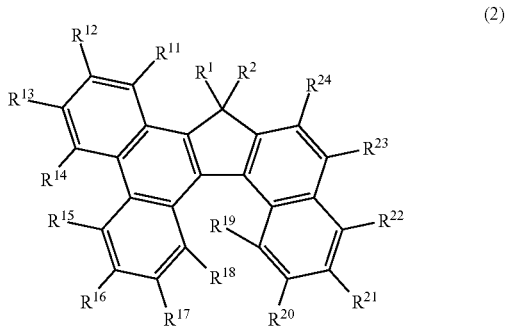

wherein:
$R^1$ and $R^2$ each independently represent a hydrogen atom, a substituted or unsubstituted alkyl group having 1 to 20 carbon atoms, a substituted or unsubstituted cycloalkyl group having 3 to 20 ring carbon atoms, a group represented by $-Si(R_{101})(R_{102})(R_{103})$, a substituted or unsubstituted aryl group having 6 to 30 ring carbon atoms, or a substituted or unsubstituted heteroaryl group having 5 to 30 ring atoms; and each of $R^{11}$ to $R^{24}$ independently represents a hydrogen atom, a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a group represented by $-Si(R_{101})(R_{102})(R_{103})$, a substituted or unsubstituted aryl group having 6 to 30 ring carbon atoms, a substituted or unsubstituted furyl group, thienyl group, benzofuranyl group, isobenzofuranyl group, benzothiophenyl group, isobenzothiophenyl group, dibenzofuranyl group, dibenzothiophenyl group, or xanthenyl group, or a group represented by $-Z-R^a$;
each Z represents a single bond, a substituted or unsubstituted arylene group having 6 to 30 ring carbon atoms, a substituted or unsubstituted dibenzofuranylene group or a substituted or unsubstituted dibenzothiophenylene group, or a divalent linking group in which 2 to 4 groups selected from the above groups are linked together;
when more than one Z occurs, groups Z may be the same or different;
$R^a$ represents a group represented by a substituted or unsubstituted aryl group having 6 to 30 ring carbon atoms, or a substituted or unsubstituted furyl group, thienyl group, benzofuranyl group, isobenzofuranyl group, benzothiophenyl group, isobenzothiophenyl group, dibenzofuranyl group, dibenzothiophenyl group, or xanthenyl group;
when more than one $R^a$ occurs, groups $R^a$ may be the same or different;
$R_{101}$ to $R_{103}$ each independently represent a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms; and when $R^1$ to $R^2$, $R^{11}$ to $R^{24}$, and $R_{101}$ to $R_{103}$ of formula (2) have a substituent, the substituent represents an alkyl group having 1 to 10 carbon atoms, a cycloalkyl group having 3 to 6 ring carbon atoms, an aryl group having 6 to 24 ring carbon atoms, an alkoxy group having 1 to 10 carbon atoms, a halogen atom, a cyano group, or a nitro group, and the substituent is not substituted with further substituent and adjacent groups of substituents is not bonded to each other to form a ring structure;

provided that one to four selected from $R^{11}$ to $R^{24}$ each represents a group represented by —Z—$R^a$.

16. The compound according to claim 15, wherein the group represented by —Z—$R^a$ is represented by any of formulae (b) to (c):

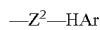

(b)

(c)

wherein:

$Z^2$ and $Z^3$ are the same as Z defined above, or a divalent linking group in which 2 to 4 groups selected from the above groups are linked together;

HAr represents a substituted or unsubstituted furyl group, thienyl group, benzofuranyl group, isobenzofuranyl group, benzothiophenyl group, isobenzothiophenyl group, dibenzofuranyl group, dibenzothiophenyl group, or xanthenyl group; and $Ar^4$ represents a substituted or unsubstituted aryl group having 14 to 30 ring carbon atoms.

17. The compound according to claim 16, wherein only one or two selected from $R^{11}$ to $R^{24}$ in formula (2) is each independently represented by any of formulae (b) to (c).

18. The compound according to claim 16, wherein only one or two selected from $R^{11}$ to $R^{24}$ in formula (2) is represented by formula (b).

19. The compound according to claim 16, wherein only one or two selected from $R^{11}$ to $R^{24}$ in formula (2) is represented by formula (c).

20. The compound according to claim 16, wherein $R^{23}$ in formula (2) is represented by any of formulae (b) to (c).

21. A compound is represented by any of formulae (3) and (4-2):

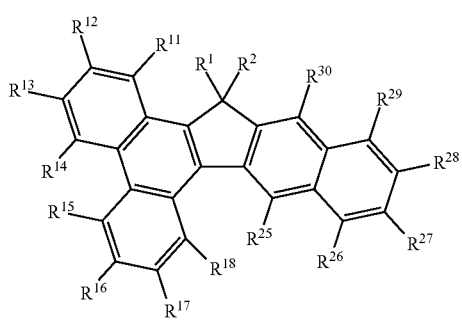

(3)

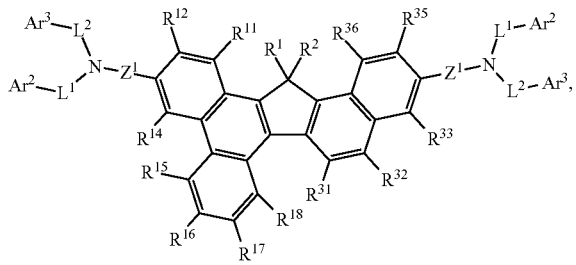

(4-2)

wherein:

$R^1$ and $R^2$ each independently represent a hydrogen atom, a substituted or unsubstituted alkyl group having 1 to 20 carbon atoms, a substituted or unsubstituted cycloalkyl group having 3 to 20 ring carbon atoms, a group represented by —Si($R_{101}$)($R_{102}$)($R_{103}$), a substituted or unsubstituted aryl group having 6 to 30 ring carbon atoms, or a substituted or unsubstituted heteroaryl group having 5 to 30 ring atoms;

$R^{11}$ to $R^{18}$, $R^{25}$ to $R^{27}$, $R^{29}$ to $R^{33}$, and $R^{35}$ to $R^{36}$ each independently represents a hydrogen atom, a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a group represented by —Si($R_{101}$)($R_{102}$)($R_{103}$), a group represented by —N($R_{104}$)($R_{105}$), a substituted or unsubstituted aryl group having 6 to 30 ring carbon atoms, a substituted or unsubstituted heteroaryl group having 5 to 30 ring atoms, or a group represented by —Z—$R^a$;

each Z represents a single bond, a substituted or unsubstituted arylene group having 6 to 30 ring carbon atoms, a substituted or unsubstituted heteroarylene group having 5 to 30 ring atoms, or a divalent linking group in which 2 to 4 groups selected from the above groups are linked together;

when more than one Z occurs, groups Z may be the same or different;

$R^a$ represents a group represented by —N($R_{104}$)($R_{105}$), a substituted or unsubstituted aryl group having 6 to 30 ring carbon atoms, or a substituted or unsubstituted heteroaryl group having 5 to 30 ring atoms;

when more than one $R^a$ occurs, groups $R^a$ may be the same or different;

$R_{101}$ to $R_{105}$ each independently represent a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms;

the group represented by —Z—$R^a$, and is represented by any of formulae (a) to (c):

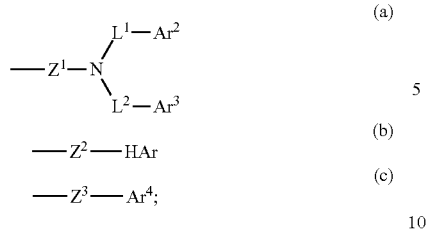

Z¹ to Z³ each independently represent a single bond, a substituted or unsubstituted arylene group having 6 to 30 ring carbon atoms, a substituted or unsubstituted heteroarylene group having 5 to 30 ring atoms, or a divalent linking group in which 2 to 4 groups selected from the arylene group and the heteroarylene group are linked together;

L¹ and L² each independently represent a single bond, a substituted or unsubstituted arylene group having 6 to 30 ring carbon atoms, a substituted or unsubstituted heteroarylene group having 5 to 30 ring atoms, or a divalent linking group in which 2 to 4 groups selected from the arylene group and the heteroarylene group are linked together;

Ar² and Ar³ each independently represent a substituted or unsubstituted aryl group having 6 to 30 ring carbon atoms, or a substituted or unsubstituted heteroaryl group having 5 to 30 ring atoms;

HAr represents a substituted or unsubstituted heteroaryl group having 5 to 30 ring atoms;

$R^{28}$ in formula (3) is represented by any of the formulae (a) to (c); and

Ar⁴ represents a substituted or unsubstituted aryl group having 14 to 30 ring carbon atoms, provided that one to three selected from $R^{11}$ to $R^{18}$, $R^{25}$ to $R^{27}$, and $R^{29}$ to $R^{30}$ of formula (3) each represent a group represented by —Z—$R^a$.

22. The compound according to claim 21, wherein the group represented by —Z—$R^a$ is represented by formula (b), and —HAr in formula (b) is a group selected from the following groups:

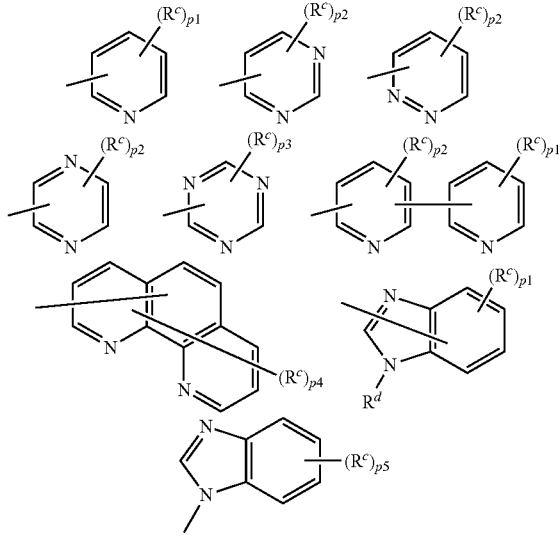

wherein each $R^c$ independently represents a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 ring carbon atoms, a substituted or unsubstituted aralkyl group having 7 to 30 carbon atoms which has an aryl group having 6 to 30 ring carbon atoms, an amino group, a mono- or dialkylamino group having an alkyl group having 1 to 20 carbon atoms, a mono- or diarylamino group having an aryl group having 6 to 30 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a mono-, di- or tri-substituted silyl group having a substituent selected from an alkyl group having 1 to 20 carbon atoms and an aryl group having 6 to 30 ring carbon atoms, a substituted or unsubstituted heteroaryl group having 5 to 30 ring atoms, a halogen atom, a cyano group, or a nitro group;

when more than one $R^c$ occurs in each group, groups $R^c$ may be the same or different;

$R^d$ represents a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 ring carbon atoms, or a substituted or unsubstituted heteroaryl group having 5 to 30 ring atoms; and each p1 independently represents an integer of 0 to 4, each p2 independently represents an integer of 0 to 3, p3 represents an integer of 0 to 2, p4 represents an integer of 0 to 7, and p5 represents an integer of 0 to 5.

23. The compound according to claim 21, wherein only one or two selected from $R^{11}$ to $R^{18}$, $R^{25}$ to $R^{27}$, and $R^{29}$ to $R^{30}$ in formula (3), and only two selected from $R^{11}$ to $R^{12}$ and $R^{14}$ to $R^{18}$ and $R^{31}$ to $R^{33}$ and $R^{35}$ to $R^{36}$ in formula (4-2) are each independently represented by any of formulae (a) to (c).

24. The compound according to claim 21, wherein only one or two selected from $R^{11}$ to $R^{18}$, $R^{25}$ to $R^{27}$, and $R^{29}$ to $R^{30}$ in formula (3), and only two selected from $R^{11}$ to $R^{12}$ and $R^{14}$ to $R^{18}$ and $R^{31}$ to $R^{33}$ and $R^{35}$ to $R^{36}$ in formula (4-2) are represented by formula (a).

25. The compound according to claim 21, wherein only one or two selected from $R^{11}$ to $R^{18}$, $R^{25}$ to $R^{27}$, and $R^{29}$ to $R^{30}$ in formula (3), and only two selected from $R^{11}$ to $R^{12}$ and $R^{14}$ to $R^{18}$ and $R^{31}$ to $R^{33}$ and $R^{35}$ to $R^{36}$ in formula (4-2) are represented by formula (b).

26. The compound according to claim 21, wherein only one or two selected from $R^{11}$ to $R^{18}$, $R^{25}$ to $R^{27}$, and $R^{29}$ to $R^{30}$ in formula (3), and only two selected from $R^{11}$ to $R^{12}$ and $R^{14}$ to $R^{18}$ and $R^{31}$ to $R^{33}$ and $R^{35}$ to $R^{36}$ in formula (4-2) are represented by formula (c).

27. The compound according to claim 21, wherein the compound is represented by formulae (3-1):

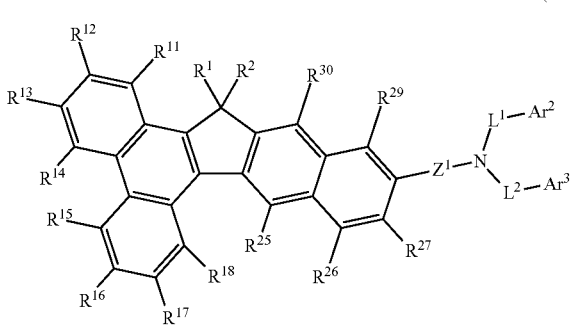

(3-1)

wherein $R^1$, $R^2$, $R^{11}$ to $R^{18}$, $R^{25}$ to $R^{27}$, $R^{29}$ to $R^{30}$, $R^{35}$, $R^{36}$, $Z^1$, $L^1$, $L^2$, $Ar^2$, and $Ar^3$ are as defined above.

28. The compound according to claim 21, wherein the compound is represented by formulae (3-2):

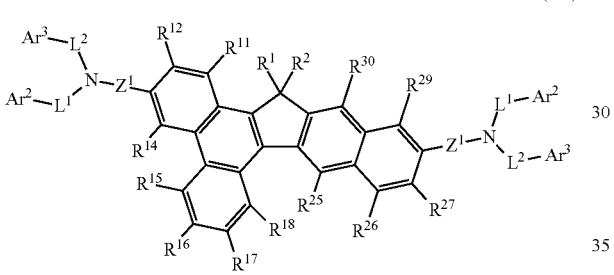

(3-2)

wherein $R^1$, $R^2$, $R^{11}$, $R^{12}$, $R^{14}$ to $R^{18}$, $R^{25}$ to $R^{27}$, $R^{29}$ to $R^{30}$ $Z^1$, $L^1$, $L^2$, $Ar^2$, and $Ar^3$ are as defined above, and more than one $Z^1$, $L^1$, $L^2$, $Ar^2$ and $Ar^3$ may be the same or different, respectively.

29. The compound according to claim 21, wherein $Z^1$ is a single bond.

30. The compound according to claim 21, wherein $Ar^2$ and $Ar^3$ each represent a substituted or unsubstituted aryl group having 6 to 30 ring carbon atoms.

31. The compound according to claim 21, wherein $L^1$ and $L^2$ are both single bonds, and $Ar^2$ and $Ar^3$ each independently represent a substituted or unsubstituted phenyl group, a substituted or unsubstituted naphthyl group, a substituted or unsubstituted phenanthrenyl group, a substituted or unsubstituted fluorenyl group, a substituted or unsubstituted dibenzofuranyl group, or a substituted or unsubstituted dibenzothiophenyl group.

32. A material for organic electroluminescence devices, the material comprising the compound according to claim 21.

33. An organic electroluminescence device, comprising:
an organic thin film layer between a cathode and an anode, wherein:
the organic thin film layer comprises one or more layers comprising a light emitting layer; and
at least one layer of the organic thin film layer comprises the compound represented by formula (3) or (4-2) according to claim 21.

34. The organic electroluminescence device according to claim 33, wherein the light emitting layer comprises the compound represented by formula (3) or (4-2).

35. The organic electroluminescence device according to claim 33, wherein the at least one layer of the organic thin film layer comprises the compound represented by formula (3) or (4-2) and an anthracene derivative represented by formula (5):

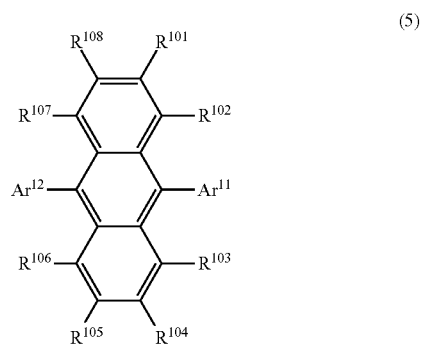

(5)

wherein $Ar^{11}$ and $Ar^{12}$ each independently represent a substituted or unsubstituted monocyclic group having 5 to 50 ring atoms or a substituted or unsubstituted fused ring group having 8 to 50 ring atoms; and $R^{101}$ to $R^{108}$ are each independently selected from a hydrogen atom, a substituted or unsubstituted monocyclic group having 5 to 50 ring atoms, a substituted or unsubstituted fused ring group having 8 to 50 ring atoms, a group comprising a combination of the monocyclic group and the fused ring group, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted silyl group, a halogen atom, and a cyano group.

36. The organic electroluminescence device according to claim 33, wherein the organic thin film layer comprises an electron transporting layer, and the electron transporting layer comprises said compound represented by formula (3) or (4-2).

37. The organic electroluminescence device according to claim 33, wherein the organic thin film layer comprises a hole transporting layer comprising the compound represented by formula (3) or (4-2).

38. The organic electroluminescence device according to claim 33, wherein the organic thin film layer comprises an electron transporting layer and a blocking layer between the electron transporting layer and the light emitting layer, and the blocking layer comprises the compound represented by formula (3) or (4-2).

39. An electronic equipment, comprising the organic electroluminescence device according to claim 33.

40. A compound is represented by any of formulae (3-1) and (4-2):

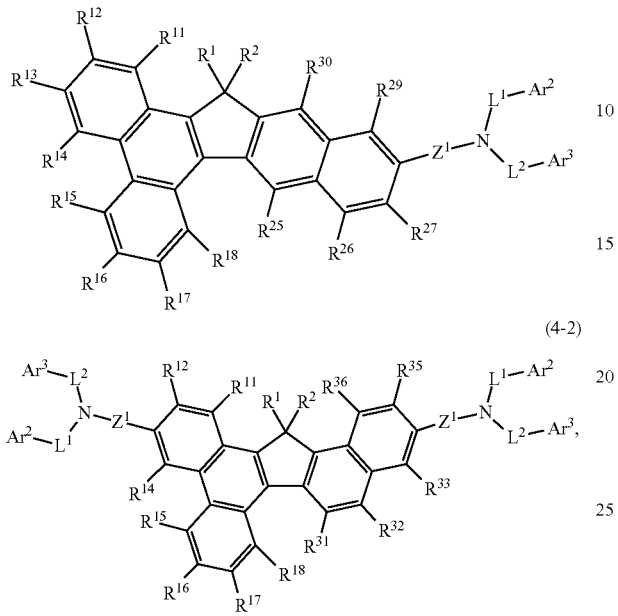

wherein:

$R^1$ and $R^2$ each independently represent a hydrogen atom, a substituted or unsubstituted alkyl group having 1 to 20 carbon atoms, a substituted or unsubstituted cycloalkyl group having 3 to 20 ring carbon atoms, a group represented by $-Si(R_{101})(R_{102})(R_{103})$, a substituted or unsubstituted aryl group having 6 to 30 ring carbon atoms, or a substituted or unsubstituted heteroaryl group having 5 to 30 ring atoms; and $R^{11}$ to $R^{18}$, $R^{25}$ to $R^{27}$, $R^{29}$ to $R^{33}$, and $R^{35}$ to $R^{36}$ each independently represents a hydrogen atom, a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a group represented by $-Si(R_{101})(R_{102})(R_{103})$, a group represented by $-N(R_{104})(R_{105})$, a substituted or unsubstituted aryl group having 6 to 30 ring carbon atoms, a substituted or unsubstituted heteroaryl group having 5 to 30 ring atoms, or a group represented by $-Z-R^a$;

$R_{101}$ to $R_{105}$ each independently represent a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms;

the group represented by $-Z-R^a$, and is represented by any of formulae (a) to (c):

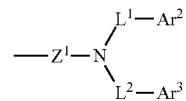 (a)

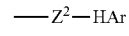 (b)

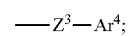 (c)

$Z^1$ to $Z^3$ each independently represent a single bond, a substituted or unsubstituted arylene group having 6 to 30 ring carbon atoms, a substituted or unsubstituted heteroarylene group having 5 to 30 ring atoms, or a divalent linking group in which 2 to 4 groups selected from the arylene group and the heteroarylene group are linked together;

$L^1$ and $L^2$ each independently represent a single bond, a substituted or unsubstituted arylene group having 6 to 30 ring carbon atoms, a substituted or unsubstituted heteroarylene group having 5 to 30 ring atoms, or a divalent linking group in which 2 to 4 groups selected from the arylene group and the heteroarylene group are linked together;

$Ar^2$ and $Ar^3$ each independently represent a substituted or unsubstituted aryl group having 6 to 30 ring carbon atoms, or a substituted or unsubstituted heteroaryl group having 5 to 30 ring atoms;

HAr represents a substituted or unsubstituted heteroaryl group having 5 to 30 ring atoms; and $Ar^4$ represents a substituted or unsubstituted aryl group having 14 to 30 ring carbon atoms, provided that one to three selected from $R^{11}$ to $R^{18}$, $R^{25}$ to $R^{27}$, and $R^{29}$ to $R^{30}$ of formula (3-1), and one or two selected from $R^{11}$ to $R^{18}$, $R^{31}$ to $R^{33}$, and $R^{35}$ to $R^{36}$ of formula (4-2) each represent a group represented by $-Z-R^a$.

41. The compound according to claim 40, wherein:
the group represented by $-Z-R^a$ is represented by formula (b):

$-Z^2-HAr$ (b);

$Z^2$ independently represents a single bond, a substituted or unsubstituted arylene group having 6 to 30 ring carbon atoms, a substituted or unsubstituted heteroarylene group having 5 to 30 ring atoms, or a divalent linking group in which 2 to 4 groups selected from the arylene group and the heteroarylene group are linked together;

—HAr in formula (b) is a group selected from the following groups:

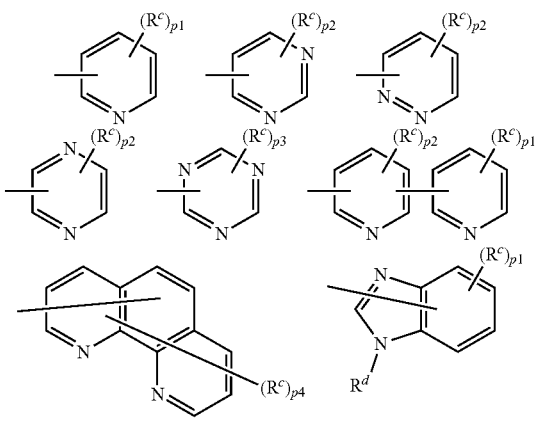

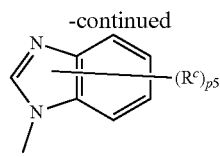

each $R^c$ independently represents a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 ring carbon atoms, a substituted or unsubstituted aralkyl group having 7 to 30 carbon atoms which has an aryl group having 6 to 30 ring carbon atoms, an amino group, a mono- or dialkylamino group having an alkyl group having 1 to 20 carbon atoms, a mono- or diarylamino group having an aryl group having 6 to 30 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a mono-, di- or tri-substituted silyl group having a substituent selected from an alkyl group having 1 to 20 carbon atoms and an aryl group having 6 to 30 ring carbon atoms, a substituted or unsubstituted heteroaryl group having 5 to 30 ring atoms, a halogen atom, a cyano group, or a nitro group;

when more than one $R^c$ occurs in each group, groups $R^c$ may be the same or different;

$R^d$ represents a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 ring carbon atoms, or a substituted or unsubstituted heteroaryl group having 5 to 30 ring atoms; and each p1 independently represents an integer of 0 to 4, each p2 independently represents an integer of 0 to 3, $p^3$ represents an integer of 0 to 2, p4 represents an integer of 0 to 7, and p5 represents an integer of 0 to 5.

42. The compound according to claim 40, wherein only one or two selected from $R^{11}$ to $R^{18}$, $R^{25}$ to $R^{27}$, and $R^{29}$ to $R^{30}$ in formula (3-1), and only two selected from $R^{11}$ to $R^{12}$ and $R^{14}$ to $R^{18}$ and $R^{31}$ to $R^{33}$ and $R^{35}$ to $R^{36}$ in formula (4-2) are each independently represented by any of the formulae (a) to (c).

43. The compound according to claim 40, wherein only one or two selected from $R^{11}$ to $R^{18}$, $R^{25}$ to $R^{27}$, and $R^{29}$ to $R^{30}$ in formula (3-1), and only two selected from $R^{11}$ to $R^{12}$ and $R^{14}$ to $R^{18}$ and $R^{31}$ to $R^{33}$ and $R^{35}$ to $R^{36}$ in formula (4-2) are represented by the formula (a).

44. The compound according to claim 40, wherein only one or two selected from $R^{11}$ to $R^{18}$, $R^{25}$ to $R^{27}$, and $R^{29}$ to $R^{30}$ in formula (3-1), and only two selected from $R^{11}$ to $R^{12}$ and $R^{14}$ to $R^{18}$ and $R^{31}$ to $R^{33}$ and $R^{35}$ to $R^{36}$ in formula (4-2) are represented by the formula (b).

45. The compound according to claim 40, wherein only one or two selected from $R^{11}$ to $R^{18}$, $R^{25}$ to $R^{27}$, and $R^{29}$ to $R^{30}$ in formula (3-1), and only two selected from $R^{11}$ to $R^{12}$ and $R^{14}$ to $R^{18}$ and $R^{31}$ to $R^{33}$ and $R^{35}$ to $R^{36}$ in formula (4-2) are represented by the formula (c).

46. The compound according to claim 40, wherein the compound is represented by formula (3-2):

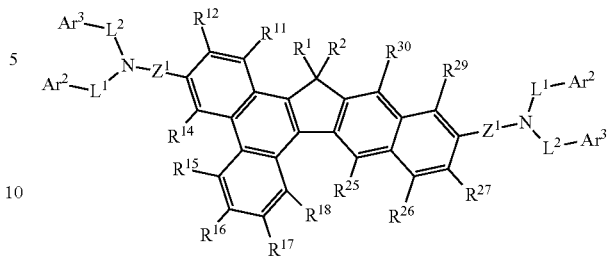

wherein $R^1$, $R^2$, $R^{11}$, $R^{12}$, $R^{14}$ to $R^{18}$, $R^{25}$ to $R^{27}$, $R^{29}$ to $R^{30}$ $Z^1$, $L^1$, $L^2$, $Ar^2$, and $Ar^3$ are as defined above, and more than one $Z^1$, $L^1$, $L^2$, $Ar^2$ and $Ar^3$ may be the same or different, respectively.

47. The compound according to claim 40, wherein $Z^1$ is a single bond.

48. The compound according to claim 40, wherein $Ar^1$ and $Ar^3$ each represent a substituted or unsubstituted aryl group having 6 to 30 ring carbon atoms.

49. The compound according to claim 40, wherein $L^1$ and $L^2$ are both single bonds, and $Ar^2$ and $Ar^3$ each independently represent a substituted or unsubstituted phenyl group, a substituted or unsubstituted naphthyl group, a substituted or unsubstituted phenanthrenyl group, a substituted or unsubstituted fluorenyl group, a substituted or unsubstituted dibenzofuranyl group, or a substituted or unsubstituted dibenzothiophenyl group.

50. A material for organic electroluminescence devices, the material comprising the compound according to claim 40.

51. An organic electroluminescence device, comprising:
an organic thin film layer between a cathode and an anode, wherein:
the organic thin film layer comprises one or more layers comprising a light emitting layer; and
at least one layer of the organic thin film layer comprises the compound represented by formula (3-1) or (4-2) according to claim 40.

52. The organic electroluminescence device according to claim 51, wherein the light emitting layer comprises the compound represented by formula (3-1) or (4-2).

53. The organic electroluminescence device according to claim 51, wherein the at least one layer of the organic thin film layer comprises the compound represented by formula (3-1) or (4-2) and an anthracene derivative represented by formula (5):

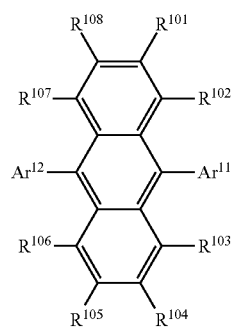

wherein $Ar^{11}$ and $Ar^{12}$ each independently represent a substituted or unsubstituted monocyclic group having 5 to 50 ring atoms or a substituted or unsubstituted fused ring group having 8 to 50 ring atoms; and $R^{101}$ to $R^{108}$ are each independently selected from a hydrogen atom, a substituted or unsubstituted monocyclic group having 5 to 50 ring atoms, a substituted or unsubstituted fused ring group having 8 to 50 ring atoms, a group comprising a combination of the monocyclic group and the fused ring group, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted silyl group, a halogen atom, and a cyano group.

54. The organic electroluminescence device according to claim 51, wherein the organic thin film layer comprises an electron transporting layer, and the electron transporting layer comprises said compound represented by formula (3-1) or (4-2).

55. The organic electroluminescence device according to claim 51, wherein the organic thin film layer comprises a hole transporting layer comprising the compound represented by formula (3-1) or (4-2).

56. The organic electroluminescence device according to claim 51, wherein the organic thin film layer comprises an electron transporting layer and a blocking layer between the electron transporting layer and the light emitting layer, and the blocking layer comprises the compound represented by formula (3-1) or (4-2).

57. An electronic equipment, comprising the organic electroluminescence device according to claim 51.

* * * * *

UNITED STATES PATENT AND TRADEMARK OFFICE
CERTIFICATE OF CORRECTION

PATENT NO. : 10,396,288 B2
APPLICATION NO. : 14/909783
DATED : August 27, 2019
INVENTOR(S) : Hirokatsu Ito et al.

It is certified that error appears in the above-identified patent and that said Letters Patent is hereby corrected as shown below:

In the Claims

At Column 917, Line 16, delete:
"$Ar^1$"
And insert:
-- $Ar^3$ --

At Column 919, Lines 10-24, delete:

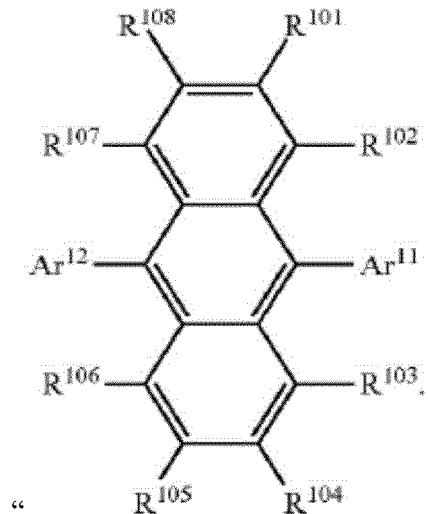

(5)

"

Signed and Sealed this
Twenty-third Day of June, 2020

Andrei Iancu
*Director of the United States Patent and Trademark Office*

And insert:
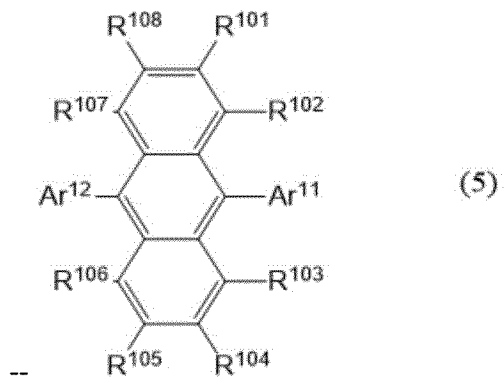
At Column 923, Line 9, delete:
""
And insert:
-- ——$Z^3$——$Ar^4$   (c); --
At Column 923, Lines 45-65, delete:
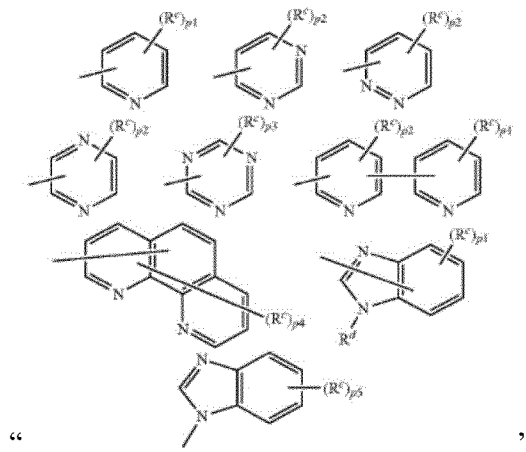
And insert:
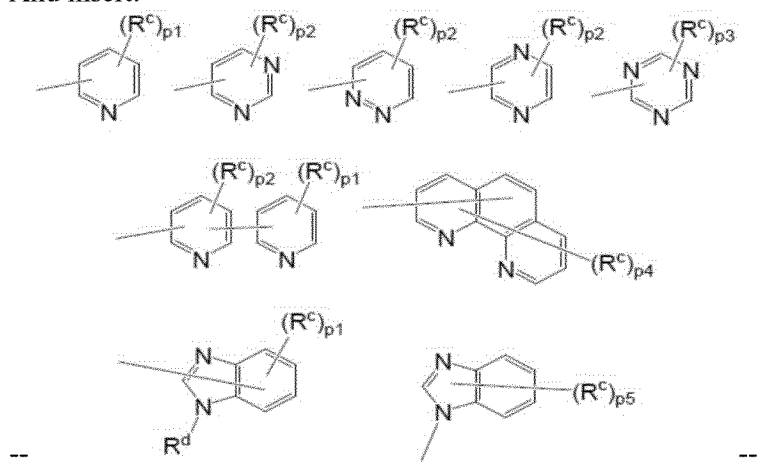

At Column 928, Line 9, delete:

"—$Z^3$—$Ar^4$;         (c)"

And insert:

-- —$Z^3$——$Ar^4$         (c); --

At Column 930, Line 21, delete:
"$Ar^1$"
And insert:
-- $Ar^2$ --